US008263606B2

(12) United States Patent
Chafeev et al.

(10) Patent No.: US 8,263,606 B2
(45) Date of Patent: Sep. 11, 2012

(54) SPIRO-OXINDOLE COMPOUNDS AND THEIR USE AS THERAPEUTIC AGENTS

(75) Inventors: Mikhail Chafeev, Burnaby (CA); Sultan Chowdhury, Surrey (CA); Lauren Fraser, Surrey (CA); Jianmin Fu, Coquitlam (CA); Jonathan Langille, Quaker Hill, CT (US); Shifeng Liu, Coquitlam (CA); Jianyu Sun, San Mateo, CA (US); Shaoyi Sun, Coquitlam (CA); Serguei Sviridov, Burnaby (CA); Mark Wood, Port Moody (CA); Alla Zenova, Vancouver (CA); Qi Jia, Burnaby (CA); Jean-Jacques Cadieux, Burnaby (CA); Simon J. Gauthier, Vancouver (CA); Amy Frances Douglas, Vancouver (CA); Tom Hsieh, Toronto (CA); Nagasree Chakka, Waltham, MA (US); Zoran Cikojevic, Port Coquitlam (CA)

(73) Assignee: Xenon Pharmaceuticals Inc., Burnaby (CA)

( * ) Notice: Subject to any disclaimer, the term of this patent is extended or adjusted under 35 U.S.C. 154(b) by 214 days.

(21) Appl. No.: 12/578,148

(22) Filed: Oct. 13, 2009

(65) Prior Publication Data
US 2010/0137299 A1   Jun. 3, 2010

Related U.S. Application Data

(60) Provisional application No. 61/106,464, filed on Oct. 17, 2008.

(51) Int. Cl.
*A61K 31/44* (2006.01)
*C07D 213/02* (2006.01)
(52) U.S. Cl. .......................................... 514/278; 546/15
(58) Field of Classification Search .................. 546/15; 514/278
See application file for complete search history.

(56) References Cited

U.S. PATENT DOCUMENTS

| | | | |
|---|---|---|---|
| 3,189,617 A | 6/1965 | Archer et al. .................. 260/319 |
| 3,723,459 A | 3/1973 | Paragamian .................... 260/325 |
| 3,845,770 A | 11/1974 | Theeuwes et al. .............. 128/260 |
| 4,045,576 A | 8/1977 | Welstead, Jr. et al. .......... 424/309 |
| 4,326,525 A | 4/1982 | Swanson et al. ................ 128/260 |
| 4,438,130 A | 3/1984 | Kaplan ......................... 424/274 |
| 4,440,785 A | 4/1984 | Walsh .......................... 424/317 |
| 4,670,566 A | 6/1987 | Walsh .......................... 548/485 |
| 4,886,788 A | 12/1989 | Skuballa et al. ................. 514/58 |
| 4,935,446 A | 6/1990 | Imaki et al. .................... 514/530 |
| 5,023,265 A | 6/1991 | Scherlock et al. .............. 514/300 |
| 5,116,854 A | 5/1992 | Marfat ......................... 514/365 |
| 5,182,289 A | 1/1993 | Ting et al. ..................... 514/278 |
| 5,278,162 A | 1/1994 | Wilkerson ..................... 514/252 |
| 5,296,478 A | 3/1994 | Teleha ........................ 514/235.2 |
| 5,453,516 A | 9/1995 | Fischer et al. ................. 548/543 |
| 5,663,431 A | 9/1997 | Di Malta et al. ............... 562/828 |
| 5,686,624 A | 11/1997 | Di Malta et al. ............... 548/410 |
| 5,696,145 A | 12/1997 | Foulon et al. .................. 514/409 |
| 5,723,625 A | 3/1998 | Keplinger et al. .............. 548/408 |
| 5,726,322 A | 3/1998 | Di Malta et al. ............... 548/410 |
| 5,728,723 A | 3/1998 | Di Malta et al. ............... 514/418 |
| 5,763,471 A | 6/1998 | Fourtillan et al. .............. 514/409 |
| 5,767,128 A | 6/1998 | Guillaumet et al. ............ 514/300 |
| 5,776,936 A | 7/1998 | Lee et al. ...................... 514/250 |
| 5,849,780 A | 12/1998 | Di Malta et al. ............... 514/409 |
| 5,994,350 A | 11/1999 | Foulon et al. ................ 514/232.8 |
| 6,046,341 A | 4/2000 | Foulon et al. .................. 548/411 |
| 6,090,818 A | 7/2000 | Foulon et al. .................. 514/278 |
| 6,110,969 A | 8/2000 | Tani et al. ..................... 514/530 |
| 6,225,347 B1 | 5/2001 | Buchmann et al. ............. 514/530 |
| 6,235,780 B1 | 5/2001 | Ohuchida et al. ............... 514/530 |
| 6,262,293 B1 | 7/2001 | Tani et al. ...................... 560/18 |
| 6,288,119 B1 | 9/2001 | Ohuchida et al. ............... 514/573 |
| 6,355,627 B1 | 3/2002 | Ishida et al. ..................... 514/58 |
| 6,414,153 B1 | 7/2002 | Kelly et al. .................... 546/113 |
| 6,670,357 B2 | 12/2003 | Leftheris et al. ................ 514/218 |
| 6,964,973 B2 | 11/2005 | Zhi et al. ....................... 514/312 |
| 7,368,470 B2 | 5/2008 | Sundermann et al. ........... 514/415 |
| 7,700,641 B2 | 4/2010 | Chafeev et al. ................ 514/409 |
| 7,799,798 B2 | 9/2010 | Chafeev et al. ................ 514/278 |
| 2002/0039790 A1 | 4/2002 | Keplinger et al. .............. 435/371 |
| 2004/0038970 A1 | 2/2004 | Thurieau et al. .............. 514/234.2 |
| 2004/0167224 A1 | 8/2004 | Ozaki et al. ................... 514/616 |
| 2005/0004137 A1 | 1/2005 | Romano ..................... 514/253.07 |
| 2005/0004138 A1 | 1/2005 | Romano ..................... 514/253.07 |
| 2005/0014764 A1 | 1/2005 | Romano et al. ............. 514/253.06 |
| 2005/0020617 A1 | 1/2005 | Bastian et al. .................. 514/300 |
| 2005/0038036 A1 | 2/2005 | Romano et al. ............. 514/253.06 |
| 2005/0075351 A1 | 4/2005 | Berg et al. ................... 514/266.2 |
| 2005/0153998 A1 | 7/2005 | Ito et al. ....................... 514/278 |

(Continued)

FOREIGN PATENT DOCUMENTS

CA        2095718 A1    5/1992

(Continued)

OTHER PUBLICATIONS

Byrn et al., Solid-State Chemistry of Drugs, Second Edition, 1999, pp. 233-247.*
Adams et al., "Bicyclic N-Hydroxyurea Inhibitors of 5-Lipoxygenase: Pharmacodynamic, Pharmacokinetic, and in Vitro Metabolic Studies Characterizing *N*-Hydroxy-*N*-(2,3-dihydro-6-(phenylmethoxy)-3-benzofuranyl)urea," *J. Med. Chem.* 39(26): 5035-5046, 1996.
Akai, "Development of Novel Asymmetric Reactions Oriented to Next-Generation Enzymatic Organic Syntheses," *Yakugaku Zasshi* 123(11): 919-931, 2003.
Al-Thebeiti and El-Zohry, "A Facile Route for the Synthesis of Some New Spiro[indoline-3,3'-indan]-2,1'-dione Derivatives," *Heterocycles* 41(11): 2475-2480, 1995.

(Continued)

*Primary Examiner* — Rebecca Anderson
(74) *Attorney, Agent, or Firm* — Seed IP Law Group PLLC

(57) ABSTRACT

This invention is directed to spiro-oxindole compounds, as stereoisomers, enantiomers, tautomers thereof or mixtures thereof; or pharmaceutically acceptable salts, solvates or prodrugs thereof, for the treatment and/or prevention of sodium channel-mediated diseases or conditions, such as pain.

25 Claims, No Drawings

U.S. PATENT DOCUMENTS

| | | | |
|---|---|---|---|
| 2005/0159473 A1 | 7/2005 | Sall et al. | 514/414 |
| 2005/0171186 A1 | 8/2005 | Fensome et al. | 514/418 |
| 2005/0256110 A1 | 11/2005 | Collins et al. | 514/224.2 |
| 2005/0256144 A1 | 11/2005 | Kath et al. | 514/275 |
| 2006/0247441 A1 | 11/2006 | Wilk | 548/408 |
| 2007/0049609 A1 | 3/2007 | Broka et al. | 514/269 |
| 2007/0072831 A1 | 3/2007 | Cai et al. | 514/80 |
| 2007/0105820 A1 | 5/2007 | Chafeev et al. | 514/80 |
| 2007/0299102 A1 | 12/2007 | Felding et al. | 514/299 |
| 2008/0103151 A9 | 5/2008 | Chafeev et al. | 514/248 |
| 2010/0099728 A1 | 4/2010 | Chafeev et al. | 514/409 |
| 2010/0125072 A1 | 5/2010 | Chafeev et al. | 514/232.8 |
| 2010/0130487 A1 | 5/2010 | Chafeev et al. | 514/232.8 |
| 2010/0160291 A1 | 6/2010 | Chafeev et al. | 514/211.09 |
| 2010/0160362 A1 | 6/2010 | Cadieux et al. | 514/278 |
| 2010/0173967 A1 | 7/2010 | Chafeev et al. | 514/409 |
| 2010/0331386 A1 | 12/2010 | Chafeev et al. | 514/409 |
| 2011/0034500 A1 | 2/2011 | Chafeev et al. | 514/278 |
| 2011/0086899 A1 | 4/2011 | Winters et al. | 514/409 |
| 2011/0087027 A1 | 4/2011 | Cadieux et al. | 546/15 |
| 2011/0251224 A1 | 10/2011 | Chafeev et al. | 514/278 |
| 2011/0269788 A1 | 11/2011 | Cadieux et al. | 514/278 |

FOREIGN PATENT DOCUMENTS

| | | |
|---|---|---|
| CA | 2107348 A1 | 7/1993 |
| CA | 2129215 A1 | 1/1995 |
| CA | 2 274 898 A1 | 6/1998 |
| CA | 2 450 550 A1 | 1/2003 |
| CA | 2 466 915 A1 | 8/2003 |
| CA | 2 487 494 A1 | 12/2003 |
| CA | 2 235 686 C | 6/2007 |
| DE | 1 956 237 A | 5/1971 |
| DE | 2113343 A1 | 9/1972 |
| EP | 0 147 805 A2 | 7/1985 |
| EP | 0 164 860 A1 | 12/1985 |
| EP | 0 175 551 A1 | 3/1986 |
| EP | 0 608 058 A1 | 7/1994 |
| EP | 1 422 217 A2 | 5/2004 |
| EP | 1 557 166 A1 | 7/2005 |
| FR | 2 722 195 A1 | 1/1996 |
| JP | 10-95766 A | 4/1998 |
| JP | 2003-505388 | 2/2003 |
| WO | WO 86/03749 A1 | 7/1986 |
| WO | WO 91/01306 A1 | 2/1991 |
| WO | WO 91/04974 A1 | 4/1991 |
| WO | WO 91/06545 A1 | 5/1991 |
| WO | WO 92/09577 A1 | 6/1992 |
| WO | WO 93/12786 A1 | 7/1993 |
| WO | WO 93/15051 A1 | 8/1993 |
| WO | WO 94/03427 A1 | 2/1994 |
| WO | WO 95/06688 A1 | 3/1995 |
| WO | WO 95/14667 A1 | 6/1995 |
| WO | WO 97/15556 A1 | 5/1997 |
| WO | WO 97/36895 A1 | 10/1997 |
| WO | WO 98/25901 A1 | 6/1998 |
| WO | WO 98/50016 A2 | 11/1998 |
| WO | WO 00/06556 A1 | 2/2000 |
| WO | WO 00/71129 A1 | 11/2000 |
| WO | WO 01/05790 A1 | 1/2001 |
| WO | WO 01/38564 A2 | 5/2001 |
| WO | WO 01/38564 A3 | 5/2001 |
| WO | WO 01/74775 A1 | 10/2001 |
| WO | WO 02/30868 A1 | 4/2002 |
| WO | WO 02/38544 A2 | 5/2002 |
| WO | WO 03/000677 A1 | 1/2003 |
| WO | WO 03/037274 A2 | 5/2003 |
| WO | WO 03/037890 A2 | 5/2003 |
| WO | WO 03/064425 A1 | 8/2003 |
| WO | WO 03/078394 A1 | 9/2003 |
| WO | WO 03/106457 A1 | 12/2003 |
| WO | WO 2004/000225 A2 | 12/2003 |
| WO | WO 2004/000227 A2 | 12/2003 |
| WO | WO 2004/048320 A1 | 6/2004 |
| WO | WO 2005/011657 A2 | 2/2005 |
| WO | WO 2005/016913 A1 | 2/2005 |
| WO | WO 2005/019208 A1 | 3/2005 |
| WO | WO 2005/035498 A1 | 4/2005 |
| WO | WO 2005/092304 A2 | 10/2005 |
| WO | WO 2005/092895 A2 | 10/2005 |
| WO | WO 2005/097107 A2 | 10/2005 |
| WO | WO 2005/097122 A2 | 10/2005 |
| WO | WO 2005/099689 A1 | 10/2005 |
| WO | WO 2005/104711 A2 | 11/2005 |
| WO | WO 2005/105753 A2 | 11/2005 |
| WO | WO 2005/110992 A1 | 11/2005 |
| WO | WO 2005/111024 A1 | 11/2005 |
| WO | WO 2006/012173 A1 | 2/2006 |
| WO | WO 2006/017075 A1 | 2/2006 |
| WO | WO 2006/023107 A1 | 3/2006 |
| WO | WO 2006/023109 A1 | 3/2006 |
| WO | WO 2006/049290 A1 | 5/2006 |
| WO | WO 2006/055752 A2 | 5/2006 |
| WO | WO 2006/087019 A1 | 8/2006 |
| WO | WO 2006/091646 A2 | 8/2006 |
| WO | WO 2006/110654 A1 | 10/2006 |
| WO | WO 2006/110917 A2 | 10/2006 |
| WO | WO 2006/113864 A2 | 10/2006 |
| WO | WO 2006/113875 A2 | 10/2006 |
| WO | WO 2008/046046 A1 | 4/2008 |
| WO | WO 2008/046049 A1 | 4/2008 |
| WO | WO 2008/046065 A1 | 4/2008 |
| WO | WO 2008/046082 A2 | 4/2008 |
| WO | WO 2008/046083 A2 | 4/2008 |
| WO | WO 2008/046084 A2 | 4/2008 |
| WO | WO 2008/046087 A2 | 4/2008 |
| WO | WO 2008/060789 A2 | 5/2008 |
| WO | WO 2008/117050 A1 | 10/2008 |
| WO | WO 2010/045197 A1 | 4/2010 |
| WO | WO 2010/045251 A2 | 4/2010 |
| WO | WO 2010/053998 * | 5/2010 |
| WO | WO 2010/053998 A1 | 5/2010 |
| WO | WO 2010/078307 A1 | 7/2010 |
| WO | WO 2010/132352 A2 | 11/2010 |
| WO | WO 2011/002708 A1 | 1/2011 |
| WO | WO 2011/047173 A2 | 4/2011 |
| WO | WO 2011/047174 A1 | 4/2011 |
| WO | WO 2011/106729 A2 | 9/2011 |

OTHER PUBLICATIONS

Alabaster et al., "The Synthesis of 5-Substituted 2,3-Dihydrobenzofurans," *Synthesis 12*: 950-952, Dec. 1988.

Alcaide et al., "Efficient Entry to Diversely Functionalized Spirocyclic Oxindoles from Isatins through Carbonyl-Addition/Cyclization Reaction Sequences," *J. Org. Chem.* 71(6): 2346-2351, 2006.

Alper et al., "Eine neuartige Methode zur Synthese von Spiro[pyrrolidin-3,3'-oxindolen]: katalysierte Ringerweiterung von Cyclopropanen mit Aldiminen," *Angew. Chem.* 111(21): 3379-3381, 1999.

Alper et al., "Facile, Novel Methodology for the Synthesis of Spiro[pyrrolidin-3,3'-oxindoles]: Catalyzed Ring Expansion Reactions of Cyclopropanes by Aldimines," *Angew. Chem. Int. Ed.* 38(21): 3186-3189, 1999.

Anger et al., "Medicinal Chemistry of Neuronal Voltage-Gated Sodium Channel Blockers," *Journal of Medicinal Chemistry* 44(2): 115-137, Jan. 18, 2001.

Autrey and Tahk, "The Synthesis and Stereochemistry of Some Isatylideneacetic Acid Derivatives," *Tetrahedron* 23: 901-917, 1967.

Bacher et al., "Oxindole alkaloids from *Uncaria tomentosa* induce apoptosis in proliferating, G0/G1-arrested and bcl-2-expressing acute lymphoblastic leukaemia cells," *British Journal of Haematology* 132: 615-622, 2005.

Banfi et al., "High Diastereoface Selection in an Ester Enolate Addition to α-Alkoxy Aldehydes: Stereoselective Synthesis of α-Methylene-β-hydroxy-γ-alkoxy Esters," *J. Org. Chem.* 49: 3784-3790, 1984.

Basavaiah et al., "$TiCl_4$ catalyzed tandem construction of C-C and C-O bonds: a simple and one-pot atom-economical stereoselective synthesis of spiro-oxindoles," *Chem. Commun.* 2621-2623, 2005.

Bean et al., "Lidocaine Block of Cardiac Sodium Channels," *J. Gen. Physiol.* 81: 613-642, May 1983.

Bennett and Xie, "A peripheral mononeuropathy in rat that produces disorders of pain sensation like those seen in man," *Pain* 33: 87-107, 1988.

Beyersbergen Van Henegouwen et al., "First Total Synthesis of *ent*-Gelsedine via a Novel Iodide-Promoted Allene *N*-Acyliminium Ion Cyclization," *J. Org. Chem.* 65(24): 8317-8325, 2000.

Beyersbergen Van Henegouwen et al., "Total Synthesis of (+)-Gelsedine," *Angw. Chem. Int. Ed.* 38(15): 2214-2217, 1999.

Billert and Beckert, "Beiträge zur Chemie der Pyrido[1,2-α]pyrazine—Reaktivität gegenüber Heterocumulenen der Kohlensäurereihe und Ketenen," *J. Prakt. Chem.* 341(4): 332-341, 1999.

Binder et al., "Disease mechanisms in neuropathic itch," *Nature Clinical Practice/Neurology* 4(6): 329-337, Jun. 2008.

Blair and Bean, "Roles of Tetrodotoxin (TTX)-Sensitive $Na^+$ Current, TTX-Resistant $Na^+$ Current, and $Ca^{2+}$ Current in the Action Potentials of Nociceptive Sensory Neurons," *Journal of Neuroscience* 22(23): 10277-10290, Dec. 1, 2002.

Bond et al., "Cyclopiamines A and B, Novel Oxindole Metabolites of *Penicillium cyclopium* Westling," *Journal of the Chemical Society, Perkin Transaction 1: Organic and Bio-Organic Chemistry* 7: 1751-1761, 1979.

Brackenbury and Djamgoz, "Activity-dependent regulation of voltage-gated $Na^+$ channel expression in Mat-LyLu rat prostate cancer cell line," *J. Physiol.* 573.2: 343-356, 2006.

Bramson et al., "Oxindole-Based Inhibitors of Cyclin-Dependent Kinase 2 (CDK2): Design, Synthesis, Enzymatic Activities, and X-ray Crystallographic Analysis," *J. Med. Chem.* 44: 4339-4358, 2001.

Braude and Lindwall, "Condensations of Isatin with Acetone by the Knoevenagel Method," *Journal of the American Chemical Society* 55: 325-327, Jan. 1933.

Caldwell et al., "Sodium channel $Na_v1.6$ is localized at nodes of Ranvier, dendrites, and synapses," *PNAS* 97(10): 5616-5620, May 9, 2000.

Cañas-Rodriguez and Leeming, "N-Phenyl-2-indolinones and N-Phenylindolines. A New Class of Antidepressant Agents," *Journal of Medicinal Chemistry* 15(7): 762-770, 1972.

Capilla et al., "Synthesis of isoquinolines and tetrahydroisoquinolines as potential antitumour agents," *Tetrahedron* 57: 8297-8303, 2001.

Carlson et al., "Potential hypolipidemic agents: VI. Syntheses of some new halo-substituted pyridine compounds. Effects on noradrenaline-stimulated free fatty acid mobilization," *Acta Pharm. Suecica* 9: 411-418, 1972.

Cassebaum and Liedel, "Beziehungen zwischen Konstitution und α-Aminosäure-dehydrogenasewirkung von Isatinen," *Journal für praktische Chemie* 4(12):91-95, 1960.

Cestèle and Catterall, "Molecular mechanisms of neurotoxin action on voltage-gated sodium channels," *Biochimie* 82: 883-892, 2000.

Chande et al., "Facile synthesis of active antitubercular, cytotoxic and antibacterial agents: a Michael addition approach," *European Journal of Medicinal Chemistry* 40: 1143-1148, 2005.

Chaplan et al., "Quantitative assessment of tactile allodynia in the rat paw," *Journal of Neuroscience Methods* 53: 55-63, 1994.

Chioni et al., "A novel adhesion molecule in human breast cancer cells: Voltage-gated $Na^+$ channel β1 subunit," *The International Journal of Biochemistry & Cell Biology* 41: 1216-1227, 2009.

Chung and Chung, "Sodium channels and neuropathic pain," *Novartis Found Symposium* 261: 19-31, 2004.

Clare et al., "Voltage-gated sodium channels as therapeutic targets," *Drug Discovery Today* 5(11): 506-520, Nov. 2000.

Claudi et al., "Synthesis and Dopamine Receptor Affinities of 2-(4-Fluoro-3-hydroxyphenyl)ethylamine and N-Substituted Derivatives," *J. Med. Chem.* 33: 2408-2412, 1990.

Coppola, "*N*-Arylation of Isatins. A Direct Route to *N*-Arylisatoic Anhydrides," *J. Heterocyclic Chem.* 24: 1249-1251, Sep./Oct. 1987.

Cossy et al., "A Convenient Route to Spiropyrrolidinyl-Oxindole Alkaloids via C-3 Substituted Ene-Pyrrolidine Carbamate Radical Cyclization," *Tetrahedron Letters* 39: 2331-2332, 1998.

Cox et al., "An *SCN9A* channelopathy causes congenital inability to experience pain," *Nature* 444: 894-898, Dec. 14, 2006.

Craner et al., "Molecular changes in neurons in multiple sclerosis: Altered axonal expression of $Na_v1.2$ and $Na_v1.6$ sodium channels and $Na^+$/$Ca^{2+}$ exchanger," *PNAS* 101(21): 8168-8173, May 25, 2004.

Cravotto et al., "Azomethine Ylide Cycloaddition/Reductive Heterocyclization Approach to Oxindole Alkaloids: Asymmetric Synthesis of (—)-Horsfiline," *J. Org. Chem.* 66(25): 8447-8453, 2001.

Creveling and Daly, "Batrachotoxinin A [$^3$H]Benzoate Binding to Sodium Channels," *Methods in Neurosciences* 8: 25-37, 1992.

Cube et al., "3-(2-Ethoxy-4-{4-[3-hydroxy-2-methyl-4-(3-methylbutanoyl)-phenoxy]butoxy}phenyl)propanoic acid: a brain penetrant allosteric potentiator at the metabotropic glutamate receptor 2 (mGluR2)," *Bioorganic & Medicinal Chemistry Letters* 15: 2389-2393, 2005.

Dallacker and Sanders, "Darstellung und Reaktionen von 5-(3'-Hydroxy-oxindol-3'-yl)-1,3-benzdioxole," *Chemiker-Zeitung* 110(11): 405-411, 1986.

Devers and Galer, "Topical Lidocaine Patch Relieves a Variety of Neuropathic Pain Conditions: An Open-Label Study," *Clinical Journal* 16(3): 205-208, Sep. 2000, obtained from URL=http://ovidsp.tx.ovid.com/spb/ovidweb.cgi, download date Apr. 18, 2008, 5 pages.

Dib-Hajj et al., "Genetics and Molecular Pathophysiology of $Na_v1.7$-Related Pain Syndromes," *Advances in Genetics* 63: 85-110, 2008.

Dib-Hajj et al., "NaN, a novel voltage-gated Na channel, is expressed preferentially in peripheral sensory neurons and down-regulated after axotomy," *Proc. Natl. Acad. Sci. USA* 95: 8963-8968, Jul. 1998.

Ding et al., "Structure-Based Design of Spiro-oxindoles as Potent, Specific Small-Molecule Inhibitors of the MDM2-p53 Interaction," *J. Med. Chem* 49(12): 3432-3435, 2006.

Diss et al., "A potential novel marker for human prostate cancer: voltage-gated sodium channel expression in vivo," *Prostate Cancer and Prostatic Diseases* 8: 266-273, 2005.

Do and Bean, "Subthreshold Sodium Currents and Pacemaking of Subthalamic Neurons: Modulation by Slow Inactivation," *Neuron* 39: 109-120, Jul. 3, 2003.

Domingo et al., "Studies on the Biosynthesis of Paraherquamide A and VM99955. A Theoretical Study of Intramolecular Diels—Alder Cycloaddition," *J. Org. Chem.* 68(7): 2895-2902, 2003.

Doyle et al., "Rhodium (II) Acetate and Nafion-H Catalyzed Decomposition of *N*-Aryldiazoamides. An Efficient Synthesis of 2(3*H*)-Indolinones," *J. Org. Chem* 53(5): 1017-1022, 1988.

Dubuisson and Dennis, "The Formalin Test: A Quantitative Study of the Analgesic Effects of Morphine, Meperidine, and Brain Stem Stimulation in Rats and Cats," *Pain* 4: 161-174, 1977.

Dutton et al., "A Total Synthesis of Gelsemine: Oxindole Spiroannelation," *J. Chem. Soc., Chem. Commun.* 765-766, 1994.

Dutton et al., "Synthesis of Hindered Spiro-Oxindoles by Photolysis of 1-(1-Alkenyl)benzotriazoles," *Tetrahedron* 55: 11927-11942, 1999.

El-Ahl, "Three-Component 1,3-Dipolar Cycloaddition Reactions in Synthesis of Spiro[pyrrolidine-2,3'-oxindoline] Derivatives," *Heteroatom Chemistry* 13(4): 324-329, 2002.

El-Gendy and Ahmedy, "Synthesis and Antimicrobial Activity of some New 2-Indolinone Derived Oximes and Spiro-Isoxazolines," *Arch. Pharm. Res.* 23(4): 310-314, 2000.

Ettinger and Argoff, "Use of Antiepileptic Drugs for Nonepileptic Conditions: Psychiatric Disorders and Chronic Pain," *Neurotherapeutics: The Journal of the American Society for Experimental NeuroTherapeutics* 4:75-83, Jan. 2007.

Feldman and Karatjas, "Extending Pummerer Reaction Chemistry. Asymmetric Synthesis of Spirocyclic Oxindoles via Chiral Indole-2-sulfoxides," *Org. Lett.* 8(18): 4137-4140, 2006.

Feldman et al., "Extending Pummerer Reaction Chemistry. Development of a Strategy for the Regio- and Stereoselective Oxidative Cyclization of 3-(ω-Nucleophile)-Tethered Indoles," *J. Org. Chem.* 70(16): 6429-6440, 2005.

Feldman and Vidulova, "Extending Pummerer Reaction Chemistry. Application to the Oxidative Cyclization of Indole Derivatives," *Organic Letters* 6(11): 1869-1871, 2004.

Fishman et al., "Intravenous Lidocaine for Treatment-resistant Pruritus," *American Journal of Medicine* 102: 584-585, Jun. 1997.

Flanagan et al., "Radical cyclisation reactions with indoles," *Tetrahedron Letters* 44: 1795-1798, 2003.

Fokas et al., "Solution Phase Synthesis of a Spiro[pyrrolidine-2,3'-oxindole] Library via a Three Component 1,3-Dipolar Cycloaddition Reaction," *Tetrahedron Letters* 39: 2235-2238, 1998.

Foster et al., "457. Furano-compounds. Part VII. A Synthesis of 2 : 3-Dihydropsoralene," *J. Chem. Soc.* 2254-2260, 1948.

Fraser et al., "Voltage-Gated Sodium Channel Expression and Potentiation of Human Breast Cancer Metastasis," *Clin. Cancer Res.* 11(15): 5381-5389, Aug. 1, 2005.

Fuchs and Funk, "Indol-2-one Intermediates: Mechanistic Evidence and Synthetic Utility. Total Syntheses of (±)-Flustramines A and C," *Org. Lett.* 7(4): 677-680, 2005.

Fuchs and See, "Basolateral amygdala inactivation abolishes conditioned stimulus- and heroin-induced reinstatement of extinguished heroin-seeking behavior in rats," *Psychopharmacology* 160: 425-433, 2002.

Fuji et al., "Direct Asymmetric Synthesis of Quaternary Carbon Centers via Addition-Elimination Process: Nitroolefination of α-Substituted δ-Lactones," *J. Am. Chem. Soc.* 111: 7921-7925, 1989.

Fujita et al., "The Beckmann Rearrangement by Means of Phosphoryl Chloride/N,N-Dimethylacetamide; A Novel and Convenient Method for Preparing Benzoxazoles," *Synthesis* 68-69, Jan. 1982.

Gálvez and García, "Synthesis of Isomeric β-Haloethylthienopyrroles," *J. Heterocyclic Chem.* 21: 393-395, Mar.-Apr. 1984.

Ganguly et al., "Solution- and solid-phase synthesis of enantiomerically pure spiro oxindoles," *Tetrahedron Letters* 43: 8981-8983, 2002.

Ganguly et al., "Synthesis of heterocyclic compounds using radical reactions and evidence for the formation of spiro radical intermediates," *Tetrahedron Letters* 45: 883-886, 2004. See also Ganguly et al., "Corrigendum to 'Synthesis of heterocyclic compounds using radical reactions and evidence for the formation of spiro radical intermediates,' [*Tetrahedron Letters* 45: 883-886, 2004]," *Tetrahedron Letters* 45: 3835, 2004.

Garden et al., "Investigation of the selective reduction of isatin derivatives. Synthesis of α-hydroxyacetophenone derivatives and ethyl spiro-3,3-(ethylenedioxy)-2-hydroxyindoline carboxylates," *Tetrahedron Letters* 44: 7617-7621, 2003.

Garden et al., "A versatile synthetic methodology for the synthesis of tryptophols," *Tetrahedron* 58: 8399-8412, 2002.

Goldberg et al., "Loss-of-function mutations in the $Na_v1.7$ gene underlie congenital indifference to pain in multiple human populations," *Clin. Genet.* 71: 311-319, 2007.

González-López De Turiso and Curran, "Radical Cyclization Approach to Spirocyclohexadienones," *Organic Letters* 7(1): 151-154, 2005.

Grigg et al., "Palladium Catalysed Ter- and Tetra-molecular Queuing Processes. One-pot Routes to 3-Spiro-2-Oxindoles and 3-Spiro-2(3H)-Benzofuranones," *Tetrahedron Letters* 37(5): 695-698, 1996.

Grigg et al., "Spiro-oxindoles via bimetallic [Pd(0)/Ag(I)] catalytic intramolecular Heck-1,3-dipolar cycloaddition cascade reactions," *Tetrahedron Letters* 43: 2605-2608, 2002.

Grigoryan et al., "Synthesis and antispasmodic activity of spiro[β-carbolineindolones] and spiro[indoleindolo[2,3-c]azepinones]," *Hayastani Kimiakan Handes* 58(3): 100-104, 2005, CAPLUS Database Accession No. 2005:876436, 4 pages, Abstract only.

Hains et al., "Upregulation of Sodium Channel $Na_v1.3$ and Functional Involvement in Neuronal Hyperexcitability Associated with Central Neuropathic Pain after Spinal Cord Injury," *Journal of Neuroscience* 23(26): 8881-8892, Oct. 1, 2003.

Hamann et al., "Motor disturbances in mice with deficiency of the sodium channel gene Scn8a show features of human dystonia," *Experimental Neurology* 184: 830-838, 2003.

Haufe et al., "The promiscuous nature of the cardiac sodium current," *Journal of Molecular and Cellular Cardiology* 42: 469-477, 2007.

Hiemstra et al., "Models of Folate Coenzymes—VIII: An Approach to Yohimbane Alkaloids Via Carbon-Fragment Transfer From $N^5$, $N^{10}$-Methylenetetrahydrofolate Models," *Tetrahedron* 39(23): 1981-1986, 1983.

Ikoma et al., "The neurobiology of itch," *Nature Reviews Neuroscience* 7: 535-547, Jul. 2006.

Inan et al., "Inhibitory effect of lidocaine on pain and itch using formalin-induced nociception and 5'-guanidinonaltrindole-induced scratching models in mice: Behavioral and neuroanatomical evidence," *European Journal of Pharmacology* 616: 141-146, 2009.

Iranpoor et al., "A novel method for the highly efficient synthesis of 1,2-benzisoxazoles under neutral conditions using the $Ph_3P$/DDQ system," *Tetrahedron Letters* 47: 8247-8250, 2006.

Ishiyama et al., "Synthesis of Arylboronates via the Palladium(0)-Catalyzed Cross-Coupling Reaction of Tetra(alkoxo)diborons with Aryl Triflates," *Tetrahedron Letters* 38(19): 3447-3450, 1997.

Islip and White, "236. Some Reactions of 2-(3-Oxindolyl)ethylamines," *Journal of the Chemical Society* 1201-1204, 1964.

Itoh et al., "Introduction of a Hydroxy Group at the Para Position and N-Iodophenylation of N-Arylamides Using Phenyliodine(III) Bis(Trifluoracetate)," *J. Org. Chem.* 67: 7424-7428, 2002.

Jarvis et al., "A-803467, a potent and selective $Na_v1.8$ sodium channel blocker, attenuates neuropathic and inflammatory pain in the rat," *PNAS* 104(20): 8520-8525, May 15, 2007.

Jorgensen and Berteau, "Thyroxine Analogs. 21. o- and m-L-Thyroxine and Related Compounds," *Journal of Medicinal Chemistry* 14(12): 1199-1202, 1971.

Julian et al., "Studies in the Indole Series. VI. On the Synthesis of Oxytryptophan and Further Studies of 3-Alkylation of Oxindoles," *Journal of the American Chemical Society* 57: 2026-2029, Nov. 1935.

Julian et al., "Studies in the Indole Series. VIII. Yohimbine (Part 1). The Mechanism of Dehydrogenation of Yohimbine and Related Compounds," *Journal of the American Chemical Society* 70: 174-179, Jan. 1948.

Kaila et al., "Synthesis and Biological Evaluation of Quinoline Salicylic Acids as P-Selectin Antagonists," *J. Med. Chem.* 50: 21-39, 2007.

Kamara et al., "The First Direct Transformation of 2,2'-Dihydroxychalcones into Coumestans," *Tetrahedron* 55: 861-868, 1999.

Kamiya et al., "A Nonsense Mutation of the Sodium Channel Gene SCN2A in a Patient with Intractable Epilepsy and Mental Decline," *Journal of Neuroscience* 24(11): 2690-2698, Mar. 17, 2004.

Kang et al., "Pteropodine and isopteropodine positively modulate the function of rat muscarinic $M_1$ and $5-HT_2$ receptors expressed in Xenopus oocyte," *European Journal of Pharmacology* 444: 39-45, 2002.

Karp et al., "Preparation of 4-Hydroxy-2-trifluoromethylthiophene: A Novel Bioisostere of α,α,α-Trifluoro-m-cresol," *Synthesis* 8: 1078-1080, 2000.

Kende et al., "Intramolecular Radical Cyclization of Phenolic Enolates," *J. Am. Chem. Soc.* 110: 2210-2218, 1988.

Kim et al., "BACE1 regulates voltage-gated sodium channels and neuronal activity," *Nature Cell Biology* 9(7): 755-764, Jul. 2007.

Kim et al., "Design, synthesis, and evaluation of dioxane-based antiviral agents targeted against the Sindbis virus capsid protein," *Bioorganic & Medicinal Chemistry Letters* 15: 3207-3211, 2005.

King et al., "Hydroxy-quinoxalines and -phenazines, and Experiments on the Preparation of Hydroxyquinoxaline Di-N-oxides," *J. Chem. Soc.* 3012-3016, 1949.

Kirmse et al., "Intramolecular Reactivity of Arylcarbenes: Derivatives of o-Tolylcarbene," *J. Org. Chem.* 59: 3821-3829, 1994.

Klugbauer et al., "Structure and functional expression of a new member of the tetrodotoxin-sensitive voltage-activated sodium channel family from human neuroendocrine cells," *EMBO J.* 14(6): 1084-1090, 1995.

Kobayashi and Furukawa, "Studies on Indole Derivatives. I. Synthesis of 3-Phenyl-9H-pyridazino-[3,4-b]indole Derivatives," *Chemical & Pharmaceutical Bulletin* 12(10): 1129-1135, Oct. 1964.

Kollmar et al., "2-Amino-3-Fluorobenzoic Acid [Benzoic acid, 2-amino-3-fluoro-]," *Organic Syntheses, Coll.* 79: 196, 2002, 5 pages.

Kornet and Thio, "Oxindole-3-spiropyrrolidines and -piperidines. Synthesis and Local Anesthetic Activity," *Journal of Medicinal Chemistry* 19(7): 892-898, 1976.

Kotha et al., "Recent applications of the Suzuki-Miyaura cross-coupling reaction in organic synthesis," *Tetrahedron* 58: 9633-9695, 2002.

Kubo et al., "Michael Additions of Indoles to 2-oxoindolin-3-ylidene Ketones," *Heterocycles* 4(10), 1675-1680, 1976.

Kumar et al., "A New Route to Spiropyrrolidinyl-oxindole Alkaloids via Iodide Ion Induced Rearrangement of [(N-Aziridinomethylthio)methylene]-2-oxindoles," *Organic Letters* 3(26): 4193-4196, 2001.

Kuzma et al., "Progress in the Development of Ultra-Long-Acting Local Anesthetics," *Regional Anesthesia* 22(6): 543-551, Nov.-Dec. 1997.

Lackey and Sternbach, "Synthesis of Substituted Quinoline-4-carboxylic Acids," *Synthesis*: 993-997, Oct. 1993.

Lai et al., "The role of voltage-gated sodium channels in neuropathic pain," *Current Opinion in Neurobiology* 13:291-297, 2003.

Laus, "Kinetics of isomerization of tetracyclic spiro oxindole alkaloids," *J. Chem. Soc., Perkin Trans. 2*: 315-317, 1998.

Laus et al., "Analysis of the kinetics of isomerization of spiro oxindole alkaloids," *J. Chem. Soc., Perkin Trans. 2*: 1931-1936, 1996.

Lee-Son et al., "Stereoselective Inhibition of Neuronal Sodium Channels by Local Anesthetics," *Anesthesiology* 77: 324-335, 1992.

Lerchner and Carreira, "Synthesis of (±)-Strychnofoline via a Highly Convergent Selective Annulation Reaction," *Chem. Eur. J.* 12: 8208-8219, 2006.

Leuwer et al., "An improved model for the binding of lidocaine and structurally related local anaesthetics to fast-inactivated voltage-operated sodium channels, showing evidence of cooperativity," *British Journal of Pharmacology* 141(1): 47-54, 2004.

Lindemann et al., "Zur Kenntnis der Indoxazene," *Justus Liebigs Annalen der Chemie* 456: 284-311, 1927.

Lindwall and MacLennan, "A Condensation of Acetophenone with Isatin by the Knoevenagel Method," *Journal of the American Chemical Society* 54: 4739-4744, Dec. 1932.

Liu et al., "Mutations in Cardiac Sodium Channels: Clinical Implications," *Am. J. Pharmacogenomics* 3(3): 173-179, 2003.

Lossin et al., "Molecular Basis of an Inherited Epilepsy," *Neuron* 34: 877-884, Jun. 13, 2002.

Loudon and Ogg, "2:3-Dihydro-3-oxobenz-1:4-oxazines," *J. Chem. Soc.*: 739-744, 1955.

Lutz and Clark, "Acid-Catalyzed Rearrangements of the γ-(Methylanilino)lactone of cis-β-(p-Bromobenzoyl)-β-methylacrylic Acid, and of trans-β-(p-Bromobenzoyl)acrylic Methylanilide, to Oxindoles," *J. Org. Chem.* 25: 193-196, Feb. 1960.

Lyalin et al., [title unavailable], *Zhurnal Organicheskoi Khimii* 20(4): 846-849, 1984.

Ma and Cai, "N,N-Dimethyl Glycine-Promoted Ullmann Coupling Reaction of Phenols and Aryl Halides," *Organic Letters* 5(21): 3799-3802, 2003.

Maercker and Theysohn, "Versuche zur Umlagerung von 2-Cyclopropyl-äthyl-Anionen," *Liebigs Ann. Chem.* 759: 132-157, 1972.

Maginnity and Gaulin, "Derivatives of o-, m- and p-Aminobenzotrifluoride," *J. Am. Chem. Soc.* 73: 3579-3580, Aug. 1951.

Majumdar et al., "1-Alkylisatins via Aldol-Retro-aldol Condensation," *J. Chem. Research (S)*, 460-461, 1996.

Mann et al., "The Synthesis of Lignans and Related Structures using Quinodimethanes and Isobenzofurans: Approaches to the Podophyllins," *J. Chem. Soc. Perkin Trans. I*: 2081-2088, 1984.

Mannaioni et al., "Tryptophan Metabolism and Hepatic Encephalopathy. Studies on the Sedative Properties of Oxindole," *Advances in experimental medicine and biology* 467: 155-167, 1999.

Mao and Baldwin, "New Spirocyclic Oxindole Synthesis Based on a Hetero Claisen Rearrangement," *Organic Letters* 6(14): 2425-2428, 2004.

Mao and Chen, "Systemic lidocaine for neuropathic pain relief," *Pain* 87: 7-17, 2000.

Marcantonio et al., "An Investigation into Causes and Effects of High Cyanide Levels in the Palladium-Catalyzed Cyanation Reaction," *Organic Letters* 6(21): 3723-3725, 2004.

Marti and Carreira, "Construction of Spiro[pyrrolidine-3,3'-oxindoles]—Recent Applications to the Synthesis of Oxindole Alkaloids," *Eur. J. Org. Chem.* 2209-2219, 2003.

Marti and Carreira, "Total Synthesis of (—)-Spirotryprostatin B: Synthesis and Related Studies," *J. Am. Chem. Soc.* 127(32): 11505-11515, 2005.

McMurtrey and Daves, Jr., "König's Adducts of N-Alkyl(aryl)aminoethanols and Quinones. 3,4-Dihydro-4-alkyl(aryl)-8a-hydroxy-2H-1,4,benzoxazin-6(8aH)-ones," *J. Org. Chem.* 35(12): 4252-4253, 1970.

McNeal et al., "[$^3$H]Batrachotoxinin A 20α-Benzoate Binding to Voltage-Sensitive Sodium Channels: A Rapid and Quantitative Assay for Local Anesthetic Activity in a Variety of Drugs," *J. Med. Chem.* 28(3): 381-388, 1985.

Meisler et al., "Sodium channel gene family: epilepsy mutations, gene interactions and modifier effects," *J. Physiol.* 588.11: 1841-1848, 2010.

Miyake et al., "Preparation and Synthetic Applications of 2-Halotryptamines: Synthesis of Elacomin and Isoelacomine," *Organic Letters* 6(5): 711-713, 2004.

Miyamoto et al., "Highly Diastereoselective One-Pot Synthesis of Spirocyclic Oxindoles through Intramolecular Ullmann Coupling and Claisen Rearrangement," *Angew. Chem. Int. Ed.* 45: 2274-2277, 2006.

Miyaura and Suzuki, "Palladium-Catalyzed Cross-Coupling Reactions of Organoboron Compounds," *Chem. Rev.* 95: 2457-2483, 1995.

Morie et al., "Asymmetric Synthesis of the Enantiomers of 2-Aminomethyl-4-(4-Fluorobenzyl)morpholine, an Intermediate of Mosapride, a Gastroprokinetic Agent," *Heterocycles* 38(5): 1033-1040, 1994.

Morinville et al., "Distribution of the Voltage-Gated Sodium Channel $Na_v1.7$ in the Rat: Expression in the Autonomic and Endocrine Systems," *Journal of Comparative Neurology* 504: 680-689, 2007.

Morton et al., "Novel solid-phase synthesis of 1,5-benzothiazepine-4-one derivatives," *Tetrahedron Letters* 41: 3029-3033, 2000.

Muci and Buchwald, "Practical Palladium Catalysts for C-N and C-O Bond Formation," *Topics in Current Chemistry* 219: 131-209, 2002.

Muhammad et al., "Two stereoisomeric pentacyclic oxindole alkaloids from *Uncaria tomentosa*; uncarine C and uncarine E," *Acta Cyst. C57*: 480-482, 2001.

Nagakura et al., "Allodynia and Hyperalgesia in Adjuvant-Induced Arthritic Rats: Time Course of Progression and Efficacy of Analgesics," *The Journal of Pharmacology and Experimental Therapeutics* 306(2): 490-497, 2003, obtained from URL=http://jpet.aspetjournals.org, download date Aug. 14, 2009.

Nagamura and Saito, "Antitumor Antibiotics: Duocarmycins," *Chemistry of Heterocyclic Compounds* 34(12): 1386-1405, 1998.

Nagamura et al., "Wagner-Meerwein Rearrangement of Duocarmycins," *Chem. Pharm. Bull.* 44(5): 933-939, May 1996.

Nair et al., "Formal dipolar cycloaddition of allylsilanes to o-quinonoid compounds: a convenient route to benzofused and spirofused heterocycles," *Tetrahedron Letters* 43: 5349-5351, 2002.

Nair et al., "N-Heterocyclic Carbene Catalyzed Reaction of Enals and 1,2-Dicarbonyl Compounds: Stereoselective Synthesis of Spiro γ-Butyrolactones," *Org. Lett.* 8(3): 507-509, 2006.

Nakamura et al., "Cancer preventive agents, Part 2: Synthesis and evaluation of 2-phenyl-4-quinolone and 9-oxo-9,10-dihydroacridine derivatives as novel antitumor promoters," *Bioorganic & Medicinal Chemistry* 13: 4396-4401, 2005.

Newkome et al., "α-Methyl Functionalization of Electron-Poor Heterocycles: Free Radical Chlorination," *Synthesis* 676-679, Aug. 1984.

Nicolaus, *Decision Making in Drug Research*, Raven Press, New York, 1983, Franz Gross (ed.), "Symbiotic Approach to Drug Design," pp. 173-186.

Niemann et al., "The Synthesis of 3'-Fluoro-*dl*-thyronine and Some of its Iodinated Derivatives," *J. Am. Chem. Soc.* 63: 609-611, Feb. 1941.

Oguri et al., "Amino Acids and Peptides. XXVIII. A New Synthesis of α-Amino Acid Derivatives by Alkylation of Schiff Bases derived from Glycine and Alanine," *Chem. Pharm. Bull.* 25(9): 2287-2291, 1977.

Okita and Isobe, "Synthesis of the Pentacyclic Intermediate for Dynemicin A and Unusual Formation of Spiro-oxindole Ring," *Tetrahedron* 50(38): 11143-11152, 1994.

Onishi et al., "Concise, Asymmetric Total Synthesis of Spirotryprostatin A," *Organic Letters* 5(17): 3135-3137, 2003.

Onishi et al., "Concise, asymmetric total synthesis of spirotryprostatin A," *Tetrahedron* 60: 9503-9515, 2004.

Orlova et al., "Synthesis of 2,3,4,5-Tetrahydro-1,5-Benzox(and Thi)azepines and Their Utilization for the Preparation of Condensed Indoles," Translated from *Khimiya Geterotsiklicheskikh Soedinenii* 9: 1262-1266, Sep. 1975, 5 pages.

Overman and Watson, "Diasteroselection in the Formation of Spirocyclic Oxindoles by the Intramolecular Heck Reaction," *J. Org. Chem* 71: 2587-2599, 2006.

Papale et al., "Heterozygous mutations of the voltage-gated sodium channel SCN8A are associated with spike-wave discharges and absence epilepsy in mice," *Human Molecular Genetics* 18(9): 1633-1641, 2009.

Pereira et al., "Severe epilepsy, retardation, and dysmorphic features with a 2q deletion including SCN1A and SCN2A," *Neurology* 63: 191-192, 2004.

Pietra and Tacconi, "α-Alkyl- and α-aryl-N-methyltryptamines," *Farmaco, Edizione Scientifica* 14: 854-866, 1959, CAPLUS Database Accession No. 1960:50362, 1 page, Abstract only.

Popp and Pajouhesh, "Potential Anticonvulsants IV: Condensation of Isatin with Benzoylacetone and Isopropyl Methyl Ketone," *Journal of Pharmaceutical Sciences* 71(9): 1052-1054, Sep. 1982.

Popp et al., "Synthesis of Potential Anticonvulsants: Consensation of Isatins with Acetone and Related Ketones," *Journal of Pharmaceutical Sciences* 69(10): 1235-1237, Oct. 1980.

Popp, "Potential Anticonvulsants. V. The Condensation of Isatins with C-Acetyl Heterocyclic Compounds," *J. Heterocyclic Chem.* 19: 589-592, May-Jun. 1982.

Priest, "Future potential and status of selective sodium channel blockers for the treatment of pain," *Current Opinion in Drug Discovery & Development* 12(5): 682-692, 2009.

Puopolo et al., "Roles of Subthreshold Calcium Current and Sodium Current in Spontaneous Firing of Mouse Midbrain Dopamine Neurons," *Journal of Neuroscience* 27(3): 645-656, Jan. 17, 2007.

Raj and Raghunathan, "A Novel Entry into a New Class of Spiro Heterocyclic Framework: A Facile Synthesis of Dispiro[oxindole-1,2,3,4-tetrahydro-naphthalen-1-one]pyrrolidines and Spiro[1,2,3,4-tetrahydro-naphthalen-1-one]pyrrolidines," *Synthetic Communications* 33(7): 1131-1139, 2003.

Raj and Raghunathan, "A novel entry into a new class of spiroheterocyclic framework: regioselective synthesis of dispiro[oxindole-cyclohexanone]-pyrrolidines and dispiro[oxindole-hexahydroindazole]pyrrolidines," *Tetrahedron* 57: 10293-10298, 2001.

Raj et al., "Synthesis, Antimicrobial and Antifungal Activity of a New Class of Spiro Pyrrolidines," *Bioorganic & Medicinal Chemistry* 11: 407-419, 2003.

Raymond et al., "Expression of Alternatively Spliced Sodium Channel α-Subunit Genes," *Journal of Biological Chemistry* 279(44): 46234-46241, Oct. 29, 2004.

Reddy et al., "Synthesis and Pharmacological Evaluation of N,N-Diarylguanidines as Potent Sodium Channel Blockers and Anticonvulsant Agents," *J. Med. Chem.* 41(17): 3298-3302, 1998.

Rehn et al., "The Three-Component Reaction between Isatin, α-Amino Acids, and Dipolarophiles," *Eur. J. Org. Chem.* 413-418, 2004.

Reimann et al., "Pain perception is altered by a nucleotide polymorphism in SCN9A," *PNAS* 107(11): 5148-5153, Mar. 16, 2010.

Ren and Dubner, "Enhanced Descending Modulation of Nociception in Rats With Persistent Hindpaw Inflamation," *Journal of Neurophysiology* 76(5): 3025-3037, Nov. 1996.

Rhodes et al., "Noninactivating voltage-gated sodium channels in severe myoclonic epilepsy of infancy," *PNAS* 101(30): 11147-11152, Jul. 27, 2004.

Rivalle and Bisagni, "Ethyl (4-N-Acylaminopyridin-3-yl)glyoxylate and 5-Azaisatin as New Synthons for a Route to Various New Polyheterocycles," *J. Heterocyclic Chem.* 34: 441-444, Mar.-Apr. 1997.

Rosevear and Wilshire, "Cyclization Reactions in Azole Chemistry: The Reaction of Some Azoles with o-Fluoro-acetophenone, o-Fluorobenzaldehyde and o-Fluorobenzophenone," *Aust. J. Chem.* 44: 1097-1114, 1991.

Ross et al., "Loss of Inhibitory Interneurons in the Dorsal Spinal Cord and Elevated Itch in Bhlhb5 Mutant Mice," *Neuron* 65: 886-898, Mar. 25, 2010.

Rossiter, "A convenient synthesis of 3-methyleneoxindoles: cytotoxic metabolites of indole-3-acetic acids," *Tetrahedron Letters* 43: 4671-4673, 2002.

Ruan et al., "Sodium channel mutations and arrhythmias," *Nature Reviews Cardiology* 6: 337-348, May 2009.

Sadler, "Separation of Isomeric Isatins," *J. Org. Chem.* 21(2): 169-170, 1956.

Sakaki et al., "Discovery of IRL 3461: A Novel and Potent Endothelin Antagonist With Balanced $ET_A/ET_B$ Affinity," *Biooganic & Medicinal Chemistry Letters* 8: 2241-2246, 1998.

Sauviat et al., "Blockade of sodium channels by Bistramide A in voltage-clamped frog skeletal muscle fibres," *Biochimica et Biophysica Acta* 1103: 109-114, 1992.

Sawyer, "Recent Advances in Diaryl Ether Synthesis," *Tetrahedron* 56: 5045-5065, 2000.

Schnyder et al., "Synthesis of Primary Aromatic Amides by Aminocarbonylation of Aryl Halides Using Formamide as an Ammonia Synthon," *J. Org. Chem.* 66: 4311-4315, 2001.

Schulenburg and Archer, "An Unusual Base-catalyzed Cyclization," *Journal of the American Chemical Society* 83(14): 3091-3096, Jul. 20, 1961.

Sebahar et al., "Asymmetric, stereocontrolled total synthesis of (+) and (—)-spirotryprostatin B via a diastereoselective azomethine ylide [1,3]-dipolar cycloaddition reaction," *Tetrahedron* 58: 6311-6322, 2002.

Shoop et al., "Anthelmintic Activity of Paraherquamide in Sheep," *J. Parasitol.* 76(3): 349-351, Jun. 1990.

Simas et al., "Regioselective Lithiation of Resorcinol Derivatives: Synthesis of Mono O-MOM- and O-Benzylresorcinols Prenylated at C-2 or C-4 Positions," *Synthesis* 6: 1017-1021, 1999.

Singh et al., "Novel cAMP PDE III Inhibitors: Imidazo[4,5-b]pyridine-2(3H)-ones and Thiazolo[4,5-b]pyridin-2(3H)-ones and Their Analogs," *J. Med. Chem.* 37: 248-254, 1994.

Smith et al., "Sodium channel protein expression enhances the invasiveness of rat and human prostate cancer cells," *FEBS Letters* 423: 19-24, 1998.

Sridhar and Raghunathan, "Rapid Access for the Synthesis of 1-N-Methyl-spiro[2.3' ]oxindole-spiro[3.7"] (3"-Aryl)-5"-methyl-3",3a",4",5",6",7"-hexahydro-2H-pyrazolo[4,3-c]pyridine-4-aryl-pyrrolidines Through Sequential 1,3-Dipolar Cycloaddition and Annulation," *Synthetic Communications* 36: 21-29, 2006.

Steinhoff et al., "Proteinase-Activated Receptor-2 Mediates Itch: A Novel Pathway for Pruritus in Human Skin," *Journal of Neuroscience* 23(15): 6176-6180, Jul. 16, 2003.

Subramaniyan et al., "A facile entry into a new class of spiroheterocycles: synthesis of dispiro[oxindolechromanone/flavanone/tetralone]pyrroloisoquinoline ring systems," *Tetrahedron* 58: 9075-9079, 2002.

Suchý et al., "Synthesis, Absolute Configuration, and Enantiomeric Enrichment of a Cruciferous Oxindole Phytoalexin, (S)-(—)-Spirobrassinin, and Its Oxazoline Analog," *J. Org. Chem.* 66: 3940-3947, 2001.

Tacconi et al., "Heterodiene Syntheses—V 1,2- versus 1,4-cycloaddition reactions of enamines to n-substituted 3-oxindolideneacetopheones," *Tetrahedron* 27: 561-579, 1971.

Takahashi et al., "Palladium(0)-Catalyzed Carbonylation on the Multipin™ System," *Tetrahedron Letters* 40: 7843-7846, 1999.

Tamaoka, "Paramyotonia Congenita and Skeletal Sodium Channelopathy," *Internal Medicine* 42(9): 769-770, Sep. 2003.

Tanelian and Brose, "Neuropathic Pain Can Be Relieved by Drugs That Are Use-dependent Sodium Channel Blockers: Lidocaine, Carbamazepine, and Mexiletine," *Anesthesiology* 74(5): 949-951, May 1991.

Ting et al., "Substituted 1,3-Dihydro-2H-pyrrolo[2,3-b]pyridin-2-ones as Potential Antiinflammatory Agents," *J. Med. Chem.* 33(10): 2697-2706, 1990.

Tokunaga et al., "Oxindole Derivatives as Orally Active Potent Growth Hormone Secretagogues," *J. Med. Chem.* 44(26): 4641-4649, 2001.

Trost and Brennan, "Palladium Asymmetric Allylic Alkylation of Prochiral Nucleophiles: Horsfiline," *Org. Lett.* 8(10): 2027-2030, 2006.

Trost and Frederiksen, "Palladium-Catalyzed Asymmetric Allylation of Prochiral Nucleophiles: Synthesis of 3-Allyl-3-Aryl Oxindoles," *Angew. Chem. Int. Ed.* 44: 308-310, 2005.

Twycross et al., "Itch: scratching more than the surface," *Q. J. Med.* 96: 7-26, 2003.

Usman et al., "1-Acetyl-3-(2-chloro-2,3-dihydrobenzofuran-3-yl)-1,2-dihydro-3-hydroxy-2-oxo-3H-indole," *Acta Cryst.* E58: o37-o39, 2002.

Venkatesan et al., "Total Synthesis of SR 121463 A, a Highly Potent and Selective Vasopressin $V_2$ Receptor Antagonist," *Journal of Organic Chemistry* 66(11): 3653-3661, Jun. 1, 2001.

Viaud et al., "Pyrrolo[2,3-b]pyridin-2(2H)-one Derivatives as Potential Non-opioid Analgesic Agents," *Pharmaceutical Sciences* 3: 283-287, 1997.

Viaud et al., "Acylation of Oxazolo[4,5-b]pyridin-2(3H)-ones, 2-Phenyloxazolo[4,5-b]pyridines and Pyrrolo[2,3-b]pyridin-2(2H)ones," *Tetrahedron* 53(14): 5159-5168, 1997.

Villamil et al., "Efficacy of lidocaine in the treatment of pruritus in patients with chronic cholestatic liver diseases," *The American Journal of Medicine* 118: 1160-1163, 2005.

Vippagunta et al., "Crystalline solids," *Advanced Drug Delivery Reviews* 48: 3-26, 2001.

Walker et al., "Limitations in Ring Rearrangement of Fused γ-Lactams Imposed by a Quaternary Carbon Atom. Cyclization of Acid Lactams to Spiro Keto Lactams," *J. Org. Chem.* 30(9): 2973-2983, Sep. 1965.

Wang and Ganesan, "A Biomimetic Total Synthesis of (—)-Spirotryprostatin B and Related Studies," *J. Org. Chem.* 65(15): 4685-4693, 2000.

Watanabe et al., "$Na_x$2/NaG Channel Is Involved in Control of Salt-Intake Behavior in the CNS," *Journal of Neuroscience* 20(20): 7743-7751, Oct. 15, 2000.

Weidmann et al., "2-[(2-Pyridylmethyl)sulfinyl]-1H-thieno[3,4-d]imidazoles. A Novel Class of Gastric $H^+/K^+$-ATPase Inhibitors," *J. Med. Chem.* 35: 438-450, 1992.

Wolff (ed.), *Burger's Medicinal Chemistry and Drug Discovery, Fifth Edition, vol. I: Principles and Practice*, John Wiley & Sons, Inc., New York, New York, 1994, pp. 975-977.

Wood et al., "Voltage-Gated Sodium Channels and Pain Pathways," *J. Neurobiol.* 61: 55-71, 2004.

Wrona et al., "Hydroxyl Radical-Mediated Oxidation of Serotonin: Potential Insights into the Neurotoxicity of Methamphetamine," *J. Neurochem.* 64(3): 1390-1400, 1995.

Wu et al., "The Effect of Hypercholesterolemia on the Sodium Inward Currents in Cardiac Myocyte," *J. Mol. Cell. Cardiol.* 27: 1263-1269, 1995.

Yang and Williams, "Palladium-Catalyzed Cyanation of Aryl Bromides Promoted by Low-Level Organotin Compounds," *Organic Letters* 6(17): 2837-2840, 2004.

Yang et al., "Nucleophilic-Type Radical Cyclizations of Indoles: Conversion of 2-Cyano 3-Substituted Indoles to Spiro-Annelated Indolines and Tetrahydrocarbazolones," *J. Org. Chem.* 58: 3100-3105, 1993.

Zhang et al., "Crystal structure of syn-1-acetyl-9'aH-8'-methoxyspiro[indole-3,2'-oxeto[3',2':4,5]furo[3,2-g][1]benzopyran]2,6'-dione," *Journal of Chemical Crystallography* 33(3): 165-168, Mar. 2003.

Zhang et al., "Photoinduced [2+2] cycloadditions (the Paterno-Büchi reaction) of 1-acetylisatin with enol ethers—regioselectivity, diastereo-selectivity and acid catalysed transformations of the spirooxetane products," *J. Chem. Soc., Perkin Trans. 1*: 345-353, 2002.

Zinser et al., "Anthelmintic paraherquamides are cholinergic antagonists in gastrointestinal nematodes and mammals," *J. vet. Pharmacol. Therap.* 25: 241-250, 2002.

Invitation to Pay Additional Fees, mailed Aug. 23, 2006, for PCTAN PCT/US2006/014845, 11 pages.

International Search Report and Written Opinion, mailed Oct. 31, 2006, for PCTAN PCT/US2006/014865, 26 pages.

International Preliminary Report on Patentability, mailed Nov. 1, 2007, for PCTAN PCT/US2006/014865, 13 pages.

Chafeev et al., entitled Oxindole Compounds and Their Uses As Therapeutic Agents, Preliminary Amendment dated Jul. 14, 2006, for U.S. Appl. No. 11/408,269, 6 pages.

Chafeev et al., entitled Oxindole Compounds and Their Uses As Therapeutic Agents, Restriction Requirement mailed Sep. 9, 2008, for U.S. Appl. No. 11/408,269, 10 pages.

Chafeev et al., entitled Oxindole Compounds and Their Uses As Therapeutic Agents, Response to Restriction Requirement dated Oct. 9, 2008, for U.S. Appl. No. 11/408,269, 3 pages.

Chafeev et al., entitled Oxindole Compounds and Their Uses As Therapeutic Agents, Office Action mailed Dec. 15, 2008, for U.S. Appl. No. 11/408,269, 29 pages.

International Search Report and Written Opinion, mailed Oct. 6, 2006, for PCTAN PCT/US2006/014352, 11 pages.

International Preliminary Report on Patentability, mailed Oct. 16, 2007, for PCTAN PCT/US2006/014352, 6 pages.

Chafeev et al., entitled Spiro-Oxindole Compounds and Their Uses As Therapeutic Agents, Preliminary Amendment dated Jul. 5, 2006, for U.S. Appl. No. 11/402,310, 6 pages.

Chafeev et al., entitled Spiro-Oxindole Compounds and Their Uses As Therapeutic Agents, Restriction Requirement mailed Feb. 10, 2009, for U.S. Appl. No. 11/402,310, 7 pages.

Chafeev et al., entitled Spiro-Oxindole Compounds and Their Uses As Therapeutic Agents, Response to Restriction Requirement dated Feb. 25, 2009, for U.S. Appl. No. 11/402,310, 109 pages.

Chafeev et al., entitled Spiro-Oxindole Compounds and Their Uses As Therapeutic Agents, Office Action mailed May 15, 2009, for U.S. Appl. No. 11/402,310, 43 pages.

Chafeev et al., entitled Spiro-Oxindole Compounds and Their Uses As Therapeutic Agents, Amendment dated Aug. 17, 2009, for U.S. Appl. No. 11/402,310, 150 pages.

Chafeev et al., entitled Spiro-Oxindole Compounds and Their Uses As Therapeutic Agents, Notice of Allowance mailed Sep. 30, 2009, for U.S. Appl. No. 11/402,310, 9 pages.

Chafeev et al., entitled Spiro-Oxindole Compounds and Their Uses As Therapeutic Agents, Statement of the Substance of the Interview, mailed Oct. 30, 2009 for U.S. Appl. No. 11/402,310, 2 pages.

Chafeev et al., entitled Spiro-Oxindole Compounds and Their Uses As Therapeutic Agents, Communication dated Nov. 17, 2009, for U.S. Appl. No. 11/402,310, 4 pages.

Sun et al., entitled Spiro-Oxindole Compounds and Their Uses As Therapeutic Agents, Office Action dated Jul. 12, 2010, for U.S. Appl. No. 12/650,218, 26 pages.

Sun et al., entitled Spiro-Oxindole Compounds and Their Uses As Therapeutic Agents, Amendment dated Nov. 10, 2010, for U.S. Appl. No. 12/650,218, 28 pages.

Sun et al., entitled Spiro-Oxindole Compounds and Their Uses As Therapeutic Agents, Notice of Allowance mailed Dec. 13, 2010, for U.S. Appl. No. 12/650,218, 19 pages.

Invitation to Pay Additional Fees, mailed Jan. 2, 2007, for PCTAN PCT/US2006/014887, 9 pages.

International Search Report and Written Opinion, mailed Mar. 15, 2007, for PCTAN PCT/US2006/014887, 22 pages.

International Preliminary Report on Patentability, mailed Nov. 1, 2007, for PCTAN PCT/US2006/014887, 12 pages.

Chafeev et al., entitled Heterocyclic Compounds and Their Uses As Therapeutic Agents, Preliminary Amendment dated Jul. 14, 2006, for U.S. Appl. No. 11/407,859, 6 pages.

Chafeev et al., entitled Heterocyclic Compounds and Their Uses As Therapeutic Agents, Restriction Requirement mailed Mar. 31, 2008, for U.S. Appl. No. 11/407,859, 9 pages.

Chafeev et al., entitled Heterocyclic Compounds and Their Uses As Therapeutic Agents, Response to Restriction Requirement dated Apr. 30, 2008, for U.S. Appl. No. 11/407,859, 39 pages.

Chafeev et al., entitled Heterocyclic Compounds and Their Uses As Therapeutic Agents, Office Action mailed Jun. 20, 2008, for U.S. Appl. No. 11/407,859, 46 pages.

Chafeev et al., entitled Heterocyclic Compounds and Their Uses As Therapeutic Agents, Amendment dated Oct. 17, 2008, for U.S. Appl. No. 11/407,859, 41 pages.

Chafeev et al., entitled Heterocyclic Compounds and Their Uses As Therapeutic Agents, Office Action mailed Jan. 15, 2009, for U.S. Appl. No. 11/407,859, 8 pages.
International Search Report and Written Opinion, mailed Aug. 11, 2006, for PCTAN PCT/US2006/013318, 15 pages.
International Preliminary Report on Patentability, mailed Oct. 16, 2007, for PCTAN PCT/US2006/013318, 9 pages.
Chafeev et al., entitled Spiroheterocyclic Compounds and Their Uses As Therapeutic Agents, Preliminary Amendment dated Jul. 7, 2006, for U.S. Appl. No. 11/402,200, 6 pages.
Chafeev et al., entitled Spiroheterocyclic Compounds and Their Uses As Therapeutic Agents, Restriction Requirement mailed Feb. 10, 2009, for U.S. Appl. No. 11/402,200, 6 pages.
Chafeev et al., entitled Spiroheterocyclic Compounds and Their Uses As Therapeutic Agents, Response to Restriction Requirement dated Feb. 27, 2009, for U.S. Appl. No. 11/402,200, 31 pages.
Chafeev et al., entitled Spiroheterocyclic Compounds and Their Uses As Therapeutic Agents, Office Action mailed Apr. 24, 2009, for U.S. Appl. No. 11/402,200, 30 pages.
Chafeev et al., entitled Spiroheterocyclic Compounds and Their Uses As Therapeutic Agents, Amendment dated Aug. 24, 2009, for U.S. Appl. No. 11/402,200, 36 pages.
Chafeev et al., entitled Spiroheterocyclic Compounds and Their Uses As Therapeutic Agents, Office Action mailed Nov. 17, 2009, for U.S. Appl. No. 11/402,200, 7 pages.
Chafeev et al., entitled Spiroheterocyclic Compounds and Their Uses As Therapeutic Agents, Amendment dated Mar. 17, 2010, for U.S. Appl. No. 11/402,200, 17 pages.
Chafeev et al., entitled Spiroheterocyclic Compounds and Their Uses As Therapeutic Agents, Notice of Allowance dated May 13, 2010, for U.S. Appl. No. 11/402,200, 16 pages.
Chafeev et al., entitled Spiroheterocyclic Compounds and Their Uses As Therapeutic Agents, Preliminary Amendment dated Oct. 25, 2010, for U.S. Appl. No. 12/855,514, 32 pages.
International Search Report and Written Opinion, mailed Mar. 3, 2008, for PCTAN PCT/US2007/081240, 16 pages.
International Preliminary Report on Patentability mailed Apr. 23, 2009, for PCTAN PCT/US2007/081240, 9 pages.
International Search Report and Written Opinion, mailed Oct. 13, 2008, for PCTAN PCT/US2007/081323, 21 pages.
International Preliminary Report on Patentability, mailed Apr. 15, 2009, for PCTAN PCT/US2007/081323, 12 pages.
International Search Report and Written Opinion, mailed Mar. 3, 2008, for PCTAN PCT/US2007/081244, 21 pages.
International Preliminary Report on Patentability, mailed Apr. 23, 2009, for PCTAN PCT/US2007/081244, 12 pages.
Invitation to Pay Additional Fees, mailed Jul. 16, 2008, for PCTAN PCT/US2007/081319, 10 pages.
International Search Report and Written Opinion, mailed Dec. 29, 2008, for PCTAN PCT/US2007/081319, 18 pages.
International Preliminary Report on Patentability, mailed Apr. 15, 2009, for PCTAN PCT/US2007/081319, 8 pages.
International Search Report and Written Opinion, mailed May 19, 2008, for PCTAN PCT/US2007/081247, 18 pages.
International Preliminary Report on Patentability, mailed Apr. 15, 2009, for PCTAN PCT/US2007/081247, 10 pages.
Chafeev et al., entitled Use of Spiro-Oxindole Compounds As Therapeutic Agents, Preliminary Amendment dated Mar. 4, 2010, for U.S. Appl. No. 12/445,264, 18 pages.
International Search Report and Written Opinion, mailed May 13, 2008, for PCTAN PCT/US2007/081318, 12 pages.
International Preliminary Report on Patentability, mailed Apr. 15, 2009, for PCTAN PCT/US2007/081318, 5 pages.
International Search Report and Written Opinion, mailed Mar. 6, 2008, for PCTAN PCT/US2007/081297, 18 pages.
International Preliminary Report on Patentability, mailed Apr. 15, 2009, for PCTAN PCT/US2007/081297, 10 pages.
Invitation to Pay Additional Fees, mailed Jan. 27, 2009, for PCTAN PCT/US2007/081320, 7 pages.
Written Opinion of the International Searching Authority, mailed Jan. 5, 2009, for PCTAN PCT/US2007/081320, 11 pages.
International Preliminary Report on Patentability, mailed May 5, 2009, for PCTAN PCT/US2007/081320, 12 pages.
International Search Report and Written Opinion, mailed Feb. 9, 2010, for PCTAN PCT/US2009/063290, 13 pages.
Winters et al., entitled Pharmaceutical Compositions for Oral Administration, Preliminary Amendment dated Dec. 27, 2010, for U.S. Appl. No. 12/905,048, 9 pages.
International Search Report and Written Opinion, mailed Oct. 1, 2010, for PCTAN PCT/US2010/040187, 13 pages.
Invitation to Pay Additional Fees, mailed Feb. 9, 2010, for PCTAN PCT/US2009/060537, 8 pages.
International Search Report and Written Opinion, mailed Oct. 6, 2010, for PCTAN PCT/US2009/060537, 18 pages.
Chafeev et al., entitled Spiro-Oxindole Compounds and Their Use As Therapeutic Agents, Preliminary Amendment dated Jan. 12, 2010, for U.S. Appl. No. 12/578,148, 57 pages.
International Search Report and Written Opinion, mailed Jan. 22, 2010, for PCTAN PCT/US2009/060455, 14 pages.
International Search Report and Written Opinion, mailed Apr. 8, 2010, for PCTAN PCT/US2009/069663, 13 pages.
Invitation to Pay Additional Fees, mailed Aug. 18, 2010, for PCTAN PCT/US2010/034223, 7 pages.
Chafeev et al., entitled Spiro-Oxindole Compounds and Their Uses As Therapeutic Agents, Amendment dated Sep. 2, 2011, for U.S. Appl. No. 12/650,196, 15 pages.
Official Action from Intellectual Property Corporation of Malaysia, dated May 31, 2011, for Patent Application No. PI 20061651, 3 pages.
Response to Official Action from Intellectual Property Corporation of Malaysia, filed Aug. 11, 2011, for Patent Application No. PI 20061651, 30 pages.
Chafeev et al., entitled Spiroheterocyclic Compounds and Their Uses As Therapeutic Agents, Office Action mailed Aug. 25, 2011, for U.S. Appl. No. 12/855,514, 43 pages.
Official Action from Intellectual Property India, mailed Mar. 28, 2011, for India Patent Application No. 4596/CHENP/2007, 4 pages.
Official Action from Intellectual Property Australia, dated Jan. 12, 2011, for Patent Application No. 2006235593, 5 pages.
Official Action from State Intellectual Property Office of China, dated Dec. 25, 2009, for Patent Application No. 200680011733.9, 4 pages.
Official Action from State Intellectual Property Office of China, dated Oct. 9, 2010, for Patent Application No. 200680011733.9, 4 pages.
Official Action from European Patent Office, dated Apr. 9, 2010, for Patent Application No. 06 750 402.7, 4 pages.
Response to Official Action from European Patent Office, dated Aug. 19, 2010, for Patent Application No. 06 750 402.7, 105 pages.
Official Action from European Patent Office, dated Sep. 14, 2010, for Patent Application No. 06 750 402.7, 3 pages.
Response to Official Action from European Patent Office, dated Jul. 6, 2011, for Patent Application No. 06 750 402.7, 175 pages.
Official Action from Israel Patent Office, dated Jan. 17, 2011, for Patent Application No. 186616, 3 pages.
Response to Official Action from Israel Patent Office, mailed Jul. 14, 2011, for Patent Application No. 186616, 5 pages.
Official Action from Intellectual Property India, mailed Apr. 29, 2011, for India Patent Application No. 4597/CHENP/2007, 2 pages.
Official Action from Intellectual Property Office of New Zealand, dated Sep. 1, 2009, for Patent Application No. 561210, 2 pages.
Response to Official Action from Intellectual Property Office of New Zealand, dated Nov. 22, 2010, for Patent Application No. 561210, 2 pages.
Official Action from Intellectual Property Office of New Zealand, dated Nov. 30, 2010, for Patent Application No. 561210, 1 page.
Response to Official Action from Intellectual Property Office of New Zealand, dated Feb. 21, 2011, for Patent Application No. 561210, 2 pages.
Official Action from Intellectual Property Office of New Zealand, dated Feb. 25, 2011, for Patent Application No. 591268, 2 pages.
Official Action from Intellectual Property Office of Republic of the Philippines, dated Sep. 22, 2010, for Patent Application No. 1-2007-502050, 2 pages.

Response to Official Action from Intellectual Property Office of the Philippines, dated Jan. 20, 2011, for Patent Application No. 1-2007-502050, 85 pages.
Translation of Official Action from Intellectual Property Office of Russia, dated Mar. 16, 2010, for Patent Application No. 2007141632/04(045572), 7 pages.
Translation of Official Action from Intellectual Property Office of Russia, dated Sep. 22, 2010, for Patent Application No. 2007141632/04(045572), 7 pages.
Chafeev et al., entitled Spiro-Oxindole Compounds and Their Uses As Therapeutic Agents, Office Action mailed Jun. 14, 2011, for U.S. Appl. No. 12/650,196, 17 pages.
Sun et al., entitled Spiro-Oxindole Compounds and Their Uses As Therapeutic Agents, Preliminary Amendment dated Jun. 24, 2011, for U.S. Appl. No. 13/078,678, 32 pages.
Official Action from European Patent Office, dated Aug. 5, 2008, for Patent Application No. 06 758 436.7, 5 pages.
Official Action from European Patent Office, dated Nov. 27, 2008, for Patent Application No. 06 740 804.7, 3 pages.
Response to Official Action from European Patent Office, dated Feb. 11, 2009, for Patent Application No. 06 740 804.7, 3 pages.
Official Action from Israel Patent Office, dated Jan. 16, 2011, for Patent Application No. 186615, 3 pages.
Response to Official Action from Israel Patent Office, dated Jul. 13, 2011, for Patent Application No. 186615, 3 pages.
Official Action from Intellectual Property of India, dated May 18, 2009, for Patent Application No. 4598/CHENP/2007, 2 pages.
Response to Official Action from Intellectual Property of India, dated Mar. 15, 2010, for Patent Application No. 4598/CHENP/2007, 27 pages.
Official Action from Intellectual Property Office of New Zealand, dated Aug. 27, 2009, for Patent Application No. 561204, 2 pages.
Response to Official Action from Intellectual Property Office of New Zealand, dated Nov. 22, 2010, for Patent Application No. 561204, 2 pages.
Official Action from Intellectual Property Office of New Zealand, dated Dec. 6, 2010, for Patent Application No. 561204, 1 page.
Response to Official Action from Intellectual Property Office of New Zealand, dated Feb. 16, 2011, for Patent Application No. 561204, 2 pages.
Translation of Official Action from Intellectual Property Office of Russia, dated Feb. 27, 2010, for Patent Application No. 2007141633/04(045573), 4 pages.
Official Action from State Intellectual Property Office of China, dated May 5, 2011, for Patent Application No. 200780038272.9, 9 pages.
Official Action from European Patent Office, dated Jul. 7, 2009, for Patent Application No. 07 868 434.7, 3 pages.
Official Action from European Patent Office, dated Jul. 23, 2010, for Patent Application No. 07 868 434.7, 6 pages.
Response to Official Action from European Patent Office, dated May 23, 2011, for Patent Application No. 07 868 434.7, 3 pages.
International Preliminary Report on Patentability, mailed May 10, 2011, for PCTAN PCT/US2009/063290, 7 pages.
Chafeev et al., entitled Enantiomers of Spiro-Oxindole Compounds and Their Uses As Therapeutic Agents, Response to Restriction Requirement and Preliminary Amendment, filed Jul. 20, 2011, for U.S. Appl. No. 12/825,168, 5 pages.
International Preliminary Report on Patentability, mailed Jun. 29, 2011, for PCTAN PCT/US2009/069663, 6 pages.
International Search Report and Written Opinion, mailed Jul. 11, 2011, for PCTAN PCT/US2010/034223, 18 pages.
International Search Report and Written Opinion, mailed Jun. 9, 2011, for PCTAN PCT/US2011/026359, 14 pages.
Goldberg, "The Significance of Molecular Type, Shape and Complementarity in Clathrate Inclusion," Topics in Current Chemistry 149: 1-44, 1988.
Guillaumet et al., "Synthese d'un analogue dioxinique du psoralene," Tetrahedron Letters 29(22): 2665-2666, 1988.
MacNicol, "Clathrates and Molecular Inclusion Phenomena," Chemical Society Reviews 7(1): 65-87, 1978.

Pouton, "Lipid formulations for oral administration of drugs: non-emulsifying, self-emulsifying and 'self-microemulsifying' drug delivery systems," European Journal of Pharmaceutical Sciences 11(Suppl 2): S93-S98, 2000.
Saenger, "Cyclodextrin Inclusion Compounds in Research and Industry," Angew. Chem. Int. Ed. Engl 19: 344-362, 1980.
Sircar et al., "Synthesis and SAR of N-Benzoyl-1-Biphenylalanine Dervatives: Discovery of TR-14035, A Dual $\alpha_4\beta_7/\alpha_4\beta_1$ Integrin Antagonist," Bioorganic & Medicinal Chemistry Letters 10: 2051-2066, 2002.
Weber and Czugler, "Functional Group Assisted Clathrate Formation—Scissor-Like and Roof-Shaped Host Molecules," Topics in Current Chemistry 149: 45-135, 1988.
Chafeev et al., entitled Spiro-Oxindole Compounds and Their Uses As Therapeutic Agents, Office Action dated Feb. 4, 2011, for U.S. Appl. No. 12/650,196, 31 pages.
Chafeev et al., entitled Spiro-Oxindole Compounds and Their Uses As Therapeutic Agents, Amendment and Winther Declaration dated May 4, 2011, for U.S. Appl. No. 12/650,196, 197 pages.
Sun et al., entitled Spiro-Oxindole Compounds and Their Uses As Therapeutic Agents, Supplemental Amendment dated Mar. 2, 2011, for U.S. Appl. No. 12/650,218, 3 pages.
International Search Report and Written Opinion, mailed Apr. 1, 2011, for PCTAN PCT/US2010/052704, 12 pages.
International Preliminary Report on Patentability, mailed Apr. 19, 2011, for PCTAN PCT/US2009/060537, 11 pages.
International Preliminary Report on Patentability, mailed Apr. 19, 2011, for PCTAN PCT/US2009/060455, 7 pages.
Chafeev et al., entitled Spiro-Oxindole Compounds and Their Use As Therapeutic Agents, Office Action dated Apr. 1, 2011, for U.S. Appl. No. 12/577,799, 49 pages.
Arcangeli et al., "Targeting Ion Channels in Cancer: A Novel Frontier in Antineoplastic Therapy," Current Medicinal Chemistry 16: 66-93, 2009.
Belikov, title unknown, Pharmaceuticheskaya himia, Moscow, Vysshaya shkola, 1993, pp. 43-47 (translation not available).
Byrn et al., "Chapter 11, Hydrates and Solvates," in Solid-State Chemistry of Drugs, Second Edition, 1999, pp. 233-247.
Catterall, "Molecular mechanisms of gating and drug block of sodium channels," 2002 Sodium channels and neuronal hyperexcitability, Wiley, Chichester (Novartis Foundation Symposium 241), p. 206-225.
Diss et al., "Expression Profiles of Voltage-Gated $Na^+$ Channel $\alpha$-Subunit Genes in Rat and Human Prostate Cancer Cell Lines," The Prostate 48:165-178, 2001.
Diss et al., "Identification and characterization of the promoter region of the Nav1.7 voltage-gated sodium channel gene (SCN9A)," Mol. Cell. Neurosci. 37: 537-547, 2008.
Hille, "Local Anesthetics: Hydrophilic and Hydrophobic Pathways for the Drug-Receptor Reaction," The Journal of General Physiology 69: 497-515, 1977.
Hille, "The pH-Dependent Rate of Action of Local Anesthetics on the Node of Ranvier," The Journal of General Physiology 69: 475-496, 1977.
Hoffman, Organic Chemistry: An Intermediate Text—Second Edition, John Wiley & Sons, Inc., Hoboken, New Jersey, 2004, 124, 138-144.
Ikoma et al., "Neuronal Sensitization for Histamine-Induced Itch in Lesional Skin of Patients With Atopic Dermatitis," Arch Dermatol. 139: 1455-1458, Nov. 2003.
Laniado et al., "Short Communication: Expression and Functional Analysis of Voltage-Activated $Na^+$ Channels in Human Prostate Cancer Cell Lines and their Contribution to Invasion in Vitro," American Journal of Pathology 150(4): 1213-1221, Apr. 1997.
Li et al., "A case of primary erythermalgia with prurigo," Clinical and Experimental Dermatology 34: e313-e314, 2009.
Namer et al., "Separate Peripheral Pathways for Pruritus in Man," J. Neurophysiol. 100: 2062-2069, 2008.
Oaklander et al., "Intractable postherpetic itch and cutaneous deafferentation after facial shingles," Pain 96: 9-12, 2002.
Patani and LaVoie, "Bioisosterism: A Rational Approach in Drug Design," Chem. Rev. 96(8): 3147-3176, 1996.

Pearn, "Neurology of ciguatera," *J.Neurol. Neurosurg. Psychiatry 70*: 4-8, 2001.

Schmelz et al., "Specific C-Receptors for Itch in Human Skin," *The Journal of Neuroscience 17*(20): 8003-8008, Oct. 15, 1997.

Stella and Nti-Addae, "Prodrug strategies to overcome poor water solubility," *Advanced Drug Delivery Reviews 59*: 677-694, 2007.

Xiao and Bennett, "C-fiber spontaneous discharge evoked by chronic inflammation is suppressed by a long-term infusion of lidocaine yielding nanogram per milliliter plasma levels," *Pain 137*: 218-228, 2008.

Zhao et al., "Voltage-gated sodium channel expression in rat and human epidermal keratinocytes: Evidence for a role in pain," *Pain 139*: 90-105, 2008.

Official Action from State Intellectual Property Office of China, dated Oct. 10, 2011, for Patent Application No. 201110027693.X, 5 pages.

Official Action from European Patent Office re extended European search report, dated Feb. 2, 2012, for Patent Application No. 11009687.2, 7 pages.

Translation of Official Action from Patent Office of Japan, dated Nov. 22, 2011, for Patent Application No. 2008-506802, 11 pages.

Chafeev et al., entitled Spiro-Oxindole Compounds and Their Uses As Therapeutic Agents, Notice of Allowance dated Sep. 20, 2011, for U.S. Appl. No. 12/650,196, 11 pages.

Sun et al., entitled Spiro-Oxindole Compounds and Their Uses As Therapeutic Agents, Restriction Requirement dated Nov. 28, 2011, for U.S. Appl. No. 13/078,678, 7 pages.

Translation of Official Action from Patent Office of Japan, dated Nov. 4, 2011, for Patent Application No. 2008-506574, 10 pages.

Chafeev et al., entitled Tricyclic Spiro-Oxindole Derivatives and Their Uses As Therapeutic Agents, Restriction Requirement mailed Jan. 26, 2012, for U.S. Appl. No. 12/445,271, 7 pages.

Official Action from State Intellectual Property Office of China, dated Oct. 28, 2010, for Patent Application No. 200780038111.X, 5 pages.

Translation of Official Action from Intellectual Property Office of Russia, dated Aug. 31, 2011, for Patent Application No. 2009117642, 4 pages.

International Preliminary Report on Patentability, mailed Jan. 4, 2012, for PCTAN PCT/US2010/040187, 7 pages.

Chafeev et al., entitled Enantiomers of Spiro-Oxindole Compounds and Their Uses As Therapeutic Agents, Restriction Requirement mailed Jun. 20, 2011, for U.S. Appl. No. 12/825,168, 8 pages.

Chafeev et al., entitled Enantiomers of Spiro-Oxindole Compounds and Their Uses As Therapeutic Agents, Office Action, mailed Aug. 29, 2011, for U.S. Appl. No. 12/825,168, 43 pages.

Chafeev et al., entitled Enantiomers of Spiro-Oxindole Compounds and Their Uses As Therapeutic Agents, Amendment filed Jan. 30, 2012, for U.S. Appl. No. 12/825,168, 8 pages.

Response to Official Action from European Patent Office, dated Jan. 10, 2012, for Patent Application No. 09 740 589.8, 4 pages.

Official Action from Intellectual Property Office of New Zealand, mailed Sep. 9, 2011, for New Zealand Patent Application No. 592275, 2 pages.

Response to Official Action from European Patent Office, dated Feb. 1, 2012, for Patent Application No. 09 741 118.5, 12 pages.

Chafeev et al., entitled Spiro-Oxindole Compounds and Their Use As Therapeutic Agents, Amendment dated Jul. 1, 2011, for U.S. Appl. No. 12/577,799, 21 pages.

Chafeev et al., entitled Spiro-Oxindole Compounds and Their Use As Therapeutic Agents, Notice of Allowance mailed Oct. 7, 2011, for U.S. Appl. No. 12/577,799, 14 pages.

International Preliminary Report on Patentability, mailed Nov. 15, 2011, for PCTAN PCT/US2010/034223, 11 pages.

* cited by examiner

SPIRO-OXINDOLE COMPOUNDS AND THEIR USE AS THERAPEUTIC AGENTS

CROSS-REFERENCE TO RELATED APPLICATION

This application claims the benefit under 37 U.S.C. §119(e) of U.S. Provisional Patent Application No. 61/106,464, filed Oct. 17, 2008, which application is incorporated herein by reference in its entirety.

FIELD OF THE INVENTION

The present invention is directed to spiro-oxindole compounds and pharmaceutical compositions comprising the compounds and methods of using the compounds and the pharmaceutical compositions in treating sodium channel-mediated diseases or conditions, such as pain, as well as other diseases and conditions associated with the mediation of sodium channels.

BACKGROUND OF THE INVENTION

Voltage-gated sodium channels, transmembrane proteins that initiate action potentials in nerve, muscle and other electrically excitable cells, are a necessary component of normal sensation, emotions, thoughts and movements (Catterall, W. A., *Nature* (2001), Vol. 409, pp. 988-990). These channels consist of a highly processed alpha subunit that is associated with auxiliary beta subunits. The pore-forming alpha subunit is sufficient for channel function, but the kinetics and voltage dependence of channel gating are in part modified by the beta subunits (Goldin et al., *Neuron* (2000), Vol. 28, pp. 365-368). Each alpha-subunit contains four homologous domains, I to IV, each with six predicted transmembrane segments. The alpha-subunit of the sodium channel, forming the ion-conducting pore and containing the voltage sensors regulating sodium ion conduction has a relative molecular mass of 260,000. Electrophysiological recording, biochemical purification, and molecular cloning have identified ten different sodium channel alpha subunits and four beta subunits (Yu, F. H., et al., *Sci. STKE* (2004), 253; and Yu, F. H., et al., *Neurosci.* (2003), 20:7577-85).

The hallmarks of sodium channels include rapid activation and inactivation when the voltage across the plasma membrane of an excitable cell is depolarized (voltage-dependent gating), and efficient and selective conduction of sodium ions through conducting pores intrinsic to the structure of the protein (Sato, C., et al., *Nature* (2001), 409:1047-1051). At negative or hyperpolarized membrane potentials, sodium channels are closed. Following membrane depolarization, sodium channels open rapidly and then inactivate. Channels only conduct currents in the open state and, once inactivated, have to return to the resting state, favoured by membrane hyperpolarization, before they can reopen. Different sodium channel subtypes vary in the voltage range over which they activate and inactivate as well as their activation and inactivation kinetics.

The sodium channel family of proteins has been extensively studied and shown to be involved in a number of vital body functions. Research in this area has identified variants of the alpha subunits that result in major changes in channel function and activities, which can ultimately lead to major pathophysiological conditions. Implicit with function, this family of proteins are considered prime points of therapeutic intervention. $Na_v1.1$ and $Na_v1.2$ are highly expressed in the brain (Raymond, C. K., et al., *J. Biol. Chem.* (2004), 279(44): 46234-41) and are vital to normal brain function. In humans, mutations in $Na_v1.1$ and $Na_v1.2$ result in severe epileptic states and in some cases mental decline (Rhodes, T. H., et al., *Proc. Natl. Acad. Sci. USA* (2004),101(30):11147-52; Kamiya, K., et al., *J. Biol. Chem.* (2004), 24(11):2690-8; Pereira, S., et al., *Neurology* (2004), 63(1):191-2). As such both channels have been considered as validated targets for the treatment of epilepsy (see PCT Published Patent Publication No. WO 01/38564).

$Na_v1.3$ is broadly expressed throughout the body (Raymond, C. K., et al., *op. cit.*). It has been demonstrated to have its expression upregulated in the dorsal horn sensory neurons of rats after nervous system injury (Hains, B. D., et al., *J. Neurosci.* (2003), 23(26):8881-92). Many experts in the field have considered $Na_v1.3$ as a suitable target for pain therapeutics (Lai, J., et al., *Curr. Opin. Neurobiol.* (2003), (3):291-72003; Wood, J. N., et al., *J. Neurobiol.* (2004), 61(1):55-71; Chung, J. M., et al., *Novartis Found Symp.* (2004), 261:19-27; discussion 27-31, 47-54). $Na_v1.4$ expression is essentially limited to muscle (Raymond, C. K., et al., *op. cit.*). Mutations in this gene have been shown to have profound effects on muscle function including paralysis, (Tamaoka A., *Intern. Med.* (2003), (9):769-70). Thus, this channel can be considered a target for the treatment of abnormal muscle contractility, spasm or paralysis.

The cardiac sodium channel, $Na_v1.5$, is expressed mainly in the heart ventricles and atria (Raymond, C. K., et al., *op. cit.*), and can be found in the sinovial node, ventricular node and possibly Purkinje cells. The rapid upstroke of the cardiac action potential and the rapid impulse conduction through cardiac tissue is due to the opening of $Na_v1.5$. As such, $Na_v1.5$ is central to the genesis of cardiac arrhythmias. Mutations in human $Na_v1.5$ result in multiple arrhythmic syndromes, including, for example, long QT3 (LQT3), Brugada syndrome (BS), an inherited cardiac conduction defect, sudden unexpected nocturnal death syndrome (SUNDS) and sudden infant death syndrome (SIDS) (Liu, H. et al., *Am. J. Pharmacogenomics* (2003), 3(3):173-9). Sodium channel blocker therapy has been used extensively in treating cardiac arrhythmias. The first antiarrhythmic drug, quinidine, discovered in 1914, is classified as a sodium channel blocker.

$Na_v1.6$ encodes an abundant, widely distributed voltage-gated sodium channel found throughout the central and peripheral nervous systems, clustered in the nodes of Ranvier of neural axons (Caldwell, J. H., et al., *Proc. Natl. Acad. Sci. USA* (2000), 97(10): 5616-20). Although no mutations in humans have been detected, $Na_v1.6$ is thought to play a role in the manifestation of the symptoms associated with multiple sclerosis and has been considered as a target for the treatment of this disease (Craner, M. J., et al., *Proc. Natl. Acad. Sci. USA* (2004), 101(21):8168-73).

$Na_v1.7$ was first cloned from the pheochromocytoma PC12 cell line (Toledo-Aral, J. J., et al., *Proc. Natl. Acad. Sci. USA* (1997), 94:1527-1532). Its presence at high levels in the growth cones of small-diameter neurons suggested that it could play a role in the transmission of nociceptive information. Although this has been challenged by experts in the field as $Na_v1.7$ is also expressed in neuroendocrine cells associated with the autonomic system (Klugbauer, N., et al., *EMBO J.* (1995), 14(6):1084-90) and as such has been implicated in autonomic processes. The implicit role in autonomic functions was demonstrated with the generation of $Na_v1.7$ null mutants; deleting $Na_v1.7$ in all sensory and sympathetic neurons resulted in a lethal perinatal phenotype. (Nassar, et al., *Proc. Natl. Acad. Sci. USA* (2004), 101(34):12706-11.). In contrast, by deleting the $Na_v1.7$ expression in a subset of sensory neurons that are predominantly nociceptive, a role in pain mechanisms, was demonstrated (Nassar, et al., *op. cit.*). Further support for $Na_v1.7$ blockers active in a subset of neurons is supported by the finding that two human heritable pain conditions, primary erythromelagia and familial rectal pain, have been shown to map to $Na_v1.7$ (Yang, Y., et al., *J. Med. Genet.* (2004), 41(3):171-4).

The expression of $Na_v1.8$ is essentially restricted to the DRG (Raymond, C. K., et al., *op. cit.*). There are no identified human mutations for $Na_v1.8$. However, $Na_v1.8$-null mutant mice were viable, fertile and normal in appearance. A pronounced analgesia to noxious mechanical stimuli, small deficits in noxious thermoreception and delayed development of inflammatory hyperalgesia suggested to the researchers that $Na_v1.8$ plays a major role in pain signalling (Akopian, A. N., et al., *Nat. Neurosci.* (1999), 2(6): 541-8). Blocking of this channel is widely accepted as a potential treatment for pain (Lai, J, et al., *op. cit.*; Wood, J. N., et al., *op. cit.*; Chung, J. M., et al., *op. cit.*). PCT Published Patent Application No. WO03/037274A2 describes pyrazole-amides and sulfonamides for the treatment of central or peripheral nervous system conditions, particularly pain and chronic pain by blocking sodium channels associated with the onset or recurrence of the indicated conditions. PCT Published Patent Application No. WO 03/037890A2 describes piperidines for the treatment of central or peripheral nervous system conditions, particularly pain and chronic pain by blocking sodium channels associated with the onset or recurrence of the indicated conditions. The compounds, compositions and methods of these inventions are of particular use for treating neuropathic or inflammatory pain by the inhibition of ion flux through a channel that includes a PN3 ($Na_v1.8$) subunit.

The tetrodotoxin insensitive, peripheral sodium channel $Na_v1.9$, disclosed by Dib-Hajj, S. D., et al. (see Dib-Hajj, S. D., et al., *Proc. Natl. Acad. Sci. USA* (1998), 95(15):8963-8) was shown to reside solely in the dorsal root ganglia. It has been demonstrated that $Na_v1.9$ underlies neurotrophin (BDNF)-evoked depolarization and excitation, and is the only member of the voltage gated sodium channel superfamily to be shown to be ligand mediated (Blum, R., Kafitz, K. W., Konnerth, A., *Nature* (2002), 419 (6908):687-93). The limited pattern of expression of this channel has made it a candidate target for the treatment of pain (Lai, J, et al., *op. cit.*; Wood, J. N., et al., *op. cit.*; Chung, J. M. et al., *op. cit.*).

NaX is a putative sodium channel, which has not been shown to be voltage gated. In addition to expression in the lung, heart, dorsal root ganglia, and Schwann cells of the peripheral nervous system, NaX is found in neurons and ependymal cells in restricted areas of the CNS, particularly in the circumventricular organs, which are involved in body-fluid homeostasis (Watanabe, E., et al., *J. Neurosci.* (2000), 20(20):7743-51). NaX-null mice showed abnormal intakes of hypertonic saline under both water- and salt-depleted conditions. These findings suggest that the NaX plays an important role in the central sensing of body-fluid sodium level and regulation of salt intake behaviour. Its pattern of expression and function suggest it as a target for the treatment of cystic fibrosis and other related salt regulating maladies.

Studies with the sodium channel blocker tetrodotoxin (TTX) used to lower neuron activity in certain regions of the brain, indicate its potential use in the treatment of addiction. Drug-paired stimuli elicit drug craving and relapse in addicts and drug-seeking behavior in rats. The functional integrity of the basolateral amygdala (BLA) is necessary for reinstatement of cocaine-seeking behaviour elicited by cocaine-conditioned stimuli, but not by cocaine itself. BLA plays a similar role in reinstatement of heroin-seeking behavior. TTX-induced inactivation of the BLA on conditioned and heroin-primed reinstatement of extinguished heroin-seeking behaviour in a rat model (Fuchs, R. A. and See, R. E., *Psychopharmacology* (2002) 160(4):425-33).

This closely related family of proteins has long been recognised as targets for therapeutic intervention. Sodium channels are targeted by a diverse array of pharmacological agents. These include neurotoxins, antiarrhythmics, anticonvulsants and local anesthetics (Clare, J. J., et al., *Drug Discovery Today* (2000) 5:506-520). All of the current pharmacological agents that act on sodium channels have receptor sites on the alpha subunits. At least six distinct receptor sites for neurotoxins and one receptor site for local anesthetics and related drugs have been identified (Cestèle, S. et al., *Biochimie* (2000), Vol. 82, pp. 883-892).

The small molecule sodium channel blockers or the local anesthetics and related antiepileptic and antiarrhythmic drugs, interact with overlapping receptor sites located in the inner cavity of the pore of the sodium channel (Catterall, W. A., *Neuron* (2000), 26:13-25). Amino acid residues in the S6 segments from at least three of the four domains contribute to this complex drug receptor site, with the IVS6 segment playing the dominant role. These regions are highly conserved and as such most sodium channel blockers known to date interact with similar potency with all channel subtypes. Nevertheless, it has been possible to produce sodium channel blockers with therapeutic selectivity and a sufficient therapeutic window for the treatment of epilepsy (e.g. lamotrignine, phenyloin and carbamazepine) and certain cardiac arrhythmias (e.g. lignocaine, tocamide and mexiletine). However, the potency and therapeutic index of these blockers is not optimal and have limited the usefulness of these compounds in a variety of therapeutic areas where a sodium channel blocker would be ideally suited.

Management of Acute and Chronic Pain

Drug therapy is the mainstay of management for acute and chronic pain in all age groups, including neonates, infants and children. The pain drugs are classified by the American Pain Society into three main categories: 1) non-opioid analgesics-acetaminophen, and non-steroidal anti-inflammatory drugs (NSAIDs), including salicylates (e.g. aspirin), 2) opioid analgesics and 3) co-analgesics.

Non-opioid analgesics such as acetaminophen and NSAIDs are useful for acute and chronic pain due to a variety of causes including surgery, trauma, arthritis and cancer. NSAIDs are indicated for pain involving inflammation because acetaminophen lacks anti-inflammatory activity. Opioids also lack anti-inflammatory activity. All NSAIDs inhibit the enzyme cyclooxygenase (COX), thereby inhibiting prostaglandin synthesis and reducing the inflammatory pain response. There are at least two COX isoforms, COX-1 and COX-2. Common non-selective COX inhibitors include, ibuprofen and naproxen. Inhibition of COX-1, which is found in platelets, GI tract, kidneys and most other human tissues, is thought to be associated with adverse effects such as gastrointestinal bleeding. The development of selective COX-2 NSAIDs, such as Celecoxib, Valdecoxib and Rofecoxib, have the benefits of non-selective NSAIDs with reduced adverse effect profiles in the gut and kidney. However, evidence now suggests that chronic use of certain selective COX-2 inhibitors can result in an increased risk of stroke occurrence.

The use of opioid analgesics is recommended by the American Pain Society to be initiated based on a pain-directed history and physical that includes repeated pain assessment. Due to the broad adverse effect profiles associated with opiate use, therapy should include a diagnosis, integrated interdisciplinary treatment plan and appropriate ongoing patient monitoring. It is further recommended that opioids be added to non-opioids to manage acute pain and cancer related pain that does not respond to non-opioids alone. Opioid analgesics act as agonists to specific receptors of the mu and kappa types in the central and peripheral nervous system. Depending on the opioid and its formulation or mode of administration it can be of shorter or longer duration. All opioid analgesics have a risk of causing respiratory depression, liver failure, addiction and dependency, and as such are not ideal for long-term or chronic pain management.

A number of other classes of drugs may enhance the effects of opioids or NSAIDSs, have independent analgesic activity in certain situations, or counteract the side effects of analgesics. Regardless of which of these actions the drug has, they are collectively termed "coanalgesics". Tricyclic antidepressants, antiepileptic drugs, local anaesthetics, glucocorticoids, skeletal muscle relaxants, anti-spasmodil agents, antihistamines, benzodiazepines, caffeine, topical agents (e.g. capsaicin), dextroamphetamine and phenothizines are all used in the clinic as adjuvant therapies or individually in the treatment of pain. The antiepeileptic drugs in particular have enjoyed some success in treating pain conditions. For instance, Gabapentin, which has an unconfirmed therapeutic target, is indicated for neuropathic pain. Other clinical trials are attempting to establish that central neuropathic pain may respond to ion channel blockers such as blockers of calcium, sodium and/or NMDA (N-methyl-D-aspartate) channels. Currently in development are low affinity NMDA channel blocking agents for the treatment of neuropathic pain. The literature provides substantial pre-clinical electrophysiological evidence in support of the use of NMDA antagonists in the treatment of neuropathic pain. Such agents also may find use in the control of pain after tolerance to opioid analgesia occurs, particularly in cancer patients.

Systemic analgesics such as NSAIDs and opioids are to be distinguished from therapeutic agents which are useful only as local analgesics/anaesthetics. Well known local analgesics such as lidocaine and xylocalne are non-selective ion channel blockers which can be fatal when administered systemically. A good description of non-selective sodium channel blockers is found in Madge, D. et al., *J. Med. Chem.* (2001), 44(2): 115-37.

Several sodium channel modulators are known for use as anticonvulsants or antidepressants, such as carbamazepine, amitriptyline, lamotrigine and riluzole, all of which target brain tetradotoxin-sensitive (TTX-S) sodium channels. Such TTX-S agents suffer from dose-limiting side effects, including dizziness, ataxia and somnolence, primarily due to action at TTX-S channels in the brain.

Sodium Channels Role in Pain

Sodium channels play a diverse set of roles in maintaining normal and pathological states, including the long recognized role that voltage gated sodium channels play in the generation of abnormal neuronal activity and neuropathic or pathological pain (Chung, J. M. et al., *op. cit.*). Damage to peripheral nerves following trauma or disease can result in changes to sodium channel activity and the development of abnormal afferent activity including ectopic discharges from axotomised afferents and spontaneous activity of sensitized intact nociceptors. These changes can produce long-lasting abnormal hypersensitivity to normally innocuous stimuli, or allodynia. Examples of neuropathic pain include, but are not limited to, post-herpetic neuralgia, trigeminal neuralgia, diabetic neuropathy, chronic lower back pain, phantom limb pain, and pain resulting from cancer and chemotherapy, chronic pelvic pain, complex regional pain syndrome and related neuralgias.

There has been some degree of success in treating neuropathic pain symptoms by using medications, such as gabapentin, and more recently pregabalin, as short-term, first-line treatments. However, pharmacotherapy for neuropathic pain has generally had limited success with little response to commonly used pain reducing drugs, such as NSAIDS and opiates. Consequently, there is still a considerable need to explore novel treatment modalities.

There remains a limited number of potent effective sodium channel blockers with a minimum of adverse events in the clinic. There is also an unmet medical need to treat neuropathic pain and other sodium channel associated pathological states effectively and without adverse side effects. The present invention provides methods to meet these critical needs.

SUMMARY OF THE INVENTION

The present invention is directed to spiro-oxindole compounds and pharmaceutical compositions comprising the compounds and methods of using the compounds and the pharmaceutical compositions of the invention for the treatment and/or prevention of sodium channel-mediated diseases or conditions, such as pain. The present invention is also directed to methods of using the compounds of the invention and pharmaceutical compositions comprising the compounds of the invention for the treatment of other sodium channel-mediated diseases or conditions, including, but not limited to central nervous conditions such as epilepsy, anxiety, depression and bipolar disease; cardiovascular conditions such as arrhythmias, atrial fibrillation and ventricular fibrillation; neuromuscular conditions such as restless leg syndrome, essential tremour and muscle paralysis or tetanus; neuroprotection against stroke, glaucoma, neural trauma and multiple sclerosis; and channelopathies such as erythromyalgia and familial rectal pain syndrome. The present invention is also directed to the use of the compounds of the invention and pharmaceutical compositions comprising the compounds of the invention for the treatment and/or prevention of diseases or conditions, such as hypercholesterolemia, benign prostatic hyperplasia, pruritis, and cancer.

Accordingly, in one aspect, the invention is directed to compounds of formula (I):

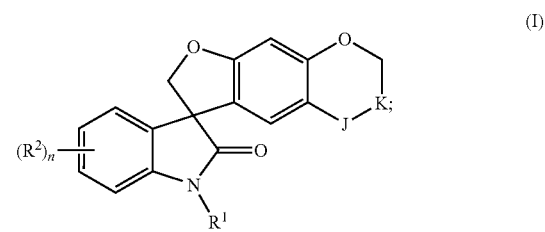

wherein:
n is 1 or 2;
one of J and K is —$CH_2$— and the other is —O—;
or both J and K are each —$CH_2$—;
$R^1$ is hydrogen, methyl, cyclopropyl, carboxymethyl, (3-carboxy)benzyl, (3-methylsulfonylamino)benzyl, [(3-methylsulfonylamino)pyridin-2-yl]methyl, [(3-carboxy)pyridin-2-yl]methyl, [(ethoxy)carbonyl]methyl, 2-cyclopropylethyl, 1,3-thiazol-5-ylmethyl, 3-methoxypropyl, (6-methylpyridin-2-yl)methyl, pyridin-3-ylmethyl, [3-(cyano)pyridine-2-yl]methyl, [3-(difluoromethyl)pyridin-2-yl]methyl, 3-(5-methyl-1,2,4-oxadiazol- 3-yl)benzyl, 4-(5-methyl-1,2,4-oxadiazol-3-yl)benzyl, [5-(trifluoromethyl)-1,2,4-oxadiazol-3-yl]methyl, [5-(trifluoromethyl)-1,3,4-oxadiazol-2-yl]methyl, [4-(trifluoromethyl)pyridin-2-yl]methyl, (4-methyl-1,2,5-oxadiazol-3-yl)methyl, pyrazin-2-ylmethyl, pyrimidin-2-ylmethyl, (1-methyl-1H-benzotriazol-5-yl)methyl, [2-(tert-butoxycarbonylamino)pyridin-5-yl]methyl, [6-(dimethylamino)pyridin-3-yl]methyl, [6-(dimethylamino)pyridin-2-yl]methyl, {6-[(diphenylmethylidene)amino]pyridin-2-yl}methyl, (5-morpholin-4-ylpyridin-2-yl)methyl, [5-(dimethylamino)pyridin-2-yl]methyl, (6-aminopyridin-2-yl)methyl, (6-oxo-1,6-dihydropyridin-3-yl)methyl, (2-hydroxypyrimidin-5-yl)methyl, (1-methyl-6-oxo-1,6-dihydropyridin-3-yl)methyl, (6-aminopyridin-3-yl)methyl, [1,2,4]triazolo[1,5-a]pyridin-6-ylmethyl, (5-hydroxypyridin-2-yl)methyl, (5-bromopyridin-2-yl)methyl, hydrazinocarbonylmethyl, [6-deoxy-D-galactopyranose]-6-yl, (6-morpholin-4-ylpyridin-3-yl)methyl, [3-(methylsulfonyl)pyridin-2-yl]methyl, (4S)-2,2-dimethyl-1,3-dioxolan-4-yl]methyl, (3-bromopyridin-2-yl)methyl, [(2-imidoformamido)pyridine-5-yl]methyl, (6-cyanopyridin-2-yl)methyl, (6-aminocarbonylpyridin-2-yl)methyl, diphenylmethyl, 4-methoxybenzyl, 2-(fluoromethyl)benzyl, 2-ethoxyethyl, 4-fluorophenyl, (2-fluorophenylaminocarbonyl)methyl, 2-(2-methoxyethoxy)ethyl, 4-isoxazol-5-ylbenzyl, 3-(benzyloxy)propyl, (2S)-2,3-dihydroxypropyl, 4-methoxybutyl, pentyl, isopentyl, hexyl, 3-nitrobenzyl, [3-(trifluoromethyl)pyridin-2-yl]methyl, [5-(trifluoromethyl)pyridin-2-yl]methyl, [(tert-butoxycarbonylamino)pyridin-2-yl]methyl, (3-(trifluoromethyl)pyridin-2-yl)methyl, (5-(trifluoromethyl)furan-2-yl)methyl, tetrahydrofuran-2-ylmethyl, 3-methylbutyl, cyanomethyl, 4-hydroxybenzyl, 3-cyanobenzyl, 4-fluoro-3-methoxybenzyl, 4-cyanobenzyl, [6-(trifluoromethyl)pyridin-3-yl]methyl, [4-(trifluoromethyl)-1,3-thiazol-2-yl]methyl, (3-fluoropyridin-2-yl)methyl, (4-fluoropyridin-2-yl)methyl, (5-fluoropyridin-3-yl)methyl, (5-fluoropyridin-2-yl)methyl, (3-chloropyridin-2-yl)methyl, (3,5-difluoropyridin-2-yl)methyl, (3-pyridin-3-ylisoxazol-5-yl)methyl, (2,2-difluorocyclopropyl)methyl, 2-oxobutyl, 2,1,3-benzothiadiazol-5-ylmethyl, 2,1,3-benzoxadiazol-5-ylmethyl, 1,3-benzothiazol-2-ylmethyl, (1-methyl-1H-benzimidazol-2-yl)methyl, [2-(1-methylethyl)-1,3-thiazol-4-yl]methyl, tert-butoxycarbonyl, [1-(tert-butoxycarbonyl)piperidin-4-yl]methyl, (2-methoxypyrimidin-5-yl)methyl, (6-methoxypyridin-3-yl)methyl, (1-oxydopyridin-2-yl)methyl, (3-aminopyridin-2-yl)methyl, piperidin-4-ylmethyl, [1-(1-methylethyl)piperidin-4-yl]methyl, (1-methylpiperidin-4-yl)methyl, morpholin-2-ylmethyl, [4-(1-methylethyl)morpholin-2-yl]methyl, (4-methylmorpholin-2-yl)methyl, (2S)-morpholin-2-ylmethyl, [(2S)-4-methylmorpholin-2-yl]methyl, [5-(difluoromethyl)furan-2-yl]methyl, tetrahydro-2H-pyran-4-ylmethyl, tetrahydro-2H-pyran-2-ylmethyl, (5-chloro-1-methyl-1H-imidazol-2-yl)methyl, (6-chloropyridin-2-yl)methyl, (4,6-dimethoxypyrimidin-2-yl)methyl, [(3-methylaminocarbonyl)pyridin-2-yl]methyl, 1-[2-(aminoethyl)aminocarbonylpyridin-3-yl]methyl, pyridin-2-ylmethyl, (2R)-1,4-dioxan-2-ylmethyl, 1,4-dioxan-2-ylmethyl, 3,4-dimethoxybenzyl, 3,5-dimethoxybenzyl, 3-hydroxypropyl, 3-phthalimidopropyl, 3-aminobenzyl, (3-aminocarbonyl)benzyl, (4-aminocarbonyl)benzyl, (3-N,N-dimethylaminocarbonyl)benzyl, 4-(benzyloxy)benzyl, 4-fluorobenzyl, 2,3-difluorobenzyl, 3,5-difluorobenzyl, 2-chloro-4-fluorobenzyl, [3-(2-fluorophenyl)aminocarbonyl]benzyl, 3-(methoxycarbonyl)benzyl, 4-(methoxycarbonyl)benzyl, 4-(ethoxycarbonyl)benzyl, 3-(dimethylamino-sulfonyl)benzyl, 3-(3-methyl-1,2,4-oxadiazol-5-yl)benzyl, 4-(3-amino-1H-pyrazol-5-yl)benzyl, 4-(3-methyl-1,2,4-oxadiazol-5-yl)benzyl, 3-(morpholin-4-ylsulfonyl)benzyl, 2-(difluoromethyl)benzyl, (3-trifluoromethoxy)benzyl, (2-fluoro-6-trifluoromethyl)benzyl, (2-fluoro-5-trifluoromethyl)benzyl, (2-trifluoromethoxy)benzyl, 3-(amino(hydroxyimino)methyl)benzyl, 2-amino-2-(hydroxyimino)ethyl, (6-(N'-hydroxyformimidamido)pyridin-3-yl)methyl, 2-(2,2,5-trimethyl-1,3-dioxan-2-yl)ethyl, (4-benzylmorpholin-2-yl)methyl, [(2S)-4-benzylmorpholin-2-yl]methyl, 2,3-dihydro-1,4-benzodioxin-6-ylmethyl, [5-(trifluoromethyl)furan-2-yl]methyl, 3-(trifluoromethyl)benzyl, [3-(trifluoromethyl)pyrazin-2-yl]methyl, [4-(trifluoromethyl)pyridin-3-yl]methyl, (5-methoxycarbonylfuran-2-yl)methyl, 5-carboxyfuran-2-ylmethyl, 5-(dimethylaminocarbonyl)furan-2ylmethyl, [2-(trifluoromethyl)pyridin-3-yl]methyl, methylcarbonyl, ethoxycarbonyl, tert-butoxycarbonyl or [(3aR,5R,5aS,8aS,8bR)-2,2,7,7-tetramethyltetrahydro-3aH-bis[1,3]dioxolo[4,5-b:4',5'-d]pyran-5-yl]methyl;

each $R^2$ is independently hydrogen, hydroxy, amino, (hexanylaminocarbonyl)amino, (cyclopentylaminocarbonyl)amino, benzylamino, (cyclohexylaminocarbonyl)amino, methylsulfonylamino, (methyl)carbonylamino, N,N-dimethylaminocarbonyl, (ethyl)carbonylamino, (butyl)carbonylamino, (tert-butyl)carbonylamino, (pentanyl)carbonylamino, (hexanyl)carbonylamino, (methoxymethyl)carbonylamino, cyclobutylcarbonylamino, [2-methoxy(ethoxymethyl)]carbonylamino, (methylsulfonyl)amino, (2-trifluoromethylphenyl)carbonylamino, (cyclohexanyl)carbonylamino, (cyclopentanyl)carbonylamino, (cyclopropanyl)carbonylamino, (phenyl)carbonylamino, bromo, cyano, fluoro, methyl, methoxy, hydroxycarbonyl, methylcarbonyl, pyrrolidinylcarbonyl, aminocarbonyl, methylaminocarbonyl, (2-methoxyethyl)aminocarbonyl, (cyclopropyl)aminocarbonyl, pentylaminocarbonyl, (cyclobutyl)aminocarbonyl, (cyclopentyl)aminocarbonyl, hexanylaminocarbonyl, (cyclohexyl)aminocarbonyl, (4-fluorophenyl)aminocarbonyl, (4-fluorobenzyl)aminocarbonyl, (pyridin-2-ylmethyl)aminocarbonyl, 2-(2-methoxyethoxy)ethoxy, [3-(trifluoromethyl)pyridin-2-yl]oxyl, quinolinyl, phenoxycarbonyl, 2-oxochromenyl, 2-oxopyrrolidinyl, morpholinyl, 2-oxopyridinyl, benzyloxyl, [3-(trifluoromethyl)pyridin-2-yl]methoxy, pyridine-2-ylmethoxy, pyridin-2-yloxy, 4-(trifluoromethyl)phenoxy, 2-methyl-1,3-thiazol-4-yl, 2-amino-1,3-thiazol-4-yl, 6-(dimethylamino)pyridin-3-yl, furan-3-yl, 1H-pyrazol-3-yl, 1H-pyrazol-4-yl, 1-methyl-1H-pyrazol-4-yl, 5-hydroxy-1H-pyrazol-3-yl, 5-methyl-1,2,4-oxadiazol-3-yl, (6-methoxypyridin-3-yl)oxy, 1,3-benzodioxol-5-yloxy, 4-fluorobenzyloxy, 3,5-dimethylisoxazol-4-yl, phenoxy, 3-methoxyphenoxy, 4-methoxyphenoxy, 3-morpholin-4-ylphenoxy, 4-fluorophenoxy, 4-methoxyphenyl or 4-phenoxyphenyl;

or two adjacent $R^2$'s, together with the adjacent carbons to which they are attached, form a fused thiazolyl ring, a fused pyridyl ring or a fused dioxinyl ring;

as a stereoisomer, enantiomer, tautomer thereof or mixtures thereof;

or a pharmaceutically acceptable salt, solvate or prodrug thereof.

In another aspect, this invention is directed to compounds of formula (II):

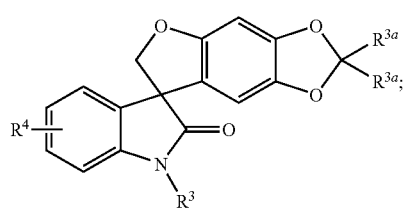

(II)

wherein:
each $R^{3a}$ is hydrogen or fluoro;
$R^3$ is hydrogen, methyl, 3-(trifluoromethyl)pyridin-2-yl]methyl, 2,5-dimethyl-1-(1-methylethyl)-1H-pyrrol-3-yl]methyl, (3-isopropylisoxazol-5-yl)methyl, (4-bromo-2-thienyl)methyl, 1-benzofuran-2-ylmethyl, [2-methyl-5-(trifluoromethyl)-1,3-oxazol-4-yl]methyl, [5-(4-chlorophenyl)-2-(trifluoromethyl)furan-3-yl]methyl, [5-chloro-1-methyl-3-(trifluoromethyl)-1H-pyrazol-4-yl]methyl, 5-methoxypyridin-3-yl, 4-bromobenzyl, [(2S)-5-oxopyrrolidin-2-yl]methyl, cyanomethyl, [5-(trifluoromethyl)-2-furyl]methyl, (5-chloro-2-thienyl)methyl, (3-chlorothiophen-2-yl)methyl, [3-(2,6-dichlorophenyl)-5-methylisoxazol-4-yl]methyl, {2-[4-(trifluoromethyl)phenyl]-1,3-thiazol-4-yl}methyl, (5-phenyl-1,3,4-oxadiazol-2-yl)methyl, [5-(4-chlorophenyl)-1,3,4-oxadiazol-2-yl]methyl, [1,3]oxazolo[4,5-b]pyridin-2-ylmethyl, (2-isopropyl-1,3-thiazol-5-yl)methyl, (2-isopropyl-1,3-oxazol-5-yl)methyl, 3-(tert-butoxycarbonylamino)-3-(cyclopropyl)propyl, 4-(methylsulfanyl)benzyl, 2-cyanoethyl, (2-bromo-1,3-thiazol-5-yl)methyl, [2-amino-4-(trifluoromethyl)-1,3-thiazol-5-yl]methyl, (2-amino-1,3-thiazol-4-yl)methyl, (5-chlorothiophen-2-yl)methyl, [2-(1-methylethyl)-1,3-thiazol-4-yl]methyl, (5-chloro-1,2,4-thiadiazol-3-yl)methyl, (5-chloro-1,2,4-thiadiazol-3-yl)methyl, 4-methoxybenzyl, (2S)-1,4-dioxan-2-ylmethyl, (2-chloro-1,3-thiazol-5-yl)methyl, [2-(dimethylamino)-1,3-thiazol-5-yl]methyl, (2-morpholin-4-yl-1,3-thiazol-5-yl)methyl, (2-piperidin-1-yl-1,3-thiazol-5-yl)methyl, (2-methoxy-1,3-thiazol-5-yl)methyl, 2-[5-(trifluoromethyl)-1,2,4-oxadiazol-3-yl]ethyl, [5-(trifluoromethyl)-1,2,4-oxadiazol-3-yl]methyl, (5-cyclopropyl-1,2,4-oxadiazol-3-yl)methyl, [5-(difluoromethyl)-1,2,4-oxadiazol-3-yl]methyl, (5-tert-butyl-1,2,4-oxadiazol-3-yl)methyl, [5-(1-methylethyl)-1,2,4-oxadiazol-3-yl]methyl, (4-methylpiperazin-1-yl)methyl, (3-methyl-2-oxo-1,3-oxazolidin-5-yl)methyl, 2-(1-(methylethyl)aminocarbonylpiperidin-3-yl)ethyl, (4-cyanothien-2-yl)methyl, [5-trifluoromethyl-4-(methyl)aminocarbonylfuran-2-yl]methyl, (5-trifluoromethyl-4-aminocarbonylfuran-2-yl)methyl, [5-trifluoromethyl-4-(dimethyl)aminocarbonylfuran-2-yl]methyl, [4-(cyclopropyl)aminocarbonyl-1,3-oxazol-2-yl]methyl, (2,4-dioxo-1,2,3,4-tetrahydropyrimidin-5-yl)methyl, or [4-(methylethyl)aminocarbonyl-1,3-oxazol-2-yl]methyl;
each $R^4$ is independently hydrogen, chloro, bromo, trifluoromethyl, cyano, 6-(dimethylamino)pyridin-3-yl, tetrahydrofuran-3-yl or furan-3-yl;
as a stereoisomer, enantiomer, tautomer thereof or mixtures thereof;
or a pharmaceutically acceptable salt, solvate or prodrug thereof.

In another aspect, this invention is directed to compounds of formula (III):

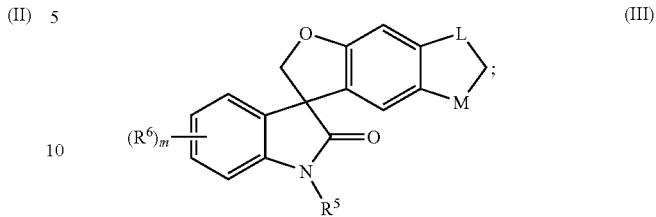

(III)

wherein:
m is 1 or 2;
one of L and M is —$CH_2$— and the other is —O—;
$R^5$ is hydrogen, methyl, pyridazin-4-ylmethyl, diphenylmethyl, 4-methoxybenzyl, 4-hydroxybenzyl, (5-(trifluoromethyl)furan-2-yl)methyl, tetrahydro-2H-pyran-2-ylmethyl, tetrahydro-2H-pyran-4-ylmethyl, tetrahydro-2H-pyran-3-ylmethyl, (2-chloro-1-methyl-1H-imidazol-5-yl)methyl, (2R)-tetrahydrofuran-2-ylmethyl, (2S)-tetrahydrofuran-2-ylmethyl, tetrahydrofuran-3-ylmethyl, tetrahydrofuran-2-ylmethyl, 3-methylbutyl, pentyl, 5-(methoxycarbonyl)furan-2-yl, 1,4-dioxan-2-ylmethyl, [1-methyl-3-(trifluoromethyl)-1H-pyrazol-4-yl]methyl, 4-methoxycarbonyl-1,3-oxazol-2-yl, 2-fluorobenzyl, 4-fluorobenzyl, benzyl, 4-phenylbenzyl, (3-bromoisoxazol-5-yl)methyl, (5-bromofuran-2-yl)methyl, oxetan-2-ylmethyl, (1-ethyl-1H-imidazol-5-yl)methyl, 3-cyanobenzyl, 4-cyanobenzyl, 4-(2-cyanophenyl)benzyl, 2-[(benzyloxy)methoxy]propyl, 2,3-dihydro-1,4-benzodioxin-6-ylmethyl, 2,1,3-benzoxadiazol-5-ylmethyl, 2,1,3-benzothiadiazol-5-ylmethyl, (4-benzylmorpholin-2-yl)methyl, [1-(tert-butoxycarbonyl)pyrrolidin-3-yl]methyl, [(2S)-1-(tert-butoxycarbonyl)pyrrolidin-2-yl]methyl, [1-(tert-butoxycarbonyl)piperidin-4-yl]methyl, [5-(trifluoromethyl)furan-2-yl]methyl, pyridin-2-ylmethyl, 4-(methylsulfanyl)benzyl, (2-methoxypyrimidin-5-yl)methyl, (2R)-1,4-dioxan-2-ylmethyl, 2-(2-methoxyethoxy)ethyl, [(2S)-5-oxopyrrolidin-2-yl]methyl, 2-(2-oxo-1,3-oxazolidin-3-yl)ethyl, 4-pyridin-2-ylbenzyl, pyrimidin-2-ylmethyl, pyrimidin-4-ylmethyl, pyrazin-2-ylmethyl, (7-fluoro-1-benzofuran-2-yl)methyl, pyridazin-3-ylmethyl, (2-oxo-1,3-oxazolidin-5-yl)methyl, 3-(benzyloxy)benzyl, (1-methyl-1H-benzimidazol-2-yl)methyl, 2H-benzotriazol-2-ylmethyl, 2-methoxycarbonylbenzyl, 4-methoxycarbonylbenzyl, 3-(benzyloxy)propyl, piperidin-4-ylmethyl, [1-(1-methylethyl)piperidin-4-yl]methyl, (1-ethylpiperidin-4-yl)methyl, (1-methylpiperidin-4-yl)methyl, (2S)-pyrrolidin-2-ylmethyl, 3-carboxybenzyl, 2-carboxybenzyl, 4-carboxybenzyl, 4-(benzyloxy)benzyl, 4-[5-(trifluoromethyl)-1,2,4-oxadiazol-3-yl]benzyl, 4-(5-methyl-1,2,4-oxadiazol-3-yl)benzyl, (5-pyridin-4-ylfuran-2-yl)methyl, 4-pyridin-3-ylbenzyl, (2'-fluorobiphenyl-4-yl)methyl, 3-(5-methyl-1,2,4-oxadiazol-3-yl)benzyl, 3-[5-(trifluoromethyl)-1,2,4-oxadiazol-3-yl]benzyl, 4-(5-methyl-4H-1,2,4-triazol-3-yl)benzyl, 3-hydroxypropyl, morpholin-2-ylmethyl, (4-methylmorpholin-2-yl)methyl, [4-(1-methylethyl)morpholin-2-yl]methyl, 4-(1H-tetrazol-5-yl)benzyl, 3-hydroxybenzyl, 4-morpholin-4-ylbenzyl, pyrrolidin-3-ylmethyl, [1-((1-methylethyl)aminocarbonyl)pyrrolidin-3-yl]methyl, [(2S)-1-methyl-5-oxopyrrolidin-2-yl]methyl, 3-(cyclohexylamino)carboxylbenzyl, 3-[(2-methoxyethyl)amino]carbonylbenzyl, 3-[(hexyl)(methyl)amino]carbonylbenzyl, 3-[(2-ethylbutyl)amino]carbonylbenzyl, 3-[(2,4-dimethylphenyl)amino]carbonylbenzyl, 3-[(2-phenylpropyl)amino]carbonylbenzyl, 3-[((1S)-1- cyclohexylethyl)amino]carbonylbenzyl, 3-[((1R)-1-cyclohexylethyl)amino]carbonylbenzyl, 2-[(4-ethylphenyl)amino]carbonylbenzyl, 2-[(2-ethylphenyl)amino]carbonylbenzyl, 2-[(2,4-dimethylphenyl)amino]carbonylbenzyl, 2-[(2-methoxyphenyl)amino]carbonylbenzyl, 2-[(2-fluorophenyl)amino]carbonylbenzyl, 2-[(3-chlorophenyl)amino]carbonylbenzyl, 2-[(3-fluoro-2-methylphenyl)amino]carbonylbenzyl, 2-[(heptyl)amino]carbonylbenzyl, 2-[(2-chlorobenzyl)amino]carbonylbenzyl, 2-(piperidin-1-yl)carbonylbenzyl, 2-[(butyl)amino]carbonylbenzyl, 2-[(3-methylphenyl)amino]carbonylbenzyl, 2-[(2-fluoro-5-methylphenyl)amino]carbonylbenzyl, 2-[(2,3-dimethylphenyl)amino]carbonylbenzyl, 2-[(2-(4-methoxyphenyl)ethyl)amino]carbonylbenzyl, 2-[(3-chlorobenzyl)amino]carbonylbenzyl, 2-[(2-(4-chlorophenyl)ethyl)amino]carbonylbenzyl, 4-[(2-methoxyphenyl)amino]carbonylbenzyl, 4-[(2-trifluoromethylphenyl)amino]carbonylbenzyl, 4-[(phenyl)amino]carbonylbenzyl, 4-[(methyl)amino]carbonylbenzyl, 4-[(2-fluorophenyl)amino]carbonylbenzyl, 4-[(2-thiophen-2-ylethyl)amino]carbonylbenzyl, 4-(amino)carbonylbenzyl, 4-[(2,3-dihydro-1H-inden-5-yl)amino]carbonylbenzyl, 4-(morpholin-1-yl)carbonylbenzyl, 4-[(2-ethylphenyl)amino]carbonylbenzyl, 4-[(2,6-dimethylphenyl)amino]carbonylbenzyl, 4-[(3-fluorophenyl)amino]carbonylbenzyl, 4-[(2,4-dimethylphenyl)amino]carbonylbenzyl, 4-[(thien-2-ylmethyl)amino]carbonylbenzyl, 4-[(ethyl)amino]carbonylbenzyl, 4-[(2-methoxyethyl)amino]carbonylbenzyl, 4-[(2-ethoxyethyl)amino]carbonylbenzyl, 4-[(cyclobutyl)amino]carbonylbenzyl, 4-[(1,3-thiazol-2-yl)amino]carbonylbenzyl, 4-[(3-fluoro-2-methylphenyl)amino]carbonylbenzyl, 4-[(2-ethylbutyl)amino]carbonylbenzyl, (aminocarbonyl)methyl, [((4-ethylphenyl)amino)carbonyl]methyl, [((2,5-dimethylphenyl)amino)carbonyl]methyl, [(diethylamino)carbonyl]methyl, [(3,3-dimethylbutylamino)carbonyl]methyl, [(3-(1-methylethoxy)propylamino)carbonyl]methyl; [(propylamino)carbonyl]methyl, [(phenyl)(methyl)aminocarbonyl]methyl, [((2,4-dimethylphenyl)amino)carbonyl]methyl, [((2,3-dimethylphenyl)amino)carbonyl]methyl, [((2,6-dimethylphenyl)amino)carbonyl]methyl, (5-carboxyfuran-2-yl)methyl, [5-(dimethylaminocarbonyl)furan-2-yl]methyl, [5-(methylaminocarbonyl)furan-2-yl]methyl, [4-(aminocarbonyl)-1,3-oxazol-2-yl]methyl, [4-((dimethylamino)carbonyl)-1,3-oxazol-2-yl]methyl, 2-hydroxypropyl, (2S)-2-hydroxypropyl, 2-(benzyloxy)propyl, 2-(4-fluorobenzyloxy)propyl, 2-(pyridin-2-yloxy)propyl, 3-hydroxybutyl, 4,4,4-trifluoro-3-hydroxybutyl, 3-aminopropyl, 3-oxopropyl, 3-[(3-methylbutyl)amino]propyl, 3-[butyl(methyl)amino]propyl, 3-[(2,2,2-trifluoroethyl)amino]propyl, 3-[(2-trifluoromethoxyphenyl)carbonylamino]propyl or 3-[(2-cyanoethyl)amino]propyl; and each R⁶ is independently hydrogen, chloro, bromo, fluoro, methyl, cyano, amino, —C(O)H, —CH₂—N(CH₃)₂, (pyrrolidin-1-yl)methyl, 6-(dimethylamino)pyridin-3-yl, 2-(4-fluorophenyl)ethenyl, dibenzo[b,d]thiophen-4-yl, benzothiophen-3-yl, 1-methyl-1H-indol-5-yl, 3,5-di(trifluoromethyl)phenyl, 4-phenoxyphenyl, 4-(2-methylpropoxy)phenyl, 4-butoxyphenyl, 4-methoxyphenyl, pyrimidin-5-yl or furan-3-yl;

or two R⁶'s, together with the adjacent carbons to which they are attached, form a fused dioxinyl ring or a fused pyridinyl ring;

as a stereoisomer, enantiomer, tautomer thereof or mixtures thereof;

or a pharmaceutically acceptable salt, solvate or prodrug thereof.

In another aspect, this invention is directed to compounds of formula (IV):

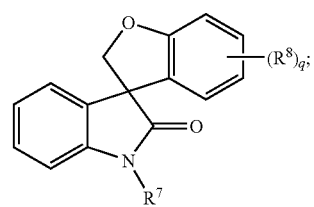

wherein:

q is 1, 2 or 3;

R⁷ is hydrogen, (5-chloro-2-thienyl)methyl, 2-(2-methoxyethoxy)ethyl, diphenylmethyl, 4-methoxybenzyl, 3-methylbutyl, benzyl, 4-bromobenzyl, 2,3-dihydro-1,4-benzodioxin-6-ylmethyl, 2-(trifluoromethyl)benzyl, [3-(trifluoromethyl)pyridin-2-yl]methyl, [5-(benzyloxy)pyridin-2-yl]methyl, piperidin-4-ylmethyl, (1-methylpiperidin-4-yl)methyl, (5-hydroxypyridin-2-yl)methyl, [5-(trifluoromethyl)furan-2-yl]methyl, (2R)-tetrahydrofuran-2-ylmethyl, pyridin-2-ylmethyl, pyridin-3-ylmethyl, tetrahydro-2H-pyran-4-ylmethyl, tetrahydro-2H-pyran-2-ylmethyl, [1-(tert-butoxycarbonyl)piperidin-4-yl]methyl, 4-[(3R)-pyrrolidin-3-ylamino]benzyl or (4-methylpiperazin-1-ylmethyl; and each R⁸ is independently hydrogen, hydroxy, bromo, chloro, cyano, fluoro, methyl, trifluoroacetyl, methoxy, 1-methylethoxy, 2-methoxyethoxy, benzyloxy, 1-(tert-butoxycarbonyl)pyrrolidin-3-yloxy, pyrrolidin-3-yloxy, amino, sulfonylamino, methylsulfonylamino, [(tert-butoxycarbonyl)pyrrolidin-3-yl]amino, 6-methoxypyridin-3-yl, 5-methyl-1,2,4-oxadiazol-3-yl, amino(hydroxyimino)methyl or (pyrrolidin-3-yl)amino;

or two R⁸ groups, together with the adjacent carbons to which they are attached, form a fused dioxinyl ring, a fused thienyl ring, a fused 1,1-dioxothienyl ring, a fused 1,2,5-oxadiazolyl ring, a fused tetrahydropyranyl ring, a fused 2,3-dihydropyrazinyl ring, a fused 3-methyl-4,5-dihydroisoxazolyl ring or a fused pyrazinyl ring, and the remaining R⁸ group, if present, is as described above;

as a stereoisomer, enantiomer, tautomer thereof or mixtures thereof;

or a pharmaceutically acceptable salt, solvate or prodrug thereof.

In another aspect, this invention is directed to compounds of formula (V):

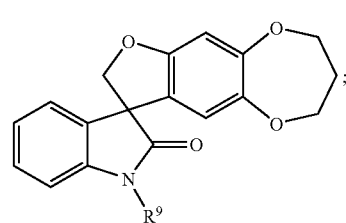

wherein:

R⁹ is hydrogen, diphenylmethyl, [5-(trifluoromethyl)furan-2-yl]methyl, (2R)-tetrahydrofuran-2-ylmethyl, pyridin-2-ylmethyl, (2R)-1,4-dioxan-2-ylmethyl, or (2S)-1,4-dioxan-2-ylmethyl;

as a stereoisomer, enantiomer, tautomer thereof or mixtures thereof;

or a pharmaceutically acceptable salt, solvate or prodrug thereof.

In another aspect, this invention is directed to compounds of formula (VI):

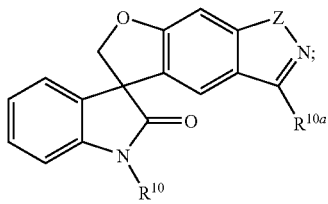

(VI)

wherein:

Z is —O— or —N(H)—;

$R^{10}$ is hydrogen, 3-methylbutyl, 4-methoxybenzyl, 2-(2-methoxyethoxy)ethyl, 4-isoxazol-5-ylbenzyl, 2-(trifluoromethyl)benzyl, [3-(trifluoromethyl)pyridin-2-yl]methyl, [4-(hydroxycarbonyl)oxazol-2-yl]methyl, [4-(N,N-dimethylaminocarbonyl) oxazol-2-yl]methyl, (4-cyanomethylcarbonyl)benzyl, [5-(trifluoromethyl)furan-2-yl]methyl, (2R)-tetrahydrofuran-2-ylmethyl, (3-fluoropyridin-2-yl)methyl, [4-(methoxycarbonyl)oxazol-2-yl]methyl, 4-(3-amino-1H-pyrazol-5-yl)benzyl, pyridin-2-ylmethyl, pyridin-3-ylmethyl or pyrazin-2-ylmethyl; and $R^{10a}$ is hydrogen, methyl or —NH$_2$;

as a stereoisomer, enantiomer, tautomer thereof or mixtures thereof;

or a pharmaceutically acceptable salt, solvate or prodrug thereof.

In another aspect, this invention is directed to compounds of formula (VII):

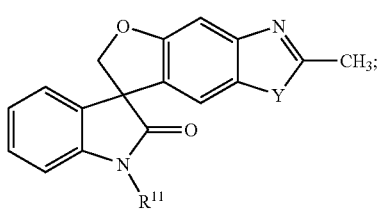

(VII)

wherein:

Y is —O— or —S—;

$R^{11}$ is hydrogen, diphenylmethyl, 3-methylbutyl, tetrahydro-2H-pyran-4-ylmethyl, (2R)-tetrahydrofuran-2-ylmethyl, pyridin-2-ylmethyl or (5-chloro-1-methyl-1H-imidazol-2-yl)methyl;

as a stereoisomer, enantiomer, tautomer thereof or mixtures thereof;

or a pharmaceutically acceptable salt, solvate or prodrug thereof.

In another aspect, this invention is directed to compounds of formula (VIII):

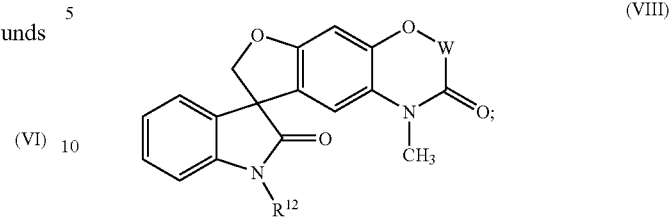

(VIII)

wherein:

W is a direct bond or —CH$_2$—; and $R^{12}$ is hydrogen, diphenylmethyl, or (2R)-tetrahydrofuran-2-ylmethyl;

as a stereoisomer, enantiomer, tautomer thereof or mixtures thereof;

or a pharmaceutically acceptable salt, solvate or prodrug thereof.

In another aspect, this invention is directed to compounds of formula (IX):

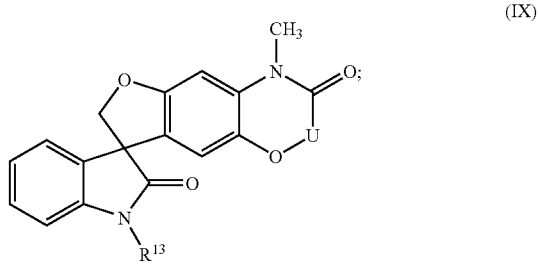

(IX)

wherein:

U is a direct bond or —CH$_2$—; and $R^{13}$ is hydrogen, diphenylmethyl, [5-(trifluoromethyl)furan-2-yl]methyl, or (2R)-tetrahydrofuran-2-ylmethyl;

as a stereoisomer, enantiomer, tautomer thereof or mixtures thereof;

or a pharmaceutically acceptable salt, solvate or prodrug thereof.

In another aspect, this invention is directed to compounds of formula (X):

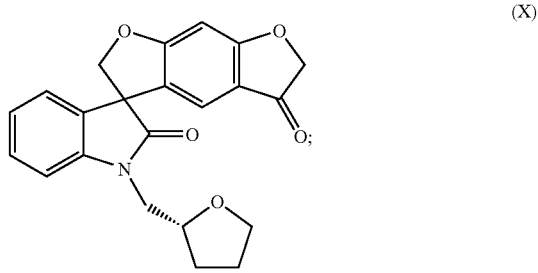

(X)

as a stereoisomer, enantiomer, tautomer thereof or mixtures thereof;

or a pharmaceutically acceptable salt, solvate or prodrug thereof.

In another aspect, this invention is directed to compounds of formula (XI):

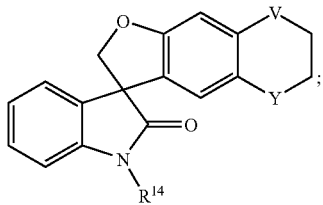

(XI)

wherein:
V is —O—, —N(CH₃)— or —CH₂— and Y is —N(CH₃)— or —CH₂—;
or V is —N(CH₃)— or —CH₂— and Y is —O—, —N(CH₃)— or —CH₂—; and
$R^{14}$ is hydrogen, [5-(trifluoromethyl)furan-2-yl]methyl, pyridin-2-ylmethyl, [3-(trifluoromethyl)pyridin-2-yl]methyl or (2R)-tetrahydrofuran-2-ylmethyl;
as a stereoisomer, enantiomer, tautomer thereof or mixtures thereof;
or a pharmaceutically acceptable salt, solvate or prodrug thereof.

In another aspect, this invention is directed to compounds of formula (XII):

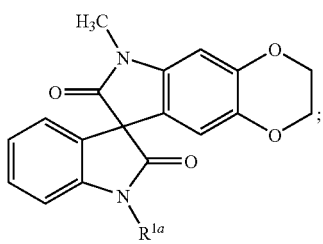

(XII)

wherein:
$R^{1a}$ is hydrogen or (pyridin-2-yl)methyl;
as a stereoisomer, enantiomer, tautomer thereof or mixtures thereof;
or a pharmaceutically acceptable salt, solvate or prodrug thereof.

In another aspect, this invention is directed to compounds of formula (XIII):

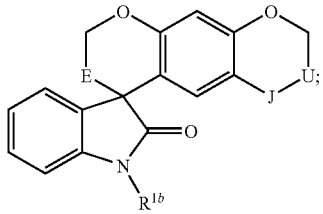

(XIII)

wherein:
E is —O— or —CH₂—;
J is —O— or —CH₂—;
U is a direct bond or —CH₂—; and
$R^{1b}$ is hydrogen, [3-(trifluoromethyl)pyridin-2-yl]methyl, diphenylmethyl, or [5-(trifluoromethyl)furan-2-yl]methyl;

as a stereoisomer, enantiomer, tautomer thereof or mixtures thereof;
or a pharmaceutically acceptable salt, solvate or prodrug thereof.

In another aspect, the invention is directed to pharmaceutical compositions comprising a pharmaceutically acceptable excipient and a therapeutically effective amount of a compound of the invention, as set forth above, as a stereoisomer, enantiomer, tautomer thereof or mixtures thereof; or as a pharmaceutically acceptable salt, solvate or prodrug thereof.

In another aspect, the invention provides methods for the treatment of pain in a mammal, preferably a human, wherein the methods comprise administering to the mammal in need thereof a therapeutically effective amount of a compound of the invention, as set forth above, as a stereoisomer, enantiomer, tautomer thereof or mixtures thereof; or a pharmaceutically acceptable salt, solvate or prodrug thereof, or a pharmaceutical composition comprising a therapeutically effective amount of a compound of the invention, as set forth above, as a stereoisomer, enantiomer, tautomer thereof or mixtures thereof, or a pharmaceutically acceptable salt, solvate or prodrug thereof, and a pharmaceutically acceptable excipient.

In another aspect, the present invention provides a method for treating or lessening the severity of a disease, condition, or disorder in a mammal where activation or hyperactivity of one or more of $Na_v1.1$, $Na_v1.2$, $Na_v1.3$, $Na_v1.4$, $Na_v1.5$, $Na_v1.6$, $Na_v1.7$, $Na_v1.8$, or $Na_v1.9$ is implicated in the disease, condition or disorder, wherein the method comprises administering to the mammal in need thereof a therapeutically effective amount of a compound of the invention, as set forth above, as a stereoisomer, enantiomer, tautomer thereof or mixtures thereof; or a pharmaceutically acceptable salt, solvate or prodrug thereof, or a pharmaceutical composition comprising a therapeutically effective amount of a compound of the invention, as set forth above, as a stereoisomer, enantiomer, tautomer thereof or mixtures thereof, or a pharmaceutically acceptable salt, solvate or prodrug thereof, and a pharmaceutically acceptable excipient.

In another aspect, the invention provides methods of treating a range of sodium channel-mediated diseases or conditions in a mammal, for example, pain associated with HIV, HIV treatment induced neuropathy, trigeminal neuralgia, post-herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritic, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, familial erythromelagia, primary erythromelagia, familial rectal pain, cancer, epilepsy, partial and general tonic seizures, restless leg syndrome, arrhythmias, fibromyalgia, neuroprotection under ischaemic conditions caused by stroke, glaucoma or neural trauma, tachy-arrhythmias, atrial fibrillation and ventricular fibrillation, wherein the methods comprise administering to the mammal in need thereof, preferably a human, a therapeutically effective amount of a compound of the invention, as set forth above, as a stereoisomer, enantiomer, tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer, tautomer thereof or mixtures thereof, or a pharmaceutically acceptable salt, solvate or prodrug thereof, and a pharmaceutically acceptable excipient.

In another aspect, the invention provides methods of treating a range of sodium channel-mediated diseases or conditions in a mammal, preferably a human, by the inhibition of ion flux through a voltage-dependent sodium channel in the mammal, wherein the methods comprise administering to the mammal in need thereof a therapeutically effective amount of a compound of the invention, as set forth above, as a stereoisomer, enantiomer, tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer, tautomer thereof or mixtures thereof, or a pharmaceutically acceptable salt, solvate or prodrug thereof, and a pharmaceutically acceptable excipient.

In another aspect, the invention provides methods of treating or preventing hypercholesterolemia in a mammal, preferably a human, wherein the methods comprise administering to the mammal in need thereof a therapeutically effective amount of a compound of the invention, as set forth above, as a stereoisomer, enantiomer, tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer, tautomer thereof or mixtures thereof, or a pharmaceutically acceptable salt, solvate or prodrug thereof, and a pharmaceutically acceptable excipient.

In another aspect, the invention provides methods of treating or preventing benign prostatic hyperplasia in a mammal, preferably a human, wherein the methods comprise administering to the mammal in need thereof a therapeutically effective amount of a compound of the invention, as set forth above, as a stereoisomer, enantiomer, tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer, tautomer thereof or mixtures thereof, or a pharmaceutically acceptable salt, solvate or prodrug thereof, and a pharmaceutically acceptable excipient.

In another aspect, the invention provides methods of treating or preventing pruritis in a mammal, preferably a human, wherein the methods comprise administering to the mammal in need thereof a therapeutically effective amount of a compound of the invention, as set forth above, as a stereoisomer, enantiomer, tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer, tautomer thereof or mixtures thereof, or a pharmaceutically acceptable salt, solvate or prodrug thereof, and a pharmaceutically acceptable excipient.

In another aspect, the invention provides methods of treating or preventing cancer in a mammal, preferably a human, wherein the methods comprise administering to the mammal in need thereof a therapeutically effective amount of a compound of the invention, as set forth above, as a stereoisomer, enantiomer, tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer, tautomer thereof or mixtures thereof, or a pharmaceutically acceptable salt, solvate or prodrug thereof, and a pharmaceutically acceptable excipient.

In another aspect, the invention provides pharmaceutical therapy in combination with one or more other compounds of the invention or one or more other accepted therapies or as any combination thereof to increase the potency of an existing or future drug therapy or to decrease the adverse events associated with the accepted therapy. In one embodiment, the present invention relates to a pharmaceutical composition combining compounds of the present invention with established or future therapies for the indications listed in the invention.

In another aspect, this invention is directed to the use of the compounds of the invention, as set forth above, as a stereoisomer, enantiomer, tautomer thereof or mixtures thereof, or a pharmaceutically acceptable salt, solvate or prodrug thereof, or the use of a pharmaceutical composition comprising a pharmaceutically acceptable excipient and a compound of the invention, as set forth above, as a stereoisomer, enantiomer, tautomer thereof or mixtures thereof, or a pharmaceutically acceptable salt, solvate or prodrug thereof, in the preparation of a medicament for the treatment of sodium channel-mediated diseases or conditions in a mammal.

DETAILED DESCRIPTION OF THE INVENTION

Definitions

Certain chemical groups named herein may be preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

In addition to the foregoing, as used in the specification and appended claims, unless specified to the contrary, the following terms have the meaning indicated:

"Amino" refers to the —$NH_2$ radical.
"Cyano" refers to the —CN radical.
"Formyl" refers to the —C(O)H radical.
"Hydroxy" refers to the —OH radical.
"Nitro" refers to the —$NO_2$ radical.
"Oxo" refers to the =O substituent.
"Thioxo" refers to the =S substituent.
"Trifluoromethyl" refers to the —$CF_3$ radical.
"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{40}$, —$OC(O)$—$R^{40}$, —$N(R^{40})_2$, —$C(O)R^{40}$, —$C(O)OR^{40}$, —$C(O)N(R^{40})_2$, —$N(R^{40})C(O)OR^{42}$, —$N(R^{40})C(O)R^{42}$, —$N(R^{40})S(O)_tR^{42}$ (where t is 1 to 2), —$S(O)_tOR^{42}$ (where t is 1 to 2), —$S(O)_pR^{42}$ (where p is 0 to 2), and —$S(O)_tN(R^{40})_2$ (where t is 1 to 2) where each $R^{40}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{42}$ is alkyl, haloalkyl, cycloalkyl, cycloalkylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{40}$, —OC(O)—$R^{40}$, —N($R^{40}$)$_2$, —C(O)$R^{40}$, —C(O)O$R^{40}$, —C(O)N($R^{40}$)$_2$, —N($R^{40}$)C(O)O$R^{42}$, —N($R^{40}$)C(O)$R^{42}$, —N($R^{40}$)S(O)$_t$$R^{42}$ (where t is 1 to 2), —S(O)$_t$O$R^{42}$ (where t is 1 to 2), —S(O)$_p$$R^{42}$ (where p is 0 to 2), and —S(O)$_t$N($R^{40}$)$_2$ (where t is 1 to 2) where each $R^{40}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{42}$ is alkyl, haloalkyl, cycloalkyl, cycloalkylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{40}$, —OC(O)—$R^{40}$, —N($R^{40}$)$_2$, —C(O)$R^{40}$, —C(O)O$R^{40}$, —C(O)N($R^{40}$)$_2$, —N($R^{40}$)C(O)O$R^{42}$, —N($R^{40}$)C(O)$R^{42}$, —N($R^{40}$)S(O)$_t$$R^{42}$ (where t is 1 to 2), —S(O)$_t$O$R^{42}$ (where t is 1 to 2), —S(O)$_p$$R^{42}$ (where p is 0 to 2), and —S(O)$_t$N($R^{40}$)$_2$ (where t is 1 to 2) where each $R^{40}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{42}$ is alkyl, haloalkyl, cycloalkyl, cycloalkylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{40}$, —OC(O)—$R^{40}$, —N($R^{40}$)$_2$, —C(O)$R^{40}$, —C(O)O$R^{40}$, —C(O)N($R^{40}$)$_2$, —N($R^{40}$)C(O)O$R^{42}$, —N($R^{40}$)C(O)$R^{42}$, —N($R^{40}$)S(O)$_t$$R^{42}$ (where t is 1 to 2), —S(O)$_t$O$R^{42}$ (where t is 1 to 2), —S(O)$_p$$R^{42}$ (where p is 0 to 2), and —S(O)$_t$N($R^4$)$_2$ (where t is 1 to 2) where each $R^{40}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{42}$ is alkyl, haloalkyl, cycloalkyl, cycloalkylalkyl, aryl, aralkyl, heterocyclyl, heterocyclylalkyl, heteroaryl or heteroarylalkyl.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may included fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group may be optionally substituted by one or more substituents independently selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{41}$—$OR^{40}$, —$R^{41}$—OC(O)—$R^{40}$, —$R^{41}$—N($R^{40}$)$_2$, —$R^{41}$—C(O)$R^{40}$, —$R^{41}$—C(O)O$R^{40}$, —$R^{41}$—C(O)N($R^{40}$)$_2$, —$R^{41}$—N($R^{40}$)C(O)O$R^{42}$, —$R^{41}$—N($R^{40}$)C(O)$R^{42}$, —$R^{41}$—N($R^{40}$)S(O)$_t$$R^{42}$ (where t is 1 to 2), —$R^{41}$—N=C(O$R^{40}$)$R^{40}$, —$R^{41}$—S(O)$_t$O$R^{42}$ (where p is 0 to 2), and —$R^{41}$—S(O)$_t$N($R^{40}$)$_2$ (where t is 1 to 2) where each $R^{40}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{41}$ is independently a direct bond or a straight or branched alkylene or alkenylene chain; and each $R^{42}$ is alkyl, haloalkyl, cycloalkyl, cycloalkylalkyl, aryl, aralkyl, heterocyclyl, heterocyclylalkyl, heteroaryl or heteroarylalkyl.

"Aralkyl" refers to a radical of the formula —$R_b$-$R_c$ where $R_b$ is an alkylene chain as defined above and $R_c$ is one or more aryl radicals as defined above, for example, benzyl, diphenylmethyl and the like. The alkylene chain part of the aralkyl radical may be optionally substituted as described above for an alkylene chain. The aryl part of the aralkyl radical may be optionally substituted as described above for an aryl group.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted by one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocyclylalkyl, heteroaryl, heteroarylalkyl, —$R^{41}$—$OR^{40}$, —$R^{41}$—OC(O)—$R^{40}$, —$R^{41}$—N($R^{40}$)$_2$, —$R^{41}$—C(O)$R^{40}$, —$R^{41}$—C(O)O$R^{40}$, —$R^{41}$—C(O)N($R^{40}$)$_2$, —$R^{41}$—N($R^{40}$)C(O)O$R^{42}$, —$R^{41}$—N($R^{40}$)C(O)$R^{42}$, —$R^{41}$—N($R^{40}$)S(O)$_t$$R^{42}$ (where t is 1 to 2), —$R^{41}$—N=C(O$R^{40}$)$R^{40}$, —$R^{41}$—S(O)$_t$O$R^{42}$ (where t is 1 to 2), —$R^{41}$—S(O)$_p$$R^{42}$ (where p is 0 to 2), and —$R^{41}$—S(O)$_t$N($R^{40}$)$_2$ (where t is 1 to 2) where each $R^{40}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{41}$ is independently a direct bond or a straight or branched alkylene or alkenylene chain; and each $R^{42}$ is alkyl, haloalkyl, cycloalkyl, cycloalkylalkyl, aryl, aralkyl, heterocyclyl, heterocyclylalkyl, heteroaryl or heteroarylalkyl.

"Cycloalkylalkyl" refers to a radical of the formula —$R_bR_g$ where $R_b$ is an alkylene chain as defined above and $R_g$ is a cycloalkyl radical as defined above. The alkylene chain and the cycloalkyl radical may be optionally substituted as defined above.

"Fused" refers to any ring system described herein which is fused to an existing ring structure in the compounds of the invention. When the fused ring system is a heterocyclyl or a heteroaryl, any carbon in the existing ring structure which becomes part of the fused ring system may be replaced with a nitrogen.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Haloalkenyl" refers to an alkenyl radical, as defined above, that is substituted by one or more halo radicals, as defined above. The alkenyl part of the haloalkyl radical may be optionally substituted as defined above for an alkenyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{41}$—$OR^{40}$, —$R^{41}$—OC(O)—$R^{40}$, —$R^{41}$—$N(R^{40})_2$, —$R^{41}$—C(O)$R^{40}$, —$R^{41}$—C(O)$OR^{40}$, —$R^{41}$—C(O)$N(R^{40})_2$, —$R^{41}$—$N(R^{40})$C(O)$OR^{42}$, —$R^{41}$—$N(R^{40})$C(O)$R^{42}$, —$R^{41}$—$N(R^{40})$S(O)$_tR^{42}$ (where t is 1 to 2), —$R^{41}$—N=C($OR^{40}$) $R^{40}$, —$R^{41}$—S(O)$_tOR^{42}$ (where t is 1 to 2), —$R^{41}$—S(O)$_pR^{42}$ (where p is 0 to 2), and —$R^{41}$—S(O)$_tN(R^{40})_2$ (where t is 1 to 2) where each $R^{40}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{41}$ is independently a direct bond or a straight or branched alkylene or alkenylene chain; and each $R^{42}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heterocyclyl" refers to a heterocyclyl radical as defined above containing at least one nitrogen. An N-heterocyclyl radical may be optionally substituted as described above for heterocyclyl radicals.

"Heterocyclylalkyl" refers to a radical of the formula —$R_bR_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. The alkylene chain of the heterocyclylalkyl radical may be optionally substituted as defined above for an alkylene chain. The heterocyclyl part of the heterocyclylalkyl radical may be optionally substituted as defined above for a heterocyclyl group.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-c]pyrimidin-4-onyl, triazolyl, tetrazolyl, triazinyl, and thiophenyl (i.e. thienyl). Unless stated otherwise specifically in the specification, a heteroaryl group may be optionally substituted by one or more substituents selected from the group consisting of alkyl, alkenyl, halo, haloalkyl, haloalkenyl, cyano, oxo, thioxo, nitro, thioxo, aryl, aralkyl, cycloalkyl, cycloalkylalkyl, heterocyclyl, heterocyclylalkyl, heteroaryl, heteroarylalkyl, —$R^{41}$—$OR^{40}$, —$R^{41}$—OC(O)—$R^{40}$, —$R^{41}$—$N(R^{40})_2$, —$R^{41}$—C(O)$R^{40}$, —$R^{41}$—C(O)$OR^{40}$, —$R^{41}$—C(O)$N(R^{40})_2$, —$R^{41}$—$N(R^{40})$C(O)$OR^{42}$, —$R^{41}$—$N(R^{40})$C(O)$R^{42}$, —$R^{41}$—$N(R^{40})$S(O)$_tR^{42}$ (where t is 1 to 2), —$R^{41}$—N=C($OR^{40}$)$R^{40}$, —$R^{41}$—S(O)$_tOR^{42}$ (where t is 1 to 2), —$R^{41}$—S(O)$_pR^{42}$ (where p is 0 to 2), and —$R^{41}$—S(O)$_tN(R^{40})_2$ (where t is 1 to 2) where each $R^{40}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{41}$ is independently a direct bond or a straight or branched alkylene or alkenylene chain; and each $R^{42}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical may be optionally substituted as described above for heteroaryl radicals.

"Heteroarylalkyl" refers to a radical of the formula —$R_bR_i$, where $R_b$ is an alkylene chain as defined above and $R_i$ is a heteroaryl radical as defined above. The heteroaryl part of the heteroarylalkyl radical may be optionally substituted as defined above for a heteroaryl group. The alkylene chain part of the heteroarylalkyl radical may be optionally substituted as defined above for an alkylene chain.

"Hydroxyalkyl" refers to a radical of the formula —$R_b$OH where $R_b$ is an alkylene chain as defined above. The —OH group can be attached to any carbon in the alkylene chain. The alkylene chain part of the heteroarylalkyl radical may additionally be optionally substituted as defined above for an alkylene chain.

"Analgesia" refers to an absence of pain in response to a stimulus that would normally be painful.

"Allodynia" refers to a condition in which a normally innocuous sensation, such as pressure or light touch, is perceived as being extremely painful.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., "Pro-drugs as Novel Delivery Systems," A.C.S. Symposium Series, Vol. 14, and in Bioreversible Carriers in Drug Design, Ed. Edward B. Roche, American Pharmaceutical Association and Pergamon Press, 1987, both of which are incorporated in full by reference herein.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable compounds of the invention being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action on the sodium channels, or binding affinity to pharmacologically important site of action on the sodium channels. Certain isotopically-labelled compounds of the invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$C and $^{13}$N, can be useful in Positron Emission Topography (PET) studies for examining substrate receptor occupancy. Isotopically-labeled compounds of the invention can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reducation, hydrolysis, amidation, esterification, and the like of the administered compound, primarily due to enzymatic processes. Accordingly, the invention includes compounds produced by a process comprising contacting a compound of this invention with a mammal for a period of time sufficient to yield a metabolic product thereof. Such products are typically are identified by administering a radiolabelled compound of the invention in a detectable dose to an animal, such as rat, mouse, guinea pig, monkey, or to human, allowing sufficient time for metabolism to occur, and isolating its coversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g. cats, dogs, swine, cattle, sheep, goats, horses, rabbits), and non-domestic animals such as wildelife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. When a functional group is described as "optionally substituted," and in turn, substitutents on the functional group are also "optionally substituted" and so on, for the purposes of this invention, such iterations are limited to five.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a sodium channel-mediated disease or condition in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(a) preventing the disease or condition from occurring in a mammal, in particular, when such mammal is predisposed to the condition but has not yet been diagnosed as having it;

(b) inhibiting the disease or condition, i.e., arresting its development;

(c) relieving the disease or condition, i.e., causing regression of the disease or condition; or (d) relieving the symptoms resulting from the disease or condition, i.e., relieving pain without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

Also within the scope of the invention are intermediate compounds of the invention and all polymorphs of the aforementioned species and crystal habits thereof.

The chemical naming protocol and structure diagrams used herein are a modified form of the I.U.P.A.C. nomenclature system, using the ACD/Name Version 9.07 software program, wherein the compounds of the invention are named herein as derivatives of a central core structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

Thus, for example, a compound of formula (I), as set forth above in the Summary of the Invention, wherein n is 1, J is —CH$_2$—, K is —O—, R$^2$ is hydrogen and R$^1$ is (2R)-tetrahydrofuran-2-ylmethyl; i.e., a compound of the following formula:

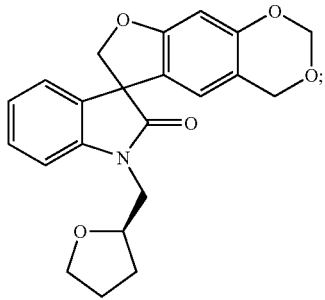

is named herein as 1'-[(2R)-tetrahydrofuran-2-ylmethyl]-4H-spiro[furo[3,2-g][1,3]benzodioxine-6,3'-indol]-2'(1'H)-one.

Embodiments Of The Invention

One embodiment of the invention is a compound of formula (I), as set forth above in the Summary of the Invention.

Of this embodiment, one embodiment is a compound of formula (I) wherein J is —O— and K is —CH$_2$—.

Of this embodiment, one embodiment is a compound of formula (I) selected from:

1'-methyl-2'-oxo-N-pentyl-1',2,2',3-tetrahydrospiro[furo[2,3-g][1,4]benzodioxine-8,3'-indole]-4'-carboxamide;
1'-(diphenylmethyl)-4',6'-dimethoxy-2,3-dihydrospiro[furo[2,3-g][1,4]benzodioxine-8,3'-indol]-2'(1'H)-one;
(8R)-1'-[(2R)-1,4-dioxan-2-ylmethyl]-2,3-dihydrospiro[furo[2,3-g][1,4]benzodioxine-8,3'-indol]-2'(1'H)-one;
1'-[(6-methylpyridin-2-yl)methyl]-2,3-dihydrospiro[furo[2,3-g][1,4]benzodioxine-8,3'-indol]-2'(1'H)-one;
1'-(pyridin-3-ylmethyl)-2,3-dihydrospiro[furo[2,3-g][1,4]benzodioxine-8,3'-indol]-2'(1'H)-one;
(R)-3,7-dihydro-2H-spiro[benzofuro[5,6-b][1,4]dioxine-8,3'-indolin]-2'-one;
(S)-2,3-dihydrospiro[furo[2,3-g][1,4]benzodioxine-8,3'-indol]-2'(1'H)-one;
(8S)-1'-{[3-(trifluoromethyl)pyridin-2-yl]methyl}-2,3-dihydrospiro[furo[2,3-g][1,4]benzodioxine-8,3'-indol]-2'(1'H)-one;
(8S)-1'-[(5-hydroxypyridin-2-yl)methyl]-2,3-dihydrospiro[furo[2,3-g][1,4]benzodioxine-8,3'-indol]-2'(1'H)-one;
1'-[(5-bromopyridin-2-yl)methyl]-2,3-dihydrospiro[furo[2,3-g][1,4]benzodioxine-8,3'-indol]-2'(1'H)-one;
1'-(diphenylmethyl)-2,3-dihydrospiro[furo[2,3-g][1,4]benzodioxine-8,3'-indol]-2'(1'H)-one;
6'-isopentyl-3,7-dihydro-2H-spiro[benzofuro[5,6-b][1,4]dioxine-8,8'-thiazolo[5,4-e]indol]-7'(6'H)-one;
6-((5-(trifluoromethyl)furan-2-yl)methyl)-2,3,3',7'-tetrahydro-2'H-spiro[[1,4]dioxino[2,3-f]indole-8,8'-benzofuro[5,6-b][1,4]dioxin]-7(6H)-one;
2,3-dihydrospiro[furo[2,3-g][1,4]benzodioxine-8,3'-indol]-2'(1'H)-one;
1'-(3-methylbutyl)-2,3-dihydrospiro[furo[2,3-g][1,4]benzodioxine-8,3'-indol]-2'(1'H)-one;
1'-(tetrahydro-2H-pyran-4-ylmethyl)-2,3-dihydrospiro[furo[2,3-g][1,4]benzodioxine-8,3'-indol]-2'(1'H)-one;
1'-(tetrahydro-2H-pyran-2-ylmethyl)-2,3-dihydrospiro[furo[2,3-g][1,4]benzodioxine-8,3'-indol]-2'(1'H)-one;
1'-[(5-chloro-1-methyl-1H-imidazol-2-yl)methyl]-2,3-dihydrospiro[furo[2,3-g][1,4]benzodioxine-8,3'-indol]-2'(1'H)-one;
1'-[(5-chloro-1-methyl-1H-imidazol-2-yl)methyl]-2,3-dihydrospiro[furo[2,3-g][1,4]benzodioxine-8,3'-indol]-2'(1'H)-one hydrochloride;
1'-(pyridin-2-ylmethyl)-2,3-dihydrospiro[furo[2,3-g][1,4]benzodioxine-8,3'-indol]-2'(1'H)-one;
1'-(pyridin-2-ylmethyl)-2,3-dihydrospiro[furo[2,3-g][1,4]benzodioxine-8,3'-indol]-2'(1'H)-one hydrochloride;
1'-[(2S)-tetrahydrofuran-2-ylmethyl]-2,3-dihydrospiro[furo[2,3-g][1,4]benzodioxine-8,3'-indol]-2'(1'H)-one;
1'-[(2R)-tetrahydrofuran-2-ylmethyl]-2,3-dihydrospiro[furo[2,3-g][1,4]benzodioxine-8,3'-indol]-2'(1'H)-one;
1'-(1,4-dioxan-2-ylmethyl)-2,3-dihydrospiro[furo[2,3-g][1,4]benzodioxine-8,3'-indol]-2'(1'H)-one;
1'-(3,4-dimethoxybenzyl)-2,3-dihydrospiro[furo[2,3-g][1,4]benzodioxine-8,3'-indol]-2'(1'H)-one;
1'-(3,5-dimethoxybenzyl)-2,3-dihydrospiro[furo[2,3-g][1,4]benzodioxine-8,3'-indol]-2'(1'H)-one;
1'-(2,3-dihydro-1,4-benzodioxin-6-ylmethyl)-2,3-dihydrospiro[furo[2,3-g][1,4]benzodioxine-8,3'-indol]-2'(1'H)-one;
(R)-1'-{[5-(trifluoromethyl)furan-2-yl]methyl}-2,3-dihydrospiro[furo[2,3-g][1,4]benzodioxine-8,3'-indol]-2'(1'H)-one;
(S)-1'-{[5-(trifluoromethyl)furan-2-yl]methyl}-2,3-dihydrospiro[furo[2,3-g][1,4]benzodioxine-8,3'-indol]-2'(1'H)-one;
(S)-1-(pyridin-2-ylmethyl)-2,3-dihydrospiro[furo[2,3-g][1,4]benzodioxine-8,3'-indol]-2'(1'H)-one;
1'-[3-(trifluoromethyl)benzyl]-2,3-dihydrospiro[furo[2,3-g][1,4]benzodioxine-8,3'-indol]-2'(1'H)-one;
methyl 5-[(2'-oxo-2,3-dihydrospiro[furo[2,3-g][1,4]benzodioxine-8,3'-indol]-1'(2'H)-yl)methyl]furan-2-carboxylate;
1'-pentyl-2,3-dihydrospiro[furo[2,3-g][1,4]benzodioxine-8,3'-indol]-2'(1'H)-one;
(8R)-1'-[(2S)-1,4-dioxan-2-ylmethyl]-2,3-dihydrospiro[furo[2,3-g][1,4]benzodioxine-8,3'-indol]-2'(1'H)-one;
(8S)-1'-[(2S)-1,4-dioxan-2-ylmethyl]-2,3-dihydrospiro[furo[2,3-g][1,4]benzodioxine-8,3'-indol]-2'(1'H)-one;
(8S)-1'-[(2R)-1,4-dioxan-2-ylmethyl]-2,3-dihydrospiro[furo[2,3-g][1,4]benzodioxine-8,3'-indol]-2'(1'H)-one;
1'-[2-(2-methoxyethoxy)ethyl]-2,3-dihydrospiro[furo[2,3-g][1,4]benzodioxine-8,3'-indol]-2'(1'H)-one;
5-[(2'-oxo-2,3-dihydrospiro[furo[2,3-g][1,4]benzodioxine-8,3'-indol]-1'(2'H)-yl)methyl]furan-2-carboxylic acid;

N,N-dimethyl-5-[(2'-oxo-2,3-dihydrospiro[furo[2,3-g][1,4]benzodioxine-8,3'-indol]-1'(2'H)-yl)methyl]furan-2-carboxamide;
(8S)-1'-{[3-(trifluoromethyl)pyridin-2-yl]methyl}-2,3-dihydrospiro[furo[2,3-g][1,4]benzodioxine-8,3'-indol]-2'(1'H)-one;
(8S)-1'-[(5-hydroxypyridin-2-yl)methyl]-2,3-dihydrospiro[furo[2,3-g][1,4]benzodioxine-8,3'-indol]-2'(1'H)-one;
1'-(diphenylmethyl)-7'-fluoro-2,3-dihydrospiro[furo[2,3-g][1,4]benzodioxine-8,3'-indol]-2'(1'H)-one;
4'-bromo-1'-(diphenylmethyl)-2,3-dihydrospiro[furo[2,3-g][1,4]benzodioxine-8,3'-indol]-2'(1'H)-one;
4'-bromo-1'-methyl-2,3-dihydrospiro[furo[2,3-g][1,4]benzodioxine-8,3'-indol]-2'(1'H)-one;
1'-(diphenylmethyl)-4'-fluoro-2,3-dihydrospiro[furo[2,3-g][1,4]benzodioxine-8,3'-indol]-2'(1'H)-one;
1'-(4-fluorophenyl)-2,3-dihydrospiro[furo[2,3-g][1,4]benzodioxine-8,3'-indol]-2'(1'H)-one;
1'-(diphenylmethyl)-4'-quinolin-3-yl-2,3-dihydrospiro[furo[2,3-g][1,4]benzodioxine-8,3'-indol]-2'(1'H)-one;
1'-(diphenylmethyl)-4'-(4-phenoxyphenyl)-2,3-dihydrospiro[furo[2,3-g][1,4]benzodioxine-8,3'-indol]-2'(1'H)-one;
5'-bromo-1'-(pyridin-2-ylmethyl)-2,3-dihydrospiro[furo[2,3-g][1,4]benzodioxine-8,3'-indol]-2'(1'H)-one;
2'-oxo-1'-(pyridin-2-ylmethyl)-1',2,2',3-tetrahydrospiro[furo[2,3-g][1,4]benzodioxine-8,3'-indole]-5'-carbonitrile;
5'-bromo-1'-(diphenylmethyl)-2,3-dihydrospiro[furo[2,3-g][1,4]benzodioxine-8,3'-indol]-2'(1'H)-one;
1'-(diphenylmethyl)-5'-methyl-2,3-dihydrospiro[furo[2,3-g][1,4]benzodioxine-8,3'-indol]-2'(1'H)-one;
phenyl 1'-methyl-2'-oxo-1',2,2',3-tetrahydrospiro[furo[2,3-g][1,4]benzodioxine-8,3'-indole]-4'-carboxylate;
4',5'-dimethoxy-1'-{[5-(trifluoromethyl)furan-2-yl]methyl}-2,3-dihydrospiro[furo[2,3-g][1,4]benzodioxine-8,3'-indol]-2'(1'H)-one;
4',7'-dimethoxy-1'-[2-(2-methoxyethoxy)ethyl]-2,3-dihydrospiro[furo[2,3-g][1,4]benzodioxine-8,3'-indol]-2'(1'H)-one;
6-[2-(2-methoxyethoxy)ethyl]-2,2',3,3'-tetrahydrospiro[1,4-dioxino[2,3-f]indole-8,8'-furo[2,3-g][1,4]benzodioxin]-7(6H)-one
6'-(4-methoxybenzyl)-2,3-dihydrospiro[furo[2,3-g][1,4]benzodioxine-8,8'-[1,3]thiazolo[5,4-e]indol]-7'(6'H)-one;
7'-fluoro-2,3-dihydrospiro[furo[2,3-g][1,4]benzodioxine-8,3'-indol]-2'(1'H)-one;
4'-bromo-2,3-dihydrospiro[furo[2,3-g][1,4]benzodioxine-8,3'-indol]-2'(1'H)-one;
4'-fluoro-2,3-dihydrospiro[furo[2,3-g][1,4]benzodioxine-8,3'-indol]-2'(1'H)-one;
4'-quinolin-3-yl-2,3-dihydrospiro[furo[2,3-g][1,4]benzodioxine-8,3'-indol]-2'(1'H)-one;
4'-(4-phenoxyphenyl)-2,3-dihydrospiro[furo[2,3-g][1,4]benzodioxine-8,3'-indol]-2'(1'H)-one;
5'-methyl-2,3-dihydrospiro[furo[2,3-g][1,4]benzodioxine-8,3'-indol]-2'(1'H)-one;
2,3-dihydrospiro[furo[2,3-g][1,4]benzodioxine-8,8'-[1,3]thiazolo[5,4-e]indol]-7'(6'H)-one;
4',6'-dimethoxy-2,3-dihydrospiro[furo[2,3-g][1,4]benzodioxine-8,3'-indol]-2'(1'H)-one;
3'-[2-(fluoromethyl)benzyl]-2,3-dihydrospiro[furo[2,3-g][1,4]benzodioxine-8,1'-inden]-2'(3'H)-one;
3-[(2'-oxo-2,3-dihydrospiro[furo[2,3-g][1,4]benzodioxine-8,3'-indol]-1'(2'H)-yl)methyl]benzonitrile;
1'-(4-fluoro-3-methoxybenzyl)-2,3-dihydrospiro[furo[2,3-g][1,4]benzodioxine-8,3'-indol]-2'(1'H)-one;
4-[(2'-oxo-2,3-dihydrospiro[furo[2,3-g][1,4]benzodioxine-8,3'-indol]-1'(2'H)-yl)methyl]benzonitrile;
1'-(4-isoxazol-5-ylbenzyl)-2,3-dihydrospiro[furo[2,3-g][1,4]benzodioxine-8,3'-indol]-2'(1'H)-one;
1'-{[6-(trifluoromethyl)pyridin-3-yl]methyl}-2,3-dihydrospiro[furo[2,3-g][1,4]benzodioxine-8,3'-indol]-2'(1'H)-one;
1'-[(5-fluoropyridin-2-yl)methyl]-2,3-dihydrospiro[furo[2,3-g][1,4]benzodioxine-8,3'-indol]-2'(1'H)-one;
1'-[(3-fluoropyridin-2-yl)methyl]-2,3-dihydrospiro[furo[2,3-g][1,4]benzodioxine-8,3'-indol]-2'(1'H)-one;
1'-(pyridin-2-ylmethyl)-4'-quinolin-3-yl-2,3-dihydrospiro[furo[2,3-g][1,4]benzodioxine-8,3'-indol]-2'(1'H)-one;
4'-(4-phenoxyphenyl)-1'-(pyridin-2-ylmethyl)-2,3-dihydrospiro[furo[2,3-g][1,4]benzodioxine-8,3'-indol]-2'(1'H)-one;
1'-[(3,5-difluoropyridin-2-yl)methyl]-2,3-dihydrospiro[furo[2,3-g][1,4]benzodioxine-8,3'-indol]-2'(1'H)-one;
3-{[(8S)-2'-oxo-2,3-dihydrospiro[furo[2,3-g][1,4]benzodioxine-8,3'-indol]-1'(2'H)-yl]methyl}benzonitrile;
(8S)-1'-[(5-fluoropyridin-2-yl)methyl]-2,3-dihydrospiro[furo[2,3-g][1,4]benzodioxine-8,3'-indol]-2'(1'H)-one;
(8S)-1'-[(3-fluoropyridin-2-yl)methyl]-2,3-dihydrospiro[furo[2,3-g][1,4]benzodioxine-8,3'-indol]-2'(1'H)-one;
(S)-1-(2-oxobutyl)-3,7-dihydro-2H-spiro[benzofuro[5,6-b][1,4]dioxine-8,3'-indolin]-2'-one;
1'-[(4-fluoropyridin-2-yl)methyl]-2,3-dihydrospiro[furo[2,3-g][1,4]benzodioxine-8,3'-indol]-2'(1'H)-one;
1'-[(3-chloropyridin-2-yl)methyl]-2,3-dihydrospiro[furo[2,3-g][1,4]benzodioxine-8,3'-indol]-2'(1'H)-one;
1'-[2-(trifluoromethyl)benzyl]-2,3-dihydrospiro[furo[2,3-g][1,4]benzodioxine-8,3'-indol]-2'(1'H)-one;
(8R)-1'-[2-(trifluoromethyl)benzyl]-2,3-dihydrospiro[furo[2,3-g][1,4]benzodioxine-8,3'-indol]-2'(1'H)-one;
5'-methyl-1'-{[3-(trifluoromethyl)pyridin-2-yl]methyl}-2,3-dihydrospiro[furo[2,3-g][1,4]benzodioxine-8,3'-indol]-2'(1'H)-one;
(8S)-1'-[2-(trifluoromethyl)benzyl]-2,3-dihydrospiro[furo[2,3-g][1,4]benzodioxine-8,3'-indol]-2'(1'H)-one;
4'-bromo-1'-(pyridin-2-ylmethyl)-2,3-dihydrospiro[furo[2,3-g][1,4]benzodioxine-8,3'-indol]-2'(1'H)-one;
1'-(2,1,3-benzothiadiazol-5-ylmethyl)-2,3-dihydrospiro[furo[2,3-g][1,4]benzodioxine-8,3'-indol]-2'(1'H)-one;
1'-(1,3-benzothiazol-2-ylmethyl)-2,3-dihydrospiro[furo[2,3-g][1,4]-benzodioxine-8,3'-indol]-2'(1'H)-one;
1'-[(1-methyl-1H-benzimidazol-2-yl)methyl]-2,3-dihydrospiro[furo[2,3-g][1,4]-benzodioxine-8,3'-indol]-2'(1'H)-one;
1'-{[2-(1-methylethyl)-1,3-thiazol-4-yl]methyl}-2,3-dihydrospiro[furo[2,3-g][1,4]benzodioxine-8,3'-indol]-2'(1'H)-one;
1'-(2,1,3-benzoxadiazol-5-ylmethyl)-2,3-dihydrospiro[furo[2,3-g][1,4]benzodioxine-8,3'-indol]-2'(1'H)-one;
tert-butyl 4-[(2'-oxo-2,3-dihydrospiro[furo[2,3-g][1,4]benzodioxine-8,3'-indol]-1'(2'H)-yl) methyl]piperidine-1-carboxylate;
1'-(2,1,3-benzoxadiazol-5-ylmethyl)-2,3-dihydrospiro[furo[2,3-g][1,4]benzodioxine-8,3'-indol]-2'(1'H)-one;
1'-{[6-(trifluoromethyl)pyridin-2-yl]methyl}-2,3-dihydrospiro[furo[2,3-g][1,4]benzodioxine-8,3'-indol]-2'(1'H)-one;
1'-{[2-(trifluoromethyl)pyridin-3-yl]methyl}-2,3-dihydrospiro[furo[2,3-g][1,4]benzodioxine-8,3'-indol]-2'(1'H)-one;
1'-{[3-(trifluoromethyl)pyrazin-2-yl]methyl}-2,3-dihydrospiro[furo[2,3-g][1,4]benzodioxine-8,3'-indol]-2'(1'H)-one;

1'-{[4-(trifluoromethyl)pyridin-3-yl]methyl}-2,3-dihydrospiro[furo[2,3-g][1,4]benzodioxine-8,3'-indol]-2'(1'H)-one;
1'-[(6-chloropyridin-2-yl)methyl]-2,3-dihydrospiro[furo[2,3-g][1,4]benzodioxine-8,3'-indol]-2'(1'H)-one;
1'-[(2-methoxypyrimidin-5-yl)methyl]-2,3-dihydrospiro[furo[2,3-g][1,4]benzodioxine-8,3'-indol]-2'(1'H)-one;
1'-[(6-methoxypyridin-3-yl)methyl]-2,3-dihydrospiro[furo[2,3-g][1,4]benzodioxine-8,3'-indol]-2'(1'H)-one;
(8S)-1'-(pyrazin-2-ylmethyl)-2,3-dihydrospiro[furo[2,3-g][1,4]benzodioxine-8,3'-indol]-2'(1'H)-one;
(8S)-1'-[(2-methoxypyrimidin-5-yl)methyl]-2,3-dihydrospiro[furo[2,3-g][1,4]benzodioxine-8,3'-indol]-2'(1'H)-one;
(8S)-1-(pyrimidin-2-ylmethyl)-2,3-dihydrospiro[furo[2,3-g][1,4]benzodioxine-8,3'-indol]-2'(1'H)-one;
4'-fluoro-1'-{[3-(trifluoromethyl)pyridin-2-yl]methyl}-2,3-dihydrospiro[furo[2,3-g][1,4]benzodioxine-8,3'-indol]-2'(1'H)-one;
1'-[(2,2-difluorocyclopropyl)methyl]-2,3-dihydrospiro[furo[2,3-g][1,4]benzodioxine-8,3'-indol]-2'(1'H)-one;
1'-methyl-2,3-dihydrospiro[furo[2,3-g][1,4]benzodioxine-8,3'-indol]-2'(1'H)-one;
1'-{[4-(trifluoromethyl)-1,3-thiazol-2-yl]methyl}-2,3-dihydrospiro[furo[2,3-g][1,4]benzodioxine-8,3'-indol]-2'(1'H)-one;
(2'-oxo-2,3-dihydrospiro[furo[2,3-g][1,4]benzodioxine-8,3'-indol]-1'(2'H)-yl)acetonitrile;
ethyl 2-[(2'-oxo-2,3-dihydrospiro[furo[2,3-g][1,4]benzodioxine-8,3'-indol]-1'(2'H)-yl)methyl]pyridine-3-carboxylate;
1'-(pyrimidin-2-ylmethyl)-2,3-dihydrospiro[furo[2,3-g][1,4]benzodioxine-8,3'-indol]-2'(1'H)-one;
1'-[(4,6-dimethoxypyrimidin-2-yl)methyl]-2,3-dihydrospiro[furo[2,3-g][1,4]benzodioxine-8,3'-indol]-2'(1'H)-one;
(S)-1'-pentyl-2,3-dihydrospiro[furo[2,3-g][1,4]benzodioxine-8,3'-indol]-2'(1'H)-one;
(R)-1'-pentyl-2,3-dihydrospiro[furo[2,3-g][1,4]benzodioxine-8,3'-indol]-2'(1'H)-one;
1'-hexyl-2,3-dihydrospiro[furo[2,3-g][1,4]benzodioxine-8,3'-indol]-2'(1'H)-one;
1'-(2-cyclopropylethyl)-2,3-dihydrospiro[furo[2,3-g][1,3]benzodioxine-8,3'-indol]-2'(1'H)-one;
1'-(2-ethoxyethyl)-2,3-dihydrospiro[furo[2,3-g][1,3]benzodioxine-8,3'-indol]-2'(1'H)-one;
1'-(4-methoxybutyl)-2,3-dihydrospiro[furo[2,3-g][1,3]benzodioxine-8,3'-indol]-2'(1'H)-one;
1'-(3-methoxypropyl)-2,3-dihydrospiro[furo[2,3-g][1,3]benzodioxine-8,3'-indol]-2'(1'H)-one;
1'-(3-nitrobenzyl)-2,3-dihydrospiro[furo[2,3-g][1,3]benzodioxine-8,3'-indol]-2'(1'H)-one;
1'-(1,3-thiazol-5-ylmethyl)-2,3-dihydrospiro[furo[2,3-g][1,3]benzodioxine-8,3'-indol]-2'(1'H)-one;
1'-{[5-(trifluoromethyl)pyridin-2-yl]methyl}-2,3-dihydrospiro[furo[2,3-g][1,3]benzodioxine-8,3'-indol]-2'(1'H)-one;
1'-{[3-(trifluoromethyl)pyridin-2-yl]methyl}-2,3-dihydrospiro[furo[2,3-g][1,3]benzodioxine-8,3'-indol]-2'(1'H)-one;
1'-[(3-pyridin-3-ylisoxazol-5-yl)methyl]-2,3-dihydrospiro[furo[2,3-g][1,3]benzodioxine-8,3'-indol]-2'(1'H)-one;
(8R)-1-{[3-(trifluoromethyl)pyridin-2-yl]methyl}-2,3-dihydrospiro[furo[2,3-g][1,3]benzodioxine-8,3'-indol]-2'(1'H)-one;
N,N-dimethyl-3-[(2'-oxo-2,3-dihydrospiro[furo[2,3-g][1,4]benzodioxine-8,3'-indol]-1'-(2'H)-yl)methyl]benzenesulfonamide;
1'-[3-(morpholin-4-ylsulfonyl)benzyl]-2,3-dihydrospiro[furo[2,3-g][1,4]benzodioxine-8,3'-indol]-2'(1'H)-one;
1'-[(4-methyl-1,2,5-oxadiazol-3-yl)methyl]-2,3-dihydrospiro[furo[2,3-g][1,4]benzodioxine-8,3'-indol]-2'(1'H)-one;
1'-(2,3-difluorobenzyl)-2,3-dihydrospiro[furo[2,3-g][1,4]benzodioxine-8,3'-indol]-2'(1'H)-one;
1'-(3,5-difluorobenzyl)-2,3-dihydrospiro[furo[2,3-g][1,4]benzodioxine-8,3'-indol]-2'(1'H)-one;
1'-(4-fluorobenzyl)-2,3-dihydrospiro[furo[2,3-g][1,4]benzodioxine-8,3'-indol]-2'(1'H)-one;
1'-(2-chloro-4-fluorobenzyl)-2,3-dihydrospiro[furo[2,3-g][1,4]benzodioxine-8,3'-indol]-2'(1'H)-one;
1'-[(1-methyl-1H-benzotriazol-5-yl)methyl]-2,3-dihydrospiro[furo[2,3-g][1,4]benzodioxine-8,3'-indol]-2'(1'H)-one;
1'-[(3-trifluoromethoxy)benzyl]-2,3-dihydrospiro[furo[2,3-g][1,4]benzodioxine-8,3'-indol]-2'(1'H)-one;
1'-[(2-fluoro-6-trifluoromethyl)benzyl]-2,3-dihydrospiro[furo[2,3-g][1,4]benzodioxine-8,3'-indol]-2'(1'H)-one;
1'-[(2-fluoro-5-trifluoromethyl)benzyl]-2,3-dihydrospiro[furo[2,3-g][1,4]benzodioxine-8,3'-indol]-2'(1'H)-one;
1'-[(2-trifluoromethoxy)benzyl]-2,3-dihydrospiro[furo[2,3-g][1,4]benzodioxine-8,3'-indol]-2'(1'H)-one;
1'-[2-(2,2,5-trimethyl-1,3-dioxan-2-yl)ethyl]-2,3-dihydrospiro[furo[2,3-g][1,4]benzodioxine-8,3'-indol]-2'(1'H)-one;
7'-fluoro-1'-(pyridin-2-ylmethyl)-3,7-dihydro-2H-spiro[benzofuro[5,6-b][1,4]dioxine-8,3'-indolin]-2'-one;
7'-fluoro-1'-'((3-(trifluoromethyl)pyridin-2-yl)methyl)-3,7-dihydro-2H-spiro[benzofuro[5,6-b][1,4]dioxine-8,3'-indolin]-2'-one;
3'-[2-(difluoromethyl)benzyl]-2,3-dihydrospiro[furo[2,3-g][1,4]benzodioxine-8,1'-inden]-2'(3'H)-one;
1'-[(5-fluoropyridin-3-yl)methyl]-2,3-dihydrospiro[furo[2,3-g][1,4]benzodioxine-8,3'-indol]-2'(1'H)-one;
(8S)-1'-[(5-fluoropyridin-3-yl)methyl]-2,3-dihydrospiro[furo[2,3-g][1,4]benzodioxine-8,3'-indol]-2'(1'H)-one;
1'-[4-(benzyloxy)benzyl]-2,3-dihydrospiro[furo[2,3-g][1,4]benzodioxine-8,3'-indol]-2'(1'H)-one;
(8S)-1'-[4-(benzyloxy)benzyl]-2,3-dihydrospiro[furo[2,3-g][1,4]benzodioxine-8,3'-indol]-2'(1'H)-one;
tert-butyl {5-[(2'-oxo-2,3-dihydrospiro[furo[2,3-g][1,4]benzodioxine-8,3'-indol]-1'(2'H)-yl)methyl]pyridin-2-yl}carbamate;
1'-[3-(benzyloxy)propyl]-2,3-dihydrospiro[furo[2,3-g][1,4]benzodioxine-8,3'-indol]-(2'H)-one;
ethyl (2'-oxo-2,3-dihydrospiro[furo[2,3-g][1,4]benzodioxine-8,3'-indol]-1'(2'H)-yl)acetate;
1'-{[(4S)-2,2-dimethyl-1,3-dioxolan-4-yl]methyl}-2,3-dihydrospiro[furo[2,3-g][1,4]-benzodioxine-8,3'-indol]-2'(1'H)-one;
4'-bromo-1'-pentyl-2,3-dihydrospiro[furo[2,3-g][1,4]benzodioxine-8,3'-indol]-2'(1'H)-one;
methyl 3-[(2'-oxo-2,3-dihydrospiro[furo[2,3-g][1,4]benzodioxine-8,3'-indol]-1'(2'H)-yl) methyl]benzoate;
1'-[(4-benzylmorpholin-2-yl)methyl]-2,3-dihydrospiro[furo[2,3-g][1,4]benzodioxine-8,3'-indol]-2'(1'H)-one;
(8S)-1'-{[(2S)-4-benzylmorpholin-2-yl]methyl}-2,3-dihydrospiro[furo[2,3-g][1,4]benzodioxine-8,3'-indol]-2'(1'H)-one;
ethyl 4-[(2'-oxo-2,3-dihydrospiro[furo[2,3-g][1,4]-benzodioxine-8,3'-indol]-1'(2'H)-yl)methyl]benzoate;
2-[3-(2'-oxo-2,3-dihydrospiro[furo[2,3-g][1,4]benzodioxine-8,3'-indol]-1'(2'H)-yl)propyl]-1H-isoindole-1,3(2H)-dione;

2-[3-(2'-oxo-2,3-dihydrospiro[furo[2,3-g][1,4]benzodioxine-8,3'-indol]-1'(2'H)-yl)propyl]-1H-isoindole-1,3(2H)-dione;

(8S)-1'-[2-(2-methoxyethoxy)ethyl]-2,3-dihydrospiro[furo[2,3-g][1,4]benzodioxine-8,3'-indol]-2'(1'H)-one;

6'-[2-(2-methoxyethoxy)ethyl]-2,3-dihydrospiro[furo[2,3-g][1,4]benzodioxine-8,8'-[1,3]thiazolo[5,4-e]indol]-7'(6'H)-one;

6'-(pyridin-2-ylmethyl)-2,3-dihydrospiro[furo[2,3-g][1,4]benzodioxine-8,8'-[1,3]thiazolo[5,4-e]indol]-7'(6'H)-one;

4',6'-dimethoxy-1'-[2-(2-methoxyethoxy)ethyl]-2,3-dihydrospiro[furo[2,3-g][1,4]benzodioxine-8,3'-indol]-2'(1'H)-one;

4',6'-dimethoxy-1'-(pyridin-2-ylmethyl)-2,3-dihydrospiro[furo[2,3-g][1,4]benzodioxine-8,3'-indol]-2'(1'H)-one;

(2'-oxo-2,3-dihydrospiro[furo[2,3-g][1,4]-benzodioxine-8,3'-indol]-1'(2'H)-yl)acetic acid;

1'-methyl-2'-oxo-1',2,2',3-tetrahydrospiro[furo[2,3-g][1,4]benzodioxine-8,3'-indole]-4'-carboxylic acid;

3'-[(3-bromopyridin-2-yl)methyl]-2,3-dihydrospiro[furo[2,3-g][1,4]benzodioxine-8,1'-inden]-2'(3'H)-one;

3'-{[3-(methylsulfonyl)pyridin-2-yl]methyl}-2,3-dihydrospiro[furo[2,3-g][1,4]benzodioxine-8,1'-inden]-2'(3'H)-one;

2-[(2'-oxo-2,2',3,3'-tetrahydrospiro[furo[2,3-g][1,4]benzodioxine-8,1'-inden]-3'-yl)methyl]pyridine-3-carbonitrile;

(8S)-1'-{[3-(difluoromethyl)pyridin-2-yl]methyl}-2,3-dihydrospiro[furo[2,3-g][1,4]benzodioxine-8,3'-indol]-2'(1'H)-one;

N'-hydroxy-3-[(2'-oxo-2,3-dihydrospiro[furo[2,3-g][1,4]benzodioxine-8,3'-indol]-1'(2'H)-yl)methyl]benzenecarboximidamide;

1'-[3-(5-methyl-1,2,4-oxadiazol-3-yl)benzyl]-2,3-dihydrospiro[furo[2,3-g][1,4]benzodioxine-8,3'-indol]-2'(1'H)-one;

1'-[4-(5-methyl-1,2,4-oxadiazol-3-yl)benzyl]-2,3-dihydrospiro[furo[2,3-g][1,4]-benzodioxine-8,3'-indol]-2'(1'H)-one;

3-[(2'-oxo-2,3-dihydrospiro[furo[2,3-g][1,4]benzodioxine-8,3'-indol]-1'(2'H)-yl)methyl]benzoic acid;

4-[(2'-oxo-2,3-dihydrospiro[furo[2,3-g][1,4]benzodioxine-8,3'-indol]-1'(2'H)-yl)methyl]benzoic acid;

N'-hydroxy-2-(2'-oxo-2,3-dihydrospiro[furo[2,3-g][1,4]benzodioxine-8,3'-indol]-1'(2'H)-yl)ethanimidamide;

1'-{[5-(trifluoromethyl)-1,2,4-oxadiazol-3-yl]methyl}-2,3-dihydrospiro[furo[2,3-g][1,4]benzodioxine-8,3'-indol]-2'(1'H)-one;

2-(2'-oxo-2,3-dihydrospiro[furo[2,3-g][1,4]benzodioxine-8,3'-indol]-1'(2'H)-yl)acetohydrazide;

1'-{[5-(trifluoromethyl)-1,3,4-oxadiazol-2-yl]methyl}-2,3-dihydrospiro[furo[2,3-g][1,4]benzodioxine-8,3'-indol]-2'(1'H)-one;

1'-(3-aminobenzyl)-2,3-dihydrospiro[furo[2,3-g][1,4]benzodioxine-8,3'-indol]-2'(1'H)-one;

N-{3-[(2'-oxo-2,3-dihydrospiro[furo[2,3-g][1,4]benzodioxine-8,3'-indol]-1'(2'H)-yl)methyl]phenyl}methanesulfonamide;

1'-[(1-oxydopyridin-2-yl)methyl]-2,3-dihydrospiro[furo[2,3-g][1,4]benzodioxine-8,3'-indol]-2'(1'H)-one;

2-[(2'-oxo-2,3-dihydrospiro[furo[2,3-g][1,4]benzodioxine-8,3'-indol]1'-(2'H)-yl)methyl]pyridine-3-carboxylic acid;

1'-[(3-aminopyridin-2-yl)methyl]-2,3-dihydrospiro[furo[2,3-g][1,4]benzodioxine-8,3'-indol]-2'(1'H)-one hydrobromide;

N-{2-[(2'-oxo-2,3-dihydrospiro[furo[2,3-g][1,4]-benzodioxine-8,3'-indol]-1'(2'H)-yl)methyl]pyridine-3-yl}methanesulfonamide;

1'-(piperidin-4-ylmethyl)-2,3-dihydrospiro[furo[2,3-g][1,4]benzodioxine-8,3'-indol]-2'(1'H)-one hydrochloride;

1'-{[1-(1-methylethyl)piperidin-4-yl]methyl}-2,3-dihydrospiro[furo[2,3-g][1,4]benzodioxine-8,3'-indol]-2'(1'H)-one hydrochloride;

1'-[(1-methylpiperidin-4-yl)methyl]-2,3-dihydrospiro[furo[2,3-g][1,4]benzodioxine-8,3'-indol]-2'(1'H)-one hydrochloride;

1'-(morpholin-2-ylmethyl)-2,3-dihydrospiro[furo[2,3-g][1,4]benzodioxine-8,3'-indol]-2'(1'H)-one;

1'-{[4-(1-methylethyl)morpholin-2-yl]methyl}-2,3-dihydrospiro[furo[2,3-g][1,4]benzodioxine-8,3'-indol]-2'(1'H)-one;

1'-[(4-methylmorpholin-2-yl)methyl]-2,3-dihydrospiro[furo[2,3-g][1,4]benzodioxine-8,3'-indol]-2'(1'H)-one;

(8S)-1-[(2S)-morpholin-2-ylmethyl]-2,3-dihydrospiro[furo[2,3-g][1,4]-benzodioxine-8,3'-indol]-2'(1'H)-one;

(8S)-1'-{[(2S)-4-methylmorpholin-2-yl]methyl}-2,3-dihydrospiro[furo[2,3-g][1,4]benzodioxine-8,3'-indol]-2'(1'H)-one;

1'-{[5-(difluoromethyl)furan-2-yl]methyl}-2,3-dihydrospiro[furo[2,3-g][1,4]benzodioxine-8,3'-indol]-2'(1'H)-one;

4-[(2'-oxo-2,3-dihydrospiro[furo[2,3-g][1,4]benzodioxine-8,3'-indol]-1'(2'H)-yl)methyl]benzamide;

3-[(2'-oxo-2,3-dihydrospiro[furo[2,3-g][1,4]benzodioxine-8,3'-indol]-1'(2'H)-yl)methyl]benzamide;

N,N-dimethyl-3-[(2'-oxo-2,3-dihydrospiro[furo[2,3-g][1,4]benzodioxine-8,3'-indol]-1'(2'H)-yl)methyl]benzamide;

N-methyl-2-[(2'-oxo-2,3-dihydrospiro[furo[2,3-g][1,4]benzodioxine-8,3'-indol]-1'(2'H)-yl)methyl]pyridine-3-carboxamide;

N-(2-aminoethyl)-2-[(2'-oxo-2,3-dihydrospiro[furo[2,3-g][1,4]benzodioxine-8,3'-indol]-1'(2'H)-yl)methyl]pyridine-3-carboxamide dihydrochloride;

N-(2-fluorophenyl)-4-[(2'-oxo-2,3-dihydrospiro[furo[2,3-g][1,4]benzodioxine-8,3'-indol]-1'(2'H)-yl)methyl]benzamide;

N-(2-fluorophenyl)-2-(2'-oxo-2,3-dihydrospiro[furo[2,3-g][1,4]benzodioxine-8,3'-indol]-1'(2'H)-yl)acetamide;

1'-methyl-4'-(2-oxo-2H-chromen-7-yl)-2,3-dihydrospiro[furo[2,3-g][1,4]benzodioxine-8,3'-indol]-2'(1'H)-one;

1'-methyl-4'-(2-oxopyrrolidin-1-yl)-2,3-dihydrospiro[furo[2,3-g][1,4]benzodioxine-8,3'-indol]-2'(1'H)-one;

1'-methyl-4'-morpholin-4-yl-2,3-dihydrospiro[furo[2,3-g][1,4]benzodioxine-8,3'-indol]-2'(1'H)-one;

1'-methyl-4'-(2-oxopyridin-1(2H)-yl)-2,3-dihydrospiro[furo[2,3-g][1,4]benzodioxine-8,3'-indol]-2'(1'H)-one;

4'-amino-1'-methyl-2,3-dihydrospiro[furo[2,3-g][1,4]benzodioxine-8,3'-indol]-2'(1'H)-one;

N-(1'-methyl-2'-oxo-1',2,2',3-tetrahydrospiro[furo[2,3-g][1,4]benzodioxine-8,3'-indol]-4'-yl)cyclobutanecarboxamide;

N-(1'-methyl-2-oxo-1',2,2',3-tetrahydrospiro[furo[2,3-g][1,4]benzodioxine-8,3'-indol]-4'-yl)-2-(trifluoromethyl)benzamide;

N-(1'-methyl-2'-oxo-1',2,2',3-tetrahydrospiro[furo[2,3-g][1,4]benzodioxine-8,3'-indol]-4'-yl)methanesulfonamide;

N-(1'-methyl-2-oxo-1',2,2',3-tetrahydrospiro[furo[2,3-g][1,4]benzodioxine-8,3'-indol]-4'-yl)cyclohexanecarboxamide;

N-(1'-methyl-2'-oxo-1',2,2',3-tetrahydrospiro[furo[2,3-g][1,4]benzodioxine-8,3'-indol]-4'-yl)cyclopentanecarboxamide;

N-(1'-methyl-2-oxo-1',2,2',3-tetrahydrospiro[furo[2,3-g][1,4]benzodioxine-8,3'-indol]-4'-yl)acetamide;

N-(t-methyl-2'-oxo-1',2,2',3-tetrahydrospiro[furo[2,3-g][1,4]benzodioxine-8,3'-indol]-4'-yl)cyclopropanecarboxamide;
N-(1'-methyl-2'-oxo-1',2,2',3-tetrahydrospiro[furo[2,3-g][1,4]benzodioxine-8,3'-indol]-4'-yl)benzamide;
2-methoxy-N-(1'-methyl-2'-oxo-1',2,2',3-tetrahydrospiro[furo[2,3-g][1,4]benzodioxine-8,3'-indol]-4'-yl)acetamide;
N-(1'-methyl-2'-oxo-1',2,2',3-tetrahydrospiro[furo[2,3-g][1,4]benzodioxine-8,3'-indol]-4'-yl)propanamide;
N-(1'-methyl-2'-oxo-1',2,2',3-tetrahydrospiro[furo[2,3-g][1,4]benzodioxine-8,3'-indol]-4'-yl)pentanamide;
2,2-dimethyl-N-(1'-methyl-2'-oxo-1',2,2',3-tetrahydrospiro[furo[2,3-g][1,4]-benzodioxine-8,3'-indol]-4'-yl)propanamide;
N-(1'-methyl-2'-oxo-1',2,2',3-tetrahydrospiro[furo[2,3-g][1,4]benzodioxine-8,3'-indol]-4'-yl)hexanamide;
N-(1'-methyl-2'-oxo-1',2,2',3-tetrahydrospiro[furo[2,3-g][1,4]benzodioxine-8,3'-indol]-4'-yl)heptanamide;
2-(2-methoxyethoxy)-N-(1'-methyl-2'-oxo-1',2,2',3-tetrahydrospiro[furo[2,3-g][1,4]benzodioxine-8,3'-indol]-4'-yl)acetamide;
1-hexyl-3-(1'-methyl-2'-oxo-1',2,2',3-tetrahydrospiro[furo[2,3-g][1,4]benzodioxine-8,3'-indol]-4'-yl)urea;
1-cyclopentyl-3-(1'-methyl-2'-oxo-1',2,2',3-tetrahydrospiro[furo[2,3-g][1,4]benzodioxine-8,3'-indol]-4'-yl)urea;
1-cyclohexyl-3-(1-methyl-2'-oxo-1',2,2',3-tetrahydrospiro[furo[2,3-g][1,4]benzodioxine-8,3'-indol]-4'-yl)urea;
N-cyclohexyl-1'-methyl-2'-oxo-1',2,2',3-tetrahydrospiro[furo[2,3-g][1,4]benzodioxine-8,3'-indole]-4'-carboxamide;
N-cyclopentyl-1'-methyl-2'-oxo-1',2,2',3-tetrahydrospiro[furo[2,3-g][1,4]benzodioxine-8,3'-indole]-4'-carboxamide;
N-cyclopropyl-1'-methyl-2'-oxo-1',2,2',3-tetrahydrospiro[furo[2,3-g][1,4]benzodioxine-8,3'-indole]-4'-carboxamide;
1'-methyl-4'-(pyrrolidin-1-ylcarbonyl)-2,3-dihydrospiro[furo[2,3-g][1,4]benzodioxine-8,3'-indol]-2'(1'H)-one;
N-(2-methoxyethyl)-1'-methyl-2'-oxo-1',2,2',3-tetrahydrospiro[furo[2,3-g][1,4]benzodioxine-8,3'-indole]-4'-carboxamide;
N-(4-fluorobenzyl)-1'-methyl-2'-oxo-1',2,2',3-tetrahydrospiro[furo[2,3-g][1,4]benzodioxine-8,3'-indole]-4'-carboxamide;
N-hexyl-1'-methyl-2'-oxo-1',2,2',3-tetrahydrospiro[furo[2,3-g][1,4]benzodioxine-8,3'-indole]-4'-carboxamide;
1'-methyl-2'-oxo-N-(pyridin-2-ylmethyl)-1',2,2',3-tetrahydrospiro[furo[2,3-g][1,4]benzodioxine-8,3'-indole]-4'-carboxamide;
N-(4-fluorophenyl)-1'-methyl-2'-oxo-1',2,2',3-tetrahydrospiro[furo[2,3-g][1,4]benzodioxine-8,3'-indole]-4'-carboxamide;
4'-amino-1'-pentyl-2,3-dihydrospiro[furo[2,3-g][1,4]benzodioxine-8,3'-indol]-2'(1'H)-one;
4'-(benzylamino)-1'-{[3-(trifluoromethyl)pyridin-2-yl]methyl}-2,3-dihydrospiro[furo[2,3-g][1,4]benzodioxine-8,3'-indol]-2'(1'H)-one;
4'-amino-1'-{[3-(trifluoromethyl)pyridin-2-yl]methyl}-2,3-dihydrospiro[furo[2,3-g][1,4]benzodioxine-8,3'-indol]-2'(1'H)-one;
4'-hydroxy-2,3-dihydrospiro[furo[2,3-g][1,4]benzodioxine-8,3'-indol]-2'(1'H)-one;
4'-hydroxy-1'-methyl-2,3-dihydrospiro[furo[2,3-g][1,4]benzodioxine-8,3'-indol]-2'(1'H)-one;
1'-methyl-4'-(pyridin-2-yloxy)-2,3-dihydrospiro[furo[2,3-g][1,4]benzodioxine-8,3'-indol]-2'(1'H)-one
4'-[2-(2-methoxyethoxy)ethoxy]-1'-methyl-2,3-dihydrospiro[furo[2,3-g][1,4]benzodioxine-8,3'-indol]-2'(1'H)-one;
1'-methyl-4'-{[3-(trifluoromethyl)pyridin-2-yl]oxy}-2,3-dihydrospiro[furo[2,3-g][1,4]benzodioxine-8,3'-indol]-2'(1'H)-one;
1'-methyl-4'-[4-(trifluoromethyl)phenoxy]-2,3-dihydrospiro[furo[2,3-g][1,4]benzodioxine-8,3'-indol]-2'(1'H)-one;
4'-(benzyloxy)-1'-methyl-2,3-dihydrospiro[furo[2,3-g][1,4]benzodioxine-8,3'-indol]-2'(1'H)-one;
1'-methyl-4'-{[3-(trifluoromethyl)pyridin-2-yl]methoxy}-2,3-dihydrospiro[furo[2,3-g][1,4]benzodioxine-8,3'-indol]-2'(1'H)-one;
4'-(6-(dimethylamino)pyridin-3-yl)-1'-(pyridin-2-ylmethyl)-3,7-dihydro-2H-spiro[benzofuro[5,6-b][1,4]dioxine-8,3'-indolin]-2'-one;
4'-(4-methoxyphenyl)-1'-(pyridin-2-ylmethyl)-3,7-dihydro-2H-spiro[benzofuro[5,6-b][1,4]dioxine-8,3'-indolin]-2'-one;
1'-methyl-4'-(1H-pyrazol-3-yl)-2,3-dihydrospiro[furo[2,3-g][1,4]benzodioxine-8,3'-indol]-2'(1'H)-one;
4'-furan-3-yl-1'-methyl-2,3-dihydrospiro[furo[2,3-g][1,4]benzodioxine-8,3'-indol]-2'(1'H)-one;
1'-methyl-4'-(1H-pyrazol-4-yl)-2,3-dihydrospiro[furo[2,3-g][1,4]benzodioxine-8,3'-indol]-2'(1'H)-one;
1'-methyl-4'-(1-methyl-1H-pyrazol-4-yl)-2,3-dihydrospiro[furo[2,3-g][1,4]benzodioxine-8,3'-indol]-2'(1'H)-one;
1'-methyl-2'-oxo-1',2,2',3-tetrahydrospiro[furo[2,3-g][1,4]benzodioxine-8,3'-indole]-4'-carbonitrile;
1'-methyl-2'-oxo-1',2,2',3-tetrahydrospiro[furo[2,3-g][1,4]benzodioxine-8,3'-indole]-4'-carboxamide;
1'-methyl-4'-(5-methyl-1,2,4-oxadiazol-3-yl)-2,3-dihydrospiro[furo[2,3-g][1,4]benzodioxine-8,3'-indol]-2'(1'H)-one;
4'-(3,5-dimethylisoxazol-4-yl)-1'-methyl-2,3-dihydrospiro[furo[2,3-g][1,4]benzodioxine-8,3'-indol]-2'(1'H)-one;
N,1'-dimethyl-2'-oxo-1,2,2',3-tetrahydrospiro[furo[2,3-g][1,4]benzodioxine-8,3'-indole]-4'-carboxamide;
N-cyclobutyl-1'-methyl-2'-oxo-1',2,2',3-tetrahydrospiro[furo[2,3-g][1,4]benzodioxine-8,3'-indole]-4'-carboxamide;
N,N,1'-trimethyl-2'-oxo-1',2,2',3-tetrahydrospiro[furo[2,3-g][1,4]benzodioxine-8,3'-indole]-4'-carboxamide;
4'-(3-methoxyphenoxy)-1'-methyl-2,3-dihydrospiro[furo[2,3-g][1,4]benzodioxine-8,3'-indol]-2'(1'H)-one;
1'-methyl-4-phenoxy-2,3-dihydrospiro[furo[2,3-g][1,4]benzodioxine-8,3'-indol]-2'(1'H)-one;
1'-methyl-4'-(3-morpholin-4-ylphenoxy)-2,3-dihydrospiro[furo[2,3-g][1,4]benzodioxine-8,3'-indol]-2'(1'H)-one;
4'-[(6-methoxypyridin-3-yl)oxy]-1'-methyl-2,3-dihydrospiro[furo[2,3-g][1,4]benzodioxine-8,3'-indol]-2'(1'H)-one;
4'-(1,3-benzodioxol-5-yloxy)-1'-methyl-2,3-dihydrospiro[furo[2,3-g][1,4]benzodioxine-8,3'-indol]-2'(1'H)-one;
4'-(4-methoxyphenoxy)-1'-methyl-2,3-dihydrospiro[furo[2,3-g][1,4]benzodioxine-8,3'-indol]-2'(1'H)-one;
1'-methyl-4-(pyridine-2-ylmethoxy)-2,3-dihydrospiro[furo[2,3-g][1,4]benzodioxine-8,3'-indol]-2'(1'H)-one;
1'-methyl-4-(4-fluorobenzyloxy)-2,3-dihydrospiro[furo[2,3-g][1,4]benzodioxine-8,3'-indol]-2'(1'H)-one;
4'-(4-fluorophenoxy)-1'-methyl-2,3-dihydrospiro[furo[2,3-g][1,4]benzodioxine-8,3'-indol]-2'(1'H)-one;
1'-(4-hydroxybenzyl)-2,3-dihydrospiro[furo[2,3-g][1,4]benzodioxine-8,3'-indol]-2'(1'H)-one;
1'-(3-hydroxypropyl)-2,3-dihydrospiro[furo[2,3-g][1,4]-benzodioxine-8,3'-indol]-2'(1'H)-one;

ethyl 2'-oxo-2,3-dihydrospiro[furo[2,3-g][1,4]benzodioxine-8,3'-indole]-1'(2'H)-carboxylate;
tert-butyl 2'-oxo-2,3-dihydrospiro[furo[2,3-g][1,4]benzodioxine-8,3'-indole]-1'(2'H)-carboxylate;
1'-{[(3aR,5R,5aS,8aS,8bR)-2,2,7,7-tetramethyltetrahydro-3aH-bis[1,3]dioxolo[4,5-b:4',5'-d]pyran-5-yl]methyl}-2,3-dihydrospiro[furo[2,3-g][1,4]benzodioxine-8,3'-indol]-2'(1'H)-one;
6-deoxy-6-(2'-oxo-2,3-dihydrospiro[furo[2,3-g][1,4]benzodioxine-8,3'-indol]-1'(2'H)-yl)-D-galactopyranose; 1'-cyclopropyl-2,3-dihydrospiro[furo[2,3-g][1,4]benzodioxine-8,3'-indol]-2'(1'H)-one;
1'-acetyl-2,3-dihydrospiro[furo[2,3-g][1,4]-benzodioxine-8,3'-indol]-2'(1'H)-one;
1-{[4-(trifluoromethyl)pyridin-2-yl]methyl}-2,3-dihydrospiro[furo[2,3-g][1,4]benzodioxine-8,3'-indol]-2'(1'H)-one;
4'-acetyl-1-methyl-2,3-dihydrospiro[furo[2,3-g][1,4]benzodioxine-8,3'-indol]-2'(1'H)-one;
1'-methyl-4'-(2-methyl-1,3-thiazol-4-yl)-2,3-dihydrospiro[furo[2,3-g][1,4]benzodioxine-8,3'-indol]-2'(1'H)-one;
4'-(2-amino-1,3-thiazol-4-yl)-1'-methyl-2,3-dihydrospiro[furo[2,3-g][1,4]benzodioxine-8,3'-indol]-2'(1'H)-one;
4'-(5-hydroxy-1H-pyrazol-3-yl)-1'-methyl-2,3-dihydrospiro[furo[2,3-g][1,4]benzodioxine-8,3'-indol]-2'(1'H)-one;
1'-[3-(3-methyl-1,2,4-oxadiazol-5-yl)benzyl]-2,3-dihydrospiro[furo[2,3-g][1,4]benzodioxine-8,3'-indol]-2'(1'H)-one;
1'-[4-(3-amino-1H-pyrazol-5-yl)benzyl]-2,3-dihydrospiro[furo[2,3-g][1,4]benzodioxine-8,3'-indol]-2'(1'H)-one hydrochloride;
1'-[4-(3-methyl-1,2,4-oxadiazol-5-yl)benzyl]-2,3-dihydrospiro[furo[2,3-g][1,4]benzodioxine-8,3'-indol]-2'(1'H)-one;
2'-oxo-1'-(pyridin-2-ylmethyl)-1',2,2',3-tetrahydrospiro[furo[2,3-g][1,4]benzodioxine-8,3'-indole]-5'-carboxamide;
1'-[(6-morpholin-4-ylpyridin-3-yl)methyl]-2,3-dihydrospiro[furo[2,3-g][1,4]benzodioxine-8,3'-indol]-2'(1'H)-one;
1'-{[6-(dimethylamino)pyridin-3-yl]methyl}-2,3-dihydrospiro[furo[2,3-g][1,4]benzodioxine-8,3'-indol]-2'(1'H)-one;
1'-{[6-(dimethylamino)pyridin-2-yl]methyl}-2,3-dihydrospiro[furo[2,3-g][1,4]benzodioxine-8,3'-indol]-2'(1'H)-one;
1'-({6-[(diphenylmethylidene)amino]pyridin-2-yl}methyl)-2,3-dihydrospiro[furo[2,3-g][1,4]benzodioxine-8,3'-indol]-2'(1'H)-one;
1'-[(5-morpholin-4-ylpyridin-2-yl)methyl]-2,3-dihydrospiro[furo[2,3-g][1,4]benzodioxine-8,3'-indol]-2'(1'H)-one;
1'-{[5-(dimethylamino)pyridin-2-yl]methyl}-2,3-dihydrospiro[furo[2,3-g][1,4]benzodioxine-8,3'-indol]-2'(1'H)-one;
1'-[(6-aminopyridin-2-yl)methyl]-2,3-dihydrospiro[furo[2,3-g][1,4]-benzodioxine-8,3'-indol]-2'(1'H)-one;
1'-[(6-oxo-1,6-dihydropyridin-3-yl)methyl]-2,3-dihydrospiro[furo[2,3-g][1,4]benzodioxine-8,3'-indol]-2'(1'H)-one;
1'-[(2-hydroxypyrimidin-5-yl)methyl]-2,3-dihydrospiro[furo[2,3-g][1,4]benzodioxine-8,3'-indol]-2'(1'H)-one;
1'-[(1-methyl-6-oxo-1,6-dihydropyridin-3-yl)methyl]-2,3-dihydrospiro[furo[2,3-g][1,4]benzodioxine-8,3'-indol]-2'(1'H)-one;
1'-[(6-aminopyridin-3-yl)methyl]-2,3-dihydrospiro[furo[2,3-g][1,4]-benzodioxine-8,3'-indol]-2'(1'H)-one;
N'-hydroxy-N-{5-[(2'-oxo-2,3-dihydrospiro[furo[2,3-g][1,4]benzodioxine-8,3'-indol]-1'(2'H)-yl)methyl]pyridin-2-yl}imidoformamide;
1'-([1,2,4]triazolo[1,5-a]pyridin-6-ylmethyl)-2,3-dihydrospiro[furo[2,3-g][1,4]-benzodioxine-8,3'-indol]-2'(1'H)-one;
1'-[(2S)-2,3-dihydroxypropyl]-2,3-dihydrospiro[furo[2,3-g][1,4]benzodioxine-8,3'-indol]-2'(1'H)-one;
6-[(2'-oxo-2,3-dihydrospiro[furo[2,3-g][1,4]benzodioxine-8,3'-indol]-1'(2'H)-yl)methyl]pyridine-2-carbonitrile; or
6-[(2'-oxo-2,3-dihydrospiro[furo[2,3-g][1,4]benzodioxine-8,3'-indol]-1'(2'H)-yl)methyl]pyridine-2-carboxamide.

Of this embodiment, another embodiment is a compound of formula (I) wherein J is —CH$_2$— and K is —O—.

Of this embodiment, one embodiment is the compound of formula (I) which is
1'-[(2R)-tetrahydrofuran-2-ylmethyl]-4H-spiro[furo[3,2-g][1,3]benzodioxine-6,3'-indol]-2'(1'H)-one.

Of this embodiment, another embodiment is a compound of formula (I) wherein both J and K are each —CH$_2$—.

Of this embodiment, one embodiment is a compound of formula (I) selected from:
1'-(diphenylmethyl)-6,7-dihydro-5H-spiro[furo[3,2-g]chromene-3,3'-indol]-2'(1'H)-one;
6,7-dihydro-5H-spiro[furo[3,2-g]chromene-3,3'-indol]-2'(1'H)-one; or
1'-[(2R)-tetrahydrofuran-2-ylmethyl]-6,7-dihydro-5H-spiro[furo[3,2-g]chromene-3,3'-indol]-2'(1'H)-one.

Another embodiment of the invention is a compound of formula (II), as set forth above in the Summary of the Invention.

Of this embodiment, one embodiment is a compound of formula (II) where each $R^{3a}$ is hydrogen.

Of this embodiment, another embodiment is a compound of formula (II) where each $R^{3a}$ is fluoro.

Of this embodiment, another embodiment is a compound of formula (II) selected from:
tert-butyl 4'-bromo-2'-oxospiro[furo[2,3-f][1,3]benzodioxole-7,3'-indole]-1'(2'H)-carboxylate;
1'-{[2,5-dimethyl-1-(1-methylethyl)-1H-pyrrol-3-yl]methyl}spiro[furo[2,3-f][1,3]benzodioxole-7,3'-indol]-2'(1'H)-one;
7'-bromospiro[furo[2,3-f][1,3]benzodioxole-7,3'-indol]-2'(1'H)-one;
1'-[(3-isopropylisoxazol-5-yl)methyl]spiro[furo[2,3-f][1,3]benzodioxole-7,3'-indol]-2'(1'H)-one;
1'-[(4-bromo-2-thienyl)methyl]spiro[furo[2,3-f][1,3]benzodioxole-7,3'-indol]-2'(1'H)-one;
1'-(1-benzofuran-2-ylmethyl)spiro[furo[2,3-f][1,3]benzodioxole-7,3'-indol]-2'(1'H)-one;
1'-{[2-methyl-5-(trifluoromethyl)-1,3-oxazol-4-yl]methyl}spiro[furo[2,3-f][1,3]benzodioxole-7,3'-indol]-2'(1'H)-one;
1'-{[5-(4-chlorophenyl)-2-(trifluoromethyl)furan-3-yl]methyl}spiro[furo[2,3-f][1,3]benzodioxole-7,3'-indol]-2'(1'H)-one;
1'-{[5-chloro-1-methyl-3-(trifluoromethyl)-1H-pyrazol-4-yl]methyl}spiro[furo[2,3-f][1,3]benzodioxole-7,3'-indol]-2'(1'H)-one;
1'-(5-methoxypyridin-3-yl)spiro[furo[2,3-f][1,3]benzodioxole-7,3'-indol]-2'(1'H)-one;
1'-(4-bromobenzyl)spiro[furo[2,3-f][1,3]benzodioxole-7,3'-indol]-2'(1'H)-one;
1'-{[(2S)-5-oxopyrrolidin-2-yl]methyl}spiro[furo[2,3-f][1,3]benzodioxole-7,3'-indol]-2'(1'H)-one;
(2'-oxospiro[furo[2,3-f][1,3]benzodioxole-7,3'-indol]-1'(2'H)-yl)acetonitrile;
7'-(trifluoromethyl)-1'-{[5-(trifluoromethyl)-2-furyl]methyl}spiro[furo[2,3-f][1,3]benzodioxole-7,3'-indol]-2'(1'H)-one;

1'-[(5-chloro-2-thienyl)methyl]-7'-(trifluoromethyl)spiro[furo[2,3-f][1,3]benzodioxole-7,3'-indol]-2'(1'H)-one;

1'-[(2-isopropyl-1,3-thiazol-5-yl)methyl]-7'-(trifluoromethyl)spiro[furo[2,3-f][1,3]benzodioxole-7,3'-indol]-2'(1'H)-one;

1'-[(2-isopropyl-1,3-oxazol-5-yl)methyl]spiro[furo[2,3-f][1,3]benzodioxole-7,3'-indol]-2'(1'H)-one;

tert-butyl [1-cyclopropyl-3-(2'-oxospiro[furo[2,3-f][1,3]benzodioxole-7,3'-indol]-1'(2'H)-yl)propyl]carbamate;

1'-[4-(methylsulfanyl)benzyl]spiro[furo[2,3-f][1,3]benzodioxole-7,3'-indol]-2'(1'H)-one;

3-(2'-oxospiro[furo[2,3-f][1,3]benzodioxole-7,3'-indol]-1'(2'H)-yl)propanenitrile;

1'-[(2-bromo-1,3-thiazol-5-yl)methyl]spiro[furo[2,3-f][1,3]benzodioxole-7,3'-indol]-2'H)-one;

1'-{[2-amino-4-(trifluoromethyl)-1,3-thiazol-5-yl]methyl}spiro[furo[2,3-f][1,3]benzodioxole-7,3'-indol]-2'(1'H)-one;

4'-chloro-2'-oxospiro[furo[2,3-f][1,3]benzodioxole-7,3'-indol]-1'(2'H)-yl)acetonitrile;

1'-[(2-amino-1,3-thiazol-4-yl)methyl]spiro[furo[2,3-f][1,3]benzodioxole-7,3'-indol]-2'(1'H)-one;

4'-bromo-1'-[(5-chlorothiophen-2-yl)methyl]spiro[furo[2,3-f][1,3]benzodioxole-7,3'-indol]-2'H)-one;

1'-[(5-chlorothiophen-2-yl)methyl]-2'-oxo-1',2'-dihydrospiro[furo[2,3-f][1,3]benzodioxole-7,3'-indole]-7'-carbonitrile;

1'-{[2-(1-methylethyl)-1,3-thiazol-4-yl]methyl}-2'-oxo-1',2'-dihydrospiro[furo[2,3-f][1,3]benzodioxole-7,3'-indole]-7'-carbonitrile;

4'-chloro-1'-[(5-chlorothiophen-2-yl)methyl]spiro[furo[2,3-f][1,3]benzodioxole-7,3'-indol]-2'H)-one;

4'-chloro-1'-{[5-(trifluoromethyl)-2-furyl]methyl}spiro[furo[2,3-f][1,3]benzodioxole-7,3'-indol]-2'(1'H)-one;

4'-chloro-1'-[(2-isopropyl-1,3-thiazol-4-yl)methyl]spiro[furo[2,3-f][1,3]benzodioxole-7,3'-indol]-2'(1'H)-one;

4'-[6-(dimethylamino)pyridin-3-yl]-1'-{[2-(1-methylethyl)-1,3-thiazol-4-yl]methyl}spiro[furo[2,3-f][1,3]benzodioxole-7,3'-indol]-2'(1'H)-one;

1'-[(5-chloro-1,2,4-thiadiazol-3-yl)methyl]spiro[furo[2,3-f][1,3]benzodioxole-7,3'-indol]-2'(1'H)-one;

4'-chloro-1'-[(5-chloro-1,2,4-thiadiazol-3-yl)methyl]spiro[furo[2,3-f][1,3]benzodioxole-7,3'-indol]-2'(1'H)-one;

1'-(4-methoxybenzyl)spiro[furo[2,3-f][1,3]benzodioxole-7,3'-indol]-2'(1'H)-one;

1'-[(2S)-1,4-dioxan-2-ylmethyl]spiro[furo[2,3-f][1,3]benzodioxole-7,3'-indol]-2'(1'H)-one;

1'-[(2-chloro-1,3-thiazol-5-yl)methyl]spiro[furo[2,3-f][1,3]benzodioxole-7,3'-indol]-2'(1'H)-one;

1'-{[2-(dimethylamino)-1,3-thiazol-5-yl]methyl}spiro[furo[2,3-f][1,3]benzodioxole-7,3'-indol]-2'(1'H)-one;

1'-[(2-morpholin-4-yl-1,3-thiazol-5-yl)methyl]spiro[furo[2,3-f][1,3]benzodioxole-7,3'-indol]-2'(1'H)-one;

1'-[(2-piperidin-1-yl-1,3-thiazol-5-yl)methyl]spiro[furo[2,3-f][1,3-f][1,3]benzodioxole-7,3'-indol]-2'(1'H)-one;

1'-[(2-methoxy-1,3-thiazol-5-yl)methyl]spiro[furo[2,3-f][1,3]benzodioxole-7,3'-indol]-2'(1'H)-one;

1'-{2-[5-(trifluoromethyl)-1,2,4-oxadiazol-3-yl]ethyl}spiro[furo[2,3-f][1,3]benzodioxole-7,3'-indol]-2'(1'H)-one;

4'-chloro-1'-{[5-(trifluoromethyl)-1,2,4-oxadiazol-3-yl]methyl}spiro[furo[2,3-f][1,3]benzodioxole-7,3'-indol]-2'(1'H)-one;

4'-chloro-1'-[(5-cyclopropyl-1,2,4-oxadiazol-3-yl)methyl]spiro[furo[2,3-f][1,3]benzodioxole-7,3'-indol]-2'(1'H)-one;

4'-chloro-1'-{[5-(difluoromethyl)-1,2,4-oxadiazol-3-yl]methyl}spiro[furo[2,3-f][1,3]benzodioxole-7,3'-indol]-2'(1'H)-one;

1'-{[5-(difluoromethyl)-1,2,4-oxadiazol-3-yl]methyl}spiro[furo[2,3-f][1,3]benzodioxole-7,3'-indol]-2'(1'H)-one;

1'-[(5-tert-butyl-1,2,4-oxadiazol-3-yl)methyl]spiro[furo[2,3-f][1,3]benzodioxole-7,3'-indol]-2'(1'H)-one;

1'-[(5-cyclopropyl-1,2,4-oxadiazol-3-yl)methyl]spiro[furo[2,3-f][1,3]benzodioxole-7,3'-indol]-2'(1'H)-one;

4'-chloro-1'-{[5-(1-methylethyl)-1,2,4-oxadiazol-3-yl]methyl}spiro[furo[2,3-f][1,3]benzodioxole-7,3'-indol]-2'(1'H)-one;

1'-{[5-(1-methylethyl)-1,2,4-oxadiazol-3-yl]methyl}spiro[furo[2,3-f][1,3]benzodioxole-7,3'-indol]-2'(1'H)-one;

1'-[(4-methylpiperazin-1-yl)methyl]spiro[furo[2,3-f][1,3]benzodioxole-7,3'-indol]-2'(1'H)-one hydrogen chloride;

1'-[(3-methyl-2-oxo-1,3-oxazolidin-5-yl)methyl]spiro[furo[2,3-f][1,3]benzodioxole-7,3'-indol]-2'(1'H)-one;

1'-{[5-(trifluoromethyl)-1,2,4-oxadiazol-3-yl]methyl}spiro[furo[2,3-f][1,3]benzodioxole-7,3'-indol]-2'(1'H)-one;

N-isopropyl-3-[2-(2'-oxospiro[furo[2,3-g][1,3]benzodioxole-7,3'-indol]-1'(2'H)-yl)ethyl]piperidine-1-carboxamide;

5-[(Z-oxospiro[furo[2,3-f][1,3]benzodioxole-7,3'-indol]-1'(2'H)-yl)methyl]thiophene-3-carbonitrile;

2'-oxo-1',2'-dihydrospiro[furo[2,3-f][1,3]benzodioxole-7,3'-indole]-7'-carbonitrile;

N-Methyl-5-[(2'-oxospiro[furo[2,3-f][1,3]benzodioxole-7,3'-indol]-1'(2'H)-yl)methyl]-2-(trifluoromethyl)furan-3-carboxamide;

5-[(2'-oxospiro[furo[2,3-f][1,3]benzodioxole-7,3'-indol]-1'(2'H)-yl)methyl]-2-(trifluoromethyl)furan-3-carboxamide;

N,N-dimethyl-5-[(2'-oxospiro[furo[2,3-f][1,3]benzodioxole-7,3'-indol]-1'(2'H)-yl)methyl]-2-(trifluoromethyl)furan-3-carboxamide;

N-cyclopropyl-2-[(2'-oxospiro[furo[2,3-f][1,3]benzodioxole-7,3'-indol]-1'(2'H)-yl)methyl]-1,3-oxazole-4-carboxamide;

N-(1-methylethyl)-2-[(2'-oxospiro[furo[2,3-f][1,3]benzodioxole-7,3'-indol]-1'(2'H)-yl)methyl]-1,3-oxazole-4-carboxamide;

1'-[(5-chloro-2-thienyl)methyl]-4'-[6-(dimethylamino)pyridin-3-yl]spiro[furo[2,3-f][1,3]benzodioxole-7,3'-indol]-2'(1'H)-one;

1'-[(5-chloro-2-thienyl)methyl]-4'-(3-furyl)spiro[furo[2,3-f][1,3]benzodioxole-7,3'-indol]-2'(1'H)-one; and 4'-[6-(dimethylamino)pyridin-3-yl]spiro[furo[2,3-f][1,3]benzodioxole-7,3'-indol]-2'(1'H)-one;

2,2-difluoro-1'-{[5-(trifluoromethyl)furan-2-yl]methyl}spiro[furo[2,3-f][1,3]benzodioxole-7,3'-indol]-2'(1'H)-one;

2,2-difluoro-1'-{[5-(trifluoromethyl)furan-2-yl]methyl}spiro[furo[2,3-f][1,3]benzodioxole-7,3'-indol]-2'(1'H)-one;

2,2-difluoro-1'-{[3-(trifluoromethyl)pyridin-2-yl]methyl}spiro[furo[2,3-f][1,3]benzodioxole-7,3'-indol]-2'(1'H)-one;

1'-[(3-chlorothiophen-2-yl)methyl]spiro[furo[2,3-f][1,3]benzodioxole-7,3'-indol]-2'(1'H)-one;

1'-{[3-(2,6-dichlorophenyl)-5-methylisoxazol-4-yl]methyl}spiro[furo[2,3-f][1,3]benzodioxole-7,3'-indol]-2'(1'H)-one;

1'-({2-[4-(trifluoromethyl)phenyl]-1,3-thiazol-4-yl}methyl)spiro[furo[2,3-f][1,3]benzodioxole-7,3'-indol]-2'(1'H)-one;

1'-[(5-phenyl-1,3,4-oxadiazol-2-yl)methyl]spiro[furo[2,3-f] [1,3]benzodioxole-7,3'-indol]-2'(1'H)-one;
1'-{[5-(4-chlorophenyl)-1,3,4-oxadiazol-2-yl]methyl}spiro [furo[2,3-f][1,3]benzodioxole-7,3'-indol]-2'(1'H)-one;
1'-([1,3]oxazolo[4,5-b]pyridin-2-ylmethyl)spiro[furo[2,3-f] [1,3]benzodioxole-7,3'-indol]-2'(1'H)-one;
(7S)-4'-furan-3-yl-1'-methylspiro[furo[2,3-f][1,3]benzodioxole-7,3'-indol]-2'(1'H)-one;
(7R)-4'-furan-3-yl-1'-methylspiro[furo[2,3-f][1,3]benzodioxole-7,3'-indol]-2'(1'H)-one;
(7R)-4'-bromo-1'-methylspiro[furo[2,3-f][1,3]benzodioxole-7,3'-indol]-2'(1'H)-one;
(7S)-4'-bromo-1-methylspiro[furo[2,3-f][1,3]benzodioxole-7,3'-indol]-2'(1'H)-one;
(7S)-4'-furan-3-ylspiro[furo[2,3-f][1,3]benzodioxole-7,3'-indol]-2'(1'H)-one;
(7R)-4'-furan-3-ylspiro[furo[2,3-f][1,3]benzodioxole-7,3'-indol]-2'(1'H)-one;
1'-methyl-4'-(tetrahydrofuran-3-yl)spiro[furo[2,3-f][1,3] benzodioxole-7,3'-indol]-2'(1'H)-one; or
6-[(2'-oxospiro[furo[2,3-f][1,3]benzodioxole-7,3'-indol]-1' (2'H)-yl)methyl]pyrimidine-2,4(1H,3H)-dione.

Another embodiment of the invention is a compound of formula (III), as set forth above in the Summary of the Invention.

Of this embodiment, one embodiment is a compound of formula (III) wherein each $R^6$ is independently hydrogen, chloro, bromo, fluoro, methyl, cyano, amino, —C(O)H, —CH$_2$—N(CH$_3$)$_2$, (pyrrolidin-1-yl)methyl, 6-(dimethylamino)pyridin-3-yl, 2-(4-fluorophenyl)ethenyl, dibenzo[b, d]thiophen-4-yl, benzothiophen-3-yl, 1-methyl-1H-indol-5-yl, 3,5-di(trifluoromethyl)phenyl, 4-phenoxyphenyl, 4-(2-methylpropoxy)phenyl, 4-butoxyphenyl, 4-methoxyphenyl, pyrimidin-5-yl or furan-3-yl.

Of this embodiment, another embodiment is a compound of formula (III) wherein two $R^6$'s, together with the adjacent carbons to which they are attached, form a fused dioxinyl ring or a fused pyridinyl ring.

Of this embodiment, another embodiment is a compound of formula (III) wherein L is —O— and M is —CH$_2$—.

Of this embodiment, one embodiment is a compound of formula (III) selected from:
(3R)-5,6-dihydrospiro[benzo[1,2-b:5,4-b']difuran-3,3'-indol]-2'(1'H)-one;
(3S)-5,6-dihydrospiro[benzo[1,2-b:5,4-b']difuran-3,3'-indol]-2'(1'H)-one;
1-(pyridazin-4-ylmethyl)-5,6-dihydrospiro[benzo[1,2-b:5,4-b']difuran-3,3'-indol]-2'(1'H)-one;
4'-chloro-1'-(diphenylmethyl)-5,6-dihydrospiro[benzo[1,2-b:5,4-b']difuran-3,3'-indol]-2'(1'H)-one;
1'-(diphenylmethyl)-5'-fluoro-5,6-dihydrospiro[benzo[1,2-b:5,4-b']difuran-3,3'-indol]-2'(1'H)-one;
1'-(diphenylmethyl)-6'-fluoro-5,6-dihydrospiro[benzo[1,2-b:5,4-b']difuran-3,3'-indol]-2'(1'H)-one;
7'-chloro-1'-(diphenylmethyl)-5,6-dihydrospiro[benzo[1,2-b:5,4-b']difuran-3,3'-indol]-2'(1'H)-one;
1'-(diphenylmethyl)-4'-fluoro-7'-methyl-5,6-dihydrospiro [benzo[1,2-b:5,4-b']difuran-3,3'-indol]-2'(1'H)-one;
1'-(diphenylmethyl)-7'-fluoro-5,6-dihydrospiro[benzo[1,2-b:5,4-b']difuran-3,3'-indol]-2'(1'H)-one;
6-((5-(trifluoromethyl)furan-2-yl)methyl)-2,3,5',6'-tetrahydro-2'H-spiro[[1,4]dioxino[2,3-f]indole-8,3'-benzofuro [6,5-b]furan]-7(6H)-one;
6-(((R)-tetrahydrofuran-2-yl)methyl)-2,3,5',6'-tetrahydro-2'H-spiro[[1,4]dioxino[2,3-f]indole-8,3'-benzofuro[6,5-b]furan]-7(6H)-one;
4'-chloro-5,6-dihydrospiro[benzo[1,2-b:5,4-b']difuran-3,3'-indol]-2'(1'H)-one;
5'-fluoro-5,6-dihydrospiro[benzo[1,2-b:5,4-b']difuran-3,3'-indol]-2'(1'H)-one;
6'-fluoro-5,6-dihydrospiro[benzo[1,2-b:5,4-b']difuran-3,3'-indol]-2'(1'H)-one;
4'-chloro-5,6-dihydrospiro[benzo[1,2-b:5,4-b']difuran-3,3'-indol]-2'(1'H)-one;
7'-fluoro-5,6-dihydrospiro[benzo[1,2-b:5,4-b']difuran-3,3'-indol]-2'(1'H)-one;
4'-fluoro-7'-methyl-5,6-dihydrospiro[benzo[1,2-b:5,4-b']difuran-3,3'-indol]-2'(1'H)-one;
1'-(tetrahydro-2H-pyran-2-ylmethyl)-5,6-dihydrospiro [benzo[1,2-b:5,4-b']difuran-3,3'-indol]-2'(1'H)-one;
1'-[(2-chloro-1-methyl-1H-imidazol-5-yl)methyl]-5,6-dihydrospiro[benzo[1,2-b:5,4-b']difuran-3,3'-indol]-2'(1'H)-one;
1'-[(2R)-tetrahydrofuran-2-ylmethyl]-5,6-dihydrospiro [benzo[1,2-b:5,4-b']difuran-3,3'-indol]-2'(1'H)-one;
1'-(3-methylbutyl)-5,6-dihydrospiro[benzo[1,2-b:5,4-b']difuran-3,3'-indol]-2'(1'H)-one;
1'-[(2S)-tetrahydrofuran-2-ylmethyl]-5,6-dihydrospiro [benzo[1,2-b:5,4-b']difuran-3,3'-indol]-2'(1'H)-one;
1'-(tetrahydro-2H-pyran-4-ylmethyl)-5,6-dihydrospiro [benzo[1,2-b:5,4-b']difuran-3,3'-indol]-2'(1'H)-one;
methyl 5-[(2'-oxo-5,6-dihydrospiro[benzo[1,2-b:5,4-b']difuran-3,3'-indol]-1'(2'H)-yl)methyl]furan-2-carboxylate;
1'-(1,4-dioxan-2-ylmethyl)-5,6-dihydrospiro[benzo[1,2-b:5, 4-b']difuran-3,3'-indol]-2'(1'H)-one;
1'-{[1-methyl-3-(trifluoromethyl)-1H-pyrazol-4-yl]methyl}-5,6-dihydrospiro[benzo[1,2-b:5,4-b']difuran-3,3'-indol]-2'(1'H)-one;
1'-(tetrahydro-2H-pyran-3-ylmethyl)-5,6-dihydrospiro [benzo[1,2-b:5,4-b']difuran-3,3'-indol]-2'(1'H)-one;
methyl 2-[(2'-oxo-5,6-dihydrospiro[benzo[1,2-b:5,4-b']difuran-3,3'-indol]-1'(2'H)-yl)methyl]-1,3-oxazole-4-carboxylate;
1'-(2-fluorobenzyl)-5,6-dihydrospiro[benzo[1,2-b:5,4-b']difuran-3,3'-indol]-2'(1'H)-one;
1'-(4-fluorobenzyl)-5,6-dihydrospiro[benzo[1,2-b:5,4-b']difuran-3,3'-indol]-2'(1'H)-one;
1'-benzyl-5,6-dihydrospiro[benzo[1,2-b:5,4-b']difuran-3,3'-indol]-2'(1'H)-one;
1'-(biphenyl-4-ylmethyl)-5,6-dihydrospiro[benzo[1,2-b:5,4-b']difuran-3,3'-indol]-2'(1'H)-one;
1'-(tetrahydrofuran-3-ylmethyl)-5,6-dihydrospiro[benzo[1, 2-b:5,4-b']difuran-3,3'-indol]-2'(1'H)-one;
1'-[(3-bromoisoxazol-5-yl)methyl]-5,6-dihydrospiro[benzo [1,2-b:5,4-b']difuran-3,3'-indol]-2'(1'H)-one;
1'-[(5-bromofuran-2-yl)methyl]-5,6-dihydrospiro[benzo[1, 2-b:5,4-b']difuran-3,3'-indol]-2'(1'H)-one;
1'-(tetrahydrofuran-2-ylmethyl)-5,6-dihydrospiro[benzo[1, 2-b:5,4-b']difuran-3,3'-indol]-2'(1'H)-one;
1'-(oxetan-2-ylmethyl)-5,6-dihydrospiro[benzo[1,2-b:5,4-b']difuran-3,3'-indol]-2'(1'H)-one;
1'-[(1-ethyl-1H-imidazol-5-yl)methyl]-5,6-dihydrospiro [benzo[1,2-b:5,4-b']difuran-3,3'-indol]-2'(1'H)-one;
3-[2'-oxo-5,6-dihydrospiro[benzo[1,2-b:5,4-b']difuran-3, 3'-indol]-1'(2'H)-yl)methyl]benzonitrile;
4-((2'-oxo-5,6-dihydro-2H-spiro[benzofuro[6,5-b]furan-3, 3'-indoline]-1-yl)methyl)benzonitrile;
4'-[(2'-oxo-5,6-dihydrospiro[benzo[1,2-b:5,4-b']difuran-3, 3'-indol]-1'(2'H)-yl)methyl]biphenyl-2-carbonitrile;
1'-{(2S)-2-[(benzyloxy)methoxy]propyl}-5,6-dihydrospiro [benzo[1,2-b:5,4-b']difuran-3,3'-indol]-2'(1'H)-one;

1'-(2,3-dihydro-1,4-benzodioxin-6-ylmethyl)-5,6-dihydrospiro[benzo[1,2-b:5,4-b']difuran-3,3'-indol]-2'(1'H)-one;

1'-(2,1,3-benzoxadiazol-5-ylmethyl)-5,6-dihydrospiro[benzo[1,2-b:5,4-b']difuran-3,3'-indol]-2'(1'H)-one;

1'-(2,1,3-benzothiadiazol-5-ylmethyl)-5,6-dihydrospiro[benzo[1,2-b:5,4-b']difuran-3,3'-indol]-2'(1'H)-one;

1'-[(4-benzylmorpholin-2-yl)methyl]-5,6-dihydrospiro[benzo[1,2-b:5,4-b']difuran-3,3'-indol]-2'(1'H)-one;

tert-butyl 3-[(2'-oxo-5,6-dihydrospiro[benzo-[1,2-b:5,4-b']difuran-3,3'-indol]-1'(2'H)-yl)methyl]pyrrolidine-1-carboxylate;

tert-butyl (2S)-2-[(2'-oxo-5,6-dihydrospiro[benzo[1,2-b:5,4-b']difuran-3,3'-indol]-1'(2'H)-yl)methyl]pyrrolidine-1-carboxylate;

tert-butyl 4-[(2'-oxo-5,6-dihydrospiro[benzo[1,2-b:5,4-b']difuran-3,3'-indol]-1'(2'H)-yl)methyl]piperidine-1-carboxylate;

4'-chloro-1'-{[5-(trifluoromethyl)furan-2-yl]methyl}-5,6-dihydrospiro[benzo[1,2-b:5,4-b']difuran-3,3'-indol]-2'(1'H)-one;

4'-chloro-1'-[(2R)-tetrahydrofuran-2-ylmethyl]-5,6-dihydrospiro[benzo[1,2-b:5,4-b']difuran-3,3'-indol]-2'(1'H)-one;

4'-bromo-1'-[(2R)-tetrahydrofuran-2-ylmethyl]-5,6-dihydrospiro[benzo[1,2-b:5,4-b']difuran-3,3'-indol]-2'(1'H)-one;

1'-[4-(methylsulfanyl)benzyl]-5,6-dihydrospiro[benzo[1,2-b:5,4-b']difuran-3,3'-indol]-2'(1'H)-one;

1'-[(2-methoxypyrimidin-5-yl)methyl]-5,6-dihydrospiro[benzo[1,2-b:5,4-b']difuran-3,3'-indol]-2'(1'H)-one;

7'-chloro-1'-((5-(trifluoromethyl)furan-2-yl)methyl)-5,6-dihydro-2H-spiro[benzofuro[6,5-b]furan-3,3'-indolin]-2'-one;

(3R)-1'-(3-methylbutyl)-5,6-dihydrospiro[benzo[1,2-b:5,4-b']difuran-3,3'-indol]-2'(1'H)-one;

(3R)-1'-pentyl-5,6-dihydrospiro[benzo[1,2-b:5,4-b']difuran-3,3'-indol]-2'(1'H)-one;

(3R)-1'-(pyridin-2-ylmethyl)-5,6-dihydrospiro[benzo[1,2-b:5,4-b']difuran-3,3'-indol]-2'-one;

(3R)-1-{[5-(trifluoromethyl)furan-2-yl]methyl}-5,6-dihydrospiro[benzo[1,2-b:5,4-b']difuran-3,3'-indol]-2'(1'H)-one;

(3S)-1'-(pyridin-2-ylmethyl)-5,6-dihydrospiro[benzo[1,2-b:5,4-b']difuran-3,3'-indol]-2'(1'H)-one;

(3S)-1'-{[5-(trifluoromethyl)furan-2-yl]methyl}-5,6-dihydrospiro[benzo[1,2-b:5,4-b']difuran-3,3'-indol]-2'(1'H)-one;

7'-chloro-1'-[(2R)-tetrahydrofuran-2-ylmethyl]-5,6-dihydrospiro[benzo[1,2-b:5,4-b']difuran-3,3'-indol]-2'(1'H)-one;

7'-fluoro-1-[(2R)-tetrahydrofuran-2-ylmethyl]-5,6-dihydrospiro[benzo[1,2-b:5,4-b']difuran-3,3'-indol]-2'(1'H)-one;

4'-fluoro-7'-methyl-1'-[(2R)-tetrahydrofuran-2-ylmethyl]-5,6-dihydrospiro[benzo[1,2-b:5,4-b']difuran-3,3'-indol]-2'(1'H)-one;

1'-[2-(2-methoxyethoxy)ethyl]-5,6-dihydrospiro[benzo[1,2-b:5,4-b']difuran-3,3'-indol]-2'(1'H)-one;

1'-{[(2S)-5-oxopyrrolidin-2-yl]methyl}-5,6-dihydrospiro[benzo[1,2-b:5,4-b']difuran-3,3'-indol]-2'(1'H)-one;

1'-[2-(2-oxo-1,3-oxazolidin-3-yl)ethyl]-5,6-dihydrospiro[benzo[1,2-b:5,4-b']difuran-3,3'-indol]-2'(1'H)-one;

1'-(4-pyridin-2-ylbenzyl)-5,6-dihydrospiro[benzo[1,2-b:5,4-b']difuran-3,3'-indol]-2'(1'H)-one;

1'-(pyrimidin-2-ylmethyl)-5,6-dihydrospiro[benzo[1,2-b:5,4-b']difuran-3,3'-indol]-2'(1'H)-one;

1'-(pyrimidin-4-ylmethyl)-5,6-dihydrospiro[benzo[1,2-b:5,4-b']difuran-3,3'-indol]-2'(1'H)-one;

1'-(pyrazin-2-ylmethyl)-5,6-dihydrospiro[benzo[1,2-b:5,4-b']difuran-3,3'-indol]-2'(1'H)-one;

1'-[(7-fluoro-1-benzofuran-2-yl)methyl]-5,6-dihydrospiro[benzo[1,2-b:5,4-b']difuran-3,3'-indol]-2'(1'H)-one;

1'-(pyridazin-3-ylmethyl)-5,6-dihydrospiro[benzo[1,2-b:5,4-b']difuran-3,3'-indol]-2'(1'H)-one;

1'-[(2-oxo-1,3-oxazolidin-5-yl)methyl]-5,6-dihydrospiro[benzo[1,2-b:5,4-b']difuran-3,3'-indol]-2'(1'H)-one;

1'-[3-(benzyloxy)benzyl]-5,6-dihydrospiro[benzo[1,2-b:5,4-b']difuran-3,3'-indol]-2'(1'H)-one;

1'-[(1-methyl-1H-benzimidazol-2-yl)methyl]-5,6-dihydrospiro[benzo[1,2-b:5,4-b']difuran-3,3'-indol]-2'(1'H)-one;

1'-(2H-benzotriazol-2-ylmethyl)-5,6-dihydrospiro[benzo[1,2-b:5,4-b']difuran-3,3'-indol]-2'(1'H)-one;

methyl 2-[(2'-oxo-5,6-dihydrospiro[benzo[1,2-b:5,4-b']difuran-3,3'-indol]-1'(2'H)-yl)methyl]benzoate;

methyl 3-[(2'-oxo-5,6-dihydrospiro[benzo[1,2-b:5,4-b']difuran-3,3'-indol]-1'(2'H)-yl)methyl]benzoate;

methyl 4-[(2'-oxo-5,6-dihydrospiro[benzo[1,2-b:5,4-b']difuran-3,3'-indol]-1'(2'H)-yl)methyl]benzoate;

1'-[3-(benzyloxy)propyl]-5,6-dihydrospiro[benzo[1,2-b:5,4-b']difuran-3,3'-indol]-2'(1'H)-one;

5'-fluoro-1-[(2R)-tetrahydrofuran-2-ylmethyl]-5,6-dihydrospiro[benzo[1,2-b:5,4-b']difuran-3,3'-indol]-2'(1'H)-one;

6'-fluoro-1'-[(2R)-tetrahydrofuran-2-ylmethyl]-5,6-dihydrospiro[benzo[1,2-b:5,4-b']difuran-3,3'-indol]-2'(1'H)-one;

1'-(piperidin-4-ylmethyl)-5,6-dihydrospiro[benzo[1,2-b:5,4-b']difuran-3,3'-indol]-2'(1'H)-one;

1'-{[1-(1-methylethyl)piperidin-4-yl]methyl}-5,6-dihydrospiro[benzo[1,2-b:5,4-b']difuran-3,3'-indol]-2'(1'H)-one hydrochloride;

1'-[(1-ethylpiperidin-4-yl)methyl]-5,6-dihydrospiro[benzo[1,2-b:5,4-b']difuran-3,3'-indol]-2'(1'H)-one;

1'-[(1-methylpiperidin-4-yl)methyl]-5,6-dihydrospiro[benzo[1,2-b:5,4-b']difuran-3,3'-indol]-2'(1'H)-one;

1'-[(2S)-pyrrolidin-2-ylmethyl]-5,6-dihydrospiro[benzo[1,2-b:5,4-b']difuran-3,3'-indol]-2'(1'H)-one;

3-[(2'-oxo-5,6-dihydrospiro[benzo[1,2-b:5,4-b']difuran-3,3'-indol]-1'(2'H)-yl)methyl]benzoic acid;

1'-{4-[5-(trifluoromethyl)-1,2,4-oxadiazol-3-yl]benzyl}-5,6-dihydrospiro[benzo[1,2-b:5,4-b']difuran-3,3'-indol]-2'(1'H)-one;

1'-[4-(5-methyl-1,2,4-oxadiazol-3-yl)benzyl]-5,6-dihydrospiro[benzo[1,2-b:5,4-b']difuran-3,3'-indol]-2'(1'H)-one;

1'-[(5-pyridin-4-ylfuran-2-yl)methyl]-5,6-dihydrospiro[benzo[1,2-b:5,4-b']difuran-3,3'-indol]-2'(1'H)-one;

1'-(4-pyridin-3-ylbenzyl)-5,6-dihydrospiro[benzo[1,2-b:5,4-b']difuran-3,3'-indol]-2'(1'H)-one;

1-[(2'-fluorobiphenyl-4-yl)methyl]-5,6-dihydrospiro[benzo[1,2-b:5,4-b']difuran-3,3'-indol]-2'(1'H)-one;

1'-[3-(5-methyl-1,2,4-oxadiazol-3-yl)benzyl]-5,6-dihydrospiro[benzo[1,2-b:5,4-b']difuran-3,3'-indol]-2'(1'H)-one;

1'-{3-[5-(trifluoromethyl)-1,2,4-oxadiazol-3-yl]benzyl}-5,6-dihydrospiro[benzo[1,2-b:5,4-b']difuran-3,3'-indol]-2'(1'H)-one;

1'-{4-(5-methyl-4H-1,2,4-triazol-3-yl)benzyl}-5,6-dihydrospiro[benzo[1,2-b:5,4-b']difuran-3,3'-indol]-2'(1'H)-one;

2-[(2'-oxo-5,6-dihydrospiro[benzo[1,2-b:5,4-b']difuran-3,3'-indol]-1'(2'H)-yl)methyl]benzoic acid;

4-[(2'-oxo-5,6-dihydrospiro[benzo[1,2-b:5,4-b']difuran-3,3'-indol]-1'(2'H)-yl)methyl]benzoic acid;

1'-(3-hydroxypropyl)-5,6-dihydrospiro[benzo[1,2-b:5,4-b']difuran-3,3'-indol]-2'(1'H)-one;

2'-oxo-1'-[(2R)-tetrahydrofuran-2-ylmethyl]-1',2',5,6-tetrahydrospiro[benzo[1,2-b:5,4-b']difuran-3,3'-indole]-4'-carbonitrile;

2'-oxo-1'-[(2R)-tetrahydrofuran-2-ylmethyl]-1',2',5,6-tetrahydrospiro[benzo[1,2-b:5,4-b']difuran-3,3'-indole]-4'-carbaldehyde;

4'-[(dimethylamino)methyl]-1'-[(2R)-tetrahydrofuran-2-ylmethyl]-5,6-dihydrospiro[benzo[1,2-b:5,4-b']difuran-3,3'-indol]-2'(1'H)-one;

4'-(pyrrolidin-1-ylmethyl)-1'-[(2R)-tetrahydrofuran-2-ylmethyl]-5,6-dihydrospiro[benzo[1,2-b:5,4-b']difuran-3,3'-indol]-2'(1'H)-one;

4'-amino-1'-[(2R)-tetrahydrofuran-2-ylmethyl]-5,6-dihydrospiro[benzo[1,2-b:5,4-b']difuran-3,3'-indol]-2'(1'H)-one;

1'-(morpholin-2-ylmethyl)-5,6-dihydrospiro[benzo[1,2-b:5,4-b']difuran-3,3'-indol]-2'(1'H)-one;

1'-[(4-methylmorpholin-2-yl)methyl]-5,6-dihydrospiro[benzo[1,2-b:5,4-b']difuran-3,3'-indol]-2'(1'H)-one;

1'-{[4-(1-methylethyl)morpholin-2-yl]methyl}-5,6-dihydrospiro[benzo[1,2-b:5,4-b']difuran-3,3'-indol]-2'(1'H)-one;

1'-methyl-5,6-dihydrospiro[benzo[1,2-b:5,4-b']difuran-3,3'-indol]-2'(1'H)-one;

1'-[4-(1H-tetrazol-5-yl)benzyl]-5,6-dihydrospiro[benzo[1,2-b:5,4-b']difuran-3,3'-indol]-2'(1'H)-one;

1'-(3-hydroxybenzyl)-5,6-dihydrospiro[benzo[1,2-b:5,4-b']difuran-3,3'-indol]-2'(1'H)-one;

1'-(4-morpholin-4-ylbenzyl)-5,6-dihydrospiro[benzo[1,2-b:5,4-b']difuran-3,3'-indol]-2'(1'H)-one;

1'-(pyrrolidin-3-ylmethyl)-5,6-dihydrospiro[benzo[1,2-b:5,4-b']difuran-3,3'-indol]-2'(1'H)-one;

N-(1-methylethyl)-3-[(2'-oxo-5,6-dihydrospiro[benzo[1,2-b:5,4-b']difuran-3,3'-indol]-1'(2'1-1)-yl)methyl]pyrrolidine-1-carboxamide;

(3S)-1'-[(2R)-tetrahydrofuran-2-ylmethyl]-5,6-dihydrospiro[benzo[1,2-b:5,4-b']difuran-3,3'-indol]-2'(1'H)-one;

(3R)-1-[(2R)-tetrahydrofuran-2-ylmethyl]-5,6-dihydrospiro[benzo[1,2-b:5,4-b']difuran-3,3'-indol]-2'(1'H)-one;

(3R)-1'-[(2S)-tetrahydrofuran-2-ylmethyl]-5,6-dihydrospiro[benzo[1,2-b:5,4-b']difuran-3,3'-indol]-2'(1'H)-one;

(3S)-1'-[(2S)-tetrahydrofuran-2-ylmethyl]-5,6-dihydrospiro[benzo[1,2-b:5,4-b']difuran-3,3'-indol]-2'(1'H)-one;

1'-{[(2S)-1-methyl-5-oxopyrrolidin-2-yl]methyl}-5,6-dihydrospiro[benzo[1,2-b:5,4-b']difuran-3,3'-indol]-2'(1'H)-one;

N-(cyclohexylmethyl)-3-[(2'-oxo-5,6-dihydrospiro[benzo[1,2-b:5,4-b']difuran-3,3'-indol]-1'(2'H)-yl)methyl]benzamide;

N-(2-methoxyethyl)-3-[(2'-oxo-5,6-dihydrospiro[benzo[1,2-b:5,4-b']difuran-3,3'-indol]-1'(2'H)-yl)methyl]benzamide;

N-hexyl-N-methyl-3-[(2'-oxo-5,6-dihydrospiro[benzo[1,2-b:5,4-b']difuran-3,3'-indol]-1'(2'H)-yl)methyl]benzamide;

N-(2-ethylbutyl)-3-[(2'-oxo-5,6-dihydrospiro[benzo[1,2-b:5,4-b']difuran-3,3'-indol]-1'(2'H)-yl)methyl]benzamide;

N-(2,4-dimethylphenyl)-3-[(2'-oxo-5,6-dihydrospiro[benzo[1,2-b:5,4-b']difuran-3,3'-indol]-1'(2'H)-yl)methyl]benzamide;

3-[(2'-oxo-5,6-dihydrospiro[benzo[1,2-b:5,4-b']difuran-3,3'-indol]-1'(2'H)-yl)methyl]-N-(2-phenylpropyl)benzamide;

N-[(1S)-1-cyclohexylethyl]-3-[(2'-oxo-5,6-dihydrospiro[benzo[1,2-b:5,4-b']difuran-3,3'-indol]-1'(2'H)-yl)methyl]benzamide;

N-[(1R)-1-cyclohexylethyl]-3-[(2'-oxo-5,6-dihydrospiro[benzo[1,2-b:5,4-b']difuran-3,3'-indol]-1'(2'H)-yl)methyl]benzamide;

N-(4-ethylphenyl)-2-[(2'-oxo-5,6-dihydrospiro[benzo[1,2-b:5,4-b']difuran-3,3'-indol]-1'(2'H)-yl)methyl]benzamide;

N-(2-ethylphenyl)-2-[(2'-oxo-5,6-dihydrospiro[benzo[1,2-b:5,4-b']difuran-3,3'-indol]-1'(2'H)-yl)methyl]benzamide;

N-(2,4-dimethylphenyl)-2-[(2'-oxo-5,6-dihydrospiro[benzo[1,2-b:5,4-b']difuran-3,3'-indol]-1'(2'H)-yl)methyl]benzamide;

N-(2-methoxyphenyl)-2-[(2'-oxo-5,6-dihydrospiro[benzo[1,2-b:5,4-b']difuran-3,3'-indol]-1'(2'H)-yl)methyl]benzamide;

N-(2-fluorophenyl)-2-[(2'-oxo-5,6-dihydrospiro[benzo[1,2-b:5,4-b']difuran-3,3'-indol]-1'(2'H)-yl)methyl]benzamide;

N-(3-chlorophenyl)-2-[(2'-oxo-5,6-dihydrospiro[benzo[1,2-b:5,4-b']difuran-3,3'-indol]-1'(2'H)-yl)methyl]benzamide;

N-(3-fluoro-2-methylphenyl)-2-[(2'-oxo-5,6-dihydrospiro[benzo[1,2-b:5,4-b']difuran-3,3'-indol]-1'(2'H)-yl)methyl]benzamide;

N-heptyl-2-[(2'-oxo-5,6-dihydrospiro[benzo[1,2-b:5,4-b']difuran-3,3'-indol]-1'(2'H)-yl)methyl]benzamide;

N-(2-chlorobenzyl)-2-[(2'-oxo-5,6-dihydrospiro[benzo[1,2-b:5,4-b']difuran-3,3'-indol]-1'(2'H)-yl)methyl]benzamide;

1'-[2-(piperidin-1-ylcarbonyl)benzyl]-5,6-dihydrospiro[benzo[1,2-b:5,4-b']difuran-3,3'-indol]-2'(1'H)-one;

N-butyl-2-[(2'-oxo-5,6-dihydrospiro[benzo[1,2-b:5,4-b']difuran-3,3'-indol]-1'(2'H)-yl)methyl]benzamide;

N-(3-methylphenyl)-2-[(2'-oxo-5,6-dihydrospiro[benzo[1,2-b:5,4-b']difuran-3,3'-indol]-1'(2'H)-yl)methyl]benzamide;

N-(2-fluoro-5-methylphenyl)-2-[(2'-oxo-5,6-dihydrospiro[benzo[1,2-b:5,4-b']difuran-3,3'-indol]-1'(2'H)-yl)methyl]benzamide;

N-(2,3-dimethylphenyl)-2-[(2'-oxo-5,6-dihydrospiro[benzo[1,2-b:5,4-b']difuran-3,3'-indol]-1'(2'H)-yl)methyl]benzamide;

N-[2-(4-methoxyphenyl)ethyl]-2-[(2'-oxo-5,6-dihydrospiro[benzo[1,2-b:5,4-b']difuran-3,3'-indol]-1'(2'H)-yl)methyl]benzamide;

N-(3-chlorobenzyl)-2-[(2'-oxo-5,6-dihydrospiro[benzo[1,2-b:5,4-b']difuran-3,3'-indol]-1'(2'H)-yl)methyl]benzamide;

N-[2-(4-chlorophenyl)ethyl]-2-[(2'-oxo-5,6-dihydrospiro[benzo[1,2-b:5,4-b']difuran-3,3'-indol]-1'(2'H)-yl)methyl]benzamide;

N-(2-methoxyphenyl)-4-[(2'-oxo-5,6-dihydrospiro[benzo[1,2-b:5,4-b']difuran-3,3'-indol]-1'(2'H)-yl)methyl]benzamide;

4-[(2'-oxo-5,6-dihydrospiro[benzo[1,2-b:5,4-b']difuran-3,3'-indol]-1'(2'H)-yl)methyl]-N-[2-(trifluoromethyl)phenyl]benzamide;

4-[(2'-oxo-5,6-dihydrospiro[benzo[1,2-b:5,4-b']difuran-3,3'-indol]-1'(2'H)-yl)methyl]-N-phenylbenzamide;

N-methyl-4-[(2'-oxo-5,6-dihydrospiro[benzo[1,2-b:5,4-b']difuran-3,3'-indol]-1'(2'H)-yl)methyl]benzamide;

N-(2-fluorophenyl)-4-[(2'-oxo-5,6-dihydrospiro[benzo[1,2-b:5,4-b']difuran-3,3'-indol]-1'(2'H)-yl)methyl]benzamide;

4-[(2'-oxo-5,6-dihydrospiro[benzo[1,2-b:5,4-b']difuran-3,3'-indol]-1'(2'H)-yl)methyl]-N-(2-thiophen-2-ylethyl)benzamide;

4-[(2'-oxo-5,6-dihydrospiro[benzo[1,2-b:5,4-b']difuran-3,3'-indol]-1'(2'H)-yl)methyl]benzamide;

N-(2,3-dihydro-1H-inden-5-yl)-4-[(2'-oxo-5,6-dihydrospiro[benzo[1,2-b:5,4-b']difuran-3,3'-indol]-1'(2'H)-yl)methyl]benzamide;

1'-[4-(morpholin-4-ylcarbonyl)benzyl]-5,6-dihydrospiro[benzo[1,2-b:5,4-b']difuran-3,3'-indol]-2'(1'H)-one;

N-(2-ethylphenyl)-4-[(2'-oxo-5,6-dihydrospiro[benzo[1,2-b:5,4-b']difuran-3,3'-indol]-1'(2'H)-yl)methyl]benzamide;

N-(2,6-dimethylphenyl)-4-[(2'-oxo-5,6-dihydrospiro[benzo[1,2-b:5,4-b']difuran-3,3'-indol]-1'(2'H)-yl)methyl]benzamide;

N-(3-fluorophenyl)-4-[(2'-oxo-5,6-dihydrospiro[benzo[1,2-b:5,4-b']difuran-3,3'-indol]-1'(2'H)-yl)methyl]benzamide;

N-(2,4-dimethylphenyl)-4-[(2'-oxo-5,6-dihydrospiro[benzo[1,2-b:5,4-b']difuran-3,3'-indol]-1'(2'H)-yl)methyl]benzamide;

4-[(2'-oxo-5,6-dihydrospiro[benzo[1,2-b:5,4-b']difuran-3,3'-indol]-1'(2'H)-yl)methyl]-N-(thiophen-2-ylmethyl)benzamide;

N-ethyl-4-[(2'-oxo-5,6-dihydrospiro[benzo[1,2-b:5,4-b']difuran-3,3'-indol]-1'(2'H)-yl)methyl]benzamide;

N-(2-methoxyethyl)-4-[(2'-oxo-5,6-dihydrospiro[benzo[1,2-b:5,4-b']difuran-3,3'-indol]-1'(2'H)-yl)methyl]benzamide;

N-(2-ethoxyethyl)-4-[(2'-oxo-5,6-dihydrospiro[benzo[1,2-b:5,4-b']difuran-3,3'-indol]-1'(2'H)-yl)methyl]benzamide;

N-cyclobutyl-4-[(2-oxo-5,6-dihydrospiro[benzo[1,2-b:5,4-b']difuran-3,3'-indol]-1(2H)-yl)methyl]benzamide;

4-[(2'-oxo-5,6-dihydrospiro[benzo[1,2-b:5,4-b']difuran-3,3'-indol]-1'(2'H)-yl)methyl]-N-1,3-thiazol-2-ylbenzamide;

N-(3-fluoro-2-methylphenyl)-4-[(2'-oxo-5,6-dihydrospiro[benzo[1,2-b:5,4-b']difuran-3,3'-indol]-1'(2'H)-yl)methyl]benzamide;

N-(2-ethylbutyl)-4-[(2'-oxo-5,6-dihydrospiro[benzo[1,2-b:5,4-b']difuran-3,3'-indol]-1'(2'H)-yl)methyl]benzamide;

2-(2'-oxo-5,6-dihydrospiro[benzo[1,2-b:5,4-b']difuran-3,3'-indol]-1'(2'H)-yl)acetamide;

N-(4-ethylphenyl)-2-(2'-oxo-5,6-dihydrospiro[benzo[1,2-b:5,4-b']difuran-3,3'-indol]-1'(2'H)-yl)acetamide;

N,N-diethyl-2-(2'-oxo-5,6-dihydrospiro[benzo[1,2-b:5,4-b']difuran-3,3'-indol]-1'(2'H)-yl)acetamide;

N-(3,3-dimethylbutyl)-2-(2'-oxo-5,6-dihydrospiro[benzo[1,2-b:5,4-b']difuran-3,3'-indol]-1'(2'H)-yl)acetamide;

N-[3-(1-methylethoxy)propyl]-2-(2'-oxo-5,6-dihydrospiro[benzo[1,2-b:5,4-b']difuran-3,3'-indol]-1'(2'H)-yl)acetamide;

2-(2'-oxo-5,6-dihydrospiro[benzo[1,2-b:5,4-b']difuran-3,3'-indol]-1'(2'H)-yl)-N-propylacetamide;

N-methyl-2-(2'-oxo-5,6-dihydrospiro[benzo[1,2-b:5,4-b']difuran-3,3'-indol]-1'(2'H)-yl)-N-phenylacetamide;

N-(2,5-dimethylphenyl)-2-(2'-oxo-5,6-dihydrospiro[benzo[1,2-b:5,4-b']difuran-3,3'-indol]-1'(2'H)-yl)acetamide;

N-(2,4-dimethylphenyl)-2-(2'-oxo-5,6-dihydrospiro[benzo[1,2-b:5,4-b']difuran-3,3'-indol]-1'(2'H)-yl)acetamide;

N-(2,3-dimethylphenyl)-2-(2'-oxo-5,6-dihydrospiro[benzo[1,2-b:5,4-b']difuran-3,3'-indol]-1'(2'H)-yl)acetamide;

N-(2,6-dimethylphenyl)-2-(2'-oxo-5,6-dihydrospiro[benzo[1,2-b:5,4-b']difuran-3,3'-indol]-1'(2'H)-yl)acetamide;

5-[(2'-oxo-5,6-dihydrospiro[benzo[1,2-b:5,4-b']difuran-3,3'-indol]-1'(2'H)-yl)methyl]furan-2-carboxylic acid;

N,N-dimethyl-5-[(2'-oxo-5,6-dihydrospiro[benzo[1,2-b:5,4-b']difuran-3,3'-indol]-1'(2'H)-yl)methyl]furan-2-carboxamide;

N-methyl-5-[(2'-oxo-5,6-dihydrospiro[benzo[1,2-b:5,4-b']difuran-3,3'-indol]-1'(2'H)-yl)methyl]furan-2-carboxamide;

2-[(2'-oxo-5,6-dihydrospiro[benzo[1,2-b:5,4-b']difuran-3,3'-indol]-1'(2'H)-yl)methyl]-1,3-oxazole-4-carboxamide;

N,N-dimethyl-2-[(2'-oxo-5,6-dihydrospiro[benzo[1,2-b:5,4-b']difuran-3,3'-indol]-1'(2'H)-yl) methyl]-1,3-oxazole-4-carboxamide;

1'-[(2S)-2-hydroxypropyl]-5,6-dihydrospiro[benzo[1,2-b:5,4-b']difuran-3,3'-indol]-2'(1'H)-one;

1'-[(2S)-2-(benzyloxy)propyl]-5,6-dihydrospiro[benzo[1,2-b:5,4-b']difuran-3,3'-indol]-2'(1'H)-one;

1'-{(2S)-2-[(4-fluorobenzyl)oxy]propyl}-5,6-dihydrospiro[benzo[1,2-b:5,4-b']difuran-3,3'-indol]-2'(1'H)-one;

1'-[(2S)-2-(pyridin-2-ylmethoxy)propyl]-5,6-dihydrospiro[benzo[1,2-b:5,4-b']difuran-3,3'-indol]-2'(1'H)-one;

1'-(3-hydroxybutyl)-5,6-dihydrospiro[benzo[1,2-b:5,4-b']difuran-3,3'-indol]-2'(1'H)-one;

1'-(4,4,4-trifluoro-3-hydroxybutyl)-5,6-dihydrospiro[benzo[1,2-b:5,4-b']difuran-3,3'-indol]-2'(1'H)-one;

3-(2'-oxo-5,6-dihydrospiro[benzo[1,2-b:5,4-b']difuran-3,3'-indol]-1'(2'H)-yl)propanal;

1'-{3-[(3-methylbutyl)amino]propyl}-5,6-dihydrospiro[benzo[1,2-b:5,4-b']difuran-3,3'-indol]-2'(1'H)-one hydrochloride;

1'-{3-[butyl(methyl)amino]propyl}-5,6-dihydrospiro[benzo[1,2-b:5,4-b']difuran-3,3'-indol]-2'(1'H)-one hydrochloride;

1'-{3-[(2,2,2-trifluoroethyl)amino]propyl}-5,6-dihydrospiro[benzo[1,2-b:5,4-b']difuran-3,3'-indol]-2'(1'H)-one hydrochloride;

3-{[3-(2'-oxo-5,6-dihydrospiro[benzo[1,2-b:5,4-b']difuran-3,3'-indol]-1'(2'H)-yl)propyl]amino}propanenitrile hydrochloride;

4'-[6-(dimethylamino)pyridin-3-yl]-1'-[(2R)-tetrahydrofuran-2-ylmethyl]-5,6-dihydrospiro[benzo[1,2-b:5,4-b']difuran-3,3'-indol]-2'(1'H)-one;

4'-[(E)-2-(4-fluorophenyl)ethenyl]-1'-[(2R)-tetrahydrofuran-2-ylmethyl]-5,6-dihydrospiro[benzo[1,2-b:5,4-b']difuran-3,3'-indol]-2'(1'H)-one;

4'-dibenzo[b,d]thiophen-4-yl-1'-[(2R)-tetrahydrofuran-2-ylmethyl]-5,6-dihydrospiro[benzo[1,2-b:5,4-b']difuran-3,3'-indol]-2'(1'H)-one;

4'-(1-benzothiophen-3-yl)-1'-[(2R)-tetrahydrofuran-2-ylmethyl]-5,6-dihydrospiro[benzo[1,2-b:5,4-b']difuran-3,3'-indol]-2'(1'H)-one;

4'-(1-methyl-1H-indol-5-yl)-1'-[(2R)-tetrahydrofuran-2-ylmethyl]-5,6-dihydrospiro[benzo[1,2-b:5,4-b']difuran-3,3'-indol]-2'(1'H)-one;

4'-[3,5-bis(trifluoromethyl)phenyl]-1'-[(2R)-tetrahydrofuran-2-ylmethyl]-5,6-dihydrospiro[benzo[1,2-b:5,4-b']difuran-3,3'-indol]-2'(1'H)-one;

4'-(4-phenoxyphenyl)-1'-[(2R)-tetrahydrofuran-2-ylmethyl]-5,6-dihydrospiro[benzo[1,2-b:5,4-b']difuran-3,3'-indol]-2'(1'H)-one;

4'-[4-(2-methylpropoxy)phenyl]-1'-[(2R)-tetrahydrofuran-2-ylmethyl]-5,6-dihydrospiro[benzo[1,2-b:5,4-b']difuran-3,3'-indol]-2'(1'H)-one;

4'-(4-butoxyphenyl)-1'-[(2R)-tetrahydrofuran-2-ylmethyl]-5,6-dihydrospiro[benzo[1,2-b:5,4-b']difuran-3,3'-indol]-2'(1'H)-one;

4'-(4-methoxyphenyl)-1'-[(2R)-tetrahydrofuran-2-ylmethyl]-5,6-dihydrospiro[benzo[1,2-b:5,4-b']difuran-3,3'-indol]-2'(1'H)-one;

4'-pyrimidin-5-yl-1'-[(2R)-tetrahydrofuran-2-ylmethyl]-5,6-dihydrospiro[benzo[1,2-b:5,4-b']difuran-3,3'-indol]-2'(1'H)-one; and 4'-[6-(dimethylamino)pyridin-3-yl]-1'-{[5-(trifluoromethyl)furan-2-yl]methyl}-5,6-dihydrospiro[benzo[1,2-b:5,4-b']difuran-3,3'-indol]-2'(1'H)-one;

6'-(diphenylmethyl)-2',3',5,6-tetrahydrospiro[benzo[1,2-b:5,4-b']difuran-3,8'-[1,4]dioxino[2,3-f]indol]-7'(6'H)-one;

3'-(4-methoxybenzyl)-5,6-dihydrospiro[benzo[1,2-b:5,4-b']difuran-3,1'-pyrrolo[3,2-f]quinolin]-2'(3'H)-one;

2',3',5,6-tetrahydrospiro[benzo[1,2-b:5,4-b']difuran-3,8'-[1,4]dioxino[2,3-f]indol]-7'(6'H)-one;

1'-[4-(benzyloxy)benzyl]-5,6-dihydrospiro[benzo[1,2-b:5,4-b']difuran-3,3'-indol]-2'(1'H)-one;

2-[3-(2'-oxo-5,6-dihydrospiro[benzo[1,2-b:5,4-b']difuran-3,3'-indol]-1'(2'H)-yl)propyl]-1H-isoindole-1,3(2H)-dione;

1'-(3-aminopropyl)-5,6-dihydrospiro[benzo[1,2-b:5,4-b']difuran-3,3'-indol]-2'(1'H)-one;

N-[3-(2'-oxo-5,6-dihydrospiro[benzo[1,2-b:5,4-b']difuran-3,3'-indol]-1'(2'H)-yl)propyl]-2-(trifluoromethoxy)benzamide; or 1'-(4-hydroxybenzyl)-5,6-dihydrospiro[benzo[1,2-b:5,4-b']difuran-3,3'-indol]-2'(1'H)-one.

Of this embodiment, another embodiment is a compound of formula (III) wherein L is —CH$_2$— and M is —O—.

Of this embodiment, one embodiment is a compound of formula (III) selected from:

1'-(pyridin-2-ylmethyl)-6,7-dihydrospiro[benzo[1,2-b:4,5-b']difuran-3,3'-indol]-2'(1'H)-one;

1'-[(2R)-tetrahydrofuran-2-ylmethyl]-6,7-dihydrospiro[benzo[1,2-b:4,5-b']difuran-3,3'-indol]-2'(1'H)-one; or 1'-[(2R)-1,4-dioxan-2-ylmethyl]-6,7-dihydrospiro[benzo[1,2-b:4,5-b']difuran-3,3'-indol]-2'(1'H)-one.

Another embodiment of the invention is a compound of formula (IV), as set forth above in the Summary of the Invention.

Of this embodiment, one embodiment is a compound of formula (IV) wherein each $R^8$ is independently hydrogen, hydroxy, bromo, chloro, cyano, fluoro, methyl, trifluoroacetyl, methoxy, 1-methylethoxy, 2-methoxyethoxy, benzyloxy, 1-(tert-butoxycarbonyl)pyrrolidin-3-yloxy, pyrrolidin-3-yloxy, amino, sulfonylamino, methylsulfonylamino, [(tert-butoxycarbonyl)pyrrolidin-3-yl]amino, 6-methoxypyridin-3-yl, 5-methyl-1,2,4-oxadiazol-3-yl, amino(hydroxyimino)methyl or (pyrrolidin-3-yl)amino.

Of this embodiment, another embodiment is a compound of formula (IV) wherein two $R^8$ groups, together with the adjacent carbons to which they are attached, form a fused dioxinyl ring, a fused thienyl ring, a fused 1,1-dioxothienyl ring, a fused 1,2,5-oxadiazolyl ring, a fused tetrahydropyranyl ring, a fused 2,3-dihydropyrazinyl ring, a fused 3-methyl-4,5-dihydroisoxazolyl ring or a fused pyrazinyl ring, and the remaining $R^8$ group, if present, is hydrogen, hydroxy, bromo, chloro, cyano, fluoro, methyl, trifluoroacetyl, methoxy, 1-methylethoxy, 2-methoxyethoxy, benzyloxy, 1-(tert-butoxycarbonyl)pyrrolidin-3-yloxy, pyrrolidin-3-yloxy, amino, sulfonylamino, methylsulfonylamino, [(tert-butoxycarbonyl)pyrrolidin-3-yl]amino, 6-methoxypyridin-3-yl, 5-methyl-1,2,4-oxadiazol-3-yl, amino(hydroxyimino)methyl or (pyrrolidin-3-yl)amino.

Of this embodiment, another embodiment is a compound of formula (IV) selected from:

1'-(pyridin-2-ylmethyl)spiro[furo[2,3-g]quinoxaline-8,3'-indol]-2'(1'H)-one;

1-(diphenylmethyl)spiro[indole-3,3'-thieno[2,3-f][1]benzofuran]-2'(1'H)-one;

1-(diphenylmethyl)spiro[indole-3,3'-thieno[2,3-f][1]benzofuran]-2'(1'H)-one 5,5'-dioxide; spiro[indole-3,3'-thieno[2,3-f][1]benzofuran]-2'(1'H)-one 5,5'-dioxide; or 1-(pyridin-2-ylmethyl)spiro[indole-3,3'-thieno[2,3-f][1]benzofuran]-2'(1'H)-one 5,5'-dioxide.

1'-(4-methoxybenzyl)-3-methylspiro[furo[2,3-f][1,2]benzisoxazole-7,3'-indol]-2'(1'H)-one;

5-(benzyloxy)-1'-[(5-chloro-2-thienyl)methyl]spiro[1-benzofuran-3,3'-indol]-2'(1'71)-one;

1-(diphenylmethyl)-6-methoxy-5-methylspiro[1-benzofuran-3,3'-indol]-2'(1'H)-one;

6-bromo-1-(diphenylmethyl)spiro[1-benzofuran-3,3'-indol]-2'(1'H)-one;

1'-(diphenylmethyl)-5,6-dimethylspiro[1-benzofuran-3,3'-indol]-2'(1'H)-one;

6-(benzyloxy)-1'-(diphenylmethyl)spiro[1-benzofuran-3,3'-indol]-2'(1'H)-one;

1'-(diphenylmethyl)-5-fluoro-6-methoxyspiro[1-benzofuran-3,3'-indol]-2'(1'H)-one;

1'-(diphenylmethyl)-5-fluorospiro[1-benzofuran-3,3'-indol]-2'(1'H)-one;

1'-(diphenylmethyl)-6-methoxyspiro[1-benzofuran-3,3'-indol]-2'(1'H)-one;

6-(benzyloxy)-1'-(3-methylbutyl)spiro[1-benzofuran-3,3'-indol]-2'(1'H)-one;

6-bromo-1-{[5-(trifluoromethyl)furan-2-yl]methyl}spiro[1-benzofuran-3,3'-indol]-2'(1'H)-one;

5-bromo-1-{[5-(trifluoromethyl)furan-2-yl]methyl}spiro[1-benzofuran-3,3'-indol]-2'(1'H)-one;

6-methoxy-5-methylspiro[1-benzofuran-3,3'-indol]-2'(1'H)-one;

6-bromospiro[1-benzofuran-3,3'-indol]-2'(1'H)-one;

5,6-dimethylspiro[1-benzofuran-3,3'-indol]-2'(1'H)-one;

5-fluoro-6-methoxyspiro[1-benzofuran-3,3'-indol]-2'(1'H)-one;

5-fluoro-spiro[1-benzofuran-3,3'-indol]-2'(1'H)-one;

6-methoxyspiro[1-benzofuran-3,3'-indol]-2'(1'H)-one;

6-hydroxyspiro[1-benzofuran-3,3'-indol]-2'(1'H)-one;

1'-(diphenylmethyl)-6-hydroxyspiro[1-benzofuran-3,3'-indol]-2'(1'H)-one;

tert-butyl 3-{[1-(diphenylmethyl)-2'-oxo-1',2'-dihydrospiro[1-benzofuran-3,3'-indol]-6-yl]oxy}pyrrolidine-1-carboxylate;

tert-butyl 3-[(2'-oxo-1',2'-dihydrospiro[1-benzofuran-3,3'-indol]-6-yl)oxy]pyrrolidine-1-carboxylate;

(3S)-6-methoxy-5-methylspiro[1-benzofuran-3,3'-indol]-2'(1'H)-one;

(3R)-6-methoxy-5-methylspiro[1-benzofuran-3,3'-indol]-2'(1'H)-one;

6-methoxy-5-methyl-1'-[(2R)-tetrahydrofuran-2-ylmethyl]spiro[1-benzofuran-3,3'-indol]-2'(1'H)-one;

6-methoxy-5-methyl-1'-(pyridin-2-ylmethyl)spiro[1-benzofuran-3,3'-indol]-2'(1'H)-one;

6-methoxy-5-methyl-1'-(tetrahydro-2H-pyran-2-ylmethyl)spiro[1-benzofuran-3,3'-indol]-2'(1'H)-one;

5-fluoro-6-methoxy-1'-(tetrahydro-2H-pyran-2-ylmethyl)spiro[1-benzofuran-3,3'-indol]-2'(1'H)-one;

5-fluoro-6-methoxy-1'-(pyridin-2-ylmethyl)spiro[1-benzofuran-3,3'-indol]-2'(1'H)-one;

5-fluoro-6-methoxy-1'-[(2R)-tetrahydrofuran-2-ylmethyl]spiro[1-benzofuran-3,3'-indol]-2'(1'H)-one;

1'-benzyl-5-fluoro-6-methoxyspiro[1-benzofuran-3,3'-indol]-2'(1'H)-one;

6-methoxy-1'-[(2R)-tetrahydrofuran-2-ylmethyl]spiro[1-benzofuran-3,3'-indol]-2'(1'H)-one;

6-bromo-1'-[1'-(2R)-tetrahydrofuran-2-ylmethyl]spiro[1-benzofuran-3,3'-indol]-2'(1'H)-one;

6-Fluoro-5-methoxy-1'-{[5-(trifluoromethyl)furan-2-yl]methyl}spiro[1-benzofuran-3,3'-indol]-2'(1'H)-one;

5,6-dimethyl-1'-(tetrahydro-2H-pyran-2-ylmethyl)spiro[1-benzofuran-3,3'-indol]-2'(1'H)-one;

5,6-dimethyl-1'-(tetrahydro-2H-pyran-4-ylmethyl)spiro[1-benzofuran-3,3'-indol]-2'(1'H)-one;

5,6-dimethyl-1'-(pyridin-2-ylmethyl)spiro[1-benzofuran-3,3'-indol]-2'(1'H)-one;

5-fluoro-6-methoxy-1'-(tetrahydro-2H-pyran-4-ylmethyl)spiro[1-benzofuran-3,3'-indol]-2'(1'H)-one;

5-fluoro-6-methoxy-1'-{[5-(trifluoromethyl)furan-2-yl]methyl}spiro[1-benzofuran-3,3'-indol]-2'(1'H)-one;

5,6-difluoro-1'-(pyridin-3-ylmethyl)spiro[1-benzofuran-3,3'-indol]-2'(1'H)-one;

5,6-difluoro-1'-{[5-(trifluoromethyl)furan-2-yl]methyl}spiro[1-benzofuran-3,3'-indol]-2'(1'H)-one;

6-methoxy-1'-(pyridin-2-ylmethyl)spiro[1-benzofuran-3,3'-indol]-2'(1'H)-one;

6-methoxy-1'-(pyridin-3-ylmethyl)spiro[1-benzofuran-3,3'-indol]-2'(1'H)-one;

6-methoxy-1'-(tetrahydro-2H-pyran-4-ylmethyl)spiro[1-benzofuran-3,3'-indol]-2'(1'H)-one;

6-methoxy-1'-(tetrahydro-2H-pyran-2-ylmethyl)spiro[1-benzofuran-3,3'-indol]-2'(1'H)-one;

6-amino-1'-[(2R)-tetrahydrofuran-2-ylmethyl]spiro[1-benzofuran-3,3'-indol]-2'(1'H)-one;

N-{2'-oxo-1'-[(2R)-tetrahydrofuran-2-ylmethyl]-1',2'-dihydrospiro[1-benzofuran-3,3'-indol]-6-yl}methanesulfonamide;

6-hydroxy-1'-(3-methylbutyl)spiro[1-benzofuran-3,3'-indol]-2'(1'H)-one;

6-hydroxy-1'-(3-methylbutyl)-5-(trifluoroacetyl)spiro[1-benzofuran-3,3'-indol]-2'(1'H)-one;

tert-butyl (3R)-3-[(2'-oxo-1'-{[5-(trifluoromethyl)furan-2-yl]methyl}-1',2'-dihydrospiro[1-benzofuran-3,3'-indol]-6-yl)amino]pyrrolidine-1-carboxylate;

6-[(3R)-pyrrolidin-3-ylamino]-1'-{[5-(trifluoromethyl)furan-2-yl]methyl}spiro[1-benzofuran-3,3'-indol]-2'(1'H)-one;

6-hydroxy-1'-[(2R)-tetrahydrofuran-2-ylmethyl]spiro[1-benzofuran-3,3'-indol]-2'(1'H)-one;

6-(1-methylethoxy)-1'-[(2R)-tetrahydrofuran-2-ylmethyl]spiro[1-benzofuran-3,3'-indol]-2'(1'H)-one;

tert-butyl (3S)-3-[(2'-oxo-1'-[(2R)-tetrahydrofuran-2-ylmethyl]-1',2'-dihydrospiro[1-benzofuran-3,3'-indol]-6-yl)oxy)pyrrolidine-1-carboxylate;

6-[(3S)-pyrrolidin-3-yloxy]-1'-[(2R)-tetrahydrofuran-2-ylmethyl]spiro[1-benzofuran-3,3'-indol]-2'(1'H)-one hydrochloride;

tert-butyl (3R)-3-({2'-oxo-1'-[(2R)-tetrahydrofuran-2-ylmethyl]-1',2'-dihydrospiro[1-benzofuran-3,3'-indol]-6-yl}oxy)pyrrolidine-1-carboxylate;

6-[(3R)-pyrrolidin-3-yloxy]-1'-[(2R)-tetrahydrofuran-2-ylmethyl]spiro[1-benzofuran-3,3'-indol]-2'(1'H)-one hydrochloride;

tert-butyl 3-[(2'-oxo-1'-{[5-(trifluoromethyl)furan-2-yl]methyl}-1',2'-dihydrospiro[1-benzofuran-3,3'-indol]-6-yl)oxy]pyrrolidine-1-carboxylate;

(3S)-6-methoxy-5-methyl-1'-[(4-methylpiperazin-1-yl)methyl]spiro[1-benzofuran-3,3'-indol]-2'(1'H)-one hydrogen chloride;

(3R)-6-methoxy-5-methyl-1'-[(4-methylpiperazin-1-yl)methyl]spiro[1-benzofuran-3,3'-indol]-2'(1'H)-one hydrogen chloride;

6-hydroxy-1'-(4-methoxybenzyl)-2'-oxo-1',2'-dihydrospiro[1-benzofuran-3,3'-indole]-5-carbonitrile;

6-fluoro-1'-(4-methoxybenzyl)-2'-oxo-1',2'-dihydrospiro[1-benzofuran-3,3'-indole]-5-carbonitrile;

1'-(diphenylmethyl)-2'-oxo-1',2'-dihydrospiro[1-benzofuran-3,3'-indole]-6-carbonitrile;

1'-(diphenylmethyl)-5,6-difluorospiro[1-benzofuran-3,3'-indol]-2'(1'H)-one;

1'-(diphenylmethyl)-6-(2-methoxyethoxy)spiro[1-benzofuran-3,3'-indol]-2'(1'H)-one;

5-(benzyloxy)-1'-(diphenylmethyl)spiro[1-benzofuran-3,3'-indol]-2'(1'H)-one;

1'-(diphenylmethyl)-5-hydroxyspiro[1-benzofuran-3,3'-indol]-2'(1'H)-one;

1'-(diphenylmethyl)-5-(2-methoxyethoxy)spiro[1-benzofuran-3,3'-indol]-2'(1'H)-one;

1'-(diphenylmethyl)-2,3-dihydrospiro[furo[2,3-f][1,4]benzodioxine-7,3'-indol]-2'(1'H)-one;

1'-(diphenylmethyl)spiro[furo[3,2-e][2,1,3]benzoxadiazole-8,3'-indol]-2'(1'H)-one;

6-chloro-1'-(diphenylmethyl)-2,3-dihydrospiro[furo[3,2-f][1,4]benzodioxine-9,3'-indol]-2'(1'H)-one;

1'-(diphenylmethyl)-9-fluoro-2,3-dihydro-spiro[furo[2,3-g][1,4]benzodioxine-8,3'-indol]-2'(1'H)-one;

1-(diphenylmethyl)-7,8-dihydro-6H-spiro[furo[2,3-g]chromene-3,3'-indol]-2'(1'H)-one;

1'-(diphenylmethyl)spiro[furo[2,3-g]quinoxaline-8,3'-indol]-2'(1'H)-one;

6-methoxy-2'-oxo-1',2'-dihydrospiro[1-benzofuran-3,3'-indole]-5-carbonitrile;

6-fluoro-2'-oxo-1',2'-dihydrospiro[1-benzofuran-3,3'-indole]-5-carbonitrile;

2'-oxo-1',2'-dihydrospiro[1-benzofuran-3,3'-indole]-6-carbonitrile;

2,3-dihydrospiro[furo[3,2-f][1,4]benzodioxine-9,3'-indol]-2'(1'H)-one;

5,6-difluorospiro[1-benzofuran-3,3'-indol]-2'(1'H)-one;

6-(2-methoxyethoxy)spiro[1-benzofuran-3,3'-indol]-2'(1'H)-one;

5-(2-methoxyethoxy)spiro[1-benzofuran-3,3'-indol]-2'(1'H)-one;

2,3-dihydrospiro[furo[2,3-f][1,4]benzodioxine-7,3'-indol]-2'(1'H)-one; spiro[furo[2,3-g]quinoxaline-8,3'-indol]-2'(1'H)-one;

2'-oxo-1'-(pyridin-2-ylmethyl)-1',2'-dihydrospiro[1-benzofuran-3,3'-indole]-6-carbonitrile;

1'-(2,3-dihydro-1,4-benzodioxin-6-ylmethyl)-2'-oxo-1',2'-dihydrospiro[1-benzofuran-3,3'-indole]-6-carbonitrile;

1'-(pyridin-2-ylmethyl)spiro[furo[3,2-e][2,1,3]benzoxadiazole-8,3'-indol]-2'(1'H)-one;

1'-(pyridin-3-ylmethyl)spiro[furo[3,2-e][2,1,3]benzoxadiazole-8,3'-indol]-2'(1'H)-one;

tert-butyl 4-[(5,6-difluoro-2'-oxospiro[1-benzofuran-3,3'-indol]-1'(2'H)-yl)methyl]piperidine-1-carboxylate;

6-(2-methoxyethoxy)-1'-(pyridin-2-ylmethyl)spiro[1-benzofuran-3,3'-indol]-2'(1'H)-one;

5-(2-methoxyethoxy)-1'-(pyridin-2-ylmethyl)spiro[1-benzofuran-3,3'-indol]-2'(1'H)-one;

1'-(pyridin-2-ylmethyl)-2,3-dihydrospiro[furo[2,3-f][1,4]benzodioxine-7,3'-indol]-2'(1'H)-one;

1'-{[3-(trifluoromethyl)pyridin-2-yl]methyl}-2,3-dihydrospiro[furo[2,3-f][1,4]benzodioxine-7,3'-indol]-2'(1'H)-one;

6-methoxy-1'-(4-methoxybenzyl)-2'-oxo-1',2'-dihydrospiro[1-benzofuran-3,3'-indole]-5-carbonitrile;

6-methoxy-2'-oxo-1'-(pyridin-2-ylmethyl)-1',2'-dihydrospiro[1-benzofuran-3,3'-indole]-5-carbonitrile;

6-fluoro-2'-oxo-1'-(pyridin-2-ylmethyl)-1',2'-dihydrospiro[1-benzofuran-3,3'-indole]-5-carbonitrile;

6-fluoro-2'-oxo-1'-[(2R)-tetrahydrofuran-2-ylmethyl]-1',2'-dihydrospiro[1-benzofuran-3,3'-indole]-5-carbonitrile;

6-fluoro-2'-oxo-1'-[2-(trifluoromethyl)benzyl]-1',2'-dihydrospiro[1-benzofuran-3,3'-indole]-5-carbonitrile;

6-fluoro-2'-oxo-1'-{[3-(trifluoromethyl)pyridin-2-yl]methyl}-1',2'-dihydrospiro[1-benzofuran-3,3'-indole]-5-carbonitrile;
1'-(4-bromobenzyl)-5,6-difluorospiro[1-benzofuran-3,3'-indol]-2'(1'H)-one;
5,6-difluoro-1'-(3-methylbutyl)spiro[1-benzofuran-3,3'-indol]-2'(1'H)-one;
5,6-difluoro-1'-(pyridin-2-ylmethyl)spiro[1-benzofuran-3,3'-indol]-2'(1'H)-one;
5,6-difluoro-1'-(tetrahydro-2H-pyran-4-ylmethyl)spiro[1-benzofuran-3,3'-indol]-2'(1'H)-one;
1'-{[5-(benzyloxy)pyridin-2-yl]methyl}spiro[furo[3,2-e][2,1,3]benzoxadiazole-8,3'-indol]-2'(1'H)-one;
6-(2-methoxyethoxy)-1'-[2-(2-methoxyethoxy)ethyl]spiro[1-benzofuran-3,3'-indol]-2'(1'H)-one;
5-(2-methoxyethoxy)-1'-[2-(2-methoxyethoxy)ethyl]spiro[1-benzofuran-3,3'-indol]-2'(1'H)-one;
1'-{[3-(trifluoromethyl)pyridin-2-yl]methyl}spiro[furo[3,2-e][2,1,3]benzoxadiazole-8,3'-indol]-2'(1'H)-one;
1'-{[3-(trifluoromethyl)pyridin-2-yl]methyl}-2,3-dihydrospiro[furo[3,2-f][1,4]benzodioxine-9,3'-indol]-2'(1'H)-one;
5,6-difluoro-1'-(piperidin-4-ylmethyl)spiro[1-benzofuran-3,3'-indol]-2'(1'H)-one hydrochloride;
5,6-difluoro-1'-[(1-methylpiperidin-4-yl)methyl]spiro[1-benzofuran-3,3'-indol]-2'(1'H)-one hydrochloride;
N',6-dihydroxy-1'-(4-methoxybenzyl)-2'-oxo-1',2'-dihydrospiro[1-benzofuran-3,3'-indole]-5-carboximidamide;
6-hydroxy-2'-oxo-1'-[(2R)-tetrahydrofuran-2-ylmethyl]-1',2'-dihydrospiro[1-benzofuran-3,3'-indole]-5-carbonitrile;
6-hydroxy-2'-oxo-1'-[2-(trifluoromethyl)benzyl]-1',2'-dihydrospiro[1-benzofuran-3,3'-indole]-5-carbonitrile;
1'-[(5-chloro-2-thienyl)methyl]-5-(6-methoxypyridin-3-yl)spiro[1-benzofuran-3,3'-indol]-2'(1'H)-one;
5,6-difluoro-1'-{4-[(3R)-pyrrolidin-3-ylamino]benzyl}spiro[1-benzofuran-3,3'-indol]-2'(1'H)-one hydrochloride;
9-fluoro-2,3-dihydro-spiro[furo[2,3-g][1,4]benzodioxine-8,3'-indol]-2'(1'H)-one;
7,8-dihydro-6H-spiro[furo[2,3-g]chromene-3,3'-indol]-2'(1'H)-one;
6-chloro-2,3-dihydrospiro[furo[3,2-f][1,4]benzodioxine-9,3'-indol]-2'(1'H)-one; spiro[furo[3,2-e][2,1,3]benzoxadiazole-8,3'-indol]-2'(1'H)-one;
6-chloro-1'-(pyridin-2-ylmethyl)-2,3-dihydrospiro[furo[3,2-f][1,4]benzodioxine-9,3'-indol]-2'(1'H)-one;
1'-(pyridin-2-ylmethyl)-2,3-dihydrospiro[furo[3,2-f][1,4]benzodioxine-9,3'-indol]-2'(1'H)-one;
9-fluoro-1'-(pyridin-2-ylmethyl)-2,3-dihydro-spiro[furo[2,3-g][1,4]benzodioxine-8,3'-indol]-2'(1'H)-one;
9-fluoro-1'-{[3-(trifluoromethyl)pyridin-2-yl]methyl}-2,3-dihydrospiro[furo[2,3-g][1,4]benzodioxine-8,3'-indol]-2'(1'H)-one;
9-fluoro-1'-[(5-hydroxypyridin-2-yl)methyl]-2,3-dihydrospiro[furo[2,3-g][1,4]benzodioxine-8,3'-indol]-2'(1'H)-one;
6-(5-methyl-1,2,4-oxadiazol-3-yl)-1'-(pyridin-2-ylmethyl)spiro[1-benzofuran-3,3'-indol]-2'(1'H)-one; and
6-chloro-1'-{[3-(trifluoromethyl)pyridin-2-yl]methyl}-2,3-dihydrospiro[furo[3,2-f][1,4]benzodioxine-9,3'-indol]-2'(1'H)-one.

Another embodiment of the invention is a compound of formula (V), as set forth above in the Summary of the Invention.

Of this embodiment, one embodiment is a compound of formula (V) selected from the group consisting of:
1'-(diphenylmethyl)-3,4-dihydro-2H-spiro[furo[2,3-h][1,5]benzodioxepine-9,3'-indol]-2'(1'H)-one;
3,4-dihydro-2H-spiro[furo[2,3-h][1,5]benzodioxepine-9,3'-indol]-2'(1'H)-one;
1'-{[5-(trifluoromethyl)furan-2-yl]methyl}-3,4-dihydro-2H-spiro[furo[2,3-h][1,5]benzodioxepine-9,3'-indol]-2'(1'H)-one;
1'-(pyridin-2-ylmethyl)-3,4-dihydro-2H-spiro[furo[2,3-h][1,5]benzodioxepine-9,3'-indol]-2'H)-one;
1'-[(2R)-tetrahydrofuran-2-ylmethyl]-3,4-dihydro-2H-spiro[furo[2,3-h][1,5]benzodioxepine-9,3'-indol]-2'(1'H)-one;
1'-[(2R)-1,4-dioxan-2-ylmethyl]-3,4-dihydro-2H-spiro[furo[2,3-h][1,5]benzodioxepine-9,3'-indol]-2'(1'H)-one; or
1'-[(2S)-1,4-dioxan-2-ylmethyl]-3,4-dihydro-2H-spiro[furo[2,3-h][1,5]benzodioxepine-9,3'-indol]-2'(1'H)-one.

Another embodiment of the invention is a compound of formula (VI), as set forth above in the Summary of the Invention.

Of this embodiment, one embodiment is a compound of formula (VI) wherein Z is —O— or —N(H)— and $R^{10a}$ is hydrogen or methyl.

Of this embodiment, one embodiment is a compound of formula (VI) wherein Z is —O— and $R^{10}$ is methyl.

Of this embodiment, one embodiment is a compound of formula (VI) wherein Z is —N(H)— and $R^{10a}$ is hydrogen.

Of this embodiment, one embodiment is a compound of formula (VI) selected from:
1'-[2-(trifluoromethyl)benzyl]-1H-spiro[furo[3,2-f]indazole-5,3'-indol]-2'(1'H)-one;
1'-(pyridin-2-ylmethyl)-1H-spiro[furo[3,2-f]indazole-5,3'-indol]-2'(1'H)-one;
1'-((3-(trifluoromethyl)pyridin-2-yl)methyl)-1,6-dihydrospiro[furo[3,24]indazole-5,3'-indolin]-2'-one;
1'-(4-methoxybenzyl)-3-methylspiro[furo[3,2-f][1,2]benzisoxazole-5,3'-indol]-2'(1'H)-one;
3-methylspiro[furo[3,2-f][1,2]benzisoxazole-5,3'-indol]-2'(1'H)-one;
3-methyl-1'-{[5-(trifluoromethyl)furan-2-yl]methyl}spiro[furo[3,2-f][1,2]benzisoxazole-5,3'-indol]-2'(1'H)-one;
3-methyl-1'-(pyridin-2-ylmethyl)spiro[furo[3,2-f][1,2]benzisoxazole-5,3'-indol]-2'(1'H)-one;
3-methyl-1'-(pyridin-3-ylmethyl)spiro[furo[3,2-f][1,2]benzisoxazole-5,3'-indol]-2'(1'H)-one;
3-methyl-1'-[(2R)-tetrahydrofuran-2-ylmethyl]spiro[furo[3,2-f][1,2]benzisoxazole-5,3'-indol]-2'(1'H)-one;
1'-(4-isoxazol-5-ylbenzyl)-3-methylspiro[furo[3,2-f][1,2]benzisoxazole-5,3'-indol]-2'(1'H)-one;
3-methyl-1'-[2-(trifluoromethyl)benzyl]spiro[furo[3,2-f][1,2]benzisoxazole-5,3'-indol]-2'(1'H)-one;
3-methyl-1'-{[3-(trifluoromethyl)pyridin-2-yl]methyl}spiro[furo[3,2-f][1,2]benzisoxazole-5,3'-indol]-2'(1'H)-one;
1'-[2-(2-methoxyethoxy)ethyl]-3-methylspiro[furo[3,2-f][1,2]benzisoxazole-5,3'-indol]-2'(1'H)-one;
3-methyl-1'-(3-methylbutyl)spiro[furo[3,2-f][1,2]benzisoxazole-5,3'-indol]-2'(1'H)-one;
3-methyl-1'-(pyrazin-2-ylmethyl)spiro[furo[3,2-f][1,2]benzisoxazole-5,3'-indol]-2'(1'H)-one;
1'-[(3-fluoropyridin-2-yl)methyl]-3-methylspiro[furo[3,2-f][1,2]benzisoxazole-5,3'-indol]-2'(1'H)-one;
methyl 2-[(3-methyl-2'-oxospiro[furo[3,2-f][1,2]benzisoxazole-5,3'-indol]-1'(2'H)-yl)methyl]-1,3-oxazole-4-carboxylate;
2-[(3-methyl-2'-oxospiro[furo[3,2-f][1,2]benzisoxazole-5,3'-indol]-1'(2'H)-yl)methyl]-1,3-oxazole-4-carboxylic acid;
N,N-dimethyl-2-[(3-methyl-2'-oxospiro[furo[3,2-f][1,2]benzisoxazole-5,3'-indol]-1'(2'H)-yl) methyl]-1,3-oxazole-4-carboxamide;

3-{4-[(3-methyl-2'-oxospiro[furo[3,2-f][1,2]benzisoxazole-5,3'-indol]-1'(2'H)-yl)methyl]phenyl}-3-oxopropanenitrile; or 1'-[4-(3-amino-1H-pyrazol-5-yl)benzyl]-3-methylspiro[furo[3,2-f][1,2]benzisoxazole-5,3'-indol]-2'(1'H)-one hydrochloride.

Of this embodiment, one embodiment is a compound of formula (VI) wherein $R^{10a}$ is —NH$_2$.

Of this embodiment, one embodiment is a compound of formula (VI) selected from:

3-amino-1'-(4-methoxybenzyl)spiro[furo[3,2-f][1,2]benzisoxazole-5,3'-indol]-2'(1'H)-one;

3-amino-1'-(pyridin-2-ylmethyl)spiro[furo[3,2-f][1,2]benzisoxazole-5,3'-indol]-2'(1'H)-one;

3-amino-1-[(2R)-tetrahydrofuran-2-ylmethyl]spiro[furo[3,2-f][1,2]benzisoxazole-5,3'-indol]-2'(1'H)-one; or 3-amino-1'-[2-(trifluoromethyl)benzyl]spiro[furo[3,2-f][1,2]benzisoxazole-5,3'-indol]-2'(1'H)-one.

Another embodiment of the invention is a compound of formula (VII), as set forth above in the Summary of the Invention.

Of this embodiment, one embodiment is a compound of formula (VII) wherein Y is —O—.

Of this embodiment, another embodiment is a compound of formula (VII) wherein Y is —S—.

Of this embodiment, another embodiment is a compound of formula (VII) selected from:

2-methylspiro[furo[2,3-f][1,3]benzothiazole-7,3'-indol]-2'(1'H)-one;

1'-(diphenylmethyl)-2-methylspiro[furo[2,3-f][1,3]benzoxazole-7,3'-indol]-2'(1'H)-one;

2-methylspiro[furo[2,3-f][1,3]benzoxazole-7,3'-indol]-2'(1'H)-one;

2-methyl-1'-(3-methylbutyl)spiro[furo[2,3-f][1,3]benzothiazole-7,3'-indol]-2'(1'H)-one;

2-methyl-1'-(tetrahydro-2H-pyran-4-ylmethyl)spiro[furo[2,3-f][1,3]benzothiazole-7,3'-indol]-2'(1'H)-one;

2-methyl-1'-[(2R)-tetrahydrofuran-2-ylmethyl]spiro[furo[2,3-f][1,3]benzoxazole-7,3'-indol]-2'(1'H)-one;

2-methyl-1'-(pyridin-2-ylmethyl)spiro[furo[2,3-f][1,3]benzothiazole-7,3'-indol]-2'(1'H)-one; or 1'-[(5-chloro-1-methyl-1H-imidazol-2-yl)methyl]-2-methylspiro[furo[2,3-f][1,3]benzothiazole-7,3'-indol]-2'(1'H)-one.

Another embodiment of the invention is a compound of formula (VIII), as set forth above in the Summary of the Invention.

Of this embodiment, one embodiment is a compound of formula (VIII) wherein W is a direct bond.

Of this embodiment, one embodiment is a compound of formula (VIII) selected from:

1'-(diphenylmethyl)-1-methylspiro[furo[3,2-f][1,3]benzoxazole-7,3'-indole]-2,2'(1'H,1'H)-dione;

1-methylspiro[furo[3,2-f][1,3]benzoxazole-7,3'-indole]-2,2'(1'H,1'H)-dione; or 1-methyl-1'-[(2R)-tetrahydrofuran-2-ylmethyl]spiro[furo[3,2-f][1,3]benzoxazole-7,3'-indole]-2,2'(1'H,1'H)-dione.

Of this embodiment, one embodiment is a compound of formula (VIII) wherein W is —CH$_2$—.

Of this embodiment, one embodiment is a compound of formula (VIII) selected from:

1'-(diphenylmethyl)-1-methyl-1H-spiro[furo[3,2-g][1,4]benzoxazine-8,3'-indole]-2,2'(1'H,3H)-dlone;

1-methyl-1H-spiro[furo[3,2-g][1,4]benzoxazine-8,3'-indole]-2,2'(1'H,3H)-dione; or 1-methyl-1'-[(2R)-tetrahydrofuran-2-yl methyl]-1H-spiro[furo[3,2-g][1,4]benzoxazine-8,3'-indole]-2,2'(1'H,3H)-dione.

Another embodiment of the invention is a compound of formula (IX), as set forth above in the Summary of the Invention.

Of this embodiment, one embodiment is a compound of formula (IX) wherein U is a direct bond.

Of this embodiment, one embodiment is a compound of formula (IX) selected from:

1'-(diphenylmethyl)-3-methylspiro[furo[2,3-f][1,3]benzoxazole-7,3'-indole]-2,2'(1'H,3H)-dione;

3-methylspiro[furo[2,3-f][1,3]benzoxazole-7,3'-indole]-2,2'(1'H,3H)-dione;

3-methyl-1'-{[5-(trifluoromethyl)furan-2-yl]methyl}spiro[furo[2,3-f][1,3]benzoxazole-7,3'-indole]-2,2'(1'H,3H)-dione; or 3-methyl-1'-(((R)-tetrahydrofuran-2-yl)methyl)-2H-spiro[benzofuro[6,5-d]oxazole-7,3'-indoline]-2,2'(3H,6H)-dione.

Of this embodiment, one embodiment is a compound of formula (IX) wherein U is —CH$_2$—.

Of this embodiment, one embodiment is a compound of formula (IX) selected from:

4-methyl-4,7-dihydrospiro[benzofuro[5,6-b][1,4]oxazine-8,3'-indoline]-2',3(2H)-dione; or 4-methyl-1'-[(2R)-tetrahydrofuran-2-ylmethyl]-2H-spiro[furo[2,3-g][1,4]benzoxazine-8,3'-indole]-2',3(1'H,4H)-dione.

Another embodiment of the invention is a compound of formula (X), as set forth above in the Summary of the Invention, which is 1'-[(2R)-tetrahydrofuran-2-ylmethyl]spiro[benzo[1,2-b:5,4-b']difuran-3,3'-indole]-2',5(1'H,6H)-dione.

Another embodiment of the invention is a compound of formula (XI), as set forth above in the Summary of the Invention.

Of this embodiment, one embodiment is a compound of formula (XI) wherein both V and Y are each —CH$_2$—.

Of this embodiment, one embodiment is a compound of formula (XI) selected from:

1-(diphenylmethyl)-5',6',7',8'-tetrahydrospiro[indole-3,3'-naphtho[2,3-b]furan]-2(1'H)-one;

5',6',7',8'-tetrahydrospiro[indole-3,3'-naphtho[2,3-b]furan]-2(1'H)-one; or

1-[(2R)-tetrahydrofuran-2-ylmethyl]-5',6', 7', 8'-tetrahydrospiro[indole-3,3'-naphtho[2,3-b]furan]-2(1'H)-one.

Of this embodiment, one embodiment is a compound of formula (XI) wherein V is —O— and Y is —N(CH$_3$)—.

Of this embodiment, one embodiment is a compound of formula (XI) selected from:

1-methyl-1-{[5-(trifluoromethyl)furan-2-yl]methyl}-2,3-dihydro-1H-spiro[furo[3,2-g][1,4]benzoxazine-8,3'-indol]-2'(1'H)-one hydrochloride; or 1-methyl-1-[(2R)-tetrahydrofuran-2-ylmethyl]-2,3-dihydro-1H-spiro[furo[3,2-g][1,4]benzoxazine-8,3'-indol]-2'(1'H)-one hydrochloride.

Of this embodiment, one embodiment is a compound of formula (XI) wherein V is —N(CH$_3$)— and Y is —O—.

Of this embodiment, one embodiment is a compound of formula (XI) which is 4-methyl-1'-[(2R)-tetrahydrofuran-2-ylmethyl]-3,4-dihydro-2H-spiro[furo[2,3-g][1,4]benzoxazine-8,3'-indol]-2'(1'H)-one.

Of this embodiment, one embodiment is a compound of formula (XI) wherein V is —CH$_2$— and Y is —O—.

Of this embodiment, one embodiment is a compound of formula (XI) selected from:

1-(pyridin-2-ylmethyl)-7,8-dihydro-6H-spiro-[furo[2,3-g] chromene-3,3'-indol]-2'(1'H)-one; or 1'-{[3-(trifluoromethyl)pyridin-2-yl]methyl}-7,8-dihydro-6H-spiro[furo[2,3-g]chromene-3,3'-indol]-2'(1'H)-one.

Another embodiment of the invention is a compound of formula (XII), as set forth above in the Summary of the Invention.

Of this embodiment, one embodiment is a compound of formula (XII) selected from:

6-methyl-1'-(pyridin-2-ylmethyl)-2,3-dihydrospiro[1,4-dioxino[2,3-f]indole-8,3'-indole]-2',7(1'H,6H)-dione; or 6-methyl-2,3-dihydrospiro[1,4-dioxino[2,3-f]indole-8,3'-indole]-2',7(1'H,6H)-dione.

Another embodiment of the invention is a compound of formula (XIII), as set forth above in the Summary of the Invention.

Of this embodiment, one embodiment is a compound of formula (XIII) selected from:

1'-(diphenylmethyl)-2,3,6,7-tetrahydrospiro[furo[3,2-g] chromene-5,3'-indol]-2'(1'H)-one;

1'-{[3-(trifluoromethyl)pyridin-2-yl]methyl}-7,8-dihydrospiro[1,4-dioxino[2,3-g][1,3]-benzodioxine-4,3'-indol]-2'(1'H)-one;

2,3,6,7-tetrahydrospiro[furo[3,2-g]chromene-5,3'-indol]-2' (1'H)-one; or

1'-{[5-(trifluoromethyl)furan-2-yl]methyl}-2,3,6,7-tetrahydrospiro[furo[3,2-g]chromene-5,3'-indol]-2'(1'H)-one.

Another embodiment of the invention is a compound of formula (Ia):

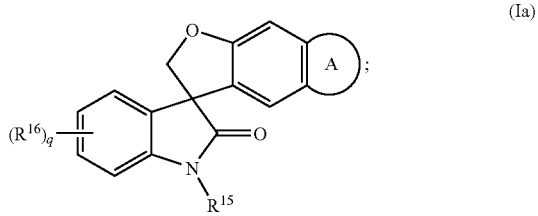

wherein:

R$^{15}$ is as defined for R$^1$, R$^3$, R$^5$, R$^7$, R$^9$, R$^{10}$, R$^{11}$, R$^{12}$, R$^{13}$ or R$^{14}$ in compounds of formula (I), formula (II), formula (III), formula (IV), formula (V), formula (VI), formula (VII), formula (VII), formula (VIII), formula (IX) and formula (XI), respectively, as set forth above in the Summary of the Invention;

R$^{16}$ is as defined for R$^2$, R$^4$ or R$^6$ in compounds of formula (I), formula (II) and formula (III), respectively, as set forth above in the Summary of the Invention; and

is a fused ring selected from the following:

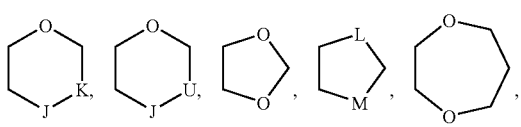

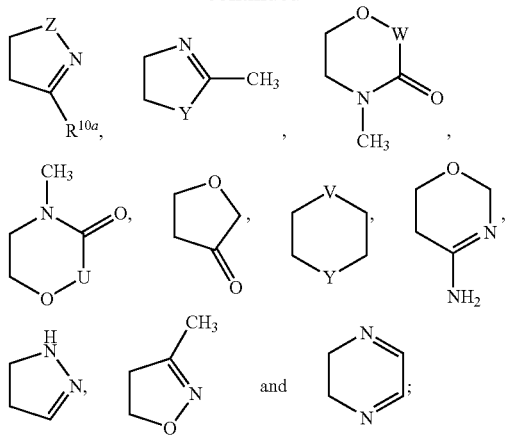

where J, K, L, M, U, V, W, Y and Z are as described as for the compounds of formula (I), formula (III), formula (VI), formula (VII), formula (VIII), formula (IX), formula (XI) and formula (XIII), as set forth above in the Summary of the Invention;

or

is a single substituent (i.e. not a fused ring) on the phenyl ring selected from —N(R$^{26}$)R$^{27}$, —OR$^{30}$ or —C(O)R$^{31}$ where R$^{26}$ and R$^{27}$ are each independently hydrogen, alkyl, optionally substituted aryl or optionally substituted heteroaryl; R$^{30}$ is alkyl, cycloalkyl or heterocyclyl, and R$^{31}$ is alkyl or haloalkyl;

as a stereoisomer, enantiomer, tautomer thereof or mixtures thereof;

or a pharmaceutically acceptable salt, solvate or prodrug thereof.

Another embodiment of the invention is a method of treating, preventing or ameliorating a disease or a condition in a mammal, preferably a human, wherein the disease or condition is selected from the group consisting of pain, depression, cardiovascular diseases, respiratory diseases, and psychiatric diseases, and combinations thereof, and wherein the method comprises administering to the mammal in need thereof a therapeutically effective amount of an embodiment of a compound of the invention, as set forth above, as a stereoisomer, enantiomer, tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer, tautomer thereof or mixtures thereof, or a pharmaceutically acceptable salt, solvate or prodrug thereof, and a pharmaceutically acceptable excipient.

One embodiment of this embodiment is wherein the disease or condition is selected from the group consisting of neuropathic pain, inflammatory pain, visceral pain, cancer pain, chemotherapy pain, trauma pain, surgical pain, post-surgical pain, childbirth pain, labor pain, neurogenic bladder, ulcerative colitis, chronic pain, persistent pain, peripherally mediated pain, dental pain, centrally mediated pain, chronic headache, migraine headache, sinus headache, tension headache, phantom limb pain, peripheral nerve injury, and combinations thereof.

Another embodiment of this embodiment is wherein the disease or condition is selected from the group consisting of pain associated with HIV, HIV treatment induced neuropathy, trigeminal neuralgia, post-herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritic, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, familial erythromelagia, primary erythromelagia, familial rectal pain, cancer, epilepsy, partial and general tonic seizures, restless leg syndrome, arrhythmias, fibromyalgia, neuroprotection under ischaemic conditions caused by stroke or neural trauma, tachy-arrhythmias, atrial fibrillation and ventricular fibrillation.

Another embodiment of the invention is the method of treating pain in a mammal, preferably a human, by the inhibition of ion flux through a voltage-dependent sodium channel in the mammal, wherein the method comprises administering to the mammal in need thereof a therapeutically effective amount of an embodiment of a compound of the invention, as set forth above, as a stereoisomer, enantiomer, tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer, tautomer thereof or mixtures thereof, or a pharmaceutically acceptable salt, solvate or prodrug thereof, and a pharmaceutically acceptable excipient.

Another embodiment of the invention is the method of treating or preventing hypercholesterolemia in a mammal, preferably a human, wherein the method comprises administering to the mammal in need thereof a therapeutically effective amount of an embodiment of a compound of the invention, as set forth above, as a stereoisomer, enantiomer, tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer, tautomer thereof or mixtures thereof, or a pharmaceutically acceptable salt, solvate or prodrug thereof, and a pharmaceutically acceptable excipient.

Another embodiment of the invention is the method of treating or preventing benign prostatic hyperplasia in a mammal, preferably a human, wherein the method comprises administering to the mammal in need thereof a therapeutically effective amount of an embodiment of a compound of the invention, as set forth above, as a stereoisomer, enantiomer, tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer, tautomer thereof or mixtures thereof, or a pharmaceutically acceptable salt, solvate or prodrug thereof, and a pharmaceutically acceptable excipient.

Another embodiment of the invention is the method of treating or preventing pruritis in a mammal, preferably a human, wherein the method comprises administering to the mammal in need thereof a therapeutically effective amount of an embodiment of a compound of the invention, as set forth above, as a stereoisomer, enantiomer, tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer, tautomer thereof or mixtures thereof, or a pharmaceutically acceptable salt, solvate or prodrug thereof, and a pharmaceutically acceptable excipient.

Another embodiment of the invention is the method of treating or preventing cancer in a mammal, preferably a human, wherein the method comprises administering to the mammal in need thereof a therapeutically effective amount of an embodiment of a compound of the invention, as set forth above, as a stereoisomer, enantiomer, tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer, tautomer thereof or mixtures thereof, or a pharmaceutically acceptable salt, solvate or prodrug thereof, and a pharmaceutically acceptable excipient.

Another embodiment of the invention is the method of decreasing ion flux through a voltage-dependent sodium channel in a cell in a mammal, wherein the method comprises contacting the cell with an embodiment of a compound of the invention, as set forth above, as a stereoisomer, enantiomer, tautomer thereof or mixtures thereof, or a pharmaceutically acceptable salt, solvate or prodrug thereof.

Specific embodiments of the compounds of the invention are described in more detail below in the Preparation of the Compounds of the Invention.

Utility and Testing of the Compounds of the Invention

The compounds of the invention modulate, preferably inhibit, ion flux through a voltage-dependent sodium channel in a mammal, especially in a human. Any such modulation, whether it be partial or complete inhibition or prevention of ion flux, is sometimes referred to herein as "blocking" and corresponding compounds as "blockers" or "inhibitors". In general, the compounds of the invention modulate the activity of a sodium channel downwards, inhibit the voltage-dependent activity of the sodium channel, and/or reduce or prevent sodium ion flux across a cell membrane by preventing sodium channel activity such as ion flux.

The compounds of the invention inhibit the ion flux through a voltage-dependent sodium channel. Preferably, the compounds are state or frequency dependent modifiers of the sodium channels, having a low affinity for the rested/closed state and a high affinity for the inactivated state. These compounds are likely to interact with overlapping sites located in the inner cavity of the sodium conducting pore of the channel similar to that described for other state-dependent sodium channel blockers (Cestèle, S., et al., *op. cit.*). These compounds may also be likely to interact with sites outside of the inner cavity and have allosteric effects on sodium ion conduction through the channel pore.

Any of these consequences may ultimately be responsible for the overall therapeutic benefit provided by these compounds.

Accordingly, the compounds of the invention are sodium channel blockers and are therefore useful for treating diseases and conditions in mammals, preferably humans, and other organisms, including all those human diseases and conditions which are the result of aberrant voltage-dependent sodium channel biological activity or which may be ameliorated by modulation of voltage-dependent sodium channel biological activity.

As defined herein, a sodium channel-mediated disease or condition refers to a disease or condition in a mammal, preferably a human, which is ameliorated upon modulation of the sodium channel and includes, but is not limited to, pain, central nervous conditions such as epilepsy, anxiety, depression and bipolar disease; cardiovascular conditions such as arrhythmias, atrial fibrillation and ventricular fibrillation; neuromuscular conditions such as restless leg syndrome and muscle paralysis or tetanus; neuroprotection against stroke, neural trauma and multiple sclerosis; and channelopathies such as erythromyalgia and familial rectal pain syndrome.

The present invention therefore relates to compounds, pharmaceutical compositions and methods of using the compounds and pharmaceutical compositions for the treatment of sodium channel-mediated diseases in mammals, preferably humans and preferably diseases related to pain, central nervous conditions such as epilepsy, anxiety, depression and bipolar disease; cardiovascular conditions such as arrhythmias, atrial fibrillation and ventricular fibrillation; neuromuscular conditions such as restless leg syndrome and muscle paralysis or tetanus; neuroprotection against stroke, neural trauma and multiple sclerosis; and channelopathies such as erythromyalgia and familial rectal pain syndrome, by administering to a mammal, preferably a human, in need of such treatment an effective amount of a sodium channel blocker modulating, especially inhibiting, agent.

Accordingly, the present invention provides a method for treating a mammal for, or protecting a mammal from developing, a sodium channel-mediated disease, especially pain, comprising administering to the mammal, especially a human, in need thereof, a therapeutically effective amount of a compound of the invention or a pharmaceutical composition comprising a therapeutically effective amount of a compound of the invention wherein the compound modulates the activity of one or more voltage-dependent sodium channels.

The general value of the compounds of the invention in mediating, especially inhibiting, the sodium channel ion flux can be determined using the assays described below in the Biological Assays section. Alternatively, the general value of the compounds in treating conditions and diseases in humans may be established in industry standard animal models for demonstrating the efficacy of compounds in treating pain. Animal models of human neuropathic pain conditions have been developed that result in reproducible sensory deficits (allodynia, hyperalgesia, and spontaneous pain) over a sustained period of time that can be evaluated by sensory testing. By establishing the degree of mechanical, chemical, and temperature induced allodynia and hyperalgesia present, several physiopathological conditions observed in humans can be modeled allowing the evaluation of pharmacotherapies.

In rat models of peripheral nerve injury, ectopic activity in the injured nerve corresponds to the behavioural signs of pain. In these models, intravenous application of the sodium channel blocker and local anesthetic lidocaine can suppress the ectopic activity and reverse the tactile allodynia at concentrations that do not affect general behaviour and motor function (Mao, J. and Chen, L. L, *Pain* (2000), 87:7-17). Allimetric scaling of the doses effective in these rat models, translates into doses similar to those shown to be efficacious in humans (Tanelian, D. L. and Brose, W. G., *Anesthesiology* (1991), 74(5):949-951). Furthermore, Lidoderm®, lidocaine applied in the form of a dermal patch, is currently an FDA approved treatment for post-herpetic neuralgia (Devers, A. and Glaler, B. S., *Clin. J. Pain* (2000), 16(3):205-8).

A sodium channel-mediated disease or condition also includes pain associated with HIV, HIV treatment induced neuropathy, trigeminal neuralgia, glossopharyngeal neuralgia, neuropathy secondary to metastatic infiltration, adiposis dolorosa, thalamic lesions, hypertension, autoimmune disease, asthma, drug addiction (e.g. opiate, benzodiazepine, amphetamine, cocaine, alcohol, butane inhalation), Alzheimer, dementia, age-related memory impairment, Korsakoff syndrome, restenosis, urinary dysfunction, incontinence, Parkinson's disease, cerebrovascular ischemia, neurosis, gastrointestinal disease, sickle cell anemia, transplant rejection, heart failure, myocardial infarction, reperfusion injury, intermittent claudication, angina, convulsion, respiratory disorders, cerebral or myocardial ischemias, long-QT syndrome, Catecholeminergic polymorphic ventricular tachycardia, ophthalmic diseases, spasticity, spastic paraplegia, myopathies, myasthenia gravis, paramyotonia congentia, hyperkalemic periodic paralysis, hypokalemic periodic paralysis, alopecia, anxiety disorders, psychotic disorders, mania, paranoia, seasonal affective disorder, panic disorder, obsessive compulsive disorder (OCD), phobias, autism, Aspergers Syndrome, Retts syndrome, disintegrative disorder, attention deficit disorder, aggressivity, impulse control disorders, thrombosis, pre clampsia, congestive cardiac failure, cardiac arrest, Freidrich's ataxia, Spinocerebellear ataxia, myelopathy, radiculopathy, systemic lupus erythamatosis, granulomatous disease, olivo-ponto-cerebellar atrophy, spinocerebellar ataxia, episodic ataxia, myokymia, progressive pallidal atrophy, progressive supranuclear palsy and spasticity, traumatic brain injury, cerebral oedema, hydrocephalus injury, spinal cord injury, anorexia nervosa, bulimia, Prader-Willi syndrome, obesity, optic neuritis, cataract, retinal haemorrhage, ischaemic retinopathy, retinitis pigmentosa, acute and chronic glaucoma, macular degeneration, retinal artery occlusion, Chorea, Huntington's chorea, cerebral edema, proctitis, post-herpetic neuralgia, eudynia, heat sensitivity, sarcoidosis, irritable bowel syndrome, Tourette syndrome, Lesch-Nyhan Syndrome, Brugado syndrome, Liddle syndrome, Crohns disease, multiple sclerosis and the pain associated with multiple sclerosis (MS), amyotrophic lateral sclerosis (ALS), disseminated sclerosis, diabetic neuropathy, peripheral neuropathy, charcot marie tooth syndrome, arthritic, rheumatoid arthritis, osteoarthritis, chondrocalcinosis, atherosclerosis, paroxysmal dystonia, myasthenia syndromes, myotonia, myotonic dystrophy, muscular dystrophy, malignant hyperthermia, cystic fibrosis, pseudoaldosteronism, rhabdomyolysis, mental handicap, hypothyroidism, bipolar depression, anxiety, schizophrenia, sodium channel toxin related illnesses, familial erythromelagia, primary erythromelagia, rectal pain, cancer, epilepsy, partial and general tonic seizures, febrile seizures, absence seizures (petit mal), myoclonic seizures, atonic seizures, clonic seizures, Lennox Gastaut, West Syndome (infantile spasms), multiresistant seizures, seizure prophylaxis (anti-epileptogenic), familial Mediterranean fever syndrome, gout, restless leg syndrome, arrhythmias, fibromyalgia, neuroprotection under ischaemic conditions caused by stroke or neural trauma, tachy-arrhythmias, atrial fibrillation and ventricular fibrillation and as a general or local anaesthetic.

As used herein, the term "pain" refers to all categories of pain and is recognized to include, but is not limited to, neuropathic pain, inflammatory pain, nociceptive pain, idiopathic pain, neuralgic pain, orofacial pain, burn pain, burning mouth syndrome, somatic pain, visceral pain, myofacial pain, dental pain, cancer pain, chemotherapy pain, trauma pain, surgical pain, post-surgical pain, childbirth pain, labor pain, reflex sympathetic dystrophy, brachial plexus avulsion, neurogenic bladder, acute pain (e.g. musculoskeletal and post-operative pain), chronic pain, persistent pain, peripherally mediated pain, centrally mediated pain, chronic headache, migraine headache, familial hemiplegic migraine, conditions associated with cephalic pain, sinus headache, tension headache, phantom limb pain, peripheral nerve injury, pain following stroke, thalamic lesions, radiculopathy, HIV pain, post-herpetic pain, non-cardiac chest pain, irritable bowel syndrome and pain associated with bowel disorders and dyspepsia, and combinations thereof.

Sodium channel blockers have clinical uses in addition to pain. Epilepsy and cardiac arrhythmias are often targets of sodium channel blockers. Recent evidence from animal models suggest that sodium channel blockers may also be useful for neuroprotection under ischaemic conditions caused by stroke or neural trauma and in patients with multiple sclerosis (MS) (Clare, J. J. et al., op. cit. and Anger, T. et al., op. cit.).

The present invention also relates to compounds, pharmaceutical compositions and methods of using the compounds and pharmaceutical compositions for the treatment or prevention of diseases or conditions such as benign prostatic hyperplasia (BPH), hypercholesterolemia, cancer and pruritis (itch).

Benign prostatic hyperplasia (BPH), also known as benign prostatic hypertrophy, is one of the most common diseases affecting aging men. BPH is a progressive condition which is characterized by a nodular enlargement of prostatic tissue resulting in obstruction of the urethra. Consequences of BPH can include hypertrophy of bladder smooth muscle, a decompensated bladder, acute urinary retention and an increased incidence of urinary tract infection.

BPH has a high public health impact and is one of the most common reasons for surgical intervention among elderly men. Attempts have been made to clarify the etiology and pathogenesis and, to that end, experimental models have been developed. Spontaneous animal models are limited to the chimpanzee and the dog. BPH in man and the dog share many common features. In both species, the development of BPH occurs spontaneously with advanced age and can be prevented by early/prepubertal castration. A medical alternative to surgery is very desirable for treating BHP and the consequences.

The prostatic epithelial hyperplasia in both man and the dog is androgen sensitive, undergoing involution with androgen deprivation and resuming epithelial hyperplasia when androgen is replaced. Cells originating from the prostate gland have been shown to express high levels of voltage gated sodium channels. Immunostaining studies clearly demonstrated evidence for voltage gated sodium channels in prostatic tissues (*Prostate Cancer Prostatic Dis.* 2005; 8(3):266-73).

Hypercholesterolemia, i.e., elevated blood cholesterol, is an established risk factor in the development of, e.g., atherosclerosis, coronary artery disease, hyperlipidemia, stroke, hyperinsulinemias, hypertension, obesity, diabetes, cardiovascular diseases (CVD), myocardial ischemia, and heart attack. Thus, lowering the levels of total serum cholesterol in individuals with high levels of cholesterol has been known to reduce the risk of these diseases. The lowering of low density lipoprotein cholesterol in particular is an essential step in the prevention of CVD. Although there are a variety of hypercholesterolemia therapies, there is a continuing need and a continuing search in this field of art for alternative therapies.

The invention provides compounds which are useful as antihypercholesterolemia agents and their related conditions. The present compounds may act in a variety of ways. While not wishing to be bound to any particular mechanism of action, the compounds may be direct or indirect inhibitors of the enzyme acyl CoA: cholesterol acyl transferase (ACAT) that results in inhibition of the esterification and transport of cholesterol across the intestinal wall. Another possibility may be that the compounds of the invention may be direct or indirect inhibitors of cholesterol biosynthesis in the liver. It is possible that some compounds of the invention may act as both direct or indirect inhibitors of ACAT and cholesterol biosynthesis.

Pruritus, commonly known as itch, is a common dermatological condition. While the exact causes of pruritis are complex and poorly understood, there has long been acknowledged to have interactions with pain. In particular, it is believed that sodium channels likely communicate or propagate along the nerve axon the itch signals along the skin. Transmission of the itch impulses results in the unpleasant sensation that elicits the desire or reflex to scratch.

From a neurobiology level, it is believed that there is a shared complexity of specific mediators, related neuronal pathways and the central processes of itch and pain and recent data suggest that there is a broad overlap between pain- and itch-related peripheral mediators and/or receptors (Ikoma et al., *Nature Reviews Neuroscience*, 7:535-547, 2006). Remarkably, pain and itch have similar mechanisms of neuronal sensitization in the peripheral nervous system and the central nervous system but exhibits intriguing differences as well.

For example, the mildly painful stimuli from scratching are effective in abolishing the itch sensation. In contrast, analgesics such as opioids can generate severe pruritus. The antagonistic interaction between pain and itch can be exploited in pruritus therapy, and current research concentrates on the identification of common targets for future analgesic and antipruritic therapy.

Compounds of the present invention have been shown to have analgesic effects in a number of animal models at oral doses ranging from 1 mg/Kg to 100 mg/Kg. The compounds of the invention can also be useful for treating pruritus.

The types of itch or skin irritation, include, but are not limited to:

a) psoriatic pruritis, itch due to hemodyalisis, aguagenic pruritus, and itching caused by skin disorders (e.g., contact dermatitis), systemic disorders, neuropathy, psychogenic factors or a mixture thereof;

b) itch caused by allergic reactions, insect bites, hypersensitivity (e.g., dry skin, acne, eczema, psoriasis), inflammatory conditions or injury;

c) itch associated with vulvar vestibulitis; and d) skin irritation or inflammatory effect from administration of another therapeutic such as, for example, antibiotics, antivirals and antihistamines.

The compounds of the invention are also useful in treating or preventing certain hormone sensitive cancers, such as prostate cancer (adenocarcinoma), breast cancer, ovarian cancer, testicular cancer, thyroid neoplasia, in a mammal, preferably a human. The voltage gated sodium channels have been demonstrated to be expressed in prostate and breast cancer cells. Up-regulation of neonatal $Na_v1.5$ occurs as an integral part of the metastatic process in human breast cancer and could serve both as a novel marker of the metastatic phenotype and a therapeutic target (*Clin. Cancer Res.* 2005, Aug. 1; 11(15): 5381-9). Functional expression of voltage-gated sodium channel alpha-subunits, specifically $Na_v1.7$, is associated with strong metastatic potential in prostate cancer (CaP) in vitro. Voltage-gated sodium channel alpha-subunits immunostaining, using antibodies specific to the sodium channel alpha subunit was evident in prostatic tissues and markedly stronger in CaP vs non-CaP patients (*Prostate Cancer Prostatic Dis.*, 2005; 8(3):266-73).

The compounds of the invention are also useful in treating or preventing symptoms in a mammal associated with BPH such as, but not limited to, acute urinary retention and urinary tract infection.

The compounds of the invention are also useful in treating or preventing certain endocrine imbalances or endocrinopathies such as congenital adrenal hyperplasia, hyperthyroidism, hypothyroidism, osteoporosis, osteomalacia, rickets, Cushing's Syndrome, Conn's syndrome, hyperaldosteronism, hypogonadism, hypergonadism, infertility, fertility and diabetes.

The present invention readily affords many different means for identification of sodium channel modulating agents that are useful as therapeutic agents. Identification of modulators of sodium channel can be assessed using a variety of in vitro and in vivo assays, e.g. measuring current, measuring membrane potential, measuring ion flux, (e.g. sodium or guanidinium), measuring sodium concentration, measuring second messengers and transcription levels, and using e.g., voltage-sensitive dyes, radioactive tracers, and patch-clamp electrophysiology.

One such protocol involves the screening of chemical agents for ability to modulate the activity of a sodium channel thereby identifying it as a modulating agent.

A typical assay described in Bean et al., *J. General Physiology* (1983), 83:613-642, and Leuwer, M., et al., *Br. J. Pharmacol* (2004), 141(1):47-54, uses patch-clamp techniques to study the behaviour of channels. Such techniques are known to those skilled in the art, and may be developed, using current technologies, into low or medium throughput assays for evaluating compounds for their ability to modulate sodium channel behaviour.

A competitive binding assay with known sodium channel toxins such as tetrodotoxin, alpha-scorpion toxins, aconitine, BTX and the like, may be suitable for identifying potential therapeutic agents with high selectivity for a particular sodium channel. The use of BTX in such a binding assay is well known and is described in McNeal, E. T., et al., *J. Med. Chem.* (1985), 28(3):381-8; and Creveling, C. R., et al., *Methods in Neuroscience, Vol. 8: Neurotoxins* (Conn PM Ed) (1992), pp. 25-37, Academic Press, New York.

These assays can be carried out in cells, or cell or tissue extracts expressing the channel of interest in a natural endogenous setting or in a recombinant setting. The assays that can be used include plate assays which measure Na+ influx through surrogate markers such as $^{14}$C-guanidine influx or determine cell depolarization using fluorescent dyes such as the FRET based and other fluorescent assays or a radiolabelled binding assay employing radiolabelled aconitine, BTX, TTX or STX. More direct measurements can be made with manual or automated electrophysiology systems. The guanidine influx assay is explained in more detail below in the Biological Assays section.

Throughput of test compounds is an important consideration in the choice of screening assay to be used. In some strategies, where hundreds of thousands of compounds are to be tested, it is not desirable to use low throughput means. In other cases, however, low throughput is satisfactory to identify important differences between a limited number of compounds. Often it will be necessary to combine assay types to identify specific sodium channel modulating compounds.

Electrophysiological assays using patch clamp techniques is accepted as a gold standard for detailed characterization of sodium channel compound interactions, and as described in Bean et al., *op. cit.* and Leuwer, M., et al., *op. cit.* There is a manual low-throughput screening (LTS) method which can compare 2-10 compounds per day; a recently developed system for automated medium-throughput screening (MTS) at 20-50 patches (i.e. compounds) per day; and a technology from Molecular Devices Corporation (Sunnyvale, Calif.) which permits automated high-throughput screening (HTS) at 1000-3000 patches (i.e. compounds) per day.

One automated patch-clamp system utilizes planar electrode technology to accelerate the rate of drug discovery. Planar electrodes are capable of achieving high-resistance, cells-attached seals followed by stable, low-noise whole-cell recordings that are comparable to conventional recordings. A suitable instrument is the PatchXpress 7000A (Axon Instruments Inc, Union City, Calif.). A variety of cell lines and culture techniques, which include adherent cells as well as cells growing spontaneously in suspension are ranked for seal success rate and stability. Immortalized cells (e.g. HEK and CHO) stably expressing high levels of the relevant sodium ion channel can be adapted into high-density suspension cultures.

Other assays can be selected which allow the investigator to identify compounds which block specific states of the channel, such as the open state, closed state or the resting state, or which block transition from open to closed, closed to resting or resting to open. Those skilled in the art are generally familiar with such assays.

Binding assays are also available, however these are of only limited functional value and information content. Designs include traditional radioactive filter based binding assays or the confocal based fluorescent system available from Evotec OAI group of companies (Hamburg, Germany), both of which are HTS.

Radioactive flux assays can also be used. In this assay, channels are stimulated to open with veratridine or aconitine and held in a stabilized open state with a toxin, and channel blockers are identified by their ability to prevent ion influx. The assay can use radioactive $^{22}$-[Na] and $^{14}$[C] guanidinium ions as tracers. FlashPlate & Cytostar-T plates in living cells avoids separation steps and are suitable for HTS. Scintillation plate technology has also advanced this method to HTS suitability. Because of the functional aspects of the assay, the information content is reasonably good.

Yet another format measures the redistribution of membrane potential using the FLIPR system membrane potential kit (HTS) available from Molecular Dynamics (a division of Amersham Biosciences, Piscataway, N.J.). This method is limited to slow membrane potential changes. Some problems may result from the fluorescent background of compounds. Test compounds may also directly influence the fluidity of the cell membrane and lead to an increase in intracellular dye concentrations. Still, because of the functional aspects of the assay, the information content is reasonably good.

Sodium dyes can be used to measure the rate or amount of sodium ion influx through a channel. This type of assay provides a very high information content regarding potential channel blockers. The assay is functional and would measure Na+ influx directly. CoroNa Red, SBFI and/or sodium green (Molecular Probes, Inc. Eugene Oreg.) can be used to measure Na influx; all are Na responsive dyes. They can be used in combination with the FLIPR instrument. The use of these dyes in a screen has not been previously described in the literature. Calcium dyes may also have potential in this format.

In another assay, FRET based voltage sensors are used to measure the ability of a test compound to directly block Na influx. Commercially available HTS systems include the VIPR™ II FRET system (Aurora Biosciences Corporation, San Diego, Calif., a division of Vertex Pharmaceuticals, Inc.) which may be used in conjunction with FRET dyes, also available from Aurora Biosciences. This assay measures subsecond responses to voltage changes. There is no requirement for a modifier of channel function. The assay measures depolarization and hyperpolarizations, and provides ratiometric outputs for quantification. A somewhat less expensive MTS version of this assay employs the FLEXstation™ (Molecular Devices Corporation) in conjunction with FRET dyes from Aurora Biosciences. Other methods of testing the compounds disclosed herein are also readily known and available to those skilled in the art.

These results provide the basis for analysis of the structure-activity relationship (SAR) between test compounds and the sodium channel. Certain substituents on the core structure of the test compound tend to provide more potent inhibitory compounds. SAR analysis is one of the tools those skilled in the art may now employ to identify preferred embodiments of the compounds of the invention for use as therapeutic agents.

Modulating agents so identified are then tested in a variety of in vivo models so as to determine if they alleviate pain, especially chronic pain or other conditions such as arrhythmias and epilepsy, benign prostatic hyperplasia (BPH), hypercholesterolemia, cancer and pruritis (itch) with minimal adverse events. The assays described below in the Biological Assays Section are useful in assessing the biological activity of the instant compounds.

Typically, a successful therapeutic agent of the present invention will meet some or all of the following criteria. Oral availability should be at or above 20%. Animal model efficacy is less than about 0.1 μg to about 100 mg/Kg body weight and the target human dose is between 0.1 μg to about 100 mg/Kg body weight, although doses outside of this range may be acceptable ("mg/Kg" means milligrams of compound per kilogram of body mass of the subject to whom it is being administered). The therapeutic index (or ratio of toxic dose to therapeutic dose) should be greater than 100. The potency (as expressed by $IC_{50}$ value) should be less than 10 μM, preferably below 1 μM and most preferably below 50 nM. The $IC_{50}$ ("Inhibitory Concentration—50%") is a measure of the amount of compound required to achieve 50% inhibition of ion flux through a sodium channel, over a specific time period, in an assay of the invention. Compounds of the present invention in the guanidine influx assay have demonstrated $IC_{50}$'s ranging from less than a nanomolar to less than 10 micromolar.

In an alternative use of the invention, the compounds of the invention can be used in in vitro or in vivo studies as exemplary agents for comparative purposes to find other compounds also useful in treatment of, or protection from, the various diseases disclosed herein.

Another aspect of the invention relates to inhibiting $Na_v1.1$, $Na_v1.2$, $Na_v1.3$, $Na_v1.4$, $Na_v1.5$, $Na_v1.6$, $Na_v1.7$, $Na_v1.8$, or $Na_v1.9$ activity in a biological sample or a mammal, preferably a human, which method comprises administering to the mammal, preferably a human, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of $Na_v1.1$, $Na_v1.2$, $Na_v1.3$, $Na_v1.4$, $Na_v1.5$, $Na_v1.6$, $Na_v1.7$, $Na_v1.8$, or $Na_v1.9$ activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

The compounds of the invention, as set forth above in the Summary of the Invention, as stereoisomers, enantiomers, tautomers thereof or mixtures thereof, or pharmaceutically acceptable salts, solvates or prodrugs thereof, and/or the pharmaceutical compositions described herein which comprise a pharmaceutically acceptable excipient and one or more compounds of the invention, as set forth above in the Summary of the Invention, as a stereoisomer, enantiomer, tautomer thereof or mixtures thereof, or a pharmaceutically acceptable salt, solvate or prodrug thereof, can be used in the preparation of a medicament for the treatment of sodium channel-mediated disease or condition in a mammal.

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier, excipient or diluent and in an amount effective to modulate, preferably inhibit, ion flux through a voltage-dependent sodium channel to treat sodium channel mediated diseases, such as pain, when administered to an animal, preferably a mammal, most preferably a human patient.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *The Science and Practice of Pharmacy*, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 Kg mammal) from about 0.001 mg/Kg (i.e., 0.07 mg) to about 100 mg/Kg (i.e., 7.0 g); preferably a therapeutically effective dose is (for a 70 Kg mammal) from about 0.01 mg/Kg (i.e., 0.7 mg) to about 50 mg/Kg (i.e., 3.5 g); more preferably a therapeutically effective dose is (for a 70 Kg mammal) from about 1 mg/Kg (i.e., 70 mg) to about 25 mg/Kg (i.e., 1.75 g).

The ranges of effective doses provided herein are not intended to be limiting and represent preferred dose ranges. However, the most preferred dosage will be tailored to the individual subject, as is understood and determinable by one skilled in the relevant arts. (see, e.g., Berkow et al., eds., *The Merck Manual*, 16$^{th}$ edition, Merck and Co., Rahway, N.J., 1992; Goodmanetna., eds., *Goodman and Cilman's The Pharmacological Basis of Therapeutics*, 10$^{th}$ edition, Pergamon Press, Inc., Elmsford, N.Y., (2001); *Avery's Drug Treatment: Principles and Practice of Clinical Pharmacology and Therapeutics*, 3rd edition, ADIS Press, LTD., Williams and Wilkins, Baltimore, Md. (1987), Ebadi, *Pharmacology*, Little, Brown and Co., Boston, (1985); Osolci al., eds., *Remington's Pharmaceutical Sciences*, 18$^{th}$ edition, Mack Publishing Co., Easton, Pa. (1990); Katzung, *Basic and Clinical Pharmacology*, Appleton and Lange, Norwalk, Conn. (1992)).

The total dose required for each treatment can be administered by multiple doses or in a single dose over the course of the day, if desired. Generally, treatment is initiated with smaller dosages, which are less than the optimum dose of the compound. Thereafter, the dosage is increased by small increments until the optimum effect under the circumstances is reached. The diagnostic pharmaceutical compound or composition can be administered alone or in conjunction with other diagnostics and/or pharmaceuticals directed to the pathology, or directed to other symptoms of the pathology. The recipients of administration of compounds and/or compositions of the invention can be any vertebrate animal, such as mammals. Among mammals, the preferred recipients are mammals of the Orders Primate (including humans, apes and monkeys), Arteriodactyla (including horses, goats, cows, sheep, pigs), Rodenta (including mice, rats, rabbits, and hamsters), and Carnivora (including cats, and dogs). Among birds, the preferred recipients are turkeys, chickens and other members of the same order. The most preferred recipients are humans.

For topical applications, it is preferred to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The compositions of the invention can be formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al., *Regional Anesthesia* 22 (6): 543-551 (1997), all of which are incorporated herein by reference.

The compositions of the invention can also be delivered through intra-nasal drug delivery systems for local, systemic, and nose-to-brain medical therapies. Controlled Particle Dispersion (CPD)™ technology, traditional nasal spray bottles, inhalers or nebulizers are known by those skilled in the art to provide effective local and systemic delivery of drugs by targeting the olfactory region and paranasal sinuses.

The invention also relates to an intravaginal shell or core drug delivery device suitable for administration to the human or animal female. The device may be comprised of the active pharmaceutical ingredient in a polymer matrix, surrounded by a sheath, and capable of releasing the compound in a substantially zero order pattern on a daily basis similar to devises used to apply testosterone as described in PCT Published Patent Application No. WO 98/50016.

Current methods for ocular delivery include topical administration (eye drops), subconjunctival injections, periocular injections, intravitreal injections, surgical implants and iontophoresis (uses a small electrical current to transportionized drugs into and through body tissues). Those skilled in the art would combine the best suited excipients with the compound for safe and effective intra-occular administration.

The most suitable route will depend on the nature and severity of the condition being treated. Those skilled in the art are also familiar with determining administration methods (e.g., oral, intravenous, inhalation, sub-cutaneous, rectal etc.), dosage forms, suitable pharmaceutical excipients and other matters relevant to the delivery of the compounds to a subject in need thereof.

Combination Therapy

The compounds of the invention may be usefully combined with one or more other compounds of the invention or one or more other therapeutic agent or as any combination thereof, in the treatment of sodium channel-mediated diseases and conditions. For example, a compound of the invention may be administered simultaneously, sequentially or separately in combination with other therapeutic agents, including, but not limited to:

opiates analgesics, e.g. morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine;

non-opiate analgesics, e.g. acetomeniphen, salicylates (e.g. aspirin);

nonsteroidal antiinflammatory drugs (NSAIDs), e.g. ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac;

anticonvulsants, e.g. carbamazepine, oxcarbazepine, lamotrigine, valproate, topiramate, gabapentin and pregabalin;

antidepressants such as tricyclic antidepressants, e.g. amitriptyline, clomipramine, despramine, imipramine and nortriptyline;

COX-2 selective inhibitors, e.g. celecoxib, rofecoxib, parecoxib, valdecoxib, deracoxib, etoricoxib, and lumiracoxib;

alpha-adrenergics, e.g. doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline;

barbiturate sedatives, e.g. amobarbital, aprobarbital, butabarbital, butabital, mephobarbital, metharbital, methohexital, pentobarbital, phenobartital, secobarbital, talbutal, theamylal and thiopental;

tachykinin (NK) antagonist, particularly an NK-3, NK-2 or NK-1 antagonist, e.g. (αR,9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl)ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

coal-tar analgesics, in particular paracetamol;

serotonin reuptake inhibitors, e.g. paroxetine, sertraline, norfluoxetine (fluoxetine desmethyl metabolite), metabolite demethylsertraline, 3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine;

noradrenaline (norepinephrine) reuptake inhibitors, e.g. maprotiline, lofepramine, mirtazepine, oxaprotiline, fezolamine, tomoxetine, mianserin, buproprion, buproprion metabolite hydroxybuproprion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics;

dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine;

acetylcholinesterase inhibitors such as donepezil;

5-HT$_3$ antagonists such as ondansetron;

metabotropic glutamate receptor (mGluR) antagonists;

local anaesthetic such as mexiletine and lidocaine;

corticosteroid such as dexamethasone;

antiarrhythimics, e.g. mexiletine and phenyloin;

muscarinic antagonists, e.g., tolterodine, propiverine, tropsium t chloride, darifenacin, solifenacin, temiverine and ipratropium;

cannabinoids;

vanilloid receptor agonists (e.g. resinferatoxin) or antagonists (e.g. capsazepine);

sedatives, e.g. glutethimide, meprobamate, methaqualone, and dichloralphenazone;

anxiolytics such as benzodiazepines, antidepressants such as mirtazapine, topical agents (e.g. lidocaine, capsacin and resiniferotoxin);

muscle relaxants such as benzodiazepines, baclofen, carisoprodol, chlorzoxazone, cyclobenzaprine, methocarbamol and orphrenadine;

anti-histamines or H1 antagonists;

NMDA receptor antagonists;

5-HT receptor agonists/antagonists;

PDEV inhibitors;

Tramadol®;

cholinergic (nicotinc) analgesics;

alpha-2-delta ligands;

prostaglandin E2 subtype antagonists;

leukotriene B4 antagonists;

5-lipoxygenase inhibitors; and

5-HT$_3$ antagonists.

Sodium channel-mediated diseases and conditions that may be treated and/or prevented using such combinations include but not limited to, pain, central and peripherally mediated, acute, chronic, neuropathic as well as other diseases with associated pain and other central nervous disorders such as epilepsy, anxiety, depression and bipolar disease; or cardiovascular disorders such as arrhythmias, atrial fibrillation and ventricular fibrillation; neuromuscular disorders such as restless leg syndrome and muscle paralysis or tetanus; neuroprotection against stroke, neural trauma and multiple sclerosis; and channelopathies such as erythromyalgia and familial rectal pain syndrome.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

Kits-of-Parts

The present invention also provides kits that contain a pharmaceutical composition which includes one or more compounds of the invention. The kit also includes instructions for the use of the pharmaceutical composition for modulating the activity of ion channels, for the treatment of pain, as well as other utilities as disclosed herein. Preferably, a commercial package will contain one or more unit doses of the pharmaceutical composition. For example, such a unit dose may be an amount sufficient for the preparation of an intravenous injection. It will be evident to those of ordinary skill in the art that compounds which are light and/or air sensitive may require special packaging and/or formulation. For example, packaging may be used which is opaque to light, and/or sealed from contact with ambient air, and/or formulated with suitable coatings or excipients.

Preparation of the Compounds of the Invention

The compounds of the invention are prepared by the methods disclosed herein and by methods similar to those described in PCT Published Patent Application, WO 2006/110917 and to those described in PCT Published Patent Application WO 2008/046049, the disclosures of which are both incorporated in full herein in their entireties, particularly with respect to the methods of preparation disclosed therein with respect to the compounds disclosed therein.

It is also understood that one skilled in the art would be able to make in a similar manner as described below the compounds of the invention by reference to the disclosures of PCT Published Patent Application, WO 2006/110917 by using the appropriate starting materials and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc., or synthesized according to sources known to those skilled in the art (see, e.g., Smith, M. B. and J. March, *Advanced Organic Chemistry: Reactions*, Mechanisms, and Structure, 5th edition (Wiley, December 2000)), or may be prepared as described in PCT Published Patent Application, WO 2006/110917, or may be prepared by methods disclosed herein.

Protecting groups may be added or removed in accordance with standard techniques, which are known to one skilled in the art and as described herein.

The use of protecting groups is described in detail in Greene, T. W. and P. G. M. Wuts, Greene's *Protective Groups in Organic Synthesis* (2006), 4$^{th}$ Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

All of the compounds described below as being prepared which may exist in free base or acid form may be converted to their pharmaceutically acceptable salts by treatment with the appropriate inorganic or organic base or acid. Salts of the compounds prepared below may be converted to their free base or acid form by standard techniques. It is understood that all polymorphs, amorphous forms, anhydrates, hydrates, solvates and salts of the compounds of the invention are intended to be within the scope of the invention. Furthermore, all compounds of the invention which contain an acid or an ester group can be converted to the corresponding ester or acid, respectively, by methods known to one skilled in the art or by methods described herein.

Alternatively, the compounds of the invention can be synthesized following the procedures set forth below in REACTION SCHEMES 1-27 where, unless indicated otherwise, q is 1 or 2, each X is halo, preferably bromo or chloro, R" is an alkyl group, $R^{15}$ is as defined for $R^1$, $R^{1a}$, $R^{1b}$, $R^3$, $R^5$, $R^7$, $R^9$, $R^{19}$, $R^{11}$, $R^{12}$, $R^{13}$ or $R^{14}$ in compounds of formula (I), formula (II), formula (III), formula (IV), formula (V), formula (VI), formula (VII), formula (VII), formula (VIII), formula (IX), formula (XI), formula (XII) and formula (XIII), $R^{16}$ is as defined for $R^2$, $R^4$ or $R^6$ in compounds of formula (I), formula (II) and formula (III), and

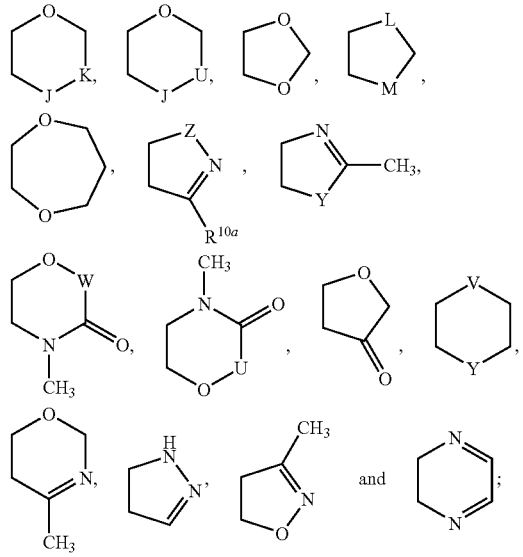

is defined as one of the following:

where J, K, L, M, U, V, W, Y and Z are as described as for the compounds of formula (I), formula (III), formula (VI), formula (VII), formula (VIII), formula (IX), formula (XI) and formula (XIII).

Preparation of Compounds of Formula (Ia), Formula (Iaa) and Formula (Iab)

Compounds of formula (Ia), formula (Iaa) and formula (Iab) are compounds of the invention, as set forth above in the Summary of the Invention. They may be prepared by the methods set forth below in REACTION SCHEMES 1 and 2 below where $R^{50a}$, $R^{50b}$, $R^{50c}$ and $R^{50d}$ are each independently hydrogen, hydroxy, bromo, chloro, cyano, fluoro, methyl, trifluoroacetyl, methoxy, 1-methylethoxy, 2-methoxyethoxy, benzyloxy, 1-(tert-butoxycarbonyl)pyrrolidin-3-yloxy, pyrrolidin-3-yloxy, amino, sulfonylamino, methylsulfonylamino, [(tert-butoxycarbonyl)pyrrolidin-3-yl]amino, 6-methoxypyridin-3-yl, 5-methyl-1,2,4-oxadiazol-3-yl, amino(hydroxyimino)methyl or (pyrrolidin-3-yl)amino; or $R^{50a}$ and $R^{50b}$, or $R^{50b}$ and $R^{50c}$, or $R^{50c}$ and $R^{50d}$, together with the adjacent carbons to which they are attached, form a fused dioxinyl ring, a fused thienyl ring, a fused 1,1-dioxothienyl ring, a fused 1,2,5-oxadiazolyl ring, a fused tetrahydropyranyl ring, a fused 2,3-dihydropyrazinyl ring, a fused 3-methyl-4,5-dihydroisoxazolyl ring or a fused pyrazinyl ring, and the remaining $R^{50a}$, $R^{50b}$, $R^{50c}$ and $R^{50d}$ group, if present, is as described above:

REACTION SCHEME 1

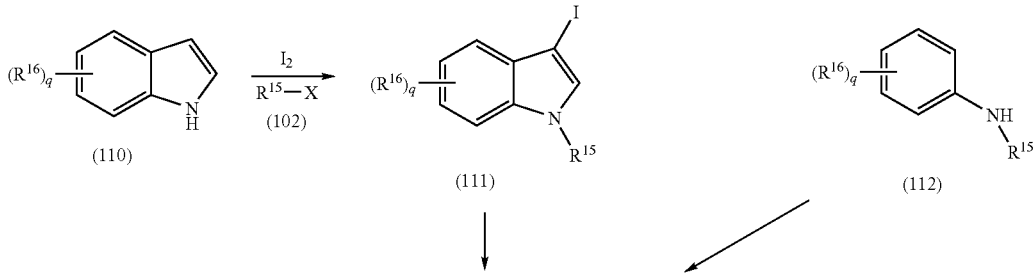

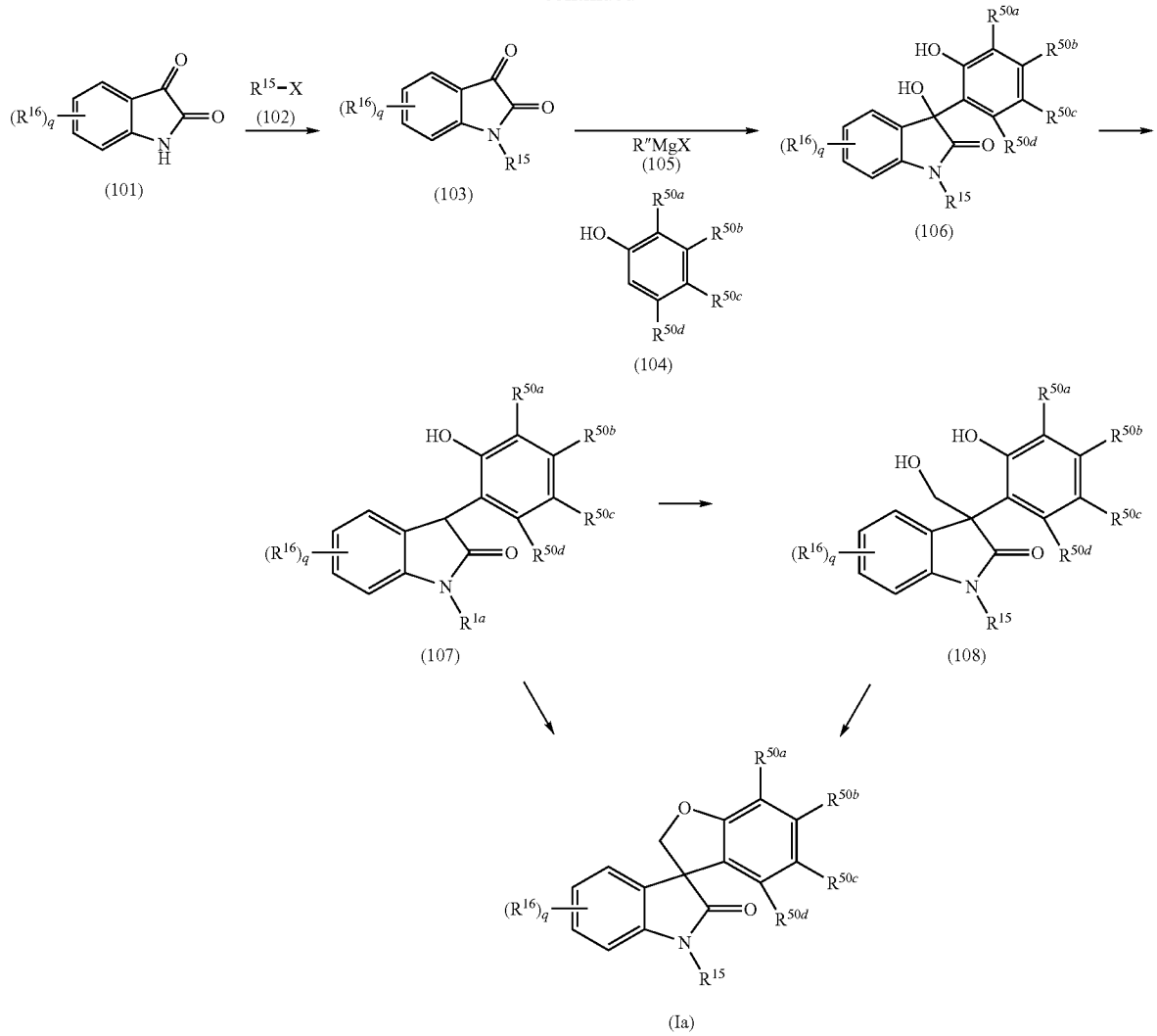

Compounds of formula (101), formula (102), formula (104), formula (105), formula (110), and formula (112) are commercially available or can be prepared according to methods known to one skilled in the art or by the methods disclosed herein or by the methods disclosed in PCT Published Patent Application WO 2006/110917.

As set forth above, compounds of formula (Ia) are prepared by first alkylating an isatin compound of formula (101) with the chloro or bromo compound of formula (102) to afford the product of formula (103). Alternatively, an indole compound of formula (110) is iodinated with iodine and alkylated with the chloro or bromo compound of formula (102) to afford the product of formula (111). Oxidation of (111) with ruthenium (III) chloride monohydrate and sodium periodate gives the isatin product of formula (103). Alternatively, treatment of an aniline compound of formula (112) with oxalyl chloride gives the istain compound of formula (103). The phenol compound of formula (104) is treated with a Grignard reagent of formula (105) at low temperature (0° C.) to form the phenoxymagnesium halide intermediate which reacts with the keto-carbonyl group of the isatin compound of formula (103) in a solvent, such as, but not limited to, methylene chloride or tetrahydrofuran, to afford the oxindole of formula (106). The compound of formula (107) is obtained after the removal of the hydroxyl group at C-3 position of the oxindole by treating the compound of formula (106) with a silane such as, but not limited to, triethylsilane. The compound of formula (107) can also be achieved by treating the compound of formula (106) with thionyl chloride/triethylamine then reduction with zinc dust. The compound of formula (107) is treated with an alkylating reagent such as, but not limited to, chloroiodomethane or 1,2-dibromoethane with a base, such as, but not limited to, cesium carbonate, in a solvent, such as, but not limited to, tetrahydrofuran or N,N-dimethylformamide to afford the compound of formula (Ia) of the invention via intramolecular cyclization. Alternatively, compound (107) is treated with a silyl compound, such as, but not limited to, trimethylsilyl chloride to generate a silyl ether intermediate which is treated with ytterbium (III) trifluoromethanesulfonate and formaldehyde to afford the compound of formula (108). The compound of formula (108) can also be obtained by treating the compound of formula (107) with a base, such as, but not limited to, LiOH, iPr$_2$NH, LDA and subsequently reacting with formaldehyde. Intramolecular cyclization of the compound of formula (108) via Mitsunobu reaction in the presence of a phosphine reagent such as, but not limited to, triphenylphosphine, tributylphosphine, or trimethylphosphine, and azadicarboxylate of diethyl, diisopropyl or di-tert-butyl, or N,N,N',N'-tetramethylazodicarboxamide in a solvent such as, but not limited to, tetrahydrofuran, ethyl acetate, or dichloromethane, affords the compound of formula (Ia) of the invention.

Compounds of formula (Ia), (Iaa) and (Iab) can also be prepared by the method illustrated below in REACTION SCHEME 2 where q, $R^{15}$, $R^{16}$, $R^{50a}$, $R^{50}$, $R^{50c}$ and $R^{50d}$ are as defined above, and PG is a nitrogen-protecting group:

Alternatively, reaction of compound of formula (202) with an alcohol (204) under Mitsunobu reaction conditions in the presence of a phosphine reagent such as, but not limited to, triphenylphosphine, tributylphosphine, or trimethyl phosphine, and azadicarboxylate of diethyl, diisopropyl, di-tent-butyl or N,N,N',N'-tetramethylazodicarboxamide in a solvent such as, but not limited to, tetrahydrofuran, ethyl acetate, or dichloromethane, provides the compound of formula (Ia).

Alternatively, reaction of compound of formula (202) with a boronic acid (205) in the presence of a copper reagent such

REACTION SCHEME 2

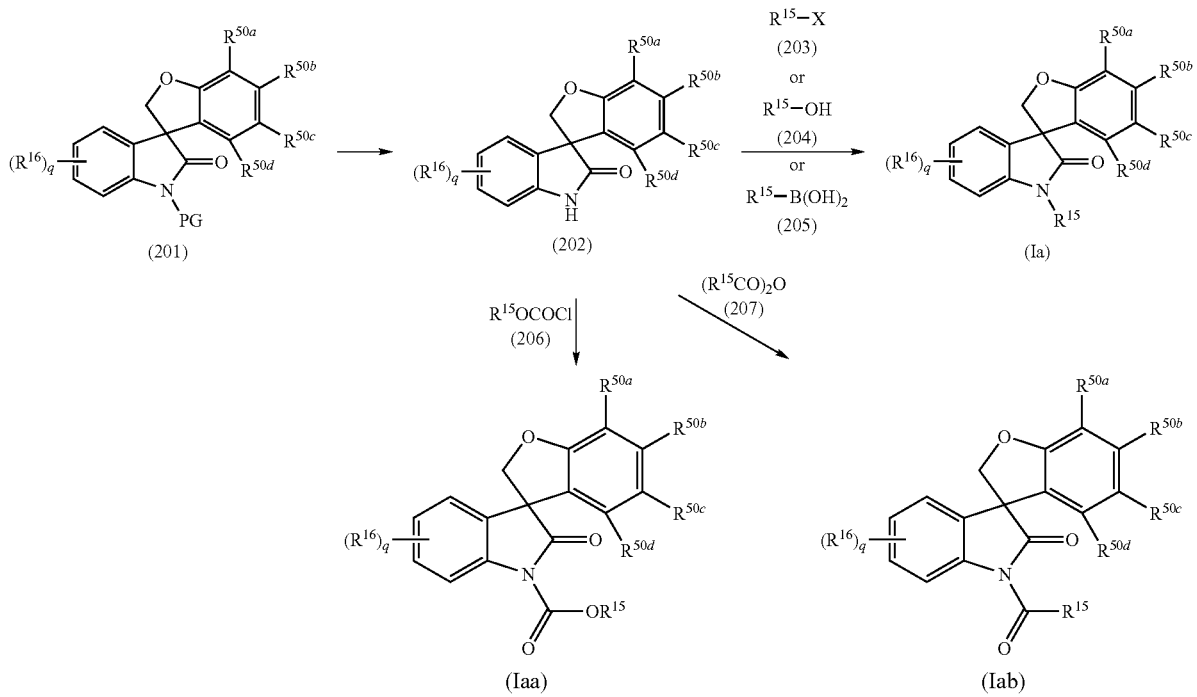

Compounds of formula (203), formula (204), formula (205), formula (206) and formula (207) are commercially available or can be prepared according to methods known to one skilled in the art or by methods disclosed herein.

Compounds of formula (201) where PG is a nitrogen-protecting group such as, but not limited to, diphenylmethyl, are synthesized through the sequence as shown in REACTION SCHEME 1 above. When the protecting group is diphenylmethyl, it is removed under a high pressure of hydrogen such as 60-120 psi to form the oxindole compound of formula (202); it can also be removed by the treatment of compound of formula (201) with triethyl silane and trifluoroacetic acid at 70° C. to 100° C. The formation of the compound of formula (Ia) is achieved by alkylation of the compound of formula (202) with an alkylating reagent $R^{15}$—X (203), where X is chloro, bromo, iodo, or OTs, alternatively, when X is chloro, the reagent is generated from the corresponding alcohol (204) by reacting with a chlorinating reagent such as, but not limited to, thionyl chloride or N-(chloromethylene)-N-methylmethanaminium chloride (Vilsmeier reagent)) in the presence of a base such as, but not limited to, sodium hydride, sodium bis(trimethylsilyl)amide, lithium hydroxide, or cesium carbonate, in a solvent such as, but not limited to, N,N-dimethylformamide, tetrahydrofuran, 2-butanone, acetone, acetonitrile or the combination of any two of them, in the presence or absence of potassium iodide.

as, but not limited to, cupric acetate, and 4-(N,N-dimethylamino)pyridine, a base such as, but not limited to, sodium hexamethyldisilazide in a solvent such as, but not limited to, toluene provides the compound of formula (Ia).

Alternatively, when $R^{15}$ is an aryl or heteroaryl group in compound (203), compound (203) reacts with compound (202) in the presence of a palladium catalyst such as, but not limited to, palladium (II) acetate, a ligand such as, but not limited to, 9,9-dimethyl-4,5-bis(diphenylphosphino)xanthene and a base such as, but not limited to, cesium carbonate in a solvent such as, but not limited to, 1,4-dioxane to provide the product of formula (Ia).

In general, treatment of compound of formula (202) with a base such as, but not limited to, sodium hydride or triethylamine, and a chloroformate reagent such as, but not limited to, ethyl chloroformate or di-tert-butyl dicarbonate provides the carbamate compound of formula (Iaa). Treatment of compound of formula (202) with an acylating reagent such as, but not limited to, acetic anhydride provides the compound of formula (Iab).

Preparation of Compounds of Formula (Ib) and Formula (Ic)

Compounds of formula (Ib) and (Ic) are compounds of the invention, as set forth above in the Summary of the Invention. They may be prepared by the methods set forth below in REACTION SCHEME 3 where

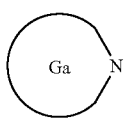

is a N-heterocycly, PG is nitrogen protecting group, q and $R^{16}$ and

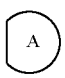

are as defined above, $R^{17}$ and $R^{18}$ are each independently hydrogen or alkyl, and $R^{19}$ is hydrogen, alkyl or aryl:

compounds of formula (302). Reductive amination of (302) with an aldehyde or a ketone (303) in the presence of a reducing agent such as, but not limited to, sodium cyanoborohydride or sodium triacetoxyborohydride, or alternatively with formaldehyde and formic acid in refluxing water, provides the amine compound of formula (Ic).

In another aspect, the urea compounds of formula (Ib) are prepared by treating an amine compound of formula (302) with an isocyanate in the presence of a base, such as, but not limited to, triethylamine or diisopropylethylamine, in a solvent such as, but not limited to, dichloromethane or chloroform.

Preparation of Compounds of Formula (Id)

Compounds of formula (Id) are compounds of the invention, as set forth above in the Summary of the Invention. They may be prepared by the methods set forth below in REACTION SCHEME 4 where q and $R^{16}$ and

REACTION SCHEME 3

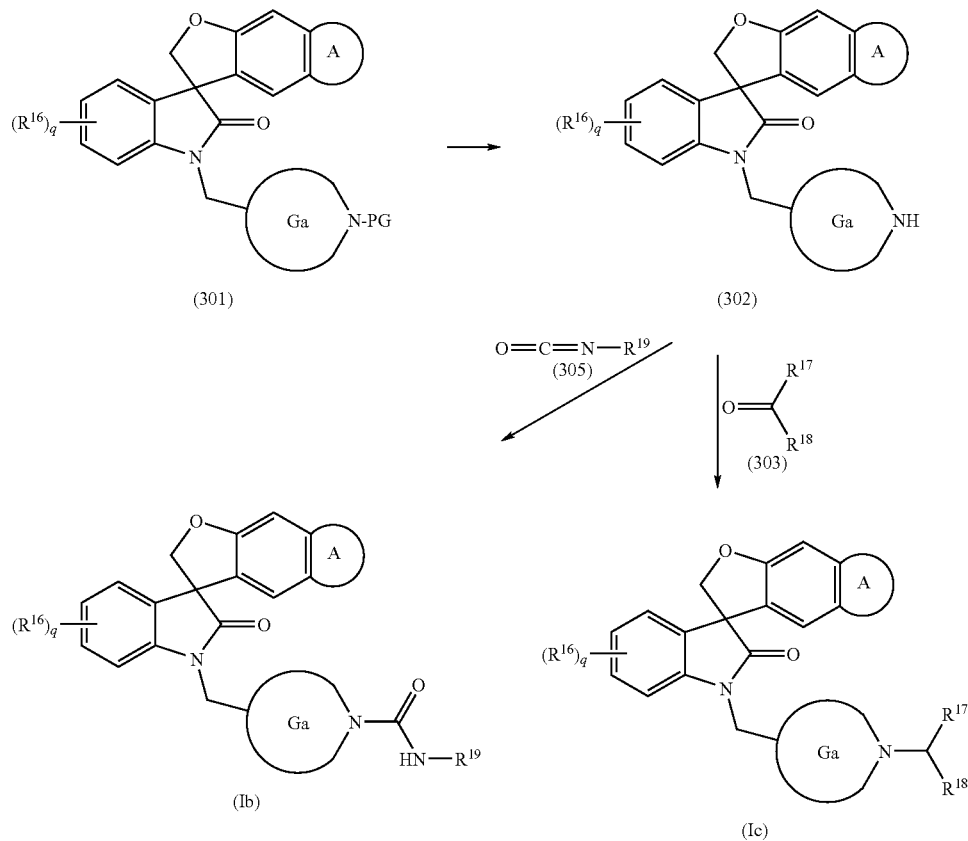

Compounds of formula (301) can be prepared according to methods known to one skilled in the art or by the methods disclosed herein or by the methods disclosed in PCT Published Patent Application WO 2006/110917. Compounds of formula (303) and formula (305) are commercially available or can be prepared according to methods known to one skilled in the art.

In general, compounds of formula (Ib) and formula (Ic) are prepared by the procedure set forth above in REACTION SCHEME 3 by deprotection of compounds of formula (301) using methods known to one skilled in the art to generate the

are as defined above, Q is an alkylene chain, an aralkyl group, or a heteroarylalkyl group (where —CN is a substituent on the aryl radical of the aralkyl group or on the heteroaryl radical of the heteroarylalkyl group) and $R^{20}$ is hydrogen, alkyl, haloalkyl or cycloalkyl:

REACTION SCHEME 4

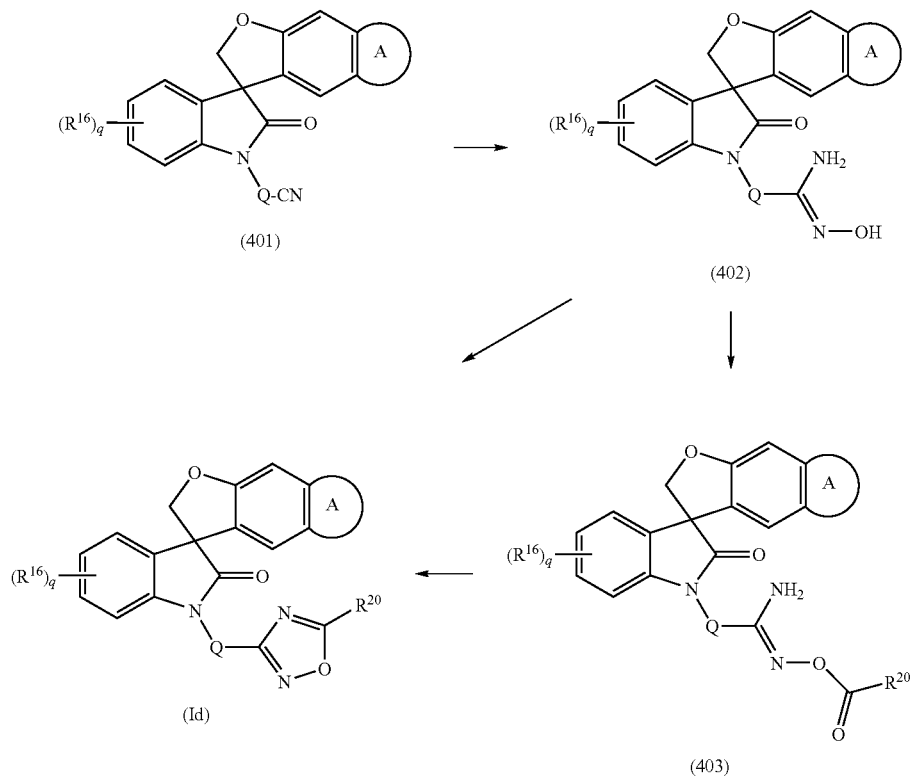

Compounds of formula (401) can be prepared according to methods known to one skilled in the art or by the methods disclosed herein or by the methods disclosed in PCT Published Patent Application WO 2006/110917.

REACTION SCHEME 4 illustrates a schematic synthesis of oxadiazole compounds for formula (Id). Compounds of formula (402) can be obtained by treating the compound of formula (401) with hydroxylamine in a solvent such as, but not limited to, dimethyl sulfoxide. A compound of formula (402) is converted to a compound of formula (Id) by reacting with an appropriately substituted anhydride or acyl chloride in the presence of a base such as, but not limited to, pyridine (also as a solvent) in a microwave reactor at a high temperature such as 170° C. Alternatively, the oxadiazole ring formation is accomplished by reacting compound (402) with an appropriately substituted anhydride or acyl chloride in the presence of a base such as, but not limited to, diisopropylamine, in a solvent such as, but not limited to, dichloromethane.

Alternatively, a compound of formula (402) can react with an appropriately substituted acyl chloride in the presence of a base such as, but not limited to, diisopropyl amine, in a solvent such as, but not limited to, dichloromethane to lead to the formation of compound of formula (403), which is then treated with a base such as, but not limited to, pyridine (also as a solvent) in a microwave reactor at a high temperature such as 170° C. to provide the compound of formula (Id).

Preparation of Compounds of Formula (Ie) and Formula (if)

Compounds of formula (Ie) and formula (If) are compounds of the invention, as set forth above in the Summary of the Invention. They may be prepared by the methods set forth below in REACTION SCHEME 5 where q, $R^{16}$ and

are as defined above,

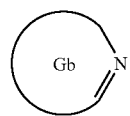

is a N-heteroaryl, and $R^{21}$ and $R^{22}$ are each independently hydrogen, alkyl, aralkyl, or aryl or $R^{21}$ and $R^{22}$, together with the nitrogen to which they are both attached, form an optionally substituted N-heteroaryl or N-heterocycle:

REACTION SCHEME 5

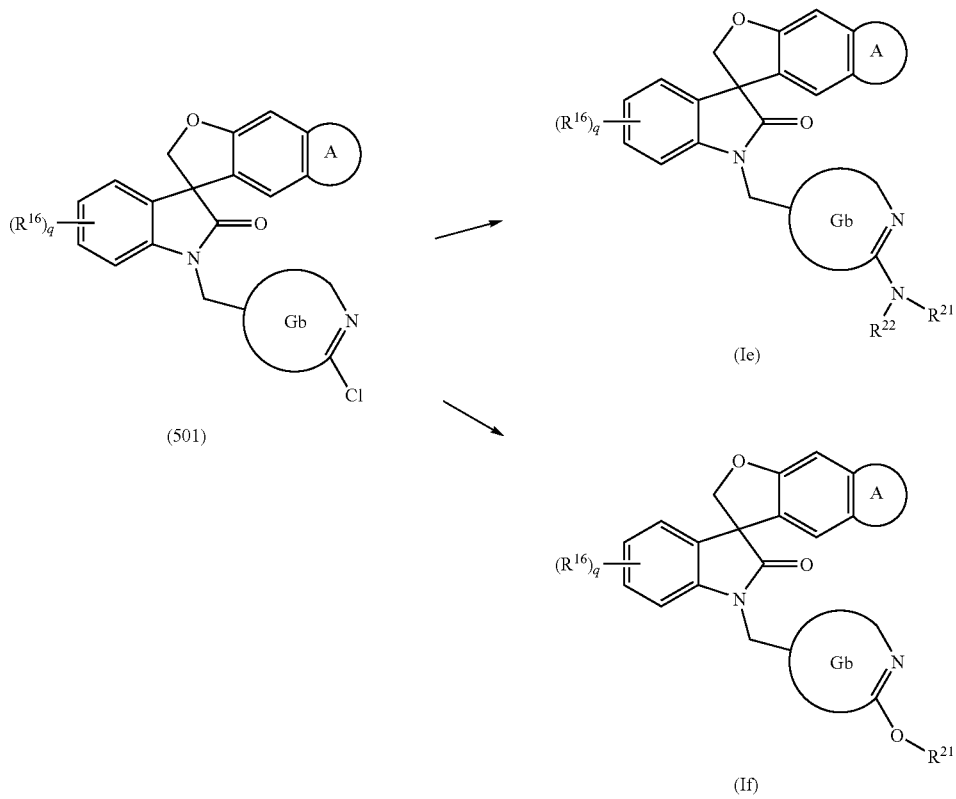

Compounds of formula (501) can be prepared according to methods known to one skilled in the art or by the methods disclosed herein or by the methods disclosed in PCT Published Patent Application WO 2006/110917.

In general, REACTION SCHEME 5 above illustrates a schematic synthesis of compounds of formula (Ie) and formula (If). A compound of formula (Ie) is obtained by treating the compound of formula (501) with an amine such as, but not limited to, dimethylamine, piperidine or morpholine in a solvent such as, but not limited to, N,N-dimethylfromamide at a high temperature, such as 120° C.

In another aspect, compound of formula (If) is obtained by treating the compound of formula (501) with an oxide nucleophile such as, but not limited to, sodium methoxide in a solvent such as, but not limited to, N,N-dimethylfromamide at high temperature such as 120° C.

Preparation of Compounds of Formula (Iq)

Compounds of formula (Ig) are compounds of the invention, as set forth above in the Summary of the Invention. They may be prepared by the methods set forth below in REACTION SCHEME 6 where q, $R^{16}$ and

are as defined above, Q is an alkylene chain, an aralkyl group or a heteroarylalkyl group (where —C(O)OR$^{23}$ is a substituent on the aryl radical of the aralkyl group or on the heteroaryl radical of the heteroarylalkyl group), $R^{23}$ is alkyl, and $R^{24}$ and $R^{25}$ are each independently hydrogen, alkyl, cycloalkyl, aryl or heteroaryl:

REACTION SCHEME 6

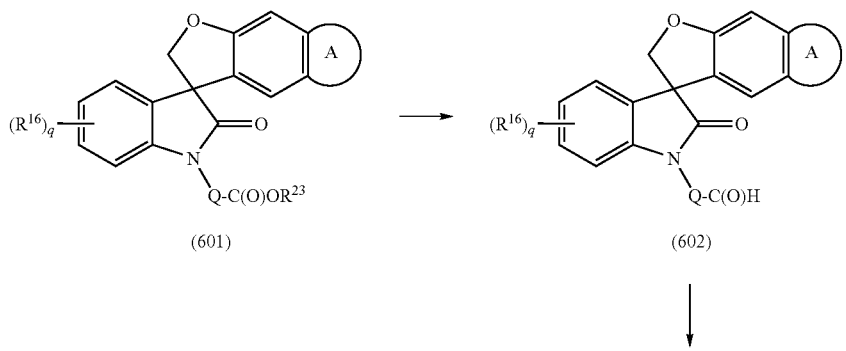

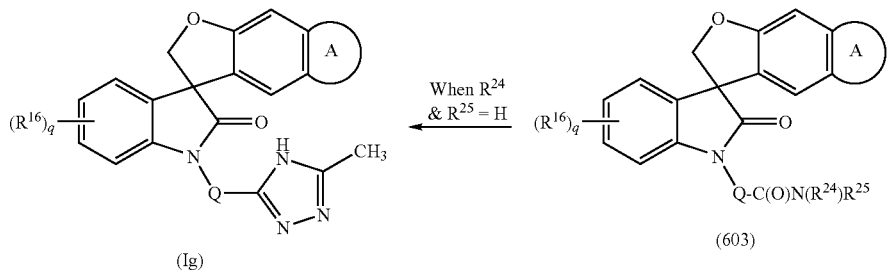

Compounds of formula (601) can be prepared according to methods known to one skilled in the art or by the methods disclosed herein or by the methods disclosed in PCT Published Patent Application WO 2006/110917.

In general, REACTION SCHEME 6 illustrates a schematic synthesis of compounds as formula (Ig). An ester compound of formula (601) is converted to the corresponding carboxylic acid of formula (602) by treatment of the ester compound of formula (601) with a base such as, but not limited to, lithium hydroxide, sodium hydroxide or potassium hydroxide, in a mixed solvent such as, but not limited to, tetrahydrofuran or methanol with water. The acid compound of formula (602) can be converted to a mixed anhydride, by treatment with iso-butyl chloroformate in the presence of a base such as, but not limited to, N-methylmorpholine, or the corresponding acid chloride, by treating with oxalyl chloride in the presence of catalytic amount of N,N-dimethylformamide in a solvent such as, but not limited to, toluene, dichloromethane or chloroform. The mixed anhydride reacts directly with, or the acid chloride react with, in the presence of a base such as, but not limited to, triethylamine or diisopropyl ethylamine, a primary or secondary amine to form the amide compound (603). When $R^{24}$ and $R^{25}$ are each hydrogen, the compound of formula (603) reacts with N,N-dimethylacetamide dimethyl acetyl in a solvent such as, but not limited to, 1,4-dioxane to generate an intermediate that reacts with hydrazine to form the triazole compound of (Ig).

Preparation of Compounds of Formula (Ih), Formula (II), Formula (IIa), Formula (IIb), Formula (Iic), Formula (ID, Formula (Ik), Formula (Ika), Formula (Ikb), Formula (Ikc), Formula (Ikd), Formula (Ike) and Formula (Ikf)

Compounds of formula (Ih), formula (Ii), formula (Iia), formula (Iib), formula (Iic), formula (IA formula (Ik), formula (Ika), formula (Ikb), formula (Ikc), formula (Ikd), formula (Ike) and formula (Ikf) are compounds of the invention, as set forth above in the Summary of the Invention. They may be prepared by the methods set forth below in REACTION SCHEMES 7 and 8 wherein q, $R^{15}$, $R^{16}$, $R^{20}$, and

⓪ A are as defined above,

⓪ Gc is aryl or heteroaryl, $R^{26}$, $R^{27}$, and $R^{28}$ are each independently hydrogen, alkyl, optionally substituted aryl or optionally substituted heteroaryl, and $R^{35}$ is alkyl, aryl or heteroaryl:

REACTION SCHEME 7

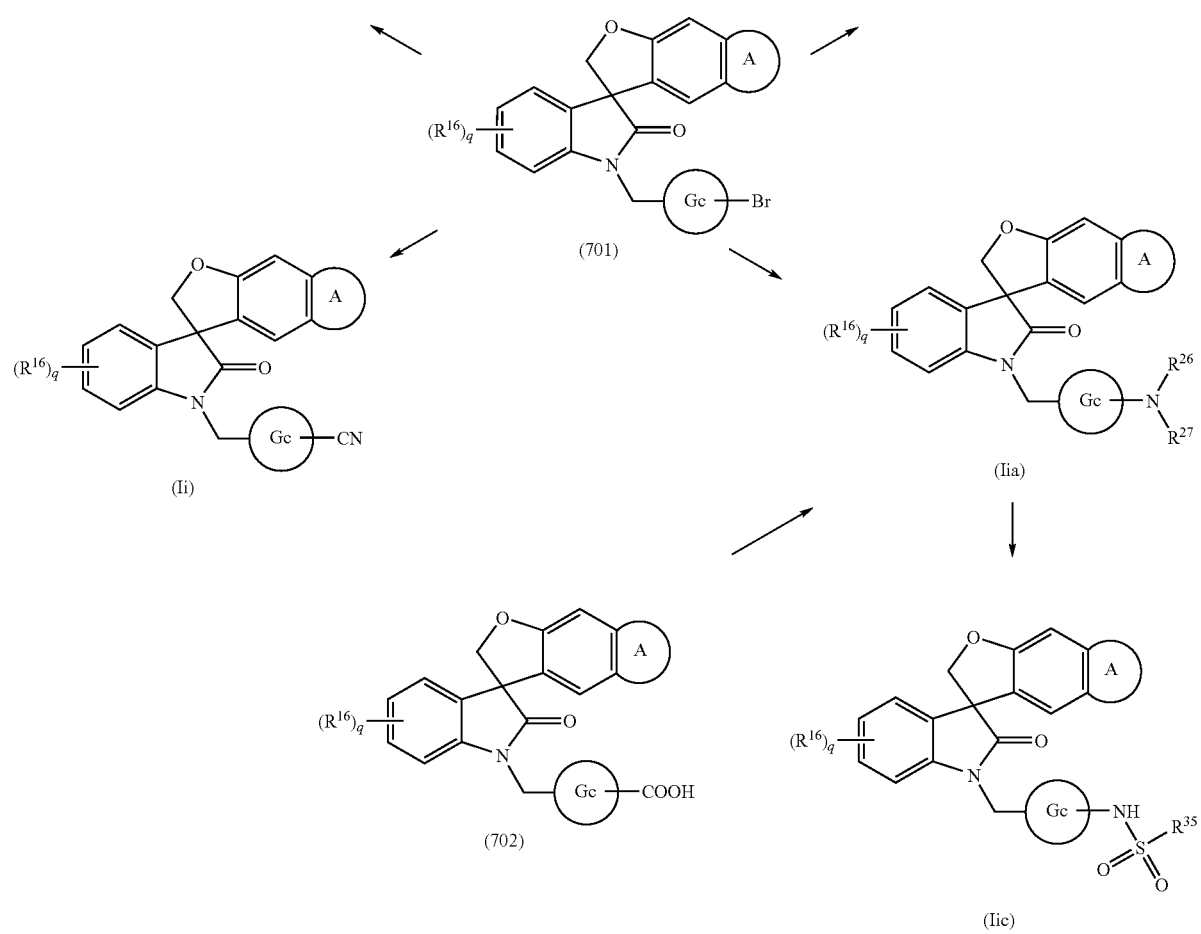
REACTION SCHEME 8
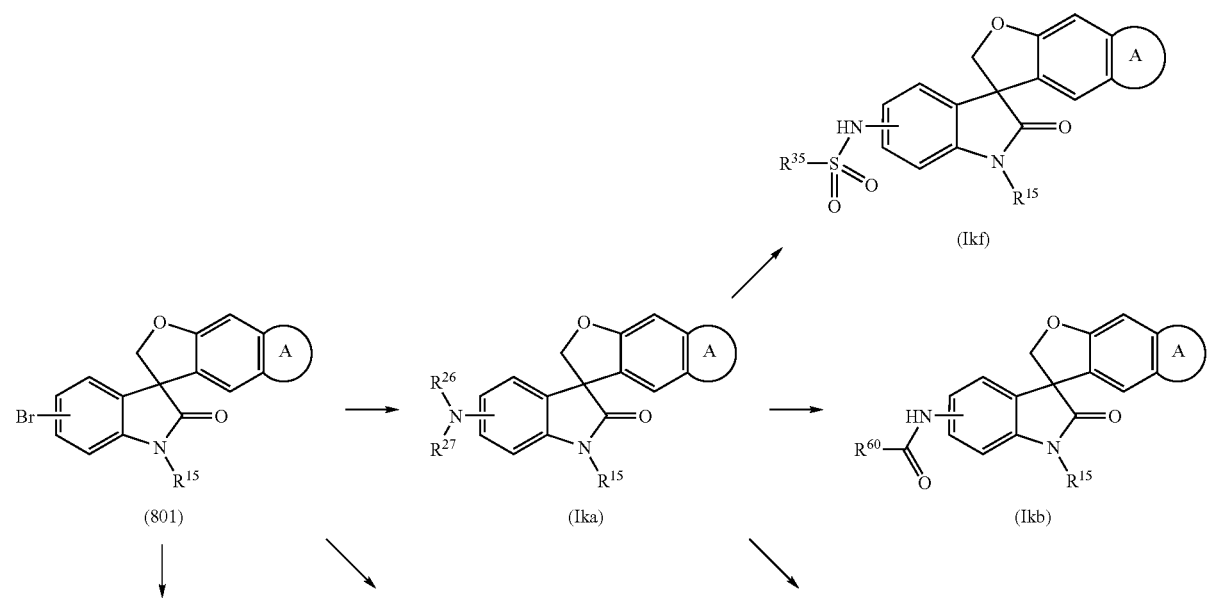

-continued

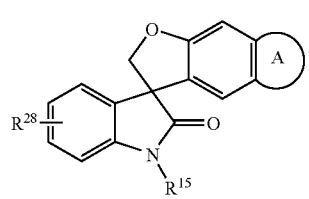

(Ij)

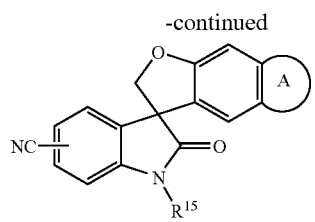

(Ik)

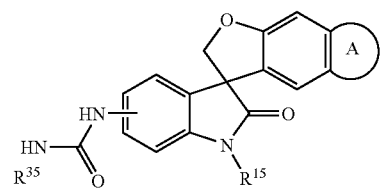

(Ikc)

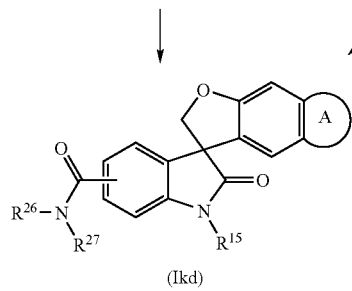

(Ikd)

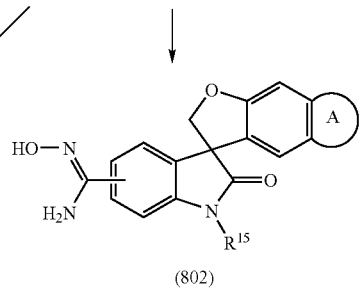

(802)

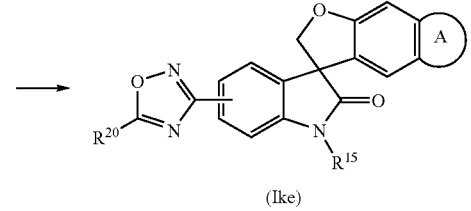

(Ike)

Compounds of formula (701) and formula (801) can be prepared according to methods known to one skilled in the art or by the methods disclosed herein or by the methods disclosed in PCT Published Patent Application WO 2006/110917.

In general, compounds of formula (Ih), formula (Ii), formula (Iia), formula (Iib), formula (Iic), formula (Ij) formula (Ik), formula (Ika), formula (Ikb), formula (Ikc), formula (Ikd), formula (Ike) and formula (Ikf) are synthesized as shown in REACTION SCHEME 7 or REACTION SCHEME 8. Compound of formula (701) or formula (801) reacts with a primary or secondary amine in the presence of a palladium catalyst such as, but not limited to, palladium acetate, tetrakis(triphenylphosphine)palladium(0) or tris(dibenzylideneacetone)dipalladium(0) with or without a ligand such as, but not limited to, triphenylphosphine, tri(o-tolyl)phosphine, 1,1'-bis(diphenylphosphino)ferrocene or 2-(di-tert-butylphosphino)biphenyl, a base such as, but not limited to, sodium carbonate, cesium carbonate or sodium tert-butoxide, in a solvent such as, but not limited to, toluene, dioxane or tetrahydrofuran, to provide the amino compound of formula (Iia) or formula (Ika) (See Muci, A. R. et al., *Topics in Current Chemistry* (2002), 219:131).

Alternatively, compound of formula (701) or formula (801) reacts with a cyclised lactam type of compound in the presence of a copper catalyst such as, but not limited to, copper (I) iodide, a ligand such as, but not limited to, 8-hydroxyquinoline or rac-trans-N,N'-dimethylcyclohexane-1,2-diamine, a base such as, but not limited to, potassium carbonate in a solvent such as, but not limited to, dimethyl sulfoxide provides the product of formula (Iia) or formula (Ika).

Alternatively, the carboxylic acid compound of formula (702) reacts with diphenyl phosphorazidate in the presence of an amine such as, but not limited to, triethylamine and tert-butanol in a solvent such as, but not limited to, toluene gives a tert-butyloxycarbonyl protected amino intermediate that leads to the formation of the amino compound of formula (Iia), where $R^{26}$ and $R^{27}$ are each hydrogen, upon acidic treatment.

Compound (701) or (801) reacts with an alkyl, vinyl, aryl or heteroaryl boronic acid or an alkyl, vinyl, aryl or heteroaryl stannane reagent in the presence of a palladium catalyst such as, but not limited to, palladium acetate, tetrakis(triphenylphosphine)palladium(0), tris(dibenzylideneacetone)dipalladium(0) with or without a ligand such as, but not limited to, triphenylphosphine, tri(o-tolyl)phosphine, 1,1'-bis(diphenylphosphino)ferrocene or 2-(di-tert-butylphosphino)biphenyl, a base such as, but not limited to, sodium carbonate, cesium carbonate, or sodium bicarbonate in a solvent such as, but not limited to, dimethoxyethane, dioxane, or tetrahydrofuran to provide the coupled product of formula (Ih) or (II) (See Kotha, S. et al., *Tetrahedron* (2002), 58:9633 and Miyaura, N. et al., *Chem. Rev.* (1995), 95:2457 and Farina, V. et al., *Org. React.* (1997), 50:1).

Compound (701) or (801) reacts with sodium cyanide, zinc cyanide or tributyltin cyanide and potassium cyanide in the presence of a nickel catalyst such as, but not limited to, nickel(II) chloride or a palladium catalyst such as, but not limited to, palladium acetate, tris(dibenzylideneacetone)dipalladium(0) and a ligand such as, but not limited to, tri(o-tolyl)phosphine, 1,1'-bis(diphenylphosphino)ferrocene or 2-(di-tert-butylphosphino)biphenyl in a solvent such as, but not limited to, N,N-dimethylformamide, 1-methylpyrrolidinone or acetonitrile to provide the cyano compounds of formula (Ii) or formula (Ik) (See Marcantonio, K. M. et al., *Org. Lett.* (2004), 6:3723-5 and Yang, C. et al., *Org. Lett.* (2004), 6:2837-40).

Compound (701) reacts with a sodium sulfonate such as, but not limited to, sodium methanesulfonate in the presence of a copper catalyst such as, but not limited to, copper iodide, and the sodium salt of L-proline in a solvent such as, but not limited to, dimethyl sulfoxide to provide the sulfone product of formula (Iib).

In compound of formula (Ika), when $R^{26}$ and $R^{27}$ are each hydrogen, it is coupled with a carboxylic acid, carried out by one skilled in the art, to provide the amide compound of formula (Ikb). Alternatively, treatment of the amino compound of formula (Ika) with an amine in the presence of a coupling agent such as, but not limited to, trichloromethyl chloroformate provide the urea compound of formula (Ikc).

Compound (801) reacts with an alcohol and carbon monoxide in the presence of a palladium catalyst such as, but not limited to, palladium acetate and a ligand such as, but not limited to, 1,3-bis(dicyclohexylphosphonium)propane bis(tetrafluoroborate) and a base such as, but not limited to, potassium carbonate in a solvent such as, but not limited to, N,N-dimethylformamide to provide the ester compound of formula (ID, where $R^{28}$ is —$COOR^{25}$ (where $R^{25}$ is as defined above). When $R^{25}$ is phenyl, the ester compound of formula (Ij) is treated with an amine in the presence of a base such as, but not limited to, potassium carbonate in a solvent such as, but not limited to, N,N-dimethylformamide to provide the amide compound of formula (Ikd). Alternatively, the ester compound of formula (Ij) is hydrolyzed using a base such as, but not limited to, lithium hydroxide or sodium hydroxide to afford an acid that can couple with an amine, carried out by one skilled in the art, to provide the amide compound of formula (Ikd). Alternatively, the hydrolysis of a nitrile compound of formula (Ik) with aqueous sodium carbonate and hydrogen peroxide in a solvent such as, but not limited to, ethanol provides the primary amide compound of formula (Ikd).

Alternatively, compounds of formula (802) can be obtained by treating the compound of formula (Ik) with hydroxylamine in a solvent such as, but not limited to, dimethyl sulfoxide. A compound of formula (802) is converted to a compound of formula (Ike) by reacting with an appropriately substituted anhydride or acyl chloride in the presence of a base such as, but not limited to, pyridine (also as a solvent) in a microwave reactor at a high temperature such as 170° C.

Alternatively, when $R^{26}$ and $R^{27}$ are each hydrogen, compounds of formula (Iia) and (Ika) react with a sulfonyl chloride reagent such as, but not limited to, methanesulfonyl chloride in the presence of a base such as, but not limited to, pyridine in a solvent such as, but not limited to, dichloromethane or chloroform to provide the sulphonamide product of formula (Iic) and (Ikf).

Preparation of Compounds of Formula (Im) and Formula (Ima)

Compounds of formula (Im) are compounds of the invention, as set forth above in the Summary of the Invention. They may be prepared by the methods set forth below in REACTION SCHEME 9 wherein q, $R^{15}$, $R^{16}$, $R^{20}$, $R^{26}$ and $R^{27}$ are as described above:

Compounds of formula (901) can be prepared according to methods known to one skilled in the art or by the methods disclosed herein or by the methods disclosed in PCT Published Patent Application WO 2006/110917.

In general, compounds of formula (Im) and formula (Ima) are synthesized as shown in REACTION SCHEME 9. A compound of formula (901) reacts with a primary or secondary amine in the presence of a palladium catalyst such as, but not limited to, palladium (II) acetate, tetrakis(triphenylphosphine)palladium(0) or tris(dibenzylideneacetone)dipalladium(0) with or without a ligand such as, but not limited to, triphenylphosphine, tri(o-tolyl)phosphine, 1,1-bis(diphenylphosphino)ferrocene or 2-(di-tert-butylphosphino)biphenyl, a base such as, but not limited to, sodium carbonate, cesium carbonate or sodium tert-butoxide in a solvent such as, but not limited to, toluene, dioxane, or tetrahydrofuran to provide the amino compound of formula (Im) (See Muci, A. R. et al., Topics in Current Chemistry (2002), 219:131).

Compound (901) reacts with sodium cyanide, zinc cyanide or tributyltin cyanide and potassium cyanide in the presence of a nickel catalyst such as, but not limited to, nickel(II) chloride or a palladium catalyst such as, but not limited to, palladium acetate, tris(dibenzylideneacetone)dipalladium(0) and a ligand such as, but not limited to, tri(o-tolyl)phosphine, 1,1'-bis(diphenylphosphino)ferrocene or 2-(di-tert-butylphosphino)biphenyl in a solvent such as, but not limited to, N,N-dimethylformamide, 1-methylpyrrolidinone or acetonitrile to provide the cyano compounds of formula (902) (See Marcantonio, K. M. et al., Org. Lett. (2004), 6:3723-5 and Yang, C. et al., Org. Lett. (2004), 6:2837-40).

A compound of formula (902) is treated with hydroxylamine and with an appropriately substituted anhydride or acyl chloride in the presence of a base such as, but not limited to, pyridine (also as a solvent) in a microwave reactor at a high temperature such as 170° C. to provide the oxadiazole product of formula (Ima).

Preparation of Compounds of Formula (In) and (Ina)

Compounds of formula (In) and (Ina) are compounds of the invention, as set forth above in the Summary of the Invention.

REACTION SCHEME 9

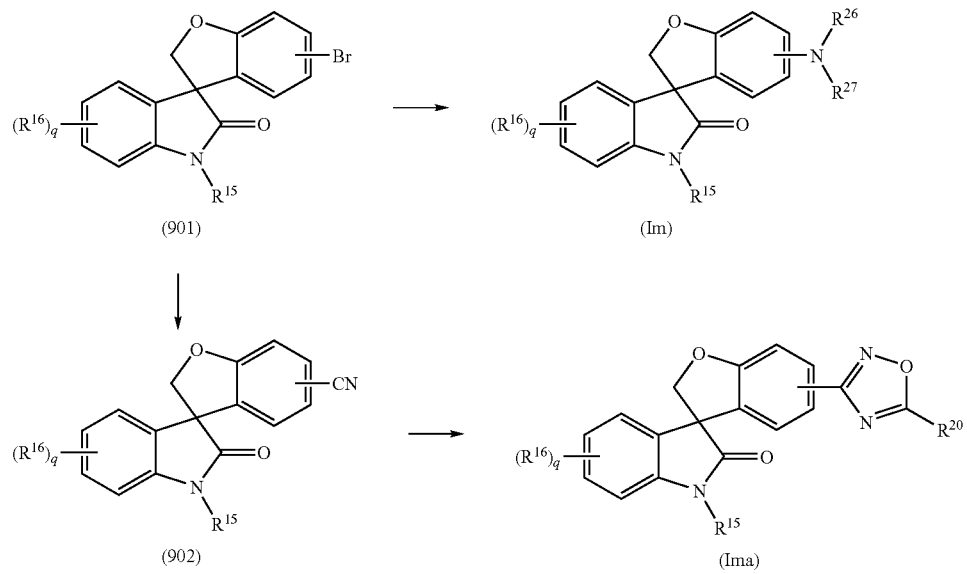

They may be prepared by the methods set forth below in REACTION SCHEME 10 wherein $R^{15}$, $R^{26}$, $R^{27}$ and

are as defined above, and $R^{29}$ is —C(O)H, alkyl, hydroxyalkyl or formyl:

in the presence of a copper reagent such as, but not limited to, copper (I) iodide, a ligand such as, but not limited to, 1-butyl-1H-imidazole and a base such as, but not limited to, potassium carbonate in a solvent such as, but not limited to, toluene provides the ether compound of formula (Ina).

Alternatively, treatment of a compound of formula (1003) with a base such as, but not limited to, cesium carbonate in a solvent such as, but not limited to, N,N-dimethylformamide and reaction with a halo reagent $R^{27}$—X gives the ether compound of formula (Ina).

REACTION SCHEME 10

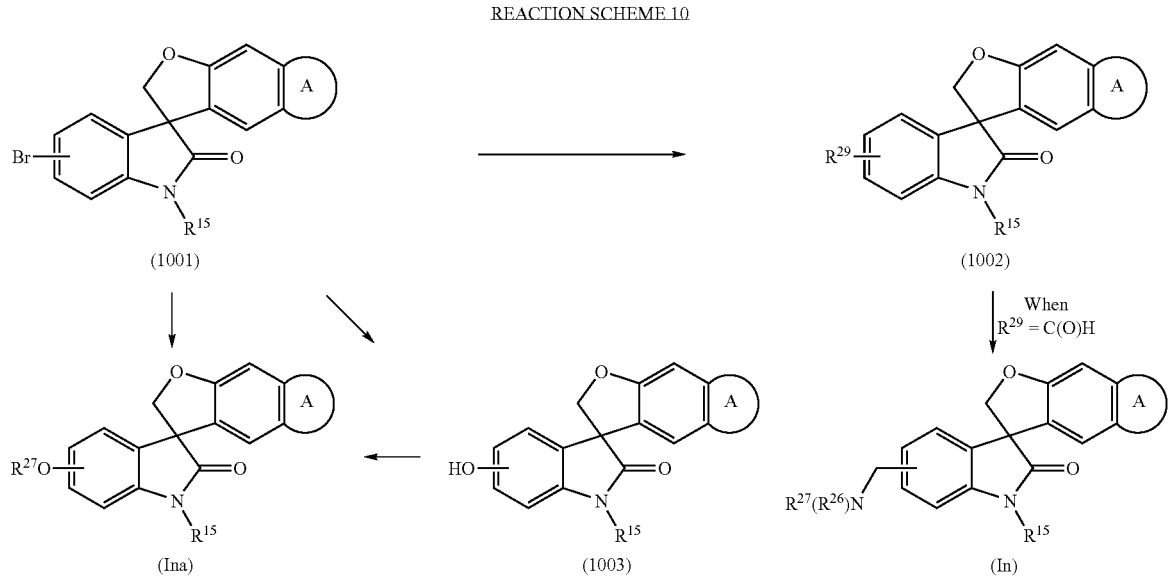

Compounds of formula (1001) can be prepared according to methods known to one skilled in the art or by the methods disclosed herein or by the methods disclosed in PCT Published Patent Application WO 2006/110917.

In general, compounds of formula (In) can be synthesized as shown in REACTION SCHEME 10. Treatment of a compound of formula (1001) with a lithium reagent such as, but not limited to, n-butyllithium or t-butyllithium in a solvent such as, but not limited to, tetrahydrofuran or diethyl ether, generates an anion that reacts with an electrophile to provide the compound of formula (1002). When the electrophile is N,N-dimethylformamide, an aldehyde compound of formula (1002) where $R^{29}$ is C(O)H is obtained, which reacts with an amine under reductive amination conditions, in the presence of a reducing agent such as, but not limited to, sodium cyanoborohydride or sodium triacetoxyborohydride, to provide the amine compound of formula (In).

Alternatively, treatment of a compound of formula (1001) with an alcohol such as, but not limited to, benzyl alcohol, phenol or substituted aryl and heteroaryl hydroxy compounds in the presence of a copper reagent such as, but not limited to, copper (I) iodide, a ligand such as, but not limited to, 3,4,7,8-tetramethyl-1,10-phenanthroline and a base such as, but not limited to, cesium carbonate in a solvent such as, but not limited to, toluene provides the ether compound of formula (Ina).

Alternatively, treatment of a compound of formula (1001) with a lithium reagent such as n-butyl lithium or t-butyl lithium, a boron reagent such as, but not limited to, trimethyl borate, followed by oxidation with hydrogen peroxide affords the hydroxy compound of formula (1003). Treatment of a compound of formula (1003) with an aryl or heteroaryl halide Preparation of Compounds of Formula (Io)

Compounds of formula (Io) are compounds of the invention, as set forth above in the Summary of the Invention. They may be prepared by the methods set forth below in REACTION SCHEME 11 wherein q, $R^{15}$ and $R^{16}$ are as defined above and $R^{30}$ is alkyl, cycloalkyl or heterocyclyl:

REACTION SCHEME 11

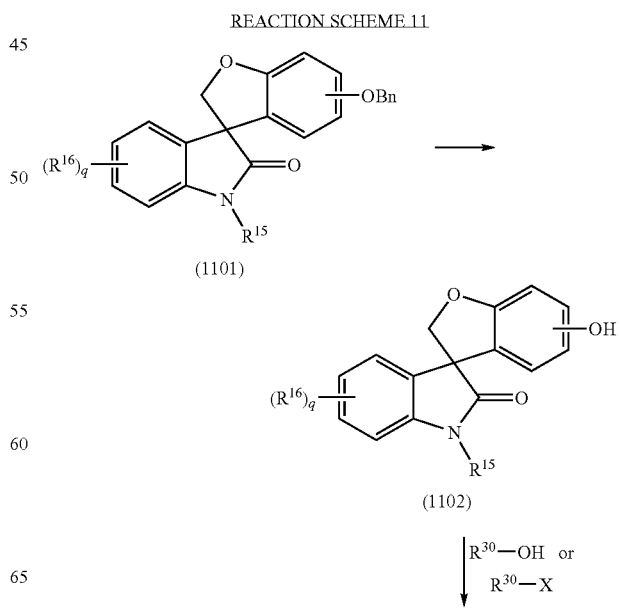

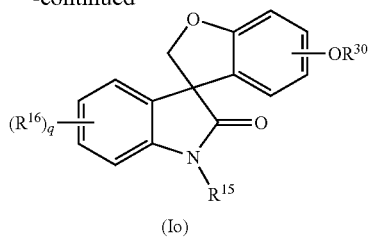

(Io)

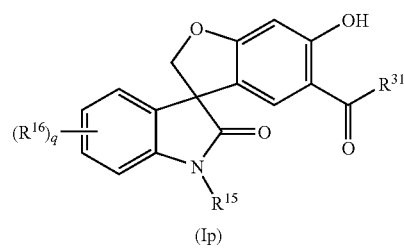

(Ip)

Compounds of formula (1101) can be prepared according to methods known to one skilled in the art or by the methods disclosed herein or by the methods disclosed in PCT Published Patent Application WO 2006/110917.

In general, REACTION SCHEME 11 illustrates a schematic synthesis of compounds of formula (Io). The benzyl protecting group of (1101) is removed selectively by hydrogenation under one atm pressure of hydrogen with a catalyst such as, but not limited to, palladium on carbon in a solvent such as, but not limited to, methanol, to provide the compound of formula (1102). The reaction of compound of formula (1102) with an alcohol ($R^{30}$—OH) under Mitsunobu reaction conditions in the presence of a phosphine reagent such as, but not limited to, triphenylphosphine, tributylphosphine, or trimethyl phosphine, and azadicarboxylate of diethyl, diisopropyl, di-tert-butyl or N,N,N,N'-tetramethylazodicarboxamide in a solvent such as, but not limited to, tetrahydrofuran, ethyl acetate, or dichloromethane, provides the compound of formula (Io).

Alternatively, treatment of compound of formula (1102) with a base such as, but not limited to, potassium carbonate or sodium hydride in a solvent such as, but not limited to N,N-dimethylformamide or tetrahydrofuran and reaction with an alkyl halide $R^{30}$—X provides the compound of formula (Io).

Preparation of Compounds of Formula (Ip)

Compounds of formula (Ip) are compounds of the invention, as set forth above in the Summary of the Invention. They may be prepared by the methods set forth below in REACTION SCHEME 12 wherein R", q, $R^{15}$ and $R^{16}$ are as defined above, and $R^{31}$ is alkyl or haloalkyl:

REACTION SCHEME 12

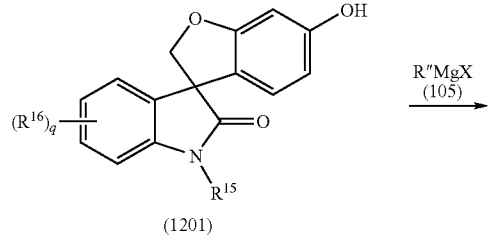

(1201)

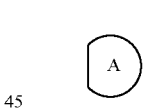

Compounds of formula (1201) can be prepared according to methods known to one skilled in the art or by the methods disclosed herein or by the methods disclosed in PCT Published Patent Application WO 2006/110917. Compounds of formula (105) are commercially available.

In general, REACTION SCHEME 12 illustrates a schematic synthesis of compounds of formula (Ip). Treatment of the alcohol compound of formula (1201) with a Grignard reagent of formula (105) at low temperature (0° C.) forms a phenoxymagnesium halide intermediate which reacts with an electrophile such as, but not limited to, trifluoroacetic anhydride in a solvent, such as, but not limited to, methylene chloride or tetrahydrofuran, to afford a compound of formula (Ip).

Preparation of Compounds of Formula (Iq), Formula (Ir) and Formula (Is)

Compounds of formula (Iq), formula (Ir) and formula (Is) are compounds of the invention, as set forth above in the Summary of the Invention. They may be prepared by the methods set forth below in REACTION SCHEME 13 wherein q, $R^{16}$, $R^{26}$, $R^{27}$ and are as defined above, and Qa is an $C_1$-$C_3$alkylene chain, $R^{32}$ is hydrogen or alkyl, and $R^{33}$ is hydrogen, alkyl, haloalkyl, cycloalkyl or heterocyclyl:

REACTION SCHEME 13

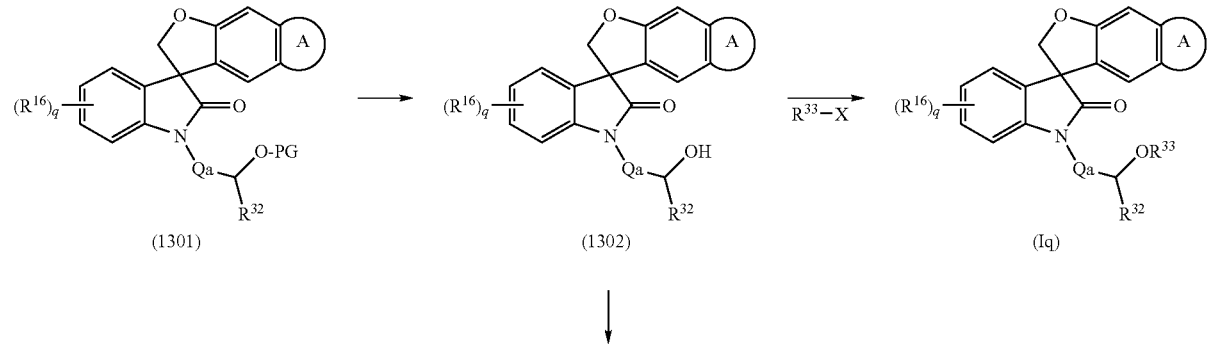

(1301)   (1302)   (Iq)

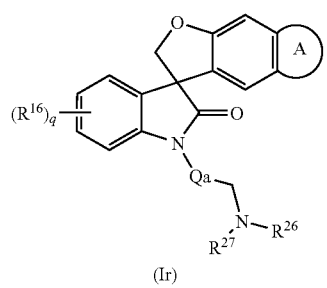
(Ir)

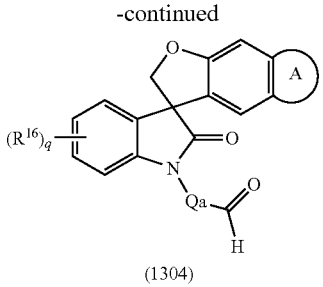
(1304)

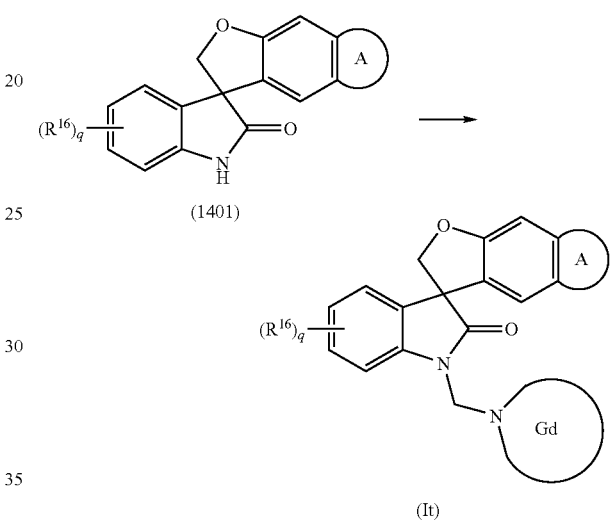
(Is)

Compounds of formula (1301) can be prepared according to methods known to one skilled in the art or by the methods disclosed herein or by the methods disclosed in PCT Published Patent Application WO 2006/110917. Compounds $R^{33}$—X are commercially available.

In general, REACTION SCHEME 13 illustrates a schematic synthesis of compounds of formula (Iq), formula (Ir) and formula (Is). The oxygen protecting group in the compound of formula (1301) is removed by using the method known to one skilled in the art to provide the alcohol compound of formula (1302). Alkylation with a halide (bromo, chloro or bromo) reagent ($R^{33}$—X) in the presence of a base such as, but not limited to, cesium carbonate, sodium hydride or potassium carbonate, in a solvent such as, but not limited to, tetrahydrofuran or N,N-dimethylformamide, provides the compound of formula (Iq). When $R^{32}$ is a hydrogen in the compound of formula (1302), the primary alcohol is oxidized by an oxidant such as, but not limited to, 1,1,1-tris(acetyloxy)-1,1-dihydro-1,2-benziodoxol-3-(1'H)-one (Dess-Martin periodinane) to form its corresponding aldehyde compound of formula (1304), which reacts with an amine under reductive amination conditions, in the presence of a reducing agent such as, but not limited to, sodium cyanoborohydride or sodium triacetoxyborohydride, to provide the amine compound of formula (Ir). In another aspect, the aldehyde compound of formula (1304) reacts with a nucleophile such as, but not limited to, methyl magnesiumbromide or the combination of trifluoromethyltrimethylsilane and cesium fluoride to form the compound of formula (Is).

Preparation of Compounds of Formula (It)

Compounds of formula (It) are compounds of the invention, as set forth above in the Summary of the Invention. They may be prepared by the methods set forth below in REACTION SCHEME 14 wherein q, $R^{16}$ and

are as defined above, and

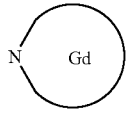

is an optionally substituted N-heterocyclyl:

REACTION SCHEME 14

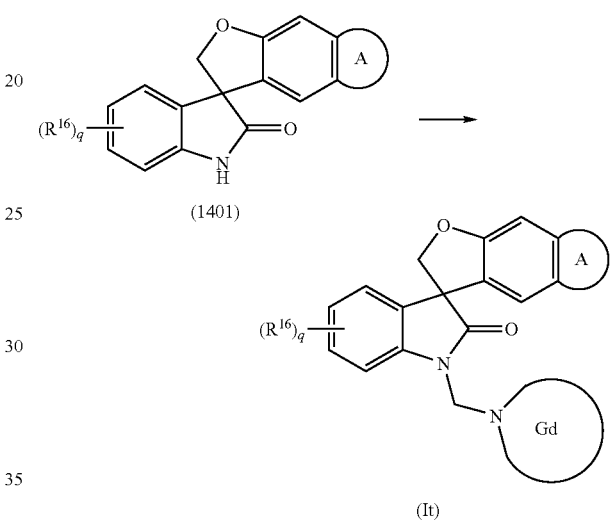

Compounds of formula (1401) can be prepared according to methods known to one skilled in the art or by the methods disclosed herein or by the methods disclosed in PCT Published Patent Application WO 2006/110917.

In general, REACTION SCHEME 14 illustrates a schematic synthesis of compounds of formula (It). Treatment of a compound of formula (1401) with formaldehyde in the presence of an optionally substituted N-heterocyclyl, such as, but not limited to, 4-methylpiperazine or piperidine, in a solvent such as, but not limited to, methanol, provides the compounds of formula (It).

Preparation of Compounds of Formula (Iu)

Compounds of formula (Iu) are compounds of the invention, as set forth above in the Summary of the Invention. They may be prepared by the methods set forth below in REACTION SCHEME 15 wherein X, q, $R^{16}$ and

are as defined above, and

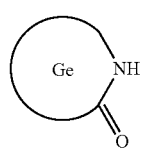

is an optionally substituted N-heteroaryl or an optionally substituted N-heterocyclyl and $R^{34}$ is alkyl or aralkyl:

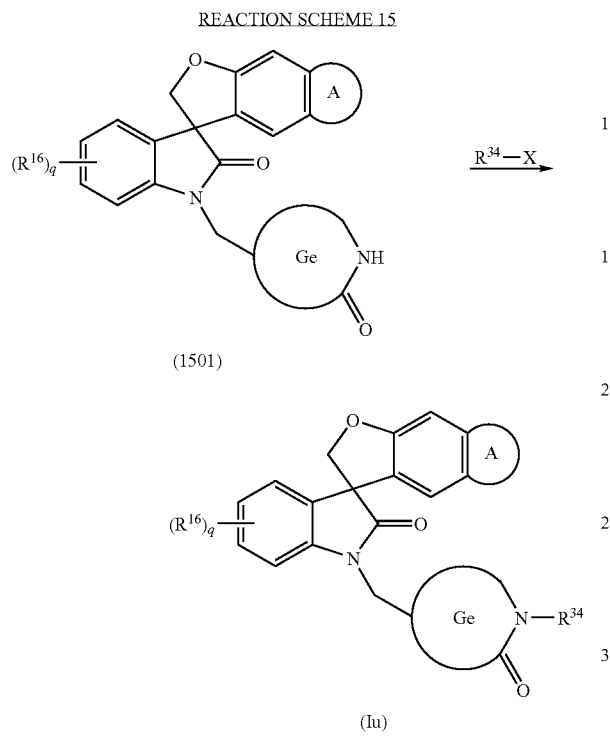

Compounds of formula (1501) can be prepared according to methods known to one skilled in the art or by the methods disclosed herein or by the methods disclosed in PCT Published Patent Application WO 2006/110917. Compounds $R^{34}$—X are commercially available.

In general, REACTION SCHEME 15 illustrates a schematic synthesis of compounds of formula (Iu). Treatment of a compound of formula (1501) with a base such as, but not limited to, sodium hydride and an alkylating reagent ($R^{34}$—X) in a solvent such as, but not limited to, tetrahydrofuran or N,N-dimethylformamide provides the compound of formula (Iu). Alternatively, the alkylation is accomplished by reacting the compound of formula (1501) with an alkylating reagent such as, but not limited to dimethyl sulfate under phase transfer reaction conditions using a base such as, but not limited to sodium hydroxide, a phase transfer catalyst such as, but not limited to tetrabutylammonium bromide in a solvent such as, but not limited to, aqueous tetrahydrofuran to provide the compound of formula (Iu).

Preparation of Compounds of Formula (Iv) and (Iva)

Compounds of formula (Iv) and (Iva) are compounds of the invention, as set forth above in the Summary of the Invention. They may be prepared by the methods set forth below in REACTION SCHEME 16 wherein $R^{15}R^{20}$ and

A are as defined above:

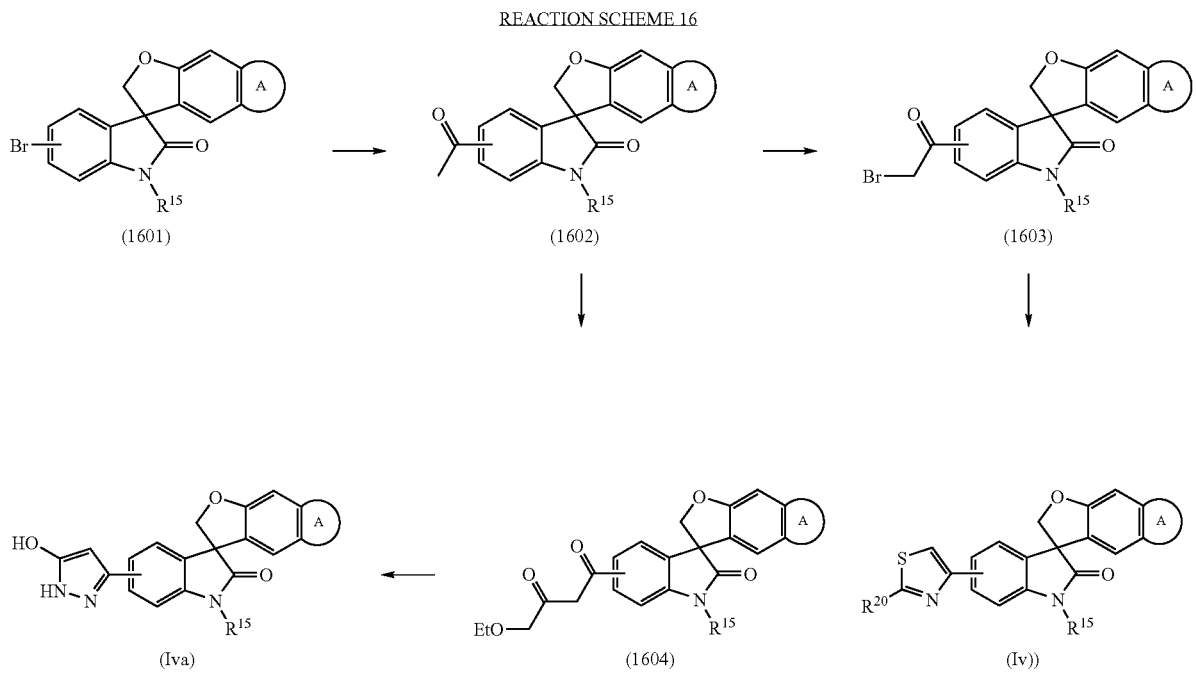

Compounds of formula (1601) can be prepared according to methods known to one skilled in the art or by the methods disclosed herein or by the methods disclosed in PCT Published Patent Application WO 2006/110917.

In general, REACTION SCHEME 16 illustrates a schematic synthesis of compounds of formula (Iv) and (Iva). Treatment of a compound of formula (1601) with a vinyl ether such as, but not limited to, butyl vinyl ether in the presence of a palladium catalyst such as, but not limited to, palladium (II) acetate, a ligand such as, but not limited to, 1,3-bis(diphenylphosphino)propane and a base such as, but not limited to, potassium carbonate in a solvent such as, but not limited to, N,N-dimethylformamide provides the compound of formula (1602). Bromination of (1602) with phenyltrimethylammonium tribromide gives the bromo compound of formula (1603). Reaction of (1603) with a sulphur containing reagent such as, but not limited to, thioacetamide or thiourea gives the thiazole compounds of formula (Iv). Alternatively, treatment of (1602) with a strong base such as, but not limited to, sodium hydride followed by the reaction with diethyl carbonate in a solvent such as, but not limited to, tetrahydrofuran gives the dicarbonyl compound of formula (1604), which is cyclised with hydrazine to provide the pyrazole compound of formula (Iva).

Preparation of Compounds of Formula (Iw)

Compounds of formula (Iw) are compounds of the invention, as set forth above in the Summary of the Invention. They may be prepared by the methods set forth below in REACTION SCHEME 17 wherein q, $R^{16}$ and are as defined above, and is an optionally substituted N-heteroaryl:

Compounds of formula (1701) can be prepared according to methods known to one skilled in the art or by the methods disclosed herein or by the methods disclosed in PCT Published Patent Application WO 2006/110917.

In general, REACTION SCHEME 17 illustrates a schematic synthesis of compounds of formula (Iw). Treatment of a compound of formula (1701) with N,N-dimethylformamide dimethyl acetal gives the imidoformamide compounds of formula (1702), which upon treatment with trifluoroacetic anhydride in a solvent such as, but not limited to, tetrahydrofuran provides the cyclized compounds of formula (Iw).

Preparation of Compounds of Formula (Ix)

Compounds of formula (Ix) are compounds of the invention, as set forth above in the Summary of the Invention. They may be prepared by the methods set forth below in REACTION SCHEME 18 where q and $R^{16}$ and are as defined above, Qb is an alkylene chain or an aralkyl group and $R^{35}$ is alkyl, aryl or heteroaryl:

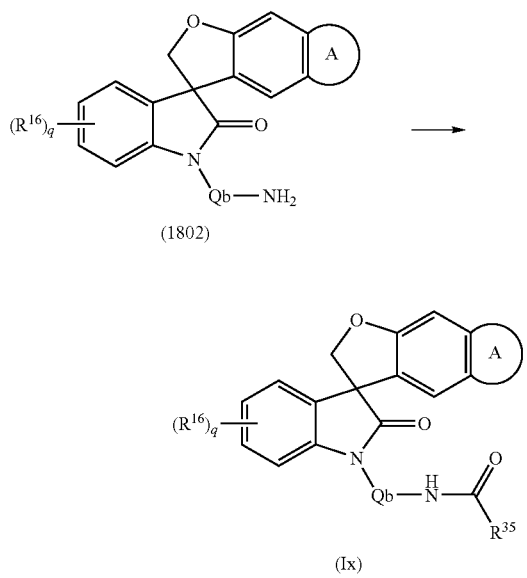

(1802)

(Ix)

Compounds of formula (1801) can be prepared according to methods known to one skilled in the art or by the methods disclosed herein or by the methods disclosed in PCT Published Patent Application WO 2006/110917.

In general, REACTION SCHEME 18 illustrates a schematic synthesis of compounds of formula (Ix). Treatment of a compound of formula (1801) with hydrazine gives the amino compounds of formula (1802), which upon reaction with an acylating reagent, carried out by one skilled in the art, provides the amide compound of formula (Ix).

Preparation of Compounds of Formula (Iy)

Compounds of formula (Iy) are compounds of the invention, as set forth above in the Summary of the Invention. They may be prepared by the methods set forth below in REACTION SCHEME 19 where q, $R^{16}$ and

are as defined above, Q is an alkylene chain, an aralkyl group, an aryl or a heteroaryl group (where —$CONH_2$ is a substituent on the aryl radical of the aralkyl group and on the heteroaryl radical of the heteroarylalkyl group) and $R^{35}$ is alkyl, aryl or heteroaryl:

Compounds of formula (1901) and (1902) can be prepared according to methods known to one skilled in the art or by the methods disclosed herein or by the methods disclosed in PCT Published Patent Application WO 2006/110917.

In general, REACTION SCHEME 19 illustrates a schematic synthesis of compounds of formula (Iy). Treatment of a compound of formula (1901) with an amide acetyl such as, but not limited to, dimethylacetamide dimethyl acetal in a solvent such as, but not limited to, 1,4-dioxane, followed by reaction with hydroxylamine in the presence of acetic acid gives the oxadiazole compound of formula (Iy).

Alternatively, treatment of the acid compound of formula (1902) with oxalyl chloride in the presence of a catalytic amount of N,N-dimethylformamide generates the corresponding acyl chloride, which upon reaction with an amidine compound such as, but not limited to, N-hydroxyacetamidine in a solvent such as, but not limited to, pyridine provides the oxadiazole product of formula (Iy).

Preparation of Compounds of Formula (Iz)

Compounds of formula (Iz) are compounds of the invention, as set forth above in the Summary of the Invention. They may be prepared by the methods set forth below in REACTION SCHEME 20 where q and $R^{16}$ and

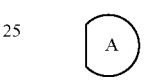

are as defined above, Q is an alkylene chain, an aralkyl group, an aryl group or a heteroaryl group:

REACTION SCHEME 20

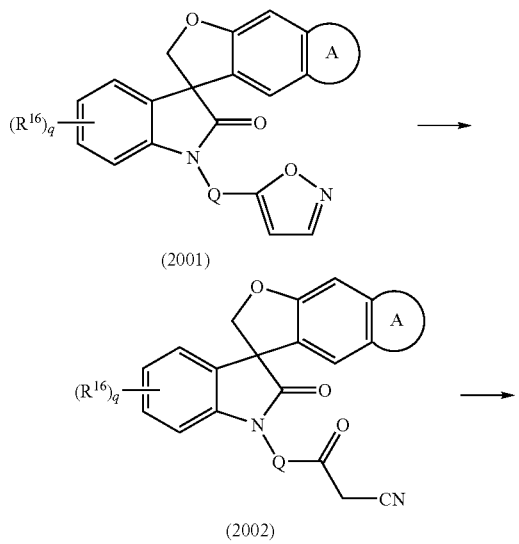

(2001)

(2002)

REACTION SCHEME 19

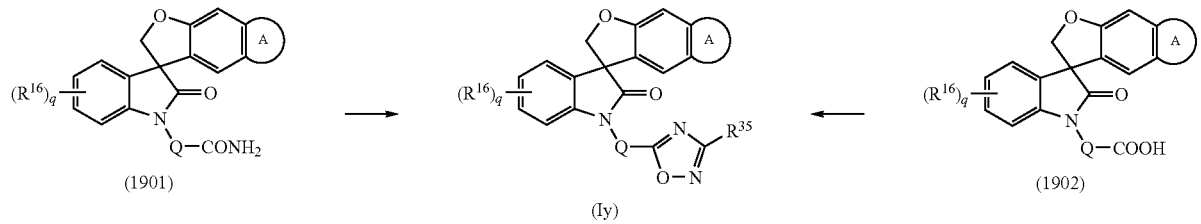

(1901)          (Iy)          (1902)

-continued

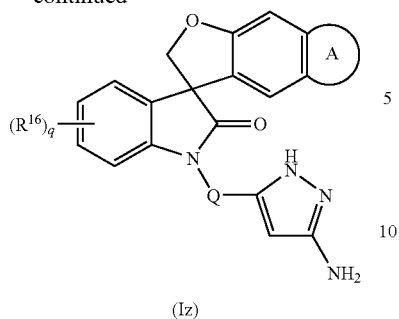

(Iz)

-continued

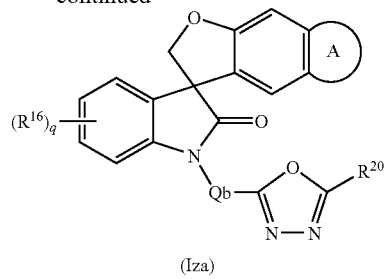

(Iza)

Compounds of formula (2001) can be prepared according to methods known to one skilled in the art or by the methods disclosed herein or by the methods disclosed in PCT Published Patent Application WO 2006/110917.

In general, REACTION SCHEME 20 illustrates a schematic synthesis of compounds of formula (Iz). Treatment of a compound of formula (2001) with a strong base such as, but not limited to, sodium hydride affords the cyano compound of formula (2002). Reaction of (2002) with hydrazine in a solvent such as, but not limited to, ethanol, provides the pyrazole compound of formula (Iz).

Preparation of Compounds of Formula (Iza)

Compounds of formula (Iza) are compounds of the invention, as set forth above in the Summary of the Invention. They may be prepared by the methods set forth below in REACTION SCHEME 21 where q, $R^{16}$, $R^{20}$ and

are as defined above, Qb is an alkylene chain or an aralkyl group, or an aryl or heteroaryl group and $R^{20}$ is alkyl, aryl or heteroaryl:

REACTION SCHEME 21

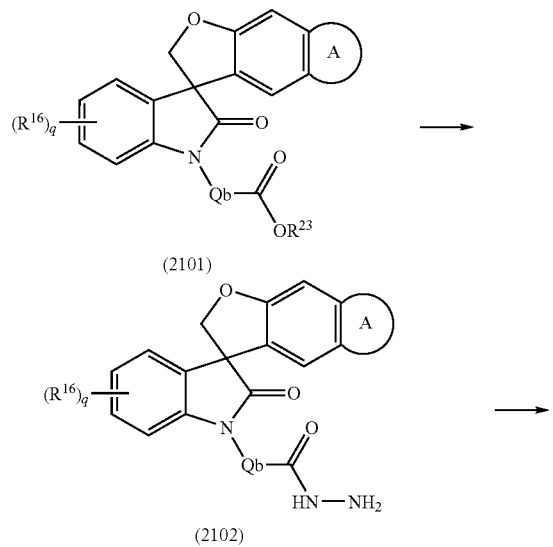

Compounds of formula (2101) can be prepared according to methods known to one skilled in the art or by the methods disclosed herein or by the methods disclosed in PCT Published Patent Application WO 2006/110917.

In general, REACTION SCHEME 21 illustrates a schematic synthesis of compounds of formula (Iza). Treatment of the ester compound of formula (2101) with hydrazine in a solvent such as, but not limited to, ethanol gives the hydrazide compound of formula (2102), which upon reaction with an appropriately substituted anhydride or acyl chloride in the presence of a base such as, but not limited to, pyridine (also as a solvent) provides the oxadiazole product of formula (Iza).

Preparation of Compounds of Formula (Izb)

Compounds of formula (Izb) are compounds of the invention, as set forth above in the Summary of the Invention. They may be prepared by the methods set forth below in REACTION SCHEME 22 where $R^{15}$ and

A are as defined above:

REACTION SCHEME 22

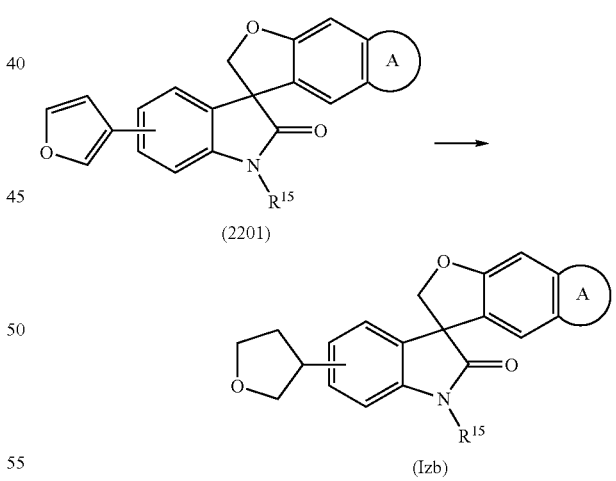

Compounds of formula (2201) can be prepared according to methods known to one skilled in the art or by the methods disclosed herein or by the methods disclosed in PCT Published Patent Application WO 2006/110917.

In general, REACTION SCHEME 22 illustrates a schematic synthesis of compounds of formula (Izb). Treatment of the furan compound of formula (2201) with hydrogen in the presence of a palladium catalyst such as, but not limited to, palladium on carbon in a solvent such as, but not limited to, ethyl acetate or methanol provides the tetrahydrofuran product of formula (Izb).

Preparation of Compounds of Formula (Izc)

Compounds of formula (Izc) are compounds of the invention, as set forth above in the Summary of the Invention. They may be prepared by the methods set forth below in REACTION SCHEME 23 where $R^{16}$ and

are as defined above, and

is a a nitrogen-containing heteroaryl:

REACTION SCHEME 23

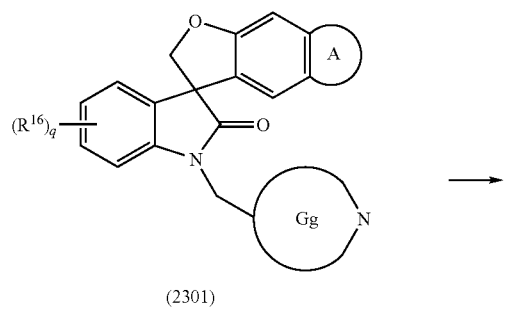

(2301)

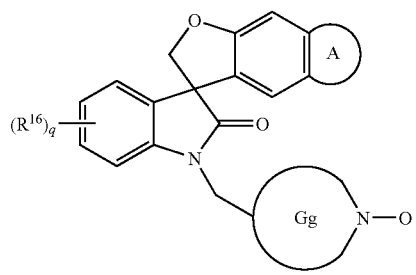

(Izc)

Compounds of formula (2301) can be prepared according to methods known to one skilled in the art or by the methods disclosed herein or by the methods disclosed in PCT Published Patent Application WO 2006/110917.

In general, REACTION SCHEME 23 illustrates a schematic synthesis of compounds of formula (Izc). Treatment of compound of formula (2301) with an oxidant such as, but not limited to, 3-chloroperbenzoic acid in a solvent such as, but not limited to, dichloromethane provides the N-oxide product of formula (Izc).

Preparation of Compounds of Formula (Izd) and (Ize)

Compounds of formula (Izd) and (Ize) are compounds of the invention, as set forth above in the Summary of the Invention. They may be prepared by the methods set forth below in REACTION SCHEME 24 where q, $R^{15}$ and $R^{16}$ are as defined above:

REACTION SCHEME 24

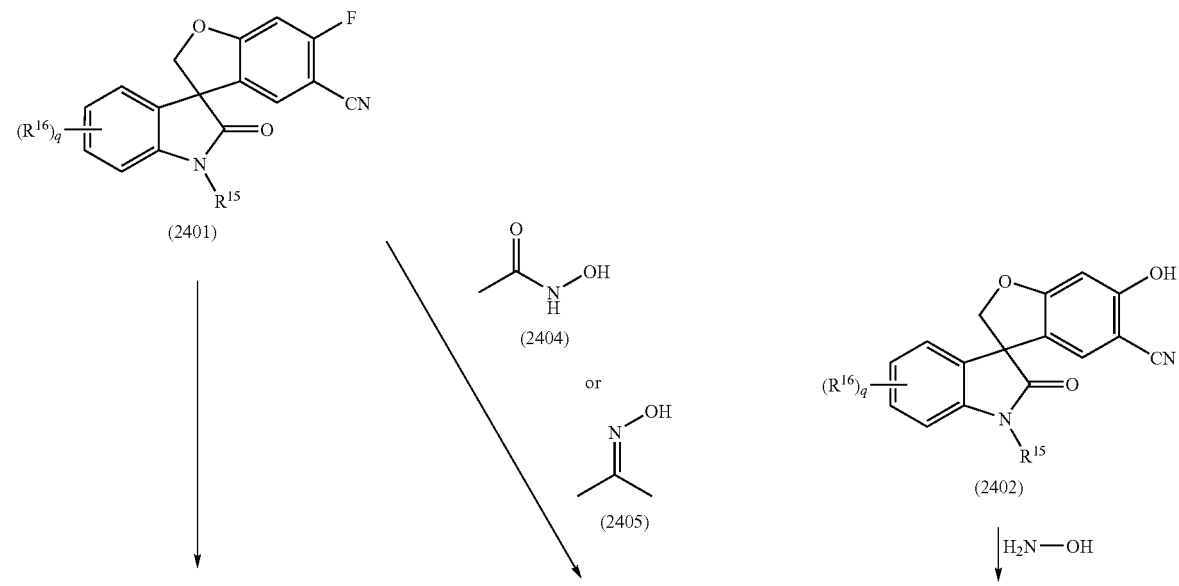

-continued

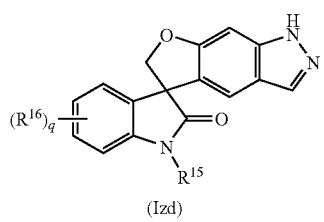 (Izd)

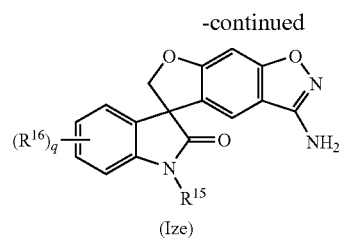 (Ize)

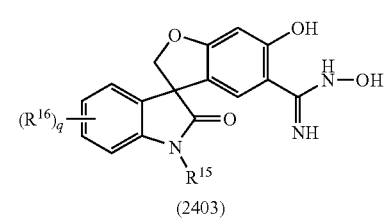 (2403)

Compounds of formula (2401) and (2402) can be prepared according to methods known to one skilled in the art or by the methods disclosed herein or by the methods disclosed in PCT Published Patent Application WO 2006/110917. Compounds (2404) and (2405) are commercially available.

In general, REACTION SCHEME 24 illustrates a schematic synthesis of compounds of formula (Izd) and (Ize). Treatment of compound of formula (2401) with hydrazine in a solvent such as, but not limited to, dimethoxyethane followed by reaction with isoamyl nitrite and hypophosphorous acid in a solvent such as, but not limited to, ethanol provides the indazole product of formula (Izd).

Treatment of compound of formula (2401) with either acetohydroxamic acid (2404) or acetone oxime (2405) in the presence of a base such as, but not limited to, cesium carbonate in a solvent such as, but not limited to, N,N-dimethylformamide provides the isooxazole product of formula (Ize). Alternatively, treatment of compound of formula (2402) with hydroxylamine gives the imidamide intermediate of formula (2403), which undergoes intramolecular Mitsunobu reaction provides the isooxazole product of formula (Ize).

Preparation of Compounds of Formula (Izf)

Compounds of formula (Izf) are compounds of the invention, as set forth above in the Summary of the Invention. They may be prepared by the methods set forth below in REACTION SCHEME 25 where q, $R^{15}$ and $R^{16}$ are as defined above:

REACTION SCHEME 25

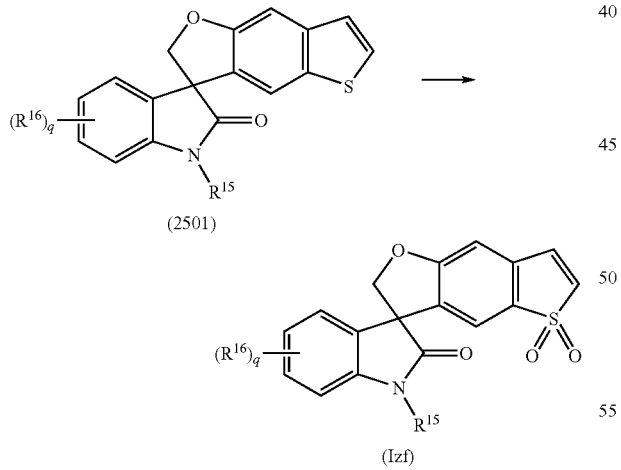

Compounds of formula (2501) can be prepared according to methods known to one skilled in the art or by the methods disclosed herein or by the methods disclosed in pct published patent application WO 2006/110917.

In general, Reaction Scheme 25 illustrates a schematic synthesis of compounds of formula (Izf). Treatment of compound of formula (2501) with an oxidant such as, but not limited to, 3-chloroperbenzoic acid in a solvent such as, but not limited to, dichloromethane provides the dioxide product of formula (Izf).

Preparation of Compounds of Formula (Izq)

Compounds of formula (Izg) are compounds of the invention, as set forth above in the Summary of the Invention. They may be prepared by the methods set forth below in REACTION SCHEME 26 where q, $R^{15}$, $R^{16}$, $R^{23}$ and

are as defined above:

REACTION SCHEME 26

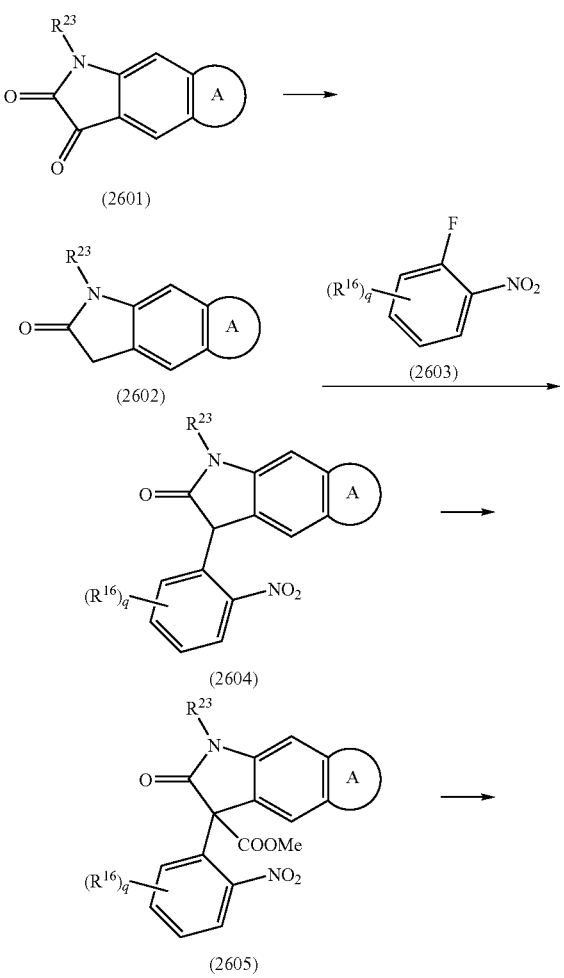

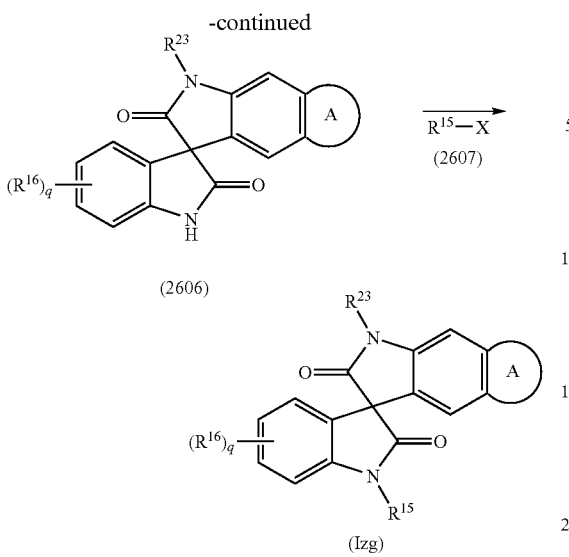

(2606)

(Izg)

Compounds of formula (2601) can be prepared according to methods known to one skilled in the art or by the methods disclosed herein or by the methods disclosed in PCT Published Patent Application WO 2006/110917. Compounds of formula (2603) and formula (2607) are commercially available or can be prepared according to methods known to one skilled in the art or by methods disclosed herein.

In general, REACTION SCHEME 26 illustrates a schematic synthesis of compounds of formula (Izg). Treatment of compound of formula (2601) with hydrazine gives the reduced compound of formula (2602). Treatment of (2602) with a strong base such as, but not limited to, sodium hydride in a solvent such as, but not limited to, N,N-dimethylformamide followed by reaction with a substituted 2-F-nitrobenzene gives the compound of formula (2604). Treatment of (2604) with a strong base such as, but not limited to, lithium bis(trimethylsilyl)amide in a solvent such as, but not limited to, tetrahydrofuran and reaction with methyl cyanoformate of formula (2605). Reduction of (2605) with hydrogen in the presence of a catalyst, palladium on carbon, in a solvent such as, but not limited to, methanol gives the cyclised product of formula (2606). Compound of formula (2606) is alkylated with the chloro or bromo compound of formula (2607) to afford the product of formula (Izg).

Preparation of Compounds of Formula (Izh)

Compounds of formula (Izh) are compounds of the invention, as set forth above in the Summary of the Invention. They may be prepared by the methods set forth below in REACTION SCHEME 27 where q, IV, $R^{16}$ and are

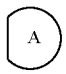

as defined above:

REACTION SCHEME 27

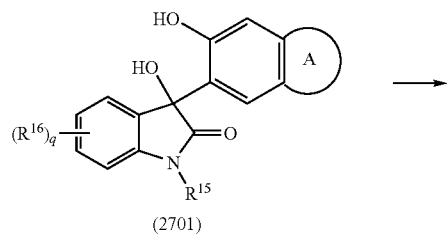

(2701)

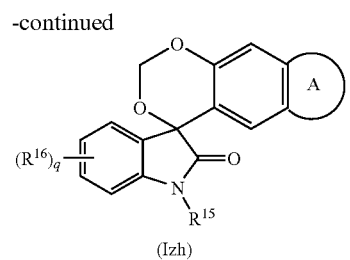

(Izh)

Compounds of formula (2701) can be prepared according to methods known to one skilled in the art or by the methods disclosed herein or by the methods disclosed in pct published patent application WO 2006/110917.

In general, Reaction Scheme 27 illustrates a schematic synthesis of compounds of formula (Izh). Treatment of compound of formula (2701) with iodochloromethane or diiodomethane in the presence of a base such as, but not limited to, cesium carbonate in a solvent such as, but not limited to, tetrahydrofuran or N,N-dimethylformamide provides the cyclized product of formula (Izh).

The following Preparations, which are directed to the preparation of intermediates used in the preparation of the compounds of the invention, the following Examples, which are directed to the preparation of the compounds of the invention, and the following Biological Examples are provided as a guide to assist in the practice of the invention, and are not intended as a limitation on the scope of the invention.

Preparation 1

Synthesis of 1,3-bis(hydroxymethyl)-3-(5-hydroxy-2-methyl-1,3-benzothiazol-6-yl)-1,3-dihydro-2H-indol-2-one A. Synthesis of 3-hydroxy-3-(5-hydroxy-2-methyl-1,3-benzothiazol-6-yl)-1,3-dihydro-2H-indol-2-one To a cooled (0° C.) solution of 2-methylbenzo[d]thiazol-5-ol (4.0 g, 24.0 mmol) in anhydrous tetrahydrofuran (50 mL) was added isopropylmagnesium chloride (2 M solution in tetrahydrofuran, 12.0 mL, 24.0 mmol). The resultant suspension was stirred at 0° C. for 0.5 h and isatin (3.1 g, 21.2 mmol) was added in one portion. The reaction mixture was stirred at ambient temperature for 48 h and was diluted with a saturated aqueous solution of ammonium chloride (80 mL) and ethyl acetate (200 mL). The phases were separated and the aqueous phase was extracted with ethyl acetate (3×50 mL). The combined organic solution was washed with brine (50 mL), dried over anhydrous sodium sulfate, filtered and concentrated in vacuo. The crude product was triturated with boiling ethyl acetate (10 mL), filtered and dried in vacuo to afford 3-hydroxy-3-(5-hydroxy-2-methyl-1,3-benzothiazol-6-yl)-1,3-dihydro-2H-indol-2-one (4.11 g, 62%) as an off-white microcrystalline solid: $^1$H NMR (300 MHz, DMSO-d$_6$) δ10.34 (s, 1H), 10.02 (br s, 1H), 8.85 (br s, 1H), 7.78 (d, J=8.6 Hz, 1H), 7.18-7.10 (m, 1H), 7.01-6.74 (m, 4H), 2.77 (br s, 3H); MS (ES+) m/z 313.1 (M+1).

B. Synthesis of 3-(5-hydroxy-2-methyl-1,3-benzothiazol-6-yl)-1,3-dihydro-2H-indol-2-one A mixture of 3-hydroxy-3-(5-hydroxy-2-methyl-1,3-benzothiazol-6-yl)-1,3-dihydro-2H-indol-2-one (4.81 g, 15.4 mmol) and 48% aqueous hydroiodic acid (25 mL) was heated at reflux for 1 h. The reaction mixture was allowed to cool to ambient temperature and was diluted with water (50 mL) and ethyl acetate (50 mL). The mixture was briefly sonicated, causing a precipitate to be deposited. The solid was collected by filtration, washed with water (20 mL) and dried in vacuo to afford 3-(5-hydroxy-2-methyl-1,3-benzothiazol-6-yl)-1,3-dihydro-2H-indol-2-one (4.52 g, 99%) as a pale yellow solid: MS (ES+) m/z 297.2 (M+1).

C. Synthesis of 1,3-bis(hydroxymethyl)-3-(5-hydroxy-2-methyl-1,3-benzothiazol-6-yl)-1,3-dihydro-2H-indol-2-one To a cooled (0° C.) suspension of 3-(5-hydroxy-2-methyl-1,3-benzothiazol-6-yl)-1,3-dihydro-2H-indol-2-one (3.66 g, 12.4 mmol), p-formaldehyde (1.85 g, 61.8 mmol) in tetrahydrofuran (30 mL) and water (30 mL) was added dropwise a solution of sodium hydroxide (2.96 g, 74.1 mmol) in water (30 mL). The reaction mixture was stirred at 0° C. for 1.5 h, and acidified to pH 5 by the dropwise addition of 10% aqueous hydrochloric acid and was diluted with ethyl acetate (50 mL). The phases were separated and the aqueous phase was extracted with ethyl acetate (3×50 mL). The combined organic solution was washed with brine (50 mL), dried over anhydrous sodium sulfate, filtered and concentrated. The crude product was purified by column chromatography with ethyl acetate in hexanes (67 to 100% gradient) to afford 1,3-bis(hydroxymethyl)-3-(5-hydroxy-2-methyl-1,3-benzothiazol-6-yl)-1,3-dihydro-2H-indol-2-one (1.80 g, 41%) as a colorless solid: $^1$H NMR (300 MHz, DMSO-d$_6$) δ 9.79 (br s, 1H), 7.75 (d, J=8.6 Hz, 1H), 7.23-7.15 (m, 1H), 7.11-7.06 (m, 1H), 6.94-6.80 (m, 3H), 6.21-6.14 (m, 1H), 5.95 (br s, 1H), 5.26-5.18 (m, 1H), 5.06-4.98 (m, 1H), 4.64-4.56 (m, 1H), 3.84-3.76 (m, 1H), 2.80 (s, 3H); MS (ES+) m/z 379.0 (M+23).

Preparation 2

Synthesis of 6-bromo-1'-{[5-(trifluoromethyl)furan-2-yl]methyl}spiro[1-benzofuran-3,3'-indol]-2'(1'H)-one

A. Synthesis of 3-(4-bromo-2-hydroxyphenyl)-3-hydroxy-1-{[5-(trifluoromethyl)furan-2-yl]methyl}-1,3-dihydro-2H-indol-2-one To a stirred solution of 3-bromophenol (4.4 g, 25.4 mmol) in tetrahydrofuran (100 mL) was added iso-propylmagnesium chloride (12.7 mL, 2 M tetrahydrofuran solution, 25.4 mol) slowly at 0° C. The mixture was allowed to stir for 30 min at 0° C., then the solvent was removed in vacuo. Dichloromethane (100 mL) was added, followed by the addition of a solution of 1-((5-(trifluoromethyl)furan-2-yl)methyl)indoline-2,3-dione (5.0 g, 16.9 mol) in dichloromethane (100 mL) at 0° C. The mixture was stirred at ambient temperature for 16 h, quenched by the addition of saturated ammonium chloride solution. The organic layer was washed with water, dried over sodium sulfate and concentrated in vacuo. The obtained solid was recrystallized from ethyl acetate/hexanes to afford 3-(4-bromo-2-hydroxyphenyl)-3-hydroxy-1-{[5-(trifluoromethyl)furan-2-yl]methyl}-1,3-dihydro-2H-indol-2-one (6.4 g, 81%) as a colorless solid: $^1$H NMR (300 MHz, DMSO-d$_6$) δ7.49-5.83 (m, 9H), 5.13-4.71 (m, 2H); MS (ES+) m/z 449.9 (M−17), 451.9 (M−17).

B. Synthesis of 3-(4-bromo-2-hydroxyphenyl)-1-{[5-(trifluoromethyl)furan-2-yl]methyl}-1,3-dihydro-2H-indol-2-one A mixture of 3-(4-bromo-2-hydroxyphenyl)-3-hydroxy-1-{[5-(trifluoromethyl)furan-2-yl]methyl}-1,3-dihydro-2H-indol-2-one (5.5 g, 11.8 mmol), triethylsilane (20.0 mL, excess) and trifluoroacetic acid (20.0 mL, excess) was stirred at ambient temperature for 16 h. The mixture was concentrated under vacuum. The residue was treated with diethyl ether to form a suspension. The filtration gave 3-(4-bromo-2-hydroxyphenyl)-1-{[5-(trifluoromethyl)furan-2-yl]methyl}-1,3-dihydro-2H-indol-2-one (4.3 g, 82%) as a colorless solid: $^1$H NMR (300 MHz, CDCl$_3$) δ 8.91 (br s, 1H), 7.36 (t, J=7.9 Hz, 1H), 7.26-7.13 (m, 2H), 7.05 (d, J=7.9 Hz, 1H), 6.97 (d, J=2.0 Hz, 1H), 6.92 (dd, J=8.5, 2.0 Hz, 1H), 6.73-6.67 (m, 2H), 6.35 (d, J=3.5 Hz, 1H), 5.08 (s, 1H), 4.95 (s, 2H); MS (ES+) m/z 452.0 (M+1), 450.0 (M+1).

C. 6-bromo-1'-{[5-(trifluoromethyl)furan-2-yl]methyl}spiro[1-benzofuran-3,3'-indol]-2'(1'H)-one To a stirred solution of 3-(4-bromo-2-hydroxyphenyl)-1-{[5-(trifluoromethyl)furan-2-yl]methyl}-1,3-dihydro-2H-indol-2-one (4.3 g, 9.5 mmol), chloroiodomethane (1.8 mL, 25.3 mmol) in tetrahydrofuran (100 mL) was added cesium carbonate (9.9 g, 30.5 mmol) under Argon. The mixture was stirred at ambient temperature for 16 h, then filtered through a pad of celite. The filtrate was concentrated under vacuum. The residue was treated with diethyl ether/hexanes to afford 6-bromo-1'-{[5-(trifluoromethyl)furan-2-yl]methyl}spiro[1-benzofuran-3,3'-indol]-2'(1'H)-one (3.46 g, 78%) as a colorless solid: $^1$H NMR (300 MHz, CDCl$_3$) δ7.30 (td, J=7.9, 1.5 Hz, 1H), 7.16-7.03 (m, 3H), 6.69 (d, J=7.9 Hz, 1H), 6.93 (dd, J=8.2, 1.8 Hz, 1H), 6.77-6.71 (m, 1H), 6.53 (d, J=8.2 Hz, 1H), 6.42-6.37 (m, 1H), 5.06 (d, J=16.1 Hz, 1H), 4.97 (d, J=9.4 Hz, 1H), 4.86 (d, J=16.1 Hz, 1H), 4.71 (d, J=9.4 Hz, 1H); $^{13}$C NMR (75 MHz, CDCl$_3$) δ176.5, 161.5, 151.8, 141.4, 131.6, 129.3, 128.0, 124.5 (d), 124.0, 114.2, 112.6 (d), 109.2 (d), 80.1, 57.5, 36.9; MS (ES+) m/z 463.9 (M+1), 465.9 (M+1).

Preparation 3

Synthesis of 1-(diphenylmethyl)-3-(2-hydroxy-4-methoxy-5-methylphenyl)-1,3-dihydro-2H-indol-2-one

A. Synthesis of 1-(diphenylmethyl)-3-hydroxy-3-(2-hydroxy-4-methoxy-5-methylphenyl)-1,3-dihydro-2H-indol-2-one To a stirred solution of 3-methoxy-4-methylphenol (Jorgensen, E. C., et al., *J. Med. Chem.* (1971), 14:1199-202) (7.5 g, 54.3 mmol) in dichloromethane (160 mL) was added iso-propylmagnesium chloride (29.0 mL, 2 M in tetrahydrofuran, 58 mmol) at 0° C. The resultant mixture was stirred at 0° C. for 30 min followed by the addition of 1-benzhydrylindoline-2,3-dione (10.4 g, 36.3 mmol). The reaction mixture was stirred at ambient temperature for 10 min and concentrated in vacuo to dryness. The residue was dissolved in ethyl acetate (300 mL) and washed with saturated ammonium chloride solution (2×200 mL). The ethyl acetate layer was dried over magnesium sulfate, filtered and concentrated in vacuo to afford 1-(diphenylmethyl)-3-hydroxy-3-(2-hydroxy-4-methoxy-5-methylphenyl)-1,3-dihydro-2H-indol-2-one (19.10 g) as a crude brown oil: MS (ES−) m/z 450.3 (M−1).

B. Synthesis of 1-(diphenylmethyl)-3-(2-hydroxy-4-methoxy-5-methylphenyl)-1,3-dihydro-2H-indol-2-one To a stirred mixture of 1-(diphenylmethyl)-3-hydroxy-3-(2-hydroxy-4-methoxy-5-methylphenyl)-1,3-dihydro-2H- indol-2-one (15.4 g, 34.1 mmol) and triethylsilane (15 mL) was added trifluoroacetic acid (15 mL) at 0° C. The solution was stirred at ambient temperature for 16 h and concentrated in vacuo to dryness. The residue was recrystallized from diethyl ether (25 mL) in a Branson ultrasonic bench top water bath to afford 1-(diphenylmethyl)-3-(2-hydroxy-4-methoxy-5-methylphenyl)-1,3-dihydro-2H-indol-2-one (11.0 g, 74%) as a colorless solid: $^1$H NMR (300 MHz, CDCl$_3$) δ7.42-7.16 (m, 12H), 7.11-7.01 (m, 2H), 6.94 (s, 1H), 6.61 (s, 1H), 6.57-6.49 (m, 1H), 6.45 (s, 1H), 5.08 (s, 1H), 3.63 (s, 3H), 2.03 (s, 3H); MS (ES+) m/z 436.3 (M+1).

Preparation 4

Synthesis of 4-chloro-1-(diphenylmethyl)-3-(6-hydroxy-2,3-dihydro-1-benzofuran-5-yl)-1,3-dihydro-2H-indol-2-one A. Synthesis of 4-chloro-1-(diphenylmethyl)-1H-indole-2,3-dione To a stirred solution of 4-chloroisatin (9.10 g, 50.0 mmol) in N,N-dimethylformamide (100 mL) was added sodium hydride (2.20 g, 55.0 mmol) at 0° C. The reaction mixture was stirred at 0° C. for 1 h, followed by the addition of bromodiphenylmethane (14.80 g, 56.8 mmol). The mixture was stirred at ambient temperature for 20 h, diluted with ethyl acetate, washed with water and brine, dried over anhydrous sodium sulfate and filtered. The filtrate was concentrated in vacuo. The residue was recrystallized from diethyl ether and hexanes to afford 4-chloro-1-(diphenylmethyl)-1H-indole-2,3-dione (14.20 g, 81%): $^1$H NMR (300 MHz, CDCl$_3$) δ 7.37-7.17 (m, 11H), 6.98-6.95 (m, 2H), 6.42 (d, J=9.0 Hz, 1H); MS (ES+) m/z 369.9 (M+23), 371.9 (M+1).

B. Synthesis of 4-chloro-1-(diphenylmethyl)-3-hydroxy-3-(6-hydroxy-2,3-dihydro-1-benzofuran-5-yl)-1,3-dihydro-2H-indol-2-one Following the procedure as described in PREPARATION 3A, and making non-critical variations using 2,3-dihydrobenzofuran-6-ol to replace 3-methoxy-4-methylphenol, and 4-chloro-1-(diphenylmethyl)-1H-indole-2,3-dione to replace 1-benzhydrylindoline-2,3-dione, 4-chloro-1-(diphenylmethyl)-3-hydroxy-3-(6-hydroxy-2,3-dihydro-1-benzofuran-5-yl)-1,3-dihydro-2H-indol-2-one was obtained (87%) as a beige solid: $^1$H NMR (300 MHz, CDCl$_3$) δ 8.66 (br s, 1H), 7.36-7.16 (m, 10H), 7.05-7.01 (m, 2H), 6.89 (s, 1H), 6.58 (s, 1H), 6.45-6.38 (m, 2H), 4.57-4.49 (m, 2H), 4.03 (br s, 1H), 3.13-2.91 (m, 2H); MS (ES+) m/z 505.9 (M+1), 507.9 (M+1).

C. Synthesis of 4-chloro-1-(diphenylmethyl)-3-(6-hydroxy-2,3-dihydro-1-benzofuran-5-yl)-1,3-dihydro-2H-indol-2-one To a stirred solution of 4-chloro-1-(diphenylmethyl)-3-hydroxy-3-(6-hydroxy-2,3-dihydro-1-benzofuran-5-yl)-1,3-dihydro-2H-indol-2-one (9.25 g, 19.1 mmol) in dichloromethane (25 mL) was added triethylsilane (10 mL). The mixture was cooled to 0° C. followed by the addition of trifluoroacetic acid (10 mL) slowly over 5 min. The resultant mixture was stirred at ambient temperature for 5 h and concentrated in vacuo to dryness. The residue was triturated in diethyl ether (25 mL) in a Branson ultrasonic bench top water bath to afford 4-chloro-1-(diphenylmethyl)-3-(6-hydroxy-2,3-dihydro-1-benzofuran-5-yl)-1,3-dihydro-2H-indol-2-one (8.90 g, quantitative) as a beige solid: MS (ES+) m/z 468.0 (M+1), 470.0 (M+1).

Preparation 5

Synthesis of 3-(4-bromo-2-hydroxyphenyl)-1-(diphenylmethyl)-1,3-dihydro-2H-indol-2-one A. Synthesis of 3-(4-bromo-2-hydroxyphenyl)-1-(diphenylmethyl)-3-hydroxy-1,3-dihydro-2H-indol-2-one To a stirred solution of 3-bromophenol (11.9 g, 69.2 mmol) in dichloromethane (160.0 mL) at 0° C. was added isopropylmagnesium chloride (2.0 M in tetrahydrofuran, 38.0 mL, 76.1 mmol). The solution was stirred at 0° C. for 30 min, then 1-benzhydrylindoline-2,3-dione (10.0 g, 34.6 mmol) was added. The reaction was stirred at ambient temperature for 16 h, then concentrated in vacuo to dryness. The residue obtained was dissolved in ethyl acetate (400.0 mL) and washed with saturated ammonium chloride solution (3×100.0 mL). The organic phase was dried over magnesium sulfate, filtered and concentrated in vacuo to dryness. Purification by flash chromatography with 30% ethyl acetate in hexanes afforded 3-(4-bromo-2-hydroxyphenyl)-1-(diphenylmethyl)-3-hydroxy-1,3-dihydro-2H-indol-2-one (11.7 g, 70%) as a beige solid: $^1$H NMR (300 MHz, CDCl$_3$) δ 9.09 (br s, 1H), 7.47-7.16 (m, 11H), 7.12-7.00 (m, 3H), 6.92-6.84 (m, 2H), 6.72-6.66 (m, 1H), 6.51-6.45 (m, 1H), 4.57 (br s, 1H); MS (ES+) m/z 484.2 (M+1), 486.2 (M+1).

B. Synthesis of 3-(4-bromo-2-hydroxyphenyl)-1-(diphenylmethyl)-1,3-dihydro-2H-indol-2-one To an ice cold stirred solution of 3-(4-bromo-2-hydroxyphenyl)-1-(diphenylmethyl)-3-hydroxy-1,3-dihydro-2H-indol-2-one (13.1 g, 27.1 mmol) in triethylsilane (25.0 mL) was added trifluoroacetic acid (25.0 mL). The solution was stirred at ambient temperature for 64 h, then concentrated in vacuo to dryness. Recrystallization from diethyl ether (25.0 mL) in a Branson ultrasonic bench top water bath afforded 3-(4-bromo-2-hydroxyphenyl)-1-(diphenylmethyl)-1,3-dihydro-2H-indol-2-one (10.1 g, 79%) as a colorless solid: $^1$H NMR (300 MHz, CDCl$_3$) δ9.17 (s, 1H), 7.40-7.03 (m, 13H), 6.99-6.92 (m, 2H), 6.79-6.74 (m, 2H), 6.58-6.50 (m, 1H), 5.10 (s, 1H); MS (ES−) m/z 468.2 (M−1), 470.2 (M−1).

Preparation 6

Synthesis of 1-(diphenylmethyl)-3-(2-hydroxy-4,5-dimethylphenyl)-1,3-dihydro-2H-indol-2-one A. Synthesis of 1-(diphenylmethyl)-3-hydroxy-3-(2-hydroxy-4,5-dimethylphenyl)-1,3-dihydro-2H-indol-2-one To a stirred solution of 3,4-dimethylphenol (2.50 g, 20.5 mmol) in tetrahydrofuran (100 mL) was added isopropylmagnesium chloride (10.2 mL, 2.0 M tetrahydrofuran solution, 20.40 mmol) at 0° C. The mixture was allowed to stir for 1 h at 0° C., then the solvent was removed in vacuo. Dichloromethane (200 mL) was added, followed by the addition of 1-(diphenylmethyl)-1H-indole-2,3-dione (5.00 g, 15.95 mmol). The mixture was stirred for 54 h at ambient temperature, quenched with saturated ammonium chloride solution. The organic layer was washed with water, brine, dried over anhydrous sodium sulfate and filtered. The filtrate was concentrated in vacuo, the residue was purified by column chromatography to give 1-(diphenylmethyl)-3-hydroxy-3-(2-hydroxy-4,5-dimethylphenyl)-1,3-dihydro-2H-indol-2-one (5.10 g, 73%): $^1$H NMR (300 MHz, CDCl$_3$) δ7.49-7.45 (m, 1H), 7.35-7.27 (m, 10H), 7.08-7.04 (m, 2H), 6.93 (s, 1H), 6.81-6.75 (m, 1H), 6.52 (s, 1H), 6.49-6.46 (m, 1H), 2.15 (s, 3H), 2.02 (s, 3H); MS (ES+) m/z 418.1 (M−17).

B. Synthesis of 1-(diphenylmethyl)-3-(2-hydroxy-4,5-dimethylphenyl)-1,3-dihydro-2H-indol-2-one Following the procedure as described in PREPARATION 4C, and making non-critical variations using 1-(diphenylmethyl)-3-hydroxy-3-(2-hydroxy-4,5-dimethylphenyl)-1,3-dihydro-2H-indol-2-one to replace 4-chloro-1-(diphenylmethyl)-3-hydroxy-3-(6-hydroxy-2,3-dihydro-1-benzofuran-5-yl)-1,3-dihydro-2H-indol-2-one, 1-(diphenylmethyl)-3-(2-hydroxy-4,5-dimethylphenyl)-1,3-dihydro-2H-indol-2-one was obtained (93%): $^1$H NMR (300 MHz, CDCl$_3$) δ 7.34-7.27 (m, 11H), 7.06-7.02 (m, 3H), 6.76 (s, 1H), 6.72 (s, 1H), 6.55-6.50 (m, 1H), 5.05 (s, 1H), 2.17 (s, 3H), 2.12 (s, 3H); MS (ES+) m/z 420.2 (M+1).

Preparation 7

Synthesis of 1-(diphenylmethyl)-5-fluoro-3-(6-hydroxy-2,3-dihydro-1-benzofuran-5-yl)-1,3-dihydro-2H-indol-2-one A. Synthesis of 1-(diphenylmethyl)-5-fluoro-1H-indole-2,3-dione To a stirred solution of 5-fluoroisatin (6.00 g, 36.3 mmol) in N,N-dimethylformamide (50 mL) was added sodium hydride (1.60 g, 40.0 mmol) at 0° C. The reaction mixture was stirred at 0° C. for 1 h followed by the addition of bromodiphenylmethane (10.0 g, 38.0 mmol). The mixture was stirred at 60° C. for 7 h, diluted with ethyl acetate, washed with water and brine, dried over anhydrous sodium sulfate and filtered. The filtrate was concentrated in vacuo to dryness, the residue was recrystallized from ethyl acetate and hexanes to give 1-(diphenylmethyl)-5-fluoro-1H-indole-2,3-dione (6.30 g, 52%): $^1$H NMR (300 MHz, CDCl$_3$) δ 7.39-7.27 (m, 11H), 7.04-6.97 (m, 2H), 6.46-6.42 (m, 1H); MS (ES+) m/z 354.2 (M+23).

B. Synthesis of 1-(diphenylmethyl)-5-fluoro-3-hydroxy-3-(6-hydroxy-2,3-dihydro-1-benzofuran-5-yl)-1,3-dihydro-2H-indol-2-one Following the procedure as described in PREPARATION 6A, and making non-critical variations using 2,3-dihydrobenzofuran-6-ol to replace 3,4-dimethylphenol, and 1-(diphenylmethyl)-5-fluoro-1H-indole-2,3-dione to replace 1-(diphenylmethyl)-1H-indole-2,3-dione, 1-(diphenylmethyl)-5-fluoro-3-hydroxy-3-(6-hydroxy-2,3-dihydro-1-benzofuran-5-yl)-1,3-dihydro-2H-indol-2-one was obtained (99%): $^1$H NMR (300 MHz, CDCl$_3$) δ 8.94 (s, 1H), 7.36-7.19 (m, 11H), 6.94 (s, 1H), 6.82-6.75 (m, 1H), 6.63 (s, 1H), 6.48-6.38 (m, 2H), 4.53 (t, J=9.0 Hz, 2H), 4.38 (br s, 1H), 3.06-3.00 (m, 2H); MS (ES+) m/z 466.4 (M−1).

C. Synthesis of 1-(diphenylmethyl)-5-fluoro-3-(6-hydroxy-2,3-dihydro-1-benzofuran-5-yl)-1,3-dihydro-2H-indol-2-one Following the procedure as described in PREPARATION 4C, and making non-critical variations using 1-(diphenylmethyl)-5-fluoro-3-hydroxy-3-(6-hydroxy-2,3-dihydro-1-benzofuran-5-yl)-1,3-dihydro-2H-indol-2-one to replace 4-chloro-1-(diphenylmethyl)-3-hydroxy-3-(6-hydroxy-2,3-dihydro-1-benzofuran-5-yl)-1,3-dihydro-2H-indol-2-one, 1-(diphenylmethyl)-5-fluoro-3-(6-hydroxy-2,3-dihydro-1-benzofuran-5-yl)-1,3-dihydro-2H-indol-2-one was obtained (94%): mp 179-181° C. (methanol); $^1$H NMR (300 MHz, CDCl$_3$) δ7.36-7.19 (m, 11H), 7.02-6.97 (m, 2H), 6.77-6.69 (m, 2H), 6.45-6.39 (m, 2H), 5.04 (s, 1H), 4.53 (t, J=9.0 Hz, 2H), 3.10-3.02 (m, 2H); MS (ES+) m/z 452.1 (M+1).

Preparation 8

Synthesis of 1-(diphenylmethyl)-6-fluoro-3-(6-hydroxy-2,3-dihydro-1-benzofuran-5-yl)-1,3-dihydro-2H-indol-2-one A. Synthesis of 1-(diphenylmethyl)-6-fluoro-1H-indole-2,3-dione Following the procedure as described in PREPARATION 4A, and making non-critical variations using 6-fluoroisatin (Sadler, P. W., J. Org. Chem. (1956), 21(2):169-70) to replace 4-chloroisatin, 1-(diphenylmethyl)-6-fluoro-1H-indole-2,3-dione was obtained (76%): mp 167-169° C. (diethyl ether); $^1$H NMR (300 MHz, DMSO-d$_6$) δ 7.41-7.27 (m, 11H), 6.77 (s, 1H), 6.30-6.26 (m, 1H), 5.82-5.80 (m, 1H); MS (ES+) m/z 354.1 (M+23).

B. Synthesis of 1-(diphenylmethyl)-6-fluoro-3-hydroxy-3-(6-hydroxy-2,3-dihydro-1-benzofuran-5-yl)-1,3-dihydro-2H-indol-2-one Following the procedure as described in PREPARATION 6A, and making non-critical variations using 2,3-dihydrobenzofuran-6-ol to replace 3,4-dimethylphenol, and 1-(diphenylmethyl)-6-fluoro-1H-indole-2,3-dione to replace 1-(diphenylmethyl)-1H-indole-2,3-dione, 1-(diphenylmethyl)-6-fluoro-3-hydroxy-3-(6-hydroxy-2,3-dihydro-1-benzofuran-5-yl)-1,3-dihydro-2H-indol-2-one was obtained (84%): mp 147-149° C.; $^1$H NMR (300 MHz, CDCl$_3$) δ 8.80 (s, 1H), 7.44-7.20 (m, 11H), 6.90 (s, 1H), 6.79-6.72 (m, 1H), 6.59 (s, 1H), 6.45 (s, 1H), 6.20-6.17 (m, 1H); MS (ES+) m/z 450.1 (M−17).

C. Synthesis of 1-(diphenylmethyl)-6-fluoro-3-(6-hydroxy-2,3-dihydro-1-benzofuran-5-yl)-1,3-dihydro-2H-indol-2-one Following the procedure as described in PREPARATION 4C, and making non-critical variations using 1-(diphenylmethyl)-6-fluoro-3-hydroxy-3-(6-hydroxy-2,3-dihydro-1-benzofuran-5-yl)-1,3-dihydro-2H-indol-2-one to replace 4-chloro-1-(diphenylmethyl)-3-hydroxy-3-(6-hydroxy-2,3-dihydro-1-benzofuran-5-yl)-1,3-dihydro-2H-indol-2-one, 1-(diphenylmethyl)-6-fluoro-3-(6-hydroxy-2,3-dihydro-1-benzofuran-5-yl)-1,3-dihydro-2H-indol-2-one was obtained (99%): mp 121-123° C. (methanol); $^1$H NMR (300 MHz, CDCl$_3$) δ 7.36-7.16 (m, 11H), 6.95 (s, 1H), 6.77-6.71 (m, 1H), 6.67 (s, 1H), 6.46 (s, 1H), 6.25-6.21 (m, 1H), 5.00 (s, 1H), 4.53 (t, J=9.0 Hz, 2H), 3.08-3.01 (m, 2H); MS (ES+) m/z 451.9 (M+1).

Preparation 9

Synthesis of 3-(6-hydroxy-3-methyl-1,2-benzisoxazol-5-yl)-1-(4-methoxybenzyl)-1,3-dihydro-2H-indol-2-one

A. Synthesis of 3-hydroxy-3-(6-hydroxy-3-methyl-1,2-benzisoxazol-5-yl)-1-(4-methoxybenzyl)-1,3-dihydro-2H-indol-2-one Following the procedure as described in PREPARATION 6A, and making non-critical variations using 3-methylbenzo[d]isoxazol-6-ol (Iranpoor, N., et al., *Tetrahedron Lett.* (2006), 47:8247) to replace 3,4-dimethylphenol, and 1-(4-methoxybenzyl)-1H-indole-2,3-dione to replace 1-(diphenylmethyl)-1H-indole-2,3-dione, 3-hydroxy-3-(6-hydroxy-3-methyl-1,2-benzisoxazol-5-yl)-1-(4-methoxybenzyl)-1,3-dihydro-2H-indol-2-one was obtained (76%): mp 199-201° C. (ethyl acetate); $^1$H NMR (300 MHz, DMSO-d$_6$) δ 7.52 (d, J=9.0 Hz, 1H), 7.37 (d, J=9.0 Hz, 2H), 7.18-7.13 (m, 1H), 7.05-7.03 (m, 1H), 6.89-6.75 (m, 5H), 4.83 (AB, 2H), 3.71 (s, 3H), 2.77 (s, 3H); MS (ES+) m/z 417.0 (M+1).

B. Synthesis of 3-(6-hydroxy-3-methyl-1,2-benzisoxazol-5-yl)-1-(4-methoxybenzyl)-1,3-dihydro-2H-indol-2-one To a stirred solution of 3-hydroxy-3-(6-hydroxy-3-methyl-1,2-benzisoxazol-5-yl)-1-(4-methoxybenzyl)-1,3-dihydro-2H-indol-2-one (3.70 g; 8.9 mmol) and triethylsilane (8.4 mL, 52.6 mmol) in dichloromethane (50 mL) was added trifluoroacetic acid (7.0 mL, 90.8 mmol). The reaction mixture was stirred at ambient temperature for 57 h, concentrated in vacuo to dryness. The residue was washed with diethyl ether-hexanes (1:2) to afford 3-(6-hydroxy-3-methyl-1,2-benzisoxazol-5-yl)-1-(4-methoxybenzyl)-1,3-dihydro-2H-indol-2-one (3.34 g, 93%): mp 195-197° C. (diethyl ether/hexanes); $^1$H NMR (300 MHz, CDCl$_3$) δ 7.37 (d, J=9.0 Hz, 2H), 7.19-7.14 (m, 1H), 7.03-6.81 (m, 6H), 6.42 (d, J=9.0 Hz, 1H), 5.46 (s, 1H), 5.04 (Aq, 2H), 3.74 (s, 3H), 2.43 (s, 3H); MS (ES+) m/z 401.0 (M+1).

Preparation 10

Synthesis of 1-benzhydryl-3-(5-fluoro-2-hydroxy-4-methoxyphenyl)indolin-2-one

A. Synthesis of 1-(diphenylmethyl)-3-(5-fluoro-2-hydroxy-4-methoxyphenyl)-3-hydroxy-1,3-dihydro-2H-indol-2-one Following the procedure as described in PREPARATION 6A, and making non-critical variations using 4-fluoro-3-methoxyphenol to replace 3,4-dimethylphenol, 1-(diphenylmethyl)-3-(5-fluoro-2-hydroxy-4-methoxyphenyl)-3-hydroxy-1,3-dihydro-2H-indol-2-one was obtained (95%): $^1$H NMR (300 MHz, CDCl$_3$) δ9.50-9.00 (br, 1H), 7.48-7.41 (m, 1H), 7.36-7.25 (m, 8H), 7.22-7.16 (m, 2H), 7.14-7.07 (m, 2H), 6.88 (s, 1H), 6.64 (d, J=7.5 Hz, 1H), 6.56-6.46 (m, 2H), 4.43-4.00 (br, 1H), 3.81 (s, 3H); MS (ES+) m/z 456.1 (M+1).

B. Synthesis of 1-(diphenylmethyl)-3-(5-fluoro-2-hydroxy-4-methoxyphenyl)-1,3-dihydro-2H-indol-2-one Following the procedure as described in PREPARATION 3B, and making non-critical variations using 1-(diphenylmethyl)-3-(5-fluoro-2-hydroxy-4-methoxyphenyl)-3-hydroxy-1,3-dihydro-2H-indol-2-one to replace 1-(diphenylmethyl)-3-hydroxy-3-(2-hydroxy-4-methoxy-5-methylphenyl)-1,3-dihydro-2H-indol-2-one, 1-(diphenylmethyl)-3-(5-fluoro-2-hydroxy-4-methoxyphenyl)-1,3-dihydro-2H-indol-2-one was obtained (73%): $^1$H NMR (300 MHz, CDCl$_3$) δ 9.33-8.84 (br, 1H), 7.41-7.25 (m, 9H), 7.22-7.04 (m, 4H), 6.92 (s, 1H), 6.71 (d, J=7.7 Hz, 1H), 6.64 (d, J=12.2 Hz, 1H), 6.56-6.49 (m, 1H), 5.09 (s, 1H), 3.84 (s, 3H); MS (ES+) m/z 440.1 (M+1).

Preparation 11

Synthesis of 1-(diphenylmethyl)-3-(5-fluoro-2-hydroxyphenyl)-1,3-dihydro-2H-indol-2-one

A. Synthesis of 1-(diphenylmethyl)-3-(5-fluoro-2-hydroxyphenyl)-3-hydroxy-1,3-dihydro-2H-indol-2-one Following the procedure as described in PREPARATION 6A, and making non-critical variations using 4-fluorophenol to replace 3,4-dimethylphenol, 1-(diphenylmethyl)-3-(5-fluoro-2-hydroxyphenyl)-3-hydroxy-1,3-dihydro-2H-indol-2-one was obtained (76%): $^1$H NMR (300 MHz, CDCl$_3$) δ7.47-7.39 (m, 1H), 7.37-7.19 (m, 10H), 7.14-7.06 (m, 2H), 6.94-6.87 (m, 3H), 6.62-6.55 (m, 1H), 6.53-6.45 (m, 1H); MS (ES+) m/z 448.0 (M+23).

B. Synthesis of 1-(diphenylmethyl)-3-(5-fluoro-2-hydroxyphenyl)-1,3-dihydro-2H-indol-2-one Following the procedure as described in PREPARATION 3B, and making non-critical variations using 1-(diphenylmethyl)-3-(5-fluoro-2-hydroxyphenyl)-3-hydroxy-1,3-dihydro-2H-indol-2-one to replace 1-(diphenylmethyl)-3-hydroxy-3-(2-hydroxy-4-methoxy-5-methylphenyl)-1,3-dihydro-2H-indol-2-one, 1-(diphenylmethyl)-3-(5-fluoro-2-hydroxyphenyl)-1,3-dihydro-2H-indol-2-one was obtained (78%): $^1$H NMR (300 MHz, CDCl$_3$) δ 8.80 (s, 1H), 7.39-7.26 (m, 9H), 7.22-7.16 (m, 2H), 7.15-7.05 (m, 2H), 7.05-6.97 (m, 1H), 6.96-6.85 (m, 2H), 6.68-6.61 (m, 1H), 6.58-6.50 (m, 1H), 5.16 (s, 1H); MS (ES+) m/z 410.0 (M+1).

Preparation 12

Synthesis of 1-(diphenylmethyl)-3-(2-hydroxy-4-methoxyphenyl)-1,3-dihydro-2H-indol-2-one

A. Synthesis of 1-(diphenylmethyl)-3-hydroxy-3-(2-hydroxy-4-methoxyphenyl)-1,3-dihydro-2H-indol-2-one Following the procedure as described in PREPARATION 6A, and making non-critical variations using 3-methoxyphenol to replace 3,4-dimethylphenol, 1-(diphenylmethyl)-3-hydroxy-3-(2-hydroxy-4-methoxyphenyl)-1,3-dihydro-2H-indol-2-one was obtained (99%): MS (ES+) m/z 420.2 (M−17), 460.2 (M+23).

B. Synthesis of 1-(diphenylmethyl)-3-(2-hydroxy-4-methoxyphenyl)-1,3-dihydro-2H-indol-2-one To a solution of 1-(diphenylmethyl)-3-hydroxy-3-(2-hydroxy-4-methoxyphenyl)-1,3-dihydro-2H-indol-2-one (27.9 g, 63.8 mmol) in dichloromethane (200 mL) were added trifluoroacetic acid (2 mL) and triethylsilane (1.5 mL) at ambient temperature. The reaction mixture was refluxed for 15 h. The mixture was concentrated in vacuo to dryness. The residue was purified by flash chromatograph using 25% ethyl acetate in hexane to afford 1-(diphenylmethyl)-3-(2-hydroxy-4-methoxyphenyl)-1,3-dihydro-2H-indol-2-one (7.40 g, 27%) as a colorless solid: $^1$H NMR (300 MHz, CDCl$_3$) δ 7.40-7.18 (m, 11H), 7.13-7.06 (m, 2H), 6.97 (s, 1H), 6.83 (d, J=8.4 Hz, 1H), 6.67-6.64 (m, 1H), 6.57-6.52 (m, 1H), 6.41 (dd, J=8.4, 2.4 Hz, 1H), 5.11 (s, 1H), 3.77 (s, 3H).

Preparation 13

Synthesis of 1-(diphenylmethyl)-3-(7-hydroxy-2,3-dihydro-1,4-benzodioxin-6-yl)-1,3-dihydro-2H-indol-2-one A. Synthesis of 1-(diphenylmethyl)-3-hydroxy-3-(7-hydroxy-2,3-dihydro-1,4-benzodioxin-6-yl)-1,3-dihydro-2H-indol-2-one Following the procedure as described in PREPARATION 6A, and making non-critical variations using 2,3-dihydrobenzo[b][1,4]dioxin-6-ol to replace 3,4-dimethylphenol, 1-(diphenylmethyl)-3-hydroxy-3-(7-hydroxy-2,3-dihydro-1,4-benzodioxin-6-yl)-1,3-dihydro-2H-indol-2-one was obtained (88%) as a pale yellow powder: mp 210-212° C. (water); $^1$H NMR (300 MHz, DMSO-d$_6$) δ9.08 (br s, 1H), 7.42-7.24 (m, 11H), 6.97-6.79 (m, 4H), 6.54 (br s, 1H), 6.29 (d, J=7.8 Hz, 1H), 6.17 (s, 1H), 4.25-4.13 (m, 4H); $^{13}$C NMR (75 MHz, DMSO-d$_6$) δ 176.8, 3.0, 142.7, 138.3, 137.8, 128.5, 128.4, 128.3, 128.0, 127.6, 127.4, 123.7, 121.6, 120.8, 115.6, 110.8, 103.3, 74.1, 64.4, 63.8, 57.2; MS (ES+) m/z 488.2 (M+23).

B. Synthesis of 1-(diphenylmethyl)-3-(7-hydroxy-2,3-dihydro-1,4-benzodioxin-6-yl)-1,3-dihydro-2H-indol-2-one Following the procedure as described in PREPARATION 4C, and making non-critical variations using 1-(diphenylmethyl)-3-hydroxy-3-(7-hydroxy-2,3-dihydro-1,4-benzodioxin-6-yl)-1,3-dihydro-2H-indol-2-one to replace 4-chloro-1-(diphenylmethyl)-3-hydroxy-3-(6-hydroxy-2,3-dihydro-1-benzofuran-5-yl)-1,3-dihydro-2H-indol-2-one, 1-(diphenylmethyl)-3-(7-hydroxy-2,3-dihydro-1,4-benzodioxin-6-yl)-1,3-dihydro-2H-indol-2-one was obtained (quantitative) as a pale pink solid: mp 157-160° C. (diethyl ether/hexanes); $^1$H NMR (300 MHz, DMSO-d$_6$) δ9.19 (br s, 1H), 7.42-7.27 (m, 10H), 6.98-6.91 (m, 3H), 6.88-6.82 (m, 1H), 6.69-6.63 (m, 1H), 6.37 (d, J=7.8 Hz, 1H), 6.30 (s, 1H), 4.81 (s, 1H), 4.21-4.11 (m, 4H); $^{13}$C NMR (75 MHz, DMSO-d$_6$) δ176.2, 149.2, 142.8, 142.6, 138.2, 137.8, 135.8, 130.1, 128.6, 128.4, 128.3, 128.2, 127.7, 1275, 126.8, 123.6, 121.7, 118.9, 117.0, 110.6, 103.8, 64.3, 63.8, 57.4, 47.4; MS (ES+) m/z 450.3 (M+1).

Preparation 14

Synthesis of 1-(diphenylmethyl)-3-(7-hydroxy-3,4-dihydro-2H-chromen-6-yl)-1,3-dihydro-2H-indol-2-one A. Synthesis of 1-(diphenylmethyl)-3-hydroxy-3-(7-hydroxy-3,4-dihydro-2H-chromen-6-yl)-1,3-dihydro-2H-indol-2-one To a cooled (0° C.) solution of chroman-7-ol (Cube, R. V., et al., *Bioorg. Med. Chem. Lett.* (2005), 15(9):2389-93) (0.55 g, 3.66 mmol) in tetrahydrofuran (11 mL) under nitrogen was added isopropylmagnesium chloride (2.4 mL, 2 M in tetrahydrofuran, 4.8 mmol). The resulting solution was stirred at 0° C. for 30 min. A suspension of 1-(diphenylmethyl)indoline-2,3-dione (1.16 g, 3.70 mmol) in dichloromethane (4 mL) was added. The reaction was stirred at 0° C. for 10 min, then warmed to ambient temperature and stirred for 15.5 h. The reaction was diluted with saturated ammonium chloride solution (10 mL) and the organic solvents were removed under reduced pressure. The residual mixture was diluted with water (50 mL) and extracted with ethyl acetate (3×25 mL). The combined organic solution was washed with brine (50 mL), dried over sodium sulfate, filtered and concentrated under reduced pressure. The residue was purified by flash column chromatography with hexanes/ethyl acetate (7:3) to afford 1-(diphenylmethyl)-3-hydroxy-3-(7-hydroxy-3,4-dihydro-2H-chromen-6-yl)-1,3-dihydro-2H-indol-2-one (1.37 g, 81%) as a light yellow solid: mp 204-206° C. (diethyl ether/hexanes); $^1$H NMR (300 MHz, CDCl$_3$) δ8.90 (s, 1H), 7.49 (dd, J=5.6, 3.2 Hz, 1H), 7.38-7.23 (m, 10H), 7.12-7.06 (m, 2H), 6.95 (s, 1H), 6.52-6.47 (m, 3H), 4.23 (s, 1H), 4.121 (dd, J=5.7, 4.5 Hz, 2H), 2.53 (t, J=6.3 Hz, 2H), 1.95-1.87 (m, 2H); MS (ES+) m/z 486.1 (M+23).

B. Synthesis of 1-(diphenylmethyl)-3-(7-hydroxy-3,4-dihydro-2H-chromen-6-yl)-1,3-dihydro-2H-indol-2-one Following the procedure as described in PREPARATION 4C, and making non-critical variations using 1-(diphenylmethyl)-3-hydroxy-3-(7-hydroxy-3,4-dihydro-2H-chromen-6-yl)-1,3-dihydro-2H-indol-2-one to replace 4-chloro-1-(diphenylmethyl)-3-hydroxy-3-(6-hydroxy-2,3-dihydro-1-benzofuran-5-yl)-1,3-dihydro-2H-indol-2-one, 1-(diphenylmethyl)-3-(7-hydroxy-3,4-dihydro-2H-chromen-6-yl)-1,3-dihydro-2H-indol-2-one was obtained (81%) as a pale yellow solid: mp 207-210° C. (hexanes): $^1$H NMR (300 MHz, CDCl$_3$) δ8.43 (br s, 1H), 7.37-7.22 (m, 11H), 7.09-7.03 (m, 2H), 6.99 (s, 1H), 6.58 (s, 1H), 6.56-6.50 (m, 1H), 6.48 (s, 1H), 5.05 (s, 1H), 4.15-4.08 (m, 2H), 2.68-2.51 (m, 2H), 1.97-1.89 (m, 2H); $^{13}$C NMR (75 MHz, CDCl$_3$) δ179.1, 155.4, 154.9, 143.4, 137.5, 137.4, 128.8, 128.7, 128.6, 128.5, 128.1, 127.9, 127.3, 125.9, 122.9, 115.8, 114.6, 112.8, 106.7, 66.5, 58.8, 47.3, 24.4, 22.6; MS (ES+) m/z 448.1 (M+1).

Preparation 15

Synthesis of 1-(diphenylmethyl)-3-(8-hydroxy-3,4-dihydro-2H-1,5-benzodioxepin-7-yl)-1,3-dihydro-2H-indol-2-one A. Synthesis of 1-(diphenylmethyl)-3-hydroxy-3-(8-hydroxy-3,4-dihydro-2H-1,5-benzo-dioxepin-7-yl)-1,3-dihydro-2H-indol-2-one Following the procedure as described in PREPARATION 14A, and making non-critical variations using 3,4-dihydro-2H-benzo[b][1,4]dioxepin-7-ol (Lange, J., et al., *Heterocycles* (2000), 53(1):197-204) to replace chroman-7-ol, 1-(diphenylmethyl)-3-hydroxy-3-(8-hydroxy-3,4-dihydro-2H-1,5-benzo-dioxepin-7-yl)-1,3-dihydro-2H-indol-2-one was obtained (70%) as a pale orange solid: mp 115-118° C. (diethyl ether/hexanes); $^1$H NMR (300 MHz, DMSO-d$_6$) δ9.25 (s, 1H), 7.42-7.29 (m, 11H), 6.98-6.80 (m, 4H), 6.58 (s, 1H), 6.30 (d, J=7.8 Hz, 1H), 6.29 (s, 1H), 4.14-3.98 (m, 4H), 2.10-2.02 (m, 2H); $^{13}$C NMR (75 MHz, DMSO-d$_6$) δ176.7, 150.9, 148.9, 143.3, 143.0, 138.2, 137.8, 132.5, 128.5, 128.4, 128.3, 128.1, 127.6, 127.4, 123.7, 122.5, 121.7, 120.2, 110.8, 107.7, 74.0, 70.71, 70.65, 57.3, 32.3; MS (ES+) m/z 502.1 (M+23).

B. Synthesis of 1-(diphenylmethyl)-3-(8-hydroxy-3,4-dihydro-2H-1,5-benzodioxepin-7-yl)-1,3-dihydro-2H-indol-2-one Following the procedure as described in PREPARATION 4C, and making non-critical variations using 1-(diphenylmethyl)-3-hydroxy-3-(8-hydroxy-3,4-dihydro-2H-1,5-benzodioxepin-7-yl)-1,3-dihydro-2H-indol-2-one to replace 4-chloro-1-(diphenylmethyl)-3-hydroxy-3-(6-hydroxy-2,3-dihydro-1-benzofuran-5-yl)-1,3-dihydro-2H-indol-2-one, 1-(diphenylmethyl)-3-(8-hydroxy-3,4-dihydro-2H-1,5-benzodioxepin-7-yl)-1,3-dihydro-2H-indol-2-one was obtained (91%) as an off-white powder: mp 193-195° C. (diethyl ether/hexanes); $^1$H NMR (300 MHz, CDCl$_3$) δ8.65 (br s, 1H), 7.39-7.27 (m, 9H), 7.23-7.20 (m, 2H), 7.13-7.04 (m, 2H), 6.96 (s, 1H), 6.73 (s, 1H), 6.60 (s, 1H), 6.53-6.50 (m, 1H), 5.09 (s, 1H), 4.25-3.99 (m, 4H), 2.22-2.06 (m, 2H); $^{13}$C NMR (75 MHz, CDCl$_3$) δ 178.9, 151.7, 151.6, 145.3, 143.3, 137.4, 137.1, 128.9, 128.8, 128.6, 128.4, 128.2, 128.0, 126.5, 126.1, 123.1, 120.2, 118.2, 112.9, 112.0, 71.0, 70.8, 58.9, 47.2, 32.3; MS (ES+) m/z 464.0 (M+1).

Preparation 16

Synthesis of 1-(diphenylmethyl)-3-(5-hydroxy-2-methyl-1,3-benzoxazol-6-yl)-1,3-dihydro-2H-indol-2-one A. Synthesis of 1-(diphenylmethyl)-3-hydroxy-3-(5-hydroxy-2-methyl-1,3-benzoxazol-6-yl)-1,3-dihydro-2H-indol-2-one To a cooled (0° C.) suspension of 2-methyl-1,3-benzoxazol-5-ol (Fujita, et al., *Synthesis* (1982):62-9) (10.3 g, 68.9 mmol) in anhydrous tetrahydrofuran (150 mL) was added isopropylmagnesium chloride (34.4 mL, 2.0 M solution in tetrahydrofuran, 68.9 mmol). The reaction mixture was stirred at 0° C. for 0.5 h, and 1-benzhydrylindoline-2,3-dione (18.8 g, 59.9 mmol) and anhydrous dichloromethane (150 mL) were added. The reaction mixture was heated at reflux for 6 days and was allowed to cool to ambient temperature. The reaction mixture was diluted with a saturated aqueous solution of ammonium chloride (200 mL) and ethyl acetate (200 mL) and the phases were separated. The aqueous phase was extracted with ethyl acetate (2×200 mL) and the combined organic solution was washed with brine (2×200 mL), dried over anhydrous sodium sulfate, filtered and concentrated in vacuo. The crude product was purified by column chromatography with hexanes/ethyl acetate (3/1), followed by recrystallization from hexanes/ethyl acetate to afford 1-(diphenylmethyl)-3-hydroxy-3-(5-hydroxy-2-methyl-1,3-benzoxazol-6-yl)-1,3-dihydro-2H-indol-2-one (3.10 g, 10%) as an off-white solid: $^1$H NMR (300 MHz, CDCl$_3$) δ8.41 (br s, 1H), 7.63-7.60 (m, 2H), 7.47-7.32 (m, 10H), 7.15 (s, 1H), 7.04-6.96 (m, 1H), 6.96-6.88 (m, 1H), 6.87 (d, J=9.0 Hz, 1H), 6.41 (d, 7.8 Hz, 1H), 4.58 (br s, 1H), 2.44 (s, 3H); MS (ES+) m/z 445.2 (M−17).

B. Synthesis of 1-(diphenylmethyl)-3-(5-hydroxy-2-methyl-1,3-benzoxazol-6-yl)-1,3-dihydro-2H-indol-2-one Following the procedure as described in PREPARATION 1B, and making non-critical variations using 1-(diphenylmethyl)-3-hydroxy-3-(5-hydroxy-2-methyl-1,3-benzoxazol-6-yl)-1,3-dihydro-2H-indol-2-one to replace 3-hydroxy-3-(5-hydroxy-2-methyl-1,3-benzothiazol-6-yl)-1,3-dihydro-2H-indol-2-one, 1-(diphenylmethyl)-3-(5-hydroxy-2-methyl-1,3-benzoxazol-6-yl)-1,3-dihydro-2H-indol-2-one was obtained (87%) as a colorless solid: MS (ES+) m/z 447.4 (M+1).

Preparation 17

Synthesis of 7-[1-(diphenylmethyl)-2-oxo-2,3-dihydro-1H-indol-3-yl]-6-hydroxy-4-methyl-2H-1,4-benzoxazin-3(4H)-one A. Synthesis of 7-[1-(diphenylmethyl)-3-hydroxy-2-oxo-2,3-dihydro-1H-indol-3-yl]-6-hydroxy-4-methyl-2H-1,4-benzoxazin-3(4H)-one Following the procedure as described in PREPARATION 14A, and making non-critical variations using 6-hydroxy-4-methyl-2H-benzo[b][1,4]oxazin-3(4H)-one (Loudon and Ogg, *J. Chem. Soc.,* 1955:739-743) to replace chroman-7-ol, 7-[1-(diphenylmethyl)-3-hydroxy-2-oxo-2,3-dihydro-1H-indol-3-yl]-6-hydroxy-4-methyl-2H-1,4-benzoxazin-3(4H)-one was obtained (27%) as an off-white solid: $^1$H NMR (300 MHz, DMSO-d$_6$) δ9.44 (s, 1H), 7.46-7.25 (m, 11H), 7.01-6.77 (m, 4H), 6.68 (s, 1H), 6.43 (s, 1H), 6.38-6.27 (m, 1H), 4.60 (s, 2H), 3.19 (s, 3H); MS (ES−) m/z 491.5 (M−1).

B. Synthesis of 7-[1-(diphenylmethyl)-2-oxo-2,3-dihydro-1H-indol-3-yl]-6-hydroxy-4-methyl-2H-1,4-benzoxazin-3(4H)-one To a solution of 7-[1-(diphenylmethyl)-3-hydroxy-2-oxo-2,3-dihydro-1H-indol-3-yl]-6-hydroxy-4-methyl-2H-1,4-benzoxazin-3(4H)-one (4.0 g, 8.1 mmol) in trifluoroacetic acid (1.8 mL, 24.4 mmol) was added triethylsilane (3.9 mL, 24.4 mmol) and the reaction mixture was stirred at ambient temperature for 16 h. The reaction mixture was concentrated in vacuo and the crude product was purified by column chromatography with ethyl acetate in hexanes (10 to 100% gradient) to afford 7-[1-(diphenylmethyl)-2-oxo-2,3-dihydro-1H-indol-3-yl]-6-hydroxy-4-methyl-2H-1,4-benzoxazin-3(4H)-one (2.66 g, 71%) as an off-white solid: $^1$H NMR (300 MHz, DMSO-d$_6$) δ9.53 (s, 1H), 7.44-7.28 (m, 10H), 6.99-6.95 (m, 3H), 6.89-6.84 (m, 2H), 6.54 (s, 1H), 6.40 (m, 1H), 4.90 (s, 1H), 4.57 (s, 2H), 3.21 (s, 3H); MS (ES+) m/z 477.0 (M+1).

Preparation 18

Synthesis of 6-[1-(diphenylmethyl)-2-oxo-2,3-dihydro-1H-indol-3-yl]-7-hydroxy-4-methyl-2H-1,4-benzoxazin-3(4H)-one A. Synthesis of 7-hydroxy-4-methyl-2H-1,4-benzoxazin-3(4H)-one To a cooled (0° C.) solution of 7-amino-4-methyl-2H-1,4-benzoxazin-3(4H)-one (10.0 g, 56 mmol) in water (80 mL) was added concentrated sulfuric acid (17 mL). After stirring at 0° C. for 10 min, a solution of sodium nitrite (4.1 g, 59 mmol) in water (10 mL) was added dropwise. After stirring for 0.5 h, the reaction mixture was added dropwise to a solution of cupric sulfate (50 g) in water (300 mL) at reflux. Once the addition was complete, the reaction mixture was allowed to cool to ambient temperature and was extracted with ethyl acetate (5×200 mL). The combined organic solution was dried over anhydrous sodium sulfate, filtered and concentrated in vacuo. The residue was purified by trituration with ice-cold ethyl acetate (25 mL) and the solid was collected by vacuum filtration, air-dried and dried under high vacuum to afford 7-hydroxy-4-methyl-2H-1,4-benzoxazin-3 (4H)-one (3.22 g, 32%) as a tan solid: $^1$H NMR (300 MHz, DMSO-$d_6$) δ9.40 (s, 1H), 6.95 (d, J=8.7 Hz, 1H), 6.45 (dd, J=8.7, 2.6 Hz, 1H), 6.40 (d, J=2.6 Hz, 1H), 4.56 (s, 2H), 3.21 (s, 3H); MS (ES+) m/z 180.1 (M+1).

B. Synthesis of 6-[1'-(diphenylmethyl)-3-hydroxy-2-oxo-2,3-dihydro-1H-indol-3-yl]-7-hydroxy-4-methyl-2H-1,4-benzoxazin-3(4H)-one Following the procedure as described in PREPARATION 16A, and making non-critical variations using 7-hydroxy-4-methyl-2H-1,4-benzoxazin-3(4H)-one to replace 2-methyl-1,3-benzoxazol-5-ol, 6-[1-(diphenylmethyl)-3-hydroxy-2-oxo-2,3-dihydro-1H-indol-3-yl]-7-hydroxy-4-methyl-2H-1, 4-benzoxazin-3(4H)-one was obtained (74%) as an off-white solid: $^1$H NMR (300 MHz, DMSO-$d_6$) δ9.54 (s, 1H), 7.55 (s, 1H), 7.42-7.30 (m, 10H), 6.99-6.94 (m, 2H), 6.88 (s, 1H), 6.86-6.80 (m, 1H), 6.71 (s, 1H), 6.35-6.30 (m, 2H), 4.61 (s, 2H), 3.32 (s, 3H); MS (ES+) tri/z 475.0 (M−17).

C. Synthesis of 6-[1-(diphenylmethyl)-2-oxo-2,3-dihydro-1H-indol-3-yl]-7-hydroxy-4-methyl-2H-1,4-benzoxazin-3(4H)-one Following the procedure as described in PREPARATION 17B, and making non-critical variations using 6-[1-(diphenylmethyl)-3-hydroxy-2-oxo-2,3-dihydro-1H-indol-3-yl]-7-hydroxy-4-methyl-2H-1,4-benzoxazin-3(4H)-one to replace 7-(1-benzhydryl-3-hydroxy-2-oxoindolin-3-yl)-6-hydroxy-4-methyl-2H-benzo[b][1,4]oxazin-3(4H)-one, 6-[1-(diphenylmethyl)-2-oxo-2,3-dihydro-1H-indol-3-yl]-7-hydroxy-4-methyl-2H-1,4-benzoxazin-3(4H)-one was obtained (65%) as an amorphous solid: MS (ES+) m/z 477.4 (M+1).

Preparation 19

Synthesis of 6-[1-(diphenylmethyl)-2-oxo-2,3-dihydro-1H-indol-3-yl]-5-hydroxy-3-methyl-1,3-benzoxazol-2(3H)-one A. Synthesis of 5-{[tert-butyl(dimethyl)silyl]oxy}-1,3-benzoxazol-2(3H)-one To a solution of 5-hydroxy-1,3-benzoxazol-2(3H)-one (Itoh, et al., J. Org. Chem. 2002 (67):7424-7428) (1.00 g, 6.6 mmol) in anhydrous N,N-dimethylformamide (10 mL) was added imidazole (0.54 g, 7.9 mmol), followed by chloro-tert-butyldimethylsilane (1.10 g, 7.3 mmol). The reaction mixture was stirred at ambient temperature for 16 h and concentrated in vacuo. The crude product was purified by column chromatography with ethyl acetate in hexanes (0 to 50% gradient) to afford 5-{[tert-butyl(dimethyl)silyl]oxy}-1,3-benzoxazol-2 (3H)-one (1.53 g, 87%) as a colorless solid: $^1$H NMR (300 MHz, CDCl$_3$) δ9.04 (br s, 1H), 7.04 (d, J=8.3 Hz, 1H), 6.60-6.53 (m, 2H), 0.98 (s, 9H), 0.19 (s, 6H).

B. Synthesis of 5-{[tert-butyl(dimethyl)sily])oxy}-3-methyl-1,3-benzoxazol-2(3H)-one To a cooled (0° C.) solution of 5-{[tert-butyl(dimethyl) silyl]oxy}-1,3-benzoxazol-2(3H)-one (1.45 g, 5.4 mmol) in anhydrous N,N-dimethylformamide (10 mL) was added sodium hydride (0.26 g, 60% dispersion in mineral oil, 6.6 mmol). The reaction mixture was stirred at 0° C. for 15 min followed by the addition of iodomethane (1.0 mL, 16 mmol). The reaction mixture was stirred at ambient temperature for 16 h and diluted with water (20 mL) and ethyl acetate (20 mL). The phases were separated and the aqueous phase was extracted with ethyl acetate (2×20 mL). The combined organic solution was washed with water (5×20 mL) and brine (2×20 mL), dried over anhydrous sodium sulfate, filtered and concentrated in vacuo. The crude product was purified by column chromatography with ethyl acetate in hexanes (0 to 25% gradient) to afford 5-{[tert-butyl(dimethyl)silyl]oxy}-3-methyl-1,3-benzoxazol-2(3H)-one (1.26 g, 83%) as a pale yellow solid: $^1$H NMR (300 MHz, CDCl$_3$) δ7.02 (d, J=8.6 Hz, 1H), 6.55 (dd, J=8.6, 2.4 Hz, 1H), 6.44 (d, J=2.4 Hz, 1H), 3.35 (s, 3H), 0.99 (s, 9H), 0.20 (s, 6H).

C. Synthesis of 5-hydroxy-3-methyl-1,3-benzoxazol-2(3H)-one

To a cooled (0° C.) solution of 5-{[tert-butyl(dimethyl) silyl]oxy}-3-methyl-1,3-benzoxazol-2(3H)-one (1.20 g, 4.3 mmol) in anhydrous tetrahydrofuran (15 mL) was added dropwise tetra-n-butylammonium fluoride (4.7 mL, 1 M in tetrahydrofuran, 4.7 mmol). The reaction mixture was stirred at ambient temperature for 16 h and concentrated in vacuo. To the residue was added ethyl acetate (10 mL) and a 1 M solution of hydrochloric acid (20 mL) and the resultant suspension was sonicated for 5 min. The product was collected by vacuum filtration, washed with ethyl acetate (10 mL), air-dried and dried under high vacuum to afford 5-hydroxy-3-methyl-1,3-benzoxazol-2(3H)-one (0.47 g, 67%) as a pink solid: $^1$H NMR (300 MHz, DMSO-$d_6$) δ 9.52 (br s, 1H), 7.09 (d, J=8.6 Hz, 1H), 6.62 (d, J=2.4 Hz, 1H), 6.47 (dd, J=8.6, 2.4 Hz, 1H), 3.27 (s, 3H); MS (ES−) m/z 164.2 (M−1).

D. Synthesis of 6-[1-(diphenylmethyl)-3-hydroxy-2-oxo-2,3-dihydro-1H-indol-3-yl]-5-hydroxy-3-methyl-1,3-benzoxazol-2(3H)-one Following the procedure as described in PREPARATION 16A, and making non-critical variations using 5-hydroxy-3-methyl-1,3-benzoxazol-2(3H)-one to replace 2-methyl-1,3-benzoxazol-5-ol, 6-[1-(diphenylmethyl)-3-hydroxy-2-oxo-2,3-dihydro-1H-indol-3-yl]-5-hydr oxy-3-methyl-1,3-benzoxazol-2(3H)-one was obtained (66%) as a pink solid: MS (ES+) m/z 461.1 (M−17).

E. Synthesis of 6-[1-(diphenylmethyl)-2-oxo-2,3-dihydro-1H-indol-3-yl]-5-hydroxy-3-methyl-1,3-benzoxazol-2(3H)-one Following the procedure as described in PREPARATION 9B, and making non-critical variations using 6-[1-(diphenylmethyl)-3-hydroxy-2-oxo-2,3-dihydro-1H-indol-3-yl]-5-hydroxy-3-methyl-1,3-benzoxazol-2(3H)-one to replace 3-hydroxy-3-(6-hydroxy-3-methyl-1,2-benzisoxazol-5-yl)-1-(4-methoxybenzyl)-1,3-dihydro-2H-indol-2-one, 6-[1-(diphenylmethyl)-2-oxo-2,3-dihydro-1H-indol-3-yl]-5-hydroxy-3-methyl-1,3-benzoxazol-2(3H)-one was obtained (98%) as a yellow amorphous solid: MS (ES+) m/z 463.4 (M+1).

Preparation 20

Synthesis of 5-[1-(diphenylmethyl)-2-oxo-2,3-dihydro-1H-indol-3-yl]-6-hydroxy-3-methyl-1,3-benzoxazol-2(3H)-one A. Synthesis of 6-{[tert-butyl(dimethyl)silyl]oxy}-3-methyl-1,3-benzoxazol-2(3H)-one To a solution of 6-hydroxy-1,3-benzoxazol-2(3H)-one (4.9 g, 32 mmol) in anhydrous N,N-dimethylformamide (40 mL) was added imidazole (2.6 g, 39 mmol) and chloro-tert-butyldimethylsilane (5.4 g, 35 mmol). The reaction mixture was stirred at ambient temperature for 16 h and diluted with ethyl acetate (100 mL). The resultant suspension was filtered and the filtrate was concentrated in vacuo. The residue was taken up in anhydrous N,N-dimethylformamide (50 mL) and cooled to 0° C. To this solution was added sodium hydride (1.6 g, 60% dispersion in mineral oil, 39 mmol) and the reaction mixture was stirred at 0° C. for 15 min. Iodomethane (6.1 mL, 97 mmol) was added and the reaction mixture was stirred at ambient temperature for 16 h. The reaction mixture was concentrated in vacuo and the residue was taken up in water (100 mL) and ethyl acetate (100 mL). The phases were separated and the aqueous phase was extracted with ethyl acetate (2×100 mL). The combined organic solution was washed with water (2×100 mL) and brine (100 mL), dried over anhydrous sodium sulfate, filtered and concentrated in vacuo. The crude product was purified by column chromatography with hexanes/ethyl acetate (5/1) to afford 6-{[tert-butyl(dimethyl)silyl]oxy}-3-methyl-1,3-benzoxazol-2(3H)-one (6.55 g, 72%) as a colorless solid: $^1$H NMR (300 MHz, CDCl$_3$) δ 6.79-6.72 (m, 2H), 6.69-6.64 (m, 1H), 3.36 (s, 3H), 0.98 (s, 9H), 0.17 (s, 6H).

B. Synthesis of 6-hydroxy-3-methyl-1,3-benzoxazol-2(3H)-one

Following the procedure as described in PREPARATION 19C, and making non-critical variations using 6-{[tert-butyl(dimethyl)silyl]oxy}-3-methyl-1,3-benzoxazol-2(3H)-one to replace 5-{[tert-butyl(dimethyl)silyl]oxy}-3-methyl-1,3-benzoxazol-2(3H)-one, 6-hydroxy-3-methyl-1,3-benzoxazol-2(3H)-one was obtained (99%) as a tan solid: $^1$H NMR (300 MHz, DMSO-d$_6$) δ9.50 (br s, 1H), 7.02 (d, J=8.4 Hz, 1H), 6.75 (d, J=2.1 Hz, 1H), 6.62 (dd, J=8.4, 2.1 Hz, 1H), 3.27 (s, 3H); MS (ES−) m/z 164.2 (M−1).

C. Synthesis of 5-[1-(diphenylmethyl)-3-hydroxy-2-oxo-2,3-dihydro-1H-indol-3-yl]-6-hydroxy-3-methyl-1,3-benzoxazol-2(3H)-one Following the procedure as described in PREPARATION 15A, and making non-critical variations using 6-hydroxy-3-methyl-1,3-benzoxazol-2(3H)-one to replace 2-methyl-1,3-benzoxazol-5-ol, 5-[1-(diphenylmethyl)-3-hydroxy-2-oxo-2,3-dihydro-1H-indol-3-yl]-6-hydroxy-3-methyl-1,3-benzoxazol-2(3H)-one was obtained (46%) as an off-white solid: $^1$H NMR (300 MHz, DMSO-d$_6$) δ9.62 (br s, 1H), 7.64 (s, 1H), 7.47-7.25 (m, 10H), 7.06-6.71 (m, 5H), 6.65 (s, 1H), 6.30 (d, J=7.9 Hz, 1H), 3.38 (s, 3H); MS (ES+) m/z 479.1 (M+1).

D. Synthesis of 5-[1-(diphenylmethyl)-2-oxo-2,3-dihydro-1H-indol-3-yl]-6-hydroxy-3-methyl-1,3-benzoxazol-2(3H)-one Following the procedure as described in PREPARATION 17B, and making non-critical variations using 5-[1-(diphenylmethyl)-3-hydroxy-2-oxo-2,3-dihydro-1H-indol-3-yl]-6-hydroxy-3-methyl-1,3-benzoxazol-2(3H)-one to replace 7-(1-benzhydryl-3-hydroxy-2-oxoindolin-3-yl)-6-hydroxy-4-methyl-2H-benzo[b][1,4]oxazin-3(4H)-one, 5-[1-(diphenylmethyl)-2-oxo-2,3-dihydro-1H-indol-3-yl]-6-hydroxy-3-methyl-1,3-benzoxazol-2(3H)-one was obtained (73%) as a pale pink solid: MS (ES+) m/z 463.4 (M+1).

Preparation 21

Synthesis of 7-chloro-1-(diphenylmethyl)-3-(6-hydroxy-2,3-dihydro-1-benzofuran-5-yl)-1,3-dihydro-2H-indol-2-one A. Synthesis of 7-chloro-1-(diphenylmethyl)-1H-indole-2,3-dione Following the procedure as described in PREPARATION 4A, and making non-critical variations using 7-chloro-1H-indole-2,3-dione to replace 4-chloro-1H-indole-2,3-dione, 7-chloro-1-(diphenylmethyl)-1H-indole-2,3-dione was obtained (38%) as an orange solid: mp 172-173° C. (hexanes/ethyl acetate); $^1$H NMR (300 MHz, DMSO-d$_6$) δ 7.71-7.60 (m, 2H), 7.36-7.27 (m, 11H), 7.22-7.17 (m, 1H).

B. Synthesis of 7-chloro-1-(diphenylmethyl)-3-hydroxy-3-(6-hydroxy-2,3-dihydro-1-benzofuran-5-yl)-1,3-dihydro-2H-indol-2-one To a cooled (0° C.) solution of 2,3-dihydrobenzofuran-6-ol (0.52 g, 3.8 mmol) in anhydrous tetrahydrofuran (25 mL) was added isopropylmagnesium chloride (2.1 mL, 2 M solution in tetrahydrofuran, 4.2 mmol). The resultant suspension was stirred at 0° C. for 0.5 h and followed by the addition of 7-chloro-1-(diphenylmethyl)-1H-indole-2,3-dione (2.11 g, 15.5 mmol) in one portion. The reaction mixture was stirred at ambient temperature for 3 h and concentrated in vacuo. The crude product was purified by column chromatography with ethyl acetate in hexanes (0% to 50% gradient) to afford 7-chloro-1-(diphenylmethyl)-3-hydroxy-3-(6-hydroxy-2,3-dihydro-1-benzofuran-5-yl)-1,3-dihydro-2H-indol-2-one (7.12 g, 95%) as a colorless solid: $^1$H NMR (300 MHz, DMSO-d$_6$) δ9.43 (s, 1H), 7.56-7.18 (m, 13H), 6.99-6.86 (m, 2H), 6.60 (s, 1H), 6.08 (s, 1H), 4.56 (t, J=8.6 Hz, 2H), 3.10 (t, J=8.6 Hz, 2H).

C. Synthesis of 7-chloro-1-(diphenylmethyl)-3-(6-hydroxy-2,3-dihydro-1-benzofuran-5-yl)-1,3-dihydro-2H-indol-2-one Following the procedure as described in PREPARATION 4C, and making non-critical variations using 7-chloro-1-(diphenylmethyl)-3-hydroxy-3-(6-hydroxy-2,3-dihydro-1-benzofuran-5-yl)-1,3-dihydro-2H-indol-2-one to replace 4-chloro-1-(diphenylmethyl)-3-hydroxy-3-(6-hydroxy-2,3-dihydro-1-benzofuran-5-yl)-1,3-dihydro-2H-indol-2-one, 7-chloro-1-(diphenylmethyl)-3-(6-hydroxy-2,3-dihydro-1-benzofuran-5-yl)-1,3-dihydro-2H-indol-2-one was obtained (64%) as a colorless solid: $^1$H NMR (300 MHz, DMSO-d$_6$) δ9.53 (s, 1H), 7.44-7.20 (m, 13H), 7.01-6.91 (m, 2H), 6.22 (s, 1H), 4.82 (s, 1H), 4.48 (t, J=8.5 Hz, 2H), 3.03 (t, J=8.5 Hz, 2H).

Preparation 22

Synthesis of 1-(diphenylmethyl)-7-fluoro-3-hydroxy-3-(6-hydroxy-2,3-dihydro-1-benzofuran-5-yl)-1,3-dihydro-2H-indol-2-one

A. Synthesis of 1-(diphenylmethyl)-7-fluoro-1H-indole-2,3-dione

Following the procedure as described in PREPARATION 4A, and making non-critical variations using 7-fluoro-1H-indole-2,3-dione (Kalia, N., et al., *J. Med. Chem.* 2007; 50:21-39) to replace 4-chloro-1H-indole-2,3-dione, 1-(diphenylmethyl)-7-fluoro-1H-indole-2,3-dione was obtained (56%) as an orange solid: $^1$H NMR (300 MHz, CDCl$_3$) δ7.52-7.47 (m, 1H), 7.42-7.30 (m, 10H), 7.29-7.21 (m, 1H), 7.13-7.05 (m, 1H), 6.99 (br s, 1H); MS (ES+) m/z 353.9 (M+23).

B. Synthesis of 1-(diphenylmethyl)-7-fluoro-3-hydroxy-3-(6-hydroxy-2,3-dihydro-1-benzofuran-5-yl)-1,3-dihydro-2H-indol-2-one Following the procedure as described in PREPARATION 21B, making non-critical variations using 1-(diphenylmethyl)-7-fluoro-1H-indole-2,3-dione to replace 7-chloro-1-(diphenylmethyl)-1H-indole-2,3-dione, 1-(diphenylmethyl)-7-fluoro-3-hydroxy-3-(6-hydroxy-2,3-dihydro-1-benzofuran-5-yl)-1,3-dihydro-2H-indol-2-one was obtained (99%) as a colorless solid: mp 121-122° C. (hexanes/ethyl acetate); $^1$H NMR (300 MHz, DMSO-d$_6$) δ9.44 (s, 1H), 7.62 (s, 1H), 7.42-7.29 m, 10H), 6.98 (s, 1H), 6.93-6.87 (m, 2H), 6.78-6.65 (m, 2H), 6.11 (s, 1H), 4.52 (t, J=8.7 Hz, 2H), 3.14 (t, J=8.6 Hz, 2H); MS (ES+) m/z 467.9 (M+1).

Preparation 23

Synthesis of 1-(diphenylmethyl)-4-fluoro-3-(6-hydroxy-2,3-dihydro-1-benzofuran-5-yl)-7-methyl-1,3-dihydro-2H-indol-2-one

A. Synthesis of 1-(diphenylmethyl)-4-fluoro-7-methyl-1H-indole-2,3-dione

Following the procedure as described in PREPARATION 4A, and making non-critical variations using 4-fluoro-7-methyl-1H-indole-2,3-dione (Cassebaum, *J. Prakt. Chem.* (1960) 12:91-92) to replace 4-chloro-1H-indole-2,3-dione, 1-(diphenylmethyl)-4-fluoro-7-methyl-1H-indole-2,3-dione was obtained (45%) as a brown solid: $^1$H NMR (300 MHz, CDCl$_3$) δ7.38-7.27 (m, 11H), 6.81 (s, 1H), 6.71 (dd, J=8.3, 8.3 Hz, 1H), 2.27 (s, 3H); MS (ES+) m/z 367.7 (M+23).

B. Synthesis of 1-(diphenylmethyl)-4-fluoro-3-hydroxy-3-(6-hydroxy-2,3-dihydro-1-benzofuran-5-yl)-7-methyl-1,3-dihydro-2H-indol-2-one Following the procedure as described in PREPARATION 21B, and making non-critical variations using 1-(diphenylmethyl)-4-fluoro-7-methyl-1H-indole-2,3-dione to replace 1-(diphenylmethyl)-7-chloro-1H-indole-2,3-dione, 1-(diphenylmethyl)-4-fluoro-3-hydroxy-3-(6-hydroxy-2,3-dihydro-1-benzofuran-5-yl)-7-methyl-1,3-dihydro-2H-indol-2-one was obtained (56%) as a colorless solid: $^1$H NMR (300 MHz, CDCl$_3$) δ8.88 (s, 1H), 7.40-7.09 (m, 11H), 6.85-6.79 (m, 2H), 6.60 (br s, 1H), 6.38 (s, 1H), 4.54 (m, 2H), 4.08 (s, 1H), 3.13-2.94 (m, 2H), 2.28 (br s, 3H); MS (ES+) m/z 503.8 (M+23).

C. Synthesis of 1-(diphenylmethyl)-4-fluoro-3-(6-hydroxy-2,3-dihydro-1-benzofuran-5-yl)-7-methyl-1,3-dihydro-2H-indol-2-one Following the procedure as described in PREPARATION 4C, and making non-critical variations using 1-(diphenylmethyl)-4-fluoro-3-hydroxy-3-(6-hydroxy-2,3-dihydro-1-benzofuran-5-yl)-7-methyl-1,3-dihydro-2H-indol-2-one to replace 4-chloro-1-(diphenylmethyl)-3-hydroxy-3-(6-hydroxy-2,3-dihydro-1-benzofuran-5-yl)-1,3-dihydro-2H-indol-2-one, 1-(diphenylmethyl)-4-fluoro-3-(6-hydroxy-2,3-dihydro-1-benzofuran-5-yl)-7-methyl-1,3-dihydro-2H-indol-2-one was obtained (61%) as a colorless solid: MS (ES+) m/z 465.7 (M+1).

Preparation 24

Synthesis of 3-(5-bromo-2-hydroxyphenyl)-1-{[5-(trifluoromethyl)furan-2-yl]methyl}-1,3-dihydro-2H-indol-2-one

A. Synthesis of 3-(5-bromo-2-hydroxyphenyl)-3-hydroxy-1-((5-(trifluoromethyl)furan-2-yl)methyl)indolin-2-one Following the procedure as described in PREPARATION 6A, and making non-critical variations using 4-bromophenol to replace 3,4-dimethylphenol, and 1-{[5-(trifluoromethyl)furan-2-yl]methyl}-1H-indole-2,3-dione to replace 1-(diphenylmethyl)-1H-indole-2,3-dione, 3-(5-bromo-2-hydroxyphenyl)-3-hydroxy-1-((5-(trifluoromethyl)furan-2-yl)methyl)indolin-2-one was obtained (62%) as a white solid: $^1$H NMR (300 MHz, CDCl$_3$) δ 8.73 (s, 1H), 7.49-7.37 (m, 2H), 7.31 (dd, J=8.8, 2.6 Hz, 1H), 7.25-7.17 (m, 1H), 7.03 (d, J=7.9 Hz, 1H), 6.93 (d, J=2.3 Hz, 1H), 6.86 (d, J=8.5 Hz, 1H), 6.74-6.68 (m, 1H), 6.38-6.32 (m, 1H), 5.00-4.81 (m, 2H), 4.09 (s, 1H); MS (ES+) m/z 449.9 (M−17), 451.3 (M−17).

B. Synthesis of 3-(5-bromo-2-hydroxyphenyl)-1-{[5-(trifluoromethyl)furan-2-yl]methyl}-1,3-dihydro-2H-indol-2-one Following the procedure as described in PREPARATION 17B, and making non-critical variations using 3-(5-bromo-2-hydroxyphenyl)-3-hydroxy-1-((5-(trifluoromethyl)furan-2-yl)methyl)indolin-2-one to replace 7-[1-(diphenylmethyl)-3-hydroxy-2-oxo-2,3-dihydro-1H-indol-3-yl]-6-hydroxy-4-methyl-2H-1,4-benzoxazin-3(4H)-one, 3-(5-bromo-2-hydroxyphenyl)-1-{[5-(trifluoromethyl)furan-2-yl]methyl}-1,3-dihydro-2H-indol-2-one was obtained (89%) as a colorless solid: $^1$H NMR (300 MHz, CDCl$_3$) δ8.78 (br s, 1H), 7.44-7.36 (m, 1H), 7.36-7.19 (m, 3H), 7.08 (d, J=7.9 Hz, 1H), 6.99 (d, J=2.3 Hz, 1H), 6.94 (d, J=8.5 Hz, 1H), 6.73-6.68 (m, 1H), 6.37-6.32 (m, 1H), 5.10 (s, 1H), 5.00-4.85 (m, 2H); MS (ES+) m/z 452.0 (M+1).

Preparation 25

Synthesis of 8-(7-hydroxy-2,3-dihydrobenzo[b][1,4]dioxin-6-yl)-6-isopentyl-6H-thiazolo[5,4-e]indol-7(8H)-one

A. Synthesis of 6-(3-methylbutyl)-6H-[1,3]thiazolo[5,4-e]indole-7,8-dione

To a stirred solution of 6H-thiazolo[5,4-e]indole-7,8-dione (2.83 g, 13.9 mmol) in a mixture of anhydrous tetrahydrofuran (120 mL) and N,N-dimethylformamide (80 mL) was added cesium carbonate (23.0 g, 70 mmol) at ambient temperature. The deep purple mixture was stirred for 0.5 h followed by the addition of 1-bromo-3-methylbutane (4.15 mL, 35.0 mmol) in one portion. The mixture was stirred at ambient temperature for 16 h and poured into 800 mL of ice-water and extracted with ethyl acetate. The orange solution was filtered through Celite, dried over magnesium sulfate and filtered.

The filtrate was concentrated in vacuo to dryness and the residue was triturated with diethyl ether to afford 6-(3-methylbutyl)-6H-[1,3]thiazolo[5,4-e]indole-7,8-dione (2.2 g, 57%): $^1$H NMR (300 MHz, CDCl$_3$) δ9.36 (s, 1H), 8.38 (d, J=8.6 Hz, 1H), 7.37 (d, J=8.6 Hz, 1H), 3.77-3.69 (m, 2H), 1.74-1.58 (m, 1H), 1.57-1.47 (m, 2H), 0.94 (d, J=6.5 Hz, 6H).

B. Synthesis of 8-hydroxy-8-(7-hydroxy-2,3-dihydro-1,4-benzodioxin-6-yl)-6-(3-methylbutyl)-6,8-dihydro-7H-[1,3]thiazolo[5,4-e]indol-7-one Following the procedure as described in PREPARATION 6A, and making non-critical variations using 2,3-dihydrobenzo[b][1,4]dioxin-6-ol to replace 3,4-dimethylphenol, and 6-(3-methylbutyl)-6H-[1,3]thiazolo[5,4-e]indole-7,8-dione to replace 1-(diphenylmethyl)-1H-indole-2,3-dione, 8-hydroxy-8-(7-hydroxy-2,3-dihydro-1,4-benzodioxin-6-yl)-6-(3-methylbutyl)-6,8-dihydro-7H-[1,3]thiazolo[5,4-e]indol-7-one was obtained (46%): $^1$H NMR (300 MHz, CDCl$_3$) δ9.00 (s, 1H), 8.80 (s, 1H), 7.96 (d, J=8.5 Hz, 1H), 7.27 (s, 1H), 7.20 (d, J=8.5 Hz, 1H), 6.55 (s, 1H), 4.15 (s, 4H), 3.81-3.59 (m, 2H), 1.79-1.55 (m, 1H), 1.56-1.42 (m, 2H), 0.93 (d, J=6.6 Hz, 6H); MS (ES+) m/z 427.0 (M+1).

C. Synthesis of 8-(7-hydroxy-2,3-dihydro-1,4-benzodioxin-6-yl)-6-(3-methylbutyl)-6,8-dihydro-7H-[1,3]thiazolo[5,4-e]indol-7-one Following the procedure as described in PREPARATION 12B, and making non-critical variations using 8-hydroxy-8-(7-hydroxy-2,3-dihydrobenzo[b][1,4]dioxin-6-yl)-6-isopentyl-6H-thiazolo[5,4-e]indol-7(8H)-one to replace 1-(diphenylmethyl)-3-hydroxy-3-(2-hydroxy-4-methoxyphenyl)-1,3-dihydro-2H-indol-2-one, 8-(7-hydroxy-2,3-dihydro-1,4-benzodioxin-6-yl)-6-(3-methylbutyl)-6,8-dihydro-7H-[1,3]thiazolo[5,4-e]indol-7-one was obtained (93%): MS (ES+) m/z 411.0 (M+1).

Preparation 26

Synthesis of 8-(6-hydroxy-2,3-dihydro-1-benzofuran-5-yl)-6-{[5-(trifluoromethyl)furan-2-yl]methyl}-2,3,6,8-tetrahydro-7H-[1,4]dioxino[2,3-f]indol-7-one A. Synthesis of 6-{[5-(trifluoromethyl)furan-2-yl]methyl}-2,3-dihydro-6H-[1,4]dioxino[2,3-f]indole-7,8-dione To a stirred solution of 2,3-dihydro-6H-[1,4]dioxino[2,3-f]indole-7,8-dione (Lackey and Sternbach, Synthesis 1993: 993-997) (3.08 g, 15.0 mmol) in dry N,N-dimethylformamide (150 mL) was added sodium hydride (0.9 g, 60% in mineral oil, 22.5 mmol) at ambient temperature. The deep purple mixture was stirred for 20 min followed by the addition of 2-(bromomethyl)-5-(trifluoromethyl)furan (3.80 g, 16.5 mmol) in one portion. The dark solution was stirred at ambient temperature for 1 h and concentrated in vacuo to dryness. The residue was mixed with water (150 mL) and stirred. The fine orange precipitation was filtered off and dried to afford 6-{[5-(trifluoromethyl)furan-2-yl]methyl}-2,3-dihydro-6H-[1,4]dioxino[2,3-f]indole-7,8-dione (4.13 g, 78%): $^1$H NMR (300 MHz, CDCl$_3$) δ7.18 (s, 1H), 6.76-6.73 (m, 1H), 6.48 (s, 1H), 6.45-6.40 (m, 1H), 4.85 (s, 2H), 4.42-4.32 (m, 2H), 4.28-4.20 (m, 2H).

B. Synthesis of 8-hydroxy-8-(6-hydroxy-2,3-dihydro-1-benzofuran-5-yl)-6-{[5-(trifluoromethyl)furan-2-yl]methyl}-2,3,6,8-tetrahydro-7H-[1,4]dioxino[2,3-f]indol-7-one Following the procedure as described in PREPARATION 6A, and making non-critical variations using 2,3-dihydrobenzofuran-6-ol to replace 3,4-dimethylphenol, and 6-{[5-(trifluoromethyl)furan-2-yl]methyl}-2,3-dihydro-6H-[1,4]dioxino[2,3-f]indole-7,8-dione to replace 1-(diphenylmethyl)-1H-indole-2,3-dione, 8-hydroxy-8-(6-hydroxy-2,3-dihydrobenzofuran-5-yl)-6-((5-(trifluoromethyl)furan-2-yl)methyl)-6,8-dihydro-2H-[1,4]dioxino[2,3-f]indol-7(3H)-one was obtained (76%): $^1$H NMR (300 MHz, CDCl$_3$) δ 9.08 (s, 1H), 7.07 (s, 1H), 6.74-6.68 (m, 1H), 6.64 (s, 1H), 6.52 (s, 1H), 6.48 (s, 1H), 6.36-6.32 (m, 1H), 4.84 (dd, J=48.7, 16.3 Hz, 2H), 4.53 (t, J=8.7 Hz, 2H), 4.32-4.20 (m, 4H), 4.16 (s, 1H), 3.08-2.94 (m, 2H); MS (ES+) m/z 471.9 (M−17).

C. Synthesis of 8-(6-hydroxy-2,3-dihydro-1-benzofuran-5-yl)-6-{[5-(trifluoromethyl)furan-2-yl]methyl}-2,3,6,8-tetrahydro-7H-[1,4]dioxino[2,3-f]indol-7-one To a solution of 8-hydroxy-8-(6-hydroxy-2,3-dihydrobenzofuran-5-yl)-6-((5-(trifluoromethyl)furan-2-yl)methyl)-6,8-dihydro-2H-[1,4]dioxino[2,3-f]indol-7(3H)-one (1.81 g, 3.70 mmol) in dichloromethane (50 mL) were added triethylsilane (6.0 mL) and trifluoroacetic acid (10 mL) at 0° C. The resultant mixture was stirred at 0° C. for 2 h and concentrated in vacuo to dryness to afford 8-(6-hydroxy-2,3-dihydro-1-benzofuran-5-yl)-6-{[5-(trifluoromethyl)furan-2-yl]methyl}-2,3,6,8-tetrahydro-7H-[1,4]dioxino[2,3-f]indol-7-one (1.70 g, 97%): MS (ES+) m/z 473.9 (M+1).

Preparation 27

Synthesis of 8-(6-hydroxy-2,3-dihydrobenzofuran-5-yl)-6-(((R)-tetrahydrofuran-2-yl)methyl)-6,8-dihydro-2H-[1,4]dioxino[2,3-f]indol-7(3H)-one A. Synthesis of 6-[(2R)-tetrahydrofuran-2-ylmethyl]-2,3-dihydro-6H-[1,4]dioxino[2,3-f]indole-7,8-dione To a stirred solution of 2H-[1,4]dioxino[2,3-f]indole-7,8 (3H,6H)-dione (2.05 g, 10.0 mmol) in dry N,N-dimethylformamide (100 mL) was added cesium carbonate (4.4 g, 12.0 mmol) at ambient temperature. The dark mixture was stirred for 1 h, followed by the addition of (R)-(tetrahydrofuran-2-yl)methyl 4-methylbenzenesulfonate (3.07 g, 12.0 mmol) in one portion and potassium iodide (0.66 g, 4.0 mmol). The dark mixture was stirred at 70° C. for 16 h. The mixture was poured into 5% hydrochloric acid solution (300 mL) and extracted with ethyl acetate. The organic layer was separated, dried over magnesium sulfate, filtered and evaporated. The residue was purified by flash column chromatography with ethyl acetate in hexanes (30 to 50% gradient) to afford 6-[(2R)-tetrahydrofuran-2-ylmethyl]-2,3-dihydro-6H-[1,4]dioxino[2,3-f]indole-7,8-dione (0.59 g, 20%): MS (ES+) m/z 290.2 (M+1).

B. Synthesis of 8-hydroxy-8-(6-hydroxy-2,3-dihydro-1-benzofuran-5-yl)-6-[(2R)-tetrahydrofuran-2-ylmethyl]-2,3,6,8-tetrahydro-7H-[1,4]dioxino[2,3-f]indol-7-one Following the procedure as described in PREPARATION 6A, and making non-critical variations using 2,3-dihydrobenzofuran-6-ol to replace 3,4-dimethylphenol, and 6-[(2R)-tetrahydrofuran-2-ylmethyl]-2,3-dihydro-6H-[1,4]dioxino[2,3-f]indole-7,8-dione to replace 1-(diphenylmethyl)-1H-indole-2,3-dione, 8-hydroxy-8-(6-hydroxy-2,3-dihydro-1-benzofuran-5-yl)-6-[(2R)-tetrahydrofuran-2-ylmethyl]-2,3,6,8-tetrahydro-7H-[1,4]dioxino[2,3-f]indol-7-one was obtained: $R_f$ 0.45 (ethyl acetate/hexanes, 1/1); MS (ES+) m/z 408.1 (M−17).

C. Synthesis of 8-(6-hydroxy-2,3-dihydro-1-benzofuran-5-yl)-6-[(2R)-tetrahydrofuran-2-ylmethyl]-2,3,6,8-tetrahydro-7H-[1,4]dioxino[2,3-f]indol-7-one Following the procedure as described in PREPARATION 12B, and making non-critical variations using 8-hydroxy-8-(6-hydroxy-2,3-dihydrobenzofuran-5-yl)-6-(((R)-tetrahydrofuran-2-yl)methyl)-6,8-dihydro-2H-[1,4]dioxino[2,3-f]indol-7(3H)-one to replace 1-(diphenylmethyl)-3-hydroxy-3-(2-hydroxy-4-methoxyphenyl)-1,3-dihydro-2H-indol-2-one, 8-(6-hydroxy-2,3-dihydro-1-benzofuran-5-yl)-6-[(2R)-tetrahydrofuran-2-ylmethyl]-2,3,6,8-tetrahydro-7H-[1,4]dioxino[2,3-f]indol-7-one was obtained (76%): $^1$H NMR (300 MHz, CDCl$_3$) δ 9.27-9.07 (m, 1H), 6.90-6.81 (m, 1H), 6.74 (s, 1H), 6.72-6.68 (m, 1H), 6.53 (s, 1H), 4.99-4.89 (m, 1H), 4.62-4.45 (m, 2H), 4.38-4.08 (m, 5H), 3.94-3.57 (m, 4H), 3.18-2.89 (m, 2H), 2.06-1.93 (m, 1H), 1.93-1.78 (m, 2H), 1.72-1.55 (m, 1H); MS (ES+) m/z 410.0 (M+1).

Preparation 28

Synthesis of 8-(7-hydroxy-2,3-dihydro-1,4-benzodioxin-6-yl)-6-{[5-(trifluoromethyl)furan-2-yl]methyl}-2,3,6,8-tetrahydro-7H-[1,4]dioxino[2,3-f]indol-7-one

A. Synthesis of 8-hydroxy-8-(7-hydroxy-2,3-dihydrobenzo[b][1,4]dioxin-6-yl)-6-((5-(trifluoromethyl)furan-2-yl)methyl)-6,8-dihydro-2H-[1,4]dioxino[2,3-f]indol-7(3H)-one Following the procedure as described in PREPARATION 6A, and making non-critical variations using 2,3-dihydrobenzo[b][1,4]dioxin-6-ol to replace 3,4-dimethylphenol, and 6-{[5-(trifluoromethyl)furan-2-yl]methyl}-2,3-dihydro-6H-[1,4]dioxino[2,3-f]indole-7,8-dione to replace 1-(diphenylmethyl)-1H-indole-2,3-dione, 8-hydroxy-8-(7-hydroxy-2,3-dihydrobenzo[b][1,4]dioxin-6-yl)-6-((5-(trifluoromethyl)furan-2-yl)methyl)-6,8-dihydro-2H-[1,4]dioxino[2,3-f]indol-7(3H)-one was obtained (80%): $^1$H NMR (300 MHz, CDCl$_3$) δ 8.78 (s, 1H), 7.07-6.97 (m, 1H), 6.71-6.65 (m, 1H), 6.60-6.55 (m, 1H), 6.51-6.47 (m, 1H), 6.40-6.35 (m, 1H), 6.31-6.25 (m, 1H), 4.89-4.69 (m, 2H), 4.34-4.04 (m, 9H); MS (ES+) m/z 487.9 (M−17).

B. Synthesis of 8-(7-hydroxy-2,3-dihydro-1,4-benzodioxin-6-yl)-6-{[5-(trifluoromethyl)furan-2-yl]methyl}-2,3,6,8-tetrahydro-7H-[1,4]dioxino[2,3-f]indol-7-one Following the procedure as described in PREPARATION 26C, and making non-critical variations using 8-hydroxy-8-(7-hydroxy-2,3-dihydrobenzo[b][1,4]dioxin-6-yl)-6-((5-(trifluoromethyl)furan-2-yl)methyl)-6,8-dihydro-2H-[1,4]dioxino[2,3-f]indol-7(3H)-one to replace 8-hydroxy-8-(6-hydroxy-2,3-dihydrobenzofuran-5-yl)-6-((5-(trifluoromethyl)furan-2-yl)methyl)-6,8-dihydro-2H-[1,4]dioxino[2,3-f]indol-7(3H)-one, 8-(7-hydroxy-2,3-dihydro-1,4-benzodioxin-6-yl)-6-{[5-(trifluoromethyl)furan-2-yl]methyl}-2,3,6,8-tetrahydro-7H-[1,4]dioxino[2,3-f]indol-7-one was obtained (89%): $^1$H NMR (300 MHz, CDCl$_3$) δ 8.46 (s, 1H), 6.86 (s, 1H), 6.69 (d, J=2.9 Hz, 1H), 6.61 (s, 1H), 6.54 (s, 1H), 6.45 (s, 1H), 6.29 (d, J=2.9 Hz, 1H), 4.95 (s, 1H), 4.89-4.74 (m, 2H), 4.31-4.06 (m, 8H).

Preparation 29

Synthesis of 3-(7-hydroxy-4-methyl-3,4-dihydro-2H-1,4-benzoxazin-6-yl)-1-{[5-(trifluoromethyl)furan-2-yl]methyl}-1,3-dihydro-2H-indol-2-one trifluoroacetate salt

A. Synthesis of 4-methyl-3,4-dihydro-2H-benzo[b][1,4]oxazin-7-ol

To a −78° C. solution of 7-bromo-4-methyl-3,4-dihydro-2H-1,4-benzoxazine (90%, 10.40 g, 41.0 mmol) in tetrahydrofuran (70 mL) under nitrogen was slowly added n-butyllithium solution (1.4 M in hexanes, 32 mL, 45 mmol) and the resulting suspension was stirred at −78° C. for 35 min. Trimethyl borate (6.0 mL, 54 mmol) was then added dropwise and the clear solution was stirred at −78° C. for 25 min and at ambient temperature for 16 h. The reaction was cooled to 0° C. and aqueous hydrogen peroxide (8.2 mL, 35%, 95 mmol) was slowly added. The resulting mixture was stirred at 0° C. for 10 min and at ambient temperature for 5 h. The insoluble material was removed by filtration and the filter cake was washed with ethyl acetate. The filtrate was concentrated under reduced pressure and the residue was taken up into ethyl acetate (100 mL) and was acidified with hydrochloric acid (100 mL, 1 M). The layers were separated and the organic solution was extracted with water (2×50 mL). The combined aqueous solution was neutralized to pH ~6-7 with 5 M sodium hydroxide and extracted with ethyl acetate (3×100 mL). This organic solution was washed with brine (200 mL) and dried over sodium sulfate and filtered. The filtrate was concentrated under reduced pressure. The residue was purified by flash column chromatography with hexanes/ethyl acetate (2:1) to afford 4-methyl-3,4-dihydro-2H-benzo[b][1,4]oxazin-7-ol (6.04 g, 89%) as a light brown solid: mp 84-87° C. (diethyl ether); $^1$H NMR (300 MHz, CDCl$_3$) δ 6.59 (d, J=9.0 Hz, 1H), 6.40-6.28 (m, 2H), 5.42 (br s, 1H), 4.30 (dd, J=4.2, 4.2 Hz, 2H), 3.19-3.09 (m, 2H), 2.80 (s, 3H); $^{13}$C NMR (75 MHz, CDCl$_3$) δ 149.1, 145.6, 130.5, 114.7, 108.0, 104.1, 65.3, 49.8, 40.1; MS (ES+) m/z 166.1 (M+1).

B. Synthesis of 3-hydroxy-3-(7-hydroxy-4-methyl-3,4-dihydro-2H-1,4-benzoxazin-6-yl)-1-{[5-(trifluoromethyl)furan-2-yl]methyl}-1,3-dihydro-2H-indol-2-one Following the procedure as described in PREPARATION 21B, and making non-critical variations using 4-methyl-3,4-dihydro-2H-benzo[b][1,4]oxazin-7-ol to replace 2,3-dihydrobenzofuran-6-ol, and 1-((5-(trifluoromethyl)furan-2-yl)methyl)indoline-2,3-dione to replace 7-chloro-1-(diphenylmethyl)-1H-indole-2,3-dione, 3-hydroxy-3-(7-hydroxy-4-methyl-3,4-dihydro-2H-1,4-benzoxazin-6-yl)-1-{[5-(trifluoromethyl)furan-2-yl]methyl}-1,3-dihydro-2H- indol-2-one was obtained (56%) as a colourless powder: mp 184-186° C. (diethyl ether/hexanes); $^1$H NMR (300 MHz, DMSO-$d_6$) δ 8.63 (s, 1H), 7.24-7.18 (m, 2H), 7.13 (s, 1H), 7.00-6.90 (m, 3H), 6.59 (d, J=3.3 Hz, 1H), 6.50 (s, 1H), 6.03 (s, 1H), 4.99 (s, 2H), 4.20 (t, J=4.1 Hz, 2H), 3.14-3.09 (m, 2H), 2.80 (s, 3H); $^{13}$C NMR (75 MHz, DMSO-$d_6$) δ 176.8, 153.8, 145.8, 144.1, 142.8, 139.3 (q, J=42 Hz), 132.7, 128.9, 128.5, 123.7, 122.2, 119.6, 119.1 (q, J=266 Hz), 114.1, 112.3, 109.1, 108.3, 103.1, 74.7, 64.9, 49.2, 39.4, 36.4; MS (ES+) m/z 461.2 (M+1).

C. Synthesis of 3-(7-hydroxy-4-methyl-3,4-dihydro-2H-1,4-benzoxazin-6-yl)-1-{[5-(trifluoromethyl)furan-2-yl]methyl}-1,3-dihydro-2H-indol-2-one trifluoroacetate salt To a cooled (0° C.) solution of triethylsilane (1.1 mL, 6.9 mmol) in trifluoroacetic acid (6.5 mL) was slowly added 3-hydroxy-3-(7-hydroxy-4-methyl-3,4-dihydro-2H-1,4-benzoxazin-6-yl)-1-{[5-(trifluoromethyl)furan-2-yl]methyl}-1,3-dihydro-2H-indol-2-one (1.00 g, 2.18 mmol) portionwise as a solid. The resulting brown solution was warmed to reflux and stirred under nitrogen for 2 h. The reaction was cooled and the solvent was removed under reduced pressure. The residue was precipitated from ethyl acetate/hexanes and collected by filtration to afford 3-(7-hydroxy-4-methyl-3,4-dihydro-2H-1,4-benzoxazin-6-yl)-1-{[5-(trifluoromethyl)furan-2-yl]methyl}-1,3-dihydro-2H-indol-2-one trifluoroacetate salt (1.09 g, 90%) as a light grey powder: mp 143-148° C. (hexanes); $^1$H NMR (300 MHz, DMSO-$d_6$) δ 8.98 (br s, 2H), 7.24-7.15 (m, 2H), 7.05-6.92 (m, 3H), 6.62 (s, 1H), 6.61 (s, 1H), 6.22 (s, 1H), 5.08 (d, J=16.7 Hz, 1H), 5.01 (d, J=16.7 Hz, 1H), 4.78 (s, 1H), 4.27-4.21 (m, 2H), 3.23-3.17 (m, 2H), 2.77 (s, 3H); MS (ES+) m/z 445.2 (M+1).

Preparation 30

Synthesis of 3-(7-hydroxy-4-methyl-3,4-dihydro-2H-1,4-benzoxazin-6-yl)-1-[(2R)-tetrahydrofuran-2-ylmethyl]-1,3-dihydro-2H-indol-2-one trifluoroacetate A. Synthesis of 1-[(2R)-tetrahydrofuran-2-ylmethyl]-1H-indole-2,3-dione Following the procedure as described in PREPARATION 4A, and making non-critical variations using isatin to replace 4-chloroisatin, and (R)-(tetrahydrofuran-2-yl)methyl 4-methylbenzenesulfonate to replace bromodiphenylmethane, 1-[(2R)-tetrahydrofuran-2-ylmethyl]-1H-indole-2,3-dione was obtained (47%) as a thick red oil: $^1$H NMR (300 MHz, CDCl$_3$) δ 7.60-7.54 (m, 2H), 7.14-7.07 (m, 2H), 4.25-4.17 (m, 1H), 3.92-3.82 (m, 2H), 3.78-3.69 (m, 2H), 2.13-2.02 (m, 1H), 1.98-1.85 (m, 2H), 1.74-1.65 (m, 1H); $^{13}$C NMR (75 MHz, CDCl$_3$) δ 183.5, 158.8, 151.8, 138.5, 125.3, 123.8, 117.7, 111.7, 68.4, 44.7, 29.3, 25.8; MS (ES+) m/z 232.1 (M+1).

B. Synthesis of 3-hydroxy-3-(7-hydroxy-4-methyl-3,4-dihydro-2H-1,4-benzoxazin-6-yl)-1-[(2R)-tetrahydrofuran-2-ylmethyl]-1,3-dihydro-2H-indol-2-one Following the procedure as described in PREPARATION 13A, and making non-critical variations using 4-methyl-3,4-dihydro-2H-benzo[b][1,4]oxazin-7-ol to replace chroman-7-ol, and 1-[(2R)-tetrahydrofuran-2-ylmethyl]-1H-indole-2,3-dione to replace 1-(diphenylmethyl)indoline-2,3-dione, 3-hydroxy-3-(7-hydroxy-4-methyl-3,4-dihydro-2H-1,4-benzoxazin-6-yl)-1-[(2R)-tetrahydrofuran-2-ylmethyl]-1,3-dihydro-2H-indol-2-one was obtained (91%) as a pale grey solid: $^1$H NMR (300 MHz, CDCl$_3$) (diastereomers) δ 8.94 (s, 0.4H), 8.80 (s, 0.6H), 7.52-7.48 (m, 1H), 7.41-7.34 (m, 1H), 7.20-7.08 (m, 2H), 6.52 (s, 1H), 6.16 (s, 1H), 4.51 (s, 0.4H), 4.44 (s, 0.6H), 4.29-4.17 (m, 3H), 3.90-3.64 (m, 4H), 3.17-2.99 (m, 2H), 2.58 (s, 3H), 2.04-1.78 (m, 3H), 1.74-1.60 (m, 1H); $^{13}$C NMR (diastereomers) (75 MHz, CDCl$_3$) δ 179.4, 179.2, 149.4, 149.3, 146.2, 143.2, 143.0, 130.2, 130.1, 129.8, 129.6, 125.9, 125.7, 123.6, 123.5, 117.6, 112.7, 112.4, 110.4, 110.3, 107.4, 79.3, 79.2, 76.9, 76.7, 68.3, 68.2, 65.3, 49.5, 44.7, 44.6, 39.5, 29.3, 29.1, 25.7, 25.6; MS (ES+) m/z 419.1 (M+23).

C. Synthesis of 3-(7-hydroxy-4-methyl-3,4-dihydro-2H-1,4-benzoxazin-6-yl)-1-[(2R)-tetrahydrofuran-2-ylmethyl]-1,3-dihydro-2H-indol-2-one trifluoroacetate Following the procedure as described in PREPARATION 12B, and making non-critical variations using 3-hydroxy-3-(7-hydroxy-4-methyl-3,4-dihydro-2H-1,4-benzoxazin-6-yl)-1-[(2R)-tetrahydrofuran-2-ylmethyl]-1,3-dihydro-2H-indol-2-one to replace 1-(diphenylmethyl)-3-hydroxy-3-(2-hydroxy-4-methoxyphenyl)-1,3-dihydro-2H-indol-2-one, 3-(7-hydroxy-4-methyl-3,4-dihydro-2H-1,4-benzoxazin-6-yl)-1-[(2R)-tetrahydrofuran-2-ylmethyl]-1,3-dihydro-2H-indol-2-one trifluoroacetate was obtained (93%) as a pink solid: $^1$H NMR (300 MHz, DMSO-$d_6$) (diastereomers) δ 9.07 (br s, 1H), 7.24-7.17 (m, 1H), 7.12-7.05 (m, 1H), 7.01-6.88 (m, 2H), 6.63, 6.57 (s, 1H), 6.24, 6.21 (s, 1H), 4.71, 4.68 (s, 1H), 4.32-4.11 (m, 3H), 3.85-3.58 (m, 4H), 3.25-3.14 (m, 2H), 2.79, 2.75 (s, 3H), 1.98-1.61 (m, 4H); MS (ES+) m/z 381.1 (M+1).

Preparation 31

Synthesis of 3-(6-hydroxy-4-methyl-3,4-dihydro-2H-1,4-benzoxazin-7-yl)-1-[(2R)-tetrahydrofuran-2-ylmethyl]-1,3-dihydro-2H-indol-2-one A. Synthesis of 3-hydroxy-3-(6-hydroxy-4-methyl-3,4-dihydro-2H-1,4-benzoxazin-7-yl)-1-[(2R)-tetrahydrofuran-2-ylmethyl]-1,3-dihydro-2H-indol-2-one Following the procedure as described in PREPARATION 14A, and making non-critical variations using 4-methyl-3,4-dihydro-2H-benzo[b][1,4]oxazin-6-ol (McMurtrey, K. D., et al., *J. Org. Chem.* (1970), 35(12):4252-3) to replace chroman-7-ol, and 1-[(2R)-tetrahydrofuran-2-ylmethyl]-1H-indole-2,3-dione to replace 1-(diphenylmethyl)indoline-2,3-dione, 3-hydroxy-3-(6-hydroxy-4-methyl-3,4-dihydro-2H-1,4-benzoxazin-7-yl)-1-[(2R)-tetrahydrofuran-2-ylmethyl]-1,3-dihydro-2H-indol-2-one was obtained (92%) as a pale brown solid: $^1$H NMR (300 MHz, CDCl$_3$) δ 9.21 (d, J=13.6 Hz, 1H), 7.46 (d, J=7.2 Hz, 1H), 7.36 (dd, J=7.8, 7.8 Hz, 1H), 7.17 (dd, J=7.5, 7.2 Hz, 1H), 7.09 (d, J=7.8 Hz, 1H), 6.40 (s, 1H), 6.18 (s, 1H), 4.25-4.06 (m, 3H), 3.87-3.63 (m, 4H), 3.27-3.17 (m, 2H), 2.87 (s, 3H), 2.02-1.74 (m, 3H), 1.71-1.57 (m, 2H); $^{13}$C NMR (75 MHz, CDCl$_3$) δ 179.8, 179.7, 151.54, 151.52, 143.1, 143.0, 138.0, 137.4, 130.12, 130.10, 129.32, 129.29, 126.1, 126.0, 123.8, 114.8, 114.6, 113.1, 113.0, 110.4, 110.3, 103.5, 79.11, 79.06, 76.9, 76.7, 68.32, 68.26, 64.6, 48.9, 44.6, 38.5, 29.3, 29.1, 25.7, 25.6; MS (ES+) m/z 418.9 (M+23).

B. Synthesis of 3-(6-hydroxy-4-methyl-3,4-dihydro-2H-1,4-benzoxazin-7-yl)-1-[(2R)-tetrahydrofuran-2-ylmethyl]-1,3-dihydro-2H-indol-2-one To a cooled (0° C.) solution of triethylsilane (1.3 mL, 8.2 mmol) in trifluoroacetic acid (8 mL) was added dropwise a solution of 3-hydroxy-3-(6-hydroxy-4-methyl-3,4-dihydro-2H-1,4-benzoxazin-7-yl)-1-[(2R)-tetrahydrofuran-2-ylmethyl]-1,3-dihydro-2H-indol-2-one (1.04 g, 2.62 mmol) in dichloromethane (3 mL). The resulting solution was warmed to reflux and stirred under nitrogen for 90 min. Once cooled, the solvent was removed under reduced pressure to afford 3-(6-hydroxy-4-methyl-3,4-dihydro-2H-1,4-benzoxazin-7-yl)-1-[(2R)-tetrahydrofuran-2-ylmethyl]-1,3-dihydro-2H-indol-2-one trifluoroacetate as a light brown foam: MS (ES+) m/z 381.0 (M+1).

Preparation 32

Synthesis of 3-(7-hydroxy-4H-1,3-benzodioxin-6-yl)-1-[(2R)-tetrahydrofuran-2-ylmethyl]-1,3-dihydro-2H-indol-2-one

A. Synthesis of 3-hydroxy-3-(7-hydroxy-4H-1,3-benzodioxin-6-yl)-1-[(2R)-tetrahydrofuran-2-ylmethyl]-1,3-dihydro-2H-indol-2-one Following the procedure as described in PREPARATION 6A, and making non-critical variations using 4H-benzo[d][1,3]dioxin-7-ol to replace 3,4-dimethylphenol, and (R)-1-((tetrahydrofuran-2-yl)methyl)indoline-2,3-dione to replace 1-(diphenylmethyl)-1H-indole-2,3-dione, 3-hydroxy-3-(7-hydroxy-4H-1,3-benzodioxin-6-yl)-1-[(2R)-tetrahydrofuran-2-ylmethyl]-1,3-dihydro-2H-indol-2-one was obtained (62%) as a colorless solid: MS (ES+) m/z 366.2 (M−17).

B. Synthesis of 3-(7-hydroxy-4H-1,3-benzodioxin-6-yl)-1-[(2R)-tetrahydrofuran-2-ylmethyl]-1,3-dihydro-2H-indol-2-one Following the procedure as described in PREPARATION 9B, and making non-critical variations using 3-hydroxy-3-(7-hydroxy-4H-1,3-benzodioxin-6-yl)-1-[(2R)-tetrahydrofuran-2-ylmethyl]-1,3-dihydro-2H-indol-2-one to replace 3-hydroxy-3-(6-hydroxy-3-methyl-1,2-benzisoxazol-5-yl)-1-(4-methoxybenzyl)-1,3-dihydro-2H-indol-2-one, 3-(7-hydroxy-4H-1,3-benzodioxin-6-yl)-1-[(2R)-tetrahydrofuran-2-ylmethyl]-1,3-dihydro-2H-indol-2-one was obtained (84%) as a colorless solid: MS (ES+) m/z 368.2 (M+1).

Preparation 33

Synthesis of (S)-2-(benzyloxymethoxy)propyl 4-methylbenzenesulfonate

To a stirred solution of (2S)-2-[(benzyloxy)methoxy]propan-1-ol (Banfi, L., et al., *J. Org. Chem.* (1984), 49:3784-90) (11.40 g, 0.058 mol) in dichloromethane (50 mL) and pyridine (20 mL) was added p-toluenesulfonyl chloride (11.0 g, 0.057 mol) at 0° C. The reaction mixture was stirred at ambient temperature for 20 h, diluted with ethyl acetate and washed with water, 5% hydrochloric acid solution, water and brine; dried over anhydrous sodium sulfate and filtered. The filtrate was concentrated in vacuo. The residue was purified by column chromatography to afford (S)-2-(benzyloxymethoxy)propyl 4-methylbenzenesulfonate (17.10 g, 84%): $^1$H NMR (300 MHz, CDCl$_3$) $\delta$ 7.77 (d, J=8.3 Hz, 2H), 7.36-7.25 (m, 7H), 4.71 (s, 2H), 4.59-4.48 (m, 2H), 4.02-3.93 (m, 3H), 2.41 (s, 3H), 1.19-1.11 (m, 3H).

Preparation 34

Synthesis of 2-(bromomethyl)-7-fluorobenzofuran

A. Synthesis of ethyl 7-fluorobenzofuran-2-carboxylate

A mixture of 3-fluoro-2-hydroxybenzaldehyde (5.00 g, 35.7 mmol), potassium carbonate (9.85 g, 71.4 mmol), and ethyl bromoacetate (4.30 ml, 39.3 mmol) in N,N-dimethylformamide (70 mL) was heated at 100° C. for 16 h. The mixture was diluted with water (500 mL) and extracted with ethyl acetate (3×150 mL). The combined organic solution was washed with brine (150 mL), dried over anhydrous magnesium sulfate, filtered, concentrated in vacuo. The residue was purified by column chromatography (hexanes/ethyl acetate, 49/1→9/1) to afford ethyl 7-fluorobenzofuran-2-carboxylate (3.86 g, 52%) as a yellowish oil: $^1$H NMR (300 MHz, CDCl$_3$) $\delta$7.56-7.54 (m, 1H), 7.47-7.42 (m, 1H), 7.28-7.14 (m, 2H), 4.46 (q, J=7.1 Hz, 2H), 1.43 (t, J=7.1 Hz, 3H).

B. Synthesis of (7-fluorobenzofuran-2-yl)methanol

To a stirred solution of ethyl 7-fluorobenzofuran-2-carboxylate (3.70 g, 17.8 mmol) in tetrahydrofuran (70 mL) was added lithium aluminum hydride (6.7 mL, 2.0 M solution in tetrahydrofuran, 13.3 mmol) at 0° C. The mixture was stirred at 0° C. for 0.5 h and solid sodium sulfate decahydrate (15.0 g) was added slowly in portions. The mixture was stirred at 0° C. for 10 min and at ambient temperature for 30 min. The solid was filtered off and washed with ethyl acetate (3×150 mL). The combined filtrate was washed with brine (150 mL), dried over anhydrous magnesium sulfate, filtered, concentrated in vacuo. The residue was purified by column chromatography (hexanes/ethyl acetate, 7/1→4/1) to afford (7-fluorobenzofuran-2-yl)methanol (2.4 g, 81%) as a colorless solid: $^1$H NMR (300 MHz, CDCl$_3$) $\delta$7.34-7.29 (m, 1H), 7.19-7.10 (m, 1H), 7.06-6.98 (m, 1H), 6.73-6.69 (m, 1H), 4.82-4.78 (m, 2H), 2.07-2.01 (m, 1H); MS (ES+) m/z 167.1 (M+1).

C. Synthesis of 2-(bromomethyl)-7-fluorobenzofuran

A mixture of (7-fluorobenzofuran-2-yl)methanol (1.38 g, 8.31 mmol), tetrabromomethane (4.41 g, 13.3 mmol) and triphenylphosphine (2.61 g, 9.97 mmol) in dichloromethane (42 mL) was stirred at 0° C. for 2 h and concentrated in vacuo to dryness. The residue was purified by column chromatography (hexanes/ethyl acetate, 49/1) to afford 2-(bromomethyl)-7-fluorobenzofuran (1.85 g, 97%) as a colorless solid: $^1$H NMR (300 MHz, CDCl$_3$) 7.34-7.29 (m, 1H), 7.20-7.12 (m, 1H), 7.10-7.02 (m, 1H), 6.82-6.77 (m, 1H), 4.60 (s, 2H).

Preparation 35

Synthesis of (R)-(1,4-dioxan-2-yl)methyl 4-methyl benzenesulfonate

To a cooled (0° C.) solution of (S)-(1,4-dioxan-2-yl)methanol (Kim, H. Y., et al., *Bioorg. Med. Chem. Lett.* (2005), 15:3207-11) (2.02 g, 17.1 mmol) and pyridine (14 mL, 173 mmol) in dichloromethane (11 mL) was added p-toluenesulfonyl chloride (3.85 g, 20.2 mmol). The reaction was stirred at 0° C. for 20 min and at ambient temperature for an additional 15.5 h. The solution was diluted with dichloromethane (100 mL) and was washed sequentially with hydrochloric acid (100 mL, 2 M), water (50 mL) and brine (50 mL). The organic solution was dried over sodium sulfate, filtered and concentrated under reduced pressure. The residue was purified by flash column chromatography with hexanes/ethyl acetate (2:1 to 3:2) to afford (R)-(1,4-dioxan-2-yl)methyl 4-methylbenzenesulfonate (3.40 g, 73%) as a colorless solid: mp 53-54° C. (dichloromethane); $^1$H NMR (300 MHz, CDCl$_3$) δ7.79 (d, J=8.4 Hz, 2H), 7.35 (d, J=8.4 Hz, 2H), 4.02 (dd, J=10.8, 5.4 Hz, 1H), 3.95 (dd, J=10.5, 4.5 Hz, 1H), 3.82-3.50 (m, 6H), 3.35 (dd, J=11.6, 9.8 Hz, 1H), 2.45 (s, 3H); MS (ES+) m/z 295.0 (M+23).

Preparation 36

Synthesis of (S)-(1,4-dioxan-2-yl)methyl 4-methylbenzenesulfonate

Following the procedure as described in PREPARATION 35, and making non-critical variations using (R)-(1,4-dioxan-2-yl)methanol (Kim, H. Y., et al., *Bioorg. Med. Chem. Lett.* (2005), 15:3207-11) to replace (S)-(1,4-dioxan-2-yl)methanol, (S)-(1,4-dioxan-2-yl)methyl 4-methylbenzenesulfonate was obtained (79%) as a colorless solid: mp 53-55° C. (dichloromethane); $^1$H NMR (300 MHz, CDCl$_3$) δ7.78 (d, J=8.1 Hz, 2H), 7.34 (d, J=8.1 Hz, 2H), 4.01 (dd, J=10.5, 5.4 Hz, 1H), 3.94 (dd, J=10.4, 4.7 Hz, 1H), 3.82-3.50 (m, 6H), 3.34 (dd, J=11.2, 10.1 Hz, 1H), 2.44 (s, 3H); $^{13}$C NMR (75 MHz, CDCl$_3$) δ145.2, 132.7, 130.0, 128.1, 72.4, 68.8, 67.8, 66.5, 66.4, 21.8; MS (ES+) m/z 294.9 (M+23).

Preparation 37

Synthesis of 7-bromo-3-(6-hydroxy-1,3-benzodioxol-5-yl)-3-(hydroxymethyl)-1,3-dihydro-2H-indol-2-one A. Synthesis of 7-bromo-3-hydroxy-3-(6-hydroxy-1,3-benzodioxol-5-yl)-1,3-dihydro-2H-indol-2-one To a solution of sesamol (7.32 g, 53.1 mmol) in anhydrous tetrahydrofuran (150 mL) were added a solution of isopropylmagnesium chloride (2.0 M in tetrahydrofuran, 30.1 mL, 60.2 mmol) at 0° C. under nitrogen. The reaction mixture was stirred at 0° C. for 30 min, followed by the addition of 7-bromo isatin (8.0 g, 35.4 mmol). The suspended mixture was stirred at ambient temperature for 16 h. The reaction mixture was diluted with a saturated aqueous solution of ammonium chloride (300 mL) and ethyl acetate (250 mL), and the phases were separated. The aqueous phase was extracted with ethyl acetate (200 mL), and the combined organic solution was washed with brine (100 mL), dried over anhydrous sodium sulfate, filtered and concentrated in vacuo. The crude solid was triturated with diethyl ether, filtered and dried under the reduced pressure to afford 7-bromo-3-hydroxy-3-(6-hydroxy-1,3-benzodioxol-5-yl)-1,3-dihydro-2H-indol-2-one (9.8 g, 77%) as a light yellow solid: $^1$H NMR (300 MHz, DMSO-d$_6$) δ10.64 (s, 1H), 9.18 (s, 1H), 7.33 (dd, J=7.8, 1.4 Hz, 1H), 7.21 (s, 1H), 6.84-6.75 (m, 2H), 6.54 (s, 1H), 6.21 (s, 1H), 5.92 (dd, J=6.1, 0.8 Hz, 2H); MS (ES+) m/z 363.8 (M+1), 365.8 (M+1).

B. Synthesis of 7-bromo-3-(6-hydroxy-1,3-benzodioxol-5-yl)-1,3-dihydro-2H-indol-2-one To a solution of 7-bromo-3-hydroxy-3-(6-hydroxy-1,3-benzodioxol-5-yl)-1,3-dihydro-2H-indol-2-one (9.50 g, 27.3 mmol) in trifluoroacetic acid (24 mL) at 0° C. was added triethyl silane (6.12 g, 52.8 mmol). The mixture was stirred at ambient temperature for 3 h. The reaction was quenched by the addition of hexanes and diethyl ether mixture (2:1, 300 mL). The precipitate was filtered, washed with hexanes and ether mixture (100 mL). The solid was dried under reduced pressure to afford 7-bromo-3-(6-hydroxy-1,3-benzodioxol-5-yl)-1,3-dihydro-2H-indol-2-one (8.40 g, 93%) as an off-white powder: $^1$H NMR (300 MHz, DMSO-d$_6$) δ 10.67 (s, 1H), 9.26 (s, 1H), 7.33-7.31 (m, 1H), 6.90-6.78 (m, 2H), 6.68 (s, 1H), 6.38 (s, 1H), 5.91 (d, J=1.0 Hz, 2H), 4.75 (s, 1H); MS (ES+) m/z 347.9 (M+1), 349.9 (M+1).

C. Synthesis of 7-bromo-3-(6-hydroxy-1,3-benzodioxol-5-yl)-3-(hydroxymethyl)-1,3-dihydro-2H-indol-2-one To a mixture of 7-bromo-3-(6-hydroxy-1,3-benzodioxol-5-yl)-1,3-dihydro-2H-indol-2-one (8.40 g, 24.1 mmol), paraformaldehyde (2.88 g, 96.0 mmol) and water (80 mL) was added sodium hydroxide (3.84 g, 96.0 mmol) at 0° C. The dark green solution was stirred at 0° C. for 4 h. The mixture was acidified with 3 N hydrochloride to pH 4 and extracted with ethyl acetate (3×100 mL). The combined ethyl acetate solution was washed with 25% ammonium chloride solution (50 mL) and brine (50 mL), dried over anhydrous sodium sulfate and concentrated in vacuo to dryness. The residue was treated with toluene (300 mL) to give an off white precipitate. The precipitate was filtered and dried under reduced pressure to give 7-bromo-3-(6-hydroxy-1,3-benzodioxol-5-yl)-3-(hydroxymethyl)-1,3-dihydro-2H-indol-2-one (4.80 g, 53%): $^1$H NMR (300 MHz, DMSO-d$_6$) δ10.48 (s, 1H), 9.16 (s, 1H), 7.27 (dd, J=8.0, 1.0 Hz, 1H), 7.01 (s, 1H), 6.87-6.74 (m, 2H), 6.22 (s, 1H), 5.91 (s, 2H), 5.03 (br, 1H), 4.12 (d, J=10.0 Hz, 1H), 3.85 (d, J=10.0 Hz, 1H); MS (ES−) m/z 376 (M−1), 378 (M−1).

Preparation 38

Synthesis of 3-[5-(benzyloxy)-2-hydroxyphenyl]-1-[(5-chlorothiphen-2-yl)methyl]-3-(hydroxymethyl)-1,3-dihydro-2H-indol-2-one A. Synthesis of 3-[5-(benzyloxy)-2-hydroxyphenyl]-1-[(5-chlorothiophen-2-yl)methyl]-3-hydroxy-1,3-dihydro-2H-indol-2-one To a pale yellow solution of 4-(benzyloxy)phenol (9.01 g, 45.0 mmol) in anhydrous tetrahydrofuran (100.0 mL) was added isopropylmagnesium chloride (26.3 mL, 52.5 mmol, 2.0 M solution in tetrahydrofuran) at 0° C. The reaction solution was stirred for 0.5 h followed by the addition of 1-((5-chlorothiophen-2-yl)methyl)indoline-2,3-dione (8.31 g, 30.0 mmol) in portions. The reaction mixture was stirred for 16 h at ambient temperature. The reaction was quenched by the addition of saturated ammonium chloride solution (50.0 mL) and concentrated in vacuo to dryness. The residue was diluted with ethyl acetate (100 mL), washed with saturated ammonium chloride solution (2×25.0 mL), brine (2×25 mL), dried over anhydrous sodium sulfate and filtered. The filtrate was concentrated in vacuo to dryness. The residue was purified by column chromatography with ethyl acetate to afford 3-[5-(benzyloxy)-2-hydroxyphenyl]-1-[(5-chlorothiophen-2-yl)methyl]-3-hydroxy-1,3-dihydro-2H-indol-2-one (4.90 g, 28%) as a colourless solid: mp 174-175° C.; $^1$H NMR (300 MHz, CDCl$_3$) δ8.45 (br, 1H), 7.40-7.27 (m, 7H), 7.14 (dd, J=7.5, 7.5 Hz, 1H), 6.92 (d, J=2.9 Hz, 1H), 6.89 (s, 1H), 6.83 (d, J=2.9 Hz, 1H), 6.79 (d, J=3.7 Hz, 1H), 6.70 (d, J=3.7 Hz, 1H), 6.43 (d, J=2.9 Hz, 1H), 4.86 (ABq, 2H), 4.84 (s, 2H); $^{13}$C NMR (75 MHz, CDCl$_3$) δ 178.3, 152.6, 149.790, 141.7, 136.8, 135.8, 130.4, 130.1, 129.1, 128.6, 127.9, 127.6, 126.3, 126.2, 126.0, 125.9, 124.3, 120.2, 116.3, 114.4, 109.6, 79.1, 70.6, 39.2; MS (ES+) m/z 478.2 (M−1), 476.2 (M−1).

B. Synthesis of 3-[5-(benzyloxy)-2-hydroxyphenyl]-1-[(5-chlorothiophen-2-yl)methyl]-1,3-dihydro-2H-indol-2-one To a solution of 3-[5-(benzyloxy)-2-hydroxyphenyl]-1-[(5-chloro-2-thienyl)methyl]-3-hydroxy-1,3-dihydro-2H-indol-2-one (4.90 g, 10.3 mmol) in dichloromethane (100.0 mL) were added trifluoroacetic acid (12.9 g, 113.2 mmol) and triethylsilane (13.2 g, 113.2 mmol). The reaction mixture was stirred at ambient temperature for 4 h, then concentrated in vacuo to dryness. The gummy residue was diluted with ethyl acetate (100.0 mL), washed with water (3×100.0 mL), dried over anhydrous sodium sulfate and filtered. The filtrate was concentrated in vacuo to dryness. The residue was triturated with diethyl ether, filtered and dried to afford 3-[5-(benzyloxy)-2-hydroxyphenyl]-1-[(5-chlorothiophen-2-yl)methyl]-1,3-dihydro-2H-indol-2-one (2.90 g, 61%) as a colourless solid: mp 173-175° C.; $^1$H NMR (300 MHz, CDCl$_3$) δ9.11 (s, 1H), 7.3-7.27 (m, 5H), 7.18 (dd, J=7.5, 7.5 Hz, 1H), 7.09 (d, J=3.8 Hz, 1H), 7.06 (dd, J=7.9 Hz, 1H), 6.97-6.86 (m, 3H), 6.79-6.68 (m, 3H), 5.04 (ABq, 2H), 4.91 (s, 2H), 4.84 (s, 1H); $^{13}$C NMR (75 MHz, CDCl$_3$) δ175.9, 151.5, 149.7, 142.8, 138.8, 137.8, 130.2, 128.8, 128.2, 128.1, 128.1, 128.0, 127.4, 126.8, 125.2, 124.2, 122.7, 117.6, 117.6, 116.3, 114.9, 109.1, 70.2, 48.1, 38.6; MS (ES+) m/z 464.3 (M+1), 462.3 (M+1).

C. Synthesis of 3-[5-(benzyloxy)-2-hydroxyphenyl]-1-[(5-chlorothiphen-2-yl)methyl]3-(hydroxymethyl)-1,3-dihydro-2H-indol-2-one To a mixture of 3-[5-(benzyloxy)-2-hydroxyphenyl]-1-[(5-chlorothiophen-2-yl)methyl]-1,3-dihydro-2H-indol-2-one (2.80 g, 6.07 mmol), para-formaldehyde (0.73 g, 24.3 mmol) in tetrahydrofuran (10.0 mL) was added an aqueous solution of sodium hydroxide (0.97 g, 24.3 mmol) in water (10.0 mL) at 0° C. The reaction solution was stirred for 2 h, then quenched by the addition of 10% aqueous hydrochloric acid solution (30.0 mL). The reaction mixture was extracted with ethyl acetate (3×50 mL). The combined organic solution was washed with saturated ammonium chloride (3×50 mL), brine (50.0 mL), dried over anhydrous sodium sulfate and filtered. The filtrate was concentrated in vacuo to dryness. The residue was triturated with diethyl ether, filtered and dried to afford 3-[5-(benzyloxy)-2-hydroxyphenyl]-1-[(5-chlorothiphen-2-yl)methyl]-3-(hydroxymethyl)-1,3-dihydro-2H-indol-2-one (2.71 g, 91%) as a colourless solid: MS (ES+) m/z 494.2 (M+1), 492.3 (M+1).

Preparation 39

Synthesis of 3-[4-(benzyloxy)-2-hydroxyphenyl]-1-(diphenylmethyl)-1,3-dihydro-2H-indol-2-one

A. Synthesis of 3-[4-(benzyloxy)-2-hydroxyphenyl]-1-(diphenylmethyl)-3-hydroxy-1,3-dihydro-2H-indol-2-one To a stirred solution of 3-(benzyloxy)phenol (8.7 g, 43.5 mmol) in tetrahydrofuran (100 mL) was added isopropylmagnesium chloride (22.7 mL, 2 M tetrahydrofuran solution, 45.4 mmol) slowly at 0° C. The mixture was allowed to stir for 30 min at 0° C., and concentrated in vacuo to dryness. Dichloromethane (100 mL) was added, followed by the addition of a solution of 1-(diphenylmethyl)-1H-indole-2,3-dione (12.4 g, 39.5 mmol) in dichloromethane (50 mL) at 0° C. The mixture was stirred at room temperature for 16 h, and quenched with saturated ammonium chloride solution. The organic layer was washed with water, dried over sodium sulfate and filtered. The filtrate was concentrated in vacuo to dryness. The obtained solid was recrystallized from ethyl acetate/hexanes to afford 3-[4-(benzyloxy)-2-hydroxyphenyl]-1-(diphenylmethyl)-3-hydroxy-1,3-dihydro-2H-indol-2-one (19.60 g, 97%) as a colorless solid: $^1$H NMR (300 MHz, CDCl$_3$) δ7.49-7.43 (m, 1H), 7.42-7.25 (m, 13H), 7.23-7.17 (m, 2H), 7.12-7.04 (m, 2H), 6.91 (s, 1H), 6.72-6.62 (m, 2H), 6.51-6.44 (m, 1H), 6.39 (dd, J=8.6, 2.4 Hz, 1H), 4.99 (s, 2H); MS (ES+) m/z 536.3 (M+23).

B. Synthesis of 3-[4-(benzyloxy)-2-hydroxyphenyl]-1-(diphenylmethyl)-1,3-dihydro-2H-indol-2-one A mixture of 3-[4-(benzyloxy)-2-hydroxyphenyl]-1-(diphenylmethyl)-3-hydroxy-1,3-dihydro-2H-indol-2-one (10.0 g, 19.5 mmol), triethylsilane (15.6 mL, 97.5 mmol) and trifluoroacetic acid (15.0 mL, 195 mmol) was mixed and stirred for 20 min at 0° C.

The mixture was concentrated under vacuum. The residue was triturated with diethyl ether to afford 3-[4-(benzyloxy)-2-hydroxyphenyl]-1-(diphenylmethyl)-1,3-dihydro-2H-indol-2-one (7.40 g, 76%) as a colorless solid: $^1$H NMR (300 MHz, CDCl$_3$) δ 7.44-7.25 (m, 14H), 7.23-7.17 (m 2H), 7.11-7.02 (m, 2H), 6.95 (s, 1H), 6.81 (d, J=8.6 Hz, 1H), 6.68 (d, J=2.5 Hz, 1H), 6.55-6.49 (m, 1H), 6.46 (dd, J=8.6, 2.6 Hz, 1H), 5.09 (s, 1H), 4.99 (s, 2H); MS (ES+) m/z 498.3 (M+1).

Preparation 40

Synthesis of N'-hydroxy-4-[(2'-oxo-5,6-dihydrospiro[benzo[1,2-b:5,4-b']difuran-3,3'-indol]-1'(2'H)-yl)methyl]benzenecarboximidamide To a stirred solution of 4-[(2'-oxo-5,6-dihydrospiro[benzo[1,2-b:5,4-b']difuran-3,3'-indol]-1'(2'H)-yl)methyl]benzonitrile (1.30 g, 32.9 mmol) in dimethyl sulfoxide (10 mL) was added 50% wt solution of hydroxylamine in water (2 mL). The reaction was heated with stirring at 80° C. for 1 h, then cooled to ambient temperature and the product was precipitated by adding distilled water (25 mL). The solid was filtered and air dried to afford N'-hydroxy-4-[(2'-oxo-5,6-dihydrospiro[benzo[1,2-b:5,4-b']difuran-3,3'-indol]-1'(2'H)-yl)methyl]benzenecarboximidamide (1.32 g, 93%) as a colorless solid: $^1$H NMR (300 MHz, CDCl$_3$) δ 9.17 (s, 1H), 7.40-7.03 (m, 13H), 6.99-6.92 (m, 2H), 6.79-6.74 (m, 2H), 6.58-6.50 (m, 1H), 5.10 (s, 1H); MS (ES+) m/z 428.0 (M+1).

Preparation 41

Synthesis of 2-(4'-chloro-2'-oxospiro[furo[2,3-f][1,3]benzodioxole-7,3'-indol]-1'(2'H)-yl)-W-[(cyclopropylcarbonyl)oxy]ethanimidamide A stirred solution of 2-(4'-chloro-2'-oxospiro[furo[2,3-f][1,3]benzodioxole-7,3'-indol]-1'(2'H)-yl)-N'-hydroxyacetimidamide (0.40 g, 1.0 mmol), diisopropylamine (0.16 g, 1.6 mmol) and cyclopropane carbonyl chloride (0.16 g, 1.6 mmol) in dichloromethane (20 mL) was stirred for 16 h at ambient temperature. The colorless solid that precipitated from the solution was filtered, washed with water (5 mL) and diethyl ether (5 mL) to afford 2-(4'-chloro-2'-oxospiro[furo[2,3-f][1,3]benzodioxole-7,3'-indol]-1'(2'H)-yl)-N'-[(cyclopropylcarbonyl)oxy]ethanimidamide as a colorless solid (0.25 g, 53%): $^1$H NMR (300 MHz, DMSO-$d_6$) δ7.31 (dd, J=8.0, 8.0 Hz, 1H), 7.02 (d, J=8.0 Hz, 2H), 6.64 (br s, 2H), 6.54 (s, 1H), 6.47 (s, 1H), 5.88 (s, 2H), 4.77 (ABq, 2H), 4.43 (ABq, 2H), 1.75-1.67 (m, 1H), 0.86-0.73 (m, 4H); $^{13}$C NMR (75 MHz, DMSO-$d_6$) 176.9, 171.9, 156.5, 153.6, 148.9, 144.8, 141.9, 130.8, 130.0, 128.6, 117.4, 108.8, 104.4, 101.8, 104.5, 101.8, 104.4, 101.8, 93.0, 77.5, 58.4, 11.7, 8.45, 8.42; MS (ES+) m/z 456.1 (M+1), 478.1 (M+23).

Preparation 42

Synthesis of N'-hydroxy-2-(2'-oxospiro[furo[2,3-f][1,3]benzodioxole-7,3'-indol]-1'(2'H)-yl)ethanimidamide To a mixture of 2'-oxospiro[furo[2,3-f][1,3]benzodioxole-7,3'-indol]-1'(2'H)-yl)acetonitrile (2.00 g, 6.25 mmol) in ethanol (40 mL) and dimethyl sulfoxide (5 mL) was added hydroxylamine (25.0 g, 1.6 mL, 50% wt solution in water). The reaction solution was stirred at ambient temperature for 2 h to form a colourless precipitate. The solid was filtered. The residue was washed with water (3×20 mL) and dried to afford N'-hydroxy-2-(2'-oxospiro[furo[2,3-f][1,3]benzodioxole-7,3'-indol]-1'(2'H)-yl)ethanimidamide (1.88 g, 85%) as a colourless solid: mp 235-238° C.; $^1$H NMR (300 MHz, DMSO-$d_6$) δ 9.20 (s, 1H), 7.26 (dd, J=7.7, 7.7 Hz, 1H), 7.10 (d, J=7.3 Hz, 1H), 6.99 (dd, J=8.6, 8.6 Hz, 2H), 6.65 (s, 1H), 6.28 (s, 1H), 5.89 (d, J=1.8 Hz, 2H), 5.49 (s, 2H), 4.70 (ABq, 2H), 4.29 (s, 2H); $^{13}$C NMR (75 MHz, DMSO-$d_6$) δ 177.1, 155.7, 148.7, 147.9, 143.0, 142.1, 132.3, 129.1, 123.7, 123.3, 120.5, 110.0, 103.9, 101.8, 93.6, 80.2, 57.8, 40.3; MS (ES+) m/z 354.18 (M+1), 337.2 (M−17).

Preparation 43

Synthesis of 3-[(2'-oxo-5,6-dihydrospiro[benzo[1,2-b:5,4-b']difuran-3,3'-indol]-1'(2'H)-yl)methyl]benzonitrile To a solution of 5,6-dihydrospiro[benzo[1,2-b:5,4-b']difuran-3,3'-indol]-2'(1'H)-one (0.97 g, 3.46 mmol) in 2-butanone (25 mL) were added cesium carbonate (3.39 g, 10.39 mmol) and α-bromo-m-tolunitrile (0.85 g, 4.33 mmol). The mixture was heated to reflux for 2 h, cooled to ambient temperature, and filtered. The solid was washed with ethyl acetate. The filtrate was concentrated in vacuo, the residue was purified by column chromatography with ethyl acetate-hexanes (1:5-1:1), followed by recrystallization from ethyl acetate and diethyl ether to afford 3-[(2'-oxo-5,6-dihydrospiro[benzo[1,2-b:5,4-b']difuran-3,3'-indol]-1'(2'H)-yl)methyl]benzonitrile (1.26 g, 92%) as a colorless solid: mp 187-193° C.; $^1$H NMR (300 MHz, CDCl$_3$) δ7.61-7.58 (m, 3H), 7.47-7.44 (m, 1H), 7.25-7.19 (m, 2H), 7.07-7.03 (m, 1H), 6.73-6.71 (m, 1H), 6.43-6.41 (m, 2H), 5.11-4.70 (m, 4H), 4.53 (d, J=9.0 Hz, 2H), 3.09-2.91 (m, 2H); $^{13}$C NMR (75 MHz, CDCl$_3$) δ 178.1, 162.0, 161.4, 141.5, 137.5, 132.6, 131.9, 131.6, 130.7, 129.9, 128.9, 124.3, 123.9, 120.2, 119.9, 118.7, 118.4, 113.1, 108.8, 93.4, 80.5, 72.5, 57.7, 43.4, 29.0; MS (ES+) m/z 394.8 (M+1).

Preparation 44

Synthesis of N'-hydroxy-3-[(2'-oxo-5,6-dihydrospiro[benzo[1,2-b:5,4-b']difuran-3,3'-indol]-1'(2'H)-yl)methyl]benzenecarboximidamide To a solution of 3-[(2'-oxo-5,6-dihydrospiro[benzo[1,2-b:5,4-b']difuran-3,3'-indol]-1'(2'H)-yl)methyl]benzonitrile (1.15 g, 2.92 mmol) in dimethyl sulfoxide (20 mL) was added hydroxylamine (50% wt in H$_2$O, 2 mL, 32.67 mmol). The reaction was stirred at 80° C. for 3 h, cooled to ambient temperature. The precipitate was collected by filtration and washed with water and diethyl ether and dried in vacuo to afford N'-hydroxy-3-[(2'-oxo-5,6-dihydrospiro[benzo[1,2-b:5,4-b']difuran-3,3'-indol]-1'(2'H) yl)methyl]benzenecarboximidamide (0.85 g, 68%): $^1$H NMR (300 MHz, CDCl$_3$) δ7.61 (m, 1H), 7.96 (m, 1H), 7.51 (m, 1H), 7.38 (m, 2H), 7.16 (m, 2H), 7.01 (m, 1H), 6.75 (m, 1H), 6.48 (s, 1H), 6.40 (s, 1H), 5.09 (d, 1H, J=15.7 Hz), 4.98 (d, 1H, J=9.0 Hz), 4.83 (m, 3H), 4.70 (d, 1H, J=9.0 Hz), 4.49 (t, 2H, J=8.6 Hz), 2.96 (m, 2H); MS (ES+) m/z 427.8 (M+1).

Preparation 45

Synthesis of 6-{[tris(1-methylethyl)silyl]oxy}spiro[1-benzofuran-3,3'-indol]-2'(1'H)-one To a solution of 6-hydroxyspiro[1-benzofuran-3,3'-indol]-2'(1'H)-one (3.0 g, 11.8 mmol) in anhydrous N,N-dimethylformamide (30 mL) under nitrogen were added imidazole (1.97 g, 28.9 mmol) and triisopropylsilyl chloride (6.03 mL, 28.5 mmol). The reaction mixture was stirred at ambient temperature for 16 h. The reaction mixture was concentrated in vacuo to dryness. The residue was extracted twice with ethyl acetate (50 mL), the combined organic phases were dried over sodium sulfate, and the filtrate was concentrated and purified by flash chromatography with 30% ethyl acetate in hexanes to give 6-{[tris(1-methylethyl)silyl]oxy}spiro[1-benzofuran-3,3'-indol]-2'(1'H)-one (2.68 g, 69% yield) as colorless solid: $^1$H NMR (300 MHz, CDCl$_3$) δ 8.48-8.08 (br, 1H), 7.29-6.90 (m, 4H), 6.10 (d, J=8.1 Hz, 1H), 6.50 (d, J=2.1 Hz, 1H), 6.35 (dd, J=8.1, 2.1 Hz, 1H), 4.96 (d, J=9.0 Hz, 1H), 4.69 (d, J=9.0 Hz, 1H), 1.34-0.98 (m, 21H).

Preparation 46

Synthesis of 1'-[(2R)-tetrahydrofuran-2-ylmethyl]-6-{[tris(1-methylethyl)silyl]oxy}spiro[1-benzofuran-3,3'-indol]-2'(1'H)-one To a solution of 6-{[tris(1-methylethyl)silyl]oxy}spiro[1-benzofuran-3,3'-indol]-2'(1'H)-one (2.46 g, 6.0 mmol) in anhydrous N,N-dimethylformamide (10 mL) at 0° C. under nitrogen was added sodium hydride (0.24 g, 6.0 mmol). The above mixture was stirred at 0° C. for 20 min, then (R)-(tetrahydrofuran-2-yl)methyl 4-methylbenzenesulfonate (1.69 g, 6.6 mmol) was added. The reaction mixture was stirred at ambient temperature for 30 min, then heated to 60° C. for 5 h. The reaction was quenched with aqueous saturated ammonium chloride (10 mL), poured into water (15 mL) and extracted with ethyl acetate (3×40 mL). The combined organic solution was washed with water (2×50 mL) and brine (50 mL), dried over sodium sulfate, filtered, and concentrated. The residue was purified by column chromatography with 25% ethyl acetate in hexanes to afford 1'-[(2R)-tetrahydrofuran-2-ylmethyl]-6-{[tris(1-methylethyl)silyl]oxy}spiro[1-benzofuran-3,3'-indol]-2'(1'H)-one (1.70 g, 58%) as a colorless oil: ¹H NMR (300 MHz, CDCl₃) δ7.33-7.26 (m, 1H), 7.14-6.98 (m, 3H), 6.53 (d, J=8.1 Hz, 1H), 6.48 (d, J=2.1 Hz, 1H), 6.32 (dd, J=8.1, 2.1 Hz, 1H), 4.95-4.90 (m, 1H), 4.66 (d, J=9.3 Hz, 1H), 4.34-4.22 (m, 1H), 4.00-3.66 (m, 4H), 2.10-1.66 (m, 4H), 1.34-0.98 (m, 21H); MS (ES+) m/z 494.2 (M+1).

Preparation 47

Synthesis of 5,6-difluorospiro[1-benzofuran-3,3'-indol]-2'(1'H)-one

A. Synthesis of 3-(4,5-difluoro-2-hydroxyphenyl)-1-(diphenylmethyl)-3-hydroxy-1,3-dihydro-2H-indol-2-one To a solution of 3,4-difluorophenol (10.33 g, 79.4 mmol) in anhydrous tetrahydrofuran (60 mL) at 0° C. under nitrogen was added isopropyl magnesium chloride (39.7 mL, 79.4 mmol), and the solution was stirred at ambient temperature for 3 h. Tetrahydrofuran was removed by rotary evaporation, and the residue was redissolved in anhydrous dichloromethane (140 mL). The solution was cooled to 0° C. under nitrogen, then N-benzhydryl isatin (13.77 g, 43.9 mmol) was added and the reaction mixture was allowed to warm to ambient temperature. After 3 days, the reaction was quenched with aqueous saturated ammonium chloride (60 mL) and concentrated in vacuo. The residue was re-dissolved in ethyl acetate (150 mL) and washed with water (2×100 mL) and brine (100 mL), dried over sodium sulfate, filtered, and concentrated. The residue was precipitated from diethyl ether to yield 3-(4,5-difluoro-2-hydroxyphenyl)-1-(diphenylmethyl)-3-hydroxy-1,3-dihydro-2H-indol-2-one (12.08 g, 61%) as a colorless solid: ¹H NMR (300 MHz, CDCl₃) δ 9.23 (br s, 1H), 7.47-7.44 (m, 1H), 7.35-7.21 (m, 9H), 7.18-7.11 (m, 2H), 6.90 (s, 1H), 6.83 (dd, J=11.2, 6.9 Hz, 1H), 6.67 (dd, J=11.2, 8.7 Hz, 1H), 6.56-6.51 (m, 1H), 4.13 (br s, 1H); MS (ES+) m/z 426.2 (M−17).

B. Synthesis of 3-(4,5-difluoro-2-hydroxyphenyl)-1-(diphenylmethyl)-1,3-dihydro-2H-indol-2-one To a solution of 3-(4,5-difluoro-2-hydroxyphenyl)-1-(diphenylmethyl)-3-hydroxy-1,3-dihydro-2H-indol-2-one (11.72 g, 26.4 mmol) in trifluoroacetic acid (60 mL) under nitrogen was added triethylsilane (10.55 mL, 66.0 mmol), and the reaction mixture was stirred for 16 h. Following concentration in vacuo, the residue was purified by column chromatography (30% ethyl acetate in hexanes). Precipitation from diethyl ether/hexanes followed by filtration yielded 3-(4,5-difluoro-2-hydroxyphenyl)-1-(diphenylmethyl)-1,3-dihydro-2H-indol-2-one (6.29 g, 56%) as a colorless solid: ¹H NMR (300 MHz, CDCl₃) δ 9.27 (br s, 1H), 7.37-7.12 (m, 12H), 6.94 (s, 1H), 6.87 (dd, J=11.3, 7.1 Hz, 1H), 6.76 (dd, J=11.2, 8.9 Hz, 1H), 6.58-6.56 (m, 1H), 5.12 (s, 1H); MS (ES+) m/z 428.2 (M+1).

C. Synthesis of 1'-(diphenylmethyl)-5,6-difluorospiro[1-benzofuran-3,3'-indol]-2'(1'H)-one To a solution of 3-(4,5-difluoro-2-hydroxyphenyl)-1-(diphenylmethyl)-1,3-dihydro-2H-indol-2-one (6.30 g, 14.7 mmol) in anhydrous tetrahydrofuran (120 mL) under argon was added cesium carbonate (14.4 g, 44.2 mmol), followed by the addition of chloroiodomethane (3.21 mL, 44.2 mmol) dropwise. After 20 h, the reaction mixture was concentrated in vacuo and re-dissolved in ethyl acetate (50 mL) and water (50 mL). The aqueous layer was extracted with ethyl acetate (6×50 mL). Some product was filtered off as a colorless precipitate. The combined organic solution was washed with water (2×150 mL) and brine (150 mL), dried over sodium sulfate, filtered, and concentrated. Precipitation from diethyl ether/hexanes afforded 1'-(diphenylmethyl)-5,6-difluorospiro[1-benzofuran-3,3'-indol]-2'(1'H)-one (4.51 g, 70%) as a colorless solid: mp 213-216° C.; ¹H NMR (300 MHz, CDCl₃) δ 7.41-7.26 (m, 10H), 7.15-7.12 (m, 1H), 7.08-6.97 (m, 3H), 6.78 (dd, J=10.5, 6.3 Hz, 1H), 6.54 (d, J=8.4 Hz, 1H), 6.44 (dd, J=9.0, 7.8 Hz, 1H), 5.03 (d, J=9.0 Hz, 1H), 4.77 (d, J=9.3 Hz, 1H); ¹³C NMR (75 MHz, CDCl₃) δ 176.8, 156.6 (d, J=11.0 Hz), 151.2 (dd, $J_{C-F}$=248.2, 14.5 Hz), 145.6 (dd, $J_{C-F}$=241.5, 13.85 Hz), 141.7, 137.4, 137.1, 131.5, 128.8, 128.8, 128.7, 128.3, 128.3, 128.1, 128.0, 124.2 (dd, J=6.4, 3.3 Hz), 123.8, 123.3, 112.4, 111.5 (dd, J=20.4, 1.6 Hz), 100.1 (d, J=22.4), 80.8, 58.9, 57.5; MS (ES+) m/z 440.2 (M+1), 462.2 (M+23).

D. Synthesis of 5,6-difluorospiro[1-benzofuran-3,3'-indol]-2'(1'H)-one

To a solution of 1-(diphenylmethyl)-5,6-difluorospiro[1-benzofuran-3,3'-indol]-2'(1'H)-one (6.06 g, 13.8 mmol) in methanol (100 mL), ethyl acetate (25 mL) and acetic acid (1 mL) under argon in a steel bomb was added palladium (20% on activated carbon, nominally 50% H₂O, 2.0 g, 3.76 mmol). The bomb was put under hydrogen (50 psi) and heated at 65° C. for 16 h. The reaction mixture was filtered through celite and washed with ethyl acetate (15 mL) and methanol (50 mL). The filtrate was concentrated and the residue was precipitated from methanol. Filtration afforded 5,6-difluorospiro[1-benzofuran-3,3'-indol]-2'(1'H)-one (3.63 g, 96%) as a colorless solid: mp>200° C.; ¹H NMR (300 MHz, CDCl₃) δ 8.00 (s, 1H), 7.32-7.27 (m, 1H), 7.15-7.05 (m, 2H), 6.97 (d, J=7.8 Hz, 1H), 6.79 (dd, J=10.3, 6.3 Hz, 1H), 6.62 (dd, J=9.0, 8.0 Hz, 1H), 5.00 (d, J=9.2 Hz, 1H), 4.73 (d, J=9.2 Hz, 1H); ¹³C NMR (75 MHz, CDCl₃) δ 179.7, 156.70 (d, J=10.9), 151.3 (dd, $J_{C-F}$=248.7, 14.3 Hz), 145.7 (dd, $J_{C-F}$=241.6, 13.8 Hz), 140.3, 131.6, 129.4, 124.0, 123.7, 123.4 (dd, J=6.3, 3.1 Hz), 111.9 (d, J=20.4 Hz), 110.7, 100.1 (d, J=22.4 Hz), 80.7, 58.4; MS (ES+) m/z 274.2 (M+1).

Preparation 48

Synthesis of N'-hydroxy-3-(2'-oxo-6H-spiro[benzofuro[6,5-d][1,3]dioxole-7,3'-indoline]-1'-yl)propanimidamide To a stirred solution of 3-(2'-oxo-6H-spiro[benzofuro[6,5-d][1,3]dioxole-7,3'-indoline]-1'-yl)propanenitrile (2.00 g, 6.0 mmol) in dimethyl sulfoxide (15.0 mL) was added hydroxylamine (50% wt solution in water, 1.6 mL, 24 mmol). The reaction was stirred at ambient temperature for 16 h, then the product was precipitated upon addition of water/ethanol (3:1, 100 mL). The solvent was decanted and the remaining solid was triturated in distilled water (75 mL). The solid was filtered and air-dried to afford N'-hydroxy-3-(2'-oxo-6H-spiro[benzofuro[6,5-d][1,3]dioxole-7,3'-indoline]-1'-yl)propanimidamide as a colorless solid (2.00 g, 91%): MS (ES+) m/z 368.2 (M+1).

Preparation 49

Synthesis of 4-chloro-3-hydroxy-3-(6-hydroxy-1,3-benzodioxol-5-yl)-1,3-dihydro-2H-indol-2-one To a solution of 1,3-benzodioxol-5-ol (4.86 g, 22.0 mmol) in anhydrous tetrahydrofuran (100 mL) was added dropwise a solution of isopropyl magnesium chloride (49.6 mmol, 24.8 mL, 2.0 M solution in tetrahydrofuran) over 10 min at 0° C. The reaction mixture was stirred for 30 min upon which time 4-chloroisatin (4.00 g, 22.0 mmol) was added in one portion. The reaction mixture was stirred at ambient temperature for 2 h and quenched by the addition of 10% aqueous hydrochloric acid (25.0 mL) and the mixture was concentrated in vacuo to dryness. The residue was diluted with ethyl acetate (100 mL), washed with saturated ammonium chloride (3×30.0 mL), dried over anhydrous sodium sulfate and filtered. The filtrate was concentrated in vacuo to dryness. The residue was triturated with hot diethyl ether to afford 4-chloro-3-hydroxy-3-(6-hydroxy-1,3-benzodioxol-5-yl)-1,3-dihydro-2H-indol-2-one (6.70 g, 95%) as a beige solid: mp 250-253° C.; $^1$H NMR (300 MHz, DMSO-d$_6$) δ 10.30, (s, 1H), 9.04 (s, 1H), 7.20 (s, 1H), 7.12 (t, J=8.0 Hz, 1H), 6.74 (d, J=8.2 Hz, 1H), 6.70 (d, J=7.7 Hz, 1H), 6.45 (s, 1H), 6.17 (s, 1H), 5.88 (d, J=6.7 Hz, 2H); $^{13}$C NMR (75 MHz, DMSO-d$_6$) δ 178.1, 148.6, 147.0, 145.6, 139.6, 130.6, 130.1, 129.6, 122.3, 118.6, 108.9, 108.4, 101.1, 97.4, 75.8; MS (ES−) adz 304.2 (M−17), 302.2 (M−17).

Preparation 50

Synthesis of 4-chloro-3-(6-hydroxy-1,3-benzo-dioxol-5-yl)-1,3-dihydro-2H-indol-2-one To a solution of 4-chloro-3-hydroxy-3-(6-hydroxy-1,3-benzodioxol-5-yl)-1,3-dihydro-2H-indol-2-one (6.00 g, 18.8 mmol) in anhydrous dichloromethane (70.0 mL) was added trifluoroacetic acid (30.7 g, 269 mmol) and triethylsilane (18.0 mL, 13.1 g, 113 mmol) at ambient temperature. The reaction mixture was stirred at ambient temperature for 2 h. The reaction mixture was quenched with water (100.0 mL) and the solid was filtered. The solid was triturated with diethyl ether to afford 4-chloro-3-(6-hydroxy-1,3-benzodioxol-5-yl)-1,3-dihydro-2H-indol-2-one (4.71 g, 83%) as a colourless solid: mp 210-225° C. (dec.); MS (ES+) m/z 304.1 (M+1), 302.1 (M+1).

Preparation 51

Synthesis of 4-chloro-3-(6-hydroxy-1,3-benzo-dioxol-5-yl)-1,3-bis(hydroxymethyl)-1,3-dihydro-2H-indol-2-one To a suspension of 4-chloro-3-(6-hydroxy-1,3-benzo-dioxol-5-yl)-1,3-dihydro-2H-indol-2-one (4.5 g, 14.9 mmol), para-formaldehyde (1.78 g, 59.4 mmol) in water (50.0 mL) was added the aqueous solution of sodium hydroxide (2.38 g, 59.4 mmol) in water (10.0 mL). The reaction mixture was stirred at 0° C. for 2 h and quenched with 10% hydrochloric acid (50.0 mL). The precipitate was filtered and washed with water (100.0 mL). The filtrate was extracted with ethyl acetate (3×50.0 mL). The combined organic solution was dried over anhydrous sodium sulfate and filtered. The filtrate was concentrated in vacuo to dryness. The residue was triturated with ethyl acetate and diethyl ether to afford 4-chloro-3-(6-hydroxy-1,3-benzodioxol-5-yl)-1,3-bis(hydroxymethyl)-1,3-dihydro-2H-indol-2-one (3.91 g, 72%) as a colourless solid: mp>210° C.; $^1$H NMR (300 MHz, DMSO-d$_6$) δ 9.04 (s, 1H), 7.17 (t, J=8.0 Hz, 1H), 6.99 (d, J=7.7 Hz, 1H), 6.86 (s, 1H), 6.83 (d, J=8.2 Hz, 1H), 6.18 (s, 1H), 5.87 (d, J=11.0 Hz, 2H), 5.03 (q, J=10.8 Hz, 2H), 4.86 (br, 1H), 4.64 (ABq, 2H); $^{13}$C NMR (75 MHz, DMSO-d$_6$) δ 177.9, 150.3, 146.9, 146.8, 139.9, 129.1, 129.0, 128.6, 122.7, 116.0, 108.8, 107.6, 101.2, 97.7, 63.6, 63.3, 56.6; MS (ES+) m/z 364.2 (M+1), 346.2 (M−17).

Preparation 52

Synthesis of 4'-chlorospiro[furo[2,3-f][1,3]benzo-dioxole-7,3'-indol]-2'(1'H)-one To a solution of 4-chloro-3-(6-hydroxy-1,3-benzodioxol-5-yl)-1,3-bis(hydroxymethyl)-1,3-dihydro-2H-indol-2-one (3.63 g, 10.0 mmol) in anhydrous tetrahydrofuran (100.0 mL) was added tributylphosphine (2.53 g, 12.5 mmol) at 0° C. followed by the solution of di-tert-butyl azodicarboxylate (2.88 g, 12.5 mmol) in anhydrous tetrahydrofuran (25.0 mL). The reaction solution was stirred at 0° C. for 1 h followed by the addition of ammonium hydroxide (100.0 mL). The reaction mixture was continued to stir for another 2 h. The reaction was quenched with 10% aqueous solution of hydrochloric acid (100.0 mL). The reaction solution was extracted with ethyl acetate (3×100.0 mL). The combined organic solution was dried over anhydrous sodium sulfate and filtered. The filtrate was concentrated in vacuo to dryness. The residue was purified by flash chromatography with ethyl acetate in hexanes to afford 4'-chlorospiro[furo[2,3-f][1,3]benzodioxole-7, 3'-indol]-2'(1'H)-one (0.98 g, 31%) as a colourless solid: mp 175-185° C.; $^1$H NMR (300 MHz, DMSO-d$_6$) δ 10.81 (s, 1H), 7.24 (t, J=8.0 Hz, 1H), 6.94 (d, J=8.2 Hz, 1H), 6.86 (d, J=7.1 Hz, 1H), 6.59 (s, 1H), 6.28 (s, 1H), 5.90 (d, J=2.5 Hz, 2H), 4.74 (ABq, J=9.5 Hz, 2H); $^{13}$C NMR (75 MHz, DMSO-d$_6$) δ 178.4, 157.0, 148.8, 144.2, 141.9, 130.9, 130.3, 129.2, 123.0, 117.5, 109.4, 103.3, 101.9, 93.3, 77.8, 58.9; MS (ES+) m/z 318.3 (M+1), 316.3 (M+1).

Preparation 53

Synthesis of 2-(4'-chloro-2'-oxospiro[furo[2,3-f][1,3]benzodioxole-7,3'-indol]-1'(2'H)-yl)-W-hydroxyethanimidamide To a solution of 4'-chloro-2'-oxospiro[furo[2,3-f][1,3]benzodioxole-7,3'-indol]-1'(2'H)-yl)acetonitrile (1.81 g, 5.10 mmol) in ethanol (25.0 mL) and dimethylsulfoxide (3.0 mL) was added hydroxylamine (0.67 g, 20.4 mL) at ambient temperature. The yellow reaction solution was stirred for 2 h upon which time yellow precipitate formed. The precipitate was filtered, washed with water (100.0 mL) and dried under vacuum to afford 2-(4'-chloro-2'-oxospiro[furo[2,3-f][1,3]benzodioxole-7,3'-indol]-1'(2'H)-yl)-N-hydroxyethanimidamide (1.54 g, 78%) as a fluffy yellow solid: mp 180-185° C.; $^1$H NMR (300 MHz, DMSO-d$_6$) δ 9.20 (s, 1H), 7.30 (d, J=8.0 Hz, 1H), 7.01 (d, J=3.8 Hz, 1H), 6.98 (d, J=3.5 Hz, 1H), 6.60 (s, 1H), 6.32 (s, 1H), 5.60 (d, J=3.8 Hz, 2H), 5.54 (br, 2H), 4.78 (ABq, J=9.6 Hz, 2H), 3.68 (s, 2H); $^{13}$C NMR (75 MHz, DMSO-d$_6$) δ 176.8, 156.6, 148.9, 147.7, 145.1, 141.9, 130.8, 129.9, 128.5, 123.5, 117.5, 109.1, 103.7, 101.9, 93.2, 77.5, 58.4, 40.9; MS (ES+) m/z 388.1 (M+1).

Preparation 54

Synthesis of 1'-[(2-oxo-1,3-oxazolidin-5-yl)methyl]spiro[furo[2,3-f][1,3]benzodioxole-7,3'-indol]-2'(1'H)-one A mixture of spiro[furo[2,3-f][1,3]benzodioxole-7,3'-indol]-2'(1'H)-one (1.37 g, 4.89 mmol), 5-(chloromethyl)-1,3-oxazolidin-2-one (1.34 g, 5.38 mmol) and cesium carbonate (2.39 g, 7.34 mmol) in N,N-dimethylformamide (8.0 mL) was stirred at ambient temperature for 11 h and filtered. The solid was washed with ethyl acetate and the filtrate was washed with water (3×15 mL), dried over sodium sulfate and filtered. The filtrate was concentrated in vacuo to dryness. The residue was purified by column chromatography to afford 1'-[(2-oxo-1,3-oxazolidin-5-yl)methyl]spiro[furo[2,3-f][1,3]benzodioxole-7,3'-indol]-2'(1'H)-one (0.56 g, 25%): mp 195-202° C.; $^1$H NMR (300 MHz, CDCl$_3$) δ 7.35-7.30 (m, 1H), 7.17-7.04 (m, 3H), 6.50 (s, 1H), 6.12 (s, 1H), 5.84 (s, 2H), 5.27 (br, 1H), 5.02-4.96 (m, 1H), 4.91-4.87 (m, 1H), 4.68-4.64 (m, 1H), 4.14-3.96 (m, 2H), 3.75-3.68 (m, 1H), 3.55-3.44 (m, 1H); $^{13}$C NMR (75 MHz, CDCl$_3$) δ 178.9, 158.5, 155.9, 149.0, 142.4, 142.2, 131.7, 129.4, 124.0, 123.9, 119.2, 109.6, 102.8, 101.6, 93.7, 80.3, 74.9, 58.1, 43.5, 43.1; MS (ES+) m/z 403.2 (M+23), 381.2 (M+1).

Preparation 55

Synthesis of 3-(6-hydroxy-1,3-benzodioxol-5-yl)-3-(hydroxymethyl)-7-(trifluoromethyl)-1,3-dihydro-2H-indol-2-one A. Synthesis of 3-hydroxy-3-(6-hydroxy-1,3-benzodioxol-5-yl)-7-(trifluoromethyl)-1,3-dihydro-2H-indol-2-one To a solution of 1,3-benzodioxol-5-ol (9.63 g, 69.7 mmol) in anhydrous tetrahydrofuran (200 mL) was added dropwise a solution of isopropyl magnesium chloride (92.9 mmol, 46.5 mL, 2.0 M solution in tetrahydrofuran) over 30 min at 0° C. 7-Trifluoromethylisatin (4.00 g, 22.0 mmol) was added in one portion. The reaction mixture was stirred at ambient temperature for 4 h and the reaction was quenched by the addition of 10% aqueous hydrochloric acid (25.0 mL) and the mixture was concentrated in vacuo to dryness. The residue was diluted with ethyl acetate (200 mL), washed with saturated ammonium chloride (3×30.0 mL), brine (3×30.0 mL), dried over anhydrous sodium sulfate and filtered. The filtrate was concentrated in vacuo to dryness. The residue was triturated with hot diethyl ether to afford 3-hydroxy-3-(6-hydroxy-1,3-benzodioxol-5-yl)-7-(trifluoromethyl)-1,3-dihydro-2H-indol-2-one (13.6 g, 83%): $^1$H NMR (300 MHz, DMSO-d$_6$) δ 10.65 (s, 1H), 9.21 (s, 1H), 7.38 (d, J=7.8 Hz, 1H), 7.22 (s, 1H), 7.07 (d, J=7.2 Hz, 1H), 6.95 (dd, J=7.7, 7.7 Hz, 1H), 6.57 (s, 1H), 6.17 (s, 1H), 5.89 (d, J=6.2 Hz, 2H); $^{13}$C NMR (75 MHz, DMSO-d$_6$) δ 179.2, 148.6, 147.3, 141.0, 139.9, 135.7, 127.9, 125.3, 124.3, 121.7, 119.8, 110.1, 107.2, 101.2, 97.7, 73.9; MS (ES-) m/z 352.2 (M-1).

B. Synthesis of 3-(6-hydroxy-1,3-benzodioxol-5-yl)-7-(trifluoromethyl)-1,3-dihydro-2H-indol-2-one To a solution of 3-hydroxy-3-(6-hydroxy-1,3-benzodioxol-5-yl)-7-(trifluoromethyl)-1,3-dihydro-2H-indol-2-one (7.06 g, 20.0 mmol) in anhydrous trifluoroacetic acid (21.0 mL, 9.12 g, 80 mmol) was added triethylsilane (12.8 mL, 9.30 g, 80.0 mmol) at ambient temperature. The reaction mixture was stirred at ambient temperature for 0.5 h. The reaction mixture was quenched with water (50.0 mL). The mixture was extracted with ethyl acetate (2×150 mL). The organic solution was washed with saturated ammonium chloride (3×75 mL), dried over sodium sulfate and filtered. The filtrate was concentrated in vacuo to dryness. The residue was triturated with diethyl ether to afford 3-(6-hydroxy-1,3-benzodioxol-5-yl)-7-(trifluoromethyl)-1,3-dihydro-2H-indol-2-one (5.94 g, 88%) as colourless solid: $^1$H NMR (300 MHz, DMSO-d$_6$) δ 10.81 (s, 1H), 9.25 (br, 1H), 7.37 (d, J=8.0 Hz, 1H), 7.12 (d, J=7.3 Hz, 1H), 6.98 (dd, J=7.7, 7.7 Hz, 1H), 6.71 (s, 1H), 5.88 (s, 2H), 4.65 (s, 1H); $^{13}$C NMR (75 MHz, DMSO-d$_6$) δ 178.7, 150.5, 147.4, 140.5, 140.1, 133.3, 127.8, 124.3, 124.2, 121.6, 115.5, 110.8, 110.3, 101.3, 98.2, 48.1; MS (ES+) m/z 338.3 (M+1).

C. Synthesis of 3-(6-hydroxy-1,3-benzodioxol-5-yl)-3-(hydroxymethyl)-7-(trifluoromethyl)-1,3-dihydro-2H-indol-2-one To a suspension of 3-(6-hydroxy-1,3-benzodioxol-5-yl)-7-(trifluoromethyl)-1,3-dihydro-2H-indol-2-one (5.64 g, 16.7 mmol), para-formaldehyde (1.78 g, 59.4 mmol) in tetrahydrofuran (20.0 mL) and water (50.0 mL) was added the aqueous solution of sodium hydroxide (2.68 g, 66.9 mmol) in water (30.0 mL). The reaction mixture was stirred at 0° C. for 1 h and quenched with 10% hydrochloric acid (50.0 mL). The mixture was extracted with ethyl acetate (3×50.0 mL). The combined organic solution was washed with saturated ammonium chloride (3×50 mL), dried over anhydrous sodium sulfate and filtered. The filtrate was concentrated in vacuo to dryness. The residue was purified by column chromatography to afford 3-(6-hydroxy-1,3-benzodioxol-5-yl)-3-(hydroxymethyl)-7-(trifluoromethyl)-1,3-dihydro-2H-indol-2-one (4.56 g, 73%) as a fluffy solid: $^1$H NMR (300 MHz, DMSO-d$_6$) δ 10.63 (s, 1H), 9.16 (s, 1H), 7.32 (d, J=7.9 Hz, 1H), 7.08 (d, J=7.2 Hz, 1H), 7.01 (s, 1H), 6.94 (dd, J=7.7, 7.7 Hz, 1H), 6.18 (s, 1H), 5.88 (s, 2H), 5.03 (br, 1H), 3.97 (ABq, J=9.9 Hz, 2H); $^{13}$C NMR (75 MHz, DMSO-d$_6$) δ 180.5, 150.3, 146.8, 141.5, 140.0, 136.0, 127.5, 123.8, 121.0, 117.7, 109.7, 108.4, 101.2, 97.9, 60.2, 55.2; MS (ES+) m/z 390.2 (M+1).

Preparation 56

Synthesis of 7'-(trifluoromethyl)spiro[furo[2,3-f][1,3]benzodioxole-7,3'-indol]-2'(1'H)-one To a solution of 3-(6-hydroxy-1,3-benzodioxol-5-yl)-3-(hydroxymethyl)-7-(trifluoromethyl)-1,3-dihydro-2H-indol-2-one (4.10 g, 11.7 mmol) in ethyl acetate (100.0 mL) was added tributylphosphine (3.4 mL, 2.83 g, 13.9 mmol) at 0° C. followed by the solution of di-tert-butyl azodicarboxylate (3.22 g, 13.9 mmol) in ethyl acetate (50.0 mL). The reaction solution was stirred at 0° C. for 30 min followed by the addition of 10% hydrochloric acid (50.0 mL). The reaction solution was washed with 10% hydrochloric acid (2×50.0 mL), saturated ammonium chloride (3×50 mL) and brine (3×50 mL). The organic solution was dried over anhydrous sodium sulfate and filtered. The filtrate was concentrated in vacuo to dryness. The residue was purified by flash chromatography to afford 7'-(trifluoromethyl)spiro[furo[2,3-f][1,3]benzodioxole-7,3'-indol]-2'(1'H)-one (3.59 g, 88%): mp 245-248° C.; $^1$H NMR (300 MHz, DMSO-d$_6$) δ 11.02 (s, 1H), 7.50 (d, J=7.9 Hz, 1H), 7.36 (d, J=7.3 Hz, 1H), 7.11 (dd, J=7.5, 7.5 Hz, 1H), 6.66 (s, 1H), 6.32 (s, 1H), 5.90 (d, J=3.1 Hz, 2H), 4.74 (ABq, 2H); $^{13}$C NMR (75 MHz, DMSO-d$_6$) δ 179.4, 156.0, 148.9, 139.7, 134.9, 128.3, 125.8, 125.7 (m), 122.9, 119.7, 112.0, 111.4 (m), 103.6, 101.9, 93.7, 80.4, 57.5; MS (ES+) m/z 350.3 (M+1).

Preparation 57

Synthesis of tert-butyl 3-[2-(2'-oxospiro[furo[2,3-f][1,3]benzodioxole-7,3'-indol]-1'(2'H)-yl)ethyl]piperidine-1-carboxylate To a mixture of spiro[furo[2,3-f][1,3]benzodioxole-7,3'-indol]-2'(1'H)-one (0.96 g, 3.41 mmol) in 2-butanone (17 mL) and acetone (17 mL) were added cesium carbonate (3.79 g, 11.6 mmol) and N-Boc-3-(2-bromoethyl)piperidine (1.00 g, 3.42 mmol) at ambient temperature. The mixture was stirred at ambient temperature for 16 h. The reaction mixture was filtered and washed with acetone (2×50 mL). The filtrate was concentrated in vacuo to dryness. The residue was purified by column chromatography with ethyl acetate in hexanes (10% to 30% gradient) to give tert-butyl 3-[2-(2'-oxospiro [furo[2,3-f][1,3]benzodioxole-7,3'-indol]-1'(2'H)-yl)ethyl] piperidine-1-carboxylate (1.48 g, 88%) as a white powder: mp 64-67° C. (diethyl ether/hexanes); $^1$H NMR (300 MHz, CDCl$_3$) δ 7.30 (dt, J=7.8, 0.9 Hz, 1H), 7.16 (d, J=7.3 Hz, 1H), 7.50 (dt, J=7.5, 0.7 Hz, 1H), 6.92 (d, J=7.8 Hz, 1H), 6.50 (s, 1H), 6.10 (d, J=1.7 Hz, 1H), 5.86 (dd, J=6.0, 1.0 Hz, 2H), 4.90 (dd, J=9.0, 0.6 Hz, 1H), 4.65 (dd, J=9.0, 3.0 Hz, 1H), 3.90-3.69 (m, 4H), 2.97-2.86 (m, 1H), 2.77-2.68 (m, 1H), 1.96-1.92 (m, 1H), 1.76-1.16 (m, 15H); $^{13}$C NMR (75 MHz, CDCl$_3$) δ 177.2, 155.8, 154.8, 148.8, 142.3, 142.2, 142.1, 132.4 (2), 128.9, 124.0, 123.2, 119.4 (2), 108.5, 102.9, 101.4, 93.6, 80.4, 79.4, 58.1, 38.2, 33.5, 30.7, 30.7, 30.6, 30.5, 28.4, 24.3; MS (ES+) m/z 515.4 (M+23).

Preparation 58

Synthesis of 3-[2-(2'-oxospiro[furo[2,3-f][1,3]benzodioxole-7,3'-indol]-1'(2'H)-yl)ethyl]piperidine To a solution of tert-butyl 3-[2-(2'-oxospiro[furo[2,3-f][1,3]benzodioxole-7,3'-indol]-1'(2'H)-yl)ethyl]piperidine-1-carboxylate (1.48 g, 3.0 mmol) in dichloromethane (20 mL) was added trifluoroacetic acid (4 mL) at 0° C. The mixture was stirred at ambient temperature for 2 h and concentrated in vacuo to dryness. The residue was diluted in dichloromethane (100 mL) and washed with saturated aqueous sodium bicarbonate solution (2×30 mL), water (30 mL), and dried over anhydrous sodium sulfate, filtered and concentrated in vacuo to dryness to give 3-[2-(2'-oxospiro[furo[2,3-f][1,3]benzodioxole-7,3'-indol]-1'(2'H)-yl)ethyl]piperidine (0.72 g, 60%): MS (ES+) m/z 393.4 (M+1).

Preparation 59

Synthesis of ethyl 5-[(2'-oxospiro[furo[2,3-f][1,3] benzodioxole-7,3'-indol]-1'(2'H)-yl)methyl]-2-(trifluoromethyl)furan-3-carboxylate To a solution of spiro[furo[2,3-f][1,3]benzodioxole-7,3'-indol]-2'(1'H)-one (4.26 g, 15.10 mmol) in 2-butanone (120 mL) was added cesium carbonate (14.76 g, 45.30 mmol) and ethyl 5-(bromomethyl)-2-(trifluoromethyl)furan-3-carboxylate (Lyalin, V. V.; et al., Zhurnal Organicheskoi Khimii (1984), 20(4):846) (4.80 g, 15.90 mmol). The reaction mixture was heated at 60° C. to 70° C. for 18 h, cooled to ambient temperature and filtered. The solid was washed with ethyl acetate. The filtrate was concentrated in vacuo, the residue was purified by column chromatography with ethyl acetate and hexanes to afford ethyl 5-[(2'-oxospiro[furo[2,3-f][1,3] benzodioxole-7,3'-indol]-1'(2'H)-yl)methyl]-2-(trifluoromethyl)furan-3-carboxylate (4.65 g, 61%): mp 162-164° C.; $^1$H NMR (300 MHz, CDCl$_3$) δ 7.23-7.17 (m, 2H), 7.12-7.06 (m, 1H), 6.94 (d, J=7.8 Hz, 1H), 6.76 (s, 1H), 6.50 (s, 1H), 5.86-5.85 (m, 2H), 5.05-4.87 (m, 3H), 4.68-4.64 (m, 1H), 4.31 (q, J=7.2 Hz, 2H), 1.32 (t, J=7.2 Hz, 3H); $^{13}$C NMR (75 MHz, CDCl$_3$) δ 177.2, 160.4, 155.9, 150.6, 149.1, 143.5, 142.5, 141.1, 132.0, 129.1, 124.2, 124.0, 120.7, 120.0, 119.0, 116.4, 111.1, 108.7, 103.0, 101.6, 93.7, 80.4, 61.7, 58.2, 36.7, 13.9; MS (ES+) m/z 502.1 (M+1).

Preparation 60

Synthesis of 5-((2'-oxo-6H-spiro[benzofuro[6,5-d][1, 3]dioxole-7,3'-indoline]-1'-yl)methyl)-2-(trifluoromethyl)furan-3-carboxylic acid To a solution of ethyl 5-[(2'-oxospiro[furo[2,3-f][1,3]benzodioxole-7,3'-indol]-1'(2'H)-yl)methyl]-2-(trifluoromethyl)furan-3-carboxylate (1.30 g, 2.59 mmol) in ethanol (8 mL) and water (1.7 mL) was added sodium hydroxide (0.12 g, 3.00 mmol). The reaction mixture was heated at reflux for 45 min, concentrated in vacuo to remove ethanol. To the residue was added water (15 mL) and the mixture was acidified to pH-3 by 10% hydrochloric acid at 0° C. The resulting mixture was extracted with ethyl acetate (3×50 mL). The organic layer was washed with water and brine, dried over anhydrous sodium sulfate and filtered. The filtrate was concentrated in vacuo to give 5-((2'-oxo-6H-spiro[benzofuro[6,5-d][1,3]dioxole-7,3'-indoline]-1'-yl)methyl)-2-(trifluoromethyl)furan-3-carboxylic acid (1.03 g, 84%): mp 195-197° C.; $^1$H NMR (300 MHz, DMSO-d$_6$) δ 7.13-7.26 (m, 1H), 7.17-7.15 (m, 2H), 7.05-7.00 (m, 2H), 6.67 (s, 1H), 6.09 (s, 1H), 5.90-5.88 (m, 2H), 5.11-4.96 (m, 2H), 4.80-4.66 (m, 2H); $^{13}$C NMR (75 MHz, DMSO-d$_6$) δ 177.0, 161.9, 155.8, 152.3, 148.9, 142.2, 141.9, 141.5, 132.1, 129.3, 124.1, 123.8, 122.2, 120.6, 120.1, 117.0, 111.8, 109.7, 103.1, 101.9, 93.8, 80.1, 57.9, 36.7; MS (ES-) m/z 472.0 (M-1).

Preparation 61

Synthesis of 1-(4-bromobenzyl)-5,6-dihydrospiro [benzo[1,2-b:5,4-b']difuran-3,3'-indol]-2'(1'H)-one A suspended mixture of 5,6-dihydrospiro[benzo[1,2-b:5, 4-b']difuran-3,3'-indol]-2'(1'H)-one (1.12 g, 4.0 mmol), 4-bromobenzyl bromide (1.00 g, 4.0 mmol) and cesium carbonate (6.50 g, 20.0 mmol) in butanone (20 mL) was refluxed for 3 h under nitrogen. The reaction mixture was cooled to ambient temperature and filtered. The solid was washed with acetone (50 mL). The filtrate was concentrated in vacuo to dryness. The residue was purified by column chromatography with a 20% to 80% gradient of ethyl acetate in hexanes to afford 1-(4-bromobenzyl)-5,6-dihydrospiro[benzo[1,2-b:5, 4-b']difuran-3,3'-indol]-2'(1'H)-one (1.60 g, 89%) as a colorless solid: $^1$H NMR (300 MHz, DMSO-d$_6$) δ 7.49-6.98 (m, 7H), 6.75 (d, J=7.7 Hz, 1H), 6.43 (s, 1H), 6.42 (s, 1H), 4.89 (ABq, 2H), 4.82 (ABq, 2H), 4.53 (t, J=8.6 Hz, 2H), 3.08-2.90 (m, 2H); $^{13}$C NMR (75 MHz, DMSO-d$_6$) δ 177.9, 161.9, 161.3, 141.8, 134.8, 132.7, 132.0, 129.2, 128.7, 124.0, 123.6, 121.7, 120.0, 120.0, 118.8, 109.0, 93.3, 80.6, 72.4, 57.7, 43.6, 29.0; MS (ES+) m/z 448.1 (M+1), 450.1 (M+1).

Preparation 62

Synthesis of methyl 2-[(2'-oxo-5,6-dihydrospiro [benzo[1,2-b:5,4-b']difuran-3,3'-indol]-1'(2'H)-yl) methyl]-1,3-oxazole-4-carboxylate A suspended mixture of 5,6-dihydrospiro[benzo[1,2-b:5, 4-b']difuran-3,3'-indol]-2'(1'H)-one (1.00 g, 3.3 mmol), methyl 2-(chloromethyl)oxazole-4-carboxylate (2.00 g, 11.4 mmol) and cesium carbonate (4.00 g, 12.3 mmol) in butanone (50 mL) was refluxed for 5 h under nitrogen. The reaction mixture was cooled to ambient temperature and filtered. The solid was washed with acetone (50 mL). The filtrate was concentrated in vacuo to dryness. The residue was purified by column chromatography with a 30% to 70% gradient of ethyl acetate in hexanes to afford methyl 2-[(2'-oxo-5,6-dihydrospiro[benzo[1,2-b:5,4-b']difuran-3,3'-indol]-1'(2'H)-yl)methyl]-1,3-oxazole-4-carboxylate (0.88 g, 61%) as a colorless solid: $^1$H NMR (300 MHz, DMSO-$d_6$) δ 8.17 (s, 1H), 7.27-6.91 (m, 4H), 6.53 (s, 1H), 6.38 (s, 1H), 5.12 (ABq, 2H), 4.81 (ABq 2H), 4.51 (t, J=8.7 Hz, 2H), 3.89 (s, 3H), 3.04-2.91 (m, 2H); $^{13}$C NMR (75 MHz, DMSO-$d_6$) δ177.6, 161.9, 161.2, 161.2, 159.2, 145.0, 141.0, 133.6, 132.5, 129.0, 124.1, 120.1, 119.9, 199.1, 108.8, 93.2, 80.5, 72.4, 57.7, 52.3, 37.2, 29.0; MS (ES+) m/z 419.2 (M+1).

Preparation 63

Synthesis of 2-[(2'-oxo-5,6-dihydrospiro[benzo[1,2-b:5,4-b']difuran-3,3'-indol]-1'(2'H)-yl)methyl]-1,3-oxazole-4-carboxylic acid A suspended mixture of methyl 2-[(2'-oxo-5,6-dihydrospiro[benzo[1,2-b:5,4-b']difuran-3,3'-indol]-1'(2'H)-yl)methyl]-1,3-oxazole-4-carboxylate (0.88 g, 2.1 mmol) and sodium hydroxide (4.00 g, 10.0 mmol) in water (50 mL) and methanol (50 mL) was stirred at 60° C. for 2 h. The reaction mixture was concentrated in vacuo to remove most of methanol and acidified with concentrated hydrochloric acid to pH 1-2. The solid residue was filtered off, washed with water (50 mL) and dried in vacuo to afford 2-[(2'-oxo-5,6-dihydrospiro[benzo[1,2-b:5,4-b']difuran-3,3'-indol]-1'(2'H)-yl)methyl]-1,3-oxazole-4-carboxylic acid (0.64 g, 75%) as a colorless solid: $^1$H NMR (300 MHz, DMSO-$d_6$) δ 8.24 (s, 1H), 7.29-6.95 (m, 4H), 6.55 (s, 1H), 6.37 (s, 1H), 5.08 (ABq, 2H), 4.74 (ABq, 2H), 4.44 (t, J=8.7 Hz, 2H), 3.01-2.80 (m, 2H); MS (ES−) m/z 403.4 (M−1).

Preparation 64

Synthesis of methyl 2-[(2'-oxospiro[furo[2,3-f][1,3]benzodioxole-7,3'-indol]-1'(2'H)-yl)methyl]-1,3-oxazole-4-carboxylate A suspended mixture of spiro[furo[2,3-f][1,3]benzodioxole-7,3'-indol]-2'(1'H)-one (1.60 g, 5.70 mmol), methyl 2-(chloromethyl)oxazole-4-carboxylate (1.00 g, 5.70 mmol) and cesium carbonate (3.71 g, 11.4 mmol) in tetrahydrofuran (10 mL) was refluxed for 16 h. The reaction mixture was cold down to ambient temperature and concentrated in vacuo. The residue was treated with water (20 mL) and extracted with ethyl acetate (3×20 mL). The combined organic solution was dried over sodium sulfate and filtered. The filtrate was concentrated in vacuo to dryness. The residue was purified by column chromatography with a 20% to 30% gradient of ethyl acetate in hexanes to afford methyl 2-[(2'-oxospiro[furo[2,3-f][1,3]benzodioxole-7,3'-indol]-1'(2'H)-yl)methyl]-1,3-oxazole-4-carboxylate (2.19 g, 92%) as a colorless solid: mp 183-185° C.; $^1$H NMR (300 MHz, DMSO-$d_6$) δ 8.86 (s, 1H), 7.28 (t, J=7.2 Hz, 1H), 7.16 (d, J=7.0 Hz, 1H), 7.09 (d, J=7.8 Hz, 1H), 7.03 (t, J=7.5 Hz, 1H), 6.66 (s, 1H), 6.41 (S, 1H), 5.90 (d, J=2.1 Hz, 2H), 5.23-5.17 (m, 2H), 4.74 (ABq, 2H), 3.74 (s, 3H); $^{13}$C NMR (75 MHz, DMSO-$d_6$) δ177.2, 161.3, 160.2, 155.6, 148.8, 146.9, 142.3, 142.0, 132.8, 132.4, 129.4, 124.1, 123.9, 120.4, 109.7, 103.9, 101.9, 93.7, 80.0, 57.9, 52.3, 37.4; MS (ES+) m/z 421.2 (M+1).

Preparation 65

Synthesis of 2-[(2'-oxospiro[furo[2,3-f][1,3]benzodioxole-7,3'-indol]-1'(2'H)-yl)methyl]-1,3-oxazole-4-carboxylic acid To a solution of methyl 2-[(2'-oxospiro[furo[2,3-f][1,3]benzodioxole-7,3'-indol]-1'(2'H)-yl)methyl]-1,3-oxazole-4-carboxylate (1.17 g, 2.79 mmol) in tetrahydrofuran (20 mL) was added a solution of sodium hydroxide (0.45 g, 11.1 mmol) in water (5 mL). The mixture was stirred at reflux for 16 h. After cooling down to ambient temperature, the mixture was acidified with concentrated hydrochloric acid (2 mL). The reaction mixture was concentrated in vacuo to remove most of tetrahydrofuran and extracted with ethyl acetate (3×25 mL). The combined organic solution was dried over sodium sulfate and filtered. The filtrate was concentrated in vacuo to dryness. The residue was triturated with diethyl ether and ethyl acetate to afford 2-[(2'-oxospiro[furo[2,3-f][1,3]benzodioxole-7,3'-indol]-1'(2'H)-yl)methyl]-1,3-oxazole-4-carboxylic acid (0.65 g, 58%) as a colorless solid: $^1$H NMR (300 MHz, DMSO-$d_6$) δ 13.07 (br, 1H), 8.74 (s, 1H), 7.29 (t, J=7.7 Hz, 1H), 7.17 (d, J=6.6 Hz, 1H), 7.10 (d, J=7.8 Hz, 1H), 7.04 (t, J=7.5 Hz, 1H), 6.66 (s, 1H), 6.34 (s, 1H), 6.04 (s, 2H), 5.20-5.08 (m, 2H), 4.73 (ABq, 2H); $^{13}$C NMR (75 MHz, DMSO-$d_6$) δ177.1, 162.2, 159.9, 155.7, 148.8, 146.4, 142.2, 142.1, 133.8, 132.2, 129.4, 124.1, 123.9, 120.3, 109.7, 103.8, 101.9, 93.7, 80.0, 57.8, 31.2; MS (ES+) m/z 407.1 (M+1).

Preparation 66

Synthesis of 4'-bromo-1'-((5-(trifluoromethyl)furan-2-yl)methyl)-5,6-dihydro-2H-spiro[benzofuro[6,5-b]furan-3,3'-indolin]-2'-one To a stirred solution of 4'-bromo-5,6-dihydro-2H-spiro[benzofuro[6,5-b]furan-3,3'-indolin]-2'-one (0.64 g, 1.8 mmol) in 2-butanone (25 mL) was added cesium carbonate (1.75 g, 5.3 mmol) followed by 2-(bromomethyl)-5-(trifluoromethyl)furan (0.51 g, 2.2 mmol). The mixture was refluxed for 16 h, cooled to ambient temperature, filtered and concentrated in vacuo to dryness. The residue was subjected to column chromatography (hexanes/ethyl acetate from 3:1 to 1:1) to afford 4'-bromo-1'-((5-(trifluoromethyl)furan-2-yl)methyl)-5,6-dihydro-2H-spiro[benzofuro[6,5-b]furan-3,3'-indolin]-2'-one (0.82 g, 90%) as a colorless solid: mp 165-167° C.; $^1$H NMR (300 MHz, CDCl$_3$) δ7.27-7.10 (m, 2H), 6.92 (td, J=6.9, 1.8 Hz, 1H), 6.77-6.70 (m, 1H), 6.44-6.33 (m, 3H), 5.15-4.96 (m, 2H), 4.91-4.76 (m, 2H), 4.53 (dt, J=8.6, 1.9 Hz, 2H), 2.98 (t, J=8.5 Hz, 2H); $^{13}$C NMR (75 MHz, CDCl$_3$) δ177.3, 162.4, 162.2, 151.6, 143.4, 141.8 (q, J=43.0 Hz), 130.2, 127.7, 120.0, 119.7, 118.8 (q, J=267.1 Hz), 118.4, 117.0, 112.6, 109.5, 107.7, 92.9, 77.1, 72.4, 59.0, 37.0, 28.9; MS (ES+) m/z 505.8 (M+1), 507.8 (M+1).

Preparation 67

Synthesis of 6-fluoro-5-methoxyspiro[1-benzofuran-3,3'-indol]-2'(1'H)-one

A. Synthesis of 1-(diphenylmethyl)-3-(4-fluoro-2-hydroxy-5-methoxyphenyl)-3-hydroxy-1,3-dihydro-2H-indol-2-one To a solution of 3-fluoro-4-methoxyphenol (Niemann, M. B. *J. Am. Chem. Soc.* (1941), 63:609) (4.60 g, 32.4 mmol) in tetrahydrofuran (60 mL) at 5° C. was added a 2 M solution of isopropylmagnesium chloride in tetrahydrofuran (18.0 mL, 36.0 mmol). Tetrahydrofuran was removed under reduced pressure and dichloromethane (60 mL) was added. To the solution was added a solution of 1-(diphenylmethyl)-1H-indole-2,3-dione (8.00 g, 25.5 mmol) in dichloromethane (60 mL) at 5° C. and the reaction mixture was stirred at ambient temperature for 16 h. The reaction mixture was quenched with saturated ammonium chloride solution (5 mL). The reaction mixture was dried over magnesium sulfate, filtered and evaporated under reduced pressure. The residue was subjected to column chromatography with 40% to 90% gradient of ethyl acetate in hexanes to afford 1-(diphenylmethyl)-3-(4-fluoro-2-hydroxy-5-methoxyphenyl)-3-hydroxy-1,3-dihydro-2H-indol-2-one (6.60 g, 57%) as a pink solid: MS (ES+) m/z 438.3 (M–17).

B. Synthesis of 1-(diphenylmethyl)-3-(4-fluoro-2-hydroxy-5-methoxyphenyl)-1,3-dihydro-2H-indol-2-one To a solution of 1-(diphenylmethyl)-3-(4-fluoro-2-hydroxy-5-methoxyphenyl)-3-hydroxy-1,3-dihydro-2H-indol-2-one (6.60 g, 14.5 mmol) in dichloroethane (100 mL) were added triethylamine (4.55 g, 45.0 mmol) and thionyl chloride (3.57 g, 30.0 mmol) at 0° C. The reaction mixture was heated at reflux for 1 h. The reaction mixture was cooled down to ambient temperature and concentrated under reduced pressure. The residue was dissolved in tetrahydrofuran (100 mL) and acetic acid (10 mL) and zinc dust (6.54 g, 100.0 mmol) were added in small portions at ambient temperature. The reaction mixture was stirred at ambient temperature for 16 h and filtered. The filtrate was concentrated in vacuo to dryness. The residue was purified by column chromatography with a 20% to 80% gradient of ethyl acetate in hexanes to afford 1-(diphenylmethyl)-3-(4-fluoro-2-hydroxy-5-methoxyphenyl)-1,3-dihydro-2H-indol-2-one (1.10 g, 17%) as a colorless solid: MS (ES+) m/z 440.2 (M+1).

C. Synthesis of 1'-(diphenylmethyl)-6-fluoro-5-methoxyspiro[1-benzofuran-3,3'-indol]-2'(1'H)-one A suspended mixture of 1-(diphenylmethyl)-3-(4-fluoro-2-hydroxy-5-methoxyphenyl)-1,3-dihydro-2H-indol-2-one (1.10 g, 2.5 mmol), chloroiodomethane (0.70 g, 4.0 mmol) and cesium carbonate (2.60 g, 8.0 mmol) in tetrahydrofuran (50 mL) was stirred at ambient temperature for 24 h. The reaction mixture was filtered. The solid was washed with acetone (50 mL). The filtrate was concentrated in vacuo to dryness. The residue was purified by column chromatography with a 20% to 70% gradient of ethyl acetate in hexanes to afford 1-(diphenylmethyl)-6-fluoro-5-methoxyspiro[1-benzofuran-3,3'-indol]-2'(1'H)-one (0.49 g, 43%) as a colorless solid: MS (ES+) m/z 452.0 (M+1).

D. Synthesis of 6-fluoro-5-methoxyspiro[1-benzofuran-3,3'-indol]-2'(1'H)-one

A suspended mixture of 1-(diphenylmethyl)-6-fluoro-5-methoxyspiro[1-benzofuran-3,3'-indol]-2'(1'H)-one (0.49 g, 1.09 mmol), triethylsilane (0.23 g, 2.0 mmol) and trifluoroacetic acid (0.57 g, 5.0 mmol) was refluxed under nitrogen for 5 h. The reaction mixture was cooled to ambient temperature and concentrated under reduced pressure. The oily residue was sonicated with hexanes (10 mL) for 10 min and a solid product was filtered off to afford 6-fluoro-5-methoxyspiro[1-benzofuran-3,3'-indol]-2'(1'H)-one (0.29 g, 92%) as a colorless solid: $^1$H NMR (300 MHz, DMSO-$d_6$) δ 9.28 (s, 1H), 7.37-6.91 (m, 4H), 6.74 (d, J=11.0 Hz, 1H), 6.39 (d, J=8.3 Hz, 1H), 4.82 (ABq, 2H), 3.68 (s, 3H); $^{13}$C NMR (75 MHz, DMSO-$d_6$) δ 180.0, 155.2, 154.9, 154.7, 151.9, 142.9, 142.7, 140.2, 132.1, 129.2, 124.1, 123.6, 122.7, 122.7, 110.4, 109.0, 108.9, 100.0, 99.7, 80.5, 58.8, 57.2; MS (ES+) m/z 285.8 (M+1).

Preparation 68

Synthesis of 1-(diphenylmethyl)-7-fluoro-3-(7-hydroxy-2,3-dihydro-1,4-benzodioxin-6-yl)-1,3-dihydro-2H-indol-2-one A. Synthesis of 7-fluoro-1-(diphenylmethyl)-1H-indole-2,3-dione Following the procedure as described in PREPARATION 26A and making non-critical variations using 7-fluoroisatin to replace 2,3-dihydro-6H-[1,4]dioxino[2,3-f]indole-7,8-dione, and bromodiphenylmethane to replace 2-(bromomethyl)-5-(trifluoromethyl)furan, 7-fluoro-1-(diphenylmethyl)-1H-indole-2,3-dione was obtained (80%): MS (ES+) m/z 353.7 (M+23).

B. Synthesis of 1-(diphenylmethyl)-7-fluoro-3-hydroxy-3-(7-hydroxy-2,3-dihydro-1,4-benzodioxin-6-yl)-1,3-dihydro-2H-indol-2-one To a cooled (0° C.) suspension of 2,3-dihydro-1,4-benzodioxin-6-ol (0.47 g, 3.0 mmol) in anhydrous tetrahydrofuran (12 mL) was added isopropylmagnesium chloride (2 M solution in tetrahydrofuran, 1.7 mL, 3.3 mmol). The reaction mixture was stirred at 0° C. for 1 h, and 7-fluoro-1-(diphenylmethyl)-1H-indole-2,3-dione (1.0 g, 3.0 mmol) and anhydrous dichloromethane (10 mL) were added. The reaction mixture was allowed to stir for 19 h at ambient temperature. The reaction mixture was concentrated in vacuo and was diluted with saturated aqueous ammonium chloride (30 mL) and ethyl acetate (30 mL). The phases were separated and the aqueous phase was extracted with ethyl acetate (2×50 mL). The combined organic extracts were washed with brine (100 mL), dried over anhydrous sodium sulfate, filtered and concentrated in vacuo. The crude product was purified by column chromatography and eluted with a 8% to 66% gradient of ethyl acetate in hexanes to afford 1-(diphenylmethyl)-7-fluoro-3-hydroxy-3-(7-hydroxy-2,3-dihydro-1,4-benzodioxin-6-yl)-1,3-dihydro-2H-indol-2-one (1.22 g, 84%) as an off-white solid: MS (ES+) m/z 475.0 (M–17).

C. Synthesis of 1-(diphenylmethyl)-7-fluoro-3-(7-hydroxy-2,3-dihydro-1,4-benzodioxin-6-yl)-1,3-dihydro-2H-indol-2-one To a solution of 1-(diphenylmethyl)-7-fluoro-3-hydroxy-3-(7-hydroxy-2,3-dihydro-1,4-benzodioxin-6-yl)-1,3-dihydro-2H-indol-2-one (4.27 g, 8.8 mmol) in trifluoroacetic acid (100 mL) at 0° C. was added triethylsilane (2.8 mL, 18 mmol) and the reaction mixture was concentrated in vacuo. The crude product was purified by column chromatography and eluted with a 0% to 66% gradient of ethyl acetate in hexanes to afford 1-(diphenylmethyl)-7-fluoro-3-(7-hydroxy-2,3-dihydro-1,4-benzodioxin-6-yl)-1,3-dihydro-2H-indol-2-one (2.5 g, 61%) as a colorless solid: MS (ES+) m/z 465.9 (M+1).

Preparation 69

Synthesis of 4'-(bromoacetyl)-1'-methyl-2,3-dihydrospiro[furo[2,3-g][1,4]benzodioxine-8,3'-indol]-2'(1'H)-one To a solution of 4'-acetyl-1-methyl-2,3-dihydrospiro[furo[2,3-g][1,4]benzodioxine-8,3'-indol]-2'(1'H)-one (0.15 g, 0.41 mmol) in anhydrous tetrahydrofuran (5 mL) was added phenyltrimethylammonium tribromide (0.16 g, 0.41 mmol) and the reaction mixture was stirred at ambient temperature for 1 h. Water (30 mL) was added and, after stirring for 5 min, the mixture was partitioned between brine (30 mL) and ethyl acetate (30 mL). The aqueous phase was extracted with ethyl acetate (2×20 mL) and the combined organic extracts were washed with brine (20 mL), dried over anhydrous sodium sulfate, filtered and concentrated in vacuo to afford a heavy yellow oil. The oil was dissolved in dichloromethane (4 mL) and diethyl ether (30 mL) was added, causing a precipitate to be deposited. The solid was collected by vacuum filtration, washed with diethyl ether (10 mL), air-dried and dried under high vacuum to afford 4'-(bromoacetyl)-1'-methyl-2,3-dihydrospiro[furo[2,3-g][1,4]benzodioxine-8,3'-indol]-2'(1'H)-one (0.125 g, 70%) as an off-white solid: $^1$H NMR (300 MHz, CDCl$_3$) δ 7.51-7.42 (m, 2H), 7.13-7.08 (m, 1H), 6.49 (s, 1H), 6.02 (s, 1H), 4.93-4.78 (m, 2H), 4.22-4.02 (m, 6H), 3.28 (s, 3H); MS (ES+) m/z 429.4 (M+1), 431.4 (M+1).

Preparation 70

Synthesis of ethyl 3-(1'-methyl-2'-oxo-1',2,2',3-tetrahydrospiro[furo[2,3-g][1,4]benzodioxine-8,3'-indol]-4'-yl)-3-oxopropanoate To a suspension of sodium hydride (60% w/w dispersion in mineral oil, 0.11 g, 2.8 mmol) in anhydrous tetrahydrofuran (10 mL) at ambient temperature was added diethyl carbonate (0.26 mL, 2.1 mmol) and the mixture was heated at reflux for 5 min. 4'-Acetyl-1'-methyl-2,3-dihydrospiro[furo[2,3-g][1,4]benzodioxine-8,3'-indol]-2'(1'H)-one (0.50 g, 1.4 mmol) was added in one portion and the reaction mixture was heated at reflux for 16 h, allowed to cool to ambient temperature and poured into water (75 mL). The mixture was extracted with dichloromethane (3×50 mL). The combined organic extracts were washed with brine (50 mL), dried over anhydrous sodium sulfate, filtered and concentrated in vacuo. The crude product was purified by column chromatography and eluted with a 0% to 10% gradient of ethyl acetate in dichloromethane, followed by recrystallization from dichloromethane/diethyl ether to afford ethyl 3-(1'-methyl-2'-oxo-1',2,2',3-tetrahydrospiro[furo[2,3-g][1,4]benzodioxine-8,3'-indol]-4'-yl)-3-oxopropanoate (0.235 g, 39%) as a pale yellow solid: $^1$H NMR (300 MHz, CDCl$_3$) δ 7.50-7.43 (m, 2H), 7.14-7.09 (m, 1H), 6.51 (s, 1H), 6.02 (s, 1H), 4.97-4.78 (m, 2H), 4.20-4.03 (m, 6H), 3.89 (d, J=15.6 Hz, 1H), 3.65 (d, J=15.6 Hz, 1H), 3.29 (s, 3H), 1.16 (t, J=7.1 Hz, 3H); MS (ES+) m/z 445.8 (M+23).

Preparation 71

Synthesis of 3-(2,2-difluoro-6-hydroxy-1,3-benzodioxol-5-yl)-1-{[5-(trifluoromethyl)furan-2-yl]methyl}-1,3-dihydro-2H-indol-2-one A. Synthesis of 3-(2,2-difluoro-6-hydroxy-1,3-benzodioxol-5-yl)-3-hydroxy-1-{[5-(trifluoromethyl)furan-2-yl]methyl}-1,3-dihydro-2H-indol-2-one To a solution of 2,2-difluoro-1,3-benzodioxol-5-ol (Jacobus et al., WO 2004/048320) (1.15 g, 6.60 mmol) in anhydrous tetrahydrofuran at 0° C. was added isopropylmagnesium chloride (2 M solution in tetrahydrofuran, 3.3 mL, 6.6 mmol). The reaction mixture was stirred at 0° C. for 0.5 h and 1-{[5-(trifluoromethyl)furan-2-yl]methyl}-1H-indole-2,3-dione (1.95 g, 6.60 mmol) was added. The reaction mixture was allowed to warm to ambient temperature and stirred for 96 h. A saturated aqueous solution of ammonium chloride (30 mL) was added and the mixture was extracted with ethyl acetate (3×30 mL). The combined organic extracts were washed with brine (2×30 mL), dried over anhydrous sodium sulfate, filtered and concentrated in vacuo. Purification of the residue by column chromatography eluted with a 0% to 35% gradient of ethyl acetate in hexanes afforded 3-(2,2-difluoro-6-hydroxy-1,3-benzodioxol-5-yl)-3-hydroxy-1-{[5-(trifluoromethyl)furan-2-yl]methyl}-1,3-dihydro-2H-indol-2-one (2.54 g, 73%) as a pale orange solid: MS (ES+) 451.3 (M−17).

B. Synthesis of 3-(2,2-difluoro-6-hydroxy-1,3-benzodioxol-5-yl)-1-{[5-(trifluoromethyl)furan-2-yl]methyl}-1,3-dihydro-2H-indol-2-one To a solution of 3-(2,2-difluoro-6-hydroxy-1,3-benzodioxol-5-yl)-3-hydroxy-1-{[5-(trifluoromethyl)furan-2-yl]methyl}-1,3-dihydro-2H-indol-2-one (2.50 g, 5.32 mmol) in anhydrous dichloromethane (10 mL) at 0° C. was added triethylsilane (4.2 mL, 26 mmol) and trifluoroacetic acid (12 mL). The reaction mixture was allowed to warm to ambient temperature and was stirred for 72 h and was concentrated in vacuo. Purification of the residue by column chromatography and eluted with a 0% to 30% gradient of ethyl acetate in hexanes afforded 3-(2,2-difluoro-6-hydroxy-1,3-benzodioxol-5-yl)-1-{[5-(trifluoromethyl)furan-2-yl]methyl}-1,3-dihydro-2H-indol-2-one (1.81 g, 75%) as a colorless amorphous solid: MS (ES+) m/z 454.2 (M+1).

Preparation 72

Synthesis of 3-(2,2-difluoro-6-hydroxy-1,3-benzodioxol-5-yl)-1-methyl-1,3-dihydro-2H-indol-2-one A. Synthesis of 3-(2,2-difluoro-6-hydroxy-1,3-benzodioxol-5-yl)-3-hydroxy-1-(methoxymethyl)-1,3-dihydro-2H-indol-2-one Following the procedure as described in PREPARATION 71A and making non-critical variations using 1-(methoxymethyl)-1H-indole-2,3-dione (Trost and Frederiksen, *Angew. Chem. Intl. Ed. Engl.* 2005, 44(2):308-310) to replace 1-{[5-(trifluoromethyl)furan-2-yl]methyl}-1H-indole-2,3-dione, 3-(2,2-difluoro-6-hydroxy-1,3-benzodioxol-5-yl)-3-hydroxy-1-(methoxymethyl)-1,3-dihydro-2H-indol-2-one was obtained (48%) as a tan amorphous solid: $^1$H NMR (300 MHz, CDCl$_3$) δ9.20 (br s, 1H), 7.50-7.40 (m, 2H), 7.29-7.21 (m, 1H), 7.13 (d, J=7.7 Hz, 1H), 6.77 (s, 1H), 6.53 (s, 1H), 4.45 (br s, 1H), 5.15-5.04 (m, 2H), 3.30 (s, 3H).

B. Synthesis of 3-(2,2-difluoro-6-hydroxy-1,3-benzodioxol-5-yl)-1-methyl-1,3-dihydro-2H-indol-2-one Following the procedure as described in PREPARATION 71B and making non-critical variations using 3-(2,2-difluoro-6-hydroxy-1,3-benzodioxol-5-yl)-3-hydroxy-1-(methoxymethyl)-1,3-dihydro-2H-indol-2-one to replace 3-(2,2-difluoro-6-hydroxy-1,3-benzodioxol-5-yl)-3-hydroxy-1-{[5-(trifluoromethyl)furan-2-yl]methyl}-1,3-dihydro-2H-indol-2-one, 3-(2,2-difluoro-6-hydroxy-1,3-benzodioxol-5-yl)-1-methyl-1,3-dihydro-2H-indol-2-one was obtained (85%) as a colorless amorphous solid: $^1$H NMR (300 MHz, CDCl$_3$) δ 7.47-7.40 (m, 1H), 7.37-7.31 (m, 1H), 7.28-7.20 (m, 2H), 6.99 (d, J=7.8 Hz, 1H), 6.85 (s, 1H), 6.60 (s, 1H), 5.10 (s, 1H), 3.25 (s, 3H); MS (ES+) m/z 320.1 (M+1).

Preparation 73

Synthesis of 3-(2,2-difluoro-6-hydroxy-1,3-benzodioxol-5-yl)-1-{[3-(trifluoromethyl)pyridin-2-yl]methyl}-1,3-dihydro-2H-indol-2-one A. Synthesis of 1-{[3-(trifluoromethyl)pyridin-2-yl]methyl}-1H-indole-2,3-dione To a cooled (0° C.) solution of 1H-indole-2,3-dione (2.08 g, 14.1 mmol) in anhydrous N,N-dimethylformamide (40 mL) was added sodium hydride (60% dispersion in mineral oil, 1.18 g, 29.6 mmol) and the resultant purple suspension was stirred at 0° C. for 15 min. To the aforementioned suspension was added, via cannula over a period of 10 min, a solution of 2-(chloromethyl)-6-(trifluoromethyl)pyridine hydrochloride (Li, J. WO 2006/34004) (3.27 g, 14.1 mmol) in anhydrous N,N-dimethylformamide (20 mL). The reaction mixture was allowed to warm to ambient temperature, stirred for 2.5 h and poured into a cooled (0° C.), well-stirred mixture of brine (60 mL) and water (60 mL). The resultant orange suspension was sonicated for 5 min, allowed to warm to ambient temperature and filtered. The filter cake was washed with water (100 mL) and hexanes (100 mL), air-dried and dried under high vacuum to afford 1-{[3-(trifluoromethyl)pyridin-2-yl]methyl}-1H-indole-2,3-dione (3.21 g, 74%) as an orange solid: $^1$H NMR (300 MHz, CDCl$_3$) δ 8.59 (d, J=4.8 Hz, 1H), 8.00 (d, J=7.9 Hz, 1H), 7.65 (d, J=7.9 Hz, 1H), 7.49-7.42 (m, 1H), 7.37-7.30 (m, 1H), 7.12-7.06 (m, 1H), 6.59 (d, J=7.9 Hz, 1H), 5.24 (s, 2H); MS (ES+) m/z 307.3 (M+1).

B. Synthesis of 3-(2,2-difluoro-6-hydroxy-1,3-benzodioxol-5-yl)-3-hydroxy-1-{[3-(trifluoromethyl)pyridin-2-yl]methyl}-1,3-dihydro-2H-indol-2-one Following the procedure described in PREPARATION 71A and making non-critical variations using 1-{[3-(trifluoromethyl)pyridin-2-yl]methyl}-1H-indole-2,3-dione to replace 1-{[5-(trifluoromethyl)furan-2-yl]methyl}-1H-indole-2,3-dione, 3-(2,2-difluoro-6-hydroxy-1,3-benzodioxol-5-yl)-3-hydroxy-1-{[3-(trifluoromethyl)pyridin-2-yl]methyl}-1,3-dihydro-2H-indol-2-one was obtained (32%) as a tan amorphous solid: MS (ES+) m/z 481.2 (M+1).

C. Synthesis of 3-(2,2-difluoro-6-hydroxy-1,3-benzodioxol-5-yl)-1-{[3-(trifluoromethyl)pyridin-2-yl]methyl}-1,3-dihydro-2H-indol-2-one Following the procedure described in PREPARATION 71B and making non-critical variations using 3-(2,2-difluoro-6-hydroxy-1,3-benzodioxol-5-yl)-3-hydroxy-1-{[3-(trifluoromethyl)pyridin-2-yl]methyl}-1,3-dihydro-2H-indol-2-one to replace 3-(2,2-difluoro-6-hydroxy-1,3-benzodioxol-5-yl)-3-hydroxy-1-{[5-(trifluoromethyl)furan-2-yl]methyl}-1,3-dihydro-2H-indol-2-one, 3-(2,2-difluoro-6-hydroxy-1,3-benzodioxol-5-yl)-1-{[3-(trifluoromethyl)pyridin-2-yl]methyl}-1,3-dihydro-2H-indol-2-one was obtained (91%) as a colorless amorphous solid: MS (ES+) m/z 465.2 (M+1).

Preparation 74

Synthesis of 6-(diphenylmethyl)-8-(6-hydroxy-2,3-dihydro-1-benzofuran-5-yl)-2,3,6,8-tetrahydro-7H-[1,4]dioxino[2,3-f]indol-7-one A. Synthesis of 6-(diphenylmethyl)-2,3-dihydro-6H-[1,4]dioxino[2,3-f]indole-7,8-dione To a cooled (0° C.) solution of 2,3-dihydro-6H-[1,4]dioxino[2,3-f]indole-7,8-dione (Lackey and Sternbach, Synthesis 1993:993-997) (1.73 g, 8.42 mmol) in anhydrous N,N-dimethylformamide (28 mL) was added sodium hydride (60% in mineral oil, 0.37 g, 9.26 mmol). The mixture was stirred at ambient temperature for 1 h and bromodiphenylmethane (2.39 g, 9.69 mmol) was added. After stirring at ambient temperature for 16 h, further bromodiphenylmethane (0.42 g, 1.68 mmol) was added. The mixture was stirred at ambient temperature for 8 h and then diluted with water (200 mL) and ethyl acetate (200 mL). The layers were separated and the aqueous layer was extracted with ethyl acetate (2×100 mL). The combined organic layers were washed with brine (150 mL), dried over anhydrous magnesium sulfate, filtered, concentrated in vacuo. The residue was purified by column chromatography, eluted with a 35% to 50% gradient of ethyl acetate in hexanes to afford 6-(diphenylmethyl)-2,3-dihydro-6H-[1,4]dioxino[2,3-f]indole-7,8-dione (0.7 g, 22%) as a red solid: $^1$H NMR (300 MHz, CDCl$_3$) δ 7.41-7.28 (m, 10H), 7.16 (s, 1H), 6.94-6.91 (m, 1H), 5.96 (s, 1H), 4.27-4.14 (m, 4H); MS (ES+) m/z 371.9 (M+1).

B. Synthesis of 6-(diphenylmethyl)-8-hydroxy-8-(6-hydroxy-2,3-dihydro-1-benzofuran-5-yl)-2,3,6,8-tetrahydro-7H-[1,4]dioxino[2,3-f]indol-7-one Following the procedure as described in PREPARATION 2A and making non-critical variations using 2,3-dihydrobenzofuran-6-ol to replace 3-bromophenol, and 6-(diphenylmethyl)-2,3-dihydro-6H-[1,4]dioxino[2,3-f]indole-7,8-dione to replace 1-((5-(trifluoromethyl)furan-2-yl)methyl)indoline-2,3-dione, 6-(diphenylmethyl)-8-hydroxy-8-(6-hydroxy-2,3-dihydro-1-benzofuran-5-yl)-2,3,6,8-tetrahydro-7H-[1,4]dioxino[2,3-f]indol-7-one was obtained (94%) as a colorless solid: MS (ES−) m/z 506.1 (M−1).

C. Synthesis of 6-(diphenylmethyl)-8-(6-hydroxy-2,3-dihydro-1-benzofuran-5-yl)-2,3,6,8-tetrahydro-7H-[1,4]dioxino[2,3-f]indol-7-one A mixture of 6-(diphenylmethyl)-8-hydroxy-8-(6-hydroxy-2,3-dihydro-1-benzofuran-5-yl)-2,3,6,8-tetrahydro-7H-[1,4]dioxino[2,3-f]indol-7-one (0.78 g, 1.5 mmol), triethylsilane (1.2 mL) and trifluoroacetic acid (1.2 mL) in dichloromethane (10 mL) was stirred at 0° C. for 1 h and then at ambient temperature for 1 h. The mixture was concentrated in vacuo to afford crude 6-(diphenylmethyl)-8-(6-hydroxy-2,3-dihydro-1-benzofuran-5-yl)-2,3,6,8-tetrahydro-7H-[1,4]dioxino[2,3-f]indol-7-one (100%): MS (ES+) m/z 492.1 (M+1).

Preparation 75

Synthesis of 1-(6-hydroxy-2,3-dihydro-1-benzofuran-5-yl)-3-(4-methoxybenzyl)-1,3-dihydro-2H-pyrrolo[3,2-f]quinolin-2-one A. Synthesis of 3-(4-methoxybenzyl)-1H-pyrrolo[3,2-f]quinoline-1,2(3H)-dione To a stirred solution of 1H-pyrrolo[3,2-f]quinoline-1,2 (3H)-dione (Bramson, H. N. et al. *J. Med. Chem.* 2001, 44

(25):4339-4358) (0.15 g, 0.76 mmol) in dry N,N-dimethylformamide (10 mL) was added sodium hydride (60% in mineral oil, 0.04 g, 0.98 mmol) at ambient temperature. The mixture was stirred at ambient temperature for 1 h and 4-methoxybenzyl bromide (0.16 mL, 1.1 mmol) was added. The mixture was stirred at ambient temperature for 16 h and was diluted with water (100 mL) and ethyl acetate (100 mL). The layers were separated and the aqueous layer was extracted with ethyl acetate (2×50 mL). The combined organic layers were washed with brine (50 mL), dried over anhydrous magnesium sulfate, filtered and concentrated in vacuo. The residue was purified by column chromatography eluted with a 50% to 65% gradient of ethyl acetate in hexanes to afford 3-(4-methoxybenzyl)-1H-pyrrolo[3,2-f]quinoline-1,2(3H)-dione (0.20 g, 82%) as a red solid: MS (ES+) m/z 319.0 (M+1).

C. Synthesis of 1-hydroxy-1-(6-hydroxy-2,3-dihydro-1-benzofuran-5-yl)-3-(4-methoxybenzyl)-1,3-dihydro-2H-pyrrolo[3,2-f]quinolin-2-one Following the procedure as described in PREPARATION 2A and making non-critical variations using 2,3-dihydrobenzofuran-6-ol to replace 3-bromophenol, and 3-(4-methoxybenzyl)-1H-pyrrolo[3,2-f]quinoline-1,2(3H)-dione to replace 1-((5-(trifluoromethyl)furan-2-yl)methyl)indoline-2,3-dione, 1-hydroxy-1-(6-hydroxy-2,3-dihydro-1-benzofuran-5-yl)-3-(4-methoxybenzyl)-1,3-dihydro-2H-pyrrolo[3,2-f]quinolin-2-one was obtained (58%) as a colorless solid: MS (ES+) m/z 455.0 (M+1).

D. Synthesis of 1-(6-hydroxy-2,3-dihydro-1-benzofuran-5-yl)-3-(4-methoxybenzyl)-1,3-dihydro-2H-pyrrolo[3,2-f]quinolin-2-one Following the procedure as described in PREPARATION 74C and making non-critical variations using 1-hydroxy-1-(6-hydroxy-2,3-dihydro-1-benzofuran-5-yl)-3-(4-methoxybenzyl)-1,3-dihydro-2H-pyrrolo[3,2-f]quinolin-2-one to replace 6-(diphenylmethyl)-8-hydroxy-8-(6-hydroxy-2,3-dihydro-1-benzofuran-5-yl)-2,3,6,8-tetrahydro-7H-[1,4]dioxino[2,3-f]indol-7-one, 1-(6-hydroxy-2,3-dihydro-1-benzofuran-5-yl)-3-(4-methoxybenzyl)-1,3-dihydro-2H-pyrrolo[3,2-f]quinolin-2-one was obtained (37%) as a colorless solid: MS (ES+) m/z 438.9 (M+1).

Preparation 76

Synthesis of 2,4-dihydroxy-5-[1-(4-methoxybenzyl)-2-oxo-2,3-dihydro-1H-indol-3-yl]benzonitrile

A. Synthesis of 2,4-dihydroxy-5-[3-hydroxy-1-(4-methoxybenzyl)-2-oxo-2,3-dihydro-1H-indol-3-yl]benzonitrile To a stirred solution of 2,4-dihydroxybenzonitrile (4.33 g, 32.1 mmol) in tetrahydrofuran (50 mL) and 1,2-dichloroethane (400 mL) was added isopropylmagnesium chloride (17.7 mL, 2.0 M solution in tetrahydrofuran, 35.4 mmol) at 0° C. The mixture was stirred at 0° C. for 1 h and at ambient temperature for 2 h, and 1-(4-methoxybenzyl)-1H-indole-2,3-dione (8.58 g, 32.1 mmol) was added to the reaction mixture. The mixture was stirred at reflux for 18 h, cooled to 0° C. and 5% v/v hydrochloric acid was added. The organic layer was separated and washed with water and brine, dried over anhydrous sodium sulfate and filtered. The filtrate was concentrated in vacuo. The residue was subjected to column chromatography and eluted with ethyl acetate/hexanes (1/1) to afford 2,4-dihydroxy-5-[3-hydroxy-1-(4-methoxybenzyl)-2-oxo-2,3-dihydro-1H-indol-3-yl]benzonitrile (10.30 g, 79%): $^1$H NMR (300 MHz, DMSO-$d_6$) δ 10.81 (s, 1H), 10.35 (s, 1H), 7.80 (s, 1H), 7.32 (d, J=9.0 Hz, 1H), 7.14-7.08 (m, 1H), 6.88-6.84 (m, 4H), 6.75-6.72 (m, 1H), 6.63 (s, 1H), 6.30 (s, 1H), 4.79 (ABq, 2H), 3.70 (s, 3H); MS (ES+) m/z 384.8 (M−17).

B. Synthesis of 2,4-dihydroxy-5-[1'-(4-methoxybenzyl)-2-oxo-2,3-dihydro-1H-indol-3-yl]benzonitrile To a stirred suspension of 2,4-dihydroxy-5-[3-hydroxy-1-(4-methoxybenzyl)-2-oxo-2,3-dihydro-1H-indol-3-yl]benzonitrile (10.3 g, 25.5 mmol) and triethylsilane (12.3 mL, 77.0 mmol) in dichloromethane (100 mL) was added trifluoroacetic acid (10.0 mL, 129 mmol). The reaction mixture was stirred at ambient temperature for 18 h and concentrated in vacuo. The residue was triturated in hexanes to afford 2,4-dihydroxy-5-[1-(4-methoxybenzyl)-2-oxo-2,3-dihydro-1H-indol-3-yl]benzonitrile (9.70 g, 98%): mp 162-163° C. (hexanes); $^1$H NMR (300 MHz, CDCl$_3$) δ 10.84 (s, 1H), 10.47 (s, 1H), 7.39 (s, 1H), 7.28 (d, J=9.0 Hz, 2H), 7.13-7.08 (m, 1H), 6.93-6.78 (m, 5H), 6.43 (s, 1H), 5.72 (s, 1H), 4.92-4.73 (m, 3H), 3.69 (s, 3H); MS (ES+) m/z 386.9 (M+1).

Preparation 77

Synthesis of 2-fluoro-4-hydroxy-5-[1-(4-methoxybenzyl)-2-oxo-2,3-dihydro-1H-indol-3-yl]benzonitrile

A. Synthesis of 2-fluoro-4-hydroxy-5-[3-hydroxy-1-(4-methoxybenzyl)-2-oxo-2,3-dihydro-1H-indol-3-yl]benzonitrile To a stirred solution of 2-fluoro-4-hydroxybenzonitrile (8.00 g, 58.3 mmol) in 1,2-dichloroethane (500 mL) and tetrahydrofuran (50 mL) was added isopropylmagnesium chloride (29.2 mL, 2.0 M solution in tetrahydrofuran, 58.4 mmol) at 0° C. The mixture was stirred at 0° C. for 1 h and at ambient temperature for 2 h. 1-(4-methoxybenzyl)-1H-indole-2,3-dione (15.0 g, 56.1 mmol) was added and the reaction mixture was stirred at reflux for 156 h. The mixture was cooled to 0° C. and 10% w/v hydrochloric acid was added. The phases were separated and the aqueous layer was extracted with dichloromethane (100 mL). The combined organic extracts were washed with water and brine, dried over anhydrous sodium sulfate and filtered. The filtrate was concentrated in vacuo. The residue was subjected to column chromatography and eluted with ethyl acetate/hexanes (1/1) to afford 2-fluoro-4-hydroxy-5-[3-hydroxy-1-(4-methoxybenzyl)-2-oxo-2,3-dihydro-1H-indol-3-yl]benzonitrile (12.30 g, 54%): $^1$H NMR (300 MHz, DMSO-$d_6$) δ 8.05 (d, J=9.0 Hz, 1H), 7.34-7.32 (m, 2H), 7.17-7.11 (m, 1H), 6.91-6.76 (m, 7H), 4.78 (ABq, 2H), 3.72 (s, 3H); MS (ES+) m/z 404.9 (M+1).

B. Synthesis of 2-fluoro-4-hydroxy-5-[1-(4-methoxybenzyl)-2-oxo-2,3-dihydro-1H-indol-3-yl]benzonitrile To a stirred suspension of 2-fluoro-4-hydroxy-5-[3-hydroxy-1-(4-methoxybenzyl)-2-oxo-2,3-dihydro-1H-indol-3-yl]benzonitrile (12.0 g, 29.7 mmol) in triethylsilane (14.2 mL, 88.9 mmol) was added trifluoroacetic acid (10.0 mL, 129 mmol). The reaction mixture was stirred at ambient temperature for 168 h and concentrated in vacuo. The residue was recrystallized from ethyl acetate/hexanes to afford 2-fluoro-4-hydroxy-5-[1-(4-methoxybenzyl)-2-oxo-2,3-dihydro-1H-indol-3-yl]benzonitrile (10.5 g, 90%): $^1$H NMR (300 MHz, CDCl$_3$) δ 7.37-7.12 (m, 7H), 6.94 (d, J=6.0 Hz, 1H), 6.85-6.79 (m, 3H), 5.07 (s, 1H), 4.88 (ABq, 2H), 3.75 (s, 3H); MS (ES+) m/z 388.9 (M+1).

Preparation 78

Synthesis of 3-(5-hydroxy-3-methyl-1,2-benzisoxazol-6-yl)-1-(4-methoxybenzyl)-1,3-dihydro-2H-indol-2-one A. Synthesis of 3-hydroxy-3-(5-hydroxy-3-methyl-1,2-benzisoxazol-6-yl)-1-(4-methoxybenzyl)-1,3-dihydro-2H-indol-2-one To a stirred solution of 3-methyl-1,2-benzisoxazol-5-ol (Lindemann, et al *Justus Liebigs Annalen der Chemie* 1927, 456:308) (3.10 g, 20.8 mmol) in 1,2-dichloroethane (200 mL) was added isopropylmagnesium chloride (10.4 mL, 2.0 M solution in tetrahydrofuran, 20.8 mmol) at 0° C. The mixture was stirred at 0° C. for 1 h and then at ambient temperature for 2 h. 1-(4-methoxybenzyl)-1H-indole-2,3-dione (5.3 g, 19.8 mmol) was added and the reaction mixture was stirred at reflux for 120 h. The mixture was cooled to 0° C. and 5% w/v hydrochloric acid was added. The organic phase was separated, washed with water and brine, dried over anhydrous sodium sulfate and filtered. The filtrate was concentrated in vacuo. The residue was subjected to column chromatography eluted with ethyl acetate/hexanes (1/1) to afford 3-hydroxy-3-(5-hydroxy-3-methyl-1,2-benzisoxazol-6-yl)-1-(4-methoxybenzyl)-1,3-dihydro-2H-indol-2-one (0.87 g, 10%): $^1$H NMR (300 MHz, DMSO-d$_6$) δ 9.68 (s, 1H), 8.01 (s, 1H), 7.37-6.76 (m, 10H), 4.83 (ABq, 2H), 3.70 (s, 3H), 2.46 (s, 3H); MS (ES+) m/z 415.0 (M−1).

B. Synthesis of 3-(5-hydroxy-3-methyl-1,2-benzisoxazol-6-yl)-1-(4-methoxybenzyl)-1,3-dihydro-2H-indol-2-one To a stirred suspension of 3-hydroxy-3-(5-hydroxy-3-methyl-1,2-benzisoxazol-6-yl)-1-(4-methoxybenzyl)-1,3-dihydro-2H-indol-2-one (0.84 g; 2.0 mmol) in triethylsilane (3.0 mL, 18.7 mmol) was added trifluoroacetic acid (15.0 mL). The reaction mixture was stirred at 50° C. for 26 h, allowed to cool to ambient temperature and concentrated in vacuo. The residue was recrystallized from ethyl acetate/hexanes to afford 3-(5-hydroxy-3-methyl-1,2-benzisoxazol-6-yl)-1-(4-methoxybenzyl)-1,3-dihydro-2H-indol-2-one (0.74 g, 92%): $^1$H NMR (300 MHz, CDCl$_3$) δ 7.34-6.80 (m, 10H), 5.29 (s, 1H), 4.87 (ABq, 2H), 3.74 (s, 3H), 2.45 (s, 3H); MS (ES+) m/z 400.9 (M+1).

Preparation 79

Synthesis of 4-bromo-3-(7-hydroxy-2,3-dihydro-1,4-benzodioxin-6-yl)-1-methyl-1,3-dihydro-2H-indol-2-one A. Synthesis of 4-bromo-1-methyl-1H-indole-2,3-dione To a stirred solution of 4-bromoisatin (90.4 g, 400 mmol) in N,N-dimethylformamide (400 mL) was added cesium carbonate (196.0 g, 600 mol) at ambient temperature. The reaction mixture was stirred for 30 min, iodomethane (37.4 mL, 600 mmol) was added and the mixture was stirred at ambient temperature for 18 h. The solid was removed by filtration, the filtrate was concentrated in vacuo, and the residue was triturated in water and washed with diethyl ether to afford 4-bromo-1-methyl-1H-indole-2,3-dione (82.0 g, 85%): $^1$H NMR (300 MHz, DMSO-d$_6$) δ 7.95-7.89 (m, 1H), 7.68-7.64 (m, 1H), 7.53-7.49 (m, 1H), 3.50 (s, 3H).

B. Synthesis of 4-bromo-3-hydroxy-3-(7-hydroxy-2,3-dihydro-1,4-benzodioxin-6-yl)-1-methyl-1,3-dihydro-2H-indol-2-one To a stirred solution of 2,3-dihydro-1,4-benzodioxin-6-ol (36.0 g, 230 mmol) in dichloromethane (1000 mL) was added isopropylmagnesium chloride (120 mL, 2.0 M solution in tetrahydrofuran, 240 mmol) at 0° C. The mixture was allowed to stir at 0° C. for 1 h and 4-bromo-1-methyl-1H-indole-2,3-dione (48.0 g, 200 mmol) was added. The reaction mixture was stirred at ambient temperature for 22 h and 5% w/v hydrochloric acid was added at 0° C. The organic layer was separated, washed with water and brine, dried over anhydrous sodium sulfate and filtered. The filtrate was concentrated in vacuo and the residue was triturated in methanol and washed with diethyl ether to afford 4-bromo-3-hydroxy-3-(7-hydroxy-2,3-dihydro-1,4-benzodioxin-6-yl)-1-methyl-1,3-dihydro-2H-indol-2-one (63.4 g, 80%): $^1$H NMR (300 MHz, DMSO-d$_6$) δ 8.80 (s, 1H), 7.21-7.13 (m, 2H), 7.01-6.93 (m, 2H), 6.45 (s, 1H), 6.03 (s, 1H), 4.17-4.10 (m, 4H), 3.08 (s, 3H); MS (ES+) m/z 373.8 (M−17), 375.8 (M−17).

C. Synthesis of 4-bromo-3-(7-hydroxy-2,3-dihydro-1,4-benzodioxin-6-yl)-1-methyl-1,3-dihydro-2H-indol-2-one To a stirred solution of 4-bromo-3-hydroxy-3-(7-hydroxy-2,3-dihydro-1,4-benzodioxin-6-yl)-1-methyl-1,3-dihydro-2H-indol-2-one (61.0 g; 155 mmol) and triethylsilane (75.0 mL, 456 mmol) in dichloromethane (300 mL) was added trifluoroacetic acid (48 mL, 623 mmol) at 0° C. The reaction mixture was stirred at ambient temperature for 20 h and concentrated in vacuo. The residue was triturated in methanol and washed with diethyl ether to afford 4-bromo-3-(7-hydroxy-2,3-dihydro-1,4-benzodioxin-6-yl)-1-methyl-1,3-dihydro-2H-indol-2-one (57.0 g, 97%): $^1$H NMR (300 MHz, CDCl$_3$) δ 7.31-7.17 (m, 3H), 6.87-6.83 (m, 1H), 6.62 (s, 1H), 6.17 (s, 1H), 4.97 (s, 1H), 4.22-4.08 (m, 4H), 3.18 (s, 3H); MS (ES+) m/z 376.1 (M+1), 378.1 (M+1).

Preparation 80

Synthesis of methyl 6-methyl-8-(2-nitrophenyl)-7-oxo-2,3,7,8-tetrahydro-6H-[1,4]dioxino[2,3-f]indole-8-carboxylate A. Synthesis of 6-methyl-2,3-dihydro-6H-[1,4]dioxino[2,3-f]indole-7,8-dione Following the procedure as described in PREPARATION 79A, and making non-critical variations using 2,3-dihydro-6H-[1,4]dioxino[2,3-f]indole-7,8-dione to replace 4-bromoisatin, 6-methyl-2,3-dihydro-6H-[1,4]dioxino[2,3-f]indole-7,8-dione was obtained (68%): $^1$H NMR (300 MHz, CDCl$_3$) δ 7.09 (s, 1H), 6.74 (s, 1H), 4.41-4.38 (m, 2H), 4.27-4.24 (m, 2H), 3.08 (s, 3H); $^{13}$C NMR (75 MHz, CDCl$_3$)$_8$; MS (ES+) m/z 220.2 (M+1).

B. Synthesis of 6-methyl-2,3,6,8-tetrahydro-7H-[1,4]dioxino[2,3-f]indol-7-one To a solution of 6-methyl-2,3-dihydro-6H-[1,4]dioxino[2,3-f]indole-7,8-dione (3.00 g, 13.7 mmol) in 1,4-dioxane (25 mL) was added hydrazine monohydrate (25 mL). The reaction mixture was stirred at reflux for 4 h, allowed to cool to ambient temperature, diluted with ethyl acetate, washed with water and brine, dried over anhydrous sodium sulfate and filtered. The filtrate was concentrated in vacuo. The residue was recrystallized from ethyl acetate/hexanes to afford 6-methyl-2,3,6,8-tetrahydro-7H-[1,4]dioxino[2,3-f]indol-7-one (2.46 g, 87%): $^1$H NMR (300 MHz, CDCl$_3$) δ 6.75 (s, 1H), 6.49 (s, 1H), 4.19-4.12 (m, 4H), 3.36 (s, 2H), 3.00 (s, 3H); MS (ES+) m/z 206.2 (M+1).

C. Synthesis of 6-methyl-8-(2-nitrophenyl)-2,3,6,8-tetrahydro-7H-[1,4]dioxino[2,3-f]indol-7-one To a stirred solution of 6-methyl-2,3,6,8-tetrahydro-7H-[1,4]dioxino[2,3-f]indol-7-one (1.03 g, 5.01 mmol) in N,N-dimethylformamide (10 mL) was added sodium hydride (60% w/w dispersion in mineral oil, 0.26 g, 6.5 mmol) at 0° C. The reaction mixture was stirred at 0° C. for 30 min, 1-fluoro-2-nitrobenzene (0.70 mL, 6.6 mmol) was added and the mixture was stirred at ambient temperature for 18 h, 10% w/v hydrochloric acid (10 mL) was added at 0° C. and the mixture was extracted with ethyl acetate (3×50 mL). The combined organic extracts were washed with water and brine, dried over anhydrous sodium sulfate and filtered. The filtrate was concentrated in vacuo. The residue was purified by column chromatography and eluted with ethyl acetate/hexanes (1/2) to afford 6-methyl-8-(2-nitrophenyl)-2,3,6,8-tetrahydro-7H-[1,4]dioxino[2,3-f]indol-7-one (0.41 g, 24%): $^1$H NMR (300 MHz, CDCl$_3$) δ 8.05-8.01 (m, 1H), 7.58-7.51 (m, 1H), 7.49-7.42 (m, 1H), 7.23-7.19 (m, 1H), 6.69 (s, 1H), 6.45 (s, 1H), 5.28 (s, 1H), 4.28-4.18 (m, 4H), 3.21 (s, 3H).

D. Synthesis of methyl 6-methyl-8-(2-nitrophenyl)-7-oxo-2,3,7,8-tetrahydro-6H-[1,4]dioxino[2,3-f]indole-8-carboxylate To a stirred solution of 6-methyl-8-(2-nitrophenyl)-2,3,6,8-tetrahydro-7H-[1,4]dioxino[2,3-f]indol-7-one (0.40 g, 1.2 mmol) in tetrahydrofuran (10 mL) was added lithium bis(trimethylsilyl)amide (1.0 M solution in tetrahydrofuran, 1.5 mL, 1.5 mmol) at 0° C. The reaction mixture was stirred at 0° C. for 10 min, methyl cyanoformate (0.12 mL, 1.5 mmol) was added and the mixture was stirred at ambient temperature for 18 h. 10% w/v hydrochloric acid (5 mL) was added at 0° C. and the mixture was extracted with ethyl acetate (3×50 mL). The combined organic extracts were washed with water and brine, dried over anhydrous sodium sulfate and filtered. The filtrate was concentrated in vacuo. The residue was purified by column chromatography and eluted with ethyl acetate/hexanes (1/2) to afford methyl 6-methyl-8-(2-nitrophenyl)-7-oxo-2,3,7,8-tetrahydro-6H-[1,4]dioxino[2,3-f]indole-8-carboxylate (0.21 g, 44%): $^1$H NMR (300 MHz, CDCl$_3$) δ 7.92-7.89 (m, 1H), 7.48-7.37 (m, 2H), 7.20-7.19 (m, 1H), 6.97 (s, 1H), 6.41 (s, 1H), 4.21-4.14 (m, 4H), 3.65 (s, 3H), 3.12 (s, 3H).

Preparation 81

Synthesis of 4-bromo-1-(diphenylmethyl)-3-(7-hydroxy-2,3-dihydro-1,4-benzodioxin-6-yl)-1,3-dihydro-2H-indol-2-one

A. Synthesis of 4-bromo-benzhydrylindoline-2,3-dione

Following the procedure as described in PREPARATION 26A and making non-critical variations using 4-bromoisatin to replace 2,3-dihydro-6H-[1,4]dioxino[2,3-f]indole-7,8-dione, and bromodiphenylmethane to replace 2-(bromomethyl)-5-(trifluoromethyl)furan, 4-bromo-benzhydrylindoline-2,3-dione was obtained (78%) as a red solid: MS (ES+) m/z 413.8 (M+23), 415.8 (M+23).

B. Synthesis of 4-bromo-1-(diphenylmethyl)-3-hydroxy-3-(7-hydroxy-2,3-dihydro-1,4-benzodioxin-6-yl)-1,3-dihydro-2H-indol-2-one Following the procedure as described in PREPARATION 2A and making non-critical variations using 2,3-dihydro-1,4-benzodioxin-6-ol to replace 3-bromophenol, and 4-bromo-1-benzhydrylindoline-2,3-dione to replace 1-((5-(trifluoromethyl)furan-2-yl)methyl)indoline-2,3-dione, 4-bromo-1-(diphenylmethyl)-3-hydroxy-3-(7-hydroxy-2,3-dihydro-1,4-benzodioxin-6-yl)-1,3-dihydro-2H-indol-2-one was obtained (99%) as a colorless solid: $^1$H NMR (300 MHz, DMSO-d$_6$) δ9.06 (s, 1H), 7.44-7.28 (m, 10H), 6.98-6.82 (m, 2H), 6.68 (s, 1H), 6.33 (d, J=7.4 Hz, 1H), 6.16 (s, 1H), 4.23-4.08 (m, 4H); MS (ES+) m/z 566.1 (M+23), 568.1 (M+23).

C. Synthesis of 4-bromo-1-(diphenylmethyl)-3-(7-hydroxy-2,3-dihydro-1,4-benzodioxin-6-yl)-1,3-dihydro-2H-indol-2-one Following the procedure as described in PREPARATION 4C, and making non-critical variations using 4-bromo-1-(diphenylmethyl)-3-hydroxy-3-(7-hydroxy-2,3-dihydro-1,4-benzodioxin-6-yl)-1,3-dihydro-2H-indol-2-one to replace 4-chloro-1-(diphenylmethyl)-3-hydroxy-3-(6-hydroxy-2,3-dihydro-1-benzofuran-5-yl)-1,3-dihydro-2H-indol-2-one, 4-bromo-1-(diphenylmethyl)-3-(7-hydroxy-2,3-dihydro-1,4-benzodioxin-6-yl)-1,3-dihydro-2H-indol-2-one was obtained (86%): as a yellow solid: $^1$H NMR (300 MHz, DMSO-d$_6$) δ9.05 (s, 1H), 7.42-7.28 (m, 10H), 6.98-6.87 (m, 3H), 6.68 (s, 1H), 6.33 (d, J=7.6 Hz, 1H), 6.16 (s, 1H), 4.22-4.16 (m, 4H).

Preparation 82

Synthesis of 1-(diphenylmethyl)-4-fluoro-3-(7-hydroxy-2,3-dihydro-1,4-benzodioxin-6-yl)-1,3-dihydro-2H-indol-2-one

A. Synthesis of 1-(diphenylmethyl)-4-fluoro-1H-indole-2,3-dione

To a solution of 1-(diphenylmethyl)-3-iodo-4-fluoroindole (8.85 g, 20.7 mmol) in a mixture of acetonitrile (25 mL) and water (5 mL) was added ruthenium (III) chloride monohydrate (0.30 g, 1.45 mmol) and sodium periodate (13.3 g, 62.2 mmol). The reaction mixture was stirred at ambient tempera ture for 16 h. The reaction mixture was diluted with ethyl acetate (100 mL), washed with water (3×25 mL), saturated aqueous ammonium chloride (3×25 mL) and brine (3×25 mL), dried over anhydrous sodium sulfate, filtered and concentrated in vacuo. The residue was crystallized from acetonitrile to afford 1-(diphenylmethyl)-4-fluoro-1H-indole-2,3-dione (1.73 g, 25%) as an orange solid: mp 168-171° C.; $^1$H NMR (300 MHz, DMSO-d$_6$) δ 7.49-7.41 (m, 1H), 7.38-7.28 (m, 10H), 6.86 (dd, J=8.8, 8.8 Hz, 1H), 6.80 (s, 1H), 6.45 (d, J=8.1 Hz, 1H); $^{13}$C NMR (75 MHz, DMSO-d$_6$) δ 178.3, 157.8, 157.7 (d, 1J$_{C-F}$=261.0 Hz), 150.6 (d, $^3$J$_{C-F}$=6.0 Hz), 139.7 (d, 2J$_{C-F}$=10.0 Hz), 137.0, 128.5, 128.3, 127.8, 110.7 (d, $^2$J$_{C-F}$=19.5 Hz), 108.8 (d, $^4$J$_{C-F}$=2.9 Hz), 106.4 (d, $^3$J$_{C-F}$=18.2 Hz), 28.7; MS (ES+) m/z 332.2 (M+23).

B. Synthesis of 1-(diphenylmethyl)-4-fluoro-3-hydroxy-3-(7-hydroxy-2,3-dihydro-1,4-benzodioxin-6-yl)-1,3-dihydro-2H-indol-2-one Following the procedure as described in PREPARATION 1A and making non-critical variations using 2,3-dihydrobenzo[b][1,4]dioxin-6-ol to replace 2-methylbenzo[d]thiazol-5-ol, and 1-(diphenylmethyl)-4-fluoro-1H-indole-2,3-dione to replace isatin, 1-(diphenylmethyl)-4-fluoro-3-hydroxy-3-(7-hydroxy-2,3-dihydro-1,4-benzodioxin-6-yl)-1,3-dihydro-2H-indol-2-one was obtained (83%) as a colourless solid: mp 209-211° C. (dec.); $^1$H NMR (300 MHz, DMSO-d$_6$) δ 9.15 (s, 1H), 7.43-7.27 (m, 11H), 7.01 (ddd, J=8.2, 8.2, 5.9 Hz, 1H), 6.87 (s, 1H), 6.79 (s, 1H), 6.61 (dd, J=8.8, 8.8 Hz, 1H), 6.21 (s, 1H), 6.16 (d, J=7.9 Hz, 1H), 4.25-4.14 (m, 4H); $^{13}$C NMR (75 MHz, DMSO-d$_6$) δ 176.2, 157.9 (d, $^1$J=248 Hz), 147.1, 145.0 (d, $^3$J$_{C-F}$=8.7 Hz), 142.7, 137.7 (d, 2J$_{C-F}$=30.9 Hz), 135.4, 130.1 (d, $^3$J$_{C-F}$=8.7 Hz), 128.4 (d, $^3$J$_{C-F}$=13.9 Hz), 128.3 (d, $^3$J$_{C-F}$=8.4 Hz), 127.5 (d, $^3$J$_{C-F}$=11.9 Hz), 119.4, 117.9 (d, $^2$J$_{C-F}$=18.9 Hz), 116.1, 109.3 (d, $^2$J$_{C-F}$=20.3 Hz), 107.2 (d, $^4$J$_{C-F}$=2.1 Hz), 103.1, 73.0, 64.2, 63.7, 57.5; MS (ES+) m/z 506.0 (M+23).

C. Synthesis of 1-(diphenylmethyl)-4-fluoro-3-(7-hydroxy-2,3-dihydro-1,4-benzodioxin-6-yl)-1,3-dihydro-2H-indol-2-one To a solution of 1-(diphenylmethyl)-4-fluoro-3-hydroxy-3-(7-hydroxy-2,3-dihydro-1,4-benzodioxin-6-yl)-1,3-dihydro-2H-indol-2-one (1.74 g, 3.60 mmol) in dichloromethane (40 mL) was added trifluoroacetic acid (1.64 g, 14.4 mmol) and triethylsilane (1.68 g, 14.4 mL). The reaction mixture was stirred at ambient temperature for 16 h and concentrated in vacuo. The residue was purified by column chromatography and eluted with a gradient of ethyl acetate in hexanes to afford 1-(diphenylmethyl)-4-fluoro-3-(7-hydroxy-2,3-dihydro-1,4-benzodioxin-6-yl)-1,3-dihydro-2H-indol-2-one (1.54 g, 92%) as a colourless solid: mp 115-118° C.; $^1$H NMR (300 MHz, DMSO-d$_6$) δ 9.17 (s, 1H), 7.42-7.26 (m, 11H), 7.01 (ddd, J=8.2, 8.2, 5.9 Hz, 1H), 6.91 (s, 1H), 6.67 (dd, J=8.8, 8.8 Hz, 1H), 6.27 (s, 1H), 6.23 (d, J=7.9 Hz, 1H), 4.99 (s, 1H), 4.20-4.14 (m, 4H); $^{13}$C NMR (75 MHz, DMSO-d$_6$) δ 176.2, 157.9 (d, $^1$J$_{C-F}$=248 Hz), 147.1, 145.0 (d, $^3$J$_{C-F}$=8.7 Hz), 142.7, 137.7 (d, $^2$J$_{C-F}$=30.9 Hz), 135.4, 130.1 (d, $^3$J$_{C-F}$=8.7 Hz), 128.4 (d, $^3$J$_{C-F}$=13.9 Hz), 128.3 (d, $^3$J$_{C-F}$=8.4 Hz), 127.5 (d, $^3$J$_{C-F}$=11.9 Hz), 119.4, 117.9 (d, $^2$J$_{C-F}$=18.9 Hz), 116.1, 109.3 (d, $^2$J$_{C-F}$=20.3 Hz), 107.2 (d, $^4$J$_{C-F}$=2.1 Hz), 103.1, 73.0, 64.2, 63.7, 57.5; MS (ES+) m/z 467.9 (M+1)

Preparation 83

Synthesis of 1-(4-fluorophenyl)-3-(7-hydroxy-2,3-dihydro-1,4-benzodioxin-6-yl)-1,3-dihydro-2H-indol-2-one A. Synthesis of 1-(4-fluorophenyl)-3-hydroxy-3-(7-hydroxy-2,3-dihydro-1,4-benzodioxin-6-yl)-1,3-dihydro-2H-indol-2-one Following the procedure as described in PREPARATION 1A and making non-critical variations using 2,3-dihydrobenzo[b][1,4]dioxin-6-ol to replace 2-methylbenzo[d]thiazol-5-ol, and 1-(4-fluorophenyl)indoline-2,3-dione (Coppola, G. M *Journal of Heterocyclic Chemistry* 1987, (24): 1249) to replace isatin, 1-(4-fluorophenyl)-3-hydroxy-3-(7-hydroxy-2,3-dihydro-1,4-benzodioxin-6-yl)-1,3-dihydro-2H-indol-2-one was obtained (23%) as a beige solid: mp 195-200° C.; $^1$H NMR (300 MHz, DMSO-d$_6$) δ 7.12 (s, 1H), 7.47-7.41 (m, 4H), 7.26 (s, 1H), 7.21-7.16 (m, 1H), 7.01-6.93 (m, 2H), 6.68 (d, J=7.8 Hz, 1H), 6.63 (s, 1H), 6.14 (s, 1H), 4.23-4.14 (m, 4H); $^{13}$C NMR (75 MHz, DMSO-d$_6$) δ 176.3, 160.9 (d, $^1$J$_{C-F}$=245 Hz), 147.1, 143.9, 142.6, 135.6, 132.0, 131.2 (d, $^4$J$_{C-F}$=2.9 Hz), 128.6 (d, $^3$J$_{C-F}$=8 Hz), 124.0, 122.4, 121.2, 116.4 (d, $^2$J$_{C-F}$=22.8 Hz), 115.1, 108.2, 103.4, 74.4, 64.3, 63.7, 57.2; MS (ES+) m/z 390.0 (M+1).

B. Synthesis of 1-(4-Fluorophenyl)-3-(7-hydroxy-2,3-dihydro-1,4-benzodioxin-6-yl)-1,3-dihydro-2H-indol-2-one Following the procedure as described in PREPARATION 82C and making non-critical variations using 1-(4-fluorophenyl)-3-hydroxy-3-(7-hydroxy-2,3-dihydro-1,4-benzodioxin-6-yl)-1,3-dihydro-2H-indol-2-one to replace 1-(diphenylmethyl)-4-fluoro-3-hydroxy-3-(7-hydroxy-2,3-dihydro-1,4-benzodioxin-6-yl)-1,3-dihydro-2H-indol-2-one, 1-(4-fluorophenyl)-3-(7-hydroxy-2,3-dihydro-1,4-benzodioxin-6-yl)-1,3-dihydro-2H-indol-2-one was obtained (59%) as a colourless solid: $^1$H NMR (300 MHz, DMSO-d$_6$) δ 9.16 (s, 1H), 7.51-7.39 (m, 4H), 7.17 (dd, J=7.6 Hz, 7.6 Hz, 1H), 7.05-6.96 (m, 2H), 6.67 (s, 1H), 6.68 (d, J=7.8 Hz, 1H), 6.27 (s, 1H), 4.84 (s, 1H), 4.19-4.12 (m, 4H): MS (ES+) m/z 378.2 (M+1).

Preparation 84

Synthesis of 4-(chloromethyl)-1-fluoro-2-methoxybenzene

To a solution of (4-fluoro-3-methoxyphenyl)methanol (Claudi, et al., J. Med. Chem. 1990, 33(9):2408) (0.90 g, 5.76 mmol) in anhydrous dichloromethane (10 mL) was added thionyl chloride (0.84 mL, 12 mmol) and anhydrous N,N-dimethylformamide (2 drops). The reaction mixture was stirred at ambient temperature for 16 h and concentrated in vacuo to afford 4-(chloromethyl)-1-fluoro-2-methoxybenzene (0.73 g, 72%) as a brown oil: $^1$H NMR (300 MHz, CDCl$_3$) δ 7.05-6.86 (m, 3H), 4.53 (s, 2H), 3.88 (s, 3H).

Preparation 85

Synthesis of 2-(chloromethyl)-3,5-difluoropyridine hydrochloride

To a solution of (3,5-difluoropyridin-2-yl)methanol (Almedia et al., WO 08/117,050) (2.15 g, 14.8 mmol) in dichloromethane (20 mL) at 0° C. was added N,N-dimethylformamide (2 drops) and thionyl chloride (2.0 mL, 27 mmol). The solution was stirred at ambient temperature for 1 h and concentrated in vacuo to afford 2-(chloromethyl)-3,5-difluoropyridine hydrochloride (2.31 g, 78%) as a brown oil: Rf=0.71 (EtOAc/Hexanes, 1/1).

Preparation 86

Synthesis of 2-(chloromethyl)-4-fluoropyridine hydrochloride

To a solution of methyl 4-fluoropicolinate (0.50 g, 3.20 mmol) in tetrahydrofuran (20 mL) at −78° C. was added slowly lithium aluminum hydride (0.15 g, 4.00 mmol). The solution was stirred at −78° C. for 2 h and water (1 mL) was added. The reaction mixture was allowed to warm to ambient temperature, dried over magnesium sulfate, filtered and concentrated in vacuo to afford (4-fluoropyridin-2-yl)methanol as a pale yellow oil. To a solution of this oil in dichloromethane (10 mL) was added thionyl chloride (1.0 mL, 13 mmol) and the solution was stirred at ambient temperature for 16 h. The solution was concentrated in vacuo to afford 2-(chloromethyl)-4-fluoropyridine hydrochloride (0.42 g, 71%) as a beige solid: $^1$H NMR (300 MHz, CDCl$_3$) δ 8.53-8.47 (m, 1H), 7.04-6.90 (m, 2H), 4.74 (s, 2H).

Preparation 87

Synthesis of 5-bromo-3-(7-hydroxy-2,3-dihydro-1,4-benzodioxin-6-yl)-1-(pyridin-2-ylmethyl)-1,3-dihydro-2H-indol-2-one A. Synthesis of 5-bromo-1-(pyridin-2-ylmethyl)-1H-indole-2,3-dione To a solution of 5-bromoisatin (10.0 g, 44.4 mmol) in anhydrous N,N-dimethylformamide (100 mL) at 0° C. was added slowly sodium hydride (60% w/w dispersion in mineral oil, 3.90 g, 97.7 mmol). The solution was stirred for 30 min and 2-(bromomethyl)pyridine hydrobromide (11.2 g, 44.4 mmol) was added. The solution was stirred at ambient temperature for 16 h and poured into ice water (1.3 L) with vigourous stirring, causing a precipitate to be deposited. The solid was collected by filtration to afford 5-bromo-1-(pyridin-2-ylmethyl)-1H-indole-2,3-dione (4.93 g, 35%) as a orange solid: $^1$H NMR (300 MHz, CDCl$_3$) δ 8.55-8.50 (m, 1H), 7.72-7.56 (m, 1H), 7.34-7.28 (m, 1H), 7.25-7.18 (m, 1H), 6.93-6.88 (m, 1H), 5.03-4.99 (m, 2H).

B. Synthesis of 5-bromo-3-hydroxy-3-(7-hydroxy-2,3-dihydro-1,4-benzodioxin-6-yl)-1-(pyridin-2-ylmethyl)-1,3-dihydro-2H-indol-2-one To a solution of 2,3-dihydrobenzo[b][1,4]dioxin-6-ol (2.55 g, 16.8 mmol) in anhydrous dichloromethane (100 mL) at 0° C. added isopropylmagnesium chloride (2 M solution in tetrahydrofuran, 10.0 mL, 19.9 mmol). The solution was stirred at 0° C. for 20 min and 5-bromo-1-(pyridin-2-ylmethyl)-1H-indole-2,3-dione (4.85 g, 15.3 mmol) was added. The reaction mixture was stirred at ambient temperature for 16 h, saturated aqueous ammonium chloride (25 mL) was added and the mixture was concentrated in vacuo. The residue was triturated with ethyl acetate (250 mL) and the solid collected by filtration to afford 5-bromo-3-hydroxy-3-(7-hydroxy-2,3-dihydro-1,4-benzodioxin-6-yl)-1-(pyridin-2-ylmethyl)-1,3-dihydro-2H-indol-2-one (7.26 g, 98%) as a beige solid: $^1$H NMR (300 MHz, DMSO-d$_6$) δ 9.20 (s, 1H), 8.71 (d, J=4.9 Hz, 1H), 8.06 (dd, J=7.80 Hz, 1H), 7.63-7.55 (m, 2H), 7.52 (d, J=8.0 Hz, 1H), 7.35 (dd, J=8.3, 2.0 Hz, 1H), 7.20 (s, 1H), 6.99 (d, J=2.0 Hz, 1H), 6.82 (d, J=8.3 Hz, 1H), 6.16 (s, 2H), 5.09 (ABq, 2H), 4.20-4.10 (m, 4H).

C. Synthesis of 5-bromo-3-(7-hydroxy-2,3-dihydro-1,4-benzodioxin-6-yl)-1-(pyridin-2-ylmethyl)-1,3-dihydro-2H-indol-2-one To a suspension of 5-bromo-3-hydroxy-3-(7-hydroxy-2,3-dihydro-1,4-benzodioxin-6-yl)-1-(pyridin-2-ylmethyl)-1,3-dihydro-2H-indol-2-one (3.60 g, 8.10 mmol) in triethylsilane (10 mL) at 0° C. was added trifluoroacetic acid (40 mL). The solution was allowed to warm to ambient temperature over 2 h and was stirred for a further 4 h. The reaction mixture was concentrated in vacuo and saturated aqueous sodium bicarbonate and ethyl acetate were added to the residue, causing a precipitate to be deposited. The solid was collected by filtration and washed sequentially with diethyl ether and hexanes to afford 5-bromo-3-(7-hydroxy-2,3-dihydro-1,4-benzodioxin-6-yl)-1-(pyridin-2-ylmethyl)-1,3-dihydro-2H-indol-2-one (4.03 g, 100%) as a pale yellow solid: $^1$H NMR (300 MHz, DMSO-d$_6$) δ 8.59-8.55 (m, 1H), 7.90-7.80 (m, 1H), 7.44-7.37 (m, 1H), 7.34-7.27 (m, 1H), 7.07 (s, 1H), 6.82-6.68 (m, 2H), 6.27 (s, 1H), 5.17-4.93 (m, 2H), 4.84 (s, 1H), 4.23-4.06 (m, 4H). MS (ES+) m/z 452.9 (M+1), 454.9 (M+1).

Preparation 88

Synthesis of 5-bromo-1-(diphenylmethyl)-3-(7-hydroxy-2,3-dihydro-1,4-benzodioxin-6-yl)-1,3-dihydro-2H-indol-2-one A. Synthesis of 5-bromo-1-(diphenylmethyl)-1H-indole-2,3-dione Following the procedure as described in PREPARATION 26A and making non-critical variations using 5-bromoisatin to replace 2,3-dihydro-6H-[1,4]dioxino[2,3-f]indole-7,8-dione, and bromodiphenylmethane to replace 2-(bromomethyl)-5-(trifluoromethyl)furan, 5-bromo-1-(diphenylmethyl)-1H-indole-2,3-dione was obtained (76%): $^1$H NMR (300 MHz, CDCl$_3$) δ 7.74-7.67 (m, 1H), 7.46-7.20 (m, 11H), 6.96 (s, 1H), 6.37 (d, J=8.5 Hz, 1H).

B. Synthesis of 5-bromo-1-(diphenylmethyl)-3-hydroxy-3-(7-hydroxy-2,3-dihydro-1,4-benzodioxin-6-yl)-1,3-dihydro-2H-indol-2-one Following the procedure as described in PREPARATION 87B and making non-critical variations using 5-bromo-1-(diphenylmethyl)-1H-indole-2,3-dione to replace 5-bromo-1-(pyridin-2-ylmethyl)-1H-indole-2,3-dione, 5-bromo-1-(diphenylmethyl)-3-hydroxy-3-(7-hydroxy-2,3-dihydro-1,4-benzodioxin-6-yl)-1,3-dihydro-2H-indol-2-one was obtained (64%) as a pale yellow solid: MS (ES+) m/z 525.9 (M−17), 527.9 (M−17).

C. Synthesis of 5-bromo-1-(diphenylmethyl)-3-(7-hydroxy-2,3-dihydro-1,4-benzodioxin-6-yl)-1,3-dihydro-2H-indol-2-one Following the procedure as described in PREPARATION 82C and making non-critical variations using 5-bromo-1-(diphenylmethyl)-3-hydroxy-3-(7-hydroxy-2,3-dihydro-1,4-benzodioxin-6-yl)-1,3-dihydro-2H-indol-2-one to replace 1-(diphenylmethyl)-4-fluoro-3-hydroxy-3-(7-hydroxy-2,3-dihydro-1,4-benzodioxin-6-yl)-1,3-dihydro-2H-indol-2-one, 5-bromo-1-(diphenylmethyl)-3-(7-hydroxy-2,3-dihydro-1,4-benzodioxin-6-yl)-1,3-dihydro-2H-indol-2-one was obtained (85%) as a colorless solid: MS (ES+) m/z 527.8 (M+1), 529.8 (M+1).

Preparation 89

Synthesis of 1-(diphenylmethyl)-3-(5-fluoro-7-hydroxy-2,3-dihydro-1,4-benzodioxin-6-yl)-1,3-dihydro-2H-indol-2-one A. Synthesis of 7-bromo-5-fluoro-2,3-dihydrobenzo[b][1,4]dioxine A solution of 5-fluoro-2,3-dihydrobenzo[b][1,4]dioxine (1.54 g, 10.0 mmol) and 1-bromopyrrolidine-2,5-dione (1.8 g, 10 mmol) in methanol (20 mL) was heated at reflux for 0.5 h, allowed to cool to ambient temperature and concentrated in vacuo. The residue was taken up in dichloromethane (50 mL) and washed with water (50 mL). The organic phase was dried over magnesium sulfate, filtered and concentrated in vacuo. Purification of the residue by column chromatography eluted with a 0% to 30% gradient of ethyl acetate in hexanes afforded 7-bromo-5-fluoro-2,3-dihydrobenzo[b][1,4]dioxine (2.04 g, 87%) as a colorless solid: MS (ES+) m/z 233.6 (M+1).

B. Synthesis of 8-fluoro-2,3-dihydrobenzo[b][1,4]dioxin-6-ol

To a solution of 7-bromo-5-fluoro-2,3-dihydrobenzo[b][1,4]dioxine (15.1 g, 64.8 mmol) in tetrahydrofuran (160 mL) at −78° C. was added a 1.6 M solution of n-butyllithium in hexanes (45 mL, 73 mmol). The reaction mixture was stirred at −78° C. for 15 min and trimethyl borate (8.5 g, 82 mmol) was added. The reaction mixture was allowed to warm to ambient temperature, stirred for 48 h and cooled to 5° C. 35% w/w aqueous hydrogen peroxide (12.6 mL, 129.6 mmol) was added, the reaction mixture was allowed to warm to ambient temperature and stirred for 3 h. The reaction mixture was diluted with ethyl acetate (200 mL) and the organic phase was washed with 1 M hydrochloric acid (50 mL) and brine (50 mL), dried over magnesium sulfate, filtered and concentrated in vacuo. Purification of the residue by column chromatography eluted with a 0% to 70% gradient of ethyl acetate in hexanes afforded 8-fluoro-2,3-dihydrobenzo[b][1,4]dioxin-6-ol (6.5 g, 59%) as a colorless solid: MS (ES+) m/z 153.0 (M−17).

C. Synthesis of 1-(diphenylmethyl)-3-(5-fluoro-7-hydroxy-2,3-dihydro-1,4-benzodioxin-6-yl)-3-hydroxy-1,3-dihydro-2H-indol-2-one A 100 mL round-bottom flask was charged with 8-fluoro-2,3-dihydrobenzo[b][1,4]dioxin-6-ol (6.4 g, 37 mmol) and tetrahydrofuran (60 mL). A 2 M solution of isopropylmagnesium chloride in tetrahydrofuran (20.0 mL, 40.0 mmol) was added at 5° C. and the reaction mixture was stirred for 15 min. The reaction mixture was concentrated in vacuo and dichloromethane (60 mL) was added, followed by a solution of 1-(diphenylmethyl)-1H-indole-2,3-dione (10.9 g, 35.0 mmol) in dichloromethane (60 mL). The reaction mixture was heated at reflux for 5 h, allowed to cool to ambient temperature and stirred for a further 16 h. Saturated aqueous ammonium chloride (30 mL) was added and the phases were separated. The organic phase was dried over magnesium sulfate, filtered and concentrated in vacuo.

Trituration of the residue in methanol (30 mL) afforded 1-(diphenylmethyl)-3-(5-fluoro-7-hydroxy-2,3-dihydro-1,4-benzodioxin-6-yl)-3-hydroxy-1,3-dihydro-2H-indol-2-one (10.8 g, 64%) as an off-white solid: MS (ES+) m/z 506.0 (M+23).

D. Synthesis of 1-(diphenylmethyl)-3-(5-fluoro-7-hydroxy-2,3-dihydro-1,4-benzodioxin-6-yl)-1,3-dihydro-2H-indol-2-one Following the procedure as described in PREPARATION 82C and making non-critical variations using 1-(diphenylmethyl)-3-(5-fluoro-7-hydroxy-2,3-dihydro-1,4-benzodioxin-6-yl)-3-hydroxy-1,3-dihydro-2H-indol-2-one to replace 1-(diphenylmethyl)-4-fluoro-3-hydroxy-3-(7-hydroxy-2,3-dihydro-1,4-benzodioxin-6-yl)-1,3-dihydro-2H-indol-2-one, 1-(diphenylmethyl)-3-(5-fluoro-7-hydroxy-2,3-dihydro-1,4-benzodioxin-6-yl)-1,3-dihydro-2H-indol-2-one was obtained (85%) as an off-white solid: MS (ES+) m/z 467.9 (M+1).

Preparation 90

Synthesis of 1-(diphenylmethyl)-3-(6-hydroxy-3,4-dihydro-2H-chromen-7-yl)-1,3-dihydro-2H-indol-2-one A 500 mL round-bottom flask was charged with chroman-6-ol (9.2 g, 61 mmol) and tetrahydrofuran (120 mL). A 2 M solution of isopropylmagnesium chloride in tetrahydrofuran (32.5 mL, 65.0 mmol) was added at 5° C. and the reaction mixture was stirred for 15 min and concentrated in vacuo. To the residue was added dichloromethane (180 mL), followed by a solution of 1-(diphenylmethyl)-1H-indole-2,3-dione (18.8 g, 60.0 mmol) in dichloromethane (180 mL) at 5° C. The reaction mixture was allowed to warm to ambient temperature and stirred for 24 h. Saturated aqueous ammonium chloride (7 mL) was added and the reaction mixture was concentrated in vacuo. Trituration of the residue in methanol/water (1/100, 200 mL) afforded 1-(diphenylmethyl)-3-hydroxy-3-(6-hydroxy-3,4-dihydro-2H-chromen-7-yl)-1,3-dihydro-2H-indol-2-one. A mixture of the 1-(diphenylmethyl)-3-hydroxy-3-(6-hydroxy-3,4-dihydro-2H-chromen-7-yl)-1,3-dihydro-2H-indol-2-one, triethylsilane (23.2 g, 200 mmol), trifluoroacetic acid (50.0 g, 438 mmol) and dichloromethane (200 mL) was stirred at ambient temperature for 20 h and concentrated in vacuo. Trituration of the residue in diethyl ether (150 mL) afforded 1-(diphenylmethyl)-3-(6-hydroxy-3,4-dihydro-2H-chromen-7-yl)-1,3-dihydro-2H-indol-2-one (24.3 g, 90%) as an off-white solid: MS (ES+) m/z 448.0 (M+1).

Preparation 91

Synthesis of 1-(diphenylmethyl)-3-(5-hydroxy-1-benzothiophene-6-yl)-1,3-dihydro-2H-indol-2-one A. Synthesis of 1-(diphenylmethyl)-3-hydroxy-3-(5-hydroxy-1-benzothiophene-6-yl)-1,3-dihydro-2H-indol-2-one To a solution of benzo[b]thiophen-5-ol (1.39 g, 9.25 mmol) in tetrahydrofuran (50 mL) at 5° C. was added a 2 M solution of isopropylmagnesium chloride in tetrahydrofuran (5.0 mL, 10 mmol). The reaction mixture was stirred at 5° C. for 15 min and concentrated in vacuo. To the residue were added 1,2-dichloroethane (100 mL) and 1-(diphenylmethyl)-1H-indole-2,3-dione (2.5 g, 8.0 mmol). The reaction mixture was heated at reflux for 3 h, allowed to cool to ambient temperature and stirred for 48 h. Saturated aqueous ammonium chloride (10 mL) was added and the phases were separated. The organic phase was dried over magnesium sulfate, filtered and concentrated in vacuo. The residue was purified by column chromatography and eluted with a 0% to 20% gradient of ethyl acetate in dichloromethane to afford 1-(diphenylmethyl)-3-hydroxy-3-(5-hydroxy-1-benzothiophen-6-yl)-1,3-dihydro-2H-indol-2-one (2.2 g, 59%) as an off-white solid: MS (ES+) m/z 486.0 (M+23).

B. Synthesis of 1-(diphenylmethyl)-3-(5-hydroxy-1-benzothiophen-6-yl)-1,3-dihydro-2H-indol-2-one Following the procedure as described in PREPARATION 82C and making non-critical variations using 1-(diphenylmethyl)-3-hydroxy-3-(5-hydroxy-1-benzothiophen-6-yl)-1,3-dihydro-2H-indol-2-one to replace 1-(diphenylmethyl)-4-fluoro-3-hydroxy-3-(7-hydroxy-2,3-dihydro-1,4-benzodioxin-6-yl)-1,3-dihydro-2H-indol-2-one, 1-(diphenylmethyl)-3-(5-hydroxy-1-benzothiophen-6-yl)-1,3-dihydro-2H-indol-2-one was obtained (94%) as an off-white solid: MS (ES+) m/z 448.1 (M+1).

Preparation 92

Synthesis of 1-(diphenylmethyl)-3-(5-hydroxy-2,1,3-benzoxadiazol-4-yl)-1,3-dihydro-2H-indol-2-one A. Synthesis of 1-(diphenylmethyl)-3-hydroxy-3-(5-hydroxy-2,1,3-benzoxadiazol-4-yl)-1,3-dihydro-2H-indol-2-one Following the procedure as described in PREPARATION 2A and making non-critical variations using 2,1,3-benzoxadiazol-5-ol to replace 3-bromophenol, and 1-(diphenylmethyl)-1H-indole-2,3-dione to replace 1-((5-(trifluoromethyl)furan-2-yl)methyl)indoline-2,3-dione, 1-(diphenylmethyl)-3-hydroxy-3-(5-hydroxy-2,1,3-benzoxadiazol-4-yl)-1,3-dihydro-2H-indol-2-one was obtained (71%) as a colorless solid: MS (ES+) m/z 472.0 (M+23).

B. Synthesis of 1-(diphenylmethyl)-3-(5-hydroxy-2,1,3-benzoxadiazol-4-yl)-1,3-dihydro-2H-indol-2-one A mixture of 1-(diphenylmethyl)-3-hydroxy-3-(5-hydroxy-2,1,3-benzoxadiazol-4-yl)-1,3-dihydro-2H-indol-2-one (21.8 g, 48.5 mmol), triethylsilane (50 mL) and trifluoroacetic acid (100.mL) was stirred at ambient temperature for 16 h, then heated to 45° C. for 1.5 h. The mixture was allowed to cool to ambient temperature and concentrated in vacuo. The residue was triturated with diethyl ether to afford 1-(diphenylmethyl)-3-(5-hydroxy-2,1,3-benzoxadiazol-4-yl)-1,3-dihydro-2H-indol-2-one (10.94 g, 52%) as a colorless solid: $^1$H NMR (300 MHz, CDCl$_3$) δ10.90-10.00 (br s, 1H), 7.61-7.31 (m, 10H), 7.18 (s, 1H), 7.06-6.89 (m, 4H), 6.55 (d, J=8.4 Hz, 1H), 6.45 (d, J=9.6 Hz, 1H), 5.57 (s, 1H); MS (ES+) m/z 456.0 (M+23).

Preparation 93

Synthesis of 3-(7-chloro-6-hydroxy-2,3-dihydro-1,4-benzodioxin-5-yl)-1-(diphenylmethyl)-1,3-dihydro-2H-indol-2-one A. Synthesis of 7-chloro-2,3-dihydrobenzo[b][1,4]dioxin-6-ol To a solution of 6-hydroxy-1,4-benzodioxane (1.52 g, 10 mmol) in N,N-dimethylformamide (10 mL) was added N-chlorosuccinimide (1.33 g, 10 mmol) at ambient temperature. The solution was stirred at ambient temperature for 16 h and concentrated in vacuo. The residue was purified by column chromatography and eluted with a 15% to 30% gradient of ethyl acetate in hexanes to afford 7-chloro-2,3-dihydrobenzo[b][1,4]dioxin-6-ol (1.79 g, 96%) as a colorless solid: $^1$H NMR (300 MHz, CDCl$_3$) δ8.02 (s, 1H), 6.83 (s, 1H), 6.56 (s, 1H), 4.27-4.16 (m, 4H).

B. Synthesis of 3-(7-chloro-6-hydroxy-2,3-dihydro-1,4-benzodioxin-5-yl)-1-(diphenylmethyl)-3-hydroxy-1,3-dihydro-2H-indol-2-one Following the procedure as described in PREPARATION 2A and making non-critical variations using 7-chloro-2,3-dihydrobenzo[b][1,4]dioxin-6-ol to replace 3-bromophenol, and 1-(diphenylmethyl)-1H-indole-2,3-dione to replace 1-((5-(trifluoromethyl)furan-2-yl)methyl)indoline-2,3-dione, 3-(7-chloro-6-hydroxy-2,3-dihydro-1,4-benzodioxin-5-yl)-1-(diphenylmethyl)-3-hydroxy-1,3-dihydro-2H-indol-2-one was obtained (18%) as a colorless solid: MS (ES+) m/z 522.1 (M+23), 524.1 (M+23).

C. Synthesis of 3-(7-chloro-6-hydroxy-2,3-dihydro-1,4-benzodioxin-5-yl)-1-(diphenylmethyl)-1,3-dihydro-2H-indol-2-one Following the procedure as described in PREPARATION 2B, and making non-critical variations using 3-(7-chloro-6-hydroxy-2,3-dihydro-1,4-benzodioxin-5-yl)-1-(diphenylmethyl)-3-hydroxy-1,3-dihydro-2H-indol-2-one to replace 3-(4-bromo-2-hydroxyphenyl)-3-hydroxy-1-{[5-(trifluoromethyl)furan-2-yl]methyl}-1,3-dihydro-2H-indol-2-one, 3-(7-chloro-6-hydroxy-2,3-dihydro-1,4-benzodioxin-5-yl)-1-(diphenylmethyl)-1,3-dihydro-2H-indol-2-one was obtained (74%) as a colorless solid: $^1$H NMR (300 MHz, CDCl$_3$) δ7.44-7.27 (m, 10H), 7.08-6.78 (m, 4H), 6.49-6.42 (m, 1H), 5.76 (s, 0.5H), 5.30 (s, 0.5H), 5.27 (s, 0.5H), 5.03 (s, 0.5H), 4.39-4.25 (m, 2H), 4.06-3.90 (m, 1H), 3.75-3.50 (m, 1H); MS (ES+) m/z 484.3 (M+1), 486.3 (M+1).

Preparation 94

Synthesis of 3-(4,5-difluoro-2-hydroxyphenyl)-1-(diphenylmethyl)-1,3-dihydro-2H-indol-2-one A. Synthesis of 3-(4,5-difluoro-2-hydroxyphenyl)-1-(diphenylmethyl)-3-hydroxy-1,3-dihydro-2H-indol-2-one Following the procedure as described in PREPARATION 2A and making non-critical variations using 3,4-difluorophenol to replace 3-bromophenol, and 1-(diphenylmethyl)-1H-indole-2,3-dione to replace 1-((5-(trifluoromethyl)furan-2-yl)methylindoline-2,3-dione, 3-(4,5-difluoro-2-hydroxyphenyl)-1-(diphenylmethyl)-3-hydroxy-1,3- dihydro-2H-indol-2-one was obtained (61%) as a colorless solid: $^1$H NMR (300 MHz, CDCl$_3$) δ 9.23 (br s, 1H), 7.47-7.44 (m, 1H), 7.35-7.21 (m, 9H), 7.18-7.11 (m, 2H), 6.90 (s, 1H), 6.83 (dd, J=11.2, 6.9 Hz, 1H), 6.67 (dd, J=11.2, 8.7 Hz, 1H), 6.56-6.51 (m, 1H), 4.13 (br s, 1H); MS (ES+) m/z 426.2 (M−17).

B. Synthesis of 3-(4,5-difluoro-2-hydroxyphenyl)-1-(diphenylmethyl)-1,3-dihydro-2H-indol-2-one Following the procedure as described in PREPARATION 2B, and making non-critical variations using 3-(4,5-difluoro-2-hydroxyphenyl)-1-(diphenylmethyl)-3-hydroxy-1,3-dihydro-2H-indol-2-one to replace 3-(4-bromo-2-hydroxyphenyl)-3-hydroxy-1-{[5-(trifluoromethyl)furan-2-yl]methyl}-1,3-dihydro-2H-indol-2-one, 3-(4,5-difluoro-2-hydroxyphenyl)-1-(diphenylmethyl)-1,3-dihydro-2H-indol-2-one was obtained (56%) as an off-white solid: $^1$H NMR (300 MHz, CDCl$_3$) δ 9.27 (br s, 1H), 7.37-7.12 (m, 12H), 6.94 (s, 1H), 6.87 (dd, J=11.3, 7.1 Hz, 1H), 6.76 (dd, J=11.2, 8.9 Hz, 1H), 6.58-6.56 (m, 1H), 5.12 (s, 1H); MS (ES+) m/z 428.2 (M+1).

Preparation 95

Synthesis of 1-(diphenylmethyl)-3-(3-hydroxy-5,6,7,8-tetrahydronaphthalen-2-yl)-1,3-dihydro-2H-indol-2-one

A. Synthesis of 1-(diphenylmethyl)-3-hydroxy-3-(3-hydroxy-5,6,7,8-tetrahydronaphthalen-2-yl)-1,3-dihydro-2H-indol-2-one Following the procedure as described in PREPARATION 2A and making non-critical variations using 5,6,7,8-tetrahydro-2-naphthol to replace 3-bromophenol, and 1-(diphenylmethyl)-1H-indole-2,3-dione to replace 1-((5-(trifluoromethyl)furan-2-yl)methyl)indoline-2,3-dione, 1-(diphenylmethyl)-3-hydroxy-3-(3-hydroxy-5,6,7,8-tetrahydronaphthalen-2-yl)-1,3-dihydro-2H-indol-2-one was obtained (76%) as a colorless solid: $^1$H NMR (300 MHz, CDCl$_3$) δ 8.73 (s, 1H), 7.52-7.49 (m, 1H), 7.32-7.28 (m, 10H), 7.09 (dd, J=5.6, 3.2 Hz, 2H), 6.95 (s, 1H), 6.75 (s, 1H), 6.51-6.48 (m, 2H), 4.31 (s, 1H), 2.70 (br s, 2H), 2.52 (br s, 2H), 1.72 (br s, 4H); MS (ES+) m/z 444.1 (M−17).

B. Synthesis of 1-(diphenylmethyl)-3-(3-hydroxy-5,6,7,8-tetrahydronaphthalen-2-yl)-1,3-dihydro-2H-indol-2-one Following the procedure as described in PREPARATION 2B, and making non-critical variations using 1-(diphenylmethyl)-3-hydroxy-3-(3-hydroxy-5,6,7,8-tetrahydronaphthalen-2-yl)-1,3-dihydro-2H-indol-2-one to replace 3-(4-bromo-2-hydroxyphenyl)-3-hydroxy-1-{[5-(trifluoromethyl)furan-2-yl]methyl}-1,3-dihydro-2H-indol-2-one, 1-(diphenylmethyl)-3-(3-hydroxy-5,6,7,8-tetrahydronaphthalen-2-yl)-1,3-dihydro-2H-indol-2-one was obtained (71%) as a colorless solid: $^1$H NMR (300 MHz, CDCl$_3$) δ 8.41 (s, 1H), 7.33-7.29 (m, 9H), 7.24-7.22 (m, 2H), 7.10-7.07 (m, 2H), 6.98 (s, 1H), 6.80 (s, 1H), 6.64 (s, 1H), 6.56-6.53 (m, 1H), 5.13 (s, 1H), 2.73 (br s, 2H), 2.60-2.56 (m, 2H), 1.74 (br s, 4H); MS (ES+) m/z 446.0 (M+1).

Preparation 96

Synthesis of 3-(7-hydroxy-2,3-dihydro-1,4-benzodioxin-6-yl)-4,5-dimethoxy-1-{[5-(trifluoromethyl)furan-2-yl]methyl}-1,3-dihydro-2H-indol-2-one

A. Synthesis of 4,5-dimethoxy-1-{[5-(trifluoromethyl)furan-2-yl]methyl}-1H-indole-2,3-dione Following the procedure as described in PREPARATION 26A and making non-critical variations using 4,5-dimethoxyindolin-2,3-dione to replace 2,3-dihydro-6H-[1,4]dioxino[2,3-f]indole-7,8-dione, 4,5-dimethoxy-1-{[5-(trifluoromethyl)furan-2-yl]methyl}-1H-indole-2,3-dione was obtained (51%) as a red solid: $^1$H NMR (300 MHz, DMSO-d$_6$) δ 7.22 (d, J=8.5 Hz, 1H), 7.17-7.12 (m, 1H), 6.77-6.70 (m, 2H), 4.94 (s, 2H), 3.96 (s, 3H), 3.72 (s, 3H).

B. Synthesis of 3-hydroxy-3-(7-hydroxy-2,3-dihydro-1,4-benzodioxin-6-O-4,5-dimethoxy-1-{[5-(trifluoromethyl)furan-2-yl]methyl}-1,3-dihydro-2H-indol-2-one Following the procedure as described in PREPARATION 2A and making non-critical variations using 2,3-dihydrobenzo[b][1,4]dioxin-6-ol to replace 3-bromophenol, and 4,5-dimethoxy-1-{[5-(trifluoromethyl)furan-2-yl]methyl}-1H-indole-2,3-dione to replace 1-((5-(trifluoromethyl)furan-2-yl)methyl)indoline-2,3-dione, 3-hydroxy-3-(7-hydroxy-2,3-dihydro-1,4-benzodioxin-6-yl)-4,5-dimethoxy-1-{[5-(trifluoromethyl)furan-2-yl]methyl}-1,3-dihydro-2H-indol-2-one was obtained (67%) as a colorless solid: $^1$H NMR (300 MHz, CDCl$_3$) δ 8.59 (s, 1H), 6.88 (d, J=8.4 Hz, 1H), 6.71-6.65 (m, 1H), 6.61 (d, J=8.4 Hz, 1H), 6.54 (s, 1H), 6.33-6.25 (m, 2H), 4.89-4.71 (m, 2H), 4.25-4.02 (m, 4H), 3.99 (s, 1H), 3.83 (s, 6H).

C. Synthesis of 3-(7-hydroxy-2,3-dihydro-1,4-benzodioxin-6-yl)-4,5-dimethoxy-1-{[5-(trifluoromethyl)furan-2-yl]methyl}-1,3-dihydro-2H-indol-2-one Following the procedure as described in PREPARATION 4C, and making non-critical variations using 3-hydroxy-3-(7-hydroxy-2,3-dihydro-1,4-benzodioxin-6-yl)-4,5-dimethoxy-1-{[5-(trifluoromethyl)furan-2-yl]methyl}-1,3-dihydro-2H-indol-2-one to replace 4-chloro-1-(diphenylmethyl)-3-hydroxy-3-(6-hydroxy-2,3-dihydro-1-benzofuran-5-yl)-1,3-dihydro-2H-indol-2-one, 3-(7-hydroxy-2,3-dihydro-1,4-benzodioxin-6-yl)-4,5-dimethoxy-1-{[5-(trifluoromethyl)furan-2-yl]methyl}-1,3-dihydro-2H-indol-2-one was obtained (83%) as a colorless solid: $^1$H NMR (300 MHz, CDCl$_3$) δ 6.86 (d, J=8.5 Hz, 1H), 6.71-6.67 (m, 1H), 6.66-6.60 (m, 2H), 6.32-6.25 (m, 2H), 5.11 (s, 1H), 4.94-4.76 (m, 2H), 4.23-4.07 (m, 5H), 3.84 (s, 3H), 3.74 (s, 3H).

Preparation 97

Synthesis of 3-(7-hydroxy-2,3-dihydro-1,4-benzodioxin-6-yl)-4,7-dimethoxy-1-[2-(2-methoxyethoxy)ethyl]-1,3-dihydro-2H-indol-2-one

A. Synthesis of 3-hydroxy-3-(7-hydroxy-2,3-dihydro-1,4-benzodioxin-6-yl)-4,7-dimethoxy-1-[2-(2-methoxyethoxy)ethyl]-1,3-dihydro-2H-indol-2-one To a solution of 4,7-dimethoxy-1H-indole-2,3-dione (1.8 g, 8.7 mmol) in anhydrous N,N-dimethylformamide (20 mL)

and anhydrous tetrahydrofuran (120 mL) at ambient temperature was added cesium carbonate (11.4 g, 35.0 mmol), The mixture was stirred at ambient temperature for 30 min and 1-bromo-2-(2-methoxyethoxy)ethane (2.35 mL, 17.4 mmol) was added in one portion. The mixture was stirred at ambient temperature for 16 h, concentrated in vacuo to a small volume and poured into ice water (300 mL). The mixture was extracted with ethyl acetate and the combined organic extracts were filtered through a pad of diatomaceous earth. The filtrate was dried over anhydrous magnesium sulfate, filtered, and concentrated in vacuo. Trituration of the residue in hexanes afforded 4,7-dimethoxy-1-[2-(2-methoxyethoxy)ethyl]-1H-indole-2,3-dione (2.2 g, 82%).

Following the procedure as described in PREPARATION 2A and making non-critical variations using 2,3-dihydrobenzo[b][1,4]dioxin-6-ol to replace 3-bromophenol, and 4,7-dimethoxy-1-[2-(2-methoxyethoxy)ethyl]-1H-indole-2,3-dione to replace 1-((5-(trifluoromethyl)furan-2-yl)methyl)indoline-2,3-dione, 3-hydroxy-3-(7-hydroxy-2,3-dihydro-1,4-benzodioxin-6-yl)-4,7-dimethoxy-1-[2-(2-methoxyethoxy)ethyl]-1,3-dihydro-2H-indol-2-one was obtained (53%): MS (ES+) m/z 443.9 (M−17).

B. Synthesis of 3-(7-hydroxy-2,3-dihydro-1,4-benzodioxin-6-yl)-4,7-dimethoxy-1-[2-(2-methoxyethoxy)ethyl]-1,3-dihydro-2H-indol-2-one Following the procedure as described in PREPARATION 4C, and making non-critical variations using 3-hydroxy-3-(7-hydroxy-2,3-dihydro-1,4-benzodioxin-6-yl)-4,7-dimethoxy-1-[2-(2-methoxyethoxy)ethyl]-1,3-dihydro-2H-indol-2-one to replace 4-chloro-1-(diphenylmethyl)-3-hydroxy-3-(6-hydroxy-2,3-dihydro-1-benzofuran-5-yl)-1,3-dihydro-2H-indol-2-one, 3-(7-hydroxy-2,3-dihydro-1,4-benzodioxin-6-yl)-4,7-dimethoxy-1-[2-(2-methoxyethoxy)ethyl]-1,3-dihydro-2H-indol-2-one was obtained (89%) as a yellow solid: MS (ES+) m/z 446.0 (M+1).

Preparation 98

Synthesis of 8-(7-hydroxy-2,3-dihydro-1,4-benzodioxin-6-yl)-6-[2-(2-methoxyethoxy)ethyl]-2,3,6,8-tetrahydro-7H-[1,4]dioxino[2,3-f]indol-7-one A. Synthesis of 6-[2-(2-methoxyethoxy)ethyl]-2,3-dihydro-6H-[1,4]dioxino[2,3-f]indole-7,8-dione Following the procedure as described in PREPARATION 97A and making non-critical variations using 2,3-dihydro-6H-[1,4]dioxino[2,3-f]indole-7,8-dione (Lackey and Sternbach, Synthesis 1993:993-997) to replace 4,7-dimethoxy-1H-indole-2,3-dione, 6-[2-(2-methoxyethoxy)ethyl]-2,3-dihydro-6H-[1,4]dioxino[2,3-f]indole-7,8-dione was obtained (82%): $^1$H NMR (300 MHz, DMSO-d$_6$) δ 7.05 (s, 1H), 6.78 (s, 1H), 4.37-4.32 (m, 2H), 4.24-4.17 (m, 2H), 3.74 (t, J=5.5 Hz, 2H), 3.56 (t, J=5.5 Hz, 2H), 3.50-3.44 (m, 2H), 3.36-3.30 (m, 2H), 3.14 (s, 3H).

B. Synthesis of 8-hydroxy-8-(7-hydroxy-2,3-dihydro-1,4-benzodioxin-6-yl)-6-[2-(2-methoxyethoxy)ethyl]-2,3,6,8-tetrahydro-7H-[1,4]dioxino[2,3-f]indol-7-one Following the procedure as described in PREPARATION 2A and making non-critical variations using 2,3-dihydrobenzo[b][1,4]dioxin-6-ol to replace 3-bromophenol, and 6-[2-(2-methoxyethoxy)ethyl]-2,3-dihydro-6H-[1,4]dioxino[2,3-f]indole-7,8-dione to replace 1-((5-(trifluoromethyl)furan-2-yl)methyl)indoline-2,3-dione, 8-hydroxy-8-(7-hydroxy-2,3-dihydro-1,4-benzodioxin-6-yl)-6-[2-(2-methoxyethoxy)ethyl]-2,3,6,8-tetrahydro-7H-[1,4]dioxino[2,3-f]indol-7-one was obtained (19%): MS (ES+) m/z 441.9 (M−17).

C. Synthesis of 8-(7-hydroxy-2,3-dihydro-1,4-benzodioxin-6-yl)-6-[2-(2-methoxyethoxy)ethyl]-2,3,6,8-tetrahydro-7H-[1,4]dioxino[2,3-f]indol-7-one Following the procedure as described in PREPARATION 4C, and making non-critical variations using 8-hydroxy-8-(7-hydroxy-2,3-dihydro-1,4-benzodioxin-6-yl)-6-[2-(2-methoxyethoxy)ethyl]-2,3,6,8-tetrahydro-7H-[1,4]dioxino[2,3-f]indol-7-one to replace 4-chloro-1-(diphenylmethyl)-3-hydroxy-3-(6-hydroxy-2,3-dihydro-1-benzofuran-5-yl)-1,3-dihydro-2H-indol-2-one, 8-(7-hydroxy-2,3-dihydro-1,4-benzodioxin-6-yl)-6-[2-(2-methoxyethoxy)ethyl]-2,3,6,8-tetrahydro-7H-[1,4]dioxino[2,3-f]indol-7-one was obtained (54%) as a pale yellow solid: MS (ES+) m/z 443.9 (M+1).

Preparation 99

Synthesis of 8-(7-hydroxy-2,3-dihydro-1,4-benzodioxin-6-yl)-6-(4-methoxybenzyl)-6,8-dihydro-7H-[1,3]thiazolo[5,4-e]indol-7-one A. Synthesis of 6-(4-methoxybenzyl)-6H-[1,3]thiazolo[5,4-e]indole-7,8-dione To a mixture of 1,3-benzo[d]thiazol-6-amine (10.0 g, 66.6 mmol) and 4-anisaldehyde (8.5 mL, 70 mmol) in 1,2-dichloroethane (350 mL) at ambient temperature was added sodium triacetoxyborohydride (28.2 g, 133.0 mmol). The mixture was stirred at ambient temperature for 16 h and 1 N aqueous sodium hydroxide was added. The organic layer was concentrated in vacuo to a small volume, causing a precipitate to be deposited. The solid was collected by filtration to afford N-(4-methoxybenzyl)-1,3-benzo[d]thiazol-6-amine (16.5 g, 90%) as a colorless solid. A mixture of oxalyl chloride (6.1 g, 48 mmol) and N-(4-methoxybenzyl)-1,3-benzo[d]thiazol-6-amine (1.3 g, 4.8 mmol) in a sealed tube was heated at 140° C. for 1 h. The mixture was allowed to cool to ambient temperature during which time a precipitate was deposited. The solid was filtered, washed with hexanes and dried to afford 6-(4-methoxybenzyl)-6H-[1,3]thiazolo[5,4-e]indole-7,8-dione (1.2 g, 76%) as an orange solid: $^1$H NMR (300 MHz, DMSO-d$_6$) δ 9.32 (s, 1H), 8.27 (d, J=8.6 Hz, 1H), 7.37 (d, J=8.6 Hz, 2H), 7.13 (d, J=8.6 Hz, 1H), 6.86 (d, J=8.6 Hz, 2H), 4.87 (s, 2H), 3.68 (s, 3H).

B. Synthesis of 8-hydroxy-8-(7-hydroxy-2,3-dihydro-1,4-benzodioxin-6-yl)-6-(4-methoxybenzyl)-6,8-dihydro-7H-[1,3]thiazolo[5,4-e]indol-7-one Following the procedure as described in PREPARATION 2A and making non-critical variations using 2,3-dihydrobenzo[b][1,4]dioxin-6-ol to replace 3-bromophenol, and 6-(4-methoxybenzyl)-6H-[1,3]thiazolo[5,4-e]indole-7,8-dione to replace 1-((5-(trifluoromethyl)furan-2-yl)methyl)indoline-2,3-dione, 8-hydroxy-8-(7-hydroxy-2,3-dihydro-1,4-benzodioxin-6-yl)-6-(4-methoxybenzyl)-6,8-dihydro-7H-[1,3]thiazolo[5,4-e]indol-7-one was obtained (39%) as a colorless solid: MS (ES+) m/z 477.1 (M+1).

C. Synthesis of 8-(7-hydroxy-2,3-dihydro-1,4-benzo-dioxin-6-yl)-6-(4-methoxybenzyl)-6,8-dihydro-7H-[1,3]thiazolo[5,4-e]indol-7-one Following the procedure as described in PREPARATION 4C, and making non-critical variations using 8-hydroxy-8-(7-hydroxy-2,3-dihydro-1,4-benzodioxin-6-yl)-6-(4-methoxybenzyl)-6,8-dihydro-7H-[1,3]thiazolo[5,4-e]indol-7-one to replace 4-chloro-1-(diphenylmethyl)-3-hydroxy-3-(6-hydroxy-2,3-dihydro-1-benzofuran-5-yl)-1,3-dihydro-2H-indol-2-one, 8-(7-hydroxy-2,3-dihydro-1,4-benzodioxin-6-yl)-6-(4-methoxybenzyl)-6,8-dihydro-7H-[1,3]thiazolo[5,4-e]indol-7-one was obtained (89%) as a colorless solid: MS (ES+) m/z 461.1 (M+1).

Preparation 100

Synthesis of 3-[4-(benzyloxy)-2-hydroxyphenyl]-1-(diphenylmethyl)-1,3-dihydro-2H-indol-2-one A. Synthesis of 3-[4-(benzyloxy)-2-hydroxyphenyl]-1-(diphenylmethyl)-3-hydroxy-1,3-dihydro-2H-indol-2-one Following the procedure as described in PREPARATION 2A and making non-critical variations using 3-(benzyloxy)phenol to replace 3-bromophenol, and 1-(diphenylmethyl)-1H-indole-2,3-dione to replace 1-((5-(trifluoromethyl)furan-2-yl)methyl)indoline-2,3-dione, 3-[4-(benzyloxy)-2-hydroxyphenyl]-1-(diphenylmethyl)-3-hydroxy-1,3-dihydro-2H-indol-2-one was obtained (75%): MS (ES+) m/z 496.0 (M−17).

B. Synthesis of 3-[4-(benzyloxy)-2-hydroxyphenyl]-1-(diphenylmethyl)-1,3-dihydro-2H-indol-2-one Following the procedure as described in PREPARATION 4C, and making non-critical variations using [4-(benzyloxy)-2-hydroxyphenyl]-1-(diphenylmethyl)-3-hydroxy-1,3-dihydro-2H-indol-2-one to replace 4-chloro-1-(diphenylmethyl)-3-hydroxy-3-(6-hydroxy-2,3-dihydro-1-benzofuran-5-yl)-1,3-dihydro-2H-indol-2-one, 3-[4-(benzyloxy)-2-hydroxyphenyl]-1-(diphenylmethyl)-1,3-dihydro-2H-indol-2-one was obtained (57%) as a colorless solid: $^1$H NMR (300 MHz, CDCl$_3$) δ9.01 (s, 1H), 7.45-7.16 (m, 15H), 7.13-7.01 (m, 2H), 6.96 (s, 1H), 6.85-6.76 (m, 1H), 6.71-6.65 (m, 1H), 6.55-6.49 (m, 1H), 6.49-6.42 (m, 1H), 5.10 (s, 1H), 4.99 (s, 2H).

Preparation 101

Synthesis of 3-[5-(benzyloxy)-2-hydroxyphenyl]-1-(diphenylmethyl)-1,3-dihydro-2H-indol-2-one A. Synthesis of 3-[5-(benzyloxy)-2-hydroxyphenyl]-1-(diphenylmethyl)-3-hydroxy-1,3-dihydro-2H-indol-2-one Following the procedure as described in PREPARATION 2A and making non-critical variations using 4-(benzyloxy)phenol to replace 3-bromophenol, and 1-(diphenylmethyl)-1H-indole-2,3-dione to replace 1-((5-(trifluoromethyl)furan-2-yl)methyl)indoline-2,3-dione, 3-[5-(benzyloxy)-2-hydroxyphenyl]-1-(diphenylmethyl)-3-hydroxy-1,3-dihydro-2H-indol-2-one was obtained (76%): $^1$H NMR (300 MHz, CDCl$_3$) δ 8.63 (s, 1H), 7.46-7.40 (m, 1H), 7.38-7.21 (m, 15H), 7.13-7.06 (m, 2H), 6.97 (d, J=8.8 Hz, 1H), 6.92 (s, 1H), 6.86 (dd, J=8.8, 3.0 Hz, 1H), 6.52-6.45 (m, 2H), 4.85 (s, 2H), 4.53 (s, 1H).

B. Synthesis of 3-[5-(benzyloxy)-2-hydroxyphenyl]-1-(diphenylmethyl)-1,3-dihydro-2H-indol-2-one Following the procedure as described in PREPARATION 4C, and making non-critical variations using 3-[5-(benzyloxy)-2-hydroxyphenyl]-1-(diphenylmethyl)-3-hydroxy-1,3-dihydro-2H-indol-2-one to replace 4-chloro-1-(diphenylmethyl)-3-hydroxy-3-(6-hydroxy-2,3-dihydro-1-benzofuran-5-yl)-1,3-dihydro-2H-indol-2-one, 3-[5-(benzyloxy)-2-hydroxyphenyl]-1-(diphenylmethyl)-1,3-dihydro-2H-indol-2-one was obtained (67%) as a colorless solid: $^1$H NMR (300 MHz, CDCl$_3$) δ8.51 (br s, 1H), 7.41-7.16 (m, 16H), 7.10-7.03 (m, 2H), 7.02-6.97 (m, 1H), 6.96 (s, 1H), 6.85-6.79 (m, 1H), 6.58-6.48 (m, 2H), 5.17 (s, 1H), 4.92 (s, 2H).

Preparation 102

Synthesis of 1-(bromomethyl)-2-(difluoromethyl)benzene

A. Synthesis of 1-(difluoromethyl)-2-methylbenzene

To a solution of o-tolualdehyde (5.00 g, 41.6 mmol) in anhydrous dichloromethane (50 mL) was added a solution of (diethylamino)sulfur trifluoride (6.70 g, 41.6 mmol) in anhydrous dichloromethane (30 mL) at ambient temperature. The mixture was stirred for 16 h at ambient temperature and saturated aqueous sodium bicarbonate (200 mL) was added. The mixture was extracted with dichloromethane (2×150 mL) and diethyl ether (100 mL). The combined organic phases were dried over sodium sulfate, filtered, and concentrated in vacuo. The resultant liquid was purified by column chromatography and eluted with dichloromethane to afford 1-(difluoromethyl)-2-methylbenzene (2.90 g, 49%) as a yellow liquid: $^1$H NMR (300 MHz, CDCl$_3$) δ7.48 (d, J=7.6 Hz, 1H), 7.35 (dd, J=7.0, 7.0 Hz, 2H), 7.24 (dd, J=14.9, 7.6 Hz, 1H), 6.78-6.70 (m, 1H), 2.42 (s, 3H).

B. Synthesis of 1-(bromomethyl)-2-(difluoromethyl)benzene

To a solution of 1-(difluoromethyl)-2-methylbenzene (2.90 g, 20.4 mmol) in carbon tetrachloride (50 mL) was added N-bromosuccinimide (3.63 g, 20.4 mmol) and 2,2'-azobis(2-methylpropionitrile) (0.167 g, 1.02 mmol). The mixture was heated at reflux for 16 h. Further 2,2'-azobis(2-methylpropionitrile) (0.167 g, 1.02 mmol) was added, the mixture was heated at reflux for 4 h, allowed to cool to ambient temperature, diluted with dichloromethane (175 mL) and washed with water (2×175 mL) and saturated sodium bicarbonate (150 mL). The organic phase was dried over sodium sulfate, filtered, and concentrated in vacuo. The resultant residue was purified by column chromatography and eluted with a 0% to 10% gradient of ethyl acetate in dichloromethane to afford 1-(bromomethyl)-2-(difluoromethyl)benzene as a yellow solid: $^1$H NMR (300 MHz, CDCl$_3$) δ7.58-7.56 (m, 1H), 7.43-7.37 (m, 3H), 6.95 (t, 55.2 Hz, 1H), 4.59 (s, 2H).

Preparation 103

Synthesis of [3-(difluoromethyl)pyridin-2-yl]methanol hydrochloride

A. Synthesis of 3-(difluoromethyl)-2-methylpyridine

To a solution of 2-methylpyridine-3-carbaldehyde (3.8 g, 31.4 mmol) in dichloromethane (60 mL) was added (diethylamino)sulfur trifluoride (4.14 mL, 31.4 mmol). After 16 h at ambient temperature, the reaction was quenched by the addition of saturated aqueous sodium bicarbonate (200 mL) and extracted with dichloromethane (200 mL). The organic phase was washed with brine (200 mL), dried over sodium sulfate, filtered, and concentrated in vacuo. The residue was purified by column chromatography and eluted with a 0% to 30% gradient of diethyl ether in dichloromethane to afford 3-(difluoromethyl)-2-methylpyridine (2.56 g, 57%) as a yellow liquid: $^1$H NMR (300 MHz, CDCl$_3$) δ8.58 (d, J=4.8 Hz, 1H), 7.80 (d, J=7.8 Hz, 1H), 7.21 (dd, J=7.8, 5.2 Hz, 1H), 6.82-6.72 (m, 1H), 2.63 (s, 3H).

B. Synthesis of 3-(difluoromethyl)-2-methylpyridine-1-oxide

To a solution of 3-(difluoromethyl)-2-methylpyridine (2.56 g, 17.9 mmol) in dichloromethane was added 3-chloroperbenzoic acid (6.01 g, 26.8 mmol) at ambient temperature. After stirring for 2 h, the mixture was diluted with a 1 M aqueous sodium hydroxide (50 mL) and extracted with dichloromethane (4×50 mL). The organic phase was washed with brine (150 mL), dried over sodium sulfate, filtered and concentrated in vacuo to afford 3-(difluoromethyl)-2-methylpyridine-1-oxide as a yellow oil (2.22 g, 78%): $^1$H NMR (300 MHz, CDCl$_3$) δ8.36 (d, J=6.5 Hz, 1H), 7.40 (d, J=7.9 Hz, 1H), 7.23 (m, 1H), 6.80-6.70 (m, 1H), 2.57 (s, 3H).

C. Synthesis of [3-(difluoromethyl)pyridin-2-yl]methanol hydrochloride 3-(Difluoromethyl)-2-methylpyridine-1-oxide (2.22 g, 14.0 mmol) and acetic anhydride (10 mL, 100 mmol) were heated at 80° C. for 1 h. The reaction mixture was allowed to cool to ambient temperature, diethyl ether (100 mL) was added and the mixture was washed with a 1 M aqueous sodium hydroxide (100 mL), water (50 mL), and brine (50 mL). The organic layer was dried over sodium sulfate, filtered and concentrated in vacuo. The residue was taken up in methanol (70 mL) and potassium carbonate (20.2 g, 14.6 mmol) was added. The mixture was stirred at ambient temperature for 1 h, concentrated in vacuo and the residue was taken up in water and extracted with ethyl acetate (3×50 mL). The organic phase was washed with brine (100 mL), dried over sodium sulfate, filtered and concentrated in vacuo. The residue was taken up in anhydrous diethyl ether and the product was precipitated by the addition of a 4 M solution of hydrogen chloride in 1,4-dioxane to afford [3-(difluoromethyl)pyridin-2-yl]methanol hydrochloride (0.700 g, 26%) as a colorless solid: $^1$H NMR (300 MHz, DMSO-d$_6$) δ 9.89 (s, 2H), 8.81 (d, J=5.2 Hz, 1H), 8.44 (d, J=7.6 Hz, 1H), 7.83 (m, 1H), 7.48-7.38 (m, 1H), 4.89 (s, 2H).

Preparation 104

Synthesis of 1-(diphenylmethyl)-3-(5-hydroxy-2,3-dihydro-1,4-benzodioxin-6-yl)-1,3-dihydro-2H-indol-2-one

A. Synthesis of 1-(diphenylmethyl)-3-hydroxy-3-(5-hydroxy-2,3-dihydro-1,4-benzodioxin-6-yl)-1,3-dihydro-2H-indol-2-one To a solution of 2,3-dihydro-1,4-benzodioxin-5-ol (3.60 g, 23.7 mmol) in anhydrous tetrahydrofuran (80 mL) at 0° C. was added isopropylmagnesium chloride (11.8 mL, 2 M solution in tetrahydrofuran, 23.7 mmol). The mixture was stirred at 0° C. for 45 min, concentrated in vacuo, and 1,2-dichloroethane (60 mL) was added. The mixture was cooled to 0° C. and a solution of 1-benzhydrylindoline-2,3-dione (4.94 g, 15.8 mmol) in 1,2-dichloroethane (70 mL) was added. The reaction mixture was allowed to warm to ambient temperature and stirred for 60 h, and heated to 83° C. and stirred for 3.5 h. The reaction mixture was allowed to cool to ambient temperature, concentrated in vacuo and saturated aqueous ammonium chloride (250 mL) was added. The mixture was extracted with ethyl acetate (250 mL followed by 2×100 mL). The organic phase was washed with water (150 mL) and brine (150 mL), dried over sodium sulfate and filtered. The filtrate was concentrated in vacuo. The residue was taken up in ethyl acetate and a solid was precipitated by the addition of hexanes to afford 1-(diphenylmethyl)-3-hydroxy-3-(5-hydroxy-2,3-dihydro-1,4-benzodioxin-6-yl)-1,3-dihydro-2H-indol-2-one (5.10 g, 69%) as a colorless solid: $^1$H NMR (300 MHz, CDCl$_3$) δ9.14 (s, 1H), 7.43-7.30 (m, 9H), 7.22 (d, J=8.7 Hz, 1H), 6.97-6.79 (m, 3H), 6.52 (s, 1H), 6.44 (d, J=8.7 Hz, 1H) 6.26 (d, J=7.8 Hz, 1H), 4.22 (s, 4H).

B. Synthesis of 1-(diphenylmethyl)-3-(5-hydroxy-2,3-dihydro-1,4-benzodioxin-6-yl)-1,3-dihydro-2H-indol-2-one Following the procedure as described in PREPARATION 4C, and making non-critical variations using 1-(diphenylmethyl)-3-hydroxy-3-(5-hydroxy-2,3-dihydro-1,4-benzodioxin-6-yl)-1,3-dihydro-2H-indol-2-one to replace 4-chloro-1-(diphenylmethyl)-3-hydroxy-3-(6-hydroxy-2,3-dihydro-1-benzofuran-5-yl)-1,3-dihydro-2H-indol-2-one, 1-(diphenylmethyl)-3-(5-hydroxy-2,3-dihydro-1,4-benzodioxin-6-yl)-1,3-dihydro-2H-indol-2-one was obtained (82%) as a colorless solid: $^1$H NMR (300 MHz, DMSO-d$_6$) δ 9.11 (s, 1H), 7.39-7.24 (m, 9H), 6.95-6.79 (m, 3H), 6.58 (d, J=8.0 Hz, 1H), 6.35-6.30 (m, 2H), 4.21 (s, 4H).

Preparation 105

Synthesis of 1-(diphenylmethyl)-3-(7-hydroxy-2,3-dihydro-1,4-benzodioxin-6-yl)-4,6-dimethoxy-1,3-dihydro-2H-indol-2-one

A. Synthesis of 1-(diphenylmethyl)-4,6-dimethoxy-1H-indole-2,3-dione

Following the procedure as described in PREPARATION 26A and making non-critical variations using 4,6-dimethoxy-1H-indole-2,3-dione to replace 2,3-dihydro-6H-[1,4]dioxino[2,3-f]indole-7,8-dione, and bromodiphenylmethane to replace 2-(bromomethyl)-5-(trifluoromethyl)furan, 1-(diphenylmethyl)-4,6-dimethoxy-1H-indole-2,3-dione was obtained (90%): $^1$H NMR (300 MHz, DMSO-d$_6$) δ7.49-7.19 (m, 10H), 6.72 (s, 1H), 6.21 (d, J=1.5 Hz, 1H), 5.87 (d, J=1.5 Hz, 1H), 3.86 (s, 3H), 3.70 (s, 3H).

B. Synthesis of 1-(diphenylmethyl)-3-hydroxy-3-(7-hydroxy-2,3-dihydro-1,4-benzodioxin-6-yl)-4,6-dimethoxy-1,3-dihydro-2H-indol-2-one Following the procedure as described in PREPARATION 2A and making non-critical variations using 4-(benzyloxy)phenol to replace 3-bromophenol, and 1-(diphenylmethyl)-4,6-dimethoxy-1H-indole-2,3-dione to replace 1-((5-(trifluoromethyl)furan-2-yl)methyl)indoline-2,3-dione, 1-(diphenylmethyl)-3-hydroxy-3-(7-hydroxy-2,3-dihydro-1,4-benzodioxin-6-yl)-4,6-dimethoxy-1,3-dihydro-2H-indol-2-one was obtained (50%) as a colorless solid: $^1$H NMR (300 MHz, CDCl$_3$) δ8.81 (s, 1H), 7.34-7.16 (m, 10H), 6.82 (s, 1H), 6.55 (s, 1H), 6.31 (s, 1H), 6.14 (d, J=1.8 Hz, 1H), 5.64 (d, J=1.8 Hz, 1H), 4.22-4.10 (m, 4H), 3.92 (s, 1H), 3.77 (s, 3H), 3.49 (s, 3H).

C. Synthesis of 1-(diphenylmethyl)-3-(7-hydroxy-2,3-dihydro-1,4-benzodioxin-6-yl)-4,6-dimethoxy-1,3-dihydro-2H-indol-2-one Following the procedure as described in PREPARATION 4C, and making non-critical variations using 1-(diphenylmethyl)-3-hydroxy-3-(7-hydroxy-2,3-dihydro-1,4-benzodioxin-6-yl)-4,6-dimethoxy-1,3-dihydro-2H-indol-2-one to replace 4-chloro-1-(diphenylmethyl)-3-hydroxy-3-(6-hydroxy-2,3-dihydro-1-benzofuran-5-yl)-1,3-dihydro-2H-indol-2-one, 1-(diphenylmethyl)-3-(7-hydroxy-2,3-dihydro-1,4-benzodioxin-6-yl)-4,6-dimethoxy-1,3-dihydro-2H-indol-2-one was obtained (92%) as a colorless solid: $^1$H NMR (300 MHz, CDCl$_3$) δ7.35-7.25 (m, 8H), 7.21-7.14 (m, 2H), 6.87 (s, 1H), 6.61 (s, 1H), 6.27 (s, 1H), 6.17 (d, J=1.8 Hz, 1H), 5.68 (d, J=1.8 Hz, 1H), 5.02 (s, 1H), 4.24-4.10 (m, 4H), 3.73 (s, 3H), 3.48 (s, 3H), 3.47 (s, 1H).

Preparation 106

Synthesis of 1-(diphenylmethyl)-3-(7-hydroxyquinoxalin-6-yl)-1,3-dihydro-2H-indol-2-one

A. Synthesis of 1-(diphenylmethyl)-3-hydroxy-3-(7-hydroxyquinoxalin-6-yl)-1,3-dihydro-2H-indol-2-one To a stirred solution of quinoxalin-6-ol (King et al.; *J. of the Chem. Society* 1949:3012.) (11.2 g, 76.66 mmol) in tetrahydrofuran (800 mL) was added isopropylmagnesium chloride (38.3 mL, 2.0 M THF solution, 76.60 mmol) at −40° C. to −30° C. The mixture was allowed to stir at 0° C. for 2 h, followed by the addition of 1-(diphenylmethyl)-1H-indole-2,3-dione (20.00 g, 63.84 mmol) in tetrahydrofuran (400 mL). The mixture was stirred at ambient temperature for 20 h, and quenched with saturated ammonium chloride solution and extracted with ethyl acetate (3×1000 mL). The organic layer was washed with water and brine, dried over anhydrous sodium sulfate and filtered. The filtrate was concentrated in vacuo, and the residue was purified by column chromatography (dichloromethane/methanol, 100/1) to give 1-(diphenylmethyl)-3-hydroxy-3-(7-hydroxyquinoxalin-6-yl)-1,3-dihydro-2H-indol-2-one (10.0 g, 34%): $^1$H NMR (300 MHz, CDCl$_3$) δ 10.21 (s, 1H), 8.47 (s, 1H), 7.97-7.92 (m, 2H), 7.60-7.58 (m, 2H), 7.54-7.49 (m, 4H), 7.46-7.35 (m, 6H), 7.14 (s, 1H), 7.05-7.00 (m, 1H), 6.89-6.87 (m, 1H), 6.56-6.52 (m, 1H).

B. Synthesis of 1-(diphenylmethyl)-3-(7-hydroxyquinoxalin-6-yl)-1,3-dihydro-2H-indol-2-one To thionyl chloride (60 mL) was added 1-(diphenylmethyl)-3-hydroxy-3-(7-hydroxyquinoxalin-6-yl)-1,3-dihydro-2H-indol-2-one (3.0 g, 6.53 mmol) at −10° C. The resulting reaction mixture was stirred at 0° C. for 1 h, and concentrated in vacuo. The residue was dissolved in acetic acid (150 mL), followed by the addition of zinc dust (4.50 g, 68.81 mmol). The resulting mixture was stirred at ambient temperature for 40 min. The solids were filtered out. The filtrate was concentrated in vacuo. The residue was dissolved in ethyl acetate (200 mL), washed with water and brine, dried over anhydrous sodium sulfate and filtered. The filtrate was concentrated in vacuo, the residue was purified by column chromatography (dichloromethane/methanol 200/1) to give 1-(diphenylmethyl)-3-(7-hydroxyquinoxalin-6-yl)-1,3-dihydro-2H-indol-2-one (2.40 g, 83%): MS (ES+) m/z 444 (M+1).

EXAMPLE 1

Synthesis of 2-methylspiro[furo[2,3-f][1,3]benzothiazole-7,3'-indol]-2'(1'H)-one

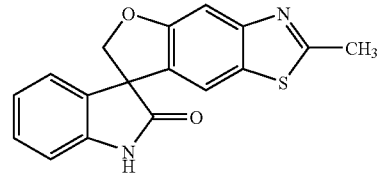

To a cooled (−78° C.) solution of 1,3-bis(hydroxymethyl)-3-(5-hydroxy-2-methyl-1,3-benzothiazol-6-yl)-1,3-dihydro-2H-indol-2-one (1.70 g, 4.7 mmol) in anhydrous tetrahydrofuran (30 mL) was added tri-n-butylphosphine (0.80 mL, 5.7 mmol), followed by diethyl azodicarboxylate (1.05 mL, 6.7 mmol). The reaction mixture was allowed to warm to ambient temperature and was stirred for 2 h. The reaction mixture was cooled to 0° C. and a 28% aqueous solution of ammonia (10 mL) was added. The reaction mixture was stirred for 1 h at 0° C. and was acidified to pH 6 by the dropwise addition of 10% aqueous hydrochloric acid. The reaction mixture was extracted with ethyl acetate (3×50 mL) and the combined organic solution was washed with brine (2×50 mL), dried over sodium sulfate, filtered and concentrated. The resultant solid was triturated with diethyl ether (50 mL), collected by vacuum filtration, washed with diethyl ether (20 mL) and dried under high vacuum to afford 2-methylspiro[furo[2,3-f][1,3]benzothiazole-7,3'-indol]-2'(1'H)-one (1.03 g, 70%): mp>250° C. (ethyl acetate); $^1$H NMR (300 MHz, DMSO-d$_6$) δ10.75 (br s, 1H), 7.89 (d, J=8.6 Hz, 1H), 7.26-7.19 (m, 1H), 7.10 (d, J=8.6 Hz, 1H), 7.02-6.86 (m, 3H), 4.86-4.74 (m, 2H), 2.60 (s, 3H); $^{13}$C NMR (75 MHz, DMSO-d$_6$) δ177.7, 160.1, 148.9, 141.7, 138.5, 132.7, 128.6, 128.0, 123.4, 122.7, 122.1, 119.9, 109.7, 108.3, 80.9, 57.8, 20.0; MS (ES+) m/z 309.1 (M+1).

EXAMPLE 1.1

Synthesis of 1-[(6-methylpyridin-2-yl)methyl]-2,3-dihydrospiro[furo[2,3-g][1,4]benzodioxine-8,3'-indol]-2'(1'H)-one

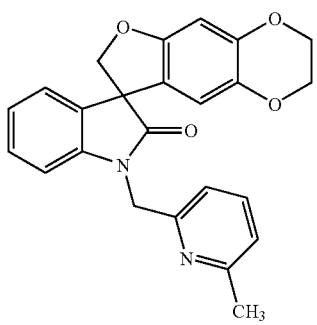

To a mixture of 2,3-dihydrospiro[furo[2,3-g][1,4]benzodioxine-8,3'-indol]-2'(1'H)-one (0.23 g, 0.79 mmol), 6-methyl-2-pyridinemethanol (0.13 g, 1.07 mmol) and triphenylphosphine (0.30 g, 1.14 mmol) in benzene (10 mL) under nitrogen was slowly added a solution of diethyl azodicarboxylate (0.22 g, 1.27 mmol) in tetrahydrofuran (6 mL). The resulting mixture was stirred at ambient temperature for 16.5 h. The solvents were removed under reduced pressure, and the residue was taken up into 2 M sodium carbonate (50 mL) and extracted with dichloromethane (3×30 mL). The combined organic solution was washed with brine (50 mL), dried with sodium sulfate, filtered and concentrated under reduced pressure. Purification by flash column chromatography with hexanes/ethyl acetate (2:1) gave 1'-[(6-methylpyridin-2-yl)methyl]-2,3-dihydrospiro[furo[2,3-g][1,4]benzodioxine-8,3'-indol]-2'(1'H)-one (0.13 g, 41%) as a colorless solid: mp 183-185° C. (hexanes/diethyl ether); $^1$H NMR (300 MHz, CDCl$_3$) δ7.56 (dd, J=7.8, 7.5 Hz, 1H), 7.23-7.16 (m, 2H), 7.10-7.00 (m, 3H), 6.90 (d, J=7.8 Hz, 1H), 6.51 (s, 1H), 6.32 (s, 1H), 5.23 (d, J=15.9 Hz, 1H), 4.958 (d, J=9.0 Hz, 1H), 4.956 (d, J=15.9 Hz, 1H), 4.68 (d, J=9.0 Hz, 1H), 4.23-4.18 (m, 2H), 4.15-4.11 (m, 2H), 2.59 (s, 3H); $^{13}$C NMR (75 MHz, CDCl$_3$) δ177.8, 158.2, 155.4, 154.7, 144.8, 142.2, 138.4, 138.2, 132.3, 129.0, 124.0, 123.7, 122.9, 121.2, 118.8, 111.8, 109.8, 99.6, 80.3, 64.7, 64.1, 58.3, 45.7, 24.1; MS (ES+) m/z 401.0 (M+1).

EXAMPLE 1.2

Synthesis of 1-(pyridin-3-ylmethyl)-2,3-dihydrospiro[furo[2,3-g][1,4]benzodioxine-8,3'-indol]-2'(1'H)-one

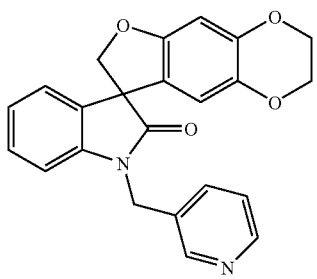

To a mixture of 2,3-dihydrospiro[furo[2,3-g][1,4]benzodioxine-8,3'-indol]-2'(1'H)-one (0.30 g, 1.00 mmol), 3-pyridinemethanol (0.15 mL, 1.50 mmol) and triphenylphosphine (0.36 g, 1.36 mmol) in tetrahydrofuran (7 mL) under nitrogen was slowly added a solution of diethyl azodicarboxylate (0.29 g, 1.67 mmol) in tetrahydrofuran (3 mL). The resulting mixture was stirred at ambient temperature for 21 h. The solvents were removed under reduced pressure, and the residue was taken up into 2 M sodium carbonate (50 mL) and extracted with dichloromethane (2×30 mL). The combined organic solution was dried with sodium sulfate, filtered and concentrated under reduced pressure. The filterate was purified by flash column chromatography with dichloromethane/isopropanol (49:1, increased to 29:1) to give a mixture of the desired product and triphenylphosphine oxide. This material was acidified with 1 M hydrochloric acid (30 mL) and extracted with diethyl ether (3×30 mL). The aqueous solution was made basic with 5 M sodium hydroxide and extracted with dichloromethane (3×30 mL). Once dried with sodium sulfate, the organic solution was concentrated under reduced pressure to afford 1-(pyridin-3-ylmethyl)-2,3-dihydrospiro[furo[2,3-g][1,4]benzodioxine-8,3'-indol]-2'(1'H)-one (0.22 g, 57%) as a colorless solid: mp 142-143° C. (diethyl ether/hexanes); $^1$H NMR (300 MHz, CDCl$_3$) δ 8.93-8.47 (m, 2H), 7.79 (d, J=7.8 Hz, 1H), 7.45-7.36 (m, 1H), 7.23 (ddd, J=7.8, 7.8, 0.9 Hz, 1H), 7.18 (d, J=7.2 Hz, 1H), 7.05 (dd, J=7.5, 7.5 Hz, 1H), 6.81 (d, J=7.8 Hz, 1H), 6.50 (s, 1H), 6.19 (s, 1H), 5.09 (d, J=15.8 Hz, 1H), 4.924 (d, J=9.0 Hz, 1H), 4.919 (d, J=15.8 Hz, 1H), 4.66 (d, J=9.0 Hz, 1H), 4.22-4.17 (m, 2H), 4.14-4.09 (m, 2H); $^{13}$C NMR (75 MHz, CDCl$_3$) δ177.8, 155.4, 148.0, 147.5, 144.9, 141.5, 138.5, 137.0, 132.2, 129.1, 124.3, 124.0, 120.8, 111.5, 109.0, 99.6, 80.2, 64.6, 64.0, 58.1, 41.7; MS (ES+) m/z 386.7 (M+1).

EXAMPLE 1.3

Synthesis of 1'-{[2,5-dimethyl-1-(1-methylethyl)-1H-pyrrol-3-yl]methyl}spiro[furo[2,3-f][1,3]benzodioxole-7,3'-indol]-2'(1'H)-one

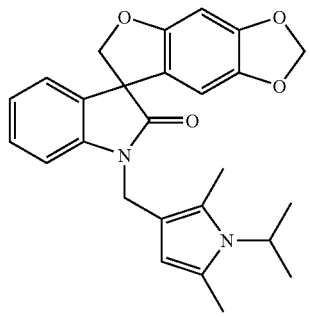

To a stirred solution of spiro[furo[2,3-f][1,3]benzodioxole-7,3'-indol]-2'(1'H)-one (0.84 g, 3.0 mmol) and (1-isopropyl-2,5-dimethyl-1H-pyrrol-3-yl)methanol (0.50 g, 3.0 mmol) in anhydrous tetrahydrofuran (15 mL) was added dropwise tributylphosphine (0.90 g, 1.5 mmol). The solution was cooled to 0° C. and diethyl azodicarboxylate (0.78 g, 4.5 mmol) was added. The solution was stirred at ambient temperature for 16 h then quenched with saturated ammonium chloride (50 mL). The aqueous solution was extracted with ethyl acetate (200 mL), dried on magnesium sulfate, filtered and concentrated in vacuo to dryness. The residue was purified by flash chromatography with ethyl acetate in hexanes (15% to 50% gradient) to afford 1'-{[2,5-dimethyl-1-(1-methylethyl)-1H-pyrrol-3-yl]methyl}spiro[furo[2,3-f][1,3]benzodioxole-7,3'-indol]-2'(1'H)-one (0.32 g, 24%) as a colorless solid: mp 169-171° C.; $^1$H NMR (300 MHz, CDCl$_3$) δ

7.27-7.20 (m, 1H), 7.11 (d, J=7.5 Hz, 1H), 7.02-6.95 (m, 2H), 6.49 (s, 1H), 6.09 (s, 1H), 5.85-5.82 (m, 2H), 5.77 (br s, 1H), 4.77 (ABq, 2H), 4.69 (ABq, 2H), 4.37 (sep, J=7.0 Hz, 1H), 2.33 (s, 3H), 2.22 (s, 3H), 1.43 (d, J=7.0 Hz, 6H); $^{13}$C NMR (75 MHz, CDCl$_3$) δ194.7, 177.2, 155.9, 148.7, 142.9, 142.2, 132.5, 128.7, 127.0, 125.5, 123.6, 122.9, 119.9, 113.0, 109.6, 107.6, 103.2, 101.4, 93.5, 80.5, 58.2, 47.3, 37.0, 22.2, 14.1, 11.5; MS (ES+) m/z 431.20 (M+1).

EXAMPLE 1.4

Synthesis of 5-(benzyloxy)-1'-[(5-chloro-2-thienyl)methyl]spiro[1-benzofuran-3,3'-indol]-2'(1'H)-one

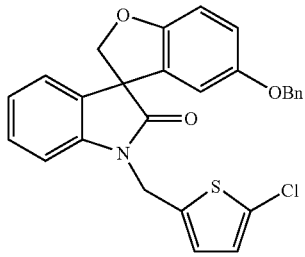

To a stirred solution of 3-[5-(benzyloxy)-2-hydroxyphenyl]-1-[(5-chloro-2-thienyl)methyl]-3-hydroxymethyl-1,3-dihydro-2H-indol-2-one (2.71 g, 5.52 mmol) in anhydrous tetrahydrofuran (60 mL) was added dropwise tributylphosphine (1.39 g, 6.90 mmol). The solution was cooled to 0° C. and di-tert-butyl azodicarboxylate (1.59 g, 6.90 mmol) was added. The solution was stirred at 0° C. for 20 min then quenched with aqueous 10% hydrochloric acid (50 mL). The aqueous solution was extracted with ethyl acetate (3×100 mL), brine (3×50 mL), dried over anhydrous sodium sulfate, filtered and concentrated in vacuo to dryness. The residue was purified by flash column chromatography with ethyl acetate in hexanes (20%) to give 5-(benzyloxy)-1'-[(5-chloro-2-thienyl)methyl]spiro[1-benzofuran-3,3'-indol]-2'(1'H)-one (2.36 g, 90%) as a colorless solid: mp 132-135° C.; $^1$H NMR (300 MHz, DMSO-d$_6$) 7.33-7.21 (m, 7H), 7.16-7.12 (m, 2H), 7.02 (ddd, J=7.4, 7.4, 1.0 Hz, 1H), 6.97 (d, J=3.8 Hz, 1H), 6.90-6.32 (m, 2H), 6.21 (d, J=2.3 Hz, 1H), 5.05 (ABq, 2H), 4.82 (s, 2H), 4.72 (ABq, 2H); $^{13}$C NMR (75 MHz, DMSO-d$_6$) δ176.6, 155.0, 153.6, 141.9, 138.6, 137.4, 132.0 130.3, 129.4, 128.8, 128.2, 128.1, 127.9, 127.1, 124.3, 123.8, 116.6, 110.8, 110.0, 109.9, 79.4, 70.4, 58.1, 38.9; MS (ES+) m/z 476.3 (M+1), 474.3 (M+1).

EXAMPLE 1.5

Synthesis of 7'-bromospiro[furo[2,3-f][1,3]benzodioxole-7,3'-indol]-2'(1'H)-one

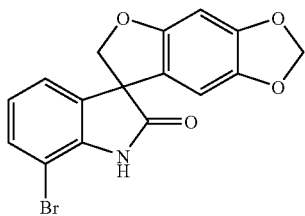

To a suspended mixture of 7-bromo-3-(6-hydroxy-1,3-benzodioxol-5-yl)-3-(hydroxymethyl)-1,3-dihydro-2H-indol-2-one (4.70 g, 12.4 mmol) in anhydrous tetrahydrofuran (120 mL) was added tributylphosphine (3.8 mL, 15.5 mmol), followed by additional of di-tert-butyl azodicarboxylate (3.58 g, 15.5 mmol) in anhydrous tetrahydrofuran (25 mL) at 0° C. The reaction mixture was stirred at 0° C. for 1 h and at ambient temperature for 16 h. The reaction was quenched by addition of saturated aqueous ammonium chloride solution (150 mL) and extracted with ethyl acetate (3×200 mL). The combined organic solution was washed with brine (100 mL), dried over anhydrous sodium sulfate, filtered and concentrated in vacuo to dryness. The residue was purified by column chromatography with ethyl acetate in hexanes (10% to 30% gradient) to give 7'-bromospiro[furo[2,3-f][1,3]benzodioxole-7,3'-indol]-2'(1'H)-one (2.4 g, 53%) as a colorless solid: mp 240° C. (dec.); $^1$H NMR (300 MHz, DMSO-d$_6$) δ10.88 (s, 1H), 7.34 (dd, J=8.1, 1.0 Hz, 1H), 7.10 (d, J=7.2 Hz, 1H), 6.93 (dd, J=8.1, 7.5 Hz, 1H), 6.68 (s, 1H), 6.36 (s, 1H), 5.93 (dd, J=2.9, 0.8 Hz, 2H), 4.77 (d, J=9.4 Hz, 1H), 4.65 (d, J=9.4 Hz, 1H); $^{13}$C NMR (75 MHz, DMSO-d$_6$) δ 178.1, 155.3, 148.2, 141.6, 141.1, 134.2, 131.4, 123.8, 122.8, 119.4, 103.1, 102.0, 101.3, 93.1, 79.9, 58.8; MS (ES+) m/z 360.2 (M+1), 362.2 (M+1); MS (ES-) m/z 358.2 (M-1), 360.2 (M-1).

EXAMPLE 1.6

Synthesis of 1'-[(3-isopropylisoxazol-5-yl)methyl]spiro[furo[2,3-f][1,3]benzodioxole-7,3'-indol]-2'(1'H)-one

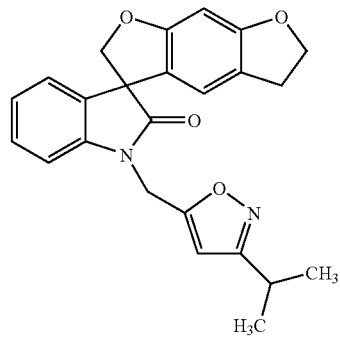

To an ice-cold stirring suspension of (3-isopropylisoxazol-5-yl)methanol (0.338 g, 2.4 mmol) in N,N-dimethylformamide (20 mL) was added a solution of N-(chloromethylene)-N-methylmethanaminium chloride (0.36 g, 2.8 mmol) in N,N-dimethylformamide (10 mL). The mixture was stirred at ambient temperature for 30 min and then transferred to a suspended mixture of spiro[furo[2,3-f][1,3]benzodioxole-7,3'-indol]-2'(1'H)-one (0.56 g, 2.0 mmol), cesium carbonate (1.95 g, 6.0 mmol) in N,N-dimethylformamide (4 mL). The reaction mixture was stirred at ambient temperature for 16 h and filtered. The solid was washed with acetone (100 mL). The filtrate was concentrated in vacuo. The residue was purified by column chromatography with ethyl acetate in hexanes (10% to 30% gradient) to give 1'-[(3-isopropylisoxazol-5-yl)methyl]spiro[furo[2,3-f][1,3]benzodioxole-7,3'-indol]-2' (1'H)-one (0.50 g, 60%) as a colorless solid: mp 132-136° C. (diethyl ether/hexanes); $^1$H NMR (300 MHz, DMSO-d$_6$) 87.34 (ddd, J=7.7, 7.7, 1.2 Hz, 1H), 7.21 (d, J=7.5 Hz, 1H), 7.14 (d, J=7.7 Hz, 1H), 7.08 (ddd, J=7.5, 7.5, 0.8 Hz, 1H), 6.71 (s, 1H), 6.49 (s, 1H), 6.21 (s, 1H), 5.93 (d, J=1.0 Hz, 2H), 5.08 (s, 2H), 4.82 (d, J=9.4 Hz, 1H), 4.72 (d, J=9.4 Hz, 1H), 3.03 (m, 1H), 1.19 (d, J=6.9 Hz, 6H); $^{13}$C NMR (75 MHz, DMSO-d$_6$) δ176.4, 168.9, 166.3, 155.2, 148.3, 141.6, 141.5, 131.4, 128.8, 123.6, 123.2, 119.5, 109.1, 102.8, 101.3, 101.1, 93.2, 79.5, 57.2, 35.6, 25.8, 21.2; MS (ES+) m/z 405.3 (M+1).

EXAMPLE 1.7

Synthesis of 1'-[(4-bromo-2-thienyl)methyl]spiro[furo[2,3-f][1,3]benzodioxole-7,3'-indol]-2'(1'H)-one

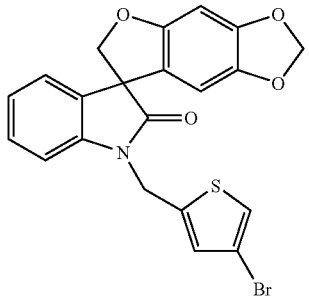

Following the procedure as described in EXAMPLE 1.6 and making non-critical variations using (4-bromothiophen-2-yl)methanol to replace (3-isopropylisoxazol-5-yl)methanol, 1'-[(4-bromo-2-thienyl)methyl]spiro[furo[2,3-f][1,3] benzodioxole-7,3'-indol]-2'(1'H)-one was obtained (47%) as a colorless solid: $^1$H NMR (300 MHz, DMSO-d$_6$) δ 7.59 (d, J=1.5 Hz, 1H), 7.35-7.18 (m, 4H), 7.06 (ddd, J=7.4, 7.4, 0.7 Hz, 1H), 6.71 (s, 1H), 6.12 (s, 1H), 5.93 (d, J=2.2 Hz, 2H), 5.11 (d, J=6.9 Hz, 2H), 4.81 (d, J=9.4 Hz, 1H), 4.70 (d, J=9.4 Hz, 1H); $^{13}$C NMR (75 MHz, DMSO-d$_6$) δ176.5, 155.4, 148.4, 141.7, 141.4, 140.9, 131.6, 129.2, 128.9, 123.8, 123.7, 123.3, 119.6, 109.4, 108.0, 102.7, 101.5, 93.4, 79.7, 57.4, 38.1; MS (ES+) m/z 478.1 (M+23), 480.1 (M+23).

EXAMPLE 1.8

Synthesis of 1'-(1-benzofuran-2-ylmethyl)spiro[furo[2,3-f][1,3]-benzodioxole-7,3'-indol]-2'(1'H)-one

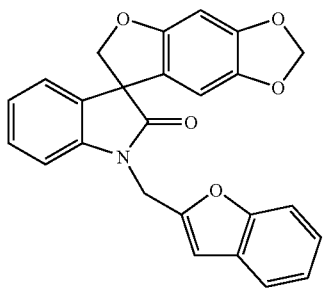

Following the procedure as described in EXAMPLE 1.6 and making non-critical variations using benzofuran-2-ylmethanol to replace (3-isopropylisoxazol-5-yl)methanol, 1-(1-benzofuran-2-ylmethyl)spiro[furo[2,3-f][1,3]benzodioxole-7,3'-indol]-2'(1'H)-one was obtained (44%) as a colorless solid: mp 167-168° C. (diethyl ether); $^1$H NMR (300 MHz, DMSO-d$_6$) δ7.60 (dd, J=7.0, 1.5 Hz, 1H), 7.50 (d, J=8.2 Hz, 1H,), 7.33-7.19 (m, 5H), 7.05 (ddd, J=7.4, 7.4, 0.9 Hz, 1H), 6.98 (s, 1H), 6.72 (s, 1H), 6.22 (s, 1H), 5.94 (d, J=4.3 Hz, 2H), 5.15 (d, J=6.0 Hz, 2H), 4.84 (d, J=9.4 Hz, 1H), 4.73 (d, J=9.4 Hz, 1H); $^{13}$C NMR (75 MHz, DMSO-d$_6$) δ176.5, 155.3, 154.3, 152.2, 148.4, 141.8, 141.7, 131.6, 128.8, 127.8, 124.4, 123.6, 123.2, 123.0, 121.1, 119.7, 110.9, 109.5, 105.2, 102.9, 101.5, 93.3, 79.7, 57.5, 37.2; MS (ES+) m/z 412.3 (M+1).

EXAMPLE 1.9

Synthesis of 1-{[2-methyl-5-(trifluoromethyl)-1,3-oxazol-4-yl]methyl}spiro[furo[2,3-f][1,3]benzodioxole-7,3'-indol]-2'(1'H)-one

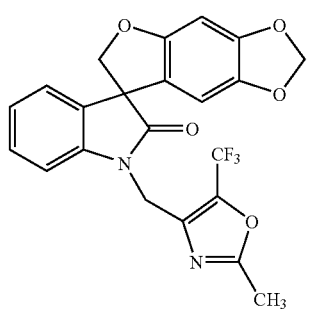

To a mixture of spiro[furo[2,3-f][1,3]benzodioxole-7,3'-indol]-2'(1'H)-one (0.281 g, 1.0 mmol) and (2-methyl-5-(trifluoromethyl)oxazol-4-yl)methanol (0.18 g, 1.0 mmol) in anhydrous tetrahydrofuran (8 mL) was added tributylphosphine (0.30 g, 1.5 mmol) at 0° C., followed by additional of N,N,N'/N'-tetramethylazodicarboxamide (0.26 g, 1.5 mmol). The reaction mixture was stirred at 0° C. for 1 h and stirred at ambient temperature for 16 h. The reaction mixture was quenched with aqueous ammonium chloride (25%, 50 mL) and extracted with ethyl acetate (3×40 mL). The combined organic solution was washed with brine (30 mL), dried over anhydrous sodium sulfate and concentrated in vacuo to dryness. The residue was purified by column chromatography with ethyl acetate in hexanes (10% to 30% gradient) to give 1'-{[2-methyl-5-(trifluoromethyl)-1,3-oxazol-4-yl]methyl}spiro[furo[2,3-f][1,3]benzodioxole-7,3'-indol]-2'(1'H)-one (0.30 g, 68%) as a colorless solid: mp 136-137° C. (diethyl ether/hexane); $^1$H NMR (300 MHz, DMSO-d$_6$) δ 7.32 (ddd, J=7.7, 1.2, 1.2 Hz, 1H), 7.19 (dd, J=7.6, 1.0 Hz, 1H), 7.07-7.03 (m, 2H), 6.70 (s, 1H), 6.29 (s, 1H), 5.93 (dd, J=5.0, 0.7 Hz, 2H), 4.98 (q, J=16.4 Hz, 2H), 4.75 (dd, J=20.8, 9.4 Hz, 2H), 2.46 (s, 3H); $^{13}$C NMR (75 MHz, DMSO-d$_6$) δ 176.5, 163.6, 155.1, 148.2, 141.9, 141.5, 137.6 (d, $^3J_{CF}$=2.1 Hz), 133.5 (q, $^2J_{CF}$=42.7 Hz), 131.6, 128.7, 123.5, 123.0, 119.8, 119.2 (q, $^1J_{CF}$=266.9 Hz), 109.0, 103.0, 101.3, 93.1, 79.3, 57.2, 34.9, 13.4; MS (ES+) m/z 445.3 (M+1).

EXAMPLE 1.10

Synthesis of (3R)-5,6-dihydrospiro[benzo[1,2-b:5,4-b']difuran-3,3'-indol]-2'(1'H)-one and (3S)-5,6-dihydrospiro[benzo[1,2-b:5,4-b']difuran-3,3'-indol]-2'(1'H)-one

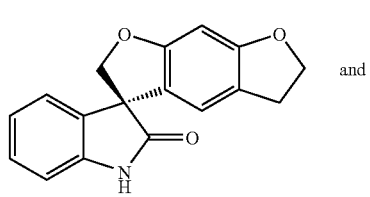

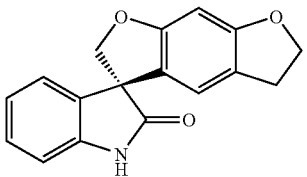

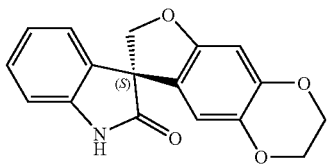

5,6-Dihydrospiro[benzo[1,2-b:5,4-b']difuran-3,3'-indol]-2'(1'H)-one (0.04 g) was dissolved with heating and sonication in dimethylsulfoxide (0.3 mL). Acetonitrile (0.3 mL) and methyl tent-butyl ether (2.0 mL) were added and the mixture was submicron filtered. The mixture was injected onto a Waters LC/MS autopurification system (Waters Inc., Milford, Mass.) equipped with a CHIRALPAK-IA (Chiral Technologies, Inc., West Chester, Pa.) HPLC column (21 mm i.d.×250 mm length, 20 μm particle diameter) and was eluted over a run time of 20 min with methyl tert-butyl ether/acetonitrile (9/1) at a flow rate of 15 mL/min with UV detection at 254 nm. 35 replicate injections were performed under these conditions, corresponding to a total of 1.40 g of the racemate. Following resolution, the appropriate fractions were concentrated to dryness in vacuo and the resultant solid was triturated with methanol (15 mL), collected by vacuum filtration and dried under high vacuum.

The first enantiomer to elute was (3S)-5,6-dihydrospiro[benzo[1,2-b:5,4-b']difuran-3,3'-indol]-2'(1'H)-one, which was obtained as a colorless solid with a 67% recovery (0.472 g): mp 255-256° C. (methanol); $^1$H NMR (300 MHz, DMSO-$d_6$) δ10.56 (br s, 1H), 7.26-7.18 (m, 1H), 7.09 (d, J=6.9 Hz, 1H), 6.98-6.89 (m, 2H), 6.49 (s, 1H), 6.38 (s, 1H), 4.77 (d, J=9.2 Hz, 1H), 4.65 (d, J=9.2 Hz, 1H), 4.52-4.43 (m, 2H), 2.99-2.91 (m, 2H); $^{13}$C NMR (75 MHz, DMSO-$d_6$) δ 178.7, 131.0, 160.6, 141.8, 133.0, 128.6, 123.8, 122.3, 120.8, 119.7, 119.0, 109.7, 92.4, 79.9, 72.1, 57.3, 28.4; MS (ES+) m/z 278.0 (M+1).

The second enantiomer to elute was (3R)-5,6-dihydrospiro[benzo[1,2-b:5,4-b']difuran-3,3'-indol]-2'(1'H)-one, which was obtained as a colorless solid with a 60% recovery (0.423 g): mp 256-257° C. (methanol); $^1$H NMR (300 MHz, DMSO-$d_6$) δ10.56 (br s, 1H), 7.26-7.18 (m, 1H), 7.09 (d, J=6.9 Hz, 1H), 6.98-6.89 (m, 2H), 6.49 (s, 1H), 6.38 (s, 1H), 4.77 (d, J=9.2 Hz, 1H), 4.65 (d, J=9.2 Hz, 1H), 4.52-4.43 (m, 2H), 2.99-2.91 (m, 2H); $^{13}$C NMR (75 MHz, DMSO-$d_6$) δ178.7, 131.0, 160.6, 141.8, 133.0, 128.6, 123.8, 122.3, 120.8, 119.7, 119.0, 109.7, 92.4, 79.9, 72.1, 57.3, 28.4; MS (ES+) m/z 278.0 (M+1).

EXAMPLE 1.11

Preparation of (R)-3,7-dihydro-2H-spiro[benzofuro[5,6-b][1,4]dioxine-8,3'-indolin]-2'-one and (S)-2,3-dihydrospiro[furo[2,3-g][1,4]benzodioxine-8,3'-indol]-2'(1'H)-one

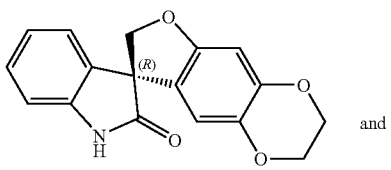

and 2,3-dihydrospiro[furo[2,3-g][1,4]benzodioxine-8,3'-indol]-2'(1'H)-one (0.14 g) was dissolved in hot dimethylsulfoxide (0.4 mL). Acetonitrile (0.4 mL) and methyl tert-butyl ether (2.2 mL) were added and the mixture was submicron filtered. The mixture was injected onto a Waters LC/MS autopurification system (Waters Inc., Milford, Mass.) equipped with a CHIRALPAK-IA (Chiral Technologies, Inc., West Chester, Pa.) HPLC column (30 mm i.d.×250 mm length, 20 μm particle diameter) and was eluted over a run time of 60 min with methyl tert-butyl ether/acetonitrile (98/2) at a flow rate of 30 mL/min with UV detection at 254 nm. Following resolution, the appropriate fractions were concentrated to dryness in vacuo and the resultant solid was triturated with water (30 mL), collected by vacuum filtration and dried under high vacuum.

The first enantiomer to elute was (R)-2,3-dihydrospiro[furo[2,3-g][1,4]benzodioxine-8,3'-indol]-2'(1'H)-one, which was obtained as a colorless solid; $^1$H NMR (300 MHz, DMSO-$d_6$) δ10.57 (s, 1H), 7.24 (ddd, J=7.7, 7.7, 1.0 Hz, 1H), 7.09 (d, J=6.9 Hz, 1H), 6.96 (dd, J=7.5, 7.5 Hz, 1H), 6.91 (d, J=7.8 Hz, 1H), 6.49 (s, 1H), 6.16 (s, 1H), 4.73 (d, J=9.0 Hz, 1H), 4.60 (d, J=9.0 Hz, 1H), 4.20-4.15 (m, 2H), 4.12-4.07 (m, 2H); MS (ES+) m/z 296.0 (M+1); $[\alpha]_D$ −36.61 (c 1.0, DMSO).

The second enantiomer to elute was (S)-2,3-dihydrospiro[furo[2,3-g][1,4]benzodioxine-8,3'-indol]-2'(1'H)-one, which was obtained as a colorless solid; $^1$H NMR (300 MHz, DMSO-$d_6$) δ10.57 (s, 1H), 7.24 (ddd, J=7.7, 7.7, 1.0 Hz, 1H), 7.09 (d, J=6.9 Hz, 1H), 6.96 (dd, J=7.5, 7.5 Hz, 1H), 6.91 (d, J=7.8 Hz, 1H), 6.49 (s, 1H), 6.16 (s, 1H), 4.73 (d, J=9.0 Hz, 1H), 4.60 (d, J=9.0 Hz, 1H), 4.20-4.15 (m, 2H), 4.12-4.07 (m, 2H); MS (ES+) m/z 296.0 (M+1); $[\alpha]_D$ +36.65 (c 1.0, DMSO).

EXAMPLE 1.12

Synthesis of (8S)-1'-{[3-(trifluoromethyl)pyridin-2-yl]methyl}-2,3-dihydrospiro[furo[2,3-g][1,4]benzodioxine-8,3'-indol]-2'(1'H)-one

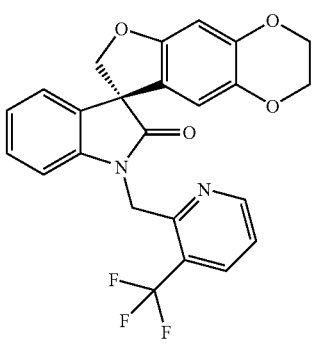

To a mixture of (3-(trifluoromethyl)pyridin-2-yl)methanol hydrochloride (5.0 g, 23.14 mmol) and thionyl chloride (5.0 g, 42.0 mmol) in dichloromethane (50 mL) at 0° C. were added two drops of N,N-dimethylformamide. The reaction mixture was allowed to warm to ambient temperature and stirred for 16 h. The solvent was removed under reduced pressure, and the residue was dissolved in N,N-dimethylformamide (50 mL). To the above solution were added (8S)-2,3-dihydrospyro[furo[2,3-g][1,4]benzodioxine-8,3'-indol]-2'(1'H)-one (4.72 g, 15.98 mmol), cesium carbonate (16.3 g, 50.03 mmol) and potassium iodide (1.0 g, 6.0 mmol). The reaction mixture was warmed up to 90° C. and stirred under nitrogen for 2.5 h. The reaction mixture was cooled to ambient temperature, concentrated to dryness under reduced pressure, and the residue was treated with water (50 mL) and sonicated for 0.5 h. The suspension was filtered, and washed with water (50 mL), dried under reduced pressure. The solid crude product was subjected to column chromatography with dichloromethane/ethyl acetate (1:100-1:4) to afford (8S)-1'-{[3-(trifluoromethyl)pyridin-2-yl]methyl}-2,3-dihydrospyro[furo[2,3-g][1,4]benzodioxine-8,3'-indol]-2'(1'H)-one (5.45 g, 75%) as a colorless solid: mp 164-165° C. (methanol); $^1$H NMR (300 MHz, DMSO-$d_6$) δ 8.62 (d, J=4.4 Hz, 1H), 8.20 (d, J=7.7 Hz, 1H), 7.51 (dd, J=7.7, 5.0 Hz, 1H), 7.23-6.82 (m, 4H), 6.47 (s, 1H), 6.43 (s, 1H), 5.21 (ABq, 2H), 4.73 (ABq, 2H), 4.18-4.04 (m, 4H); $^{13}$C NMR (75 MHz, DMSO-$d_6$) δ 177.5, 155.0, 152.9, 152.8, 144.5, 143.3, 138.2, 135.5, 135.4, 132.4, 129.1, 126.1, 124.1, 123.9, 123.7, 123.4, 123.3, 122.8, 122.5, 122.0, 112.2, 109.4, 99.0, 79.6, 64.6, 64.0, 57.7, 42.4, 42.3; MS (ES+) m/z 454.9.

EXAMPLE 1.13

Synthesis of (8S)-1'-[(5-hydroxypyridin-2-yl)methyl]-2,3-dihydrospiro[furo[2,3-g][1,4]benzodioxine-8,3'-indol]-2'(1'H)-one

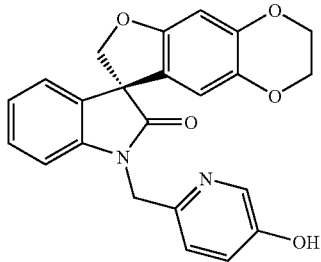

To a mixture of (8S)-2,3-dihydrospyro[furo[2,3-g][1,4]benzodioxine-8,3'-indol]-2'(1'H)-one (1.3 g, 4.4 mmol), (5-(benzyloxy)pyridin-2-yl)methanol (1.23 g, 5.72 mmol) and tributylphosphine (1.26 g, 6.23 mml) in tetrahydrofuran (150 mL) at 0° C. was added diethyl azodicarboxylate (1.15 g, 6.62 mmol). The reaction mixture was allowed to warm to ambient temperature and stirred for 48 h. The reaction mixture was diluted with ethyl acetate (100 mL) and filtered, and the filtrate was concentrated under reduced pressure. The residue was dissolved in dichloromethane (150 mL), washed with 1 M hydrochloric acid in water (3×30 mL), 1 M sodium hydroxide in water (3×30 mL), dried over magnesium sulfate, filtered, and the filtrate was concentrated to dryness. The residue was sonicated with methanol (30 mL), and the solid product was filtered off to afford (8S)-1'-{[5-(benzyloxy)pyridine-2-yl]methyl}-2,3-dihydrospyro[furo[2,3-g][1,4]-benzodioxine-8,3'-indol]-2'(1'H)-one (1.54 g, 87%). To a mixture of (8S)-1'-{[5-(benzyloxy)pyridine-2-yl]methyl}-2,3-dihydrospyro[furo[2,3-g][1,4]benzodioxine-8,3'-indol]-2'(1'H)-one (1.54 g, 3.12 mmol) and ammonium formate (1.0 g, 15.86 mmol) in methanol (50 mL) was added 10% palladium on carbon (0.5 g). The reaction mixture was heated at reflux for 1 h under nitrogen. The reaction mixture was cooled to ambient temperature, filtered, and the filtrate was concentrated under reduced pressure. The residue was subjected to column chromatography with dichloromethanemethanol (20:1-10:1) to afford (8S)-1'-[(5-hydroxypyridin-2-yl)methyl]-2,3-dihydrospyro[furo[2,3-g][1,4]benzodioxine-8,3'-indol]-2'(1'H)-one (0.93 g, 50%) as a colorless solid: mp 256-258° C. (chloroform-hexane); $^1$H NMR (300 MHz, DMSO-$d_6$) δ 8.51 (s, 1H), 7.96 (d, J=2.7 Hz, 1H), 7.23-6.85 (m, 6H), 6.45 (s, 1H), 6.34 (s, 1H), 4.97 (ABq, 2H), 4.79 (ABq, 2H), 4.08-3.91 (m, 2H), 3.78-3.56 (m, 2H); $^{13}$C NMR (75 MHz, DMSO-$d_6$) δ178.4, 155.3, 152.9, 145.7, 144.6, 142.2, 138.3, 137.3, 132.1, 128.8, 124.3, 124.0, 123.7, 122.5, 120.5, 111.7, 109.5, 99.4, 79.7, 64.4, 63.4, 58.2, 44.9; MS (ES+) m/z 402.8 (M+1).

EXAMPLE 1.14

Synthesis of 1'-[(5-bromopyridin-2-yl)methyl]-2,3-dihydrospiro[furo[2,3-g][1,4]benzodioxine-8,3'-indol]-2'(1'H)-one

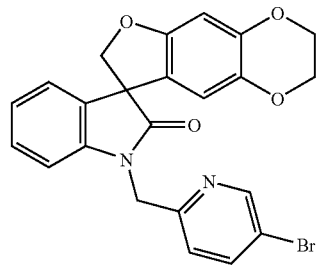

Following the procedure as described in EXAMPLE 1.2 and making non-critical variations using (5-bromopyrid-2-yl)methanol to replace 3-pyridinemethanol, 1'-[(5-bromopyridin-2-yl)methyl]-2,3-dihydrospiro[furo[2,3-g][1,4]benzodioxine-8,3'-indol]-2'-(1'H)-one was obtained (32%) as a colorless solid: mp 201-202° C.; $^1$H NMR (300 MHz, CDCl$_3$) δ8.63 (d, J=2.4 Hz, 1H), 7.79 (dd, J=8.4, 2.1 Hz, 1H), 7.24-7.16 (m, 3H), 7.04 (dd, J=7.5, 7.5 Hz, 1H), 6.88 (d, J=7.8 Hz, 1H), 6.51 (s, 1H), 6.28 (s, 1H), 5.15 (d, J=15.9 Hz, 1H), 4.94 (d, J=9.0 Hz, 1H), 4.91 (d, J=15.9 Hz, 1H), 4.67 (d, J=9.0 Hz, 1H), 4.22-4.11 (m, 4H); $^{13}$C NMR (75 MHz, CDCl$_3$) δ177.5, 155.3, 154.1, 150.6, 144.7, 141.9, 139.7, 138.3, 132.2, 128.9, 123.9, 123.6, 123.1, 121.0, 119.9, 111.6, 109.4, 99.4, 80.1, 64.5, 63.9, 58.1, 45.5; MS (ES+) m/z 465.1 (M+1), 467.1 (M+1).

EXAMPLE 1.15

Synthesis of 1'-{[5-(4-chlorophenyl)-2-(trifluoromethyl)furan-3-yl]methyl}spiro[furo[2,3-f][1,3]benzodioxole-7,3'-indol]-2'(1'H)-one

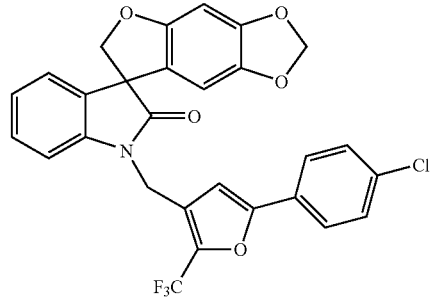

Following the procedure as described in EXAMPLE 1.6 and making non-critical variations using (5-(4-chlorophenyl)-2-(trifluoromethyl)furan-3-yl)methanol to replace (3-isopropylisoxazol-5-yl)methanol, 1-{[5-(4-chlorophenyl)-2-(trifluoromethyl)furan-3-yl]methyl}spiro[furo[2,3-f][1,3]benzodioxole-7,3'-indol]-2'(1'H)-one was obtained (35%) as a colorless solid: mp 114-116° C.; ¹H NMR (300 MHz, CDCl₃) δ7.55 (d, J=8.7 Hz, 2H), 7.34 (d, J=8.7 Hz, 2H), 7.28 (dd, J=7.8, 7.8 Hz, 1H), 7.18 (d, J=7.5 Hz, 1H), 7.06 (dd, J=7.5, 7.5 Hz, 1H), 6.87 (d, J=7.8 Hz, 1H), 6.57 (s, 1H), 6.53 (s, 1H), 6.09 (s, 1H), 5.87 (s, 2H), 4.96 (ABq, 2H), 4.82, (ABq, 2H); ¹³C NMR (75 MHz, CDCl₃) δ 177.8, 156.0, 155.2, 149.1, 142.4, 141.4, 137.7, 135.1, 131.9, 129.2, 129.1, 127.8, 127.1, 125.9, 124.7, 124.2, 123.9, 121.6, 119.2, 113.9, 108.6, 106.6, 102.8, 101.6, 93.8, 80.3, 58.2, 34.4; MS (ES+) m/z 540.3 (M+1), 542.3 (M+1).

EXAMPLE 1.16

Synthesis of 1'-{[5-chloro-1-methyl-3-(trifluoromethyl)-1H-pyrazol-4-yl]methyl}spiro[furo[2,3-f][1,3]benzodioxole-7,3'-indol]-2'(1'H)-one

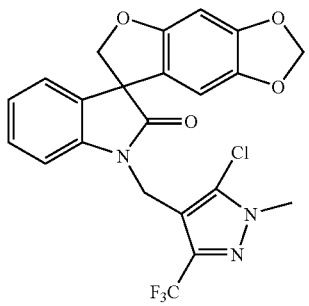

Following the procedure as described in EXAMPLE 1.6 and making non-critical variations using (5-chloro-1-methyl-3-(trifluoromethyl)-1H-pyrazol-4-yl)methanol (Nakatani et al., EP 2002/743670) to replace (3-isopropylisoxazol-5-yl)methanol, 1'-{[5-chloro-1-methyl-3-(trifluoromethyl)-1H-pyrazol-4-yl]methyl}spiro[furo[2,3-f][1,3]benzodioxole-7,3'-indol]-2'(1'H)-one was obtained (70%) as a colorless solid: mp 180-182° C.; ¹H NMR (300 MHz, CDCl₃) δ7.26-7.12 (m, 2H), 7.03 (dd, J=7.5, 7.5 Hz, 1H), 6.75 (d, J=7.8 Hz, 1H), 6.49 (s, 1H), 6.14 (s, 1H), 5.84 (d, J=5.3 Hz, 2H), 4.92 (s, 2H), 4.75 (ABq, 2H), 3.86 (s, 3H); ¹³C NMR (75 MHz, CDCl₃) δ177.3, 156.2, 148.9, 142.4, 141.6, 139.6 (q, J=37.9 Hz), 132.0, 128.9, 128.7, 124.1, 123.6, 122.7, 119.0, 110.6, 108.9, 103.4, 101.5, 93.6, 80.9, 58.2, 37.2, 33.5; MS (ES+) m/z 478.3 (M+1), 480.3 (M+1).

EXAMPLE 1.17

Synthesis of 1'-(5-methoxypyridin-3-yl)spiro[furo[2,3-f][1,3]benzodioxole-7,3'-indol]-2'(1'H)-one

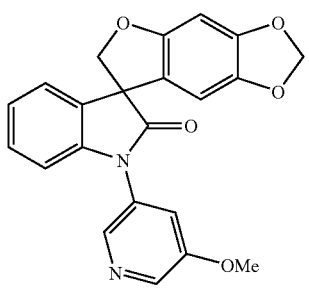

A 10 mL pressure tube was charged with spiro[furo[2,3-f][1,3]benzodioxole-7,3'-indol]-2'(1'H)-one (0.28 g, 1.0 mmol), 3-bromo-5-methoxypyridine (0.26 g, 1.4 mmol), palladium (II) acetate (0.038 g, 0.2 mmol), 9,9-dimethyl-4,5-bis(diphenylphosphino)xanthene (0.14 g, 0.24 mmol), cesium carbonate (0.46 g, 1.4 mmol) and 1,4-dioxane (1.2 mL). The reaction mixture was heated at 100° C. for 25 min under microwave irradiation and allowed to cool to ambient temperature. The mixture was diluted with dichloromethane (20 mL) and filtered through a pad of diatomaceous earth. The filtrate was concentrated in vacuo and the residue purified by column chromatography eluted with a 0% to 15% gradient of ethyl acetate in hexanes to afford 1'-(5-methoxypyridin-3-yl)spiro[furo[2,3-f][1,3]benzodioxole-7,3'-indol]-2'(1'H)-one (0.097 g, 25%) as a brown solid: ¹H NMR (300 MHz, CDCl₃) δ8.37 (d, J=6.2 Hz, 2H), 7.39-7.34 (m, 1H), 7.32-7.24 (m, 2H), 7.18-7.09 (m, 1H), 6.95 (d, J=7.9 Hz, 1H), 6.53 (s, 1H), 6.25 (s, 1H), 5.88 (d, J=6.2 Hz, 2H), 4.89 (ABq, 2H), 3.90 (s, 3H); ¹³C NMR (75 MHz, CDCl₃) δ177.0, 156.3, 156.0, 149.1, 142.5, 141.9, 138.9, 137.3, 131.9, 129.1, 129.0, 128.2, 124.5, 119.2, 118.5, 109.6, 103.0, 101.6, 93.7, 80.7, 58.5, 56.0; MS (ES+) m/z 389.3 (M+1).

EXAMPLE 2

Synthesis of 1'-(diphenylmethyl)-6-methoxy-5-methylspiro[1-benzofuran-3,3'-indol]-2'(1'H)-one

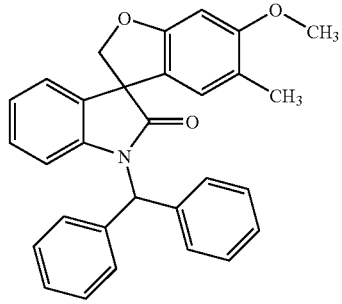

To a mixture of 1-(diphenylmethyl)-3-(2-hydroxy-4-methoxy-5-methylphenyl)-1,3-dihydro-2H-indol-2-one (10.6 g, 24.4 mmol) and cesium carbonate (23.8 g, 73.1 mmol) in tetrahydrofuran (100 mL) was added chloroiodomethane (6.35 g, 36.6 mmol) under nitrogen. The mixture was stirred at ambient temperature for 3 h, then filtered through a pad of silica and rinsed with tetrahydrofuran (500 mL). The filtrate was concentrated in vacuo to dryness. The residue was recrystallized from diethyl ether (20 mL) to afford 1-(diphenylmethyl)-6-methoxy-5-methylspiro[1-benzofuran-3,3'-indol]-2'(1'H)-one (7.9 g, 72%) as a colorless solid: ¹H NMR (300 MHz, CDCl₃) δ7.41-7.27 (m, 10H), 7.15 (dd, J=7.1, 1.5 Hz, 1H), 7.07 (s, 1H), 7.05-6.92 (m, 2H), 6.55-6.49 (m, 2H), 6.34 (s, 1H), 4.86 (ABq, 2H), 3.80 (s, 3H), 2.01 (s, 3H); ¹³C NMR (75 MHz, CDCl₃) δ178.1, 160.2, 159.2, 141.8, 137.8, 137.4, 132.9, 128.70, 128.66, 128.48, 128.46, 128.2, 128.0, 127.9, 124.2, 123.8, 123.1, 119.6, 112.2, 93.8, 80.4, 58.7, 57.7, 55.6, 16.1; MS (ES+) m/z 448.3 (M+1).

EXAMPLE 2.1

Synthesis of 4'-chloro-1'-(diphenylmethyl)-5,6-dihydrospiro[benzo[1,2-b:5,4-b']difuran-3,3'-indol]-2'(1'H)-one

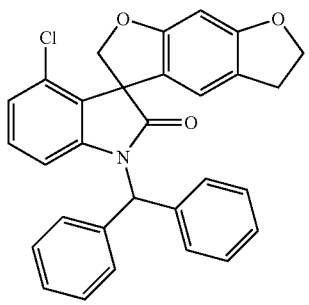

Following the procedure as described in EXAMPLE 2 and making non-critical variations using 4-chloro-1-(diphenylmethyl)-3-(6-hydroxy-2,3-dihydro-1-benzofuran-5-yl)-1,3-dihydro-2H-indol-2-one to replace 1-(diphenylmethyl)-3-(2-hydroxy-4-methoxy-5-methylphenyl)-1,3-dihydro-2H-indol-2-one, 4'-chloro-1'-(diphenylmethyl)-5,6-dihydrospiro[benzo[1,2-b:5,4-b']difuran-3,3'-indol]-2'(1'H)-one was obtained (49%) as a colorless solid: MS (ES+) m/z 479.9 (M+1), 481.9 (M+1).

EXAMPLE 2.2

Synthesis of 6-bromo-1'-(diphenylmethyl)spiro[1-benzofuran-3,3'-indol]-2'(1'H)-one

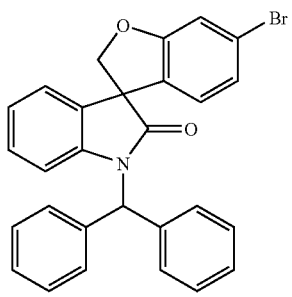

To a stirred solution of 3-(4-bromo-2-hydroxyphenyl)-1-(diphenylmethyl)-1,3-dihydro-2H-indol-2-one (10.1 g, 22.6 mmol) and cesium carbonate (22.1 g, 67.8 mmol) in tetrahydrofuran (100.0 mL) was added chloroiodomethane (5.88 g, 33.9 mmol). The mixture was stirred at ambient temperature for 3 h, then filtered through a pad of silica gel followed by tetrahydrofuran rinses (500.0 mL). The filtrate was concentrated in vacuo to dryness, and recrystallized from diethyl ether (20.0 mL) in a Branson ultrasonic bench top water bath to afford 6-bromo-1-(diphenylmethyl)spiro[1-benzofuran-3, 3'-indol]-2'(1'H)-one (7.3 g, 67%) as a colorless solid: $^1$H NMR (300 MHz, CDCl$_3$) δ7.44-7.25 (m, 10H), 7.15-7.09 (m, 2H), 7.07-6.90 (m, 4H), 6.56-6.49 (m, 2H), 5.03 (d, J=9.1 Hz, 1H), 4.76 (d, J=9.1 Hz, 1H); MS (ES+) m/z 482.1 (M+1), 484.0 (M+1).

EXAMPLE 2.3

Synthesis of 1'-(diphenylmethyl)-5,6-dimethylspiro[1-benzofuran-3,3'-indol]-2'(1'H)-one

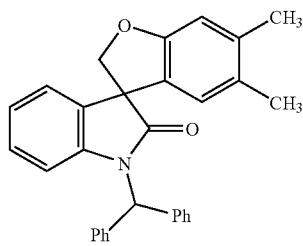

Following the procedure as described in EXAMPLE 2 and making non-critical variations using 1-(diphenylmethyl)-3-hydroxy-3-(2-hydroxy-4,5-dimethylphenyl)-1,3-dihydro-2H-indol-2-one to replace 1-(diphenylmethyl)-3-(2-hydroxy-4-methoxy-5-methylphenyl)-1,3-dihydro-2H-indol-2-one, 1'-(diphenylmethyl)-5,6-dimethylspiro[1-benzofuran-3,3'-indol]-2'(1'H)-one was obtained (54%) as a colorless solid: mp 193-195° C. (ethyl acetate/hexanes); $^1$H NMR (300 MHz, CDCl$_3$) δ7.38-7.32 (m, 10H), 7.14-6.92 (m, 4H), 6.75-6.78 (m, 1H), 6.55-6.50 (m, 1H), 6.37-6.31 (m, 1H), 4.99-4.94 (m, 1H), 4.73-4.65 (m, 1H), 2.20 (s, 3H), 2.05 (s, 3H); $^{13}$C NMR (75 MHz, CDCl$_3$) δ177.9, 159.0, 141.7, 138.4, 137.7, 137.4, 132.8, 129.4, 128.6, 128.4, 128.1, 127.9, 127.8, 126.3, 123.8, 123.0, 112.2, 111.4, 79.7, 58.7, 57.8, 20.3, 19.3; MS (ES+) m/z 432.3 (M+1).

EXAMPLE 2.4

Synthesis of 1'-(diphenylmethyl)-5'-fluoro-5,6-dihydrospiro[benzo[1,2-b:5,4-b']difuran-3,3'-indol]-2'(1'H)-one

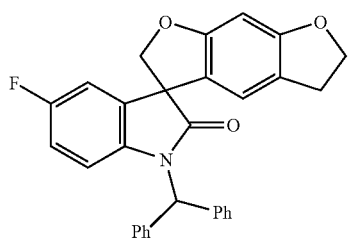

Following the procedure as described in EXAMPLE 2 and making non-critical variations using 1-(diphenylmethyl)-5-fluoro-3-(6-hydroxy-2,3-dihydro-1-benzofuran-5-yl)-1,3-dihydro-2H-indol-2-one to replace 1-(diphenylmethyl)-3-(2-hydroxy-4-methoxy-5-methylphenyl)-1,3-dihydro-2H-indol-2-one, 1'-(diphenylmethyl)-5'-fluoro-5,6-dihydrospiro[benzo[1,2-b:5,4-b']difuran-3,3'-indol]-2'(1'H)-one was obtained (71%) as a colorless solid: mp 228-229° C. (ethyl acetate/hexanes); $^1$H NMR (300 MHz, CDCl$_3$) δ 7.39-7.25 (m, 10H), 7.06 (s, 1H), 6.90-6.87 (m, 1H), 6.72-6.65 (m, 1H), 6.42-6.38 (m, 3H), 4.83 (ABq, 2H), 4.53 (t, J=9.0 Hz, 2H), 3.02-2.97 (m, 2H); MS (ES+) m/z 464.1 (M+1).

EXAMPLE 2.5

Synthesis of 1'-(diphenylmethyl)-6'-fluoro-5,6-dihydrospiro[benzo[1,2-b:5,4-b']difuran-3,3'-indol]-2'(1'H)-one

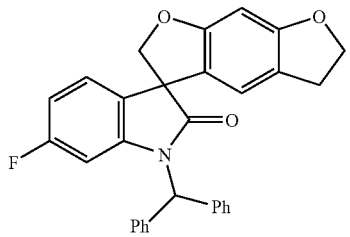

Following the procedure as described in EXAMPLE 2 and making non-critical variations using 1-(diphenylmethyl)-6-fluoro-3-(6-hydroxy-2,3-dihydro-1-benzofuran-5-yl)-1,3-dihydro-2H-indol-2-one to replace 1-(diphenylmethyl)-3-(2-hydroxy-4-methoxy-5-methylphenyl)-1,3-dihydro-2H-indol-2-one, 1'-(diphenylmethyl)-6'-fluoro-5,6-dihydrospiro[benzo[1,2-b:5,4-b']difuran-3,3'-indol]-2'(1'H)-one was obtained (87%) as a colorless solid: mp 194-196° C. (methanol); $^1$H NMR (300 MHz, CDCl$_3$) δ7.42-7.25 (m, 10H), 7.10-7.04 (m, 2H), 6.67-6.61 (m, 1H), 6.40-6.39 (m, 2H), 6.23-6.19 (m, 1H), 4.81 (ABq, 2H), 4.53 (t, J=9.0 Hz, 2H), 2.99 (t, J=9.0 Hz, 2H); MS (ES+) m/z 463.8 (M+1).

EXAMPLE 2.6

Synthesis of 1'-(4-methoxybenzyl)-3-methylspiro[furo[3,2-f][1,2]benzisoxazole-5,3'-indol]-2'(1'H)-one

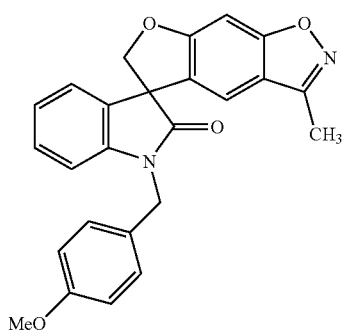

Following the procedure as described in EXAMPLE 2 and making non-critical variations using 3-(6-hydroxy-3-methyl-1,2-benzisoxazol-5-yl)-1-(4-methoxybenzyl)-1,3-dihydro-2H-indol-2-one to replace 1-(diphenylmethyl)-3-(2-hydroxy-4-methoxy-5-methylphenyl)-1,3-dihydro-2H-indol-2-one, 1'-(4-methoxybenzyl)-3-methylspiro[furo[3,2-f][1,2]benzisoxazole-5,3'-indol]-2'(1'H)-one was obtained (95%) as a colorless solid: mp 138-139° C. (ethyl acetate/hexanes); $^1$H NMR (300 MHz, CDCl$_3$) δ 7.46 (d, J=9.0 Hz, 2H), 7.35 (d, J=9.0 Hz, 2H), 7.21-7.18 (m, 1H), 7.11-7.09 (m, 1H), 6.96 (d, J=9.0 Hz, 1H), 6.94-6.88 (m, 2H), 6.79 (d, J=9.0 Hz, 1H), 5.16-4.79 (m, 4H), 3.78 (s, 3H), 2.45 (s, 3H); MS (ES+) m/z 412.9 (M+1).

EXAMPLE 2.7

Synthesis of 1'-benzhydryl-6-(benzyloxy)-2H-spiro[benzofuran-3,3'-indolin]-2'-one

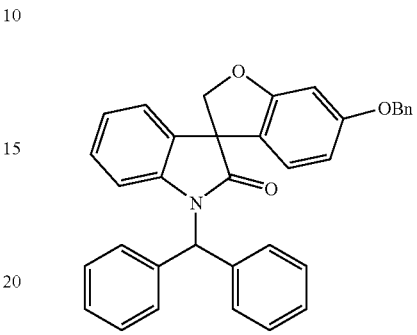

To a stirred solution of 3-[4-(benzyloxy)-2-hydroxyphenyl]-1-(diphenylmethyl)-1,3-dihydro-2H-indol-2-one (7.4 g, 14.8 mmol), chloroiodomethane (2.7 mL, 37.0 mmol) in anhydrous tetrahydrofuran (200 mL) was added cesium carbonate (15.4 g, 47.4 mmol) under argon. The mixture was stirred at ambient temperature for 16 h, then filtered through a pad of celite. The filtrate was concentrated under vacuum. The residue was purified by column chromatography (ethyl acetate/hexanes, 1/5) followed by the treatment with diethyl ether/hexanes to afford 1'-benzhydryl-6-(benzyloxy)-2H-spiro[benzofuran-3,3'-indolin]-2'-one (4.1 g, 55%) as a colorless solid: $^1$H NMR (300 MHz, CDCl$_3$) δ7.42-7.25 (m, 15H), 7.16-7.09 (m, 1H), 7.07-6.90 (m, 3H), 6.62-6.38 (m, 4H), 5.03-4.90 (m, 3H), 4.73 (d, J=9.0 Hz, 1H); MS (ES+) m/z 510.1 (M+1).

EXAMPLE 2.8

Synthesis of 1'-(diphenylmethyl)-5-fluoro-6-methoxyspiro[1-benzofuran-3,3'-indol]-2'(1'H)-one

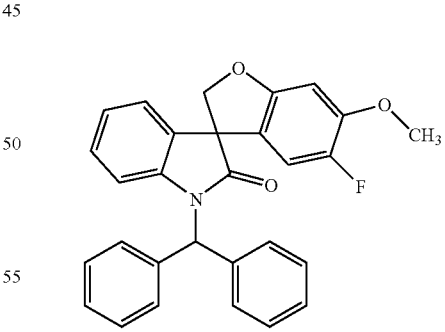

Following the procedure as described in EXAMPLE 2 and making non-critical variations using 1-(diphenylmethyl)-3-(5-fluoro-2-hydroxy-4-methoxyphenyl)-1,3-dihydro-2H-indol-2-one to replace 1-(diphenylmethyl)-3-(2-hydroxy-4-methoxy-5-methylphenyl)-1,3-dihydro-2H-indol-2-one, 1'-(diphenylmethyl)-5-fluoro-6-methoxyspiro[1-benzofuran-3,3'-indol]-2'(1'H)-one was obtained (73%) as a colorless solid: $^1$H NMR (300 MHz, CDCl$_3$) δ7.43-7.22 (m, 10H), 7.16-7.09 (m, 1H), 7.06-6.92 (m, 3H), 6.60 (d, J=6.8 Hz, 1H), 6.54-6.48

(m, 1H), 6.37 (d, J=10.0 Hz, 1H), 4.99 (d, J=9.0 Hz, 1H), 4.72 (d, J=9.0 Hz, 1H), 3.85 (s, 3H); MS (ES+) m/z 452.1 (M+1).

EXAMPLE 2.9

Synthesis of 1'-(diphenylmethyl)-5-fluorospiro[1-benzofuran-3,3'-indol]-2'(1'H)-one

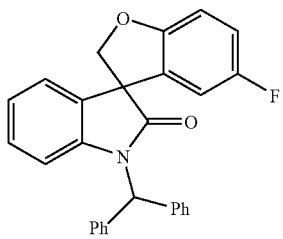

Following the procedure as described in EXAMPLE 2 and making non-critical variations using 1-(diphenylmethyl)-3-(5-fluoro-2-hydroxyphenyl)-1,3-dihydro-2H-indol-2-one to replace 1-(diphenylmethyl)-3-(2-hydroxy-4-methoxy-5-methylphenyl)-1,3-dihydro-2H-indol-2-one, 1-(diphenylmethyl)-5-fluorospiro[1-benzofuran-3,3'-indol]-2'(1'H)-one was obtained (56%) as a colorless solid: mp 182-184° C.; $^1$H NMR (300 MHz, CDCl$_3$) δ7.43-7.25 (m, 10H), 7.17-7.10 (m, 1H), 7.07-6.84 (m, 5H), 6.56-6.49 (m, 1H), 6.39-6.32 (m, 1H), 5.01 (t, J=9.0 Hz, 2H), 4.74 (t, J=9.0 Hz, 2H); $^{13}$C NMR (75 MHz, CDCl$_3$) δ 177.0, 159.3, 156.8, 156.1, 141.7, 137.5, 137.2, 131.9, 130.3, 130.2, 128.8, 128.7, 128.6, 128.4, 128.3, 128.1, 127.9, 123.8, 123.3, 116.5, 116.1, 112.4, 110.9, 110.8, 110.6, 110.2, 80.3, 58.8, 58.0; MS (ES+) m/z 444.0 (M+23).

EXAMPLE 2.10

Synthesis of 1'-(diphenylmethyl)-6-methoxyspiro[1-benzofuran-3,3'-indol]-2'(1'H)-one

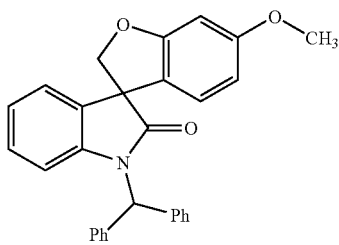

Following the procedure as described in EXAMPLE 2 and making non-critical variations using 1-(diphenylmethyl)-3-(2-hydroxy-4-methoxyphenyl)-1,3-dihydro-2H-indol-2-one to replace 1-(diphenylmethyl)-3-(2-hydroxy-4-methoxy-5-methylphenyl)-1,3-dihydro-2H-indol-2-one, 1'-(diphenylmethyl)-6-methoxyspiro[1-benzofuran-3,3'-indol]-2'(1'H)-one was obtained (74%) as a colorless solid: $^1$H NMR (300 MHz, CDCl$_3$) δ7.42-7.27 (m, 10H), 7.16-6.92 (m, 4H), 6.59-6.49 (m, 3H), 6.37 (dd, J=8.4, 2.4 Hz, 1H), 5.02 (d, J=9.0 Hz, 1H), 4.75 (d, J=9.0 Hz, 1H), 3.77 (s, 3H); MS (ES+) m/z 434.3 (M+1), 456.3 (M+23).

EXAMPLE 2.11

Synthesis of 1'-(diphenylmethyl)-2,3-dihydrospiro[furo[2,3-g][1,4]benzodioxine-8,3'-indol]-2'(1'H)-one

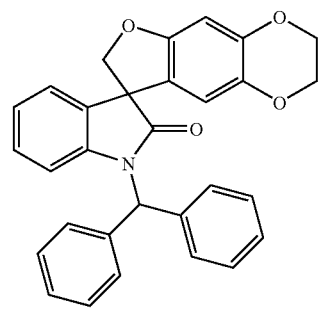

Following the procedure as described in EXAMPLE 2 and making non-critical variations using 1-(diphenylmethyl)-3-(7-hydroxy-2,3-dihydro-1,4-benzodioxin-6-yl)-1,3-dihydro-2H-indol-2-one to replace 1-(diphenylmethyl)-3-(2-hydroxy-4-methoxy-5-methylphenyl)-1,3-dihydro-2H-indol-2-one, 1'-(diphenylmethyl)-2,3-dihydrospiro[furo[2,3-g][1,4]benzodioxine-8,3'-indol]-2'(1'H)-one was obtained (68%) as a colorless solid: mp 183-185° C. (methanol); $^1$H NMR (300 MHz, CDCl$_3$) δ7.41-7.28 (m, 10H), 7.15 (dd, J=6.8, 1.4 Hz, 1H), 7.06 (s, 1H), 7.04-6.93 (m, 2H), 6.52-6.48 (m, 2H), 6.21 (s, 1H), 4.95 (d, J=8.9 Hz, 1H), 4.69 (d, J=8.9 Hz, 1H), 4.22-4.17 (m, 2H), 4.15-4.10 (m, 2H); $^{13}$C NMR (75 MHz, CDCl$_3$) δ177.8, 155.3, 144.7, 141.8, 138.4, 137.7, 137.5, 132.6, 128.83, 128.75, 128.5, 128.44, 128.36, 128.02, 127.98, 123.9, 123.2, 121.5, 112.3, 111.6, 99.5, 80.4, 64.6, 64.0, 58.8, 57.9; MS (ES+) m/z 462.3 (M+1).

EXAMPLE 2.12

Synthesis of 1'-(diphenylmethyl)-6,7-dihydro-5H-spiro[furo[3,2-g]chromene-3,3'-indol]-2'(1'H)-one

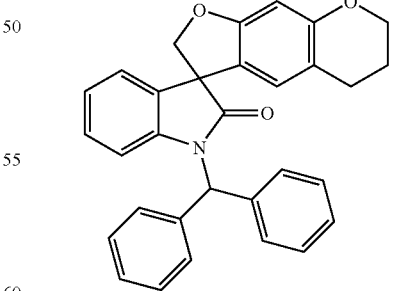

Following the procedure as described in EXAMPLE 2 and making non-critical variations using 1-(diphenylmethyl)-3-(7-hydroxy-3,4-dihydro-2H-chromen-6-yl)-1,3-dihydro-2H-indol-2-one to replace 1-(diphenylmethyl)-3-(2-hydroxy-4-methoxy-5-methylphenyl)-1,3-dihydro-2H-indol-2-one, 1-(diphenylmethyl)-6,7-dihydro-5H-spiro[furo[3,2-g]chromene-3,3'-indol]-2'(1'H)-one was obtained (70%) as an off-white solid: mp 208-211° C. (hexanes); $^1$H NMR (300 MHz, CDCl$_3$) δ7.41-7.29 (m, 10H), 7.16 (dd, J=6.6, 1.8 Hz, 1H), 7.08 (s, 1H), 7.05-6.94 (m, 2H), 6.52 (d, J=7.8 Hz, 1H), 6.41 (s, 1H), 6.28 (s, 1H), 4.96 (d, J=9.0 Hz, 1H), 4.70 (d, J=9.0 Hz, 1H), 4.11 (dd, J=5.1, 5.1 Hz, 2H), 2.56 (t, J=6.3 Hz, 2H), 1.94-1.86 (m, 2H); $^{13}$C NMR (75 MHz, CDCl$_3$) δ178.1, 160.1, 156.3, 141.8, 137.9, 137.5, 132.9, 128.75, 128.73, 128.53, 128.52, 128.2, 128.00, 127.96, 132.9, 132.8, 123.2, 121.3, 115.2, 112.3, 98.9, 80.3, 66.6, 58.8, 57.5, 24.8, 22.3; MS (ES+) m/z 460.1 (M+1).

EXAMPLE 2.13

Synthesis of 1'-(diphenylmethyl)-3,4-dihydro-2H-spiro[furo[2,3-h][1,5]benzodioxepine-9,3'-indol]-2'(1'H)-one

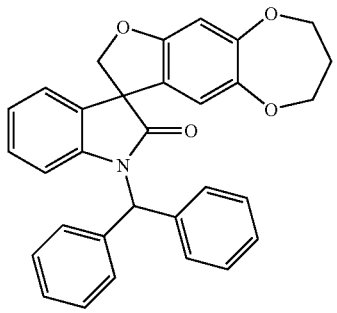

Following the procedure as described in EXAMPLE 2 and making non-critical variations using 1-(diphenylmethyl)-3-(8-hydroxy-3,4-dihydro-2H-1,5-benzo-dioxepin-7-yl)-1,3-dihydro-2H-indol-2-one to replace 1-(diphenylmethyl)-3-(2-hydroxy-4-methoxy-5-methylphenyl)-1,3-dihydro-2H-indol-2-one, 1'-(diphenylmethyl)-3,4-dihydro-2H-spiro[furo[2,3-h][1,5]benzodioxepine-9,3'-indol]-2'(1'H)-one was obtained (75%) as a pale pink solid: mp 165-168° C. (ethyl acetate/methanol); $^1$H NMR (300 MHz, CDCl$_3$) δ 7.42-7.28 (m, 10H), 7.15 (dd, J=7.2, 1.4 Hz, 1H), 7.06 (s, 1H), 7.04-6.94 (m, 2H), 6.61 (s, 1H), 6.50 (d, J=7.5 Hz, 1H), 6.35 (s, 1H), 4.98 (d, J=9.0 Hz, 1H), 4.71 (d, J=9.0 Hz, 1H), 4.29-4.22 (m, 1H), 4.16-4.03 (m, 2H), 4.01-3.93 (m, 1H), 2.24-2.01 (m, 2H); $^{13}$C NMR (75 MHz, CDCl$_3$) δ177.7, 156.9, 153.1, 146.4, 141.8, 137.7, 137.6, 132.5, 128.9, 128.8, 128.6, 128.44, 128.41, 128.0, 124.0, 123.4, 123.2, 116.1, 112.3, 103.6, 80.7, 70.92, 70.88, 58.8, 57.8, 32.3; MS (ES+) m/z 476.1 (M+1).

EXAMPLE 2.14

Synthesis of 1'-(diphenylmethyl)-2-methylspiro[furo[2,3-f][1,3]benzoxazole-7,3'-indol]-2'(1'H)-one

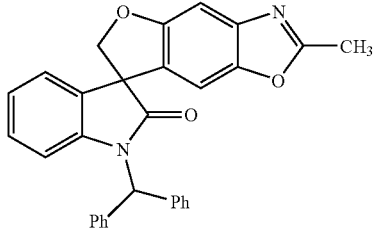

Following the procedure as described in EXAMPLE 2 and making non-critical variations using 1-(diphenylmethyl)-3-(5-hydroxy-2-methyl-1,3-benzoxazol-6-yl)-1,3-dihydro-2H-indol-2-one to replace 1-(diphenylmethyl)-3-(2-hydroxy-4-methoxy-5-methylphenyl)-1,3-dihydro-2H-indol-2-one, 1-(diphenylmethyl)-2-methylspiro[furo[2,3-f][1,3]benzoxazole-7,3'-indol]-2'(1'H)-one was obtained (68%) as a colorless solid: mp 240-242° C. (dichloromethane); $^1$H NMR (300 MHz, CDCl$_3$) δ7.66 (d, J=7.2 Hz, 2H), 7.45-7.29 (m, 9H), 7.11-6.97 (m, 4H), 6.89 (t, J=7.2 Hz, 1H), 6.46 (d, J=7.8 Hz, 1H), 6.01 (d, J=5.7 Hz, 1H), 5.41 (d, J=5.7 Hz, 1H), 2.47 (s, 3H); $^{13}$C NMR (75 MHz, CDCl$_3$) δ 175.1, 164.5, 151.3, 146.2, 143.7, 138.6, 138.0, 137.3, 129.9, 129.8, 129.0, 128.9, 128.8, 128.3, 128.0, 127.7, 124.6, 122.8, 114.0, 112.7, 111.8, 110.7, 88.7, 75.8, 58.6, 14.8; MS (ES+) m/z 497.1 (M+39).

EXAMPLE 2.15

Synthesis of 1'-(diphenylmethyl)-1-methyl-1H-spiro[furo[3,2-g][1,4]benzoxazine-8,3'-indole]-2,2'(1'H,3H)-dione

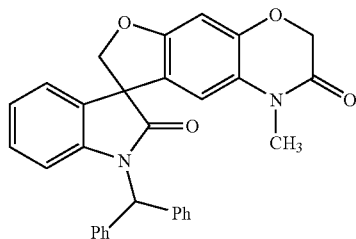

Following the procedure as described in EXAMPLE 2 and making non-critical variations using 6-[1-(diphenylmethyl)-2-oxo-2,3-dihydro-1H-indol-3-yl]-7-hydroxy-4-methyl-2H-1,4-benzoxazin-3(4H)-one to replace 1-(diphenylmethyl)-3-(2-hydroxy-4-methoxy-5-methylphenyl)-1,3-dihydro-2H-indol-2-one, 1'-(diphenylmethyl)-1-methyl-1H-spiro[furo[3,2-g][1,4]benzoxazine-8,3'-indole]-2,2'(1'H,3H)-dione was obtained (32%) as a colorless solid: $^1$H NMR (300 MHz, DMSO-d$_6$) δ7.47-7.23 (m, 11H), 7.19-7.10 (m, 1H), 7.07-6.98 (m, 1H), 6.88 (s, 1H), 6.72 (s, 1H), 6.64 (d, J=7.9 Hz, 1H), 6.20 (s, 1H), 4.93 (d, J=9.4 Hz, 1H), 4.82 (d, J=9.4 Hz, 1H), 4.57 (s, 2H), 3.01 (s, 3H); MS (ES+) m/z 489.0 (M+1).

EXAMPLE 2.16

Synthesis of 1'-(diphenylmethyl)-3-methylspiro[furo[2,3-f][1,3]benzoxazole-7,3'-indole]-2,2'(1'H,3H)-dione

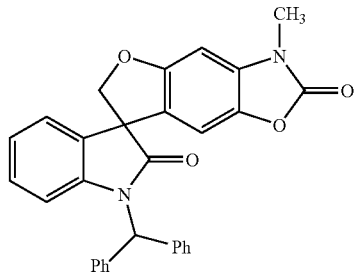

Following the procedure as described in EXAMPLE 2 and making non-critical variations using 6-[1-(diphenylmethyl)-2-oxo-2,3-dihydro-1H-indol-3-yl]-5-hydroxy-3-methyl-1,3-benzoxazol-2(3H)-one to replace 1-(diphenylmethyl)-3-(2- hydroxy-4-methoxy-5-methylphenyl)-1,3-dihydro-2H-indol-2-one, 1-(diphenylmethyl)-3-methylspiro[furo[2,3-f][1,3]benzoxazole-7,3'-indole]-2,2'(1'H,3H)-dione was obtained (40%) as a colorless solid: mp 228-229° C. (ethyl acetate); ¹H NMR (300 MHz, CDCl₃) δ 7.42-7.28 (m, 10H), 7.15-6.96 (m, 4H), 6.60 (s, 1H), 6.55 (d, J=7.2 Hz, 1H), 6.44 (s, 1H), 5.04 (d, J=9.0 Hz, 1H), 4.77 (d, J=9.0 Hz, 1H), 3.38 (s, 3H); ¹³C NMR (75 MHz, CDCl₃) δ177.6, 157.7, 155.3, 142.0, 137.7, 137.4, 137.2, 133.2, 132.1, 129.0, 128.9, 128.6, 128.5, 128.3, 128.2, 124.0, 123.5, 122.6, 112.6, 105.4, 92.0, 80.6, 59.1, 58.0, 28.5; MS (ES+) m/z 475.1 (M+1).

EXAMPLE 2.17

Synthesis of 1'-(diphenylmethyl)-1-methylspiro[furo[3,2-f][1,3]benzoxazole-7,3'-indole]-2,2'(1'H,1'H)-dione

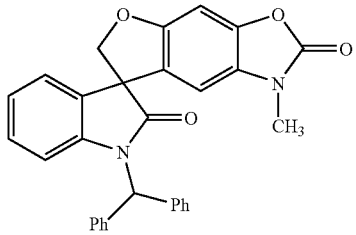

Following the procedure as described in EXAMPLE 2 and making non-critical variations using 5-[1-(diphenylmethyl)-2-oxo-2,3-dihydro-1H-indol-3-yl]-6-hydroxy-3-methyl-1,3-benzoxazol-2(3H)-one to replace 1-(diphenylmethyl)-3-(2-hydroxy-4-methoxy-5-methylphenyl)-1,3-dihydro-2H-indol-2-one, 1'-(diphenylmethyl)-1-methylspiro[furo[3,2-f][1,3]benzoxazole-7,3'-indole]-2,2'(1'H,1'H)-dione was obtained (65%) as a colorless solid: ¹H NMR (300 MHz, DMSO-d₆) δ7.47-7.28 (m, 11H), 7.18-7.11 (m, 2H), 7.06-6.99 (m, 1H), 6.89 (s, 1H), 6.64 (d, J=7.9 Hz, 1H), 6.45 (s, 1H), 4.92 (d, J=9.4 Hz, 1H), 4.81 (d, J=9.4 Hz, 1H), 3.18 (s, 3H); MS (ES+) m/z 475.0 (M+1).

EXAMPLE 2.18

Synthesis of 7'-chloro-1'-(diphenylmethyl)-5,6-dihydrospiro[benzo[1,2-b:5,4-b']difuran-3,3'-indol]-2'(1'H)-one

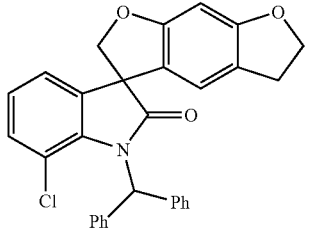

Following the procedure as described in EXAMPLE 2 and making non-critical variations using 7-chloro-1-(diphenylmethyl)-3-(6-hydroxy-2,3-dihydro-1-benzofuran-5-yl)-1,3-dihydro-2H-indol-2-one to replace 1-(diphenylmethyl)-3-(2-hydroxy-4-methoxy-5-methylphenyl)-1,3-dihydro-2H-indol-2-one, 7'-chloro-1'-(diphenylmethyl)-5,6-dihydrospiro[benzo[1,2-b:5,4-b']difuran-3,3'-indol]-2'(1'H)-one was obtained (80%) as a colorless solid: ¹H NMR (300 MHz, DMSO-d₆) δ7.45-7.06 (m, 14H), 6.38-6.32 (m, 2H), 4.75 (s, 2H), 4.48 (t, J=8.7 Hz, 2H), 2.94 (t, J=8.7 Hz, 2H).

EXAMPLE 2.19

Synthesis of 1'-(diphenylmethyl)-4'-fluoro-7'-methyl-5,6-dihydrospiro[benzo[1,2-b:5,4-b']difuran-3,3'-indol]-2'(1'H)-one

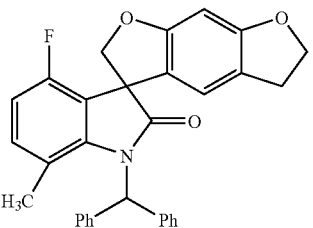

Following the procedure as described in EXAMPLE 2 and making non-critical variations using 1-(diphenylmethyl)-7-fluoro-3-(6-hydroxy-2,3-dihydro-1-benzofuran-5-yl)-1,3-dihydro-2H-indol-2-one to replace 1-(diphenylmethyl)-3-(2-hydroxy-4-methoxy-5-methylphenyl)-1,3-dihydro-2H-indol-2-one, 1'-(diphenylmethyl)-4'-fluoro-7'-methyl-5,6-dihydrospiro[benzo[1,2-b:5,4-b']difuran-3,3'-indol]-2'(1'H)-one was obtained (89%) as a colorless solid: mp 81-82° C. (hexanes/ethyl acetate); ¹H NMR (300 MHz, DMSO-d₆) δ7.44-7.23 (m, 10H), 7.18-7.22 (m, 1H), 6.94 (br s, 1H), 6.85-6.78 (m, 1H), 6.45 (s, 1H), 6.33 (s, 1H), 4.83 (d, J=9.5 Hz, 1H), 4.69 (d, J=9.5 Hz, 1H), 4.52-4.50 (m, 2H), 3.08-2.86 (m, 2H), 2.33 (br s, 3H); m/z 477.9 (M+1).

EXAMPLE 2.20

Synthesis of 1'-(diphenylmethyl)-7'-fluoro-5,6-dihydrospiro[benzo[1,2-b:5,4-b']difuran-3,3'-indol]-2'(1'H)-one

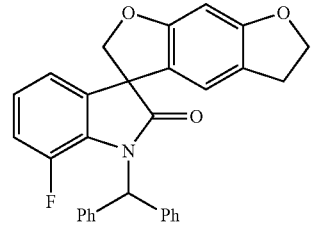

Following the procedure as described in EXAMPLE 2 and making non-critical variations using 7-fluoro-1-(diphenylmethyl)-3-(6-hydroxy-2,3-dihydro-1-benzofuran-5-yl)-1,3-dihydro-2H-indol-2-one to replace 1-(diphenylmethyl)-3-(2-hydroxy-4-methoxy-5-methylphenyl)-1,3-dihydro-2H-indol-2-one, 1'-(diphenylmethyl)-7'-fluoro-5,6-dihydrospiro[benzo[1,2-b:5,4-b']difuran-3,3'-indol]-2'(1'H)-one was obtained (70%) as a colorless solid: mp 183-184° C. (hexanes/ethyl acetate); ¹H NMR (300 MHz, DMSO-d₆) δ7.45-7.22 (m, 10H), 7.13-7.05 (m, 3H), 6.98 (s, 1H), 6.44-6.43 (m, 2H), 4.91 (d, J=9.5 Hz, 1H), 4.80 (d, J=9.5 Hz, 1H), 4.51 (t, J=8.9 Hz, 2H), 2.97 (t, J=8.6 Hz, 2H); MS (ES+) m/z 463.9 (M+1).

EXAMPLE 2.21

Synthesis of 6-(benzyloxy)-1'-(3-methylbutyl)spiro [1-benzofuran-3,3'-indol]-2'(1'H)-one

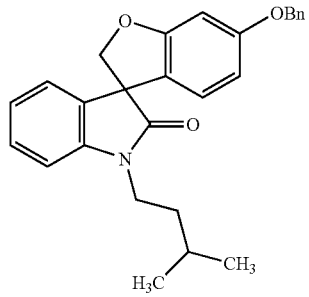

Following the procedure as described in EXAMPLE 2 and making non-critical variations using 3-[4-(benzyloxy)-2-hydroxyphenyl]-1-(3-methylbutyl)-1,3-dihydro-2H-indol-2-one to replace 1-(diphenylmethyl)-3-(2-hydroxy-4-methoxy-5-methylphenyl)-1,3-dihydro-2H-indol-2-one, 6-(benzyloxy)-1'-(3-methylbutyl)spiro[1-benzofuran-3,3'-indol]-2'(1'H)-one was obtained (67%): $^1$H NMR (300 MHz, CDCl$_3$) δ 7.41-7.28 (m, 7H), 7.14-7.12 (m, 1H), 7.04-6.99 (m, 1H), 6.90-6.87 (m, 1H), 6.59-6.55 (m, 1H), 6.44-6.30 (m, 1H), 5.00 (s, 2H), 4.79 (ABq, 2H), 3.87-3.64 (m, 2H), 1.71-1.56 (m, 3H), 0.98 (d, J=6.0 Hz, 6H); MS (ES+) m/z 414.3 (M+1).

EXAMPLE 2.22

Synthesis of 6-bromo-1'-((5-(trifluoromethyl)furan-2-yl)methyl)-2H-spiro[benzofuran-3,3'-indol]-2'-one

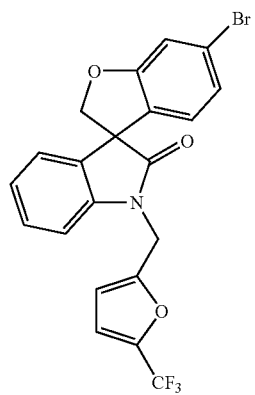

Following the procedure as described in EXAMPLE 2 and making non-critical variations using 3-(4-bromo-2-hydroxyphenyl)-1-((5-(trifluoromethyl)furan-2-yl)methyl)indolin-2-one to replace 1-(diphenylmethyl)-3-(2-hydroxy-4-methoxy-5-methylphenyl)-1,3-dihydro-2H-indol-2-one, 6-bromo-1'-((5-(trifluoromethyl)furan-2-yl)methyl)-2H-spiro[benzofuran-3,3'-indol]-2'-one was obtained (78%) as a colorless solid: $^1$H NMR (300 MHz, CDCl$_3$) δ 7.30 (ddd, J=7.9, 7.9, 1.5 Hz, 1H), 7.16-7.03 (m, 3H), 6.69 (d, J=7.9 Hz, 1H), 6.93 (dd, J=8.2, 1.8 Hz, 1H), 6.77-6.71 (m, 1H), 6.53 (d, J=8.2 Hz, 1H), 6.42-6.37 (m, 1H), 5.06 (d, J=16.1 Hz, 1H), 4.97 (d, J=9.4 Hz, 1H), 4.86 (d, J=16.1 Hz, 1H), 4.71 (d, J=9.4 Hz, 1H); $^{13}$C NMR (75 MHz, CDCl$_3$) δ176.5, 161.5, 151.8, 141.4, 131.6, 129.3, 128.0, 124.5 (d), 124.0, 114.2, 112.6 (d), 109.2 (d), 80.1, 57.5, 36.9; MS (ES+) m/z 463.9 (M+1), 465.9 (M+1).

EXAMPLE 2.23

Synthesis of 5-bromo-1'-((5-(trifluoromethyl)furan-2-yl)methyl)-2H-spiro[benzofuran-3,3'-indolin]-2'-one

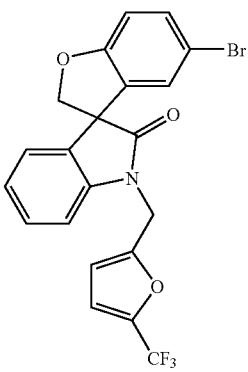

Following the procedure as described in EXAMPLE 2 and making non-critical variations using 3-(5-bromo-2-hydroxyphenyl)-1-((5-(trifluoromethyl)furan-2-yl)methyl)indolin-2-one to replace 1-(diphenylmethyl)-3-(2-hydroxy-4-methoxy-5-methylphenyl)-1,3-dihydro-2H-indol-2-one, 5-bromo-1'-((5-(trifluoromethyl)furan-2-yl)methyl)-2H-spiro[benzofuran-3,3'-indolin]-2'-one was obtained (78%) as a colorless solid: $^1$H NMR (300 MHz, CDCl$_3$) δ 7.36-7.27 (m, 2H), 7.17-6.98 (m, 3H), 6.8 (d, J=8.6 Hz, 1H), 6.78-6.72 (m, 2H), 6.39 (d, J=3.4 Hz, 1H), 5.07-5.87 (m, 3H), 4.69 (d, J=9.1 Hz, 1H); MS (ES+) m/z 463.9 (M+1), 465.9 (M+1).

EXAMPLE 2.24

Synthesis of 6'-isopentyl-3,7-dihydro-2H-spiro[benzofuro[5,6-b][1,4]dioxine-8,8'-thiazolo[5,4-e]indol]-7'(6'H)-one

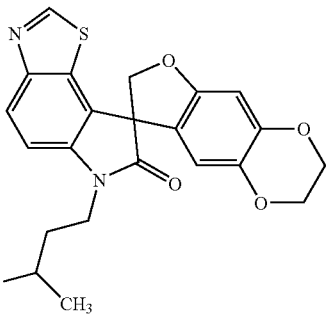

Following the procedure as described in EXAMPLE 2 and making non-critical variations using 8-(7-hydroxy-2,3-dihydrobenzo[b][1,4]dioxin-6-yl)-6-isopentyl-6H-thiazolo[5,4-e]indol-7(8H)-one to replace 1-(diphenylmethyl)-3-(2-hydroxy-4-methoxy-5-methylphenyl)-1,3-dihydro-2H-indol-2-one, 6'-isopentyl-3,7-dihydro-2H-spiro[benzofuro[5,6-b][1,4]dioxine-8,8'-thiazolo[5,4-e]indol]-7'(6'H)-one was obtained (17%) as a colorless solid: mp 169-171° C.; $^1$H NMR (300 MHz, CDCl$_3$) δ8.89 (s, 1H), 8.18 (d, J=8.5 Hz, 1H), 7.19 (d, J=8.5 Hz, 1H), 6.59 (s, 1H), 6.21 (s, 1H), 4.84 (ABq, 2H), 4.30-4.17 (m, 2H), 4.17-4.08 (m, 2H), 4.03-3.89

(m, 1H), 3.90-3.75 (m, 1H), 1.91-1.51 (m, 3H), 1.04 (d, J=6.1 Hz, 6H); MS (ES+) m/z 423.1 (M+1).

EXAMPLE 2.25

Synthesis of 6-((5-(trifluoromethyl)furan-2-yl)methyl)-2,3,5',6'-tetrahydro-2'H-spiro[f-[1,4]dioxino[2,3-f]indole-8,3'-benzofuro[6,5-b]furan]-7(6H)-one

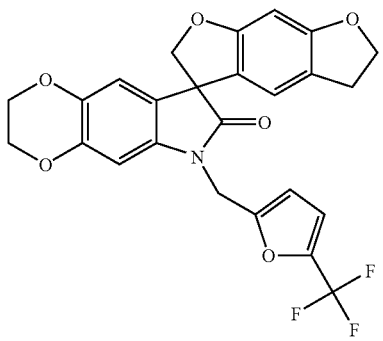

Following the procedure as described in EXAMPLE 2 and making non-critical variations using 8-(6-hydroxy-2,3-dihydrobenzofuran-5-yl)-6-((5-(trifluoromethyl)furan-2-yl)methyl)-6,8-dihydro-2H-[1,4]dioxino[2,3-f]indol-7(3H)-one to replace 1-(diphenylmethyl)-3-(2-hydroxy-4-methoxy-5-methylphenyl)-1,3-dihydro-2H-indol-2-one, 6-((5-(trifluoromethyl)furan-2-yl)methyl)-2,3,5',6'-tetrahydro-2'H-spiro[[1,4]dioxino[2,3-f]indole-8,3'-benzofuro[6,5-b]furan]-7(6H)-one was obtained (42%) as a colorless solid: mp 189-191° C.; $^1$H NMR (300 MHz, CDCl$_3$) δ6.77-6.73 (m, 1H), 6.72 (s, 1H), 6.52-6.45 (m, 2H), 6.43-6.36 (m, 2H), 4.91 (ABq, 2H), 4.77 (ABq, 2H), 4.53 (t, J=8.6 Hz, 2H), 4.27-4.14 (m, 4H), 3.10-2.90 (m, 2H); $^{13}$C NMR (75 MHz, CDCl$_3$) δ 177.6, 161.8, 161.0, 151.9, 143.9, 140.1, 135.2, 124.9, 120.2, 120.0, 118.8, 113.6, 112.6 (d, J=2.8 Hz, 10), 109.2, 98.8, 93.1, 80.4, 72.4, 64.6, 64.0, 57.5, 37.0, 28.9; MS (ES+) m/z 485.9 (M+1).

EXAMPLE 2.26

Synthesis of 6-(((R)-tetrahydrofuran-2-yl)methyl)-2,3,5',6'-tetrahydro-2'H-spiro[[1,4]dioxino[2,3-f]indole-8,3'-benzofuro[6,5-b]furan]-7(6H)-one

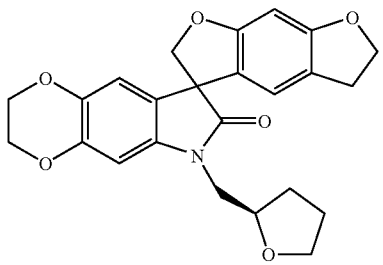

Following the procedure as described in EXAMPLE 2 and making non-critical variations using 8-(6-hydroxy-2,3-dihydrobenzofuran-5-yl)-6-(((R)-tetrahydrofuran-2-yl)methyl)-6,8-dihydro-2H-[1,4]dioxino[2,3-f]indol-7(3H)-one to replace 1-(diphenylmethyl)-3-(2-hydroxy-4-methoxy-5-methylphenyl)-1,3-dihydro-2H-indol-2-one, 6-(((R)-tetrahydrofuran-2-yl)methyl)-2,3,5',6'-tetrahydro-2'H-spiro[[1,4]dioxino[2,3-f]indole-8,3'-benzofuro[6,5-b]furan]-7(6H)-one was obtained (39%) as a colorless solid: mp 220-225° C.; $^1$H NMR (300 MHz, CDCl$_3$) δ6.65 (s, 1H), 6.64-6.60 (m, 1H), 6.51-6.46 (m, 1H), 6.36 (s, 1H), 4.72 (dd, J=84.4, 8.9 Hz, 2H), 4.51 (dd, J=8.6, 8.6 Hz, 2H), 4.25-4.19 (m, 2H), 4.19-4.13 (m, 2H), 3.94-3.82 (m, 2H), 3.80-3.67 (m, 2H), 3.64-3.52 (m, 1H), 2.98 (t, J=8.6 Hz, 2H), 2.08-1.94 (m, 1H), 1.94-1.80 (m, 2H), 1.74-1.60 (m, 1H); MS (ES+) m/z 421.9 (M+1).

EXAMPLE 2.27

Synthesis of 6-((5-(trifluoromethyl)furan-2-yl)methyl)-2,3,3',7'-tetrahydro-2'H-spiro[[1,4]dioxino[2,3-f]indole-8,8'-benzofuro[5,6-b][1,4]dioxin]-7(6H)-one

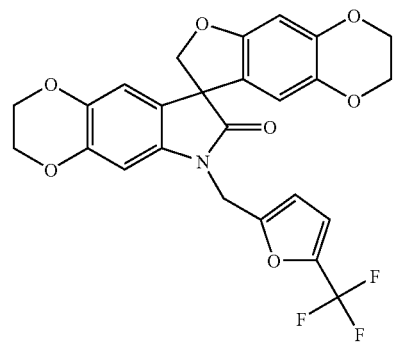

Following the procedure as described in EXAMPLE 2 and making non-critical variations using 8-(7-hydroxy-2,3-dihydrobenzo[b][1,4]dioxin-6-yl)-6-((5-(trifluoromethyl)furan-2-yl)methyl)-6,8-dihydro-2H-[1,4]dioxino[2,3-f]indol-7(3H)-one to replace 1-(diphenylmethyl)-3-(2-hydroxy-4-methoxy-5-methylphenyl)-1,3-dihydro-2H-indol-2-one, 6-((5-(trifluoromethyl)furan-2-yl)methyl)-2,3,3',7'-tetrahydro-2'H-spiro[[1,4]dioxino[2,3-f]indole-8,8'-benzofuro[5,6-b][1,4]dioxin]-7(6H)-one was obtained (76%) as a colorless solid: mp 176-178° C.; $^1$H NMR (300 MHz, CDCl$_3$) δ 6.75-6.67 (m, 2H), 6.49-6.43 (m, 2H), 6.37-6.31 (m, 1H), 6.22-6.16 (m, 1H), 4.87 (ABq, 2H), 4.69 (ABq, 2H), 4.26-4.04 (m, 8H); $^{13}$C NMR (75 MHz, CDCl$_3$ δ 177.2, 155.0, 152.0, 151.9, 144.6, 144.0, 140.1, 138.3, 135.2, 124.3, 120.9, 113.7, 112.6, 112.6, 111.5, 109.1, 99.3, 98.9, 80.0, 64.6, 64.5, 64.0, 63.9, 57.8, 37.0; MS (ES+) m/z 501.9 (M+1).

EXAMPLE 2.28

Synthesis of 1-methyl-1'-{[5-(trifluoromethyl)furan-2-yl]methyl}-2,3-dihydro-1H-spiro[furo[3,2-g][1,4]benzoxazine-8,3'-indol]-2'(1'H)-one hydrochloride

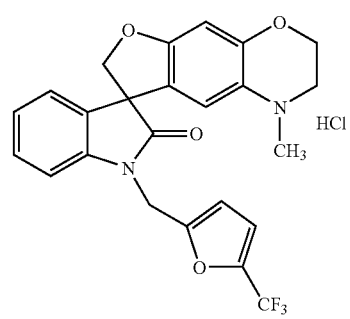

Following the procedure as described in EXAMPLE 2 and making non-critical variations using 3-(7-hydroxy-4-methyl-3,4-dihydro-2H-1,4-benzoxazin-6-yl)-1-{[5-(trifluoromethyl)furan-2-yl]methyl}-1,3-dihydro-2H-indol-2-one trifluoroacetate salt to replace 1-(diphenylmethyl)-3-(2-hydroxy-4-methoxy-5-methylphenyl)-1,3-dihydro-2H-indol-2-one, 1-methyl-1'-{[5-(trifluoromethyl)furan-2-yl]methyl}-2,3-dihydro-1H-spiro[furo[3,2-g][1,4]benzoxazine-8,3'-indol]-2'(1'H)-one was obtained. To a suspension of 1-methyl-1'-{[5-(trifluoromethyl)furan-2-yl]methyl}-2,3-dihydro-1H-spiro[furo[3,2-g][1,4]benzoxazine-8,3'-indol]-2'(1'H)-one (0.59 g, 1.3 mmol) in methanol (8.5 mL) was added 4 M hydrochloric acid in 1,4-dioxane (1.5 mL, 6.0 mmol) and the resulting solution was stirred at ambient temperature for 35 min. The solvent was removed and the residue was dried under reduced pressure. The residue was then precipitated by addition of hexanes, sonicated and the solvent was removed under reduced pressure. This process was repeated several times, until the solid formed a fine suspension in hexanes. The material was then collected by filtration and air-dried to afford 1-methyl-1'-{[5-(trifluoromethyl)furan-2-yl]methyl}-2,3-dihydro-1H-spiro[furo[3,2-g][1,4]benzoxazine-8,3'-indol]-2'(1'H)-one hydrochloride (0.60 g, 94%) as a pale gray powder: mp 105° C. (dec.) (hexanes); $^1$H NMR (300 MHz, DMSO-$d_6$) δ7.33 (ddd, J=7.8, 7.5, 0.9 Hz, 1H), 7.22-7.17 (m, 3H), 7.07 (dd, J=7.5, 7.5 Hz, 1H), 6.74 (d, J=3.3 Hz, 1H), 6.48 (s, 1H), 6.25-6.19 (m, 1H), 5.10 (d, J=16.2 Hz, 1H), 5.02 (d, J=16.2 Hz, 1H), 4.76 (d, J=9.3 Hz, 1H), 4.65 (d, J=9.3 Hz, 1H), 4.33-4.22 (m, 2H), 3.27-3.18 (m, 2H), 2.68 (s, 3H); $^{13}$C NMR (75 MHz, DMSO-$d_6$) δ176.4, 157.2, 153.2, 147.9, 141.9, 139.6 (q, J=42.0 Hz), 131.3, 129.0, 123.9, 123.4, 121.5, 119.0 (q, J=267 Hz), 114.2 (q, J=2.8 Hz), 112.4, 109.9, 109.3, 98.8, 79.9, 62.7, 57.1, 48.8, 48.6, 41.5, 36.6; MS (ES+) m/z 457.1 (M+1); Anal. Calcd. for $C_{24}H_{19}FN_2O_4$·HCl: C, 58.49; H, 4.09; N, 5.68. Found: C, 58.85; H, 3.74; N, 5.37.

EXAMPLE 2.29

Synthesis of 1-methyl-1'-[(2R)-tetrahydrofuran-2-ylmethyl]-2,3-dihydro-1H-spiro[furo[3,2-g][1,4]benzoxazine-8,3'-indol]-2'(1'H)-one hydrochloride

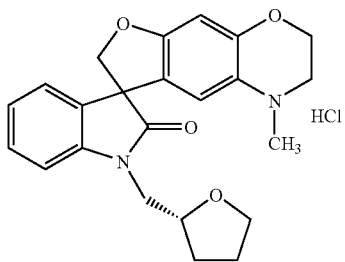

Following the procedure as described in EXAMPLE 2 and making non-critical variations using 3-(7-hydroxy-4-methyl-3,4-dihydro-2H-1,4-benzoxazin-6-yl)-1-[(2R)-tetrahydrofuran-2-ylmethyl]-1,3-dihydro-2H-indol-2-one trifluoroacetate to replace 1-(diphenylmethyl)-3-(2-hydroxy-4-methoxy-5-methylphenyl)-1,3-dihydro-2H-indol-2-one, 1-methyl-1'-[(2R)-tetrahydrofuran-2-ylmethyl]-2,3-dihydro-1H-spiro[furo[3,2-g][1,4]benzoxazine-8,3'-indol]-2'(1'H)-one was obtained (72%) as a colorless solid. Following the procedure described in EXAMPLE 2.28 and making non-critical variations using 1-methyl-1'-[(2R)-tetrahydrofuran-2-ylmethyl]-2,3-dihydro-1H-spiro[furo-[3,2-g][1,4]benzoxazine-8,3'-indol]-2'(1'H)-one to replace 1-methyl-1'-{[5-(trifluoromethyl)furan-2-yl]methyl}-2,3-dihydro-1H-spiro[furo[3,2-g][1,4]benzoxazine-8,3'-indol]-2'(1'H)-one, 1-methyl-1'-[(2R)-tetrahydrofuran-2-ylmethyl]-2,3-dihydro-1H-spiro[furo-[3,2-g][1,4]benzoxazine-8,3'-indol]-2'(1'H)-one hydrochloride was obtained (83%) as a colorless solid: mp>135° C. (dec.) (hexanes); $^1$H NMR (300 MHz, DMSO-$d_6$) (diastereomers) δ7.83 (br s, 1H), 7.36-7.29 (m, 1H), 7.22 (d, J=8.1 Hz, 1H), 7.15 (d, J=7.5 Hz, 1H), 7.07-7.00 (m, 1H), 6.51 (br s, 1H), 6.44, 6.40 (br s, 1H), 4.82-4.59 (m, 2H), 4.38-4.26 (m, 2H), 4.25-4.14 (m, 1H), 3.87-3.69 (m, 3H), 3.66-3.59 (m, 1H), 3.36-3.24 (m, 2H), 2.78, 2.75 (br s, 3H), 2.02-1.72 (m, 3H), 1.68-1.55 (m, 1H); $^{13}$C NMR (75 MHz, DMSO-$d_6$) (diastereomers) δ 176.8, 158.2, 157.8, 148.3, 143.1, 142.9, 131.5, 131.2, 128.9, 128.8, 123.6, 123.5, 122.9, 122.3, 114.0, 113.3, 109.9, 109.8, 98.9, 79.9, 79.8, 75.7, 75.6, 67.3, 62.3, 57.0, 48.9, 43.9, 43.7, 42.3, 42.1, 28.7, 28.5, 25.2, 25.1; MS (ES+) m/z 393.1 (M+1).

EXAMPLE 2.30

Synthesis of 4-methyl-1'-[(2R)-tetrahydrofuran-2-ylmethyl]-3,4-dihydro-2H-spiro[furo[2,3-g][1,4]benzoxazine-8,3'-indol]-2'(1'H)-one

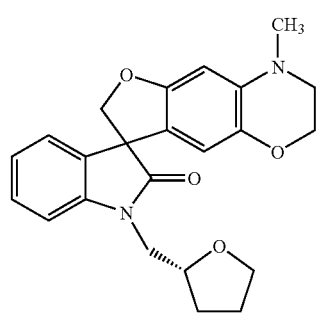

Following the procedure as described in EXAMPLE 2 and making non-critical variations using 3-(6-hydroxy-4-methyl-3,4-dihydro-2H-1,4-benzoxazin-7-yl)-1-[(2R)-tetrahydrofuran-2-ylmethyl]-1,3-dihydro-2H-indol-2-one trifluoroacetate to replace 1-(diphenylmethyl)-3-(2-hydroxy-4-methoxy-5-methylphenyl)-1,3-dihydro-2H-indol-2-one, 4-methyl-1'-[(2R)-tetrahydrofuran-2-ylmethyl]-3,4-dihydro-2H-spiro[furo[2,3-g][1,4]benzoxazine-8,3'-indol]-2'(1'H)-one was obtained (62%) as a pale yellow solid: mp 138-140° C. (diethyl ether/hexanes); $^1$H NMR (300 MHz, CDCl$_3$) (diastereomers) δ 7.26 (dd, J=7.7, 7.7 Hz, 1H), 7.16-6.99 (m, 3H), 6.29 (s, 1H), 6.122, 6.117 (s, 1H), 4.86 (d, J=8.9 Hz, 1H), 4.61 (d, J=8.9 Hz, 1H), 4.31-4.21 (m, 1H), 4.13 (dd, J=4.5, 4.5 Hz, 2H), 3.99-3.66 (m, 4H), 3.23 (dd, J=4.5, 4.2 Hz, 2H), 2.87 (s, 3H), 2.07-1.83 (m, 3H), 1.81-1.67 (m, 1H); $^{13}$C NMR (75 MHz, CDCl$_3$) (diastereomers) δ178.5, 178.3, 156.1, 143.1, 142.9, 139.0, 137.8, 132.7, 132.6, 128.7, 128.6, 123.84, 123.76, 123.2, 116.41, 116.35, 110.26, 110.22, 109.7, 109.4, 94.4, 80.2, 80.1, 77.3, 76.8, 68.38, 68.35, 64.5, 58.3, 49.2, 44.64, 44.58, 39.0, 29.4, 29.0, 25.9, 25.7; MS (ES+) m/z 393.0 (M+1).

EXAMPLE 2.31

Synthesis of 1'-[(2R)-tetrahydrofuran-2-ylmethyl]-4H-spiro[furo[3,2-g][1,3]benzodioxine-6,3'-indol]-2'(1'H)-one

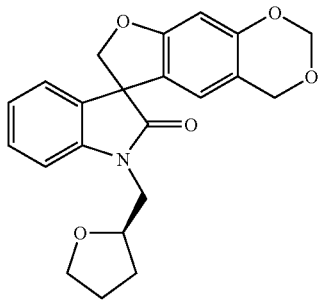

Following the procedure as described in EXAMPLE 2 and making non-critical variations using 3-(7-hydroxy-4H-1,3-benzodioxin-6-yl)-1-[(2R)-tetrahydrofuran-2-ylmethyl]-1,3-dihydro-2H-indol-2-one to replace 1-(diphenylmethyl)-3-(2-hydroxy-4-methoxy-5-methylphenyl)-1,3-dihydro-2H-indol-2-one, 1'-[(2R)-tetrahydrofuran-2-ylmethyl]-4H-spiro[furo[3,2-g][1,3]benzodioxine-6,3'-indol]-2'(1'H)-one was obtained (3%) as a colorless solid: $^1$H NMR (300 MHz, CDCl$_3$) δ 7.38-6.99 (m, 4H), 6.47 (s, 1H), 6.30 (d, J=3.6 Hz, 1H), 5.15 (ABq, 2H), 4.89 (d, J=9.0 Hz, 1H), 4.71-4.61 (m, 3H), 4.30-4.20 (m, 1H), 3.96-3.64 (m, 4H), 2.10-1.60 (m, 4H); $^{13}$C NMR (75 MHz, CDCl$_3$) δ 177.8, 177.8, 160.5, 160.5, 153.9, 142.8, 142.7, 132.3, 132.2, 128.8 (2C), 123.6, 123.3, 122.4, 122.3, 119.6 (2C), 113.9, 109.6, 109.5, 99.2, 91.2, 80.3, 76.9, 68.2, 68.1, 66.2, 57.5 (2C), 44.7, 44.6, 29.2, 29.0, 25.6, 25.5; MS (ES+) m/z 379.9 (M+1), 401.8 (M+23).

EXAMPLE 2.32

Synthesis of 1'-(diphenylmethyl)-2,3,6,7-tetrahydrospiro[furo[3,2-g]chromene-5,3'-indol]-2'(1'H)-one

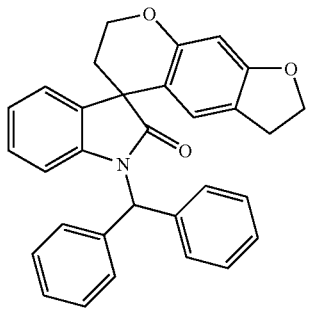

A suspension of 1-(diphenylmethyl)-3-(6-hydroxy-2,3-dihydro-1-benzofuran-5-yl)-1,3-dihydro-2H-indol-2-one (5.1 g, 11.8 mmol), 1,2-dibromoethane (4.7 g, 25.0 mmol) and cesium carbonate (24.4 g, 75.0 mmol) in tetrahydrofuran (200 mL) was stirred under argon at ambient temperature for 16 h and at 50° C. for 7 h. The reaction mixture was filtered and the filtrate was evaporated under reduced pressure. The residue was subjected to column chromatography with dichloromethane/methanol (100/1-20/1) to afford 1'-(diphenylmethyl)-2,3,6,7-tetrahydrospiro[furo[3,2-g]chromene-5,3'-indol]-2'(1'H)-one (2.11 g, 39%) as a colorless solid: MS (ES+) m/z 459.8 (M+1).

EXAMPLE 2.33

Synthesis of 1'-(diphenylmethyl)-7'-fluoro-2,3-dihydrospiro[furo[2,3-g][1,4]benzodioxine-8,3'-indol]-2'(1'H)-one

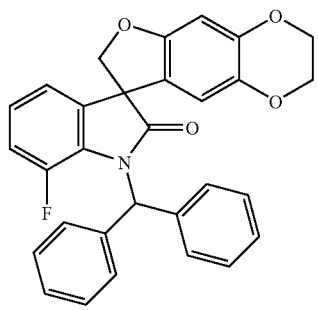

Following the procedure as described in EXAMPLE 2 and making non-critical variations using 1-(diphenylmethyl)-7-fluoro-3-(7-hydroxy-2,3-dihydro-1,4-benzodioxin-6-yl)-1,3-dihydro-2H-indol-2-one to replace 1-(diphenylmethyl)-3-(2-hydroxy-4-methoxy-5-methylphenyl)-1,3-dihydro-2H-indol-2-one, 1'-(diphenylmethyl)-7'-fluoro-2,3-dihydrospiro[furo[2,3-g][1,4]benzodioxine-8,3'-indol]-2'(1'H)-one was obtained (55%) as a colorless solid: MS (ES+) m/z 479.9 (M+1).

EXAMPLE 2.34

Synthesis of 2,2-difluoro-1'-{[5-(trifluoromethyl)furan-2-yl]methyl}spiro[furo[2,3-f][1,3]benzodioxole-7,3'-indol]-2'(1'H)-one

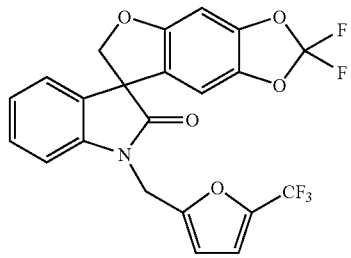

Following the procedure as described in EXAMPLE 2 and making non-critical variations using 3-(2,2-difluoro-6-hydroxy-1,3-benzodioxol-5-yl)-1-{[5-(trifluoromethyl)furan-2-yl]methyl}-1,3-dihydro-2H-indol-2-one to replace 1-(diphenylmethyl)-3-(2-hydroxy-4-methoxy-5-methylphenyl)-1,3-dihydro-2H-indol-2-one, 2,2-difluoro-1'-{[5-(trifluoromethyl)furan-2-yl]methyl}spiro[furo[2,3-f][1,3]benzodioxole-7,3'-indol]-2'(1'H)-one was obtained (55%) as an off-white solid: mp 59-60° C. (recrystallized from the melt); $^1$H NMR (300 MHz, CDCl$_3$) δ7.37-7.30 (m, 1H), 7.21-7.15 (m, 1H), 7.14-7.07 (m, 1H), 7.02 (d, J=7.9 Hz, 1H), 6.79-6.74 (m, 1H), 6.72 (s, 1H), 6.44-6.40 (m, 1H), 6.36 (s, 1H), 5.12-

4.83 (m, 3H), 4.73 (d, J=9.1 Hz, 1H); $^{13}$C NMR (75 MHz, CDCl$_3$) δ 176.7, 157.0, 151.8, 144.7, 142.2, 141.7, 141.5, 138.5, 135.4, 132.0, 131.4, 129.6, 128.6, 124.2, 122.4, 120.7, 117.1, 112.8, 109.6, 109.3, 104.6, 94.4, 80.6, 58.0, 37.1; MS (ES+) m/z 465.7 (M+1).

EXAMPLE 2.35

Synthesis of 2,2-difluoro-1'-{[5-(trifluoromethyl)furan-2-yl]methyl}spiro[furo[2,3-f][1,3]benzodioxole-7,3'-indol]-2'(1'H)-one

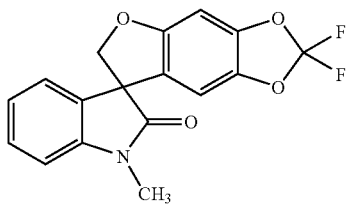

Following the procedure as described in EXAMPLE 2 and making non-critical variations using 3-(2,2-difluoro-6-hydroxy-1,3-benzodioxol-5-yl)-1-methyl-1,3-dihydro-2H-indol-2-one to replace 1-(diphenylmethyl)-3-(2-hydroxy-4-methoxy-5-methylphenyl)-1,3-dihydro-2H-indol-2-one, 2,2-difluoro-1'-{[5-(trifluoromethyl)furan-2-yl]methyl}spiro[furo[2,3-f][1,3]benzodioxole-7,3'-indol]-2'(1'H)-one (10%) was obtained as a pale yellow solid: mp 176-178° C. (hexanes/ethyl acetate); $^1$H NMR (300 MHz, CDCl$_3$) δ 7.39-7.32 (m, 1H), 7.18-7.05 (m, 2H), 6.92 (d, J=7.8 Hz, 1H), 6.72 (s, 1H), 6.40 (s, 1H), 4.96 (d, J=9.1 Hz, 1H), 4.70 (d, J=9.1 Hz, 1H), 3.29 (s, 3H); $^{13}$C NMR (75 MHz, CDCl$_3$) δ 177.0, 157.1, 144.7, 143.1, 138.4, 132.0, 131.7, 129.5, 124.0, 123.8, 122.5, 108.7, 104.8, 94.4, 80.8, 58.2, 26.9; MS (ES+) m/z 331.9 (M+1).

EXAMPLE 2.36

Synthesis of 2,2-difluoro-1'-{[3-(trifluoromethyl)pyridin-2-yl]methyl}spiro[furo[2,3-f][1,3]benzodioxole-7,3'-indol]-2'(1'H)-one

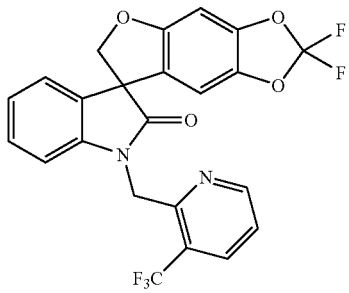

Following the procedure as described in EXAMPLE 2 and making non-critical variations using 3-(2,2-difluoro-6-hydroxy-1,3-benzodioxol-5-yl)-1-{[3-(trifluoromethyl)pyridin-2-yl]methyl}-1,3-dihydro-2H-indol-2-one to replace 1-(diphenylmethyl)-3-(2-hydroxy-4-methoxy-5-methylphenyl)-1,3-dihydro-2H-indol-2-one, 2,2-difluoro-1'-{[3-(trifluoromethyl)pyridin-2-yl]methyl}spiro[furo[2,3-f][1,3]benzodioxole-7,3'-indol]-2'(1'H)-one was obtained (23%) as a colorless solid: mp 200-201° C. (ether/hexanes); $^1$H NMR (300 MHz, acetone-d$_6$) δ 8.75 (d, J=4.1 Hz, 1H), 8.24 (d, J=7.9 Hz, 1H), 7.62-7.55 (m, 1H), 7.30-7.22 (m, 2H), 7.10-6.84 (m, 4H), 5.42 (d, J=17.4 Hz, 1H), 5.22 (d, J=17.4 Hz, 1H), 5.01 (d, J=9.2 Hz, 1H), 4.91 (d, J=9.2 Hz, 1H); $^{13}$C NMR (75 MHz, acetone-d$_6$) δ 177.6, 158.1, 153.5, 153.4, 144.9, 144.0, 138.6, 135.7, 132.8, 129.9, 126.9, 125.3, 124.9, 124.6, 124.0, 123.7, 123.3, 109.9, 106.6, 98.4, 81.3, 58.7, 42.9; MS (ES+) m/z 477.0 (M+1).

EXAMPLE 2.37

Synthesis of 6'-(diphenylmethyl)-2',3',5,6-tetrahydrospiro[benzo[1,2-b:5,4-b']difuran-3,8'-[1,4]dioxino[2,3-f]indol]-7'(6'H)-one

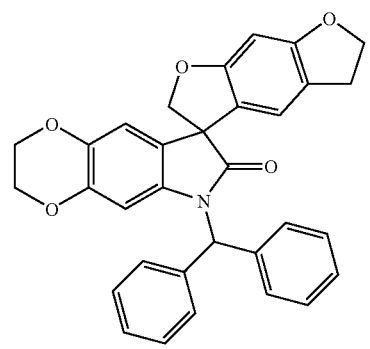

Following the procedure as described in EXAMPLE 2 and making non-critical variations using 6-(diphenylmethyl)-8-(6-hydroxy-2,3-dihydro-1-benzofuran-5-yl)-2,3,6,8-tetrahydro-7H-[1,4]dioxino[2,3-f]indol-7-one to replace 1-(diphenylmethyl)-3-(2-hydroxy-4-methoxy-5-methylphenyl)-1,3-dihydro-2H-indol-2-one, 6'-(diphenylmethyl)-2',3',5,6-tetrahydrospiro[benzo[1,2-b:5,4-b']difuran-3,8'-[1,4]dioxino[2,3-f]indol]-7'(6'H)-one was obtained (67%) as a colorless solid: MS (ES+) m/z 504.0 (M+1).

EXAMPLE 2.38

Synthesis of 3'-(4-methoxybenzyl)-5,6-dihydrospiro[benzo[1,2-b:5,4-b']difuran-3,1'-pyrrolo[3,2-f]quinolin]-2'(3'H)-one

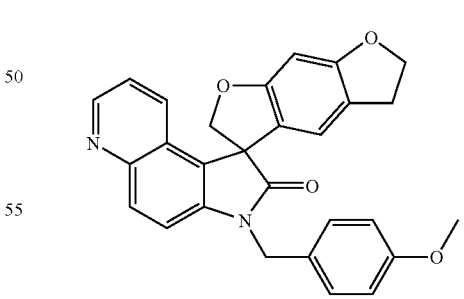

Following the procedure as described in EXAMPLE 2 and making non-critical variations using 1-(6-hydroxy-2,3-dihydro-1-benzofuran-5-yl)-3-(4-methoxybenzyl)-1,3-dihydro-2H-pyrrolo[3,2-f]quinolin-2-one to replace 1-(diphenylmethyl)-3-(2-hydroxy-4-methoxy-5-methylphenyl)-1,3-dihydro-2H-indol-2-one, 3'-(4-methoxybenzyl)-5,6-dihydrospiro[benzo[1,2-b:5,4-b']difuran-3,1'-pyrrolo[3,2-f]quinolin]-2'(3'H)-one was obtained (9%) as a yellow solid:

mp 169-170° C.; $^1$H NMR (300 MHz, CDCl$_3$) δ 8.75 (s, 1H), 8.10 (m, 1H), 7.92 (m, 1H), 7.43-7.28 (m, 4H), 6.92-6.86 (m, 2H), 6.51 (s, 1H), 6.44 (m, 1H), 5.17-5.06 (m, 2H), 4.97-4.88 (m, 2H), 4.58-4.49 (m, 2H), 3.79 (s, 3H), 3.09-2.82 (m, 2H); $^{13}$C NMR (75 MHz, CDCl$_3$) δ 179.1, 162.2, 161.0, 159.3, 148.0, 144.6, 140.2, 130.9, 128.8, 127.8, 127.6, 124.8, 122.4, 120.4, 119.8, 118.9, 114.4, 113.9, 93.4, 79.6, 72.4, 58.5, 55.3, 43.9, 29.0; MS (ES+) m/z 451.0 (M+1).

EXAMPLE 2.39

Synthesis of 6-hydroxy-1'-(4-methoxybenzyl)-2'-oxo-1',2'-dihydrospiro[1-benzofuran-3,3'-indole]-5-carbonitrile

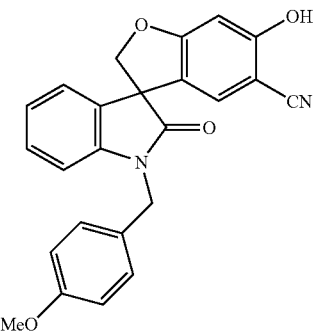

To a stirred solution of 2,4-dihydroxy-5-[1-(4-methoxybenzyl)-2-oxo-2,3-dihydro-1H-indol-3-yl]benzonitrile (9.40 g, 24.3 mmol) and chloroiodomethane (4.40 mL, 60.4 mmol) in tetrahydrofuran (250 mL) was added cesium carbonate (23.8 g, 73.0 mmol) under nitrogen. The reaction mixture was stirred at ambient temperature for 20 h and 5% w/v hydrochloric acid was added. The mixture was extracted with ethyl acetate (3×200 mL). The combined organic extracts were washed with water and brine, and dried over anhydrous sodium sulfate and filtered. The filtrate was concentrated in vacuo. The residue was subjected to column chromatography and eluted with ethyl acetate to afford 6-hydroxy-1-(4-methoxybenzyl)-2'-oxo-1,2'-dihydrospiro[1-benzofuran-3,3'-indole]-5-carbonitrile (2.57 g, 26%): mp 112-114° C. (ethyl acetate/hexanes); $^1$H NMR (300 MHz, DMSO-d$_6$) δ 11.32 (s, 1H), 7.29-7.16 (m, 4H), 7.02-6.97 (m, 2H), 6.89-6.85 (m, 3H), 6.54 (s, 1H), 4.93-4.77 (m, 4H), 3.68 (s, 3H); MS (ES+) m/z 398.8 (M+1).

EXAMPLE 2.40

Synthesis of 6-fluoro-1'-(4-methoxybenzyl)-2'-oxo-1',2'-dihydrospiro[1-benzofuran-3,3'-indole]-5-carbonitrile

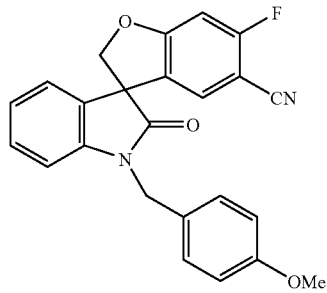

To a stirred solution of 2-fluoro-4-hydroxy-5-[1-(4-methoxybenzyl)-2-oxo-2,3-dihydro-1H-indol-3-yl]benzonitrile (10.50 g, 27.03 mmol) and chloroiodomethane (5.00 mL, 68.7 mmol) in tetrahydrofuran (200 mL) and N,N-dimethylformamide (50 mL) was added cesium carbonate (26.40 g, 81.02 mmol) under nitrogen. The reaction mixture was stirred at ambient temperature for 20 h and filtered through a pad of diatomaceous earth. The filtrate was concentrated in vacuo. The residue was subjected to column chromatography and eluted with ethyl acetate/hexanes (1/3) to afford 6-fluoro-1'-(4-methoxybenzyl)-2'-oxo-1',2'-dihydrospiro[1-benzofuran-3,3'-indole]-5-carbonitrile (5.27 g, 48%): mp 142-143° C.; $^1$H NMR (300 MHz, CDCl$_3$) δ 7.29-7.23 (m, 3H), 7.11-7.02 (m, 2H), 6.89-6.85 (m, 4H), 6.77 (d, J=9.0 Hz, 1H), 5.12-4.75 (m, 4H), 3.78 (s, 3H); MS (ES+) m/z 400.7 (M+1).

EXAMPLE 2.41

Synthesis of 1'-(4-methoxybenzyl)-3-methylspiro[furo[2,3-f][1,2]benzisoxazole-7,3'-indol]-2'(1'H)-one

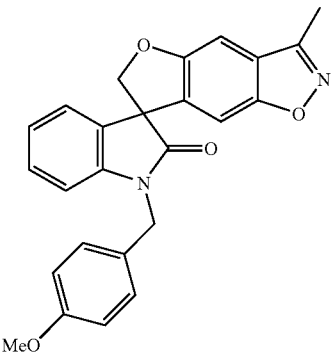

Following the procedure as described in EXAMPLE 2 and making non-critical variations using 3-(5-hydroxy-3-methyl-1,2-benzisoxazol-6-yl)-1-(4-methoxybenzyl)-1,3-dihydro-2H-indol-2-one to replace 1-(diphenylmethyl)-3-(2-hydroxy-4-methoxy-5-methylphenyl)-1,3-dihydro-2H-indol-2-one, 1'-(4-methoxybenzyl)-3-methylspiro[furo[2,3-f][1,2]benzisoxazole-7,3'-indol]-2'(1'H)-one was obtained (17%): mp 183-184° C. (ethyl acetate/hexanes); $^1$H NMR (300 MHz, CDCl$_3$) δ 7.29-7.21 (m, 3H), 7.13-7.10 (m, 1H), 7.05 (s, 1H), 7.03-6.98 (m, 1H), 6.89-6.86 (m, 3H), 6.82 (s, 1H), 5.07-5.00 (m, 2H), 4.79-4.74 (m, 2H), 3.78 (s, 3H), 2.51 (s, 3H); MS (ES+) m/z 412.8 (M+1).

EXAMPLE 2.42

Synthesis of 4'-bromo-1'-(diphenylmethyl)-2,3-dihydrospiro[furo[2,3-g][1,4]benzodioxine-8,3'-indol]-2'(1'H)-one

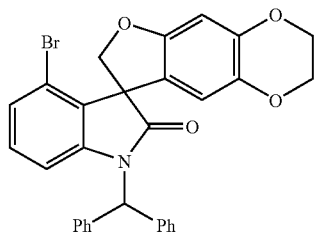

Following the procedure as described in EXAMPLE 2 and making non-critical variations using 4-bromo-1-(diphenylmethyl)-3-(7-hydroxy-2,3-dihydro-1,4-benzodioxin-6-yl)-1,3-dihydro-2H-indol-2-one to replace 1-(diphenylmethyl)-3-(2-hydroxy-4-methoxy-5-methylphenyl)-1,3-dihydro-2H- indol-2-one, 4'-bromo-1'-(diphenylmethyl)-2,3-dihydrospiro[furo[2,3-g][1,4]benzodioxine-8,3'-indol]-2'(1'H)-one was obtained (66%) as a colorless solid: $^1$H NMR (300 MHz, DMSO-d$_6$) δ 7.47-7.16 (m, 12H), 6.85 (s, 1H), 6.82-6.76 (m, 1H), 6.57 (s, 1H), 5.92 (s, 1H), 5.66 (ABq, 2H), 4.22-4.14 (m, 4H).

EXAMPLE 2.43

Synthesis of 4'-bromo-1'-methyl-2,3-dihydrospiro[furo[2,3-g][1,4]benzodioxine-8,3'-indol]-2'(1'H)-one

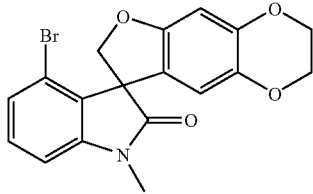

Following the procedure as described in EXAMPLE 2.40 and making non-critical variations using 4-bromo-3-(7-hydroxy-2,3-dihydro-1,4-benzodioxin-6-yl)-1-methyl-1,3-dihydro-2H-indol-2-one to replace 2-fluoro-4-hydroxy-5-[1-(4-methoxybenzyl)-2-oxo-2,3-dihydro-1H-indol-3-yl]benzonitrile, 4'-bromo-1'-methyl-2,3-dihydrospiro[furo[2,3-g][1,4]benzodioxine-8,3'-indol]-2'(1'N)-one was obtained (95%): $^1$H NMR (300 MHz, CDCl$_3$) δ 7.23-7.14 (m, 2H), 6.87-6.79 (m, 1H), 6.43 (s, 1H), 6.16 (s, 1H), 4.93 (ABq, 2H), 4.22-4.07 (m, 4H), 3.24 (s, 3H); MS (ES+) m/z 387.9 (M+1), 389.9 (M+1).

EXAMPLE 2.44

Synthesis of 1'-(diphenylmethyl)-4'-fluoro-2,3-dihydrospiro[furo[2,3-g][1,4]benzodioxine-8,3'-indol]-2'(1'H)-one

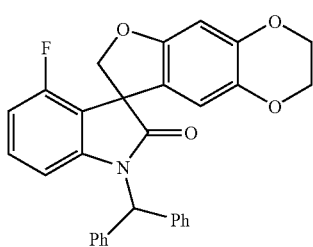

Following the procedure as described in EXAMPLE 2 and making non-critical variations using 1-(diphenylmethyl)-4-fluoro-3-(7-hydroxy-2,3-dihydro-1,4-benzodioxin-6-yl)-1,3-dihydro-2H-indol-2-one to replace 1-(diphenylmethyl)-3-(2-hydroxy-4-methoxy-5-methylphenyl)-1,3-dihydro-2H-indol-2-one, 1-(diphenylmethyl)-4'-fluoro-2,3-dihydrospiro[furo[2,3-g][1,4]benzodioxine-8,3'-indol]-2'(1'H)-one was obtained (83%) as a colorless solid: mp 196-198° C.; $^1$H NMR (300 MHz, DMSO-d$_6$) δ 7.46-7.26 (m, 10H), 7.19 (ddd, J=8.2, 8.2, 6.1 Hz, 1H), 6.89 (s, 1H), 6.83 (dd, J=8.9, 8.9 Hz, 1H), 6.50 (s, 1H), 6.46 (d, J=8.0 Hz, 1H), 6.09 (s, 1H), 4.83 (q, J=9.6 Hz, 2H), 4.14 (dd, J=5.3, 3.2 Hz, 4H); $^{13}$C NMR (75 MHz, DMSO-d$_6$) δ 176.3, 157.9 (d, $^1J_{C-F}$=247 Hz), 144.3, 143.8 (d, $^3J_{C-F}$=8.4 Hz), 137.2 (d, $^3J_{C-F}$=13.6 Hz), 130.5 (d, $^3J_{C-F}$=8.6 Hz), 128.1, 127.8 (d, $^3J_{C-F}$=9.0 Hz), 119.2, 117.3 (d, $^2J_{C-F}$=19.0 Hz), 110.4, 110.0 (d, $^2J_{C-F}$=19.7 Hz), 107.8 (d, $^4J_{C-F}$=2.8 Hz), 98.7, 77.5, 64.1, 63.5, 58.6, 55.8 (d, $^4J_{C-F}$=2.8 Hz); MS (ES+) m/z 480.0 (M+1),

EXAMPLE 2.45

Synthesis of 1'-(4-fluorophenyl)-2,3-dihydrospiro[furo[2,3-g][1,4]benzodioxine-8,3'-indol]-2'(1'H)-one

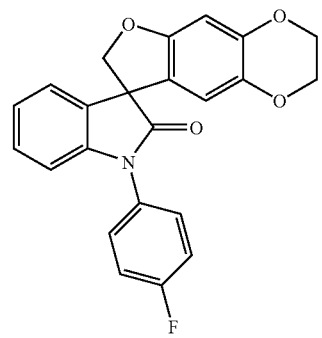

Following the procedure as described in EXAMPLE 2 and making non-critical variations using 1-(4-fluorophenyl)-3-(7-hydroxy-2,3-dihydro-1,4-benzodioxin-6-yl)-1,3-dihydro-2H-indol-2-one to replace 1-(diphenylmethyl)-3-(2-hydroxy-4-methoxy-5-methylphenyl)-1,3-dihydro-2H-indol-2-one, 1-(4-fluorophenyl)-2,3-dihydrospiro[furo[2,3-g][1,4]benzodioxine-8,3'-indol]-2'(1'H)-one was obtained (71%) as a colorless solid: mp 210-212° C.; $^1$H NMR (300 MHz, DMSO-d$_6$) δ 7.63-7.59 (m, 2H), 7.45-7.39 (m, 2H), 7.31-7.23 (m, 2H), 7.10 (dd, J=7.3, 7.3 Hz, 1H), 6.75 (d, J=7.8 Hz, 1H), 6.52 (s, 1H), 6.46 (s, 1H), 4.80 (q, J=9.4 Hz, 2H), 4.21-4.09 (m, 4H); $^{13}$C NMR (75 MHz, DMSO-d$_6$) δ 176.1, 161.2 (d, $^1J_{C-F}$=245 Hz), 154.6, 144.1, 143.0, 137.7, 131.6, 130.4 (d, $^4J_{C-F}$=2.9 Hz), 129.4 (d, $^3J_{C-F}$=8.9 Hz), 128.6, 123.7, 123.3, 121.1, 116.4 (d, $^2J_{C-F}$=22.8 Hz), 111.5, 109.0, 98.6, 79.6, 64.1, 63.5, 57.2; MS (ES+) m/z 390.0 (M+1).

EXAMPLE 2.46

Synthesis of 1'-(diphenylmethyl)-4'-quinolin-3-yl-2,3-dihydrospiro[furo[2,3-g][1,4]benzodioxine-8,3'-indol]-2'(1'H)-one

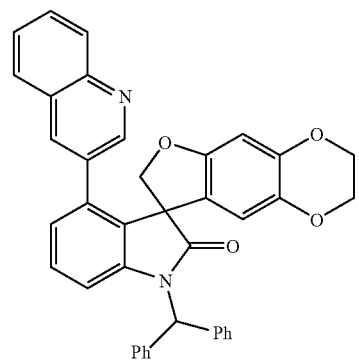

A 10 mL microwave reaction vessel was charged with 4'-bromo-1-(diphenylmethyl)-2,3-dihydrospiro[furo[2,3-g]

[1,4]benzodioxine-8,3'-indol]-2'(1'H)-one (0.38 g, 1.40 mmol), tetrakis(triphenylphosphine)palladium (0.080 g, 0.14 mmol), quinolin-3-ylboronic acid (0.20 g, 2.3 mmol), 2 M aqueous sodium carbonate (1.8 mL) and N,N-dimethylformamide (3.mL). The reaction mixture was irradiated at 150° C. for 15 min in a microwave reactor. The reaction was repeated and both reaction mixtures were combined, poured into distilled water (75 mL) and extracted with ethyl acetate (150 mL). The combined organic extracts were washed with water (3×50 mL) and brine (100 mL), dried over magnesium sulfate, filtered and concentrated in vacuo. The residue was purified by column chromatography and eluted with a 20% to 50% gradient of ethyl acetate in hexanes to afford 1'-(diphenylmethyl)-4'-quinolin-3-yl-2,3-dihydrospiro[furo[2,3-g][1,4]benzodioxine-8,3'-indol]-2'(1'H)-one (0.29 g, 35%) as a light yellow solid: MS (ES+) m/z 589.0 (M+1).

EXAMPLE 2.47

Synthesis of 1'-(diphenylmethyl)-4'-(4-phenoxyphenyl)-2,3-dihydrospiro[furo[2,3-g][1,4]benzodioxine-8,3'-indol]-2'(1'H)-one

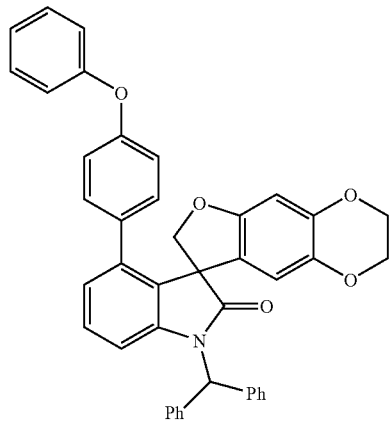

Following the procedure as described in EXAMPLE 2.46 and making non-critical variations using 4-phenoxyphenylboronic acid to replace quinolin-3-ylboronic acid, 1'-(diphenylmethyl)-4'-(4-phenoxyphenyl)-2,3-dihydrospiro[furo[2,3-g][1,4]benzodioxine-8,3'-indol]-2'(1'H)-one was obtained (99%) as a colorless solid: MS (ES+) m/z 630.0 (M+1).

EXAMPLE 2.48

Synthesis of 1'-(diphenylmethyl)-2'-oxo-1',2'-dihydrospiro[1-benzofuran-3,3'-indole]-6-carbonitrile

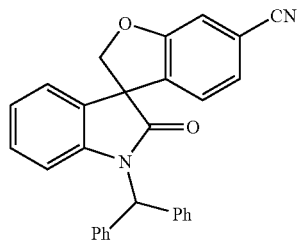

A 10 mL microwave reaction vessel was charged with 6-bromo-1'-(diphenylmethyl)spiro[1-benzofuran-3,3'-indol]-2'(1'H)-one (0.51 g, 1.1 mmol), nickel chloride hexahydrate (0.25 g, 1.1 mmol), sodium cyanide (0.10 g, 2.1 mmol) and 1-methyl-2-pyrrolidinone (1 mL). The solution was irradiated at 200° C. for 20 min in a microwave reactor. The solution was allowed to cool to ambient temperature, diluted with ethyl acetate (25 mL) and filtered. The filtrate was washed with brine (3×15 mL), dried over magnesium sulfate, filtered and concentrated in vacuo. The residue was purified by column chromatography and eluted with a 15% to 50% gradient of ethyl acetate in hexanes to afford 1'-(diphenylmethyl)-2'-oxo-1,2'-dihydrospiro[1-benzofuran-3,3'-indole]-6-carbonitrile (0.50 g, 100%) as a colorless solid: $^1$H NMR (300 MHz, CDCl$_3$) δ 7.44-7.22 (m, 10H), 7.21-7.18 (m, 1H), 7.14-6.93 (m, 5H), 6.72 (d, J=7.8 Hz, 1H), 6.55 (d, J=7.5 Hz, 1H), 5.07 (d, J=9.2 Hz, 1H), 4.80 (d, J=9.2 Hz, 1H).

EXAMPLE 2.49

Synthesis of 5'-bromo-1'-(pyridin-2-ylmethyl)-2,3-dihydrospiro[furo[2,3-g][1,4]-benzodioxine-8,3'-indol]-2'(1'H)-one

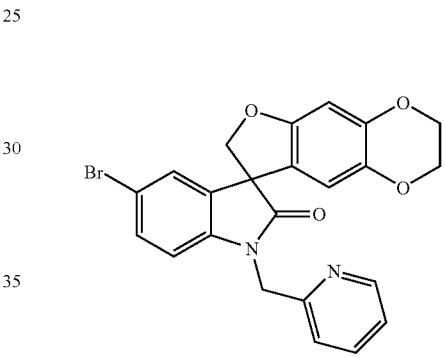

To a solution of 5-bromo-3-(7-hydroxy-2,3-dihydro-1,4-benzodioxin-6-yl)-1-(pyridin-2-ylmethyl)-1,3-dihydro-2H-indol-2-one (2.00 g, 4.40 mmol) in anhydrous N,N-dimethylformamide (25 mL) was added cesium carbonate (4.30 g, 13.2 mmol) and chloroiodomethane (0.85 g, 4.9 mmol). The solution was stirred at ambient temperature for 16 h and poured into water (100 mL). The mixture was extracted with ethyl acetate (3×50 mL) and the combined ethyl acetate extracts were washed with brine (2×35 mL), dried over magnesium sulfate, filtered and concentrated in vacuo. The residue was triturated in dichloromethane/diethyl ether (2/5, 14 mL) to afford 5'-bromo-1'-(pyridin-2-ylmethyl)-2,3-dihydrospiro[furo[2,3-g][1,4]benzodioxine-8,3'-indol]-2'(1'H)-one (1.44 g, 72%) as a beige solid: mp>250° C. (dichloromethane/diethyl ether); $^1$H NMR (300 MHz, CDCl$_3$) δ 8.57-8.52 (m, 1H), 7.69-7.61 (m, 1H), 7.33-7.27 (m, 3H), 7.26-7.16 (m, 1H), 6.77 (d, J=8.3 Hz, 1H), 6.49 (s, 1H), 6.30 (s, 1H), 5.16 (d, J=15.8 Hz, 1H), 4.97-4.87 (m, 2H), 4.64 (d, J=9.0 Hz, 1H), 4.22-4.08 (m, 4H); $^{13}$C NMR (75 MHz, CDCl$_3$) δ 176.9, 155.2, 155.1, 149.6, 144.9, 141.1, 138.4, 137.2, 134.2, 131.7, 127.0, 122.9, 121.7, 120.4, 116.1, 111.7, 111.1, 99.5, 80.0, 64.5, 63.9, 58.2, 46.1; MS (ES+) m/z 465.0 (M+1), 467.0 (M+1).

EXAMPLE 2.50

Synthesis of 2'-oxo-1'-(pyridin-2-ylmethyl)-1',2,2',3-tetrahydrospiro[furo[2,3-g][1,4]benzodioxine-8,3'-indole]-5'-carbonitrile

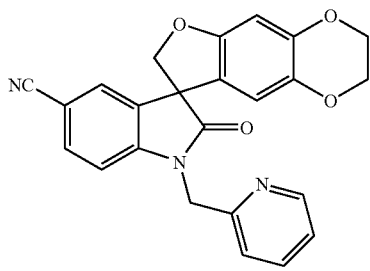

Following the procedure as described in EXAMPLE 2.48 and making non-critical variations using 5'-bromo-1-(pyridin-2-ylmethyl)-2,3-dihydrospiro[furo[2,3-g][1,4]benzodioxine-8,3'-indol]-2'(1'H)-one to replace 6-bromo-1'-(diphenylmethyl)spiro[1-benzofuran-3,3'-indol]-2'(1'H)-one, ylmethyl)-1',2,2',3-tetrahydrospiro[furo[2,3-g][1,4]benzodioxine-8,3'-indole]-5'-carbonitrile was obtained (83%) as a colorless solid: mp 198-199° C. (ethyl acetate/hexanes); $^1$H NMR (300 MHz, CDCl$_3$) δ 8.56-8.52 (m, 1H), 7.65-7.68 (m, 1H), 7.51 (dd, J=8.2, 1.4 Hz, 1H), 7.40-7.38 (m, 1H), 7.30-7.18 (m, 2H), 7.01 (d, J=8.2 Hz, 1H), 6.51 (s, 1H), 6.29 (s, 1H), 5.20 (d, J=15.8 Hz, 1H), 4.96 (d, J=15.5 Hz, 1H), 4.92 (d, J=8.9 Hz, 1H), 4.64 (d, J=9.1 Hz, 1H), 4.23-4.09 (m, 4H); $^{13}$C NMR (75 MHz, CDCl$_3$) δ 177.1, 155.2, 154.4, 149.7, 146.0, 145.1, 138.6, 137.2, 133.9, 133.4, 127.2, 123.1, 122.0, 119.8, 118.7, 111.6, 110.2, 106.7, 99.7, 79.8, 64.5, 63.9, 57.8, 46.1; MS (ES+) m/z 412.0 (M+1).

EXAMPLE 2.51

Synthesis of 5'-bromo-1'-(diphenylmethyl)-2,3-dihydrospiro[furo[2,3-g][1,4]benzodioxine-8,3'-indol]-2'(1'H)-one

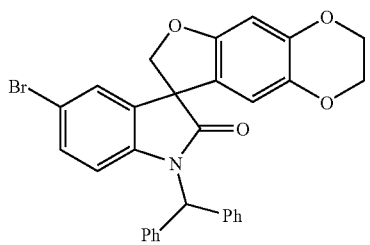

Following the procedure as described in EXAMPLE 2 and making non-critical variations using 5-bromo-1-(diphenylmethyl)-3-(7-hydroxy-2,3-dihydro-1,4-benzodioxin-6-yl)-1,3-dihydro-2H-indol-2-one to replace 1-(diphenylmethyl)-3-(2-hydroxy-4-methoxy-5-methylphenyl)-1,3-dihydro-2H-indol-2-one, 5'-bromo-1'-(diphenylmethyl)-2,3-dihydrospiro[furo[2,3-g][1,4]benzodioxine-8,3'-indol]-2'(1'H)-one was obtained (76%) as a colorless solid: MS (ES+) m/z 539.9 (M+1), 541.1 (M+1).

EXAMPLE 2.52

Synthesis of 1'-(diphenylmethyl)-5'-methyl-2,3-dihydrospiro[furo[2,3-g][1,4]benzodioxine-8,3'-indol]-2'(1'H)-one

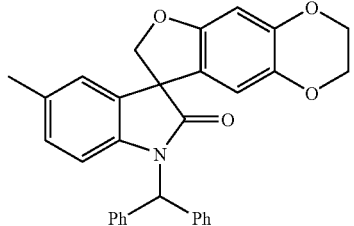

To a 10 mL reaction vessel was added tri-o-tolylphosphine (0.022 g, 0.075 mmol), palladium acetate trimer (0.013 g, 0.020 mmol), triethylamine (0.13 g, 1.30 mmol), N,N-dimethylformamide (1.5 mL), tetramethyltin (0.20 g, 1.1 mmol) and 1'-(diphenylmethyl)-5'-bromo-2,3-dihydrospiro[furo[2,3-g][1,4]benzodioxine-8,3'-indol]-2'(1'H)-one (0.50 g, 0.93 mmol). The reaction vessel was sealed, heated at 110° C. for 16 h, allowed to cool to ambient temperature and poured into water (50 mL). The mixture was extracted with ethyl acetate (2×100 mL) and the combined organic extracts were washed with brine (2×50 mL), dried over magnesium sulfate, filtered and concentrated in vacuo. The residue was purified by column chromatography and eluted with 15% ethyl acetate in hexanes followed by recrystallization from diethyl ether to afford 1'-(diphenylmethyl)-5'-methyl-2,3-dihydrospiro[furo[2,3-g][1,4]benzodioxine-8,3'-indol]-2'(1'H)-one (0.38 g, 86%) as a colorless solid: MS (ES+) m/z 476.0 (M+1).

EXAMPLE 2.53

Synthesis of phenyl 1'-methyl-2'-oxo-1',2,2',3-tetrahydrospiro[furo[2,3-g][1,4]benzodioxine-8,3'-indole]-4'-carboxylate

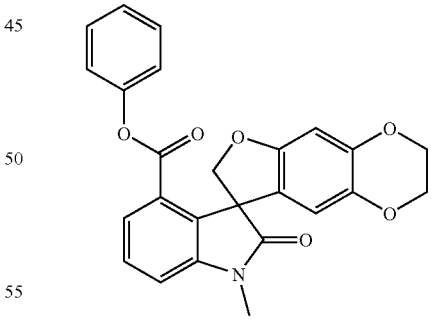

To a high pressure steel reaction vessel were added 4'-bromo-1-methylspiro[furo[2,3-f][1,3]benzodioxole-7,3'-indol]-2'(1'H)-one (10 g, 26 mmol), palladium acetate (0.35 g, 1.55 mmol), 1,3-bis(dicyclohexylphosphonium)propane bis(tetrafluoroborate) (0.64 g, 1.0 mmol), phenol (2.92 g, 31.0 mmol), potassium carbonate (5.34 g, 39.8 mmol), activated 4 Å molecular sieves (4.00 g) and N,N-dimethylformamide (30.0 mL). The reaction vessel was purged with nitrogen for 10 min, sealed, pressurized with carbon monoxide to 150 psi and stirred at 120° C. for 82 h. The mixture was poured into water (100 mL) and extracted with ethyl acetate (3×100 mL). The combined organic extracts were washed with brine (2×50 mL), dried over magnesium sulfate, filtered and concentrated in vacuo. The residue was purified by column chromatography and eluted with a 15% to 75% gradient of ethyl acetate in hexanes followed by recrystallization form dichloromethane/diethyl ether to afford phenyl 1'-methyl-2'-oxo-1',2,2',3-tetrahydrospiro[furo[2,3-g][1,4]benzodioxine-8,3'-indole]-4'-carboxylate (3.30 g, 30%) as a colorless solid: mp 184-186° C. (diethyl ether); $^1$H NMR (300 MHz, CDCl$_3$) δ 7.85 (d, J=8.0 Hz, 1H), 7.49 (dd, J=7.9, 7.9 Hz, 1H), 7.35-7.11 (m, 4H), 6.84-6.78 (m, 2H), 6.24 (s, 1H), 6.12 (s, 1H), 5.11 (d, J=8.5 Hz, 1H), 4.87 (d, J=8.5 Hz, 1H), 4.18-4.05 (m, 4H), 3.29 (s, 3H); MS (ES+) m/z 451.92 (M+23).

EXAMPLE 2.54

Synthesis of 1'-{[3-(trifluoromethyl)pyridin-2-yl]methyl}-7,8-dihyrdospiro[1,4-dioxino[2,3-g][1,3]benzodioxine-4,3'-indol]-2'(1'H)-one

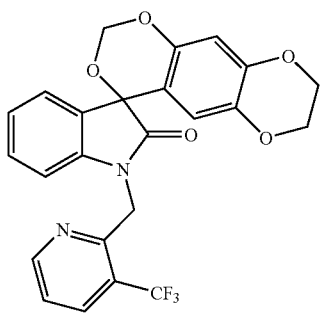

A 100 mL flask was charged under argon with 3-hydroxy-3-(7-hydroxy-2,3-dihydro-1,4-benzodioxin-6-yl)-1-{[3-(trifluoromethyl)pyridine-2-yl]methyl}-1,3-dihydro-2H-indol-2-one (0.46 g, 1.0 mmol), chloroiodomethane (0.36 g, 2.0 mmol), cesium carbonate (1.3 g, 4.0 mmol) and anhydrous tetrahydrofuran (50 mL). The reaction mixture was heated at reflux for 3 h, allowed to cool to ambient temperature and filtered. The filtrate was concentrated in vacuo and the residue was purified by column chromatography and eluted with a 0% to 50% gradient of ethyl acetate in dichloromethane to afford 1-{[3-(trifluoromethyl)pyridin-2-yl]methyl}-7,8-dihyrdospiro[1,4-dioxino[2,3-g][1,3]benzodioxine-4,3'-indol]-2'(1'H)-one (0.16 g, 34%) as an off-white solid: mp>250° C. (methanol); $^1$H NMR (300 MHz, CDCl$_3$) δ 8.65 (d, J=4.5 Hz, 1H), 7.96 (d, J=7.8 Hz, 1H), 7.35-7.14 (m, 3H), 6.95-7.03 (m, 1H), 6.68 (s, 1H), 6.57 (d, J=7.8 Hz, 1H), 6.52 (s, 1H), 5.70 (ABq, 2H), 5.21 (ABq, 2H), 4.25-4.01 (m, 4H); $^{13}$C NMR (75 MHz, CDCl$_3$) δ 176.3, 152.3, 152.2, 147.8, 144.1, 143.3, 138.9, 134.3, 134.2, 134.2, 134.1, 130.7, 130.2, 129.2, 125.6, 125.2, 124.8, 124.4, 124.0, 123.5, 122.2, 122.0, 114.9, 114.2, 108.7, 105.3, 88.3, 77.2, 64.5, 64.0, 41.8, 41.7.

EXAMPLE 2.55

Synthesis of 1'-(diphenylmethyl)-9-fluoro-2,3-dihydro-spiro[furo[2,3-g][1,4]benzodioxine-8,3'-indol]-2'(1'H)-one

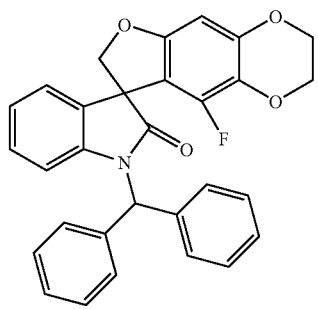

Following the procedure as described in EXAMPLE 2 and making non-critical variations using 1-(diphenylmethyl)-3-(5-fluoro-7-hydroxy-2,3-dihydro-1,4-benzodioxin-6-yl)-1,3-dihydro-2H-indol-2-one to replace 1-(diphenylmethyl)-3-(2-hydroxy-4-methoxy-5-methylphenyl)-1,3-dihydro-2H-indol-2-one, 1'-(diphenylmethyl)-9-fluoro-2,3-dihydro-spiro[furo[2,3-g][1,4]benzodioxine-8,3'-indol]-2'(1'H)-one was obtained (95%) as an off-white solid: MS (ES+) m/z 479.8 (M+1).

EXAMPLE 2.56

Synthesis of 1-(diphenylmethyl)-7,8-dihydro-6H-spiro[furo[2,3-g]chromene-3,3'-indol]-2'(1'H)-one

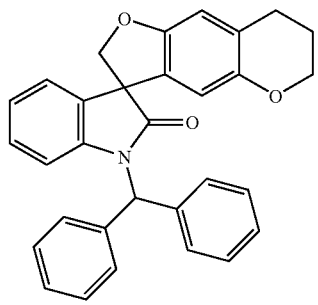

Following the procedure as described in EXAMPLE 2 and making non-critical variations using 1-(diphenylmethyl)-3-(6-hydroxy-3,4-dihydro-2H-chromen-7-yl)-1,3-dihydro-2H-indol-2-one to replace 1-(diphenylmethyl)-3-(2-hydroxy-4-methoxy-5-methylphenyl)-1,3-dihydro-2H-indol-2-one, 1-(diphenylmethyl)-7,8-dihydro-6H-spiro[furo[2,3-g]chromene-3,3'-indol]-2'(1'H)-one was obtained (93%) as an off-white solid: MS (ES+) m/z 460.0 (M+1).

EXAMPLE 2.57

Synthesis of 1-(diphenylmethyl)spiro[indole-3,3'-thieno[2,3-f][1]benzofuran]-2(1'H)-one

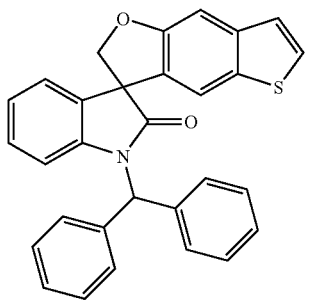

Following the procedure as described in EXAMPLE 2 and making non-critical variations using 1-(diphenylmethyl)-3-(5-hydroxy-1-benzothiophen-6-yl)-1,3-dihydro-2H-indol-2-one to replace 1-(diphenylmethyl)-3-(2-hydroxy-4-methoxy-5-methylphenyl)-1,3-dihydro-2H-indol-2-one, 1-(diphenylmethyl)spiro[indole-3,3'-thieno[2,3-f][1]benzofuran]-2(1'H)-one was obtained (54%) as an off-white solid: MS (ES+) m/z 460.2 (M+1).

EXAMPLE 2.58

Synthesis of 1-(diphenylmethyl)spiro[indole-3,3'-thieno[2,3-f][1]benzofuran]-2(1'H)-one 5,5'-dioxide

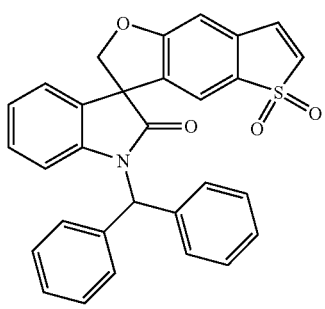

To a solution of 1-(diphenylmethyl)spiro[indole-3,3'-thieno[2,3-f][1]benzofuran]-2(1'H)-one (1.12 g, 2.44 mmol) in dichloromethane (50 mL) at ambient temperature was added 3-chloroperbenzoic acid (77% w/w, 0.65 g, 2.9 mmol) and the mixture was stirred for 16 h. The reaction mixture was diluted with dichloromethane (100 mL), washed with saturated aqueous sodium bicarbonate (3×150 mL), dried over magnesium sulfate, filtered and concentrated in vacuo. The residue was purified by column chromatography and eluted with a 0% to 20% gradient of ethyl acetate in dichloromethane to afford 1-(diphenylmethyl)spiro[indole-3,3'-thieno[2,3-f][1]benzofuran]-2(1'H)-one 5,5'-dioxide (0.98 g, 82%) as an off-white solid: MS (ES+) m/z 492.0 (M+1).

EXAMPLE 2.59

Synthesis of 1'-(diphenylmethyl)spiro[furo[3,2-e][2,1,3]benzoxadiazole-8,3'-indol]-2'(1'H)-one

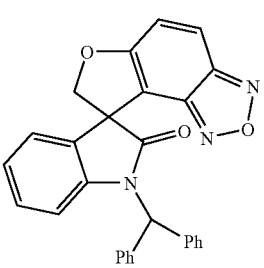

Following the procedure as described in EXAMPLE 2 and making non-critical variations using 1-(diphenylmethyl)-3-(5-hydroxy-2,1,3-benzoxadiazol-4-yl)-1,3-dihydro-2H-indol-2-one to replace 1-(diphenylmethyl)-3-(2-hydroxy-4-methoxy-5-methylphenyl)-1,3-dihydro-2H-indol-2-one, 1'-(diphenylmethyl)spiro[furo[3,2-e][2,1,3]benzoxadiazole-8,3'-indol]-2'(1'H)-one was obtained (50%) as a colorless solid: $^1$H NMR (300 MHz, CDCl$_3$) δ7.82 (d, J=9.6 Hz, 1H), 7.58-6.92 (m, 15H), 6.55 (d, J=7.8 Hz, 1H), 5.25 (d, J=9.3 Hz, 1H), 4.99 (d, J=9.3 Hz, 1H); MS (ES+) m/z 446 (M+1).

EXAMPLE 2.60

Synthesis of 6-chloro-1'-(diphenylmethyl)-2,3-dihydrospiro[furo[3,2-f][1,4]benzodioxine-9,3'-indol]-2'(1'H)-one

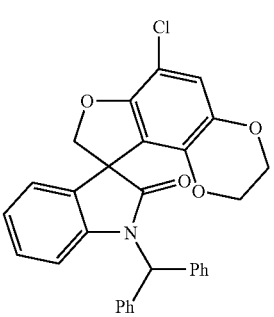

Following the procedure as described in EXAMPLE 2.40 and making non-critical variations using 3-(7-chloro-6-hydroxy-2,3-dihydro-1,4-benzodioxin-5-yl)-1-(diphenylmethyl)-1,3-dihydro-2H-indol-2-one to replace 2-fluoro-4-hydroxy-5-[1-(4-methoxybenzyl)-2-oxo-2,3-dihydro-1H-indol-3-yl]benzonitrile, 6-chloro-1'-(diphenylmethyl)-2,3-dihydrospiro[furo[3,2-f][1,4]benzodioxine-9,3'-indol]-2'(1'H)-one was obtained (65%) as a colorless solid: $^1$H NMR (300 MHz, CDCl$_3$) δ7.42-7.26 (m, 10H), 7.20-7.15 (m, 1H), 7.11 (s, 1H), 7.03-6.95 (m, 2H), 6.78 (s, 1H), 6.50-6.45 (m, 1H), 5.02 (d, J=8.7 Hz, 1H), 4.76 (d, J=8.7 Hz, 1H), 4.12-3.84 (m, 4H); MS (ES+) m/z 496.2 (M+1).

EXAMPLE 2.61

Synthesis of 1'-(diphenylmethyl)-5,6-difluorospiro [1-benzofuran-3,3'-indol]-2'(1'H)-one

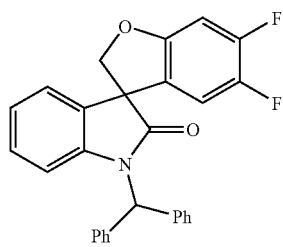

Following the procedure as described in EXAMPLE 2 and making non-critical variations using 3-(4,5-difluoro-2-hydroxyphenyl)-1-(diphenylmethyl)-1,3-dihydro-2H-indol-2-one to replace 1-(diphenylmethyl)-3-(2-hydroxy-4-methoxy-5-methylphenyl)-1,3-dihydro-2H-indol-2-one, 1'-(diphenylmethyl)-5,6-difluorospiro[1-benzofuran-3,3'-indol]-2'(1'H)-one was obtained (70%) as a colorless solid: mp 213-216° C.; $^1$H NMR (300 MHz, CDCl$_3$) δ 7.41-7.26 (m, 10H), 7.15-7.12 (m, 1H), 7.08-6.97 (m, 3H), 6.78 (dd, J=10.5, 6.3 Hz, 1H), 6.54 (d, J=8.4 Hz, 1H), 6.44 (dd, J=9.0, 7.8 Hz, 1H), 5.03 (d, J=9.0 Hz, 1H), 4.77 (d, J=9.3 Hz, 1H); $^{13}$C NMR (75 MHz, CDCl$_3$) δ 176.8, 156.6 (d, J=11.0 Hz), 151.2 (dd, $J_{C-F}$=248.2, 14.5 Hz), 145.6 (dd, $J_{C-F}$=241.5, 13.9 Hz), 141.7, 137.4, 137.1, 131.5, 128.8, 128.8, 128.7, 128.3, 128.3, 128.1, 128.0, 124.2 (dd, J=6.4, 3.3 Hz), 123.8, 123.3, 112.4, 111.5 (dd, J=20.4, 1.6 Hz), 100.1 (d, J=22.4), 80.8, 58.9, 57.5; MS (ES+) m/z 440.2 (M+1).

EXAMPLE 2.62

Synthesis of 1-(diphenylmethyl)-5',6',7',8'-tetrahydrospiro[indole-3,3'-naphtho[2,3-b]furan]-2(1'H)-one

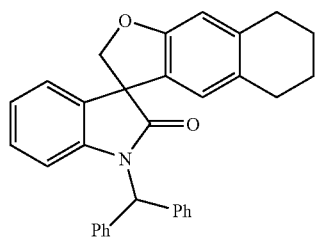

Following the procedure as described in EXAMPLE 2 and making non-critical variations using 1-(diphenylmethyl)-3-(3-hydroxy-5,6,7,8-tetrahydronaphthalen-2-yl)-1,3-dihydro-2H-indol-2-one to replace 1-(diphenylmethyl)-3-(2-hydroxy-4-methoxy-5-methylphenyl)-1,3-dihydro-2H-indol-2-one, 1-(diphenylmethyl)-5',6',7',8'-tetrahydrospiro[indole-3,3'-naphtho[2,3-b]furan]-2(1'H)-one was obtained (81%) as a colorless solid: $^1$H NMR (300 MHz, CDCl$_3$) δ 7.37-7.32 (m, 10H), 7.17-7.14 (m, 1H), 7.07 (s, 1H), 7.05-6.94 (m, 2H), 6.67 (s, 1H), 6.52 (d, J=7.6 Hz, 1H), 6.33 (s, 1H), 4.96 (d, J=8.9 Hz, 1H), 4.69 (d, J=8.9 Hz, 1H), 2.73 (br s, 2H), 2.54 (br s, 1H), 1.72-1.70 (m, 4H); MS (ES+) m/z 457.9 (M+1).

EXAMPLE 2.63

Synthesis of 4',5'-dimethoxy-1'-{[5-(trifluoromethyl)furan-2-yl]methyl}-2,3-dihydrospiro[furo[2,3-g][1,4]benzodioxine-8,3'-indol]-2'(1'H)-one

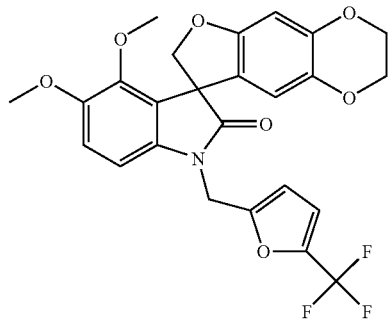

Following the procedure as described in EXAMPLE 2 and making non-critical variations using 3-(7-hydroxy-2,3-dihydro-1,4-benzodioxin-6-yl)-4,5-dimethoxy-1-{[5-(trifluoromethyl)furan-2-yl]methyl}-1,3-dihydro-2H-indol-2-one to replace 1-(diphenylmethyl)-3-(2-hydroxy-4-methoxy-5-methylphenyl)-1,3-dihydro-2H-indol-2-one, 4',5'-dimethoxy-1'-{[5-(trifluoromethyl)furan-2-yl]methyl}-2,3-dihydrospiro[furo[2,3-g][1,4]benzodioxine-8,3'-indol]-2'(1'H)-one was obtained (77%): mp 62-65° C.; $^1$H NMR (300 MHz, CDCl$_3$) δ 6.80 (d, J=8.4 Hz, 1H), 6.74-6.69 (m, 1H), 6.62 (d, J=8.4 Hz, 1H), 6.45 (s, 1H), 6.38-6.32 (m, 1H), 6.20 (s, 1H), 4.90 (ABq, 2H), 4.85-4.81 (m, 2H), 4.18-4.05 (m, 4H), 3.78 (s, 3H), 3.40 (s, 3H); $^{13}$C NMR (75 MHz, CDCl$_3$) δ 177.0, 155.6, 152.3, 152.2, 149.9, 146.6, 144.6, 137.9, 135.1, 125.0, 120.3, 112.7, 111.1, 109.2, 103.7, 99.1, 78.2, 64.5, 63.9, 60.4, 57.7, 56.3, 37.1; MS (ES+) m/z 503.9 (M+1).

EXAMPLE 2.64

Synthesis of 4',7'-dimethoxy-1'-[2-(2-methoxyethoxy)ethyl]-2,3-dihydrospiro[furo[2,3-g][1,4]benzodioxine-8,3'-indol]-2'(1'H)-one

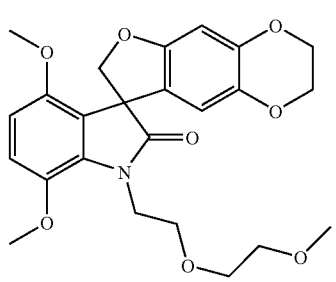

Following the procedure as described in EXAMPLE 2 and making non-critical variations using 3-(7-hydroxy-2,3-dihydro-1,4-benzodioxin-6-yl)-4,7-dimethoxy-1-[2-(2-methoxyethoxy)ethyl]-1,3-dihydro-2H-indol-2-one to replace 1-(diphenylmethyl)-3-(2-hydroxy-4-methoxy-5-methylphenyl)-1,3-dihydro-2H-indol-2-one, 4',7'-dimethoxy-1'-[2-(2- methoxyethoxy)ethyl]-2,3-dihydrospiro[furo[2,3-g][1,4]benzodioxine-8,3'-indol]-2'(1'H)-one was obtained (24%): mp 109-110° C.; ¹H NMR (300 MHz, CDCl₃) δ6.80 (d, J=9.0 Hz, 1H), 6.47 (d, J=9.0 Hz, 1H), 6.39 (s, 1H), 6.24 (s, 1H), 4.76 (ABq, 2H), 4.26-4.03 (m, 6H), 3.81 (s, 3H), 3.77-3.69 (m, 2H), 3.64-3.59 (m, 2H), 3.59 (s, 3H), 3.49-3.43 (m, 2H), 3.31 (s, 3H); ¹³C NMR (75 MHz, CDCl₃) δ178.4, 155.6, 150.4, 144.1, 139.7, 137.6, 131.0, 120.2, 119.5, 113.4, 111.1, 106.1, 98.7, 71.9, 69.8, 68.8, 64.5, 63.8, 59.0, 57.5, 56.4, 56.0, 41.2; MS (ES+) m/z 457.9 (M+1).

EXAMPLE 2.65

Synthesis of 6-[2-(2-methoxyethoxy)ethyl]-2,2',3,3'-tetrahydrospiro[1,4-dioxino[2,3-f]indole-8,8'-furo[2,3-g][1,4]benzodioxin]-7(6H)-one

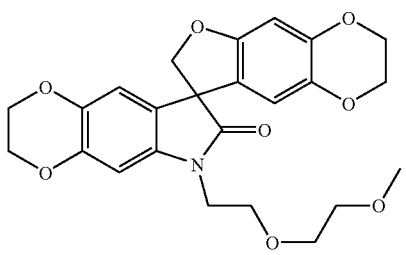

Following the procedure as described in EXAMPLE 2 and making non-critical variations using 8-(7-hydroxy-2,3-dihydro-1,4-benzodioxin-6-yl)-6-[2-(2-methoxyethoxy)ethyl]-2,3,6,8-tetrahydro-7H-[1,4]dioxino[2,3-f]indol-7-one to replace 1-(diphenylmethyl)-3-(2-hydroxy-4-methoxy-5-methylphenyl)-1,3-dihydro-2H-indol-2-one, 6-[2-(2-methoxyethoxy)ethyl]-2,2',3,3'-tetrahydrospiro[1,4-dioxino[2,3-f]indole-8,8'-furo[2,3-g][1,4]benzodioxin]-7(6H)-one was obtained (74%): mp 146-148° C.; ¹H NMR (300 MHz, CDCl₃) δ6.64 (s, 1H), 6.56 (s, 1H), 6.43 (s, 1H), 6.22 (s, 1H), 4.67 (ABq, 2H), 4.27-4.03 (m, 8H), 3.98-3.65 (m, 4H), 3.65-3.55 (m, 2H), 3.52-3.45 (m, 2H), 3.34 (s, 3H); ¹³C NMR (75 MHz, CDCl₃) δ 177.6, 155.0, 144.4, 143.8, 139.6, 138.2, 136.4, 124.7, 121.4, 113.3, 111.5, 99.3, 99.2, 80.1, 71.9, 70.4, 68.1, 64.6, 64.5, 64.1, 63.9, 59.0, 57.8, 40.3; MS (ES+) m/z 455.9 (M+1).

EXAMPLE 2.66

Synthesis of 6'-(4-methoxybenzyl)-2,3-dihydrospiro[furo[2,3-g][1,4]benzodioxine-8,8'-[1,3]thiazolo[5,4-e]indol]-7'(6'H)-one

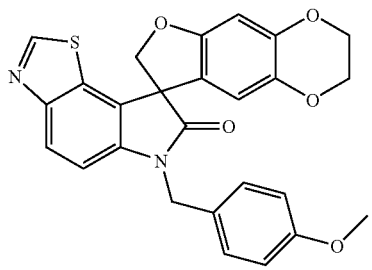

Following the procedure as described in EXAMPLE 2 and making non-critical variations using 8-(7-hydroxy-2,3-dihydro-1,4-benzodioxin-6-yl)-6-(4-methoxybenzyl)-6,8-dihydro-7H-[1,3]thiazolo[5,4-e]indol-7-one to replace 1-(diphenylmethyl)-3-(2-hydroxy-4-methoxy-5-methylphenyl)-1,3-dihydro-2H-indol-2-one, 6'-(4-methoxybenzyl)-2,3-dihydrospiro[furo[2,3-g][1,4]benzodioxine-8,8'-[1,3]thiazolo[5,4-e]indol]-7'(6'H)-one was obtained (80%) as a colorless solid: ¹H NMR (300 MHz, CDCl₃) δ8.76 (s, 1H), 7.99 (d, J=8.5 Hz, 1H), 7.30 (d, J=8.6 Hz, 2H), 7.05 (d, J=8.5 Hz, 1H), 6.88 (d, J=8.6 Hz, 2H), 6.58 (s, 1H), 6.21 (s, 1H), 4.99 (ABq, 2H), 4.86 (ABq, 2H), 4.25-4.04 (m, 4H), 3.79 (s, 3H); MS (ES+) m/z 473.1 (M+1).

EXAMPLE 2.67

Synthesis of 1'-(diphenylmethyl)-6-hydroxyspiro[1-benzofuran-3,3'-indol]-2'(1'H)-one

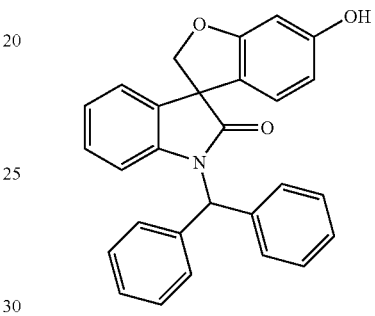

To a stirred solution of 6-(benzyloxy)-1-(diphenylmethyl)spiro[1-benzofuran-3,3'-indol]-2'(1'H)-one (0.22 g, 0.44 mmol) in dichloromethane (3 mL) at ambient temperature was added iodotrimethylsilane (0.12 g, 0.61 mmol). The mixture was stirred at ambient temperature for 3 h and concentrated in vacuo. The residue was purified by column chromatography to afford 1'-(diphenylmethyl)-6-hydroxyspiro[1-benzofuran-3,3'-indol]-2'(1'H)-one (2.25 g, 67%): ¹H NMR (300 MHz, CDCl₃) δ7.46-7.25 (m, 10H), 7.17-7.09 (m, 1H), 7.08-7.02 (m, 1H), 7.02-6.91 (m, 2H), 6.57-6.37 (m, 2H), 6.32 (s, 1H), 6.24-6.12 (m, 1H), 5.70 (s, 1H), 4.85 (ABq, 2H).

EXAMPLE 2.68

Synthesis of 1'-(diphenylmethyl)-6-(2-methoxyethoxy)spiro[1-benzofuran-3,3'-indol]-2'(1'H)-one

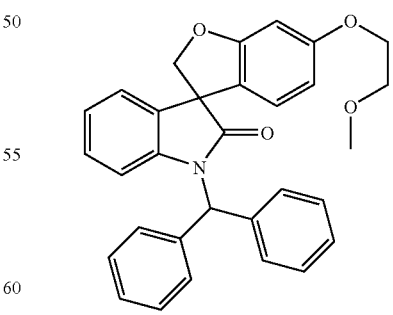

To a solution of 1'-(diphenylmethyl)-6-hydroxyspiro[1-benzofuran-3,3'-indol]-2'(1'H)-one (2.9 g, 6.9 mmol) in anhydrous N,N-dimethylformamide (30 mL) was added at ambient temperature potassium carbonate (2.9 g, 21 mmol). The mixture was stirred at ambient temperature for 10 min and 2-bromoethyl methyl ether (1.9 g, 14 mmol) was added. The mixture was stirred at 40° C. for 7 h, allowed to cool to ambient temperature and poured into water (300 mL), causing a precipitate to be deposited.

The solid was collected by filtration to afford 1'-(diphenylmethyl)-6-(2-methoxyethoxy)spiro[1-benzofuran-3,3'-indol]-2'(1'H)-one (2.84 g, 85%) as a colorless solid: $^1$H NMR (300 MHz, CDCl$_3$) δ7.46-7.22 (m, 10H), 7.16-7.10 (m, 1H), 7.06 (s, 1H), 7.03-6.92 (m, 2H), 6.89-6.74 (m, 2H), 6.57-6.45 (m, 1H), 6.30-6.23 (m, 1H), 4.85 (ABq, 2H), 3.92-3.87 (m, 2H), 3.72-3.55 (m, 2H), 3.39 (s, 3H).

EXAMPLE 2.69

Synthesis of 5-(benzyloxy)-1'-(diphenylmethyl)spiro[1-benzofuran-3,3'-indol]-2'(1'H)-one

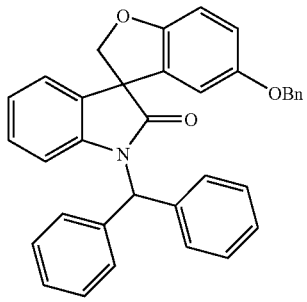

Following the procedure as described in EXAMPLE 2 and making non-critical variations using 3-[5-(benzyloxy)-2-hydroxyphenyl]-1-(diphenylmethyl)-1,3-dihydro-2H-indol-2-one to replace 1-(diphenylmethyl)-3-(2-hydroxy-4-methoxy-5-methylphenyl)-1,3-dihydro-2H-indol-2-one, 5-(benzyloxy)-1'-(diphenylmethyl)spiro[1-benzofuran-3,3'-indol]-2'(1'H)-one was obtained (88%): $^1$H NMR (300 MHz, CDCl$_3$) δ7.43-7.26 (m, 15H), 7.17-7.10 (m, 1H), 7.06 (s, 1H), 7.05-6.91 (m, 2H), 6.90-6.76 (m, 2H), 6.55-6.46 (m, 1H), 6.30-6.23 (m, 1H), 4.85 (ABq, 2H), 4.79 (s, 2H).

EXAMPLE 2.70

Synthesis of 1'-(diphenylmethyl)-5-hydroxyspiro[1-benzofuran-3,3'-indol]-2'(1'H)-one

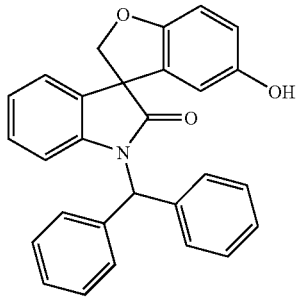

Following the procedure as described in EXAMPLE 2.68 and making non-critical variations using 5-(benzyloxy)-1'-(diphenylmethyl)spiro[1-benzofuran-3,3'-indol]-2'(1'H)-one to replace 6-(benzyloxy)-1'-(diphenylmethyl)spiro[1-benzofuran-3,3'-indol]-2'(1'H)-one, 1'-(diphenylmethyl)-5-hydroxyspiro[1-benzofuran-3,3'-indol]-2'(1'H)-one was obtained (78%) as a colorless solid: $^1$H NMR (300 MHz, CDCl$_3$) δ8.22 (br s, 1H), 7.30-7.08 (m, 10H), 7.02-6.93 (m, 1H), 6.88 (s, 1H), 6.85-6.75 (m, 2H), 6.65-6.49 (m, 2H), 6.38-6.26 (m, 1H), 6.13-6.02 (m, 1H), 4.65 (ABq, 2H).

EXAMPLE 2.71

Synthesis of 1'-(diphenylmethyl)-5-(2-methoxyethoxy)spiro[1-benzofuran-3,3'-indol]-2'(1'H)-one

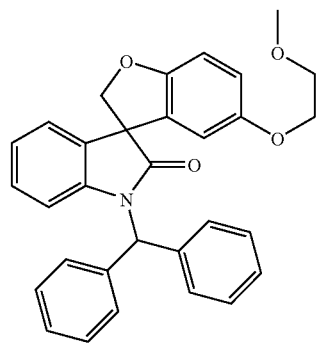

Following the procedure as described in EXAMPLE 2.68 and making non-critical variations using 1-(diphenylmethyl)-5-hydroxyspiro[1-benzofuran-3,3'-indol]-2'(1'H)-one to replace 1'-(diphenylmethyl)-6-hydroxyspiro[1-benzofuran-3,3'-indol]-2'(1'H)-one, 1'-(diphenylmethyl)-5-(2-methoxyethoxy)spiro[1-benzofuran-3,3'-indol]-2'(1'H)-one was obtained (90%) as a colorless solid: $^1$H NMR (300 MHz, CDCl$_3$) δ7.44-7.25 (m, 10H), 7.15-7.07 (m, 1H), 7.04 (s, 1H), 7.00-6.90 (m, 2H), 6.58-6.44 (m, 3H), 6.41-6.33 (m, 1H), 4.86 (ABq, 2H), 4.15-3.98 (m, 2H), 3.75-3.66 (m, 2H), 3.41 (s, 3H).

EXAMPLE 2.72

Synthesis of 1'-(diphenylmethyl)-2,3-dihydrospiro[furo[2,3-f][1,4]benzodioxine-7,3'-indol]-2'(1'H)-one

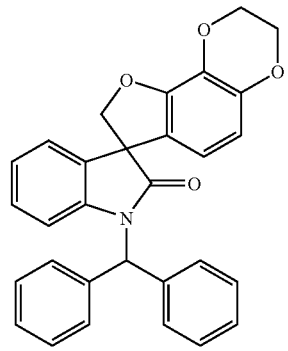

Following the procedure as described in EXAMPLE 2 and making non-critical variations using 1-(diphenylmethyl)-3-(5-hydroxy-2,3-dihydro-1,4-benzodioxin-6-yl)-1,3-dihydro-2H-indol-2-one to replace 1-(diphenylmethyl)-3-(2-hydroxy-4-methoxy-5-methylphenyl)-1,3-dihydro-2H-indol-2-one, 1'-(diphenylmethyl)-2,3-dihydrospiro[furo[2,3-f][1, 4]benzodioxine-7,3'-indol]-2'(1'H)-one was obtained (85%) as a colorless solid: $^1$H NMR (300 MHz, DMSO-d$_6$) δ7.47-7.22 (m, 12H), 7.10 (ddd, J=7.8, 7.8, 1.2 Hz, 1H), 6.99 (dd, J=7.4, 7.4 Hz, 1H), 6.88 (s, 1H), 6.58 (d, J=7.8 Hz, 1H), 6.32 (d, J=8.3 Hz, 1H), 6.04 (d, J=8.3 Hz, 1H), 4.93 (d, J=9.5 Hz, 1H), 4.81 (d, J=9.5 Hz, 1H), 4.27 (s, 4H); $^{13}$C NMR (75 MHz, DMSO-d$_6$) δ 176.8, 148.8, 144.7, 142.0, 137.6, 137.5, 131.6, 129.3, 128.7, 128.5, 128.3, 128.1, 127.9, 127.7, 127.6, 123.9, 122.9, 122.4, 113.8, 111.0, 109.9, 80.1, 64.1, 63.9, 58.1, 57.1; MS (ES+) m/z 461.9 (M+1).

EXAMPLE 2.73

Synthesis of 1'-(diphenylmethyl)-4',6'-dimethoxy-2,3-dihydrospiro[furo[2,3-g][1,4]benzodioxine-8,3'-indol]-2'(1'H)-one

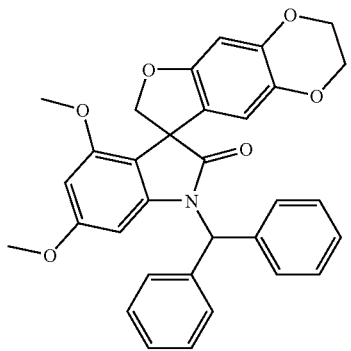

Following the procedure as described in EXAMPLE 2 and making non-critical variations using 1-(diphenylmethyl)-3-(7-hydroxy-2,3-dihydro-1,4-benzodioxin-6-yl)-4,6-dimethoxy-1,3-dihydro-2H-indol-2-one to replace 1-(diphenylmethyl)-3-(2-hydroxy-4-methoxy-5-methylphenyl)-1,3-dihydro-2H-indol-2-one, 1-(diphenylmethyl)-4',6'-dimethoxy-2,3-dihydrospiro[furo[2,3-g][1,4]benzodioxine-8,3'-indol]-2'(1'H)-one was obtained (96%) as a colorless solid: $^1$H NMR (300 MHz, CDCl$_3$) δ 7.41-7.24 (m, 10H), 6.97 (s, 1H), 6.42 (s, 1H), 6.19 (s, 1H), 6.04 (d, J=1.8 Hz, 1H), 5.69 (d, J=1.8 Hz, 1H), 4.81 (ABq, 2H), 4.21-4.06 (m, 4H), 3.62 (s, 3H), 3.47 (s, 3H); MS (ES+) m/z 522.1 (M+1).

EXAMPLE 2.74

Synthesis of 1'-(diphenylmethyl)spiro[furo[2,3-g]quinoxaline-8,3'-indol]-2'(1'H)-one

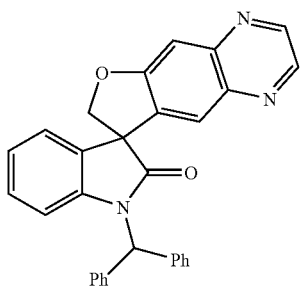

Following the procedure as described in EXAMPLE 2.40 and making non-critical variations using 1-(diphenylmethyl)-3-(7-hydroxyquinoxalin-6-yl)-1,3-dihydro-2H-indol-2-one to replace 2-fluoro-4-hydroxy-5-[1-(4-methoxybenzyl)-2-oxo-2,3-dihydro-1H-indol-3-yl]benzonitrile, 1'-(diphenylmethyl)spiro[furo[2,3-g]quinoxaline-8,3'-indol]-2'(1'H)-one was obtained (34%): $^1$H NMR (300 MHz, CDCl$_3$) δ 8.57 (d, J=1.5 Hz, 1H), 8.46 (d, J=1.5 Hz, 1H), 8.07-8.04 (m, 1H), 7.63-6.86 (m, 15H), 6.55-6.52 (m, 1H), 5.10 (ABq, 2H).

EXAMPLE 3

Synthesis of 6-methoxy-5-methylspiro[1-benzofuran-3,3'-indol]-2'(1'H)-one

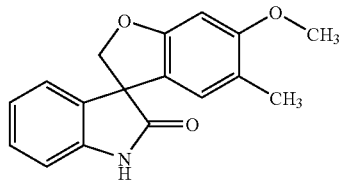

A stirred solution of 1-(diphenylmethyl)-6-methoxy-5-methylspiro[1-benzofuran-3,3'-indol]-2'(1'H)-one (7.2 g, 16.1 mmol), triethylsilane (15 mL) and trifluoroacetic acid (50 mL) was refluxed for 14 h. The solution was concentrated in vacuo and precipitated from hexanes to afford 6-methoxy-5-methylspiro[1-benzofuran-3,3'-indol]-2'(1'H)-one (3.9 g, 86%) as a colorless solid: mp>250° C.; $^1$H NMR (300 MHz, DMSO-d$_6$) δ10.54 (s, 1H), 7.23-7.14 (m, 1H), 7.03 (d, J=6.9 Hz, 1H), 6.95-6.86 (m, 2H), 6.58 (s, 1H), 6.41 (s, 1H), 4.68 (ABq, 2H), 3.73 (s, 3H), 1.91 (s, 3H); $^{13}$C NMR (75 MHz, DMSO-d$_6$) δ179.2, 160.4, 158.9, 142.2, 133.4, 129.1, 124.4, 124.2, 122.7, 120.3, 118.5, 110.2, 94.3, 80.1, 58.0, 56.0, 16.0; MS (ES+) m/z 282.2 (M+1).

EXAMPLE 3.1

Synthesis of 4'-chloro-5,6-dihydrospiro[benzo[1,2-b:5,4-b']difuran-3,3'-indol]-2'(1'H)-one

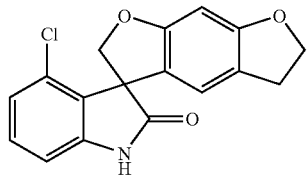

Following the procedure as described in EXAMPLE 3 and making non-critical variations using 1'-(diphenylmethyl)-4'-chloro-5,6-dihydrospiro[benzo[1,2-b:5,4-b']difuran-3,3'-indol]-2'(1'H)-one to replace 1'-(diphenylmethyl)-6-methoxy-5-methylspiro[1-benzofuran-3,3'-indol]-2'(1'H)-one, 4'-chloro-5,6-dihydrospiro[benzo[1,2-b:5,4-b']difuran-3,3'-indol]-2'(1'H)-one was obtained (70%) as a colorless solid: mp>200° C.; $^1$H NMR (300 MHz, DMSO-d$_6$) δ10.80 (s, 1H), 7.23 (dd, J=8.0, 8.0 Hz, 1H), 6.93 (d, J=8.0 Hz, 1H), 6.87 (d, J=7.7 Hz, 1H), 6.49 (s, 1H), 6.31 (s, 1H), 4.84 (d, J=9.6 Hz, 1H), 4.68 (d, J=9.6 Hz, 1H), 4.46 (t, J=8.7, Hz, 2H), 2.92 (t, J=8.6 Hz, 2H); $^{13}$C NMR (75 MHz, DMSO-d$_6$) δ182.8, 166.0, 165.8, 148.3, 134.9, 134.3, 133.8, 127.1, 123.9, 123.2, 122.4, 113.4, 96.5, 81.8, 76.6, 62.4, 32.9; MS (ES+) m/z 313.9 (M+1), 315.9 (M+1).

EXAMPLE 3.2

Synthesis of 6-bromospiro[1-benzofuran-3,3'-indol]-2'(1'H)-one

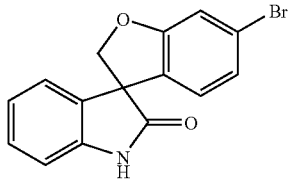

Following the procedure as described in EXAMPLE 3 and making non-critical variations using 6-bromo-1'-(diphenylmethyl)spiro[1-benzofuran-3,3'-indol]-2'(1'H)-one to replace 1'-(diphenylmethyl)-6-methoxy-5-methylspiro[1-benzofuran-3,3'-indol]-2'(1'H)-one, 6-bromospiro[1-benzofuran-3,3'-indol]-2'(1'H)-one was obtained (89%) as a colorless solid: MS (ES+) m/z 316.1 (M+1), 318.1 (M+1).

EXAMPLE 3.3

Synthesis of 5,6-dimethylspiro[1-benzofuran-3,3'-indol]-2'(1'H)-one

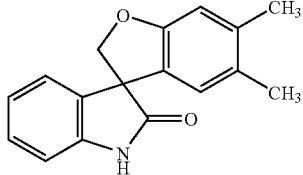

Following the procedure as described in EXAMPLE 3 and making non-critical variations using 1'-(diphenylmethyl)-5,6-dimethylspiro[1-benzofuran-3,3'-indol]-2'(1'H)-one to replace 1'-(diphenylmethyl)-6-methoxy-5-methylspiro[1-benzofuran-3,3'-indol]-2'(1'H)-one, 5,6-dimethylspiro[1-benzofuran-3,3'-indol]-2'(1'H)-one was obtained (88%) as a colorless solid: mp 206-207° C. (ethyl acetate/hexanes); $^1$H NMR (300 MHz, DMSO-d$_6$) δ10.5 (s, 1H), 7.23-7.18 (m, 1H), 7.03-7.01 (m, 1H), 6.94-6.88 (m, 2H), 6.73 (s, 1H), 6.43 (s, 1H), 4.68 (ABq, 2H), 2.13 (s, 3H), 1.99 (s, 3H); $^{13}$C NMR (75 MHz, DMSO-d$_6$) δ178.9, 159.1, 142.2, 138.0, 133.3, 129.1, 127.0, 124.2, 124.1, 122.7, 111.2, 110.2, 79.5, 58.2, 20.2, 19.1; MS (ES+) m/z 266.3 (M+1).

EXAMPLE 3.4

Synthesis of 5'-fluoro-5,6-dihydrospiro[benzo[1,2-b:5,4-b']difuran-3,3'-indol]-2'(1'H)-one

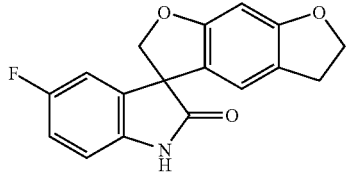

Following the procedure as described in EXAMPLE 3 and making non-critical variations using 1'-(diphenylmethyl)-5'-fluoro-5,6-dihydrospiro[benzo[1,2-b:5,4-b']difuran-3,3'-indol]-2'(1'H)-one to replace 1'-(diphenylmethyl)-6-methoxy-5-methylspiro[1-benzofuran-3,3'-indol]-2'(1'H)-one, 5'-fluoro-5,6-dihydrospiro[benzo[1,2-b:5,4-b']furan-3,3'-indol]-2'(1'H)-one was obtained (91%) as a colorless solid: mp 257-259° C. (diethyl ether); $^1$H NMR (300 MHz, CDCl$_3$) δ10.35 (s, 1H), 6.86-6.73 (m, 3H), 6.43 (s, 1H), 6.22 (s, 1H), 4.64 (ABq, 2H), 4.43 (t, J=9.0 Hz, 2H), 2.93-2.90 (m, 2H); MS (ES+) m/z 298.0 (M+1).

EXAMPLE 3.5

Synthesis of 6'-fluoro-5,6-dihydrospiro[benzo[1,2-b:5,4-b']difuran-3,3'-indol]-2'(1'H)-one

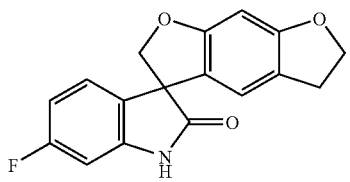

Following the procedure as described in EXAMPLE 3 and making non-critical variations using 1'-(diphenylmethyl)-6'-fluoro-5,6-dihydrospiro[benzo[1,2-b:5,4-b']difuran-3,3'-indol]-2'(1'H)-one to replace 1'-(diphenylmethyl)-6-methoxy-5-methylspiro[1-benzofuran-3,3'-indol]-2'(1'H)-one, 6'-fluoro-5,6-dihydrospiro[benzo[1,2-b:5,4-b']difuran-3,3'-indol]-2'(1'H)-one was obtained (71%) as a colorless solid: mp 249-251° C. (diethyl ether); $^1$H NMR (300 MHz, DMSO-d$_6$) δ10.74 (s, 1H), 7.18-7.13 (m, 1H), 6.79-6.42 (m, 2H), 6.55 (s, 1H), 6.42 (s, 1H), 4.74 (ABq, 2H), 4.52 (t, J=9.0 Hz, 2H), 2.99 (t, J=9.0 Hz, 2H); MS (ES+) m/z 298.0 (M+1).

EXAMPLE 3.6

Synthesis of 3-methylspiro[furo[3,2-f][1,2]benzisoxazole-5,3'-indol]-2'(1'H)-one

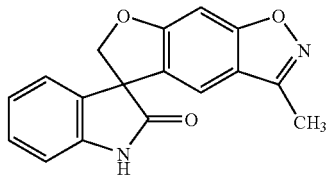

To a stirred solution of 1-(4-methoxybenzyl)-3-methylspiro[furo[3,2-f][1,2]benzisoxazole-5,3'-indol]-2'(1'H)-one (3.00 g, 7.76 mmol) in dichloromethane (20 mL) and trifluoroacetic acid (20 mL) was added trifluoromethanesulfonic acid (6.8 mL, 76.8 mmol). The reaction mixture was stirred at ambient temperature for 22 h, and concentrated in vacuo. The residue was basified with saturated sodium bicarbonate solution and extracted with ethyl acetate. The combined organic solution was washed with water and brine, dried over anhydrous sodium sulfate and filtered. The filtrate was concentrated in vacuo. The residue was purified by column chromatography with ethyl acetate in hexanes (gradient 30% to 80%) to give 3-methylspiro[furo[3,2-f][1,2]benzisoxazole-5,3'-indol]-2'(1'H)-one (1.72 g, 76%): mp 226-227° C. (ethyl acetate/hexanes); $^1$H NMR (300 MHz, DMSO-d$_6$) δ10.82 (s, 1H), 7.69 (d, J=9.0 Hz, 1H), 7.27 (m, 1H), 7.11-7.04 (m, 2H), 6.97-6.90 (m, 2H), 4.89 (AB, 2H), 2.40 (s, 3H); MS (ES+) m/z 292.9 (M+1).

EXAMPLE 3.7

Synthesis of 5-fluoro-6-methoxyspiro[1-benzofuran-3,3'-indol]-2'(1'H)-one

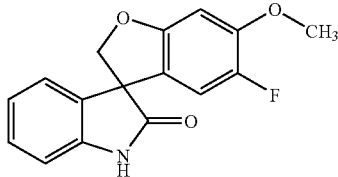

Following the procedure as described in EXAMPLE 3 and making non-critical variations using 1'-(diphenylmethyl)-5-fluoro-6-methoxyspiro[1-benzofuran-3,3'-indol]-2'(1'H)-one to replace 1-(diphenylmethyl)-6-methoxy-5-methylspiro[1-benzofuran-3,3'-indol]-2'(1'H)-one, 5-fluoro-6-methoxyspiro[1-benzofuran-3,3'-indol]-2'(1'H)-one was obtained (82%) as a colorless solid: mp 222-225° C.; $^1$H NMR (300 MHz, CDCl$_3$) δ8.33 (s, 1H), 7.29-7.21 (m, 1H), 7.12 (d, J=6.7 Hz, 1H), 7.03 (ddd, J=7.5, 7.5, 0.9 Hz, 1H), 6.93 (d, J=7.8 Hz, 1H), 6.59 (d, J=6.8 Hz, 1H), 6.52 (d, J=10.1 Hz, 1H), 4.96 (d, J=9.1 Hz, 1H), 4.68 (d, J=9.1 Hz, 1H), 3.85 (s, 3H); $^{13}$C NMR (75 MHz, CDCl$_3$) δ179.9, 157.2, 149.3, 149.1 (d, J=12.4 Hz), 146.1, 140.2, 132.2, 129.1, 123.8 (d, J=42.8 Hz), 118.6 (d, J=7.1 Hz), 110.7, 110.4, 96.3, 80.5, 58.6, 56.4; MS (ES+) m/z 286.2 (M+1).

EXAMPLE 3.8

Synthesis of 5-fluoro-spiro[1-benzofuran-3,3'-indol]-2'(1'H)-one

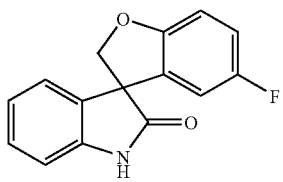

Following the procedure as described in EXAMPLE 3 and making non-critical variations using 1'-(diphenylmethyl)-5-fluorospiro[1-benzofuran-3,3'-indol]-2'(1'H)-one to replace 1'-(diphenylmethyl)-6-methoxy-5-methylspiro[1-benzofuran-3,3'-indol]-2'(1'H)-one, 5-fluoro-spiro[1-benzofuran-3,3'-indol]-2'(1'H)-one was obtained (87%): mp 224-226° C.; $^1$H NMR (300 MHz, DMSO-d$_6$) δ10.65 (s, 1H), 7.23 (ddd, J=7.7, 7.7, 0.9 Hz, 1H), 7.09 (d, J=7.0 Hz, 1H), 7.06-6.87 (m, 4H), 6.58 (dd, J=8.0, 2.7 Hz, 1H), 4.80 (d, J=9.3 Hz, 1H), 4.67 (d, J=9.3 Hz, 1H); $^{13}$C NMR (75 MHz, DMSO-d$_6$) δ178.2, 158.9, 157.1, 142.3, 132.4, 131.3, 131.1, 129.5, 124.3, 122.8, 116.5, 116.2, 111.0, 110.9, 110.7, 110.4, 80.2, 58.4; MS (ES+) m/z 260.0 (M+1).

EXAMPLE 3.9

Synthesis of 6-methoxyspiro[1-benzofuran-3,3'-indol]-2'(1'H)-one

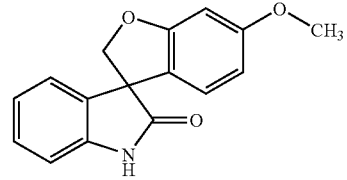

Following the procedure as described in EXAMPLE 3 and making non-critical variations using 1-(diphenylmethyl)-6-methoxyspiro[1-benzofuran-3,3'-indol]-2'(1'H)-one to replace 1-(diphenylmethyl)-6-methoxy-5-methylspiro[1-benzofuran-3,3'-indol]-2'(1'H)-one, 6-methoxyspiro[1-benzofuran-3,3'-indol]-2'(1'H)-one was obtained (98%) as a colorless solid: $^1$H NMR (300 MHz, CDCl$_3$) δ8.23-8.11 (br, 1H), 7.30-6.90 (m, 4H), 6.69 (d, J=8.4 Hz, 1H), 6.54 (d, J=2.4 Hz, 1H), 6.39 (dd, J=8.4, 1.8 Hz, 1H), 4.98 (d, J=9.0 Hz, 1H), 4.71 (d, J=9.0 Hz, 1H), 3.78 (s, 3H); MS (ES+) m/z 268.3 (M+1).

EXAMPLE 3.10

Synthesis of 2,3-dihydrospiro[furo[2,3-g][1,4]benzodioxine-8,3'-indol]-2'(1'H)-one

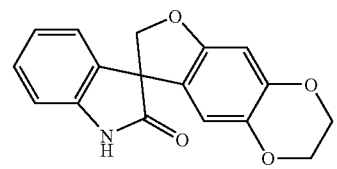

Following the procedure as described in EXAMPLE 3 and making non-critical variations using 1'-(diphenylmethyl)-2,3-dihydrospiro[furo[2,3-g][1,4]benzodioxine-8,3'-indol]-2'(1'H)-one to replace 1'-(diphenylmethyl)-6-methoxy-5-methylspiro[1-benzofuran-3,3'-indol]-2'(1'H)-one, 2,3-dihydrospiro[furo[2,3-g][1,4]benzodioxine-8,3'-indol]-2'(1'H)-one was obtained (89%) as a colorless solid: mp>250° C. (diethyl ether); $^1$H NMR (300 MHz, DMSO-d$_6$) δ10.57 (s, 1H), 7.24 (ddd, J=7.7, 7.7, 1.0 Hz, 1H), 7.09 (d, J=6.9 Hz, 1H), 6.96 (dd, J=7.5, 7.5 Hz, 1H), 6.91 (d, J=7.8 Hz, 1H), 6.49 (s, 1H), 6.16 (s, 1H), 4.73 (d, J=9.2 Hz, 1H), 4.60 (d, J=9.2 Hz, 1H), 4.20-4.15 (m, 2H), 4.13-4.08 (m, 2H); $^{13}$C NMR (75 MHz, DMSO-d$_6$) δ178.3, 154.6, 144.0, 141.7, 137.7, 132.5, 128.7, 123.7, 122.2, 121.4, 111.1, 109.8, 98.6, 79.4, 64.2, 63.6, 57.6; MS (ES+) m/z 296.3 (M+1).

EXAMPLE 3.11

Synthesis of 3,4-dihydro-2H-spiro[furo[2,3-h][1,5]benzodioxepine-9,3'-indol]-2'(1'H)-one

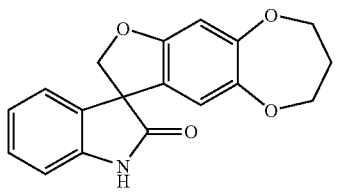

Following the procedure as described in EXAMPLE 3 and making non-critical variations using 1'-(diphenylmethyl)-3,4-dihydro-2H-spiro[furo[2,3-h][1,5]benzo-dioxepine-9,3'-indol]-2'(1'H)-one to replace 1'-(diphenylmethyl)-6-methoxy-5-methylspiro[1-benzofuran-3,3'-indol]-2'(1'H)-one, 3,4-dihydro-2H-spiro[furo[2,3-h][1,5]benzodioxepine-9,3'-indol]-2'(1'H)-one was obtained (70%) as a colorless solid: mp 235-236° C. (methanol); $^1$H NMR (300 MHz, DMSO-d$_6$) δ10.60 (s, 1H), 7.24 (dd, J=7.8, 7.2 Hz, 1H), 7.11 (d, J=7.2 Hz, 1H), 6.97 (dd, J=7.8, 7.5 Hz, 1H), 6.92 (d, J=7.8 Hz, 1H), 6.58 (s, 1H), 6.27 (s, 1H), 4.78 (d, J=9.3 Hz, 1H), 4.65 (d, J=9.3 Hz, 1H), 4.14-4.01 (m, 2H), 3.98-3.87 (m, 2H), 2.06-1.97 (m, 2H); $^{13}$C NMR (75 MHz, DMSO-d$_6$) δ178.2, 156.3, 152.5, 145.8, 141.8, 132.4, 128.8, 123.8, 123.7, 122.3, 115.6, 109.8, 103.0, 79.8, 70.7, 57.6, 31.9; MS (ES+) m/z 310.0 (M+1).

EXAMPLE 3.12

Synthesis of 2-methylspiro[furo[2,3-f][1,3]benzoxazole-7,3'-indol]-2'(1'H)-one

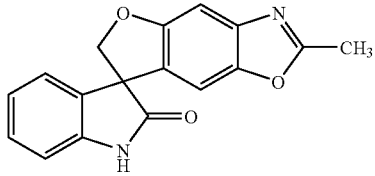

Following the procedure as described in EXAMPLE 3 and making non-critical variations using 1'-(diphenylmethyl)-2-methylspiro[furo[2,3-f][1,3]benzoxazole-7,3'-indol]-2'(1'H)-one to replace 1'-(diphenylmethyl)-6-methoxy-5-methylspiro[1-benzofuran-3,3'-indol]-2'(1'H)-one, 2-methylspiro[furo[2,3-f][1,3]benzoxazole-7,3'-indol]-2'(1'H)-one was obtained (62%) as a colorless solid: mp 242-244° C. (diethyl ether); $^1$H NMR (300 MHz, CDCl$_3$) δ8.20 (br s, 1H), 7.36 (d, J=8.7 Hz, 1H), 7.30-7.24 (m, 1H), 7.08 (d, J=7.5 Hz, 1H), 7.00 (d, J=8.7 Hz, 1H), 6.99-6.93 (m, 1H), 6.96 (d, J=7.8 Hz, 1H), 5.96 (d, J=6.0 Hz, 1H), 5.42 (d, J=5.0 Hz, 1H), 2.41 (s, 3H); $^{13}$C NMR (75 MHz, CDCl$_3$) δ176.2, 165.2, 151.4, 146.1, 142.0, 138.2, 130.6, 130.1, 125.0, 123.1, 114.3, 111.5, 110.9, 88.4, 76.3, 14.6; MS (ES+) m/z 331.1 (M+39).

EXAMPLE 3.13

Synthesis of 3-methylspiro[furo[2,3-f][1,3]benzoxazole-7,3'-indole]-2,2'(1'H,3H)-dione

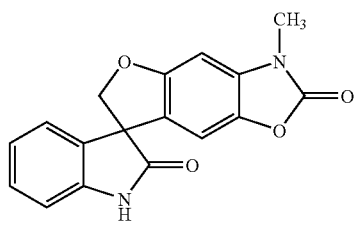

Following the procedure as described in EXAMPLE 3 and making non-critical variations using 1'-(diphenylmethyl)-3-methylspiro[furo[2,3-f][1,3]benzoxazole-7,3'-indole]-2,2'(1'H,3H)-dione to replace 1'-(diphenylmethyl)-6-methoxy-5-methylspiro[1-benzofuran-3,3'-indol]-2'(1'H)-one, 3-methylspiro[furo[2,3-f][1,3]benzoxazole-7,3'-indole]-2,2'(1'H,3H)-dione was obtained (88%) as a colorless solid: mp>250° C. (diethyl ether); $^1$H NMR (300 MHz, DMSO-d$_6$) δ10.64 (br s, 1H), 7.30-7.22 (m, 1H), 7.09 (d, J=7.0 Hz, 1H), 7.01-6.90 (m, 3H), 6.75 (s, 1H), 4.82 (d, J=9.3 Hz, 1H), 4.70 (d, J=9.3 Hz, 1H), 3.30 (s, 3H); $^{13}$C NMR (75 MHz, DMSO-d$_6$) δ178.2, 157.0, 154.5, 141.8, 136.2, 132.8, 132.4, 128.9, 123.8, 122.3, 122.0, 109.9, 104.9, 92.3, 79.8, 57.8, 28.2; MS (ES+) m/z 309.1 (M+1).

EXAMPLE 3.14

Synthesis of 1-methylspiro[furo[3,2-f][1,3]benzoxazole-7,3'-indole]-2,2'(1'H,1'H)-dione

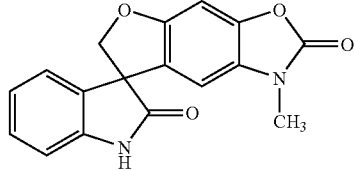

Following the procedure as described in EXAMPLE 3 and making non-critical variations using 1'-(diphenylmethyl)-1-methylspiro[furo[3,2-f][1,3]benzoxazole-7,3'-indole]-2,2'(1'H,1'H)-dione to replace 1'-(diphenylmethyl)-6-methoxy-5-methylspiro[1-benzofuran-3,3'-indol]-2'(1'H)-one, 1-(diphenylmethyl)-1-methylspiro[furo[3,2-f][1,3]benzoxazole-7,3'-indole]-2,2'(1'H,1'H)-dione was obtained (53%) as a colorless solid: mp>250° C. (methanol); $^1$H NMR (300 MHz, DMSO-d$_6$) δ10.69 (br s, 1H), 7.30-7.25 (m, 1H), 7.14-7.08 (m, 2H), 7.01-6.92 (m, 2H), 6.69 (s, 1H), 4.82 (d, J=9.3 Hz, 1H), 4.70 (d, J=9.3 Hz, 1H), 3.20 (s, 3H); $^{13}$C NMR (75 MHz, DMSO-d$_6$) δ178.2, 156.1, 154.2, 142.5, 141.9, 132.4, 128.9, 126.0, 124.0, 122.4, 109.9, 104.0, 93.9, 79.8, 57.8, 28.1; MS (ES+) m/z 308.9 (M+1).

EXAMPLE 3.15

Synthesis of 7'-chloro-5,6-dihydrospiro[benzo[1,2-b:5,4-b']difuran-3,3'-indol]-2'(1'H)-one

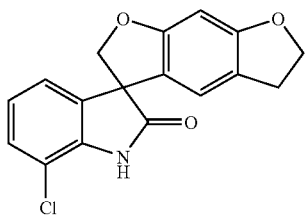

Following the procedure as described in EXAMPLE 3 and making non-critical variations using 7-chloro-1-(diphenylmethyl)-3-(6-hydroxy-2,3-dihydro-1-benzofuran-5-yl)-1,3-dihydro-2H-indol-2-one to replace 1-(diphenylmethyl)-6-methoxy-5-methylspiro[1-benzofuran-3,3'-indol]-2'(1'H)-one, 7'-chloro-5,6-dihydrospiro[benzo[1,2-b:5,4-b']difuran-3,3'-indol]-2'(1'H)-one was obtained (78%) as a colorless solid: mp>250° C. (diethyl ether); $^1$H NMR (300 MHz, DMSO-$d_6$) δ11.01 (s, 1H), 7.30 (d, J=8.0 Hz, 1H), 7.70 (d, J=7.1 Hz, 1H), 7.00-6.94 (m, 1H), 6.56 (s, 1H), 6.40 (s 1H), 4.80 (d, J=9.4 Hz, 1H), 4.68 (d, J=9.4 Hz, 1H), 4.49 (m, 2H), 2.95 (m, 2H); $^{13}$C NMR (75 MHz, DMSO-$d_6$) δ178.5, 161.0, 160.5, 139.4, 134.7, 128.4, 123.4, 122.3, 120.1, 119.8, 118.9, 113.8, 92.3, 79.8, 72.0, 58.0, 28.2; MS (ES+) m/z 313.7 (M+1), 315.7 (M+1).

EXAMPLE 3.16

Synthesis of 7'-fluoro-5,6-dihydrospiro[benzo[1,2-b:5,4-b']difuran-3,3'-indol]-2'(1'H)-one

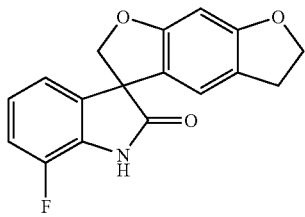

Following the procedure as described in EXAMPLE 3 and making non-critical variations using 7-fluoro-1-(diphenylmethyl)-3-(6-hydroxy-2,3-dihydro-1-benzofuran-5-yl)-1,3-dihydro-2H-indol-2-one to replace 1-(diphenylmethyl)-6-methoxy-5-methylspiro[1-benzofuran-3,3'-indol]-2'(1'H)-one, 7'-fluoro-5,6-dihydrospiro[benzo[1,2-b:5,4-b']difuran-3,3'-indol]-2'(1'H)-one was obtained (97%) as a colorless solid: mp>250° C. (diethyl ether); $^1$H NMR (300 MHz, DMSO-$d_6$) δ11.01 (s, 1H), 7.30 (d, J=8.0 Hz, 1H), 7.70 (d, J=7.1 Hz, 1H), 7.00-6.94 (m, 1H), 6.56 (s, 1H), 6.40 (s 1H), 4.80 (d, J=9.4 Hz, 1H), 4.68 (d, J=9.4 Hz, 1H), 4.49 (m, 2H), 2.95 (m, 2H); $^{13}$C NMR (75 MHz, DMSO-$d_6$) δ178.5, 161.0, 160.5, 139.4, 134.7, 128.4, 123.4, 122.3, 120.1, 119.8, 118.9, 113.8, 92.3, 79.8, 72.0, 58.0, 28.2; MS (ES+) m/z 298.0 (M+1).

EXAMPLE 3.17

Synthesis of 4'-fluoro-7'-methyl-5,6-dihydrospiro[benzo[1,2-b:5,4-b']difuran-3,3'-indol]-2'(1'H)-one

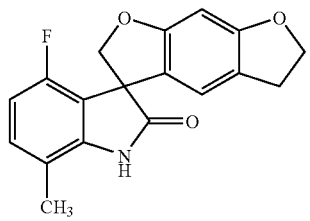

Following the procedure as described in EXAMPLE 3 and making non-critical variations using 1'-(diphenylmethyl)-4'-fluoro-7'-methyl-5,6-dihydrospiro[benzo[1,2-b:5,4-b']difuran-3,3'-indol]-2'(1'H)-one to replace 1-(diphenylmethyl)-6-methoxy-5-methylspiro[1-benzofuran-3,3'-indol]-2'(1'H)-one, 4'-fluoro-7'-methyl-5,6-dihydrospiro[benzo[1,2-b:5,4-b']difuran-3,3'-indol]-2'(1'H)-one was obtained (76%) as a colorless solid: mp>250° C. (diethylether); $^1$H NMR (300 MHz, DMSO-$d_6$) δ10.84 (s, 1H), 7.12-7.07 (m, 1H), 6.72-6.65 (m, 1H), 6.59 (s, 1H), 6.37 (s, 1H), 4.78-4.73 (m, 2H), 4.50 (t, J=8.7 Hz, 2H), 2.97 (d, J=8.7 Hz, 2H), 2.20 (s, 3H); MS (ES+) m/z 311.9 (M+1).

EXAMPLE 3.18

Synthesis of 6-hydroxyspiro[1-benzofuran-3,3'-indol]-2'(1'1-1)-one

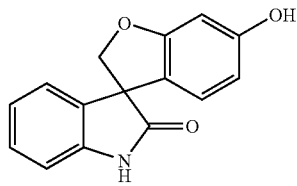

A suspension of 6-(benzyloxy)-1'-(diphenylmethyl)spiro[1-benzofuran-3,3'-indol]-2'(1'H)-one (0.60 g, 1.2 mmol) in methanol (20 mL) was degassed by bubbling through nitrogen for 1 h before palladium hydroxide on carbon (20%, 0.08 g, 0.12 mmol) was added. The mixture was stirred under 120 psi hydrogen at 60° C. for 16 h. The mixture was filtered through a pad of celite, and the filtrate was concentrated in vacuo. The residue obtained was recrystallized from ethyl acetate and hexanes to afford 6-hydroxy-2H-spiro[benzofuran-3,3'-indolin]-2'-one (0.25 g, 83%) as a colorless solid: $^1$H NMR (300 MHz, DMSO-$d_6$) δ 10.86-9.35 (br, 2H), 7.19 (td, J=7.6, 1.2 Hz, 1H), 7.03 (d, J=7.3 Hz, 1H), 6.96-6.84 (m, 2H), 6.42 (d, J=8.2 Hz, 1H), 6.29 (d, J=2.1 Hz, 1H), 6.17 (dd, J=8.2, 2.1 Hz, 1H), 4.72 (d, J=9.2 Hz, 1H), 4.59 (d, J=9.2 Hz, 1H); MS (ES+) m/z 254.1 (M+1).

EXAMPLE 3.19

Synthesis of tert-butyl (3S)-3-{[1'-(diphenylmethyl)-2'-oxo-1',2'-dihydrospiro[1-benzofuran-3,3'-indol]-6-yl]oxy}pyrrolidine-1-carboxylate

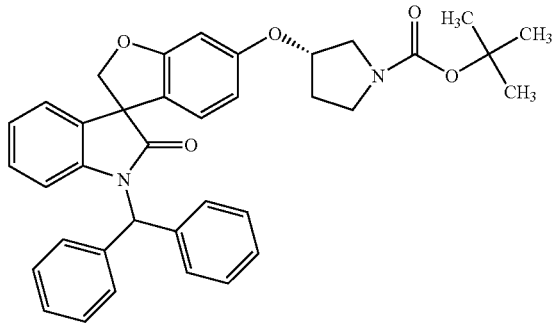

To a solution of 1'-(diphenylmethyl)-6-hydroxyspiro[1-benzofuran-3,3'-indol]-2'(1'H)-one (0.45 g, 1.07 mol), tert-butyl (3R)-3-hydroxypyrrolidine-1-carboxylate (0.60 g, 3.22 mmol) and triphenylphosphine (0.70 g, 2.68 mmol) in tetrahydrofuran (50 mL) was added diethyl azodicarboxylate (0.42 mL, 2.68 mmol) slowly at 0° C. The mixture was stirred to 16 h at ambient temperature, then concentrated in vaccuo. The residue was purified by column chromatography (ethyl acetate/hexanes-1:2) to afford tert-butyl (3S)-3-{[1'-(diphenylmethyl)-2'-oxo-1',2'-dihydrospiro[1-benzofuran-3,3'-indol]-6-yl]oxy}pyrrolidine-1-carboxylate as an oil (0.52 g, 83%): $^1$H NMR (300 MHz, CDCl$_3$) δ7.43-7.25 (m, 10H), 7.16-7.06 (m, 1H), 7.07-6.91 (m, 3H), 6.58-6.43 (m, 3H), 6.38-6.25 (m, 1H), 5.00 (d, J=9.0 Hz, 1H), 4.80 (s, 1H), 4.73 (d, J=9.0 Hz, 1H), 3.65-3.36 (m, 4H), 2.22-1.95 (m, 2H), 1.45 (s, 9H); MS (ES+) m/z 611.3 (M+23).

EXAMPLE 3.20

Synthesis of tert-butyl (3S)-3-[(2'-oxo-1',2'-dihydrospiro[1-benzofuran-3,3'-indol]-6-yl)oxy]pyrrolidine-1-carboxylate

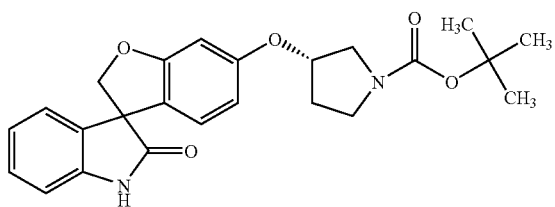

A suspension of tert-butyl (3S)-3-{[1'-(diphenylmethyl)-2'-oxo-1',2'-dihydrospiro[1-benzofuran-3,3'-indol]-6-yl]oxy}pyrrolidine-1-carboxylate (0.50 g, 0.85 mmol) in methanol (20 mL) was degassed by bubbling through nitrogen for one hour before palladium hydroxide on carbon (20%, 0.084 g) was added. The mixture was stirred under 120 psi hydrogen at 60° C. for 48 h. The mixture was filtered through a pad of celite, the filtrate was concentrated in vacuo. The obtained residue was recrystallized from ethyl acetate and hexanes to afford tert-butyl (3S)-3-[(2'-oxo-1',2'-dihydrospiro[1-benzofuran-3,3'-indol]-6-yl)oxy]pyrrolidine-1-carboxylate (0.25 g, 70%) as a colorless solid: $^1$H NMR (300 MHz, CDCl$_3$) δ8.01 (br s, 1H), 7.29-7.09 (m, 1H), 7.12 (d, J=7.0 Hz, 1H), 7.02 (dd, J=7.5, 0.8 Hz, 1H), 6.92 (d, J=7.7 Hz, 1H), 6.66 (d, J=8.3 Hz, 1H), 6.47 (d, J=2.1 Hz, 1H), 6.33 (dd, J=8.3, 2.1 Hz, 1H), 4.96 (d, J=9.1 Hz, 1H), 4.81 (s, 1H), 4.69 (d, J=9.1 Hz, 1H), 3.64-3.37 (m, 4H), 2.22-1.96 (m, 2H), 1.45 (s, 9H); MS (ES+) m/z 445.0 (M+23).

EXAMPLE 3.21

Synthesis of 6,7-dihydro-5H-spiro[furo[3,2-g]chromene-3,3'-indol]-2'(1'H)-one

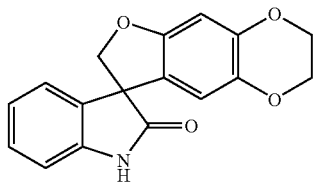

A solution of 1'-(diphenylmethyl)-6,7-dihydro-5H-spiro[furo[3,2-g]chromene-3,3'-indol]-2'(1'H)-one (0.61 g, 1.32 mmol) and triethylsilane (0.67 mL, 4.2 mmol) in trifluoroacetic acid (4.5 mL) was stirred at reflux under nitrogen for 2.5 h. Once cooled, the reaction was diluted with water (40 mL) and extracted with ethyl acetate (3×25 mL). The combined organic solution was washed with brine (50 mL), dried (sodium sulfate), filtered and concentrated under reduced pressure. The residue was dissolved into 10% diethyl ether in dichloromethane (5 mL) and, after standing at ambient temperature, yielded a colorless precipitate. This material was collected by filtration and washed with hexanes. Drying in air provided 6,7-dihydro-5H-spiro[furo[3,2-g]chromene-3,3'-indol]-2'(1'H)-one (0.25 g, 63%) as a colorless solid. An additional portion (0.14 g, 37%) of product was also recovered by concentrating the filtrate and triturating the residual solid with hexanes: mp 216-220° C. (hexanes); $^1$H NMR (300 MHz, DMSO-d$_6$) δ10.58 (s, 1H), 7.23 (ddd, J=7.8, 7.5, 0.9 Hz, 1H), 7.08 (d, J=7.2 Hz, 1H), 6.98-6.91 (m, 2H), 6.36 (s, 1H), 6.31 (s, 1H), 4.74 (d, J=9.0 Hz, 1H), 4.61 (d, J=9.0 Hz, 1H), 4.05 (dd, J=5.1, 4.8 Hz, 2H), 2.61-2.45 (m, 2H), 1.84-1.77 (m, 2H); $^{13}$C NMR (75 MHz, DMSO-d$_6$) δ178.6, 159.5, 155.4, 141.8, 132.9, 128.6, 123.8, 123.6, 122.3, 121.4, 114.8, 109.7, 97.9, 79.5, 66.0, 57.3, 23.9, 21.7; MS (ES+) m/z 294.1 (M+1).

EXAMPLE 3.22

Synthesis of 1-methyl-1H-spiro[furo[3,2-g][1,4]benzoxazine-8,3'-indole]-2,2'(1'H,3H)-dione

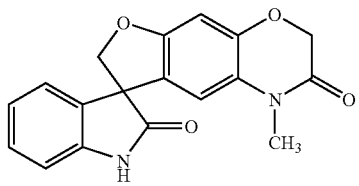

Following the procedure as described in EXAMPLE 3 and making non-critical variations using 1'-(diphenylmethyl)-1-methyl-1H-spiro[furo[3,2-g][1,4]benzoxazine-8,3'-indole]-2,2'(1'H,3H)-dione to replace 1-(diphenylmethyl)-6-methoxy-5-methylspiro[1-benzofuran-3,3'-indol]-2'(1'H)-one, 1-methyl-1H-spiro[furo[3,2-g][1,4]benzoxazine-8,3'-indole]-2,2'(1'H,3H)-dione was obtained (73%) as a colorless solid: mp>250° C. (ethyl acetate); $^1$H NMR (300 MHz, DMSO-d$_6$) δ 10.62 (br s, 1H), 7.29-7.22 (m, 1H), 7.11 (d, J=7.1 Hz, 1H), 7.02-6.90 (m, 2H), 6.70 (s, 1H), 6.48 (s, 1H), 4.80 (d, J=9.2 Hz, 1H), 4.66 (d, J=9.2 Hz, 1H), 4.58 (s, 2H), 3.07 (s, 3H); $^{13}$C NMR (75 MHz, DMSO-d$_6$) δ178.1, 163.3, 156.7, 146.2, 141.9, 132.3, 128.9, 124.0, 123.9, 122.9, 122.3, 109.9, 99.1, 80.3, 67.1, 57.7, 28.0; MS (ES+) m/z 322.9 (M+1).

EXAMPLE 3.23

Synthesis of 4-methyl-4,7-dihydrospiro[benzofuro[5,6-b][1,4]oxazine-8,3'-indoline]-2',3(2H)-dione

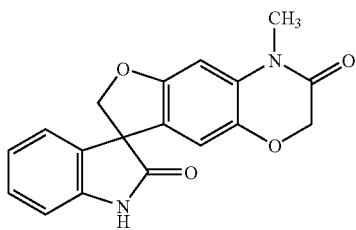

A solution of 7-[1-(diphenylmethyl)-2-oxo-2,3-dihydro-1H-indol-3-yl]-6-hydroxy-4-methyl-2H-1,4-benzoxazin-3(4H)-one (3.4 g, 7.1 mmol) in anhydrous tetrahydrofuran (30 mL) was deoxygenated for 1 h with dry argon. Cesium carbonate (8.1 g, 25 mmol) and chloroiodomethane (1.5 mL, 21 mmol) were added and the heterogeneous reaction mixture was stirred at ambient temperature for 16 h. The reaction mixture was filtered through a pad of diatomaceous earth and the pad was washed with ethyl acetate (50 mL). The filtrate was concentrated in vacuo and the crude product was purified by column chromatography with ethyl acetate in hexanes (10% to 70% gradient) to afford 6-[1-(diphenylmethyl)-2-oxo-2,3-dihydro-1H-indol-3-yl]-5-hydroxy-3-methyl-1,3-benzoxazol-2(3H)-one. To a solution containing 6-[1-(diphenylmethyl)-2-oxo-2,3-dihydro-1H-indol-3-yl]-5-hydroxy-3-methyl-1,3-benzoxazol-2(3H)-one (1.0 g, 20 mmol), in trifluoroacetic acid (10 mL) was added triethylsilane (1.6 mL, 10 mmol) and the reaction mixture was heated at reflux for 16 h. The reaction mixture was concentrated in vacuo and the crude product was purified by column chromatography with ethyl acetate in hexanes (10% to 60% gradient) to afford 4-methyl-4,7-dihydrospiro[benzofuro[5,6-b][1,4]oxazine-8,3'-indoline]-2',3(2H)-dione (0.52 g, 78%) as an off-white solid: mp>250° C.; $^1$F1 NMR (300 MHz, DMSO-d$_6$) δ10.63 (s, 1H), 7.28-7.23 (m, 1H), 7.10 (d, J=7.1 Hz, 1H), 6.99-6.90 (m, 2H), 6.87 (s, 1H), 6.36 (s, 1H), 4.81 (d, J=9.3 Hz, 1H), 4.70 (d, J=9.3 Hz, 1H), 4.51 (s, 2H), 3.26 (s, 3H); $^{13}$C NMR (75 MHz, DMSO-d$_6$) δ178.0, 164.4, 156.0, 141.7, 139.2, 132.2, 130.7, 128.8, 123.7, 123.0, 122.2, 110.8, 109.8, 97.8, 79.7, 67.0, 57.6, 28.1; MS (ES−) m/z 321.2 (M−1).

EXAMPLE 3.24

Synthesis of 2,3,6,7-tetrahydrospiro[furo[3,2-g]chromene-5,3'-indol]-1'(1'H)-one

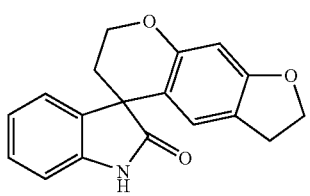

Following the procedure as described in EXAMPLE 3 and making non-critical variations using 1-(diphenylmethyl)-2,3,6,7-tetrahydrospiro[furo[3,2-g]chromene-5,3'-indol]-2'(1'H)-one to replace 1-(diphenylmethyl)-6-methoxy-5-methylspiro[1-benzofuran-3,3'-indol]-2'(1'H)-one, 2,3,6,7-tetrahydrospiro[furo[3,2-g]chromene-5,3'-indol]-2'(1'H)-one was obtained (63%) as a colorless solid: $^1$H NMR (300 MHz, CDCl$_3$) δ 9.33 (s, 1H), 7.32-6.90 (m, 4H), 6.38 (s, 1H), 6.34 (s, 1H), 4.80-4.71 (m, 1H), 4.46 (t, J=8.6 Hz, 2H), 4.37-4.29 (m, 1H), 2.93 (t, J=8.5 Hz, 2H), 2.30-2.13 (m, 2H); $^{13}$C NMR (75 MHz, CDCl$_3$) δ182.7, 160.6, 155.5, 140.5, 135.9, 128.3, 124.0, 123.8, 123.0, 120.3, 112.1, 110.1, 98.5, 71.9, 62.0, 48.5, 32.4, 28.9; MS (ES+) m/z 293.8 (M+1)

EXAMPLE 3.25

Synthesis of (3S)-6-methoxy-5-methylspiro[1-benzofuran-3,3'-indol]-2'(1'H)-one

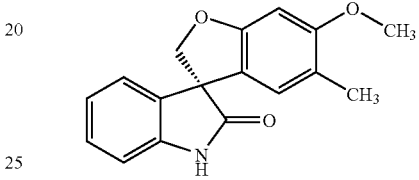

6-Methoxy-5-methylspiro[1-benzofuran-3,3'-indol]-2'(1'H)-one (2.16 g, 0.10 g per run) was resolved on a semi-prep chiral IA column with 10% acetonitrile in tert-butyl methylether. (3S)-6-methoxy-5-methylspiro[1-benzofuran-3,3'-indol]-2'(1'H)-one was isolated as a crystalline colorless solid (0.96 g, 89% recovery): ee>99% (analytical chiralpak IA, 1:1 acetonitrile/tert-butyl methylether); mp>250° C.; $^1$H NMR (300 MHz, DMSO-d$_6$) δ10.57 (s, 1H), 7.23 (ddd, J=7.6, 7.6, 1.3 Hz, 1H), 7.07 (d, J=6.8 Hz, 1H), 6.99-6.89 (m, 1H), 6.61 (s, 1H), 6.45 (s, 1H), 4.81-4.74 (m, 1H), 4.64 (d, J=9.2 Hz, 1H), 3.77 (s, 1H), 1.95 (s, 1H); $^{13}$C NMR (75 MHz, DMSO-d$_6$) δ179.2, 160.4, 158.9, 142.2, 133.4, 129.1, 124.4, 124.2, 122.7, 120.3, 118.4, 110.2, 94.3, 80.1, 58.0, 56.0, 16.0; MS (ES+) m/z 282.0 (M+1).

EXAMPLE 3.26

Synthesis of (3R)-6-methoxy-5-methylspiro[1-benzofuran-3,3'-indol]-2'(1'H)-one

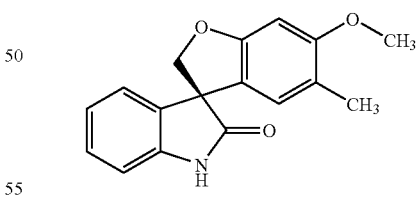

6-Methoxy-5-methylspiro[1-benzofuran-3,3'-indol]-2'(1'H)-one (2.16 g, 0.10 g per run) was resolved on a semi-prep chiral IA column with 10% acetonitrile in tert-butyl methylether. (R)-6-methoxy-5-methyl-2H-spiro[benzofuran-3,3'-indolin]-2'-one was isolated as a crystalline colorless solid (0.81 g, 75% recovery): ee>99% (analytical chiralpak IA, 1:1 acetonitrile/tert-butyl methylether); mp>250° C.; $^1$H NMR (300 MHz, DMSO-d$_6$) δ10.57 (s, 1H), 7.23 (ddd, J=7.6, 7.6, 1.3 Hz, 1H), 7.07 (d, J=6.8 Hz, 1H), 6.99-6.89 (m, 1H), 6.61 (s, 1H), 6.45 (s, 1H), 4.81-4.74 (m, 1H), 4.64 (d, J=9.2 Hz, 1H), 3.77 (s, 1H), 1.95 (s, 1H); $^{13}$C NMR (75 MHz, DMSO-d$_6$) δ 179.2, 160.4, 158.9, 142.2, 133.4, 129.1, 124.4, 124.2, 122.7, 120.3, 118.4, 110.2, 94.3, 80.1, 58.0, 56.0, 16.0; MS (ES+) m/z 282.1 (M+1).

EXAMPLE 3.27

Synthesis of 7'-fluoro-2,3-dihydrospiro[furo[2,3-g][1,4]benzodioxine-8,3'-indol]-2'(1'H)-one

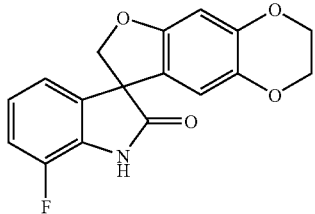

To a solution of 1'-(diphenylmethyl)-7'-fluoro-2,3-dihydrospiro[furo[2,3-g][1,4]benzodioxine-8,3'-indol]-2'(1'H)-one (0.59 g, 1.2 mmol) in trifluoroacetic acid (25 mL) was added triethylsilane (0.6 mL, 3.7 mmol). The reaction mixture was heated at reflux for 1 h, allowed to cool to ambient temperature and concentrated in vacuo. The residue was purified by column chromatography and eluted with a gradient of ethyl acetate in hexanes, followed by sequential trituration in acetonitrile and ethyl acetate, to afford 7'-fluoro-2,3-dihydrospiro[furo[2,3-g][1,4]benzodioxine-8,3'-indol]-2'(1'H)-one (0.101 g, 26%) as an off-white solid: MS (ES+) m/z 314.2 (M+1).

EXAMPLE 3.28

Synthesis of 2',3',5,6-tetrahydrospiro[benzo[1,2-1):5,4-b']difuran-3,8'-[1,4]dioxino[2,3-f]indol]-7'(6'H)-one

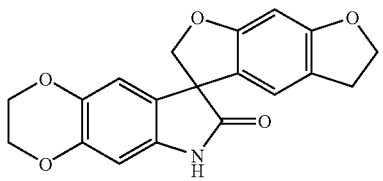

To a solution of 6'-(diphenylmethyl)-2',3',5,6-tetrahydrospiro[benzo[1,2-b:5,4-b']difuran-3,8'-[1,4]dioxino[2,3-f]indol]-7'(6'H)-one (0.5 g, 1.0 mmol) in trifluoroacetic acid (7 mL) was added triethylsilane (0.47 mL, 3.0 mmol). The reaction mixture was heated at reflux for 3.5 h and concentrated in vacuo. The residue was triturated in methanol to afford 2',3',5,6-tetrahydrospiro[benzo[1,2-b:5,4-b']difuran-3,8'-[1,4]dioxino[2,3-f]indol]-7'(6'H)-one (0.076 g, 23%) as a colorless solid: mp>250° C.; $^1$H NMR (300 MHz, DMSO-d$_6$) δ 10.30 (s, 1H), 6.61 (s, 1H), 6.50 (s, 1H), 6.40 (s, 1H), 6.36 (s, 1H), 4.66 (ABq, J=36.8, 9.2 Hz, 2H), 4.54-4.44 (m, 2H), 4.24-4.11 (m, 4H), 3.02-2.92 (m, 2H); $^{13}$C NMR (75 MHz, CDCl$_3$) δ 178.8, 160.8, 160.4, 143.3, 138.7, 135.4, 125.1, 120.9, 119.5, 118.9, 113.0, 99.0, 92.2, 79.7, 72.0, 64.2, 63.7, 57.1, 28.3; MS (ES+) m/z 337.9 (M+1).

EXAMPLE 3.29

Synthesis of 6-methoxy-2'-oxo-1',2'-dihydrospiro[1-benzofuran-3,3'-indole]-5-carbonitrile

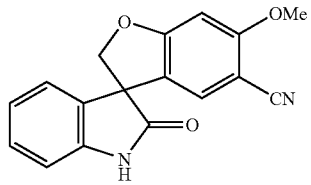

To a stirred solution of 6-methoxy-1-(4-methoxybenzyl)-2'-oxo-1',2'-dihydrospiro[1-benzofuran-3,3'-indole]-5-carbonitrile (0.50 g, 1.2 mmol) in dichloromethane (5 mL) and trifluoroacetic acid (5 mL) was added trifluoromethanesulfonic acid (1.0 mL, 11 mmol). The reaction mixture was stirred at ambient temperature for 18 h and concentrated in vacuo. The residue was basified with saturated aqueous sodium bicarbonate and extracted with ethyl acetate. The organic phase was washed with water and brine, dried over anhydrous sodium sulfate and filtered. The filtrate was concentrated in vacuo. The residue was purified by column chromatography to afford 6-methoxy-2'-oxo-1',2'-dihydrospiro[1-benzofuran-3,3'-indole]-5-carbonitrile (0.34 g, 96%): mp 185-186° C.; $^1$H NMR (300 MHz, CDCl$_3$) δ 8.46 (s, 1H), 7.30-7.25 (m, 1H), 7.11-7.03 (m, 2H), 6.97-6.94 (m, 2H), 6.56 (s, 1H), 4.91 (ABq, 2H), 3.90 (s, 3H); MS (ES+) m/z 292.9 (M+1).

EXAMPLE 3.30

Synthesis of 6-fluoro-2'-oxo-1',2'-dihydrospiro[1-benzofuran-3,3'-indole]-5-carbonitrile

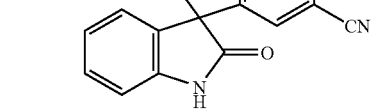

Following the procedure as described in EXAMPLE 3.29 and making non-critical variations using 6-fluoro-1-(4-methoxybenzyl)-2'-oxo-1',2'-dihydrospiro[1-benzofuran-3,3'-indole]-5-carbonitrile to replace of 6-methoxy-1-(4-methoxybenzyl)-2'-oxo-1',2'-dihydrospiro[1-benzofuran-3,3'-indole]-5-carbonitrile, 6-fluoro-2'-oxo-1',2'-dihydrospiro[1-benzofuran-3,3'-indole]-5-carbonitrile was obtained (85%): mp 222-224° C.; $^1$H NMR (300 MHz, DMSO-d$_6$) δ 10.70 (s, 1H), 7.40-7.38 (m, 1H), 7.28-7.23 (m, 2H), 7.17-7.15 (m, 1H), 6.99-6.90 (m, 2H), 4.91 (ABq, 2H); MS (ES+) m/z 280.9 (M+1).

EXAMPLE 3.31

Synthesis of 6-methyl-2,3-dihydrospiro[1,4-dioxino[2,3-f]indole-8,3'-indole]-2',7(1'H,6H)-dione

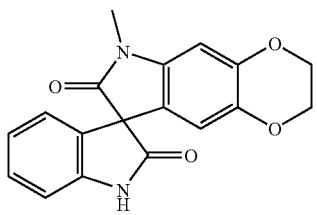

A suspension of methyl 6-methyl-8-(2-nitrophenyl)-7-oxo-2,3,7,8-tetrahydro-6H-[1,4]dioxino[2,3-f]indole-8-carboxylate (0.21 g, 0.54 mmol) and 10% w/w palladium on carbon (0.1 g) in methanol (20 mL) was hydrogenated at 1 atm and at ambient temperature for 20 h. The mixture was filtered through a pad of diatomaceous earth and the filtrate was concentrated in vacuo. The residue was subjected to column chromatography to afford 6-methyl-2,3-dihydrospiro[1,4-dioxino[2,3-f]indole-8,3'-indole]-2',7(1'H,6H)-dione (0.07 g, 40%): MS (ES+) m/z 323.0 (M+1).

EXAMPLE 3.32

Synthesis of 4'-bromo-2,3-dihydrospiro[furo[2,3-g][1,4]benzodioxine-8,3'-indol]-2'(1'H)-one

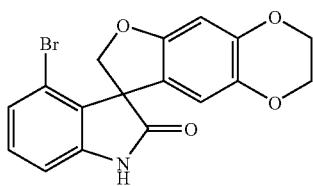

A mixture of 4'-bromo-1'-(diphenylmethyl)-2,3-dihydrospiro[furo[2,3-g][1,4]benzodioxine-8,3'-indol]-2'(1W)-one (5.38 g, 9.96 mmol), triethylsilane (7.93 mL, 49.8 mmol) and trifluoroacetic acid (25.9 mL, 348 mmol) was heated at 75° C. for 8 h. The reaction mixture was allowed to cool to ambient temperature, concentrated in vacuo. The residue was triturated in diethyl ether, purified by column chromatography and eluted with a 0% to 25% gradient of ethyl acetate in dichloromethane to afford 4'-bromo-2,3-dihydrospiro[furo[2,3-g][1,4]benzodioxine-8,3'-indol]-2'(1'H)-one (1.79 g, 48%) as a colorless solid: mp>250° C.; $^1$H NMR (300 MHz, DMSO-$d_6$) δ 10.89 (s, 1H), 7.27 (dd, J=7.9, 7.9 Hz, 1H), 7.14 (d, J=7.8 Hz, 1H), 6.94 (d, J=7.6 Hz, 1H), 6.53 (s, 1H), 5.98 (s, 1H), 5.63 (ABq, 2H), 4.20-4.12 (m, 4H); $^{13}$C NMR (75 MHz, DMSO-$d_6$) δ 176.3, 148.7, 145.1, 144.3, 139.1, 133.0, 128.7, 126.8, 120.0, 112.6, 112.2, 110.2, 105.4, 87.7, 77.6, 64.7, 64.3; MS (ES+) m/z 359.6 (M+1), 361.6 (M+1).

EXAMPLE 3.33

Synthesis of 4'-fluoro-2,3-dihydrospiro[furo[2,3-g][1,4]benzodioxine-8,3'-indol]-2'(1'H)-one

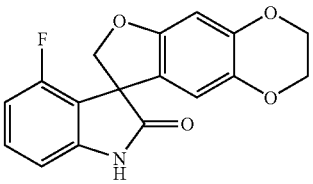

A solution of 1'-(diphenylmethyl)-4'-fluoro-2,3-dihydrospiro[furo[2,3-g][1,4]benzodioxine-8,3'-indol]-2'(1'H)-one (1.18 g, 2.45 mmol) and triethylsilane (1.21 g, 9.84 mmol) in trifluoroacetic acid (20 mL) was heated at 65° C. for 16 h. After cooling to ambient temperature, the reaction mixture was concentrated in vacuo. The residue was recrystallized from N,N'-dimethylformamide/water to afford 4'-fluoro-2,3-dihydrospiro[furo[2,3-g][1,4]benzodioxine-8,3'-indol]-2'(1'H)-one (0.65 g, 84%) as a colourless solid: mp 282-285° C.; $^1$H NMR (300 MHz, DMSO-$d_6$) δ 10.83 (s, 1H), 7.30 (ddd, J=8.2, 8.2, 5.9 Hz, 1H), 6.78 (d, J=8.0 Hz, 1H), 6.75 (d, J=9.2 Hz, 1H), 6.47 (s, 1H), 6.27 (s, 1H), 4.71 (dd, J=9.4 Hz, 2H), 4.14 (dd, J=5.3, 3.2 Hz, 4H); $^{13}$C NMR (75 MHz, DMSO-$d_6$) δ 176.3, 160.9 (d, $^1J_{C-F}$=244 Hz), 147.0, 143.3 (d, $^2J_{C-F}$=96.3 Hz), 135.5, 131.9, 131.2 (d, $^4J_{C-F}$=2.9 Hz), 128.6, 128.5, 123.2 (d, $^2J_{C-F}$=120 Hz), 116.4 (d, $^3J_{C-F}$=22.8 Hz), 115.1, 108.2, 103.3, 74.3, 64.2, 63.7; MS (ES+) m/z 313.1 (M+1).

EXAMPLE 3.34

Synthesis of 4'-quinolin-3-yl-2,3-dihydrospiro[furo[2,3-g][1,4]benzodioxine-8,3'-indol]-2'(1'H)-one

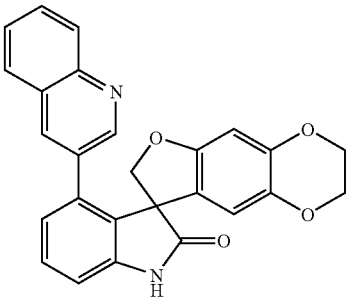

Following the procedure as described in EXAMPLE 3 and making non-critical variations using 1-(diphenylmethyl)-4'-quinolin-3-yl-2,3-dihydrospiro[furo[2,3-g][1,4]benzodioxine-8,3'-indol]-2'(1'H)-one to replace 1'-(diphenylmethyl)-6-methoxy-5-methylspiro[1-benzofuran-3,3'-indol]-2'(1'H)-one, 4'-quinolin-3-yl-2,3-dihydrospiro[furo[2,3-g][1,4]benzodioxine-8,3'-indol]-2'(1'H)-one was obtained (99%) as a light yellow solid: mp 221-224° C. (ethyl acetate/hexanes); $^1$H NMR (300 MHz, DMSO-$d_6$) δ 10.79 (s, 1H), 8.41 (d, J=2.2 Hz, 1H), 7.96 (d, J=8.3 Hz, 1H), 7.75-7.68 (m, 1H), 7.58-7.53 (m, 2H), 7.40-7.33 (m, 2H), 7.04-7.00 (m, 1H), 6.93-6.88 (m, 1H), 6.36 (s, 1H), 5.84 (s, 1H), 4.42 (d, J=9.5 Hz, 1H), 4.25 (d, J=9.5 Hz, 1H), 4.25-4.05 (m, 4H); $^{13}$C NMR (75 MHz, DMSO-$d_6$) δ 179.0, 155.1, 150.5, 146.9, 144.6, 142.6, 138.3, 136.4, 135.5, 131.8, 130.1, 129.5, 129.1, 128.6, 127.3, 127.0, 124.8, 123.0, 111.2, 110.4, 98.9, 78.27, 64.7, 64.2, 58.4; MS (ES+) m/z 422.8 (M+1).

EXAMPLE 3.35

Synthesis of 4'-(4-phenoxyphenyl)-2,3-dihydrospiro[furo[2,3-g][1,4]benzodioxine-8,3'-indol]-2'(1'H)-one

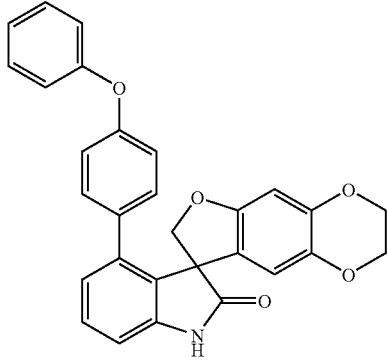

Following the procedure as described in EXAMPLE 3 and making non-critical variations using 1-(diphenylmethyl)-4'-(4-phenoxyphenyl)-2,3-dihydrospiro[furo[2,3-g][1,4]benzodioxine-8,3'-indol]-2'(1'H)-one to replace 1'-(diphenylmethyl)-6-methoxy-5-methylspiro[1-benzofuran-3,3'-indol]-2'(1'H)-one, 4'-(4-phenoxyphenyl)-2,3-dihydrospiro[furo[2,3-g][1,4]benzodioxine-8,3'-indol]-2'(1'H)-one was obtained (74%) as an off-white solid: mp 243-246° C. (diethyl ether); $^1$H NMR (300 MHz, CDCl$_3$) δ 8.63-8.53 (m, 2H), 8.07 (d, J=8.5 Hz, 1H), 7.74-7.64 (m, 2H), 7.57-7.39 (m, 2H), 7.36-7.19 (m, 3H), 7.02-6.93 (m, 2H), 6.50 (s, 1H), 5.96 (s, 1H), 5.28 (d, J=15.8 Hz, 1H), 4.98 (d, J=15.8 Hz, 1H), 4.69 (d, J=9.2 Hz, 1H), 4.34 (d, J=9.2 Hz, 1H), 4.32-4.08 (m, 4H); $^{13}$C NMR (75 MHz, CDCl$_3$) δ 177.8, 155.4, 150.3, 149.6, 147.2, 144.8, 142.7, 138.2, 137.2, 136.3, 135.7, 131.2, 130.4, 129.7, 129.2, 128.0, 126.9, 128.0, 126.9, 125.6, 122.9, 122.7, 121.8, 111.3, 109.5, 99.6, 64.6, 64.1, 58.4, 46.3; MS (ES+) m/z 463.9 (M+1).

EXAMPLE 3.36

Synthesis of 2'-oxo-1',2'-dihydrospiro[1-benzofuran-3,3'-indole]-6-carbonitrile

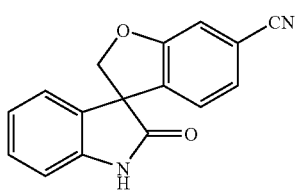

To a suspension of 1'-(diphenylmethyl)-2'-oxo-1',2'-dihydrospiro[1-benzofuran-3,3'-indole]-6-carbonitrile (1.9 g, 4.4 mmol) in triethylsilane (5.0 mL) was added trifluoroacetic acid (10.0 mL). The solution was heated at reflux for 6 h, allowed to cool to ambient temperature and concentrated in vacuo to obtain 2'-oxo-1',2'-dihydrospiro[1-benzofuran-3,3'-indole]-6-carbonitrile (0.86 g, 74%) as a colorless solid which was carried forward without purification MS (ES+) m/z 263.0 (M+1).

EXAMPLE 3.37

Synthesis of 5'-methyl-2,3-dihydrospiro[furo[2,3-g][1,4]benzodioxine-8,3'-indol]-2'(1'H)-one

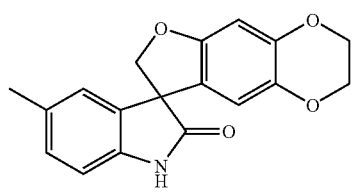

To a suspension of 1-(diphenylmethyl)-5'-methyl-2,3-dihydrospiro[furo[2,3-g][1,4]benzodioxine-8,3'-indol]-2'(1'H)-one (0.33 g, 0.70 mmol) in triethylsilane (2 mL) was added trifluoroacetic acid (5 mL). The reaction mixture was heated at 65° C. for 16 h, allowed to cool to ambient temperature and concentrated in vacuo to afford 5'-methyl-2,3-dihydrospiro[furo[2,3-g][1,4]benzodioxine-8,3'-indol]-2'(1'H)-one (0.21 g, 60%): MS (ES+) m/z 309.9 (M+1).

EXAMPLE 3.38

Synthesis of 9-fluoro-2,3-dihydro-spiro[furo[2,3-g][1,4]benzodioxine-8,3'-indol]-2'(1'H)-one

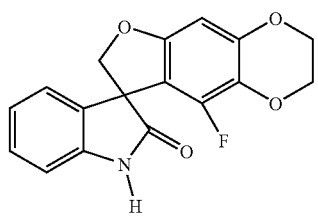

Following the procedure as described in EXAMPLE 3 and making non-critical variations using 1'-(diphenylmethyl)-9-fluoro-2,3-dihydro-spiro[furo[2,3-g][1,4]benzodioxine-8,3'-indol]-2'(1'H)-one to replace 1'-(diphenylmethyl)-6-methoxy-5-methylspiro[1-benzofuran-3,3'-indol]-2'(1'H)-one, 9-fluoro-2,3-dihydro-spiro[furo[2,3-g][1,4]benzodioxine-8,3'-indol]-2'(1'H)-one was obtained (72%) as a colorless solid: MS (ES+) m/z 313.8 (M+1).

Example 3.39

Synthesis of 7,8-dihydro-6H-spiro[furo[2,3-g]chromene-3,3'-indol]-2'(1'H)-one

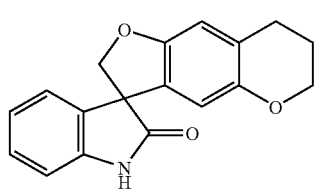

Following the procedure as described in EXAMPLE 3 and making non-critical variations using 1-(diphenylmethyl)-7,8-dihydro-6H-spiro[furo[2,3-g]chromene-3,3'-indol]-2'(1'H)-one to replace 1'-(diphenylmethyl)-6-methoxy-5-methylspiro[1-benzofuran-3,3'-indol]-2'(1'H)-one, 7,8-dihydro-6H- spiro[furo[2,3-g]chromene-3,3'-indol]-2'(1'H)-one was obtained (68%) as an off-white solid: MS (ES+) m/z 293.8 (M+1).

EXAMPLE 3.40

Synthesis of spiro[indole-3,3'-thieno[2,3-f][1]benzofuran]-2(1'H)-one 5,5'-dioxide

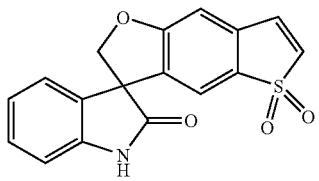

Following the procedure as described in EXAMPLE 3 and making non-critical variations using 1-(diphenylmethyl) spiro[indole-3,3'-thieno[2,3-f][1]benzofuran]-2(1'H)-one 5,5'-dioxide to replace 1-(diphenylmethyl)-6-methoxy-5-methylspiro[1-benzofuran-3,3'-indol]-2'(1'H)-one, spiro[indole-3,3'-thieno[2,3-f][1]benzofuran]-2(1'H)-one 5,5'-dioxide was obtained (43%) as an off-white solid: $^1$H NMR (300 MHz, CDCl$_3$) δ 11.01-10.88 (m, 1H), 7.86-7.67 (m, 1H), 7.40-6.96 (m, 6H), 6.40-6.30 (m, 1H), 5.07-4.80 (m, 2H); $^{13}$C NMR (75 MHz, CDCl$_3$) δ 177.7, 165.5, 141.8, 135.1, 131.6, 130.1, 128.9, 128.1, 127.2, 126.5, 124.8, 124.0, 123.3, 111.3, 110.9, 80.9, 56.7; MS (ES+) m/z 325.8 (M+1).

EXAMPLE 3.41

Synthesis of spiro[furo[3,2-e][2,1,3]benzoxadiazole-8,3'-indol]-2'(1'H)-one

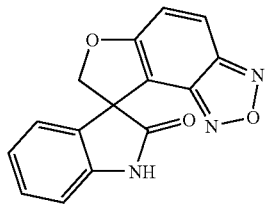

Following the procedure as described in EXAMPLE 3 and making non-critical variations using 1'-(diphenylmethyl) spiro[furo[3,2-e][2,1,3]benzoxadiazole-8,3'-indol]-2'(1'H)-one to replace 1'-(diphenylmethyl)-6-methoxy-5-methylspiro[1-benzofuran-3,3'-indol]-2'(1'H)-one, spiro[furo[3,2-e][2,1,3]benzoxadiazole-8,3'-indol]-2'(1'H)-one was obtained (88%) as a colorless solid: mp>220° C.; $^1$H NMR (300 MHz, DMSO-d$_6$) δ 11.69 (s, 1H), 8.96-8.89 (m, 1H), 8.47-8.40 (m, 1H), 8.16-7.70 (m, 4H), 5.93 (d, J=9.3 Hz, 1H), 5.82 (d, J=9.3 Hz, 1H); MS (ES+) m/z 280.0 (M+1).

EXAMPLE 3.42

Synthesis of 6-chloro-2,3-dihydrospiro[furo[3,2-f][1,4]benzodioxine-9,3'-indol]-2'(1'H)-one

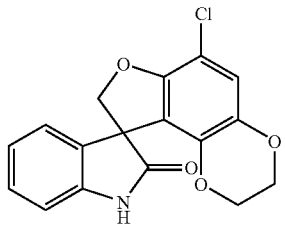

Following the procedure as described in EXAMPLE 3 and making non-critical variations using 6-chloro-t-(diphenylmethyl)-2,3-dihydrospiro[furo[3,2-f][1,4]benzodioxine-9,3'-indol]-2'(1'H)-one to replace 1'-(diphenylmethyl)-6-methoxy-5-methylspiro[1-benzofuran-3,3'-indol]-2'(1'H)-one, 6-chloro-2,3-dihydrospiro[furo[3,2-f][1,4]benzodioxine-9,3'-indol]-2'(1'H)-one was obtained (81%) as a colorless solid: mp 255-257° C.; $^1$H NMR (300 MHz, DMSO-d$_6$) δ10.66 (s, 1H), 7.23 (dd, J=7.5, 1.2 Hz, 1H), 7.11 (d, J=7.5 Hz, 1H), 6.96 (dd, J=7.5, 7.5 Hz, 1H), 6.92-6.85 (m, 2H), 4.72 (ABq, 2H), 4.14-3.92 (m, 4H); $^{13}$C NMR (75 MHz, DMSO-d$_6$) δ176.7, 151.0, 141.6, 138.9, 138.1, 131.0, 128.7, 123.5, 122.2, 117.3, 117.1, 109.6, 104.8, 81.1, 64.4, 63.6, 57.3; MS (ES+) m/z 330.1 (M+1), 332.1 (M+1).

EXAMPLE 3.43

Synthesis of 2,3-dihydrospiro[furo[3,2-f][1,4]benzodioxine-9,3'-indol]-2'(1'H)-one

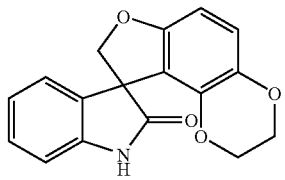

6-chloro-1-(diphenylmethyl)-2,3-dihydrospiro[furo[3,2-f][1,4]benzodioxine-9,3'-indol]-2'(1'H)-one (2.1 g, 4.24 mmol) was suspended in methanol (20 mL) and ethyl acetate (80 mL) in a steel bomb and palladium on carbon (20% w/w, 0.45 g) was added. The bomb was pressurized with hydrogen gas (120 psi) and the mixture was stirred at 60° C. for 16 h. The reaction mixture was allowed to cool to ambient temperature and filtered through a pad of diatomaceous earth. The filtrate was concentrated in vacuo and the residue triturated with ethyl acetate to afford 2,3-dihydrospiro[furo[3,2-f][1,4]benzodioxine-9,3'-indol]-2'(1'H)-one (0.522 g, 42%) as a colorless solid: mp 259-261° C.; $^1$H NMR (300 MHz, CD$_3$OD) δ7.27-7.18 (m, 1H), 7.09-6.88 (m, 3H), 6.70 (d, J=8.7 Hz, 1H), 6.39 (d, J=8.7 Hz, 1H), 4.75 (d, J=9.3 Hz, 1H), 4.59 (d, J=9.0 Hz, 1H), 4.12-3.90 (m, 4H); $^{13}$C NMR (75 MHz, CD$_3$OD) δ181.0, 157.5, 142.4, 141.3, 139.6, 133.9, 129.8, 124.5, 124.0, 119.0, 117.1, 111.0, 102.9, 82.4, 66.0, 65.2, 59.1; MS (ES+) m/z 296.2 (M+1).

EXAMPLE 3.44

Synthesis of 5,6-difluorospiro[1-benzofuran-3,3'-indol]-2'(1'H)-one

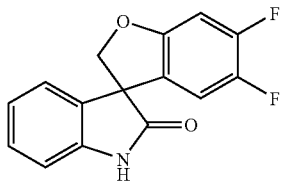

To a solution of 1-(diphenylmethyl)-5,6-difluorospiro[1-benzofuran-3,3'-indol]-2'(1'1-1)-one (6.06 g, 13.8 mmol) in methanol (100 mL), ethyl acetate (25 mL) and acetic acid (1 mL) in a steel bomb was added palladium on carbon (20% w/w, 2.0 g). The bomb was pressurized with hydrogen (50 psi) and the reaction mixture was heated at 65° C. for 16 h. The reaction mixture allowed to cool to ambient temperature and was filtered through a pad of diatomaceous earth. The pad was washed with ethyl acetate (15 mL) and methanol (50 mL). The filtrate was concentrated in vacuo and the residue was triturated in methanol to afford 5,6-difluorospiro[1-benzofuran-3,3'-indol]-2'(1'H)-one (3.63 g, 96%) as a colorless solid. mp>200° C.; $^1$H NMR (300 MHz, CDCl$_3$) δ 8.00 (s, 1H), 7.32-7.27 (m, 1H), 7.15-7.05 (m, 2H), 6.97 (d, J=7.8 Hz, 1H), 6.79 (dd, J=10.3, 6.3 Hz, 1H), 6.62 (dd, J=9.0, 8.0 Hz, 1H), 5.00 (d, J=9.2 Hz, 1H), 4.73 (d, J=9.2 Hz, 1H); $^{13}$C NMR (75 MHz, CDCl$_3$) δ179.7, 156.70 (d, $J_{C-F}$=10.9 Hz), 151.3 (dd, $J_{C-F}$=248.7, 14.3 Hz), 145.7 (dd, $J_{C-F}$=241.6, 13.8 Hz), 140.3, 131.6, 129.4, 124.0, 123.7, 123.4 (dd, $J_{C-F}$=6.3, 3.1 Hz), 111.9 (d, $J_{C-F}$=20.4 Hz), 110.7, 100.1 (d, $J_{C-F}$=22.4 Hz), 80.7, 58.4; MS (ES+) m/z 274.2 (M+1).

EXAMPLE 3.45

Synthesis of 5',6',7',8'-tetrahydrospiro[indole-3,3'-naphtho[2,3-b]furan]-2(1'H)-one

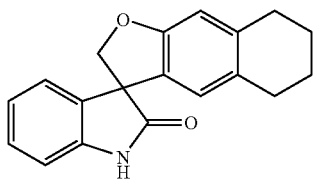

Following the procedure as described in EXAMPLE 3 and making non-critical variations using 1-(diphenylmethyl)-5',6',7',8'-tetrahydrospiro[indole-3,3'-naphtho[2,3-b]furan]-2(1'H)-one to replace 1'-(diphenylmethyl)-6-methoxy-5-methylspiro[1-benzofuran-3,3'-indol]-2'(1'H)-one, 5',6',7',8'-tetrahydrospiro[indole-3,3'-naphtho[2,3-b]furan]-2(1'H)-one was obtained (80%) as a colorless solid: mp>230° C.; $^1$H NMR (300 MHz, CDCl$_3$) δ 8.13 (s, 1H), 7.33-7.19 (m, 1H), 7.16 (d, J=7.4 Hz, 1H), 7.04 (dd, J=7.5, 7.5 Hz, 1H), 6.95 (d, J=7.7 Hz, 1H), 6.68 (s, 1H), 6.49 (s, 1H), 4.92 (d, J=9.0 Hz, 1H), 4.65 (d, J=9.0 Hz, 1H), 2.76-2.72 (m, 2H), 2.58-2.56 (m, 2H), 1.71 (t, J=3.2 Hz, 4H); $^{13}$C NMR (75 MHz, CDCl$_3$) δ180.5, 158.7, 140.4, 139.0, 132.9, 130.2, 128.8, 126.0, 124.1, 123.6, 123.3, 110.3, 110.2, 79.6, 58.6, 30.0, 29.0, 23.2, 23.0; MS (ES+) m/z 292.0 (M+1).

EXAMPLE 3.46

Synthesis of 6-(2-methoxyethoxy)spiro[1-benzofuran-3,3'-indol]-2'(1'H)-one

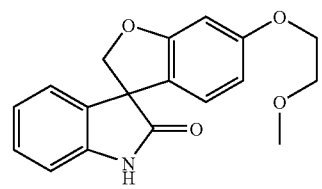

Following the procedure as described in EXAMPLE 3 and making non-critical variations using 1'-(diphenylmethyl)-6-(2-methoxyethoxy)spiro[1-benzofuran-3,3'-indol]-2'(1'H)-one to replace 1'-(diphenylmethyl)-6-methoxy-5-methylspiro[1-benzofuran-3,3'-indol]-2'(1'H)-one, 6-(2-methoxyethoxy)spiro[1-benzofuran-3,3'-indol]-2'(1'H)-one was obtained (69%): mp 172-174° C.; $^1$H NMR (300 MHz, CDCl$_3$) δ8.56 (s, 1H), 7.23-7.18 (m, 1H), 7.15-7.06 (m, 1H), 7.06-6.97 (m, 1H), 6.97-6.89 (m, 1H), 6.89-6.82 (m, 1H), 6.82-6.74 (m, 1H), 6.38 (s, 1H), 4.80 (ABq, 2H), 4.03-3.80 (m, 2H), 3.67-3.54 (m, 2H), 3.35 (s, 3H); MS (ES+) m/z 312.0 (M+1).

EXAMPLE 3.47

Synthesis of 5-(2-methoxyethoxy)spiro[1-benzofuran-3,3'-indol]-2'(1'H)-one

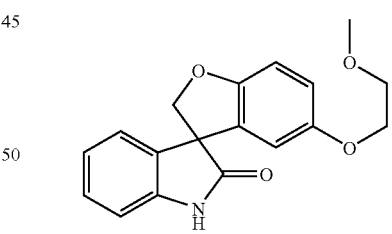

Following the procedure as described in EXAMPLE 3 and making non-critical variations using 1-(diphenylmethyl)-5-(2-methoxyethoxy)spiro[1-benzofuran-3,3'-indol]-2'(1'H)-one to replace 1'-(diphenylmethyl)-6-methoxy-5-methylspiro[1-benzofuran-3,3'-indol]-2'(1'H)-one, 5-(2-methoxyethoxy)spiro[1-benzofuran-3,3'-indol]-2'(1'H)-one was obtained (30%): $^1$H NMR (300 MHz, CDCl$_3$) δ8.38 (s, 1H), 7.24-7.18 (m, 1H), 7.15-7.07 (m, 1H), 7.06-6.97 (m, 1H), 6.96-6.88 (m, 1H), 6.70-6.61 (m, 1H), 6.54 (s, 1H), 6.43-6.35 (m, 1H), 4.82 (ABq, 2H), 4.13-3.98 (m, 2H), 3.75-3.67 (m, 2H), 3.42 (s, 1H).

EXAMPLE 3.48

Synthesis of 2,3-dihydrospiro[furo[2,3-f][1,4]benzo-dioxine-7,3'-indol]-2'(1'H)-one

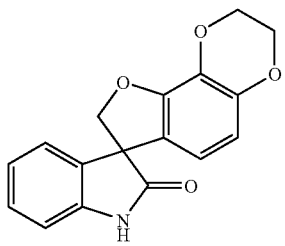

Following the procedure as described in EXAMPLE 3 and making non-critical variations using 1'-(diphenylmethyl)-2,3-dihydrospiro[furo[2,3-f][1,4]benzodioxine-7,3'-indol]-2'(1'H)-one to replace 1'-(diphenylmethyl)-6-methoxy-5-methylspiro[1-benzofuran-3,3'-indol]-2'(1'H)-one, 2,3-dihydrospiro[furo[2,3-f][1,4]benzodioxine-7,3'-indol]-2'(1'H)-one was obtained (30%) as a colorless solid: mp>250° C.; $^1$H NMR (300 MHz, DMSO-$d_6$) δ 10.56 (s, 1H), 7.23 (ddd, J=7.7, 7.7, 0.5 Hz, 1H), 7.13 (d, J=7.2 Hz, 1H), 6.99-6.90 (m, 2H), 6.21 (ABq, 2H), 4.76 (ABq, 2H), 4.26 (s, 4H); $^{13}$C NMR (75 MHz, DMSO-$d_6$) δ 178.3, 148.7, 144.5, 141.8, 132.3, 129.2, 128.6, 123.8, 122.5, 122.2, 114.1, 109.7, 80.2, 64.1, 63.9, 57.7; MS (ES+) m/z 295.9 (M+1).

EXAMPLE 3.49

Synthesis of 2,3-dihydrospiro[furo[2,3-g][1,4]benzo-dioxine-8,8'-[1,3]thiazolo[5,4-e]indol]-7'(6'H)-one

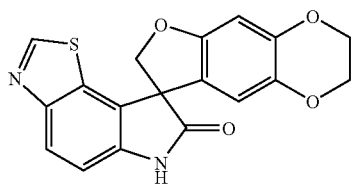

To a solution of 6'-(4-methoxybenzyl)-2,3-dihydrospiro[furo[2,3-g][1,4]benzodioxine-8,8'-[1,3]thiazolo[5,4-e]indol]-7'(6'H)-one (1.9 g, 4.0 mmol) in dichloromethane (40 mL) and trifluoroacetic acid (40 mL) was added at ambient temperature trifluoromethanesulfonic acid (1.8 mL, 20 mmol). The mixture was stirred at ambient temperature for 16 h and concentrated in vacuo. Water was added to the residue and the mixture was extracted with ethyl acetate. The combined organic extracts were washed with saturated aqueous sodium bicarbonate and water, dried over anhydrous magnesium sulfate, filtered, and concentrated in vacuo. The residue was purified by column chromatography and eluted with 50% ethyl acetate in hexanes to afford 2,3-dihydrospiro[furo[2,3-g][1,4]benzodioxine-8,8'-[1,3]thiazolo[5,4-e]indol]-7'(6'H)-one (0.65 g, 44%): $^1$H NMR (300 MHz, CDCl$_3$) δ10.86 (s, 1H), 9.06 (s, 1H), 7.97 (d, J=8.5 Hz, 1H), 7.14 (d, J=8.5 Hz, 1H), 6.54 (s, 1H), 6.21 (s, 1H), 4.68 (s, 2H), 4.19-4.01 (m, 4H); MS (ES+) m/z 353.1 (M+1).

EXAMPLE 3.50

Synthesis of 4',6'-dimethoxy-2,3-dihydrospiro[furo[2,3-g][1,4]benzodioxine-8,3'-indol]-2'(1'H)-one

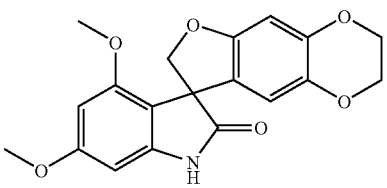

Following the procedure as described in EXAMPLE 3 and making non-critical variations using 1-(diphenylmethyl)-4',6'-dimethoxy-2,3-dihydrospiro[furo[2,3-g][1,4]benzodioxine-8,3'-indol]-2'(1'H)-one to replace 1'-(diphenylmethyl)-6-methoxy-5-methylspiro[1-benzofuran-3,3'-indol]-2'(1'H)-one, 4',6'-dimethoxy-2,3-dihydrospiro[furo[2,3-g][1,4]benzodioxine-8,3'-indol]-2'(1'H)-one was obtained (55%): $^1$H NMR (300 MHz, CDCl$_3$) δ10.42 (s, 1H), 6.35 (s, 1H), 6.15 (d, J=2.0 Hz, 1H), 6.10 (d, J=2.0 Hz, 1H), 6.08 (s, 1H), 4.58 (ABq, 2H), 4.17-4.03 (m, 4H), 3.72 (s, 3H), 3.58 (s, 3H); MS (ES+) m/z 356.1 (M+1).

EXAMPLE 3.51

Synthesis of spiro[furo[2,3-g]quinoxaline-8,3'-indol]-2'(1'H)-one

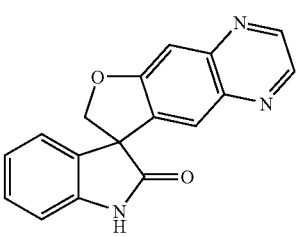

Following the procedure as described in EXAMPLE 3 and making non-critical variations using 1'-(diphenylmethyl)spiro[furo[2,3-g]quinoxaline-8,3'-indol]-2'(1'H)-one to replace 1-(diphenylmethyl)-6-methoxy-5-methylspiro[1-benzofuran-3,3'-indol]-2'(1'H)-one, spiro[furo[2,3-g]quinoxaline-8,3'-indol]-2'(1'H)-one was obtained (22%): mp 206-207° C. (ethyl acetate/hexanes); $^1$H NMR (300 MHz, DMSO-$d_6$) δ 10.78 (s, 1H), 8.68-8.61 (m, 2H), 8.06 (d, J=9.0 Hz, 1H), 7.68 (d, J=9.0 Hz, 1H), 7.21-7.18 (m, 1H), 7.03-6.86 (m, 3H), 6.96 (ABq, 2H); MS (ES+) m/z 289.8 (M+1).

EXAMPLE 4

Synthesis of 1'-(tetrahydro-2H-pyran-2-ylmethyl)-5,6-dihydrospiro[benzo[1,2-b:5,4-b']difuran-3,3'-indol]-2'(1'H)-one

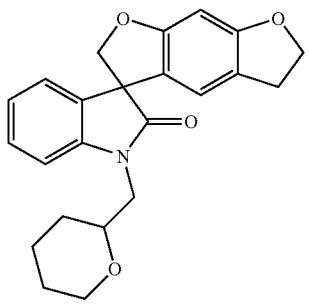

A mixture of 5,6-dihydrospiro[benzo[1,2-b:5,4-b']difuran-3,3'-indol]-2'(1'H)-one (0.28 g, 1.0 mmol), 2-(bromomethyl)tetrahydro-2H-pyran (0.36 g, 2.0 mmol) and cesium carbonate (1.00 g, 3.0 mmol) was stirred in butanone at 80° C. for 3 h. Upon cooling to ambient temperature, the reaction mixture was filtered, and the filtrate was evaporated under reduced pressure. The residue was subjected to column chromatography with ethyl acetate-hexanes (1:5-1:1) to afford 1'-(tetrahydro-2H-pyran-2-ylmethyl)-5,6-dihydrospiro[benzo[1,2-b:5,4-b']difuran-3,3'-indol]-2'(1'H)-one (0.31 g, 82%) as a colorless solid: $^1$H NMR (300 MHz, CDCl$_3$) δ7.38-6.94 (m, 4H), 6.47 (d, J=2.9 Hz, 1H), 6.38 (s, 1H), 4.79 (ABq, 2H), 4.50 (t, J=8.6 Hz, 2H), 4.01-3.61 (m, 4H), 3.37 (t, J=11.1 Hz, 1H), 2.97 (t, J=8.4 Hz, 2H), 1.97-1.27 (m, 6H); $^{13}$C NMR (75 MHz, CDCl$_3$) δ178.1 (2C), 161.7 (2C), 161.3, 161.2, 143.2, 143.1, 132.8, 132.7, 128.6 (2C), 123.5, 123.1, 123.1, 120.6, 120.5, 119.8 (2C), 119.0, 118.9, 109.7, 93.2, 93.1, 80.6, 75.7, 75.5, 72.3, 68.4 (2C), 57.7, 57.6, 45.8, 45.7, 29.6, 29.5, 29.1, 25.8, 23.0; MS (ES+) m/z 378.3 (M+1).

EXAMPLE 4.1

Synthesis of 1'-(4-bromobenzyl)spiro[furo[2,3-f][1,3]benzodioxole-7,3'-indol]-2'(1'H)-one

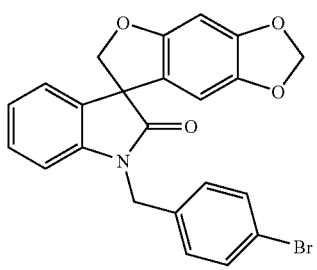

A mixture of spiro[furo[2,3-f][1,3]benzodioxole-7,3'-indol]-2'(1'H)-one (1.05 g, 3.73 mmol), 4-bromobenzyl bromide (1.21 g, 4.84 mmol) and cesium carbonate (1.84 g, 5.65 mmol) in 2-butanone (25 mL) was stirred at ambient temperature for 16 h. The mixture was diluted with ethyl acetate and filtered through Celite. The filtrate was concentrated to dryness under reduced pressure. The residue was purified by flash column chromatography with hexanes/ethyl acetate (9:1, increased to 1:1) to afford 1-(4-bromobenzyl)spiro[furo[2,3-f][1,3]benzodioxole-7,3'-indol]-2'(1'H)-one (1.42 g, 84%) as a colorless solid: mp 148-150° C. (hexanes); $^1$H NMR (300 MHz, CDCl$_3$) δ7.48 (d, J=8.4 Hz, 2H), 7.25-7.17 (m, 4H), 7.05 (dd, J=7.5, 7.5 Hz, 1H), 6.77 (d, J=7.8 Hz, 1H), 6.53 (s, 1H), 6.12 (s, 1H), 5.89 (s, 1H), 5.88 (s, 1H), 5.02 (d, J=15.6 Hz, 1H), 4.97 (d, J=9.0 Hz, 1H), 4.78 (d, J=15.6 Hz, 1H), 4.70 (d, J=9.0 Hz, 1H); $^{13}$C NMR (75 MHz, CDCl$_3$) δ177.8, 156.1, 149.1, 142.5, 141.9, 134.9, 132.3, 132.2, 129.3, 129.1, 124.2, 123.8, 122.0, 119.4, 109.3, 103.1, 101.7, 93.8, 80.6, 58.4, 43.7; MS (ES+) m/z 452.0 (M+1), 450.0 (M+1).

EXAMPLE 4.2

Synthesis of 1'-[(2-chloro-1-methyl-1H-imidazol-5-yl)methyl]-5,6-dihydrospiro[benzo[1,2-b:5,4-b']difuran-3,3'-indol]-2'(1'H)-one

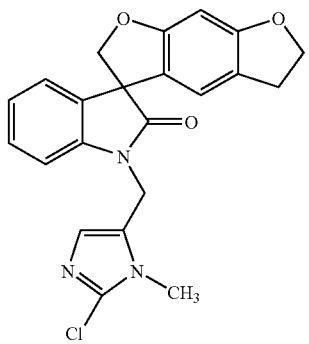

Following the procedure as described in EXAMPLE 4 and making non-critical variations using 2-chloro-5-(chloromethyl)-1-methyl-1H-imidazole to replace 2-(bromomethyl)tetrahydro-2H-pyran, 1'-[(2-chloro-1-methyl-1H-imidazol-5-yl)methyl]-5,6-dihydrospiro[benzo[1,2-b:5,4-b']difuran-3,3'-indol]-2'(1'H)-one was obtained (42%) as a colorless solid: $^1$H NMR (300 MHz, CDCl$_3$) δ 7.42-7.01 (m, 4H), 6.94 (s, 1H), 6.42 (s, 1H), 6.40 (s, 1H), 5.03 (ABq, 2H), 4.77 (ABq, 2H), 4.52 (t, J=8.6 Hz, 2H), 3.59 (s, 3H), 2.97 (t, J=8.6 Hz, 2H); $^{13}$C NMR (75 MHz, CDCl$_3$) δ177.7, 162.0, 161.4, 141.7, 141.7, 132.0, 129.1, 124.2, 124.0, 123.8, 120.1, 119.8, 119.6, 118.8, 110.5, 93.3, 80.6, 72.4, 57.7, 37.8, 31.0, 29.0; MS (ES+) m/z 408.0 (M+1), 410.0 (M+1).

EXAMPLE 4.3

Synthesis of 1'-[(2R)-tetrahydrofuran-2-ylmethyl]-5,6-dihydrospiro[benzo[1,2-b:5,4-b']difuran-3,3'-indol]-2'(1'H)-one

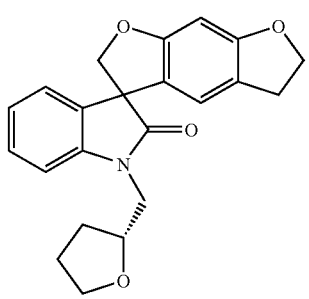

Following the procedure as described in EXAMPLE 4 and making non-critical variations using (R)-(tetrahydrofuran-2-yl)methyl 4-methylbenzenesulfonate to replace 2-(bromomethyl)tetrahydro-2H-pyran, 1'-[(2R)-tetrahydrofuran-2-ylmethyl]-5,6-dihydrospiro[benzo[1,2-b:5,4-b']difuran-3,3'-indol]-2'(1'H)-one was obtained (30%) as a colorless solid:

$^1$H NMR (300 MHz, CDCl$_3$) δ 7.31-6.98 (m, 4H), 6.48 (s, 1H), 6.39 (s, 1H), 4.78 (ABq, 2H), 4.52 (t, J=8.6 Hz, 2H), 4.32-4.22 (m, 1H), 3.91-3.69 (m, 4H), 2.97 (t, J=8.4 Hz, 2H), 2.09-1.64 (m, 4H); $^{13}$C NMR (75 MHz, CDCl$_3$) δ178.3, 161.7, 161.3, 142.8, 132.8, 128.7, 123.6, 123.2, 120.5, 119.8, 118.9, 109.6, 93.2, 80.7, 76.8, 72.4, 68.2, 57.7, 44.6, 29.1, 29.0, 25.7; MS (ES+) m/z 364.1 (M+1).

EXAMPLE 4.4

Synthesis of 1'-(3-methylbutyl)-5,6-dihydrospiro[benzo[1,2-b:5,4-b']difuran-3,3'-indol]-2'(1'H)-one

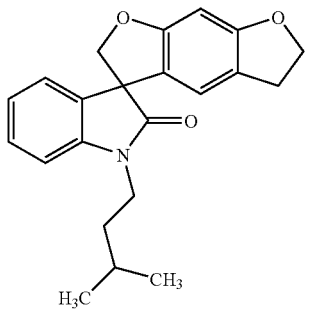

Following the procedure as described in EXAMPLE 4 and making non-critical variations using 1-bromo-3-methylbutane to replace 2-(bromomethyl)tetrahydro-2H-pyran, 1'-(3-methylbutyl)-5,6-dihydrospiro[benzo[1,2-b:5,4-b']difuran-3,3'-indol]-2'(1'H)-one was obtained (58%) as a colorless solid: $^1$H NMR (300 MHz, CDCl$_3$) δ 7.36-6.84 (m, 4H), 6.44 (s, 1H), 6.39 (s, 1H), 4.77 (ABq, 2H), 4.51 (t, J=8.6 Hz, 2H), 3.88-3.64 (m, 2H), 3.04-2.90 (m, 2H), 1.75-1.54 (m, 3H), 0.99 (d, J=6.2 Hz, 6H); $^{13}$C NMR (75 MHz, CDCl$_3$) δ 177.6, 161.7, 161.3, 142.4, 133.1, 128.7, 123.9, 123.1, 120.4, 119.8, 118.8, 108.5, 93.2, 80.6, 72.4, 57.7, 38.8, 36.2, 29.1, 26.1, 22.6, 22.5; MS (ES+) m/z 350.1 (M+1).

EXAMPLE 4.5

Synthesis of 1-[(2S)-tetrahydrofuran-2-ylmethyl]-5,6-dihydrospiro[benzo[1,2-b:5,4-b']difuran-3,3'-indol]-2'(1'H)-one

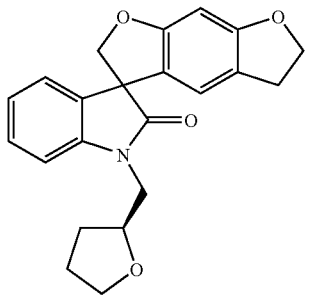

Following the procedure as described in EXAMPLE 4 and making non-critical variations using (S)-(tetrahydrofuran-2-yl)methyl 4-methylbenzenesulfonate to replace 2-(bromomethyl)tetrahydro-2H-pyran, 1'-[(2S)-tetrahydrofuran-2-ylmethyl]-5,6-dihydrospiro[benzo[1,2-b:5,4-b']difuran-3,3'-indol]-2'(1'H)-one was obtained (56%) as a colorless solid: $^1$H NMR (300 MHz, CDCl$_3$) δ 7.34-6.96 (m, 4H), 6.48 (d, J=1.51 Hz, 1H), 6.38 (s, 1H), 4.77 (ABq, 2H), 4.50 (t, J=8.6 Hz, 2H), 4.32-4.21 (m, 1H), 3.98-3.64 (m, 4H), 2.96 (t, J=8.7 Hz, 2H), 2.09-1.63 (m, 4H); $^{13}$C NMR (75 MHz, CDCl$_3$) δ 178.3, 178.2, 161.7, 161.3, 142.9, 142.9, 142.8, 132.8, 132.7, 128.7, 128.7, 123.7, 123.6, 123.2, 119.0, 118.9, 109.6, 109.5, 93.1, 80.7, 80.7, 76.9, 76.8, 72.4, 68.3, 68.2, 57.7, 57.7, 44.7, 44.6, 29.3, 29.1 (2C), 25.7, 25.6; MS (ES+) m/z 364.3 (M+1).

EXAMPLE 4.6

Synthesis of 1'-(tetrahydro-2H-pyran-4-ylmethyl)-5,6-dihydrospiro[benzo[1,2-b:5,4-b']difuran-3,3'-indol]-2'(1'H)-one

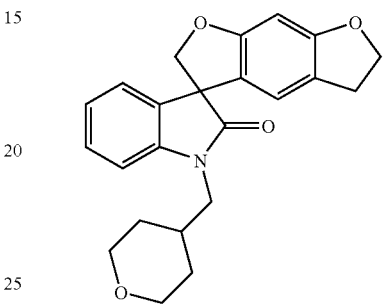

Following the procedure as described in EXAMPLE 4 and making non-critical variations using 4-(bromomethyl)tetrahydro-2H-pyran to replace 2-(bromomethyl)tetrahydro-2H-pyran, 1-(tetrahydro-2H-pyran-4-ylmethyl)-5,6-dihydrospiro[benzo[1,2-b:5,4-b']difuran-3,3'-indol]-2'(1'H)-one was obtained (69%) as a colorless solid: $^1$H NMR (300 MHz, CDCl$_3$) δ 7.37-6.85 (m, 4H), 6.43 (s, 1H), 6.39 (s, 1H), 4.76 (ABq, 2H), 4.51 (t, J=8.6 Hz, 2H), 3.97 (ABq, 2H), 3.77-3.52 (m, 2H), 3.40-3.28 (m, 2H), 3.03-2.91 (m, 2H), 2.19-2.02 (m, 1H), 1.65-1.38 (m, 4H); $^{13}$C NMR (75 MHz, CDCl$_3$) δ178.1, 161.8, 161.4, 142.8, 132.8, 128.8, 124.1, 123.3, 120.2, 119.9, 118.8, 108.6, 93.3, 80.8, 72.4, 67.5, 57.7, 46.1, 33.9, 30.8, 29.1; MS (ES+) m/z 378.3 (M+1).

EXAMPLE 4.7

Synthesis of methyl 5-[(2'-oxo-5,6-dihydrospiro[benzo[1,2-b:5,4-b']difuran-3,3'-indol]-1'(2'H)-yl)methyl]furan-2-carboxylate

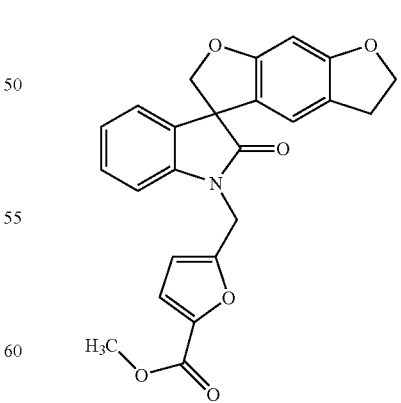

Following the procedure as described in EXAMPLE 4 and making non-critical variations using methyl 5-(chloromethyl)furan-2-carboxylate to replace 2-(bromomethyl)tetrahydro-2H-pyran, methyl 5-[(2'-oxo-5,6-dihydrospiro[benzo[1,2-b:5,4-b']difuran-3,3'-indol]-1'(2'H)-yl)methyl]

furan-2-carboxylate was obtained (70%) as a colorless solid: $^1$H NMR (300 MHz, CDCl$_3$) δ 7.28-6.23 (m, 5H), 6.49 (s, 1H), 6.39 (s, 1H), 6.37 (d, J=3.49 Hz, 1H), 4.99 (ABq, 2H), 4.80 (ABq, 2H), 4.51 (t, J=8.6 Hz, 2H), 3.85 (s, 3H), 3.05-2.92 (m, 2H); $^{13}$C NMR (75 MHz, CDCl$_3$) δ177.5, 161.9, 161.3, 158.8, 153.5, 144.2, 141.4, 132.6, 128.9, 124.0, 123.8, 120.1, 120.0, 119.0, 110.2, 109.0, 93.2, 80.5, 72.4, 57.7, 52.0, 37.4, 29.1; MS (ES+) m/z 418.1 (M+1).

EXAMPLE 4.8

Synthesis of 1'-(1,4-dioxan-2-ylmethyl)-5,6-dihydrospiro[benzo[1,2-b:5,4-b']difuran-3,3'-indol]-2'(1'H)-one

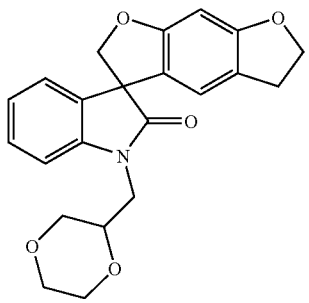

Following the procedure as described in EXAMPLE 4 and making non-critical variations using 2-(iodomethyl)-1,4-dioxane to replace 2-(bromomethyl)tetrahydro-2H-pyran, 1'-(1,4-dioxan-2-ylmethyl)-5,6-dihydrospiro[benzo[1,2-b:5,4-b']difuran-3,3'-indol]-2'(1'H)-one was obtained (48%) as a colorless solid: $^1$H NMR (300 MHz, CDCl$_3$) δ 7.39-6.96 (m, 4H), 6.45 (d, J=8.1 Hz, 1H), 6.38 (s, 1H), 4.89 (ABq, 2H), 4.65 (ABq, 2H), 4.51 (t, J=8.6 Hz, 2H), 3.99-3.33 (m, 9H), 3.05-2.85 (m, 2H); $^{13}$C NMR (75 MHz, CDCl$_3$) δ178.2, 178.1, 161.8, 161.8, 161.3, 161.2, 142.6, 132.7, 132.6, 128.8, 128.7, 123.8, 123.7, 123.4, 120.3, 120.2, 120.0, 119.9, 118.9, 118.8, 109.5, 109.3, 93.2, 80.6, 80.5, 73.2, 72.4, 69.3, 69.2, 66.7, 66.6, 66.4, 57.6, 41.7 (2C), 29.1; MS (ES+) m/z 380.1 (M+1).

EXAMPLE 4.9

Synthesis of 1'-{[1-methyl-3-(trifluoromethyl)-1H-pyrazol-4-yl]methyl}-5,6-dihydrospiro[benzo[1,2-b:5,4-b']difuran-3,3'-indol]-2'(1'H)-one

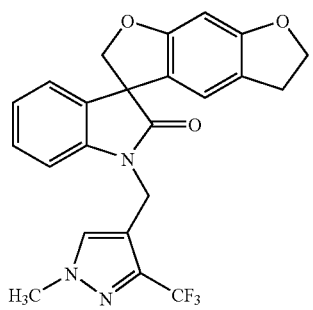

Following the procedure as described in EXAMPLE 4 and making non-critical variations using 4-(chloromethyl)-1-methyl-3-(trifluoromethyl)-1H-pyrazole to replace 2-(bromomethyl)tetrahydro-2H-pyran, 1'-{[1-methyl-3-(trifluoromethyl)-1H-pyrazol-4-yl]methyl}-5,6-dihydrospiro[benzo[1,2-b:5,4-b']difuran-3,3'-indol]-2'(1'H)-one was obtained (32%) as a colorless solid: $^1$H NMR (300 MHz, CDCl$_3$) δ 7.39 (s, 1H), 7.29-6.84 (m, 4H), 6.42 (s, 1H), 6.38 (s, 1H), 4.89 (s, 2H), 4.79 (ABq, 2H), 4.51 (t, J=8.6 Hz, 2H), 3.86 (s, 3H), 2.97 (t, J=8.6 Hz, 2H); $^{13}$C NMR (75 MHz, CDCl$_3$) δ178.0, 161.9, 161.4, 141.6, 139.9, 139.4, 138.9, 138.4, 132.5, 131.9, 128.9, 124.1, 123.7, 123.4, 120.0, 119.9, 119.8, 118.8, 115.4, 108.8, 93.3, 80.6, 72.4, 57.6, 39.7, 34.0, 29.0; MS (ES+) m/z 442.0 (M+1).

EXAMPLE 4.10

Synthesis of 1'-(tetrahydro-2H-pyran-3-ylmethyl)-5,6-dihydrospiro[benzo[1,2-b:5,4-b']difuran-3,3'-indol]-2'(1'H)-one

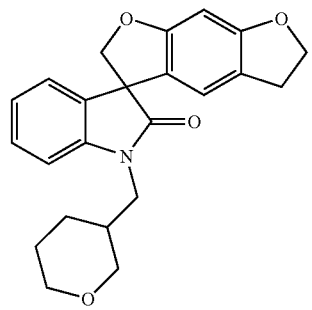

Following the procedure as described in EXAMPLE 4 and making non-critical variations using 3-(bromomethyl)tetrahydro-2H-pyran to replace 2-(bromomethyl)tetrahydro-2H-pyran, 1'-(tetrahydro-2H-pyran-3-ylmethyl)-5,6-dihydrospiro[benzo[1,2-b:5,4-b']difuran-3,3'-indol]-2'(1'H)-one was obtained (45%) as a colorless solid: $^1$H NMR (300 MHz, CDCl$_3$) δ 7.42-6.83 (m, 4H), 6.44 (d, J=2.3 Hz, 1H), 6.39 (s, 1H), 4.88 (dd, J=8.9, 1.9 Hz, 1H), 4.63 (d, J=8.9 Hz, 1H), 4.51 (t, J=8.6 Hz, 2H), 3.89-3.24 (m, 6H), 3.08-2.86 (m, 2H), 2.26-2.09 (m, 1H), 1.91-1.29 (m, 5H); $^{13}$C NMR (75 MHz, CDCl$_3$) δ178.0, 178.0, 161.8, 161.4, 161.3, 142.5, 142.4, 132.8, 132.8, 128.8, 124.0 (2C), 123.4, 120.2, 120.1, 120.0, 119.9, 118.8 (2C), 108.6, 93.2, 93.2, 80.8, 72.4 (2C), 71.2, 71.0, 68.5, 68.4, 57.7 (2C), 42.5, 42.4, 34.8, 29.1, 27.5, 27.4, 25.1, 24.8; MS (ES+) m/z 378.1 (M+1).

EXAMPLE 4.11

Synthesis of methyl 2-[(2'-oxo-5,6-dihydrospiro[benzo[1,2-b:5,4-b']difuran-3,3'-indol]-1'(2'H)-yl)methyl]-1,3-oxazole-4-carboxylate Following the procedure as described in EXAMPLE 4 and making non-critical variations using methyl 2-(bromomethyl)oxazole-4-carboxylate to replace 2-(bromomethyl)tetrahydro-2H-pyran, methyl 2-[(2'-oxo-5,6-dihydrospiro[benzo[1,2-b:5,4-b']difuran-3,3'-indol]-1'(2'H)-yl)methyl]-1,3-oxazole-4-carboxylate was obtained (61%) as a colorless solid: $^1$H NMR (300 MHz, CDCl$_3$) δ 8.17 (s, 1H), 7.27-6.91 (m, 4H), 6.53 (s, 1H), 6.38 (s, 1H), 5.12 (ABq, 2H), 4.81 (ABq 2H), 4.51 (t, J=8.7 Hz, 2H), 3.89 (s, 3H), 3.04-2.91 (m, 2H); $^{13}$C NMR (75 MHz, CDCl$_3$) δ177.6, 161.9, 161.2 (2C), 159.2, 145.0, 141.0, 133.6, 132.5, 129.0, 124.1, 120.1, 119.9, 199.1, 108.8, 93.2, 80.5, 72.4, 57.7, 52.3, 37.2, 29.0.

EXAMPLE 4.12

Synthesis of 1'-(2-fluorobenzyl)-5,6-dihydrospiro[benzo[1,2-b:5,4-b']difuran-3,3'-indol]-2'(1'H)-one

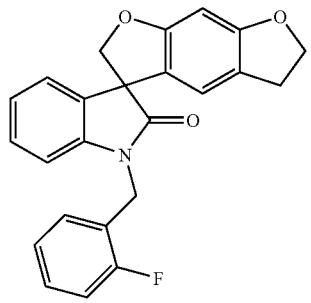

Following the procedure as described in EXAMPLE 4 and making non-critical variations using 1-(bromomethyl)-2-fluorobenzene to replace 2-(bromomethyl)tetrahydro-2H-pyran, 1'-(2-fluorobenzyl)-5,6-dihydrospiro[benzo[1,2-b:5,4-b']difuran-3,3'-indol]-2'(1'H)-one was obtained (81%) as a colorless solid: $^1$H NMR (300 MHz, CDCl$_3$) δ 7.41-6.81 (m, 8H), 6.47 (s, 1H), 6.41 (s, 1H), 5.02 (ABq, 2H), 4.83 (ABq, 2H), 4.52 (t, J=8.7 Hz, 2H), 3.08-2.89 (m, 2H); $^{13}$C NMR (75 MHz, CDCl$_3$) δ178.0, 162.3, 161.9, 161.4, 159.0, 141.9, 132.7, 129.7, 129.7 (2C), 129.6, 128.9, 124.7, 124.6, 123.9, 123.5, 122.9, 122.7, 120.2, 120.0, 119.0, 115.8, 115.5, 109.1, 109.0, 93.3, 80.7, 72.4, 57.8, 37.6, 37.5, 29.1; MS (ES+) m/z 387.9 (M+1).

EXAMPLE 4.13

Synthesis of 1'(4-fluorobenzyl)-5,6-dihydrospiro[benzo[1,2-b:5,4-b']difuran-3,3'-indol]-2'(1')-one

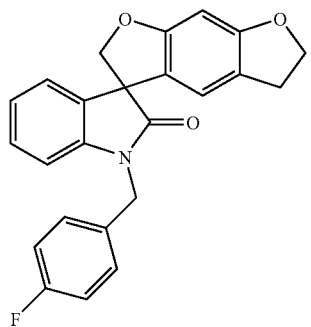

Following the procedure as described in EXAMPLE 4 and making non-critical variations using 1-(bromomethyl)-4-fluorobenzene to replace 2-(bromomethyl)tetrahydro-2H-pyran, 1'-(4-fluorobenzyl)-5,6-dihydrospiro[benzo[1,2-b:5,4-b']difuran-3,3'-indol]-2'(1'H)-one was obtained (80%) as a colorless solid: $^1$H NMR (300 MHz, CDCl$_3$) δ 7.41-6.94 (m, 7H), 6.79 (d, J=7.8 Hz, 1H), 6.44 (s, 1H), 6.41 (s, 1H), 4.91 (ABq, 2H), 4.83 (Abq, 2H), 4.53 (t, J=8.7 Hz, 2H), 3.08-2.89 (m, 2H); $^{13}$C NMR (75 MHz, CDCl$_3$) δ 178.0, 164.0, 161.9, 161.4, 160.7, 141.9, 132.8, 131.7, 131.6, 129.3, 129.2, 128.7, 124.0, 123.5, 120.2, 120.0, 118.8, 116.0, 115.7, 109.1, 93.3, 80.6, 72.4, 57.7, 43.5, 29.1; MS (ES+) m/z 387.9 (M+1).

EXAMPLE 4.14

Synthesis of 1'-benzyl-5,6-dihydrospiro[benzo[1,2-b:5,4-b']difuran-3,3'-indol]-2'(1'H)-one

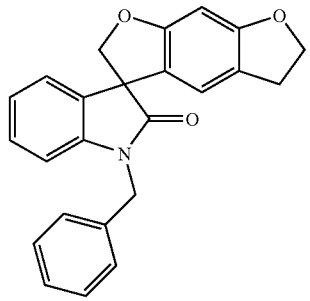

Following the procedure as described in EXAMPLE 4 and making non-critical variations using benzyl bromide to replace 2-(bromomethyl)tetrahydro-2H-pyran, 1'-benzyl-5,6-dihydrospiro[benzo[1,2-b:5,4-b']difuran-3,3'-indol]-2'(1'H)-one was obtained (89%) as a colorless solid: $^1$H NMR (300 MHz, CDCl$_3$) δ 7.43-6.96 (m, 8H), 6.80 (d, J=7.8 Hz, 1H), 6.48 (s, 1H), 6.42 (s, 1H), 4.96 (ABq, 2H), 4.84 (ABq, 2H), 4.53 (t, J=8.7 Hz, 2H), 3.05-2.92 (m, 2H); $^{13}$C NMR (75 MHz, CDCl$_3$) δ178.0, 161.8, 161.4, 142.2, 135.8, 132.8, 128.9, 128.7, 127.8, 127.4, 123.9, 123.4, 120.3, 120.0, 118.9, 109.3, 93.3, 80.7, 72.4, 57.8, 44.2, 29.1; MS (ES+) m/z 369.9 (M+1).

EXAMPLE 4.15

Synthesis of 1'-(biphenyl-4-ylmethyl)-5,6-dihydrospiro[benzo[1,2-b:5,4-b']difuran-3,3'-indol]-2'(1'H)-one

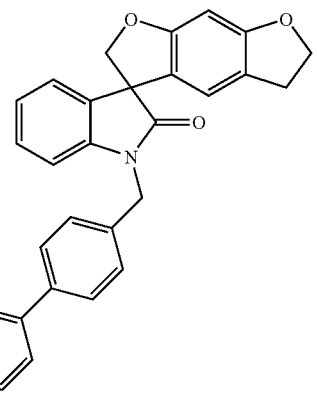

Following the procedure as described in EXAMPLE 4 and making non-critical variations using 4-(chloromethyl)biphenyl to replace 2-(bromomethyl)tetrahydro-2H-pyran, 1'-(biphenyl-4-ylmethyl)-5,6-dihydrospiro[benzo[1,2-b:5,4-b']difuran-3,3'-indol]-2'(1'H)-one was obtained (39%) as a colorless solid: ¹H NMR (300 MHz, CDCl₃) δ 7.67-6.81 (m, 13H), 6.50 (s, 1H), 6.44 (s, 1H), 5.00 (ABq, 2H), 4.86 (ABq, 2H), 4.54 (t, J=8.7 Hz, 2H), 3.09-2.90 (m, 2H); ¹³C NMR (75 MHz, CDCl₃) δ 178.0, 161.9, 161.4, 142.1, 140.8, 140.5, 134.8, 132.8, 128.8, 127.9, 127.6, 127.5, 127.1, 123.9, 123.5, 120.3, 120.0, 118.9, 109.3, 93.3, 80.7, 72.4, 57.8, 43.9, 29.1; MS (ES+) m/z 445.9 (M+1).

EXAMPLE 4.16

Synthesis of 1'-(tetrahydrofuran-3-ylmethyl)-5,6-dihydrospiro[benzo[1,2-b:5,4-b']difuran-3,3'-indol]-2'(1'H)-one

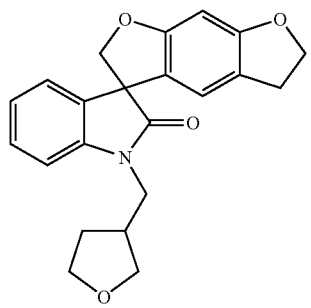

Following the procedure as described in EXAMPLE 4 and making non-critical variations using 3-(bromomethyl)tetrahydrofuran to replace 2-(bromomethyl)tetrahydro-2H-pyran, 1'-(tetrahydrofuran-3-ylmethyl)-5,6-dihydrospiro[benzo[1,2-b:5,4-b']difuran-3,3'-indol]-2'(1'H)-one was obtained (83%) as a colorless solid: ¹H NMR (300 MHz, CDCl₃) δ7.39-6.89 (m, 4H), 6.42 (s, 1H), 6.39 (s, 1H), 4.77 (ABq, 2H), 4.51 (t, J=8.6 Hz, 2H), 4.01-3.54 (m, 6H), 3.04-2.91 (m, 2H), 2.89-2.75 (m, 1H), 2.10-1.95 (m, 1H), 1.82-1.68 (m, 1H); ¹³C NMR (75 MHz, CDCl₃) δ178.1, 178.0, 161.8, 161.3, 142.4 (2C), 132.8 (2C), 128.8, 124.0 (2C), 123.4, 120.2, 120.1, 119.9 (2C), 118.7, 118.6, 108.4, 108.3, 93.2 (2C), 80.6, 72.3, 71.1, 70.9, 67.6, 67.5, 57.6, 42.8, 42.7, 38.0 (2C), 29.8 (2C), 29.1; MS (ES+) m/z 364.0 (M+1).

EXAMPLE 4.17

Synthesis of 1-[(3-bromoisoxazol-5-yl)methyl]-5,6-dihydrospiro[benzo[1,2-b:5,4-b']difuran-3,3'-indol]-2'(1'H)-one

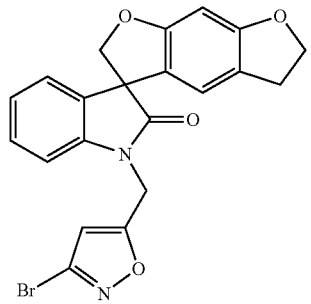

Following the procedure as described in EXAMPLE 4 and making non-critical variations using 3-bromo-5-(bromomethyl)isoxazole to replace 2-(bromomethyl)tetrahydro-2H-pyran, 1-[(3-bromoisoxazol-5-yl)methyl]-5,6-dihydrospiro[benzo[1,2-b:5,4-b']difuran-3,3'-indol]-2'(1'H)-one was obtained (58%) as a colorless solid: ¹H NMR (300 MHz, CDCl₃) δ7.36-6.88 (m, 4H), 6.44 (s, 1H), 6.40 (s, 1H), 6.33 (s, 1H), 5.05 (ABq, 2H), 4.80 (ABq, 2H), 4.53 (t, J=8.6 Hz, 2H), 3.07-2.89 (m, 2H); ¹³C NMR (75 MHz, CDCl₃) δ178.1, 161.7, 161.2, 142.8, 132.6, 128.6, 123.6, 123.2, 120.3, 119.8, 118.8, 109.4, 93.1, 80.6, 76.9, 72.3, 68.2, 57.6, 44.6, 29.2, 29.0, 25.5; MS (ES+) m/z 438.7 (M+1), 440 (M+1).

EXAMPLE 4.18

Synthesis of 1'-[(5-bromofuran-2-yl)methyl]-5,6-dihydrospiro[benzo[1,2-b:5,4-b']difuran-3,3'-indol]-2'(1'H)-one

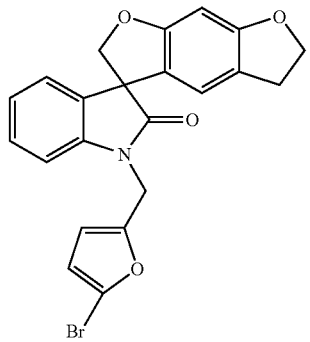

Following the procedure as described in EXAMPLE 4 and making non-critical variations using 2-bromo-5-(bromomethyl)furan to replace 2-(bromomethyl)tetrahydro-2H-pyran, 1'-[(5-bromofuran-2-yl)methyl]-5,6-dihydrospiro[benzo[1,2-b:5,4-b']difuran-3,3'-indol]-2'(1'H)-one was obtained (94%) as a colorless solid: ¹H NMR (300 MHz, CDCl₃) δ7.33-6.96 (m, 4H), 6.46 (s, 1H), 6.40 (s, 1H), 6.28 (dd, J=23.3, 3.3 Hz, 2H), 4.89 (ABq, 2H), 4.80 (ABq, 2H), 4.52 (t, J=8.6 Hz, 2H), 3.07-2.88 (m, 2H); ¹³C NMR (75 MHz, CDCl₃) δ 177.4, 161.8, 161.2, 151.0, 141.5, 132.7, 128.7, 123.8, 123.6, 121.6, 120.1, 119.9, 118.9, 112.3, 111.4, 109.0, 93.2, 80.4, 72.4, 57.6, 37.0, 29.0; MS (ES+) m/z: 437.7 (M+1), 439.7 (M+1).

EXAMPLE 4.19

Synthesis of 1'-(tetrahydrofuran-2-ylmethyl)-5,6-dihydrospiro[benzo[1,2-b:5,4-b']difuran-3,3'-indol]-2'(1'H)-one

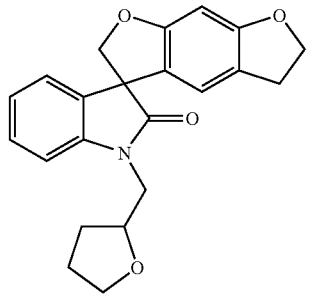

Following the procedure as described in EXAMPLE 4 and making non-critical variations using 2-(bromomethyl)tetrahydrofuran to replace 2-(bromomethyl)tetrahydro-2H-pyran, t-(tetrahydrofuran-2-ylmethyl)-5,6-dihydrospiro[benzo[1,2-b:5,4-b']difuran-3,3'-indol]-2'(1'H)-one was obtained (64%) as a colorless solid: $^1$H NMR (300 MHz, CDCl$_3$) δ7.37-6.95 (m, 4H), 6.48 (d, J=1.2 Hz, 1H), 6.38 (s, 1H), 4.78 (ABq, 2H), 4.50 (t, J=8.7 Hz, 2H), 4.31-4.21 (m, 1H), 3.98-3.65 (m, 4H), 2.96 (t, J=8.7 Hz, 2H), 2.09-1.64 (m, 4H); $^{13}$C NMR (75 MHz, CDCl$_3$) δ178.3, 178.2, 161.7, 161.2, 142.8 (2C), 132.7, 132.6, 128.7, 123.6, 123.2, 120.4 (2C), 119.8, 118.9 (2C), 109.5, 109.4, 93.1, 80.7, 80.6, 76.9, 76.8, 72.3, 68.2, 68.1, 57.6 (2C), 44.6, 44.5, 29.2, 29.0, 25.6, 25.5; MS (ES+) m/z 363.8 (M+1).

EXAMPLE 4.20

Synthesis of 1-(oxetan-2-ylmethyl)-5,6-dihydrospiro[benzo[1,2-b:5,4-b']difuran-3,3'-indol]-2'(1'H)-one

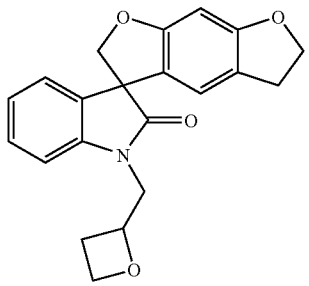

Following the procedure as described in EXAMPLE 4 and making non-critical variations using oxetan-2-ylmethyl 4-methylbenzenesulfonate to replace 2-(bromomethyl)tetrahydro-2H-pyran, 1'-(oxetan-2-ylmethyl)-5,6-dihydrospiro[benzo[1,2-b:5,4-b']difuran-3,3'-indol]-2'(1'H)-one was obtained (28%) as a colorless solid: $^1$H NMR (300 MHz, CDCl$_3$) δ 7.34-6.95 (m, 4H), 6.41 (d, J=9.2 Hz, 1H), 6.38 (s, 1H), 5.04-4.90 (m, 1H), 4.80-4.62 (m, 2H), 4.52-4.30 (m, 4H), 4.08-3.76 (m, 2H), 2.91 (t, J=8.6 Hz, 2H), 2.70-2.56 (m, 1H), 2.44-2.33 (m, 1H); $^{13}$C NMR (75 MHz, CDCl$_3$) δ178.0, 177.8, 161.5, 161.0 (2C), 143.5, 143.4, 132.5, 132.4, 129.0, 128.9, 123.8, 123.7, 123.3, 121.0 (2C), 120.3, 119.3, 119.2, 110.3, 110.2, 92.9 (2C), 80.3 (2C), 79.8, 79.6, 72.5, 68.0, 57.3 (2C), 45.8 (2C), 28.8, 28.7, 25.0, 24.7; MS (ES+) m/z 349.8 (M+1).

EXAMPLE 4.21

Synthesis of 1'-[(1-ethyl-1H-imidazol-5-yl)methyl]-5,6-dihydrospiro[benzo[1,2-b:5,4-b']difuran-3,3'-indol]-2'(1'H)-one

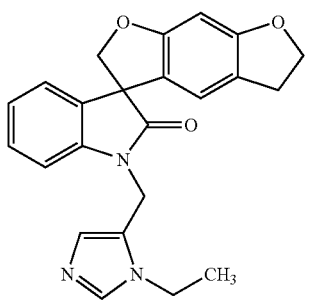

Following the procedure as described in EXAMPLE 4 and making non-critical variations using 5-(chloromethyl)-1-ethyl-1H-imidazol-3-ium chloride to replace 2-(bromomethyl)tetrahydro-2H-pyran, 1'-[(1-ethyl-1H-imidazol-5-yl)methyl]-5,6-dihydrospiro[benzo[1,2-b:5,4-b']difuran-3,3'-indol]-2'(1'H)-one was obtained (57%) as a colorless solid: $^1$H NMR (300 MHz, CDCl$_3$) δ7.34-6.95 (m, 4H), 6.41 (d, J=9.2 Hz, 1H), 6.38 (s, 1H), 5.04-4.90 (m, 1H), 4.80-4.62 (m, 2H), 4.52-4.30 (m, 4H), 4.08-3.76 (m, 2H), 2.91 (t, J=8.6 Hz, 2H), 2.70-2.56 (m, 1H), 2.44-2.33 (m, 1H); $^{13}$C NMR (75 MHz, CDCl$_3$) δ178.0, 177.8, 161.5, 161.0 (2C), 143.5, 143.4, 132.5, 132.4, 129.0, 128.9, 123.8, 123.7, 123.3, 121.0 (2C), 120.3, 119.3, 119.2, 110.3, 110.2, 92.9 (2C), 80.3 (2C), 79.8, 79.6, 72.5, 68.0, 57.3 (2C), 45.8 (2C), 28.8, 28.7, 25.0, 24.7; MS (ES+) m/z 349.8.

EXAMPLE 4.22

Synthesis of 3-[(2'-oxo-5,6-dihydrospiro[benzo[1,2-b:5,4-b']difuran-3,3'-indol]-1'(2'H)-yl)methyl]benzonitrile

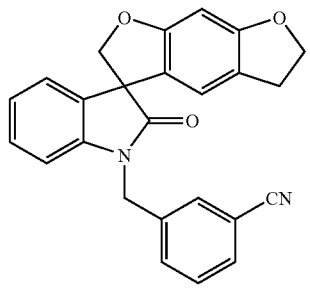

To a solution of 5,6-dihydrospiro[benzo[1,2-b:5,4-b']difuran-3,3'-indol]-2'(1'H)-one (0.97 g, 3.46 mmol) in 2-butanone (25 mL) were added cesium carbonate (3.39 g, 10.39 mmol) and α-bromo-m-tolunitrile (0.85 g, 4.33 mmol). The mixture was heated to reflux for 2 h, cooled to ambient temperature, and filtered. The solid was washed with ethyl acetate. The filtrate was concentrated in vacuo, the residue was purified by column chromatography with ethyl acetate-hexanes (1:5-1:1), followed by recrystallization from ethyl acetate and diethyl ether to afford 3-[(2'-oxo-5,6-dihydrospiro[benzo[1,2-b:5,4-b']difuran-3,3'-indol]-1'(2'H)-yl)methyl]benzonitrile (1.26 g, 92%) as a colorless solid: mp 187-193° C.; $^1$H NMR (300 MHz, CDCl$_3$) δ7.61-7.58 (m, 3H), 7.47-7.44 (m, 1H), 7.25-7.19 (m, 2H), 7.07-7.03 (m, 1H), 6.73-6.71 (m, 1H), 6.43-6.41 (m, 2H), 5.11-4.70 (m, 4H), 4.53 (d, J=9.0 Hz, 2H), 3.09-2.91 (m, 2H); $^{13}$C NMR (75 MHz, CDCl$_3$) δ178.1, 162.0, 161.4, 141.5, 137.5, 132.6, 131.9, 131.6, 130.7, 129.9, 128.9, 124.3, 123.9, 120.2, 119.9, 118.7, 118.4, 113.1, 108.8, 93.4, 80.5, 72.5, 57.7, 43.4, 29.0; MS (ES+) m/z 394.8 (M+1).

EXAMPLE 4.23

Synthesis of 4-((2'-oxo-5,6-dihydro-2H-spiro[benzofuro[6,5-b]furan-3,3'-indoline]-1'-yl)methyl)benzonitrile

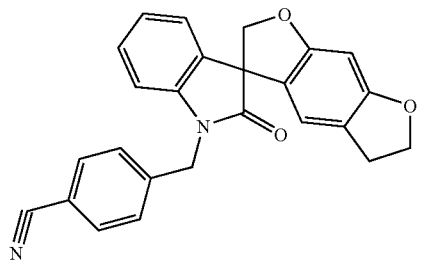

Following the procedure as described in EXAMPLE 4.22 and making non-critical variations using 4-(bromomethyl) benzonitrile to replace α-bromo-m-tolunitrile, 4-((2'-oxo-5, 6-dihydro-2H-spiro[benzofuro[6,5-b]furan-3,3'-indoline]-1'-yl)methyl)benzonitrile was obtained (88%) as a colorless solid: mp 69-71° C.; ¹H NMR (300 MHz, CDCl₃) δ7.73-7.56 (m, 2H), 7.50-7.40 (m, 2H), 7.22-7.15 (m, 2H), 7.10-7.00 (m, 1H), 6.75-6.66 (m, 1H), 6.47-6.38 (m, 2H), 4.99 (ABq, 2H), 4.83 (ABq, 2H), 4.54 (t, J=8.6 Hz, 2H), 3.06-2.92 (m, 2H); MS (ES+) m/z 395.0 (M+1).

EXAMPLE 4.24

Synthesis of 4'-[(2'-oxo-5,6-dihydrospiro[benzo[1,2-b:5,4-b']difuran-3,3'-indol]-1'(2'H)-yl)methyl]biphenyl-2-carbonitrile

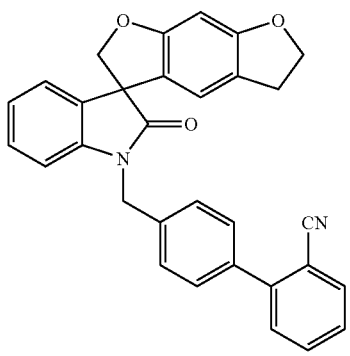

Following the procedure as described in EXAMPLE 4 and making non-critical variations using 4-bromomethyl-2-cyanobiphenyl to replace 2-(bromomethyl)tetrahydro-2H-pyran, 4'-[(2'-oxo-5,6-dihydrospiro[benzo[1,2-b:5,4-b']difuran-3,3'-indol]-1'(2'H)-yl)methyl]biphenyl-2-carbonitrile was obtained (81%) as a colorless solid: mp 192-194° C.; ¹H NMR (300 MHz, CDCl₃) δ7.74 (d, J=7.7 Hz, 1H), 7.63 (ddd, J=7.6, 7.6, 1.1 Hz, 1H), 7.58-7.39 (m, 6H), 7.27-7.15 (m, 2H), 7.04 (dd, J=7.5, 7.5 Hz, 1H), 6.85 (d, J=7.8 Hz, 1H), 6.51 (s, 1H), 6.42 (s, 1H), 5.12 (d, J=15.7 Hz, 1H), 5.00 (d, J=9.0 Hz, 1H), 4.91 (d, J=15.7 Hz, 1H), 4.72 (d, J=9.0 Hz, 1H), 4.53 (t, J=8.6 Hz, 2H), 3.09-2.90 (m, 2H); ¹³C NMR (75 MHz, CDCl₃) δ178.0, 161.9, 161.4, 144.8, 142.1, 137.7, 133.9, 133.0, 132.8, 130.1, 129.3, 128.9, 127.8, 124.0, 123.6, 120.2, 120.0, 119.0, 118.7, 111.1, 109.3, 93.3, 80.7, 72.4, 57.8, 43.9, 29.1; MS (ES+) m/z 471.0 (M+1).

EXAMPLE 4.25

Synthesis of 1'-{(2S)-2-[(benzyloxy)methoxy]propyl}-5,6-dihydrospiro[benzo[1,2-b:5,4-b']difuran-3,3'-indol]-2'(1'H)-one

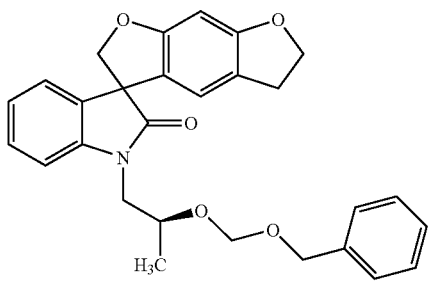

Following the procedure as described in EXAMPLE 4 and making non-critical variations using (S)-2-(benzyloxymethoxy)propyl 4-methylbenzenesulfonate to replace 2-(bromomethyl)tetrahydro-2H-pyran, 1'-{(2S)-2-[(benzyloxy)methoxy]propyl}-5,6-dihydrospiro[benzo[1,2-b:5,4-b']difuran-3,3'-indol]-2'(1'H)-one was obtained (61%) as a colorless solid: mp 49-52° C.; ¹H NMR (300 MHz, CDCl₃,) (diastereomers) δ7.36-7.22 (m, 4H), 7.20-6.99 (m, 5H), 6.44 (d, J=12.8 Hz, 1H), 6.39 (s, 1H), 4.89-4.61 (m, 4H), 4.56-4.33 (m, 4H), 4.28-4.13 (m, 1H), 3.96-3.70 (m, 2H), 3.03-2.70 (m, 2H), 1.29 (dd, J=6.1, 3.1 Hz, 3H); ¹³C NMR (75 MHz, CDCl₃) (diastereomers) δ178.1, 161.6 (2), 143.0 (2), 137.6 (2), 132.7 (2), 128.7 (2), 128.5, 127.8 (2), 127.6 (2), 123.8 (2), 123.2 (2), 120.3 (2), 119.9 (2), 119.0, 109.6 (2), 93.2 (2), 93.0 (2), 80.7 (2), 72.4 (2), 71.5 (2), 69.5 (2), 57.6 (2), 46.2 (2), 29.0 (2), 18.3 (2); MS (ES+) m/z 479.9 (M+23).

EXAMPLE 4.26

Synthesis of 1'-(2,3-dihydro-1,4-benzodioxin-6-ylmethyl)-5,6-dihydrospiro[benzo[1,2-b:5,4-b']difuran-3,3'-indol]-2'(1'H)-one

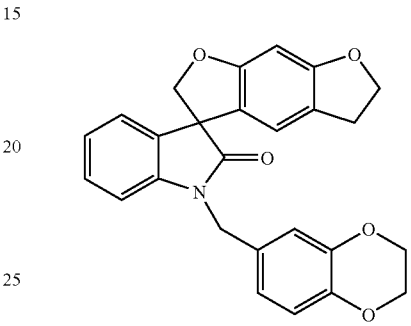

Following the procedure as described in EXAMPLE 4 and making non-critical variations using 6-(bromomethyl)-2,3-dihydrobenzo[b][1,4]dioxine to replace 2-(bromomethyl)tetrahydro-2H-pyran, 1'-(2,3-dihydro-1,4-benzodioxin-6-ylmethyl)-5,6-dihydrospiro[benzo[1,2-b:5,4-b']difuran-3,3'-indol]-2'(1'H)-one was obtained (86%) as a colorless solid: mp 173-175° C. (diethyl ether/hexanes); ¹H NMR (300 MHz, CDCl₃) δ 7.21 (dd, J=7.8, 7.8 Hz, 1H), 7.16 (d, J=6.9 Hz, 1H), 7.02 (dd, J=7.5, 7.02 Hz, 1H), 6.86-6.80 (m, 4H), 6.49 (s, 1H), 6.43 (s, 1H), 4.98 (d, J=9.0 Hz, 1H), 4.94 (d, J=15.2 Hz, 1H), 4.75 (d, J=15.2 Hz, 1H), 4.70 (d, J=9.0 Hz, 1H), 4.54 (t, J=8.6 Hz, 2H), 4.24 (s, 4H), 3.09-2.92 (m, 2H); ¹³C NMR (75 MHz, CDCl₃) δ177.9, 161.9, 161.4, 143.8, 143.3, 142.3, 132.9, 129.1, 128.8, 123.9, 123.4, 120.6, 120.4, 120.0, 119.1, 117.7, 116.5, 109.5, 93.3, 80.8, 72.5, 64.45, 64.41, 57.8, 43.7, 29.2; MS (ES+) m/z 428.0 (M+1).

EXAMPLE 4.27

Synthesis of 1'-(2,1,3-benzoxadiazol-5-ylmethyl)-5,6-dihydrospiro[benzo[1,2-b:5,4-b']difuran-3,3'-indol]-2'(1'H)-one

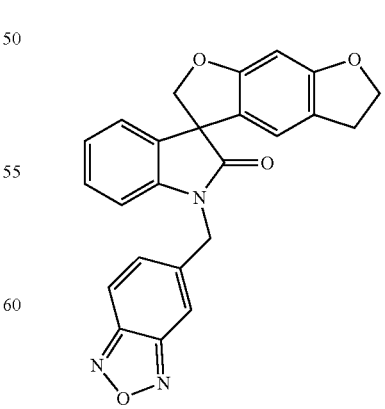

Following the procedure as described in EXAMPLE 4 and making non-critical variations using 5-(bromomethyl)-2,1,3-benzoxadiazole to replace 2-(bromomethyl)tetrahydro-2H- pyran, 1'-(2,1,3-benzoxadiazol-5-ylmethyl)-5,6-dihydrospiro[benzo[1,2-b:5,4-b']difuran-3,3'-indol]-2'(1'H)-one was obtained (74%) as a colorless solid: mp 169-171° C.; $^1$H NMR (300 MHz, DMSO-d$_6$) δ8.06 (d, J=8.6 Hz, 1H), 8.01 (s, 1H), 7.49 (dd, J=9.3, 1.3 Hz, 1H), 7.28-7.14 (m, 2H), 7.12-6.98 (m, 2H), 6.46 (s, 1H), 6.40 (s, 1H), 5.14-4.97 (m, 2H), 4.89 (d, J=9.5 Hz, 1H), 4.74 (d, J=9.5 Hz, 1H), 4.57-4.35 (m, 2H), 3.04-2.82 (m, 2H); $^{13}$C NMR (75 MHz, DMSO-d$_6$) δ177.9, 161.7, 161.2, 149.3, 148.9, 142.4, 141.8, 133.2, 132.7, 129.2, 124.2, 123.8, 120.9, 120.4, 119.4, 117.3, 113.5, 109.8, 93.0, 80.4, 72.6, 65.4, 57.4, 43.7, 28.8; MS (ES+) m/z 411.9 (M+1).

EXAMPLE 4.28

Synthesis of 1'-(2,1,3-benzothiadiazol-5-ylmethyl)-5,6-dihydrospiro[benzo[1,2-b:5,4-b']difuran-3,3'-indol]-2'(1'H)-one

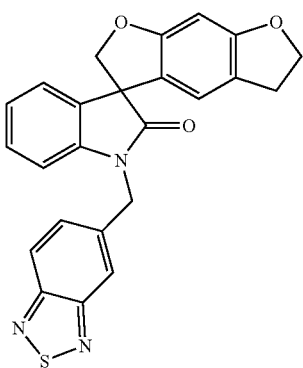

Following the procedure as described in EXAMPLE 4 and making non-critical variations using 5-(bromomethyl)-2,1,3-benzothiadiazole to replace 2-(bromomethyl)tetrahydro-2H-pyran, 1'-(2,1,3-benzothiadiazol-5-ylmethyl)-5,6-dihydrospiro[benzo[1,2-b:5,4-b']difuran-3,3'-indol]-2'(1'H)-one was obtained (74%) as a colorless solid: mp 162-164° C.; $^1$H NMR (300 MHz, DMSO-d$_6$) δ8.12-8.04 (m, 2H), 7.63 (dd, J=9.3, 1.5 Hz, 1H), 7.27-7.14 (m, 2H), 7.09 (d, J=7.7 Hz, 1H), 7.00 (dd, J=7.5, 7.5 Hz, 1H), 6.42 (s, 1H), 6.40 (s, 1H), 5.23-5.05 (m, 2H), 4.88 (d, J=9.5 Hz, 1H), 4.73 (d, J=9.5 Hz, 1H), 4.55-4.38 (m, 2H), 3.04-2.82 (m, 2H); $^{13}$C NMR (75 MHz, DMSO-d$_6$) δ177.8, 161.7, 161.2, 154.7, 154.2, 142.5, 139.0, 132.6, 130.2, 129.2, 124.2, 123.7, 122.3, 120.9, 120.4, 119.6, 119.3, 109.9, 93.0, 80.3, 72.6, 57.5, 43.5, 28.8; MS (ES+) m/z 427.9 (M+1).

EXAMPLE 4.29

Synthesis of 1'-[(4-benzylmorpholin-2-yl)methyl]-5,6-dihydrospiro[benzo[1,2-b:5,4-b']difuran-3,3'-indol]-2'(1'H)-one

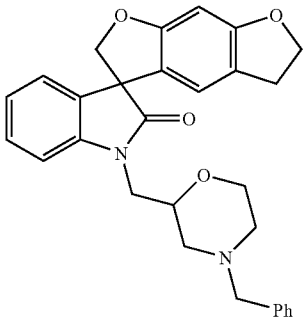

Following the procedure as described in EXAMPLE 4 and making non-critical variations using 4-benzyl-2-(chloromethyl)morphine to replace 2-(bromomethyl)tetrahydro-2H-pyran, 1-[(4-benzylmorpholin-2-yl)methyl]-5,6-dihydrospiro[benzo[1,2-b:5,4-b']difuran-3,3'-indol]-2'(1'H)-one was obtained (10%) as a colorless solid: mp 65-70° C.; $^1$H NMR (300 MHz, CDCl$_3$) δ7.35-7.00 (m, 9H), 6.49-6.39 (m, 2H), 4.92-4.84 (m, 1H), 4.69-4.49 (m, 3H), 3.93-3.42 (m, 7H), 3.02-2.54 (m, 4H), 2.22-2.00 (m, 2H); MS (ES+) m/z 469.1 (M+1).

EXAMPLE 4.30

Synthesis of tert-butyl 3-[(2'-oxo-5,6-dihydrospiro[benzo-[1,2-b:5,4-b']difuran-3,3'-indol]-1'(2'H)-yl)methyl]pyrrolidine-1-carboxylate

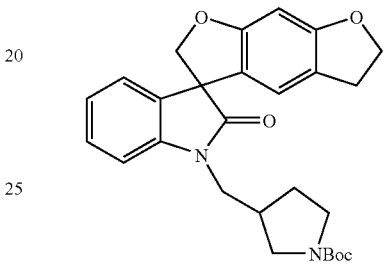

Following the procedure as described in EXAMPLE 4 and making non-critical variations using tert-butyl 3-(bromomethyl)pyrrolidine-1-carboxylate to replace 2-(bromomethyl)tetrahydro-2H-pyran, tert-butyl 3-[(2'-oxo-5,6-dihydrospiro[benzo-[1,2-b:5,4-b']difuran-3,3'-indol]-1'(2'H)-yl)methyl]pyrrolidine-1-carboxylate was obtained (85%) as a pale yellow solid: $^1$H NMR (300 MHz, CDCl$_3$) (diastereomers) δ7.30 (dd, J=7.5, 7.5 Hz, 1H), 7.18 (d, J=7.5 Hz, 1H), 7.07 (dd, J=7.2, 6.9 Hz, 1H), 6.90 (d, J=7.5 Hz, 1H), 6.46 (s, 1H), 6.42 (s, 1H), 4.91 (d, J=9.0 Hz, 1H), 4.66 (d, J=9.0 Hz, 1H), 4.54 (t, J=8.6 Hz, 2H), 3.95-3.44 (m, 3H), 3.41-3.27 (m, 1H), 3.24-3.13 (m, 1H), 3.06-2.92 (m, 2H), 2.82-2.68 (m, 1H), 2.05-1.92 (m, 1H), 1.82-1.69 (m, 1H), 1.46 (s, 9H), 0.93-0.85 (m, 1H); MS (ES+) m/z 485.3 (M+23).

EXAMPLE 4.31

Synthesis of tent-butyl (2S)-2-[(2'-oxo-5,6-dihydrospiro[benzo[1,2-b:5,4-b']difuran-3,3'-indol]-1'(2'H)-yl)methyl]pyrrolidine-1-carboxylate

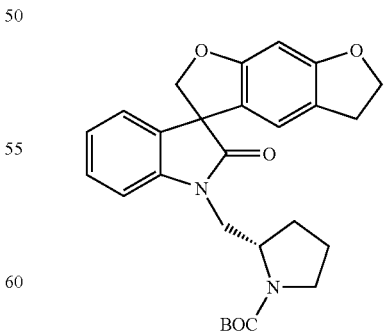

Following the procedure as described in EXAMPLE 4.22 and making non-critical variations using (S)-tert-butyl 2-(tosyloxymethyl)pyrrolidine-1-carboxylate (Fuji, K., et al., *J. Am. Chem. Soc.* (1989), 111(20):7921-5) to replace α-bromo-m-tolunitrile, tert-butyl (2S)-2-[(2'-oxo-5,6-dihydrospiro[benzo[1,2-b:5,4-b']difuran-3,3'-indol]-1'(2'H)-yl)methyl]pyrrolidine-1-carboxylate was obtained (80%) as a colorless solid: $^1$H NMR (300 MHz, CDCl$_3$) (diastereomers) δ7.37-7.25 (m, 2H), 7.20-7.00 (m, 2H), 6.54-6.41 (m, 2H), 4.96-4.88 (m, 1H), 4.70-4.64 (m, 1H), 4.534 (t, J=8.6 Hz, 1H), 4.527 (t, J=8.6 Hz, 1H), 4.31-4.19 (m, 1H), 3.99-3.85 (m, 1H), 3.80-3.67 (m, 1H), 3.49-3.22 (m, 2H), 3.05-2.91 (m, 2H), 2.10-1.77 (m, 4H), 1.48 (s, 4.5H), 1.42 (s, 4.5H); MS (ES+) m/z 485.1 (M+23).

EXAMPLE 4.32

Synthesis of tert-butyl 4-[(2'-oxo-5,6-dihydrospiro[benzo[1,2-b:5,4-b']difuran-3,3'-indol]-1'(2'H)-yl)methyl]piperidine-1-carboxylate

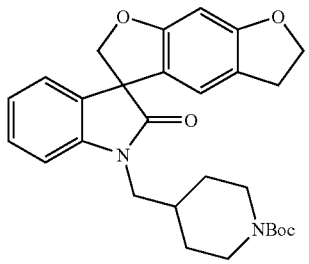

Following the procedure as described in EXAMPLE 4 and making non-critical variations using tert-butyl 4-(tosyloxymethyl)piperidine-1-carboxylate to replace 2-(bromomethyl)tetrahydro-2H-pyran, tert-butyl 4-[(2'-oxo-5,6-dihydrospiro[benzo[1,2-b:5,4-b']difuran-3,3'-indol]-1'(2'H)-yl)methyl]piperidine-1-carboxylate was obtained (99%) as a colorless solid: $^1$H NMR (300 MHz, CDCl$_3$) δ7.30 (ddd, J=7.8, 7.5, 1.2 Hz, 1H), 7.17 (d, J=7.5 Hz, 1H), 7.06 (dd, J=7.5, 7.5 Hz, 1H), 6.90 (d, J=7.8 Hz, 1H), 6.45 (s, 1H), 6.42 (s, 1H), 4.91 (d, J=9.0 Hz, 1H), 4.66 (d, J=9.0 Hz, 1H), 4.54 (t, J=8.6 Hz, 2H), 4.20-4.06 (m, 2H), 3.72 (dd, J=14.0, 7.5 Hz, 1H), 3.58 (d, J=14.0, 6.6 Hz, 1H), 3.08-2.92 (m, 2H), 2.75-2.61 (m, 2H), 2.11-1.96 (m, 1H), 1.73-1.60 (m, 2H), 1.45 (s, 9H), 1.33-1.22 (m, 2H); MS (ES+) m/z 499.2 (M+23).

EXAMPLE 4.33

Synthesis of 4'-chloro-1'-{[5-(trifluoromethyl)furan-2-yl]methyl}-5,6-dihydrospiro[benzo[1,2-b:5,4-b']difuran-3,3'-indol]-2'(1'H)-one

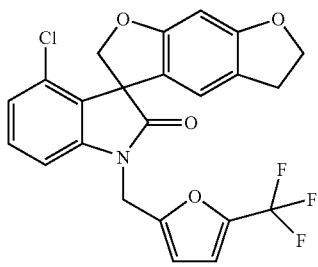

Following the procedure as described in EXAMPLE 4 and making non-critical variations using 4'-chloro-5,6-dihydrospiro[benzo[1,2-b:5,4-b']difuran-3,3'-indol]-2'(1'H)-one to replace 5,6-dihydrospiro[benzo[1,2-b:5,4-b']difuran-3,3'-indol]-2'(1'H)-one, and 2-(bromomethyl)-5-(trifluoromethyl)furan to replace 2-(bromomethyl)tetrahydro-2H-pyran, 4'-chloro-1'-{[5-(trifluoromethyl)furan-2-yl]methyl}-5,6-dihydrospiro[benzo[1,2-b:5,4-b']difuran-3,3'-indol]-2'(1'H)-one was obtained (73%) as a colorless solid: mp 166-169° C.; $^1$H NMR (300 MHz, CDCl$_3$) δ7.29-7.18 (m, 1H), 7.01 (d, J=8.2 Hz, 1H), 6.89 (d, J=7.82 Hz, 1H), 6.74 (d, J=2.3 Hz, 1H), 6.45-6.34 (m, 2H), 5.11 (d, J=16.2 Hz, 1H), 4.99 (d, J=9.2 Hz, 1H), 4.88 (d, J=9.2 Hz, 1H), 4.81 (d, J=16.2 Hz, 1H), 4.52 (t, J=8.6 Hz, 2H), 2.98 (t, J=8.60 Hz, 2H); $^{13}$C NMR (75 MHz, CDCl$_3$) δ177.2, 162.2, 162.0, 151.6, 143.1, 141.8 (q, J=43.0 Hz), 131.6, 130.0, 128.7, 124.6, 118.8 (q, J=267.1 Hz), 119.7, 118.4, 117.1, 112.7, 109.5, 107.2, 92.9, 77.1, 72.4, 58.2, 37.1, 28.9; MS (ES+) m/z 461.9 (M+1), 463.9 (M+1).

EXAMPLE 4.34

Synthesis of 4'-chloro-1'-[(2R)-tetrahydrofuran-2-ylmethyl]-5,6-dihydrospiro[benzo[1,2-b:5,4-b']difuran-3,3'-indol]-2'(1'H)-one

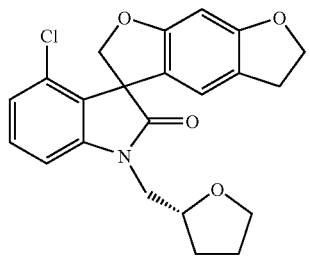

Following the procedure as described in EXAMPLE 4 and making non-critical variations using 4'-chloro-5,6-dihydrospiro[benzo[1,2-b:5,4-b']difuran-3,3'-indol]-2'(1'H)-one to replace 5,6-dihydrospiro[benzo[1,2-b:5,4-b']difuran-3,3'-indol]-2'(1'H)-one, and (R)-(tetrahydrofuran-2-yl)methyl 4-methylbenzenesulfonate to replace 2-(bromomethyl)tetrahydro-2H-pyran, 4'-chloro-1'-[(2R)-tetrahydrofuran-2-yl-methyl]-5,6-dihydrospiro[benzo[1,2-b:5,4-b']difuran-3,3'-indol]-2'(1'H)-one was obtained (80%) as a colorless solid: mp 78-82° C.; $^1$H NMR (300 MHz, DMSO-d$_6$) δ7.32-7.09 (m, 1H), 7.05-6.92 (m, 1H), 6.44 (s, 1H), 6.35 (s, 1H), 4.96 (dd, J=9.1, 1.1 Hz, 1H), 4.85 (d, J=9.1 Hz, 1H), 4.51 (t, J=8.7 Hz, 1H), 4.31-4.16 (m, 1H), 4.00-3.59 (m, 1H), 2.98 (t, J=8.6 Hz, 1H), 2.12-1.80 (m, 1H), 1.76-1.61 (m, 1H); $^{13}$C NMR (75 MHz, DMSO-d$_6$) δ178.0 (2), 162.1 (2), 162.0, 144.7, 131.1 (2), 129.8 (2), 128.7 (2), 123.9, 119.4 (2), 118.4 (2), 117.5 (2), 108.1 (2), 92.9, 77.5, 76.9 (2), 72.3, 68.2 (2), 58.1 (2), 44.9 (2), 29.1 (2), 29.0 (2), 25.6 (2); MS (ES+) m/z 397.9 (M+1), 399.9 (M+1).

EXAMPLE 4.35

Synthesis of 4'-bromo-1'-[(2R)-tetrahydrofuran-2-ylmethyl]-5,6-dihydrospiro[benzo[1,2-b:5,4-b']difuran-3,3'-indol]-2'(1'H)-one

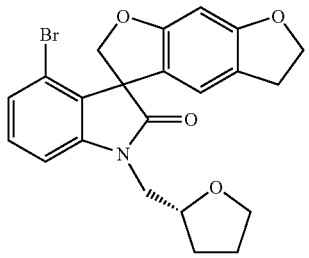

Following the procedure as described in EXAMPLE 4 and making non-critical variations using 4'-bromo-5,6-dihydrospiro[benzo[1,2-b:5,4-b']difuran-3,3'-indol]-2'(1'H)-one to replace 5,6-dihydrospiro[benzo[1,2-b:5,4-b']difuran-3,3'-indol]-2'(1'H)-one, and (R)-(tetrahydrofuran-2-yl)methyl 4-methylbenzenesulfonate to replace 2-(bromomethyl)tetrahydro-2H-pyran, 4'-bromo-1'-[(2R)-tetrahydrofuran-2-ylmethyl]-5,6-dihydrospiro[benzo[1,2-b:5,4-b']difuran-3,3'-indol]-2'(1'H)-one was obtained (75%) as a colorless solid: mp 137-141° C.; $^1$H NMR (300 MHz, DMSO-d$_6$) (diastereomers) δ7.30-7.10 (m, 3H), 6.42-6.37 (m, 1H), 6.32 (s, 1H), 4.88 (d, J=9.63 Hz, 1H), 4.70-4.63 (m, 1H), 4.46 (t, J=8.6 Hz, 2H), 4.18-4.05 (m, 1H), 3.85-3.52 (m, 4H), 2.93 (t, J=8.5 Hz, 2H), 2.01-1.67 (m, 3H), 1.64-1.49 (m, 1H); $^{13}$C NMR (75 MHz, DMSO-d$_6$) δ177.5 (2), 162.2, 161.8, 145.7, 130.9, 130.2 (2), 126.6, 119.9 (2), 119.0 (2), 118.9 (2), 118.1, 92.5, 77.5, 76.3, 76.1, 72.5, 67.7 (2), 65.4, 58.7, 44.5, 29.0 (2), 28.7, 25.5; MS (ES+) m/z 443.9 (M+1), 445.9 (M+1).

EXAMPLE 4.36

Synthesis of 1'-(3-methylbutyl)-2,3-dihydrospiro[furo[2,3-g][1,4]benzodioxine-8,3'-indol]-2'(1'H)-one

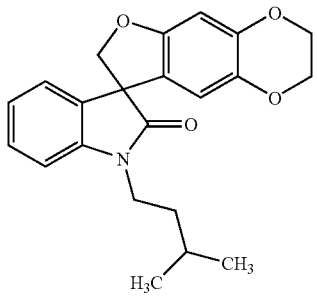

Following the procedure as described in EXAMPLE 4 and making non-critical variations using 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, and 1-bromo-3-methylbutane to replace 2-(bromomethyl)tetrahydro-2H-pyran, 1'-(3-methylbutyl)-2,3-dihydrospiro[furo[2,3-g][1,4]benzodioxine-8,3'-indol]-2'(1'H)-one was obtained (64%) as a colorless solid: mp 134-137° C. (hexanes); $^1$H NMR (300 MHz, CDCl$_3$) δ7.30 (ddd, J=7.7, 7.7, 1.3 Hz, 1H), 7.15 (dd, J=7.2, 0.9 Hz, 1H), 7.03 (ddd, J=7.4, 7.4, 0.7 Hz, 1H), 6.89 (d, J=7.8 Hz, 1H), 6.49 (s, 1H), 6.20 (s, 1H), 4.88 (d, J=9.0 Hz, 1H), 4.62 (d, J=9.0 Hz, 1H), 4.21-4.16 (m, 2H), 4.14-4.09 (m, 2H), 3.89-3.80 (m, 1H), 3.73-3.63 (m, 1H), 1.75-1.59 (m, 3H), 1.00 (d, J=6.3 Hz, 6H); $^{13}$C NMR (75 MHz, CDCl$_3$) δ177.3, 155.4, 144.6, 142.5, 138.3, 132.8, 128.9, 124.0, 123.2, 121.3, 111.6, 108.6, 99.4, 80.2, 64.6, 64.0, 58.1, 38.9, 36.3, 26.2, 22.7, 22.6; MS (ES+) m/z 366.3 (M+1); Anal. Calcd for C$_{22}$H$_{23}$NO$_4$: C, 72.31; H, 6.34; N, 3.83. Found: C, 72.21; H, 6.31; N, 3.55.

EXAMPLE 4.37

Synthesis of t-(tetrahydro-2H-pyran-4-ylmethyl)-2,3-dihydrospiro[furo[2,3-g][1,4]benzodioxine-8,3'-indol]-2'(1'H)-one

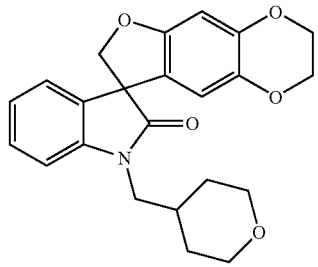

Following the procedure as described in EXAMPLE 4 and making non-critical variations using 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, and 4-(bromomethyl)tetrahydro-2H-pyran to replace 2-(bromomethyl)tetrahydro-2H-pyran, 1'-(tetrahydro-2H-pyran-4-ylmethyl)-2,3-dihydrospiro[furo[2,3-g][1,4]benzodioxine-8,3'-indol]-2'(1'H)-one was obtained (95%) as a colorless solid: mp 129-131° C. (hexanes); $^1$H NMR (300 MHz, CDCl$_3$) δ7.29 (ddd, J=7.9, 7.9, 1.3 Hz, 1H), 7.16 (d, J=7.5 Hz, 1H), 7.04 (ddd, J=7.4, 7.4, 1.0 Hz, 1H), 6.89 (d, J=8.1 Hz, 1H), 6.50 (s, 1H), 6.18 (s, 1H), 4.87 (d, J=8.9 Hz, 1H), 4.62 (d, J=8.9 Hz, 1H), 4.22-4.16 (m, 2H), 4.15-4.09 (m, 2H), 4.03-3.94 (m, 2H), 3.74 (dd, J=13.8, 7.7 Hz, 1H), 3.55 (dd, J=13.8, 7.1 Hz, 1H), 3.42-3.30 (m, 2H), 2.20-2.03 (m, 1H), 1.66-1.56 (m, 2H), 1.53-1.40 (m, 2H); $^{13}$C NMR (75 MHz, CDCl$_3$) δ177.8, 155.4, 144.7, 142.8, 138.4, 132.5, 128.9, 124.2, 123.4, 121.1, 111.5, 108.7, 99.5, 80.4, 67.6, 67.5, 64.6, 64.0, 58.1, 46.2, 34.0, 30.93, 30.86; MS (ES+) m/z 394.2 (M+1); Anal. Calcd for C$_{23}$H$_{23}$NO$_5$: C, 70.21; H, 5.89; N, 3.56. Found: C, 70.15; H, 5.92; N, 3.20.

EXAMPLE 4.38

Synthesis of 1-(tetrahydro-2H-pyran-2-ylmethyl)-2,3-dihydrospiro[furo[2,3-g][1,4]benzodioxine-8,3'-indol]-2'(1'H)-one

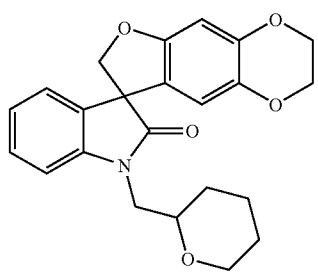

Following the procedure as described in EXAMPLE 4 and making non-critical variations using 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, 1'-(tetrahydro-2H-pyran-2-ylmethyl)-2,3-dihydrospiro[furo[2,3-g][1,4]benzodioxine-8,3'-indol]-2'(1'H)- one was obtained (45%) as a colorless solid: mp 158-166° C. (hexanes); $^1$H NMR (300 MHz, CDCl$_3$) (diastereomers) δ7.31-7.25 (m, 1H), 7.13 (d, J=7.5 Hz, 1H), 7.08-7.00 (m, 2H), 6.48 (s, 1H), 6.24 (s, 0.5H), 6.22 (s, 0.5H), 4.89 (d, J=9.0 Hz, 0.5H), 4.88 (d, J=9.0 Hz, 0.5H), 4.64 (d, J=9.0 Hz, 0.5H), 4.63 (d, J=9.0 Hz, 0.5H), 4.21-4.16 (m, 2H), 4.14-4.09 (m, 2H), 4.01-3.93 (m, 1H), 3.91-3.82 (m, 1H), 3.74-3.63 (m, 2H), 3.44-3.33 (m, 1H), 1.91-1.81 (m, 1H), 1.68-1.31 (m, 5H); $^{13}$C NMR (75 MHz, CDCl$_3$) (diastereomers) δ177.89, 177.80, 155.30, 155.27, 144.61, 143.25, 143.11, 138.34, 132.46, 132.35, 128.78, 128.73, 123.66, 123.64, 123.19, 123.17, 121.51, 121.45, 111.76, 111.62, 109.90, 109.77, 99.41, 99.36, 80.14, 75.75, 75.58, 68.57, 68.53, 64.63, 64.02, 58.08, 58.04, 45.83, 45.77, 29.70, 29.57, 25.88, 23.13; MS (ES+) m/z 394.2 (M+1); Anal. Calcd for C$_{23}$H$_{23}$NO$_5$: C, 70.21; H, 5.89; N, 3.56. Found: C, 70.03; H, 5.97; N, 3.17.

EXAMPLE 4.39

Synthesis of 1'-[(5-chloro-1-methyl-1H-imidazol-2-yl)methyl]-2,3-dihydrospiro[furo[2,3-g][1,4]benzodioxine-8,3'-indol]-2'(1'H)-one

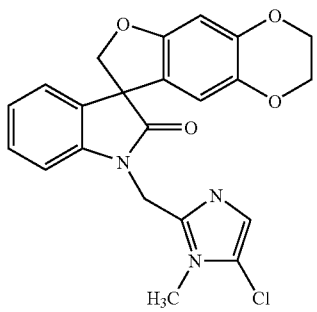

Following the procedure as described in EXAMPLE 4 and making non-critical variations using 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, and 5-chloro-2-(chloromethyl)-1-methyl-1H-imidazole hydrochloride to replace 2-(bromomethyl)tetrahydro-2H-pyran, 1'-[(5-chloro-1-methyl-1H-imidazol-2-yl)methyl]-2,3-dihydrospiro[furo[2,3-g][1,4]benzodioxine-8,3'-indol]-2'(1'H)-one was obtained (94%) as a colorless solid: mp 91-95° C. (dichloromethane); $^1$H NMR (300 MHz, CDCl$_3$) δ7.39 (d, J=7.8 Hz, 1H), 7.27 (ddd, J=7.7, 7.7, 1.2 Hz, 1H), 7.14 (dd, J=7.2, 0.9 Hz, 1H), 7.05 (ddd, J=7.4, 7.4, 0.8 Hz, 1H), 6.94 (s, 1H), 6.50 (s, 1H), 6.18 (s, 1H), 5.12 (d, J=15.6 Hz, 1H), 4.93 (d, J=15.6 Hz, 1H), 4.87 (d, J=9.0 Hz, 1H), 4.62 (d, J=9.0 Hz, 1H), 4.21-4.16 (m, 2H), 4.13-4.08 (m, 2H), 3.59 (s, 3H); $^{13}$C NMR (75 MHz, CDCl$_3$) δ177.3, 155.4, 144.8, 141.9, 141.7, 138.5, 131.6, 129.3, 124.8, 124.0, 123.8, 120.7, 119.5, 111.5, 110.7, 99.6, 80.3, 64.6, 64.0, 58.1, 38.2, 31.0; MS (ES+) m/z 426.2 (M+1), 424.2 (M+1).

EXAMPLE 4.40

Synthesis of 1'-[(5-chloro-1-methyl-1H-imidazol-2-yl)methyl]-2,3-dihydrospiro[furo[2,3-g][1,4]benzodioxine-8,3'-indol]-2'(1'H)-one hydrochloride

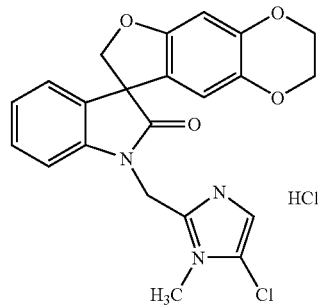

Following the procedure as described in EXAMPLE 2.28 and making non-critical variations using 1'-[(5-chloro-1-methyl-1H-imidazol-2-yl)methyl]-2,3-dihydrospiro[furo[2,3-g][1,4]benzodioxine-8,3'-indol]-2'(1'H)-one to replace 1-methyl-1'-{[5-(trifluoromethyl)furan-2-yl]methyl}-2,3-dihydro-1H-spiro[furo[3,2-g][1,4]benzoxazine-8,3'-indol]-2'(1'H)-one, 1'-[(5-chloro-1-methyl-1H-imidazol-2-yl)methyl]-2,3-dihydrospiro[furo[2,3-g][1,4]benzodioxine-8,3'-indol]-2'(1'H)-one hydrochloride was obtained (82%) as a colorless solid: 207-208° C. (hexanes); $^1$H NMR (300 MHz, DMSO-d$_6$) δ7.80 (s, 1H), 7.40 (d, J=7.8 Hz, 1H), 7.31 (dd, J=7.8, 7.2 Hz, 1H), 7.18 (d, J=7.2 Hz, 1H), 7.08 (dd, J=7.5, 7.2 Hz, 1H), 6.50 (s, 1H), 6.42 (s, 1H), 5.30 (s, 2H), 4.83 (d, J=9.6 Hz, 1H), 4.66 (d, J=9.6 Hz, 1H), 4.20-4.15 (m, 2H), 4.13-4.08 (m, 2H), 3.70 (s, 3H); $^{13}$C NMR (75 MHz, DMSO-d$_6$) δ177.0, 154.8, 144.2, 141.8, 141.7, 137.9, 132.1, 128.6, 123.6, 123.5, 121.0, 120.9, 118.0, 111.9, 109.8, 98.6, 79.9, 64.2, 63.6, 57.3, 35.8, 31.9; MS (ES+) m/z 426.2 (M+1), 424.2 (M+1); Anal. Calcd for C$_{22}$H$_{18}$ClN$_3$O$_4$HCl.H$_2$O: C, 55.24; H, 4.43; N, 8.78. Found: C, 55.51; H, 4.18; N, 8.58.

EXAMPLE 4.41

Synthesis of 1-(pyridin-2-ylmethyl)-2,3-dihydrospiro[furo[2,3-g][1,4]benzodioxine-8,3'-indol]-2'(1'H)-one

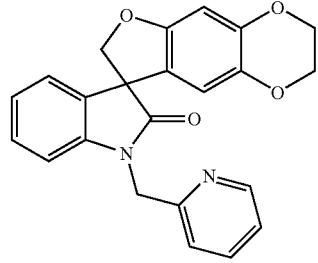

Following the procedure as described in EXAMPLE 4 and making non-critical variations using 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, and 2-(bromomethyl)pyridine hydrobromide to replace 2-(bromomethyl)tetrahydro-2H-pyran, 1'-(pyridin-2-ylmethyl)-2,3-dihydrospiro[furo[2,3-g][1,4]benzodioxine-8,3'-indol]-2'(1'H)-one was obtained (80%) as a colorless solid: mp 208-209° C. (hexanes); $^1$H NMR (300 MHz, CDCl$_3$) δ8.58 (d, J=4.8 Hz, 1H), 7.65 (ddd, J=7.7, 7.7, 1.7 Hz, 1H), 7.28-7.15 (m, 4H), 7.02 (dd, J=7.5, 7.5 Hz, 1H), 6.89 (d, J=7.8 Hz, 1H), 6.51 (s, 1H), 6.31 (s, 1H), 5.21 (d, J=16.0 Hz, 1H), 4.97 (d, J=16.0 Hz, 1H), 4.96 (d, J=8.7 Hz, 1H), 4.68 (d, J=8.7 Hz, 1H), 4.22-4.17 (m, 2H), 4.15-4.10 (m, 2H); $^{13}$C NMR (75 MHz, CDCl$_3$) δ 177.6, 155.6, 155.3, 149.6, 144.6, 142.2, 138.3, 137.1, 132.2, 128.9, 123.8, 123.5, 122.8, 121.6, 121.1, 111.8, 109.6, 99.4, 80.2, 64.5, 63.9, 58.2, 46.1; MS (ES+) m/z 387.2 (M+1).

EXAMPLE 4.42

Synthesis of 1'-(pyridin-2-ylmethyl)-2,3-dihydrospiro[furo[2,3-g][1,4]benzodioxine-8,3'-indol]-2'(1'H)-one hydrochloride

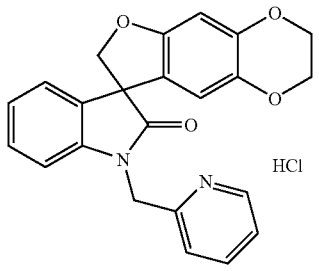

Following the procedure as described in EXAMPLE 2.28 and making non-critical variations using 1'-(pyridin-2-ylmethyl)-2,3-dihydrospiro[furo[2,3-g][1,4]benzo-dioxine-8,3'-indol]-2'(1'H)-one to replace 1-methyl-1'-{[5-(trifluoromethyl)furan-2-yl]methyl}-2,3-dihydro-1H-spiro[furo[3,2-g][1,4]benzoxazine-8,3'-indol]-2'(1'H)-one, 1'-(pyridin-2-ylmethyl)-2,3-dihydrospiro[furo[2,3-g][1,4]benzodioxine-8,3'-indol]-2'(1'H)-one hydrochloride was obtained (89%) as a pale yellow powder: mp 206-208° C. (hexanes); $^1$H NMR (300 MHz, DMSO-d$_6$) δ8.68 (dd, J=4.8, 0.9 Hz, 1H), 8.13 (ddd, J=7.7, 7.7, 1.0 Hz, 1H), 7.65-7.58 (m, 2H), 7.26 (ddd, J=7.7, 7.7, 1.1 Hz, 1H), 7.19 (d, J=7.2 Hz, 1H), 7.07-7.01 (m, 2H), 6.51 (s, 1H), 6.35 (s, 1H), 5.24 (d, J=17.1 Hz, 1H), 5.17 (d, J=17.1 Hz, 1H), 4.83 (d, J=9.3 Hz, 1H), 4.70 (d, J=9.3 Hz, 1H), 4.21-4.16 (m, 2H), 4.14-4.09 (m, 2H); $^{13}$C NMR (75 MHz, DMSO-d$_6$) δ177.0, 154.7, 153.5, 146.2, 144.2, 142.2, 141.2, 137.8, 131.9, 128.8, 124.2, 123.6, 123.23, 123.21, 121.2, 111.7, 109.3, 98.7, 79.5, 64.2, 63.6, 57.3, 43.3; MS (ES+) m/z 387.2 (M+1); Anal. Calcd for C$_{23}$H$_{18}$N$_2$O$_4$.HCl.0.3H$_2$O: C, 64.42; H, 4.62; N, 6.53. Found: C, 64.72; H, 4.55; N, 6.13.

EXAMPLE 4.43

Synthesis of 1-[(2S)-tetrahydrofuran-2-ylmethyl]-2,3-dihydrospiro[furo[2,3-g][1,4]benzodioxine-8,3'-indol]-2'(1'H)-one

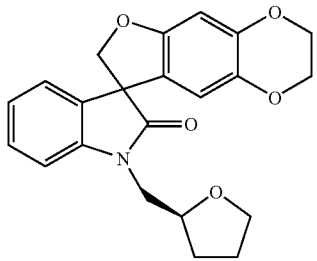

Following the procedure as described in EXAMPLE 4 and making non-critical variations using 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, and (S)-(tetrahydrofuran-2-yl)methyl 4-methylbenzenesulfonate to replace 2-(bromomethyl)tetrahydro-2H-pyran, 1-[(2S)-tetrahydrofuran-2-ylmethyl]-2,3-dihydrospiro[furo[2,3-g][1,4]benzodioxine-8,3'-indol]-2'(1'H)-one was obtained (69%) as a colorless solid: mp 173-175° C. (methanol); $^1$H NMR (300 MHz, CDCl$_3$) (diastereomers) δ7.32-7.25 (m, 1H), 7.16-7.00 (m, 3H), 6.49 (s, 1H), 6.24 (s, 1H), 4.88 (d, J=8.9 Hz, 1H), 4.63 (d, J=8.9 Hz, 1H), 4.31-4.22 (m, 1H), 4.21-4.17 (m, 2H), 4.14-4.09 (m, 2H), 3.99-3.67 (m, 4H), 2.09-1.66 (m, 4H); $^{13}$C NMR (75 MHz, CDCl$_3$) (diastereomers) δ178.1, 177.9, 155.3, 144.6, 143.0, 142.9, 138.4, 132.4, 132.3, 128.9, 128.8, 123.8, 123.7, 123.3, 121.4, 121.3, 111.7, 111.6, 109.8, 109.5, 99.4, 80.3, 80.2, 77.1, 76.8, 68.35, 68.31, 64.6, 64.0, 58.09, 58.06, 44.7, 29.4, 29.0, 25.9, 25.7; MS (ES+) m/z 380.2 (M+1).

EXAMPLE 4.44

Synthesis of 1'-[(2R)-tetrahydrofuran-2-ylmethyl]-2,3-dihydrospiro[furo[2,3-g][1,4]benzodioxine-8,3'-indol]-2'(1'H)-one

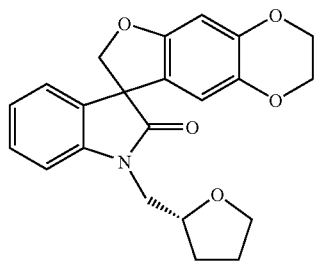

Following the procedure as described in EXAMPLE 4 and making non-critical variations using 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, and (R)-(tetrahydrofuran-2-yl)methyl 4-methylbenzenesulfonate to replace 2-(bromomethyl)tetrahydro-2H-pyran, 1'-[(2R)-tetrahydrofuran-2-ylmethyl]-2,3-dihydrospiro[furo[2,3-g][1,4]benzodioxine-8,3'-indol]-2'(1'H)-one was obtained (55%) as a colorless solid: mp 174-176° C. (hexanes); $^1$H NMR (300 MHz, CDCl$_3$) (diastereomers) δ7.32-7.25 (m, 1H), 7.16-7.00 (m, 3H), 6.49 (s, 1H), 6.24 (s, 1H), 4.88 (d, J=8.7 Hz, 1H), 4.63 (d, J=8.7 Hz, 1H), 4.31-4.22 (m, 1H), 4.21-4.17 (m, 2H), 4.14-4.09 (m, 2H), 3.99-3.67 (m, 4H), 2.09-1.82 (m, 3H), 1.78-1.66 (m, 1H); $^{13}$C NMR (75 MHz, CDCl$_3$) (diastereomers) δ178.1, 177.9, 155.3, 144.6, 143.0, 142.9, 138.4, 132.4, 132.3, 128.9, 128.8, 123.8, 123.7, 123.3, 121.4, 121.3, 111.7, 111.6, 109.8, 109.5, 99.4, 80.29, 80.26, 77.1, 76.8, 68.4, 68.3, 64.6, 64.0, 58.10, 58.08, 44.7, 29.4, 29.1, 25.9, 25.7; MS (ES+) m/z 380.2 (M+1).

EXAMPLE 4.45

Synthesis of 1'-(1,4-dioxan-2-ylmethyl)-2,3-dihydrospiro[furo[2,3-g][1,4]benzodioxine-8,3'-indol]-2'(1'H)-one

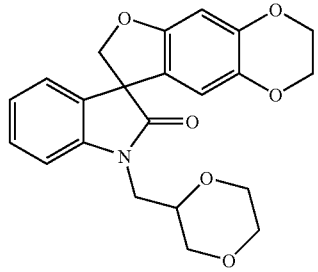

A mixture of 2,3-dihydrospiro[furo[2,3-g][1,4]benzodioxine-8,3'-indol]-2'(1'H)-one (0.30 g, 1.03 mmol), 2-(iodomethyl)-1,4-dioxane (0.31 g, 1.35 mmol) and cesium carbonate (0.52 g, 1.58 mmol) in 2-butanone (7 mL) was stirred at reflux under nitrogen for 4 h. Once cooled, the reaction was diluted with ethyl acetate and the suspension was filtered through Celite. The filtrate was concentrated under reduced pressure and the residue was purified by flash column chromatography with dichloromethane/diethyl ether (14:1) to afford 1'-(1,4-dioxan-2-ylmethyl)-2,3-dihydrospiro[furo[2,3-g][1,4]benzodioxine-8,3'-indol]-2'(1'H)-one as an inseparable mixture with unreacted lactam (0.36 g). A mixture of this material, benzyl bromide (0.12 mL, 1.00 mmol) and cesium carbonate (0.50 g, 1.55 mmol) in 2-butanone (7 mL) was then stirred at reflux under nitrogen for 15 h. Work-up as described above and purified by flash column chromatography with (hexanes/ethyl acetate) (2:1, increased to 1:1) afforded 1'-(1,4-dioxan-2-ylmethyl)-2,3-dihydrospiro[furo[2,3-g][1,4]benzodioxine-8,3'-indol]-2'(1'H)-one (0.24 g, 58%) as a colorless solid, along with 1'-benzyl-2,3-dihydrospiro[furo[2,3-g][1,4]benzodioxine-8,3'-indol]-2'(1'H)-one (0.09 g, 24%) as a colorless solid. Characterization for 1-(1,4-dioxan-2-ylmethyl)-2,3-dihydrospiro[furo[2,3-g][1,4]benzodioxine-8,3'-indol]-2'(1'H)-one: mp 160-165° C. (hexanes); $^1$H NMR (300 MHz, CDCl$_3$) (diastereomers) δ7.26-7.34 (m, 1H), 7.16 (d, J=7.5 Hz, 1H), 7.01-7.09 (m, 2H), 6.49 (s, 1H), 6.24 (s, 0.5H), 6.21 (s, 0.5H), 4.88 (d, J=8.9 Hz, 0.5 Hz), 4.87 (d, J=8.9 Hz, 0.5H), 4.64 (d, J=8.9 Hz, 0.5H), 4.63 (d, J=8.9 Hz, 0.5H), 4.22-4.16 (m, 2H), 4.15-4.09 (m, 2H), 3.99-3.78 (m, 4H), 3.76-3.55 (m, 4H), 3.47-3.37 (m, 1H); $^{13}$C NMR (75 MHz, CDCl$_3$) (diastereomers) δ177.9, 177.8, 156.3, 155.3, 144.71, 144.69, 142.72, 142.66, 138.42, 138.39, 132.4, 132.3, 128.91, 128.85, 123.9, 123.8, 123.5, 121.3, 121.1, 111.7, 111.6, 109.6, 109.4, 99.49, 99.46, 80.2, 80.0, 73.32, 73.29, 69.4, 69.2, 66.8, 66.7, 66.52, 66.48, 64.6, 64.0, 58.1, 58.0, 41.85, 41.76; MS (ES+) m/z 396.2 (M+1).

EXAMPLE 4.46

Synthesis of 1'-(3,4-dimethoxybenzyl)-2,3-dihydrospiro[furo[2,3-g][1,4]benzodioxine-8,3'-indol]-2'(1'H)-one

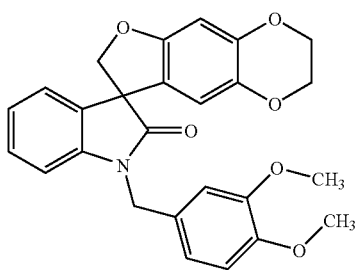

Following the procedure as described in EXAMPLE 4 and making non-critical variations using 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, and 3,4-dimethoxybenzyl bromide (Oguri, T., et al., Chem. Pharm. Bull. (1977), 25:2287-91) to replace 2-(bromomethyl)tetrahydro-2H-pyran, 1'-(3,4-dimethoxybenzyl)-2,3-dihydrospiro[furo[2,3-g][1,4]benzodioxine-8,3'-indol]-2'(1'H)-one was obtained (100%) as a colorless solid: mp 209-211° C. (hexanes/diethyl ether); $^1$H NMR (300 MHz, CDCl$_3$) δ7.23-7.14 (m, 2H), 7.01 (dd, J=7.5, 7.5 Hz, 1H), 6.92-6.80 (m, 4H), 6.51 (s, 1H), 6.21 (s, 1H), 5.09 (d, J=15.3 Hz, 1H), 4.94 (d, J=9.0 Hz, 1H), 4.68 (d, J=15.3 Hz, 1H), 4.67 (d, J=9.0 Hz, 1H), 4.22-4.16 (m, 2H), 4.13-4.08 (m, 2H), 3.86 (s, 3H), 3.84 (s, 3H); $^{13}$C NMR (75 MHz, CDCl$_3$) δ177.7, 155.3, 149.5, 148.8, 144.7, 142.2, 138.4, 132.4, 128.9, 128.4, 124.0, 123.5, 121.3, 120.0, 111.5, 111.2, 110.5, 109.5, 99.6, 80.1, 64.6, 64.0, 58.2, 56.02, 55.99, 44.1; MS (ES+) m/z 446.0 (M+1).

EXAMPLE 4.47

Synthesis of 1'-(3,5-dimethoxybenzyl)-2,3-dihydrospiro[furo[2,3-g][1,4]benzodioxine-8,3'-indol]-2'(1'H)-one

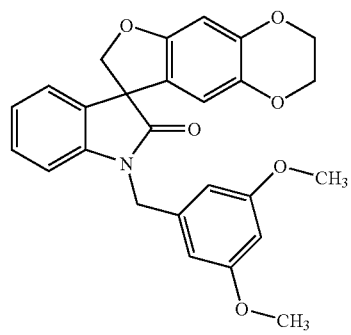

Following the procedure as described in EXAMPLE 4 and making non-critical variations using 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, and 3,5-dimethoxybenzyl bromide to replace 2-(bromomethyl)tetrahydro-2H-pyran, 1'(3,5-dimethoxybenzyl)-2,3-dihydrospiro[furo[2,3-g][1,4]benzodioxine-8,3'-indol]-2'(1'H)-one was obtained (97%) as a colorless solid: mp 192-195° C. (diethyl ether/hexanes); $^1$F1 NMR (300 MHz, CDCl$_3$) δ7.23-7.15 (m, 2H), 7.02 (dd, J=7.5, 7.5 Hz, 1H), 6.81 (d, J=7.5 Hz, 1H), 6.51 (s, 1H), 6.47 (d, J=1.8 Hz, 2H), 6.37 (t, J=1.8 Hz, 1H), 6.25 (s, 1H), 5.04 (d, J=15.5 Hz, 1H), 4.95 (d, J=9.0 Hz, 1H), 4.72 (d, J=15.5 Hz, 1H), 4.68 (d, J=9.0 Hz, 1H), 4.22-4.16 (m, 2H), 4.14-4.09 (m, 2H), 3.76 (s, 6H); $^{13}$C NMR (75 MHz, CDCl$_3$) δ177.7, 161.3, 155.4, 144.7, 142.2, 138.5, 138.2, 132.3, 129.0, 123.9, 123.5, 121.2, 111.6, 109.5, 105.4, 99.8, 99.6, 80.2, 64.6, 64.0, 58.2, 55.5, 44.3; MS (ES+) m/z 446.0 (M+1).

EXAMPLE 4.48

Synthesis of 1-(2,3-dihydro-1,4-benzodioxin-6-ylmethyl)-2,3-dihydrospiro[furo[2,3-g][1,4]benzodioxine-8,3'-indol]-2'(1'H)-one

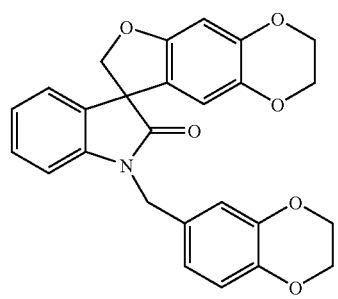

Following the procedure as described in EXAMPLE 4 and making non-critical variations using 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'

(1'H)-one, and 6-(bromomethyl)-2,3-dihydrobenzo[b][1,4]dioxine (Capilla, A. S. et al., *Tetrahedron*, (2001), 57:8297-304) to replace 2-(bromomethyl)tetrahydro-2H-pyran, 1-(2,3-dihydro-1,4-benzodioxin-6-ylmethyl)-2,3-dihydrospiro[furo[2,3-g][1,4]-benzodioxine-8,3'-indol]-2'(1'H)-one was obtained (100%) as a colorless solid: mp 120-123° C. (hexanes/diethyl ether); $^1$H NMR (300 MHz, CDCl$_3$) δ7.20 (ddd, J=7.8, 7.5, 1.2 Hz, 1H), 7.15 (dd, J=7.4, 0.8 Hz, 1H), 7.01 (ddd, J=7.5, 7.4, 0.7 Hz, 1H), 6.85-6.79 (m, 4H), 6.50 (s, 1H), 6.24 (s, 1H), 4.93 (d, J=8.7 Hz, 1H), 4.92 (d, J=15.5 Hz, 1H), 4.76 (d, J=15.5 Hz, 1H), 4.65 (d, J=8.7 Hz, 1H), 4.23 (s, 4H), 4.22-4.17 (m, 2H), 4.14-4.10 (m, 2H); $^{13}$C NMR (75 MHz, CDCl$_3$) δ177.5, 155.4, 144.7, 143.8, 143.3, 142.3, 138.4, 132.4, 129.0, 128.9, 123.9, 123.4, 121.2, 120.5, 117.8, 116.5, 111.8, 109.5, 99.5, 80.4, 64.6, 64.44, 64.41, 64.0, 58.2, 43.8; MS (ES+) m/z 444.0 (M+1).

EXAMPLE 4.49

Synthesis of (R)-1'-{[5-(trifluoromethyl)furan-2-yl]methyl}-2,3-dihydrospiro[furo[2,3-g][1,4]-benzodioxine-8,3'-indol]-2'(1'H)-one

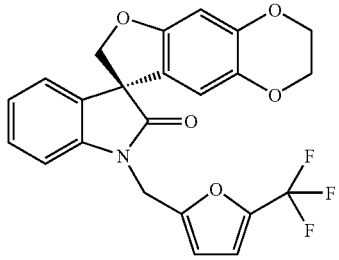

Following the procedure as described in EXAMPLE 4 and making non-critical variations using (R)-(2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, and 2-(bromomethyl)-5-(trifluoromethyl)furan to replace 2-(bromomethyl)tetrahydro-2H-pyran, (R)-1'-{[5-(trifluoromethyl)furan-2-yl]methyl}-2,3-dihydrospiro[furo[2,3-g][1,4]benzodioxine-8,3'-indol]-2'(1'H)-one was obtained (92%) as a colorless solid: mp 64-68° C. (methanol/water); $^1$H NMR (300 MHz, CDCl$_3$) δ7.30 (ddd, J=7.8, 7.7, 1.0 Hz, 1H), 7.18 (d, J=7.2 Hz, 1H), 7.07 (dd, J=7.5, 7.2 Hz, 1H), 6.99 (d, J=8.1 Hz, 1H), 6.76-6.72 (m, 1H), 6.50 (s, 1H), 6.38 (d, J=3.3 Hz, 1H), 6.19 (s, 1H), 5.06 (d, J=16.5 Hz, 1H), 4.89 (d, J=16.5 Hz, 1H), 4.90 (d, J=9.0 Hz, 1H), 4.64 (d, J=9.0 Hz, 1H), 4.22-4.16 (m, 2H), 4.14-4.09 (m, 2H); $^{13}$C NMR (75 MHz, CDCl$_3$) δ177.2, 155.3, 152.2, 144.8, 141.8 (q, J=43.0 Hz), 141.5, 138.5, 132.2, 129.1, 124.2, 123.9, 120.9, 118.9 (d, J=267 Hz), 112.8 (d, J=2.8 Hz), 111.6, 109.3, 109.0, 99.5, 80.1, 64.6, 64.0, 58.1, 37.1; MS (ES+) m/z 443.9 (M+1).

EXAMPLE 4.50

Synthesis of (S)-1'-{[5-(trifluoromethyl)furan-2-yl]methyl}-2,3-dihydrospiro[furo[2,3-g][1,4]benzodioxine-8,3'-indol]-2'(1'H)-one

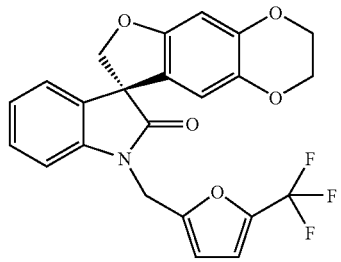

Following the procedure as described in EXAMPLE 4 and making non-critical variations using (S)-(2,3-dihydrospiro[furo[2,3-g][1,4]-benzodioxine-8,3'-indol]-2'(1'H)-one to replace 5,6-dihydrospiro[benzo[1,2-b:5,4-b']difuran-3,3'-indol]-2'(1'H)-one, and 2-(bromomethyl)-5-(trifluoromethyl)furan to replace 2-(bromomethyl)tetrahydro-2H-pyran, (S)-1'-{[5-(trifluoromethyl)furan-2-yl]methyl}-2,3-dihydrospiro[furo[2,3-g][1,4]benzodioxine-8,3'-indol]-2'(1'H)-one was obtained (95%) as a colorless solid: mp 53-56° C. (methanol/water); $^1$H NMR (300 MHz, CDCl$_3$) δ7.30 (dd, J=7.8, 7.8 Hz, 1H), 7.18 (d, J=7.2 Hz, 1H), 7.08 (dd, J=7.5, 7.5 Hz, 1H), 6.99 (d, J=8.1 Hz, 1H), 6.74 (dd, J=2.1, 0.9 Hz, 1H), 6.50 (s, 1H), 6.38 (d, J=3.0 Hz, 1H), 6.19 (s, 1H), 5.06 (d, J=16.2 Hz, 1H), 4.90 (d, J=9.0 Hz, 1H), 4.89 (d, J=16.2 Hz, 1H), 4.64 (d, J=9.0 Hz, 1H), 4.22-4.17 (m, 2H), 4.14-4.09 (m, 2H); $^{13}$C NMR (75 MHz, CDCl$_3$) δ177.2, 155.3, 152.2, 144.8, 141.8 (q, J=43.0 Hz), 141.5, 138.5, 132.2, 129.1, 124.2, 123.9, 120.9, 118.9 (q, J=267 Hz), 112.8 (q, J=2.8 Hz), 111.6, 109.3, 109.0, 99.5, 80.1, 64.6, 64.0, 58.1, 37.1; MS (ES+) m/z 443.9 (M+1).

EXAMPLE 4.51

Synthesis of (S)-1'-(pyridin-2-ylmethyl)-2,3-dihydrospiro[furo[2,3-g][1,4]benzodioxine-8,3'-indol]-2'(1'H)-one

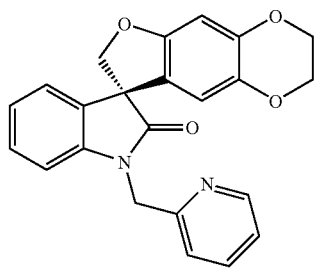

Following the procedure as described in EXAMPLE 4 and making non-critical variations using (S)-2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, and 2-(bromomethyl)pyridine hydrobromide to replace 2-(bromomethyl)tetrahydro-2H-pyran, (S)-1'-(pyridin-2-ylmethyl)-2,3-dihydrospiro[furo[2,3-g][1,4]benzodioxine-8,3'-indol]-2'(1'H)-one was obtained (95%) as a colorless solid: mp 144-146° C. (diethyl ether/hexanes); $^1$H NMR (300 MHz, CDCl₃) δ8.59 (dd, J=5.1, 0.6 Hz, 1H), 7.73 (ddd, J=7.8, 7.5, 1.5 Hz, 1H), 7.33-7.27 (m, 2H), 7.22 (ddd, J=7.7, 7.7, 1.3 Hz, 1H), 7.17 (dd, J=7.4, 0.9 Hz, 1H), 7.03 (ddd, J=7.5, 7.5, 0.9 Hz, 1H), 6.95 (d, J=7.8 Hz, 1H), 6.51 (s, 1H), 6.29 (s, 1H), 5.26 (d, J=15.9 Hz, 1H), 5.04 (d, J=15.9 Hz, 1H), 4.96 (d, J=9.0 Hz, 1H), 4.68 (d, J=9.0 Hz, 1H), 4.22-4.18 (m, 2H), 4.15-4.11 (m, 2H); ¹³C NMR (75 MHz, CDCl₃) δ177.7, 155.4, 155.3, 148.6, 144.8, 142.0, 138.4, 138.2, 132.2, 129.0, 124.0, 123.7, 123.3, 122.3, 121.1, 111.8, 109.7, 99.5, 80.3, 64.6, 64.0, 58.2, 45.5; MS (ES+) m/z 387.0 (M+1).

EXAMPLE 4.52

Synthesis of 1'-(pyridin-2-ylmethyl)-6,7-dihydrospiro[benzo[1,2-b:4,5-b']difuran-3,3'-indol]-2'(1'H)-one

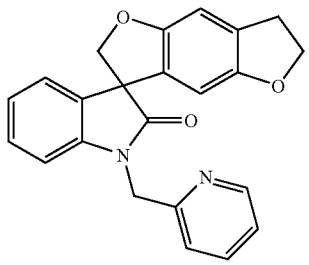

Following the procedure as described in EXAMPLE 4 and making non-critical variations using 6,7-dihydrospiro[benzo[1,2-b:4,5-b']difuran-3,3'-indol]-2'(1'H)-one to replace 5,6-dihydrospiro[benzo[1,2-b:5,4-b']difuran-3,3'-indol]-2'(1'H)-one, and 2-(bromomethyl)pyridine hydrobromide to replace 2-(bromomethyl)tetrahydro-2H-pyran, 1'-(pyridin-2-ylmethyl)-6,7-dihydrospiro[benzo[1,2-b:4,5-b']difuran-3,3'-indol]-2'(1'H)-one was obtained (67%) as a colorless solid: mp 198-200° C. (diethyl ether/hexanes); ¹H NMR (300 MHz, CDCl₃) δ8.59 (d, J=4.8 Hz, 1H), 7.71 (dd, J=7.8, 7.5 Hz, 1H), 7.32-7.15 (m, 4H), 7.02 (dd, J=7.5, 7.5 Hz, 1H), 6.94 (d, J=7.8 Hz, 1H), 6.82 (s, 1H), 6.17 (s, 1H), 5.27 (d, J=15.6 Hz, 1H), 5.01 (d, J=15.6 Hz, 1H), 4.98 (d, J=9.0 Hz, 1H), 4.70 (d, J=9.0 Hz, 1H), 4.49 (td, J=8.7, 0.7 Hz, 2H), 3.15 (t, J=8.7 Hz, 2H); ¹³C NMR (75 MHz, CDCl₃) δ177.7, 155.3, 155.2, 154.9, 148.6, 142.1, 138.3, 132.1, 129.1, 128.9, 127.6, 124.0, 123.7, 123.3, 122.3, 109.7, 107.2, 104.0, 80.1, 71.8, 58.6, 45.5, 30.4; MS (ES+) m/z 370.9 (M+1).

EXAMPLE 4.53

Synthesis of 1'-[(2R)-tetrahydrofuran-2-ylmethyl]-6,7-dihydro-5H-spiro[furo[3,2-g]chromene-3,3'-indol]-2'(1'H)-one

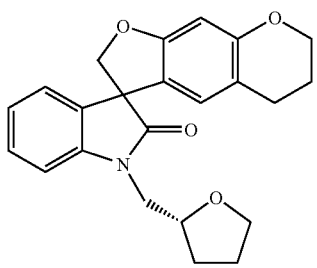

Following the procedure as described in EXAMPLE 4 and making non-critical variations using 6,7-dihydro-5H-spiro[furo[3,2-g]chromene-3,3'-indol]-2'(1'H)-one to replace 5,6-dihydrospiro[benzo[1,2-b:5,4-b']difuran-3,3'-indol]-2'(1'H)-one, and (R)-(tetrahydrofuran-2-yl)methyl 4-methylbenzenesulfonate to replace 2-(bromomethyl)tetrahydro-2H-pyran, 1'-[(2R)-tetrahydrofuran-2-ylmethyl]-6,7-dihydro-5H-spiro[furo[3,2-g]chromene-3,3'-indol]-2'(1'H)-one was obtained (57%) as an off-white solid: mp 151-156° C. (diethyl ether); ¹H NMR (300 MHz, CDCl₃) (diastereomers) δ7.32-7.26 (m, 1H), 7.16-7.02 (m, 3H), 6.40 (s, 1H), 6.38 (s, 1H), 4.89 (d, J=9.0 Hz, 1H), 4.644, 4.640 (d, J=9.0 Hz, 1H), 4.32-4.24 (m, 1H), 4.11 (dd, J=5.4, 4.8 Hz, 2H), 3.99-3.69 (m, 4H), 2.63-2.52 (m, 2H), 2.10-1.85 (m, 5H), 1.79-1.67 (m, 1H); ¹³C NMR (75 MHz, CDCl₃) (diastereomers) δ178.3, 178.2, 160.2, 156.3, 143.0, 132.8, 132.7, 128.8, 128.7, 123.88, 123.86, 123.82, 123.76, 123.3, 121.1, 121.0, 115.24, 115.20, 109.7, 109.5, 98.9, 80.43, 80.40, 77.1, 77.0, 68.4, 68.3, 66.7, 57.8, 57.7, 44.8, 44.7, 29.4, 29.1, 25.8, 25.7, 24.8, 24.7, 22.4; MS (ES+) m/z 378.1 (M+1).

EXAMPLE 4.54

Synthesis of 1-{[5-(trifluoromethyl)furan-2-yl]methyl}-3,4-dihydro-2H-spiro[furo[2,3-h][1,5]benzodioxepine-9,3'-indol]-2'(1'H)-one

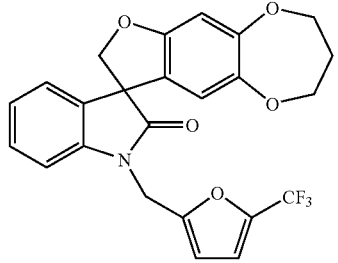

Following the procedure as described in EXAMPLE 4 and making non-critical variations using 3,4-dihydro-2H-spiro[furo[2,3-h][1,5]benzodioxepine-9,3'-indol]-2'(1'H)-one to replace 5,6-dihydrospiro[benzo[1,2-b:5,4-b']difuran-3,3'-indol]-2'(1'H)-one, and 2-(bromomethyl)-5-(trifluoromethyl)furan to replace 2-(bromomethyl)tetrahydro-2H-pyran, 1-{[5-(trifluoromethyl)furan-2-yl]methyl}-3,4-dihydro-2H-spiro[furo[2,3-h][1,5]benzodioxepine-9,3'-indol]-2'(1'H)-one was obtained (97%) as a colorless solid: mp 162-164° C. (water/methanol); ¹H NMR (300 MHz, CDCl₃) δ7.30 (ddd, J=7.8, 7.8, 1.2 Hz, 1H), 7.18 (d, J=7.5 Hz, 1H), 7.07 (dd, J=7.5, 7.5 Hz, 1H), 6.98 (d, J=7.8 Hz, 1H), 6.76-6.73 (m, 1H), 6.60 (s, 1H), 6.39 (d, J=3.3 Hz, 1H), 6.32 (s, 1H), 5.07 (d, J=16.4 Hz, 1H), 4.94 (d, J=9.0 Hz, 1H), 4.89 (d, J=16.4 Hz, 1H), 4.68 (d, J=9.0 Hz, 1H), 4.29-4.21 (m, 1H), 4.14-4.02 (m, 2H), 3.99-3.91 (m, 1H), 2.23-2.00 (m, 2H); ¹³C NMR (75 MHz, CDCl₃) δ177.1, 156.8, 153.2, 152.1 (q, J=1.3 Hz), 146.4, 141.8 (q, J=42.9 Hz), 141.4, 132.1, 129.1, 124.2, 124.0, 122.9, 118.9 (q, J=267 Hz), 116.1, 112.8 (q, J=2.7 Hz), 109.4, 109.0, 103.6, 80.4, 70.91, 70.90, 58.0, 37.1, 32.3; MS (ES+) m/z 457.9 (M+1).

EXAMPLE 4.55

Synthesis of 1'-(pyridin-2-ylmethyl)-3,4-dihydro-2H-spiro[furo[2,3-h][1,5]benzodioxepine-9,3'-indol]-2'(1'H)-one

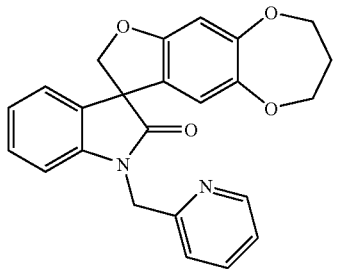

Following the procedure as described in EXAMPLE 4 and making non-critical variations using 3,4-dihydro-2H-spiro[furo[2,3-h][1,5]benzodioxepine-9,3'-indol]-2'(1'H)-one to replace 5,6-dihydrospiro[benzo[1,2-b:5,4-b']difuran-3,3'-indol]-2'(1'H)-one, and 2-(bromomethyl)pyridine hydrobromide to replace 2-(bromomethyl)tetrahydro-2H-pyran, 1'-(pyridin-2-ylmethyl)-3,4-dihydro-2H-spiro[furo[2,3-h][1,5]benzodioxepine-9,3'-indol]-2'(1'H)-one was obtained (90%) as a colorless solid: mp 122-123° C. (diethyl ether/hexanes); $^1$H NMR (300 MHz, CDCl$_3$) δ8.59 (d, J=4.8 Hz, 1H), 7.71 (ddd, J=7.8, 7.5, 1.2 Hz, 1H), 7.31-7.15 (m, 4H), 7.03 (dd, J=7.5, 7.5 Hz, 1H), 6.92 (d, J=7.8 Hz, 1H), 6.61 (s, 1H), 6.42 (s, 1H), 5.24 (d, J=15.9 Hz, 1H), 5.04 (d, J=15.9 Hz, 1H), 4.98 (d, J=9.0 Hz, 1H), 4.71 (d, J=9.0 Hz, 1H), 4.28-4.20 (m, 1H), 4.14-4.05 (m, 2H), 4.02-3.94 (m, 1H), 2.22-2.02 (m, 2H); $^{13}$C NMR (75 MHz, CDCl$_3$) δ177.5, 156.8, 155.4, 153.1, 149.1, 146.3, 142.1, 137.7, 132.2, 129.0, 124.0, 123.7, 123.1, 123.0, 121.9, 116.2, 109.6, 103.6, 80.5, 70.87, 70.85, 58.1, 45.9, 32.2; MS (ES+) m/z 401.0 (M+1).

EXAMPLE 4.56

Synthesis of 2-methyl-1'-(3-methylbutyl)spiro[furo[2,3-f][1,3]benzothiazole-7,3'-indol]-2'(1'H)-one

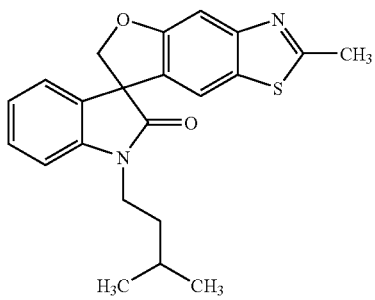

Following the procedure as described in EXAMPLE 4 and making non-critical variations using 2-methylspiro[furo[2,3-f][1,3]benzothiazole-7,3'-indol]-2'(1'H)-one to replace 5,6-dihydrospiro[benzo[1,2-b:5,4-b']difuran-3,3'-indol]-2'(1'H)-one, and 1-bromo-3-methylbutane to replace 2-(bromomethyl)tetrahydro-2H-pyran, 2-methyl-t-(3-methylbutyl)spiro[furo[2,3-f][1,3]benzothiazole-7,3'-indol]-2'(1'H)-one was obtained (71%) as a colorless solid: mp 137-138° C. (hexanes/ethyl acetate); $^1$H NMR (300 MHz, CDCl$_3$) δ7.60 (d, J=8.6 Hz, 1H), 7.32-7.27 (m, 1H), 7.13-7.08 (m, 1H), 7.03-6.92 (m, 3H), 5.03 (d, J=8.8 Hz, 1H), 4.78 (d, J=8.8 Hz, 1H), 4.12-4.01 (m, 1H), 3.71-3.60 (m, 1H), 2.56 (s, 3H), 1.93-1.61 (m, 3H), 1.06-1.00 (m, 6H); $^{13}$C NMR (75 MHz, CDCl$_3$) δ176.8, 169.3, 160.4, 149.4, 142.8, 132.9, 129.1, 128.7, 123.6, 122.8, 122.2, 120.4, 108.6, 108.4, 81.1, 58.2, 39.2, 36.1, 26.0, 23.0, 22.5, 20.3; MS (ES+) m/z 378.5 (M+1).

EXAMPLE 4.57

Synthesis of 2-methyl-1'-(tetrahydro-2H-pyran-4-ylmethyl)spiro[furo[2,3-f][1,3]benzothiazole-7,3'-indol]-2'(1'H)-one

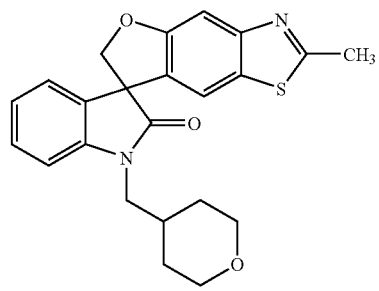

Following the procedure as described in EXAMPLE 4 and making non-critical variations using 2-methylspiro[furo[2,3-f][1,3]benzothiazole-7,3'-indol]-2"(1'H)-one to replace 5,6-dihydrospiro[benzo[1,2-b:5,4-b']difuran-3,3'-indol]-2'(1'H)-one, and 4-(bromomethyl)tetrahydropyran to replace 2-(bromomethyl)tetrahydro-2H-pyran, 2-methyl-1'-(tetrahydro-2H-pyran-4-ylmethyl)spiro[furo[2,3-f][1,3]benzothiazole-7,3'-indol]-2'(1'H)-one was obtained (44%) as a colorless solid: mp 186-187° C. (hexanes/ethyl acetate); $^1$H NMR (300 MHz, CDCl$_3$) δ7.66-7.60 (m, 1H), 7.34-7.27 (m, 1H), 7.13-7.07 (m, 1H), 7.06-6.91 (m, 3H), 5.04-4.97 (m, 1H), 4.78-4.72 (m, 1H), 4.07-3.93 (m, 3H), 3.52-3.35 (m, 3H), 2.52 (s, 3H), 2.32-2.15 (m, 1H), 2.07-1.95 (m, 1H), 1.91-1.80 (m, 1H), 1.57-1.42 (m, 2H); $^{13}$C NMR (75 MHz, CDCl$_3$) δ177.4, 169.3, 160.6, 149.2, 143.1, 132.7, 129.1, 128.7, 123.7, 123.0, 122.3, 119.9, 108.7, 108.5, 81.5, 67.9, 62.4, 58.1, 46.6, 34.3, 30.9, 20.2, 14.6; MS (ES+) m/z 407.0 (M+1).

EXAMPLE 4.58

Synthesis of 2-methyl-1'-[(2R)-tetrahydrofuran-2-ylmethyl]spiro[furo[2,3-f][1,3]benzoxazole-7,3'-indol]-2'(1'H)-one

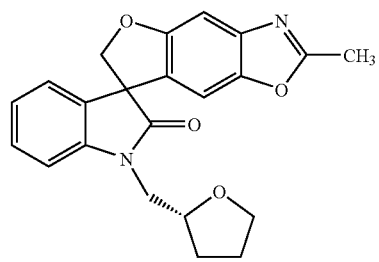

Following the procedure as described in EXAMPLE 4 and making non-critical variations using 2-methylspiro[furo[2,3-f][1,3]benzoxazole-7,3'-indol]-2'(1'H)-one to replace 5,6-dihydrospiro[benzo[1,2-b:5,4-b']difuran-3,3'-indol]-2"(1'H)-one, and (R)-(tetrahydrofuran-2-yl)methyl 4-methylbenzenesulfonate to replace 2-(bromomethyl)tetrahydro-2H-pyran, 2-methyl-1'-[(2R)-tetrahydrofuran-2-ylmethyl]spiro[furo[2,3-f][1,3]benzoxazole-7,3'-indol]-2'(1'H)-one was obtained (52%) as a colorless solid: mp 188-190° C. (ethyl acetate); ¹H NMR (300 MHz, CDCl₃) δ7.37-7.30 (m, 2H), 7.23-7.05 (m, 2H), 6.98-6.93 (m, 2H), 6.00-5.93 (m, 1H), 5.43-5.38 (m, 1H), 4.42-4.26 (m, 1H), 4.05-3.75 (m, 4H), 2.35-2.33 (m, 3H) 2.09-1.79 (m, 4H); ¹³C NMR (75 MHz, CDCl₃) δ175.6, 175.3, 164.4, 164.3, 151.2, 151.1, 146.2, 146.1, 144.9, 144.6, 138.7, 138.6, 130.5, 130.4, 129.6, 124.6, 124.4, 123.0 (2C), 114.0, 113.9, 111.8, 111.6, 110.6, 110.5, 110.3, 109.8, 88.7, 88.4, 76.1, 76.0, 68.5, 68.3, 44.7, 44.4, 29.8, 28.9, 26.2, 25.7, 14.7, 14.6; MS (ES+) m/z 414.9 (M+39).

EXAMPLE 4.59

Synthesis of 1-methyl-1'-[(2R)-tetrahydrofuran-2-ylmethyl]-1H-spiro[furo[3,2-g][1,4]benzoxazine-8,3'-indole]-2,2'(1'H-3H)-dione

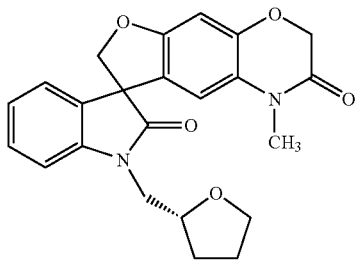

Following the procedure as described in EXAMPLE 4 and making non-critical variations using 1-methyl-1H-spiro[furo[3,2-g][1,4]benzoxazine-8,3'-indole]-2,2'(1'H,3H)-dione to replace 5,6-dihydrospiro[benzo[1,2-b:5,4-b']difuran-3,3'-indol]-2"(1'H)-one, and (R)-(tetrahydrofuran-2-yl)methyl 4-methylbenzenesulfonate to replace 2-(bromomethyl)tetrahydro-2H-pyran, 1-methyl-1'-[(2R)-tetrahydrofuran-2-ylmethyl]-1H-spiro[furo[3,2-g][1,4]benzoxazine-8,3'-indole]-2,2'(1'H,3H)-dione was obtained (69%) as an off-white solid: mp 79-81° C. (diethyl ether); ¹H NMR (300 MHz, CDCl₃) δ7.33 (dd, J=7.8, 7.8 Hz, 1H), 7.16-7.04 (m, 3H), 6.63-6.62 (m, 1H), 6.39-6.32 (m, 1H), 4.96-4.92 (m, 1H), 4.72-4.67 (m, 1H), 4.54 (s, 2H), 4.37-4.26 (m, 1H), 3.98-3.85 (m, 2H), 3.82-3.70 (m, 2H), 3.15 (s, 3H), 2.13-2.00 (m, 1H), 1.98-1.88 (m, 2H), 1.78-1.65 (m, 1H); ¹³C NMR (75 MHz, CDCl₃) δ177.7 (2C), 163.9 (2C), 157.4, 157.3, 146.9 (2C), 143.1, 142.6, 132.2, 131.9, 129.2, 129.1, 124.4 (2C), 123.8 (2C), 123.5, 123.1, 122.8, 109.8, 109.7, 109.6, 100.1 (2C), 80.8, 80.6, 76.9, 76.2, 68.4, 68.2, 67.7, 58.1 (2C), 44.9, 44.6, 29.3, 29.1, 28.5, 28.4, 25.7 (2C); MS (ES+) m/z 429.1 (M+23), 407.1 (M+1).

EXAMPLE 4.60

Synthesis of 1-methyl-1'-[(2R)-tetrahydrofuran-2-ylmethyl]spiro[furo[3,2-f][1,3]benzoxazole-7,3'-indole]-2,2'(1'H,1'H)-dione

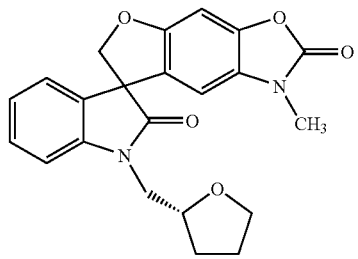

Following the procedure as described in EXAMPLE 4 and making non-critical variations using 1-methylspiro[furo[3,2-f][1,3]benzoxazole-7,3'-indole]-2,2'(1'H,1'H)-dione to replace 5,6-dihydrospiro[benzo[1,2-b:5,4-b']difuran-3,3'-indol]-2"(1'H)-one, and (R)-(tetrahydrofuran-2-yl)methyl 4-methylbenzenesulfonate to replace 2-(bromomethyl)tetrahydro-2H-pyran, 1-methyl-1'-[(2R)-tetrahydrofuran-2-ylmethyl]spiro[furo[3,2-g][1,3]benzoxazole-7,3'-indole]-2,2'(1'H,1'H)-dione was obtained (32%) as a colorless solid: mp>250° C. (toluene/hexanes); ¹H NMR (300 MHz, CDCl₃) δ7.38-7.29 (m, 1H), 7.17-7.03 (m, 3H), 6.90-6.85 (m, 1H), 6.40-6.28 (m, 1H), 4.99-4.92 (m, 1H), 4.75-4.67 (m, 1H), 4.36-4.25 (m, 1H), 4.01-3.67 (m, 4H), 3.25-3.21 (m, 3H), 2.14-1.85 (m, 3H), 1.79-1.65 (m, 1H); ¹³C NMR (75 MHz, CDCl₃) δ177.6, 157.0, 156.9, 155.0, 143.5 (2C), 143.1, 142.6, 132.2, 131.9, 129.3, 129.2, 126.2, 124.1, 123.8, 123.6, 109.8, 109.8, 103.1, 103.0, 94.7 (2C), 80.5, 80.4, 77.1, 76.3, 68.4, 68.2, 58.2 (2C), 45.0, 44.7, 29.3, 29.2, 28.3, 28.2, 25.7; MS (ES+) m/z 393.0 (M+1).

EXAMPLE 4.61

Synthesis of 6-methoxy-5-methyl-1'-[(2R)-tetrahydrofuran-2-ylmethyl]spiro[1-benzofuran-3,3'-indol]-2'(1'H)-one

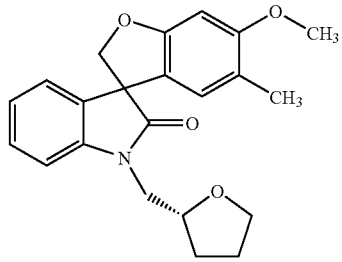

Following the procedure as described in EXAMPLE 4 and making non-critical variations using 6-methoxy-5-methyl-spiro[1-benzofuran-3,3'-indol]-2'(1'H)-one to replace 5,6-dihydrospiro[benzo[1,2-b:5,4-b']difuran-3,3'-indol]-2"(1'H)-one, and (R)-(tetrahydrofuran-2-yl)methyl 4-methylbenzenesulfonate to replace 2-(bromomethyl)tetrahydro-2H-pyran, 6-methoxy-5-methyl-1'-[(2R)-tetrahydrofuran-2-ylmethyl]spiro[1-benzofuran-3,3'-indol]-2'(1'H)-one was obtained (72%) as a colorless solid: mp 151-153° C.; ¹H NMR (300 MHz, CDCl₃) δ7.27 (dd, J=7.7, 7.7

Hz, 1H), 7.15-6.98 (m, 3H), 6.48 (s, 1H), 6.44 (s, 1H), 4.90 (d, J=8.9 Hz, 1H), 4.65 (dd, J=8.9, 2.3 Hz, 1H), 4.32-4.21 (m, 1H), 3.99-3.61 (m, 4H), 3.78 (s, 3H), 2.10-1.63 (m, 4H), 1.99 (s, 3H); $^{13}$C NMR (75 MHz, CDCl$_3$) δ 178.3 (2), 160.3, 159.1, 142.9 (2), 132.6 (2), 128.7 (2), 124.2 (2), 123.7 (2), 119.5 (2), 119.2 (2), 109.5 (2), 93.7, 80.4 (2), 77.0 (2), 68.2 (2), 57.9, 55.5, 44.6 (2), 29.1 (2), 25.6 (2), 15.9 (2); MS (ES+) m/z 366.3 (M+1).

EXAMPLE 4.62

Synthesis of 6-methoxy-5-methyl-1'-(pyridin-2-ylmethyl)spiro[1-benzofuran-3,3'-indol]-2'(1'H)-one

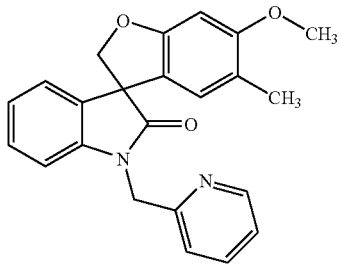

Following the procedure as described in EXAMPLE 4 and making non-critical variations using 6-methoxy-5-methyl-spiro[1-benzofuran-3,3'-indol]-2'(1'H)-one to replace 5,6-dihydrospiro[benzo[1,2-b:5,4-b']difuran-3,3'-indol]-2"(1'H)-one, and 2-(bromomethyl)pyridine hydrobromide to replace 2-(bromomethyl)tetrahydro-2H-pyran, 6-methoxy-5-methyl-1'-(pyridin-2-ylmethyl)spiro[1-benzofuran-3,3'-indol]-2'(1'H)-one was obtained (82%) as a colorless solid: mp 142-144° C.; $^1$H NMR (300 MHz, CDCl$_3$) δ 8.56 (d, J=4.8 Hz, 1H), 7.67-7.60 (m, 1H), 7.28-7.11 (m, 4H), 7.00 (dd, J=7.5, 7.5 Hz, 1H), 6.90 (d, J=7.8 Hz, 1H), 6.50 (s, 2H), 5.09 (ABq, 2H), 4.84 (ABq, 2H), 3.79 (s, 3H), 2.00 (s, 3H); $^{13}$C NMR (75 MHz, CDCl$_3$) δ 178.0, 160.3, 159.2, 155.7, 149.5, 142.5, 142.2, 137.1, 132.6, 128.7, 124.3, 123.8, 123.5, 122.8, 121.7, 119.5, 119.2, 109.5, 93.8, 80.3, 58.0, 46.1, 22.6, 16.0; MS (ES+) m/z 373.3 (M+1).

EXAMPLE 4.63

Synthesis of 6-methoxy-5-methyl-1'-(tetrahydro-2H-pyran-2-ylmethyl)spiro[1-benzofuran-3,3'-indol]-2'(1'H)-one

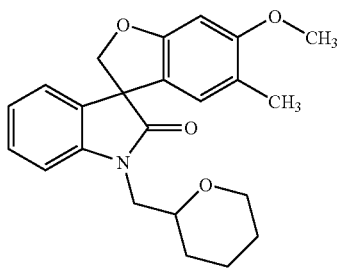

Following the procedure as described in EXAMPLE 4 and making non-critical variations using 6-methoxy-5-methyl-spiro[1-benzofuran-3,3'-indol]-2'(1'H)-one to replace 5,6-dihydrospiro[benzo[1,2-b:5,4-b']difuran-3,3'-indol]-2'(1'H)-one, 6-methoxy-5-methyl-1'-(tetrahydro-2H-pyran-2-ylmethyl)spiro[1-benzofuran-3,3'-indol]-2'(1'H)-one was obtained (68%) as a colorless solid: mp 180-182° C.; $^1$H NMR (300 MHz, CDCl$_3$) δ 7.28 (dd, J=7.8, 7.8 Hz, 1H), 7.13-6.97 (m, 3H), 6.47 (s, 1H), 6.43 (d, J=4.3 Hz, 1H), 4.91 (dd, J=8.9, 2.1 Hz, 1H), 4.66 (dd, J=8.9, 3.3 Hz, 1H), 4.02-3.59 (m, 4H), 3.79 (s, 3H), 3.43-3.31 (m, 1H), 1.99 (s, 3H), 1.92-1.77 (m, 1H), 1.71-1.26 (m, 5H); MS (ES+) m/z 380.4 (M+1).

EXAMPLE 4.64

Synthesis of 5-fluoro-6-methoxy-1'-(tetrahydro-2H-pyran-2-ylmethyl)spiro[1-benzofuran-3,3'-indol]-2'(1'H)-one

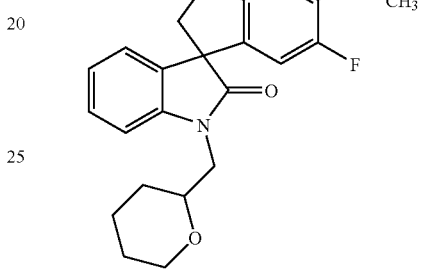

Following the procedure as described in EXAMPLE 4 and making non-critical variations using 5-fluoro-6-methoxyspiro[1-benzofuran-3,3'-indol]-2'(1'H)-one to replace 5,6-dihydrospiro[benzo[1,2-b:5,4-b']difuran-3,3'-indol]-2"(1'H)-one, 5-fluoro-6-methoxy-1-(tetrahydro-2H-pyran-2-ylmethyl)spiro[1-benzofuran-3,3'-indol]-2'(1'H)-one was obtained (99%) as a colorless solid: mp 131-133° C.; $^1$H NMR (300 MHz, CDCl$_3$) δ 7.31-7.24 (m, 1H), 7.13-6.98 (m, 3H), 6.61-6.55 (m, 1H), 6.47-6.39 (m, 1H), 4.96-4.89 (m, 1H), 4.71-4.63 (m, 1H), 4.00-3.76 (m, 5H), 3.73-3.59 (m, 2H), 3.42-3.30 (m, 1H), 1.91-1.79 (m, 1H), 1.70-1.27 (m, 5H); $^{13}$C NMR (75 MHz, CDCl$_3$) δ 177.5, 177.4, 157.10, 157.08, 157.05, 157.03, 149.2, 149.0, 148.8, 146.1, 143.2, 143.0, 131.9, 131.8, 128.9, 128.8, 123.52, 123.50, 123.18, 123.15, 119.4, 119.3, 119.2, 110.6, 110.5, 110.3, 110.2, 109.9, 109.8, 96.2, 80.4, 75.6, 75.4, 68.4, 68.3, 57.96, 57.95, 57.92, 56.4, 45.7, 45.6, 29.5, 29.4, 25.7, 23.0; MS (ES+) m/z 384.2 (M+1).

EXAMPLE 4.65

Synthesis of 5-fluoro-6-methoxy-1'-(pyridin-2-ylmethyl)spiro[1-benzofuran-3,3'-indol]-2'(1'H)-one

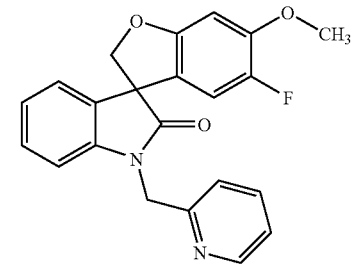

Following the procedure as described in EXAMPLE 4 and making non-critical variations using 5-fluoro-6-methoxyspiro[1-benzofuran-3,3'-indol]-2'(1'H)-one to replace 5,6-dihydrospiro[benzo[1,2-b:5,4-b']difuran-3,3'-indol]-2"(1'H)-one, and 2-(bromomethyl)pyridine hydrobromide to replace 2-(bromomethyl)tetrahydro-2H-pyran, 5-fluoro-6-methoxy-1'-(pyridin-2-ylmethyl)spiro[1-benzofuran-3,3'-indol]-2'(1'H)-one was obtained (77%) as a colorless solid: mp 142-144° C.; $^1$H NMR (300 MHz, CDCl$_3$) δ 8.59-8.53 (m, 1H), 7.65 (ddd, J=7.7, 7.7, 1.7 Hz, 1H), 7.28-7.10 (m, 4H), 7.01 (dd, J=7.5, 7.5 Hz, 1H), 6.88 (d, J=7.8 Hz, 1H), 6.60 (d, J=6.8 Hz, 1H), 6.52 (d, J=10.1 Hz, 1H), 5.20 (d, J=15.8 Hz, 1H), 5.03-4.90 (m, 2H), 4.72 (d, J=9.0 Hz, 1H), 3.86 (s, 3H); $^{13}$C NMR (75 MHz, CDCl$_3$) δ177.3, 157.2 (d), 155.4, 149.6, 149.3, 149.1, 149.0, 146.1, 142.1, 137.1, 131.8, 129.0, 123.8, 123.6, 122.8, 121.6, 119.0 (d), 110.7, 110.4, 109.6, 96.3, 80.5, 58.1, 56.4, 46.0; MS (ES+) m/z 377.2 (M+1).

EXAMPLE 4.66

Synthesis of 5-fluoro-6-methoxy-1'-[(2R)-tetrahydrofuran-2-ylmethyl]spiro[1-benzofuran-3,3'-indol]-2'(1'H)-one

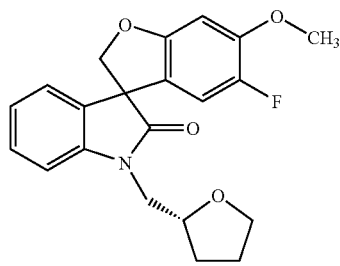

Following the procedure as described in EXAMPLE 4 and making non-critical variations using 5-fluoro-6-methoxyspiro[1-benzofuran-3,3'-indol]-2'(1'H)-one to replace 5,6-dihydrospiro[benzo[1,2-b:5,4-b']difuran-3,3'-indol]-2"(1'H)-one, and (R)-(tetrahydrofuran-2-yl)methyl 4-methylbenzenesulfonate to replace 2-(bromomethyl)tetrahydro-2H-pyran, 5-fluoro-6-methoxy-1'-[(2R)-tetrahydrofuran-2-ylmethyl]spiro[1-benzofuran-3,3'-indol]-2'(1'H)-one was obtained (42%) as a colorless solid: mp 106-116° C.; $^1$H NMR (300 MHz, CDCl$_3$) δ7.28 (dd, J=7.6, 7.6 Hz, 1H), 7.14-6.98 (m, 3H), 6.58 (d, J=6.8 Hz, 1H), 6.49-6.40 (m, 1H), 4.92 (d, J=9.0 Hz, 1H), 4.66 (d, J=9.0 Hz, 1H), 4.31-4.19 (m, 1H), 3.98-3.64 (m, 7H), 2.09-1.80 (m, 3H), 1.76-1.61 (m, 1H); $^{13}$C NMR (75 MHz, CDCl$_3$) δ177.7, 177.5, 157.1, 149.3, 149.1, 148.9, 146.1, 142.8, 131.9, 131.7, 129.0, 128.9, 123.7, 123.6, 123.3, 119.3, 119.2, 110.6, 110.5, 110.3, 110.2, 109.8, 109.6, 96.3, 80.6, 76.7, 68.2, 68.1, 58.0, 56.4, 44.6, 29.2, 29.0, 25.7, 25.5; MS (ES+) m/z 370.2 (M+1).

EXAMPLE 4.67

Synthesis of 1'-benzyl-5-fluoro-6-methoxyspiro[1-benzofuran-3,3'-indol]-2'(1'H)-one

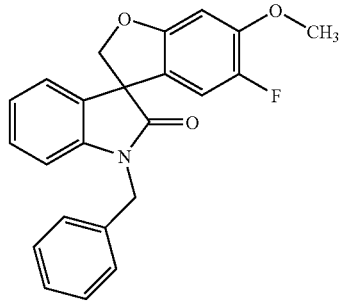

Following the procedure as described in EXAMPLE 4 and making non-critical variations using 5-fluoro-6-methoxyspiro[1-benzofuran-3,3'-indol]-2'(1'H)-one to replace 5,6-dihydrospiro[benzo[1,2-b:5,4-b']difuran-3,3'-indol]-2"(1'H)-one, and benzylbromide to replace 2-(bromomethyl)tetrahydro-2H-pyran, 1-benzyl-5-fluoro-6-methoxyspiro[1-benzofuran-3,3'-indol]-2'(1'H)-one was obtained (86%) as a colorless solid: mp 160-162° C.; $^1$H NMR (300 MHz, CDCl$_3$) δ7.39-7.26 (m, 5H), 7.20 (ddd, J=7.6, 7.6, 1.2 Hz, 1H), 7.16-7.09 (m, 1H), 7.06-6.97 (m, 1H), 6.79 (d, J=7.8 Hz, 1H), 6.61 (d, J=6.8 Hz, 1H), 6.43 (d, J=10.1 Hz, 1H), 5.05 (d, J=15.5 Hz, 1H), 4.99 (d, J=9.0 Hz, 1H), 4.83 (d, J=15.5 Hz, 1H), 4.70 (d, J=9.0 Hz, 1H), 3.86 (s, 3H); $^{13}$C NMR (75 MHz, CDCl$_3$) δ 182.3, 173.3, 166.3, 165.6, 147.9, 137.5, 133.7, 128.5, 128.0, 126.1, 124.9, 124.6, 114.2, 97.5, 84.9, 77.3, 62.0, 47.6, 33.5; MS (ES+) m/z 376.0 (M+1).

EXAMPLE 4.68

Synthesis of 6-methoxy-1'-[(2R)-tetrahydrofuran-2-ylmethyl]spiro[1-benzofuran-3,3'-indol]-2'(1'H)-one

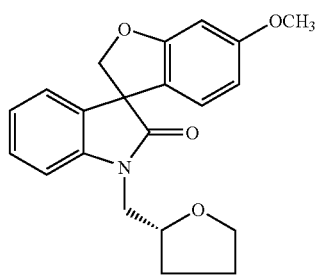

Following the procedure as described in EXAMPLE 4 and making non-critical variations using 6-methoxyspiro[1-benzofuran-3,3'-indol]-2'(1'H)-one to replace 5,6-dihydrospiro[benzo[1,2-b:5,4-b']difuran-3,3'-indol]-2'(1'H)-one, and (R)-(tetrahydrofuran-2-yl)methyl 4-methylbenzenesulfonate to replace 2-(bromomethyl)tetrahydro-2H-pyran, 6-methoxy-1'-[(2R)-tetrahydrofuran-2-ylmethyl]spiro[1-benzofuran-3,3'-indol]-2'(1'H)-one was obtained (54%) as a colorless liquid: $^1$H NMR (300 MHz, CDCl$_3$) (diastereomers) δ7.32-7.25 (m, 1H), 7.16-6.99 (m, 3H), 6.61 (d, J=8.1 Hz, 1H), 6.52 (d, J=2.1 Hz, 1H), 6.36 (dd, J=8.1, 2.1 Hz, 1H), 4.94 (d, J=9.0 Hz, 1H), 4.69 (d, J=9.0 Hz, 1H), 4.32-4.22 (m, 1H), 4.00-3.66 (m, 4H), 3.77 (s, 3H), 2.10-1.66 (m, 4H); $^{13}$C NMR (75 MHz, CDCl$_3$) (diastereomers) δ178.0, 177.9, 162.0, 161.4, 142.9, 142.8, 132.4, 132.3, 128.7, 128.6, 123.6, 123.5 (2C), 123.4, 123.2, 121.0, 120.9, 109.6, 109.3, 107.4 (2C), 96.5, 80.5, 80.4, 76.8, 76.7, 68.2, 68.1, 57.5, 55.5, 44.5 (2C), 29.2, 28.9, 25.6, 25.5; MS (ES+) m/z 352.1 (M+1).

EXAMPLE 4.69

Synthesis of 6-bromo-1'-[(2R)-tetrahydrofuran-2-ylmethyl]spiro[1-benzofuran-3,3'-indol]-2'(1'H)-one

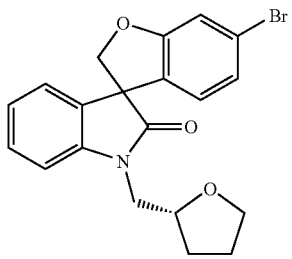

To a stirred solution of 6-bromospiro[1-benzofuran-3,3'-indol]-2'(1'H)-one (1.3 g, 4.3 mmol) in 2-butanone (40.0 mL) was added cesium carbonate (4.2 g, 12.9 mmol) and (R)-(tetrahydrofuran-2-yl)methyl 4-methylbenzenesulfonate (1.4 g, 5.4 mmol). The reaction was refluxed for 16 h, filtered and concentrated in vacuo to dryness. The residue was purified by flash chromatography with 25% ethyl acetate in hexanes to afford 6-bromo-1'-[(2R)-tetrahydrofuran-2-ylmethyl]spiro[1-benzofuran-3,3'-indol]-2'(1'H)-one (1.75 g, 100%) as a colorless solid: MS (ES+) m/z 400.0 (M+1), 402.0 (M+1).

EXAMPLE 4.70

Synthesis of 1'-{[5-(trifluoromethyl)furan-2-yl]methyl}-2,3,6,7-tetrahydrospiro[furo[3,2-g]chromene-5,3'-indol]-2'(1'H)-one

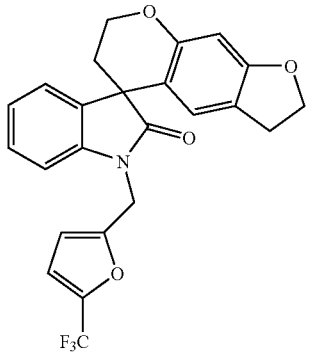

Following the procedure as described in EXAMPLE 4 and making non-critical variations using 2,3,6,7-tetrahydrospiro[furo[3,2-g]chromene-5,3'-indol]-2'(1'H)-one to replace 5,6-dihydrospiro[benzo[1,2-b:5,4-b']difuran-3,3'-indol]-2"(1'H)-one, acetone to replace butanone, and 2-(bromomethyl)-5-(trifluoromethyl)furan to replace 2-(bromomethyl)tetrahydro-2H-pyran, 1'-{[5-(trifluoromethyl)furan-2-yl]methyl}-2,3,6,7-tetrahydrospiro[furo[3,2-g]chromene-5,3'-indol]-2'(1'H)-one was obtained (43%) as a colorless solid: $^1$H NMR (300 MHz, CDCl$_3$) δ7.36-6.93 (m, 4H), 6.76-6.70 (m, 1H), 6.38 (d, J=3.5 Hz, 1H), 6.36 (s, 1H), 6.21 (s, 1H), 4.98 (ABq, 2H), 4.80-4.69 (m, 1H), 4.45 (t, J=8.6 Hz, 2H), 4.36-4.28 (m, 1H), 2.92 (t, J=8.5 Hz, 2H), 2.23-2.16 (m, 2H); $^{13}$C NMR (75 MHz, CDCl$_3$) δ179.3, 160.6, 155.5, 152.2, 152.1, 141.8, 141.6, 141.3, 135.2, 128.3, 124.1, 123.5, 123.5, 120.6, 120.4, 117.0, 112.6 (2C), 112.5 (2C), 112.1, 109.1, 108.6, 98.6, 71.8, 62.0, 47.8, 36.7, 32.4, 28.8; MS (ES+) m/z 441.7 (M+1).

EXAMPLE 4.71

Synthesis of 1'-[4-(methylsulfanyl)benzyl]-5,6-dihydrospiro[benzo[1,2-b:5,4-b']difuran-3,3'-indol]-2'(1'H)-one

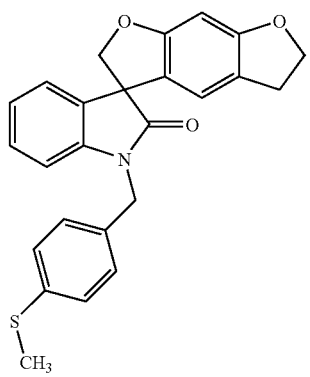

Following the procedure as described in EXAMPLE 4.22 and making non-critical variations using (4-(bromomethyl)phenyl)(methyl)sulfane to replace α-bromo-m-tolunitrile, 1'-[4(methylsulfanyl)benzyl]-5,6-dihydrospiro[benzo[1,2-b:5,4-b']difuran-3,3'-indol]-2'(1'H)-one was obtained (61%) as a colorless solid: MS (ES+) m/z: 416.2 (M+1).

EXAMPLE 4.72

Synthesis of 1'-{[(2S)-5-oxopyrrolidin-2-yl]methyl}spiro[furo[2,3-f][1,3]benzodioxole-7,3'-indol]-2'(1'H)-one

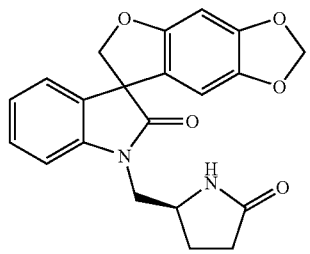

Following the procedure as described in EXAMPLE 4 and making non-critical variations using (R)-3-bromomethyl-2-pyrrolidinone to replace 2-(bromomethyl)tetrahydro-2H-pyran, and spiro[furo[2,3-f][1,3]benzodioxole-7,3'-indol]-2'(1'H)-one to replace 5,6-dihydrospiro[benzo[1,2-b:5,4-b']difuran-3,3'-indol]-2"(1'H)-one, 1'-{[(2S)-5-oxopyrrolidin-2-yl]methyl}spiro[furo[2,3-f][1,3]benzodioxole-7,3'-indol]-2'(1'H)-one was obtained (47%) as a colorless solid: mp 121-130° C.; $^1$H NMR (300 MHz, CD$_3$OD) δ7.34 (dd, J=7.6, 7.6 Hz, 1H), 7.22-7.06 (m, 4H), 6.48 (d, J=1.9 Hz, 1H), 6.15 (d, J=9.3 Hz, 1H), 5.82 (d, J=1.4 Hz, 2H), 4.86-4.81 (m, 2H), 4.64 (dd, J=9.3, 3.8 Hz, 1H), 4.13-4.06 (m, 1H), 3.85-3.83 (m, 2H), 2.43-2.18 (m, 2H), 2.00-1.88 (m, 1H); $^{13}$C NMR (75 MHz, CD$_3$OD) δ177.9, 177.4, 177.3, 154.7, 154.6, 147.5, 147.4, 141.2, 140.8, 140.8 136.0, 130.8, 130.6, 127.3 127.2, 127.0, 126.3, 123.4, 122.0, 121.9, 121.9 118.0, 117.8, 107.4, 101.1, 100.0, 99.9, 91.3, 91.3, 78.8, 78.7, 56.8 (2C), 51.4, 51.2, 43.2 (2C), 27.6, 22.6, 18.6; MS (ES+) m/z 401.2 (M+23), 379.2 (M+1).

EXAMPLE 4.73

Synthesis of (2'-oxospiro[furo[2,3-f][1,3]benzodioxole-7,3'-indol]-1'(2'H)-yl)acetonitrile

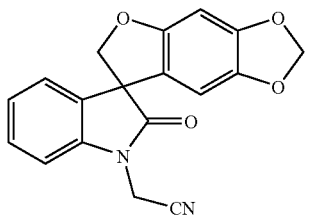

Following the procedure as described in EXAMPLE 4 and making non-critical variations using chloroacetonitrile to replace 2-(bromomethyl)tetrahydro-2H-pyran, and spiro[furo[2,3-f][1,3]benzodioxole-7,3'-indol]-2'(1'H)-one to replace 5,6-dihydrospiro[benzo[1,2-b:5,4-b']difuran-3,3'-indol]-2'(1'H)-one, (2'-oxospiro[furo[2,3-f][1,3]benzodioxole-7,3'-indol]-1'(2'H)-yl)acetonitrile was obtained (61%) as a colorless solid: mp 170-172° C.; $^1$H NMR (300 MHz, DMSO-d$_6$) δ7.38 (dt, J=7.7, 1.2 Hz, 1H), 7.26 (d, J=7.7 Hz, 1H), 7.20 (d, J=7.3 Hz, 1H), 7.11 (dt, J=7.7, 1.1 Hz, 1H), 6.66 (s, 1H), 6.21 (s, 1H), 5.89 (d, J=1.5 Hz, 2H), 4.94 (ABq, J=17.9 Hz, 2H), 4.73 (ABq, J=9.5 Hz, 2H); $^{13}$C NMR (75 MHz, DMSO-d$_6$) δ176.8, 155.8, 148.9, 142.232, 141.0, 131.9, 129.4, 124.3, 124.3, 119.8, 116.0, 109.7, 103.5, 101.9, 93.8, 80.1, 57.8, 28.8; MS (ES+) m/z 321.3 (M+1).

EXAMPLE 4.74

Synthesis of 7'-(trifluoromethyl)-1'-{[5-(trifluoromethyl)-2-furyl]methyl}spiro[furo[2,3-f][1,3]benzodioxole-7,3'-indol]-2'(1'H)-one

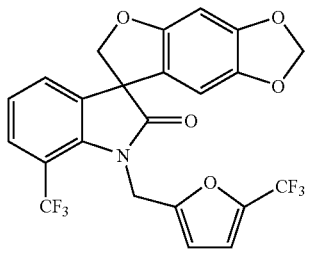

Following the procedure as described in EXAMPLE 4 and making non-critical variations using 5-bromomethyl-2-(trifluoromethyl)furan to replace 2-(bromomethyl)tetrahydro-2H-pyran, and 7'-(trifluoromethyl)spiro[furo[2,3-f][1,3]benzodioxole-7,3'-indol]-2'(1'H)-one to replace 5,6-dihydrospiro[benzo[1,2-b:5,4-b'd]furan-3,3'-indol]-2"(1'H)-one, 7'-(trifluoromethyl)-1'-{[5-(trifluoromethyl)-2-furyl]methyl}spiro[furo[2,3-f][1,3]benzodioxole-7,3'-indol]-2'(1'H)-one was obtained (43%) as a colorless solid: mp 95-98° C.; $^1$H NMR (300 MHz, CDCl$_3$) δ7.59 (d, J=8.1 Hz, 1H), 7.36 (d, J=7.3 Hz, 1H), 7.15 (dd, J=7.8, 7.8 Hz, 1H), 6.69 (d, J=3.2 Hz, 1H), 6.50 (s, 1H), 6.23 (d, J=3.0 Hz, 1H), 6.10 (s, 1H), 5.86 (d, J=3.0 Hz, 2H), 5.23 (ABq, 2H), 4.78 (ABq, 2H); $^{13}$C NMR (75 MHz, CDCl$_3$) δ178.6, 156.0, 152.2, 149.3, 142.7, 141.4 (q), 139.1, 135.1, 127.9, 127.0 (m), 122.9 (d), 121.1 (d), 119.3 (d), 118.7, 113.4 (q), 112.5, 108.2, 102.8, 101.7, 93.7, 80.8, 56.9, 39.4; MS (ES+) m/z 498.4 (M+1).

EXAMPLE 4.75

Synthesis of 1-[(5-chloro-2-thienyl)methyl]-7'-(trifluoromethyl)spiro[furo[2,3-f][1,3]benzodioxole-7,3'-indol]-2'(1'H)-one

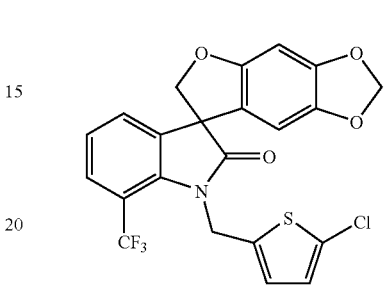

Following the procedure as described in EXAMPLE 4 and making non-critical variations using 2-chloro-5-(chloromethyl)thiophene to replace 2-(bromomethyl)tetrahydro-2H-pyran, and 7'-(trifluoromethyl)spiro[furo[2,3-f][1,3]benzodioxole-7,3'-indol]-2'(1'H)-one to replace 5,6-dihydrospiro[benzo[1,2-b:5,4-b']difuran-3,3'-indol]-2"(1'H)-one, 1'-[(5-chloro-2-thienyl)methyl]-7'-(trifluoromethyl)spiro[furo[2,3-f][1,3]benzodioxole-7,3'-indol]-2'(1'H)-one was obtained (95%) as a colorless solid: mp 165-166° C.; $^1$H NMR (300 MHz, DMSO-d$_6$) δ 7.66 (d, J=8.0 Hz, 1H), 7.49 (d, J=7.2 Hz, 1H), 7.24 (dd, J=7.8, 7.8 Hz, 1H), 6.93 (d, J=3.8 Hz, 1H), 6.80 (d, J=3.8 Hz, 1H), 6.70 (s, 1H), 6.22 (s, 1H), 5.91 (d, J=4.4 Hz, 2H), 5.09 (ABq, 2H), 4.78 (ABq, 2H); $^{13}$C NMR (75 MHz, DMSO-d$_6$) δ178.9, 156.2, 149.2, 142.4, 139.9 (2C), 138.7, 135.4, 129.1, 127.4, 127.2, 126.9, 125.9, 123.9, 119.4, 111.5, 103.5, 102.0, 93.9, 80.7, 56.5, 42.3; MS (ES+) m/z 481.2 (M+1), 479.9 (M+1).

EXAMPLE 4.76

Synthesis of 1'-[(2-isopropyl-1,3-thiazol-5-yl)methyl]-7'-(trifluoromethyl)spiro[furo[2,3-f][1,3]benzodioxole-7,3'-indol]-2'(1'H)-one

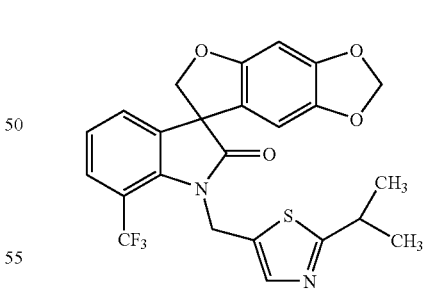

Following the procedure as described in EXAMPLE 4 and making non-critical variations using 5-chloromethyl-2-(isopropyl)thiazole to replace 2-(bromomethyl)tetrahydro-2H-pyran, and 7'-(trifluoromethyl)spiro[furo[2,3-f][1,3]benzodioxole-7,3'-indol]-2'(1'H)-one to replace 5,6-dihydrospiro[benzo[1,2-b:5,4-b']difuran-3,3'-indol]-2"(1'H)-one, 1'-[(2-isopropyl-1,3-thiazol-5-yl)methyl]-7'-(trifluoromethyl)spiro[furo[2,3-f][1,3]benzodioxole-7,3'-indol]-2'(1'H)-one was obtained (51%) as a colorless solid: mp 101-103° C.; $^1$H NMR (300 MHz, DMSO-d$_6$) δ7.61 (d, J=8.1 Hz, 1H), 7.48 (d, J=6.8 Hz, 1H), 7.23 (dd J=7.8, 7.8 Hz, 1H), 7.18 (s, 1H), 6.69

(s, 1H), 6.48 (s, 1H), 5.91 (s, 2H), 5.08 (ABq, 2H), 4.77 (ABq, 2H), 3.21-3.16 (m, 1H), 1.22 (d, J=6.9 Hz, 6H); $^{13}$C NMR (75 MHz, DMSO-d$_6$) δ178.7, 177.4, 156.0, 150.7, 149.0, 142.3, 140.7, 135.6, 128.7, 125.7, 124.5 (d), 123.6, 119.8, 113.3, 111.5 (m), 103.9, 101.9, 93.8, 80.8, 56.6, 43.3, 32.8, 23.3; MS (ES+) m/z 489.4 (M+1).

EXAMPLE 4.77

Synthesis of 1'-[(2-isopropyl-1,3-oxazol-5-yl)methyl]spiro[furo[2,3-f][1,3]benzodioxole-7,3'-indol]-2'(1'H)-one

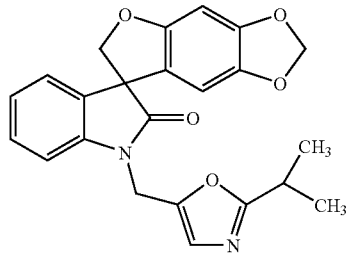

Following the procedure as described in EXAMPLE 4 and making non-critical variations using 5-chloromethyl-2-isopropyloxazole to replace 2-(bromomethyl)tetrahydro-2H-pyran, and spiro[furo[2,3-f][1,3]benzodioxole-7,3'-indol]-2'(1'H)-one to replace 5,6-dihydrospiro[benzo[1,2-b:5,4-b']difuran-3,3'-indol]-2'(1'H)-one, 1'-[(2-isopropyl-1,3-oxazol-5-yl)methyl]spiro[furo[2,3-f][1,3]benzodioxole-7,3'-indol]-2'(1'H)-one was obtained (11%) as a colorless solid: mp 75-77° C.; $^1$H NMR (300 MHz, CDCl$_3$) δ7.42 (s, 1H), 7.26 (dd, J=7.4, 7.4 Hz, 1H), 7.15 (d, J=7.3 Hz, 1H), 7.07-7.00 (m, 2H), 6.48 (s, 1H), 6.15 (s, 1H), 5.83 (d, J=4.2 Hz, 2H), 4.83 (ABq, 2H), 4.78 (ABq, 2H), 3.10-2.95 (m, 1H), 1.30 (d, J=7.0 Hz, 6H); $^{13}$C NMR (75 MHz, DMSO-d$_6$) δ177.3, 169.4, 155.8, 148.9, 142.3, 141.8, 135.3, 135.1, 132.2, 128.9, 123.8, 123.5, 119.5, 109.6, 103.1, 101.5, 93.6, 80.3, 58.2, 36.6, 28.5, 20.4, 20.3; MS (ES+) m/z 405.4 (M+1).

EXAMPLE 4.78

Synthesis of tert-butyl [1-cyclopropyl-3-(2'-oxospiro[furo[2,3-f][1,3]benzodioxole-7,3'-indol]-1'(2'H)-yl)propyl]carbamate

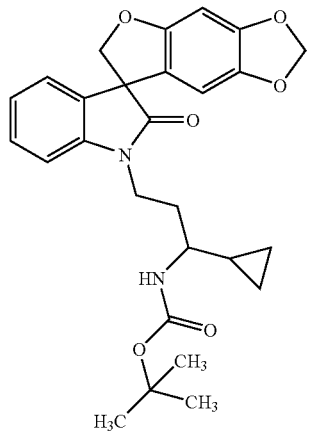

Following the procedure as described in EXAMPLE 4 and making non-critical variations using tert-butyl-3-bromomethyl-1-cyclopropyl carbamate to replace 2-(bromomethyl)tetrahydro-2H-pyran, and spiro[furo[2,3-f][1,3]benzodioxole-7,3'-indol]-2'(1'H)-one to replace 5,6-dihydrospiro[benzo[1,2-b:5,4-b']difuran-3,3'-indol]-2'(1'H)-one, tert-butyl [1-cyclopropyl-3-(2'-oxospiro[furo[2,3-f][1,3]benzodioxole-7,3'-indol]-1'(2'H)-yl)propyl]carbamate was obtained (91%) as a fluffy yellow solid: $^1$H NMR (300 MHz, CDCl$_3$) δ7.28 (dd, J=7.7, 7.7 Hz, 1H), 7.13 (d, J=6.9 Hz, 1H), 7.02 (dd, J=7.2, 7.2 Hz, 1H), 6.90 (d, J=7.8 Hz, 1H), 6.47 (s, 1H), 6.11 (d, J=4.9 Hz, 1H), 5.83 (d, J=5.5 Hz, 2H), 4.88 (dd, J=8.9, 7.0, Hz, 1H), 4.69 (br, 1H), 4.62 (dd, J=8.9, 1.7 Hz, 1H), 3.93-3.73 (m, 2H), 2.99 (br, 1H), 2.14-1.81 (m, 2H), 1.30 (s, 9H), 0.95-0.80 (m, 1H), 0.58-0.19 (m, 4H); $^{13}$C NMR (75 MHz, CDCl$_3$) δ177.3, 177.3, 155.9, 155.7, 155.6, 148.8, 142.3, 142.2, 132.4, 129.0, 123.9, 123.3, 119.5, 119.4, 108.6, 103.1, 103.0, 101.5, 93.6, 80.4 (2C), 65.9, 58.2, 37.8, 37.5, 32.9, 32.7, 28.4, 16.1 (2C), 15.3, 3.9, 3.8, 3.0, 2.9; MS (ES+) m/z 501.3, (M+23), 479.28 (M+1), 423.2 (M−56), 379.3 (M−100).

EXAMPLE 4.79

Synthesis of 1'-[4-(methylsulfanyl)benzyl]spiro[furo[2,3-f][1,3]benzodioxole-7,3'-indol]-2'(1'H)-one

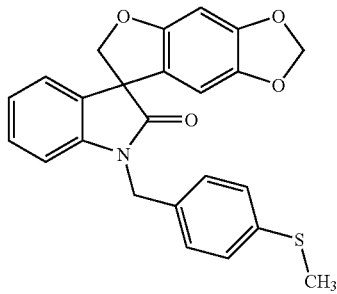

Following the procedure as described in EXAMPLE 4 and making non-critical variations using 4-(methylthio)benzyl bromide to replace 2-(bromomethyl)tetrahydro-2H-pyran, and spiro[furo[2,3-f][1,3]benzodioxole-7,3'-indol]-2'(1'H)-one to replace 5,6-dihydrospiro[benzo[1,2-b:5,4-b']difuran-3,3'-indol]-2'(1'H)-one, 1'-[4-(methylsulfanyl)benzyl]spiro[furo[2,3-f][1,3]benzodioxole-7,3'-indol]-2'(1'H)-one was obtained (86%) as a colorless solid: mp 128-130° C.; $^1$H NMR (300 MHz, DMSO-d$_6$) δ7.28-7.19 (m, 5H), 7.14 (d, J=7.0 Hz, 1H), 7.00 (d, J=7.5 Hz, 1H), 6.96 (d, J=7.8 Hz, 1H), 6.68 (s, 1H), 6.14 (s, 1H), 5.89 (d, J=1.9 Hz, 2H), 4.87-4.79 (m, 3H), 4.67 (d, J=9.3 Hz, 1H), 2.40 (s, 3H); $^{13}$C NMR (75 MHz, DMSO-d$_6$) δ177.3, 155.9, 148.8, 142.6, 142.2, 137.8, 133.3, 132.1, 129.3, 128.4, 126.6, 124.2, 123.6, 120.1, 109.9, 103.3, 101.9, 93.8, 80.4, 57.9, 43.2, 15.1; MS (ES+) m/z 418.1 (M+1).

EXAMPLE 4.80

Synthesis of 3-(2'-oxospiro[furo[2,3-f][1,3]benzodioxole-7,3'-indol]-1'(2'H)-yl)propanenitrile

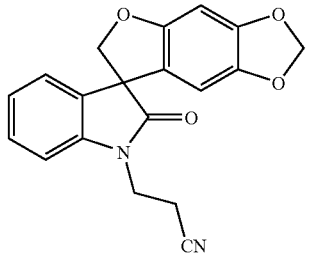

Following the procedure as described in PREPARATION 44 and making non-critical variations using 3-bromopropionitrile to replace α-bromo-m-tolunitrile, and spiro[furo[2,3-f][1,3]benzodioxole-7,3'-indol]-2'(1'H)-one to replace 5,6-dihydrospiro[benzo[1,2-b:5,4-b']difuran-3,3'-indol]-2'(1'H)- one, 3-(2'-oxospiro[furo[2,3-f][1,3]benzodioxole-7,3'-indol]-1'(2'H)-yl)propanenitrile was obtained (86%) as a colorless solid: mp 200-202° C.; $^1$H NMR (300 MHz, DMSO-d$_6$) δ7.32 (ddd, J=7.6, 7.4, 1.2 Hz, 1H), 7.24 (d, J=7.6 Hz, 1H), 7.15 (d, J=6.7 Hz, 1H), 7.04 (ddd, J=7.4, 7.4, 1.0 Hz, 1H), 6.66 (s, 1H), 6.24 (s, 1H), 5.89 (d, J=2.2 Hz, 2H), 4.69 (ABq, J=9.3 Hz, 2H), 4.10-3.88 (m, 2H), 2.95 (t, J=6.5 Hz, 2H); $^{13}$C NMR (75 MHz, DMSO-d$_6$) δ 177.1, 155.8, 148.8, 142.2, 141.9, 132.3, 129.3, 124.1, 123.7, 120.1, 119.1, 109.8 103.6, 101.9, 93.7, 80.3, 57.9, 35.9, 16.2; MS (ES+) m/z 335.1 (M+1).

EXAMPLE 4.81

Synthesis of 1'-[(2-bromo-1,3-thiazol-5-yl)methyl]spiro[furo[2,3-f][1,3]benzodioxole-7,3'-indol]-2'(1'H)-one

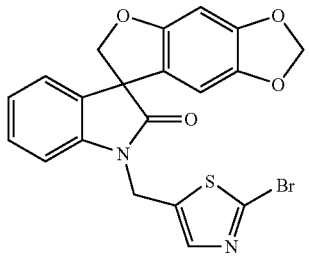

Following the procedure as described in EXAMPLE 4 and making non-critical variations using 2-bromo-(5-bromomethyl)thiazole to replace 2-(bromomethyl)tetrahydro-2H-pyran, and spiro[furo[2,3-f][1,3]benzodioxole-7,3'-indol]-2'(1'H)-one to replace 5,6-dihydrospiro[benzo[1,2-b:5,4-b']difuran-3,3'-indol]-2'(1'H)-one, 1'-[(2-bromo-1,3-thiazol-5-yl)methyl]spiro[furo[2,3-f][1,3]benzodioxole-7,3'-indol]-2'(1'H)-one was obtained (94%) as a colorless solid: mp 215-217° C.; $^1$H NMR (300 MHz, DMSO-d$_6$) δ7.81 (s, 1H), 7.34-7.24 (m, 2H), 7.15 (d, J=7.2 Hz, 1H), 7.03 (ddd, J=7.3, 7.3, 1.3 Hz, 1H), 6.67 (s, 1H), 6.13 (s, 1H), 5.89 (d, J=3.9 Hz, 2H), 5.11 (s, 2H), 4.69 (ABq, 2H); $^{13}$C NMR (75 MHz, DMSO-d$_6$) δ177.0, 155.9, 148.9, 142.9, 142.2, 141.7, 138.2, 136.4, 132.1, 129.4, 124.3, 123.9, 119.9, 109.7, 103.4, 101.9, 93.8, 80.2, 57.8, 36.3; MS (ES+) m/z 458.9 (M+1), 456.9 (M+1).

EXAMPLE 4.82

Synthesis of 1'-{[2-amino-4-(trifluoromethyl)-1,3-thiazol-5-yl]methyl}spiro[furo[2,3-f][1,3]benzodioxole-7,3'-indol]-2'(1'H)-one

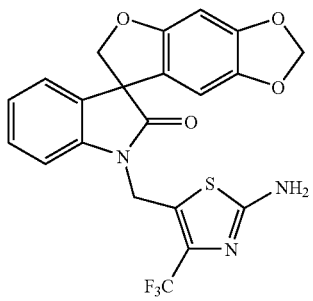

Following the procedure as described in EXAMPLE 4 and making non-critical variations using 5-(chloromethyl)-4-(trifluoromethyl)thiazol-2-amine to replace 2-(bromomethyl)tetrahydro-2H-pyran, and spiro[furo[2,3-f][1,3]benzodiox-ole-7,3'-indol]-2"(1'H)-one to replace 5,6-dihydrospiro[benzo[1,2-b:5,4-b']difuran-3,3'-indol]-2'(1'H)-one, 1'-{[2-amino-4-(trifluoromethyl)-1,3-thiazol-5-yl]methyl}spiro[furo[2,3-f][1,3]benzodioxole-7,3'-indol]-2'(1'H)-one was obtained (4.0%) as a colorless solid: mp 165-167° C.; $^1$H NMR (300 MHz, DMSO-d$_6$) δ7.39 (br, 2H), 7.32 (dd, J=7.7, 7.7 Hz, 1H), 7.18 (d, J=6.7 Hz, 1H), 7.05 (dd, J=7.5, 7.5 Hz, 1H), 6.98 (d, J=7.8 Hz, 1H), 6.69 (s, 1H), 6.12 (s, 1H), 5.91 (s, 2H), 5.02 (ABq, 2H), 4.70 (ABq, 2H); $^{13}$C NMR (75 MHz, DMSO-d$_6$) δ176.8, 167.9, 155.9, 148.9, 142.2, 141.8, 134.7 (q, $^1J_{CF}$=135 Hz), 132.1, 129.5, 124.5, 123.9, 123.8 (m), 119.9, 109.2, 103.2, 101.9, 93.9, 80.2, 57.8, 40.9; MS (ES+) m/z 462.1 (M+1).

EXAMPLE 4.83

Synthesis of 6-fluoro-5-methoxy-1'-{[5-(trifluoromethyl)furan-2-yl]methyl}spiro[1-benzofuran-3,3'-indol]-2'(1'H)-one

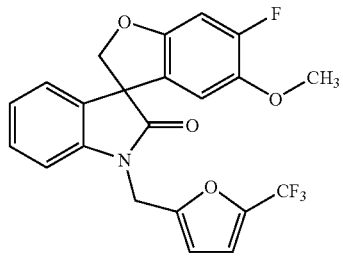

Following the procedure as described in EXAMPLE 4 and making non-critical variations using 5-bromomethyl-2-(trifluoromethyl)furan to replace 2-(bromomethyl)tetrahydro-2H-pyran, and 6-fluoro-5-methoxyspiro[1-benzofuran-3,3'-indol]-2'(1'H)-one to replace 5,6-dihydrospiro[benzo[1,2-b:5,4-b']difuran-3,3'-indol]-2"(1'H)-one, 6-fluoro-5-methoxy-1'-{[5-(trifluoromethyl)furan-2-yl]methyl}spiro[1-benzofuran-3,3'-indol]-2'(1'H)-one was obtained (43%) as a colorless solid: mp 132-134° C.; $^1$H NMR (300 MHz, CDCl$_3$) δ7.58 (d, J=9.4 Hz, 1H), 7.27 (dd, J=7.7, 7.7 Hz, 1H), 7.06-7.01 (m, 2H), 6.84 (d, J=7.9 Hz, 1H), 6.71-6.67 (m, 2H), 6.62 (d, J=12.1 Hz, 1H), 6.34 (d, J=3.4 Hz, 1H), 6.10 (d, J=3.4 Hz, 1H), 4.90 (d, J=16.3 Hz, 1H), 4.57 (d, J=12.8 Hz, 1H), 4.45 (d, J=12.7 Hz, 1H), 4.41 (d, J=16.2 Hz, 1H), 3.91 (s, 3H); MS (ES+) m/z 433.9 (M+1).

EXAMPLE 4.84

Synthesis of 4'-chloro-2'-oxospiro[furo[2,3-f][1,3]benzodioxole-7,3'-indol]-1'(2'H)-yl)acetonitrile

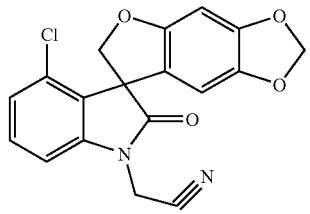

Following the procedure as described in EXAMPLE 4 and making non-critical variations using chloroacetonitrile to replace 2-(bromomethyl)tetrahydro-2H-pyran, and 4'-chlorospiro[furo[2,3-f][1,3]benzodioxole-7,3'-indol]-2'(1'H)-one to replace 5,6-dihydrospiro[benzo[1,2-b:5,4-b']difuran- 3,3'-indol]-2''(1'H)-one, 4'-chloro-2'-oxospiro[furo[2,3-f][1,3]benzodioxole-7,3'-indol]-1'(2'H)-yl)acetonitrile was obtained (94%) as a colorless solid: mp 122-123° C.; $^1$H NMR (300 MHz, DMSO-d$_6$) δ7.41 (dd, J=8.0, 8.0 Hz, 1H), 7.27 (d, J=7.9 Hz, 1H), 7.11 (d, J=8.1 Hz, 1H), 6.62 (s, 1H), 6.29 (s, 1H), 5.90 (d, J=1.9 Hz, 2H), 4.95 (ABq, 2H), 4.79 (ABq, 2H); $^{13}$C NMR (75 MHz, DMSO-d$_6$) δ176.4, 156.7, 149.2, 143.0, 141.9, 131.1, 130.4, 128.4, 124.6, 116.8, 115.8, 108.8, 103.3, 101.9, 93.4, 77.6, 58.3, 29.2; MS (ES+) m/z 355.2 (M+1).

EXAMPLE 4.85

Synthesis of 1'-[(2-amino-1,3-thiazol-4-yl)methyl]spiro[furo[2,3-f][1,3]benzodioxole-7,3'-indol]-2'(1'H)-one

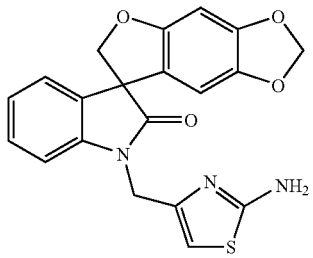

Following the procedure as described in EXAMPLE 4 and making non-critical variations using 2-amino-(5-chloromethyl)thiazole to replace 2-(bromomethyl)tetrahydro-2H-pyran, and spiro[furo[2,3-f][1,3]benzodioxole-7,3'-indol]-2'(1'H)-one to replace 5,6-dihydrospiro[benzo[1,2-b:5,4-b']difuran-3,3'-indol]-2'(1'H)-one, 1'-[(2-amino-1,3-thiazol-4-yl)methyl]spiro[furo[2,3-f][1,3]benzodioxole-7,3'-indol]-2'(1'H)-one was obtained (73%) as a yellow solid: mp 230-235° C.; $^1$H NMR (300 MHz, DMSO-d$_6$) δ7.24 (dd, J=7.7, 7.7 Hz, 1H), 7.12 (d, J=7.2 Hz, 1H), 7.04-6.96 (m, 2H), 6.93 (s, 2H), 6.65 (s, 1H), 6.37 (s, 1H), 6.22 (s, 1H), 5.89 (s, 2H), 4.76 (d, J=9.3 Hz, 1H), 4.67-4.59 (m, 3H); $^{13}$C NMR (75 MHz, DMSO-d$_6$) δ177.6, 166.8, 155.9, 148.9, 146.8, 143.9, 142.3, 131.8, 129.6, 129.6, 124.3, 120.3, 109.9, 109.8, 103.1, 101.9, 93.9, 80.4, 57.8, 14.8; MS (ES+) m/z 394.3 (M+1).

EXAMPLE 4.86

Synthesis of 4'-bromo-1'-[1(5-chloro-2-thienyl)methyl]spiro[furo[2,3-f][1,3]benzodioxole-7,3'-indol]-2'(1'H)-one

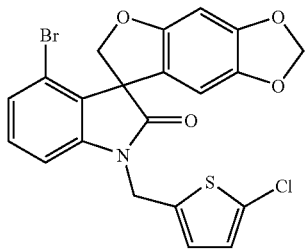

Following the procedure as described in EXAMPLE 4 and making non-critical variations using 2-chloro-5-(chloromethyl)thiophene to replace 2-(bromomethyl)tetrahydro-2H-pyran, and 4'-bromospiro[furo[2,3-f][1,3]benzodioxole-7,3'-indol]-2'(1'H)-one to replace 5,6-dihydrospiro[benzo[1,2-b:5,4-b']difuran-3,3'-indol]-2'(1'H)-one, 4'-bromo-1'-[1(5-chloro-2-thienyl)methyl]spiro[furo[2,3-f][1,3]benzodioxole-7,3'-indol]-2'(1'H)-one was obtained (95%) as a colorless solid: mp 85-87° C.; $^1$H NMR (300 MHz, DMSO-d$_6$) δ 7.19-7.11 (m, 2H), 6.88-6.85 (m, 2H), 6.76 (d, J=3.8 Hz, 1H), 6.47 (s, 1H), 6.06 (s, 1H), 5.87 (d, J=5.8 Hz, 2H), 4.97 (ABq, 2H), 4.91 (d, J=9.2 Hz, 2H); $^{13}$C NMR (75 MHz, DMSO-d$_6$) δ176.9, 157.2, 156.9, 149.3, 143.3, 142.1, 136.3, 130.3, 129.8, 127.7, 126.3, 126.0, 120.2, 116.1, 107.9, 102.6, 101.6, 93.3, 77.2, 59.5, 39.4; MS (ES+) m/z 490.3 (M+1), 488.2 (M+1).

EXAMPLE 4.87

Synthesis of 1'-[(5-chloro-2-thienyl)methyl]-2'-oxo-1',2'-dihydrospiro[furo[2,3-f][1,3]benzodioxole-7,3'-indole]-7'-carbonitrile

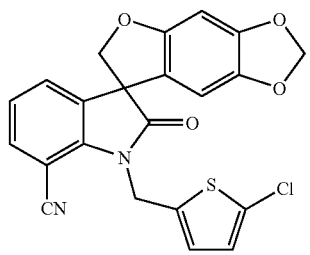

Following the procedure as described in EXAMPLE 4 and making non-critical variations using 2-chloro-5-(chloromethyl)thiophene to replace 2-(bromomethyl)tetrahydro-2H-pyran, and 2'-oxo-1',2'-dihydrospiro[furo[2,3-f][1,3]benzodioxole-7,3'-indole]-7'-carbonitrile to replace 5,6-dihydrospiro[benzo[1,2-b:5,4-b']difuran-3,3'-indol]-2'(1'H)-one, 1'-[(5-chloro-2-thienyl)methyl]-2'-oxo-1',2'-dihydrospiro[furo[2,3-f][1,3]benzodioxole-7,3'-indole]-7'-carbonitrile was obtained (78%) as a colorless solid: mp 192-193° C. (diethyl ether); $^1$H NMR (300 MHz, DMSO-d$_6$) δ 7.72 (dd, J=8.0, 1.1 Hz, 1H), 7.54 (dd, J=7.4, 1.1 Hz, 1H), 7.21 (dd, J=7.7, 7.7 Hz, 1H), 7.03 (s, 2H), 6.73 (s, 1H), 6.35 (s, 1H), 5.95 (dd, J=4.0, 0.7 Hz, 2H), 5.29 (d, J=1.5 Hz, 2H), 4.78 (dd, J=20.4, 9.6 Hz, 2H); $^{13}$C NMR (75 MHz, DMSO-d$_6$) δ 177.0, 155.5, 148.7, 143.2, 141.8, 137.6, 133.6, 133.2, 128.8, 127.7, 126.6, 126.5, 123.7, 118.5, 116.9, 103.0, 101.5, 93.4, 92.6, 79.5, 56.4, 40.0; MS (ES+) m/z 437.3 (M+1), 439.3 (M+1).

EXAMPLE 4.88

Synthesis of 1'-[(2-isopropyl-1,3-thiazol-4-yl)methyl]-2'-oxo-1',2'-dihydrospiro[furo[2,3-f][1,3]benzodioxole-7,3'-indole]-7'-carbonitrile

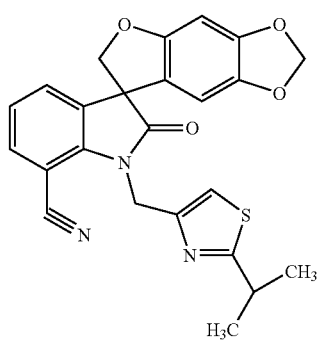

Following the procedure as described in EXAMPLE 4 and making non-critical variations using 4-(chloromethyl)-2-isopropylthiazole to replace 2-(bromomethyl)tetrahydro-2H-pyran, and 2'-oxo-1',2'-dihydrospiro[furo[2,3-f][1,3]benzodioxole-7,3'-indole]-7'-carbonitrile to replace 5,6-dihydrospiro[benzo[1,2-b:5,4-b']difuran-3,3'-indol]-2'(1'H)-one, 1-[(2-isopropyl-1,3-thiazol-4-yl)methyl]-2'-oxo-1',2'-dihydrospiro[furo[2,3-f][1,3]benzodioxole-7,3'-indole]-7'-carbonitrile was obtained (74%) as a colorless solid: mp=162-163° C. (diethyl ether/hexanes); $^1$H NMR (300 MHz, DMSO-d$_6$) δ 7.66 (dd, J=8.0, 1.2 Hz, 1H), 7.52 (dd, J=7.4, 1.2 Hz, 1H), 7.39 (s, 1H), 7.19 (dd, J=7.7, 7.7 Hz, 1H), 6.72 (s, 1H), 6.42 (s, 1H), 5.94 (s, 2H), 5.25 (ABq, 2H), 4.80 (ABq, 2H), 3.28-3.15 (m, 1H), 1.26 (d, J=6.9 Hz, 6H); $^{13}$C NMR (75 MHz, DMSO-d$_6$) δ 177.5, 176.9, 155.4, 149.7, 148.6, 144.0, 141.8, 133.8, 133.1, 128.4, 123.4, 119.0, 116.5, 114.3, 103.1, 101.5, 93.3, 93.1, 79.4, 56.5, 40.9, 32.4, 22.7; MS (ES+) m/z 446.2 (M+1).

EXAMPLE 4.89

Synthesis of 4'-chloro-1'-[(5-chloro-2-thienyl)methyl]spiro[furo[2,3-f][1,3]benzodioxole-7,3'-indol]-2'(1'H)-one

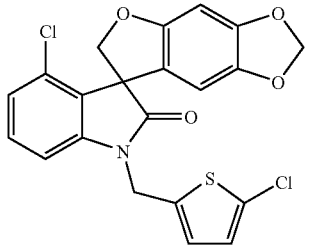

Following the procedure as described in EXAMPLE 4 and making non-critical variations using 2-chloro-5-(chloromethyl)thiophene to replace 2-(bromomethyl)tetrahydro-2H-pyran, and 4'-chlorospiro[furo[2,3-f][1,3]benzodioxole-7,3'-indol]-2'(1'H)-one to replace 5,6-dihydrospiro[benzo[1,2-b:5,4-b']difuran-3,3'-indol]-2'(1'H)-one, 4'-chloro-1'-[(5-chloro-2-thienyl)methyl]spiro[furo[2,3-f][1,3]benzodioxole-7,3'-indol]-2'(1'H)-one was obtained (67%) as a colorless solid: mp 167-168° C. (diethyl ether/hexanes); $^1$H NMR (300 MHz, DMSO-d$_6$) δ 7.36 (dd, J=8.0, 8.0 Hz, 1H), 7.20-7.18 (m, 2H), 7.08 (dd, J=8.0, 0.7 Hz, 1H), 6.77 (d, J=3.4 Hz, 1H), 6.66 (s, 1H), 6.12 (s, 1H), 5.94 (s, 2H), 5.09 (ABq, 2H), 4.92 (d, J=9.8 Hz, 1H), 4.75 (d, J=9.8 Hz, 1H); $^{13}$C NMR (75 MHz, DMSO-d$_6$) δ 176.1, 156.2, 148.5, 143.3, 141.5, 137.5, 130.5, 129.8, 127.8, 127.7, 127.3, 126.5, 123.6, 116.5, 108.3, 102.4, 101.4, 92.9, 77.0, 57.8, 38.7; MS (ES+) m/z 446.2 (M+1), 448.2 (M+1).

EXAMPLE 4.90

Synthesis of 4'-chloro-1'-{[5-(trifluoromethyl)-2-furyl]methyl}spiro[furo[2,3-f][1,3]benzodioxole-7,3'-indol]-2'(1'H)-one

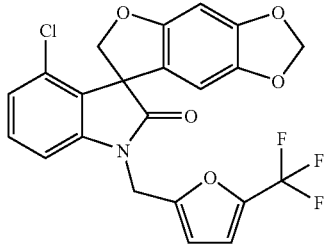

Following the procedure as described in EXAMPLE 4 and making non-critical variations using 2-bromomethyl-5-(trifluoromethyl)furan to replace 2-(bromomethyl)tetrahydro-2H-pyran, and 4'-chlorospiro[furo[2,3-f][1,3]benzodioxole-7,3'-indol]-2'(1'H)-one to replace 5,6-dihydrospiro[benzo[1,2-b:5,4-b']difuran-3,3'-indol]-2"(1'H)-one, 4'-chloro-1'-{[5-(trifluoromethyl)-2-furyl]methyl}spiro[furo[2,3-f][1,3]benzodioxole-7,3'-indol]-2'(1'H)-one was obtained (43%) as a colorless solid: $^1$H NMR (300 MHz, DMSO-d$_6$) δ 7.36 (dd, J=8.0, 8.0 Hz, 1H), 7.20-7.18 (m, 2H), 7.08 (dd, J=0.7 Hz, 8.0 Hz, 1H), 6.77 (d, J=3.4 Hz, 1H), 6.66 (s, 1H), 6.12 (s, 1H), 5.94 (s, 2H), 5.09 (ABq, 2H), 4.92 (d, J=9.8 Hz, 1H), 4.75 (d, J=9.8 Hz, 1H); $^{13}$C NMR (75 MHz, DMSO-d$_6$) δ 176.1, 156.1, 152.7, 148.6, 143.4, 141.5, 139.5 (q, $^2J_{CF}$=42 Hz), 130.5, 129.7, 127.9, 123.6, 118.8 (q, $^1J_{CF}$=267 Hz), 116.6, 114.0 (d, $^3J_{CF}$=3 Hz), 109.9, 108.2, 102.2, 101.4, 92.9, 76.9, 57.9, 36.7; MS (ES+) m/z 464.3 (M+1), 466.3 (M+1).

EXAMPLE 4.91

Synthesis of 4'-chloro-1'-[(2-isopropyl-1,3-thiazol-4-yl)methyl]spiro[furo[2,3-f][1,3]benzodioxole-7,3'-indol]-2'(1'H)-one

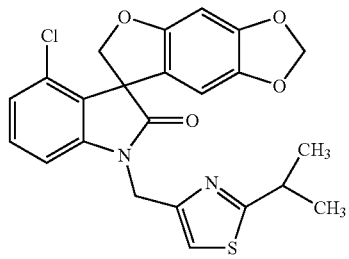

Following the procedure as described in EXAMPLE 4 and making non-critical variations using 4-(chloromethyl)-2-isopropylthiazole to replace 2-(bromomethyl)tetrahydro-2H-pyran, and 4'-chlorospiro[furo[2,3-f][1,3]benzodioxole-7,3'-indol]-2'(1'H)-one to replace 5,6-dihydrospiro[benzo[1,2-b:5,4-b']difuran-3,3'-indol]-2"(1'H)-one, 4'-chloro-1'-[(2-isopropyl-1,3-thiazol-4-yl)methyl]spiro[furo[2,3-f][1,3]benzodioxole-7,3'-indol]-2'(1'H)-one was obtained (62%) as a colorless solid: mp 147-148° C. (diethyl ether/hexanes); $^1$H NMR (300 MHz, DMSO-d$_6$) δ 7.47 (s, 1H), 7.31 (dd, J=8.0, 8.0 Hz, 1H), 7.04 (d, J=8.0 Hz, 2H), 6.65 (s, 1H), 6.33 (s, 1H), 5.94 (s, 2H), 5.09 (d, J=16 Hz, 1H), 4.93 (d, J=9.7 Hz, 1H), 4.91 (d, J=16 Hz, 1H), 4.76 (d, J=9.7 Hz, 1H); $^{13}$C NMR (75 MHz, DMSO-d$_6$) δ 177.5, 176.1, 156.1, 149.5, 148.5, 144.1, 141.4, 130.3, 129.6, 128.1, 123.2, 116.9, 115.2, 108.5, 102.7, 101.4, 92.8, 76.9, 57.9, 40.2, 32.4, 22.7, 22.6; MS (ES+) m/z 455.3 (M+1), 457.3 (M+1).

EXAMPLE 4.92

Synthesis of 4'-[6-(dimethylamino)pyridin-3-yl]-1'-{[2-(1-methylethyl)-1,3-thiazol-4-yl]methyl}spiro[furo[2,3-f][1,3]benzodioxole-7,3'-indol]-2'(1'H)-one

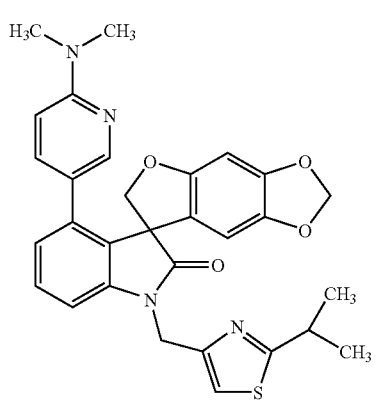

Following the procedure as described in EXAMPLE 4 and making non-critical variations using 4-(chloromethyl)-2-isopropylthiazole to replace 2-(bromomethyl)tetrahydro-2H-pyran, and 4'-[6-(dimethylamino)pyridin-3-yl]spiro[furo[2,3-f][1,3]benzodioxole-7,3'-indol]-2'(1'H)-one to replace 5,6-dihydrospiro[benzo[1,2-b:5,4-b']difuran-3,3'-indol]-2'(1'H)-one, 4'-[6-(dimethylamino)pyridin-3-yl]-1'-{[2-(1-methylethyl)-1,3-thiazol-4-yl]methyl}spiro[furo[2,3-f][1,3]benzodioxole-7,3'-indol]-2'(1'H)-one was obtained (73%) as a colorless solid: mp 164-165° C. (diethyl ether); $^1$H NMR (300 MHz, DMSO-$d_6$) δ 7.58 (d, J=2.3 Hz, 1H), 7.49 (s, 1H), 7.32 (dd, J=7.8, 7.8 Hz, 1H), 7.06 (d, J=7.9 Hz, 1H), 6.82-6.76 (m, 2H), 6.42-6.37 (m, 3H), 5.96 (d, J=19.0 Hz, 2H), 5.11 (d, J=16.0 Hz, 1H), 4.89 (d, J=16.0 Hz, 1H), 4.57 (d, J=9.4 Hz, 1H), 4.42 (d, J=9.4 Hz, 1H), 3.29-3.20 (m, 1H), 2.99 (s, 6H), 1.31 (d, J=6.9 Hz, 6H); $^{13}$C NMR (75 MHz, DMSO-$d_6$) δ 177.5, 176.9, 157.9, 155.4, 149.9, 148.3, 146.6, 142.6, 141.5, 136.8 (2C), 129.2, 128.8, 125.2, 121.7, 121.1, 115.3, 108.6, 104.3, 102.6, 101.3, 93.2, 77.2, 57.8, 37.6, 32.4, 22.8, 22.7; MS (ES+) m/z 541.3 (M+1).

EXAMPLE 4.93

Synthesis of 3'-[2-(fluoromethyl)benzyl]-2,3-dihydrospiro[furo[2,3-g][1,4]benzodioxine-8,1-inden]-2'(3'H)-one

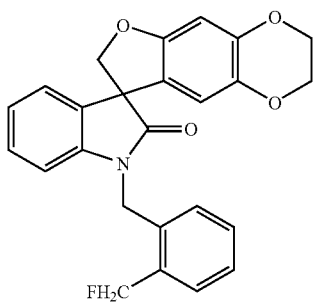

Following the procedure as described in EXAMPLE 4 and making non-critical variations using 1-(bromomethyl)-2-(fluoromethyl)benzene (Kirmse, W. et al. *J. Org. Chem.* (1994), 59(14):3821-3829) to replace 2-(bromomethyl)tetrahydro-2H-pyran, and 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2"(1'H)-one, 3'-[2-(fluoromethyl)benzyl]-2,3-dihydrospiro[furo[2,3-g][1,4]benzodioxine-8,1'-inden]-2'(3'H)-one was obtained (53%) as a colorless solid: mp 188-190° C.; $^1$H NMR (300 MHz, DMSO-$d_6$) δ 7.50 (d, J=6.6 Hz, 1H), 7.39-7.35 (m, 2H), 7.27-7.15 (m, 3H), 7.04 (dd, J=7.5, 7.5 Hz, 1H), 6.87 (d, J=7.8 Hz, 1H), 6.54 (s, 1H), 6.23 (s, 1H), 5.69-5.60 (m, 2H), 5.10-4.98 (m, 2H), 4.76 (ABq, 2H), 4.20-4.11 (m, 4H); $^{13}$C NMR (75 MHz, DMSO-$d_6$) δ 177.3, 155.3, 144.7, 142.8, 138.3, 135.3 (d, $J_{C-F}$=2.8 Hz), 134.2 (d, $J_{C-F}$=15.5 Hz), 132.1, 130.4 (d, $J_{C-F}$=7.1 Hz), 130.0 (d, $J_{C-F}$=3.3 Hz), 129.3, 128.1, 126.9 (d, $J_{C-F}$=1.8 Hz), 124.2, 123.6, 121.5, 111.7, 109.9, 99.3, 82.9 (d, $J_{C-F}$=160.6 Hz), 80.1, 64.7, 64.1, 57.8, 55.4; MS (ES+) m/z 439.9 (M+23).

EXAMPLE 4.94

Synthesis of 3-[(2'-oxo-2,3-dihydrospiro[furo[2,3-g][1,4]benzodioxine-8,3'-indol]-1'(2'H)-yl)methyl]benzonitrile

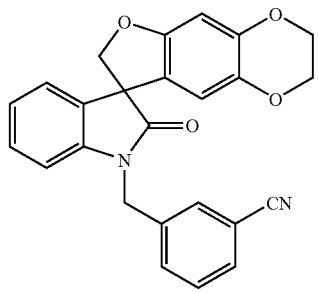

Following the procedure as described in EXAMPLE 4 and making non-critical variations using α-bromo-m-tolunitrile to replace 2-(bromomethyl)tetrahydro-2H-pyran, and 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, 3-[(2'-oxo-2,3-dihydrospiro[furo[2,3-g][1,4]-benzodioxine-8,3'-indol]-1'(2'H)-yl)methyl]benzonitrile was obtained (66%) as a colorless solid: mp 173-178° C. (ethyl acetate/diethyl ether); $^1$H NMR (300 MHz, CDCl$_3$) δ 7.60-7.63 (m, 3H), 7.44-7.47 (m, 1H), 7.21-7.24 (m, 2H), 7.05 (t, J=7.5 Hz, 1H), 6.72 (d, J=7.5 Hz, 1H), 6.50 (s, 1H), 6.18 (s, 1H), 4.93-4.97 (m, 3H), 4.66-4.69 (m, 1H), 4.13-4.17 (m, 4H); $^{13}$C NMR (75 MHz, CDCl$_3$) δ 177.7, 155.3, 144.8, 141.5, 138.4, 137.4, 132.1, 131.8, 131.7, 130.9, 129.9, 129.0, 124.3, 123.9, 120.7, 118.4, 113.1, 111.4, 108.8, 99.5, 80.1, 64.5, 63.9, 58.0, 43.4; MS (ES+) m/z 410.8 (M+1).

EXAMPLE 4.95

Synthesis of 1-(4-fluoro-3-methoxybenzyl)-2,3-dihydrospiro[furo[2,3-g][1,4]benzodioxine-8,3'-indol]-2'(1'H)-one

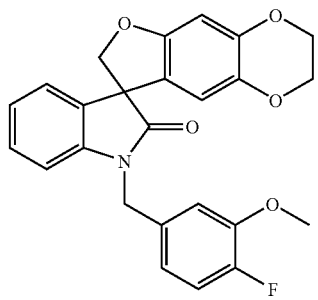

Following the procedure as described in EXAMPLE 4 and making non-critical variations using 4-(chloromethyl)-1-fluoro-2-methoxybenzene to replace 2-(bromomethyl)tetrahydro-2H-pyran, and 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2"(1'H)-one, 1'-(4-fluoro-3-methoxybenzyl)-2,3-dihydrospiro[furo[2,3-g][1,4]benzodioxine-8,3'-indol]-2'(1'H)-one was obtained (82%) as a colorless solid: mp 161-163° C. (hexanes); $^1$H NMR (300 MHz, CDCl$_3$) δ 7.23-7.15 (m, 2H), 7.05-7.00 (m, 2H), 6.94-6.77 (m, 3H), 6.49 (s, 1H), 6.18 (s, 1H), 5.09-5.04 (m, 1H), 4.97-4.91 (m, 1H), 4.71-4.61 (m, 2H), 4.19-4.08 (m, 4H), 3.83 (s, 3H); $^{13}$C NMR (75 MHz, CDCl$_3$) δ 177.6, 155.2, 153.6, 150.4, 148.1, 144.7, 141.9, 138.3, 132.2, 128.8, 124.0, 123.6, 121.0, 119.8, 116.1, 112.4, 111.3, 109.2, 99.5, 79.9, 64.5, 63.9, 58.0, 56.2, 43.8; MS (ES+) m/z 433.8 (M+1).

EXAMPLE 4.96

Synthesis of 4-[(2'-oxo-2,3-dihydrospiro[furo[2,3-g][1,4]benzodioxine-8,3'-indol]-1'(2'H)-yl)methyl]benzonitrile

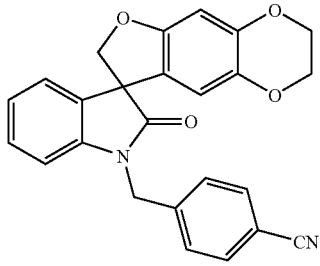

Following the procedure as described in EXAMPLE 4 and making non-critical variations using 4-(bromomethyl)benzonitrile to replace 2-(bromomethyl)tetrahydro-2H-pyran, and 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2"(1'H)-one, 4-[(2'-oxo-2,3-dihydrospiro[furo[2,3-g][1,4]benzodioxine-8,3'-indol]-1'(2'H)-yl)methyl]benzonitrile was obtained (85%) as a colorless solid: mp 69-72° C. (ethyl acetate/hexanes); $^1$H NMR (300 MHz, CDCl$_3$) δ 7.67-7.58 (m, 2H), 7.49-7.39 (m, 2H), 7.23-7.15 (m, 2H), 7.07-7.00 (m, 1H), 6.69 (d, J=7.8 Hz, 1H), 6.50 (s, 1H), 6.18 (s, 1H), 5.10 (d, J=16.1 Hz, 1H), 4.92 (d, J=9.0 Hz, 1H), 4.85 (d, J=16.1 Hz, 1H), 4.65 (d, J=9.0 Hz, 1H), 4.22-4.08 (m, 4H); MS (ES+) m/z 410.9 (M+1).

EXAMPLE 4.97

Synthesis of 1'-(4-isoxazol-5-ylbenzyl)-2,3-dihydrospiro[furo[2,3-g][1,4]benzodioxine-8,3'-indol]-2'(1'H)-one

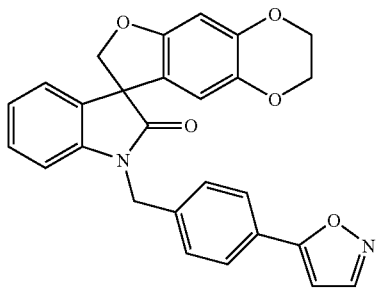

Following the procedure as described in EXAMPLE 4 and making non-critical variations using 5-(4-(bromomethyl)phenyl)isoxazole (0.20 g, 0.84 mmol) to replace 2-(bromomethyl)tetrahydro-2H-pyran, and 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2"(1'H)-one, 1-(4-isoxazol-5-ylbenzyl)-2,3-dihydrospiro[furo[2,3-g][1,4]benzodioxine-8,3'-indol]-2'(1'H)-one was obtained (70%) as a colorless solid: mp 209-212° C. (ethyl acetate/hexanes); $^1$H NMR (300 MHz, CDCl$_3$) δ8.28-8.25 (m, 1H), 7.77 (d, J=8.0 Hz, 2H), 7.42 (d, J=8.0 Hz, 2H), 7.23-7.13 (m, 2H), 7.02 (dd, J=7.5, 7.5 Hz, 1H), 6.75 (d, J=7.8 Hz, 1H), 6.52-6.47 (m, 2H), 6.22 (s, 1H), 5.11 (d, J=15.8 Hz, 1H), 4.94 (d, J=8.9 Hz, 1H), 4.84 (d, J=15.8 Hz, 1H), 4.66 (d, J=8.9 Hz, 1H), 4.22-4.08 (m, 4H); $^{13}$C NMR (75 MHz, CDCl$_3$) δ177.6, 168.8, 155.3, 150.9, 144.7, 141.9, 138.4, 138.0, 132.2, 128.9, 128.0, 126.9, 126.5, 126.2, 124.1, 123.6, 120.9, 111.5, 109.2, 99.5, 98.9, 80.2, 64.5, 64.0, 58.1, 43.9, 29.7; MS (ES+) m/z 453.0 (M+1).

EXAMPLE 4.98

Synthesis of 1-{[6-(trifluoromethyl)pyridin-3-yl]methyl}-2,3-dihydrospiro[furo[2,3-g][1,4]benzodioxine-8,3'-indol]-2'(1'H)-one

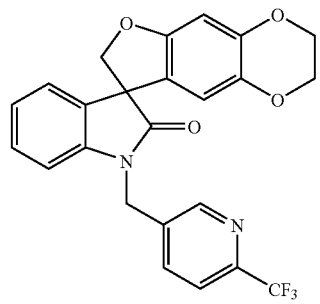

Following the procedure as described in EXAMPLE 4 and making non-critical variations using 5-chloromethyl-2-(trifluoromethyl)pyridine to replace 2-(bromomethyl)tetrahydro-2H-pyran, and 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2"(1'H)-one, 1'-{[6-(trifluoromethyl)pyridin-3-yl]methyl}-2,3-dihydrospiro[furo[2,3-g][1,4]-benzodioxine-8,3'-indol]-2'(1'H)-one was obtained (90%) as a colorless solid: mp 204-207° C. (dichloromethane); $^1$H NMR (300 MHz, CDCl$_3$) δ 8.74 (d, J=1.6 Hz, 1H), 7.82 (dd, J=8.1, 1.6 Hz, 1H), 7.66 (d, J=8.1 Hz, 1H), 7.27-7.15 (m, 1H), 7.03-7.05 (m, 1H), 6.75 (d, J=7.8 Hz, 1H), 6.50 (s, 1H), 6.18 (s, 1H), 5.11 (d, J=16.0 Hz, 1H), 4.92 (d, J=16.1 Hz, 1H), 4.91 (d, J=9.0 Hz, 1H), 4.64 (d, J=9.0 Hz, 1H), 4.22-4.07 (m, 1H); $^{13}$C NMR (75 MHz, CDCl$_3$) δ 177.7, 155.3, 149.0, 147.9 (q, J=139.5 Hz), 144.8, 141.2, 138.4, 136.5, 134.9, 132.1, 129.1, 124.4, 124.1, 121.4, 120.8 (q, J=10.8 Hz), 120.5, 111.4, 108.6, 99.6, 80.1, 64.5, 63.9, 58.0, 41.3; MS (ES+) m/z 429.9 (M+1).

EXAMPLE 4.99

Synthesis of 1'-(4-isoxazol-5-ylbenzyl)-3-methylspiro[furo[3,2-f][1,2]benzisoxazole-5,3'-indol]-2'(1'H)-one

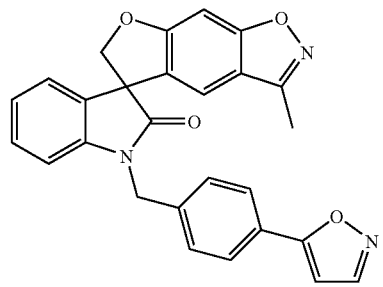

Following the procedure as described in EXAMPLE 4 and making non-critical variations using 5-(4-(bromomethyl)

phenyl)isoxazole (0.20 g, 0.84 mmol) to replace 2-(bromomethyl)tetrahydro-2H-pyran, and 3-methylspiro[furo[3,2-f][1,2]benzisoxazole-5,3'-indol]-2'(1'H)-one to replace 5,6-dihydrospiro[benzo[1,2-b:5,4-b']difuran-3,3'-indol]-2"(1'H)-one, 1'-(4-isoxazol-5-ylbenzyl)-3-methylspiro[furo[3,2-f][1,2]benzisoxazole-5,3'-indol]-2'(1'H)-one was obtained (60%) as a colorless solid: mp 192-194° C.; $^1$H NMR (300 MHz, DMSO-$d_6$) δ 8.25 (d, J=1.8 Hz, 1H), 7.81 (d, J=8.3 Hz, 2H), 7.55 (d, J=8.2 Hz, 2H), 7.47 (d, J=8.6 Hz, 1H), 7.27-7.09 (m, 2H), 7.02-6.95 (m, 2H), 6.75 (d, J=7.8 Hz, 1H), 6.50 (d, J=1.8 Hz, 1H), 5.32 (d, J=16.2 Hz, 1H), 5.15 (d, J=9.1 Hz, 1H), 4.89 (d, J=9.1 Hz, 1H), 4.83 (d, J=16.2 Hz, 1H), 2.45 (s, 3H); $^{13}$C NMR (75 MHz, DMSO-$d_6$) δ 176.3, 169.0, 164.0, 158.2, 155.0, 150.8, 141.9, 137.4, 130.5, 129.4, 127.8, 126.8, 123.8, 123.7, 123.1, 118.0, 109.7, 108.9, 108.0, 98.9, 81.4, 56.4, 53.5, 44.1, 9.8; MS (ES+) m/z 449.9 (M+1).

EXAMPLE 4.100

Synthesis of 1-[(5-fluoropyridin-2-yl)methyl]-2,3-dihydrospiro[furo[2,3-g][1,4]benzodioxine-8,3'-indol]-2'(1'H)-one

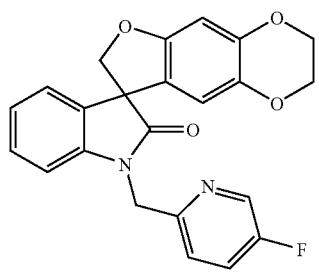

Following the procedure as described in EXAMPLE 4 and making non-critical variations using 2-(chloromethyl)-5-fluoropyridine hydrochloride (Cai, Z. et al. US 2007/0072831) to replace 2-(bromomethyl)tetrahydro-2H-pyran, and 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, 1-[(5-fluoropyridin-2-yl)methyl]-2,3-dihydrospiro[furo[2,3-g][1,4]benzodioxine-8,3'-indol]-2'(1'H)-one was obtained (99%) as a colorless solid: mp 174-176° C.; $^1$H NMR (300 MHz, CDCl$_3$) δ 8.40 (d, J=2.7 Hz, 1H), 7.41-7.11 (m, 4H), 7.01 (t, J=7.4 Hz, 1H), 6.89 (d, J=7.8 Hz, 1H), 6.48 (s, 1H), 6.25 (s, 1H), 5.16 (d, J=15.7 Hz, 1H), 4.98-4.88 (m, 2H), 4.65 (d, J=8.9 Hz, 1H), 4.20-4.07 (m, 4H); $^{13}$C NMR (75 MHz, CDCl$_3$) δ 177.5, 160.2, 157.2, 155.3, 151.5, 151.5, 144.7, 142.0, 138.3, 137.8, 137.5, 132.2, 128.8, 124.1, 123.9, 123.8, 123.6, 122.9, 122.8, 121.0, 111.6, 109.4, 99.4, 80.1, 64.5, 63.9, 58.1, 45.4; MS (ES+) m/z 404.9 (M+1).

EXAMPLE 4.101

Synthesis of 1-[(3-fluoropyridin-2-yl)methyl]-2,3-dihydrospiro[furo[2,3-g][1,4]benzodioxine-8,3'-indol]-2'(1'H)-one

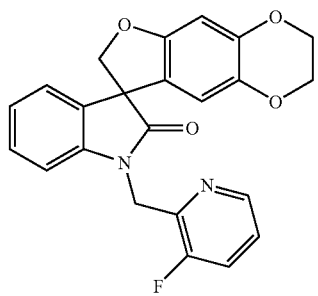

Following the procedure as described in EXAMPLE 4 and making non-critical variations using 2-(chloromethyl)-3-fluoropyridine hydrochloride (Weidmann, K. et al., J. Med. Chem. (1992), (35):438) to replace 2-(bromomethyl)tetrahydro-2H-pyran, and 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2"(1'H)-one, 1'-[(3-fluoropyridin-2-yl)methyl]-2,3-dihydrospiro[furo[2,3-g][1,4]benzodioxine-8,3'-indol]-2'(1'H)-one was obtained (25%) as a colorless solid: mp 247-249° C. (dichloromethane/ether); $^1$H NMR (300 MHz, CDCl$_3$) δ 8.35 (td, J=4.6, 1.34 Hz, 1H), 7.43-7.33 (m, 1H), 7.27-7.11 (m, 3H), 7.02-6.95 (m, 1H), 6.80-6.75 (m, 1H), 6.47 (s, 1H), 6.44 (s, 1H), 5.31 (dd, J=16.2, 1.5 Hz, 1H), 5.04 (dd, J=16.2, 1.4 Hz, 1H), 4.95 (d, J=8.9 Hz, 1H), 4.67 (d, J=8.9 Hz, 1H), 4.20-4.07 (m, 4H); $^{13}$C NMR (75 MHz, CDCl$_3$) δ 177.5, 159.6, 156.2, 155.2, 145.4, 145.3, 144.5, 142.9, 142.8, 142.2, 138.3, 132.6, 128.6, 124.3, 123.8, 123.3, 123.1, 121.3, 112.2, 109.0, 99.2, 80.2, 64.5, 63.9, 58.1, 40.7; MS (ES+) m/z 404.7 (M+1).

EXAMPLE 4.102

Synthesis of 1-(pyridin-2-ylmethyl)-4'-quinolin-3-yl-2,3-dihydrospiro[furo[2,3-g][1,4]benzodioxine-8,3'-indol]-2'(1'H)-one

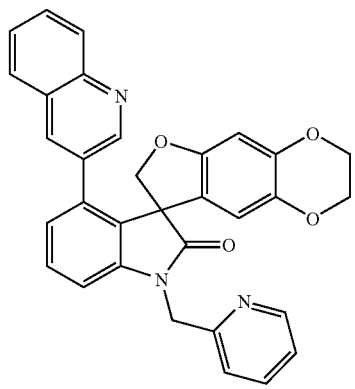

Following the procedure as described in EXAMPLE 4 and making non-critical variations using 2-(bromomethyl)pyridine hydrobromide to replace 2-(bromomethyl)tetrahydro- 2H-pyran, and 4'-quinolin-3-yl-2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, 1-(pyridin-2-ylmethyl)-4'-quinolin-3-yl-2,3-dihydrospiro[furo[2,3-g][1,4]benzodioxine-8,3'-indol]-2'(1'H)-one was obtained (73%) as a colorless solid: mp 228-230° C. (ethyl acetate/hexanes); $^1$H NMR (300 MHz, CDCl$_3$) δ 10.70 (s, 1H), 7.42-7.32 (m, 2H), 7.26 (t, J=7.8 Hz, 1H), 7.13-7.05 (m, 1H), 6.96-6.90 (m, 3H), 6.79-6.70 (m, 5H), 6.23 (s, 1H), 6.12 (s, 1H), 4.47 (d, J=9.3 Hz, 1H), 4.32 (d, J=9.3 Hz, 1H), 4.15-4.01 (m, 4H); $^{13}$C NMR (75 MHz, CDCl$_3$) δ 177.8, 155.4, 150.3, 149.6, 147.2, 144.8, 142.7, 138.2, 137.2, 136.4, 135.7, 131.2, 130.4, 129.2, 128.0, 126.9, 125.9, 122.9, 122.7, 121.8, 111.3, 109.5, 99.6, 64.6, 64.1, 46.3; MS (ES+) m/z 513.9 (M+1).

EXAMPLE 4.103

Synthesis of 4'-(4-phenoxyphenyl)-1'-(pyridin-2-ylmethyl)-2,3-dihydrospiro[furo[2,3-g][1,4]benzodioxine-8,3'-indol]-2'(1'H)-one

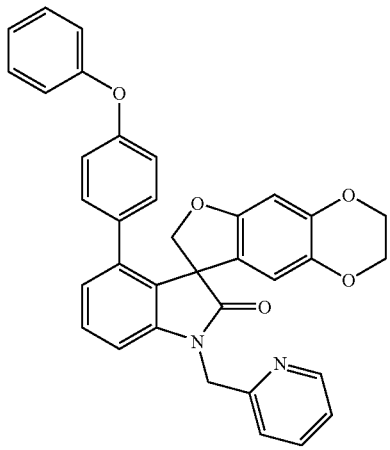

Following the procedure as described in EXAMPLE 4 and making non-critical variations using 2-(bromomethyl)pyridine hydrobromide to replace 2-(bromomethyl)tetrahydro-2H-pyran, and 4'-(4-phenoxyphenyl)-2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2"(1'H)-one, 4'-(4-phenoxyphenyl)-1'-(pyridin-2-ylmethyl)-2,3-dihydrospiro[furo[2,3-g][1,4]benzodioxine-8,3'-indol]-2'(1'H)-one was obtained (90%) as a colorless solid: mp 196-199° C. (dichloromethane/ether); $^1$H NMR (300 MHz, CDCl$_3$) δ 8.61-8.57 (m, 1H), 7.69-7.65 (m, 1H), 7.40-7.18 (m, 5H), 7.12-7.05 (m, 1H), 7.02-6.97 (m, 2H), 6.93-6.86 (m, 2H), 6.84-6.71 (m, 4H), 6.39 (s, 1H), 6.21 (s, 1H), 5.26 (d, J=15.8 Hz, 1H), 4.95 (d, J=15.8 Hz, 1H), 4.73 (d, J=9.0 Hz, 1H), 4.43 (d, J=9.0 Hz, 1H), 4.20-4.07 (m, 4H); $^{13}$C NMR (75 MHz, CDCl$_3$) δ 178.2, 157.4, 156.3, 155.6, 149.6, 144.7, 142.4, 139.8, 137.9, 137.1, 133.5, 130.4, 130.1, 129.7, 128.7, 125.4, 123.1, 122.8, 122.3, 121.7, 118.6, 118.4, 111.2, 108.7, 99.3, 77.9, 64.5, 64.0, 58.5, 46.2; MS (ES+) m/z 555.0 (M+1).

EXAMPLE 4.104

Synthesis of 1-[(3,5-difluoropyridin-2-yl)methyl]-2,3-dihydrospiro[furo[2,3-g][1,4]benzodioxine-8,3'-indol]-2'(1'H)-one

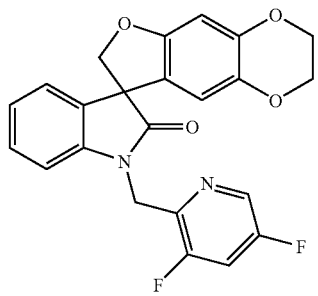

Following the procedure as described in EXAMPLE 4 and making non-critical variations using 2-(chloromethyl)-3,5-difluoropyridine hydrochloride to replace 2-(bromomethyl)tetrahydro-2H-pyran, and 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2"(1'H)-one, 1'-[(3,5-difluoropyridin-2-yl)methyl]-2,3-dihydrospiro[furo[2,3-g][1,4]benzodioxine-8,3'-indol]-2'(1'H)-one was obtained (64%) as a colorless solid: mp 220-222° C. (ethyl acetate/hexanes); $^1$H NMR (300 MHz, CDCl$_3$) δ 8.27 (d, J=1.7 Hz, 1H), 7.26-7.11 (m, 3H), 7.04-6.96 (m, 1H), 6.77 (d, J=7.7 Hz, 1H), 6.49-6.46 (m, 1H), 6.39-6.36 (m, 1H), 5.27 (d, J=16.1 Hz, 1H), 5.00 (d, J=16.1 Hz, 1H), 4.95-4.90 (m, 1H), 4.68-4.63 (m, 1H), 4.20-4.06 (m, 4H); $^{13}$C NMR (75 MHz, CDCl$_3$) δ 177.5, 159.7, 156.2, 155.3, 144.6, 142.0, 139.0, 138.9, 138.3, 133.8, 133.6, 132.5, 123.9, 123.4, 121.2, 112.0, 111.6, 108.9, 99.2, 80.1, 64.5, 63.9, 58.1, 40.3; MS (ES+) m/z 422.8 (M+1).

EXAMPLE 4.105

Synthesis of 2'-oxo-1'-(pyridin-2-ylmethyl)-1',2'-dihydrospiro[1-benzofuran-3,3'-indole]-6-carbonitrile

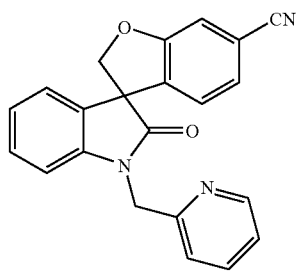

Following the procedure as described in EXAMPLE 4 and making non-critical variations using 2-(bromomethyl)pyridine hydrobromide to replace 2-(bromomethyl)tetrahydro-2H-pyran, and 2'-oxo-1',2'-dihydrospiro[1-benzofuran-3,3'-indole]-6-carbonitrile to replace 5,6-dihydrospiro[benzo[1,2-b:5,4-b']difuran-3,3'-indol]-2'(1'H)-one, 2'-oxo-1'-(pyridin-2-ylmethyl)-1',2'-dihydrospiro[1-benzofuran-3,3'-indole]-6-carbonitrile was obtained (89%) as a colorless solid: mp 151-153° C. (diethyl ether/hexanes); $^1$H NMR (300 MHz, CDCl$_3$) δ 8.55 (d, J=3.9 Hz, 1H), 7.66 (t, J=7.5 Hz, 1H), 7.34-6.84 (m, 9H), 5.19 (d, J=15.8 Hz, 1H), 5.07 (d, J=9.2 Hz, 1H), 4.97 (d, J=15.8 Hz, 1H), 4.79 (d, J=9.2 Hz, 1H); $^{13}$C NMR (75 MHz, CDCl$_3$) δ 176.3, 160.7, 155.1, 149.7, 142.3, 137.1, 134.8, 131.2, 129.5, 125.8, 124.6, 123.8, 122.9, 121.8, 118.5, 113.8, 113.3, 109.9, 80.21, 77.5, 57.9, 46.1; MS (ES+) m/z 353.9 (M+1).

EXAMPLE 4.106

Synthesis of 3-{[(8S)-2'-oxo-2,3-dihydrospiro[furo[2,3-g][1,4]benzodioxine-8,3'-indol]-1'(2'H)-yl]methyl}benzonitrile

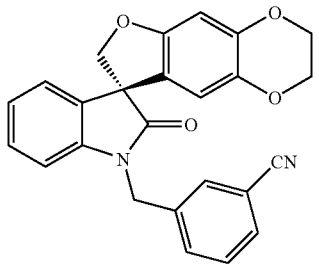

Following the procedure as described in EXAMPLE 4 and making non-critical variations using 3-(bromomethyl)benzonitrile to replace 2-(bromomethyl)tetrahydro-2H-pyran, and (8S)-2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, 3-{[(8S)-2'-oxo-2,3-dihydrospiro[furo[2,3-g][1,4]-benzodioxine-8,3'-indol]-1'(2'H)-yl]methyl}benzonitrile was obtained (75%) as a colorless solid: mp 94-96° C. (isopropyl alcohol); $^1$H NMR (300 MHz, CDCl$_3$) δ 7.65-7.52 (m, 4H), 7.49-7.42 (m, 2H), 7.23-7.15 (m, 1H), 7.08-7.01 (m, 1H), 6.75-6.70 (m, 1H), 6.49 (s, 1H), 6.18 (s, 1H), 5.03 (d, J=15.8 Hz, 1H), 4.95-4.84 (m, 2H), 4.66 (d, J=9.0 Hz, 1H), 4.20-4.07 (m, 3H); $^{13}$C NMR (75 MHz, CDCl$_3$) δ 177.6, 155.3, 144.8, 141.5, 138.4, 137.4, 132.1, 131.8, 130.9, 129.9, 129.0, 124.3, 123.9, 120.7, 118.4, 113.1, 111.4, 108.8, 99.5, 80.1, 64.5, 63.9, 58.0, 43.4, 29.7; MS (ES+) m/z 411.0 (M+1). Anal. Calcd. for C$_{25}$H$_{18}$N$_2$O$_4$: C, 73.16; H, 4.42; N, 6.83. Found: C, 72.92; H, 5.05; N, 6.50.

EXAMPLE 4.107

Synthesis of (8S)-1'-[(5-fluoropyridin-2-yl)methyl]-2,3-dihydrospiro[furo[2,3-g][1,4]benzodioxine-8,3'-indol]-2'(1'H)-one

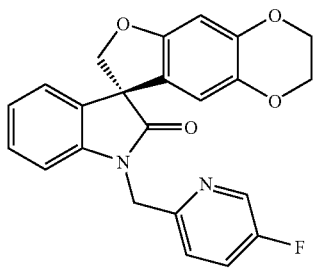

Following the procedure as described in EXAMPLE 4 and making non-critical variations using 5-(chloromethyl)-2-fluoropyridine hydrochloride to replace 2-(bromomethyl)tetrahydro-2H-pyran, and (8S)-2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, (8S)-1'-[(5-fluoropyridin-2-yl)methyl]-2,3-dihydrospiro[furo[2,3-g][1,4]benzodioxine-8,3'-indol]-2'(1'H)-one was obtained (68%) as a colorless solid: mp 210-212° C. (isopropyl alcohol); $^1$H NMR (300 MHz, CDCl$_3$) δ 8.40 (d, J=2.6

Hz, 1H), 7.41-7.11 (m, 4H), 7.05-6.97 (m, 1H), 6.89 (d, J=7.8 Hz, 1H), 6.49 (s, 1H), 6.25 (s, 1H), 5.16 (d, J=15.7 Hz, 1H), 4.99-4.88 (m, 2H), 4.65 (d, J=8.9 Hz, 1H), 4.20-4.06 (m, 4H); $^{13}$C NMR (75 MHz, CDCl$_3$) δ 177.5, 160.6, 157.2, 155.3, 151.5, 144.7, 142.0, 138.3, 137.8, 137.5, 132.2, 128.8, 124.1, 123.9, 123.8, 123.6, 122.9, 121.0, 111.6, 109.4, 99.4, 80.1, 54.5, 63.9, 58.1, 45.4; MS (ES+) m/z 404.9 (M+1). Anal. Calcd. for O$_{23}$H$_{17}$N$_2$O$_4$: C, 68.31; H, 4.24; N, 6.93. Found: C, 67.81; H, 4.39; N, 6.85.

EXAMPLE 4.108 and Example 4.109

Synthesis of (8S)-1'-[(3-fluoropyridin-2-yl)methyl]-2,3-dihydrospiro[furo[2,3-g][1,4]benzodioxine-8,3'-indol]-2'(1'H)-one and (S)-1'-(2-oxobutyl)-3,7-dihydro-2H-spiro[benzofuro[5,6-b][1,4]dioxine-8,3'-indolin]-2'-one

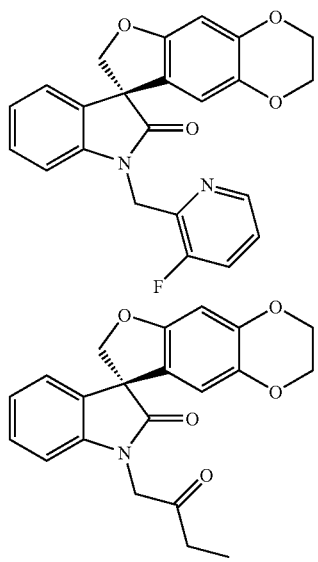

Following the procedure as described in EXAMPLE 4 and making non-critical variations using 2-(chloromethyl)-3-fluoropyridine hydrochloride to replace 2-(bromomethyl)tetrahydro-2H-pyran, and (8S)-2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, (8S)-1'-[(3-fluoropyridin-2-yl)methyl]-2,3-dihydrospiro[furo[2,3-g][1,4]benzodioxine-8,3'-indol]-2'(1'H)-one was obtained (33%) as a colorless solid: mp 125-126° C. (diethyl ether); $^1$H NMR (300 MHz, CDCl$_3$) δ 8.38-8.32 (m, 1H), 7.43-7.34 (m, 1H), 7.28-7.11 (m, 3H), 7.02-6.95 (m, 1H), 6.78 (d, J=7.6 Hz, 1H), 6.48 (s, 1H), 6.44 (s, 1H), 5.31 (d, J=16.2 Hz, 1H), 5.04 (d, J=16.2 Hz, 1H), 4.95 (d, J=8.9 Hz, 1H), 4.67 (d, J=8.9 Hz, 1H), 4.21-4.07 (m, 4H); $^{13}$C NMR (75 MHz, CDCl$_3$) δ 177.5, 159.6, 156.2, 155.2, 145.4, 144.5, 142.9, 142.8, 142.2, 138.3, 132.6, 128.6, 124.3, 123.8, 123.3, 123.1, 121.3, 112.2, 109.0, 99.2, 80.2, 64.5, 63.9, 58.1, 40.7; MS (ES+) m/z 404.9 (M+1). Anal. Calcd. for C$_{23}$H$_{17}$FN$_2$O$_4$: C, 68.31; H, 4.24; N, 6.93. Found: C, 67.27; H, 4.24; N, 6.93.

(S)-1'-(2-oxobutyl)-3,7-dihydro-2H-spiro[benzofuro[5,6-b][1,4]dioxine-8,3'-indolin]-2'-one was isolated (6%) as a byproduct from this reaction as a colorless solid: mp 182-183° C. (diethyl ether); $^1$H NMR (300 MHz, CDCl$_3$) δ 7.28-7.20 (m, 1H), 7.17 (d, J=7.2 Hz, 1H), 7.07-7.00 (m, 1H), 6.63 (d, J=7.8 Hz, 1H), 6.47 (s, 1H), 6.37 (s, 1H), 4.89 (d, J=9.0 Hz, 1H), 4.68-4.56 (m, 2H), 4.44 (d, J=17.9 Hz, 1H), 4.20-4.07 (m, 4H), 2.54 (q, J=7.3 Hz, 2H), 1.11 (t, J=7.3 Hz, 3H); $^{13}$C NMR (75 MHz, CDCl$_3$) δ 203.5, 177.6, 155.2, 144.6, 141.9, 138.4, 132.2, 128.8, 124.0, 123.7, 120.9, 111.9, 108.2, 99.3, 80.0, 64.5, 63.9, 58.0, 48.9, 33.2, 7.4; MS (ES+) m/z 366.0 (M+1).

EXAMPLE 4.110

Synthesis of 1-[(4-fluoropyridin-2-yl)methyl]-2,3-dihydrospiro[furo[2,3-g][1,4]benzodioxine-8,3'-indol]-2'(1'H)-one

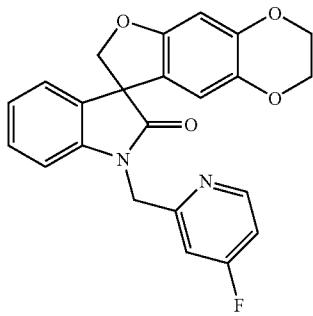

Following the procedure as described in EXAMPLE 4 and making non-critical variations using 2-(chloromethyl)-4-fluoropyridine hydrochloride to replace 2-(bromomethyl)tetrahydro-2H-pyran, and 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2"(1'H)-one, 1'-[(4-fluoropyridin-2-yl)methyl]-2,3-dihydrospiro[furo[2,3-g][1,4]benzodioxine-8,3'-indol]-2'(1'H)-one was obtained (54%) as a colorless solid: mp 228-231° C. (diethyl ether); $^1$H NMR (300 MHz, CDCl$_3$) δ 8.52 (dd, J=8.38, 5.56 Hz, 1H), 7.24-7.14 (m, 2H), 7.06-6.90 (m, 3H), 6.85 (d, J=7.8 Hz, 1H), 6.49 (s, 1H), 6.30 (s, 1H), 5.15 (d, J=16.0 Hz, 1H), 5.02-4.91 (m, 2H), 4.67 (d, J=8.9 Hz, 1H), 4.21-4.07 (m, 4H); $^{13}$C NMR (75 MHz, CDCl$_3$) δ 177.6, 171.0, 167.6, 158.9 (2), 155.3, 152.0 (2), 144.7, 141.9, 138.4, 132.2, 128.9, 124.0, 123.7, 120.9, 111.7, 111.0, 110.8, 109.7, 109.5, 109.3, 99.4, 80.1, 64.5, 63.9, 58.1, 45.8, 11.9; MS (ES+) m/z 404.9 (M+1).

EXAMPLE 4.111

Synthesis of 1'-(2,3-dihydro-1,4-benzodioxin-6-ylmethyl)-2'-oxo-1',2'-dihydrospiro[1-benzofuran-3,3'-indole]-6-carbonitrile

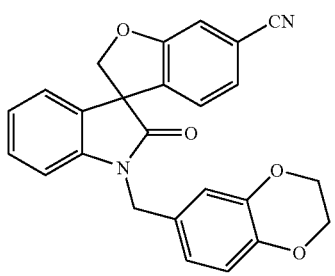

Following the procedure as described in EXAMPLE 4 and making non-critical variations using 6-(chloromethyl)-2,3-dihydrobenzo[b][1,4]dioxine (Capilla, A. S. et al., *Tetrahedron* (2001), 57:8297) to replace 2-(bromomethyl)tetrahydro-2H-pyran, and 2'-oxo-1'-(pyridin-2-ylmethyl)-1',2'-dihydrospiro[1-benzofuran-3,3'-indole]-6-carbonitrile to replace 5,6-dihydrospiro[benzo[1,2-b:5,4-b']difuran-3,3'-indol]-2'(1'H)-one, 1'-(2,3-dihydro-1,4-benzodioxin-6-ylmethyl)-2'-oxo-1',2'-dihydrospiro[1-benzofuran-3,3'-indole]-6-carbonitrile was obtained (54%) as a colorless solid: mp 181-183° C. (dichloromethane/diethyl ether); $^1$H NMR (300 MHz, CDCl$_3$) δ 7.29-7.16 (m, 1H), 7.15-6.97 (m, 3H), 6.89-6.75 (m, 5H), 5.04 (d, J=9.2 Hz, 1H), 4.94 (d, J=15.3 Hz, 1H), 4.80-4.67 (m, 2H), 4.25-4.19 (m, 4H); $^{13}$C NMR (75 MHz, CDCl$_3$) δ 176.2, 160.8, 143.8, 143.3, 142.2, 134.7, 131.3, 129.5, 128.5, 125.8, 124.4, 123.8, 123.7, 120.5, 118.5, 117.8, 116.3, 113.8, 113.3, 109.8, 80.2, 64.3 (2C), 57.8, 43.8.

EXAMPLE 4.112

Synthesis of 1-[(3-chloropyridin-2-yl)methyl]-2,3-dihydrospiro[furo[2,3-g][1,4]benzodioxine-8,3'-indol]-2'(1'H)-one

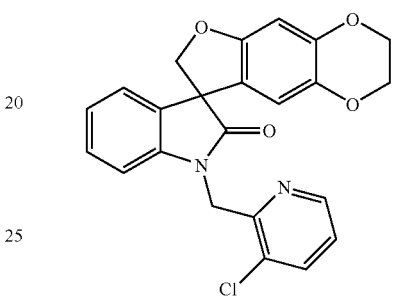

Following the procedure as described in EXAMPLE 4 and making non-critical variations using 3-chloro-2-(chloromethyl)pyridine hydrochloride to replace 2-(bromomethyl)tetrahydro-2H-pyran, and 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2"(1'H)-one, 1'-[(3-chloropyridin-2-yl)methyl]-2,3-dihydrospiro[furo[2,3-g][1,4]benzodioxine-8,3'-indol]-2'(1'H)-one was obtained (67%) as a colorless solid: mp 176-178° C. (ethyl acetate/hexanes); $^1$H NMR (300 MHz, CDCl$_3$) δ 8.35-8.31 (m, 1H), 7.47 (d, J=7.6 Hz, 1H), 7.27-7.15 (m, 3H), 7.09-7.02 (m, 1H), 6.75 (d, J=7.8 Hz, 1H), 6.50 (d, J=1.5 Hz, 1H), 6.23 (d, J=1.4 Hz, 1H), 5.13 (d, J=16.8 Hz, 1H), 5.02-4.89 (m, 2H), 4.67 (dd, J=8.9, 1.3 Hz, 1H), 4.22-4.06 (m, 4H); $^{13}$C NMR (75 MHz, CDCl$_3$) δ 177.8, 155.4, 150.0, 148.9, 144.8, 141.4, 138.4, 136.9, 132.0, 129.1, 129.8, 124.2, 124.0, 123.0, 120.6, 111.4, 109.1, 99.6, 80.2, 64.5, 63.9, 58.1, 41.2.

EXAMPLE 4.113

Synthesis of 1'-[2-(trifluoromethyl)benzyl]-2,3-dihydrospiro[furo[2,3-g][1,4]benzodioxine-8,3'-indol]-2'(1'H)-one

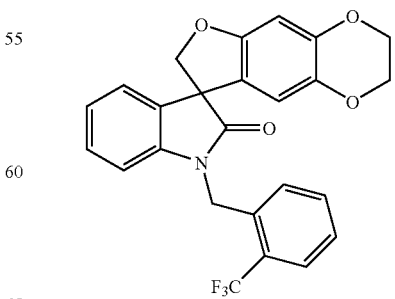

Following the procedure as described in EXAMPLE 4 and making non-critical variations using 1-(chloromethyl)-2-(trifluoromethyl)benzene to replace 2-(bromomethyl)tetrahydro-2H-pyran, and 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2''(1'H)-one, 1'-[2-(trifluoromethyl)benzyl]-2,3-dihydrospiro[furo[2,3-g][1,4]benzodioxine-8,3'-indol]-2'(1'H)-one was obtained (55%) as a colorless solid: mp 207-208° C. (dichloromethane/diethyl ether); ¹H NMR (300 MHz, CDCl₃) δ 7.72 (d, J=7.6 Hz, 1H), 7.51-7.42 (m, 2H), 7.42-7.34 (m, 3H), 7.22-7.12 (m, 1H), 7.07-7.00 (m, 1H), 6.61 (d, J=7.7 Hz, 1H), 6.52 (s, 1H), 6.31 (s, 1H), 5.26 (d, J=17.1 Hz, 1H), 5.07 (d, J=17.0 Hz, 1H), 4.97 (d, J=8.9 Hz, 1H), 4.70 (d, J=8.9 Hz, 1H), 4.24-4.09 (m, 4H); ¹³C NMR (75 MHz, CDCl₃) δ 177.9, 155.4, 144.8, 141.8, 138.4, 133.9, 132.5, 132.1, 129.0, 128.3 (q, J=30.8 Hz), 127.7, 126.8, 126.4 (q, J=5.8 Hz), 124.4 (q, J=273.7 Hz), 124.1, 123.8, 120.8, 111.5, 109.2, 99.5, 80.3, 64.5, 63.9, 58.2, 40.6; MS (ES+) m/z 454.1 (M+1).

EXAMPLE 4.114

Synthesis of (8R)-1'-[2-(trifluoromethyl)benzyl]-2,3-dihydrospiro[furo[2,3-g][1,4]benzodioxine-8,3'-indol]-2'(1'H)-one

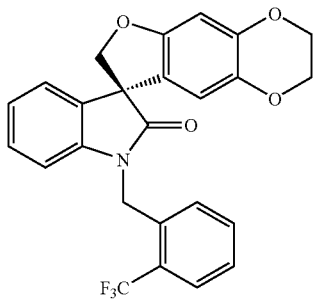

Following the procedure as described in EXAMPLE 4 and making non-critical variations using 1-(bromomethyl)-2-(trifluoromethyl)benzene to replace 2-(bromomethyl)tetrahydro-2H-pyran, and (8R)-2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, (8R)-1'-[2-(trifluoromethyl)benzyl]-2,3-dihydrospiro[furo[2,3-g][1,4]benzodioxine-8,3'-indol]-2'(1'H)-one was obtained (87%) as a colorless solid: mp 137-138° C. (diethyl ether); ¹H NMR (300 MHz, CDCl₃) δ 7.72 (d, J=7.6 Hz, 1H), 7.52-7.33 (m, 2H), 7.22-7.13 (m, 3H), 7.07-7.00 (m, 1H), 6.62 (d, J=7.8 Hz, 1H), 6.52 (s, 1H), 6.31 (s, 1H), 5.26 (d, J=17.1 Hz, 1H), 5.08 (d, J=17.1 Hz, 1H), 4.97 (d, J=8.9 Hz, 1H), 4.70 (d, J=8.9 Hz, 1H), 4.23-4.09 (m, 4H); ¹³C NMR (75 MHz, CDCl₃) δ 177.9, 155.4, 144.8, 141.8, 138.4, 133.9, 132.5, 132.1, 129.0, 127.9 (q, ²J$_{C-F}$=30.8 Hz), 127.6, 126.8, 126.4 (q, ⁵J$_{C-F}$=5.8 Hz), 124.4 (q, ¹J$_{C-F}$=273.8 Hz), 124.1, 123.8, 120.8, 111.6, 109.2, 99.6, 80.3, 64.5, 64.0, 58.2, 40.6 (q, J=3.4 Hz); MS (ES+) m/z 454.0 (M+1). Anal. Calcd. for C₂₆H₁₈F₃NO₄: C, 66.22; H, 4.00; N, 3.09. Found: C, 66.16; H, 4.11; N, 3.07.

EXAMPLE 4.115

Synthesis of 5'-methyl-1'-{[3-(trifluoromethyl)pyridin-2-yl]methyl}-2,3-dihydrospiro[furo[2,3-g][1,4]benzodioxine-8,3'-indol]-2'(1'H)-one

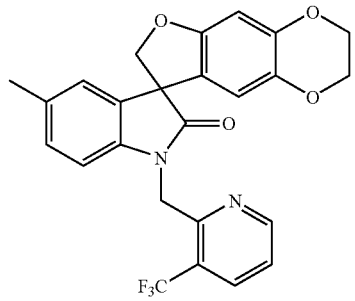

Following the procedure as described in EXAMPLE 4 and making non-critical variations using 2-(chloromethyl)-3-(trifluoromethyl)pyridine hydrochloride to replace 2-(bromomethyl)tetrahydro-2H-pyran, and 5'-methyl-2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, (5'-methyl-1'-{[3-(trifluoromethyl)pyridin-2-yl]methyl}-2,3-dihydrospiro[furo[2,3-g][1,4]-benzodioxine-8,3'-indol]-2'(1'H)-one was obtained (62%) as a colorless solid: mp 137-139° C. (diethyl ether); ¹H NMR (300 MHz, DMSO-d₆) δ 8.63 (d, J=4.6 Hz, 1H), 8.22 (d, J=7.5 Hz, 1H), 7.57-7.50 (m, 1H), 7.02-6.94 (m, 2H), 6.72 (d, J=7.9 Hz, 1H), 6.47 (s, 1H), 6.40 (s, 1H), 5.29-5.03 (ABq, 2H), 4.76-4.64 (ABq, 2H), 4.18-4.06 (m, 4H), 2.18 (s, 3H); ¹³C NMR (75 MHz, DMSO-d₆) δ 177.4, 155.0, 153.0, 152.9, 144.5, 140.9, 138.2, 135.5 (q, ⁴J=5.31 Hz), 132.5, 132.5, 129.3, 124.5, 124.4 (q, ¹J=273.6 Hz), 123.5 (q, 2J=32.3 Hz), 123.5, 122.2, 112.3, 109.3, 99.1, 79.7, 64.7, 64.1, 57.8, 42.4 (q, J=3.1 Hz), 21.0; MS (ES+) m/z 469.0 (M+1).

EXAMPLE 4.116

Synthesis of (8S)-1'-[2-(trifluoromethyl)benzyl]-2,3-dihydrospiro[furo[2,3-g][1,4]benzodioxine-8,3'-indol]-2'(1'H)-one

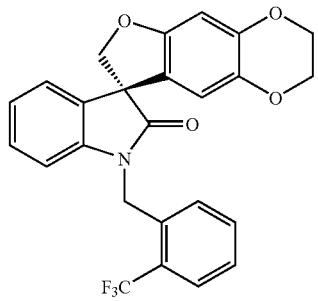

Following the procedure as described in EXAMPLE 4 and making non-critical variations using 2-(trifluoromethyl)benzyl bromide to replace 2-(bromomethyl)tetrahydro-2H-pyran, and (8S)-2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2''(1'H)-one, (8S)-1'-[2-(trifluoromethyl)benzyl]-2,3-dihydrospiro[furo[2,3-g][1,4]benzodioxine-8,3'-indol]-2'(1'H)-one was obtained (82%) as a colorless solid: mp 137-138° C. (diethyl ether); ¹H NMR (300 MHz, CDCl₃) δ 7.72 (d, J=7.7 Hz, 1H), 7.52-7.33 (m, 2H), 7.22-7.12 (m, 3H), 7.07-7.00 (m, 1H), 6.61 (d, J=7.7 Hz, 1H), 6.52 (s, 1H), 6.31 (s, 1H), 5.26 (d, J=17.1 Hz, 1H), 5.07 (d, J=17.1 Hz, 1H), 4.97 (d, J=8.9 Hz, 1H), 4.70 (d, J=8.9 Hz, 1H), 4.23-4.09 (m, 4H); ¹³C NMR (75 MHz, CDCl₃) δ 177.9, 155.4, 144.8, 141.8, 138.4, 133.9, 132.5, 132.1, 129.0, 127.9 (q, ²$J_{C-F}$=30.8 Hz), 127.6, 126.8, 126.4 (q, ⁵$J_{C-F}$=5.8 Hz), 124.4 (q, ¹$J_{C-F}$=273.8 Hz), 124.1, 123.8, 120.8, 111.6, 109.2, 99.6, 80.3, 64.5, 64.0, 58.2, 40.6 (q, J=3.4 Hz); MS (ES+) m/z 454.0 (M+1); Anal. Calcd. for C₂₅H₁₈F₃NO₄: C, 66.22; H, 4.00; N, 3.09. Found: C, 66.06; H, 3.98; N, 3.12.

EXAMPLE 4.117

Synthesis of 4'-bromo-1'-(pyridin-2-ylmethyl)-2,3-dihydrospiro[furo[2,3-g][1,4]benzodioxine-8,3'-indol]-2'(1'H)-one

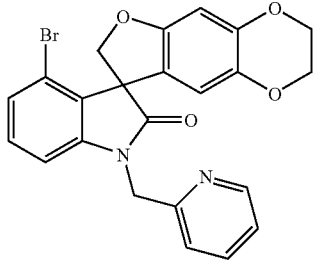

Following the procedure as described in EXAMPLE 4 and making non-critical variations using 2-(bromomethyl)pyridine hydrobromide to replace 2-(bromomethyl)tetrahydro-2H-pyran, and 4'-bromo-2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2''(1'H)-one, 4'-bromo-1'-(pyridin-2-ylmethyl)-2,3-dihydrospiro[furo[2,3-g][1,4]benzodioxine-8,3'-indol]-2'(1'H)-one was obtained (75%) as a colorless solid: MS (ES+) m/z 465.7 (M+1), 466.7 (M+1).

EXAMPLE 4.118

Synthesis of 1'-(2,1,3-benzothiadiazol-5-ylmethyl)-2,3-dihydrospiro[furo[2,3-g][1,4]benzodioxine-8,3'-indol]-2'(1'H)-one

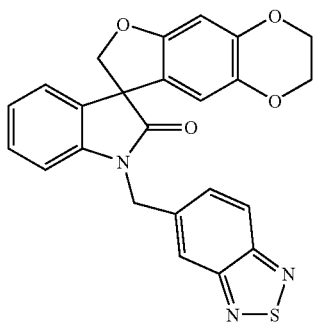

Following the procedure as described in EXAMPLE 4 and making non-critical variations using 5-(bromomethyl)-2,1,3-benzothiadiazole to replace 2-(bromomethyl)tetrahydro-2H-pyran, and 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2''(1'H)-one, 1'-(2,1,3-benzothiadiazol-5-ylmethyl)-2,3-dihydrospiro[furo[2,3-g][1,4]benzodioxine-8,3'-indol]-2'(1'H)-one was obtained (80%) as a colorless solid: mp 189-191° C.; ¹H NMR (300 MHz, CDCl₃) δ8.04-7.90 (m, 2H), 7.63-7.55 (m, 1H), 7.22-7.15 (m, 2H), 7.08-7.00 (m, 1H), 6.86-6.79 (m, 1H), 6.53 (s, 1H), 6.26 (s, 1H), 5.22 (d, J=15.9 Hz, 1H), 5.04 (d, J=15.9 Hz, 1H), 4.97 (d, J=9.0 Hz, 1H), 4.70 (d, J=9.0 Hz, 1H), 4.24-4.10 (m, 4H); MS (ES+) m/z 443.8 (M+1).

EXAMPLE 4.119

Synthesis of 1-(1,3-benzothiazol-2-ylmethyl)-2,3-dihydrospiro[furo[2,3-g][1,4]benzodioxine-8,3'-indol]-2'(1'H)-one

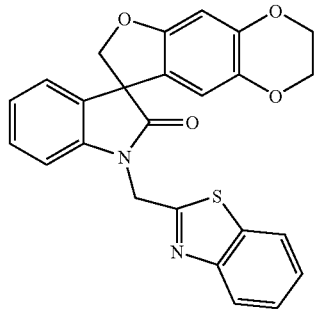

Following the procedure as described in EXAMPLE 4 and making non-critical variations using 2-(bromomethyl)-1,3-benzothiazole to replace 2-(bromomethyl)tetrahydro-2H-pyran, and 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, 1'-(1,3-benzothiazol-2-ylmethyl)-2,3-dihydrospiro[furo[2,3-g][1,4]benzodioxine-8,3'-indol]-2'(1'H)-one was obtained (77%) as a colorless solid: mp 164-166° C.; ¹H NMR (300 MHz, CDCl₃) δ8.04 (d, J=8.1 Hz, 1H), 7.85 (d, J=8.1 Hz, 1H), 7.54-7.46 (m, 1H), 7.43-7.35 (m, 1H), 7.24-7.17 (m, 2H), 7.05 (dd, J=7.5, 7.5 Hz, 1H), 6.97 (d, J=7.8 Hz, 1H), 6.53 (s, 1H), 6.41 (s, 1H), 5.53 (d, J=16.2 Hz, 1H), 5.24 (d, J=16.2 Hz, 1H), 4.97 (d, J=9.0 Hz, 1H), 4.69 (d, J=9.0 Hz, 1H), 4.24-4.11 (m, 4H); ¹³C NMR (75 MHz, CDCl₃) δ177.2, 165.9, 155.3, 152.9, 144.7, 141.2, 138.3, 135.3, 132.1, 128.9, 126.3, 125.5, 124.0, 123.9, 123.2, 121.9, 120.8, 111.8, 109.2, 99.4, 64.5, 63.9, 58.0, 42.6; MS (ES+) m/z 442.8 (M+1).

EXAMPLE 4.120

Synthesis of 1'-[(1-methyl-1H-benzimidazol-2-yl)methyl]-2,3-dihydrospiro[furo[2,3-g][1,4]benzodioxine-8,3'-indol]-2'(1'H)-one

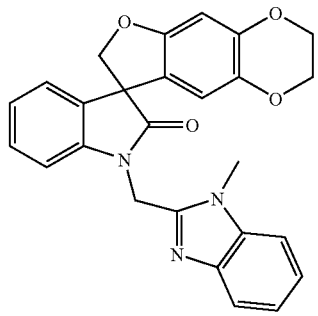

Following the procedure as described in EXAMPLE 4 and making non-critical variations using 2-(bromomethyl)-1-methyl-1H-benzoimidazole to replace 2-(bromomethyl)tetrahydro-2H-pyran, and 2,3-dihydrospiro[furo[2,3-g][1,4]benzodioxine-8,3'-indol]-2'(1'H)-one to replace 5,6-dihydrospiro

[benzo[1,2-b:5,4-b']difuran-3,3'-indol]-2"(1'H)-one, 1'-[(1-methyl-1H-benzimidazol-2-yl)methyl]-2,3-dihydrospiro[furo[2,3-g][1,4]benzodioxine-8,3'-indol]-2'(1'H)-one was obtained (20%) as a colorless solid: mp>240° C.; $^1$H NMR (300 MHz, CDCl$_3$) δ7.58-7.53 (m, 2H), 7.30-7.14 (m, 5H), 7.06-6.99 (m, 1H), 6.60 (s, 1H), 6.51 (s, 1H), 5.28 (ABq, 2H), 4.81 (d, J=9.3 Hz, 1H), 4.71 (d, J=9.3 Hz, 1H), 4.22-4.10 (m, 4H), 3.85 (s, 3H); $^{13}$C NMR (75 MHz, CDCl$_3$) δ 176.6, 154.5, 149.1, 144.1, 142.3, 141.7, 137.8, 136.1, 131.9, 128.5, 123.3, 123.0, 122.1, 121.5, 121.4, 118.6, 112.0, 110.1, 109.7, 98.5, 79.3, 64.1, 63.6, 57.3, 37.1, 29.8; MS (ES+) m/z 440.0 (M+1).

EXAMPLE 4.121

Synthesis of 1'-{[2-(1-methylethyl)-1,3-thiazol-4-yl]methyl}-2,3-dihydrospiro[furo[2,3-g][1,4]benzodioxine-8,3'-indol]-2'(1'H)-one

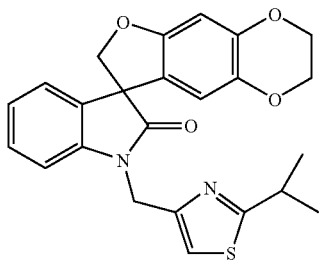

Following the procedure as described in EXAMPLE 4 and making non-critical variations using 4-(chloromethyl)-2-isopropylthiazole to replace 2-(bromomethyl)tetrahydro-2H-pyran, and 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, 1'-{[2-(1-methylethyl)-1,3-thiazol-4-yl]methyl}-2,3-dihydrospiro[furo[2,3-g][1,4]benzodioxine-8,3'-indol]-2'(1'H)-one was obtained (95%) as a colorless solid: mp 60-63° C.; $^1$H NMR (300 MHz, CDCl$_3$) δ7.28-7.21 (m, 1H), 7.16 (d, J=7.4 Hz, 1H), 7.06-6.98 (m, 2H), 6.92 (s, 1H), 6.50 (s, 1H), 6.26 (s, 1H), 5.15 (d, J=16.2 Hz, 1H), 4.95 (d, J=16.2 Hz, 1H), 4.93 (d, J=9.0 Hz, 1H), 4.66 (d, J=9.0 Hz, 1H), 4.22-4.08 (m, 4H), 3.37-3.22 (m, 1H), 1.39 (d, J=6.9 Hz, 6H); $^{13}$C NMR (75 MHz, CDCl$_3$) δ 178.5, 177.2, 155.2, 150.2, 144.6, 142.1, 138.3, 132.2, 128.8, 123.7, 123.4, 121.1, 114.1, 111.6, 109.7, 99.4, 80.1, 64.5, 63.9, 58.1, 40.6, 33.3, 23.1; MS (ES+) m/z 434.9 (M+1).

EXAMPLE 4.122

Synthesis of 1-(2,1,3-benzoxadiazol-5-ylmethyl)-2,3-dihydrospiro[furo[2,3-g][1,4]benzodioxine-8,3'-indol]-2'(1'H)-one

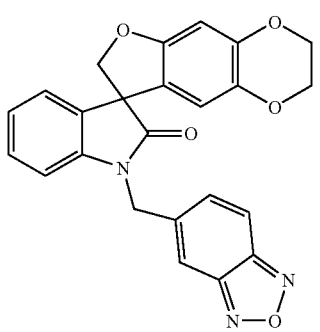

Following the procedure as described in EXAMPLE 4 and making non-critical variations using 5-(bromomethyl)-2,1,3-benzooxadiazole to replace 2-(bromomethyl)tetrahydro-2H-pyran, and 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, 1'-(2,1,3-benzoxadiazol-5-ylmethyl)-2,3-dihydrospiro[furo[2,3-g][1,4]benzodioxine-8,3'-indol]-2'(1'H)-one was obtained (44%) as a colorless solid: mp 164-166° C.; $^1$H NMR (300 MHz, CDCl$_3$) δ7.86 (d, J=9.3 Hz, 1H), 7.75 (s, 1H), 7.43-7.37 (m, 1H), 7.25-7.19 (m, 2H), 7.08 (dd, J=7.5, 7.5 Hz, 1H), 6.82 (d, J=7.8 Hz, 1H), 6.53 (s, 1H), 6.23 (s, 1H), 5.13 (d, J=16.2 Hz, 1H), 4.95 (d, J=9.0 Hz, 1H), 4.94 (d, J=16.2 Hz, 1H), 4.70 (d, J=9.0 Hz, 1H), 4.24-4.10 (m, 4H); $^{13}$C NMR (75 MHz, CDCl$_3$) δ177.7, 155.3, 149.0, 148.7, 144.8, 141.4, 139.7, 138.4, 132.0, 131.4, 129.0, 124.3, 124.0, 120.6, 117.8, 113.9, 111.4, 108.8, 99.6, 80.1, 64.5, 63.9, 58.0, 44.0; MS (ES+) m/z 427.9 (M+1).

EXAMPLE 4.123

Synthesis of tert-butyl 4-[(2'-oxo-2,3-dihydrospiro[furo[2,3-g][1,4]benzodioxine-8,3'-indol]-1'(2'H)-yl)methyl]piperidine-1-carboxylate

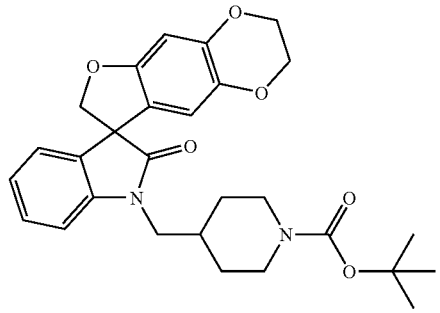

Following the procedure as described in EXAMPLE 4 and making non-critical variations using tert-butyl 4-(tosyloxymethyl)piperidine-1-carboxylate to replace 2-(bromomethyl)tetrahydro-2H-pyran, and 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, tert-butyl 4-[(2'-oxo-2,3-dihydrospiro[furo[2,3-g][1,4]benzodioxine-8,3'-indol]-1'(2'H)-yl)methyl]piperidine-1-carboxylate was obtained (99%) as a colorless solid: $^1$H NMR (300 MHz, CDCl$_3$) δ 7.34-7.26 (m, 1H), 7.14-7.19 (m, 1H), 7.08-7.01 (m, 1H), 6.88 (d, J=7.8 Hz, 1H), 6.50 (s, 1H), 6.19 (s, 1H), 4.87 (d, J=9.0 Hz, 1H), 4.62 (d, J=9.0 Hz, 1H), 4.23-4.06 (m, 6H), 3.80-3.44 (m, 2H), 2.76-2.59 (m, 2H), 2.11-1.93 (m, 1H), 1.74-1.60 (m, 2H), 1.45 (s, 9H), 1.37-1.20 (m, 2H).

EXAMPLE 4.124

Synthesis of 1'-(pyridin-2-ylmethyl)spiro[furo[3,2-e][2,1,3]benzoxadiazole-8,3'-indol]-2'(1'H)-one

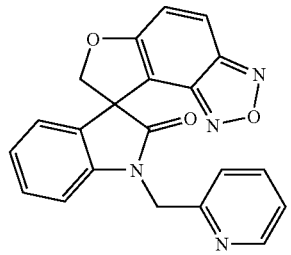

Following the procedure as described in EXAMPLE 4 and making non-critical variations using 2-(bromomethyl)pyridine to replace 2-(bromomethyl)tetrahydro-2H-pyran, and spiro[furo[3,2-e][2,1,3]benzoxadiazole-8,3'-indol]-2'(1'H)-one to replace 5,6-dihydrospiro[benzo[1,2-b:5,4-b']difuran-3,3'-indol]-2'(1'H)-one, 1'-(pyridin-2-ylmethyl)spiro[furo[3,2-e][2,1,3]benzoxadiazole-8,3'-indol]-2'(1'H)-one was obtained (81%) as a colorless solid: mp 180-182° C.; $^1$H NMR (300 MHz, CDCl$_3$) δ8.63-8.59 (m, 1H), 7.84 (d, J=9.6 Hz, 1H), 7.77-7.70 (m, 1H), 7.57 (d, J=7.8 Hz, 1H), 7.32 (d, J=9.6 Hz, 1H), 7.28-7.16 (m, 3H), 7.04 (ddd, J=7.5, 7.5, 0.9 Hz, 1H), 6.88 (d, J=7.8 Hz, 1H), 5.45 (d, J=16.2 Hz, 1H), 5.28 (d, J=9.6 Hz, 1H), 5.01 (d, J=9.6 Hz, 1H), 4.92 (d, J=16.2 Hz, 1H); $^{13}$C NMR (75 MHz, CDCl$_3$) δ176.1, 163.0, 155.1, 149.4, 148.3, 144.9, 142.2, 137.3, 129.8, 129.7, 123.7, 123.67, 122.8, 121.9, 121.6, 119.4, 110.1, 107.0, 82.0, 57.4, 46.5; MS (ES+) m/z 371.0 (M+1).

EXAMPLE 4.125

Synthesis of 1-(pyridin-3-ylmethyl)spiro[furo[3,2-e][2,1,3]benzoxadiazole-8,3'-indol]-2'(1'H)-one

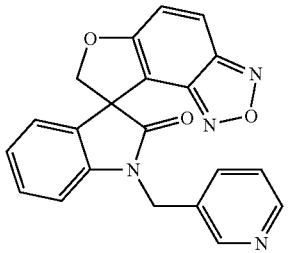

Following the procedure as described in EXAMPLE 4 and making non-critical variations using 3-(bromomethyl)pyridine hydrobromide to replace 2-(bromomethyl)tetrahydro-2H-pyran, and spiro[furo[3,2-e][2,1,3]benzoxadiazole-8,3'-indol]-2'(1'H)-one to replace 5,6-dihydrospiro[benzo[1,2-b:5,4-b']difuran-3,3'-indol]-2"(1'H)-one, 1'-(pyridin-3-ylmethyl)spiro[furo[3,2-e][2,1,3]benzoxadiazole-8,3'-indol]-2'(1'H)-one was obtained (47%) as a colorless solid: mp 230-232° C.; $^1$H NMR (300 MHz, CDCl$_3$) δ 8.74 (s, 1H), 8.59 (d, J=2.7 Hz, 1H), 7.88-7.82 (m, 2H), 7.39-7.16 (m, 4H), 7.04 (dd, J=7.5, 7.5 Hz, 1H), 6.80 (d, J=7.8 Hz, 1H), 5.35-5.24 (m, 2H), 4.99 (d, J=9.3 Hz, 1H), 4.84 (d, J=15.9 Hz, 1H); $^{13}$C NMR (75 MHz, CDCl$_3$) δ176.1, 162.9, 149.4, 148.8, 148.3, 144.8, 141.7, 135.1, 130.8, 129.8, 129.7, 123.9, 121.8, 119.4, 109.6, 106.9, 81.9, 57.2, 42.0; MS (ES+) m/z 371.1 (M+1).

EXAMPLE 4.126

Synthesis of 6-chloro-1'-(pyridin-2-ylmethyl)-2,3-dihydrospiro[furo[3,2-f][1,4]benzodioxine-9,3'-indol]-2'(1'H)-one

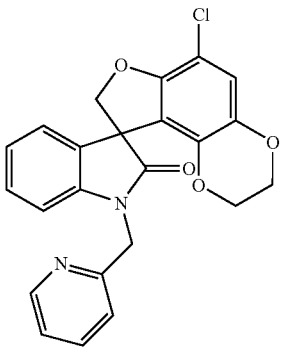

Following the procedure as described in EXAMPLE 4 and making non-critical variations using 2-(bromomethyl)pyridine to replace 2-(bromomethyl)tetrahydro-2H-pyran, and 6-chloro-2,3-dihydrospiro[furo[3,2-f][1,4]benzodioxine-9,3'-indol]-2'(1'H)-one to replace 5,6-dihydrospiro[benzo[1,2-b:5,4-b']difuran-3,3'-indol]-2'(1'H)-one, 6-chloro-1'-(pyridin-2-ylmethyl)-2,3-dihydrospiro[furo[3,2-f][1,4]benzodioxine-9,3'-indol]-2'(1'H)-one was obtained (81%) as a colorless solid: mp 197-199° C.; $^1$H NMR (300 MHz, CDCl$_3$) δ8.60 (d, J=2.1 Hz, 1H), 7.60 (ddd, J=7.5, 7.5, 1.5 Hz, 1H), 7.32 (d, J=7.5 Hz, 1H), 7.25-7.15 (m, 3H), 7.02 (dd, J=7.5, 7.5 Hz, 1H), 6.83 (d, J=7.5 Hz, 1H), 6.79 (s, 1H), 5.35 (d, J=16.2 Hz, 1H), 5.00 (d, J=9.3 Hz, 1H), 4.89 (d, J=16.2 Hz, 1H), 4.74 (d, J=9.0 Hz, 1H), 4.16-3.86 (m, 4H); $^{13}$C NMR (75 MHz, CDCl$_3$) δ175.9, 155.8, 151.7, 149.5, 141.8, 138.6, 138.3, 136.7, 130.9, 128.9, 123.6, 123.4, 122.6, 121.4, 118.2, 116.8, 109.4, 106.8, 81.7, 64.5, 63.8, 57.7, 46.3; MS (ES+) m/z 421.2 (M+1), 423.2 (M+1).

EXAMPLE 4.127

Synthesis of 1-(pyridin-2-ylmethyl)-2,3-dihydrospiro[furo[3,2-f][1,4]benzodioxine-9,3'-indol]-2'(1'H)-one

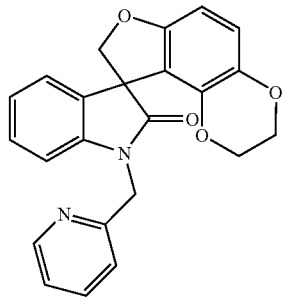

Following the procedure as described in EXAMPLE 4 and making non-critical variations using 2-(bromomethyl)pyridine to replace 2-(bromomethyl)tetrahydro-2H-pyran, and 2,3-dihydrospiro[furo[3,2-f][1,4]benzodioxine-9,3'-indol]-2'(1'H)-one to replace 5,6-dihydrospiro[benzo[1,2-b:5,4-b']difuran-3,3'-indol]-2"(1'H)-one, 1-(pyridin-2-ylmethyl)-2,3-dihydrospiro[furo[3,2-f][1,4]benzodioxine-9,3'-indol]-2'(1'H)-one was obtained (38%) as a colorless solid: mp 132-134° C.; $^1$H NMR (300 MHz, CDCl$_3$) δ8.60 (d, J=1.2 Hz, 1H), 7.60 (ddd, J=7.5, 7.5, 1.5 Hz, 1H), 7.38-7.13 (m, 4H), 7.01 (dd, J=7.2, 7.2 Hz, 1H), 6.82 (d, J=7.8 Hz, 1H), 6.74 (d, J=8.4 Hz, 1H), 6.47 (d, J=8.4 Hz, 1H), 5.38 (d, J=16.2 Hz, 1H), 4.96-4.83 (m, 2H), 4.65 (d, J=8.7 Hz, 1H), 4.17-3.86 (m, 4H); $^{13}$C NMR (75 MHz, CDCl$_3$) δ176.6, 156.0, 155.9, 149.4, 141.7, 139.6, 138.0, 136.7, 131.5, 128.6, 123.5, 123.2, 122.6, 121.4, 118.1, 115.7, 109.2, 102.4, 81.4, 64.5, 63.8, 57.2, 46.2; MS (ES+) m/z 387.2 (M+1).

EXAMPLE 4.128

Synthesis of tert-butyl 4-[(5,6-difluoro-2'-oxospiro[1-benzofuran-3,3'-indol]-1'(2'H)-yl)methyl]piperidine-1-carboxylate

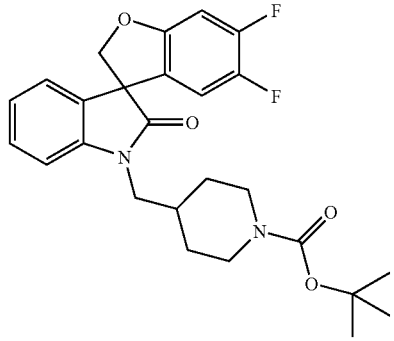

Following the procedure as described in EXAMPLE 4 and making non-critical variations using tert-butyl 4-(tosyloxymethyl)piperidine-1-carboxylate to replace 2-(bromomethyl)tetrahydro-2H-pyran, and 5,6-difluorospiro[1-benzofuran-3,3'-indol]-2'(1'H)-one to replace 5,6-dihydrospiro[benzo[1,2-b:5,4-b']difuran-3,3'-indol]-2'(1'H)-one, tert-butyl 4-[(5,6-difluoro-2'-oxospiro[1-benzofuran-3,3'-indol]-1'(2'H)-yl)methyl]piperidine-1-carboxylate was obtained (57%) as a colorless solid: $^1$H NMR (300 MHz, CDCl$_3$) δ 7.34 (ddd, J=9.0, 7.6, 1.5 Hz, 1H), 7.16-7.06 (m, 2H), 6.92 (d, J=7.8 Hz, 1H), 6.78 (dd, J=10.3, 6.3 Hz, 1H), 6.49 (dd, J=10.3, 6.3 Hz, 1H), 4.95 (d, J=9.0 Hz, 1H), 4.70 (d, J=9.0 Hz, 1H), 4.13 (br s, 2H), 3.74-3.56 (m, 2H), 2.69 (t, J=12.4 Hz, 2H), 2.07-1.96 (m, 1H), 1.68-1.63 (m, 2H), 1.45 (s, 9H), 1.32-1.26 (m, 2H); MS (ES+) m/z 493.3 (M+23).

EXAMPLE 4.129

Synthesis of 1-[(2R)-tetrahydrofuran-2-ylmethyl]-5',6',7',8'-tetrahydrospiro[indole-3,3'-naphtho[2,3-b]furan]-2(1'H)-one

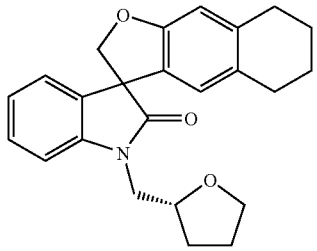

Following the procedure as described in EXAMPLE 4 and making non-critical variations using (R)-(tetrahydrofuran-2-yl)methyl 4-methylbenzenesulfonate to replace 2-(bromomethyl)tetrahydro-2H-pyran, and 5',6',7',8'-tetrahydrospiro[indole-3,3'-naphtho[2,3-b]furan]-2(1'H)-one to replace 5,6-dihydrospiro[benzo[1,2-b:5,4-b']difuran-3,3'-indol]-2''(1'H)-one, 1-[(2R)-tetrahydrofuran-2-ylmethyl]-5',6',7',8'-tetrahydrospiro[indole-3,3'-naphtho[2,3-b]furan]-2(1'H)-one was obtained (80%) as a colorless solid: mp 139-141° C.; $^1$H NMR (300 MHz, CDCl$_3$) δ 7.32-7.27 (m, 1H), 7.15-7.01 (m, 3H), 6.66 (s, 1H), 6.41 (s, 1H), 4.88 (dd, J=8.9, 0.9 Hz, 1H), 4.63 (dd, J=8.9, 2.5 Hz, 1H), 4.32-4.24 (m, 1H), 4.00-3.69 (m, 4H), 2.75-2.71 (m, 2H), 2.54 (br s, 2H), 2.10-1.86 (m, 3H), 1.78-1.69 (m, 5H); $^{13}$C NMR (75 MHz, CDCl$_3$) δ178.0, 158.6, 142.9, 138.8, 132.4, 130.0, 128.6, 126.5, 123.6, 123.4, 123.2, 110.1, 109.5 79.7, 76.9, 68.2, 57.9, 44.6, 29.9, 29.2, 29.0, 25.6, 23.2, 23.0; MS (ES+) m/z 375.9 (M+1).

EXAMPLE 4.130

Synthesis of 1-(pyridin-2-ylmethyl)spiro[furo[2,3-g]quinoxaline-8,3'-indol]-2'(1'H)-one

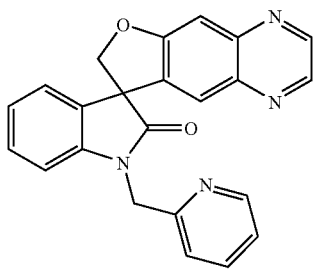

Following the procedure as described in EXAMPLE 4 and making non-critical variations using 2-(bromomethyl)pyridine hydrobromide to replace 2-(bromomethyl)tetrahydro-2H-pyran, and 7H-spiro[furo[2,3-g]quinoxaline-8,3'-indolin]-2'-one to replace 5,6-dihydrospiro[benzo[1,2-b:5,4-b']difuran-3,3'-indol]-2''(1'H)-one, 1'-(pyridin-2-ylmethyl)spiro[furo[2,3-g]quinoxaline-8,3'-indol]-2'(1'H)-one was obtained (93%) as a pale orange solid: mp 232-233° C.; $^1$H NMR (300 MHz, CDCl$_3$) δ8.64 (m, 1H), 8.59 (d, J=1.5 Hz, 1H), 8.44 (d, J=1.5 Hz, 1H), 8.05 (d, J=9.3 Hz, 1H), 7.83 (d, J=8.1 Hz, 1H), 7.77-7.67 (m, 1H), 7.56 (d, J=9.0 Hz, 1H), 7.28-7.17 (m, 2H), 7.10 (d, J=7.2 Hz, 1H), 6.96 (t, J=7.5 Hz, 1H), 6.84 (d, J=7.8 Hz, 1H), 5.56 (d, J=16.5 Hz, 1H), 5.25 (d, J=9.0 Hz, 1H), 4.97 (d, J=9.0 Hz, 1H), 4.91 (d, J=16.5 Hz, 1H); $^{13}$C NMR (75 MHz, CDCl$_3$) δ177.2, 162.5, 155.9, 149.4, 144.9, 142.3, 142.1, 139.8, 139.8, 136.9, 132.6, 132.4, 128.8, 123.3, 123.2, 122.6, 121.9, 121.4, 116.6, 109.6, 82.6, 57.7, 46.5; MS (ES+) m/z 381.2 (M+1).

EXAMPLE 5

Synthesis of 1-[(2-methoxypyrimidin-5-yl)methyl]-5,6-dihydrospiro[benzo[1,2-b:5,4-b']difuran-3,3'-indol]-2'(1'H)-one

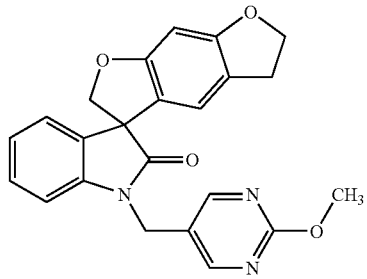

To a stirred solution of 5,6-dihydrospiro[benzo[1,2-b:5,4-b']difuran-3,3'-indol]-2'(1'H)-one (0.28 g, 1.0 mmol) in dry N,N-dimethylformamide (6 mL) was added cesium carbonate (2.30 g, 7.1 mmol) at ambient temperature. The mixture was stirred at ambient temperature for 30 min, and 5-(chloromethyl)-2-methoxypyrimidine (0.34 g, 2.1 mmol) in dry N,N-dimethylformamide (3 mL) was added dropwise. The mixture was stirred at ambient temperature for 16 h, and additional cesium carbonate (0.68 g, 2.1 mmol) and 5-(chloromethyl)-2-methoxypyrimidine (0.20 g, 1.3 mmol) were added. The mixture was stirred at ambient temperature for 64 h. Water (60 mL) was added and the mixture was extracted with ethyl acetate (3×60 mL). The combined organic solution was washed with brine (100 mL), dried over anhydrous magnesium sulfate, filtered, and concentrated in vacuo The residue was purified by column chromatography (hexanes/ethyl acetate 1:1) to afford 1-[(2-methoxypyrimidin-5-yl)methyl]-5,6-dihydrospiro[benzo[1,2-b:5,4-b']difuran-3,3'-indol]-2'(1'H)-one (0.29 g, 73%) as a colorless solid: mp 203-204° C.; $^1$H NMR (300 MHz, CDCl$_3$) δ8.57 (s, 2H), 7.30-7.23 (m, 1H), 7.22-7.17 (m, 1H), 7.11-7.04 (m, 1H), 6.86-6.81 (m, 1H), 6.44-6.41 (m, 2H), 4.89 (ABq, 2H), 4.81 (ABq, 2H), 4.59-4.50 (m, 2H), 4.01 (s, 3H), 3.10-2.90 (m, 2H); $^{13}$C NMR (75 MHz, CDCl$_3$) δ177.9, 165.4, 161.9, 161.3, 158.8, 141.1, 132.7, 128.8, 124.3, 123.9, 122.8, 120.1, 119.7, 118.7, 108.5, 93.3, 80.5, 72.4, 57.6, 55.1, 38.8, 29.0; MS (ES+) m/z 402.1 (M+1).

EXAMPLE 5.1

Synthesis of 7'-chloro-1'-((5-(trifluoromethyl)furan-2-yl)methyl)-5,6-dihydro-2H-spiro[benzofuro[6,5-b]furan-3,3'-indolin]-2'-one

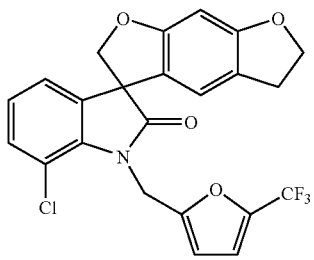

Following the procedure as described in EXAMPLE 5 and making non-critical variations using T-chloro-5,6-dihydrospiro[benzo[1,2-b:5,4-b']difuran-3,3'-indol]-2'(1'H)-one to replace 5,6-dihydrospiro[benzo[1,2-b:5,4-b']difuran-3,3'-indol]-2'(1'H)-one, and 2-(bromomethyl)-5-(trifluoromethyl)furan to replace 5-(chloromethyl)-2-methoxypyrimidine, 7'-chloro-1'-((5-(trifluoromethyl)furan-2-yl)methyl)-5,6-dihydro-2H-spiro[benzofuro[6,5-b]furan-3,3'-indolin]-2'-one was obtained (30%) as a colorless solid: mp 210-211° C. (diethyl ether); $^1$H NMR (300 MHz, DMSO-$d_6$) δ7.34-7.31 (m, 1H), 7.21-7.16 (m, 2H), 7.10-7.05 (m, 1H), 6.67-6.65 (m, 1H), 6.49 (s, 1H), 6.43 (s, 1H), 5.34 (s, 2H), 4.85 (d, J=9.6 Hz, 1H), 4.74 (d, J=9.6 Hz, 1H), 4.57-4.48 (m, 2H), 2.94 (t, J=3.0 Hz, 2H); $^{13}$C NMR (75 MHz, DMSO-$d_6$) δ177.4, 161.2, 160.4, 154.1, 139.4, 138.9, 137.2, 135.4, 130.5, 124.6, 122.8, 120.6, 120.1, 119.9, 118.7, 117.1, 114.3, 114.2, 108.7, 92.4, 79.8, 72.0, 56.6, 28.1.

EXAMPLE 5.2

Synthesis of (3R)-1-(3-methylbutyl)-5,6-dihydrospiro[benzo[1,2-b:5,4-b']difuran-3,3'-indol]-2'(1'H)-one

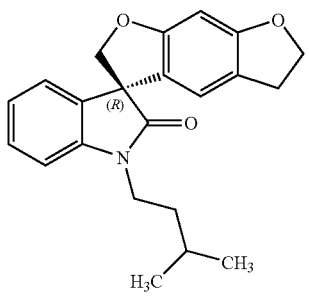

Following the procedure as described in EXAMPLE 5 and making non-critical variations using (3R)-5,6-dihydrospiro[benzo[1,2-b:5,4-b']difuran-3,3'-indol]-2'(1'H)-one to replace 5,6-dihydrospiro[benzo[1,2-b:5,4-b']difuran-3,3'-indol]-2'(1'H)-one, and 1-bromo-3-methylbutane to replace 5-(chloromethyl)-2-methoxypyrimidine, (3R)-1-(3-methylbutyl)-5,6-dihydrospiro[benzo[1,2-b:5,4-b']difuran-3,3'-indol]-2'(1'H)-one was obtained (86%) as a colorless solid: mp 86-87° C. (diethyl ether); $^1$H NMR (300 MHz, CDCl$_3$) δ7.33-7.26 (m, 1H), 7.17 (d, J=7.4 Hz, 1H), 7.07-7.02 (m, 1H), 6.90 (d, J=7.8 Hz, 1H), 6.45 (s, 1H), 6.41 (s, 1H), 4.92 (d, J=8.9 Hz, 1H), 4.66 (d, J=8.9 Hz, 1H), 4.52 (t, J=8.6 Hz, 2H), 3.88-3.65 (m, 2H), 3.02-3.96 (m, 2H), 1.74-1.58 (m, 3H), 1.00 (d, J=6.3 Hz, 6H); $^{13}$C NMR (75 MHz, CDCl$_3$) δ177.5, 161.7, 161.2, 142.3, 133.1, 128.6, 123.8, 123.0, 120.3, 119.8, 118.7, 108.4, 93.1, 80.5, 72.3, 57.6, 38.7, 36.1, 29.0, 26.0, 22.5, 22.4; MS (ES+) m/z 349.9 (M+1).

EXAMPLE 5.3

Synthesis of (3R)-1'-pentyl-5,6-dihydrospiro[benzo[1,2-b:5,4-b']difuran-3,3'-indol]-2'(1'H)-one

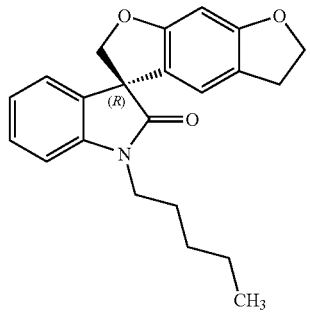

Following the procedure as described in EXAMPLE 5 and making non-critical variations using (3R)-5,6-dihydrospiro[benzo[1,2-b:5,4-b']difuran-3,3'-indol]-2'(1'H)-one to replace 5,6-dihydrospiro[benzo[1,2-b:5,4-b']difuran-3,3'-indol]-2'(1'H)-one, and 1-bromopentane to replace 5-(chloromethyl)-2-methoxypyrimidine, (3R)-1'-pentyl-5,6-dihydrospiro[benzo[1,2-b:5,4-b']difuran-3,3'-indol]-2'(1'H)-one was obtained (78%) as a colorless solid: mp 128-129° C. (diethyl ether); $^1$H NMR (300 MHz, CDCl$_3$) δ7.33-7.26 (m, 1H), 7.17 (d, J=7.1 Hz, 1H), 7.07-7.02 (m, 1H), 6.91 (d, J=7.8 Hz, 1H), 6.49 (s, 1H), 6.41 (s, 1H), 4.92 (d, J=8.9 Hz, 1H), 4.67 (d, J=8.9 Hz, 1H), 8.64 (t, J=4.5 Hz, 2H), 3.87-3.63 (m, 2H), 2.99 (t, J=4.5 Hz, 2H), 1.79-1.69 (m, 2H), 1.40-1.35 (m, 4H), 0.94-0.89 (m, 3H); $^{13}$C NMR (75 MHz, CDCl$_3$) δ177.5, 161.6, 161.2, 142.4, 133.0, 128.6, 123.8, 123.0, 120.3, 119.7, 118.7, 108.4, 93.1, 80.5, 72.3, 57.6, 40.3, 29.0, 27.1, 22.3, 13.9; MS (ES+) m/z 349.9 (M+1).

EXAMPLE 5.4

Synthesis of (3R)-1-(pyridin-2-ylmethyl)-5,6-dihydrospiro[benzo[1,2-b:5,4-b']difuran-3,3'-indol]-2'(1'H)-one

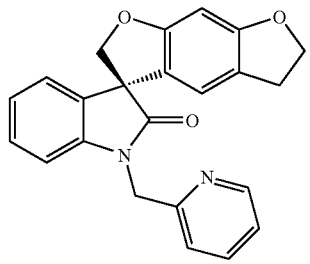

Following the procedure as described in EXAMPLE 5 and making non-critical variations using (3R)-5,6-dihydrospiro[benzo[1,2-b:5,4-b']difuran-3,3'-indol]-2'(1'H)-one to replace 5,6-dihydrospiro[benzo[1,2-b:5,4-b']difuran-3,3'-indol]-2'(1'H)-one, and (2-bromomethyl)pyridine hydrobromide to replace 5-(chloromethyl)-2-methoxypyrimidine, (3R)-1-(pyridin-2-ylmethyl)-5,6-dihydrospiro[benzo[1,2-b:5,4-b']difuran-3,3'-indol]-2'(1'H)-one was obtained (77%) as a colorless solid: mp 154-156° C. (diethyl ether); 1H NMR (300 MHz, DMSO-$d_6$) δ8.53-8.51 (m, 1H), 7.82-7.77 (m, 1H), 7.38-7.13 (m, 4H), 7.05-6.99 (m, 1H), 6.98-6.92 (m, 1H), 6.61 (s, 1H), 6.42 (s, 1H), 5.10 (d, J=16.4 Hz, 1H), 5.00 (d, J=16.4 Hz, 1H), 4.86 (d, J=9.3 Hz, 1H), 4.75 (d, J=9.3 Hz, 1H), 4.49 (t, J=8.7 Hz, 2H), 2.98 (t, J=8.7 Hz, 2H); $^{13}$C NMR (75 MHz, DMSO-d$_6$) δ177.0, 161.0, 160.4, 155.2, 149.2, 142.4, 137.0, 132.2, 128.5, 123.4, 122.8, 122.6, 121.5, 120.6, 119.7, 119.2, 109.2, 92.3, 79.7, 72.0, 56.8, 44.7, 28.2; MS (ES+) m/z 371.0 (M+1).

EXAMPLE 5.5

Synthesis of (3R)-1'-{[5-(trifluoromethyl)furan-2-yl]methyl}-5,6-dihydrospiro[benzo[1,2-b:5,4-b']difuran-3,3'-indol]-2'(1'H)-one

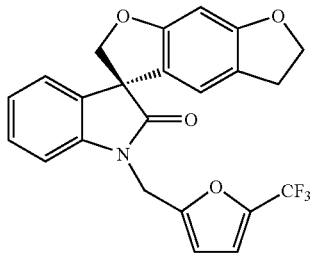

Following the procedure as described in EXAMPLE 5 and making non-critical variations using (3R)-5,6-dihydrospiro[benzo[1,2-b:5,4-b']difuran-3,3'-indol]-2'(1'H)-one to replace 5,6-dihydrospiro[benzo[1,2-b:5,4-b']difuran-3,3'-indol]-2'(1'H)-one, and 2-(bromomethyl)-5-(trifluoromethyl)furan to replace 5-(chloromethyl)-2-methoxypyrimidine, (3R)-1'-{[5-(trifluoromethyl)furan-2-yl]methyl}-5,6-dihydrospiro[benzo[1,2-b:5,4-b']difuran-3,3'-indol]-2'(1'H)-one was obtained (83%) as a colorless solid: mp 68-70° C. (diethyl ether); $^1$H NMR (300 MHz, CDCl$_3$) δ7.32-7.26 (m, 1H), 7.20 (d, J=7.4 Hz, 1H), 7.10-7.05 (m, 1H), 6.98 (d, J=7.8 Hz, 1H), 6.75-6.74 (m, 1H), 6.45 (s, 1H), 6.42 (s, 2H), 5.12 (d, J=16.2 Hz, 1H), 4.96 (d, J=9.0 Hz, 1H), 4.85 (d, J=16.2 Hz, 1H), 4.70 (d, J=9.0 Hz, 1H), 4.54 (t, J=8.6 Hz, 2H), 3.07-2.90 (m, 2H); $^{13}$C NMR (75 MHz, CDCl$_3$) δ177.4, 161.8, 161.1, 151.9, 141.9, 141.2, 132.5, 128.8, 123.9, 123.7, 120.5, 120.0 (2C), 118.7, 112.6, 112.5, 109.2, 108.7, 93.1, 80.3, 72.3, 57.6, 36.8, 28.9; MS (ES+) m/z 427.9 (M+1).

EXAMPLE 5.6

Synthesis of (3S)-1'-(pyridin-2-ylmethyl)-5,6-dihydrospiro[benzo[1,2-b:5,4-b']difuran-3,3'-indol]-2'(1'H)-one

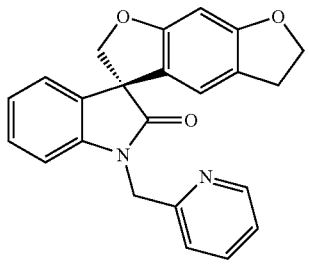

Following the procedure as described in EXAMPLE 5 and making non-critical variations using (3S)-5,6-dihydrospiro[benzo[1,2-b:5,4-b']difuran-3,3'-indol]-2'(1'H)-one to replace 5,6-dihydrospiro[benzo[1,2-b:5,4-b']difuran-3,3'-indol]-2'(1'H)-one, and (2-bromomethyl)pyridine hydrobromide to replace 5-(chloromethyl)-2-methoxypyrimidine, (3S)-1'-(pyridin-2-ylmethyl)-5,6-dihydrospiro[benzo[1,2-b:5,4-b']difuran-3,3'-indol]-2'(1'H)-one was obtained (77%) as a colorless solid: mp 154-156° C. (diethyl ether); mp 84-85° C. (diethyl ether); $^1$H NMR (300 MHz, DMSO-d$_6$) δ8.53-8.51 (m, 1H), 7.82-7.77 (m, 1H), 7.38-7.13 (m, 4H), 7.05-6.99 (m, 1H), 6.98-6.92 (m, 1H), 6.61 (s, 1H), 6.42 (s, 1H), 5.10 (d, J=16.4 Hz, 1H), 5.00 (d, J=16.4 Hz, 1H), 4.86 (d, J=9.3 Hz, 1H), 4.75 (d, J=9.3 Hz, 1H), 4.49 (t, J=8.7 Hz, 2H), 2.98 (t, J=8.7 Hz, 2H); $^{13}$C NMR (75 MHz, DMSO-d$_5$) δ177.0, 161.0, 160.4, 155.2, 149.2, 142.4, 137.0, 132.2, 128.5, 123.4, 122.8, 122.6, 121.5, 120.6, 119.7, 119.2, 109.2, 92.3, 79.7, 72.0, 56.8, 44.7, 28.2; MS (ES+) m/z 371.0 (M+1).

EXAMPLE 5.7

Synthesis of (3S)-1'-{[5-(trifluoromethyl)furan-2-yl]methyl}-5,6-dihydrospiro[benzo[1,2-b:5,4-b']difuran-3,3'-indol]-2'(1'H)-one

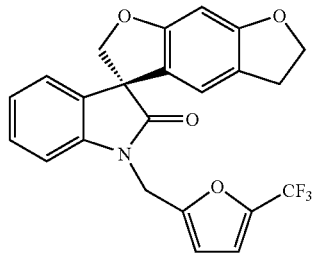

Following the procedure as described in EXAMPLE 5 and making non-critical variations using (3S)-5,6-dihydrospiro[benzo[1,2-b:5,4-b']difuran-3,3'-indol]-2'(1'H)-one to replace 5,6-dihydrospiro[benzo[1,2-b:5,4-b']difuran-3,3'-indol]-2'(1'H)-one, and 2-(bromomethyl)-5-(trifluoromethyl)furan to replace 5-(chloromethyl)-2-methoxypyrimidine, (3S)-1'-{[5-(trifluoromethyl)furan-2-yl]methyl}-5,6-dihydrospiro[benzo[1,2-b:5,4-b']difuran-3,3'-indol]-2'(1'H)-one was obtained (83%) as a colorless solid: mp 64-65° C. (diethyl ether); $^1$H NMR (300 MHz, CDCl$_3$) δ 7.32-7.26 (m, 1H), 7.20 (d, J=7.4 Hz, 1H), 7.10-7.05 (m, 1H), 6.98 (d, J=7.8 Hz, 1H), 6.75-6.74 (m, 1H), 6.45 (s, 1H), 6.42 (s, 2H), 5.12 (d, J=16.2 Hz, 1H), 4.96 (d, J=9.0 Hz, 1H), 4.85 (d, J=16.2 Hz, 1H), 4.70 (d, J=9.0 Hz, 1H), 4.54 (t, J=8.6 Hz, 2H), 3.07-2.90 (m, 2H); $^{13}$C NMR (75 MHz, CDCl$_3$) δ177.4, 161.8, 161.1, 151.9, 141.9, 141.2, 132.5, 128.8, 123.9, 123.7, 120.5, 120.0 (2C), 118.7, 112.6, 112.5, 109.2, 108.7, 93.1, 80.3, 72.3, 57.6, 36.8, 28.9; MS (ES+) m/z 427.9 (M+1).

EXAMPLE 5.8

Synthesis of 3-methyl-1'-{[5-(trifluoromethyl)furan-2-yl]methyl}spiro[furo[2,3-f][1,3]benzoxazole-7,3'-indole]-2,2'(1'H,3H)-dione

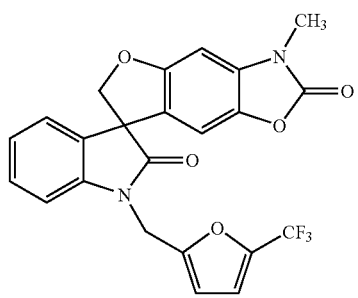

Following the procedure as described in EXAMPLE 5 and making non-critical variations using 3-methylspiro[furo[2,3-f][1,3]benzoxazole-7,3'-indole]-2,2'(1'H,3H)-dione to replace 5,6-dihydrospiro[benzo[1,2-b:5,4-b']difuran-3,3'-indol]-2'(1'H)-one, and 2-(bromomethyl)-5-(trifluoromethyl)furan to replace 5-(chloromethyl)-2-methoxypyrimidine, 3-methyl-1'-{[5-(trifluoromethyl)furan-2-yl]methyl}spiro[furo[2,3-f][1,3]benzoxazole-7,3'-indole]-2,2'(1'H,3H)-dione was obtained (59%) as a colorless solid: mp 198-199° C. (diethyl ether); $^1$H NMR (300 MHz, DMSO-$d_6$) δ 7.37-7.30 (m, 1H), 7.23-7.18 (m, 3H), 7.12-7.03 (m, 2H), 6.77 (s, 1H), 6.56 (s, 1H), 5.17-4.99 (m, 2H), 4.91-4.75 (m, 2H), 3.31 (s, 3H); $^{13}$C NMR (75 MHz, DMSO-$d_6$) δ176.2, 156.8, 154.3, 152.9, 141.5, 136.1, 132.9, 131.4, 128.9, 123.6, 123.3, 121.5, 114.0 (2C), 109.8, 109.2, 104.2, 92.4, 79.3, 57.2, 36.4, 28.1; MS (ES+) m/z 456.4 (M+1).

EXAMPLE 5.9

Synthesis of 1'-{[6-(trifluoromethyl)pyridin-2-yl]methyl}-2,3-dihydrospiro[furo[2,3-g][1,4]benzodioxine-8,3'-indol]-2'(1'H)-one

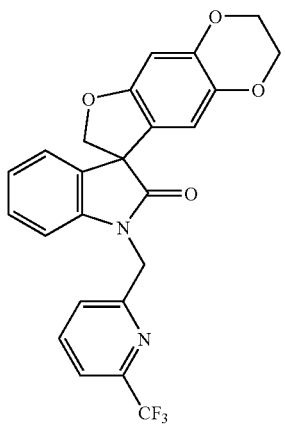

A heterogeneous mixture of 2,3-dihydrospiro[furo[2,3-g][1,4]benzodioxine-8,3'-indol]-2'(1'H)-one (0.41 g, 1.4 mmol), cesium carbonate (1.1 g, 3.5 mmol), 2-(chloromethyl)-6-(trifluoromethyl)pyridine (0.33 g, 1.7 mmol) and N,N-dimethylformamide (10 mL) was stirred at ambient temperature for 16 h. The mixture was diluted with water (100 mL) and ethyl acetate (100 mL). The layers were separated and the aqueous layer was extracted with ethyl acetate (2×70 mL). The combined organic layers was washed with brine (100 mL), dried over anhydrous magnesium sulfate, filtered, and concentrated in vacuo. The residue was purified by column chromatography and eluted with a 25% to 35% gradient of ethyl acetate in hexanes to afford 1'-{[6-(trifluoromethyl)pyridin-2-yl]methyl}-2,3-dihydrospiro[furo[2,3-g][1,4]-benzodioxine-8,3'-indol]-2'(1'H)-one (0.44 g, 70%) as a colorless solid: mp 195-196° C.; $^1$H NMR (300 MHz, DMSO-$d_6$) δ8.15-8.07 (m, 1H), 7.85-7.79 (m, 1H), 7.75-7.70 (m, 1H), 7.28-7.15 (m, 2H), 7.07-7.00 (m, 1H), 6.97-6.91 (m, 1H), 6.52 (s, 1H), 6.29 (s, 1H), 5.16 (ABq, J=42.6, 16.9 Hz, 2H), 4.75 (ABq, J=37.3, 9.3 Hz, 2H), 4.22-4.08 (m, 4H); $^{13}$C NMR (300 MHz, DMSO-$d_6$) δ 176.8, 156.5, 154.6, 146.0 (q, $J_{C-F}$=33.7 Hz), 144.1, 142.3, 139.4, 137.8, 131.7, 128.6, 125.4, 123.5, 123.0, 121.4 (q, $J_{C-F}$=272.7 Hz), 121.1, 119.5 (m), 111.4, 109.1, 98.6, 79.5, 64.1, 63.5, 57.2, 44.2; MS (ES+) m/z 455.0 (M+1).

EXAMPLE 5.10

Synthesis of 1'-{[2-(trifluoromethyl)pyridin-3-yl]methyl}-2,3-dihydrospiro[furo[2,3-g][1,4]benzodioxine-8,3'-indol]-2'(1'H)-one

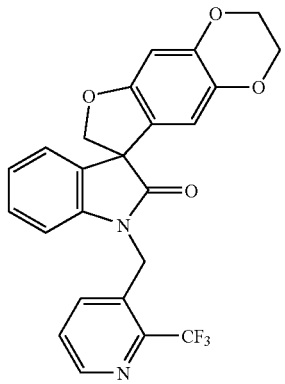

Following the procedure as described in Example 5.9, making non-critical variations using 3-(chloromethyl)-2-(trifluoromethyl)pyridine to replace 2-(chloromethyl)-6-(trifluoromethyl)pyridine, 1-{[2-(trifluoromethyl)pyridin-3-yl]methyl}-2,3-dihydrospiro[furo[2,3-g][1,4]-benzodioxine-8,3'-indol]-2'(1'H)-one was obtained (63%) as a colorless solid: mp 219-220° C.; $^1$H NMR (300 MHz, DMSO-$d_6$) δ8.70-8.65 (m, 1H), 7.77-7.66 (m, 2H), 7.33-7.21 (m, 2H), 7.13-7.05 (m, 1H), 6.90-6.83 (m, 1H), 6.52 (s, 1H), 6.37 (s, 1H), 5.14 (s, 2H), 4.78 (ABq, J=42.3, 9.4 Hz, 2H), 4.23-4.07 (m, 4H); $^{13}$C NMR (300 MHz, DMSO-$d_6$) δ 177.0, 154.7, 147.9, 144.2, 143.4 (q, $J_{C-F}$=33.3 Hz), 142.0, 137.8, 136.3, 131.7, 130.8, 128.9, 127.7, 123.8, 123.3, 122.1 (q, $J_{C-F}$=275.6 Hz), 120.9, 111.6, 109.0, 98.7, 79.6, 64.2, 63.5, 57.2, 48.5; MS (ES+) m/z 455.0 (M+1).

EXAMPLE 5.11

Synthesis of 1-{[3-(trifluoromethyl)pyrazin-2-yl]methyl}-2,3-dihydrospiro[furo[2,3-g][1,4]benzodioxine-8,3'-indol]-2'(1'H)-one

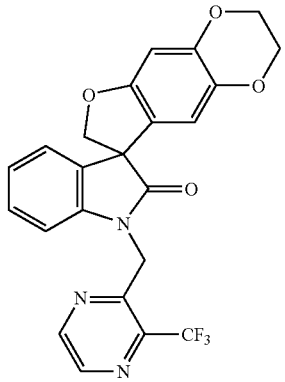

Following the procedure as described in Example 5.9, making non-critical variations using 2-(bromomethyl)-3-(trifluoromethyl)pyrazine to replace 2-(chloromethyl)-6-(trifluoromethyl)pyridine, 1'-{[3-(trifluoromethyl)pyrazin-2-yl]methyl}-2,3-dihydrospiro[furo[2,3-g][1,4]benzodioxine-8, 3'-indol]-2'(1'H)-one was obtained (72%) as a colorless solid: mp 230-232° C.; $^1$H NMR (300 MHz, CDCl$_3$) δ8.69-8.66 (m, 1H), 8.60-8.57 (m, 1H), 7.23-7.15 (m, 2H), 7.08-7.01 (m, 1H), 6.63-6.58 (m, 1H), 6.52 (s, 1H), 6.51 (s, 1H), 5.33 (ABq, J=79.0, 17.6 Hz, 2H), 4.85 (ABq, J=75.4, 8.9 Hz, 2H), 4.23-4.11 (m, 4H); $^{13}$C NMR (300 MHz, CDCl$_3$) δ 178.1, 155.1, 148.9, 146.8, 144.6, 142.1, 141.8, 141.7 (q, $J_{C-F}$=36.1 Hz), 138.2, 132.6, 128.7, 124.0, 123.6, 121.6 (q, $J_{C-F}$ 273.4 Hz), 121.2, 112.2, 108.2, 99.2, 80.0, 64.5, 63.9, 58.1, 41.2 (q, $J_{C-F}$=3.9 Hz); MS (ES+) m/z 455.9 (M+1).

EXAMPLE 5.12

Synthesis of 1'-{[4-(trifluoromethyl)pyridin-3-yl]methyl}-2,3-dihydrospiro[furo[2,3-g][1,4]benzodioxine-8,3'-indol]-2'(1'H)-one

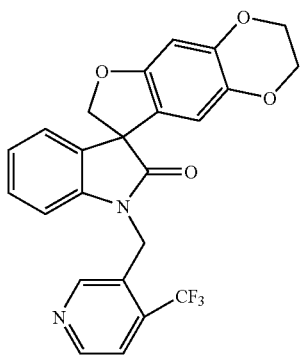

Following the procedure as described in Example 5.9, making non-critical variations using 3-(chloromethyl)-4-(trifluoromethyl)pyridine hydrochloride to replace 3-(chloromethyl)-2-(trifluoromethyl)pyridine, 1'-{[4-(trifluoromethyl)pyridin-3-yl]methyl}-2,3-dihydrospiro[furo[2,3-g][1,4]benzodioxine-8,3'-indol]-2'(1'H)-one was obtained (51%) as a colorless solid: mp 131-132° C.; $^1$H NMR (300 MHz, CDCl$_3$) δ8.78-8.72 (m, 1H), 8.51 (s, 1H), 7.64-7.60 (m, 1H), 7.25-7.18 (m, 2H), 7.12-7.05 (m, 1H), 6.65-6.60 (m, 1H), 6.53 (s, 1H), 6.32 (s, 1H), 5.32-5.11 (m, 2H), 4.84 (ABq, J=78.9, 8.9 Hz, 2H), 4.24-4.10 (m, 4H); $^{13}$C NMR (300 MHz, CDCl$_3$) δ 177.9, 155.3, 149.9, 148.9, 144.8, 141.3, 138.4, 135.8 (q, $J_{C-F}$=32.8 Hz), 132.0, 129.1, 128.1, 124.3, 124.1, 123.0 (q, $J_{C-F}$=275.0 Hz), 120.4, 119.6 (m), 111.6, 108.8, 99.5, 80.2, 64.5, 63.9, 58.1, 38.8 (m); MS (ES+) m/z 455.0 (M+1).

EXAMPLE 5.13

Synthesis of 1'-[(6-chloropyridin-2-yl)methyl]-2,3-dihydrospiro[furo[2,3-g][1,4]benzodioxine-8,3'-indol]-2'(1'H)-one

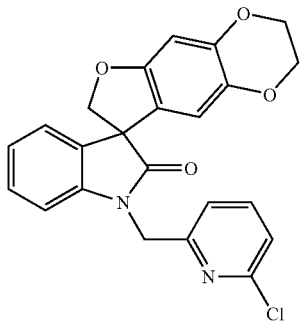

Following the procedure as described in Example 5.9, making non-critical variations using 2-chloro-6-(chloromethyl)pyridine hydrochloride to replace 3-(chloromethyl)-2-(trifluoromethyl)pyridine, 1'-[(6-chloropyridin-2-yl)methyl]-2,3-dihydrospiro[furo[2,3-g][1,4]benzodioxine-8,3'-indol]-2'(1'H)-one was obtained (90%) as a colorless solid: mp 181-182° C.; $^1$H NMR (300 MHz, CDCl$_3$) δ7.67-7.59 (m, 1H), 7.28-7.22 (m, 2H), 7.22-7.13 (m, 2H), 7.08-7.02 (m, 1H), 6.90-6.84 (m, 1H), 6.52 (s, 1H), 6.32 (s, 1H), 5.23-5.14 (m, 1H), 4.98-4.89 (m, 2H), 4.70-4.65 (m, 1H), 4.24-4.09 (m, 4H); $^{13}$C NMR (300 MHz, CDCl$_3$) δ 177.5, 156.4, 155.2, 151.2, 144.6, 141.7, 139.7, 138.3, 132.1, 128.9, 123.9, 123.7, 123.4, 120.8, 119.9, 111.6, 109.3, 99.4, 80.1, 64.5, 63.9, 58.1, 45.4; MS (ES+) m/z 420.7 (M+1), 422.7 (M+1).

EXAMPLE 5.14

Synthesis of 1'-[(2-methoxypyrimidin-5-yl)methyl]-2,3-dihydrospiro[furo[2,3-g][1,4]benzodioxine-8,3'-indol]-2'(1'H)-one

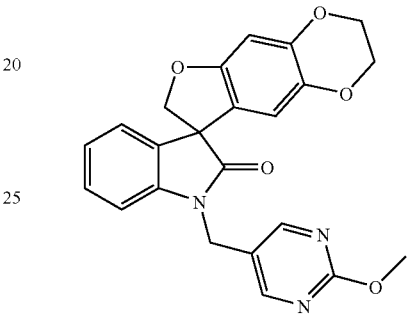

Following the procedure as described in Example 5.9, making non-critical variations using 5-(chloromethyl)-2-methoxypyrimidine hydrochloride to replace 3-(chloromethyl)-2-(trifluoromethyl)pyridine, 1'-[(2-methoxypyrimidin-5-yl)methyl]-2,3-dihydrospiro[furo[2,3-g][1,4] benzodioxine-8,3'-indol]-2'(1'H)-one was obtained (47%) as a colorless solid: mp 248-249° C.; $^1$H NMR (300 MHz, DMSO-d$_6$) δ8.64 (s, 2H), 7.34-7.27 (m, 1H), 7.21-7.14 (m, 2H), 7.08-7.01 (m, 1H), 6.51 (s, 1H), 6.10 (s, 1H), 4.98-4.85 (m, 2H), 4.73 (ABq, J=49.9, 9.4 Hz, 2H), 4.21-4.06 (m, 4H), 3.89 (s, 3H); $^{13}$C NMR (300 MHz, CDCl$_3$) δ 176.8, 164.6, 158.9, 154.6, 144.1, 141.6, 137.7, 131.8, 128.7, 123.6, 123.5, 123.1, 121.0, 110.9, 109.2, 98.7, 79.3, 64.1, 63.5, 57.1, 54.6, 38.0; MS (ES+) m/z 418.2 (M+1).

EXAMPLE 5.15

Synthesis of 1'-[(6-methoxypyridin-3-yl)methyl]-2,3-dihydrospiro[furo[2,3-g][1,4]-benzodioxine-8,3'-indol]-2'(1'H)-one

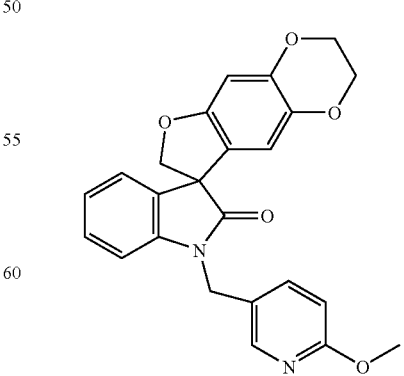

Following the procedure as described in Example 5.9, making non-critical variations using 5-(chloromethyl)-2-methoxypyridine hydrochloride to replace 3-(chloromethyl)-

2-(trifluoromethyl)pyridine, 1-[(6-methoxypyridin-3-yl)methyl]-2,3-dihydrospiro[furo[2,3-g][1,4]benzodioxine-8,3'-indol]-2'(1'H)-one was obtained (34%) as a colorless solid: mp 161-162° C.; $^1$H NMR (300 MHz, DMSO-$d_6$) δ 8.26-8.22 (m, 1H), 7.69-7.63 (m, 1H), 7.32-7.25 (m, 1H), 7.19-7.08 (m, 2H), 7.07-7.00 (m, 1H), 6.84-6.79 (m, 1H), 6.52 (s, 1H), 6.05 (s, 1H), 4.91-4.86 (m, 2H), 4.73 (ABq, J=42.8, 9.4 Hz, 2H), 4.22-4.06 (m, 4H), 3.82 (s, 3H); $^{13}$C NMR (75 MHz, DMSO-$d_6$) δ 176.7, 163.0, 154.6, 145.9, 144.1, 141.8, 138.5, 137.7, 131.7, 128.7, 125.0, 123.6, 123.1, 121.1, 110.8, 110.7, 109.3, 98.8, 79.3, 64.1, 63.5, 57.2, 53.1; MS (ES+) m/z 416.9 (M+1).

EXAMPLE 5.16

Synthesis of (8S)-1'-(pyrazin-2-ylmethyl)-2,3-dihydrospiro[furo[2,3-g][1,4]benzodioxine-8,3'-indol]-2'(1'H)-one

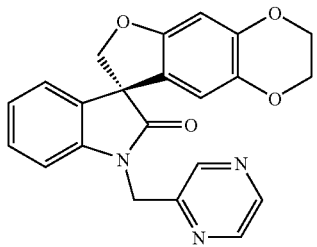

Following the procedure as described in Example 5.9, making non-critical variations using 2-(chloromethyl)pyrazine to replace 3-(chloromethyl)-2-(trifluoromethyl)pyridine, and (8S)-2,3-dihydrospiro[furo[2,3-g][1,4]benzodioxine-8,3'-indol]-2'(1'H)-one to replace 2,3-dihydrospiro[furo[2,3-g][1,4]benzodioxine-8,3'-indol]-2'(1'H)-one, (8S)-1'-(pyrazin-2-ylmethyl)-2,3-dihydrospiro[furo[2,3-g][1,4]benzodioxine-8,3'-indol]-2(1'H)-one was obtained (62%) as a colorless solid: mp 216-218° C.; $^1$H NMR (300 MHz, CDCl$_3$) δ 8.65-8.62 (m, 1H), 8.58-8.50 (m, 2H), 7.27-7.15 (m, 2H), 7.09-7.01 (m, 1H), 6.91-6.85 (m, 1H), 6.51 (s, 1H), 6.31 (s, 1H), 5.13 (ABq, J=55.5, 16.1 Hz, 2H), 4.81 (ABq, J=81.0, 9.0 Hz, 2H), 4.24-4.09 (m, 4H); $^{13}$C NMR (300 MHz, CDCl$_3$) δ177.5, 155.2, 151.2, 144.6, 144.2, 143.9, 143.8, 141.7, 138.3, 132.2, 128.8, 124.0, 123.7, 120.8, 111.7, 109.1, 99.4, 80.0, 64.5, 63.8, 58.0, 43.7; MS (ES+) m/z 387.8 (M+1); Anal. Calcd for $C_{22}H_{17}N_3O_4$: C, 68.21; H, 4.42; N, 10.85. Found: C, 67.81; H, 4.39; N, 10.84.

EXAMPLE 5.17

Synthesis of (8S)-1'-[(2-methoxypyrimidin-5-yl)methyl]-2,3-dihydrospiro[furo[2,3-g][1,4]benzodioxine-8,3'-indol]-2'(1'H)-one

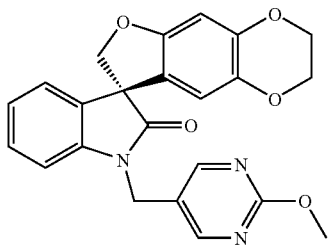

Following the procedure as described in Example 5.9 and making non-critical variations using 5-(chloromethyl)-2-methoxypyrimidine hydrochloride to replace 3-(chloromethyl)-2-(trifluoromethyl)pyridine, and (8S)-2,3-dihydrospiro[furo[2,3-g][1,4]benzodioxine-8,3'-indol]-2'(1'H)-one to replace 2,3-dihydrospiro[furo[2,3-g][1,4]benzodioxine-8,3'-indol]-2'(1'H)-one, (8S)-1'-[(2-methoxypyrimidin-5-yl)methyl]-2,3-dihydrospiro[furo[2,3-g][1,4]benzodioxine-8,3'-indol]-2'(1'H)-one was obtained (54%) as a colorless solid: mp 102-104° C.; $^1$H NMR (300 MHz, CDCl$_3$) δ 8.56 (s, 2H), 7.30-7.22 (m, 1H), 7.21-7.15 (m, 1H), 7.11-7.02 (m, 1H), 6.85-6.81 (m, 1H), 6.51 (s, 1H), 6.17 (s, 1H), 4.98-4.77 (m, 3H), 4.66-4.61 (m, 1H), 4.24-4.09 (m, 4H), 4.00 (s, 3H); $^{13}$C NMR (300 MHz, CDCl$_3$) δ 177.5, 165.4, 158.8, 155.2, 144.7, 141.2, 138.4, 132.2, 128.9, 124.3, 123.9, 122.7, 120.5, 111.4, 108.5, 99.5, 80.1, 64.5, 63.9, 57.9, 55.1, 38.9; MS (ES+) m/z 417.8 (M+1); Anal. Calcd for $C_{23}H_{19}N_3O_5$: C, 66.18; H, 4.59; N, 10.07. Found: C, 65.94; H, 4.68; N, 9.77.

EXAMPLE 5.18

Synthesis of (8S)-1'-(pyrimidin-2-ylmethyl)-2,3-dihydrospiro[furo[2,3-g][1,4]benzodioxine-8,3'-indol]-2'(1'H)-one

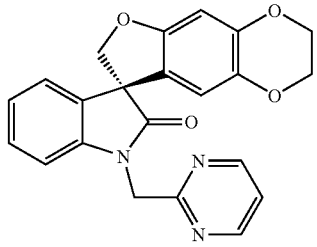

Following the procedure as described in Example 5.9, making non-critical variations using 2-(chloromethyl)pyrimidine hydrochloride to replace 3-(chloromethyl)-2-(trifluoromethyl)pyridine, and (8S)-2,3-dihydrospiro[furo[2,3-g][1,4]benzodioxine-8,3'-indol]-2'(1'H)-one to replace 2,3-dihydrospiro[furo[2,3-g][1,4]benzodioxine-8,3'-indol]-2'(1'H)-one, (8S)-1'-(pyrimidin-2-ylmethyl)-2,3-dihydrospiro[furo[2,3-g][1,4]benzodioxine-8,3'-indol]-2'(1'H)-one was obtained (59%) as a colorless solid: mp 210-212° C.; $^1$H NMR (300 MHz, CDCl$_3$) δ 8.72-8.68 (m, 2H), 7.23-7.14 (m, 3H), 7.06-6.99 (m, 1H), 6.74-6.69 (m, 1H), 6.56 (s, 1H), 6.50 (s, 1H), 5.21 (ABq, J=82.1, 17.0 Hz, 2H), 4.86 (ABq, J=81.2, 8.9 Hz, 2H), 4.22-4.10 (m, 4H); $^{13}$C NMR (300 MHz, CDCl$_3$) δ 177.8, 164.6, 157.5, 155.1, 144.5, 142.2, 138.2, 132.6, 128.6, 123.8, 123.3, 121.5, 119.8, 112.3, 108.7, 99.1, 80.0, 64.5, 63.9, 58.1, 45.7; MS (ES+) m/z 387.9 (M+1); Anal. Calcd for $C_{22}H_{17}N_3O_4$: C, 68.21; H, 4.42; N, 10.85. Found: C, 68.17; H, 4.41; N, 10.76.

EXAMPLE 5.19

Synthesis of 6-methyl-1'-(pyridin-2-ylmethyl)-2,3-dihydrospiro[1,4-dioxino[2,3-f]indole-8,3'-indole]-2',7(1H,6H)-dione

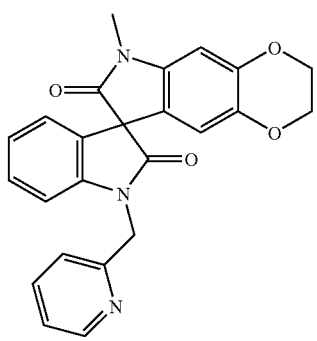

To a stirred solution of 6-methyl-2,3-dihydrospiro[1,4-dioxino[2,3-f]indole-8,3'-indole]-2',7(1H,6H)-dione (0.07 g, 0.21 mmol) in N,N-dimethylformamide (5 mL) was added cesium carbonate (0.20 g, 0.61 mmol) at 0° C. The reaction mixture was stirred at 0° C. for 30 min, 2-(bromomethyl)pyridine hydrobromide (0.08 g, 0.31 mmol) was added and the mixture was stirred at ambient temperature for 18 h. The mixture was diluted with water and ethyl acetate. The organic phase was washed with water and brine, dried over anhydrous sodium sulfate and filtered. The filtrate was concentrated in vacuo. The residue was purified by column chromatography and eluted with ethyl acetate/hexanes (3/2) to afford 6-methyl-1-(pyridin-2-ylmethyl)-2,3-dihydrospiro[1,4-dioxino[2,3-f]indole-8,3'-indole]-2',7(1'H,6H)-dione (0.02 g, 26%): mp 87-89° C. (ethyl acetate/hexanes); $^1$H NMR (300 MHz, CDCl$_3$) δ 8.64-8.63 (m, 1H), 7.71-7.62 (m, 2H), 7.26-7.17 (m, 2H), 6.96-6.47 (m, 3H), 6.47 (s, 1H), 6.46 (s, 1H), 5.33 (s, 2H), 4.24-4.06 (m, 4H), 3.22 (s, 3H); MS (ES+) m/z 414.0 (M+1).

EXAMPLE 5.20

Synthesis of 4'-fluoro-1-{[3-(trifluoromethyl)pyridin-2-yl]methyl}-2,3-dihydrospiro[furo[2,3-g][1,4]benzodioxine-8,3'-indol]-2'(1'H)-one

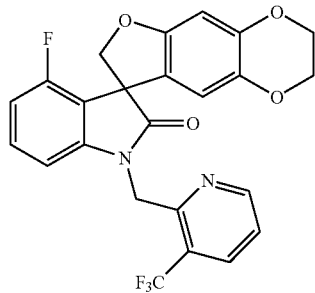

A mixture of 4'-fluoro-2,3-dihydrospiro[furo[2,3-g][1,4]benzodioxine-8,3'-indol]-2'(1'H)-one (0.31 g, 1.00 mmol), 2-(chloromethyl)-3-(trifluoromethyl)pyridine hydrochloride (0.29 g, 1.50 mmol) and cesium carbonate (0.98 g, 3.00 mmol) in N,N' dimethylformamide (10 mL) was heated at 60° C. for 2 h and was filtered while hot. The filtrate was allowed to cool to ambient temperature and water was added, causing a precipitate to be deposited. The solid was collected by filtration, washed with water (50 mL) and dried under vacuum. The residue was recrystallized from N,N' dimethylformamide/water to afford 4'-fluoro-1'-{[3-(trifluoromethyl)pyridin-2-yl]methyl}-2,3-dihydrospiro[furo[2,3-g][1,4]benzodioxine-8,3'-indol]-2'(1'H)-one (0.39 g, 82%) as a beige solid: mp 245-247° C.; $^1$H NMR (300 MHz, DMSO-d$_6$) δ 8.68 (d, J=4.5 Hz, 1H), 8.27 (d, J=7.65 Hz, 1H), 7.59 (dd, J=7.8, 4.9 Hz, 1H), 7.30 (ddd, J=8.2, 8.2, 5.8 Hz, 1H), 6.86 (d, J=9.0 Hz, 1H), 6.82 (d, J=7.8 Hz, 1H), 6.54 (s, 1H), 6.49 (s, 1H), 5.25 (ABq, J=17.4 Hz, 2H), 4.79 (q, J=9.4 Hz, 2H), 4.22-4.10 (m, 4H); $^{13}$C NMR (75 MHz, DMSO-d$_6$) δ 176.5, 157.9 (d, $^1J_{C-F}$=247 Hz), 154.6, 152.3, 152.1 (d, $^5J_{C-F}$=1.2 Hz), 144.9 (d, $^4J_{C-F}$=8.9 Hz), 144.3, 137.6, 135.1 (q, $^4J_{C-F}$=4.9 Hz), 130.8 (d, $^4J_{C-F}$=8.6 Hz), 125.6 (q, $^1J_{C-F}$=274 Hz), 123.0, 122.9 (d, $^2J_{C-F}$=32.3 Hz), 119.4, 117.1 (d, $^3J_{C-F}$=19.3 Hz), 111.5, 109.9 (d, $^3J_{C-F}$=19.9 Hz), 105.7 (d, $^5J_{C-F}$=2.9 Hz), 98.4, 77.4, 64.1, 63.5, 56.0 (d, $^5J_{C-F}$=1.7 Hz), 42.3 (q, $^5J_{C-F}$=3.3 Hz); MS (ES+) m/z 460.9 (M+1).

EXAMPLE 5.21

Synthesis of 1'-[(2,2-difluorocyclopropyl)methyl]-2,3-dihydrospiro[furo[2,3-g][1,4]benzodioxine-8,3'-indol]-2'(1'H)-one

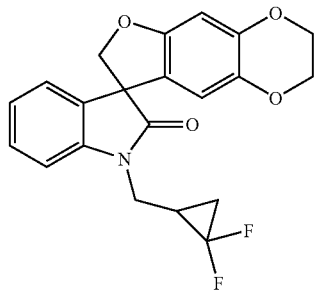

A mixture of 2,3-dihydrospiro[furo[2,3-g][1,4]benzodioxine-8,3'-indol]-2'(1'H)-one (0.29 g, 1.00 mmol), 2-(bromomethyl)-1,1-difluorocyclopropane (0.21 g, 1.20 mmol), cesium carbonate (0.65 g, 2.00 mmol) and N,N'-dimethylformamide (2.5 mL) was heated at 40° C. for 2 h and filtered while hot. The filtrate was allowed to cool to ambient temperature and water was added, causing a precipitate to be deposited. The solid was collected by filtration, washed with water and dried under vacuum. The residue was recrystallized from ethanol/diethyl ether to afford 1'-[(2,2-difluorocyclopropyl)methyl]-2,3-dihydrospiro[furo[2,3-g][1,4]benzodioxine-8,3'-indol]-2'(1'H)-one (0.28 g, 73%) as a colourless solid: mp 162-164° C.; $^1$H NMR (300 MHz, DMSO-d$_6$) δ 7.35 (ddd, J=7.8, 7.8, 0.9 Hz, 1H), 7.23 (dd, J=7.9 Hz, 1H), 7.17 (d, J=6.9 Hz, 1H), 7.06 (dd, J=7.4, 7.4 Hz, 1H), 6.51 (d, J=1.9 Hz, 1H), 6.13 (d, J=6.2 Hz, 1H), 4.71 (dd, J=9.3 Hz, 1H), 4.69 (dd, J=9.3 Hz, 1H), 4.17 (dd, J=3.7 Hz, 2H), 4.10 (dd, J=3.4 Hz, 2H), 3.87 (d, J=6.9 Hz, 2H), 2.33-2.14 (m, 1H), 1.74-1.60 (m, 1H), 1.48-1.29 (m, 1H); $^{13}$C NMR (75 MHz, DMSO-d$_6$) δ 176.5 (d, $^4J_{C-F}$=15.9 Hz), 154.5 (d, $^6J_{C-F}$=1.4 Hz), 144.1 (d, $^6J_{C-F}$=1.9 Hz), 141.9, 137.7 (d, $^5J_{C-F}$=3.9 Hz), 131.7 (d, $^6J_{C-F}$=2.3 Hz), 128.8, 123.5, 122.9 (d, $^6J_{C-F}$=1.6 Hz), 121.2 (d, $^5J_{C-F}$=4.1 Hz), 114.3 (q, $^1J_{C-F}$=283.4 Hz), 110.9 (d, $^2J_{C-F}$=18.1 Hz), 109.1, 98.7 (d, $^5J_{C-F}$=3.6 Hz), 79.2 (d, $^5J_{C-F}$=3.7 Hz), 64.1, 63.5, 57.1 (d, $^6J_{C-F}$=2.4 Hz), 36.6 (t, $^3J_{C-F}$=5.9 Hz), 20.1 (t, $^2J_{C-F}$=17.4 Hz), 14.7 (t, $^2J_{C-F}$=10.7 Hz); MS (ES+) m/z 386.2 (M+1).

EXAMPLE 5.22

Synthesis of 1'-methyl-2,3-dihydrospiro[furo[2,3-g][1,4]benzodioxine-8,3'-indol]-2'(1'H)-one

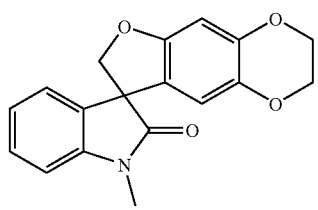

Following the procedure as described in EXAMPLE 5.21 and making non-critical variations using dimethyl sulfate to replace 2-(bromomethyl)-1,1-difluorocyclopropane, 1'-methyl-2,3-dihydrospiro[furo[2,3-g][1,4]benzodioxine-8,3'-indol]-2'(1'H)-one was obtained (28%) as a colourless solid: mp 152-154° C.; $^1$H NMR (300 MHz, DMSO-d$_6$) δ 7.34 (d, J=7.6 Hz, 1H), 7.15-7.01 (m, 3H), 6.50 (s, 1H), 6.18 (s, 1H), 4.67 (d, J=9.3 Hz, 2H), 4.13 (dd, J=4.5, 2.8 Hz, 4H), 3.14 (s, 3H); $^{13}$C NMR (75 MHz, DMSO-d$_6$) δ 176.9, 155.1, 144.5, 143.7, 138.2, 132.2, 129.2, 123.7, 123.3, 121.7, 111.8, 109.3, 99.1, 79.9, 64.6, 64.0, 57.6, 26.9; MS (ES+) m/z 310.2 (M+1).

EXAMPLE 5.23

Synthesis of 1-{[4-(trifluoromethyl)-1,3-thiazol-2-yl]methyl}-2,3-dihydrospiro[furo[2,3-g][1,4]benzodioxine-8,3'-indol]-2'(1'H)-one

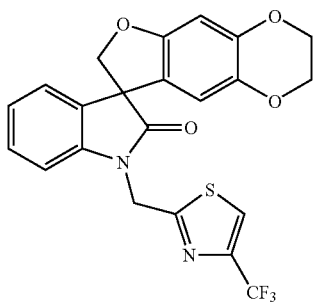

Following the procedure as described in EXAMPLE 5.21 and making non-critical variations using 2-(bromomethyl)-4-(trifluoromethyl)thiazole to replace 2-(bromomethyl)-1,1-difluorocyclopropane, 1'-{[4-(trifluoromethyl)-1,3-thiazol-2-yl]methyl}-2,3-dihydrospiro[furo[2,3-g][1,4] benzodioxine-8,3'-indol]-2'(1'H)-one was obtained (58%) as a colourless solid: mp 169-170° C.; $^1$H NMR (300 MHz, DMSO-d$_6$) δ 8.49 (s, 1H), 7.32 (dd, J=7.7, 7.7 Hz, 1H), 7.21 (d, J=6.9 Hz, 1H), 7.15 (d, J=7.8 Hz, 1H), 7.08 (dd, J=7.3, 7.3 Hz, 1H), 6.53 (s, 1H), 6.22 (s, 1H), 5.36 (ABq, J=16.9 Hz, 2H), 4.74 (dd, J=9.4 Hz, 2H), 4.14 (dd, J=4.7, 3.1 Hz, 4H); $^{13}$C NMR (75 MHz, DMSO-d$_6$) δ 176.5, 168.6, 154.5, 144.1, 143.3, 142.2 (d, $^2J_{C-F}$=36.5 Hz), 137.8, 131.6, 128.8, 124.5 (q, $^3J_{C-F}$=6.6 Hz), 123.7, 123.4, 120.9, 120.3 (q, $^1J_{C-F}$=270 Hz), 111.1, 109.1, 98.7, 79.2, 64.1, 63.5, 57.1, 41.1; MS (ES+) m/z 460.9 (M+1).

EXAMPLE 5.24

Synthesis of (2'-oxo-2,3-dihydrospiro[furo[2,3-g][1,4]benzodioxine-8,3'-indol]-1'(2'H)-yl)acetonitrile

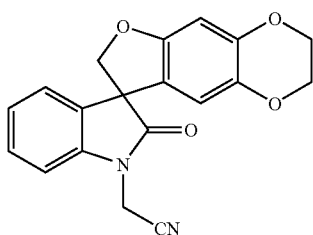

Following the procedure as described in Example 5.9 and making non-critical variations using bromoacetonitrile to replace 2-(chloromethyl)-6-(trifluoromethyl)pyridine, (2'-oxo-2,3-dihydrospiro[furo[2,3-g][1,4]benzodioxine-8,3'-indol]-1'(2'H)-yl)acetonitrile was obtained (54%) as a colorless solid: mp 161-162° C. (diethyl ether); $^1$H NMR (300 MHz, CDCl$_3$) δ 7.35-7.38 (m, 1H), 7.23-7.10 (m, 2H), 7.04 (d, J=7.8 Hz, 1H), 6.48 (s, 1H), 6.21 (s, 1H), 4.87 (d, J=9.1 Hz, 1H), 4.67 (d, J=3.7 Hz, 2H), 4.63 (d, J=9.1 Hz, 1H), 4.20-4.05 (m, 4H); $^{13}$C NMR (75 MHz, CDCl$_3$) δ 176.6, 155.2, 144.9, 139.7, 138.5, 131.6, 129.3, 124.8, 124.4, 120.1, 113.6, 111.6, 108.7, 99.6, 79.9, 64.5, 63.9, 57.9, 28.0; MS (ES+) m/z 334.9 (M+1).

EXAMPLE 5.25

Synthesis of 9-fluoro-1'-(pyridin-2-ylmethyl)-2,3-dihydro-spiro[furo[2,3-g][1,4]benzodioxine-8,3'-indol]-2'(1'H)-one

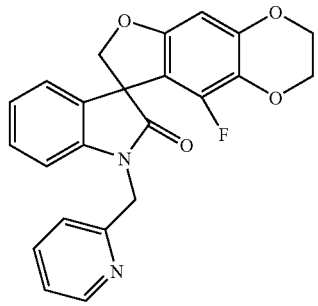

A 50 mL round bottom flask was charged with 9-fluoro-2,3-dihydro-spiro[furo[2,3-g][1,4]benzodioxine-8,3'-indol]-2'(1'H)-one (0.63 g, 2.0 mmol), 2-(bromomethyl)pyridine hydrobromide (0.51 g, 2.0 mmol), cesium carbonate (3.26 g, 10.0 mmol) and N,N-dimethylformamide (20 mL). The reaction mixture was heated at 90° C. for 1 h, allowed to cool to ambient temperature, filtered and the filtrate concentrated in vacuo. Purification of the residue by column chromatography and eluted with a 0% to 70% gradient of ethyl acetate in dichloromethane afforded 9-fluoro-1'-(pyridin-2-ylmethyl)-2,3-dihydro-spiro[furo[2,3-g][1,4]benzodioxine-8,3'-indol]-2'(1'H)-one (0.46 g, 57%) as an off-white solid: $^1$H NMR (300 MHz, DMSO-d$_6$) δ 8.45 (d, J=4.3 Hz, 1H), 7.71-7.77 (m, 1H), 7.40-6.87 (m, 6H), 6.19 (d, J=1.8 Hz, 1H), 5.02 (ABq, 2H), 4.84 (ABq, 2H), 4.27-4.09 (m, 4H); $^{13}$C NMR (75 MHz, DMSO-d$_6$) δ 176.7, 155.6, 149.6, 143.1, 142.1, 142.0, 139.2, 139.2, 138.5, 137.5, 135.3, 133.9, 133.7, 131.5, 129.3, 124.1, 123.4, 123.2, 122.7, 122.7, 122.1, 109.9, 106.6, 106.6, 80.8, 64.7, 64.1, 58.0, 58.0, 45.2; MS (ES+) m/z 404.8 (M+1).

EXAMPLE 5.26

Synthesis of 9-fluoro-1'-{[3-(trifluoromethyl)pyridin-2-yl]methyl}-2,3-dihydrospiro[furo[2,3-g][1,4]benzodioxine-8,3'-indol]-2'(1'H)-one

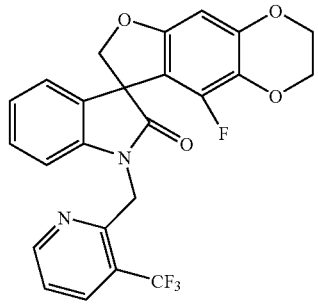

Following the procedure as described in EXAMPLE 5.25 and making non-critical variations using 2-(chloromethyl)-3-(trifluoromethyl)pyridine hydrochloride to replace 2-(bromomethyl)pyridine hydrobromide, 9-fluoro-1'-{[3-(trifluoromethyl)pyridin-2-yl]methyl}-2,3-dihydrospiro[furo[2,3-g][1,4]benzodioxine-8,3'-indol]-2'(1'H)-one was obtained (25%) as a colorless solid: $^1$H NMR (300 MHz, DMSO-d$_6$) δ 8.62 (d, J=4.3 Hz, 1H), 8.21 (d, J=7.4 Hz, 1H), 7.53 (dd, J=7.7, 5.0 Hz, 1H), 7.28-6.83 (m, 4H), 6.29 (d, J=1.8 Hz, 1H), 5.20 (ABq, 2H), 4.84 (ABq, 2H), 4.27-4.10 (m, 4H); $^{13}$C NMR (75 MHz, DMSO-d$_6$) δ 176.9, 152.8, 143.4, 142.0, 141.9, 139.2, 139.2, 138.5, 135.5, 135.4, 135.4, 135.2, 133.9, 133.7, 131.5, 129.3, 126.1, 124.1, 123.7, 123.4, 123.4, 123.2, 122.8, 122.8, 122.5, 109.6, 106.8, 106.8, 80.6, 64.7, 64.1, 58.0, 58.0, 42.4, 42.4; MS (ES+) m/z 472.9 (M+1).

EXAMPLE 5.27

Synthesis of 9-fluoro-1'-[(5-hydroxypyridin-2-yl)methyl]-2,3-dihydrospiro[furo[2,3-g][1,4]benzodioxine-8,3'-indol]-2'(1'H)-one

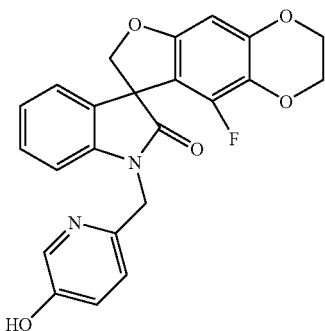

Following the procedure as described in EXAMPLE 5.25 and making non-critical variations using 5-(benzyloxy)-2-(chloromethyl)pyridine hydrochloride to replace 2-(bromomethyl)pyridine hydrobromide, 1'-{[5-(benzyloxy)pyridine-2-yl]methyl}-9-fluoro-2,3-dihydrospiro[furo[2,3-g][1,4]benzodioxine-8,3'-indol]-2'(1'H)-one (59%) was obtained as a colorless solid: MS (ES+) m/z 511.0 (M+1). A mixture of the 1'-{[5-(benzyloxy)pyridine-2-yl]methyl}-9-fluoro-2,3-dihydrospiro[furo[2,3-g][1,4]benzodioxine-8,3'-indol]-2'(1'H)-one from the last step, palladium on carbon (10% w/w, 0.2 g), methanol (50 mL) and acetic acid (1 drop) was hydrogenated at a pressure of 50 psi at ambient temperature for 5 h. The reaction mixture was filtered and the filtrate was concentrated in vacuo. The residue was purified by column chromatography and eluted with a 0% to 70% gradient of ethyl acetate in dichloromethane to afford 9-fluoro-1'-[(5-hydroxypyridin-2-yl)methyl]-2,3-dihydrospiro[furo[2,3-g][1,4]benzodioxine-8,3'-indol]-2'(1'H)-one (0.37 g, 46%) as an off-white solid: $^1$H NMR (300 MHz, DMSO-d$_6$) δ9.88 (s, 1H), 8.00 (d, J=2.6 Hz, 1H), 7.25-7.09 (m, 4H), 7.01-6.87 (m, 2H), 6.12 (d, J=1.8 Hz, 1H), 4.88 (ABq, 2H), 4.82 (ABq, 2H), 4.29-4.09 (m, 4H); $^{13}$C NMR (75 MHz, DMSO-d$_6$) δ176.0, 152.8, 145.2, 142.6, 141.5, 141.4, 138.7, 138.0, 137.1, 134.8, 133.4, 133.2, 131.0, 128.8, 123.5, 123.0, 122.8, 122.4, 122.2, 109.5, 106.0, 80.2, 64.3, 63.6, 57.5, 44.2; MS (ES+) m/z 421.1 (M+1).

EXAMPLE 5.28

Synthesis of 1'-(pyridin-2-ylmethyl)-7,8-dihydro-6H-spiro-[furo[2,3-g]chromene-3,3'-indol]-2'(1'H)-one

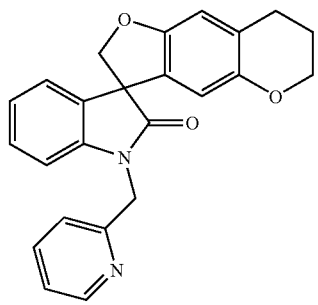

Following the procedure as described in EXAMPLE 5.25 and making non-critical variations using 7,8-dihydro-6H-spiro[furo[2,3-g]chromene-3,3'-indol]-2'(1'H)-one to replace 9-fluoro-2,3-dihydro-spiro[furo[2,3-g][1,4]benzodioxine-8,3'-indol]-2'(1'H)-one, 1-(pyridin-2-ylmethyl)-7,8-dihydro-6H-spiro-[furo[2,3-g]chromene-3,3'-indol]-2'(1'H)-one was obtained (87%) as an off-white solid: $^1$H NMR (300 MHz, DMSO-d$_6$) δ 8.46 (d, J=4.8 Hz, 1H), 7.71-7.77 (m, 1H), 7.37-6.88 (m, 6H), 6.64 (s, 1H), 6.18 (s, 1H), 5.03 (ABq, 2H), 4.72 (ABq, 2H), 4.04-3.84 (m, 2H), 2.66 (t, J=6.4 Hz, 2H), 1.88-1.67 (m, 2H); $^{13}$C NMR (75 MHz, DMSO-d$_6$) δ177.1, 155.7, 154.3, 149.7, 149.4, 143.0, 137.5, 132.3, 129.1, 128.6, 123.9, 123.6, 123.4, 123.1, 122.0, 111.5, 110.4, 109.8, 79.3, 66.2, 58.0, 45.2, 25.2, 22.1; MS (ES+) m/z 384.8 (M+1).

EXAMPLE 5.29

Synthesis of 1-{[3-(trifluoromethyl)pyridin-2-yl]methyl}-7,8-dihydro-6H-spiro[furo[2,3-g]chromene-3,3'-indol]-2'(1'H)-one

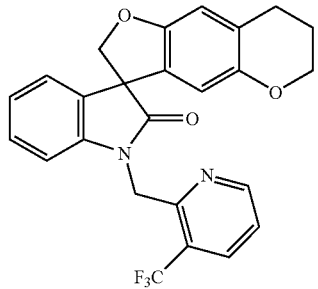

Following the procedure as described in EXAMPLE 5.25 and making non-critical variations using 7,8-dihydro-6H-spiro[furo[2,3-g]chromene-3,3'-indol]-2'(1'H)-one to replace 9-fluoro-2,3-dihydro-spiro[furo[2,3-g][1,4]benzodioxine-8,3'-indol]-2'(1'H)-one, and 2-(chloromethyl)-3-(trifluoromethyl)pyridine hydrochloride to replace 2-(bromomethyl)pyridine hydrobromide, 1-{[3-(trifluoromethyl)pyridin-2-yl]methyl}-7,8-dihydro-6H-spiro[furo[2,3-g]chromene-3,3'-indol]-2'(1'H)-one was obtained (2%) as a colorless solid: $^1$H NMR (300 MHz, DMSO-d$_6$) δ 8.65 (d, J=4.4 Hz, 1H), 8.25 (d, J=7.8 Hz, 1H), 7.56 (dd, J=7.8, 5.0 Hz, 1H), 7.20-7.26 (m, 1H), 7.15 (d, J=6.9 Hz, 1H), 7.01 (t, J=7.4 Hz, 1H), 6.88 (d, J=7.8 Hz, 1H), 6.65 (s, 1H), 6.31 (s, 1H), 5.22 (ABq, J=39.2 Hz, 2H), 4.72 (ABq, J=18.8 Hz, 2H), 4.04-3.95 (m, 2H), 2.70

(t, J=6.4 Hz, 2H), 1.89-1.77 (m, 2H); $^{13}$C NMR (75 MHz, DMSO-d$_6$) δ177.1, 155.7, 154.3, 149.7, 149.4, 143.0, 137.5, 132.3, 129.1, 128.6, 123.9, 123.6, 123.4, 123.1, 122.0, 111.5, 110.4, 109.8, 79.3, 66.2, 58.0, 45.2, 25.2, 22.1; MS (ES+) m/z 453.2 (M+1).

EXAMPLE 5.30

Synthesis of ethyl 2-[(2'-oxo-2,3-dihydrospiro[furo[2,3-g][1,4]benzodioxine-8,3'-indol]-1'(2'H)-yl)methyl]pyridine-3-carboxylate

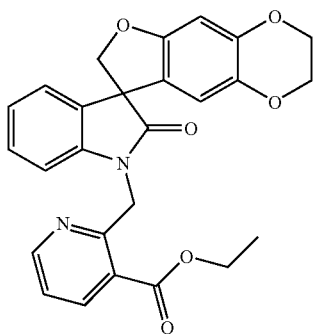

A 50 mL round-bottom flask was charged with 2,3-dihydrospiro[furo[2,3-g][1,4]benzodioxine-8,3'-indol]-2'(1'H)-one (2.0 g, 6.8 mmol), ethyl 2-(bromomethyl)nicotinate (2.3 g, 9.4 mmol), cesium carbonate (6.62 g, 20.3 mmol), potassium iodide (0.17 g, 1.0 mmol) and N,N-dimethylformamide (30 mL). The reaction mixture was stirred under nitrogen at 95° C. for 1 h, allowed to cool to ambient temperature and concentrated in vacuo. Purification of the residue by column chromatography and eluted with a 0% to 30% gradient of ethyl acetate in dichloromethane afforded ethyl 2-[(2'-oxo-2,3-dihydrospiro[furo[2,3-g][1,4]benzodioxine-8,3'-indol]-1'(2'H)-yl)methyl]pyridine-3-carboxylate (2.4 g, 79%) as an off-white solid: MS (ES+) m/z 459.0 (M+1).

EXAMPLE 5.31

Synthesis of 1-(pyridin-2-ylmethyl)spiro[indole-3,3'-thieno[2,3-f][1]benzofuran]-2(1'H)-one 5,5'-dioxide

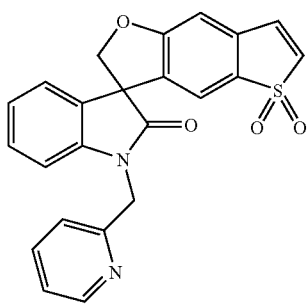

Following the procedure as described in EXAMPLE 5.25 and making non-critical variations using spiro[indole-3,3'-thieno[2,3-f][1]benzofuran]-2(1'H)-one 5,5'-dioxide to replace 9-fluoro-2,3-dihydro-spiro[furo[2,3-g][1,4]benzodioxine-8,3'-indol]-2'(1'1-1)-one, 1-(pyridin-2-ylmethyl)spiro[indole-3,3'-thieno[2,3-f][1]benzofuran]-2(1'H)-one 5,5'-dioxide was obtained (43%) as an off-white solid: $^1$H NMR (300 MHz, CDCl$_3$) δ 8.44 (d, J=4.8 Hz, 1H), 7.87-6.91 (m, 11H), 5.11 (ABq, 2H), 4.96 (ABq, 2H); $^{13}$C NMR (75 MHz, CDCl$_3$) δ 176.0, 165.5, 155.2, 149.4, 143.0, 137.6, 134.3, 131.1, 129.9, 129.1, 128.6, 128.5, 126.4, 124.4, 124.1, 123.8, 123.3, 122.9, 111.4, 110.4, 81.3, 56.4, 44.8; MS (ES+) m/z 416.9 (M+1).

EXAMPLE 5.32

Synthesis of 1'-(pyrimidin-2-ylmethyl)-2,3-dihydrospiro[furo[2,3-g][1,4]-benzodioxine-8,3'-indol]-2'(1'H)-one

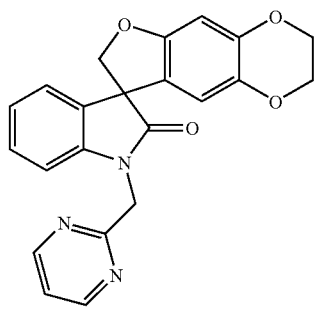

Following the procedure as described in EXAMPLE 5 and making non-critical variations using 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, and 2-(chloromethyl)pyrimidine hydrochloride to replace 5-(chloromethyl)-2-methoxypyrimidine, 1-(pyrimidin-2-ylmethyl)-2,3-dihydrospiro[furo[2,3-g][1,4]benzodioxine-8,3'-indol]-2'(1'H)-one was obtained (90%): mp 278-279° C.; $^1$H NMR (300 MHz, CDCl$_3$) δ8.67 (d, J=4.9 Hz, 2H), 7.20-7.11 (m, 3H), 7.05-6.94 (m, 1H), 6.72-6.67 (m, 1H), 6.54 (s, 1H), 6.47 (s, 1H), 5.19 (ABq, 2H), 4.83 (ABq, 2H), 4.21-4.02 (m, 4H); $^{13}$C NMR (75 MHz, CDCl$_3$) δ177.8, 164.6, 157.5, 155.1, 144.5, 142.2, 138.2, 132.6, 128.6, 123.8, 123.3, 121.5, 119.8, 112.3, 108.7, 99.1, 80.0, 64.5, 63.9, 58.1, 45.7; MS (ES+) m/z 387.9 (M+1).

EXAMPLE 5.33

Synthesis of 1'-[(4,6-dimethoxypyrimidin-2-yl)methyl]-2,3-dihydrospiro[furo[2,3-g][1,4]benzodioxine-8,3'-indol]-2'(1'H)-one

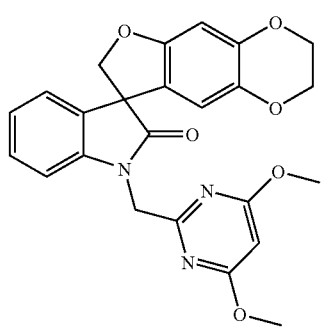

Following the procedure as described in EXAMPLE 5 and making non-critical variations using 2,3-dihydrospiro[furo[2,3-g][1,4]benzodioxine-8,3'-indol]-2'(1'H)-one to replace 5,6-dihydrospiro[benzo[1,2-b:5,4-b']difuran-3,3'-indol]-2'(1'H)-one, and 2-(chloromethyl)-4,6-dimethoxypyrimidine to replace 5-(chloromethyl)-2-methoxypyrimidine, 1'-[(4,6-dimethoxypyrimidin-2-yl)methyl]-2,3-dihydrospiro[furo[2, 3-g][1,4]benzodioxine-8,3'-indol]-2'(1'H)-one was obtained (90%): mp 169-170° C.; $^1$H NMR (300 MHz, CDCl$_3$) δ7.21-7.11 (m, 2H), 7.06-6.95 (m, 1H), 6.81-6.67 (m, 1H), 6.49 (s, 1H), 6.37 (s, 1H), 5.89 (s, 1H), 4.98 (ABq, 2H), 4.80 (ABq, 2H), 4.23-4.00 (m, 4H), 3.80 (s, 6H); MS (ES+) m/z 447.9 (M+1).

EXAMPLE 5.34

Synthesis of 6-(2-methoxyethoxy)-1'-(pyridin-2-ylmethyl)spiro[1-benzofuran-3,3'-indol]-2'(1'H)-one

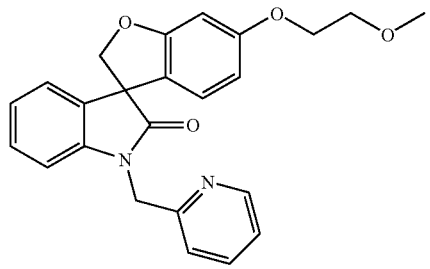

Following the procedure as described in EXAMPLE 5 and making non-critical variations using 6-(2-methoxyethoxy)spiro[1-benzofuran-3,3'-indol]-2'(1'H)-one to replace 5,6-dihydrospiro[benzo[1,2-b:5,4-b']difuran-3,3'-indol]-2'(1'H)-one, and 2-(bromomethyl)pyridine hydrobromide to replace 5-(chloromethyl)-2-methoxypyrimidine, 6-(2-methoxyethoxy)-1'-(pyridin-2-ylmethyl)spiro[1-benzofuran-3,3'-indol]-2'(1'H)-one was obtained (72%): mp 94-95° C.; $^1$H NMR (300 MHz, CDCl$_3$) δ8.56 (d, J=4.7 Hz, 1H), 7.69-7.59 (m, 1H), 7.25-7.09 (m, 4H), 7.05-6.95 (m, 1H), 6.92-6.82 (m, 2H), 6.81-6.73 (m, 1H), 6.37 (s, 1H), 5.08 (ABq, 2H), 4.83 (ABq, 2H), 3.93 (t, J=4.7 Hz, 2H), 3.62 (t, J=4.7 Hz, 2H), 3.36 (s, 3H); $^{13}$C NMR (75 MHz, CDCl$_3$ δ 177.2, 155.5, 155.1, 153.7, 149.5, 142.1, 137.1, 132.0, 129.6, 128.9, 123.8, 123.5, 122.8, 121.6, 115.8, 110.5, 110.4, 109.5, 79.8, 71.0, 68.1, 59.1, 58.5, 46.1; MS (ES+) m/z 403.0 (M+1).

EXAMPLE 5.35

Synthesis of 5-(2-methoxyethoxy)-1'-(pyridin-2-ylmethyl)spiro[1-benzofuran-3,3'-indol]-2'(1'H)-one

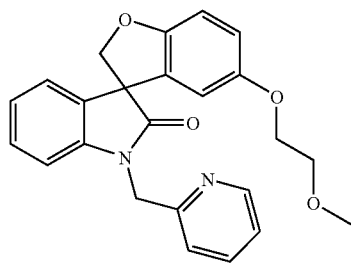

Following the procedure as described in EXAMPLE 5 and making non-critical variations using 5-(2-methoxyethoxy)spiro[1-benzofuran-3,3'-indol]-2'(1'H)-one to replace 5,6-dihydrospiro[benzo[1,2-b:5,4-b']difuran-3,3'-indol]-2'(1'H)-one, and 2-(bromomethyl)pyridine hydrobromide to replace 5-(chloromethyl)-2-methoxypyrimidine, 5-(2-methoxyethoxy)-1'-(pyridin-2-ylmethyl)spiro[1-benzofuran-3,3'-indol]-2'(1'H)-one was obtained (65%): mp 140-142° C.; $^1$H NMR (300 MHz, CDCl$_3$) δ8.57 (d, J=4.8 Hz, 1H), 7.65 (t, J=7.6 Hz, 1H), 7.25-7.11 (m, 4H), 7.06-6.97 (m, 1H), 6.89 (d, J=7.8 Hz, 1H), 6.68-6.62 (m, 1H), 6.59-6.54 (m, 1H), 6.44-6.38 (m, 1H), 5.09 (ABq, 2H), 4.87 (ABq, 2H), 4.11-4.05 (m, 2H), 3.77-3.68 (m, 2H), 3.43 (s, 3H); $^{13}$C NMR (75 MHz, CDCl$_3$) δ 177.6, 162.1, 160.7, 155.6, 149.5, 142.1, 137.0, 132.4, 128.8, 123.8, 123.6, 123.5, 122.7, 121.6, 121.1, 109.5, 108.2, 97.3, 80.5, 70.9, 67.6, 59.2, 57.7, 46.1; MS (ES+) m/z 403.0 (M+1).

EXAMPLE 5.36

Synthesis of 1-(pyridin-2-ylmethyl)-2,3-dihydrospiro[furo[2,3-f][1,4]benzodioxine-7,3'-indol]-2'(1'H)-one

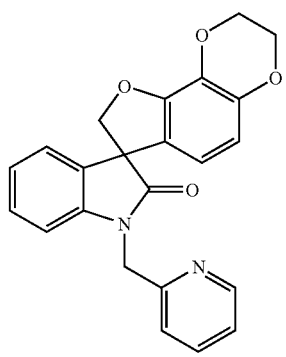

Following the procedure as described in EXAMPLE 5.30 and making non-critical variations using 2,3-dihydrospiro[furo[2,3-f][1,4]-benzodioxine-7,3'-indol]-2'(1'H)-one to replace 2,3-dihydrospiro[furo[2,3-g][1,4]benzodioxine-8,3'-indol]-2'(1'H)-one, and 2-(bromomethyl)pyridine hydrobromide to replace ethyl 2-(bromomethyl)nicotinate, (pyridin-2-ylmethyl)-2,3-dihydrospiro[furo[2,3-f][1,4]benzodioxine-7,3'-indol]-2'(1'H)-one was obtained (57%) as a colorless solid: mp 205-206° C.; $^1$H NMR (300 MHz, DMSO-d$_6$) δ8.52 (d, 1H, J=4.7 Hz), 7.79 (ddd, J=7.7, 7.7, 1.7 Hz, 1H), 7.35-7.20 (m, 4H), 7.02 (dd, J=7.5, 7.5 Hz, 1H), 6.93 (d, J=7.7 Hz, 1H), 6.29 (ABq, 2H), 5.04 (ABq, 2H), 4.84 (ABq, 2H), 4.27 (s, 4H); $^{13}$C NMR (75 MHz, DMSO-d$_6$) δ176.7, 155.2, 149.2, 148.8, 144.6, 142.5, 137.0, 131.6, 129.2, 128.6, 123.6, 122.9, 122.6, 122.4, 121.4, 114.4, 109.8, 109.2, 80.2, 64.1, 63.9, 57.3, 44.8; MS (ES+) m/z 387.7 (M+1).

EXAMPLE 5.37

Synthesis of 1'-{[3-(trifluoromethyl)pyridin-2-yl]methyl}-2,3-dihyrospiro[furo[2,3-f][1,4]benzodioxine-7,3'-indol]-2'(1'H)-one

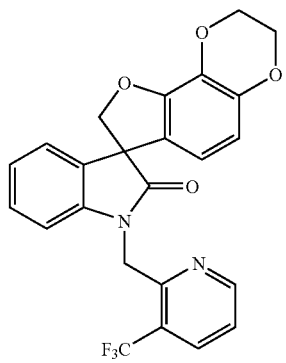

A mixture of (3-(trifluoromethyl)pyridin-2-yl)methanol hydrochloride (0.324 g, 1.52 mmol) and thionyl chloride (0.174 mL, 2.39 mmol) in anhydrous dichloromethane (10 mL) was stirred at ambient temperature for 16 h. The reaction mixture was concentrated in vacuo and anhydrous N,N-dimethylformamide (10 mL) was added. To this mixture was added 2,3-dihydrospiro[furo[2,3-f][1,4]benzodioxine-7,3'-indol]-2'(1'H)-one (0.300 g, 1.01 mmol), cesium carbonate (0.926 g, 2.84 mmol), potassium iodide (0.094 g, 0.57 mmol) and anhydrous N,N-dimethylformamide (15 mL) and the mixture was heated at 90° C. for 1 h. The reaction mixture was allowed to cool to ambient temperature, concentrated in vacuo, and the resulting residue was taken up in water (50 mL), sonicated and filtered. The solid was purified by column chromatography and eluted with a 0% to 40% gradient of ethyl acetate in dichloromethane followed by recrystallization from methanol to afford 1'-{[3-(trifluoromethyl)pyridin-2-yl]methyl}-2,3-dihyrospiro[furo[2,3-f][1,4]benzodioxine-7,3'-indol]-2'(1'H)-one (0.123 g, 27%) as a colorless solid: mp 206-207° C.; $^1$H NMR (300 MHz, DMSO-$d_6$) δ 8.72 (d, J=4.4 Hz, 1H), 8.24 (d, J=7.9 Hz, 1H), 7.55 (dd, J=7.8, 5.0 Hz, 1H), 7.26-7.20 (m, 2H), 7.01 (dd, J=11.3, 3.8 Hz, 1H), 6.88 (d, J=7.6 Hz, 1H), 6.36 (s, 2H), 5.22 (ABq, 2H), 4.83 (ABq, 2H), 4.27 (s, 4H); $^{13}$C NMR (75 MHz, DMSO-$d_6$) δ 177.0, 152.6, 152.4, 148.7, 144.6, 142.9, 134.9, 131.7, 129.1, 128.6, 123.5, 123.0, 122.8, 122.6, 122.5, 122.0, 114.8, 110.0, 108.9, 80.1, 64.1, 63.9, 57.3, 41.8; MS (ES+) m/z 455.0 (M+1).

EXAMPLE 5.38

Synthesis of 6-[(2'-oxospiro[furo[2,3-f][1,3]benzodioxole-7,3'-indol]-1'(2'H)-yl)methyl]pyrimidine-2,4(1H,3H)-dione

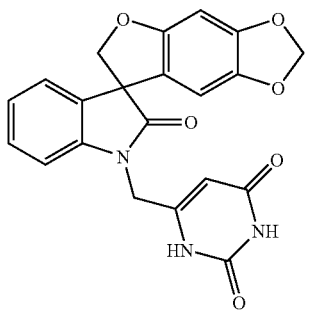

Following the procedure as described in EXAMPLE 5.25 and making non-critical variations using 6-(chloromethyl)uracil to replace 2-(bromomethyl)pyridine hydrobromide, and spiro[furo[2,3-f][1,3]benzodioxole-7,3'-indol]-2'(1'H)-one to replace 9-fluoro-2,3-dihydro-spiro[furo[2,3-g][1,4]benzodioxine-8,3'-indol]-2'(1'H)-one, 6-[(2'-oxospiro[furo[2,3-f][1,3]benzodioxole-7,3'-indol]-1'(2'H)-yl)methyl]pyrimidine-2,4(1H,3H)-dione was obtained (5%) as an off-white solid: mp>300° C.; $^1$H NMR (300 MHz, DMSO-$d_6$) δ 11.11 (s, 1H), 11.05 (s, 1H), 7.29 (dd, J=7.7, 7.7 Hz, 1H), 7.18 (d, J=6.8 Hz, 1H), 7.05 (dd, J=7.5, 7.5 Hz, 1H), 7.03 (dd, J=7.7, 7.7 Hz, 1H), 6.66 (s, 1H), 6.26 (s, 1H), 5.90 (s, 2H), 5.14 (s, 1H), 4.75 (ABq, 2H), 4.60 (ABq, 2H); $^{13}$C NMR (75 MHz, DMSO-$d_6$) δ 177.4, 164.2, 155.9, 151.8, 151.5, 148.8, 142.3, 142.2, 132.1, 129.4, 124.2, 123.9, 120.1, 109.8, 103.6, 101.9, 96.9, 93.8, 80.4, 57.9, 40.5; MS (ES+) m/z 406.3 (M+1).

EXAMPLE 6

Synthesis of 1'-[(5-chloro-1,2,4-thiadiazol-3-yl)methyl]spiro[furo[2,3-f][1,3]benzodioxole-7,3'-indol]-2'(1'H)-one

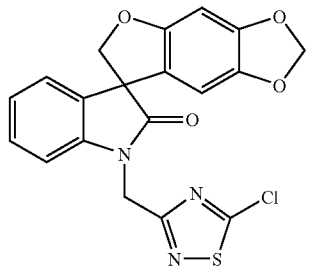

To a stirred solution of spiro[furo[2,3-f][1,3]benzodioxole-7,3'-indol]-2'(1'H)-one (1.33 g, 4.73 mmol) in acetone (50 mL) and 2-butanone (10 mL) were added cesium carbonate (3.10 g, 9.46 mmol) and 5-chloro-3-(chloromethyl)-1,2,4-thiadiazole (1.00 g, 5.92 mmol). The reaction was stirred at ambient temperature for 16 h, then filtered and concentrated in vacuo to dryness. The residue was purified by flash chromatography with ethyl acetate in hexanes (15% to 50% gradient) to afford 1'-[(5-chloro-1,2,4-thiadiazol-3-yl)methyl]spiro[furo[2,3-f][1,3]benzodioxole-7,3'-indol]-2'(1'H)-one (0.43 g, 22%) as a colorless solid: mp 114-116° C.; $^1$H NMR (300 MHz, DMSO-$d_6$) δ 7.29 (dd, J=7.7, 7.7 Hz, 1H), 7.21 (d, J=7.0 Hz, 1H), 7.08-7.03 (m, 2H), 6.71 (s, 1H), 6.32 (s, 1H), 5.93 (d, J=3.0 Hz, 2H), 5.24 (ABq, 2H), 4.78 (ABq, 2H); $^{13}$C NMR (75 MHz, DMSO-$d_6$) δ 177.2, 174.2, 170.6, 155.7, 148.8, 142.4, 142.2, 132.2, 129.3, 124.1, 123.7, 120.4, 109.8, 103.5, 101.9, 93.8, 79.9, 57.9, 41.6; MS (ES+) m/z 414.1 (M+1), 416.1 (M+1).

EXAMPLE 6.1

Synthesis of 4'-chloro-1'-[(5-chloro-1,2,4-thiadiazol-3-yl)methyl]spiro[furo[2,3-f][1,3]benzodioxole-7,3'-indol]-2'(1'H)-one

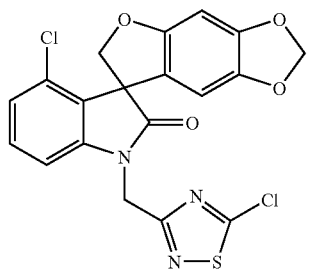

Following the procedure as described in EXAMPLE 6 and making non-critical variations using 4'-chlorospiro[furo[2,3-f][1,3]benzodioxole-7,3'-indol]-2'(1'H)-one to replace spiro[furo[2,3-f][1,3]benzodioxole-7,3'-indol]-2'(1'H)-one, 4'-chloro-1'-[(5-chloro-1,2,4-thiadiazol-3-yl)methyl]spiro[furo[2,3-f][1,3]benzodioxole-7,3'-indol]-2'(1'H)-one was obtained (17%) as a colorless solid: mp 174-176° C.; $^1$H NMR (300 MHz, CDCl$_3$) δ 7.17 (dd, J=8.0 Hz, 1H), 7.00 (d, J=7.8 Hz, 1H), 6.67 (d, J=7.8 Hz, 1H), 6.46 (s, 1H), 6.34 (s, 1H), 5.86 (ABq, 2H), 5.16 (ABq, 2H), 4.95 (ABq, 2H); $^{13}$C NMR (75 MHz, CDCl$_3$) δ 177.2, 174.9, 169.4, 156.8, 149.2, 143.3, 142.1, 131.7, 130.1, 128.4, 124.5, 166.5, 107.2, 103.2, 101.5, 93.2, 77.2, 58.8, 41.6; MS (ES+) m/z 447.9 (M+1), 449.9 (M+1).

EXAMPLE 6.2

Synthesis of 5,6-dimethyl-1'-(tetrahydro-2H-pyran-2-ylmethyl)spiro[1-benzofuran-3,3'-indol]-2'(1'H)-one

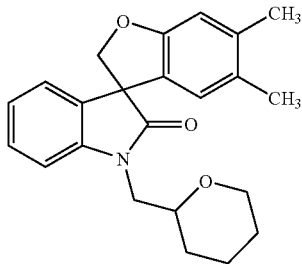

Following the procedure as described in EXAMPLE 6 and making non-critical variations using 5,6-dimethylspiro[1-benzofuran-3,3'-indol]-2'(1'H)-one to replace spiro[furo[2,3-f][1,3]benzodioxole-7,3'-indol]-2'(1'H)-one, and 2-(bromomethyl)-tetrahydro-2H-pyran to replace 5-chloro-3-(chloromethyl)-1,2,4-thiadiazole, 5,6-dimethyl-1'-(tetrahydro-2H-pyran-2-ylmethyl)spiro[1-benzofuran-3,3'-indol]-2'(1'H)-one was obtained (72%) as a colorless solid: $^1$H NMR (300 MHz, CDCl$_3$) δ7.28 (dd, J=7.6, 7.6 Hz, 1H), 7.15-6.97 (m, 1H), 6.75 (s, 1H), 6.47 (d, J=4.9 Hz, 1H), 4.89 (dd, J=8.9, 1.8 Hz, 1H), 4.65 (dd, J=8.9, 2.9 Hz, 1H), 4.03-3.60 (m, 2H), 3.44-3.32 (m, 1H), 2.19 (s, 3H), 2.05 (s, 3H), 1.92-1.80 (m, 1H), 1.73-1.27 (m, 1H); $^{13}$C NMR (75 MHz, CDCl$_3$) δ178.0, 159.1, 143.2, 138.3, 132.6, 129.3, 128.6, 126.3, 123.9, 123.6, 123.1, 111.4, 109.7, 79.7, 75.6, 68.4, 58.0, 45.7, 29.6, 25.8, 23.0, 20.3, 19.4; MS (ES+) m/z 364.3 (M+1).

EXAMPLE 6.3

Synthesis of 1'-[(3-chlorothiophen-2-yl)methyl]spiro[furo[2,3-f][1,3]benzodioxole-7,3'-indol]-2'(1'H)-one

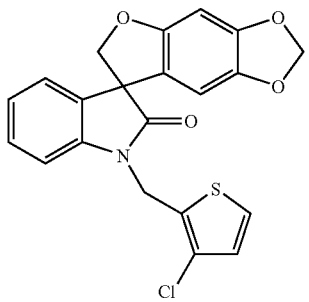

Following the procedure as described in EXAMPLE 6 and making non-critical variations using 3-chloro-2-chloromethylthiophene (Morton et al. *Tetrahedron Lett.* (2000), 41:3029-3034) to replace 5-chloro-3-(chloromethyl)-1,2,4-thiadiazole, 1'-[(3-chlorothiophen-2-yl)methyl]spiro[furo[2,3-f][1,3]benzodioxole-7,3'-indol]-2'(1'H)-one was obtained (38%) as an off-white solid: mp 161-163° C.; $^1$H NMR (300 MHz, CDCl$_3$) δ 7.29-7.20 (m, 2H), 7.15 (d, J=7.3 Hz, 1H), 7.08-6.93 (m, 2H), 6.88 (d, J=5.2 Hz, 1H), 6.51 (s, 1H), 6.16 (s, 1H), 5.86 (d, J=2.7 Hz, 2H), 5.09 (ABq, 2H), 4.80 (ABq, 2H); $^{13}$C NMR (75 MHz, CDCl$_3$) δ177.3, 156.0, 148.9, 142.4, 141.2, 132.1, 131.4, 129.0, 127.6, 125.1, 124.1, 124.0, 123.7, 119.3, 109.2, 103.2, 101.5, 93.6, 80.5, 58.3, 37.0; MS (ES+) m/z 412.1 (M+1).

EXAMPLE 6.4

Synthesis of 1'-{[3-(2,6-dichlorophenyl)-5-methylisoxazol-4-yl]methyl}spiro[furo[2,3-f][1,3]benzodioxole-7,3'-indol]-2'(1'H)-one

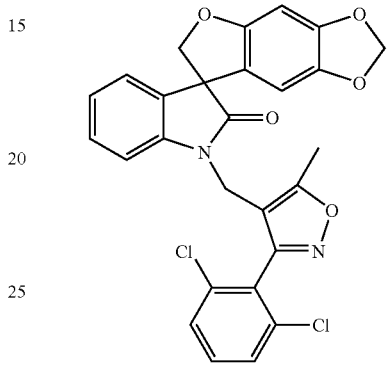

Following the procedure as described in EXAMPLE 6 and making non-critical variations using 4-(chloromethyl)-3-(2,6-dichlorophenyl)-5-methyl isoxazole to replace 5-chloro-3-(chloromethyl)-1,2,4-thiadiazole, and acetone as the solvent, 1'-{[3-(2,6-dichlorophenyl)-5-methylisoxazol-4-yl]methyl}spiro[furo[2,3-f][1,3]benzodioxole-7,3'-indol]-2'(1'H)-one was obtained (71%) as a colorless solid: mp 190-192° C.; $^1$H NMR (300 MHz, CDCl$_3$) δ7.39-7.22 (m, 3H), 7.10-7.01 (m, 1H), 7.00-6.88 (m, 2H), 6.46 (s, 1H), 6.20 (d, J=8.2 Hz, 1H), 6.02 (s, 1H), 5.83 (d, J=4.1 Hz, 2H), 4.59 (ABq, 2H), 4.58 (ABq, 2H), 2.64 (s, 3H); $^{13}$C NMR (75 MHz, CDCl$_3$) δ177.4, 169.2, 158.6, 156.0, 148.9, 142.3, 141.5, 136.0, 135.6, 131.8, 131.6, 128.6, 128.3, 128.1, 127.9, 123.9, 123.2, 119.0, 110.2, 107.7, 103.1, 101.5, 93.6, 80.6, 57.9, 33.3, 11.7; MS (ES+) m/z 521.3 (M+1), 523.3 (M+1).

EXAMPLE 6.5

Synthesis of 1'-({2-[4-(trifluoromethyl)phenyl]-1,3-thiazol-4-yl}methyl)spiro[furo[2,3-f][1,3]benzodioxole-7,3'-indol]-2'(1'H)-one

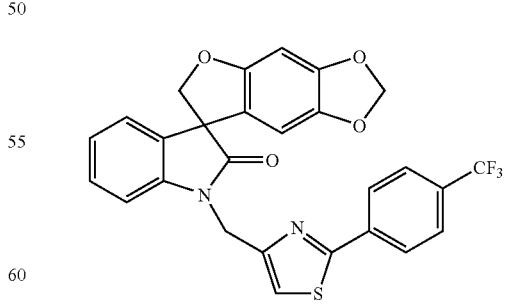

Following the procedure as described in EXAMPLE 6 and making non-critical variations using 4-(chloromethyl)-2-[4-(trifluoromethyl)phenyl]-1,3-thiazole to replace 5-chloro-3-(chloromethyl)-1,2,4-thiadiazole, and acetone as the solvent, 1'-({2-[4-(trifluoromethyl)phenyl]-1,3-thiazol-4-yl}methyl)spiro[furo[2,3-f][1,3]benzodioxole-7,3'-indol]-2'(1'H)-one was obtained (36%) as a colorless solid: mp 151-153° C.; $^1$H NMR (300 MHz, CDCl$_3$) δ8.02 (d, J=8.2 Hz, 2H), 7.67 (d, J=8.2 Hz, 2H), 7.30-7.21 (m, 2H), 7.17 (d, J=7.2 Hz, 1H), 7.09-7.00 (m, 2H), 6.51 (s, 1H), 6.18 (s, 1H), 5.85 (s, 2H), 5.13 (ABq, 2H), 4.83 (ABq, 2H); $^{13}$C NMR (75 MHz, CDCl$_3$) δ177.4, 166.8, 155.9, 152.5, 148.9, 142.3, 141.9, 136.4, 132.2, 131.7 (q, J=32.6 Hz), 128.9, 126.7, 126.0 (q, J=3.7 Hz), 125.7, 123.9, 123.6, 122.1, 119.5, 117.0, 109.5, 103.1, 101.5, 93.7, 80.3, 58.3, 40.4; MS (ES+) m/z 523.4 (M+1).

EXAMPLE 6.6

Synthesis of 1'-[(5-phenyl-1,3,4-oxadiazol-2-yl)methyl]spiro[furo[2,3-f][1,3]benzodioxole-7,3'-indol]-2'(1'H)-one

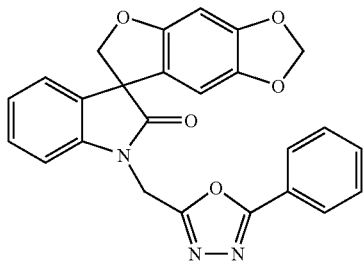

Following the procedure as described in EXAMPLE 6 and making non-critical variations using 2-(chloromethyl)-5-phenyl-1,3,4-oxadiazole to replace 5-chloro-3-(chloromethyl)-1,2,4-thiadiazole, and 2-butanone as the solvent, 1'-[(5-phenyl-1,3,4-oxadiazol-2-yl)methyl]spiro[furo[2,3-f][1,3]benzodioxole-7,3'-indol]-2'(1'H)-one was obtained (76%) as a colorless solid: mp 151-153° C.; mp 158-160° C.; $^1$H NMR (300 MHz, CDCl$_3$) δ8.02-7.94 (m, 2H), 7.56-7.41 (m, 3H), 7.27 (dd, J=7.5, 7.5 Hz, 1H), 7.18 (d, J=7.8 Hz, 1H), 7.06 (d, J=7.5, 7.5 Hz, 1H), 7.04 (d, J=7.8 Hz, 1H), 6.50 (s, 1H), 6.20 (s, 1H), 5.85 (s, 2H), 5.26 (ABq, 2H), 4.83 (ABq, 2H); $^{13}$C NMR (75 MHz, CDCl$_3$) δ177.3, 165.8, 161.0, 155.9, 149.1, 142.5, 140.8, 132.1, 131.8, 129.3, 129.2, 127.0, 124.2, 124.1, 123.3, 119.1, 109.0, 103.1, 101.6, 93.7, 80.2, 58.2, 35.1; MS (ES+) m/z 440.3 (M+1).

EXAMPLE 6.7

Synthesis of 1-{[5-(4-chlorophenyl)-1,3,4-oxadiazol-2-yl]methyl}spiro[furo[2,3-f][1,3]benzodioxole-7,3'-indol]-2'(1'H)-one

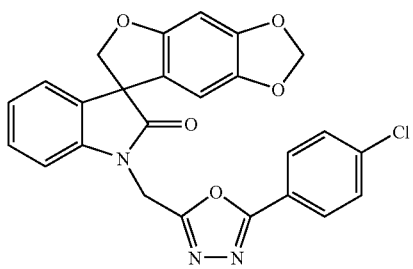

Following the procedure as described in EXAMPLE 6 and making non-critical variations using 2-(chloromethyl)-5-(4-chlorophenyl)-1,3,4-oxadiazole to replace 5-chloro-3-(chloromethyl)-1,2,4-thiadiazole, and 2-butanone as the solvent, 1'-{[5-(4-chlorophenyl)-1,3,4-oxadiazol-2-yl]methyl}spiro[furo[2,3-f][1,3]benzodioxole-7,3'-indol]-2'(1'H)-one was obtained (72%) as a colorless solid: mp 161-162° C.; $^1$H NMR (300 MHz, CDCl$_3$) δ7.91 (d, J=8.5 Hz, 2H), 7.44 (d, J=8.5 Hz, 2H), 7.27 (dd, J=7.7, 7.7 Hz, 1H), 7.19 (d, J=7.4 Hz, 1H), 7.07 (d, J=7.5, 7.5 Hz, 1H), 7.04 (d, J=7.8 Hz, 1H), 6.50 (s, 1H), 6.17 (s, 1H), 5.85 (s, 2H), 5.25 (ABq, 2H), 4.82 (ABq, 2H); $^{13}$C NMR (75 MHz, CDCl$_3$) δ177.3, 165.0, 161.2, 155.9, 149.1, 142.5, 140.7, 138.4, 131.8, 129.6, 129.3, 128.3, 124.3, 124.2, 121.7, 119.1, 109.0, 103.0, 101.6, 93.7, 80.2, 58.2, 35.0; MS (ES+) m/z 474.2 (M+1), 476.2 (M+1).

EXAMPLE 6.8

Synthesis of 1'-([1,3]oxazolo[4,5-b]pyridin-2-ylmethyl)spiro[furo[2,3-f][1,3]benzodioxole-7,3'-indol]-2'(1'H)-one

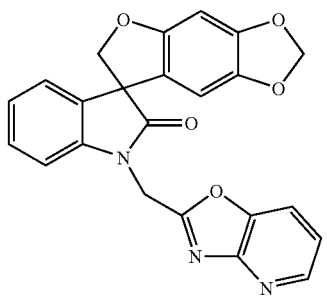

Following the procedure as described in EXAMPLE 6 and making non-critical variations using 2-(chloromethyl)[1,3]oxazolo[4,5-b]pyridine to replace 5-chloro-3-(chloromethyl)-1,2,4-thiadiazole, and 2-butanone as the solvent, 1'-([1,3]oxazolo[4,5-b]pyridin-2-ylmethyl)spiro[furo[2,3-f][1,3]benzodioxole-7,3'-indol]-2'(1'H)-one was obtained (11%) as a colorless solid: mp 202-204° C.; $^1$H NMR (300 MHz, CDCl$_3$) δ8.56 (d, J=4.9 Hz, 1H), 7.81 (d, J=8.2 Hz, 1H), 7.34-7.16 (m, 3H), 7.06 (dd, J=7.5, 7.5 Hz, 1H), 6.98 (d, J=7.8 Hz, 1H), 6.51 (s, 1H), 6.28 (s, 1H), 5.86 (d, J=3.6 Hz, 2H), 5.30 (ABq, 2H), 4.85 (ABq, 2H); $^{13}$C NMR (75 MHz, CDCl$_3$) δ117.4, 163.3, 155.9, 155.0, 149.1, 146.9, 143.4, 142.4, 141.0, 131.9, 129.2, 127.8, 124.1, 120.7, 119.2, 118.8, 109.0, 103.3, 101.6, 93.6, 80.4, 58.3, 38.0; MS (ES+) m/z 414.3 (M+1).

EXAMPLE 7

Synthesis of 1'-(4-methoxybenzyl)spiro[furo[2,3-f][1,3]benzodioxole-7,3'-indol]-2'(1'H)-one

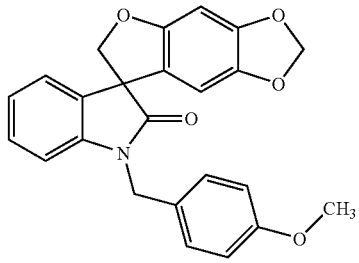

A mixture of spiro[furo[2,3-f][1,3]benzodioxole-7,3'-indol]-2'(1'H)-one (1.99 g, 7.08 mmol), 4-methoxybenzyl chloride (1.30 mL, 9.6 mmol), potassium iodide (0.17 g, 0.99 mmol) and cesium carbonate (4.68 g, 14.4 mmol) in 2-butanone (45 mL) was stirred at reflux under nitrogen for 16 h. The reaction was cooled, diluted with ethyl acetate and filtered through Celite. The filtrate was concentrated under reduced pressure and the residue was purified by flash column chromatography with hexanes/ethyl acetate (4:1) to afford 1'-(4-methoxybenzyl)spiro[furo[2,3-f][1,3]benzodioxole-7, 3'-indol]-2'(1'H)-one (2.52 g, 89%) as a colorless solid: mp 147-148° C. (hexanes); ¹H NMR (300 MHz, CDCl₃) δ7.28 (d, J=8.7 Hz, 2H), 7.21 (ddd, J=7.8, 7.5, 1.2 Hz, 1H), 7.16 (dd, J=7.5, 0.6 Hz, 1H), 7.02 (ddd, J=7.7, 7.4, 1.0 Hz, 1H), 6.88 (d, J=8.7 Hz, 2H), 6.83 (d, J=7.8 Hz, 1H), 6.53 (s, 1H), 6.13 (s, 1H), 5.88 (d, J=1.2 Hz, 1H), 5.87 (d, J=1.2 Hz, 1H), 5.02 (d, J=15.3 Hz, 1H), 4.97 (d, J=9.0 Hz, 1H), 4.76 (d, J=15.3 Hz, 1H), 4.69 (d, J=9.0 Hz, 1H), 3.79 (s, 3H); MS (ES+) m/z 402.2 (M+1).

EXAMPLE 7.1

Synthesis of 1'-[3-(trifluoromethyl)benzyl]-2,3-dihydrospiro[furo[2,3-g][1,4]benzodioxine-8,3'-indol]-2'(1'H)-one

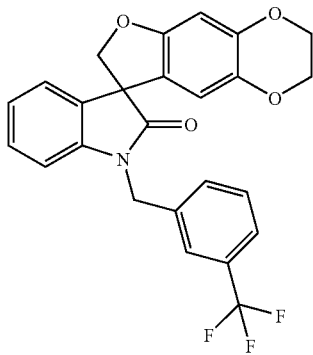

Following the procedure as described in EXAMPLE 7 and making non-critical variations using 2,3-dihydrospiro[furo[2,3-g][1,4]benzodioxine-8,3'-indol]-2'(1'H)-one to replace spiro[furo[2,3-f][1,3]benzodioxole-7,3'-indol]-2'(1'H)-one, and 3-(trifluoromethyl)benzyl chloride to replace 4-methoxybenzyl chloride, 1'-[3-(trifluoromethyl)benzyl]-2,3-dihydrospiro[furo[2,3-g][1,4]benzodioxine-8,3'-indol]-2'(1'H)-one was obtained (92%) as a colorless solid: mp 131-134° C. (diethyl ether/hexanes); ¹H NMR (300 MHz, CDCl₃) δ7.62-7.43 (m, 4H), 7.25-7.18 (m, 2H), 7.05 (dd, J=7.5, 7.5 Hz, 1H), 6.75 (d, J=7.5 Hz, 1H), 6.52 (s, 1H), 6.23 (s, 1H), 5.14 (d, J=15.9 Hz, 1H), 4.95 (d, J=9.0 Hz, 1H), 4.88 (d, J=15.9 Hz, 1H), 4.68 (d, J=9.0 Hz, 1H), 4.23-4.18 (m, 2H), 4.15-4.11 (m, 2H); ¹³C NMR (75 MHz, CDCl₃) δ177.8, 155.4, 144.8, 141.8, 138.5, 137.0, 132.3, 131.4 (q, J=32.4 Hz), 130.7, 129.7, 129.0, 124.9 (q, J=3.7 Hz), 124.25, 124.22 (q, J=3.7 Hz), 124.0 (q, J=272.4 Hz), 123.8, 120.9, 111.6, 109.1, 99.6, 80.2, 64.7, 64.0, 58.2, 43.8; MS (ES+) m/z 453.9 (M+1).

EXAMPLE 7.2

Synthesis of methyl 5-[(2'-oxo-2,3-dihydrospiro[furo[2,3-g][1,4]benzodioxine-8,3'-indol]-1'(2'H)-yl)methyl]furan-2-carboxylate

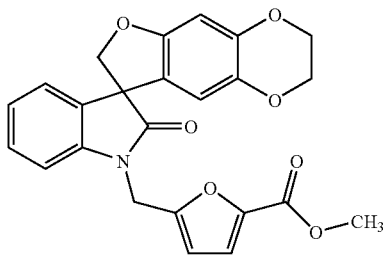

Following the procedure as described in EXAMPLE 7 and making non-critical variations using 2,3-dihydrospiro[furo[2,3-g][1,4]benzodioxine-8,3'-indol]-2'(1'H)-one to replace spiro[furo[2,3-f][1,3]benzodioxole-7,3'-indol]-2'(1'H)-one, and methyl 5-(chloromethyl)-2-furoate to replace 4-methoxybenzyl chloride, methyl 5-[(2'-oxo-2,3-dihydrospiro[furo[2,3-g][1,4]benzodioxine-8,3'-indol]-1'(2'H)-yl)methyl]furan-2-carboxylate was obtained (92%) as a colorless solid: mp 88-92° C. (hexanes/diethyl ether); ¹H NMR (300 MHz, CDCl₃) δ7.28 (ddd, J=7.8, 7.5, 1.2 Hz, 1H), 7.17 (dd, J=7.2, 0.9 Hz, 1H), 7.12 (d, J=3.6 Hz, 1H), 7.06 (ddd, J=7.8, 7.8, 0.9 Hz, 1H), 6.96 (d, J=7.8 Hz, 1H), 6.50 (s, 1H), 6.37 (d, J=3.6 Hz, 1H), 6.24 (s, 1H), 5.12 (d, J=16.5 Hz, 1H), 4.91 (d, J=9.0 Hz, 1H), 4.90 (d, J=16.5 Hz, 1H), 4.64 (d, J=9.0 Hz, 1H), 4.22-4.18 (m, 2H), 4.14-4.10 (m, 2H), 3.89 (s, 3H); ¹³C NMR (75 MHz, CDCl₃) δ177.2, 158.9, 155.3, 153.4, 144.8, 144.4, 141.4, 138.4, 132.2, 129.1, 124.1, 123.9, 120.9, 119.1, 111.7, 110.3, 109.1, 99.5, 80.1, 64.6, 64.0, 58.1, 52.1, 37.4; MS (ES+) m/z 433.9 (M+1).

EXAMPLE 7.3

Synthesis of (S)-1-pentyl-2,3-dihydrospiro[furo[2,3-g][1,4]benzodioxine-8,3'-indol]-2'(1'H)-one

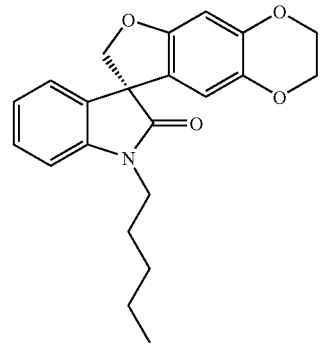

A suspension of (S)-2,3-dihydrospiro[furo[2,3-g][1,4]benzodioxine-8,3'-indol]-2'(1'H)-one (1.0 g, 3.4 mmol), cesium carbonate (3.3 g, 10.2 mmol) and 1-bromopentane (1.02 g, 6.77 mmol) in anhydrous 1,4-dioxane (25 mL) was heated at reflux under nitrogen for 2 h. The reaction mixture was allowed to cool to ambient temperature, filtered and concentrated in vacuo. Purification of the residue by column chromatography and eluted with a 15% to 50% gradient of ethyl acetate in hexanes, followed by recrystallization from methanol afforded (S)-1-pentyl-2,3-dihydrospiro[furo[2,3-g][1,4]benzodioxine-8,3'-indol]-2'(1'H)-one as an off-white solid (0.89 g, 72%): mp 111-113° C. (ethyl acetate/hexanes); ¹H NMR (300 MHz, CDCl₃) δ 7.23-7.30 (m, 1H), 7.13 (dd, J=7.4, 0.9 Hz, 1H), 7.00-7.03 (m, 1H), 6.89 (d, J=7.8 Hz, 1H), 6.46 (s, 1H), 6.19 (s, 1H), 4.73 (ABq, 2H), 4.19-4.05 (m, 4H), 3.86-3.59 (m, 2H), 1.82-1.62 (m, 2H), 1.43-1.28 (m, 4H), 0.89 (t, J=6.9 Hz, 3H); ¹³C NMR (75 MHz, CDCl₃) δ177.2, 155.2, 144.5, 142.4, 138.2, 132.5, 128.7, 123.9, 123.0, 121.1, 111.4, 108.5, 99.3, 80.1, 64.5, 63.9, 58.0, 40.3, 29.0, 27.1, 22.3, 14.0; MS (ES+) m/z 366.0 (M+1).

EXAMPLE 7.4

Synthesis of (R)-1'-pentyl-2,3-dihydrospiro[furo[2,3-g][1,4]benzodioxine-8,3'-indol]-2'(1'H)-one

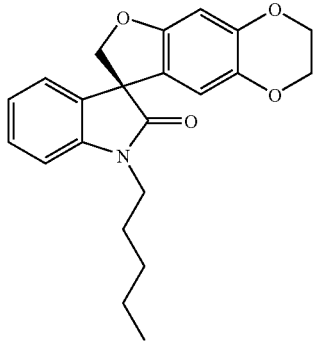

Following the procedure as described in EXAMPLE 7.3 and making non-critical variations using (R)-2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, (R)-1'-pentyl-2,3-dihydrospiro[furo[2,3-g][1,4]benzodioxine-8,3'-indol]-2'(1'H)-one was obtained (74%) as a colorless solid: $^1$H NMR (300 MHz, CDCl$_3$) δ 7.25-7.30 (m, 1H), 7.16-7.11 (m, 1H), 6.99-7.04 (m, 1H), 6.89 (d, J=7.8 Hz, 1H), 6.47 (s, 1H), 6.19 (s, 1H), 4.73 (ABq, 2H), 4.20-4.06 (m, 4H), 3.86-3.59 (m, 2H), 1.82-1.63 (m, 2H), 1.42-1.28 (m, 4H), 0.89 (t, J=6.8 Hz, 3H); $^{13}$C NMR (75 MHz, CDCl$_3$) δ 177.2, 155.2, 144.5, 142.4, 138.2, 132.5, 128.7, 123.9, 123.0, 121.2, 111.4, 108.5, 99.3, 80.1, 64.5, 63.9, 58.0, 40.3, 29.0, 27.1, 22.3, 14.0; MS (ES+) m/z 366.1 (M+1).

EXAMPLE 7.5

Synthesis of t-hexyl-2,3-dihydrospiro[furo[2,3-g][1,4]benzodioxine-8,3'-indol]-2'(1'H)-one

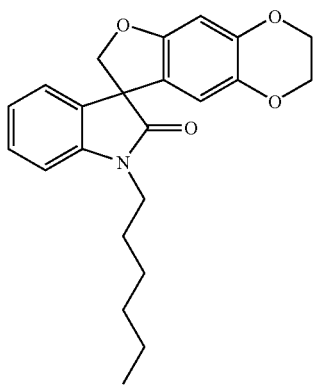

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 1-bromohexane to replace 1-bromopentane, 1'-hexyl-2,3-dihydrospiro[furo[2,3-g][1,4]benzodioxine-8,3'-indol]-2'(1'H)-one was obtained (83%) as a colorless solid: $^1$H NMR (300 MHz, CDCl$_3$) δ 7.25-7.29 (dt, J=7.74, 7.71, 1.05 Hz, 1H), 7.13 (d, J=7.4 Hz, 1H), 6.98-7.04 (m, 1H), 6.89 (d, J=7.8 Hz, 1H), 6.46 (s, 1H), 6.19 (s, 1H), 4.73 (ABq, 2H), 4.19-4.05 (m, 4H), 3.86-3.59 (m, 2H), 1.80-1.63 (m, 2H), 1.44-1.22 (m, 6H), 0.87 (t, J=6.9 Hz, 3H); $^{13}$C NMR (75 MHz, CDCl$_3$) δ 177.2, 155.2, 144.5, 142.4, 138.2, 132.5, 128.7, 123.9, 123.0, 121.2, 111.4, 108.5, 99.3, 80.1, 64.5, 63.9, 58.0, 40.3, 31.4, 27.4, 26.5, 22.5, 14.0; MS (ES+) m/z 379.9 (M+1).

EXAMPLE 7.6

Synthesis of 1'-(2-cyclopropylethyl)-2,3-dihydrospiro[furo[2,3-g][1,3]benzodioxine-8,3'-indol]-2(1'H)-one

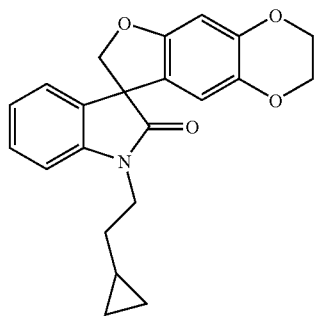

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 2-cyclopropylethyl 4-methylbenzenesulfonate to replace 1-bromopentane, 1'-(2-cyclopropylethyl)-2,3-dihydrospiro[furo[2,3-g][1,3]benzodioxine-8,3'-indol]-2'(1'H)-one was obtained (59%) as a colorless solid: $^1$H NMR (300 MHz, CDCl$_3$) δ 7.12 (d, J=7.4 Hz, 2H), 6.96-7.04 (m, 1H), 6.90 (d, J=7.8 Hz, 1H), 6.45 (s, 1H), 6.19 (s, 1H), 4.72 (ABq, 2H), 4.19-4.03 (m, 4H), 3.94-3.71 (m, 2H), 0.79-0.64 (m, 1H), 0.50-0.37 (m, 2H), 0.11-0.04 (m, 2H); $^{13}$C NMR (75 MHz, CDCl$_3$) δ 177.2, 155.2, 144.5, 142.6, 138.2, 132.4, 128.7, 123.9, 123.0, 121.1, 111.5, 108.5, 99.3, 80.1, 64.5, 63.9, 57.9, 40.4, 32.4, 8.6, 4.4; MS (ES+) m/z 364.0 (M+1).

EXAMPLE 7.7

Synthesis of 1-(2-ethoxyethyl)-2,3-dihydrospiro[furo[2,3-g][1,3]benzodioxine-8,3'-indol]-2'(1'H)-one

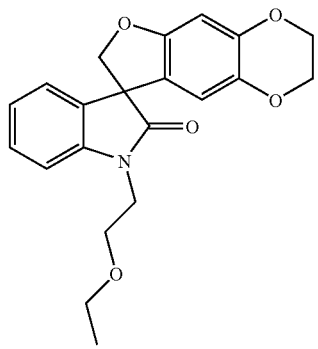

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 1-bromo-2-ethoxyethane to replace 1-bromopentane, 1-(2-ethoxyethyl)-2,3-dihydrospiro[furo[2,3-g][1,3]benzodioxine-8,3'-indol]-2'(1'H)-one was obtained (50%) as a colorless solid: $^1$H NMR (300

MHz, CDCl₃) δ 7.31-7.21 (m, 1H), 7.14-7.09 (m, 1H), 7.07-6.97 (m, 2H), 6.46 (s, 1H), 6.21 (s, 1H), 4.74 (ABq, 2H), 4.19-4.05 (m, 4H), 4.03-3.80 (m, 2H), 3.74-3.61 (m, 2H), 3.49 (q, J=7.0 Hz, 2H), 1.14 (t, J=7.0 Hz, 3H); ¹³C NMR (75 MHz, CDCl₃) δ177.5, 155.1, 144.5, 142.6, 138.2, 132.3, 128.6, 123.6, 123.1, 121.2, 111.5, 109.2, 99.2, 80.0, 67.4, 66.6, 64.5, 63.9, 57.9, 40.4, 15.1; MS (ES+) m/z 368.1 (M+1).

EXAMPLE 7.8

Synthesis of 1'-(4-methoxybutyl)-2,3-dihydrospiro[furo[2,3-g][1,3]benzodioxine-8,3'-indol]-2'(1'H)-one

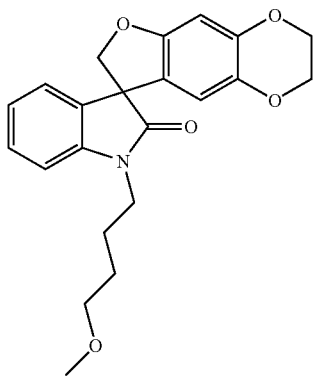

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 1-bromo-4-methoxybutane to replace 1-bromopentane, 1'-(4-methoxybutyl)-2,3-dihydrospiro[furo[2,3-g][1,3]benzodioxine-8,3'-indol]-2'(1'H)-one was obtained (93%) as a colorless solid: ¹H NMR (300 MHz, CDCl₃) δ 7.30-6.86 (m, 4H), 6.45 (s, 1H), 6.18 (s, 1H), 4.72 (ABq, 2H), 4.18-4.04 (m, 4H), 3.88-3.63 (m, 2H), 3.44-3.37 (m, 2H), 3.30 (s, 3H), 1.88-1.56 (m, 4H); ¹³C NMR (75 MHz, CDCl₃) δ177.2, 155.2, 144.5, 142.3, 138.2, 132.5, 128.8, 123.9, 123.1, 121.1, 111.4, 108.6, 99.3, 80.1, 72.0, 64.5, 63.9, 58.6, 57.9, 40.0, 26.9, 24.3; MS (ES+) m/z 381.9 (M+1).

EXAMPLE 7.9

Synthesis of 1-(3-methoxypropyl)-2,3-dihydrospiro[furo[2,3-g][1,3]benzodioxine-8,3'-indol]-2'(1'H)-one

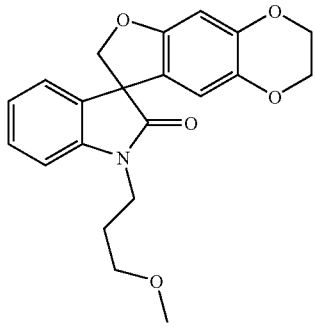

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 1-bromo-3-methoxypropane to replace 1-bromopentane, 1'-(3-methoxypropyl)-2,3-dihydrospiro[furo[2,3-g][1,3]benzodioxine-8,3'-indol]-2'(1'H)-one was obtained (71%) as a colorless solid: ¹H NMR (300 MHz, CDCl₃) δ 7.30-6.93 (m, 4H), 6.46 (s, 1H), 6.18 (s, 1H), 4.72 (ABq, 2H), 4.19-4.04 (m, 4H), 3.94-3.72 (m, 2H), 3.41 (t, J=5.9 Hz, 2H), 3.30 (s, 3H), 2.01-1.91 (m, 2H); ¹³C NMR (75 MHz, CDCl₃) δ177.3, 155.2, 144.5, 142.5, 138.2, 132.4, 128.8, 123.8, 123.1, 121.1, 111.4, 108.5, 99.3, 80.0, 69.7, 64.5, 63.9, 58.7, 57.9, 37.6, 27.8; MS (ES+) m/z 367.9 (M+1).

EXAMPLE 7.10

Synthesis of 1'-(3-nitrobenzyl)-2,3-dihydrospiro[furo[2,3-g][1,3]benzodioxine-8,3'-indol]-2'(1'H)-one

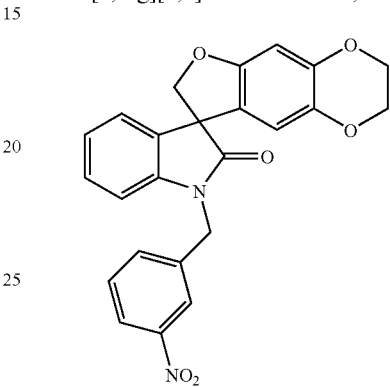

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 1-(bromomethyl)-3-nitrobenzene to replace 1-bromopentane, 1-(3-nitrobenzyl)-2,3-dihydrospiro[furo[2,3-g][1,3]benzodioxine-8,3'-indol]-2'(1'H)-one was obtained (72%) as a colorless solid: ¹H NMR (300 MHz, CDCl₃) δ 8.19 (s, 1H), 8.12 (d, J=8.1 Hz, 1H), 7.77 (d, J=7.7 Hz, 1H), 7.60-7.66 (m, 1H), 7.28-6.97 (m, 4H), 6.49 (s, 1H), 6.13 (s, 1H), 5.07 (ABq, 2H), 4.73 (ABq, 2H), 4.18-4.03 (m, 4H); ¹³C NMR (75 MHz, CDCl₃) δ 177.4, 155.2, 148.4, 144.7, 142.3, 139.1, 138.3, 134.2, 132.1, 130.8, 129.3, 124.2, 123.7, 122.9, 122.3, 121.5, 111.5, 109.8, 99.3, 79.9, 64.6, 64.0, 57.7, 42.8; MS (ES+) m/z 430.9 (M+1).

EXAMPLE 7.11

Synthesis of 1'-(1,3-thiazol-5-ylmethyl)-2,3-dihydrospiro[furo[2,3-g][1,3]benzodioxine-8,3'-indol]-2'(1'H)-one

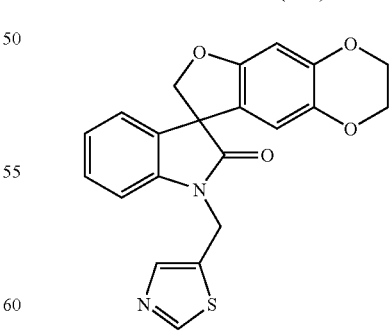

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 5-(chloromethyl)thiazole to replace 1-bromopentane, 1'-(1,3-thiazol-5-ylmethyl)-2,3-dihydrospiro[furo[2,3-g][1,3]benzodioxine-8,3'-indol]-2'(1'H)-one was obtained (56%) as a colorless solid: $^1$H NMR (300 MHz, CDCl$_3$) δ 8.72 (s, 1H), 7.89 (s, 1H), 7.29-6.86 (m, 4H), 6.47 (d, J=2.0 Hz, 1H), 6.16 (d, J=2.0 Hz, 1H), 5.13 (ABq, 2H), 4.74 (ABq, 2H), 4.20-4.03 (m, 4H); $^{13}$C NMR (75 MHz, CDCl$_3$) δ 177.0, 155.2, 153.8, 144.7, 142.6, 141.0, 138.3, 133.0, 132.2, 128.9, 124.1, 123.8, 120.7, 111.5, 108.7, 99.4, 79.9, 64.5, 63.9, 57.9, 36.2; MS (ES+) m/z 392.4 (M+1).

EXAMPLE 7.12

Synthesis of 1'-{[5-(trifluoromethyl)pyridin-2-yl]methyl}-2,3-dihydrospiro[furo[2,3-g][1,3]benzodioxine-8,3'-indol]-2'(1'H)-one

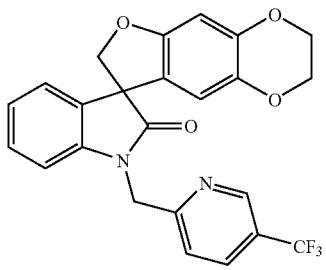

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 2-(chloromethyl)-5-(trifluoromethyl)pyridine to replace 1-bromopentane, 1'-{[5-(trifluoromethyl)pyridin-2-yl]methyl}-2,3-dihydrospiro[furo[2,3-g][1,3]benzodioxine-8,3'-indol]-2'(1'H)-one was obtained (53%) as a colorless solid: $^1$H NMR (300 MHz, CDCl$_3$) δ 8.83 (s, 1H), 7.89 (dd, J=8.2, 2.0 Hz, 1H), 7.42-6.81 (m, 5H), 6.50 (s, 1H), 6.28 (s, 1H), 5.13 (ABq, 2H), 4.80 (ABq, 2H), 4.22-4.07 (m, 4H); $^{13}$C NMR (75 MHz, CDCl$_3$) δ 177.6, 159.4, 155.2, 146.5, 146.5, 144.7, 141.7, 138.3, 134.3, 134.3, 134.2, 132.1, 128.9, 126.1, 125.6, 125.1, 124.0, 123.7, 121.4, 120.8, 111.6, 109.2, 99.4, 80.0, 64.5, 63.9, 58.1, 45.7; MS (ES+) m/z 454.9 (M+1).

EXAMPLE 7.13

Synthesis of 1-{[3-(trifluoromethyl)pyridin-2-yl]methyl}-2,3-dihydrospiro[furo[2,3-g][1,3]benzodioxine-8,3'-indol]-2'(1'H)-one

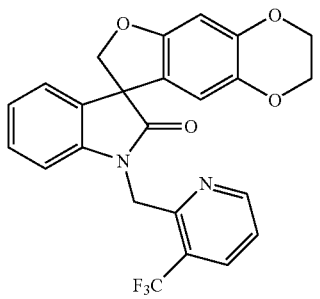

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 2-(chloromethyl)-3-(trifluoromethyl)pyridine hydrochloride to replace 1-bromopentane, 1'-{[3-(trifluoromethyl)pyridin-2-yl]methyl}-2,3-dihydrospiro[furo[2,3-g][1,3]benzodioxine-8,3'-indol]-2'(1'H)-one was obtained (40%) as a colorless solid: $^1$H NMR (300 MHz, CDCl$_3$) δ 8.62 (d, J=4.7 Hz, 1H), 7.96 (d, J=7.9 Hz, 1H), 7.32-6.96 (m, 4H), 6.71-6.54 (m, 2H), 6.48 (s, 1H), 5.22-5.28 (m, 2H), 4.80-4.90 (m, 2H), 4.21-4.06 (m, 4H); $^{13}$C NMR (75 MHz, CDCl$_3$) δ 178.1, 155.1, 152.3, 144.5, 142.3, 138.2, 134.3, 134.2, 134.1, 134.1, 132.7, 129.2, 128.6, 125.6, 124.9, 124.5, 124.1, 123.8, 123.6, 123.2, 122.1, 122.0, 121.6, 112.4, 108.5, 99.1, 80.0, 64.5, 63.9, 58.2, 42.2, 42.2; MS (ES+) m/z 454.8 (M+1).

EXAMPLE 7.14

Synthesis of 1'-[(3-pyridin-3-ylisoxazol-5-yl)methyl]-2,3-dihydrospiro[furo[2,3-g][1,3]benzodioxine-8,3'-indol]-2'(1'H)-one

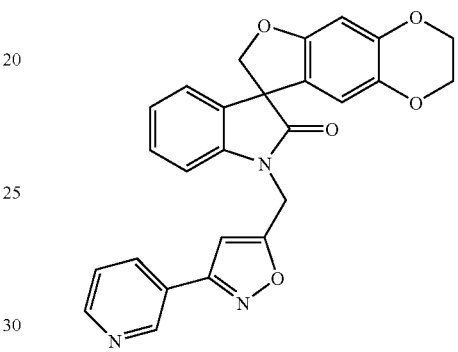

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 5-(chloromethyl)-3-(pyridin-3-yl)isoxazole to replace 1-bromopentane, 1'-[(3-pyridin-3-ylisoxazol-5-yl)methyl]-2,3-dihydrospiro[furo[2,3-g][1,3]benzodioxine-8,3'-indol]-2'(1'H)-one was obtained (40%) as a colorless solid: $^1$H NMR (300 MHz, CDCl$_3$) 8.96 (s, 1H), 8.65 (d, J=4.7 Hz, 1H), 8.07 (d, J=8.4 Hz, 1H), 7.39-6.98 (m, 5H), 6.58 (s, 1H), 6.47 (s, 1H), 6.20 (s, 1H), 5.10 (ABq, 2H), 4.76 (ABq, 2H), 4.20-4.03 (m, 4H); $^{13}$C NMR (75 MHz, CDCl$_3$) δ 177.2, 167.7, 160.3, 155.2, 151.2, 147.9, 144.7, 141.0, 138.3, 134.0, 131.9, 129.1, 124.7, 124.1, 124.1, 123.7, 120.5, 111.5, 108.8, 100.9, 99.4, 79.9, 64.5, 63.8, 57.9, 35.8; MS (ES+) m/z 453.9 (M+1).

EXAMPLE 7.15

Synthesis of (8R)-1'-{[3-(trifluoromethyl)pyridin-2-yl]methyl}-2,3-dihydrospiro[furo[2,3-g][1,3]benzodioxine-8,3'-indol]-2'(1'H)-one

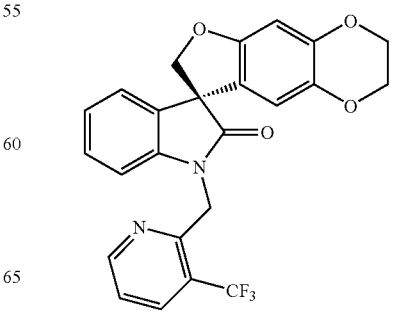

Following the procedure as described in EXAMPLE 7.3 and making non-critical variations using (R)-2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 2-(chloromethyl)-3-(trifluoromethyl)pyridine hydrochloride to replace 1-bromopentane, (8R)-1'-{[3-(trifluoromethyl)pyridin-2-yl]methyl}-2,3-dihydrospiro[furo[2,3-g][1,3]benzodioxine-8,3'-indol]-2'(1'H)-one was obtained (72%) as a colorless solid: $^1$H NMR (300 MHz, CDCl$_3$) δ 8.63 (d, J=4.5 Hz, 1H), 7.97 (d, J=7.8 Hz, 1H), 7.34-6.96 (m, 4H), 6.62 (s, 1H), 6.59 (d, J=7.8 Hz, 1H), 6.48 (s, 1H), 5.26 (ABq, 2H), 4.85 (, 2H), 4.21-4.08 (m, 4H); $^{13}$C NMR (75 MHz, CDCl$_3$) δ 178.1, 155.1, 152.3, 144.5, 142.3, 138.2, 134.3, 134.2, 134.1, 134.0, 132.7, 128.5, 125.6, 124.9, 124.5, 124.1, 123.8, 123.2, 122.1, 122.0, 121.6, 112.4, 108.5, 99.1, 80.0, 64.5, 63.9, 58.2, 42.2, 42.2; MS (ES+) m/z 454.8 (M+1).

EXAMPLE 7.16

Synthesis of N,N-dimethyl-3-[(2'-oxo-2,3-dihydrospiro[furo[2,3-g][1,4]benzodioxine-8,3'-indol]-1'-(2'H)-yl)methyl]benzenesulfonamide

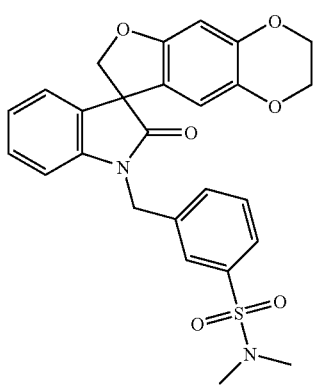

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]-benzodioxine-8,3'-indol]-2'(1'H)-one, and 3-(chloromethyl)-N,N-dimethylbenzenesulfonamide to replace 1-bromopentane, N,N-dimethyl-3-[(2'-oxo-2,3-dihydrospiro[furo[2,3-g][1,4]benzodioxine-8,3'-indol]-1-(2'H)-yl)methyl]benzenesulfonamide was obtained (40%) as a colorless solid: $^1$H NMR (300 MHz, DMSO-d$_6$) δ 7.72-7.62 (m, 4H), 7.29-6.99 (m, 4H), 6.50 (s, 1H), 6.07 (s, 1H), 5.06 (ABq, 2H), 4.71 (ABq, 2H), 4.19-4.05 (m, 4H), 2.50 (s, 6H); $^{13}$C NMR (75 MHz, DMSO-d$_6$) δ 176.9, 154.7, 144.2, 141.9, 137.8, 134.9, 131.8, 131.5, 129.9, 128.8, 126.6, 125.9, 123.8, 123.2, 120.9, 110.9, 109.3, 98.8, 79.4, 64.2, 63.5, 57.2, 42.5, 37.4; MS (ES+) m/z 492.7 (M+1).

EXAMPLE 7.17

Synthesis of 1'-[3-(morpholin-4-ylsulfonyl)benzyl]-2,3-dihydrospiro[furo[2,3-g][1,4]benzodioxine-8,3'-indol]-2'(1'H)-one

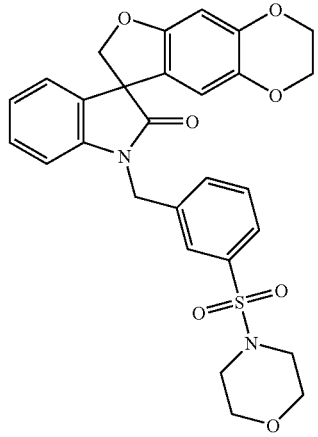

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 4-(3-(chloromethyl)phenylsulfonyl)morpholine to replace 1-bromopentane, 1'-[3-(morpholin-4-ylsulfonyl)benzyl]-2,3-dihydrospiro[furo[2,3-g][1,4]benzodioxine-8,3'-indol]-2'(1'H)-one was obtained (40%) as a colorless solid: $^1$H NMR (300 MHz, DMSO-d$_6$) δ 7.73-7.64 (m, 4H), 7.29-7.18 (m, 2H), 7.05 (dd, J=7.3, 5.6 Hz, 2H), 6.52 (s, 1H), 6.11 (s, 1H), 5.09 (ABq, 2H), 4.74 (dd, J=9.3 Hz, 2H), 4.04-4.21 (m, 4H), 3.56 (t, J=4.5 Hz, 4H), 2.84-2.65 (m, 4H); $^{13}$C NMR (75 MHz, DMSO-d$_6$) δ 176.9, 154.8, 144.2, 141.9, 138.0, 137.9, 134.7, 132.2, 131.6, 130.1, 128.8, 126.7, 125.9, 123.9, 123.3, 121.0, 110.9, 109.5, 98.9, 79.5, 65.2, 64.2, 63.6, 57.3, 45.8, 42.5; MS (ES+) m/z 534.9 (M+1).

EXAMPLE 7.18

Synthesis of 1'-[(4-methyl-1,2,5-oxadiazol-3-yl)methyl]-2,3-dihydrospiro[furo[2,3-g][1,4]benzodioxine-8,3'-indol]-2'(1'H)-one

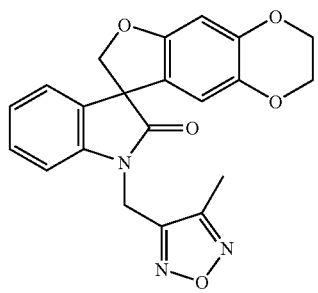

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 3-(chloromethyl)-4-methyl-1,2,5-oxadiazole to replace 1-bromopentane, 1'-[(4-methyl-1,2,5-oxadiazol-3-yl)methyl]-2,3-dihydrospiro[furo[2,3-g][1,4]benzodioxine-8,3'-indol]-2'(1'H)-one was obtained (69%) as a colorless solid: ¹H NMR (300 MHz, DMSO-$d_6$) δ 7.36-7.28 (m, 1H), 7.22-7.03 (m, 3H), 6.52 (s, 1H), 6.23 (s, 1H), 5.19 (ABq, 2H), 4.73 (ABq, 2H), 4.22-4.07 (m, 4H), 2.41 (s, 3H); ¹³C NMR (75 MHz, DMSO-$d_6$) δ 176.6, 154.6, 151.4, 151.3, 144.2, 141.6, 137.8, 131.8, 128.7, 123.6, 123.4, 121.1, 111.2, 109.3, 98.7, 79.3, 64.2, 63.6, 57.2; MS (ES+) m/z 414.0 (M+23).

EXAMPLE 7.19

Synthesis of 1-(2,3-difluorobenzyl)-2,3-dihydrospiro[furo[2,3-g][1,4]benzodioxine-8,3'-indol]-2'(1'H)-one

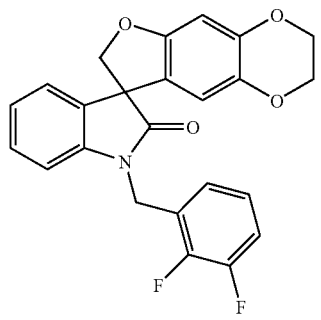

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]-benzodioxine-8,3'-indol]-2'(1'H)-one, and 1-(bromomethyl)-2,3-difluorobenzene to replace 1-bromopentane, 1-(2,3-difluorobenzyl)-2,3-dihydrospiro[furo[2,3-g][1,4]benzodioxine-8,3'-indol]-2'(1'H)-one was obtained (47%) as a colorless solid: ¹H NMR (300 MHz, DMSO-$d_6$) δ 7.45-7.10 (m, 5H), 7.01-7.08 (m, 1H), 6.99 (d, J=7.8 Hz, 1H), 6.52 (s, 1H), 6.14 (s, 1H), 5.04 (ABq, 2H), 4.74 (ABq, 2H), 4.22-4.06 (m, 4H); ¹³C NMR (75 MHz, DMSO-$d_6$) δ 176.6, 154.7, 144.2, 141.9, 137.8, 131.6, 128.9, 125.7, 125.6, 125.2, 124.4, 123.7, 123.2, 121.0, 116.9, 116.7, 111.1, 109.1, 98.8, 79.5, 64.2, 63.6, 57.2; MS (ES+) m/z 421.8 (M+1).

EXAMPLE 7.20

Synthesis of 1'-(3,5-difluorobenzyl)-2,3-dihydrospiro[furo[2,3-g][1,4]benzodioxine-8,3'-indol]-2'(1'H)-one

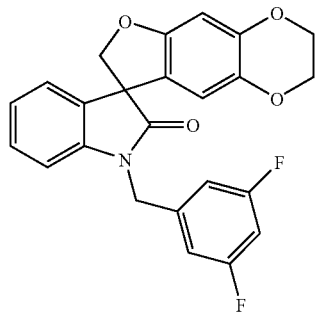

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 1-(bromomethyl)-3,5-difluorobenzene to replace 1-bromopentane, 1'-(3,5-difluorobenzyl)-2,3-dihydrospiro[furo[2,3-g][1,4]benzodioxine-8,3'-indol]-2'(1'H)-one was obtained (72%) as a colorless solid: ¹H NMR (300 MHz, DMSO-$d_6$) δ 7.22-7.32 (m, 1H), 7.24-7.14 (m, 2H), 7.13-7.00 (m, 4H), 6.53 (s, 1H), 6.11 (s, 1H), 4.96 (s, 2H), 4.77 (ABq, 2H), 4.23-4.07 (m, 4H); ¹³C NMR (75 MHz, DMSO-$d_6$) δ 176.6, 154.7, 144.2, 141.9, 137.8, 131.6, 128.9, 125.7, 125.6, 125.2, 124.4, 123.7, 123.2, 121.0, 116.9, 116.7, 111.1, 109.1, 98.8, 79.5, 64.2, 63.6, 57.2; MS (ES+) m/z 421.8 (M+1).

EXAMPLE 7.21

Synthesis of 1'-(4-fluorobenzyl)-2,3-dihydrospiro[furo[2,3-g][1,4]benzodioxine-8,3'-indol]-2'(1'H)-one

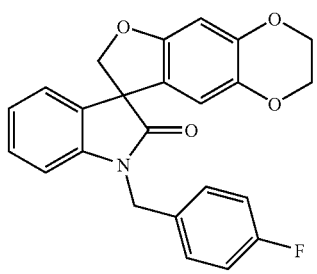

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 1-(bromomethyl)-4-fluorobenzene to replace 1-bromopentane, 1'-(4-fluorobenzyl)-2,3-dihydrospiro[furo[2,3-g][1,4]benzodioxine-8,3'-indol]-2'(1'H)-one was obtained (73%) as a colorless solid: ¹H NMR (300 MHz, DMSO-$d_6$) δ 7.45-7.37 (m, 2H), 7.31-7.23 (m, 1H), 7.23-7.14 (m, 3H), 7.07-6.99 (m, 2H), 6.53 (s, 1H), 6.09 (s, 1H), 4.92 (ABq, 2H), 4.74 (ABq, 2H), 4.22-4.07 (m, 4H); ¹³C NMR (75 MHz, DMSO-$d_6$) δ 176.7, 154.7, 144.2, 142.1, 137.8, 132.6, 132.5, 132.0, 129.4, 129.3, 128.8, 123.7, 123.1, 121.2, 115.7, 115.4, 111.0, 109.4, 98.8, 79.4, 64.2, 63.6, 57.2, 42.4; MS (ES+) m/z 403.8 (M+1).

EXAMPLE 7.22

Synthesis of 1'-(2-chloro-4-fluorobenzyl)-2,3-dihydrospiro[furo[2,3-g][1,4]benzodioxine-8,3'-indol]-2'(1'H)-one

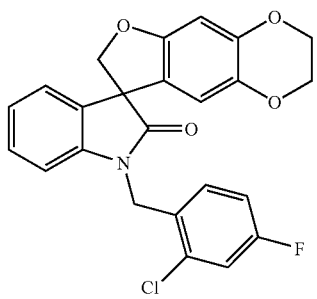

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 1-(bromomethyl)-2-chloro-4-fluorobenzene to replace 1-bromopentane, 1'-(2-chloro-4- fluorobenzyl)-2,3-dihydrospiro[furo[2,3-g][1,4]benzodioxine-8,3'-indol]-2'(1'H)-one was obtained (81%) as a colorless solid: $^1$H NMR (300 MHz, DMSO-$d_6$) δ 7.52-7.60 (m, 1H), 7.35-7.17 (m, 4H), 7.10-7.02 (m, 1H), 6.89 (d, J=7.8 Hz, 1H), 6.52 (s, 1H), 6.24 (s, 1H), 4.97 (ABq 2H), 4.75 (ABq, 2H), 4.22-4.08 (m, 4H); $^{13}$C NMR (75 MHz, DMSO-$d_6$) δ 176.7, 154.8, 144.2, 142.1, 137.8, 132.9, 131.7, 130.1, 129.5, 129.4, 128.9, 123.8, 123.2, 121.0, 117.2, 116.9, 114.9, 111.3, 109.3, 98.8, 79.6, 64.2, 63.6, 57.2, 41.1; MS (ES+) m/z 437.6 (M+1).

EXAMPLE 7.23

Synthesis of 1'-[(1-methyl-1H-benzotriazol-5-yl)methyl]-2,3-dihydrospiro[furo[2,3-g][1,4]-benzodioxine-8,3'-indol]-2'(1'H)-one

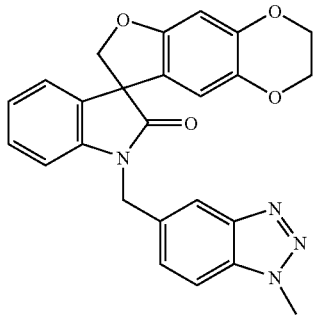

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 5-(chloromethyl)-1-methyl-1H-benzo[d][1,2,3]triazole to replace 1-bromopentane, 1'-[(1-methyl-1H-benzotriazol-5-yl)methyl]-2,3-dihydrospiro[furo[2,3-g][1,4]benzodioxine-8,3'-indol]-2'(1'H)-one was obtained (15%) as a colorless solid: $^1$H NMR (300 MHz, DMSO-$d_6$) δ 8.08 (s, 1H), 7.86 (d, J=8.6 Hz, 1H), 7.52 (dd, J=8.6, 1.2 Hz, 1H), 7.20-7.28 (m, 1H), 7.18 (d, J=6.9 Hz, 1H), 7.08 (d, J=7.7 Hz, 1H), 7.02 (t, J=7.4 Hz, 1H), 6.54 (s, 1H), 6.08 (s, 1H), 5.10 (ABq, 2H), 4.77 (ABq, 2H), 4.28 (s, 3H), 4.22-4.07 (m, 4H); $^{13}$C NMR (75 MHz, DMSO-$d_6$) δ 176.8, 154.7, 145.2, 144.2, 142.0, 137.8, 132.9, 132.4, 131.7, 128.8, 126.7, 123.7, 123.1, 121.2, 117.6, 111.3, 110.9, 109.5, 98.9, 79.4, 64.2, 63.6, 57.3, 43.1, 34.2; MS (ES+) m/z 440.9 (M+1).

EXAMPLE 7.24

Synthesis of 1'-[(3-trifluoromethoxy)benzyl]-2,3-dihydrospiro[furo[2,3-g][1,4]benzodioxine-8,3'-indol]-2'(1'H)-one

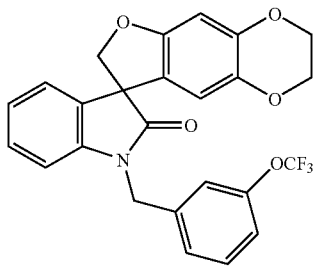

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 1-(bromomethyl)-3-(trifluoromethoxy)benzene to replace 1-bromopentane, 1'-[(3-trifluoromethoxy)benzyl]-2,3-dihydrospiro[furo[2,3-g][1,4]benzodioxine-8,3'-indol]-2'(1'H)-one was obtained (62%) as a colorless solid: $^1$H NMR (300 MHz, DMSO-$d_6$) δ 7.47-7.55 (m, 1H), 7.41-7.34 (m, 2H), 7.33-7.24 (m, 2H), 7.22-7.17 (m, 1H), 7.09-7.00 (m, 2H), 6.53 (s, 1H), 6.08 (s, 1H), 5.00 (ABq, 2H), 4.75 (ABq, 2H), 4.22-4.07 (m, 4H); $^{13}$C NMR (75 MHz, DMSO-$d_6$) δ 176.9, 154.7, 148.6, 148.5, 144.2, 142.0, 139.3, 137.9, 131.6, 130.8, 128.8, 126.2, 123.7, 123.2, 121.1, 120.1, 120.0 (q, $J_{C-F}$=256.4 Hz), 119.7, 110.9, 109.3, 98.8, 79.4, 64.2, 63.6, 57.2, 42.5; MS (ES+) m/z 469.9 (M+1).

EXAMPLE 7.25

Synthesis of t-[(2-fluoro-6-trifluoromethyl)benzyl]-2,3-dihydrospiro[furo[2,3-g][1,4]benzodioxine-8,3'-indol]-2'(1'H)-one

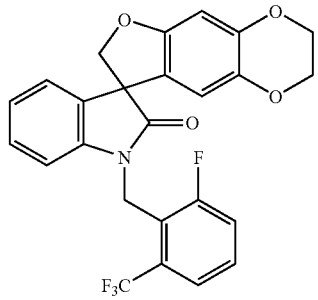

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1W)-one, and 2-(bromomethyl)-1-fluoro-3-(trifluoromethyl)benzene to replace 1-bromopentane, 1'-[(2-fluoro-6-trifluoromethyl)benzyl]-2,3-dihydrospiro[furo[2,3-g][1,4]benzodioxine-8,3'-indol]-2'(1'H)-one was obtained (68%) as a colorless solid: $^1$H NMR (300 MHz, DMSO-$d_6$) δ 7.73-7.53 (m, 3H), 7.24 (ddd, J=7.7, 7.7, 1.2 Hz, 1H), 7.16 (dd, J=7.3, 0.9 Hz, 1H), 7.02 (t, J=7.5 Hz, 1H), 6.81 (d, J=7.8 Hz, 1H), 6.51 (s, 1H), 6.14 (s, 1H), 5.14 (ABq, 2H), 4.67 (ABq, 2H), 4.22-4.07 (m, 4H); $^{13}$C NMR (75 MHz, DMSO-$d_6$) δ 176.4, 163.0, 159.7, 154.7, 144.2, 142.2, 137.8, 131.7, 130.7, 130.6, 129.4, 129.3, 129.0, 128.7, 125.4, 125.3, 123.7, 123.0, 122.7, 121.7, 121.5, 121.0, 120.8, 120.5, 111.2, 108.6, 98.7, 79.6, 64.2, 63.6, 56.9, 36.3; MS (ES+) m/z 471.8 (M+1).

EXAMPLE 7.26

Synthesis of 1'-[(2-fluoro-5-trifluoromethyl)benzyl]-2,3-dihydrospiro[furo[2,3-g][1,4]benzodioxine-8,3'-indol]-2'(1'H)-one

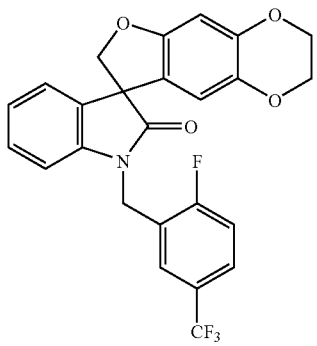

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 2-(bromomethyl)-1-fluoro-4-(trifluoromethyl)benzene to replace 1-bromopentane, 1'-[(2-fluoro-5-trifluoromethyl)benzyl]-2,3-dihydrospiro[furo[2,3-g][1,4]benzodioxine-8,3'-indol]-2'(1'H)-one was obtained (75%) as a colorless solid: $^1$H NMR (300 MHz, DMSO-$d_6$) δ 7.84-7.76 (m, 1H), 7.75-7.69 (m, 1H), 7.50-7.55 (m, 1H), 7.26-7.33 (m, 1H), 7.20 (d, J=6.8 Hz, 1H), 7.10-7.00 (m, 2H), 6.53 (s, 1H), 6.05 (s, 1H), 5.08 (ABq, 2H), 4.74 (ABq, 2H), 4.22-4.06 (m, 4H); $^{13}$C NMR (75 MHz, DMSO-$d_6$) δ 176.7, 164.0, 160.7, 154.7, 144.2, 141.8, 137.9, 131.6, 128.9, 127.5, 127.47, 127.39, 127.3, 126.9, 126.8, 126.7, 126.2, 126.1, 125.7, 125.6, 125.3, 125.2, 124.8, 124.6, 123.8, 123.7 (q, $J_{C-F}$=271.8 Hz), 123.3, 121.1, 117.3, 116.9, 110.8, 109.1, 98.9, 79.4, 64.2, 63.6, 57.2, 37.7; MS (ES+) m/z 471.8 (M+1).

EXAMPLE 7.27

Synthesis of 1'-[(2-trifluoromethoxy)benzyl]-2,3-dihydrospiro[furo[2,3-g][1,4]benzodioxine-8,3'-indol]-2'(1'H)-one

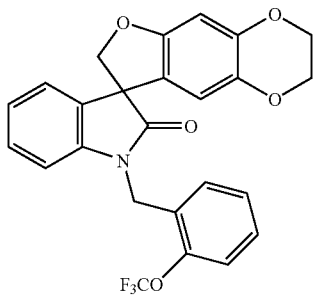

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 1-(bromomethyl)-2-(trifluoromethoxy)benzene to replace 1-bromopentane, 1'-[(2-trifluoromethoxy)benzyl]-2,3-dihydrospiro[furo[2,3-g][1,4]benzodioxine-8,3'-indol]-2'(1'H)-one was obtained (42%) as a colorless solid: $^1$H NMR (300 MHz, DMSO-$d_6$) δ 7.51-7.33 (m, 4H), 7.21-7.29 (m, 1H), 7.19 (d, J=7.1 Hz, 1H), 7.02-7.06 (m, 1H), 6.86 (d, J=7.8 Hz, 1H), 6.52 (s, 1H), 6.21 (s, 1H), 5.00 (ABq, 2H), 4.75 (ABq, 2H), 4.22-4.07 (m, 4H); $^{13}$C NMR (75 MHz, DMSO-$d_6$) δ 176.7, 154.7, 146.4, 144.2, 142.1, 137.8, 131.7, 129.6, 129.1, 128.8, 128.3, 127.8, 123.7, 123.2, 121.1, 120.9, 120.2, (q, $J_{C-F}$ 253.9 Hz), 111.3, 109.0, 98.8, 79.5, 64.2, 63.6, 57.2; MS (ES+) m/z 469.8 (M+1).

EXAMPLE 7.28

Synthesis of 1'-[2-(2,2,5-trimethyl-1,3-dioxan-2-yl)ethyl]-2,3-dihydrospiro[furo[2,3-g][1,4]benzodioxine-8,3'-indol]-2'(1'H)-one

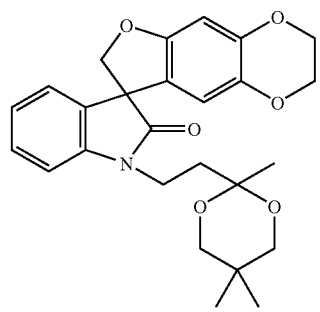

Following the procedure as described in EXAMPLE 7.3 and making non-critical variations using 2,3-dihydrospiro[furo[2,3-g][1,4]benzodioxine-8,3'-indol]-2'(1'H)-one to replace (S)-2,3-dihydrospiro[furo[2,3-g][1,4]benzodioxine-8,3'-indol]-2'(1'H)-one, and 2-(2-bromoethyl)-2,5,5-trimethyl-1,3-dioxane to replace 1-bromopentane, 1'-[2-(2,2,5-trimethyl-1,3-dioxan-2-yl)ethyl]-2,3-dihydrospiro[furo[2,3-g][1,4]benzodioxine-8,3'-indol]-2'(1'H)-one was obtained (23%) as a colorless solid: $^1$H NMR (300 MHz, CDCl$_3$) δ 7.33-7.38 (m, 1H), 7.15 (d, J=7.7 Hz, 1H), 7.04 (t, J=6.9 Hz, 2H), 6.50 (s, 1H), 6.14 (s, 1H), 4.67 (ABq, 2H), 4.22-4.05 (m, 4H), 3.96-3.71 (m, 2H), 3.49 (ABq, 4H), 2.09-1.84 (m, 2H), 1.41 (s, 3H), 1.00 (s, 3H), 0.82 (s, 3H); $^{13}$C NMR (75 MHz, CDCl$_3$) δ 176.2, 154.6, 144.1, 142.3, 137.8, 132.0, 128.9, 123.6, 122.7, 121.3, 111.2, 108.7, 98.7, 97.5, 79.3, 69.4, 64.2, 63.6, 57.1, 35.6, 34.9, 29.5, 22.6, 21.9, 19.7; MS (ES+) m/z 451.7 (M+1).

EXAMPLE 8

Synthesis of 1'-[(2S)-1,4-dioxan-2-ylmethyl]spiro[furo[2,3-f][1,3]benzodioxole-7,3'-indol]-2'(1'H)-one

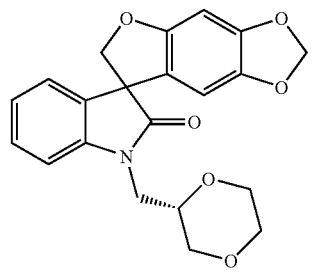

A mixture of spiro[furo[2,3-f][1,3]benzodioxole-7,3'-indol]-2'(1'H)-one (0.30 g, 1.07 mmol) and cesium carbonate (0.56 g, 1.71 mmol) in N,N-dimethylformamide (7 mL) was stirred at ambient temperature under nitrogen for 40 min. To this mixture was added potassium iodide (0.05 g, 0.28 mmol) and (R)-(1,4-dioxan-2-yl)methyl 4-methylbenzenesulfonate (0.38 g, 1.40 mmol). The reaction was warmed to 60° C. and stirred for 2 h. The solvent was removed under reduced pressure, and the residue was suspended in ethyl acetate and filtered through Celite. The filtrate was concentrated under reduced pressure and the product was purified by flash column chromatography with dichloromethane/t-butyl methyl ether (19:1) to afford 1'-[(2S)-1,4-dioxan-2-ylmethyl]spiro[furo[2,3-f][1,3]benzodioxole-7,3'-indol]-2'(1'H)-one (0.38 g, 93%) as a colorless solid: mp 147-149° C. (ethyl acetate/hexanes); $^1$H NMR (300 MHz, CDCl$_3$) (diastereomers) δ7.34-7.28 (m, 1H), 7.17 (d, J=7.2 Hz, 1H), 7.09-7.02 (m, 2H), 6.51 (s, 1H), 6.16, 6.12 (s, 1H), 5.89-5.86 (m, 2H), 4.81, 4.80 (2ABq, 2H), 3.99-3.55 (m, 8H), 3.46-3.38 (m, 1H); $^{13}$C NMR (75 MHz, CDCl$_3$) (diastereomers) δ178.0, 177.9, 156.0, 155.9, 149.01, 148.98, 142.7, 142.6, 142.5, 142.4, 132.3, 132.2, 129.02, 128.97, 123.94, 123.87, 123.6, 119.7, 119.5, 109.6, 109.4, 103.14, 103.07, 101.64, 101.62, 93.74, 93.72, 80.5, 80.4, 73.3, 73.2, 69.4, 69.2, 66.8, 66.7, 66.53, 66.49, 58.3, 58.2, 41.9, 41.7; MS (ES+) m/z 381.9 (M+1).

EXAMPLE 8.1

Synthesis of 7'-chloro-1'-[(2R)-tetrahydrofuran-2-ylmethyl]-5,6-dihydrospiro[benzo[1,2-b:5,4-b']difuran-3,3'-indol]-2'(1'H)-one

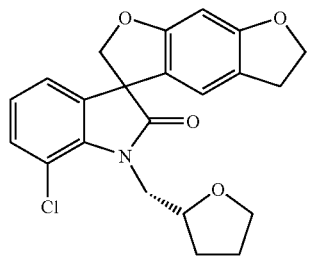

Following the procedure as described in EXAMPLE 8 and making non-critical variations using 7'-chloro-5,6-dihydrospiro[benzo[1,2-b:5,4-b']difuran-3,3'-indol]-2'(1'H)-one to replace spiro[furo[2,3-f][1,3]benzodioxole-7,3'-indol]-2'(1'H)-one, and (R)-(tetrahydrofuran-2-yl)methyl 4-methylbenzenesulfonate to replace (R)-(1,4-dioxan-2-yl)methyl 4-methylbenzenesulfonate, 7'-chloro-1'-[(2R)-tetrahydrofuran-2-ylmethyl]-5,6-dihydrospiro[benzo[1,2-b:5,4-b']difuran-3,3'-indol]-2'(1'H)-one was obtained (98%) as a colorless solid: mp 192-193° C. (hexanes/ethyl acetate); $^1$H NMR (300 MHz, DMSO-d$_6$) δ7.23-7.18 (m, 1H), 7.08-6.98 (m, 2H), 6.53 (d, J=17.6 Hz, 1H), 6.42 (d, J=2.0 Hz, 1H), 4.80-4.69 (m, 2H), 4.53-4.47 (m, 2H), 4.20-4.11 (m, 1H), 3.95-3.60 (m, 4H), 2.99-2.93 (m, 2H), 2.04-1.59 (m, 4H); $^{13}$C NMR (75 MHz, DMSO-d$_6$) δ177.7, 177.6, 161.1 (2C), 160.5, 160.3, 138.3, 138.0, 135.8, 135.4, 130.7, 130.6, 124.1, 122.7, 122.6, 120.5, 120.2, 119.9, 119.8, 119.2, 118.8, 114.3, 114.2, 92.4, 92.2, 80.0, 76.3, 76.1, 72.0, 72.0, 67.2, 66.9, 56.7, 56.5, 45.0, 44.9, 28.3, 28.2, 24.9, 24.9; MS (ES+) m/z 397.7 (M+1), 399.7 (M+1).

EXAMPLE 8.2

Synthesis of 7'-fluoro-1'-[(2R)-tetrahydrofuran-2-ylmethyl]-5,6-dihydrospiro[benzo[1,2-b:5,4-b']difuran-3,3'-indol]-2'(1'H)-one

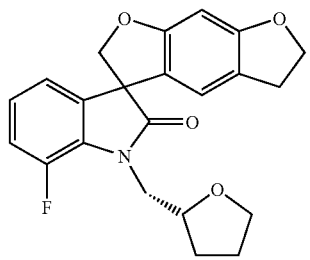

Following the procedure as described in EXAMPLE 8 and making non-critical variations using 7'-fluoro-5,6-dihydrospiro[benzo[1,2-b:5,4-b']difuran-3,3'-indol]-2'(1'H)-one to replace spiro[furo[2,3-f][1,3]benzodioxole-7,3'-indol]-2'(1'H)-one, and (R)-(tetrahydrofuran-2-yl)methyl 4-methylbenzenesulfonate to replace (R)-(1,4-dioxan-2-yl)methyl 4-methylbenzenesulfonate, 7'-fluoro-1'-[(2R)-tetrahydrofuran-2-ylmethyl]-5,6-dihydrospiro[benzo[1,2-b:5,4-b']difuran-3,3'-indol]-2'(1'H)-one was obtained (28%) as a colorless solid: mp 169-170° C. (diethyl ether); $^1$H NMR (300 MHz, DMSO-d$_6$) δ7.35-7.32 (m, 1H), 7.15-7.01 (m, 2H), 6.56 (d, J=28.1 Hz, 1H), 6.41 (d, J=2.9 Hz, 1H), 4.78-4.67 (m, 2H), 4.52-4.46 (m, 2H), 4.30-3.93 (m, 3H), 3.82-3.93 (m, 2H), 2.99-2.91 (m, 2H), 2.06-1.58 (m, 4H); $^{13}$C NMR (75 MHz, DMSO-d$_6$) δ176.7, 156.8, 156.7, 154.3, 142.9, 142.7, 136.1, 136.0, 132.8, 131.5, 131.3, 128.7 (2C), 123.3 (2C), 122.7, 121.9, 121.8, 109.7, 109.6, 109.5, 104.5, 104.4, 92.4, 79.5, 75.6, 75.4, 67.1, 67.0, 57.2, 43.8, 43.7, 28.5, 28.4, 28.1, 25.0, 24.9.

EXAMPLE 8.3

Synthesis of 4'-fluoro-7'-methyl-1'-[(2R)-tetrahydrofuran-2-ylmethyl]-5,6-dihydrospiro[benzo[1,2-b:5,4-b']difuran-3,3'-indol]-2'(1'H)-one

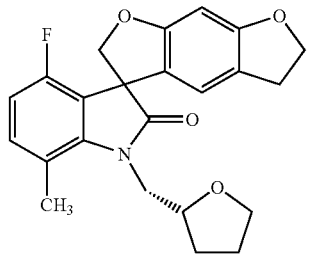

Following the procedure as described in EXAMPLE 8 and making non-critical variations using 4'-fluoro-7'-methyl-5,6-dihydrospiro[benzo[1,2-b:5,4-b']difuran-3,3'-indol]-2'(1'H)-one to replace spiro[furo[2,3-f][1,3]benzodioxole-7,3'-indol]-2'(1'H)-one, and (R)-(tetrahydrofuran-2-yl)methyl 4-methylbenzenesulfonate to replace (R)-(1,4-dioxan-2-yl)methyl 4-methylbenzenesulfonate, 4'-fluoro-7'-methyl-1'-[(2R)-tetrahydrofuran-2-ylmethyl]-5,6-dihydrospiro[benzo[1,2-b:5,4-b']difuran-3,3'-indol]-2'(1'H)-one was obtained (76%) as a colorless solid: mp 175-176° C. (diethyl ether); $^1$H NMR (300 MHz, CD$_3$OD) δ7.14-7.06 (m, 1H), 6.71-6.52 (m, 2H), 6.25 (d, J=2.3 Hz, 1H), 4.80-4.78 (m, 2H), 4.51 (t, J=8.6

Hz, 2H), 4.26-3.69 (m, 5H), 3.00 (t, J=8.6 Hz, 2H), 2.56 (s, 3H), 2.16-1.87 (m, 3H), 1.78-1.69 (m, 1H); MS (ES+) m/z 396.0 (M+1).

EXAMPLE 8.4

Synthesis of 1'-pentyl-2,3-dihydrospiro[furo[2,3-g][1,4]benzodioxine-8,3'-indol]-2'(1'H)-one

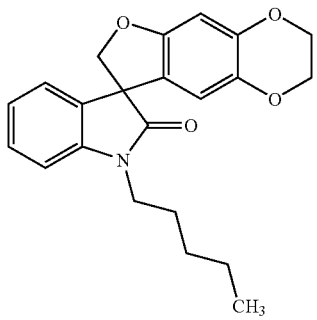

Following the procedure as described in EXAMPLE 8 and making non-critical variations using 2,3-dihydrospiro[furo[2,3-g][1,4]benzodioxine-8,3'-indol]-2'(1'H)-one to replace spiro[furo[2,3-f][1,3]benzodioxole-7,3'-indol]-2'(1'H)-one, and 1-bromopentane to replace (R)-(1,4-dioxan-2-yl)methyl 4-methylbenzenesulfonate, 1'-pentyl-2,3-dihydrospiro[furo[2,3-g][1,4]benzodioxine-8,3'-indol]-2'(1'H)-one was obtained (91%) as a colorless solid: mp 129-130° C. (diethyl ether/hexanes); $^1$H NMR (300 MHz, CDCl$_3$) δ 7.29 (ddd, J=8.0, 7.7, 1.5 Hz, 1H), 7.16 (d, J=7.5 Hz, 1H), 7.04 (dd, J=7.5, 7.5 Hz, 1H), 6.90 (d, J=7.8 Hz, 1H), 6.49 (s, 1H), 6.21 (s, 1H), 4.88 (d, J=9.0 Hz, 1H), 4.63 (d, J=9.0 Hz, 1H), 4.23-4.17 (m, 2H), 4.14-4.09 (m, 2H), 3.87-3.77 (m, 1H), 3.72-3.62 (m, 1H), 1.77-1.68 (m, 2H), 1.45-1.30 (m, 4H), 0.91 (t, J=6.6 Hz, 3H); $^{13}$C NMR (75 MHz, CDCl$_3$) δ177.3, 155.3, 144.6, 142.5, 138.3, 132.7, 128.9, 124.0, 123.2, 121.3, 111.6, 108.7, 99.4, 80.2, 64.6, 64.0, 58.1, 40.4, 29.1, 27.2, 22.4, 14.1; MS (ES+) m/z 366.0 (M+1).

EXAMPLE 8.5

Synthesis of (8R)-1'-[(2R)-1,4-dioxan-2-ylmethyl]-2,3-dihydrospiro[furo[2,3-g][1,4]benzodioxine-8,3'-indol]-2'(1'H)-one

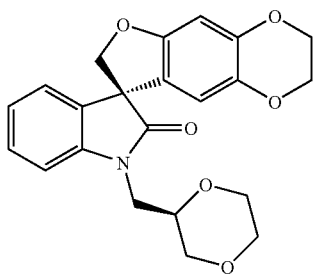

Following the procedure as described in EXAMPLE 8 and making non-critical variations using (R)-2,3-dihydrospiro[furo[2,3-g][1,4]benzodioxine-8,3'-indol]-2'(1'H)-one to replace spiro[furo[2,3-f][1,3]benzodioxole-7,3'-indol]-2'(1'H)-one, and (S)-2-(iodomethyl)-1,4-dioxane (Kim, H.Y. et al., *Bioorg. Med. Chem. Lett.* (2005), 15:3207-11) to replace (R)-(1,4-dioxan-2-yl)methyl 4-methylbenzenesulfonate, (8R)-1'-[(2R)-1,4-dioxan-2-ylmethyl]-2,3-dihydrospiro[furo[2,3-g][1,4]benzodioxine-8,3'-indol]-2'(1'H)-one was obtained (51%) as a colorless solid: mp 198-199° C. (diethyl ether/hexanes); $^1$H NMR (300 MHz, CDCl$_3$) δ7.30 (ddd, J=7.8, 7.8, 1.1 Hz, 1H), 7.16 (d, J=7.8 Hz, 1H), 7.08-7.02 (m, 2H), 6.49 (s, 1H), 6.24 (s, 1H), 4.88 (d, J=9.0 Hz, 1H), 4.64 (d, J=9.0 Hz, 1H), 4.22-4.16 (m, 2H), 4.13-4.08 (m, 2H), 3.98-3.78 (m, 4H), 3.75-3.56 (m, 4H), 3.47-3.38 (m, 1H); $^{13}$C NMR (75 MHz, CDCl$_3$) δ177.9, 155.3, 144.7, 142.7, 138.4, 132.4, 128.9, 123.8, 123.5, 121.3, 111.7, 109.6, 99.5, 80.1, 73.3, 69.2, 66.7, 66.5, 64.6, 64.0, 58.1, 41.8; MS (ES+) m/z 396.0 (M+1).

EXAMPLE 8.6

Synthesis of (8R)-1'-[(2S)-1,4-dioxan-2-ylmethyl]-2,3-dihydrospiro[furo[2,3-g][1,4]benzodioxine-8,3'-indol]-2'(1'H)-one

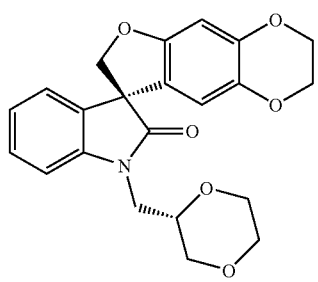

Following the procedure as described in EXAMPLE 8 and making non-critical variations using (R)-2,3-dihydrospiro[furo[2,3-g][1,4]benzodioxine-8,3'-indol]-2'(1'H)-one to replace spiro[furo[2,3-f][1,3]benzodioxole-7,3'-indol]-2'(1'H)-one, (8R)-1'-[(2S)-1,4-dioxan-2-ylmethyl]-2,3-dihydrospiro[furo[2,3-g][1,4]benzodioxine-8,3'-indol]-2'(1'H)-one was obtained (88%) as a colorless solid: mp 207-209° C. (diethyl ether/hexanes); $^1$H NMR (300 MHz, CDCl$_3$) δ7.30 (ddd, J=7.7, 7.7, 1.3 Hz, 1H), 7.15 (dd, J=7.5, 0.9 Hz, 1H), 7.08-7.02 (m, 2H), 6.49 (s, 1H), 6.21 (s, 1H), 4.87 (d, J=9.0 Hz, 1H), 4.63 (d, J=9.0 Hz, 1H), 4.21-4.16 (m, 2H), 4.13-4.08 (m, 2H), 3.98-3.79 (m, 4H), 3.75-3.56 (m, 4H), 3.41 (dd, J=11.6, 9.8 Hz, 1H); $^{13}$C NMR (75 MHz, CDCl$_3$) δ177.8, 155.3, 144.7, 142.7, 138.4, 132.3, 128.9, 123.9, 123.5, 121.1, 111.6, 109.4, 99.5, 80.2, 73.3, 69.4, 66.8, 66.5, 64.6, 64.0, 58.0, 41.9; MS (ES+) m/z 396.0 (M+1).

EXAMPLE 8.7

Synthesis of (8S)-1'-[(2S)-1,4-dioxan-2-ylmethyl]-2,3-dihydrospiro[furo[2,3-g][1,4]benzodioxine-8,3'-indol]-2'(1'H)-one

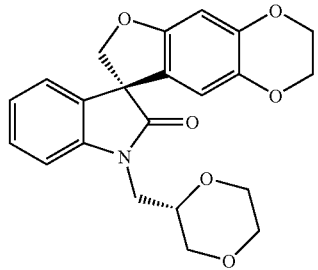

Following the procedure as described in EXAMPLE 8 and making non-critical variations using (S)-2,3-dihydrospiro

[furo[2,3-g][1,4]benzodioxine-8,3'-indol]-2'(1'H)-one to replace spiro[furo[2,3-f][1,3]benzodioxole-7,3'-indol]-2'(1'H)-one, (8S)-1'-[(2S)-1,4-dioxan-2-ylmethyl]-2,3-dihydrospiro[furo[2,3-g][1,4]benzodioxine-8,3'-indol]-2'(1'H)-one was obtained (92%) as a colorless solid: mp 198-200° C. (diethyl ether/hexanes); $^1$H NMR (300 MHz, CDCl$_3$) δ7.30 (ddd, J=7.8, 7.5, 1.2 Hz, 1H), 7.15 (dd, J=7.5, 1.2 Hz, 1H), 7.08-7.01 (m, 2H), 6.49 (s, 1H), 6.24 (s, 1H), 4.88 (d, J=9.0 Hz, 1H), 4.64 (d, J=9.0 Hz, 1H), 4.21-4.16 (m, 2H), 4.14-4.09 (m, 2H), 3.98-3.79 (m, 4H), 3.74-3.55 (m, 4H), 3.42 (dd, J=11.6, 9.5 Hz, 1H); $^{13}$C NMR (75 MHz, CDCl$_3$) δ177.9, 155.2, 144.7, 142.7, 138.4, 132.4, 128.9, 123.8, 123.5, 121.3, 111.7, 109.6, 99.5, 80.0, 73.3, 69.2, 66.7, 66.5, 64.6, 64.0, 58.1, 41.8; MS (ES+) m/z 396.0 (M+1).

EXAMPLE 8.8

Synthesis of (8S)-1'-[(2R)-1,4-dioxan-2-ylmethyl]-2,3-dihydrospiro[furo[2,3-g][1,4]benzodioxine-8,3'-indol]-2'(1'H)-one

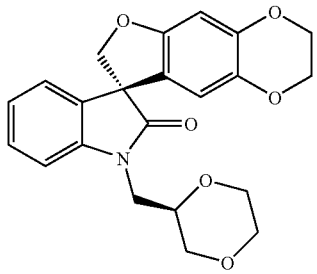

Following the procedure as described in EXAMPLE 8 and making non-critical variations using (S)-2,3-dihydrospiro[furo[2,3-g][1,4]benzodioxine-8,3'-indol]-2'(1'H)-one to replace spiro[furo[2,3-f][1,3]benzodioxole-7,3'-indol]-2'(1'H)-one, and (S)-(1,4-dioxan-2-yl)methyl 4-methylbenzenesulfonate to replace (R)-(1,4-dioxan-2-yl)methyl 4-methylbenzenesulfonate, (8S)-1'-[(2R)-1,4-dioxan-2-ylmethyl]-2,3-dihydrospiro[furo[2,3-g][1,4]benzodioxine-8,3'-indol]-2'(1'H)-one was obtained (84%) as a colorless solid: mp 207-210° C. (diethyl ether/hexanes); $^1$H NMR (300 MHz, CDCl$_3$) δ 7.30 (ddd, J=7.7, 7.7, 1.2 Hz, 1H), 7.15 (dd, J=7.5 Hz, 0.9 Hz, 1H), 7.08-7.02 (m, 2H), 6.49 (s, 1H), 6.21 (s, 1H), 4.87 (d, J=9.0 Hz, 1H), 4.63 (d, J=9.0 Hz, 1H), 4.21-4.16 (m, 2H), 4.13-4.09 (m, 2H), 3.98-3.77 (m, 4H), 3.75-3.56 (m, 4H), 3.41 (dd, J=11.7, 9.9 Hz, 1H); $^{13}$C NMR (75 MHz, CDCl$_3$) δ177.8, 155.3, 144.7, 142.7, 138.4, 132.3, 128.9, 123.9, 123.5, 121.1, 111.6, 109.4, 99.5, 80.2, 73.3, 69.4, 66.8, 66.5, 64.6, 64.0, 58.0, 41.9; MS (ES+) m/z 396.0 (M+1).

EXAMPLE 8.9

Synthesis of 1'-[(2R)-tetrahydrofuran-2-ylmethyl]-6,7-dihydrospiro[benzo[1,2-b:4,5-b']difuran-3,3'-indol]-2'(1'H)-one

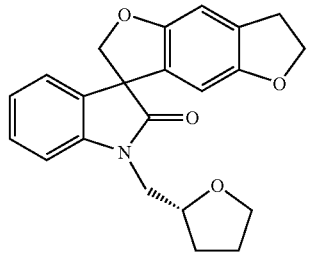

Following the procedure as described in EXAMPLE 8 and making non-critical variations using 6,7-dihydrospiro[benzo[1,2-b:4,5-b']difuran-3,3'-indol]-2'(1'H)-one to replace spiro[furo[2,3-f][1,3]benzodioxole-7,3'-indol]-2'(1'H)-one, and (R)-(tetrahydrofuran-2-yl)methyl 4-methylbenzenesulfonate to replace (R)-(1,4-dioxan-2-yl)methyl 4-methylbenzenesulfonate, 1'-[(2R)-tetrahydrofuran-2-ylmethyl]-6,7-dihydrospiro[benzo[1,2-b:4,5-b']difuran-3,3'-indol]-2'(1'H)-one was obtained (57%) as a colorless solid: mp 162-164° C. (diethyl ether/hexanes); $^1$H NMR (300 MHz, CDCl$_3$) (diastereomers) δ7.29 (dd, J=7.8, 7.8 Hz, 1H), 7.16-7.00 (m, 3H), 6.79 (s, 1H), 6.12 (s, 1H), 4.91 (d, J=9.0 Hz, 1H), 4.65 (d, J=9.0 Hz, 1H), 4.48 (t, J=8.7 Hz, 2H), 4.31-4.22 (m, 1H), 4.00-3.67 (m, 4H), 3.14 (t, J=8.7 Hz, 2H), 2.09-1.82 (m, 3H), 1.78-1.67 (m, 1H); $^{13}$C NMR (75 MHz, CDCl$_3$) (diastereomers) δ178.0, 177.8, 155.1, 154.9, 143.1, 142.9, 132.3, 132.2, 128.94, 128.88, 128.7, 127.91, 127.86, 123.8, 123.7, 123.4, 109.9, 109.5, 107.1, 104.01, 103.96, 80.2, 80.1, 77.1, 76.8, 71.7, 68.4, 68.3, 58.52, 58.49, 44.7, 30.4, 29.4, 29.0, 25.9, 25.7; MS (ES+) m/z 364.0 (M+1).

EXAMPLE 8.10

Synthesis of 1'-[(2R)-1,4-dioxan-2-ylmethyl]-6,7-dihydrospiro[benzo[1,2-b:4,5-b']difuran-3,3'-indol]-2'(1'H)-one

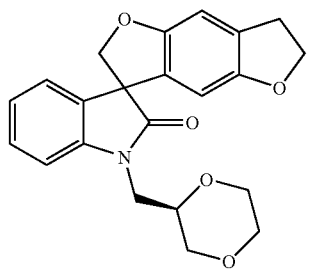

Following the procedure as described in EXAMPLE 8 and making non-critical variations using 6,7-dihydrospiro[benzo[1,2-b:4,5-b']difuran-3,3'-indol]-2'(1'H)-one to replace spiro

[furo[2,3-f][1,3]benzodioxole-7,3'-indol]-2'(1'H)-one, and (S)-(1,4-dioxan-2-yl)methyl 4-methylbenzenesulfonate to replace (R)-(1,4-dioxan-2-yl)methyl 4-methylbenzenesulfonate, 1'-[(2R)-1,4-dioxan-2-ylmethyl]-6,7-dihydrospiro[benzo[1,2-b:4,5-b']difuran-3,3'-indol]-2'(1'H)-one was obtained (97%) as a colorless solid: mp 162-164° C. (diethyl ether/hexanes); $^1$H NMR (300 MHz, CDCl$_3$) (diastereomers) δ 7.302, 7.298 (ddd, J=7.8, 7.7, 1.3 Hz, 1H), 7.17-7.14 (m, 1H), 7.07-7.02 (m, 2H), 6.79 (s, 1H), 6.12, 6.09 (s, 1H), 4.91, 4.90 (d, J=8.9 Hz, 1H), 4.66, 4.65 (d, J=8.9 Hz, 1H), 4.48 (t, J=8.7 Hz, 2H), 3.98-3.78 (m, 4H), 3.75-3.55 (m, 4H), 3.45-3.37 (m, 1H), 3.14 (t, J=8.7 Hz, 2H); $^{13}$C NMR (75 MHz, CDCl$_3$) (diastereomers) δ177.9, 177.7, 155.1, 155.0, 154.92, 154.88, 142.8, 142.7, 132.3, 132.2, 128.94, 128.89, 128.84, 128.80, 127.8, 127.7, 123.9, 123.8, 123.5, 109.6, 109.4, 107.19, 107.16, 104.0, 103.9, 80.0, 79.9, 73.3, 71.7, 69.4, 69.2, 66.8, 66.7, 66.52, 66.48, 58.46, 58.43, 41.9, 41.8, 30.4; MS (ES+) m/z 380.0 (M+1).

EXAMPLE 8.11

Synthesis of 1'-[(2R)-tetrahydrofuran-2-ylmethyl]-3,4-dihydro-2H-spiro[furo[2,3-h][1,5]benzodioxepine-9,3'-indol]-2'(1'H)-one

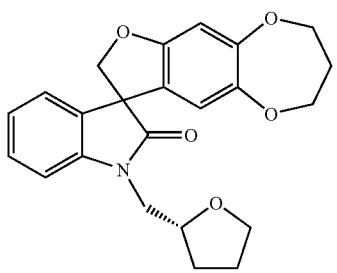

Following the procedure as described in EXAMPLE 8 and making non-critical variations using 3,4-dihydro-2H-spiro[furo[2,3-h][1,5]benzodioxepine-9,3'-indol]-2'(1'H)-one to replace spiro[furo[2,3-f][1,3]benzodioxole-7,3'-indol]-2'(1'H)-one, and (R)-(tetrahydrofuran-2-yl)methyl 4-methylbenzenesulfonate to replace (R)-(1,4-dioxan-2-yl)methyl 4-methylbenzenesulfonate, 1'-[(2R)-tetrahydrofuran-2-ylmethyl]-3,4-dihydro-2H-spiro[furo[2,3-h][1,5]benzodioxepine-9,3'-indol]-2'(1'H)-one was obtained (80%) as a colorless solid: mp 134-138° C. (diethyl ether/hexanes); $^1$H NMR (300 MHz, CDCl$_3$) (diastereomers) δ7.29 (dd, J=7.8, 7.8 Hz, 1H), 7.14-7.01 (m, 3H), 6.58 (s, 1H), 6.36 (s, 1H), 4.91 (d, J=9.0 Hz, 1H), 4.66 (d, J=9.0 Hz, 1H), 4.31-4.18 (m, 2H), 4.12-4.04 (m, 2H), 4.01-3.68 (m, 5H), 2.21-1.85 (m, 5H), 1.77-1.66 (m, 1H); $^{13}$C NMR (75 MHz, CDCl$_3$) (diastereomers) δ178.0, 177.8, 156.8, 153.0, 146.3, 143.0, 142.9, 132.3, 132.2, 128.94, 128.90, 123.9, 123.8, 123.4, 123.34, 123.28, 116.14, 116.10, 109.8, 109.6, 103.5, 80.58, 77.1, 76.9, 70.9, 68.4, 68.3, 58.04, 58.02, 44.7, 32.3, 29.4, 29.1, 25.9, 25.7; MS (ES+) m/z 394.1 (M+1).

EXAMPLE 8.12

Synthesis of 1'-[(2R)-1,4-dioxan-2-ylmethyl]-3,4-dihydro-2H-spiro[furo[2,3-h][1,5]benzodioxepine-9,3'-indol]-2'(1'H)-one

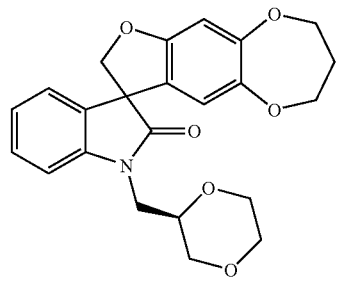

Following the procedure as described in EXAMPLE 8 and making non-critical variations using 3,4-dihydro-2H-spiro[furo[2,3-h][1,5]benzodioxepine-9,3'-indol]-2'(1'H)-one to replace spiro[furo[2,3-f][1,3]benzodioxole-7,3'-indol]-2'(1'H)-one, and (S)-2-(iodomethyl)-1,4-dioxane to replace (R)-(1,4-dioxan-2-yl)methyl 4-methylbenzenesulfonate, 1'-[(2R)-1,4-dioxan-2-ylmethyl]-3,4-dihydro-2H-spiro[furo[2,3-h][1,5]benzodioxepine-9,3'-indol]-2'(1'H)-one was obtained (61%) as a colorless solid: mp 144-147° C. (diethyl ether/hexanes); $^1$H NMR (300 MHz, CDCl$_3$) (diastereomers) δ 7.30 (ddd, J=7.7, 7.7, 1.0 Hz, 1H), 7.14 (d, J=6.9 Hz, 1H), 7.08-7.02 (m, 2H), 6.59 (s, 1H), 6.36, 6.33 (s, 1H), 4.91, 4.90 (d, J=9.0 Hz, 1H), 4.67, 4.66 (d, J=9.0 Hz, 1H), 4.28-4.19 (m, 1H), 4.15-4.02 (m, 2H), 3.99-3.78 (m, 5H), 3.75-3.57 (m, 4H), 3.46-3.39 (m, 1H), 2.22-2.00 (m, 2H); $^{13}$C NMR (75 MHz, CDCl$_3$) (diastereomers) δ177.8, 177.7, 156.8, 156.7, 153.0, 146.4, 146.3, 142.65, 142.63, 132.3, 132.2, 129.0, 128.9, 124.0, 123.9, 123.6, 123.2, 123.1, 116.1, 116.0, 109.6, 109.4, 103.58, 103.56, 80.5, 80.4, 73.34, 73.30, 70.9, 69.4, 69.2, 66.8, 66.7, 66.52, 66.49, 57.98, 57.96, 41.9, 41.8, 32.3; MS (ES+) m/z 410.0 (M+1).

EXAMPLE 8.13

Synthesis of 1'-[(2S)-1,4-dioxan-2-ylmethyl]-3,4-dihydro-2H-spiro[furo[2,3-h][1,5]benzodioxepine-9,3'-indol]-2'(1'H)-one

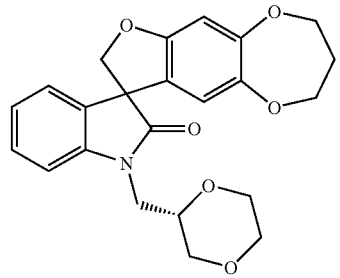

Following the procedure as described in EXAMPLE 8 and making non-critical variations using 3,4-dihydro-2H-spiro[furo[2,3-h][1,5]benzodioxepine-9,3'-indol]-2'(1'H)-one to replace spiro[furo[2,3-f][1,3]-benzodioxole-7,3'-indol]-2'(1'H)-one, and (S)-(1,4-dioxan-2-yl)methyl 4-methylbenzenesulfonate to replace (R)-(1,4-dioxan-2-yl)methyl 4-methylbenzenesulfonate, 1'-[(2S)-1,4-dioxan-2-ylmethyl]-3,4-dihydro-2H-spiro[furo[2,3-h][1,5]benzodioxepine-9,3'-indol]-2'(1'H)-one was obtained (91%) as a colorless solid: mp 137-139° C. (hexanes/diethyl ether); $^1$H NMR (300 MHz, CDCl$_3$) (diastereomers) δ 7.33-7.27 (m, 1H), 7.14 (d, J=7.2 Hz, 1H), 7.08-7.01 (m, 2H), 6.58 (s, 1H), 6.36, 6.33 (s, 1H), 4.91, 4.90 (d, J=9.0 Hz, 1H), 4.67, 4.66 (d, J=9.0 Hz, 1H), 4.28-4.20 (m, 1H), 4.14-4.02 (m, 2H), 3.99-3.78 (m, 5H), 3.76-3.57 (m, 4H), 3.46-3.38 (m, 1H), 2.22-2.00 (m, 2H); $^{13}$C NMR (75 MHz, CDCl$_3$) (diastereomers) δ177.8, 177.7, 156.8, 156.7, 153.08, 153.05, 146.38, 146.35, 142.65, 142.63, 132.3, 132.2, 129.0, 128.9, 124.0, 123.9, 123.6, 123.2, 123.1, 116.1, 116.0, 109.6, 109.4, 103.59, 103.56, 80.5, 80.4, 73.34, 73.31, 70.9, 69.4, 69.2, 66.8, 66.7, 66.52, 66.49, 57.98, 57.96, 41.9, 41.8, 32.3; MS (ES+) m/z 410.0 (M+1).

EXAMPLE 8.14

Synthesis of 3-methyl-1'-(((R)-tetrahydrofuran-2-yl)methyl)-2H-spiro[benzofuro[6,5-d]oxazole-7,3'-indoline]-2,2'(3H,6H)-dione

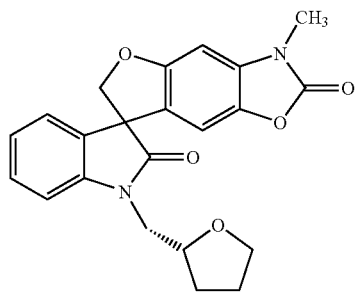

Following the procedure as described in EXAMPLE 8 and making non-critical variations using 3-methylspiro[furo[2,3-f][1,3]benzoxazole-7,3'-indole]-2,2'(1'H,3H)-dione to replace spiro[furo[2,3-f][1,3]benzodioxole-7,3'-indol]-2'(1'H)-one, and (R)-(tetrahydrofuran-2-yl)methyl 4-methylbenzenesulfonate to replace (R)-(1,4-dioxan-2-yl)methyl 4-methyl benzenesulfonate, 3-methyl-1'-(((R)-tetrahydrofuran-2-yl)methyl)-2H-spiro[benzofuro[6,5-d]oxazole-7,3'-indoline]-2,2'(3H,6H)-dione was obtained (69%) as a colorless solid: mp 186-187° C. (diethyl ether); $^1$H NMR (300 MHz, DMSO-d$_6$) δ7.36-7.29 (m, 1H), 7.23 (d, J=8.2 Hz, 1H), 7.14 (d, J=8.2 Hz, 1H), 7.06-7.02 (m, 2H), 6.63 (d, J=6.9 Hz, 1H), 4.85-4.73 (m, 2H), 4.24-4.16 (m, 1H), 3.81-3.59 (m, 4H), 3.31 (s, 3H), 2.00-1.75 (m, 3H), 1.69-1.55 (m, 1H); $^{13}$C NMR (75 MHz, DMSO-d$_6$) δ177.2, 157.3, 154.9, 143.4, 136.6, 133.3, 131.9, 129.3, 123.9, 123.3, 122.3, 110.2, 105.0, 92.9, 80.0, 76.1, 67.7, 57.7, 44.3, 29.1, 28.6, 25.5; MS (ES+) m/z 392.7 (M+1).

EXAMPLE 8.15

Synthesis of 7'-fluoro-1'-(pyridin-2-ylmethyl)-3,7-dihydro-2H-spiro[benzofuro[5,6-b][1,4]dioxine-8,3'-indolin]-2'-one

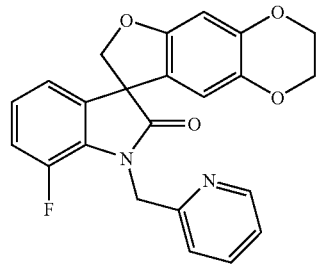

Following the procedure as described in EXAMPLE 8 and making non-critical variations using 7'-fluoro-2,3-dihydrospiro[furo[2,3-g][1,4]benzodioxine-8,3'-indol]-2'(1'H)-one to replace spiro[furo[2,3-f][1,3]benzodioxole-7,3'-indol]-2'(1'H)-one, and 2-(bromomethyl)pyridine hydrobromide to replace (R)-(1,4-dioxan-2-yl)methyl 4-methylbenzenesulfonate, 7'-fluoro-1'-(pyridin-2-ylmethyl)-3,7-dihydro-2H-spiro[benzofuro[5,6-b][1,4]dioxine-8,3'-indolin]-2'-one was obtained (38%) as a colorless solid: mp 205-207° C. (dichloromethane); $^1$H NMR (300 MHz, CDCl$_3$) δ8.55 (d, J=4.8 Hz, 1H), 7.69-7.63 (m, 1H), 7.23-7.16 (m, 2H), 6.99-6.89 (m, 3H), 6.50 (s, 2H), 5.35 (d, J=16.4 Hz, 1H), 5.17 (d, J=16.4 Hz, 1H), 4.97 (d, J=8.9 Hz, 1H), 4.70 (d, J=8.9 Hz, 1H), 4.22-4.19 (m, 2H), 4.15-4.13 (m, 2H); $^{13}$C NMR (75 MHz, CDCl$_3$) δ 177.5, 155.7, 155.1, 149.6, 144.7, 138.4, 136.7, 124.0, 124.0, 122.4, 121.0, 120.7, 119.7, 119.6, 116.7, 116.5, 112.1, 99.3, 80.3, 64.5, 63.9, 58.4, 47.0; MS (ES+) m/z 405.0 (M+1).

EXAMPLE 8.16

Synthesis of 7'-fluoro-1-((3-(trifluoromethyl)pyridin-2-yl)methyl)-3,7-dihydro-2H-spiro[benzofuro[5,6-b][1,4]dioxine-8,3'-indolin]-2'-one

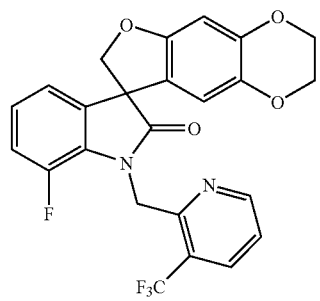

Following the procedure as described in EXAMPLE 8 and making non-critical variations using 7'-fluoro-2,3-dihydrospiro[furo[2,3-g][1,4]benzodioxine-8,3'-indol]-2'(1'H)- one to replace spiro[furo[2,3-f][1,3]benzodioxole-7,3'-indol]-2'(1'H)-one, and 2-(chloromethyl)-3-(trifluoromethyl)pyridine hydrochloride to replace (R)-(1,4-dioxan-2-yl)methyl 4-methylbenzenesulfonate, 7'-fluoro-1'-((3-(trifluoromethyl)pyridin-2-yl)methyl)-3,7-dihydro-2H-spiro[benzofuro[5,6-b][1,4]dioxine-8,3'-indolin]-2'-one was obtained (40%) as a colorless solid: mp 241-243° C. (dichloromethane); $^1$H NMR (300 MHz, CDCl$_3$) δ8.62 (d, J=4.7 Hz, 1H), 7.97 (d, J=7.8 Hz, 1H), 7.34-7.30 (m, 1H), 7.00-6.86 (m, 3H), 6.68 (s, 1H), 6.50 (s, 1H), 5.54 (d, J=17.1 Hz, 1H), 5.37 (d, J=17.1 Hz, 1H), 4.99 (d, J=9.0 Hz, 1H), 4.73 (d, J=9.0 Hz, 1H), 4.21-4.19 (m, 2H), 4.15-4.14 (m, 2H); $^{13}$C NMR (75 MHz, CDCl$_3$) δ177.9, 155.1, 153.0, 151.9, 149.2, 145.9, 144.7, 138.3, 135.5, 134.3, 129.2, 123.9, 121.9, 121.3, 119.6, 116.4, 116.2, 112.5, 99.2, 80.2, 64.6, 63.9, 58.5, 44.2; MS (ES+) m/z 473.0 (M+1).

EXAMPLE 8.17

Synthesis of 3'-[2-(difluoromethyl)benzyl]-2,3-dihydrospiro[furo[2,3-g][1,4]benzodioxine-8,1'-inden]-2'(3'H)-one

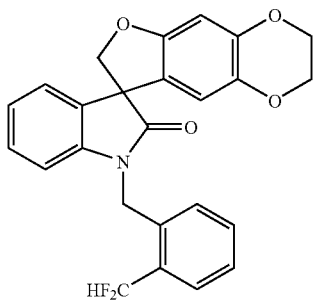

Following the procedure as described in EXAMPLE 8 and making non-critical variations using 2,3-dihydrospiro[furo[2,3-g][1,4]benzodioxine-8,3'-indol]-2'(1'H)-one to replace spiro[furo[2,3-f][1,3]benzodioxole-7,3'-indol]-2'(1'H)-one, and 1-(bromomethyl)-2-(difluoromethyl)benzene to replace (R)-(1,4-dioxan-2-yl)methyl 4-methylbenzenesulfonate, 3'-[2-(difluoromethyl)benzyl]-2,3-dihydrospiro[furo[2,3-g][1,4]benzodioxine-8,1'-inden]-2'(3'H)-one was obtained (52%) as a colorless solid: mp 191-193° C.; $^1$H NMR (300 MHz, DMSO-d$_6$) δ7.67 (d, J=7.4 Hz, 1H), 7.52-7.46 (m, 2H), 7.37 (s, 1H), 7.26-7.20 (m, 3H), 7.06 (dd, J=7.4, 7.4 Hz, 1H), 6.85 (d, J=7.8 Hz, 1H), 6.53 (s, 1H), 6.24 (s, 1H), 5.17-5.04 (m, 2H), 4.77 (ABq, 2H), 4.20-4.11 (m, 4H); $^{13}$C NMR (75 MHz, DMSO-d$_6$) δ177.4, 155.3, 144.7, 142.6, 138.3, 134.5 (t, $J_{C-F}$=3.8 Hz), 132.1, 131.9, 131.8 (t, $J_{C-F}$=21.3 Hz), 129.3, 128.3, 127.4, 127.0 (t, $J_{C-F}$=7.7 Hz), 124.3, 123.7, 121.5, 114.9 (t, $J_{C-F}$=236.0 Hz), 111.8, 109.8, 99.3, 80.1, 64.7, 64.1, 57.8; MS (ES+) m/z 435.7 (M+1).

EXAMPLE 8.18

Synthesis of 1'-[(5-fluoropyridin-3-yl)methyl]-2,3-dihydrospiro[furo[2,3-g][1,4]benzodioxine-8,3'-indol]-2'(1'H)-one

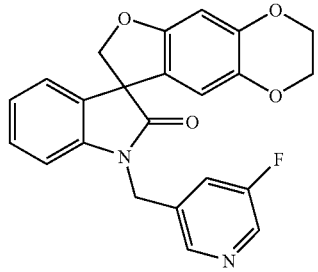

Following the procedure as described in EXAMPLE 8 and making non-critical variations using 2,3-dihydrospiro[furo[2,3-g][1,4]benzodioxine-8,3'-indol]-2'(1'H)-one to replace spiro[furo[2,3-f][1,3]benzodioxole-7,3'-indol]-2'(1'H)-one, and 3-(chloromethyl)-5-fluoropyridine hydrochloride (Carlson et al., *Acta Pharmaceutica Suecica*, 1972, 9, 411-414) to replace (R)-(1,4-dioxan-2-yl)methyl 4-methylbenzenesulfonate, 1'-[(5-fluoropyridin-3-yl)methyl]-2,3-dihydrospiro[furo[2,3-g][1,4]benzodioxine-8,3'-indol]-2'(1'H)-one was obtained (71%) as a colorless solid: $^1$H NMR (300 MHz, CDCl$_3$) δ 8.45-8.38 (m, 2H), 7.37-7.34 (m, 1H), 7.24-7.14 (m, 2H), 7.04-7.00 (m, 1H), 6.78-6.75 (m, 1H), 6.46 (s, 1H), 6.17 (s, 1H), 5.03-4.85 (m, 3H), 4.64-4.61 (m, 1H), 4.16-4.04 (m, 4H); $^{13}$C NMR (75 MHz, CDCl$_3$) δ 177.6, 155.3, 144.7, 144.6, 141.4, 138.4, 138.1, 137.8, 132.1, 129.0, 124.3, 123.9, 122.1, 121.9, 120.6, 111.4, 108.8, 99.5, 80.1, 64.5, 63.9, 58.0, 41.1; MS (ES+) m/z 405.0 (M+1).

EXAMPLE 8.19

Synthesis of (8S)-1'-[(5-fluoropyridin-3-yl)methyl]-2,3-dihydrospiro[furo[2,3-g][1,4]benzodioxine-8,3'-indol]-2'(1'H)-one

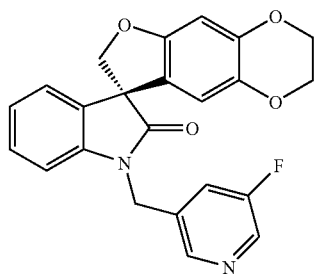

To a solution of (8S)-2,3-dihydrospiro[furo[2,3-g][1,4]benzodioxine-8,3'-indol]-2'(1'H)-one (0.40 g, 1.35 mmol) in 2-butanone (15 mL) was added cesium carbonate (1.76 g, 5.40 mmol), 3-(chloromethyl)-5-fluoropyridine hydrochloride (0.49 g, 2.69 mmol) and potassium iodide (0.085 g, 38 mol %). This mixture was stirred under nitrogen at ambient temperature for 72 h. Further, cesium carbonate (1.76 g, 5.40 mmol), 3-(chloromethyl)-5-fluoropyridine hydrochloride (0.49 g, 2.69 mmol) and tetra-n-butylammonium iodide (0.08 g, 0.22 mmol) were added and the reaction mixture was heated at reflux for 48 h, allowed to cool to ambient temperature, filtered and concentrated in vacuo. The residue was purified by column chromatography and eluted with a 10% to 40% gradient of ethyl acetate in hexanes and recrystallized from diethyl ether to afford (8S)-1'-[(5-fluoropyridin-3-yl)methyl]-2,3-dihydrospiro[furo[2,3-g][1,4]benzodioxine-8,3'-indol]-2'(1'H)-one (102.1 mg, 19%) as a yellow solid: mp 197-200° C. (diethyl ether); $^1$H NMR (300 MHz, CDCl$_3$) δ 8.48-8.42 (m, 2H), 7.40-7.37 (m, 1H), 7.26-7.17 (m, 2H), 7.08-7.03 (m, 1H), 6.78-6.76 (m, 1H), 6.50 (s, 1H), 6.18 (s, 1H), 5.06-4.88 (m, 3H), 4.66-4.63 (m, 1H), 4.20-4.09 (m, 4H); $^{13}$C NMR (75 MHz, CDCl$_3$) δ 177.7, 155.3, 144.8, 144.4, 141.3, 138.4, 138.0, 137.7, 132.1, 129.0, 124.3, 124.0, 122.4, 122.2, 120.5, 111.4, 108.7, 99.5, 80.1, 64.5, 63.9, 58.0, 41.1; MS (ES+) m/z 404.9 (M+1).

EXAMPLE 9

Synthesis of 3-methyl-1'-{[5-(trifluoromethyl)furan-2-yl]methyl}spiro[furo[3,2-f][1,2]benzisoxazole-5,3'-indol]-2'(1'H)-one

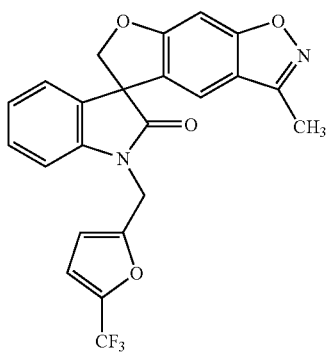

To a stirred solution of 3-methylspiro[furo[3,2-f][1,2]benzisoxazole-5,3'-indol]-2'(1'H)-one (0.29 g, 1.00 mmol) in N,N-dimethylformamide (10 mL) was added sodium hydride (0.05 g, 1.25 mmol) at 0° C. The reaction mixture was stirred at 0° C. for 30 min, then 2-(bromomethyl)-5-(trifluoromethyl)furan (0.25 mL, 1.80 mmol) was added. The mixture was stirred at ambient temperature for 20 h, diluted with ethyl acetate, washed with water and brine, and dried over anhydrous sodium sulfate and filtered. The filtrate was concentrated in vacuum. The residue was purified by column chromatography with ethyl acetate in hexanes (10% to 40% gradient) to afford 3-methyl-1'-{[5-(trifluoromethyl)furan-2-yl]methyl}spiro[furo[3,2-f][1,2]benzisoxazole-5,3'-indol]-2'(1'H)-one (0.35 g, 80%): mp 111-112° C. (diethyl ether/hexanes); $^1$H NMR (300 MHz, CDCl$_3$) δ 7.46 (d, J=9.0 Hz, 1H), 7.33-7.27 (m, 1H), 7.15-7.12 (m, 1H), 7.06-7.01 (m, 3H), 6.77-6.76 (m, 1H), 6.55-6.52 (m, 1H), 5.20-4.85 (m, 4H), 2.44 (s, 3H); $^{13}$C NMR (75 MHz, CDCl$_3$) δ 175.7, 163.9, 158.1, 154.9, 151.6, 141.4, 130.2, 129.5, 123.9, 123.1, 120.7, 117.9, 117.1, 112.9, 109.3, 108.9, 108.8, 107.9, 81.2, 56.2, 37.5, 9.8; MS (ES+) m/z 462.9 (M+23).

EXAMPLE 9.1

Synthesis of 1'-[2-(2-methoxyethoxy)ethyl]-5,6-dihydrospiro[benzo[1,2-b:5,4-b']difuran-3,3'-indol]-2'(1'H)-one

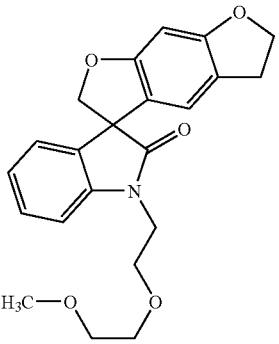

Following the procedure as described in EXAMPLE 9 and making non-critical variations using 5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, and 1-bromo-2-(2-methoxyethoxy)ethane to replace 2-(bromomethyl)-5-(trifluoromethyl)furan, 5,6-dihydrospiro[benzo[1,2-b:5,4-b']difuran-3,3'-indol]-2'(1'H)-one was obtained (68%) as a colorless solid: mp 105-107° C.; 1H NMR (300 MHz, CDCl$_3$) δ7.32-7.24 (m, 1H), 7.18-7.12 (m, 1H), 7.07-7.00 (m, 2H), 6.49 (s, 1H), 6.40 (s, 1H), 4.80 (ABq, 2H), 4.53 (t, J=8.6 Hz, 2H), 4.09-3.88 (m, 2H), 3.83-3.73 (m, 2H), 3.68-3.60 (m, 2H), 3.53-3.46 (m, 2H), 3.34 (s, 3H), 3.04-2.94 (m, 2H); $^{13}$C NMR (75 MHz, CDCl$_3$) δ177.9, 161.7, 161.2, 142.5, 132.8, 128.6, 123.7, 123.2, 120.3, 119.8, 118.9, 109.1, 93.1, 80.5, 72.3, 71.9, 70.3, 68.1, 59.0, 57.6, 40.1, 29.0; MS (ES+) m/z 382.1 (M+1).

EXAMPLE 9.2

Synthesis of 1'-{[(2S)-5-oxopyrrolidin-2-yl]methyl}-5,6-dihydrospiro[benzo[1,2-b:5,4-b']difuran-3,3'-indol]-2'(1'H)-one

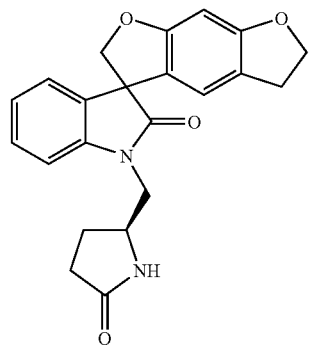

Following the procedure as described in EXAMPLE 9 and making non-critical variations using 5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, and (S)-(5-oxopyrrolidin-2-yl)methyl 4-methylbenzenesulfonate to replace 2-(bromomethyl)-5-(trifluoromethyl)furan, 1'-{[(2S)-5-oxopyrrolidin-2-yl]methyl}-5,6-dihydrospiro[benzo[1,2-b:5,4-b']difuran-3,3'-indol]-2'(1'H)-one was obtained (47%) as a colorless solid: mp 133-136° C.; $^1$H NMR (300 MHz, CDCl$_3$) δ7.35-7.27 (m, 1H), 7.24-7.14 (m, 1H), 7.14-7.03 (m, 1H), 7.00-6.85 (m, 1H), 6.54-6.42 (m, 1H), 6.42-6.37 (m, 1H), 4.93 (t, J=9.3 Hz, 1H), 4.67 (dd, J=9.3, 3.0 Hz, 1H), 4.53 (t, J=8.5 Hz, 2H), 4.18-4.04 (m, 1H), 3.93 (dt, J=13.9, 4.6 Hz, 1H), 3.72 (dt, J=13.9, 4.6 Hz, 1H), 3.07-2.80 (m, 3H), 2.42-2.15 (m, 3H), 2.06-1.81 (m, 1H); $^{13}$C NMR (75 MHz, CDCl$_3$) δ178.6, 178.5, 161.8 (2C), 161.3, 161.2, 142.2, 142.1, 132.6, 132.5, 129.0 (2C), 128.9, 128.8, 124.1, 123.6, 119.9 (3C), 119.7, 118.8, 108.3, 93.2, 93.1, 80.6, 80.5, 72.3, 57.5, 53.2, 53.1, 45.2 (2C), 29.6, 29.6, 28.9, 24.7 (2C); MS (ES+) m/z 377.1 (M+1).

EXAMPLE 9.3

Synthesis of 1'-[2-(2-oxo-1,3-oxazolidin-3-yl)ethyl]-5,6-dihydrospiro[benzo[1,2-b:5,4-b']difuran-3,3'-indol]-2'(1'H)-one

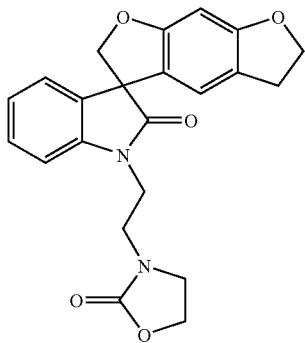

Following the procedure described in EXAMPLE 9 and making non-critical variations using 5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, and 2-(2-oxooxazolidin-3-yl)ethyl 4-methylbenzenesulfonate to replace 2-(bromomethyl)-5-(trifluoromethyl)furan, 1'-[2-(2-oxo-1,3-oxazolidin-3-yl)ethyl]-5,6-dihydrospiro[benzo[1,2-b:5,4-b']difuran-3,3'-indol]-2'(1'H)-one was obtained (46%) as a colorless solid: mp 185-186° C.; $^1$H NMR (300 MHz, CDCl$_3$) δ7.33 (dd, J=7.8, 7.8 Hz, 1H), 7.18 (d, J=7.3 Hz, 1H), 7.08 (dd, J=7.3, 7.3 Hz, 1H), 6.99 (d, J=7.8 Hz, 1H), 6.50 (s, 1H), 6.40 (s, 1H), 4.78 (ABq, 2H), 4.53 (t, J=8.6 Hz, 2H), 4.33-4.22 (m, 1H), 4.21-4.00 (m, 2H), 3.93-3.58 (m, 4H), 3.57-3.43 (m, 1H), 3.05-2.91 (m, 2H); $^{13}$C NMR (75 MHz, CDCl$_3$) δ 178.8, 161.8, 161.3, 158.7, 141.7, 132.4, 129.0, 124.1, 123.7, 120.0, 119.0, 108.3, 93.2, 80.5, 72.5, 62.1, 57.7, 44.3, 41.7, 37.3, 29.0; MS (ES+) m/z 393.3 (M+1).

EXAMPLE 9.4

Synthesis of 1-(4-pyridin-2-ylbenzyl)-5,6-dihydrospiro[benzo[1,2-b:5,4-b']difuran-3,3'-indol]-2'(1'H)-one

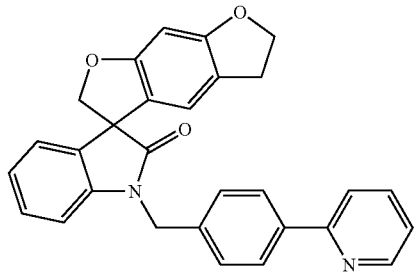

Following the procedure as described in EXAMPLE 9 and making non-critical variations using 5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, and 2-(4-(chloromethyl)phenyl)pyridine to replace 2-(bromomethyl)-5-(trifluoromethyl)furan, 1'-(4-pyridin-2-ylbenzyl)-5,6-dihydrospiro[benzo[1,2-b:5,4-b']difuran-3,3'-indol]-2'(1'H)-one was obtained (67%) as a colorless solid: mp 217-219° C.; $^1$H NMR (300 MHz, CDCl$_3$) δ 8.66 (d, J=4.3 Hz, 1H), 7.96 (d, J=8.0 Hz, 2H), 7.78-7.64 (m, 2H), 7.44 (d, J=8.0 Hz, 2H), 7.25-7.11 (m, 3H), 7.00 (dd, J=7.6, 7.6 Hz, 1H), 6.79 (d, J=7.6 Hz, 1H), 6.49 (s, 1H), 6.42 (s, 1H), 5.00 (ABq, 2H), 4.85 (ABq, 2H), 4.52 (t, J=8.6 Hz, 2H), 3.09-2.87 (m, 2H); $^{13}$C NMR (75 MHz, CDCl$_3$) δ177.9, 161.7, 161.2, 156.7, 149.6, 141.9, 138.9, 136.7, 136.4, 132.6, 128.6, 127.8, 127.3, 123.8, 123.4, 122.2, 120.4, 120.1, 119.9, 118.8, 109.3, 93.2, 80.6, 72.3, 57.7, 43.8, 29.0; MS (ES+) m/z 447.1 (M+1).

EXAMPLE 9.5

Synthesis of 1'-(pyrimidin-2-ylmethyl)-5,6-dihydrospiro[benzo[1,2-b:5,4-b']difuran-3,3'-indol]-2'(1'H)-one

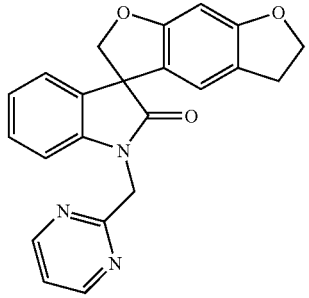

Following the procedure as described in EXAMPLE 9 and making non-critical variations using 5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, and 2-(chloromethyl)pyrimidine to replace 2-(bromomethyl)-5-(trifluoromethyl)furan, (pyrimidin-2-ylmethyl)-5,6-dihydrospiro[benzo[1,2-b:5,4-b']difuran-3,3'-indol]-2'(1'H)-one was obtained (84%) as a colorless solid: mp 203-205° C.; $^1$H NMR (300 MHz, CDCl$_3$) δ8.68 (d, J=4.9 Hz, 2H), 7.24-7.15 (m, 3H), 7.03 (dd, J=7.5, 7.5 Hz, 1H), 6.75 (s, 1H), 6.73 (d, J=7.7 Hz, 1H), 6.42 (s, 1H), 5.22 (ABq, 2H), 4.89 (ABq, 2H), 4.53 (t, J=8.6 Hz, 2H), 3.07-2.93 (m, 2H) $^{13}$C NMR (75 MHz, CDCl$_3$) δ178.0, 164.6, 161.6, 161.1, 157.4, 142.2, 132.9, 128.4, 123.7, 123.2, 120.5, 119.7, 119.7, 119.4, 108.7, 93.0, 80.5, 72.2, 57.7, 45.7, 29.0; MS (ES+) m/z 372.3 (M+1).

EXAMPLE 9.6

Synthesis of 1-(pyrimidin-4-ylmethyl)-5,6-dihydrospiro[benzo[1,2-b:5,4-b']difuran-3,3'-indol]-2'(1'H)-one

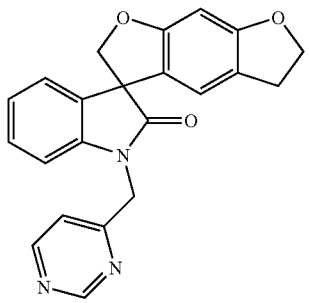

Following the procedure as described in EXAMPLE 9 and making non-critical variations using 5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, and 4-(chloromethyl)pyrimidine to replace 2-(bromomethyl)-5-(trifluoromethyl)furan, (pyrimidin-4-ylmethyl)-5,6-dihydrospiro[benzo[1,2-b:5,4-b']difuran-3,3'-indol]-2'(1'H)-one was obtained (70%) as a colorless solid: mp 158-160° C.; $^1$H NMR (300 MHz, CDCl$_3$) δ 9.16 (s, 1H), 8.68 (d, J=4.1 Hz, 1H), 7.30-7.15 (m, 3H), 7.05 (dd, J=7.5, 7.5 Hz, 1H), 6.79 (d, J=7.7 Hz, 1H), 6.55 (s, 1H), 6.39 (s, 1H), 5.04 (ABq, 2H), 4.84 (ABq, 2H), 4.51 (t, J=8.6 Hz, 2H), 3.06-2.91 (m, 2H); $^{13}$C NMR (75 MHz, CDCl$_3$) δ 177.9, 164.1, 161.8, 161.2, 158.6, 157.3, 141.5, 132.4, 128.7, 124.0, 123.7, 119.9, 119.8, 118.9, 108.8, 93.1, 80.5, 72.3, 57.6, 44.9, 28.9; MS (ES+) m/z 372.3 (M+1).

EXAMPLE 9.7

Synthesis of 1'-(pyrazin-2-ylmethyl)-5,6-dihydrospiro[benzo[1,2-b:5,4-b']difuran-3,3'-indol]-2'(1'H)-one

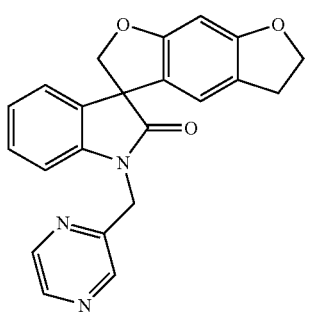

Following the procedure as described in EXAMPLE 9 and making non-critical variations using 5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, and 2-(chloromethyl)pyrazine to replace 2-(bromomethyl)-5-(trifluoromethyl)furan, 1'-(pyrazin-2-ylmethyl)-5,6-dihydrospiro[benzo[1,2-b:5,4-b']difuran-3,3'-indol]-2'(1'H)-one was obtained (27%) as a colorless solid: mp 143-144° C.; $^1$H NMR (300 MHz, CDCl$_3$) δ8.64 (br s, 1H), 8.58-8.59 (m, 2H), 7.24-7.17 (m, 2H), 7.09-7.02 (m, 1H), 6.91-6.86 (m, 1H), 6.54 (s, 1H), 6.43 (s, 1H), 5.14 (ABq, 2H), 4.85 (ABq, 2H), 4.59-4.50 (m, 2H), 3.10-2.91 (m, 2H); $^{13}$C NMR (75 MHz, CDCl$_3$) δ177.9, 161.9, 161.3, 151.4, 144.2, 143.9, 143.8, 141.6, 132.7, 128.8, 124.0, 123.8, 120.0, 119.9, 119.0, 109.1, 93.2, 80.6, 72.4, 57.8, 43.8, 29.0; MS (ES+) m/z 372.3 (M+1).

EXAMPLE 9.8

Synthesis of 1'-[(7-fluoro-1-benzofuran-2-yl)methyl]-5,6-dihydrospiro[benzo[1,2-b:5,4-b']difuran-3,3'-indol]-2'(1'H)-one

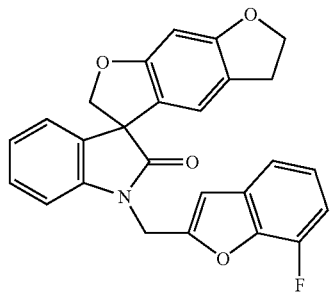

Following the procedure as described in EXAMPLE 9 and making non-critical variations using 5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, and 2-(bromomethyl)-7-fluorobenzofuran to replace 2-(bromomethyl)-5-(trifluoromethyl)furan, 1'-[(7-fluoro-1-benzofuran-2-yl)methyl]-5,6-dihydrospiro[benzo[1,2-b:5,4-b']difuran-3,3'-indol]-2'(1'H)-one was obtained (83%) as a colorless solid: mp 192-193° C.; $^1$H NMR (300 MHz, CDCl$_3$) δ7.31-7.24 (m, 2H), 7.22-6.96 (m, 5H), 6.77-6.74 (m, 1H), 6.56 (s, 1H), 6.43 (s, 1H), 5.31-5.23 (m, 1H), 5.03-4.95 (m, 2H), 4.75-4.68 (m, 1H), 4.59-4.49 (m, 2H), 3.10-2.91 (m, 2H); $^{13}$C NMR (75 MHz, CDCl$_3$) δ177.6, 161.8, 161.2, 152.8, 147.8 (d, $J_{C-F}$=249.7 Hz), 141.9 (d, $J_{C-F}$=11.3 Hz), 141.4, 132.7, 131.6 (d, $J_{C-F}$=3.2 Hz), 128.8, 123.9, 123.7, 123.6, 120.1 (d, $J_{C-F}$=5.2 Hz), 119.0, 116.6 (d, $J_{C-F}$=3.9 Hz), 110.8 (d, $J_{C-F}$=16.1 Hz), 109.0, 105.6 (d, $J_{C-F}$=2.1 Hz), 93.2, 80.4, 72.4, 57.7, 37.5, 29.0; MS (ES+) m/z 428.3 (M+1).

EXAMPLE 9.9

Synthesis of 1'-(pyridazin-3-ylmethyl)-5,6-dihydrospiro[benzo[1,2-b:5,4-b']difuran-3,3'-indol]-2'(1'H)-one

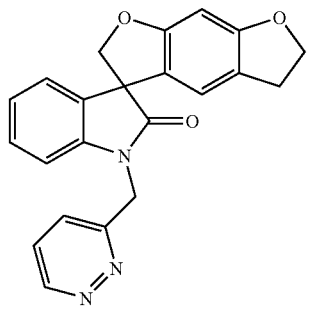

Following the procedure as described in EXAMPLE 9 and making non-critical variations using 5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, and 3-(chloromethyl)pyridazine to replace 2-(bromomethyl)-5-(trifluoromethyl)furan, 1'-(pyridazin-3-ylmethyl)-5,6-dihydrospiro[benzo[1,2-b:5,4-b']difuran-3,3'-indol]-2'(1'H)-one was obtained (13%) as a colorless solid: mp 81-82° C.; $^1$H NMR (300 MHz, CDCl$_3$) δ9.18-9.14 (m, 1H), 7.58-7.44 (m, 2H), 7.28-7.15 (m, 2H), 7.12-7.02 (m, 2H), 6.47 (s, 1H), 6.43 (s, 1H), 5.39-5.22 (m, 2H), 4.84 (ABq, 2H), 4.60-4.49 (m, 2H), 3.10-2.91 (m, 2H); $^{13}$C NMR (75 MHz, CDCl$_3$) δ178.1, 161.9, 161.4, 158.4, 151.1, 141.6, 132.4, 129.0, 127.3, 126.0, 123.9, 123.8, 120.0, 119.9, 118.8, 109.6, 93.3, 80.6, 72.4, 57.8, 44.6, 29.0; MS (ES+) m/z 372.3 (M+1).

EXAMPLE 9.10

Synthesis of 1'-[(2-oxo-1,3-oxazolidin-5-yl)methyl]-5,6-dihydrospiro[benzo[1,2-b:5,4-b']difuran-3,3'-indol]-2'(1'H)-one

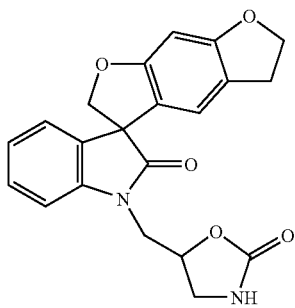

Following the procedure as described in EXAMPLE 9 and making non-critical variations using 5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, and 5-chloromethyl-2-oxazolidinone to replace 2-(bromomethyl)-5-(trifluoromethyl)furan, [(2-oxo-1,3-oxazolidin-5-yl)methyl]-5,6-dihydrospiro[benzo[1,2-b:5,4-b']difuran-3,3'-indol]-2'(1'H)-one was obtained (32%) as a colorless solid: mp 197-198° C.; $^1$H NMR (300 MHz, DMSO-d$_6$) δ7.58 (s, 1H), 7.37-7.29 (m, 1H), 7.26-7.20 (m, 1H), 7.19-7.13 (m, 1H), 7.09-7.01 (m, 1H), 6.49-6.39 (m, 2H), 4.98-4.75 (m, 2H), 4.74-4.66 (m, 1H), 4.54-4.45 (m, 2H), 4.15-3.84 (m, 2H), 3.67-3.56 (m, 1H), 3.31-3.23 (m, 1H), 3.02-2.90 (m, 2H); $^{13}$C NMR (75 MHz, DMSO-d$_6$) δ177.9, 177.6, 161.2, 160.6, 160.5, 158.3, 142.6 (2C), 132.2, 132.0, 128.7, 128.6, 123.5, 123.4, 123.0, 120.6, 120.5, 119.9, 119.0, 118.9, 109.7, 109.6, 92.5, 92.4, 79.8, 73.3, 73.2, 72.1, 56.8, 43.1, 42.7, 42.6, 28.4; MS (ES+) m/z 379.3 (M+1).

EXAMPLE 9.11

Synthesis of 1'-[3-(benzyloxy)benzyl]-5,6-dihydrospiro[benzo[1,2-b:5,4-b']difuran-3,3'-indol]-2'(1'H)-one

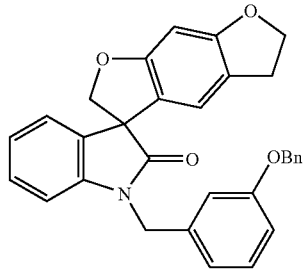

Following the procedure as described in EXAMPLE 9 and making non-critical variations using 5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, and 1-(benzyloxy)-3-(bromomethyl)benzene to replace 2-(bromomethyl)-5-(trifluoromethyl)furan, 1'-[3-(benzyloxy)benzyl]-5,6-dihydrospiro[benzo[1,2-b:5,4-b']difuran-3,3'-indol]-2'(1'H)-one was obtained (82%) as a colorless solid: mp 66-68° C.; $^1$H NMR (300 MHz, CDCl$_3$) δ7.43-7.14 (m, 8H), 7.06-6.99 (m, 1H), 6.97-6.87 (m, 3H), 6.81-6.75 (m, 1H), 6.48 (s, 1H), 6.43 (s, 1H), 5.10-5.00 (m, 3H), 4.85-4.75 (m, 1H), 4.84 (ABq, 2H), 4.56-4.47 (m, 2H), 2.98-2.88 (m, 2H); $^{13}$C NMR (75 MHz, CDCl$_3$) δ 177.9, 161.8, 161.3, 159.2, 142.1, 137.4, 136.6, 132.7, 129.9, 128.7, 128.6, 128.0, 127.5, 123.8, 123.4, 120.2, 119.9 (2C), 118.8, 114.0, 113.9, 109.3, 93.2, 80.5, 72.3, 70.0, 57.7, 44.0, 29.0; MS (ES+) m/z 476.1 (M+1).

EXAMPLE 9.12

Synthesis of 1'-[(1-methyl-1H-benzimidazol-2-yl)methyl]-5,6-dihydrospiro[benzo[1,2-b:5,4-b']difuran-3,3'-indol]-2'(1'H)-one

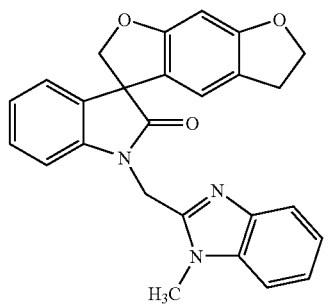

Following the procedure as described in EXAMPLE 9 and making non-critical variations using 5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, and 2-(bromomethyl)-1-methyl-1H-benzo[d]imidazole to replace 2-(bromomethyl)-5-(trifluoromethyl)furan, 1'-[(1-methyl-1H-benzimidazol-2-yl)methyl]-5,6-dihydrospiro[benzo[1,2-b:5,4-b']difuran-3,3'-indol]-2'(1'H)-one was obtained (70%) as a colorless solid: mp 244-246° C.; $^1$H NMR (300 MHz, CDCl$_3$) δ7.95-7.86 (m, 1H), 7.70 (d, J=7.6 Hz, 1H), 7.49-7.40 (m, 2H), 7.32 (dd, J=7.6, 7.6 Hz, 1H), 7.16

(d, J=7.6 Hz, 1H), 7.07 (dd, J=7.6, 7.6 Hz, 1H), 6.52-6.36 (m, 2H), 5.51 (ABq, 2H), 4.81 (ABq, 2H), 4.55 (t, J=8.6 Hz, 2H), 3.92 (s, 3H), 2.99 (t, J=8.6 Hz, 2H); MS (ES+) m/z 424.1 (M+1).

EXAMPLE 9.13

Synthesis of 1'-(2H-benzotriazol-2-ylmethyl)-5,6-dihydrospiro[benzo[1,2-b:5,4-b']difuran-3,3'-indol]-2'(1'H)-one

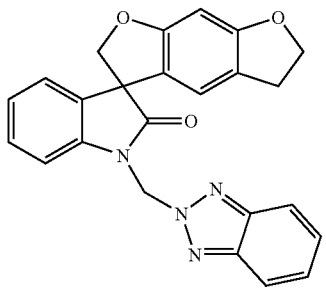

Following the procedure as described in EXAMPLE 9 and making non-critical variations using 5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, and 2-(chloromethyl)-2H-benzo[d][1,2,3]triazo to replace 2-(bromomethyl)-5-(trifluoromethyl)furan, 1'-(2H-benzotriazol-2-ylmethyl)-5,6-dihydrospiro[benzo[1,2-b:5,4-b']difuran-3,3'-indol]-2'(1'H)-one was obtained (67%) as a colorless solid: mp 102-105° C.; $^1$H NMR (300 MHz, CDCl$_3$) δ8.14-7.96 (m, 1H), 7.89-7.80 (m, 1H), 7.53-7.44 (m, 2H), 7.42-7.34 (m, 1H), 7.33-7.26 (m, 1H), 7.17-7.10 (m, 1H), 7.10-7.02 (m, 1H), 6.58 (ABq, 2H), 6.41 (s, 1H), 6.19 (s, 1H), 4.77 (ABq, 2H), 4.51 (t, J=8.6 Hz, 2H), 2.89 (t, J=8.6 Hz, 2H); MS (ES+) m/z 411.1 (M+1).

EXAMPLE 9.14

Synthesis of methyl 2-[(2'-oxo-5,6-dihydrospiro[benzo[1,2-b:5,4-b']difuran-3,3'-indol]-1'(2'H)-yl)methyl]benzoate

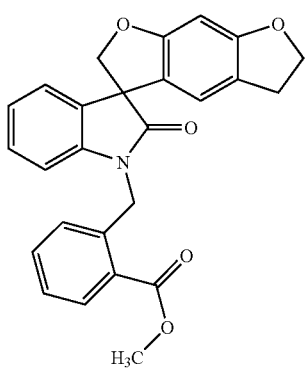

Following the procedure as described in EXAMPLE 9 and making non-critical variations using 5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, and methyl 2-(bromomethyl)benzoate to replace 2-(bromomethyl)-5-(trifluoromethyl)furan, methyl 2-[(2'-oxo-5,6-dihydrospiro[benzo[1,2-b:5,4-b']difuran-3,3'-indol]-1'(2'H)-yl)methyl]benzoate was obtained (79%) as a colorless solid: $^1$H NMR (300 MHz, CDCl$_3$) δ8.04 (dd, J=7.7, 1.3 Hz, 1H), 7.43 (ddd, J=7.5, 7.5, 1.5 Hz, 1H), 7.38-7.29 (m, 1H), 7.22-7.11 (m, 3H), 7.07-6.99 (m, 1H), 6.70 (d, J=7.7 Hz, 1H), 6.55 (s, 1H), 6.43 (s, 1H), 5.52-5.34 (m, 2H), 5.00 (d, J=8.9 Hz, 1H), 4.74 (d, J=8.9 Hz, 1H), 4.54 (t, J=8.7 Hz, 2H), 3.95 (s, 3H), 3.08-2.94 (m, 2H); $^{13}$C NMR (75 MHz, CDCl$_3$) δ178.2, 167.5, 161.8, 161.4, 142.3, 137.5, 132.8, 132.7, 131.4, 129.1, 128.8, 128.6, 128.0, 127.4, 126.5, 123.9, 123.5, 120.2, 120.0, 119.0, 109.4, 93.3, 80.8, 72.4, 65.9, 57.9, 52.3, 42.4, 29.1, 15.3; MS (ES+) m/z 427.9 (M+1).

EXAMPLE 9.15

Synthesis of methyl 3-[(2'-oxo-5,6-dihydrospiro[benzo[1,2-b:5,4-b']difuran-3,3'-indol]-1'(2'H)-yl)methyl]benzoate

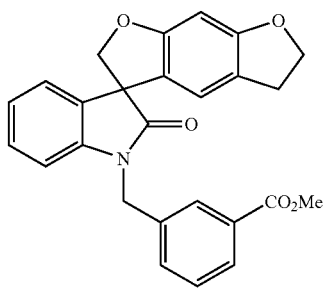

Following the procedure as described in EXAMPLE 9 and making non-critical variations using 5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, and methyl 3-(bromomethyl)benzoate to replace 2-(bromomethyl)-5-(trifluoromethyl)furan, methyl 3-[(2'-oxo-5,6-dihydrospiro[benzo[1,2-b:5,4-b']difuran-3,3'-indol]-1'(2'H)-yl)methyl]benzoate was obtained (93%) as a colorless solid: mp 97-98° C. (hexanes/ethyl acetate); $^1$H NMR (300 MHz, CDCl$_3$) δ8.04 (s, 1H), 8.02-7.96 (m, 1H), 7.58-7.52 (m, 1H), 7.49-7.42 (m, 1H), 7.25-7.17 (m, 2H), 7.09-7.00 (m, 1H), 6.78 (d, J=7.5 Hz, 1H), 6.56 (s, 1H), 6.45 (s, 1H), 5.16 (d, J=15.7 Hz, 1H), 5.02 (d, J=9.0 Hz, 1H), 4.89 (d, J=15.7 Hz, 1H), 4.74 (d, J=9.0 Hz, 1H), 4.60-4.52 (m, 2H), 3.93 (s, 3H), 3.13-2.96 (m, 2H); $^{13}$C NMR (75 MHz, CDCl$_3$) δ178.1, 166.7, 162.0, 161.4, 141.9, 136.3, 132.8, 131.9, 130.9, 129.3, 129.2, 128.9, 128.4, 124.1, 123.7, 120.2, 120.1, 119.1, 109.2, 93.4, 80.7, 72.5, 57.9, 52.3, 43.9, 29.2; MS (ES+) m/z 428.1 (M+1).

EXAMPLE 9.16

Synthesis of methyl 4-[(2'-oxo-5,6-dihydrospiro[benzo[1,2-b:5,4-b']difuran-3,3'-indol]-1'(2'H)-yl)methyl]benzoate

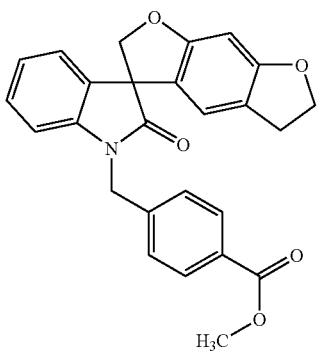

Following the procedure as described in EXAMPLE 9 and making non-critical variations using 5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, and methyl 4-(bromomethyl)benzoate to replace 2-(bromomethyl)-5-(trifluoromethyl)furan, methyl 4-[(2'-oxo-5,6-dihydrospiro[benzo[1,2-b:5,4-b']difuran-3,3'-indol]-1'(2'H)-yl)methyl]benzoate was obtained (95%) as a colorless solid: mp 136-140° C.; $^1$H NMR (300 MHz, CDCl$_3$) δ8.01 (d, J=8.1 Hz, 2H), 7.39 (d, J=8.1 Hz, 2H), 7.17 (d, J=7.4 Hz, 2H), 7.02 (dd, J=7.4, 7.4 Hz, 1H), 6.72 (d, J=7.6 Hz, 1H), 6.48 (s, 1H), 6.44 (s, 1H), 4.99 (ABq, 2H), 4.84 (ABq, 2H), 4.54 (t, J=8.6 Hz, 2H), 3.89 (s, 3H), 3.06-2.92 (m, 2H); MS (ES+) m/z 428.1 (M+1).

EXAMPLE 9.17

Synthesis of 1'-[3-(benzyloxy)propyl]-5,6-dihydrospiro[benzo[1,2-b:5,4-b']difuran-3,3'-indol]-2'(1'H)-one

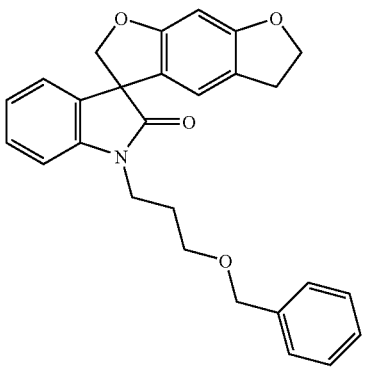

Following the procedure as described in EXAMPLE 9 and making non-critical variations using 5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, and benzyl 3-bromopropyl ether to replace 2-(bromomethyl)-5-(trifluoromethyl)furan, 1'-[3-(benzyloxy)propyl]-5,6-dihydrospiro[benzo[1,2-b:5,4-b']difuran-3,3'-indol]-2'(1'H)-one was obtained (89%) as a colorless solid: mp 112-113° C. (ethyl acetate/hexanes); $^1$H NMR (300 MHz, CDCl$_3$) δ 7.35-7.27 (m, 6H), 7.14 (d, J=6.0 Hz, 1H), 7.06-6.95 (m, 2H), 6.41-6.39 (m, 2H), 4.63 (AB, 2H), 4.54-4.48 (m, 4H), 3.94-3.80 (m, 2H), 3.54 (t, J=6.0 Hz, 2H), 2.95 (t, J=9.0 Hz, 2H), 2.07-1.99 (m, 2H); MS (ES+) m/z 428.1 (M+1).

EXAMPLE 9.18

Synthesis of 5'-fluoro-1'-[(2R)-tetrahydrofuran-2-ylmethyl]-5,6-dihydrospiro[benzo[1,2-b:5,4-b']difuran-3,3'-indol]-2'(1'H)-one

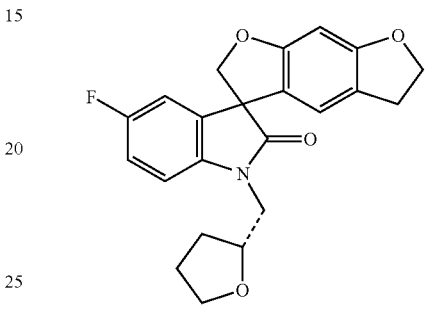

Following the procedure as described in EXAMPLE 9 and making non-critical variations using 5'-fluoro-5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, and (R)-(tetrahydrofuran-2-yl)methyl 4-methylbenzenesulfonate to replace 2-(bromomethyl)-5-(trifluoromethyl)furan, 5'-fluoro-1'-[(2R)-tetrahydrofuran-2-ylmethyl]-5,6-dihydrospiro[benzo[1,2-b:5,4-b']difuran-3,3'-indol]-2'(1'H)-one was obtained (60%) as a colorless solid: mp 167-169° C. (diethyl ether); $^1$H NMR (300 MHz, CDCl$_3$) δ 7.06-6.85 (m, 3H), 6.47 (s, 1H), 6.39 (s, 1H), 4.76 (ABq, 2H), 4.52 (t, J=9.0 Hz, 2H), 4.28-4.20 (m, 1H), 3.89-3.69 (m, 4H), 2.98-2.95 (m, 2H), 2.10-1.63 (m, 4H); $^{13}$C NMR (75 MHz, CDCl$_3$) δ 178.0, 161.9, 161.2, 157.9, 138.7, 134.3, 120.0, 118.8, 115.1, 114.8, 111.7, 111.4, 110.5, 93.3, 80.5, 72.4, 68.2, 58.0, 44.8, 29.0, 28.9, 25.7; MS (ES+) m/z 382.1 (M+1).

EXAMPLE 9.19

Synthesis of 6'-fluoro-1'-[(2R)-tetrahydrofuran-2-ylmethyl]-5,6-dihydrospiro[benzo[1,2-b:5,4-b']difuran-3,3'-indol]-2'(1'H)-one

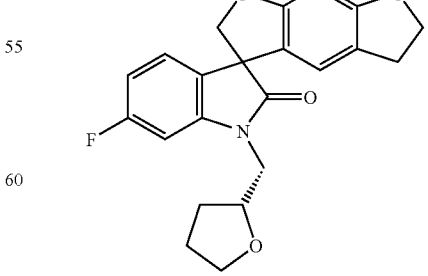

Following the procedure as described in EXAMPLE 9 and making non-critical variations using 6'-fluoro-5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, and (R)-(tetrahydrofuran-2-yl)methyl 4-methylbenzenesulfonate to replace 2-(bromomethyl)-5-(trifluoromethyl)furan, 6'-fluoro-1'-[(2R)-tetrahydrofuran-2-ylmethyl]-5,6-dihydrospiro[benzo[1,2-b:5,4-b']difuran-3,3'-indol]-2'(1'H)-one was obtained (47%) as a colorless solid: mp 137-139° C. (diethyl ether/hexanes); $^1$H NMR (300 MHz, CDCl$_3$) $\delta$ 7.08-7.03 (m, 1H), 6.88-6.83 (m, 1H), 6.73-6.66 (m, 1H), 6.46 (s, 1H), 6.38 (s, 1H), 4.74 (ABq, 2H), 4.52 (t, J=9.0 Hz, 2H), 4.25-4.20 (m, 1H), 3.96-3.60 (m, 4H), 2.98 (t, J=9.0 Hz, 2H), 2.08-1.86 (m, 3H), 1.73-1.64 (m, 1H); $^{13}$C NMR (75 MHz, CDCl$_3$) $\delta$178.0, 161.9, 161.2, 128.1, 124.7, 120.0, 118.8, 109.5, 109.2, 98.8, 98.4, 93.2, 80.6, 72.4, 68.3, 57.3, 44.8, 29.2, 28.9, 25.7; MS (ES+) m/z 382.0 (M+1).

EXAMPLE 9.20

Synthesis of 1'-[2-(2-methoxyethoxy)ethyl]-2,3-dihydrospiro[furo[2,3-g][1,4]benzodioxine-8,3'-indol]-2'(1'H)-one

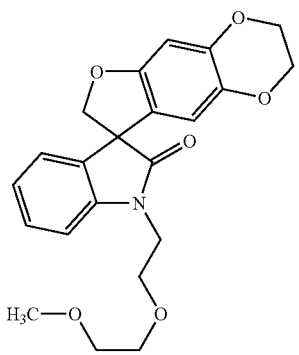

Following the procedure as described in EXAMPLE 9 and making non-critical variations using 2,3-dihydrospiro[furo[2,3-g][1,4]benzodioxine-8,3'-indol]-2'(1'H)-one to replace 3-methylspiro[furo[3,2-f][1,2]benzisoxazole-5,3'-indol]-2'(1'H)-one, and 1-bromo-2-(2-methoxyethoxy)ethane to replace 2-(bromomethyl)-5-(trifluoromethyl)furan, 1'-[2-(2-methoxyethoxy)ethyl]-2,3-dihydrospiro[furo[2,3-g][1,4]benzodioxine-8,3'-indol]-2'(1'H)-one was obtained (65%) as a colorless solid: mp 90-91° C.; $^1$H NMR (300 MHz, CDCl$_3$) $\delta$7.32-7.20 (m, 1H), 7.14-7.09 (m, 1H), 7.05-6.97 (m, 2H), 6.46 (s, 1H), 6.21 (s, 1H), 4.73 (ABq, 2H), 4.19-4.12 (m, 2H), 4.12-4.05 (m, 2H), 4.05-3.96 (m, 1H), 3.94-3.83 (m, 1H), 3.64-3.57 (m, 2H), 3.51-3.44 (m, 2H), 3.32 (s, 3H); $^{13}$C NMR (75 MHz, CDCl$_3$) $\delta$177.6, 155.2, 144.5, 142.5, 138.3, 132.3, 128.7, 123.7, 123.2, 121.2, 111.6, 109.2, 99.3, 80.0, 71.9, 70.4, 68.2, 64.5, 63.9, 59.0, 58.0, 402; MS (ES+) m/z 397.9 (M+1).

EXAMPLE 9.21

Synthesis of 2-methyl-1'-(pyridin-2-ylmethyl)spiro[furo[2,3-f][1,3]benzothiazole-7,3'-indol]-2'(1'H)-one

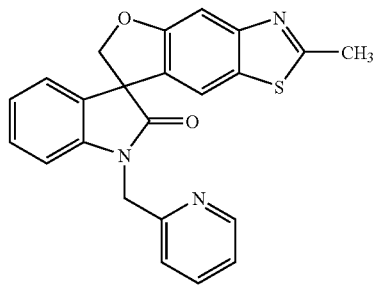

Following the procedure as described in EXAMPLE 9 and making non-critical variations using 2-methylspiro[furo[2,3-f][1,3]benzothiazole-7,3'-indol]-2'(1'H)-one to replace 3-methylspiro[furo[3,2-f][1,2]benzisoxazole-5,3'-indol]-2'(1'H)-one, and 2-(bromomethyl)pyridine hydrobromide to replace 2-(bromomethyl)-5-(trifluoromethyl)furan, 2-methyl-1'-(pyridin-2-ylmethyl)spiro[furo[2,3-f][1,3]benzothiazole-7,3'-indol]-2'(1'H)-one was obtained (38%) as a colorless solid: mp 249-250° C. (ethyl acetate); $^1$H NMR (300 MHz, DMSO-d$_6$) $\delta$8.63-8.59 (m, 1H), 7.95 (d, J=8.6 Hz, 1H), 7.85-7.70 (m, 2H), 7.38-7.31 (m, 1H), 7.27-7.1 (m, 3H), 7.02-6.95 (m, 1H), 6.85 (d, J=7.8 Hz, 1H), 5.31 (d, J=16.9 Hz, 1H), 4.96-4.84 (m, 3H), 2.67 (s, 3H); $^{13}$C NMR (75 MHz, DMSO-d$_6$) $\delta$176.4, 170.2, 160.2, 155.7, 149.3, 148.5, 142.3, 137.0, 131.9, 128.8, 128.1, 123.4, 123.1, 122.7, 120.7, 119.5, 109.3, 108.4, 81.0, 57.4, 45.6, 20.1; MS (ES+) m/z 400.0 (M+1).

EXAMPLE 9.22

Synthesis of 1'-[(5-chloro-1-methyl-1H-imidazol-2-yl)methyl]-2-methylspiro[furo[2,3-f][1,3]benzothiazole-7,3'-indol]-2'(1'H)-one

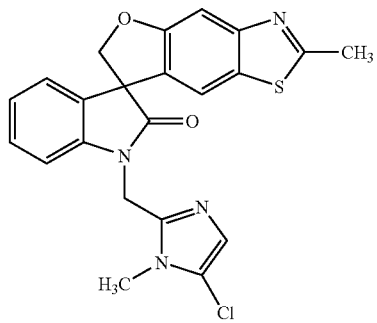

Following the procedure as described in EXAMPLE 9 and making non-critical variations using methylspiro[furo[2,3-f][1,3]benzothiazole-7,3'-indol]-2'(1'H)-one to replace 3-methylspiro[furo[3,2-f][1,2]benzisoxazole-5,3'-indol]-2'(1'H)-one, and 5-chloro-2-(chloromethyl)-1-methyl-1H-imidazole hydrochloride to replace 2-(bromomethyl)-5-(trifluoromethyl)furan, 1'-[(5-chloro-1-methyl-1H-imidazol-2-yl)methyl]-2-methylspiro[furo[2,3-f][1,3]benzothiazole-7,3'-indol]-2'(1'H)-one was obtained (68%) as a colorless solid: mp 177-178° C. (hexanes/ethyl acetate); $^1$H NMR (300 MHz, CDCl₃) δ7.63 (dd, J=8.6, 1.1 Hz, 1H), 7.47 (d, J=7.9 Hz, 1H), 7.29-7.23 (m, 1H), 7.08-6.92 (m, 4H), 5.42 (d, J=15.4 Hz, 1H), 5.08-5.00 (m, 1H), 4.85-4.74 (m, 2H), 3.67 (s, 3H), 2.51 (s, 3H); ¹³C NMR (75 MHz, CDCl₃) δ176.8, 169.6, 160.5, 149.1, 142.1, 141.8, 132.1, 129.1, 124.6, 123.7, 123.3, 122.5, 119.6, 119.3, 110.7, 108.7, 81.3, 60.5, 58.2, 38.4, 31.2, 20.2; MS (ES+) m/z 437.0 (M+1), 439.0 (M+1).

EXAMPLE 9.23

Synthesis of 4-methyl-1'-(((R)-tetrahydrofuran-2-yl)methyl)-4,7-dihydrospiro[benzofuro[5,6-b][1,4]oxazine-8,3'-indoline]-2',3(2H)-dione

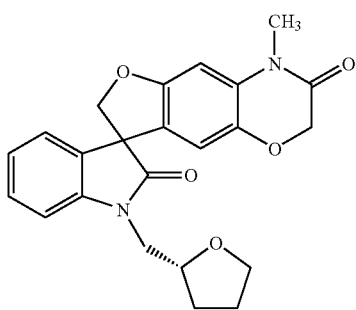

Following the procedure as described in EXAMPLE 9 and making non-critical variations using 4-methyl-2H-spiro[furo[2,3-g][1,4]benzoxazine-8,3'-indole]-2',3(1'H,4H)-dione to replace 3-methylspiro[furo[3,2-f][1,2]benzisoxazole-5,3'-indol]-2'(1'H)-one, and (R)-(tetrahydrofuran-2-yl)methyl 4-methylbenzenesulfonate to replace 2-(bromomethyl)-5-(trifluoromethyl)furan, 4-methyl-1'-(((R)-tetrahydrofuran-2-yl)methyl)-4,7-dihydrospiro[benzofuro[5,6-b][1,4]oxazine-8,3'-indoline]-2',3(2H)-dione was obtained (11%) as a colorless solid: ¹H NMR (300 MHz, (CD₃)₂CO) δ7.35-7.30 (m, 1H), 7.23-7.13 (m, 2H), 7.08-6.99 (m, 1H), 6.75 (s, 1H), 6.35 (d, J=10.1 Hz, 1H), 4.92-4.87 (m, 1H), 4.74 (d, J=9.2 Hz, 1H), 4.45-4.44 (m, 2H), 4.31-4.20 (m, 1H), 3.97-3.62 (m, 4H), 3.33 (s, 3H), 1.95-1.66 (m, 4H); ¹³C NMR (75 MHz, (CD₃)₂CO) δ178.8, 178.7, 166.1, 158.4 (2C), 145.3, 145.1, 141.5, 133.9, 133.7, 133.2, 130.6, 130.5, 125.6, 125.3 (2C), 125.1 (2C), 124.6, 124.3, 112.9, 112.7, 111.6, 111.5, 99.2, 99.1, 82.0, 81.8 (2C), 79.6, 78.2, 77.9, 75.7, 69.4, 69.3, 69.1, 59.6, 59.5, 46.0, 45.8, 30.7, 30.4, 29.8, 29.4, 27.2, 27.1; MS (ES+) m/z 406.9 (M+1).

EXAMPLE 9.24

Synthesis of 3-methyl-1'-(pyridin-2-ylmethyl)spiro[furo[3,2-f][1,2]benzisoxazole-5,3'-indol]-2'(1'H)-one

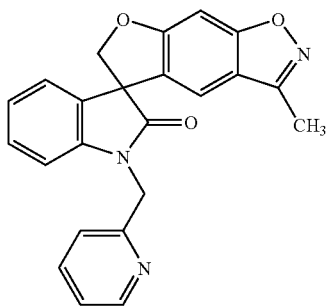

Following the procedure as described in EXAMPLE 9 and making non-critical variations using 2-(bromomethyl)pyridine to replace 2-(bromomethyl)-5-(trifluoromethyl)furan, 3-methyl-1'-(pyridin-2-ylmethyl)spiro[furo[3,2-f][1,2]benzisoxazole-5,3'-indol]-2'(1'H)-one was obtained (24%) as a colorless solid: mp 142-143° C. (ethyl acetate/hexanes); ¹H NMR (300 MHz, CDCl₃) δ8.58 (d, J=6.0 Hz, 1H), 7.75-7.69 (m, 1H), 7.75-7.69 (m, 1H), 7.52-7.46 (m, 2H), 7.23-7.11 (m, 3H), 7.01-6.96 (m, 2H), 6.85 (d, J=6.0 Hz, 1H), 5.45-4.89 (m, 4H), 2.45 (s, 3H); ¹³C NMR (75 MHz, CDCl₃) δ176.1, 164.0, 158.2, 155.3, 154.9, 149.3, 142.0, 137.3, 130.4, 129.4, 123.7, 123.6, 123.0, 122.7, 121.5, 117.9, 109.9, 108.9, 108.0, 81.4, 56.4, 46.4, 9.8; MS (ES+) m/z 383.9 (M+1).

EXAMPLE 9.25

Synthesis of 3-methyl-1'-(pyridin-3-ylmethyl)spiro[furo[3,2-f][1,2]benzisoxazole-5,3'-indol]-2'(1'H)-one

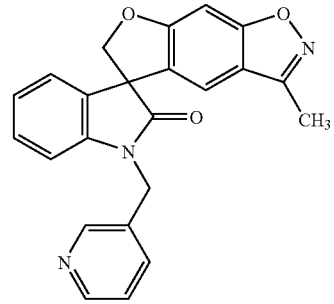

Following the procedure as described in EXAMPLE 9 and making non-critical variations using 3-(bromomethyl)pyridine to replace 2-(bromomethyl)-5-(trifluoromethyl)furan, 3-methyl-1'-(pyridin-3-ylmethyl)spiro[furo[3,2-f][1,2]benzisoxazole-5,3'-indol]-2'(1'H)-one was obtained (65%) as a colorless solid: mp 176-177° C. (ethyl acetate/hexanes); ¹H NMR (300 MHz, CDCl₃) δ 8.71 (d, J=3.0 Hz, 1H), 8.56-8.54 (m, 1H), 7.81 (d, J=6.0 Hz, 1H), 7.46 (d, J=9.0 Hz, 1H), 7.35-7.30 (m, 1H), 7.23-7.11 (m, 2H), 7.01-6.96 (m, 2H), 6.77 (d, J=9.0 Hz, 1H), 5.28-4.81 (m, 4H), 2.44 (s, 3H); ¹³C NMR (75 MHz, CDCl₃) δ 176.2, 164.0, 158.1, 155.0, 154.9, 149.4, 148.8, 141.5, 135.1, 131.0, 130.4, 129.4, 124.0, 123.9, 123.8, 123.1, 117.9, 109.4, 108.9, 108.0, 81.3, 56.3, 41.9, 9.8; MS (ES+) m/z 383.9 (M+1).

EXAMPLE 9.26

Synthesis of 3-methyl-1'-[(2R)-tetrahydrofuran-2-ylmethyl]spiro[furo[3,2-f][1,2]benzisoxazole-5,3'-indol]-2'(1'H)-one

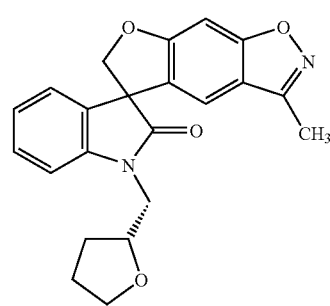

Following the procedure as described in EXAMPLE 9 and making non-critical variations using (R)-(tetrahydrofuran-2-yl)methyl 4-methylbenzenesulfonate to replace 2-(bromomethyl)-5-(trifluoromethyl)furan, 3-methyl-1'-[(2R)-tetrahydrofuran-2-ylmethyl]spiro[furo[3,2-f][1,2]benzisoxazole-5,3'-indol]-2'(1'H)-one was obtained (50%) as a colorless solid: mp 134-135° C. (ethyl acetate/hexanes); $^1$H NMR (300 MHz, CDCl$_3$) δ7.43 (d, J=9.0 Hz, 1H), 7.32-6.93 (m, 5H), 4.94 (ABq, 2H), 4.36-4.28 (m, 1H), 4.06-3.73 (m, 4H), 2.42 (s, 3H), 2.14-1.77 (m, 4H); $^{13}$C NMR (75 MHz, CDCl$_3$) δ 176.8, 176.3, 164.0, 158.2, 154.8, 143.2, 142.6, 130.4, 129.3, 123.5, 123.3, 122.9, 117.9, 110.5, 109.6, 109.1, 107.9, 81.4, 81.3, 77.8, 77.5, 68.4, 68.3, 56.3, 56.2, 44.9, 44.6, 29.4, 28.5, 26.1, 25.6, 9.8; MS (ES+) m/z 377.0 (M+1).

EXAMPLE 9.27

Synthesis of 5,6-dimethyl-1'-(tetrahydro-2H-pyran-4-ylmethyl)spiro[1-benzofuran-3,3'-indol]-2'(1'H)-one

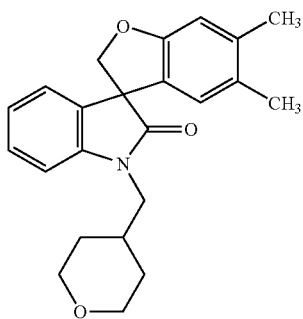

Following the procedure as described in EXAMPLE 9 and making non-critical variations using 5,6-dimethylspiro[1-benzofuran-3,3'-indol]-2'(1'H)-one to replace 3-methylspiro[furo[3,2-f][1,2]benzisoxazole-5,3'-indol]-2'(1'H)-one, and 4-bromomethyltetrahydropyrane to replace 2-(bromomethyl)-5-(trifluoromethyl)furan, 5,6-dimethyl-1'-(tetrahydro-2H-pyran-4-ylmethyl)spiro[1-benzofuran-3,3'-indol]-2'(1'H)-one was obtained (55%) as a colorless solid: mp 199-201° C. (ethyl acetate/hexanes); $^1$H NMR (300 MHz, CDCl$_3$) δ 7.32-7.27 (m, 1H), 7.14-7.12 (m, 1H), 7.05-7.00 (m, 2H), 6.91-6.89 (m, 1H), 6.75 (s, 1H), 6.41 (s, 1H), 4.71 (ABq, 2H), 4.12-3.95 (m, 2H), 3.75-3.54 (m, 2H), 3.39-3.28 (m, 2H), 2.19-2.02 (m, 7H), 1.62-1.28 (m, 4H); $^{13}$C NMR (75 MHz, CDCl$_3$) δ177.9, 159.1, 142.8, 138.5, 132.6, 129.4, 128.7, 125.8, 124.0, 123.7, 123.2, 111.4, 108.5, 79.9, 67.4, 58.0, 46.0, 33.9, 30.8, 20.3, 19.3; MS (ES+) m/z 364.3 (M+1).

EXAMPLE 9.28

Synthesis of 5,6-dimethyl-1'-(pyridin-2-ylmethyl)spiro[1-benzofuran-3,3'-indol]-2'(1'H)-one

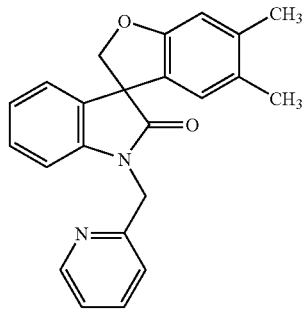

Following the procedure as described in EXAMPLE 9 and making non-critical variations using 5,6-dimethyl-1'-(tetrahydro-2H-pyran-4-ylmethyl)spiro[1-benzofuran-3,3'-indol]-2'(1'H)-one to replace 3-methylspiro[furo[3,2-f][1,2]benzisoxazole-5,3'-indol]-2'(1'H)-one, and 2-(bromomethyl)pyridine to replace 2-(bromomethyl)-5-(trifluoromethyl)furan, 5,6-dimethyl-1'-(pyridin-2-ylmethyl)spiro[1-benzofuran-3,3'-indol]-2'(1'H)-one was obtained (76%) as a colorless solid: mp 165-168° C. (ethyl acetate/hexanes); $^1$H NMR (300 MHz, DMSO-d$_6$) δ8.67 (d, J=6.0 Hz, 1H), 8.12-8.06 (m, 1H), 7.59-7.55 (m, 2H), 7.26-7.23 (m, 1H), 7.21-7.20 (m, 1H), 7.03-6.98 (m, 2H), 6.76 (s, 1H), 6.55 (s, 1H), 5.18 (s, 2H), 4.74 (ABq, 2H), 2.13 (s, 3H), 2.01 (s, 3H); $^{13}$C NMR (75 MHz, DMSO-d$_6$) δ177.5, 159.1, 154.0, 146.7, 142.6, 141.5, 138.3, 132.6, 129.1, 126.7, 124.5, 124.4, 124.1, 123.7, 123.5, 111.3, 109.7, 79.5, 57.8, 43.7, 20.2, 19.2; MS (ES+) m/z 357.2 (M+1).

EXAMPLE 9.29

Synthesis of 5-fluoro-6-methoxy-1-(tetrahydro-2H-pyran-4-ylmethyl)spiro[1-benzofuran-3,3'-indol]-2'(1'H)-one

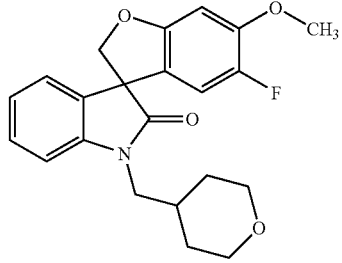

Following the procedure as described in EXAMPLE 9 and making non-critical variations using 5-fluoro-6-methoxyspiro[1-benzofuran-3,3'-indol]-2'(1'H)-one to replace 3-methylspiro[furo[3,2-f][1,2]benzisoxazole-5,3'-indol]-2'(1'H)-one, and 4-(bromomethyl)tetrahydropyran to replace 2-(bromomethyl)-5-(trifluoromethyl)furan, 5-fluoro-6-methoxy-1'-(tetrahydro-2H-pyran-4-ylmethyl)spiro[1-benzofuran-3,3'-indol]-2'(1'H)-one was obtained (82%) as a colorless solid: $^1$H NMR (300 MHz, CDCl$_3$) δ7.30 (ddd, J=7.7, 7.7, 1.3 Hz, 1H), 7.16-7.00 (m, 2H), 6.89 (d, J=7.8 Hz, 1H), 6.59 (d, J=6.8 Hz, 1H), 6.38 (d, J=10.0 Hz, 1H), 4.90 (d, J=9.0 Hz, 1H), 4.65 (d, J=9.0 Hz, 1H), 4.02-3.92 (m, 2H), 3.85 (s, 3H), 3.76-3.51 (m, 2H), 3.35 (t, J=11.5 Hz, 2H), 2.18-2.00

(m, 1H), 1.65-1.37 (m, 4H); $^{13}$C NMR (75 MHz, CDCl$_3$) δ177.4, 157.3 (d, J=1.7 Hz), 149.3, 149.1, 149.0, 146.1, 142.7, 131.9, 129.1, 123.7 (d, J=49.0 Hz), 118.9 (d, J=6.4 Hz), 110.3 (d, J=21.7 Hz), 96.4, 80.7, 67.41, 67.39, 57.9, 56.4, 46.1, 33.9, 30.8, 30.7; MS (ES+) m/z 384.2 (M+1).

EXAMPLE 9.30

Synthesis of 5-fluoro-6-methoxy-1'-{[5-(trifluoromethyl)furan-2-yl]methyl}spiro[1-benzofuran-3,3'-indol]-2'(1'H)-one

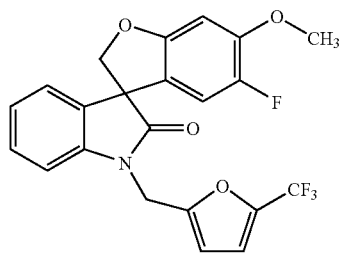

Following the procedure as described in EXAMPLE 9 and making non-critical variations using 5-fluoro-6-methoxyspiro[1-benzofuran-3,3'-indol]-2'(1'H)-one to replace 3-methylspiro[furo[3,2-f][1,2]benzisoxazole-5,3'-indol]-2'(1'H)-one, 5-fluoro-6-methoxy-1'-{[5-(trifluoromethyl)furan-2-yl]methyl}spiro[1-benzofuran-3,3'-indol]-2'(1'H)-one was obtained (67%) as a colorless solid: mp 45-47° C.; $^1$H NMR (300 MHz, CDCl$_3$) δ7.32 (dd, J=7.8, 1.2 Hz, 1H), 7.20-6.98 (m, 3H), 6.77-6.73 (m, 1H), 6.61 (d, J=6.6 Hz, 1H), 6.44-6.38 (m, 2H), 5.05 (d, J=16.2 Hz, 1H), 4.96 (d, J=9.3 Hz, 1H), 4.90 (d, J=16.2 Hz, 1H), 4.70 (d, J=9.3 Hz, 1H), 3.87 (s, 3H); $^{13}$C NMR (75 MHz, CDCl$_3$) δ 176.8, 157.1 (d, J=1.8 Hz), 151.8 (d, J=1.4 Hz), 149.2, 149.1 (d, J=12.3 Hz), 146.1, 141.5 (q, J=42.6 Hz), 141.3, 131.6, 129.2, 124.0, 123.9, 118.7 (d, J=265.4 Hz), 118.6 (d, J=7.3 Hz), 112.6 (q, J=2.8 Hz), 110.3 (d, J=21.6 Hz), 109.1 (d, J=25.1 Hz), 96.3, 80.4, 57.9 (d, J=1.3 Hz), 56.4, 36.9; MS (ES+) m/z 433.9 (M+1).

EXAMPLE 9.31

Synthesis of 5,6-difluoro-1'-(pyridin-3-ylmethyl)spiro[1-benzofuran-3,3'-indol]-2'(1'H)-one

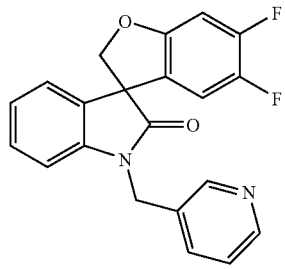

Following the procedure as described in EXAMPLE 9 and making non-critical variations using 5,6-difluorospiro[1-benzofuran-3,3'-indol]-2'(1'H)-one to replace 3-methylspiro[furo[3,2-f][1,2]benzisoxazole-5,3'-indol]-2'(1'H)-one, and 3-(bromomethyl)pyridine hydrobromide to replace 2-(bromomethyl)-5-(trifluoromethyl)furan, 5,6-difluoro-1'-(pyridin-3-ylmethyl)spiro[1-benzofuran-3,3'-indol]-2'(1'H)-one was obtained (57%) as a colorless solid: mp 175-177° C.; $^1$H NMR (300 MHz, CD$_3$OD) δ 8.98 (s, 1H), 8.84 (d, J=5.4 Hz, 1H), 8.67 (d, J=8.4 Hz, 1H), 8.12 (dd, J=8.1, 6.0 Hz, 1H), 7.37 (ddd, J=7.5, 7.5, 1.2 Hz, 1H), 7.26 (d, J=6.9 Hz, 1H), 7.18 (d, J=7.8 Hz, 1H), 7.15 (d, J=7.8 Hz, 1H), 6.93 (dd, J=10.5, 6.3 Hz, 1H), 6.76 (dd, J=9.6, 7.8 Hz, 1H), 5.27 (s, 1H), 5.26 (s, 1H), 5.00 (d, J=9.6 Hz, 1H), 4.83 (d, J=9.6 Hz, 1H); MS (ES+) m/z 365.2 (M+1).

EXAMPLE 9.32

Synthesis of 5,6-difluoro-1'-{[5-(trifluoromethyl)furan-2-yl]methyl}spiro[1-benzofuran-3,3'-indol]-2'(1'H)-one

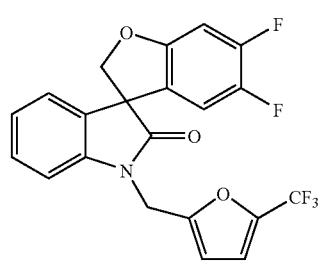

Following the procedure as described in EXAMPLE 9 and making non-critical variations using 5,6-difluorospiro[1-benzofuran-3,3'-indol]-2'(1'H)-one to replace 3-methylspiro[furo[3,2-f][1,2]benzisoxazole-5,3'-indol]-2'(1'H)-one, 5,6-difluoro-1'-{[5-(trifluoromethyl)furan-2-yl]methyl}spiro[1-benzofuran-3,3'-indol]-2'(1'H)-one was obtained (64%) as a colorless solid: $^1$H NMR (300 MHz, CDCl$_3$) δ 7.34 (dd, J=7.5 Hz, 1H), 7.21-6.99 (m, 3H), 6.82-6.74 (m, 2H), 6.53-6.39 (m, 2H), 5.07 (d, J=15.9 Hz, 1H), 4.98 (d, J=9.3 Hz, 1H), 4.90 (d, J=15.9 Hz, 1H), 4.73 (d, J=9.3 Hz, 1H); MS (ES+) m/z 422 (M+1).

EXAMPLE 9.33

Synthesis of 6-methoxy-1'-(pyridin-2-ylmethyl)-2H-spiro[benzofuran-3,3'-indolin]-2'-one

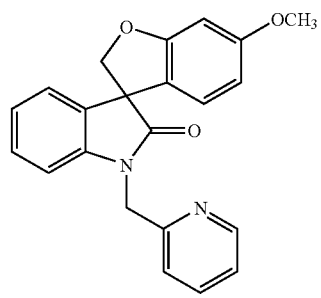

Following the procedure as described in EXAMPLE 9 and making non-critical variations using 6-methoxyspiro[1-benzofuran-3,3'-indol]-2'(1'H)-one to replace 3-methylspiro[furo[3,2-f][1,2]benzisoxazole-5,3'-indol]-2'(1'H)-one, and 2-(bromomethyl)pyridine hydrobromide to replace 2-(bromomethyl)-5-(trifluoromethyl)furan, 6-methoxy-1'-(pyridin-2-ylmethyl)-2H-spiro[benzofuran-3,3'-indolin]-2'-one was obtained (67%) as a colorless solid: mp 122-123° C.; $^1$H NMR (300 MHz, CDCl$_3$) δ 8.56 (s, 1H), 7.63 (dd, J=7.8, 7.8

Hz, 1H), 7.32-7.09 (m, 3H), 7.0 (dd, J=7.5, 7.5 Hz, 1H), 6.88 (d, J=7.8 Hz, 1H), 6.65 (d, J=7.8 Hz, 1H), 6.52 (d, J=2.1 Hz, 1H), 6.36 (dd, J=7.8, 2.1 Hz, 1H), 5.18 (d, J=15.9 Hz, 1H), 4.98 (d, J=15.9 Hz, 1H), 5.00 (d, J=8.7 Hz, 1H), 4.72 (d, J=8.7 Hz, 1H), 3.74 (s, 3H); $^{13}$C NMR (75 MHz, CDCl$_3$) δ177.6, 162.1, 161.5, 155.5, 149.4, 142.1, 137.0, 132.3, 128.7, 123.7, 123.6, 123.4, 122.7, 121.5, 120.8, 109.4, 107.5, 96.5, 80.4, 57.6, 55.5, 46.0; MS (ES+) m/z 359.4 (M+1).

EXAMPLE 9.34

Synthesis of 6-methoxy-1'-(pyridin-3-ylmethyl)spiro [1-benzofuran-3,3'-indol]-2'(1'H)-one

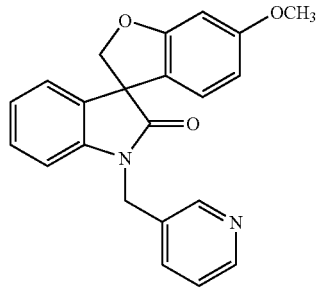

Following the procedure as described in EXAMPLE 9 and making non-critical variations using 6-methoxyspiro[1-benzofuran-3,3'-indol]-2'(1'H)-one to replace 3-methylspiro [furo[3,2-f][1,2]benzisoxazole-5,3'-indol]-2'(1'H)-one, and 3-(bromomethyl)pyridine hydrobromide to replace 2-(bromomethyl)-5-(trifluoromethyl)furan, 6-methoxy-1'-(pyridin-3-ylmethyl)spiro[1-benzofuran-3,3'-indol]-2'(1'H)-one was obtained (63%) as a colorless solid: mp 164-165° C.; $^1$H NMR (300 MHz, CDCl$_3$) δ 8.56 (s, 1H), 8.55 (d, J=3.9 Hz, 1H), 7.67 (d, J=7.8 Hz, 1H), 7.33-7.13 (m, 3H), 7.03 (dd, J=7.5, 7.5 Hz, 1H), 6.80 (d, J=7.8 Hz, 1H), 6.61-6.51 (m, 2H), 6.37 (dd, J=8.4, 2.1 Hz, 1H), 5.08 (d, J=15.6 Hz, 1H), 4.98 (d, J=9.0 Hz, 1H), 4.86 (d, J=15.6 Hz, 1H), 4.72 (d, J=9.0 Hz, 1H), 3.76 (s, 3H); $^{13}$C NMR (75 MHz, CDCl$_3$) δ177.7, 162.1, 161.6, 149.3, 148.8, 141.5, 135.2, 132.4, 131.5, 128.8, 124.0, 123.8, 123.7, 123.4, 120.5, 108.8, 107.5, 96.6, 80.4, 57.5, 55.5, 41.6; MS (ES+) m/z 359.4 (M+1).

EXAMPLE 9.35

Synthesis of 6-methoxy-1'-(tetrahydro-2H-pyran-4-ylmethyl)spiro[1-benzofuran-3,3'-indol]-2'(1'H)-one

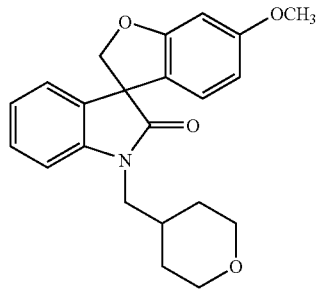

Following the procedure as described in EXAMPLE 9 and making non-critical variations using 6-methoxyspiro[1-benzofuran-3,3'-indol]-2'(1'H)-one to replace 3-methylspiro [furo[3,2-f][1,2]benzisoxazole-5,3'-indol]-2'(1'H)-one, and 4-(bromomethyl)tetrahydro-2H-pyran to replace 2-(bromomethyl)-5-(trifluoromethyl)furan, 6-methoxy-1'-(tetrahydro-2H-pyran-4-ylmethyl)spiro[1-benzofuran-3,3'-indol]-2'(1'H)-one was obtained (84%) as a colorless foam; $^1$H NMR (300 MHz, CDCl$_3$) δ 7.31 (dd, J=7.5, 1.2 Hz, 1H), 7.15 (dd, J=7.5, 1.2 Hz, 1H), 7.04 (dd, J=7.5 Hz, 1H), 6.91 (d, J=7.8 Hz, 1H), 6.57 (d, J=8.4 Hz, 1H), 6.53 (d, J=2.4 Hz, 1H), 6.36 (dd, J=8.4, 2.4 Hz, 1H), 4.93 (d, J=9.0 Hz, 1H), 4.68 (d, J=9.0 Hz, 1H), 4.03-3.94 (m, 2H), 3.77 (s, 3H), 3.80-3.30 (m, 4H), 2.21-2.05 (m, 1H), 1.74-1.38 (m, 4H); $^{13}$C NMR (75 MHz, CDCl$_3$) δ 177.8, 162.1, 161.5, 142.7, 132.6, 128.7, 123.9, 123.3, 123.2, 120.8, 108.5, 107.5, 96.6, 80.6, 67.4, 67.3, 57.5, 55.5, 46.0, 33.9, 30.8, 30.7; MS (ES+) m/z 366.4 (M+1).

EXAMPLE 9.36

Synthesis of 6-methoxy-1'-(tetrahydro-2H-pyran-2-ylmethyl)spiro[1-benzofuran-3,3'-indol]-2'(1'H)-one

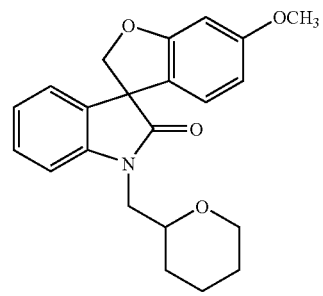

Following the procedure as described in EXAMPLE 9 and making non-critical variations using 6-methoxyspiro[1-benzofuran-3,3'-indol]-2'(1'H)-one to replace 3-methylspiro [furo[3,2-f][1,2]benzisoxazole-5,3'-indol]-2'(1'H)-one, and 2-(bromomethyl)tetrahydro-2H-pyran to replace 2-(bromomethyl)-5-(trifluoromethyl)furan, 6-methoxy-1'-(tetrahydro-2H-pyran-2-ylmethyl)spiro[1-benzofuran-3,3'-indol]-2'(1'H)-one was obtained (54%) as a colorless foam; $^1$H NMR (300 MHz, CDCl$_3$) δ 7.28 (dd, J=7.5, 7.5 Hz, 1H), 7.20-6.98 (m, 3H), 6.66-6.49 (m, 2H), 6.41-6.33 (m, 1H), 4.99-4.91 (m, 1H), 4.74-4.66 (m, 1H), 4.02-3.31 (m, 8H), 1.92-1.19 (m, 6H); MS (ES+) m/z 366.4 (M+1).

EXAMPLE 9.37

Synthesis of 1'-[4-(benzyloxy)benzyl]-2,3-dihydrospiro[furo[2,3-g][1,4]benzodioxine-8,3'-indol]-2'(1'H)-one

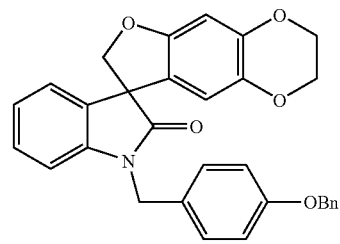

To a solution of 2,3-dihydrospiro[furo[2,3-g][1,4]benzodioxine-8,3'-indol]-2'(1'H)-one (2.0 g, 6.8 mmol) in dry N,N- dimethylformamide (45 mL) was added sodium hydride (60% in mineral oil, 0.35 g, 8.8 mmol) at ambient temperature. The mixture was stirred at ambient temperature for 1 h and 4-benzyloxybenzyl chloride (2.2 g, 9.4 mmol) was added in one portion, followed by potassium iodide (0.06 g, 0.34 mmol). The mixture was stirred at ambient temperature for 16 h and diluted with water (200 mL) and ethyl acetate (200 mL). The layers were separated and the aqueous layer was extracted with ethyl acetate (2×100 mL). The combined organic layers were washed with brine (150 mL), dried over anhydrous magnesium sulfate, filtered and concentrated in vacuo. The residue was purified by column chromatography and eluted with a 25% to 35% gradient of ethyl acetate in hexanes to afford 1'-[4-(benzyloxy)benzyl]-2,3-dihydrospiro[furo[2,3-g][1,4]benzodioxine-8,3'-indol]-2'(1'H)-one (2.49 g, 75%) as a colorless solid: mp 87-89° C.; $^1$H NMR (300 MHz, CDCl$_3$) δ 7.45-7.24 (m, 7H), 7.24-7.12 (m, 2H), 7.05-6.92 (m, 3H), 6.84-6.79 (m, 1H), 6.51 (s, 1H), 6.22 (s, 1H), 5.06-4.90 (m, 4H), 4.82-4.62 (m, 2H), 4.24-4.08 (m, 4H); $^{13}$C NMR (75 MHz, CDCl$_3$) δ 177.4, 158.4, 155.2, 144.6, 142.1, 138.3, 136.8, 132.3, 128.7 (2C), 128.6, 128.0 (2C), 127.5, 123.8, 123.3, 121.0, 115.2, 111.5, 109.3, 99.4, 80.2, 70.0, 64.5, 63.9, 58.0, 43.6; MS (ES+) m/z 492.0 (M+1).

EXAMPLE 9.38

Synthesis of 1'-[4-(benzyloxy)benzyl]-5,6-dihydrospiro[benzo[1,2-b:5,4-b']difuran-3,3'-indol]-2'(1'H)-one

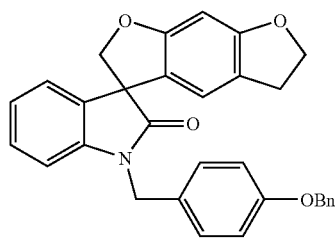

Following the procedure as described in EXAMPLE 9.37 and making non-critical variations using 5,6-dihydro-2H-spiro[benzofuro[6,5-b]furan-3,3'-indolin]-2'-one to replace 2,3-dihydrospiro[furo[2,3-g][1,4]benzodioxine-8,3'-indol]-2'(1'H)-one, 1'-[4-(benzyloxy)benzyl]-5,6-dihydrospiro[benzo[1,2-b:5,4-b']difuran-3,3'-indol]-2'(1'H)-one was obtained (77%) as a colorless solid: mp 169-170° C.; $^1$H NMR (300 MHz, CDCl$_3$) δ 7.45-7.13 (m, 9H), 7.05-6.91 (m, 3H), 6.86-6.79 (m, 1H), 6.46 (s, 1H), 6.43 (s, 1H), 5.06-4.94 (m, 4H), 4.83-4.75 (m, 1H), 4.73-4.66 (m, 1H), 4.59-4.50 (m, 2H), 3.09-2.89 (m, 2H); $^{13}$C NMR (75 MHz, CDCl$_3$) δ 177.9, 161.8, 161.3, 158.4, 142.1, 136.8, 132.8, 128.8, 128.6 (2C), 128.2, 128.0, 127.4, 123.8, 123.3, 120.3, 119.9, 118.9, 115.1, 109.2, 93.2, 80.6, 72.4, 70.0, 57.7, 43.6, 29.0; MS (ES+) m/z 476.0 (M+1).

EXAMPLE 9.39

Synthesis of (8S)-1'-[4-(Benzyloxy)Benzyl]-2,3-Dihydrospiro[Furo[2,3-g][1,4]Benzodioxine-8,3'-Indol]-2'(1'H)-One

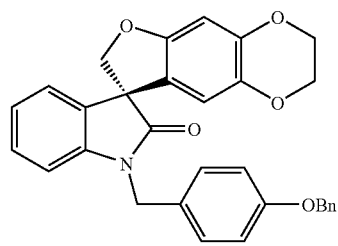

Following the procedure described in EXAMPLE 9 and making non-critical variations using (8S)-2,3-dihydrospiro[furo[2,3-g][1,4]benzodioxine-8,3'-indol]-2'(1'H)-one to replace 3-methylspiro[furo[3,2-f][1,2]benzisoxazole-5,3'-indol]-2'(1'H)-one, and 4-benzyloxybenzyl chloride to replace 2-(bromomethyl)-5-(trifluoromethyl)furan, (8S)-1'-[4-(benzyloxy)benzyl]-2,3-dihydrospiro[furo[2,3-g][1,4]benzodioxine-8,3'-indol]-2'(1'H)-one was obtained (95%) as a colorless solid: mp 151-153° C.; $^1$H NMR (300 MHz, DMSO-d$_6$) δ7.45-7.23 (m, 8H), 7.18-7.14 (m, 1H), 7.05-6.97 (m, 4H), 6.53 (s, 1H), 6.06 (s, 1H), 5.07 (s, 2H), 4.86 (ABq, J=27.9, 15.6 Hz, 2H), 4.73 (ABq, J=39.9, 9.3 Hz, 2H), 4.22-4.07 (m, 4H); $^{13}$C NMR (75 MHz, DMSO-d$_6$) δ 176.6, 157.7, 154.6, 144.1, 142.1, 137.8, 136.9, 131.7, 128.7, 128.6, 128.4, 128.3, 127.8, 127.6, 123.5, 122.9, 121.2, 114.9, 110.8, 109.4, 98.8, 79.4, 69.1, 64.1, 63.5, 57.2, 42.4; MS (ES+) m/z 491.8 (M+1).

EXAMPLE 9.40

Synthesis of tert-butyl {5-[(2'-oxo-2,3-dihydrospiro[furo[2,3-g][1,4]benzodioxine-8,3'-indol]-1'(2'H)-yl)methyl]pyridin-2-yl}carbamate

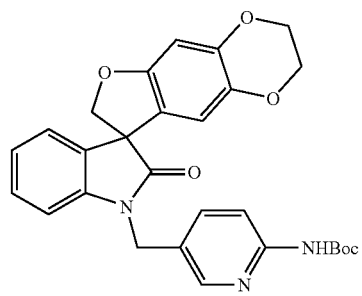

Following the procedure as described in EXAMPLE 9 and making non-critical variations using 2,3-dihydrospiro[furo[2,3-g][1,4]benzodioxine-8,3'-indol]-2'(1'H)-one to replace 3-methylspiro[furo[3,2-f][1,2]benzisoxazole-5,3'-indol]-2'(1'H)-one, and tert-butyl [5-(bromomethyl)pyridin-2-yl]carbamate to replace 2-(bromomethyl)-5-(trifluoromethyl)furan, tert-butyl {5-[(2'-oxo-2,3-dihydrospiro[furo[2,3-g][1,4]benzodioxine-8,3'-indol]-1'(2'H)-yl)methyl]pyridin-2-yl}carbamate was obtained (74%) as a colorless solid: mp 238-239° C.; $^1$H NMR (300 MHz, DMSO-d$_6$) δ9.81 (s, 1H), 8.30-8.27 (m, 1H), 7.79-7.73 (m, 1H), 7.73-7.66 (m, 1H), 7.31-7.24 (m, 1H), 7.20-7.14 (m, 1H), 7.12-6.99 (m, 2H), 6.52 (s, 1H), 6.06 (s, 1H), 4.89 (ABq, J=22.9, 15.5 Hz, 2H), 4.74 (ABq, J=44.4, 9.3 Hz, 2H), 4.23-4.05 (m, 4H), 1.45 (s, 9H); $^{13}$C NMR (75 MHz, DMSO-d$_6$) δ 176.7, 154.6, 152.6, 151.8, 146.9, 144.1, 141.8, 137.8, 137.2, 131.6, 128.7, 126.2, 123.6, 123.1, 121.1, 112.2, 110.8, 109.3, 98.8, 79.5, 79.3, 64.1, 63.5, 57.2, 27.9; MS (ES+) m/z 502.1 (M+1).

EXAMPLE 9.41

Synthesis of 3-methyl-1'-[2-(trifluoromethyl)benzyl]spiro[furo[3,2-f][1,2]benzisoxazole-5,3'-indol]-2'(1'H)-one

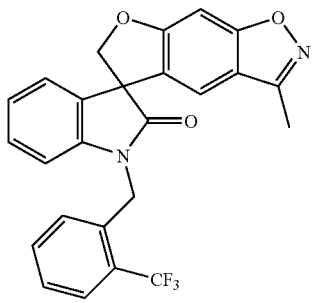

Following the procedure as described in EXAMPLE 9 and making non-critical variations using 2-(trifluoromethyl)benzyl bromide to replace 2-(bromomethyl)-5-(trifluoromethyl)furan, 3-methyl-1'-[2-(trifluoromethyl)benzyl]spiro[furo[3,2-f][1,2]benzisoxazole-5,3'-indol]-2'(1'H)-one was obtained (60%): mp 192-194° C. (ethyl acetate/hexanes); $^1$H NMR (300 MHz, CDCl$_3$) δ 7.73-7.70 (m, 1H), 7.66-7.57 (m, 2H), 7.50-7.48 (m, 1H), 7.41-7.36 (m, 1H), 7.22-7.14 (m, 2H), 7.05-6.98 (m, 2H), 6.68-6.64 (m, 1H), 5.54-4.90 (m, 4H), 2.47 (s, 3H); $^{13}$C NMR (75 MHz, CDCl$_3$) δ 176.5, 164.1, 158.1, 155.0, 141.8, 133.3, 132.8, 130.4, 129.5, 127.7, 127.5, 127.4, 127.3, 126.3, 126.1, 123.8, 123.1, 117.9, 109.6, 108.9, 108.0, 81.5, 56.4, 40.9, 9.8; MS (ES+) m/z 450.8 (M+1).

EXAMPLE 9.42

Synthesis of 3-methyl-1'-{[3-(trifluoromethyl)pyridin-2-yl]methyl}spiro[furo[3,2-f][1,2]benzisoxazole-5,3'-indol]-2'(1'H)-one

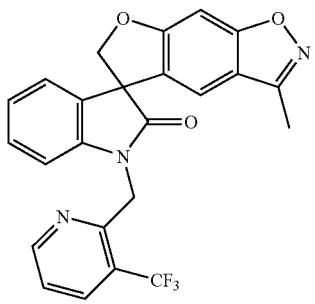

Following the procedure as described in EXAMPLE 9 and making non-critical variations using 2-(chloromethyl)-3-(trifluoromethyl)pyridine to replace 2-(bromomethyl)-5-(trifluoromethyl)furan, 3-methyl-1'-{[3-(trifluoromethyl)pyridin-2-yl]methyl}spiro[furo[3,2-f][1,2]benzisoxazole-5,3'-indol]-2'(1'H)-one was obtained (87%): mp 221-222° C. (ethyl acetate); $^1$H NMR (300 MHz, DMSO-d$_6$) δ 8.66-8.64 (m, 1H), 8.21-8.18 (m, 1H), 7.75-7.72 (m, 1H), 7.54-7.49 (m, 1H), 7.29-7.20 (m, 2H), 7.10-7.07 (m, 1H), 7.02-6.97 (m, 2H), 5.27 (s, 2H), 4.96 (ABq, 2H), 2.41 (s, 3H); $^{13}$C NMR (75 MHz, DMSO-d$_6$) δ 176.7, 164.4, 158.0, 155.7, 155.6, 153.1, 152.7, 143.7, 135.4, 135.3, 130.0, 129.7, 126.1, 124.5, 124.3, 123.5, 123.3, 123.1, 122.5, 117.9, 109.9, 108.9, 108.4, 81.7, 56.0, 42.8, 9.8; MS (ES+) m/z 451.8 (M+1).

EXAMPLE 9.43

Synthesis of 1'-[3-(benzyloxy)propyl]-2,3-dihydrospiro[furo[2,3-g][1,4]-benzodioxine-8,3'-indol]-2'(1'H)-one

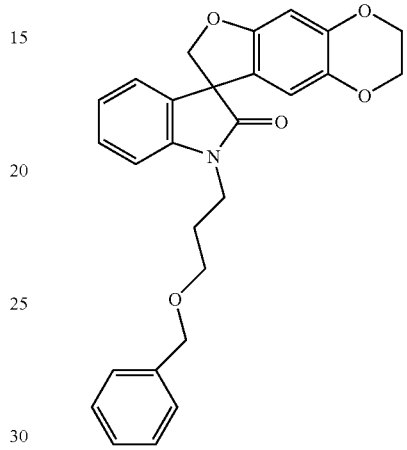

Following the procedure as described in EXAMPLE 9 and making non-critical variations using benzyl 3-bromopropyl ether to replace 2-(bromomethyl)-5-(trifluoromethyl)furan, and 2,3-dihydrospiro[furo[2,3-g][1,4]benzodioxine-8,3'-indol]-2'(1'H)-one to replace 3-methylspiro[furo[3,2-f][1,2]benzisoxazole-5,3'-indol]-2'(1'H)-one, 1'-[3-(benzyloxy)propyl]-2,3-dihydrospiro[furo[2,3-g][1,4]-benzodioxine-8,3'-indol]-2'(1'H)-one was obtained (94%): mp 37-38° C. (ethyl acetate/hexanes); $^1$H NMR (300 MHz, CDCl$_3$) δ 7.33-7.23 (m, 6H), 7.14-7.12 (m, 1H), 7.02-6.94 (m, 2H), 6.47 (d, J=0.9 Hz, 1H), 6.18 (d, J=0.9 Hz, 1H), 4.70 (ABq, 2H), 4.47 (s, 1H), 4.18-4.08 (m, 4H), 3.96-3.78 (m, 2H), 3.53 (t, J=6.3 Hz, 2H), 2.01 (d, J=6.6 Hz, 2H); MS (ES+) m/z 443.9 (M+1).

EXAMPLE 9.44

Synthesis of ethyl (2'-oxo-2,3-dihydrospiro[furo[2,3-g][1,4]benzodioxine-8,3'-indol]-1'(2'H)-yl)acetate

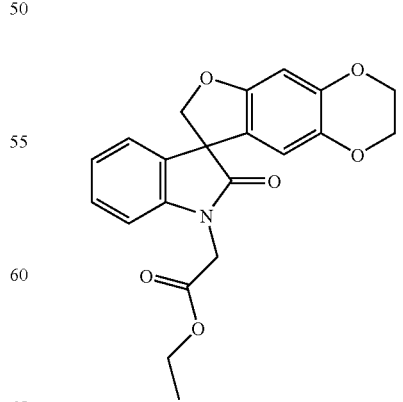

Following the procedure as described in EXAMPLE 9 and making non-critical variations using ethyl bromoacetate to replace 2-(bromomethyl)-5-(trifluoromethyl)furan, and 2,3-dihydrospiro[furo[2,3-g][1,4]benzodioxine-8,3'-indol]-2'(1'H)-one to replace 3-methylspiro[furo[3,2-f][1,2]benzisoxazole-5,3'-indol]-2'(1'H)-one, ethyl (2'-oxo-2,3-dihydrospiro[furo[2,3-g][1,4]benzodioxine-8,3'-indol]-1'(2'H)-yl)acetate was obtained (90%): mp 58-59° C. (ethyl acetate/hexanes); $^1$H NMR (300 MHz, CDCl$_3$) δ 7.29-7.23 (m, 1H), 7.18-7.15 (m, 1H), 7.08-7.02 (m, 1H), 6.77-6.74 (m, 1H), 6.47 (s, 1H), 6.34 (s, 1H), 4.89-4.39 (m, 4H), 4.25-4.15 (m, 4H), 4.11-4.08 (m, 2H), 1.26 (t, J=9.0 Hz, 3H); MS (ES+) m/z 381.8 (M+1).

EXAMPLE 9.45

Synthesis of 1'-{[(4S)-2,2-dimethyl-1,3-dioxolan-4-yl]methyl}-2,3-dihydrospiro[furo[2,3-g][1,4]benzodioxine-8,3'-indol]-2'(1'H)-one

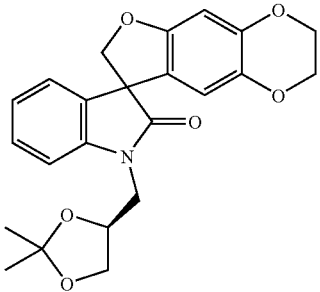

Following the procedure as described in EXAMPLE 9 and making non-critical variations using (S)-(2,2-dimethyl-1,3-dioxolan-4-yl)methyl 4-methylbenzenesulfonate to replace 2-(bromomethyl)-5-(trifluoromethyl)furan, and 2,3-dihydrospiro[furo[2,3-g][1,4]benzodioxine-8,3'-indol]-2'(1'H)-one to replace 3-methylspiro[furo[3,2-f][1,2]benzisoxazole-5,3'-indol]-2'(1'H)-one, 1'-{[(4S)-2,2-dimethyl-1,3-dioxolan-4-yl]methyl}-2,3-dihydrospiro[furo[2,3-g][1,4]benzodioxine-8,3'-indol]-2'(1'H)-one was obtained (98%): mp 55-57° C. (ethyl acetate/hexanes); $^1$H NMR (300 MHz, CDCl$_3$) δ 7.30-6.99 (m, 4H), 6.47-6.20 (m, 2H), 4.88-4.84 (m, 1H), 4.63-4.59 (m, 1H), 4.48-4.40 (m, 1H), 4.17-3.77 (m, 8H), 1.35-1.28 (m, 6H); MS (ES+) m/z 410.1 (M+1).

EXAMPLE 9.46

Synthesis of 6-methoxy-1'-(4-methoxybenzyl)-2'-oxo-1',2'-dihydrospiro[1-benzofuran-3,3'-indole]-5-carbonitrile

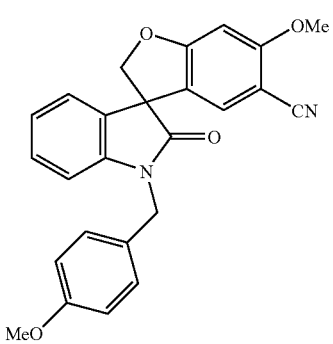

Following the procedure as described in EXAMPLE 9 and making non-critical variations using iodomethane to replace 2-(bromomethyl)-5-(trifluoromethyl)furan, and 6-hydroxy-1'-(4-methoxybenzyl)-2'-oxo-1',2'-dihydrospiro[1-benzofuran-3,3'-indole]-5-carbonitrile to replace 3-methylspiro[furo[3,2-f][1,2]benzisoxazole-5,3'-indol]-2'(1'H)-one, 6-methoxy-1'-(4-methoxybenzyl)-2'-oxo-1',2'-dihydrospiro[1-benzofuran-3,3'-indole]-5-carbonitrile was obtained (62%): mp 207-208° C. (ethyl acetate/hexanes); $^1$H NMR (300 MHz, CDCl$_3$) δ 7.27-7.20 (m, 3H), 7.10-6.99 (m, 2H), 6.90-6.83 (m, 4H), 6.56 (s, 1H), 5.07-4.74 (m, 4H), 3.90 (s, 3H), 3.78 (s, 3H); MS (ES+) m/z 412.9 (M+1).

EXAMPLE 9.47

Synthesis of 6-methoxy-2'-oxo-1'-(pyridin-2-ylmethyl)-1',2'-dihydrospiro[1-benzofuran-3,3'-indole]-5-carbonitrile

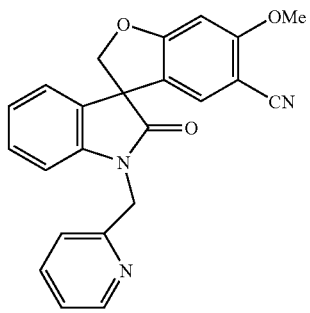

Following the procedure as described in EXAMPLE 9 and making non-critical variations using 2-(bromomethyl)pyridine hydrobromide to replace 2-(bromomethyl)-5-(trifluoromethyl)furan, and 6-methoxy-2'-oxo-1',2'-dihydrospiro[1-benzofuran-3,3'-indole]-5-carbonitrile to replace 3-methylspiro[furo[3,2-f][1,2]benzisoxazole-5,3'-indol]-2'(1'H)-one, 6-methoxy-2'-oxo-1'-(pyridin-2-ylmethyl)-1',2'-dihydrospiro[1-benzofuran-3,3'-indole]-5-carbonitrile was obtained (80%): mp 187-189° C. (ethyl acetate/hexanes); $^1$H NMR (300 MHz, CDCl$_3$) δ 8.57-8.55 (m, 1H), 7.70-7.64 (m, 1H), 7.27-7.20 (m, 3H), 7.12-7.00 (m, 3H), 6.91-6.89 (m, 1H), 6.55 (s, 1H), 4.97 (ABq, 2H), 3.90 (s, 3H); $^{13}$C NMR (75 MHz, CDCl$_3$) δ 176.7, 165.8, 164.1, 154.9, 149.6, 142.3, 137.1, 131.2, 129.4, 128.8, 123.7, 123.6, 122.9, 122.0, 121.7, 116.7, 109.8, 94.6, 81.2, 56.9, 56.3, 45.9; MS (ES+) m/z 383.8 (M+1).

EXAMPLE 9.48

Synthesis of 6-fluoro-2'-oxo-1'-(pyridin-2-ylmethyl)-1',2'-dihydrospiro[1-benzofuran-3,3'-indole]-5-carbonitrile

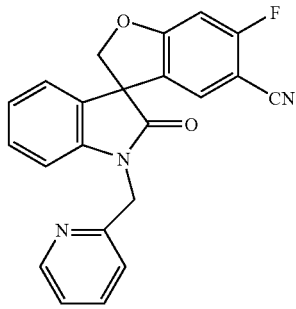

Following the procedure as described in EXAMPLE 9 and making non-critical variations using 2-(bromomethyl)pyridine hydrobromide to replace 2-(bromomethyl)-5-(trifluoromethyl)furan, and 6-fluoro-2'-oxo-1',2'-dihydrospiro[1-benzofuran-3,3'-indole]-5-carbonitrile to replace 3-methylspiro[furo[3,2-f][1,2]benzisoxazole-5,3'-indol]-2'(1'H)-one, 6-fluoro-2'-oxo-1'-(pyridin-2-ylmethyl)-1',2'-dihydrospiro[1-benzofuran-3,3'-indole]-5-carbonitrile was obtained (55%): mp 108-109° C.; ¹H NMR (300 MHz, DMSO-d₆) δ 7.71-7.66 (m, 1H), 7.29-7.20 (m, 3H), 7.15-7.03 (m, 3H), 6.93-6.90 (m, 1H), 6.79-6.76 (m, 1H), 5.26-4.85 (m, 4H); MS (ES+) m/z 371.9 (M+1).

EXAMPLE 9.49

Synthesis of 6-fluoro-2'-oxo-1'-[(2R)-tetrahydrofuran-2-ylmethyl]-1',2'-dihydrospiro[1-benzofuran-3,3'-indole]-5-carbonitrile

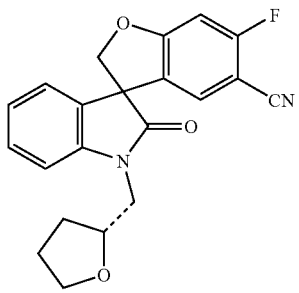

Following the procedure as described in EXAMPLE 9 and making non-critical variations using (R)-(tetrahydrofuran-2-yl)methyl 4-methylbenzenesulfonate to replace 2-(bromomethyl)-5-(trifluoromethyl)furan, and 6-fluoro-2'-oxo-1',2'-dihydrospiro[1-benzofuran-3,3'-indole]-5-carbonitrile to replace 3-methylspiro[furo[3,2-f][1,2]benzisoxazole-5,3'-indol]-2'(1'H)-one, 6-fluoro-2'-oxo-1'-[(2R)-tetrahydrofuran-2-ylmethyl]-1',2'-dihydrospiro[1-benzofuran-3,3'-indole]-5-carbonitrile was obtained (34%): ¹H NMR (300 MHz, CDCl₃) δ 7.37-7.27 (m, 1H), 7.12-7.06 (m, 3H), 7.01-6.92 (m, 1H), 6.79-6.74 (m, 1H), 4.94 (ABq, 2H), 4.31-4.21 (m, 1H), 3.91-3.72 (m, 4H), 2.12-1.84 (m, 4H); MS (ES+) m/z 364.9 (M+1).

EXAMPLE 9.50

Synthesis of 6-fluoro-2'-oxo-1'-[2-(trifluoromethyl)benzyl]-1',2'-dihydrospiro[1-benzofuran-3,3'-indole]-5-carbonitrile

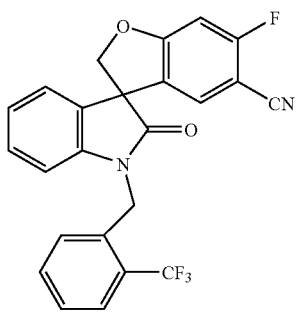

Following the procedure as described in EXAMPLE 9 and making non-critical variations using 2-(trifluoromethyl)benzyl bromide to replace 2-(bromomethyl)-5-(trifluoromethyl)furan, and 6-fluoro-2'-oxo-1',2'-dihydrospiro[1-benzofuran-3,3'-indole]-5-carbonitrile to replace 3-methylspiro[furo[3,2-f][1,2]benzisoxazole-5,3'-indol]-2'(1'H)-one, 6-fluoro-2'-oxo-1'-[2-(trifluoromethyl)benzyl]-1',2'-dihydrospiro[1-benzofuran-3,3'-indole]-5-carbonitrile was obtained (55%): mp 193-195° C. (ethyl acetate/hexanes); ¹H NMR (300 MHz, CDCl₃) δ 7.76-7.73 (m, 1H), 7.53-7.39 (m, 2H), 7.27-7.22 (m, 1H), 7.17-7.07 (m, 3H), 7.01-6.99 (m, 1H), 6.82-6.79 (m, 1H), 6.70-6.67 (m, 1H), 5.27-5.09 (m, 3H), 4.90-4.87 (m, 1H); MS (ES+) m/z 419.0 (M−19).

EXAMPLE 9.51

Synthesis of 6-fluoro-2'-oxo-1'-{[3-(trifluoromethyl)pyridin-2-yl]methyl}-1',2'-dihydrospiro[1-benzofuran-3,3'-indole]-5-carbonitrile

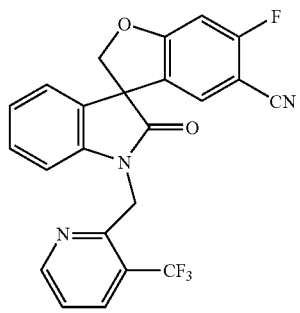

Following the procedure as described in EXAMPLE 9 and making non-critical variations using 2-(chloromethyl)-3-(trifluoromethyl)pyridine to replace 2-(bromomethyl)-5-(trifluoromethyl)furan, and 6-fluoro-2'-oxo-1',2'-dihydrospiro[1-benzofuran-3,3'-indole]-5-carbonitrile to replace 3-methylspiro[furo[3,2-f][1,2]benzisoxazole-5,3'-indol]-2'(1'H)-one, 6-fluoro-2'-oxo-1'-{[3-(trifluoromethyl)pyridin-2-yl]methyl}-1',2'-dihydrospiro[1-benzofuran-3,3'-indole]-5-carbonitrile was obtained (67%): mp 209-211° C. (ethyl acetate/hexanes); ¹H NMR (300 MHz, DMSO-d₆) δ 8.65 (d, J=6.0 Hz, 1H), 8.23 (d, J=6.0 Hz, 1H), 7.58-7.54 (m, 1H), 7.42-7.40 (m, 1H), 7.31-7.23 (m, 3H), 7.06-7.01 (m, 1H), 6.93-6.91 (m, 1H), 5.21 (s, 2H), 5.03 (s, 2H); MS (ES+) m/z 440.2 (M+1).

EXAMPLE 9.52

Synthesis of 4'-bromo-1'-pentyl-2,3-dihydrospiro[furo[2,3-g][1,4]benzodioxine-8,3'-indol]-2'(1'H)-one

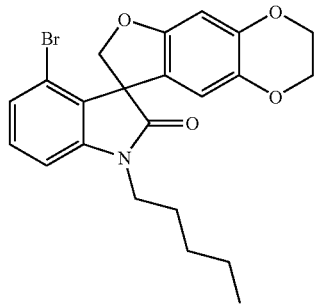

Following the procedure as described in EXAMPLE 9 and making non-critical variations using 1-iodopentane to replace 2-(bromomethyl)-5-(trifluoromethyl)furan, and 4'-bromo-2,3-dihydrospiro[furo[2,3-g][1,4]benzodioxine-8,3'-indol]-2'

(1'H)-one to replace 3-methylspiro[furo[3,2-f][1,2]benzisoxazole-5,3'-indol]-2'(1'H)-one, 4'-bromo-1'-pentyl-2,3-dihydrospiro[furo[2,3-g][1,4]benzodioxine-8,3'-indol]-2'(1'H)-one was obtained (54%) as a colorless solid: $^1$H NMR (300 MHz, CDCl$_3$) δ 7.20-7.15 (m, 2H), 6.87-6.83 (m, 1H), 6.45 (s, 1H), 6.16 (s, 1H), 4.89 (ABq, 2H), 4.20-4.11 (m, 4H), 3.85-3.59 (m, 2H), 1.72-1.67 (m, 2H), 1.38-1.25 (m, 4H), 0.92-0.85 (m, 3H); $^{13}$C NMR (75 MHz, CDCl$_3$) δ 117.0, 156.4, 144.7, 144.5, 137.9, 130.13, 130.10, 126.9, 119.9, 118.1, 111.0, 107.5, 98.9, 76.8, 64.4, 63.8, 59.3, 40.5, 28.9, 27.0, 22.3, 13.9; MS (ES+) m/z 443.9 (M+1), 445.9 (M+1).

EXAMPLE 9.53

Synthesis of methyl 3-[(2'-oxo-2,3-dihydrospiro[furo[2,3-g][1,4]benzodioxine-8,3'-indol]-1'(2'H)-yl)methyl]benzoate

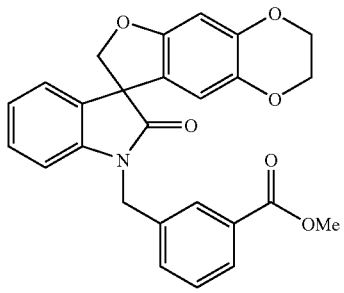

Following the procedure as described in EXAMPLE 9 and making non-critical variations using methyl 3-bromomethylbenzoate to replace 2-(bromomethyl)-5-(trifluoromethyl)furan, and 2,3-dihydrospiro[furo[2,3-g][1,4]benzodioxine-8,3'-indol]-2'(1'H)-one to replace 3-methylspiro[furo[3,2-f][1,2]benzisoxazole-5,3'-indol]-2'(1'H)-one, methyl 3-[(2'-oxo-2,3-dihydrospiro[furo[2,3-g][1,4]benzodioxine-8,3'-indol]-1'(2'H)-yl)methyl]benzoate was obtained (99%) as a colorless solid: mp 89-97° C. (ethyl acetate/diethyl ether); $^1$H NMR (300 MHz, CDCl$_3$) δ 7.98-7.95 (m, 2H), 7.51-7.42 (m, 2H), 7.19-7.14 (m, 2H), 7.03-7.01 (m, 1H), 6.73-6.70 (m, 1H), 6.50 (s, 1H), 6.27 (s, 1H), 5.19-5.13 (m, 1H), 4.95-4.92 (m, 1H), 4.84-4.79 (m, 1H), 4.67-4.64 (m, 1H), 4.19-4.11 (m, 4H), 3.90 (s, 3H) $^{13}$C NMR (75 MHz, CDCl$_3$) δ 177.6, 166.7, 153.3, 144.7, 141.7, 138.4, 136.1, 132.3, 131.7, 130.8, 129.2, 128.9, 128.1, 124.0, 123.6, 120.9, 111.6, 109.2, 99.4, 80.2, 64.5, 63.9, 58.1, 52.3, 43.8, 29.7; MS (ES+) m/z 443.8 (M+1).

EXAMPLE 9.54

Synthesis of 1'-[2-(2-methoxyethoxy)ethyl]-3-methylspiro[furo[3,2-f][1,2]benzisoxazole-5,3'-indol]-2'(1'H)-one

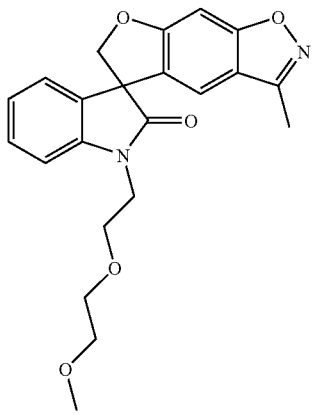

Following the procedure as described in EXAMPLE 9 and making non-critical variations using 1-bromo-2-(2-methoxyethoxy)ethane to replace 2-(bromomethyl)-5-(trifluoromethyl)furan, 1'-[2-(2-methoxyethoxy)ethyl]-3-methylspiro[furo[3,2-f][1,2]benzisoxazole-5,3'-indol]-2'(1'H)-one was obtained (98%) as a colorless oil: $^1$H NMR (300 MHz, CDCl$_3$) δ 7.45-7.42 (m, 1H), 7.30-7.27 (m, 1H), 7.14-7.07 (m, 2H), 7.01-6.94 (m, 2H), 5.09-5.06 (m, 1H), 4.85-4.82 (m, 1H), 4.08-3.98 (m, 2H), 3.84-3.80 (m, 2H), 3.68-3.65 (m, 2H), 3.51-3.49 (m, 2H), 3.34 (s, 3H), 2.42 (s, 3H); $^{13}$C NMR (75 MHz, CDCl$_3$) δ 176.1, 163.9, 154.8, 142.8, 130.4, 129.2, 123.5, 123.3, 122.8, 117.9, 109.8, 107.9, 81.2, 72.0, 70.7, 68.6, 59.0, 56.3, 40.8, 30.9, 9.8; MS (ES+) m/z 394.8 (M+1).

EXAMPLE 9.55

Synthesis of 3-methyl-1'-(3-methylbutyl)spiro[furo[3,2-f][1,2]benzisoxazole-5,3'-indol]-2'(1'H)-one

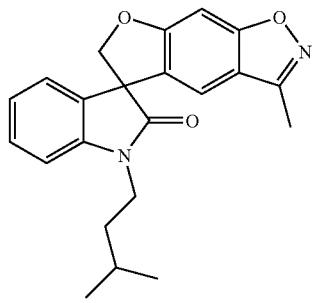

Following the procedure as described in EXAMPLE 9 and making non-critical variations using 1-bromo-3-methylbutane to replace 2-(bromomethyl)-5-(trifluoromethyl)furan, 3-methyl-1'-(3-methylbutyl)spiro[furo[3,2-f][1,2]benzisoxazole-5,3'-indol]-2'(1'H)-one was obtained (71%) as a colorless solid: mp 135-138° C. (hexanes); $^1$H NMR (300 MHz, CDCl$_3$) δ 7.45-7.42 (m, 1H), 7.33-7.28 (m, 1H), 7.11-7.09 (m, 1H), 7.01-6.94 (m, 3H), 5.07 (d, J=9.0 Hz, 1H), 4.82 (d, J=9.0 Hz, 1H), 3.94-3.87 (m, 1H), 3.77-3.70 (m, 1H), 2.43 (s, 3H), 1.77-1.63 (m, 3H), 1.01-0.98 (m, 6H); $^{13}$C NMR (75 MHz, CDCl$_3$) δ 175.7, 163.9, 158.3, 154.8, 142.5, 130.8, 129.3, 123.7, 123.1, 122.8, 117.9, 109.2, 108.9, 107.9, 81.2, 56.3, 39.1, 36.0, 26.0, 22.6, 22.4, 9.8; MS (ES+) m/z 362.8 (M+1).

EXAMPLE 9.56

Synthesis of 3-methyl-1'-(pyrazin-2-ylmethyl)spiro[furo[3,2-f][1,2]benzisoxazole-5,3'-indol]-2'(1'H)-one

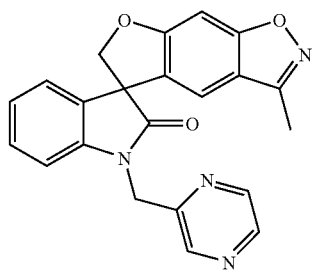

Following the procedure as described in EXAMPLE 9 and making non-critical variations using 2-(chloromethyl)pyrazine (Newkome, G. R. et al., *Synthesis*, (1984) 8:676) to replace 2-(bromomethyl)-5-(trifluoromethyl)furan, 3-methyl-1'-(pyrazin-2-ylmethyl)spiro[furo[3,2-f][1,2]benzisoxazole-5,3'-indol]-2'(1'H)-one was obtained (20%) as a colorless solid: mp 170-173° C. (methanol/hexanes); $^1$H NMR (300 MHz, CDCl$_3$) δ 8.81 (s, 1H), 8.63-8.47 (m, 2H), 7.48-7.45 (m, 1H), 7.21-6.91 (m, 5H), 5.34-5.29 (m, 1H), 5.16-5.06 (m, 2H), 4.90-4.87 (m, 1H), 2.44 (s, 3H); $^{13}$C NMR (75 MHz, CDCl$_3$) δ 176.2, 163.9, 158.1, 154.9, 151.0, 144.1, 141.7, 130.4, 129.4, 123.9, 123.1, 118.0, 109.6, 108.9, 107.9, 81.2, 56.4, 44.3, 9.8; MS (ES+) m/z 384.7 (M+1).

EXAMPLE 9.57

Synthesis of 1'-[(3-fluoropyridin-2-yl)methyl]-3-methylspiro[furo[3,2-f][1,2]benzisoxazole-5,3'-indol]-2'(1'H)-one

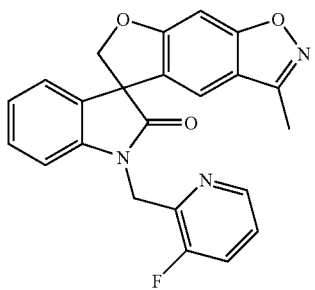

Following the procedure as described in Example 9 and making non-critical variations using 2-(chloromethyl)-3-fluoropyridine to replace 2-(bromomethyl)-5-(trifluoromethyl)furan, 1'-[(3-fluoropyridin-2-yl)methyl]-3-methylspiro[furo[3,2-f][1,2]benzisoxazole-5,3'-indol]-2'(1'H)-one was obtained (52%) as a colorless solid: mp 167-169° C. (diethyl ether); $^1$H NMR (300 MHz, CDCl$_3$) δ 8.38-8.36 (m, 1H), 7.47-7.37 (m, 2H), 7.27-7.18 (m, 3H), 7.10-7.08 (m, 1H), 6.99-6.94 (m, 2H), 5.29-5.14 (m, 3H), 4.88-4.85 (m, 1H), 2.44 (s, 3H); $^{13}$C NMR (75 MHz, CDCl$_3$) δ 176.0, 164.1, 158.4, 156.3, 154.8, 145.3, 143.0, 142.4, 130.3, 129.2, 124.4, 123.6, 123.5, 123.3, 122.9, 117.9, 109.7, 108.9, 107.9, 81.6, 56.4, 41.3, 9.8; MS (ES+) m/z 401.8 (M+1).

EXAMPLE 9.58

Synthesis of methyl 2-[(3-methyl-2'-oxospiro[furo[3,2-f][1,2]benzisoxazole-5,3'-indol]-1'(2'H)-yl)methyl]-1,3-oxazole-4-carboxylate

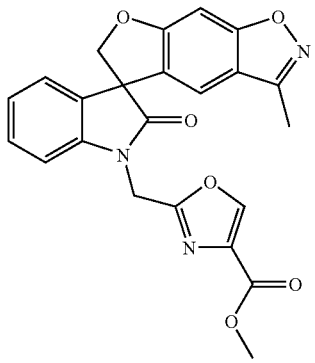

Following the procedure as described in EXAMPLE 9 and making non-critical variations using methyl 2-(chloromethyl)oxazole-4-carboxylate to replace 2-(bromomethyl)-5-(trifluoromethyl)furan, methyl 2-[(3-methyl-2'-oxospiro[furo[3,2-f][1,2]benzisoxazole-5,3'-indol]-1'(2'H)-yl)methyl]-1,3-oxazole-4-carboxylate was obtained (80%) as a colorless solid: mp 148-152° C. (dichloromethane); $^1$H NMR (300 MHz, CDCl$_3$) δ 8.23 (s, 1H), 7.48-7.45 (m, 1H), 7.30-7.27 (m, 1H), 7.13-7.11 (m, 1H), 7.06-6.95 (m, 3H), 5.20 (s, 2H), 5.14-5.11 (m, 1H), 4.88-4.85 (m, 1H), 3.91 (s, 3H), 2.43 (s, 3H); $^{13}$C NMR (75 MHz, CDCl$_3$) δ 175.8, 163.9, 161.2, 159.0, 158.2, 154.9, 145.3, 141.1, 133.5, 130.1, 129.6, 124.1, 123.2, 118.0, 109.3, 108.7, 107.9, 81.2, 56.3, 52.3, 37.5, 30.9, 9.8; MS (ES+) m/z 431.8 (M+1).

EXAMPLE 9.59

Synthesis of methyl 4-[(2'-oxo-2,3-dihydrospiro[furo[2,3-g][1,4]benzodioxine-8,3'-indol]-1'(2'H)-yl)methyl]benzoate

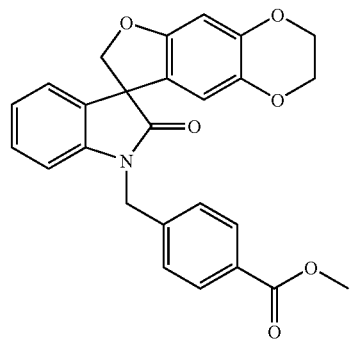

To a solution of 2,3-dihydrospiro[furo[2,3-g][1,4]benzodioxine-8,3'-indol]-2'(1'H)-one (3.50 g, 11.9 mmol) in anhydrous tetrahydrofuran (75 mL) at 0° C., was added sodium hydride (60% w/w dispersion in mineral oil, 0.72 g, 17.9 mmol). The solution was stirred at 0° C. for 0.5 h and methyl 4-(bromomethyl)benzoate (3.00 g, 13.1 mmol) was added. The solution was stirred at ambient temperature for 16 h, further sodium hydride (60% w/w dispersion in mineral oil, 0.30 g, 7.5 mmol) and methyl 4-(bromomethyl)benzoate (0.50 g, 2.2 mmol) were added and the mixture was stirred for 1 h, filtered and concentrated in vacuo. The residue was purified by column chromatography and eluted with a 25% to 50% gradient of ethyl acetate in hexanes to afford methyl 4-[(2'-oxo-2,3-dihydrospiro[furo[2,3-g][1,4]benzodioxine-8,3'-indol]-1'(2'H)-yl)methyl]benzoate (4.51 g, 86%) as a colorless solid: mp 167-169° C. (ethyl acetate/hexanes); $^1$H NMR (300 MHz, CDCl$_3$) δ 8.00 (d, J=8.4 Hz, 2H), 7.37 (d, J=8.4 Hz, 2H), 7.15 (d, J=7.4 Hz, 2H), 7.03-6.96 (m, 1H), 6.73-6.68 (m, 1H), 6.48 (s, 1H), 6.22 (s, 1H), 5.10 (d, J=15.9 Hz, 1H), 4.92 (d, J=8.9 Hz, 1H), 4.84 (d, J=16.0 Hz, 1H), 4.65 (d, J=8.9 Hz, 1H), 4.19-4.04 (m, 4H), 3.87 (s, 3H); $^{13}$C NMR (75 MHz, CDCl$_3$) δ 177.6, 166.6, 155.3, 144.7, 141.8, 140.9, 138.4, 132.2, 130.3, 129.8, 128.9, 127.3, 124.0, 123.6, 120.9, 111.5, 109.2, 99.5, 80.1, 64.5, 63.9, 58.1, 52.2, 43.9; MS (ES+) m/z 443.9 (M+1).

EXAMPLE 9.60

Synthesis of 1'-[(4-benzylmorpholin-2-yl)methyl]-2,3-dihydrospiro[furo[2,3-g][1,4]benzodioxine-8,3'-indol]-2'(1'H)-one

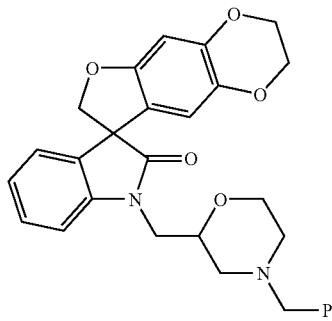

To a suspension of sodium hydride (60% w/w dispersion in mineral oil, 0.48 g, 12 mmol) in N,N-dimethylformamide (10 mL) at 0° C. was added 2,3-dihydrospiro[furo[2,3-g][1,4]benzodioxine-8,3'-indol]-41H)-one (2.95 g, 10 mmol). The reaction mixture was stirred for 30 min and 4-benzyl-2-(chloromethyl)morpholine (2.71 g, 12 mmol) and potassium iodide (0.10 g, 0.60 mmol) were added. The reaction mixture was heated at 100° C. for 16 h, allowed to cool to ambient temperature and concentrated in vacuo. The residue was purified by column chromatography and eluted with ethyl acetate/hexanes (3/7) to afford 1'-[(4-benzylmorpholin-2-yl)methyl]-2,3-dihydrospiro[furo[2,3-g][1,4]benzodioxine-8,3'-indol]-2'(1'H)-one (0.75 g, 74%) as a colorless solid: mp 88-100° C.; $^1$H NMR (mixture of diasteroisomers, 300 MHz, CDCl$_3$) δ7.35-7.20 (m, 6H), 7.16-7.11 (m, 1H), 7.07-7.00 (m, 2H), 6.48 (s, 1H), 6.25 (s, 0.5H), 6.20 (s, 0.5H), 4.90-4.80 (m, 1H), 4.64-4.57 (m, 1H), 4.22-4.08 (m, 4H), 3.98-3.40 (m, 7H), 2.87-2.56 (m, 2H), 2.23-1.98 (m, 2H); MS (ES+) m/z 485.0 (M+1).

EXAMPLE 9.61

Synthesis of (8S)-1'-{[(2S)-4-benzylmorpholin-2-yl]methyl}-2,3-dihydrospiro[furo[2,3-g][1,4]benzodioxine-8,3'-indol]-2'(1'H)-one

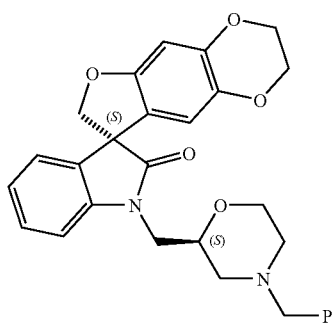

Following the procedure as described in EXAMPLE 9.60 and making non-critical variations using (S)-4-benzyl-2-(chloromethyl)morpholine (Toshiya, M. et al., *Heterocycles* (1994), 38(5):1033-1040) to replace 4-benzyl-2-(chloromethyl)morpholine, and (8S)-2,3-dihydrospiro[furo[2,3-g][1,4]benzodioxine-8,3'-indol]-2'(1'H)-one to replace 2,3-dihydrospiro[furo[2,3-g][1,4]benzodioxine-8,3'-indol]-2'(1'H)-one, (8S)-1'-{[(2S)-4-benzylmorpholin-2-yl]methyl}-2,3-dihydrospiro[furo[2,3-g][1,4]benzodioxine-8,3'-indol]-2'(1'H)-one was obtained (99%): MS (ES+) m/z 485.0 (M+1).

EXAMPLE 9.62

Synthesis of 1'-(4-bromobenzyl)-5,6-difluorospiro[1-benzofuran-3,3'-indol]-2'(1'H)-one

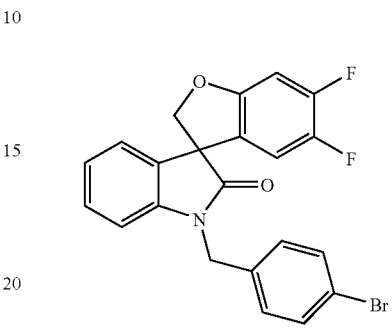

Following the procedure as described in EXAMPLE 9 and making non-critical variations using 4-bromobenzyl bromide to replace 2-(bromomethyl)-5-(trifluoromethyl)furan, and 5,6-difluorospiro[1-benzofuran-3,3'-indol]-2'(1'H)-one to replace 3-methylspiro[furo[3,2-f][1,2]benzisoxazole-5,3'-indol]-2'(1'H)-one, 1'-(4-bromobenzyl)-5,6-difluorospiro[1-benzofuran-3,3'-indol]-2'(1'H)-one was obtained (54%) as a pale yellow oil: $^1$H NMR (300 MHz, CDCl$_3$) δ7.51 (s, 1H), 7.48 (s, 1H), 7.23-7.04 (m, 5H), 6.82-6.77 (m, 2H), 6.50 (dd, J=8.9, 8.9 Hz, 1H), 5.03-4.96 (m, 2H), 4.84-4.72 (m, 2H); MS (ES+) m/z 442.1 (M+1), 444.1 (M+1).

EXAMPLE 9.63

Synthesis of 5,6-difluoro-1'-(3-methylbutyl)spiro[1-benzofuran-3,3'-indol]-2'(1'H)-one

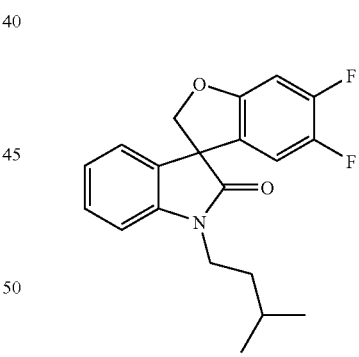

Following the procedure as described in EXAMPLE 9 and making non-critical variations using 1-bromo-3-methylbutane to replace 2-(bromomethyl)-5-(trifluoromethyl)furan, and 5,6-difluorospiro[1-benzofuran-3,3'-indol]-2'(1'H)-one to replace 3-methylspiro[furo[3,2-f][1,2]benzisoxazole-5,3'-indol]-2'(1'H)-one, 5,6-difluoro-1'-(3-methylbutyl)spiro[1-benzofuran-3,3'-indol]-2'(1'H)-one was obtained (96%) as a pale yellow oil: $^1$H NMR (300 MHz, CDCl$_3$) δ 7.34 (t, J=7.7 Hz, 1H), 7.16-7.04 (m, 2H), 6.93 (d, J=7.8 Hz, 1H), 6.77 (dd, J=10.3, 6.3 Hz, 1H), 6.50 (t, J=8.5 Hz, 1H), 4.95 (d, J=9.1 Hz, 1H), 4.70 (d, J=9.1 Hz, 1H), 3.88-3.67 (m, 2H), 1.72-1.60 (m, 3H), 1.01 (d, 6.2 Hz, 6H); $^{13}$C NMR (75 MHz, CDCl$_3$) δ176.3, 156.6 (d, J$_{C-F}$=11.0 Hz), 151.1 (dd, J$_{C-F}$=248.1, 14.5 Hz), 145.6 (dd, J$_{C-F}$=241.3, 14.0 Hz), 142.3, 131.6, 129.2, 123.8, 123.3, 111.5 (d, J=20.5 Hz), 108.7, 99.9 (d, J=22.3 Hz), 80.7, 57.7, 38.8, 36.0, 26.0, 22.4, 22.3; MS (ES+) m/z 344.4 (M+1).

EXAMPLE 9.64

Synthesis of 5,6-difluoro-1'-(pyridin-2-ylmethyl)spiro[1-benzofuran-3,3'-indol]-2'(1'H)-one

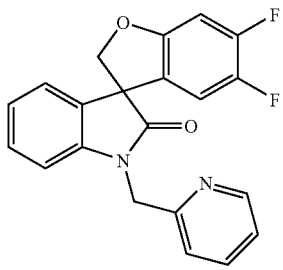

Following the procedure as described in EXAMPLE 9 and making non-critical variations using 2-(bromomethyl)pyridine hydrobromide to replace 2-(bromomethyl)-5-(trifluoromethyl)furan, and 5,6-difluorospiro[1-benzofuran-3,3'-indol]-2'(1'H)-one to replace 3-methylspiro[furo[3,2-f][1,2]benzisoxazole-5,3'-indol]-2'(1'H)-one, 5,6-difluoro-1'-(pyridin-2-ylmethyl)spiro[1-benzofuran-3,3'-indol]-2'(1'H)-one was obtained (29%) as a pale yellow oil: $^1$H NMR (300 MHz, CDCl$_3$) δ 8.58 (d, J=4.1 Hz, 1H), 7.71 (ddd, J=9.4, 7.7, 1.7 Hz, 1H), 7.31-7.22 (m, 3H), 7.15 (dd, J=7.4, 0.9 Hz, 1H), 7.05 (ddd, J=8.4, 7.5, 0.9 Hz, 1H), 6.94 (d, J=7.8 Hz, 1H), 6.79 (dd, J=10.3, 6.3 Hz, 1H), 6.66 (dd, J=9.2, 7.9 Hz, 1H), 5.23 (d, J=15.9 Hz, 1H), 5.06-4.96 (m, 2H), 4.77 (d, J=9.1 Hz, 1H); MS (ES+) m/z 365.3 (M+1).

EXAMPLE 9.65

Synthesis of 5,6-difluoro-1'-(tetrahydro-2H-pyran-4-ylmethyl)spiro[1-benzofuran-3,3'-indol]-2'(1'H)-one

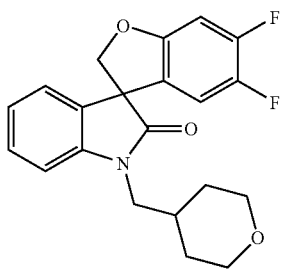

Following the procedure as described in EXAMPLE 9 and making non-critical variations using 4-(bromomethyl)tetrahydro-2H-pyran to replace 2-(bromomethyl)-5-(trifluoromethyl)furan, and 5,6-difluorospiro[1-benzofuran-3,3'-indol]-2'(1'H)-one to replace 3-methylspiro[furo[3,2-f][1,2]benzisoxazole-5,3'-indol]-2'(1'H)-one, 5,6-difluoro-1'-(tetrahydro-2H-pyran-4-ylmethyl)spiro[1-benzofuran-3,3'-indol]-2'(1'H)-one was obtained (32%) as a pale yellow oil: $^1$H NMR (300 MHz, CDCl$_3$) δ 7.34 (ddd, J=9.1, 7.7, 1.5 Hz, 1H), 7.16-7.05 (m, 2H), 6.93 (d, J=7.9 Hz, 1H), 6.78 (dd, J=10.3, 6.3 Hz, 1H), 6.49 (dd, J=9.1, 7.8 Hz, 1H), 4.95 (d, J=9.0 Hz, 1H), 4.70 (d, J=9.0 Hz, 1H), 4.00 (dd, J=11.6, 2.5 Hz, 2H), 3.75-3.56 (m, 2H), 3.37 (ddd, J=14.0, 11.6, 2.3 Hz, 2H), 2.15-2.08 (m, 1H), 1.62-1.41 (m, 4H); $^{13}$C NMR (75 MHz, CDCl$_3$) δ 176.8, 156.7 (d, $J_{C-F}$=10.9 Hz), 151.1 (dd, $J_{C-F}$=248.4, 14.5 Hz), 145.6 (dd, $J_{C-F}$=241.4, 14.0 Hz), 142.6, 131.3, 129.3, 124.0, 123.7 (dd, $J_{C-F}$=6.1, 3.1 Hz), 123.5, 111.5 (d, $J_{C-F}$=20.4 Hz), 108.8, 100.1 (d, $J_{C-F}$=22.3 Hz), 80.9, 67.3, 57.7, 46.1, 33.8, 30.7; MS (ES+) m/z 372.1 (M+1).

EXAMPLE 9.66

Synthesis of 2-[3-(2'-oxo-5,6-dihydrospiro[benzo[1,2-b:5,4-b']difuran-3,3'-indol]-1'(2'H)-yl)propyl]-1H-isoindole-1,3(2H)-dione

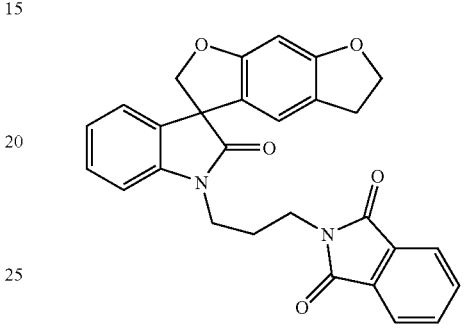

Following the procedure as described in EXAMPLE 9 and making non-critical variations using N-(3-bromopropyl)phthalimide to replace 2-(bromomethyl)-5-(trifluoromethyl)furan, and 5,6-dihydrospiro[benzo[1,2-b:5,4-b']difuran-3,3'-indol]-2'(1'H)-one to replace 3-methylspiro[furo[3,2-f][1,2]benzisoxazole-5,3'-indol]-2'(1'H)-one, 2-[3-(2'-oxo-5,6-dihydrospiro[benzo[1,2-b:5,4-b']difuran-3,3'-indol]-1'(2'H)-yl)propyl]-1H-isoindole-1,3(2H)-dione was obtained (39%) as a pale yellow solid: mp 214-217° C.; $^1$H NMR (300 MHz, CDCl$_3$) δ 7.84 (dd, J=5.6, 3.0 Hz, 2H), 7.72 (dd, J=5.5, 3.0 Hz, 2H), 7.31-7.28 (m, 1H), 7.18 (dd, J=7.4, 0.8 Hz, 1H), 7.04 (ddd, J=8.4, 7.5, 0.8 Hz, 1H), 6.88 (d, J=7.8 Hz, 1H), 6.58 (s, 1H), 6.40 (s, 1H), 4.94 (d, J=9.0 Hz, 1H), 4.69 (d, J=9.0 Hz, 1H), 4.53 (t, J=8.6 Hz, 2H), 3.98-3.89 (m, 1H), 3.85-3.75 (m, 3H), 3.01 (ddd, J=10.6, 8.4, 1.7 Hz, 2H), 2.20-2.10 (m, 2H); $^{13}$C NMR (75 MHz, CDCl$_3$) δ177.7, 168.1, 161.7, 161.2, 141.9, 134.0, 133.0, 131.9, 128.7, 124.0, 123.3, 123.2, 120.2, 119.9, 118.9, 108.2, 93.1, 80.4, 72.4, 57.6, 38.0, 35.7, 29.0, 26.8; MS (ES+) m/z 466.9 (M+1).

EXAMPLE 9.67

Synthesis of 1-{[5-(benzyloxy)pyridin-2-yl]methyl}spiro[furo[3,2-e][2,1,3]benzoxadiazole-8,3'-indol]-2'(1'H)-one

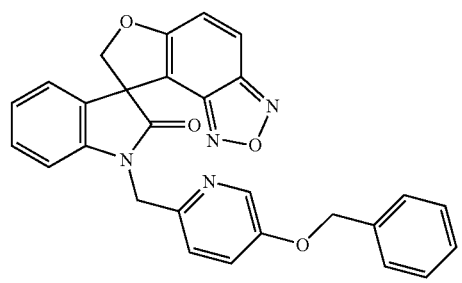

To a solution of 7H-spiro[benzofuro[4,5-c][1,2,5]oxadiazole-8,3'-indolin]-2'-one (0.400 g, 1.4 mmol) in anhydrous N,N-dimethylformamide (7 mL) was added sodium hydride (60% w/w dispersion in mineral oil, 0.086 g, 3.6 mmol) at 0° C. and the mixture was stirred for 20 minutes. 5-(Benzyloxy)-2-(chloromethyl)pyridine (0.44 g, 1.9 mmol) was added and the reaction mixture was stirred at ambient temperature for 19 h. Potassium iodide (~10 mg, catalytic amount) was added and the reaction mixture was stirred at 60° C. for 2 h, at ambient temperature for 43 h, at 60° C. for 7 h and at ambient temperature for 3 days. Saturated aqueous ammonium chloride (7 mL) and water (30 mL) were added and the mixture was extracted with ethyl acetate (3×10 mL). The combined organic extracts were washed with water (2×20 mL) and brine (20 mL), dried over sodium sulfate, filtered and concentrated in vacuo. The residue was purified by column chromatography and eluted with hexanes/ethyl acetate (3/2), followed by trituration in hexanes to afford 1-{[5-(benzyloxy)pyridin-2-yl]methyl}spiro[furo[3,2-e][2,1,3]benzoxadiazole-8,3'-indol]-2'(1'H)-one (0.034 g, 5%) as a pale yellow solid: mp 209-212° C.; $^1$H NMR (300 MHz, CDCl$_3$) δ 8.36 (d, J=2.7 Hz, 1H), 7.83 (d, J=9.6 Hz, 1H), 7.50 (d, J=8.7 Hz, 1H), 7.45-7.23 (m, 8H), 7.18 (d, J=7.5 Hz, 1H), 7.03 (t, J=7.5 Hz, 1H), 6.92 (J=7.8 Hz, 1H), 5.39 (d, J=15.9 Hz, 1H), 5.27 (d, J=9.6 Hz, 1H), 5.11 (s, 2H), 4.99 (d, J=9.3 Hz, 1H), 4.87 (d, J=15.9 Hz, 1H); $^{13}$C NMR (75 MHz, CDCl$_3$) δ176.0, 163.0, 154.4, 148.3, 147.1, 144.9, 142.2, 137.8, 136.0, 129.8, 129.7, 128.7, 128.3, 127.6, 123.7, 123.6, 122.4, 122.3, 121.9, 119.3, 110.2, 107.0, 82.0, 70.4, 57.4, 46.0; MS (ES+) m/z 477.2 (M+1).

EXAMPLE 9.68

Synthesis of ethyl 4-[(2'-oxo-2,3-dihydrospiro[furo [2,3-g][1,4]benzodioxine-8,3'-indol]-1'(2'H)-yl)methyl]benzoate

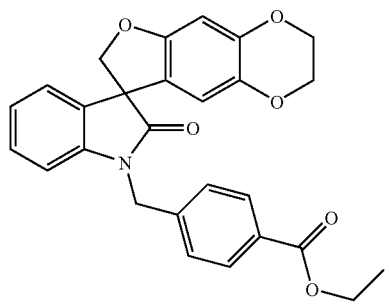

Following the procedure as described in EXAMPLE 9.67 and making non-critical variations using 2,3-dihydrospiro [furo[2,3-g][1,4]benzodioxine-8,3'-indol]-2'(1'H)-one to replace 7H-spiro[benzofuro[4,5-c][1,2,5]oxadiazole-8,3'-indolin]-2'-one, and ethyl 4-(bromomethyl)benzoate to replace 5-(benzyloxy)-2-(chloromethyl)pyridine, ethyl 4-[(2'-oxo-2,3-dihydrospiro[furo[2,3-g][1,4]benzodioxine-8,3'-indol]-1'(2'H)-yl)methyl]benzoate was obtained (95%) as a colorless solid: $^1$H NMR (300 MHz, CDCl$_3$) δ 8.03 (d, J=8.4 Hz, 2H), 7.39 (d, J=8.1 Hz, 2H), 7.21-7.16 (m, 2H), 7.03 (t, J=7.5 Hz, 1H), 6.72 (d, J=7.5 Hz, 1H), 6.52 (s, 1H), 6.24 (s, 1H), 5.14 (d, J=15.9 Hz, 1H), 4.95 (d, J=9.0 Hz, 1H), 4.87 (d, J=15.9 Hz, 1H), 4.67 (d, J=8.7 Hz, 1H), 4.36 (q, J=7.1 Hz, 2H), 4.22-4.19 (m, 2H), 4.15-4.12 (m, 2H), 1.38 (t, J=7.1 Hz, 3H); MS (ES+) m/z 458.1 (M+1).

EXAMPLE 9.69

Synthesis of 2-[3-(2'-oxo-2,3-dihydrospiro[furo[2,3-g][1,4]benzodioxine-8,3'-indol]-1'(2'H)-yl)propyl]-1H-isoindole-1,3(2H)-dione

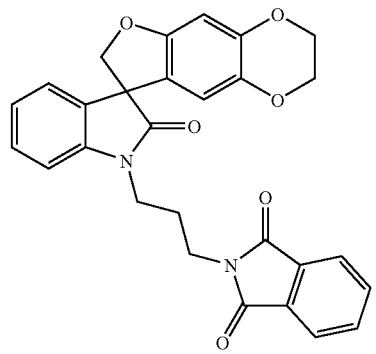

Following the procedure as described in EXAMPLE 9.67 and making non-critical variations using 2,3-dihydrospiro [furo[2,3-g][1,4]benzodioxine-8,3-indol]-2'(1'H)-one to replace 7H-spiro[benzofuro[4,5-c][1,2,5]oxadiazole-8,3'-indolin]-2'-one, and N-(3-bromopropyl)phthalimide to replace 5-(benzyloxy)-2-(chloromethyl)pyridine, 2-[3-(2'-oxo-2,3-dihydrospiro[furo[2,3-g][1,4]benzodioxine-8,3'-indol]-1' (2'H)-yl)propyl]-1H-isoindole-1,3(2H)-dione was obtained (92%) as a pale yellow solid: $^1$H NMR (300 MHz, CDCl$_3$) δ 7.85-7.82 (m, 2H), 7.74-7.69 (m, 2H), 7.29-7.24 (m, 1H), 7.15 (d, J=7.2 Hz, 1H), 7.08-7.00 (m, 1H), 6.87 (d, J=7.8 Hz, 1H), 6.48 (s, 1H), 6.29 (s, 1H), 4.89 (d, J=9.0 Hz, 1H), 4.64 (d, J=9.0 Hz, 1H), 4.18-4.10 (m, 4H), 3.94-3.77 (m, 4H), 2.19-2.10 (m, 2H).

EXAMPLE 9.70

Synthesis of (8S)-1'-[2-(2-methoxyethoxy)ethyl]-2,3-dihydrospiro[furo[2,3-g][1,4]benzodioxine-8,3'-indol]-2'(1'H)-one

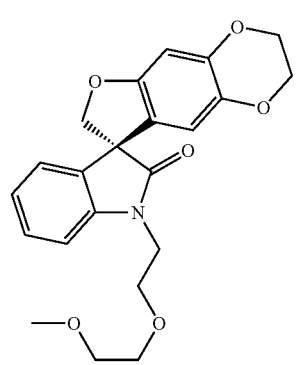

To a solution of (8S)-2,3-dihydrospiro[furo[2,3-g][1,4] benzodioxine-8,3'-indol]-2'(1'H)-one (0.27 g, 0.9 mmol) in dry N,N-dimethylformamide (15 mL) was added sodium hydride (60% w/w dispersion in mineral oil, 0.054 g, 1.4 mmol) at ambient temperature. The mixture was stirred at ambient temperature for 15 minutes and 1-bromo-2-(2-methoxyethoxy)ethane (0.33 g, 1.8 mmol) was added in one portion. The mixture was stirred at 60° C. for 6 h and concentrated in vacuo. Water (50 mL) was added to the residue and the mixture was extracted with ethyl acetate. The combined organic layers were dried over anhydrous magnesium sulfate, filtered and concentrated in vacuo. The residue was purified by column chromatography and eluted with 40% ethyl acetate in hexanes to afford (8S)-1'-[2-(2-methoxyethoxy)ethyl]-2,3-dihydrospiro[furo[2,3-g][1,4]benzodioxine-8,3'-indol]-2'(1'H)-one (0.31 g, 85%) as a colorless oil: $^1$H NMR (300 MHz, CDCl$_3$) δ 7.32-7.20 (m, 1H), 7.15-7.08 (m, 1H), 7.05-6.96 (m, 2H), 6.46 (s, 1H), 6.21 (s, 1H), 4.73 (ABq, 2H), 4.20-4.04 (m, 4H), 4.05-3.83 (m, 2H), 3.80-3.69 (m, 2H), 3.64-3.56 (m, 2H), 3.51-3.44 (m, 2H), 3.32 (s, 3H); $^{13}$C NMR (75 MHz, CDCl$_3$) δ 177.5, 155.1, 144.5, 142.5, 138.2, 132.3, 128.6, 123.7, 123.2, 121.2, 111.5, 109.2, 99.3, 80.0, 71.9, 70.4, 68.1, 64.5, 63.9, 59.0, 57.9, 40.2; MS (ES+) m/z 397.9 (M+1).

EXAMPLE 9.71

Synthesis of 6'-[2-(2-methoxyethoxy)ethyl]-2,3-dihydrospiro[furo[2,3-g][1,4]benzodioxine-8,8'-[1,3]thiazolo[5,4-e]indol]-7'(6'H)-one

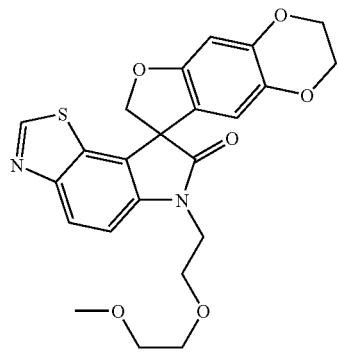

Following the procedure as described in EXAMPLE 9.70 and making non-critical variations using 2,3-dihydrospiro[furo[2,3-g][1,4]benzodioxine-8,8'-[1,3]thiazolo[5,4-e]indol]-7'(6'H)-one to replace (8S)-2,3-dihydrospiro[furo[2,3-g][1,4]benzodioxine-8,3'-indol]-2'(1'H)-one, 6'-[2-(2-methoxyethoxy)ethyl]-2,3-dihydrospiro[furo[2,3-g][1,4]benzodioxine-8,8'-[1,3]thiazolo[5,4-e]indol]-7'(6'H)-one was obtained (37%): mp 156-158° C.; $^1$H NMR (300 MHz, CDCl$_3$) δ 8.77 (s, 1H), 8.07 (d, J=8.6 Hz, 1H), 7.32 (d, J=8.6 Hz, 1H), 6.56 (s, 1H), 6.23 (s, 1H), 4.83 (ABq, 2H), 4.23-4.04 (m, 6H), 3.85-3.77 (m, 2H), 3.67-3.61 (m, 2H), 3.52-3.46 (m, 1H), 3.32 (s, 3H); MS (ES+) m/z 455.1 (M+1).

EXAMPLE 9.72

Synthesis of 6'-(pyridin-2-ylmethyl)-2,3-dihydrospiro[furo[2,3-g][1,4]-benzodioxine-8,8'-[1,3]thiazolo[5,4-e]indol]-7'(6'H)-one

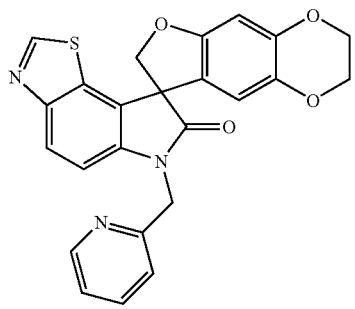

Following the procedure as described in EXAMPLE 9.70 and making non-critical variations using 2,3-dihydrospiro[furo[2,3-g][1,4]-benzodioxine-8,8'-[1,3]thiazolo[5,4-e]indol]-7'(6'H)-one to replace (8S)-2,3-dihydrospiro[furo[2,3-g][1,4]benzodioxine-8,3'-indol]-2'(1'H)-one, and 2-(bromomethyl)pyridine hydrobromide to replace 1-bromo-2-(2-methoxyethoxy)ethane, 6'-(pyridin-2-ylmethyl)-2,3-dihydrospiro[furo[2,3-g][1,4]benzodioxine-8,8'-[1,3]thiazolo[5,4-e]indol]-7'(6'H)-one was obtained (41%) as a colorless solid: mp 156-158° C.; $^1$H NMR (300 MHz, CDCl$_3$) δ 8.75 (s, 1H), 8.60-8.53 (m, 1H), 7.98 (d, J=8.2 Hz, 1H), 7.69-7.61 (m, 1H), 7.32-7.26 (m, 1H), 7.23-7.17 (m, 1H), 7.13 (d, J=8.2 Hz, 1H), 6.56 (s, 1H), 6.30 (s, 1H), 5.17 (ABq, 2H), 4.87 (ABq, 2H), 4.24-4.03 (m, 4H); MS (ES+) m/z 444.1 (M+1).

EXAMPLE 9.73

Synthesis of 4',6'-dimethoxy-1'-[2-(2-methoxyethoxy)ethyl]-2,3-dihydrospiro[furo[2,3-g][1,4]benzodioxine-8,3'-indol]-2'(1'H)-one

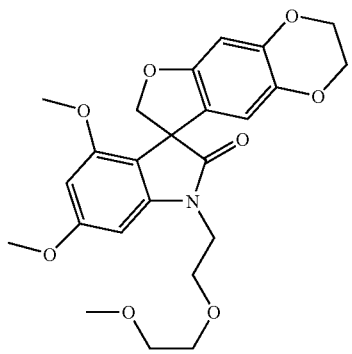

Following the procedure as described in EXAMPLE 9.70 and making non-critical variations using 4',6'-dimethoxy-2,3-dihydrospiro[furo[2,3-g][1,4]benzodioxine-8,3'-indol]-2'(1'H)-one to replace (8S)-2,3-dihydrospiro[furo[2,3-g][1,4]benzodioxine-8,3'-indol]-2'(1'H)-one, 4',6'-dimethoxy-1'-[2-(2-methoxyethoxy)ethyl]-2,3-dihydrospiro[furo[2,3-g][1,4]benzodioxine-8,3'-indol]-2'(1'H)-one was obtained (80%) as a colorless solid: mp 158-160° C.; $^1$H NMR (300 MHz, DMSO-d$_6$) δ 6.43 (s, 1H), 6.33 (d, J=4.2 Hz, 1H), 6.20 (s, 1H), 6.06 (d, J=4.2 Hz, 1H), 4.70-4.46 (m, 2H), 4.19-3.99 (m, 4H), 3.79-3.72 (m, 2H), 3.65-3.52 (m, 4H), 3.52-3.42 (m, 2H), 3.38-3.24 (m, 6H), 3.18-3.11 (m, 3H); $^{13}$C NMR (75 MHz, CDCl$_3$) δ178.8, 162.0, 156.7, 155.6, 155.5, 144.7, 144.1, 137.6, 120.4, 110.9, 109.2, 98.8, 92.9, 89.2, 71.0, 70.4, 68.3, 64.4, 63.9, 59.0, 56.9, 55.6, 55.5, 40.3; MS (ES+) m/z 458.1 (M+1).

EXAMPLE 9.74

Synthesis of 4',6'-dimethoxy-1'-(pyridin-2-ylmethyl)-2,3-dihydrospiro[furo[2,3-g][1,4]benzodioxine-8,3'-indol]-2'(1'H)-one

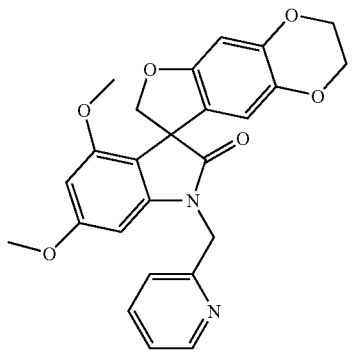

Following the procedure as described in EXAMPLE 9.70 and making non-critical variations using 4',6'-dimethoxy-2,3-dihydrospiro[furo[2,3-g][1,4]benzodioxine-8,3'-indol]-2'(1'H)-one to replace (8S)-2,3-dihydrospiro[furo[2,3-g][1,4]-benzodioxine-8,3'-indol]-2'(1'H)-one, and 2-(bromomethyl)pyridine hydrobromide to replace 1-bromo-2-(2-methoxyethoxy)ethane, 4',6'-dimethoxy-1'-(pyridin-2-ylmethyl)-2,3-dihydrospiro[furo[2,3-g][1,4]benzodioxine-8,3'-indol]-2'(1'H)-one was obtained (78%) as a colorless solid: mp 187-188° C.; $^1$H NMR (300 MHz, DMSO-d$_6$) δ8.59-8.34 (m, 1H), 7.86-7.66 (m, 1H), 7.44-7.19 (m, 2H), 6.51-6.32 (m, 1H), 6.32-6.14 (m, 3H), 5.17-4.80 (m, 2H), 4.79-4.50 (m, 2H), 4.25-3.95 (m, 4H), 3.66 (s, 3H), 3.61 (s, 3H); $^{13}$C NMR (75 MHz, CDCl$_3$) δ178.7, 162.0, 156.7, 155.8, 155.6, 149.4, 144.3, 144.2, 137.7, 137.1, 122.7, 121.5, 120.3, 111.1, 108.9, 98.9, 93.1, 89.5, 64.5, 63.9, 57.1, 55.6, 46.2; MS (ES+) m/z 447.1 (M+1).

EXAMPLE 9.75

Synthesis of 6-(2-methoxyethoxy)-1'-[2-(2-methoxyethoxy)ethyl]spiro[1-benzofuran-3,3'-indol]-2'(1'H)-one

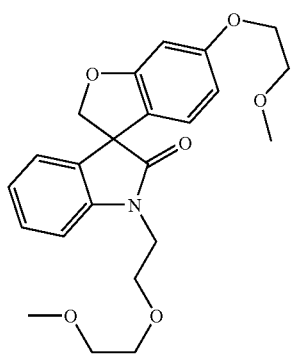

Following the procedure as described in EXAMPLE 9.70 and making non-critical variations using 6-(2-methoxyethoxy)spiro[1-benzofuran-3,3'-indol]-2'(1'H)-one to replace (8S)-2,3-dihydrospiro[furo[2,3-g][1,4]benzodioxine-8,3'-indol]-2'(1'H)-one, 6-(2-methoxyethoxy)-1'-[2-(2-methoxyethoxy)ethyl]spiro[1-benzofuran-3,3'-indol]-2'(1'H)-one was obtained (94%) as a colorless oil: $^1$H NMR (300 MHz, DMSO-d$_6$) δ7.32-7.27 (m, 1H), 7.12 (d, J=7.2 Hz, 1H), 7.07-6.98 (m, 2H), 6.85 (d, J=8.7 Hz, 1H), 6.76 (dd, J=8.7, 2.6 Hz, 1H), 6.32 (d, J=2.6 Hz, 1H), 4.78 (ABq, 2H), 4.08-3.88 (m, 4H), 3.82-3.74 (m, 2H), 3.68-3.59 (m, 4H), 3.52-3.47 (m, 2H), 3.37 (s, 3H), 3.34 (s, 3H); MS (ES+) m/z 414.1 (M+1).

EXAMPLE 9.76

Synthesis of 5-(2-methoxyethoxy)-1'-[2-(2-methoxyethoxy)ethyl]spiro[1-benzofuran-3,3'-indol]-2'(1'H)-one

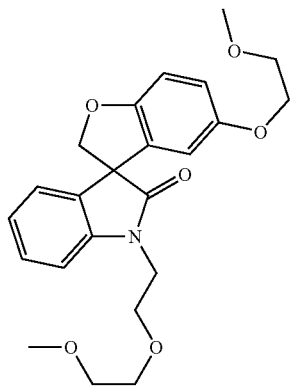

Following the procedure as described in EXAMPLE 9.70 and making non-critical variations using 5-(2-methoxyethoxy)spiro[1-benzofuran-3,3'-indol]-2'(1'H)-one to replace (8S)-2,3-dihydrospiro[furo[2,3-g][1,4]benzodioxine-8,3'-indol]-2'(1'H)-one, 5-(2-methoxyethoxy)-1'-[2-(2-methoxyethoxy)ethyl]spiro[1-benzofuran-3,3'-indol]-2'(1'H)-one was obtained (80%) as a colorless oil: $^1$H NMR (300 MHz, DMSO-d$_6$) δ7.31-7.27 (m, 1H), 7.15-7.10 (m, 1H), 7.06-6.99 (m, 2H), 6.63-6.58 (m, 1H), 6.56-6.53 (m, 1H), 6.42-6.36 (m, 1H), 4.81 (ABq, 2H), 4.11-4.02 (m, 2H), 3.83-3.76 (m, 2H), 3.75-3.70 (m, 2H), 3.69-3.54 (m, 4H), 3.52-3.45 (m, 2H), 3.43 (s, 3H), 3.33 (s, 3H); MS (ES+) m/z 414.1 (M+1).

EXAMPLE 10

Synthesis of 1-(pyridazin-4-ylmethyl)-5,6-dihydrospiro[benzo[1,2-b:5,4-b']difuran-3,3'-indol]-2'(1'H)-one

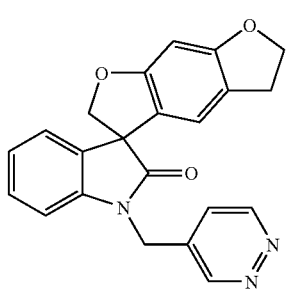

To a stirred suspension of 5,6-dihydro-2H-spiro[benzofuro[6,5-b]furan-3,3'-indolin]-2'-one (0.20 g, 0.72 mmol) and pyridazin-4-ylmethanol (0.08 g, 0.72 mmol) in dry tetrahydrofuran (5 mL) was added at 0° C. tributylphosphine (0.27 mL, 1.1 mmol), followed by N,N,N',N'-tetramethylazodicarboxamide (0.19 g, 1.1 mmol). The mixture was stirred at 0° C. for 15 min and at ambient temperature for 64 h. Saturated aqueous solution of ammonium chloride (10 mL) was added and the mixture was extracted with ethyl acetate (4×100 mL). The combined organic solution was washed with water (2×60 mL), brine (100 mL), dried over anhydrous magnesium sulfate, filtered, and concentrated in vacuo. The residue was purified by column chromatography (hexanes/ethyl acetate from 1:1 to 1:3) to afford 1-(pyridazin-4-ylmethyl)-5,6-dihydrospiro[benzo[1,2-b:5,4-b']difuran-3,3'-indol]-2'(1'H)-one (0.03 g, 11%): mp 187-189° C.; $^1$H NMR (300 MHz, CDCl$_3$) δ 9.25-9.16 (m, 2H), 7.44-7.39 (m, 1H), 7.29-7.21 (m, 2H), 7.14-7.07 (m, 1H), 6.74-6.69 (m, 1H), 6.47 (s, 1H), 6.44 (s, 1H), 5.00 (ABq, 2H), 4.85 (ABq, 2H), 4.60-4.52 (m, 2H), 3.11-2.93 (m, 2H); $^{13}$C NMR (75 MHz, CD$_3$OD) δ178.1, 162.1, 161.4, 151.3, 150.7, 141.0, 135.5, 132.5, 129.0, 124.7, 124.5, 124.3, 120.2, 119.5, 118.7, 108.4, 93.4, 80.6, 72.4, 57.7, 41.0, 29.0; MS (ES+) m/z 372.3 (M+1);

EXAMPLE 11

Synthesis of 1'-[(2-chloro-1,3-thiazol-5-yl)methyl]spiro[furo[2,3-f][1,3]benzodioxole-7,3'-indol]-2'(1'H)-one

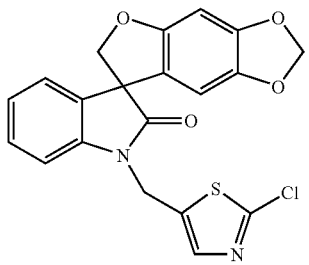

A mixture of 2-bromothiazole-5-methanol (0.80 g, 4.12 mmol) in thionyl chloride (10 mL) was refluxed for 3 h, and the mixture was evaporated to dryness and dried in vacuo. The residue was re-dissolved in 2-butanone (15 mL), followed by addition of cesium carbonate (2.61 g, 8.0 mmol) and spiro[furo[2,3-f][1,3]benzodioxole-7,3'-indol]-2'(1'H)-one (1.12 g, 4.0 mmol). The reaction mixture was refluxed for 16 h, then concentrated to dryness in vacuo. The residue was taken up in ethyl acetate (200 mL), washed by water (50 mL) and brine (50 mL). The organic phase was dried over sodium sulfate, filtered, and the filtrate was concentrated to dryness. The residue was purified by flash chromatography with 25% ethyl acetate in hexanes to afford 1'-[(2-chloro-1,3-thiazol-5-yl)methyl]spiro[furo[2,3-f][1,3]benzodioxole-7,3'-indol]-2'(1'H)-one (0.70 g, 38%) as a colorless solid: $^1$H NMR (300 MHz, CDCl$_3$) δ 7.58 (s, 1H), 7.30 (ddd, J=7.5, 7.5, 1.2 Hz, 1H), 7.22-7.17 (m, 1H), 7.09 (ddd, J=7.5, 7.5, 0.9 Hz, 1H), 6.91 (d, J=7.8 Hz, 1H), 6.52 (s, 1H), 6.09 (s, 1H), 5.90-5.86 (m, 2H), 5.16-5.08 (m, 1H), 4.97 (d, J=15.9 Hz, 1H), 4.92 (d, J=9.0 Hz, 1H), 4.66 (d, J=9.0 Hz, 1H); MS (ES+) m/z 413.0 (M+1), 415.0 (M+1).

EXAMPLE 11.1

Synthesis of 1'-{[2-(dimethylamino)-1,3-thiazol-5-yl]methyl}spiro[furo[2,3-f][1,3]benzodioxole-7,3'-indol]-2'(1'H)-one

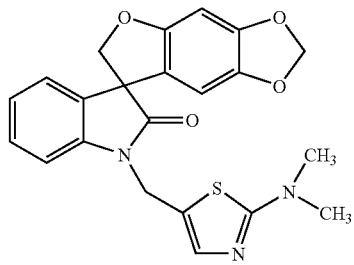

To a solution of 1'-[(2-chloro-1,3-thiazol-5-yl)methyl]spiro[furo[2,3-f][1,3]benzodioxole-7,3'-indol]-2'(1'H)-one (0.10 g, 0.24 mmol) in N,N-dimethylformamide (5 mL) was added 2 M dimethyl amine in tetrahydrofuran (2.0 mL, 4.0 mmol) under nitrogen in a sealed tube. The reaction mixture was heated at 120° C. for 16 h. The reaction was quenched with the water, then extracted with ethyl acetate (2×50 mL). The combined organic solution was dried over sodium sulfate, filtered, and the filtrate was concentrated to dryness. The residue was purified by flash chromatography with 30% ethyl acetate in hexanes to afford 1'-{[2-(dimethylamino)-1,3-thiazol-5-yl]methyl}spiro[furo[2,3-f][1,3]benzodioxole-7,3'-indol]-2'(1'H)-one (0.08 g, 76%) as a colorless solid: mp 200-202° C.; $^1$H NMR (300 MHz, CDCl$_3$) δ 7.27 (ddd, J=7.5, 7.5, 0.9 Hz, 1H), 7.20 (s, 1H), 7.15 (d, J=7.5 Hz, 1H), 7.08-6.95 (m, 2H), 6.51 (s, 1H), 6.14 (s, 1H), 5.91-5.84 (m, 2H), 5.05 (d, J=15.6 Hz, 1H), 4.93 (d, J=9.0 Hz, 1H), 4.84 (d, J=15.6 Hz, 1H), 4.65 (d, J=9.0 Hz, 1H), 3.06 (s, 6H); $^{13}$C NMR (75 MHz, CDCl$_3$) δ177.2, 172.0, 156.1, 149.0, 142.5, 141.5, 139.1, 132.4, 129.1, 124.1, 123.7, 119.7, 119.5, 109.2, 103.3, 101.6, 93.7, 80.5, 58.2, 40.4, 37.2; MS (ES+) m/z 422.1 (M+1).

EXAMPLE 11.2

Synthesis of 1'-[(2-morpholin-4-yl-1,3-thiazol-5-yl)methyl]spiro[furo[2,3-f][1,3]benzodioxole-7,3'-indol]-2'(1'H)-one

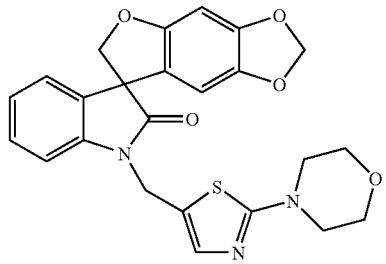

Following the procedure as described in EXAMPLE 11.1 and making non-critical variations using morpholine to replace dimethyl amine, 1'-[(2-morpholin-4-yl-1,3-thiazol-5-yl)methyl]spiro[furo[2,3-f][1,3]benzodioxole-7,3'-indol]-2'(1'H)-one was obtained (71%) as a colorless solid: mp 97-99° C.; $^1$H NMR (300 MHz, CDCl$_3$) δ 7.28 (dd, J=7.5, 7.5, Hz, 1H), 7.23 (s, 1H), 7.16 (d, J=7.5 Hz, 1H), 7.05 (dd, J=7.5, 7.5 Hz, 1H), 6.97 (d, J=7.5 Hz, 1H), 6.51 (s, 1H), 6.11 (s, 1H), 5.91-5.84 (m, 2H), 5.05 (d, J=15.6 Hz, 1H), 4.92 (d, J=9.0 Hz, 1H), 4.85 (d, J=15.6 Hz, 1H), 4.64 (d, J=9.0 Hz, 1H), 3.78 (t, J=4.8 Hz, 4H), 3.43 (t, J=4.8 Hz, 4H); $^{13}$C NMR (75 MHz, CDCl$_3$) δ 177.3, 172.3, 156.1, 149.1, 142.5, 141.4, 138.6, 132.4, 129.1, 124.2, 123.8, 120.9, 119.4, 109.1, 103.3, 101.7, 93.8, 80.5, 66.2, 58.2, 48.6, 37.0; MS (ES+) m/z 464.1 (M+1).

EXAMPLE 11.3

Synthesis of 1'-[(2-piperidin-1-yl-1,3-thiazol-5-yl)methyl]spiro[furo[2,3-f][1,3]benzodioxole-7,3'-indol]-2'(1'H)-one

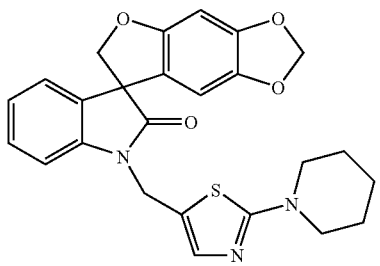

Following the procedure as described in EXAMPLE 11.1 and making non-critical variations using piperidine to replace dimethyl amine, 1'-[(2-piperidin-1-yl-1,3-thiazol-5-yl)methyl]spiro[furo[2,3-f][1,3]benzodioxole-7,3'-indol]-2'(1'H)-one was obtained (98%) as a colorless solid: mp 195-197° C.; $^1$H NMR (300 MHz, CDCl$_3$) δ7.27 (ddd, J=7.5, 7.5, 0.9 Hz, 1H), 7.17 (s, 1H), 7.16 (d, J=7.5 Hz, 1H), 7.04 (dd, J=7.5, 7.5 Hz, 1H), 6.98 (d, J=7.5 Hz, 1H), 6.51 (s, 1H), 6.14 (s, 1H), 5.90-5.84 (m, 2H), 5.04 (d, J=15.6 Hz, 1H), 4.92 (d, J=9.0 Hz, 1H), 4.85 (d, J=15.6 Hz, 1H), 4.65 (d, J=9.0 Hz, 1H), 3.46-3.36 (m, 4H), 1.70-1.57 (m, 6H); $^{13}$C NMR (75 MHz, CDCl$_3$) δ177.2, 172.3, 156.1, 149.0, 142.5, 141.5, 138.6, 132.4, 129.1, 124.1, 123.7, 119.5, 119.4, 109.2, 103.3, 101.6, 93.7, 80.5, 58.2, 49.8, 37.1, 25.1, 24.1; MS (ES+) m/z 462.1 (M+1).

EXAMPLE 11.4

Synthesis of 1'-[(2-methoxy-1,3-thiazol-5-yl)methyl]spiro[furo[2,3-f][1,3]benzodioxole-7,3'-indol]-2'(1'H)-one

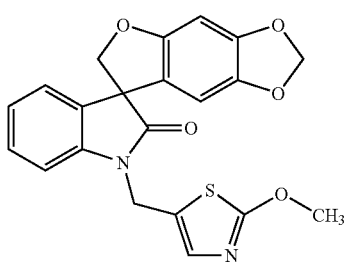

Following the procedure as described in EXAMPLE 11.1 and making non-critical variations using sodium methoxide to replace dimethyl amine, 1'-[(2-methoxy-1,3-thiazol-5-yl)methyl]spiro[furo[2,3-f][1,3]benzodioxole-7,3'-indol]-2'(1'H)-one was obtained (19%) as a colorless solid: mp 164-166° C.; $^1$H NMR (300 MHz, CDCl$_3$) δ 7.28 (ddd, J=7.5, 7.5, 1.2 Hz, 1H), 7.20-7.13 (m, 2H), 7.06 (dd, J=7.5, 7.5 Hz, 1H), 6.95 (d, J=8.1 Hz, 1H), 6.51 (s, 1H), 6.11 (s, 1H), 5.90-5.84 (m, 2H), 5.05 (d, J=15.6 Hz, 1H), 4.92 (d, J=9.0 Hz, 1H), 4.85 (d, J=15.6 Hz, 1H), 4.65 (d, J=9.0 Hz, 1H), 4.03 (s, 3H); $^{13}$C NMR (75 MHz, CDCl$_3$) δ177.2, 175.7, 156.1, 149.1, 142.5, 141.3, 136.2, 132.4, 129.1, 124.7, 124.3, 123.9, 119.3, 108.9, 103.2, 101.7, 93.8, 80.5, 58.4, 58.2, 37.2; MS (ES+) m/z 409.1 (M+1).

EXAMPLE 11.5

Synthesis of 1-(piperidin-4-ylmethyl)-5,6-dihydrospiro[benzo[1,2-b:5,4-b']difuran-3,3'-indol]-2'(1'H)-one

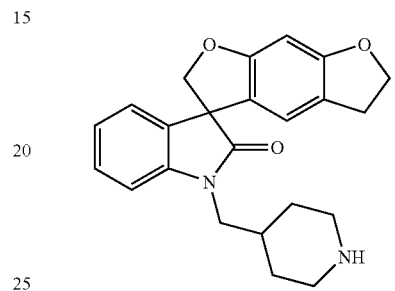

A solution of tert-butyl 4-[(2'-oxo-5,6-dihydrospiro[benzo[1,2-b:5,4-b']difuran-3,3'-indol]-1'(2'H)-yl)methyl]piperidine-1-carboxylate (0.94 g, 1.98 mmol) and trifluoroacetic acid (2 mL) in dichloromethane (10 mL) was stirred at ambient temperature for 1.5 h. The reaction was made basic with 1 M sodium hydroxide solution (30 mL) and extracted with dichloromethane (3×25 mL). The combined organic solution was dried over sodium sulfate, filtered and concentrated under reduced pressure to afford 1-(piperidin-4-ylmethyl)-5,6-dihydrospiro[benzo[1,2-b:5,4-b']difuran-3,3'-indol]-2'(1'H)-one (0.73 g, 98%) as a colorless solid: $^1$H NMR (300 MHz, CDCl$_3$) δ7.30 (dd, J=7.8, 7.5 Hz, 1H), 7.16 (d, J=6.9 Hz, 1H), 7.05 (dd, J=7.5, 7.5 Hz, 1H), 6.90 (d, J=7.8 Hz, 1H), 6.45 (s, 1H), 6.41 (s, 1H), 4.91 (d, J=8.9 Hz, 1H), 4.66 (d, J=8.9 Hz, 1H), 4.54 (t, J=8.6 Hz, 2H), 3.71 (dd, J=13.9, 7.5 Hz, 1H), 3.57 (dd, J=13.9, 7.1 Hz, 1H), 3.21-3.11 (m, 2H), 2.99 (td, J=8.7, 2.7 Hz, 2H), 2.74 (br s, 1H), 2.67-2.56 (m, 2H), 2.08-1.94 (m, 1H), 1.77-1.66 (m, 2H), 1.44-1.30 (m, 2H).

EXAMPLE 11.6

Synthesis of 1'-{[1-(1-methylethyl)piperidin-4-yl]methyl}-5,6-dihydrospiro[benzo[1,2-b:5,4-b']difuran-3,3'-indol]-2'(1'H)-one

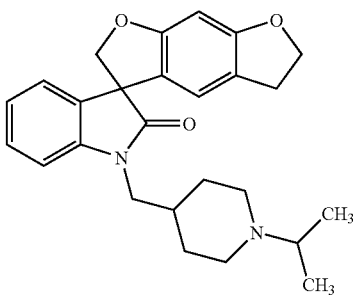

A solution of 1'-(piperidin-4-ylmethyl)-5,6-dihydrospiro[benzo[1,2-b:5,4-b']difuran-3,3'-indol]-2'(1'H)-one (0.29 g, 0.77 mmol), acetone (0.10 mL, 1.4 mmol), sodium cyanoborohydride (0.10 g, 1.51 mmol) and acetic acid (6 drops) in methanol (4 mL), sealed in a well-stoppered round-bottomed flask, was stirred at 60° C. for 16 h. The reaction was cooled, diluted with saturated aqueous sodium bicarbonate (30 mL) and extracted with dichloromethane (3×25 mL). The organic solution was dried over sodium sulfate, filtered and concentrated under reduced pressure. Purification by flash column chromatography with dichloromethane/methanol (14:1) afforded 1'-{[1-(1-methylethyl)piperidin-4-yl]methyl}-5,6-dihydrospiro[benzo[1,2-b:5,4-b']difuran-3,3'-indol]-2'(1'H)-one (0.21 g, 64%) as a colorless foam: $^1$H NMR (300 MHz, CD$_3$OD) δ 7.33 (ddd, J=7.8, 7.5, 0.9 Hz, 1H), 7.14-7.05 (m, 3H), 6.44 (s, 1H), 6.32 (s, 1H), 4.81 (d, J=9.2 Hz, 1H), 4.65 (d, J=9.2 Hz, 1H), 4.99 (t, J=8.7 Hz, 2H), 3.74 (dd, J=14.0, 7.2 Hz, 1H), 3.65 (dd, J=14.0, 7.1 Hz, 1H), 3.02-2.91 (m, 4H), 2.77 (septet, J=6.6 Hz, 1H), 2.30-2.18 (m, 2H), 2.00-1.84 (m, 1H), 1.81-1.71 (m, 2H), 1.50-1.34 (m, 2H), 1.08 (d, J=6.6 Hz, 6H); $^{13}$C NMR (75 MHz, CD$_3$OD) δ180.3, 163.2, 162.9, 144.1, 134.1, 123.0, 124.8, 124.6, 121.6, 121.4, 120.0, 110.5, 93.7, 81.7, 73.5, 59.2, 56.2, 49.5, 49.4, 46.6, 36.0, 30.7 (2C), 29.9, 18.3, 18.3; MS (ES+) m/z 419.2 (M+1).

EXAMPLE 11.7

Synthesis of 1'-{[1-(1-methylethyl)piperidin-4-yl]methyl}-5,6-dihydrospiro[benzo[1,2-b:5,4-b']difuran-3,3'-indol]-2'(1'H)-one hydrochloride

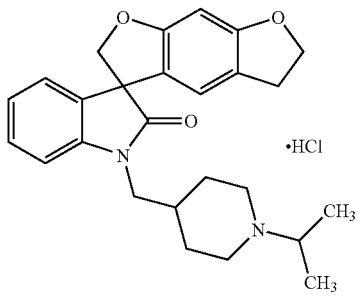

A solution of 1'-{[1-(1-methylethyl)piperidin-4-yl]methyl}-5,6-dihydrospiro[benzo-[1,2-b:5,4-b']difuran-3,3'-indol]-2'(1'H)-one (0.21 g, 0.49 mmol) and 4 M hydrochloric acid in 1,4-dioxane (0.50 mL, 2.0 mmol) in methanol (1.5 mL) was stirred at ambient temperature for 30 min. The solvent was removed under reduced pressure, the residue was suspended in ethyl acetate/hexanes and the resulting precipitate was collected by filtration. The precipitate was dried to afford 1-{[1-(1-methylethyl)piperidin-4-yl]methyl}-5,6-dihydrospiro[benzo[1,2-b:5,4-b']difuran-3,3'-indol]-2'(1'H)-one hydrochloride (0.17 g, 76%) as a colorless powder: mp 167° C. (dec.) (hexanes); $^1$H NMR (300 MHz, CD$_3$OD) δ7.36 (ddd, J=7.8, 7.2, 1.2 Hz, 1H), 7.19-7.08 (m, 3H), 6.48 (s, 1H), 6.33 (s, 1H), 4.83 (d, J=9.3 Hz, 1H), 4.67 (d, J=9.3 Hz, 1H), 4.51 (t, J=8.6 Hz, 2H), 3.80 (dd, J=14.3, 7.5 Hz, 1H), 3.73 (dd, J=14.3, 7.1 Hz, 1H), 3.54-3.42 (m, 3H), 3.07-2.96 (m, 4H), 2.31-2.16 (m, 1H), 2.09-1.98 (m, 2H), 1.76-1.60 (m, 2H), 1.35 (d, J=6.6 Hz, 6H); $^{13}$C NMR (75 MHz, CD$_3$OD) δ180.4, 163.3, 162.9, 143.8, 134.0, 130.1, 124.9, 124.8, 121.5 (2C), 120.1, 110.4, 93.7, 81.8, 73.5, 59.7, 59.3, 49.5, 45.8, 34.1, 29.9, 28.7, 28.67, 17.0; MS (ES+) m/z 419.3 (M+1); Anal.

Calcd. for $C_{26}H_{30}N_2O_3 \cdot HCl \cdot 2H_2O$: C, 63.60; H, 7.18; N, 5.71. Found: C, 63.80; H, 6.83; N, 5.67.

EXAMPLE 11.8

Synthesis of 1'-[(1-ethylpiperidin-4-yl)methyl]-5,6-dihydrospiro[benzo[1,2-b:5,4-b']difuran-3,3'-indol]-2'(1'H)-one

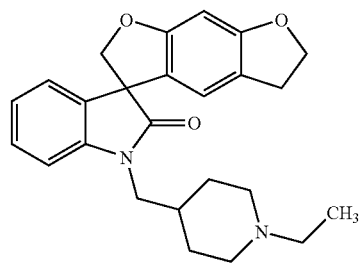

A mixture of 1'-(piperidin-4-ylmethyl)-5,6-dihydrospiro[benzo[1,2-b:5,4-b']difuran-3,3'-indol]-2'(1'H)-one (0.37 g, 0.99 mmol), acetaldehyde (0.08 mL, 1.4 mmol) and sodium triacetoxyborohydride (0.32 g, 1.51 mmol) in 1,2-dichloroethane (4 mL) was stirred at ambient temperature for 17.5 h. The orange reaction mixture was diluted with saturated aqueous sodium bicarbonate (30 mL) and was extracted with dichloromethane (3×25 mL). The organic solution was dried over sodium sulfate, filtered and concentrated under reduced pressure. Purification by flash column chromatography with dichloromethane/methanol (19:1) afforded 1'-[(1-ethylpiperidin-4-yl)methyl]-5,6-dihydrospiro[benzo[1,2-b:5,4-b']difuran-3,3'-indol]-2'(1'H)-one (0.32 g, 80%) as a yellow foam: $^1$H NMR (300 MHz, CDCl$_3$) δ7.29 (ddd, J=7.8, 7.8, 1.4 Hz, 1H), 7.15 (dd, J=7.5, 0.9 Hz, 1H), 7.04 (ddd, J=7.5, 7.5, 0.8 Hz, 1H), 6.90 (d, J=8.1 Hz, 1H), 6.45 (s, 1H), 6.41 (s, 1H), 4.90 (d, J=9.0 Hz, 1H), 4.66 (d, J=9.0 Hz, 1H), 4.53 (t, J=8.6 Hz, 2H), 3.73 (dd, J=14.0, 7.4 Hz, 1H), 3.60 (dd, J=14.0, 7.1 Hz, 1H), 3.10-2.95 (m, 4H), 2.52 (q, J=7.1 Hz, 2H), 2.14-1.87 (m, 3H), 1.83-1.72 (m, 2H), 1.67-1.52 (m, 2H), 1.15 (t, J=7.1 Hz, 3H); $^{13}$C NMR (75 MHz, CDCl$_3$) δ178.2, 161.9, 161.5, 143.0, 132.9, 128.9, 124.1, 123.4, 120.3, 120.0, 118.9, 108.8, 93.4, 80.9, 72.5, 57.8, 52.6, 45.8, 34.5, 29.6, 29.5, 29.2, 11.7; MS (ES+) m/z 405.2 (M+1).

EXAMPLE 11.9

Synthesis of 1'-[(1-ethylpiperidin-4-yl)methyl]-5,6-dihydrospiro[benzo[1,2-b:5,4-b']difuran-3,3'-indol]-2'(1'H)-one hydrochloride

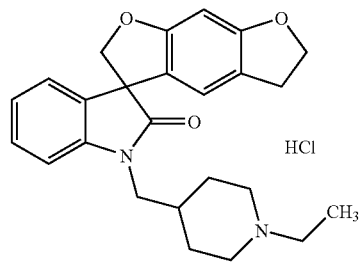

A solution of 1'-[(1-ethylpiperidin-4-yl)methyl]-5,6-dihydrospiro[benzo[1,2-b:5,4-b']difuran-3,3'-indol]-2'(1'H)-one (0.17 g, 0.41 mmol) and hydrogen chloride (4.0 M in 1,4-dioxane, 0.40 mL, 1.6 mmol) in methanol (1.0 mL) was stirred at ambient temperature for 35 min. The solvent was removed under reduced pressure, the residue was suspended in ethyl acetate/hexanes and the precipitate was collected by filtration and washed with hexanes. The precipitate was dried to afford 1'-[(1-ethylpiperidin-4-yl)methyl]-5,6-dihydrospiro[benzo[1,2-b:5,4-b']difuran-3,3'-indol]-2'(1'H)-one hydrochloride (0.18 g, 100%) as an off-white powder: mp 135° C. (dec.) (hexanes); $^1$H NMR (300 MHz, CD$_3$OD) δ7.36 (dd, J=6.9, 6.6 Hz, 1H), 7.20-7.07 (m, 3H), 6.49 (s, 1H), 6.32 (s, 1H), 4.83 (d, J=9.2 Hz, 1H), 4.67 (d, J=9.2 Hz, 1H), 4.50 (t, J=8.3 Hz, 2H), 3.84-3.68 (m, 2H), 3.65-3.54 (m, 2H), 3.21-3.10 (m, 2H), 3.02-2.87 (m, 4H), 2.31-2.16 (m, 1H), 2.08-1.95 (m, 2H), 1.76-1.58 (m, 2H), 1.35 (t, J=6.2 Hz, 3H); $^{13}$C NMR (75 MHz, CD$_3$OD) δ180.4, 163.2, 162.9, 143.8, 133.9, 130.1, 124.9, 124.8, 121.5 (2C), 120.1, 110.5, 93.7, 81.8, 73.5, 59.2, 53.4, 53.0, 45.9, 34.0, 29.9, 28.7 (2C), 9.7; MS (ES+) m/z 405.2 (M+1).

EXAMPLE 11.10

Synthesis of 1'-[(1-methylpiperidin-4-yl)methyl]-5,6-dihydrospiro[benzo[1,2-b:5,4-b']difuran-3,3'-indol]-2'(1'H)-one

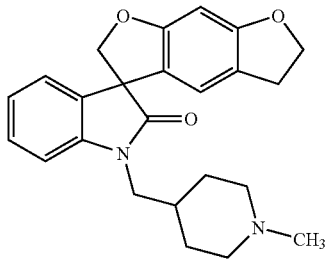

A mixture of 1'-(piperidin-4-ylmethyl)-5,6-dihydrospiro[benzo[1,2-b:5,4-b']difuran-3,3'-indol]-2'(1'H)-one (0.354 g, 0.94 mmol), formaldehyde solution (37% in water, 0.80 mL, 10.6 mmol) and formic acid (0.80 mL, 21.2 mmol) in water (2 mL) was stirred at 80° C. for 14.5 h. The reaction was diluted with 1 M sodium hydroxide (25 mL) and extracted with dichloromethane (3×25 mL). The organic solution was dried over sodium sulfate, filtered and concentrated under reduced pressure. Purification by flash column chromatography with methanol/dichloromethane/ammonium hydroxide (32:1:0.17, increased to 19:1:0.2) afforded 1-[(1-methylpiperidin-4-yl)methyl]-5,6-dihydrospiro[benzo[1,2-b:5,4-b']difuran-3,3'-indol]-2'(1'H)-one (0.18 g, 48%) as a colorless solid: mp 155-158° C. (hexanes); $^1$H NMR (300 MHz, CDCl$_3$) δ7.30 (dd, J=7.8, 7.5 Hz, 1H), 7.16 (d, J=6.9 Hz, 1H), 7.04 (dd, J=7.5, 7.2 Hz, 1H), 6.89 (d, J=7.8 Hz, 1H), 6.45 (s, 1H), 6.41 (s, 1H), 4.91 (d, J=9.0 Hz, 1H), 4.66 (d, J=9.0 Hz, 1H), 4.54 (t, J=8.6 Hz, 2H), 3.72 (dd, J=14.0, 7.4 Hz, 1H), 3.58 (dd, J=14.0, 6.9 Hz, 1H), 2.99 (td, J=8.3, 1.2 Hz, 2H), 2.91-2.82 (m, 2H), 2.27 (s, 3H), 1.97-1.80 (m, 3H), 1.75-1.65 (m, 2H), 1.53-1.38 (m, 2H); $^{13}$C NMR (75 MHz, CDCl$_3$) δ178.1, 161.9, 161.5, 143.0, 133.0, 128.8, 124.1, 123.3, 120.3, 120.0, 118.9, 108.7, 93.3, 80.9, 72.5, 57.7, 55.3, 46.5, 46.1, 34.3, 30.3, 29.2; MS (ES+) m/z 391.2 (M+1); Anal. Calcd. for C$_{24}$H$_{26}$N$_2$O$_3$: C, 73.82; H, 6.71; N, 7.17. Found: C, 73.46; H, 7.10; N, 7.22.

EXAMPLE 11.11

Synthesis of 1'-[(2S)-pyrrolidin-2-ylmethyl]-5,6-dihydrospiro[benzo[1,2-b:5,4-b']difuran-3,3'-indol]-2'(1'H)-one

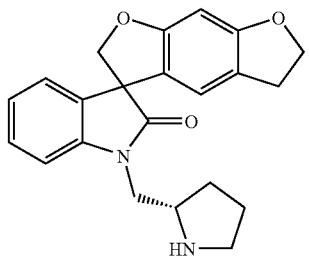

Following the procedure described in EXAMPLE 11.5 and making non-critical variations using tert-butyl (2S)-2-[(2'-oxo-5,6-dihydrospiro[benzo[1,2-b:5,4-b']difuran-3,3'-indol]-1'(2'H)-yl)methyl]pyrrolidine-1-carboxylate to replace tert-butyl 4-[(2'-oxo-5,6-dihydrospiro[benzo[1,2-b:5,4-b']difuran-3,3'-indol]-1'(2'H)-yl)methyl]piperidine-1-carboxylate, tetrahydrofuran to replace dichloromethane, 1'-[(2S)-pyrrolidin-2-ylmethyl]-5,6-dihydrospiro[benzo[1,2-b:5,4-b']difuran-3,3'-indol]-2'(1'H)-one was obtained (89%) as a pale yellow solid: mp 83-86° C. (hexanes); $^1$H NMR (300 MHz, CDCl$_3$) (diastereomers) δ7.29 (dd, J=7.8, 7.5 Hz, 1H), 7.16 (d, J=7.5 Hz, 1H), 7.07-6.99 (m, 2H), 6.52, 6.46 (s, 1H), 6.40 (s, 1H), 4.95, 4.91 (d, J=9.0 Hz, 1H), 4.66 (d, J=9.0 Hz, 1H), 4.53 (t, J=8.7 Hz, 2H), 3.91-3.71 (m, 2H), 3.69-3.60 (m, 1H), 3.14-2.90 (m, 5H), 1.98-1.70 (m, 3H), 1.66-1.51 (m, 1H); MS (ES+) m/z 363.1 (M+1).

EXAMPLE 11.12

Synthesis of 3-[(2'-oxo-5,6-dihydrospiro[benzo[1,2-b:5,4-b']difuran-3,3'-indol]-1'(2'H)-yl)methyl]benzoic acid

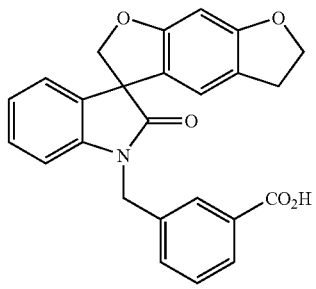

To a solution of methyl 3-[(2'-oxo-5,6-dihydrospiro[benzo[1,2-b:5,4-b']difuran-3,3'-indol]-1'(2'H)-yl)methyl]benzoate (2.80 g, 6.5 mmol) in tetrahydrofuran (30 mL) and water (10 mL) was added lithium hydroxide monohydrate (0.82 g, 19 mmol). The reaction mixture was stirred at ambient temperature for 16 h. Most of the tetrahydrofuran was removed in vacuo and the resultant solution was washed with diethyl ether (2×50 mL). The aqueous phase was rendered acidic to litmus by the addition of 1 M hydrochloric acid and extracted with ethyl acetate (3×50 mL). The combined organic solution was dried over anhydrous sodium sulfate, filtered and concentrated in vacuo. The residue was triturated with diethyl ether (50 mL) and the solid was collected by vacuum filtration, washed with diethyl ether (20 mL), air-dried and dried under high vacuum to afford 3-[(2'-oxo-5,6-dihydrospiro[benzo[1,2-b:5,4-b']difuran-3,3'-indol]-1'(2'H)-yl)methyl]benzoic acid (2.20 g, 81%) as a colorless solid: mp>250° C. (water); $^1$H NMR (300 MHz, DMSO-$d_6$) δ13.06 (br s, 1H), 7.89-7.82 (m, 2H), 7.66 (d, J=7.6 Hz, 1H), 7.55-7.47 (m, 1H), 7.29-7.16 (m, 2H), 7.07-6.96 (m, 2H), 6.49 (s, 1H), 6.42 (s, 1H), 5.17-4.72 (m, 4H), 4.55-4.45 (m, 2H), 3.06-2.88 (m, 2H); $^{13}$C NMR (75 MHz, DMSO-$d_6$) δ177.2, 167.1, 161.2, 160.7, 142.0, 136.9, 132.2, 131.8, 131.2, 129.1, 128.8, 128.4, 127.3, 123.8, 123.2, 120.5, 120.0, 118.9, 109.3, 92.5, 79.7, 72.1, 57.0, 42.5; MS (ES+) m/z 414.0 (M+1).

EXAMPLE 11.13

Synthesis of 1'-{4-[5-(trifluoromethyl)-1,2,4-oxadiazol-3-yl]benzyl}-5,6-dihydrospiro[benzo[1,2-b:5,4-b']difuran-3,3'-indol]-2'(1'H)-one

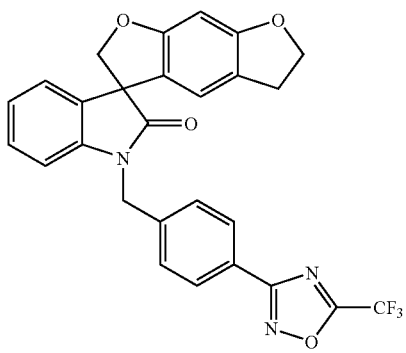

A stirred solution of N'-hydroxy-4-[(2'-oxo-5,6-dihydrospiro[benzo[1,2-b:5,4-b']difuran-3,3'-indol]-1'(2'H)-yl)methyl]benzenecarboximidamide (0.40 g, 0.94 mmol) and trifluoroacetic anhydride (0.4 mL) in pyridine (2 mL) was heated at 170° C. in a microwave reactor for 30 min. The solution was concentrated in vacuo to dryness, purified by flash chromatography with ethyl acetate in hexanes (20% to 40% gradient) to afford 1'-{4-[5-(trifluoromethyl)-1,2,4-oxadiazol-3-yl]benzyl}-5,6-dihydrospiro[benzo[1,2-b:5,4-b']difuran-3,3'-indol]-2'(1'H)-one (0.34 g, 71%) as a colorless solid: mp 178-179° C.; $^1$H NMR (300 MHz, CDCl$_3$) δ8.09 (d, J=8.2 Hz, 2H), 7.49 (d, J=8.2 Hz, 2H), 7.24-7.16 (m, 2H), 7.04 (dd, J=7.5, 7.5 Hz, 1H), 6.76 (d, J=7.7 Hz, 1H), 6.48 (s, 1H), 6.42 (s, 1H), 5.15 (d, J=15.9 Hz, 1H), 4.99 (d, J=9.0 Hz, 1H), 4.90 (d, J=15.9 Hz, 1H), 4.71 (d, J=9.0 Hz, 1H), 4.54 (t, J=8.62 Hz, 2H), 3.07-2.93 (m, 2H); $^{13}$C NMR (75 MHz, CDCl$_3$) δ194.7, 178.0, 168.8, 162.0, 161.4, 141.8, 140.4, 132.7, 128.8, 128.3, 128.1, 124.5, 124.1, 123.7, 120.0, 118.8, 116.0 (q, J=273.8 Hz), 109.1, 93.4, 80.7, 72.4, 57.8, 43.9, 29.1; MS (ES+) m/z 506.0 (M+1).

EXAMPLE 11.14

Synthesis of 1'-[4-(5-methyl-1,2,4-oxadiazol-3-yl)benzyl]-5,6-dihydrospiro[benzo[1,2-b:5,4-b']difuran-3,3'-indol]-2'(1'H)-one

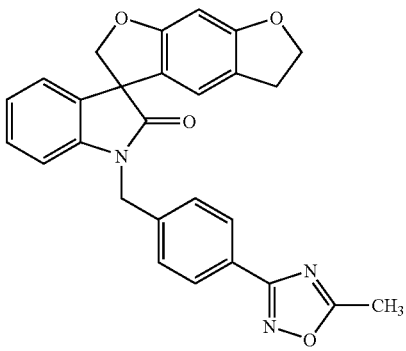

Following the procedure as described in EXAMPLE 11.13 and making non-critical variations using acetyl chloride to replace trifluoroacetic anhydride, 1'-[4-(5-methyl-1,2,4-oxadiazol-3-yl)benzyl]-5,6-dihydrospiro[benzo[1,2-b:5,4-b']difuran-3,3'-indol]-2'(1'H)-one was obtained (82%) as a colorless solid: mp 185-186° C.; $^1$H NMR (300 MHz, CDCl$_3$) δ8.03 (d, J=8.1 Hz, 2H), 7.44 (d, J=8.0 Hz, 2H), 7.25-7.14 (m, 2H), 7.02 (dd, J=7.5, 7.5 Hz, 1H), 6.77 (d, J=8.2 Hz, 1H), 6.47 (s, 1H), 6.42 (s, 1H), 5.13 (d, J=15.8 Hz, 1H), 4.98 (d, J=9.0 Hz, 1H), 4.86 (d, J=15.8 Hz, 1H), 4.71 (d, J=9.0 Hz, 1H), 4.53 (t, J=8.6 Hz, 2H), 3.10-2.89 (m, 2H), 2.63 (s, 3H); $^{13}$C NMR (75 MHz, CDCl$_3$) δ178.0, 176.7, 168.0, 161.9, 161.4, 141.9, 139.0, 132.7, 128.8, 127.9 (2C), 126.4, 124.0, 123.6, 120.1, 120.0, 118.8, 109.0, 93.3, 80.6, 72.4, 57.8, 43.9, 29.1, 12.4; MS (ES+) m/z 451.9 (M+1).

EXAMPLE 11.15

Synthesis of 1'-[(5-pyridin-4-ylfuran-2-yl)methyl]-5,6-dihydrospiro[benzo[1,2-b:5,4-b']difuran-3,3'-indol]-2'(1'H)-one

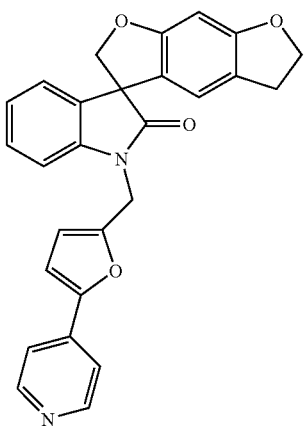

A mixture of 1-[(5-bromofuran-2-yl)methyl]-5,6-dihydrospiro[benzo[1,2-b:5,4-b']difuran-3,3'-indol]-2'(1'H)-one (0.22 g, 0.5 mmol), pyridin-4-ylboronic acid (0.09 g, 0.75 mmol), tetrakis(triphenylphosphine) palladium (0.06 g, 0.05 mmol) and sodium carbonate (1 mL of 2 M water solution, 2.0 mmol) in N,N-dimethylformamide (4 mL) was heated in microwave reactor at 150° C. for 15 min. The reaction mixture was subjected to column chromatography with ethyl acetate/hexanes (1:1) to afford 1'-[(5-pyridin-4-ylfuran-2-yl)methyl]-5,6-dihydrospiro[benzo[1,2-b:5,4-b']difuran-3,3'-indol]-2'(1'H)-one (0.15 g, 66%) as a colorless solid: $^1$H NMR (300 MHz, CDCl$_3$) δ 8.55 (s, 2H), 7.52-7.00 (m, 6H), 6.83 (d, J=3.4 Hz, 1H), 6.48 (d, J=3.4 Hz, 1H), 6.40 (s, 1H), 6.38 (s, 1H), 5.00 (ABq, 2H), 4.81 (ABq, 2H), 4.52-4.44 (m, 2H), 2.87 (t, J=8.6 Hz, 2H); $^{13}$C NMR (75 MHz, CDCl$_3$) δ 177.5, 161.8, 161.2, 151.0, 150.8, 149.7, 141.6, 137.3, 132.6, 128.7, 124.0, 123.7, 120.1, 119.9, 118.8, 117.7, 111.2, 110.0, 108.9, 93.2, 80.4, 72.3, 57.6, 37.2, 28.9; MS (ES+) m/z 436.8 (M+1).

EXAMPLE 11.16

Synthesis of 1'-(4-pyridin-3-ylbenzyl)-5,6-dihydrospiro[benzo[1,2-b:5,4-b']difuran-3,3'-indol]-2'(1'H)-one

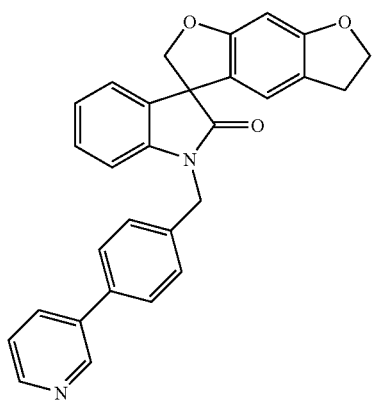

Following the procedure as described in EXAMPLE 11.15 and making non-critical variations using pyridin-3-ylboronic acid to replace pyridin-4-ylboronic acid, and 1'-(4-bromobenzyl)-)-5,6-dihydrospiro[benzo[1,2-b:5,4-b']difuran-3,3'-indol]-2'(1'H)-one to replace 1'-[(5-bromofuran-2-yl)methyl]-5,6-dihydrospiro[benzo[1,2-b:5,4-b']difuran-3,3'-indol]-2'(1'H)-one, 1'-(4-pyridin-3-ylbenzyl)-5,6-dihydrospiro[benzo[1,2-b:5,4-b']difuran-3,3'-indol]-2'(1'H)-one was obtained (42%) as a colorless solid: $^1$H NMR (300 MHz, CDCl$_3$) δ 8.73-8.69 (m, 1H), 8.49-8.44 (m, 1H), 7.95-7.88 (m, 1H), 7.59-6.79 (m, 9H), 6.45 (s, 1H), 6.35 (s, 1H), 5.11-5.01 (m, 1H), 5.11-4.81 (m, 3H), 4.67 (dd, J=9.1, 1.42 Hz, 1H), 4.48 (t, J=8.6 Hz, 2H), 3.05-2.86 (m, 2H); $^{13}$C NMR (75 MHz, CDCl$_3$) δ 181.4, 164.7, 164.2, 150.4, 150.0, 144.8, 139.7, 139.6, 138.9, 138.3, 135.4, 131.8, 131.1, 130.5, 127.1, 126.8, 126.7, 123.0, 121.8, 112.3, 96.0, 83.4, 75.3, 60.8, 46.6, 31.8; MS (ES+) m/z 446.8 (M+1).

EXAMPLE 11.17

Synthesis of 1'-[(2'-fluorobiphenyl-4-yl)methyl]-5,6-dihydrospiro[benzo[1,2-b:5,4-b']difuran-3,3'-indol]-2'(1'H)-one

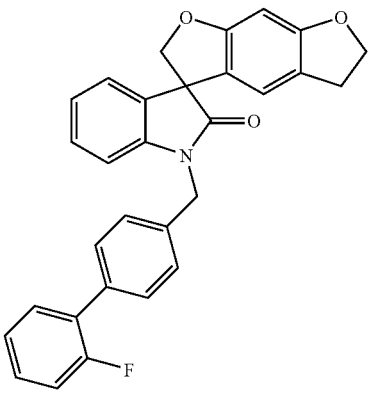

Following the procedure as described in EXAMPLE 11.15 and making non-critical variations using 2-fluorophenylboronic acid to replace pyridin-4-ylboronic acid, and 1-(4-bromobenzyl)-5,6-dihydrospiro[benzo[1,2-b:5,4-b']difuran-3,3'-indol]-2'(1'H)-one to replace 1'-[(5-bromofuran-2-yl)methyl]-5,6-dihydrospiro[benzo[1,2-b:5,4-b']difuran-3,3'-indol]-2'(1'H)-one, 1-[(2'-fluorobiphenyl-4-yl)methyl]-5,6-dihydrospiro[benzo[1,2-b:5,4-b']difuran-3,3'-indol]-2'(1'H)-one was obtained (34%) as a colorless solid: $^1$H NMR (300 MHz, CDCl$_3$) δ8.72-7.91 (m, 12H), 7.61 (s, 1H), 7.54 (s, 1H), 6.11 (ABq, 2H), 5.97 (ABq, 2H), 5.64 (t, J=8.6 Hz, 2H), 4.20-4.01 (m, 2H); $^{13}$C NMR (75 MHz, CDCl$_3$) δ177.9, 161.8, 161.3, 158.0, 142.1, 135.3 (2C), 135.2, 132.8, 130.6 (2C), 129.5, 129.4, 129.2, 129.1, 128.7, 128.4, 128.3, 127.5, 124.4 (2C), 123.9, 123.4, 120.2, 119.9, 118.9, 116.3, 116.0, 109.3, 93.2, 80.6, 72.4, 57.7, 43.9, 29.0.

EXAMPLE 11.18

Synthesis of 1'-{2-[5-(trifluoromethyl)-1,2,4-oxadiazol-3-yl]ethyl}spiro[furo[2,3-f][1,3]benzodioxole-7,3'-indol]-2'(1'H)-one

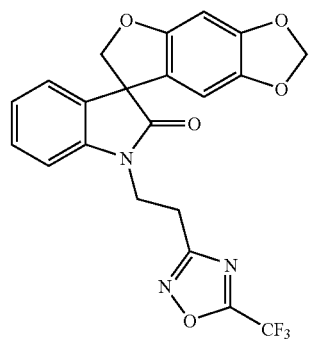

To a stirred solution of N'-hydroxy-3-(2'-oxo-6H-spiro[benzofuro[6,5-d][1,3]dioxole-7,3'-indoline]-1-yl)propanimidamide (0.50 g, 1.4 mmol) and diisopropylamine (0.3 mL, 2.0 mmol) in dichloromethane (20 mL) was added trifluoromethylacetic anhydride (0.3 mL, 2.0 mmol). The solution was stirred at ambient temperature for 1 h, then partitioned with saturated solution of ammonium chloride in water (10 mL) and the aqueous layer was extracted with dichloromethane (2×25 mL). The combined organic solution was dried over sodium sulfate, filtered and concentrated in vacuo to dryness. The residue was purified by flash chromatography with ethyl acetate in hexanes (15% to 50% gradient) to afford 1-{2-[5-(trifluoromethyl)-1,2,4-oxadiazol-3-yl]ethyl}spiro[furo[2,3-f][1,3]benzodioxole-7,3'-indol]-2'(1'H)-one (0.20 g, 33%) as a colorless solid: mp 45-48° C.; $^1$H NMR (300 MHz, CDCl$_3$) δ7.27-7.20 (m, 1H), 7.14 (d, J=7.1 Hz, 1H), 7.03 (dd, J=7.5, 7.5 Hz, 1H), 6.76 (d, J=7.8 Hz, 1H), 6.48 (s, 1H), 6.23 (s, 1H), 5.87-5.83 (m, 2H), 4.74 (ABq, 2H), 4.27-4.05 (m, 2H), 3.28 (td, J=6.4, 1.5 Hz, 2H); $^{13}$C NMR (75 MHz, CDCl$_3$) δ177.6, 168.8, 166.0 (q, J=44.5 Hz), 155.9, 148.9, 142.4, 141.4, 132.4, 128.8, 124.3, 123.6, 119.1, 115.8 (q, J=273.9 Hz), 107.8, 103.3, 101.5, 93.5, 80.5, 58.1, 37.8, 24.2; MS (ES+) m/z 446.1 (M+1).

EXAMPLE 11.19

Synthesis of 4'-chloro-1'-{[5-(trifluoromethyl)-1,2,4-oxadiazol-3-yl]methyl}spiro[furo[2,3-f][1,3]benzodioxole-7,3'-indol]-2'(1'H)-one

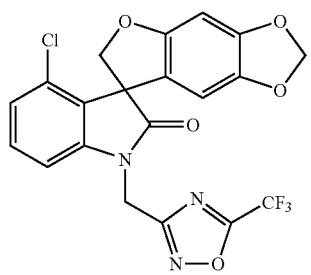

To a stirred solution of 2-(4'-chloro-2'-oxospiro[furo[2,3-f][1,3]benzodioxole-7,3'-indol]-1'(2'H)-yl)-N'-hydroxyacetimidamide (0.39 g, 1.0 mmol) and diisopropylamine (0.20 mL, 1.5 mmol) in dichloromethane (20 mL) was added trifluoromethylacetic anhydride (0.21 mL, 1.5 mmol). The solution was stirred for 2 h at ambient temperature then concentrated in vacuo and dissolved in ethyl acetate (50 mL). The ethyl acetate solution was washed with saturated solution of ammonium chloride in water (2×25 mL), dried over sodium sulfate, filtered and concentrated in vacuo to dryness. The residue was purified by flash chromatography with ethyl acetate in hexanes (15% to 50% gradient) to afford 1'-{2-[5-(trifluoromethyl)-1,2,4-oxadiazol-3-yl]ethyl}spiro[furo[2,3-f][1,3]benzodioxole-7,3'-indol]-2'(1'H)-one (0.13 g, 29%) as a colorless solid: mp 138-140° C.; $^1$H NMR (300 MHz, DMSO-d$_6$) δ7.34 (dd, J=8.0, 8.0 Hz, 1H), 7.15 (d, J=7.9 Hz, 1H), 7.07 (d, J=8.1 Hz, 1H), 6.67 (s, 1H), 6.27 (s, 1H), 5.30 (ABq, 2H), 4.81 (ABq, 2H); $^{13}$C NMR (75 MHz, DMSO-d$_6$) δ176.8, 167.6, 165.8 (q, J=106.3 Hz), 156.6, 149.1, 143.7, 142.0, 131.0, 130.3, 128.4, 124.3, 117.1, 116.0 (q, J=273.2 Hz), 109.0, 103.2, 102.0, 93.4, 77.3, 58.4, 36.1; MS (ES+) m/z 466.0 (M+1).

EXAMPLE 11.20

Synthesis of 4'-chloro-1'-[(5-cyclopropyl-1,2,4-oxadiazol-3-yl)methyl]spiro[furo[2,3-f][1,3]benzodioxole-7,3'-indol]-2'(1'H)-one

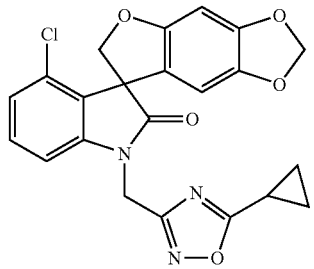

A stirred solution of 2-(4'-chloro-2'-oxospiro[furo[2,3-f][1,3]benzodioxole-7,3'-indol]-1'(2'H)-yl)-N'-[(cyclopropylcarbonyl)oxy]ethanimidamide (0.24 g, 0.52 mmol) in pyridine (1 mL) was heated at 170° C. for 30 min in a microwave reactor. The solution was concentrated in vacuo to dryness, purified by flash chromatography with ethyl acetate in hexanes (15% to 50% gradient) to afford 4'-chloro-1'-[(5-cyclopropyl-1,2,4-oxadiazol-3-yl)methyl]spiro[furo[2,3-f][1,3]benzodioxole-7,3'-indol]-2'(1'H)-one (0.36 g, 16%) as a colorless solid: mp 180-182° C.; $^1$H NMR (300 MHz, CDCl$_3$) δ7.19 (dd, J=8.1, 8.1 Hz, 1H), 6.99 (d, J=8.4 Hz, 1H), 6.77 (d, J=7.8 Hz, 1H), 6.46 (s, 1H), 6.28 (s, 1H), 5.86 (d, J=1.2 Hz, 1H), 5.04 (ABq, 2H), 4.94 (ABq, 2H), 2.20-2.10 (m, 1H). 1.26-1.12 (m, 4H); $^{13}$C NMR (75 MHz, CDCl$_3$) δ182.9, 177.0, 165.4, 156.8, 149.2, 143.0, 142.1, 131.6, 130.0, 128.4, 124.6, 116.5, 107.4, 103.0, 101.5, 93.2, 58.7, 36.1, 10.57, 10.53, 7.8; MS (ES+) m/z 438.1 (M+1).

EXAMPLE 11.21

Synthesis of 4'-chloro-1'-{1-[5-(difluoromethyl)-1,2,4-oxadiazol-3-yl]ethyl}spiro[furo[2,3-f][1,3]benzodioxole-7,3'-indol]-2'(1'H)-one

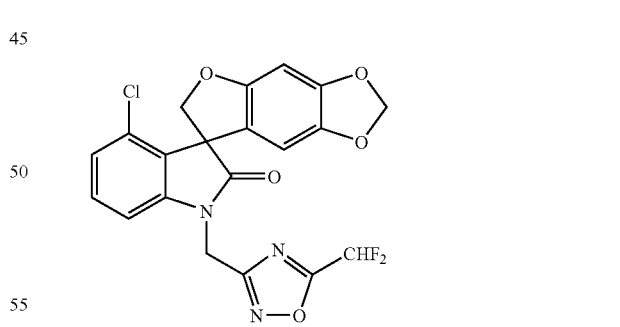

Following the procedure as described in EXAMPLE 11.19 and making non-critical variations using difluoromethylacetic anhydride to replace trifluoromethylacetic anhydride, 4'-chloro-1'-{1-[5-(difluoromethyl)-1,2,4-oxadiazol-3-yl]ethyl}spiro[furo[2,3-f][1,3]benzodioxole-7,3'-indol]-2'(1'H)-one was obtained (35%) as a colorless solid: mp 179-182° C.; $^1$H NMR (300. MHz, CDCl$_3$) δ7.25-7.17 (m, 1H), 7.03 (d, J=8.1 Hz, 1H), 6.76 (d, J=7.6 Hz, 1H), 6.76 (t, J=52.0 Hz, 1H), 6.47 (s, 1H), 6.24 (s, 1H), 5.86 (ABq, 2H), 5.15 (ABq, 2H), 4.94 (ABq, 2H); $^{13}$C NMR (75 MHz, CDCl$_3$) δ177.1, 170.6 (t, J=30.2 Hz), 166.3, 156.8, 149.3, 142.6, 142.2, 131.9, 130.3, 128.2, 124.9, 116.1, 107.1, 105.3 (t, J=244.5 Hz), 102.9, 101.6, 93.3, 58.7, 35.8; MS (ES+) m/z 448.1 (M+1).

EXAMPLE 11.22

Synthesis of 1-{[5-(difluoromethyl)-1,2,4-oxadiazol-3-yl]methyl}spiro[furo[2,3-f][1,3]benzodioxole-7,3'-indol]-2'(1'H)-one

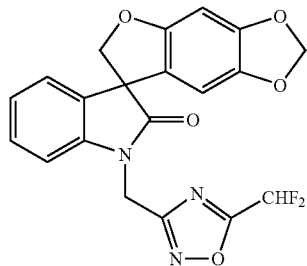

Following the procedure as described in EXAMPLE 11.19 and making non-critical variations using difluoromethylacetic anhydride to replace trifluoromethylacetic anhydride, and N'-hydroxy-2-(2'-oxo-6H-spiro[benzofuro[6,5-d][1,3]dioxole-7,3'-indoline]-1'-yl)acetimidamide to replace 2-(4'-chloro-2'-oxospiro[furo[2,3-f][1,3]benzodioxole-7,3'-indol]-1'(2'H)-yl)-N'-hydroxyacetimidamide, 1'-{[5-(difluoromethyl)-1,2,4-oxadiazol-3-yl]methyl}spiro[furo[2,3-f][1,3]benzodioxole-7,3'-indol]-2'(1'H)-one was obtained (67%) as a colorless solid: mp 137-139° C.; ¹H NMR (300 MHz, CDCl₃) δ7.30-7.17 (m, 2H), 7.08 (dd, J=7.5, 7.5 Hz, 1H), 6.85 (d, J=7.8 Hz, 1H), 6.76 (t, J=52.0 Hz, 1H), 6.50 (s, 1H), 6.26 (s, 1H), 6.85 (m, 2H), 5.16 (ABq, 2H), 4.82 (ABq, 2H); ¹³C NMR (75 MHz, CDCl₃) δ177.4, 170.5, 166.5, 155.8, 149.0, 142.4, 140.8, 132.2, 129.1, 124.2, 124.1, 119.2, 108.6, 105.4 (t, J=244.2 Hz), 103.3, 101.5, 93.6, 80.2, 58.2, 35.6; MS (ES+) m/z 414.1 (M+1).

EXAMPLE 11.23

Synthesis of 1'-[(5-tert-butyl-1,2,4-oxadiazol-3-yl)methyl]spiro[furo[2,3-f][1,3]benzodioxole-7,3'-indol]-2'(1'H)-one

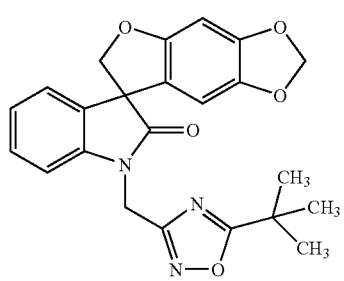

To a stirred solution of N'-hydroxy-2-(2'-oxo-6H-spiro[benzofuro[6,5-c][1,3]dioxole-7,3'-indoline]-1-yl)acetimidamide (0.20 g, 0.57 mmol) and diisopropylamine (0.40 mL, 2.9 mmol) in dichloromethane (10 mL) was added trimethylacetic anhydride (0.2 mL, 1.1 mmol). The solution was stirred at ambient temperature for 2 h then concentrated in vacuo to afford the intermediate 2-(2'-oxo-6H-spiro[benzofuro[6,5-d][1,3]dioxole-7,3'-indoline]-1-yl)-N'-(pivaloyloxy)acetimidamide. The crude residue was dissolved in pyridine (3 mL) and heated at 170° C. for 30 min in a microwave reactor. The solution was concentrated in vacuo to dryness, purified by flash chromatography with ethyl acetate in hexane (15% to 50% gradient) to afford 1'-[(5-tert-butyl-1,2,4-oxadiazol-3-yl)methyl]spiro[furo[2,3-f][1,3]benzodioxole-7,3'-indol]-2'(1'H)-one (0.16 g, 67%) as a colorless solid: mp 183-185° C.; ¹H NMR (300 MHz, CDCl₃) δ7.27-7.16 (m, 2H), 7.05 (dd, J=7.5, 7.5 Hz, 1H), 6.85 (d, J=7.5 Hz, 1H), 6.48 (s, 1H), 6.35 (s, 1H), 5.84 (d, J=3.3 Hz, 2H), 5.05 (ABq, 2H), 4.83 (ABq, 2H), 1.39 (s, 9H); ¹³C NMR (75 MHz, CDCl₃) δ187.4, 177.4, 165.5, 155.7, 148.9, 142.4, 141.2, 132.4, 128.9, 123.9, 123.8, 119.7, 108.8, 103.5, 101.5, 93.5, 80.1, 58.3, 36.1, 33.7, 28.3; MS (ES+) m/z 420.2 (M+1).

EXAMPLE 11.24

Synthesis of 1'-[(5-cyclopropyl-1,2,4-oxadiazol-3-yl)methyl]spiro[furo[2,3-f][1,3]benzodioxole-7,3'-indol]-2'(1'H)-one

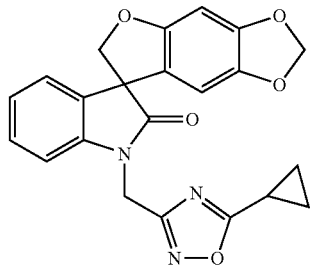

Following the procedure as described in EXAMPLE 11.23 and making non-critical variations using cyclopropane carboxylic acid chloride to replace trimethylacetic anhydride, 1'-[(5-cyclopropyl-1,2,4-oxadiazol-3-yl)methyl]spiro[furo[2,3-f][1,3]benzodioxole-7,3'-indol]-2'(1'H)-one was obtained (20%) as a colorless solid: mp 136-137° C.; ¹H NMR (300 MHz, CDCl₃) δ7.24 (dd, J=7.7, 7.7 Hz, 1H), 7.17 (d, J=7.3 Hz, 1H), 7.05 (dd, J=7.5, 7.5 Hz, 1H), 6.86 (d, J=7.5 Hz, 1H), 6.48 (s, 1H), 6.30 (s, 1H), 5.84 (d, J=3.8 Hz, 2H), 5.00 (ABq, J=16.4 Hz, 2H), 4.82 (ABq, J=9.0 Hz, 2H), 2.20-2.09 (m, 1H), 1.21-1.16 (m, 4H); ¹³C NMR (75 MHz, CDCl₃) δ182.7, 177.3, 165.6, 155.7, 148.9, 142.4, 141.2, 132.3, 128.9, 123.9, 123.8, 119.6, 108.9, 103.5, 101.5, 93.5, 80.2, 58.2, 35.8, 10.50, 10.46, 7.8; MS (ES+) m/z 404.1 (M+1).

EXAMPLE 11.25

Synthesis of 4'-chloro-1'-{[5-(1-methylethyl)-1,2,4-oxadiazol-3-yl]methyl}spiro[furo[2,3-f][1,3]benzodioxole-7,3'-indol]-2'(1'H)-one

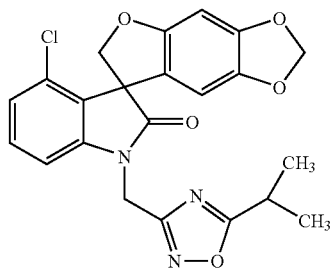

Following the procedure as described in EXAMPLE 11.23 and making non-critical variations using isobutyryl chloride

EXAMPLE 11.26

Synthesis of 1'-{[5-(1-methylethyl)-1,2,4-oxadiazol-3-yl]methyl}spiro[furo[2,3-f][1,3]benzodioxole-7,3'-indol]-2'(1'H)-one

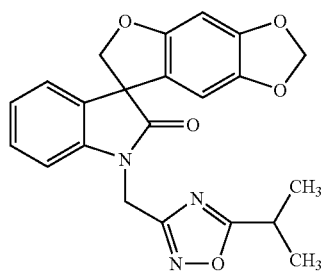

to replace trimethylacetic anhydride, and 2-(4'-chloro-2'-oxospiro[furo[2,3-f][1,3]benzodioxole-7,3'-indol]-1'(2'H)-yl)-N'-hydroxyacetimidamide to replace N'-hydroxy-2-(2'-oxo-6H-spiro[benzofuro[6,5-d][1,3]dioxole-7,3'-indoline]-1'-yl)acetimidamide, 4'-chloro-1'-{[5-(1-methylethyl)-1,2,4-oxadiazol-3-yl]methyl}spiro[furo[2,3-f][1,3]benzodioxole-7,3'-indol]-2'(1'H)-one was obtained (26%) as a colorless solid: mp 165-167° C.; $^1$H NMR (300 MHz, CDCl$_3$) δ 7.19 (dd, J=8.0, 8.0 Hz, 1H), 7.00 (dd, J=8.2, 0.8 Hz, 1H), 6.77 (dd, J=7.8, 0.7 Hz, 1H), 6.46 (s, 1H), 6.32 (s, 1H), 5.85 (ABq, 2H), 5.04 (ABq, 2H), 4.95 (ABq, 2H), 3.17 (sep, J=7.0 Hz, 1H), 1.36 (d, J=7.0 Hz, 6H); $^{13}$C NMR (75 MHz, CDCl$_3$) δ 185.2, 177.1, 165.3, 156.7, 149.2, 143.0, 142.1, 131.6, 130.1, 128.4, 124.6, 116.5, 107.3, 103.1, 101.5, 93.2, 77.1, 58.8, 36.2, 27.5, 20.1, 20.0; MS (ES+) m/z 440.1 (M+1).

A stirred solution of N'-hydroxy-2-(2'-oxospiro[furo[2,3-f][1,3]benzodioxole-7,3'-indol]-1'(2'H)-yl)ethanimidamide (0.35 g, 1.0 mmol) and isobutyric anhydride (250 mL, 1.5 mmol) in pyridine (3 mL) was heated at 170° C. in a microwave reactor for 30 min. The solution was concentrated in vacuo to dryness, purified by flash chromatography with ethyl acetate in hexanes (15% to 50% gradient) to afford 1-[(5-tert-butyl-1,2,4-oxadiazol-3-yl)methyl]spiro[furo[2,3-f][1,3]benzodioxole-7,3'-indol]-2'(1'H)-one (0.26 g, 64%) as a colorless solid: mp 196-199° C.; $^1$H NMR (300 MHz, CDCl$_3$) δ 7.28-7.15 (m, 2H), 7.05 (dd, J=7.5 Hz, 1H), 6.86 (d, J=7.8 Hz, 1H), 6.49 (s, 1H), 6.34 (s, 1H), 6.86-6.82 (m, 2H), 5.06 (ABq, 2H), 4.83 (ABq, 2H), 3.18 (sep, J=7.0 Hz, 1H), 1.36 (d, J=7.0 Hz, 6H); $^{13}$C NMR (75 MHz, CDCl$_3$) δ 185.0, 177.4, 165.6, 155.7, 148.9, 142.4, 141.2, 132.3, 128.9, 123.9, 123.8, 119.7, 108.9, 103.5, 101.5, 93.5, 80.1, 58.2, 36.0, 27.5, 20.1, 20.0; MS (ES+) m/z 406.2 (M+1).

EXAMPLE 11.27

Synthesis of 1'-[3-(5-methyl-1,2,4-oxadiazol-3-yl)benzyl]-5,6-dihydrospiro[benzo[1,2-b:5,4-b']difuran-3,3'-indol]-2'(1'H)-one

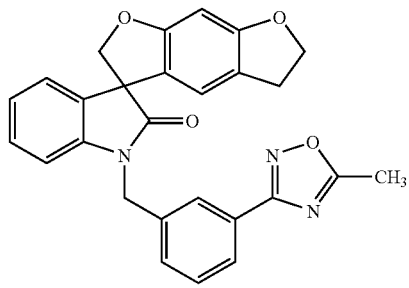

To a solution of N'-hydroxy-3-[(2'-oxo-5,6-dihydrospiro[benzo[1,2-b:5,4-b']difuran-3,3'-indol]-1'(2'H)-yl)methyl]benzenecarboximidamide (0.36 g, 0.84 mmol) in pyridine (3 mL) was added acetyl chloride (0.12 mL, 1.68 mmol). The reaction was stirred in a microwave reactor (170° C., 200 watts, 200 psi) for 30 min. The mixture was concentrated in vacuo. The residue was purified by column chromatography with ethyl acetate in hexanes (25% to 40% gradient), and recrystallized from ethyl acetate and diethylether to afford 1'-[3-(5-methyl-1,2,4-oxadiazol-3-yl)benzyl]-5,6-dihydrospiro[benzo[1,2-b:5,4-b']difuran-3,3'-indol]-2'(1'H)-one (0.27 g, 71%) as a colorless solid: mp 209-213° C.; $^1$H NMR (300 MHz, CDCl$_3$) δ 8.06-8.03 (m, 1H), 7.99-7.96 (m, 1H), 7.48-7.44 (m, 2H), 7.19-7.12 (m, 2H), 7.03-6.98 (m, 1H), 6.77-6.74 (m, 1H), 6.58 (s, 1H), 6.42 (s, 1H), 5.18 (d, J=15.8 Hz, 1H), 5.00 (d, J=9.0 Hz, 1H), 4.85 (d, J=15.8 Hz, 1H), 4.72 (d, J=9.0 Hz, 1H), 4.56-4.50 (m, 2H), 3.07-2.95 (m, 2H), 2.63 (s, 3H); $^{13}$C NMR (75 MHz, CDCl$_3$) δ 178.0, 176.7, 168.1, 161.9, 161.3, 141.9, 136.6, 132.8, 129.9, 129.6, 128.8, 127.5, 126.9, 126.0, 124.0, 123.6, 120.2, 120.1, 119.1, 109.2, 93.2, 80.6, 72.4, 57.8, 43.8, 29.1, 12.4; MS (ES+) m/z 451.8 (M+1).

EXAMPLE 11.28

Synthesis of 1'-{3-[5-(trifluoromethyl)-1,2,4-oxadiazol-3-yl]benzyl}-5,6-dihydrospiro[benzo[1,2-b:5,4-b']difuran-3,3'-indol]-2'(1'H)-one

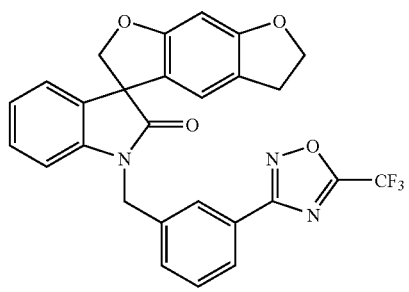

Following the procedure as described in EXAMPLE 11.27 and making non-critical variations using trifluoroacetic anhydride to replace acetyl chloride, 1'-{3-[5-(trifluoromethyl)-1,2,4-oxadiazol-3-yl]benzyl}-5,6-dihydrospiro[benzo[1,2-b:5,4-b']difuran-3,3'-indol]-2'(1'H)-one was obtained (71%) as a colorless solid: mp 182-188° C.; $^1$H NMR (300 MHz, CDCl₃) δ 8.12-7.97 (m, 2H), 7.60-7.51 (m, 2H), 7.25-7.17 (m, 2H), 7.06-7.00 (m, 1H), 6.76-6.72 (m, 1H), 6.57 (s, 1H), 6.42 (s, 1H), 5.22 (d, J=15.9 Hz, 1H), 5.00 (d, J=9.0 Hz, 1H), 4.86 (d, J=15.9 Hz, 1H), 4.72 (d, J=9.0 Hz, 1H), 4.57-4.51 (m, 2H), 3.07-2.92 (m, 2H); $^{13}$C NMR (75 MHz, CDCl₃) δ 178.1, 168.8, 161.9, 161.4, 141.7, 137.1, 132.8, 131.1, 129.9, 128.8, 127.3, 126.1, 125.6, 124.1, 123.7, 120.2, 120.1, 119.0, 109.1, 93.3, 80.6, 72.5, 65.9, 57.8, 43.7, 29.0, 15.3; MS (ES+) m/z 505.8 (M+1).

EXAMPLE 11.29

Synthesis of 1'-[4(5-methyl-4H-1,2,4-triazol-3-yl)benzyl]-5,6-dihydrospiro[benzo[1,2-b:5,4-b']difuran-3,3'-indol]-2'(1'H)-one

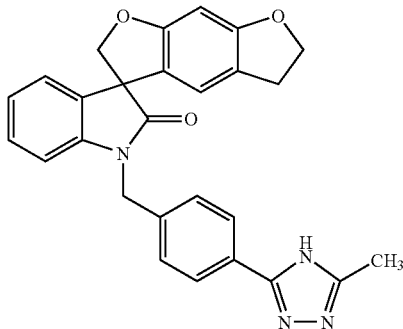

To a solution of 4-[(2'-oxo-5,6-dihydrospiro[benzo[1,2-b:5,4-b']difuran-3,3'-indol]-1'(2'H)-yl)methyl]benzamide (0.40 g, 0.96 mmol) in 1,4-dioxane (15 mL) was added N,N-dimethylacetamide dimethyl acetal (1.42 mL, 9.71 mmol). The reaction was heated to reflux for 18 h, concentrated in vacuo. To the above residue were added acetic acid (15 mL) and hydrazine monohydrate (0.15 mL, 3.17 mmol). The reaction was stirred at 90° C. for 6 h, cooled to ambient temperature, quenched with saturated sodium bicarbonate (15 mL), and extracted with chloroform. The combined organic solution was washed with water and brine, dried over anhydrous sodium sulfate and filtered. The filtrate was concentrated in vacuo. The residue was purified by column chromatography with 5% methanol in ethyl acetate, and recrystallized from dichloromethane and hexanes to afford 1'-[4-(5-methyl-4H-1,2,4-triazol-3-yl)benzyl]-5,6-dihydrospiro[benzo[1,2-b:5,4-b']difuran-3,3'-indol]-2'(1'H)-one (0.07 g, 16%) as a colorless solid: mp 169-180° C. (hexanes); $^1$H NMR (300 MHz, CDCl₃) δ 10.72 (s, 1H), 8.01 (d, J=8.1 Hz, 2H), 7.41 (d, J=8.1 Hz, 2H), 7.15 (d, J=7.5 Hz, 2H), 7.01 (t, J=7.5 Hz, 1H), 6.79 (d, J=7.7 Hz, 1H), 6.45 (s, 1H), 6.40 (s, 1H), 5.19-4.09 (m, 4H), 4.53-4.47 (m, 2H), 2.95-2.90 (m, 2H), 2.50 (s, 3H); $^{13}$C NMR (75 MHz, CDCl₃) δ 178.3, 161.9, 161.4, 141.9, 136.9, 132.7, 128.8, 127.8, 126.9, 123.9, 123.6, 120.0, 119.9, 118.8, 109.4, 93.2, 80.6, 72.4, 57.8, 44.0, 28.9, 11.7; MS (ES+) m/z 450.8 (M+1).

EXAMPLE 11.30

Synthesis of 2-[(2'-oxo-5,6-dihydrospiro[benzo[1,2-b:5,4-b']difuran-3,3'-indol]-1'(2'H)-yl)methyl]benzoic acid

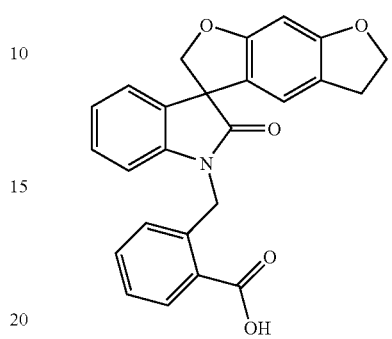

Lithium hydroxide monohydrate (1.48 g, 35.2 mmol) was added to a solution of methyl 2-[(2'-oxo-5,6-dihydrospiro[benzo[1,2-b:5,4-b']difuran-3,3'-indol]-1'(2'H)-yl)methyl]benzoate (6.00 g, 14.2 mmol) in a mixed solvent (tetrahydrofuran/water=2/1 v/v, 180 mL), and stirred at ambient temperature for 16 h. Most of tetrahydrofuran was removed under vacuum, and 150 mL water was added. The solution was extracted with 50 mL of mixed solvent (ethyl acetate/hexanes: 1/3 v/v). The water layer was acidified with 1 N HCl solution until pH 2. After filtration and air dry, 2-[(2'-oxo-5,6-dihydrospiro[benzo[1,2-b:5,4-b']difuran-3,3'-indol]-1'(2'H)-yl)methyl]benzoic acid was obtained (5.60 g, 96%) as a colorless solid: $^1$H NMR (300 MHz, DMSO-d₆) δ 13.2 (br s, 1H), 7.95 (dd, J=7.7, 1.2 Hz, 1H), 7.51 (ddd, J=7.5, 7.5, 1.2 Hz, 1H), 7.37 (dd, J=7.5, 7.5 Hz, 1H), 7.24-7.14 (m, 2H), 7.12-6.96 (m, 2H), 6.81 (d, J=7.7 Hz, 1H), 6.58 (s, 1H), 6.40 (s, 1H), 5.39-5.18 (m, 2H), 4.86 (d, J=8.9 Hz, 1H), 4.74 (d, J=8.9 Hz, 1H), 4.47 (t, J=8.7 Hz, 2H), 3.95 (s, 3H), 2.95 (t, J=8.7 Hz, 2H); $^{13}$C NMR (75 MHz, DMSO-d₆) δ 177.8, 168.7, 161.6, 161.2, 143.0, 137.6, 133.0, 132.6, 131.5, 129.8, 129.2, 127.7, 126.4, 124.2, 123.6, 120.9, 120.4, 119.7, 109.7, 92.9, 80.5, 72.6, 57.5, 42.5, 28.8; MS (ES+) m/z 414.0 (M+1).

EXAMPLE 11.31

Synthesis of 4-[(2'-oxo-5,6-dihydrospiro[benzo[1,2-b:5,4-b']difuran-3,3'-indol]-1'(2'H)-yl)methyl]benzoic acid

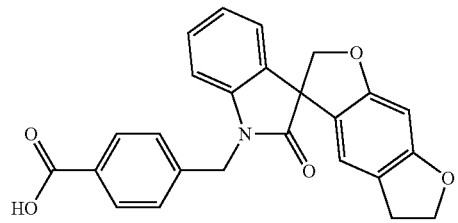

Following the procedure as described in EXAMPLE 11.30 and making non-critical variations using methyl 4-[(2'-oxo-5,6-dihydrospiro[benzo[1,2-b:5,4-b']difuran-3,3'-indol]-1'(2'H)-yl)methyl]benzoate to replace methyl 2-[(2'-oxo-5,6-dihydrospiro[benzo[1,2-b:5,4-b']difuran-3,3'-indol]-1'(2'H)-yl)methyl]benzoate, 4-[(2'-oxo-5,6-dihydrospiro[benzo[1,2-b:5,4-b']difuran-3,3'-indol]-1'(2'H)-yl)methyl]benzoic acid was obtained (95%) as a colorless solid: $^1$H NMR (300 MHz, CDCl$_3$) δ12.93 (s, 1H), 7.90 (d, J=8.1 Hz, 2H), 7.43 (d, J=8.1 Hz, 2H), 7.22 (dd, J=7.4 Hz, 1H), 7.16 (d, J=7.4 Hz, 1H), 7.00 (dd, J=7.4 Hz, 1H), 6.94 (d, J=7.4 Hz, 1H), 6.45 (s, 1H), 6.40 (s, 1H), 4.98 (ABq, 2H), 4.77 (ABq, 2H), 4.47 (t, J=8.9 Hz, 2H), 3.01-2.85 (m, 2H); MS (ES+) m/z 414.1 (M+1).

EXAMPLE 11.32

Synthesis of 5-[(2'-oxo-2,3-dihydrospiro[furo[2,3-g][1,4]benzodioxine-8,3'-indol]-1'(2'H)-yl)methyl]furan-2-carboxylic acid

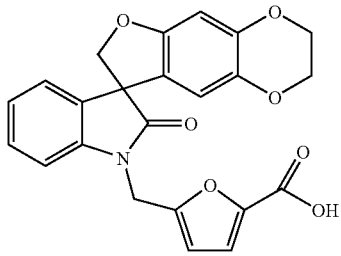

A mixture of methyl 5-[(2'-oxo-2,3-dihydrospiro[furo[2,3-g][1,4]benzodioxine-8,3'-indol]-1'(2'H)-yl)methyl]furan-2-carboxylate (1.38 g, 3.17 mmol) and lithium hydroxide (0.76 g, 31.7 mmol) in tetrahydrofuran (10 mL) and water (10 mL) was stirred at 60° C. for 2 h. The reaction mixture was acidified with 1 M hydrochloric acid (50 mL) and extracted with dichloromethane (3×30 mL). The combined organic solution was washed with brine (50 mL), dried over sodium sulfate, filtered and concentrated under reduced pressure to afford 5-[(2'-oxo-2,3-dihydrospiro[furo[2,3-g][1,4]benzodioxine-8,3'-indol]-1'(2'H)-yl)methyl]furan-2-carboxylic acid (1.36 g, quantitative) as a colorless solid: mp 192-195° C. (diethyl ether); $^1$H NMR (300 MHz, CDCl$_3$) δ8.40 (br s, 1H), 7.27 (dd, J=7.8, 7.8 Hz, 1H), 7.25 (d, J=3.3 Hz, 1H), 7.18 (d, J=7.5 Hz, 1H), 7.06 (dd, J=7.5, 7.5 Hz, 1H), 6.94 (d, J=7.8 Hz, 1H), 6.50 (s, 1H), 6.45 (d, J=3.3 Hz, 1H), 6.31 (s, 1H), 5.19 (d, J=16.5 Hz, 1H), 4.92 (d, J=9.3 Hz, 1H), 4.87 (d, J=16.5 Hz, 1H), 4.66 (d, J=9.3 Hz, 1H), 4.21-4.07 (m, 4H); $^{13}$C NMR (75 MHz, CDCl$_3$) δ177.4, 162.8, 155.2, 154.4, 144.8, 143.7, 141.3, 138.6, 132.3, 129.1, 124.2, 124.0, 121.1, 120.9, 111.8, 110.7, 109.0, 99.5, 80.0, 64.7, 64.0, 58.2, 37.5; MS (ES+) m/z 419.9 (M+1).

EXAMPLE 11.33

Synthesis of N,N-dimethyl-5-[(2'-oxo-2,3-dihydrospiro[furo[2,3-g][1,4]benzodioxine-8,3'-indol]-1'(2'H)-yl)methyl]furan-2-carboxamide

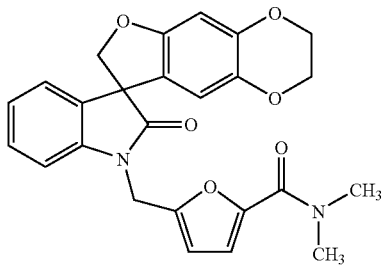

A solution of 5-[(2'-oxo-2,3-dihydrospiro[furo[2,3-g][1,4]benzodioxine-8,3'-indol]-1'(2'H)-yl)methyl]furan-2-carboxylic acid (0.42 g, 1.00 mmol), dimethylamine hydrochloride (0.17 g, 2.04 mmol), N-(3-dimethylaminopropyl)-N'-ethylcarbodiimide hydrochloride (0.26 g, 1.35 mmol), 1-hydroxybenzotriazole hydrate (0.21 g, 1.54 mmol) and 4-methylmorpholine (0.30 mL, 2.7 mmol) in N,N-dimethylformamide (10 mL) was stirred at ambient temperature for 16 h. The solvent was removed under reduced pressure, the residue was taken up into ethyl acetate (75 mL) and washed sequentially with 1 M hydrochloric acid (2×50 mL), water (50 mL) and brine (50 mL). The organic phase was further diluted with dichloromethane until all the material was in solution, then was dried over sodium sulfate, filtered and concentrated under reduced pressure. Purification by flash column chromatography with dichloromethane/methanol (29:1) afforded N,N-dimethyl-5-[(2'-oxo-2,3-dihydrospiro[furo[2,3-g][1,4]benzodioxine-8,3'-indol]-1'(2'H)-yl)methyl]furan-2-carboxamide (0.34 g, 77%) as a colorless solid: mp 224-226° C. (diethyl ether/hexanes); $^1$H NMR (300 MHz, DMSO-d$_6$) δ7.32 (dd, J=7.5, 7.5 Hz, 1H), 7.22-7.14 (m, 2H), 7.05 (dd, J=7.8, 7.5 Hz, 1H), 6.96 (m, 1H), 6.62 (m, 1H), 6.51 (s, 1H), 6.06 (s, 1H), 5.06 (d, J=16.4 Hz, 1H), 4.97 (d, J=16.4 Hz, 1H), 4.76 (d, J=9.3 Hz, 1H), 4.66 (d, J=9.3 Hz, 1H), 4.22-4.14 (m, 2H), 4.14-4.06 (m, 2H), 3.05 (br s, 3H), 2.94 (br s, 3H); $^{13}$C NMR (75 MHz, DMSO-d$_6$) δ176.4, 158.9, 154.6, 150.8, 147.2, 144.2, 141.8, 137.8, 131.6, 128.8, 123.6, 123.3, 121.2, 116.5, 111.0, 109.9, 109.4, 98.8, 79.3, 64.2, 63.6, 57.2, 37.7, 36.7, 35.8; MS (ES+) m/z 446.9 (M+1).

EXAMPLE 11.34

Synthesis of 1'-(3-hydroxypropyl)-5,6-dihydrospiro[benzo[1,2-b:5,4-b']difuran-3,3'-indol]-2'(1'H)-one

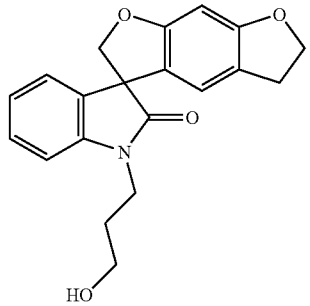

A suspension of 1'-[3-(benzyloxy)propyl]-5,6-dihydrospiro[benzo[1,2-b:5,4-b']difuran-3,3'-indol]-2'(1'H)-one (2.70 g, 6.31 mmol) and 10% palladium on carbon (1.00 g, 0.94 mmol) in methanol (50 mL) was hydrogenated for 20 h. The reaction mixture was filtered through a pad of celite. The filtrate was concentrated in vacuo, and the residue was subjected to column chromatography with ethyl acetate in hexanes (20% to 50% gradient) to afford 1-(3-hydroxypropyl)-5,6-dihydrospiro[benzo[1,2-b:5,4-b']difuran-3,3'-indol]-2'(1'H)-one (2.07 g, 97%): mp 54-56° C. (ethyl acetate/hexanes); $^1$H NMR (300 MHz, CDCl$_3$) δ 7.33-7.28 (m, 1H), 7.19-7.17 (m, 1H), 7.09-7.04 (m, 1H), 6.94 (d, J=9.0 Hz, 1H), 6.45 (s, 1H), 6.41 (s, 1H), 4.77 (ABq, 2H), 4.53 (t, J=6.0 Hz, 2H), 4.02-3.84 (m, 2H), 3.63-3.54 (m, 2H), 3.07-2.90 (m, 3H), 1.94-1.83 (m, 2H); MS (ES+) m/z 338.1 (M+1).

EXAMPLE 11.35

Synthesis of 2'-oxo-1'-[(2R)-tetrahydrofuran-2-ylmethyl]-1',2',5,6-tetrahydrospiro[benzo[1,2-b:5,4-b']difuran-3,3'-indole]-4'-carbonitrile

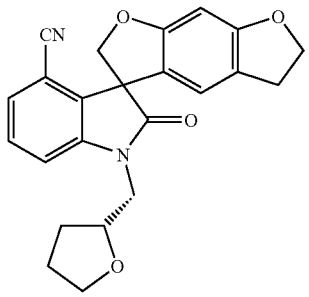

To a stirred solution of 4'-bromo-1-[(2R)-tetrahydrofuran-2-ylmethyl]-5,6-dihydrospiro[benzo[1,2-b:5,4-b']difuran-3,3'-indol]-2'(1'H)-one (0.20 g, 0.45 mmol), potassium hexacyanoferrate(II) trihydrate (0.04 g, 0.1 mmol) in N,N-dimethylacetamide (5 mL) was added palladium(II) acetate (0.01 g, 0.04 mmol) followed with the addition of sodium carbonate (0.10 g, 0.9 mmol). The mixture was stirred at 130° C. for 18 h. The mixture was filtered through a pad of celite, and the filtrate was concentrated in vacuo. The residue was subjected to column chromatography (ethyl acetate/hexanes, 1/2) to afford 2'-oxo-1'-[(2R)-tetrahydrofuran-2-ylmethyl]-1',2',5,6-tetrahydrospiro[benzo[1,2-b:5,4-b']difuran-3,3'-indole]-4'-carbonitrile (0.03 g, 16%): $^1$H NMR (300 MHz, CDCl$_3$) δ7.41-7.25 (m, 3H), 6.46-6.38 (m, 2H), 4.98-4.88 (m, 2H), 4.53 (t, J=8.7 Hz, 2H), 4.28-4.15 (m, 1H), 4.03-3.62 (m, 4H), 2.98 (t, J=8.7 Hz, 2H), 2.14-2.00 (m, 1H), 1.97-1.83 (m, 2H), 1.74-1.59 (m, 1H); MS (ES+) m/z 389.0 (M+1).

EXAMPLE 11.36

Synthesis of 2'-oxo-1'-[(2R)-tetrahydrofuran-2-ylmethyl]-1',2',5,6-tetrahydrospiro[benzo[1,2-b:5,4-b']difuran-3,3'-indole]-4'-carbaldehyde

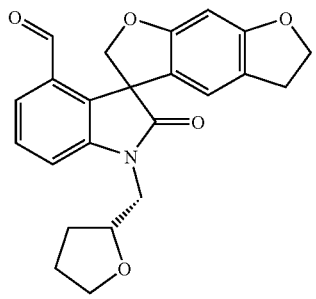

To a stirred solution of 4'-bromo-1-[(2R)-tetrahydrofuran-2-ylmethyl]-5,6-dihydrospiro[benzo[1,2-b:5,4-b']difuran-3,3'-indol]-2'(1'H)-one (0.80 g, 1.8 mmol) in anhydrous tetrahydrofuran was added tert-butyllithium (2.7 mL 1.7 M in pentane, 4.5 mmol) at −78° C. The mixture was stirred at −78° C. for 45 min, followed by the addition of N,N-dimethylformamide (1.4 mL, 18.1 mmol). The mixture was kept at −78° C. for 30 min before quenched with saturated ammonium chloride solution. The mixture was extracted with ethyl acetate (3×30 mL). The combined organic solution was dried over anhydrous sodium sulfate and filtered. The filtrate was concentrated in vacuo. The residue was subjected to column chromatography (ethyl acetate/hexanes, 1/2) to afford 2'-oxo-1'-[(2R)-tetrahydrofuran-2-ylmethyl]-1',2',5,6-tetrahydrospiro[benzo[1,2-b:5,4-b']difuran-3,3'-indole]-4'-carbaldehyde (0.19 g, 26%) as a colorless solid: $^1$H NMR (300 MHz, CDCl$_3$) δ9.94 (s, 1H), 7.56 (dd, J=7.8, 1.2 Hz, 1H), 7.45 (dd, J=7.8, 7.8 Hz, 1H), 7.39-7.33 (m, 1H), 6.42 (s, 1H), 6.41 (s, 1H), 4.98 (d, J=9.2 Hz, 1H), 4.86 (d, J=9.2 Hz, 1H), 4.51 (t, J=8.7 Hz, 2H), 4.31-4.19 (m, 1H), 4.05-3.66 (m, 4H), 3.04-2.85 (m, 2H), 2.14-2.00 (m, 1H), 1.97-1.83 (m, 2H), 1.77-1.63 (m, 1H); MS (ES+) m/z 392.0 (M+1).

EXAMPLE 11.37

Synthesis of 4'-[(dimethylamino)methyl]-1'-[(2R)-tetrahydrofuran-2-ylmethyl]-5,6-dihydrospiro[benzo[1,2-b:5,4-b']difuran-3,3'-indol]-2'(1'H)-one

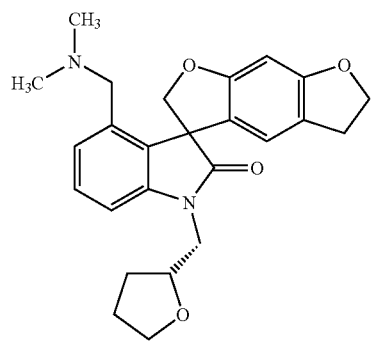

To a stirred solution of 2'-oxo-1'-[(2R)-tetrahydrofuran-2-ylmethyl]-1',2',5,6-tetrahydrospiro[benzo[1,2-b:5,4-b']difuran-3,3'-indole]-4'-carbaldehyde (0.10 g, 0.26 mmol) and dimethylamine (0.19 mL, 0.38 mmol) in dichloroethane was added sodium triacetoxyborohydride (0.10 g, 0.46 mmol) at 0° C. The mixture was stirred at ambient temperature for 18 h, and quenched with water. The mixture was extracted with ethyl acetate (3×20 mL). The combined organic solution was dried over anhydrous sodium sulfate and filtered. The filtrate was concentrated in vacuo. The residue was subjected to column chromatography (methanol/ethyl acetate, 5/100) to afford 4'-[(dimethylamino)methyl]-1'-[(2R)-tetrahydrofuran-2-ylmethyl]-5,6-dihydrospiro[benzo[1,2-b:5,4-b']difuran-3,3'-indol]-2'(1'H)-one (0.05 g, 46%) as a colorless solid: $^1$H NMR (300 MHz, CDCl$_3$) δ7.29-7.20 (m, 1H), 7.07 (d, J=7.9 Hz, 1H), 6.98 (t, J=7.0 Hz, 1H), 6.45-6.39 (m, 1H), 6.38 (s, 1H), 5.07 (dd, J=8.8, 2.1 Hz, 1H), 4.88 (d, J=8.8 Hz, 1H), 4.52 (t, J=8.6 Hz, 1H), 4.33-4.21 (m, 1H), 3.98-3.62 (m, 4H), 3.33 (dd, J=13.2, 3.3 Hz, 1H), 3.03-2.88 (m, 2H), 2.80 (d, J=13.2 Hz, 1H), 2.09-1.63 (m, 10H); MS (ES+) m/z 421.0 (M+1).

EXAMPLE 11.38

Synthesis of 4'-(pyrrolidin-1-ylmethyl)-1'-[(2R)-tetrahydrofuran-2-ylmethyl]-5,6-dihydrospiro[benzo[1,2-b:5,4-b']difuran-3,3'-indol]-2'(1'H)-one

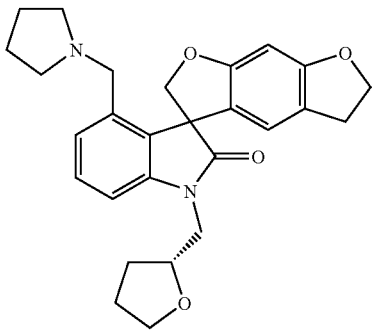

Following the procedure as described in EXAMPLE 11.37 and making non-critical variations using pyrrolidine to replace dimethylamine, 4'-(pyrrolidin-1-ylmethyl)-1'-[(2R)-tetrahydrofuran-2-ylmethyl]-5,6-dihydrospiro[benzo[1,2-b:5,4-b']difuran-3,3'-indol]-2'(1'H)-one was obtained (75%): $^1$H NMR (300 MHz, CDCl$_3$) δ7.29-7.20 (m, 1H), 7.09 (d, J=7.9 Hz, 1H), 6.98 (dd, J=7.0, 7.0 Hz, 1H), 6.45-6.39 (m, 1H), 6.36 (s, 1H), 5.10 (dd, J=8.8, 2.1 Hz, 1H), 4.87 (d, J=8.8 Hz, 1H), 4.51 (t, J=8.6 Hz, 1H), 4.32-4.20 (m, 1H), 3.98-3.62 (m, 4H), 3.58 (dd, J=13.2, 3.3 Hz, 1H), 3.03-2.89 (m, 3H), 2.40-1.59 (m, 12H); MS (ES+) m/z 447.1 (M+1).

EXAMPLE 11.39

Synthesis of 4'-amino-1'-[(2R)-tetrahydrofuran-2-ylmethyl]-5,6-dihydrospiro[benzo[1,2-b:5,4-b']difuran-3,3'-indol]-2'(1'H)-one

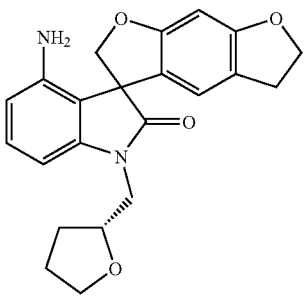

To a stirred solution of 4'-bromo-1'-[(2R)-tetrahydrofuran-2-ylmethyl]-5,6-dihydrospiro[benzo[1,2-b:5,4-b']difuran-3,3'-indol]-2'(1'H)-one (0.20 g, 0.45 mmol), benzophenone imine (0.11 mL, 0.68 mmol) and rac-2,2'-bis(diphenylphosphine)-1,1'-binaphthyl (0.10 g, 0.16 mmol) in toluene (5 mL) was added tris(dibenzylideneacetone) dipalladium(0) (0.05 g, 0.05 mmol) followed by the addition of sodium tert-butoxide (0.09 g, 0.9 mmol). The mixture was stirred at 90° C. for 18 h, filtered through a pad of celite. The filtrate was concentrated in vacuo, and the obtained residue was dissolved in tetrahydrofuran (15 mL). Hydrochloride solution (2 mL of 2 M solution) was added to the above mixture. The mixture was stirred at ambient temperature for 3 h. The mixture was neutralized with sodium bicarbonate solution, and extracted with ethyl acetate (3×30 mL). The combined organic solution was dried over anhydrous sodium sulfate and filtered. The filtrate was concentrated in vacuo. The residue was subjected to column chromatography (hexanes/ethyl acetate, 1/2) to afford 4'-amino-1'-[(2R)-tetrahydrofuran-2-ylmethyl]-5,6-dihydrospiro[benzo[1,2-b:5,4-b']difuran-3,3'-indol]-2'(1'H)-one (0.07 g, 46%) as a colorless solid: mp 190-192° C.; $^1$H NMR (300 MHz, CDCl$_3$) δ7.06 (dd, J=7.9, 7.9 Hz, 1H), 6.60 (d, J=10.6 Hz, 1H), 6.48 (dd, J=7.8, 3.0 Hz, 1H), 6.38 (s, 1H), 6.32 (d, J=8.2 Hz, 1H), 4.80 (s, 2H), 4.52 (t, J=8.6 Hz, 2H), 4.33-4.22 (m, 1H), 3.94-3.62 (m, 4H), 3.59 (s, 2H), 2.99 (t, J=8.8 Hz, 2H), 2.08-1.80 (m, 3H), 1.78-1.64 (m, 1H); MS (ES+) m/z 378.8 (M+1).

EXAMPLE 11.40 AND EXAMPLE 11.41

Synthesis of 1'-(morpholin-2-ylmethyl)-5,6-dihydrospiro[benzo[1,2-b:5,4-b']difuran-3,3'-indol]-2'(1'H)-one and 1'-[(4-methylmorpholin-2-yl)methyl]-5,6-dihydrospiro[benzo[1,2-b:5,4-b']difuran-3,3'-indol]-2'(1'H)-one

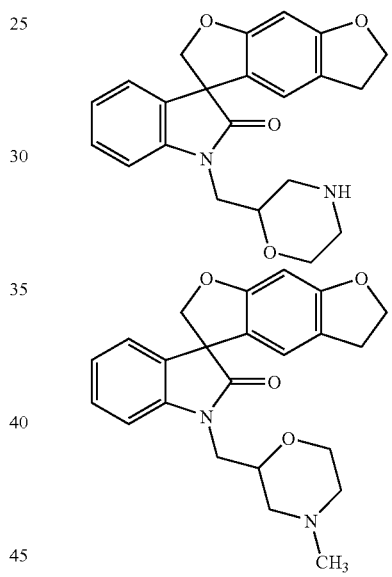

1-[(4-Benzylmorpholin-2-yl)methyl]-5,6-dihydrospiro[benzo[1,2-b:5,4-b']difuran-3,3'-indol]-2'(1'H)-one (0.19 g, 0.41 mmol) was suspended in methanol (20 mL) and ethyl acetate (20 mL) in a steel bomb, then 20% palladium hydroxide on carbon (0.03 g, 0.04 mmol) was added. Hydrogenation was done at 120 psi in the steel bomb for 16 h. The reaction mixture was filtered through a pad of celite, and the filtrate was concentrated to dryness. The residue was purified by column chromatography (ethyl acetate/methanol/ammonia, 10:1:0.1) to afford 1'-[(4-methylmorpholin-2-yl)methyl]-5,6-dihydrospiro[benzo[1,2-b:5,4-b']difuran-3,3'-indol]-2'(1'H)-one (0.015 g, 10%) as a colorless foam as the first fraction: $^1$H NMR (300 MHz, CDCl$_3$) δ7.34-7.25 (m, 1H), 7.17-6.99 (m, 3H), 6.48 (s, 0.5H), 6.44 (s, 0.5H), 6.39 (s, 1H), 4.94-4.88 (m, 1H), 4.69-4.63 (m, 1H), 4.52 (t, J=8.7 Hz, 2H), 4.00-3.55 (m, 5H), 2.97 (t, J=8.7 Hz, 2H), 2.76 (d, J=8.4 Hz, 1H), 2.60 (d, J=8.4 Hz, 1H), 2.26 (s, 3H), 2.18-1.88 (m, 2H); $^{13}$C NMR (75 MHz, CDCl$_3$) δ 178.1, 178.0, 161.8, 161.7, 161.2, 161.18, 142.7, 142.67, 132.7, 132.6, 128.7, 128.6), 123.7, 123.6, 123.3, 123.2, 120.4, 120.3, 119.8, 119.7, 118.9, 118.8, 109.6, 109.4, 93.2, 93.16, 80.5, 80.4, 73.7, 73.6, 72.3, 66.8, 66.6, 58.3 58.0, 57.6, 54.7, 54.6, 46.4, 46.3, 43.2, 43.17, 29.0; MS (ES+) m/z 393.0 (M+1), and 1-(morpholin-2-ylmethyl)-5,6-dihydrospiro[benzo[1,2-b:5,4-b']difuran-3,3'-indol]-2'(1'H)-one (0.04 g, 26%) as a colorless foam as the second fraction: MS (ES+) m/z 379.0 (M+1).

EXAMPLE 11.42

Synthesis of 1'-{[4-(1-methylethyl)morpholin-2-yl]methyl}-5,6-dihydrospiro[benzo[1,2-b:5,4-b']difuran-3,3'-indol]-2'(1'H)-one

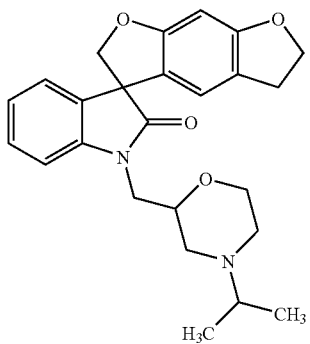

To a solution of acetone (0.04 mL, 0.53 mmol) in dichloroethane (5 mL) was added 1'-(morpholin-2-ylmethyl)-5,6-dihydrospiro[benzo[1,2-b:5,4-b']difuran-3,3'-indol]-2'(1'H)-one (0.04 g, 0.11 mmol) and sodium triacetoxyhydroborate (0.11 g, 0.53 mmol), then the mixture was stirred at ambient temperature for 16 h. The reaction mixture was concentrated to dryness, and the residue was purified by flash chromatography with ethyl acetate/methanol/ammonium hydroxide (15/1/0.1) to afford 1'-{[4-(1-methylethyl)morpholin-2-yl]methyl}-5,6-dihydrospiro[benzo[1,2-b:5,4-b']difuran-3,3'-indol]-2'(1'H)-one (0.02 g, 54%) as a colorless foam; $^1$H NMR (300 MHz, CDCl$_3$) δ7.38-7.25 (m, 1H), 7.18-7.04 (m, 3H), 6.50 (s, 0.5H), 6.44 (s, 0.5H), 6.41 (s, 1H), 4.92 (d, J=9.0 Hz, 1H), 4.68 (d, J=9.0 Hz, 1H), 4.53 (t, J=8.7 Hz, 2H), 4.00-3.55 (m, 5H), 2.97 (t, J=8.7 Hz, 2H), 2.85-2.55 (m, 3H), 2.37-2.03 (m, 2H), 1.05-0.98 (m, 6H); MS (ES+) m/z 421.0 (M+1).

EXAMPLE 11.43

Synthesis of 1'-methyl-5,6-dihydrospiro[benzo[1,2-b:5,4-b']difuran-3,3'-indol]-2'(1'H)-one

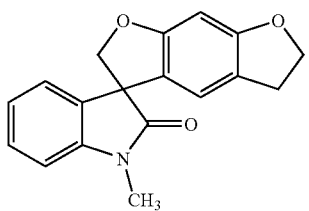

To a stirred solution of 5,6-dihydrospiro[benzo[1,2-b:5,4-b']difuran-3,3'-indol]-2'(1'H)-one (0.06 g, 0.20 mmol) in anhydrous N,N-dimethylformamide (10 mL) was added sodium hydride (60% in mineral oil, 0.20 g, 0.50 mmol) at ambient temperature. The mixture was stirred for 15 min, and iodomethane (0.14 g, 1.0 mmol) was added in one portion. The reaction mixture was stirred at ambient temperature for 1 h, and then concentrated to dryness. The residue was purified by flash chromatography with ethyl acetate in hexanes (0% to 30% gradient) to afford 1'-methyl-5,6-dihydrospiro[benzo[1,2-b:5,4-b']difuran-3,3'-indol]-2'(1'H)-one (0.06 g, 88%): mp 187-190° C.; $^1$H NMR (300 MHz, CDCl$_3$) δ7.32 (dd, J=7.4, 7.4 Hz, 1H), 7.17 (d, J=7.4 Hz, 1H), 7.06 (t, J=7.4 Hz, 1H), 6.91 (d, J=7.4 Hz, 1H), 6.49 (s, 1H), 6.40 (s, 1H), 4.79 (ABq, 2H), 4.52 (t, J=8.5 Hz, 2H), 3.28 (s, 3H), 2.98 (t, J=8.5 Hz, 2H); $^{13}$C NMR (75 MHz, CDCl$_3$) δ 177.7, 161.6, 161.1, 142.9, 132.7, 128.6, 123.6, 123.2, 120.0, 119.7, 118.8, 108.1, 93.0, 80.4, 72.2, 57.6, 28.9, 26.6; MS (ES+) m/z 294.1 (M+1).

EXAMPLE 11.44

Synthesis of 1'-[4-(1H-tetrazol-5-yl)benzyl]-5,6-dihydrospiro[benzo[1,2-b:5,4-b']difuran-3,3'-indol]-2'(1'H)-one

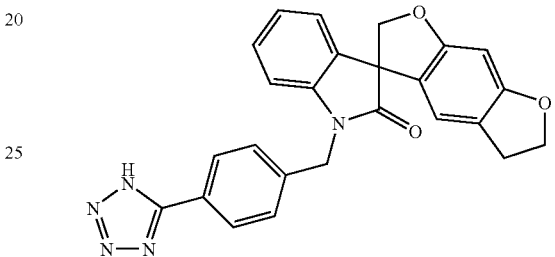

A round bottom flask was charged with 4-[(2'-oxo-5,6-dihydrospiro[benzo[1,2-b:5,4-b']difuran-3,3'-indol]-1'(2'H)-yl)methyl]benzonitrile (0.50 g, 1.27 mmol), sodium azide (0.21 g, 3.17 mmol), and triethylamine hydrochloride (0.45 g, 3.17 mmol) in toluene (20 mL). The reaction mixture was refluxed under argon for 24 h. After cooling to ambient temperature, the product was extracted with water. 36% hydrochloric acid was added dropwise to the aqueous layer. The solid was filtrated and dried under reduced pressure to afford 1'-[4-(1H-tetrazol-5-yl)benzyl]-5,6-dihydrospiro[benzo[1,2-b:5,4-b']difuran-3,3'-indol]-2'(1'H)-one (0.38 g, 58%); $^1$H NMR (300 MHz, CDCl$_3$) δ8.02 (d, J=8.0 Hz, 2H), 7.55 (d, J=8.0 Hz, 2H), 7.22 (t, J=7.6 Hz, 1H), 7.16 (d, J=7.6 Hz, 1H), 7.05-6.94 (m, 2H), 6.47 (s, 1H), 6.40 (s, 1H), 5.01 (ABq, 2H), 4.79 (ABq, 2H), 4.53-4.38 (m, 2H), 3.03-2.82 (m, 2H); $^{13}$C NMR (75 MHz, CD$_3$OD) δ177.6, 161.6, 161.2, 142.5, 140.1, 132.6, 129.1, 128.6, 127.9, 124.2, 123.6, 120.8, 120.4, 119.4, 109.8, 92.9, 80.3, 72.5, 57.4, 43.3, 28.8; MS (ES+) m/z 437.9 (M+1).

EXAMPLE 11.45

Synthesis of 1'-(3-hydroxybenzyl)-5,6-dihydrospiro[benzo[1,2-b:5,4-b']difuran-3,3'-indol]-2'(1'H)-one

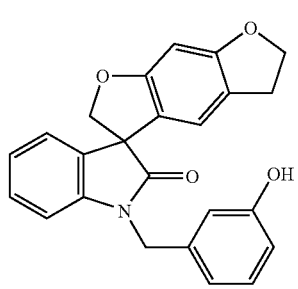

A mixture of 1'-[3-(benzyloxy)benzyl]-5,6-dihydrospiro[benzo[1,2-b:5,4-b']difuran-3,3'-indol]-2'(1'H)-one (1.30 g, 2.7 mmol) and 10% wt. palladium on carbon (0.25 g) in dry methanol (14 mL) was hydrogenated at ambient temperature under a balloon pressure for 16 h. The mixture was filtered through a pad of celite and concentrated in vacuo to dryness. The residue was subjected to column chromatography (hexanes/ethyl acetate from 2:1 to 1:1) to afford 1'-(3-hydroxybenzyl)-5,6-dihydrospiro[benzo[1,2-b:5,4-b']difuran-3,3'-indol]-2'(1'H)-one (0.97 g, 93%) as a colorless solid: mp 225-227° C.; $^1$H NMR (300 MHz, CDCl$_3$) δ9.48 (s, 1H), 7.30-7.22 (m, 1H), 7.20-7.11 (m, 2H), 7.06-6.94 (m, 2H), 6.81-6.76 (m, 1H), 6.72-6.69 (m, 1H), 6.68-6.63 (m, 1H), 6.46 (s, 1H), 6.43 (s, 1H), 4.85 (ABq, 2H), 4.79 (ABq, 2H), 4.55-4.46 (m, 2H), 3.02-2.92 (m, 2H); $^{13}$C NMR (75 MHz, CDCl$_3$) δ177.0, 161.1, 160.6, 157.6, 142.2, 137.6, 132.0, 129.7, 128.6, 123.6, 123.0, 120.4, 119.9, 118.9, 117.7, 114.4, 113.6, 109.4, 92.5, 79.8, 72.1, 56.9, 42.9, 28.3; MS (ES+) m/z 386.0 (M+1).

EXAMPLE 11.46

Synthesis of t-(4-morpholin-4-ylbenzyl)-5,6-dihydrospiro[benzo[1,2-b:5,4-b']difuran-3,3'-indol]-2' (1'H)-one

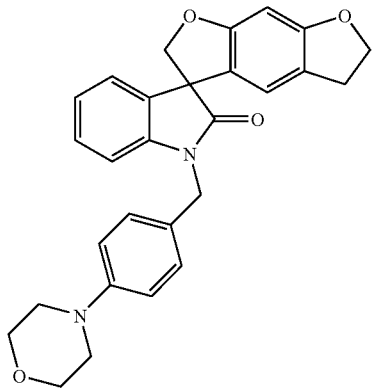

A suspension of 1'-(4-bromobenzyl)-5,6-dihydrospiro[benzo[1,2-b:5,4-b']difuran-3,3'-indol]-2'(1'H)-one (0.45 g, 1.0 mmol), morpholine (0.26 g, 3.0 mmol), dicyclohexyloxalylhydrazide (0.14 g, 0.5 mmol), tetrabutylammonium bromide (0.34 g, 1 mmol), copper (II) oxide (0.05 g, 0.6 mmol) and cesium carbonate (0.65 g, 2.0 mmol) was heated in microwave reactor at 130° C. for 10 min. The reaction mixture was concentrated under reduced pressure, and the residue was subjected to column chromatography with dichloromethanemethanol (100:1-10:1) to afford 1'-(4-morpholin-4-ylbenzyl)-5,6-dihydrospiro[benzo[1,2-b:5,4-b']difuran-3,3'-indol]-2'(1'H)-one as a colorless solid: $^1$H NMR (300 MHz, CDCl$_3$) δ 7.35-6.74 (m, 8H), (0.09 g, 19%), 6.45 (s, 1H), 6.41 (s, 1H), 4.87 (ABq, 2H), 4.81 (ABq, 2H), 4.52 (t, J=8.7, 8.7 Hz, 2H), 4.01-3.74 (m, 4H), 3.25-3.07 (m, 4H), 3.05-2.90 (m, 2H); $^{13}$C NMR (75 MHz, CDCl$_3$) δ 177.8, 161.8, 161.3, 142.1, 132.8, 128.6 (2C), 123.8, 123.3, 120.2, 119.9, 118.9, 116.0, 109.3, 93.2, 80.6, 72.3, 66.6, 57.7, 49.4, 43.6, 29.0; MS (ES+) m/z 454.87 (M+1).

EXAMPLE 11.47

Synthesis of 6-amino-1'-[(2R)-tetrahydrofuran-2-ylmethyl]spiro[1-benzofuran-3,3'-indol]-2'(1'H)-one

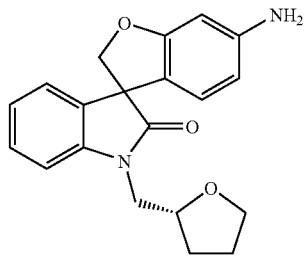

To a stirred solution of 6-bromo-1'-[(2R)-tetrahydrofuran-2-ylmethyl]spiro[1-benzofuran-3,3'-indol]-2'(1'H)-one (1.65 g, 4.1 mmol), benzophenone imine (0.90 g, 4.92 mmol), tris(dibenzylideneacetone)dipalladium(0) (0.46 g, 0.51 mmol), 2,2'-bis(diphenylphosphino)-1,1'-binaphthyl (0.96 g, 1.6 mmol) in toluene (50.0 mL) was added sodium tert-butoxide (0.55 g, 5.8 mmol). The solution was heated at reflux for 2 h, cooled to ambient temperature, diluted with ethyl acetate (75 mL), filtered through celite and concentrated in vacuo to dryness. The residue was dissolved in tetrahydrofuran (150 mL) and 3 M hydrochloric acid (15 mL). The solution was diluted in ethyl acetate (250 mL), and adjusted to basic with 5 M NaOH. The aqueous phase was further extracted with ethyl acetate (2×100 mL). The combined organic solution was dried over magnesium sulfate, filtered and concentrated in vacuo to dryness. The residue was purified by flash chromatography with ethyl acetate in hexanes (15% to 50% gradient) to afford 6-amino-1'-[(2R)-tetrahydrofuran-2-ylmethyl]spiro[1-benzofuran-3,3'-indol]-2' (1'H)-one (0.84 g, 61%) as a colorless solid: mp 71-74° C.; $^1$H NMR (300 MHz, CDCl$_3$, mixture of diastereomers) δ7.29-7.22 (m, 1H), 7.14-6.95 (m, 3H), 6.46 (d, J=8.1 Hz, 1H), 6.26 (d, J=2.0 Hz, 1H), 6.10 (dd, J=8.1, 2.0 Hz, 1H), 4.75 (ABq, 2H), 4.31-4.19 (m, 1H), 3.99-3.61 (m, 6H), 2.08-1.80 (m, 3H), 1.77-1.61 (m, 1H); $^{13}$C NMR (75 MHz, CDCl$_3$, mixture of diastereomers) δ178.3 (2), 162.1, 148.4, 142.9 (2), 132.7 (2), 128.6 (2), 123.7, 123.6 (2), 123.2 (2), 118.8 (2), 109.4 (2), 108.4, 97.2, 80.3 (2), 68.2 (2), 57.6 (2), 44.5 (2), 29.1 (2), 25.6 (2); MS (ES+) m/z 337.0 (M+1).

EXAMPLE 11.48

Synthesis of N-{2'-oxo-1'-[(2R)-tetrahydrofuran-2-ylmethyl]-1',2'-dihydrospiro[1-benzofuran-3,3'-indol]-6-yl}methanesulfonamide

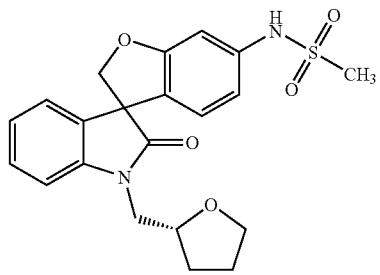

To a stirred solution of 6-amino-1-[(2R)-tetrahydrofuran-2-ylmethyl]spiro[1-benzofuran-3,3'-indol]-2'(1'H)-one (0.20 g, 0.6 mmol), triethylamine (0.09 g, 0.9 mmol) in dichloromethane was added methanesulfonyl chloride (0.07 g, 0.6 mmol). The solution was stirred at 0° C. for 4 h, then concentrated in vacuo to dryness. The residue was purified by flash chromatography with ethyl acetate in hexanes (50% to 75% gradient) to afford N-{2'-oxo-1'-[(2R)-tetrahydrofuran-2-yl-methyl]-1',2'-dihydrospiro[1-benzofuran-3,3'-indol]-6-yl}methanesulfonamide (0.15 g, 61%) as a colorless solid: ¹H NMR (300 MHz, CDCl₃) (diastereomers) δ7.75 (d, J=5.5 Hz, 1H), 7.28 (dd, J=7.4, 7.4 Hz, 1H), 7.13-6.97 (m, 3H), 6.75 (dd, J=8.3, 1.4 Hz, 1H), 6.59-6.42 (m, 2H), 4.93 (d, J=9.2 Hz, 1H), 4.66 (d, J=9.2 Hz, 1H), 4.38-4.20 (m, 1H), 3.99-3.64 (m, 4H), 2.92 (s, 3H), 2.16-1.77 (m, 3H), 1.77-1.61 (m, 1H); ¹³C NMR (75 MHz, CDCl₃) (diastereomers) δ178.2 (2), 161.7 (2), 142.8 (2), 138.9, 131.9 (2), 129.0 (2), 125.0 (2), 124.0 (2), 123.7 (2), 113.1 (2), 109.8 (2), 102.5 (2), 80.3 (2), 68.2 (2), 57.7 (2), 44.7 (2), 39.2, 25.6 (2); MS (ES+) m/z 415.0 (M+1).

EXAMPLE 11.49

Synthesis of 6-hydroxy-1'-(3-methylbutyl)spiro[1-benzofuran-3,3'-indol]-2'(1'H)-one

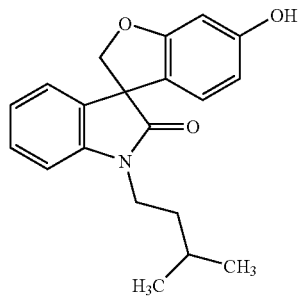

A suspension of 6-(benzyloxy)-1'-(3-methylbutyl)spiro[1-benzofuran-3,3'-indol]-2'(1'H)-one (7.80 g, 18.86 mmol) and 10% palladium on carbon (2.00 g, 1.88 mmol) in methanol (150 mL) was hydrogenated for 54 h. The mixture was filtered through a pad of celite, the filtrate was concentrated in vacuo, and the residue was crystallized from diethyl ether to give 6-hydroxy-1'-(3-methylbutyl)spiro[1-benzofuran-3,3'-indol]-2'(1'H)-one (5.20 g, 85%) as a colorless solid: mp 101-103° C. (diethyl ether); ¹H NMR (300 MHz, CDCl₃) δ7.32-7.27 (m, 1H), 7.16-7.14 (m, 1H), 7.07-7.02 (m, 1H), 6.92-6.89 (m, 1H), 6.40-6.38 (m, 1H), 6.20-6.12 (m, 2H), 4.77 (AB, 2H), 3.86-3.70 (m, 2H), 1.64-1.59 (m, 3H), 0.99 (d, J=6.0 Hz, 6H); MS (ES+) m/z 324.3 (M+1).

EXAMPLE 11.50

Synthesis of 6-hydroxy-1'-(3-methylbutyl)-5-(trifluoroacetyl)spiro[1-benzofuran-3,3'-indol]-2'(1'H)-one

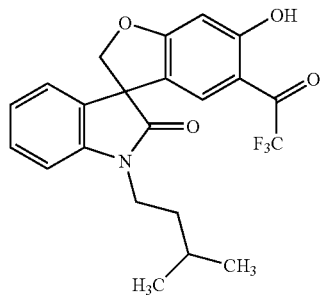

To a stirred solution of 6-hydroxy-1'-(3-methylbutyl)spiro[1-benzofuran-3,3'-indol]-2'(1'H)-one (1.00 g, 3.10 mmol) in tetrahydrofuran (30 mL) was added isopropylmagnesium chloride (1.6 mL, 2.0M tetrahydronfuran solution, 3.20 mmol) at 0° C. The mixture was allowed to stir at 0° C. for 1 h, then trifluoroacetic anhydride (0.8 mL, 5.75 mmol) was added. The mixture was stirred at ambient temperature for 52 h, quenched with saturated sodium bicarbonate solution and stirred for 30 min. The resulting solution was extracted with ethyl acetate. The organic layer was washed with water and brine, dried over anhydrous sodium sulfate and filtered. The filtrate was concentrated in vacuo. The residue was subjected to column chromatography with ethyl acetate in hexanes (gradient: 10% to 30%) to give 6-hydroxy-1'-(3-methylbutyl)-5-(trifluoroacetyl)spiro[1-benzofuran-3,3'-indol]-2'(1'H)-one (0.12 g, 9%): mp 87-88° C. (ethyl acetate/hexanes); ¹H NMR (300 MHz, CDCl₃) δ 11.78 (s, 1H), 7.38-7.32 (m, 1H), 7.14-7.03 (m, 3H), 7.07-7.02 (m, 1H), 6.94-6.89 (d, J=9.0 Hz, 1H), 6.58 (s, 1H), 4.90 (ABq, 2H), 3.95-3.86 (m, 1H), 3.71-3.62 (m, 1H), 1.66-1.59 (m, 3H), 0.98 (d, J=6.0 Hz, 6H); MS (ES+) m/z 420.1 (M+1).

EXAMPLE 11.51

Synthesis of tert-butyl (3R)-3-[(2'-oxo-1'-{[5-(trifluoromethyl)furan-2-yl]methyl}-1',2'-dihydrospiro [1-benzofuran-3,3'-indol]-6-yl)amino]pyrrolidine-1-carboxylate

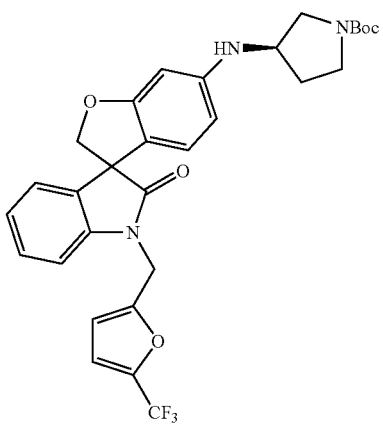

To a stirred solution of 6-bromo-1'-{[5-(trifluoromethyl)furan-2-yl]methyl}spiro[1-benzofuran-3,3'-indol]-2'(1'H)-one (0.80 g, 1.73 mmol), (R)-1-Boc-3-aminopyrrolidine (0.48 g, 2.59 mmol) and (2-biphenyl)di-tert-butylphosphine (0.08 g, 0.28 mmol) in toluene (15 mL) was added palladium (II) acetate (0.09 g, 0.14 mmol) followed by the addition of sodium tert-butoxide (0.42 g, 4.3 mmol). The mixture was stirred at 100° C. for 18 h. The mixture was filtered through a pad of celite, and the filtrate was concentrated in vacuo. The residue was subjected to column chromatography (ethyl acetate/hexane; 1/2) to afford tert-butyl (3R)-3-[(2'-oxo-1'-{[5-(trifluoromethyl)furan-2-yl]methyl}-1',2'-dihydrospiro [1-benzofuran-3,3'-indol]-6-yl)amino]pyrrolidine-1-carboxylate (0.47 g, 48%): ¹H NMR (300 MHz, CDCl₃) δ7.32-7.24 (m, 1H), 7.17 (d, J=7.4 Hz, 1H), 7.05 (dd, J=7.4 Hz, 1H), 6.95 (d, J=7.8 Hz, 1H), 6.76-6.69 (m, 1H), 6.45 (d, J=8.2 Hz, 1H), 6.36 (d, J=3.2 Hz, 1H), 6.19 (d, J=2.0 Hz, 1H), 6.02 (dd, J=8.2, 2.0 Hz, 1H), 5.05 (d, J=16.2 Hz, 1H), 4.95-4.81 (m, 2H), 4.65 (d, J=9.0 Hz, 1H), 4.00-3.90 (m, 1H), 3.88-3.76 (m, 1H), 3.73-3.57 (m, 1H), 3.52-3.34 (m, 2H), 3.30-3.11 (m, 1H), 2.23-2.06 (m, 1H), 1.96-1.77 (m, 1H), 1.45 (s, 9H); MS (ES+) m/z 570.2 (M+1).

EXAMPLE 11.52

Synthesis of 6-[(3R)-pyrrolidin-3-ylamino]-1'-{[5-(trifluoromethyl)furan-2-yl]methyl}spiro[1-benzofuran-3,3'-indol]-2'(1'H)-one

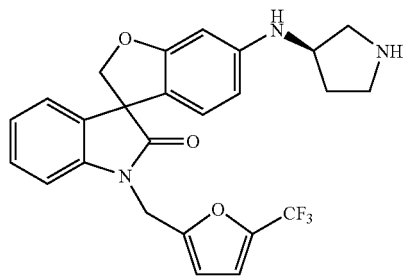

To a stirred solution of tert-butyl (3R)-3-[(2'-oxo-1-{[5-(trifluoromethyl)furan-2-yl]methyl}-1',2'-dihydrospiro[1-benzofuran-3,3'-indol]-6-yl)amino]pyrrolidine-1-carboxylate (0.22 g, 0.47 mmol) in methanol (10 mL) was added 4 M hydrogen chloride in dioxane (2 mL, 8.0 mmol). The mixture was stirred at ambient temperature for 16 h. Solvent and excess hydrogen chloride were removed under vacuum. The residue was treated with methanol and diethyl ether to form a solid. 6-[(3R)-Pyrrolidin-3-ylamino]-1'-{[5-(trifluoromethyl)furan-2-yl]methyl}spiro[1-benzofuran-3,3'-indol]-2'(1'H)-one was obtained through filtration (0.12 g, 47%) as a colorless solid: mp 122-125° C.; $^1$H NMR (300 MHz, CD$_3$OD) δ7.40 (dd, J=7.9, 7.9 Hz, 1H), 7.26-7.13 (m, 3H), 7.05-6.99 (m, 1H), 6.68 (d, J=3.2 Hz, 1H), 6.58-6.47 (m, 2H), 6.34 (d, J=8.2 Hz, 1H), 5.24 (d, J=16.7 Hz, 1H), 5.05 (d, J=16.7 Hz, 1H), 4.94 (d, J=9.1 Hz, 1H), 4.78 (d, J=9.1 Hz, 1H), 4.31-4.24 (m, 1H), 3.67-3.42 (m, 4H), 2.53-2.35 (m, 1H), 2.27-2.11 (m, 1H); $^{13}$C NMR (75 MHz, CD$_3$OD) δ178.1, 162.3 (m), 152.8, 141.5, 132.2, 128.7, 123.7, 123.6, 123.4, 120.8, 117.3, 112.8 (m), 109.5, 109.1, 79.8, 57.7, 54.2 (m), 49.4, 44.3, 36.3, 29.5; MS (ES+) m/z 470.2 (M+1).

EXAMPLE 11.53

Synthesis of 6-hydroxy-1'-[(2R)-tetrahydrofuran-2-ylmethyl]spiro[1-benzofuran-3,3'-indol]-2'(1'H)-one

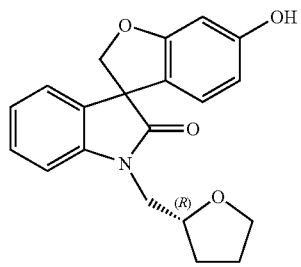

To a solution of 1'-[(2R)-tetrahydrofuran-2-ylmethyl]-6-{[tris(1-methylethyl)silyl]oxy}spiro[1-benzofuran-3,3'-indol]-2'(1'H)-one (1.69 g, 3.43 mmol) in anhydrous tetrahydrofuran (15 mL) under nitrogen was added tetrabutylammonium fluoride (1 M solution in tetrahydrofuran, 10 mL, 10 mmol), and the mixture was stirred at ambient temperature for 16 h. The reaction mixture was concentrated, and the residue was re-dissolved in ethyl acetate (25 mL), washed with water (2×20 mL) and brine (20 mL), dried over sodium sulfate, filtered, and concentrated. The residue was purified by column chromatography with 40% ethyl acetate in hexanes to afford 6-hydroxy-1'-[(2R)-tetrahydrofuran-2-ylmethyl]spiro[1-benzofuran-3,3'-indol]-2'(1'H)-one (1.00 g, 86%) as a colorless solid: mp 72-74° C.; $^1$H NMR (300 MHz, CDCl$_3$) δ7.29 (ddd, J=7.5, 7.5, 1.2 Hz, 1H), 7.18-7.01 (m, 3H), 6.80-6.67 (br., 1H), 6.44 (d, J=8.4 Hz, 1H), 6.24 (d, J=2.1 Hz, 1H), 6.17-6.09 (m, 1H), 4.96-4.90 (m, 1H), 4.69-4.63 (m, 1H), 4.36-4.24 (m, 1H), 4.00-3.71 (m, 4H), 2.12-1.61 (m, 4H); MS (ES+) m/z 338.1 (M+1).

EXAMPLE 11.54

Synthesis of 6-(1-methylethoxy)-1'-[(2R)-tetrahydrofuran-2-ylmethyl]spiro[1-benzofuran-3,3'-indol]-2'(1'H)-one

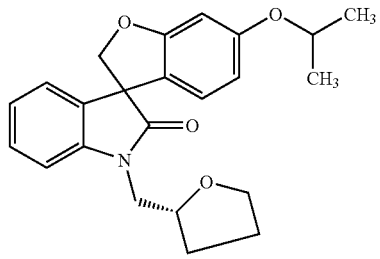

To a stirred solution of triphenylphosphine (0.23 g, 0.89 mmol) in anhydrous tetrahydronfuran (200 mL) at 0° C. under nitrogen were added diethyl azodicarboxylate (0.14 mL, 0.89 mmol), isopropanol (0.23 mL, 2.97 mmol) and 6-hydroxy-1'-[(2R)-tetrahydrofuran-2-ylmethyl]spiro[1-benzofuran-3,3'-indol]-2'(1'H)-one (0.20 g, 0.59 mmol). The reaction mixture was stirred at ambient temperature for 16 h, and then the reaction was quenched with ammonium chloride solution. The solvent was removed, and the residue was dissolved in ethyl acetate (100 mL), which was washed with water, brine, dried over sodium sulfate and filtered. The filtrate was concentrated to dryness, and the residue was purified by flash chromatograph with 25% ethyl acetate in hexanes to afford 6-(1-methylethoxy)-1'-[(2R)-tetrahydrofuran-2-ylmethyl]spiro[1-benzofuran-3,3'-indol]-2'(1'H)-one (0.19 g, 85%) as colorless liquid; $^1$H NMR (300 MHz, CDCl$_3$) δ7.33-7.25 (m, 1H), 7.16-6.99 (m, 3H), 6.58 (d, J=8.4 Hz, 1H), 6.50 (d, J=1.8 Hz, 1H), 6.33 (dd, J=8.4, 2.1 Hz, 1H), 4.93 (d, J=9.0 Hz, 1H), 4.68 (d, J=9.0 Hz, 1H), 4.53-4.43 (m, 1H), 4.33-4.23 (m, 1H), 4.00-3.66 (m, 4H), 2.10-1.66 (m, 4H), 1.31 (d, J=6.0 Hz, 6H); MS (ES+) m/z 380.0 (M+1), 402.0 (M+23).

EXAMPLE 11.55

Synthesis of tert-butyl (3S)-3-({2'-oxo-1'-[(2R)-tetrahydrofuran-2-ylmethyl]-1',2'-dihydrospiro[1-benzofuran-3,3'-indol]-6-yl}oxy)pyrrolidine-1-carboxylate

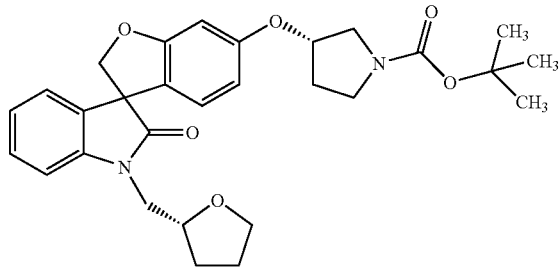

Following the procedure as described in EXAMPLE 11.54 and making non-critical variations using (R)-tert-butyl 3-hydroxypyrrolidine-1-carboxylate to replace isopropanol, tert-butyl (3S)-3-({2'-oxo-1'-[(2R)-tetrahydrofuran-2-ylmethyl]-1',2'-dihydrospiro[1-benzofuran-3,3'-indol]-6-yl}oxy)pyrrolidine-1-carboxylate was obtained (75%) as a colorless solid: $^1$H NMR (300 MHz, CDCl$_3$) δ7.33-7.26 (m, 1H), 7.17-7.00 (m, 3H), 6.64-6.57 (m, 1H), 6.50-6.45 (m, 1H), 6.35-6.28 (m, 1H), 4.94 (d, J=9.0 Hz, 1H), 4.85-4.78 (m, 1H), 4.69 (d, J=9.0 Hz, 1H), 4.33-4.22 (m, 1H), 4.00-3.40 (m, 8H), 2.22-1.65 (m, 6H), 1.47 (s, 9H); MS (ES+) m/z 529.1 (M+23).

EXAMPLE 11.56

Synthesis of 6-[(3S)-pyrrolidin-3-yloxy]-1'-[(2R)-tetrahydrofuran-2-ylmethyl]spiro[1-benzofuran-3,3'-indol]-2'(1'H)-one hydrochloride

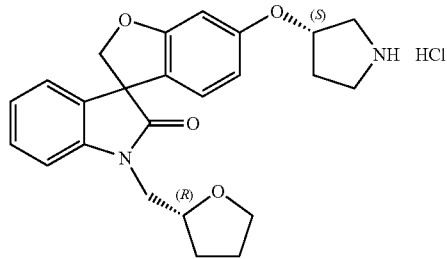

To a stirred solution of tert-butyl (3S)-3-({2'-oxo-1'-[(2R)-tetrahydrofuran-2-ylmethyl]-1',2'-dihydrospiro[1-benzofuran-3,3'-indol]-6-yl}oxy)pyrrolidine-1-carboxylate (0.33 g, 0.65 mmol) in dichloromethane (5 mL) was added 4 M hydrogen chloride in dioxane (4 mL, 16 mmol). The mixture was stirred at ambient temperature for 3 h, then anhydrous diethyl ether (20 mL) was added. The white solid was precipitated out, filtered, washed with diethyl ether and dried to afford 6-[(3S)-pyrrolidin-3-yloxy]-1'-[(2R)-tetrahydrofuran-2-ylmethyl]spiro[1-benzofuran-3,3'-indol]-2'(1'H)-one hydrochloride (0.24 g, 82%) as a colorless solid: mp 119-121° C.; $^1$H NMR (300 MHz, CD$_3$OD) δ7.38-7.03 (m, 4H), 6.68-6.59 (m, 2H), 6.48-6.41 (m, 1H), 5.20-5.14 (m, 1H), 4.92-4.85 (m, 1H), 4.73 (d, J=9.3 Hz, 1H), 4.37-4.24 (m, 1H), 4.00-3.38 (m, 8H), 2.36-1.66 (m, 6H); MS (ES+) m/z 407.1 (M+1).

EXAMPLE 11.57

Synthesis of tent-butyl (3R)-3-({2'-oxo-1'-[(2R)-tetrahydrofuran-2-ylmethyl]-1',2'-dihydrospiro[1-benzofuran-3,3'-indol]-6-yl}oxy)pyrrolidine-1-carboxylate

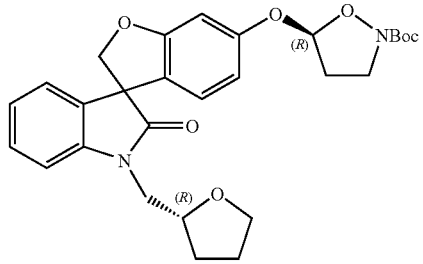

Following the procedure as described in EXAMPLE 11.54 and making non-critical variations using (S)-tert-butyl 3-hydroxypyrrolidine-1-carboxylate to replace isopropanol, tert-butyl (3R)-3-({2'-oxo-1'-[(2R)-tetrahydrofuran-2-ylmethyl]-1',2'-dihydrospiro[1-benzofuran-3,3'-indol]-6-yl}oxy)pyrrolidine-1-carboxylate was obtained (80%) as a colorless solid: $^1$H NMR (300 MHz, CDCl$_3$) δ7.34-7.26 (m, 1H), 7.16-7.00 (m, 3H), 6.60 (d, J=8.1 Hz, 1H), 6.47 (d, J=2.1 Hz, 1H), 6.32 (d, J=8.4, 2.1 Hz, 1H), 4.94 (d, J=9.0 Hz, 1H), 4.85-4.78 (m, 1H), 4.69 (d, J=9.0 Hz, 1H), 4.33-4.22 (m, 1H), 4.00-3.39 (m, 8H), 2.23-1.65 (m, 6H), 1.47 (s, 9H); MS (ES+) m/z 529.1 (M+23).

EXAMPLE 11.58

Synthesis of 6-[(3R)-pyrrolidin-3-yloxy]-1'-[(2R)-tetrahydrofuran-2-ylmethyl]spiro[1-benzofuran-3,3'-indol]-2'(1'H)-one hydrochloride

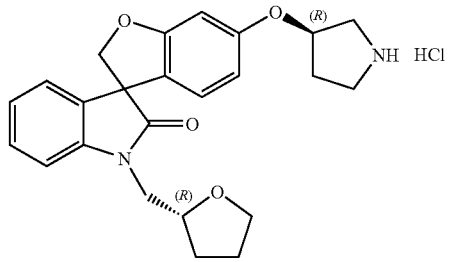

Following the procedure as described in EXAMPLE 11.56 and making non-critical variations using tert-butyl (3R)-3-({2'-oxo-1'-[(2R)-tetrahydrofuran-2-ylmethyl]-1',2'-dihydrospiro[1-benzofuran-3,3'-indol]-6-yl}oxy)pyrrolidine-1-carboxylate to replace tert-butyl (3S)-3-({2'-oxo-1'-[(2R)-tetrahydrofuran-2-ylmethyl]-1',2'-dihydrospiro[1-benzofuran-3,3'-indol]-6-yl}oxy)pyrrolidine-1-carboxylate, 6-[(3R)-pyrrolidin-3-yloxy]-1'-[(2R)-tetrahydrofuran-2-ylmethyl]spiro[1-benzofuran-3,3'-indol]-2'(1'H)-one hydrochloride was obtained (87%) as a colorless solid: mp 120-130° C.; $^1$H NMR (300 MHz, CD$_3$OD) δ7.38-7.04 (m, 4H), 6.68-6.59 (m, 2H), 6.48-6.41 (m, 1H), 5.20-5.14 (m, 1H), 4.92-4.85 (m, 1H), 4.73-4.70 (m, 1H), 4.36-4.24 (m, 1H), 3.99-3.38 (m, 8H), 2.36-1.66 (m, 6H); MS (ES+) m/z 407.1 (M+1).

EXAMPLE 11.59

Synthesis of tert-butyl 3-[(2'-oxo-1'-{[5-(trifluoromethyl)furan-2-yl]methyl}-1',2'-dihydrospiro[1-benzofuran-3,3'-indol]-6-yl)oxy]pyrrolidine-1-carboxylate

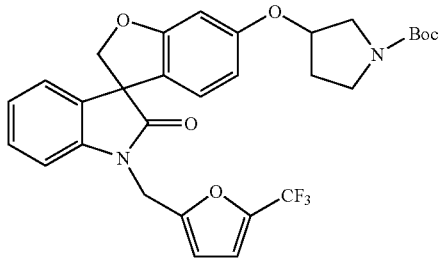

To a stirred solution of tert-butyl 3-[(2'-oxo-1',2'-dihydrospiro[1-benzofuran-3,3'-indol]-6-yl)oxy]pyrrolidine-1-carboxylate (0.19 g, 0.45 mol) in N,N-dimethyl formamide (10 mL) was added sodium hydride (0.02 g, 0.54 mmol) slowly at 0° C. After 30 min, 2-(bromomethyl)-5-(trifluoromethyl)furan (0.12 g, 0.54 mmol) was added. The mixture was stirred at ambient temperature for 16 h, and then quenched with saturated ammonium chloride (10 mL). The mixture was extracted with ethyl acetate (3×20 mL). The combined organic solution was dried over anhydrous sodium sulfate and filtered. The filtrate was concentrated in vacuo. The residue was subjected to column chromatography (ethyl acetate/hexanes, 1/2) to afford tert-butyl 3-[(2'-oxo-1-{[5-(trifluoromethyl)furan-2-yl]methyl}-1',2'-dihydrospiro[1-benzofuran-3,3'-indol]-6-yl)oxy]pyrrolidine-1-carboxylate (0.14 g, 55%) as a colorless solid: $^1$H NMR (300 MHz, CDCl$_3$) δ7.29 (t, J=7.7 Hz, 1H), 7.16 (d, J=7.4 Hz, 1H), 7.06 (t, J=7.5 Hz, 1H), 6.97 (d, J=7.8 Hz, 1H), 6.76-6.70 (m, 1H), 6.54 (d, J=8.2 Hz, 1H), 6.47 (s, 1H), 6.40-6.35 (m, 1H), 6.30 (d, J=8.2 Hz, 1H), 5.06 (d, J=16.2 Hz, 1H), 4.95 (d, J=9.0 Hz, 1H), 4.86 (d, J=16.2 Hz, 1H), 4.80 (br s, 1H), 4.69 (d, J=9.0 Hz, 1H), 3.64-3.37 (m, 4H), 2.22-1.96 (m, 2H), 1.45 (s, 9H); MS (ES+) m/z 593.2 (M+23).

EXAMPLE 11.60

Synthesis of 1'-[(2R)-tetrahydrofuran-2-ylmethyl] spiro[benzo[1,2-b:5,4-b']difuran-3,3'-indole]-2',5 (1'H,6H)-dione

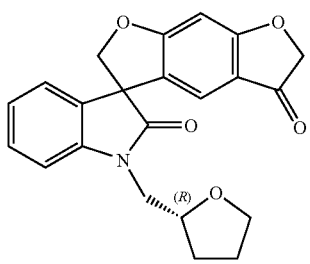

To a solution of ({2'-oxo-1'-[(2R)-tetrahydrofuran-2-ylmethyl]-1',2'-dihydrospiro[1-benzofuran-3,3'-indol]-6-yl}oxy)acetic acid (0.42 g, 1.06 mmol) in benzene were added oxaly chloride (0.28 mL, 3.18 mmol) and a drop of N,N-dimethyl formamide, then the reaction mixture was refluxed for 16 h. The mixture was evaporated to dryness and dried over high vacuum pump. The residue was re-dissolved in anhydrous dichloromethane (30 mL), and then aluminum trichloride (0.21 g, 1.59 mmol) was added. The reaction mixture was stirred at ambient temperature for 16 h, and then refluxed for 2 h. The reaction was quenched by saturated ammonium chloride, and then extracted with dichloromethane (2×50 mL). The combined organic phase was dried over sodium sulfate, filtered, concentrated and purified by flash chromatography with 50% ethyl acetate in hexanes to give 1-[(2R)-tetrahydrofuran-2-ylmethyl]spiro[benzo[1,2-b: 5,4-b']difuran-3,3'-indole]-2',5(1'H,6H)-dione (0.28 g, 69%) as a colorless solid: mp 142-144° C.; $^1$H NMR (300 MHz, CDCl$_3$) δ7.36-7.29 (m, 1H), 7.16-7.00 (m, 4H), 6.64-6.60 (m, 1H), 5.08 (d, J=9.3 Hz, 1H), 4.85-4.80 (m, 1H), 4.61 (s, 2H), 4.31-4.19 (m, 1H), 3.98-3.68 (m, 4H), 2.11-1.84 (m, 3H), 1.76-1.62 (m, 1H); MS (ES+) m/z 377.9 (M+1), 399.9 (M+23).

EXAMPLE 11.61

Synthesis of 1'-(pyrrolidin-3-ylmethyl)-5,6-dihydrospiro[benzo[1,2-b:5,4-b']difuran-3,3'-indol]-2' (1'H)-one

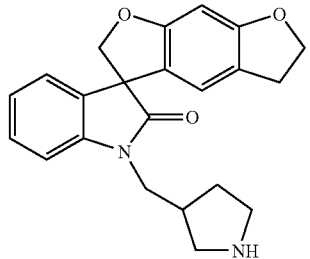

Following the procedure described in EXAMPLE 11.5 and making non-critical variations using tert-butyl 3-[(2'-oxo-5, 6-dihydrospiro[benzo-[1,2-b:5,4-b']difuran-3,3'-indol]-1' (2'H)-yl)methyl]pyrrolidine-1-carboxylate to replace tert-butyl 4-[(2'-oxo-5,6-dihydrospiro[benzo[1,2-b:5,4-b']difuran-3,3'-indol]-1'(2'H)-yl)methyl]piperidine-1-carboxylate, tetrahydrofuran to replace dichloromethane, 1-(pyrrolidin-3-ylmethyl)-5,6-dihydrospiro[benzo[1,2-b:5,4-b']difuran-3,3'-indol]-2'(1'H)-one was obtained (66%) as a colorless solid: mp 85-95° C. (dichloromethane); $^1$H NMR (300 MHz, CDCl$_3$) (diastereomers) δ7.309 (dd, J=7.8, 1.2 Hz, 0.5 Hz), 7.305 (dd, J=7.8, 1.2 Hz, 0.5H), 7.180 (d, J=7.5, Hz, 0.5H), 7.177 (d, J=7.5 Hz, 0.5H), 7.063 (dd, J=7.5, 0.6 Hz, 0.5H), 7.060 (dd, J=7.5, 0.6 Hz, 0.5H), 6.96 (d, J=7.8 Hz, 1H), 6.452 (s, 0.5H), 6.450 (s, 0.5H), 6.41 (s, 1H), 4.92 (d, J=9.0 Hz, 0.5H), 4.91 (d, J=9.0 Hz, 0.5H), 4.67 (d, J=9.0 Hz, 0.5H), 4.66 (d, J=9.0 Hz, 0.5H), 4.54 (t, J=8.7 Hz, 2H), 3.85 (dd, J=14.1, 8.7 Hz, 0.5H), 3.83 (dd, J=13.8, 7.8 Hz, 0.5H), 3.67 (dd, J=13.8, 7.5 Hz, 0.5H), 3.65 (dd, J=13.9, 6.8 Hz, 0.5H), 3.18-2.92 (m, 4H), 2.84-2.65 (m, 2H), 2.55-2.36 (m, 2H), 2.02-1.89 (m, 1H), 1.67-1.53 (m, 1H); $^{13}$C NMR (75 MHz, CDCl$_3$) (diastereomers) δ 178.2, 161.9, 161.4, 142.41, 142.38, 132.9, 128.9, 124.1, 123.5, 120.3, 120.2, 120.1, 120.0, 118.8, 108.7, 93.3, 80.7, 72.48, 72.47, 57.8, 50.4, 46.30, 46.25, 43.41, 43.39, 37.8, 29.91, 29.86, 29.13; MS (ES+) m/z 363.3 (M+1).

EXAMPLE 11.62

Synthesis of N-(1-methylethyl)-3-[(2'-oxo-5,6-dihydrospiro[benzo[1,2-b:5,4-b']difuran-3,3'-indol]-1'(2'H)-yl)methyl]pyrrolidine-1-carboxamide

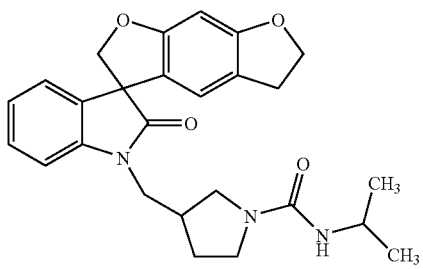

To a solution of 1'-(pyrrolidin-3-ylmethyl)-5,6-dihydrospiro[benzo[1,2-b:5,4-b']difuran-3,3'-indol]-2'(1'H)-one (0.24 g, 0.65 mmol) and triethylamine (0.15 mL, 1.1 mmol) in dichloromethane (5 mL) was added isopropyl isocyanate (0.10 mL, 1.0 mmol) and the solution was stirred at ambient temperature for 35 min. The reaction was diluted with saturated sodium bicarbonate (40 mL) and was extracted with dichloromethane (3×20 mL). The combined organic solution was dried over sodium sulfate, filtered and concentrated under reduced pressure. Purification by flash column chromatography with dichloromethane/diethyl ether (2/1) afforded N-(1-methylethyl)-3-[(2'-oxo-5,6-dihydrospiro[benzo[1,2-b:5,4-b']difuran-3,3'-indol]-1'(2'H)-yl)methyl]pyrrolidine-1-carboxamide (0.24 g, 81%) as a colorless solid: mp 107-115° C. (hexanes); $^1$H NMR (300 MHz, CDCl$_3$) (diastereomers) δ7.31 (dd, J=7.6, 7.6 Hz, 0.5H), 7.30 (dd, J=7.7, 7.7 Hz, 0.5H), 7.18 (d, J=6.8 Hz, 1H), 7.07 (dd, J=7.5, 7.5 Hz, 1H), 6.90 (d, J=7.8 Hz, 1H), 6.45 (s, 1H), 6.42 (s, 1H), 4.912 (d, J=9.0 Hz, 0.5H), 4.906 (d, J=8.9 Hz, 0.5H), 4.67 (d, J=8.9 Hz, 0.5H), 4.66 (d, J=9.0 Hz, 0.5H), 4.53 (t, J=8.6 Hz, 2H), 4.03-3.44 (m, 6H), 3.35-3.17 (m, 2H), 3.00 (t, J=8.5 Hz, 2H), 2.77 (septet, J=6.9 Hz, 1H), 2.09-1.98 (m, 1H), 1.87-1.73 (m, 1H), 1.15 (d, J=5.7 Hz, 3H), 1.14 (d, J=6.0 Hz, 3H); $^{13}$C NMR (75 MHz, CDCl$_3$) (diastereomers) δ178.33, 178.26, 162.0, 161.4, 156.3, 142.41, 142.36, 132.80, 132.75, 129.0, 124.25, 124.23, 123.6, 120.16, 120.10, 120.07, 118.9, 118.8, 108.4, 93.39, 93.36, 80.8, 72.5, 57.8, 49.2, 44.7, 44.6, 42.6, 42.5, 42.43, 42.40, 37.7, 37.5, 29.35, 29.32, 29.1, 23.7; MS (ES+) m/z 448.2 (M+1).

EXAMPLE 11.63

Synthesis of 1'-[(4-methylpiperazin-1-yl)methyl]spiro[furo[2,3-f][1,3]benzodioxole-7,3'-indol]-2'(1'H)-one hydrogen chloride

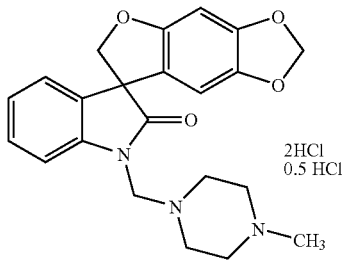

A stirred solution of spiro[furo[2,3-f][1,3]benzodioxole-7,3'-indol]-2'(1'H)-one (1.0 g, 3.6 mmol), N-methylpiperazine (3.6 g, 36.0 mmol) and formaldehyde (37% wt solution in water, 2.9 mL, 36.0 mmol) in methanol was refluxed for 20 h. The solution was concentrated in vacuo to dryness and recrystallized from ether in hexanes to afford the free base form of 1'-[(4-methylpiperazin-1-yl)methyl]spiro[furo[2,3-f][1,3]benzodioxole-7,3'-indol]-2'(1'H)-one as a pale orange solid (1.15 g, 81%). To a solution of 1'-[(4-methylpiperazin-1-yl)methyl]spiro[furo[2,3-f][1,3]benzodioxole-7,3'-indol]-2'(1'H)-one (0.50 g, 12.7 mmol) in methanol (5 mL) was added hydrochloric acid saturated methanol (10 mL). The precipitate that formed was filtered and dried in vacuo to afford 1'-[(4-methylpiperazin-1-yl)methyl]spiro[furo[2,3-f][1,3]benzodioxole-7,3'-indol]-2'(1'H)-one hydrogen chloride (0.65 g, quantitative) as a colorless solid: mp>175° C. (dec.); $^1$H NMR (300 MHz, DMSO-d$_6$) δ11.59 (br s, 1H), 9.43 (br s, 1H), 7.41 (d, J=7.9 Hz, 1H), 7.31 (dd, J=7.6, 7.6 Hz, 1H), 7.15 (d, J=6.6 Hz, 1H), 7.06 (dd, J=7.4, 7.4 Hz, 1H), 6.66 (s, 1H), 6.47 (s, 1H), 5.89 (s, 2H), 4.86-4.73 (m, 3H), 4.61 (d, J=9.5 Hz, 1H), 3.54-3.28 (m, 4H), 3.27-2.94 (m, 4H), 2.71 (s, 3H); MS (ES+) m/z 394.0 (M+1). Anal. Calcd. for C$_{20}$H$_{23}$N$_3$O$_4$.2HCl.0.5H$_2$O: C, 55.59; H, 5.51; N, 8.84. Found: C, 55.47; H, 5.43; N, 8.78.

EXAMPLE 11.64

Synthesis of (3S)-6-methoxy-5-methyl-1'-[(4-methylpiperazin-1-yl)methyl]spiro[1-benzofuran-3,3'-indol]-2'(1'H)-one hydrogen chloride

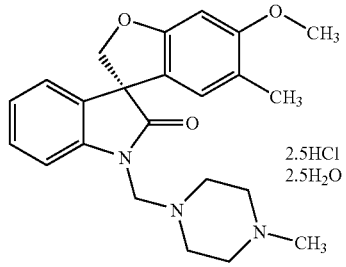

A stirred solution of (3S)-6-methoxy-5-methylspiro[1-benzofuran-3,3'-indol]-2'(1'H)-one (0.50 g, 1.8 mmol), N-methylpiperazine (1.80 g, 17.8 mmol) and formaldehyde (37% wt solution in water, 1.45 mL, 17.8 mmol) in methanol was refluxed for 3 h. The solution was concentrated in vacuo to dryness and dissolved in methanol (5 mL) and hydrochloric acid saturated methanol (10 mL). The solution was again concentrated in vacuo to dryness, dissolved in distilled water (25 mL) and the product was precipitated upon addition of 5 M NaOH (15 mL). The solid was filtered and air dried to afford (3S)-6-methoxy-5-methyl-1'-[(4-methylpiperazin-1-yl)methyl]spiro[1-benzofuran-3,3'-indol]-2'(1'H)-one (0.65 g, 93%). To a stirred solution of the above product (0.20 g) in methanol (1 mL) was added hydrochloric acid saturated methanol (2 mL). The solution was stirred for 20 min, then diethyl ether (25 mL) was added and the suspension was filtered and air dried to afford (3S)-6-methoxy-5-methyl-1'-[(4-methylpiperazin-1-yl)methyl]spiro[1-benzofuran-3,3'-indol]-2'(1'H)-one hydrogen chloride (0.19 g, 71%) as a colorless solid: mp>200° C. (dec.); $^1$H NMR (300 MHz, CDCl$_3$) δ7.71 (s, 2H), 7.42 (d, J=7.9 Hz, 1H), 7.33 (dd, J=7.5, 7.5 Hz, 1H), 7.17-7.03 (m, 2H), 6.69 (s, 1H), 6.62 (s, 1H), 4.89-4.70 (m, 2H), 4.65 (d, J=9.40 Hz, 1H), 3.77 (s, 3H), 3.52-2.91 (m, 5H), 2.72 (s, 3H), 1.98 (s, 3H); MS (ES+) m/z 394.0 (M+1);

Anal. Calcd. for $C_{23}H_{27}N_3O_3 \cdot 2.5HCl \cdot 2.5H_2O$: C, 52.15; H, 6.57; N, 7.93. Found: C, 52.07; H, 6.32; N, 8.50.

EXAMPLE 11.65

Synthesis of (3R)-6-methoxy-5-methyl-1'-[(4-methylpiperazin-1-yl)methyl]spiro[1-benzofuran-3,3'-indol]-2'(1'H)-one hydrogen chloride

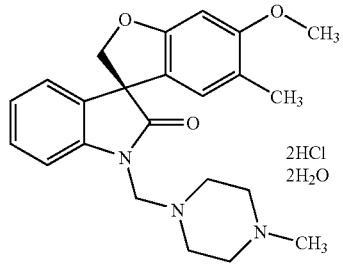

Following the procedure as described in EXAMPLE 11.64 and making non-critical variations using (3R)-6-methoxy-5-methylspiro[1-benzofuran-3,3'-indol]-2'(1'H)-one to replace (3S)-6-methoxy-5-methylspiro[1-benzofuran-3,3'-indol]-2'(1'H)-one, (3R)-6-methoxy-5-methyl-1'-[(4-methylpiperazin-1-yl)methyl]spiro[1-benzofuran-3,3'-indol]-2'(1'H)-one hydrogen chloride was obtained (27%) as a colorless solid: mp>200° C. (dec.); $^1$H NMR (300 MHz, CDCl$_3$) δ7.57-7.49 (m, 2H), 7.39 (d, J=7.9 Hz, 1H), 7.29 (t, J=7.5 Hz, 1H), 7.15-6.99 (m, 2H), 6.65 (s, 1H), 6.59 (s, 1H), 4.87-4.67 (m, 2H), 4.62 (d, J=9.4 Hz, 1H), 3.73 (s, 3H), 3.51-2.86 (m, 5H), 2.69 (s, 3H), 1.95 (s, 3H); MS (ES+) m/z 393.99 (M+1); Anal. Calcd. for $C_{23}H_{27}N_3O_3 \cdot 2HCl \cdot 2H_2O$: C, 54.98; H, 6.62; N, 8.36. Found: C, 54.92; H, 6.33; N, 8.32.

EXAMPLE 11.66

Synthesis of (3S)-1'-[(2R)-tetrahydrofuran-2-ylmethyl]-5,6-dihydrospiro[benzo[1,2-b:5,4-b']difuran-3,3'-indol]-2'(1'H)-one

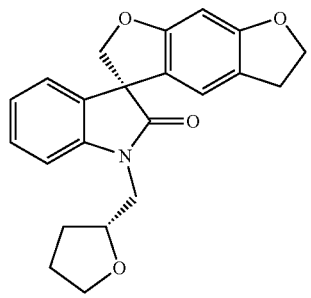

1'-[(2R)-Tetrahydrofuran-2-ylmethyl]-5,6-dihydrospiro[benzo[1,2-b:5,4-b']difuran-3,3'-indol]-2'(1'H)-one was resolved on chiral semi-prep HPLC IA column with 99% tert-butylmethyl ether and 1% acetonitrile to afford (3S)-1'-[(2R)-tetrahydrofuran-2-ylmethyl]-5,6-dihydrospiro[benzo[1,2-b:5,4-b']difuran-3,3'-indol]-2'(1'H)-one (66%): $^1$H NMR (300 MHz, CDCl$_3$) δ7.34-6.97 (m, 4H), 6.48 (s, 1H), 6.38 (s, 1H), 4.77 (ABq, 2H), 4.50 (t, J=8.6 Hz, 2H), 4.32-4.21 (m, 1H), 3.92-3.68 (m, 4H), 2.96 (t, J=8.4 Hz, 2H), 2.10-1.64 (m, 4H); $^{13}$C NMR (75 MHz, CDCl$_3$) δ 178.2, 161.7, 161.2, 142.8, 132.7, 128.6, 123.6, 123.2, 120.4, 119.8, 118.9, 109.5, 93.1, 80.7, 76.8, 72.3, 68.1, 57.6, 44.5, 29.0, 29.0, 25.6; MS (ES+) m/z 363.8 (M+1).

EXAMPLE 11.67

Synthesis of (3R)-1'-[(2R)-tetrahydrofuran-2-ylmethyl]-5,6-dihydrospiro[benzo[1,2-b:5,4-b']difuran-3,3'-indol]-2'(1'H)-one

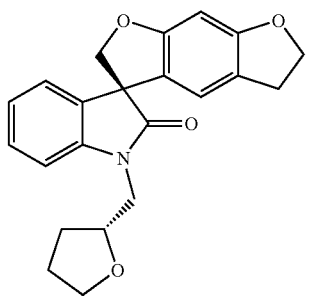

1'-[(2R)-Tetrahydrofuran-2-ylmethyl]-5,6-dihydrospiro[benzo[1,2-b:5,4-b']difuran-3,3'-indol]-2'(1'H)-one was resolved on chiral semi-prep HPLC IA column with tert-butylmethyl ether (99%) and acetonitrile (1%) to afford (3R)-1'-[(2R)-tetrahydrofuran-2-ylmethyl]-5,6-dihydrospiro[benzo[1,2-b:5,4-b']difuran-3,3'-indol]-2'(1'H)-one (66%): $^1$H NMR (300 MHz, CDCl$_3$) δ 7.35-6.98 (m, 4H), 6.47 (s, 1H), 6.38 (s, 1H), 4.78 (Abq, 2H), 4.51 (t, J=8.6 Hz, 2H), 4.31-4.21 (m, 1H), 3.99-3.63 (m, 4H), 3.03-2.90 (m, 2H), 2.10-1.62 (m, 4H); $^{13}$C NMR (75 MHz, CDCl$_3$) δ178.1, 161.7, 161.2, 142.8, 132.6, 128.6, 123.6, 123.2, 120.3, 119.8, 118.8, 109.4, 93.1, 80.6, 76.9, 72.3, 68.2, 57.6, 44.6, 29.2, 29.0, 25.5; MS (ES+) m/z 363.8 (M+1).

EXAMPLE 11.68

Synthesis of (3R)-1-[(2S)-tetrahydrofuran-2-ylmethyl]-5,6-dihydrospiro[benzo[1,2-b:5,4-b']difuran-3,3'-indol]-2'(1'H)-one

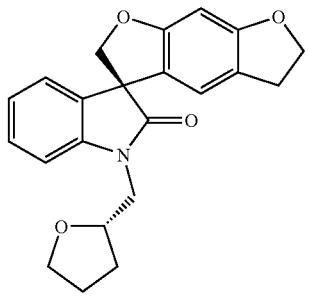

1'-[(2S)-Tetrahydrofuran-2-ylmethyl]-5,6-dihydrospiro[benzo[1,2-b:5,4-b']difuran-3,3'-indol]-2'(1'H)-one was resolved on chiral semi-prep HPLC IA column with tert-butylmethyl ether (100%) to afford (3R)-1'-[(2S)-tetrahydrofuran-2-ylmethyl]-5,6-dihydrospiro[benzo[1,2-b:5,4-b']difuran-3,3'-indol]-2'(1'H)-one (64%): $^1$H NMR (300 MHz, CDCl$_3$) δ7.32-6.98 (m, 4H), 6.47 (s, 1H), 6.38 (s, 1H), 4.77 (ABq, 2H), 4.51 (t, J=8.6 Hz, 2H), 4.31-4.21 (m, 1H), 3.98-3.64 (m, 4H), 3.05-2.88 (m, 2H), 2.09-1.64 (m, 4H); $^{13}$C NMR (75 MHz, CDCl$_3$) δ 178.2, 161.7, 161.2, 142.8, 132.6, 128.6, 123.6, 123.2, 120.3, 119.8, 118.8, 109.4, 93.1, 80.6, 76.9, 72.3, 68.2, 57.6, 44.6, 29.2, 29.0, 25.5; MS (ES+) m/z 363.8 (M+1).

EXAMPLE 11.69

Synthesis of (3S)-1'-[(2S)-tetrahydrofuran-2-ylmethyl]-5,6-dihydrospiro[benzo[1,2-b:5,4-b']difuran-3,3'-indol]-2'(1'H)-one

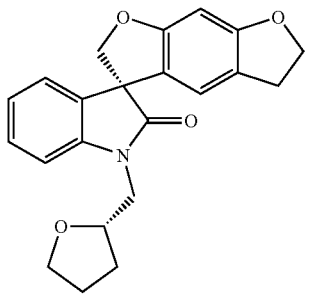

1'-[(2S)-Tetrahydrofuran-2-ylmethyl]-5,6-dihydrospiro[benzo[1,2-b:5,4-b']difuran-3,3'-indol]-2'(1'H)-one was resolved on chiral semi-prep HPLC IA column with tert-butylmethyl ether (100%) to afford (3S)-1'-[(2S)-tetrahydrofuran-2-ylmethyl]-5,6-dihydrospiro[benzo[1,2-b:5,4-b']difuran-3,3'-indol]-2'(1'H)-one (64%): $^1$H NMR (300 MHz, CDCl$_3$) δ 7.32-6.97 (m, 4H), 6.48 (s, 1H), 6.38 (s, 1H), 4.77 (ABq, 2H), 4.51 (t, J=8.3 Hz, 2H), 4.32-4.21 (m, 1H), 3.91-3.68 (m, 4H), 2.97 (t, J=8.5 Hz, 2H), 2.10-1.63 (m, 4H); $^{13}$C NMR (75 MHz, CDCl$_3$) δ 178.3, 161.7, 161.2, 142.8, 132.7, 128.6, 123.6, 123.2, 120.4, 119.8, 118.9, 109.5, 93.1, 80.6, 76.8, 72.3, 68.1, 57.6, 44.5, 29.0, 25.6; MS (ES+) m/z 363.8 (M+1).

EXAMPLE 11.70

Synthesis of 1'-{[(2S)-1-methyl-5-oxopyrrolidin-2-yl]methyl}-5,6-dihydrospiro[benzo[1,2-b:5,4-b']difuran-3,3'-indol]-2'(1'H)-one

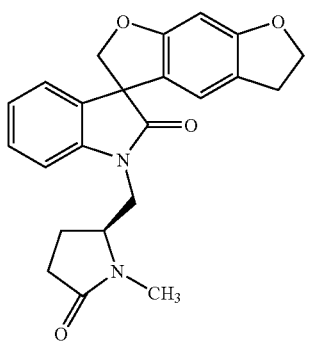

To a stirred solution of 1-{[(2S)-5-oxopyrrolidin-2-yl]methyl}-5,6-dihydrospiro[benzo[1,2-b:5,4-b']difuran-3,3'-indol]-2'(1'H)-one (0.235 g, 0.623 mmol) in dry N,N-dimethylformamide (10 mL) was added sodium hydride (60% in mineral oil, 0.04 g, 1.04 mmol) at ambient temperature. The mixture was stirred for 15 min, and iodomethane (0.28 g, 2.0 mmol) was added in one portion. The reaction mixture was stirred at ambient temperature for 1 h, and concentrated to dryness. The residue was purified by flash chromatography (hexanes/ethyl acetate; gradient 0% to 30%) to afford 1'-{[(2S)-1-methyl-5-oxopyrrolidin-2-yl]methyl}-5,6-dihydrospiro[benzo[1,2-b:5,4-b']difuran-3,3'-indol]-2'(1'H)-one (0.15 g, 62%) as colorless solid: mp 72-76° C.; $^1$H NMR (300 MHz, CDCl$_3$) δ7.33 (dd, J=7.5, 7.5 Hz, 1H), 7.20 (d, J=7.5 Hz, 1H), 7.09 (dd, J=7.5, 7.5 Hz, 1H), 6.91 (d, J=7.5 Hz, 1H), 6.46-6.38 (m, 2H), 4.77 (ABq, 2H), 4.53 (t, J=8.6 Hz, 2H), 4.03-3.75 (m, 3H), 3.11-2.83 (m, 5H), 2.61-2.42 (m, 1H), 2.42-2.27 (m, 1H), 2.26-2.07 (m, 1H), 2.03-1.84 (m, 1H); $^{13}$C NMR (75 MHz, CDCl$_3$) δ178.4, 178.4, 175.1, 175.0, 161.8, 161.3, 161.2, 142.1, 141.9, 132.5, 132.4, 128.9 (2C), 124.3, 124.2, 123.7 (2C), 120.0, 119.9, 119.7, 119.6, 118.6, 118.5, 108.0, 93.2, 80.5, 72.3, 58.1, 58.0, 57.5 (2C), 43.0, 42.9, 29.3, 29.2, 28.9, 28.7 (2C), 22.6 (20); MS (ES+) m/z 391.1 (M+1).

EXAMPLE 11.71

Synthesis of 1-[(3-methyl-2-oxo-1,3-oxazolidin-5-yl)methyl]spiro[furo[2,3-f][1,3]benzodioxole-7,3'-indol]-2'(1'H)-one

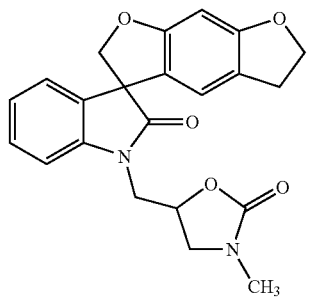

A mixture of 1'-[(2-oxo-1,3-oxazolidin-5-yl)methyl]spiro[furo[2,3-f][1,3]benzodioxole-7,3'-indol]-2'(1'H)-one (0.32 g, 0.84 mmol), tetrabutylammonium bromide (0.05 g, 0.16 mmol), aqueous sodium hydroxide (0.10 g, 2.52 mmol) and dimethyl sulfate (0.21 g, 1.68 mmol) in anhydrous tetrahydrofuran (5 mL), was stirred at an ambient temperature for 1 h. The mixture was concentrated in vacuo to dryness. The residue was purified by column chromatography with ethyl acetate (30%) in hexanes to afford 1'-[(3-methyl-2-oxo-1,3-oxazolidin-5-yl)methyl]spiro[furo[2,3-f][1,3]benzodioxole-7,3'-indol]-2'(1'H)-one (0.13 g, 40%): mp 98-102° C.; $^1$H NMR (300 MHz, CDCl$_3$) δ 7.39 (dd, J=7.7, 7.7 Hz, 1H), 7.18 (d, J=7.4 Hz, 1H), 7.07 (dd, J=7.5, 7.5 Hz, 1H), 6.88 (d, J=7.8 Hz, 1H), 6.49 (s, 1H), 6.05 (s, 1H), 5.84 (d, J=6.2 Hz, 2H), 4.74 (ABq, 2H), 3.93-3.88 (m, 2H), 3.82-3.74 (m, 1H), 2.92 (d, J=4.0 Hz, 3H), 2.55-2.40 (m, 1H), 2.36-2.26 (m, 1H), 2.20-2.07 (m, 1H), 1.95-1.85 (m, 1H); $^{13}$C NMR (75 MHz, CDCl$_3$) δ 178.2, 178.1, 175.2, 175.1, 156.1, 156.0, 149.1, 142.5, 142.4, 142.2, 142.0, 132.1, 132.0, 129.2, 124.5, 124.4, 123.9, 123.8, 119.0, 118.9, 108.1, 102.8, 102.7, 101.6, 93.8, 93.7, 80.5, 80.4, 58.2, 58.1, 58.0, 57.9, 43.1, 43.0, 29.3, 29.2, 28.8, 28.7, 22.8, 22.7; MS (ES+) m/z 417.3 (M+1).

EXAMPLE 11.72

Synthesis of 1-{[5-(trifluoromethyl)-1,2,4-oxadiazol-3-yl]methyl}spiro[furo[2,3-f][1,3]benzodioxole-7,3'-indol]-2'(1'H)-one

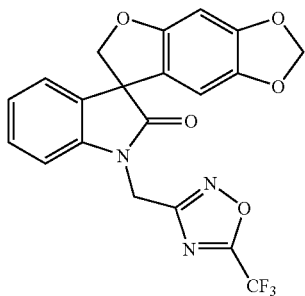

To a mixture of N'-hydroxy-2-(2'-oxospiro[furo[2,3-f][1,3]benzodioxole-7,3'-indol]-1'(2'H)-yl)ethanimidamide (0.53 g, 1.50 mmol) in dichloromethane (30 mL) was added diisopropylethyl amine (3.88 g, 3.00 mmol) and trifluoroacetic anhydride (0.41 g, 1.95 mmol) at 0° C. to give a clear yellow solution. The reaction solution was stirred for 2 h. The organic layer was washed with saturated aqueous ammonium chloride (3×15 mL), brine (3×15 mL), dried over anhydrous sodium sulfate and filtered. The filtrate was concentrated to dryness under reduced pressure. The residue was purified by column chromatography with ethyl acetate in hexanes (30%) to afford 1'-{[5-(trifluoromethyl)-1,2,4-oxadiazol-3-yl]methyl}spiro[furo[2,3-f][1,3]benzodioxole-7,3'-indol]-2'(1'H)-one (0.47 g, 73%) as a colourless solid: mp 139-140° C.; $^1$H NMR (300 MHz, DMSO-$d_6$) δ 7.30 (ddd, J=7.7, 7.7, 1.2 Hz, 1H), 7.19 (d, J=7.4 Hz, 1H), 7.14 (d, J=7.8 Hz, 1H), 7.05 (ddd, J=7.5, 7.5, 0.8 Hz, 1H), 6.67 (s, 1H), 6.23 (s, 1H), 5.89 (d, J=3.8 Hz, 2H), 5.28 (ABq, 2H), 4.74 (ABq, 2H); $^{13}$C NMR (75 MHz, DMSO-$d_6$) 177.1, 167.8, 165.5 (d, $^2J_{CF}$=42 Hz), 155.7, 148.9, 142.2, 141.8, 132.1, 129.3, 124.2, 124.0, 120.2, 116.1 (d, $^1J_{CF}$=273 Hz), 109.9, 103.5, 101.9, 93.8, 79.9, 57.9, 35.9; MS (ES+) m/z 432.2 (M+1).

EXAMPLE 11.73

Synthesis of N-isopropyl-3-[2-(2'-oxospiro[furo[2,3-f][1,3]benzodioxole-7,3'-indol]-1'(2'H)-yl)ethyl]piperidine-1-carboxamide

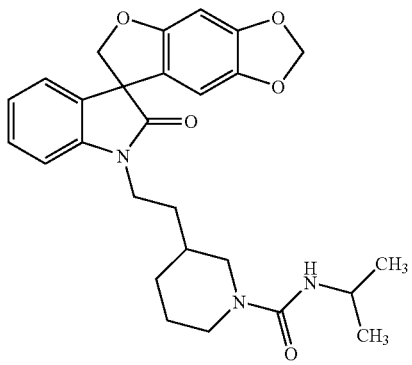

To a mixture of 1-(2-piperidin-3-ylethyl)spiro[furo[2,3-f][1,3]benzodioxole-7,3'-indol]-2'(1'H)-one (0.82 g, 2.09 mmol) and diisopropylethylamine (1.08 g, 8.37 mmol) in anhydrous dichloromethane (25 mL) was added isopropyl isocyanate (0.36 g, 4.18 mmol) at 0° C. The reaction mixture was stirred at ambient temperature for 16 h. The reaction was quenched by addition of saturated aqueous ammonium chloride solution (100 mL) and extracted with dichloromethane (3×50 mL). The combined organic solution was washed with brine (80 mL), dried over anhydrous sodium sulfate, filtered and concentrated in vacuo to dryness. The residue was purified by column chromatography with methanol in dichloromethane (2% to 10% gradient) to give N-isopropyl-3-[2-(2'-oxospiro[furo[2,3-f][1,3]benzodioxole-7,3'-indol]-1'(2'H)-yl)ethyl]piperidine-1-carboxamide (0.21 g, 21%) as a colorless solid: mp 206-208° C. (ethyl acetate/hexanes); $^1$H NMR (300 MHz, DMSO-$d_6$) δ 7.34 (ddd, J=7.8, 7.8, 1.0 Hz, 1H), 7.16 (dd, J=6.4, 6.4 Hz, 2H), 7.05 (dd, J=7.3, 7.3 Hz, 1H), 6.69 (s, 1H), 6.16 (s, 1H), 5.97 (d, J=7.6 Hz, 1H), 5.92 (s, 2H), 4.77 (d, J=9.3 Hz, 1H), 4.66 (d, J=9.3 Hz, 1H), 3.84-3.60 (m, 5H), 2.66 (t, J=10.7 Hz, 1H), 2.55-2.47 (m, 1H), 1.85-1.81 (m, 1H), 1.57-1.10 (m, 6H), 1.03 (d, J=6.6 Hz, 3H), 0.97 (d, J=6.6 Hz, 3H); $^{13}$C NMR (75 MHz, DMSO-$d_6$) δ 176.6, 156.5, 155.4, 148.2, 142.2, 141.7, 131.9, 128.9, 123.6, 122.9, 119.7, 109.0, 102.8, 101.4, 93.3, 79.8, 57.4, 48.8, 43.9, 41.7, 37.5, 33.0, 30.6, 30.5, 24.4, 22.9, 22.8; MS (ES+) m/z 478.5 (M+1).

EXAMPLE 11.74

Synthesis of 5-[(2'-oxospiro[furo[2,3-][1,3']benzodioxole-7,3'-indol]-1'(2'H)-yl)methyl]thiophene-3-carbonitrile

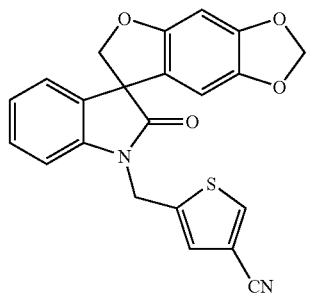

To a suspended mixture of 1'-[(4-bromo-2-thienyl)methyl]spiro[furo[2,3-f][1,3]benzodioxole-7,3'-indol]-2'(1'H)-one (0.456 g, 1.0 mmol) and zinc cyanide (0.117 g, 1.0 mmol) in anhydrous N,N-dimethylformamide (5 mL) was added tetrakis(triphenylphosphine)palladium (0.04 g, 0.03 mmol). The reaction mixture was put into a microwave reactor set at 100 W at 133° C. for 7 min. The solid was filtered and washed with ethyl acetate (40 mL). The filtrate was concentrated in vacuo to dryness. The residue was purified by column chromatography with ethyl acetate in hexanes (10% to 30% gradient) to give 5-[(2'-oxospiro[furo[2,3-f][1,3]benzodioxole-7,3'-indol]-1'(2'H)-yl)methyl]thiophene-3-carbonitrile (0.25 g, 62%) as a colorless solid: mp 207-209° C. (dichloromethane/hexane); $^1$H NMR (300 MHz, DMSO-$d_6$) δ8.48 (d, J=1.3 Hz, 1H), 7.63 (d, J=1.3 Hz, 1H), 7.33 (dd, J=7.8, 1.1 Hz, 1H), 7.23-7.19 (m, 2H), 7.06 (d, J=7.4, 0.8 Hz, 1H), 6.71 (s, 1H), 6.15 (s, 1H), 5.93 (d, J=1.5 Hz, 2H), 5.14 (d, J=4.6 Hz, 2H), 4.81 (d, J=9.4 Hz, 1H), 4.69 (d, J=9.4 Hz, 1H); $^{13}$C NMR (75 MHz, DMSO-$d_6$) δ176.5, 155.4, 148.3, 141.7, 141.5, 141.3, 137.8, 131.5, 128.8, 127.9, 123.7, 123.3, 119.4, 115.1, 109.3, 108.7, 102.8, 101.4, 93.3, 79.7, 57.3, 37.9; MS (ES+) m/z 403.2 (M+1).

EXAMPLE 11.75

Synthesis of 2'-oxo-1',2'-dihydrospiro[furo[2,3-f][1,3]benzodioxole-7,3'-indole]-7'-carbonitrile

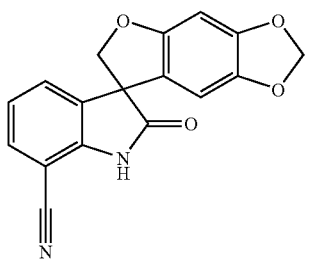

To a suspended mixture of 7'-bromospiro[furo[2,3-f][1,3]benzodioxole-7,3'-indol]-2'(1'H)-one (0.44 g, 1.2 mmol) and zinc cyanide (0.28 g, 2.4 mmol) in anhydrous N,N-dimethylformamide (12 mL) was added tetrakis(triphenylphosphine)palladium (0.14 g, 0.12 mmol). The reaction mixture was refluxed for 3 h. The solid was filtered and washed with ethyl acetate (40 mL). The filtrate was concentrated in vacuo to dryness. The residue was purified by column chromatography with ethyl acetate in hexanes (20% to 30% gradient) to afford 2'-oxo-1',2'-dihydrospiro[furo[2,3-f][1,3]benzodioxole-7,3'-indole]-7'-carbonitrile (0.28 g, 76%) as a colorless solid: mp 205-207° C.; $^1$H NMR (300 MHz, DMSO-$d_6$) δ 11.55 (s, 1H), 7.62 (dd, J=8.0 Hz, 1.1 Hz, 1H), 7.41 (d, J=7.0 Hz, 1H), 7.12-7.07 (m, 1H), 6.69 (s, 1H), 6.44 (s, 1H), 5.93 (dd, J=3.4, 0.8 Hz, 2H), 4.78 (d, J=9.5 Hz, 1H), 4.67 (d, J=9.5 Hz, 1H); $^{13}$C NMR (75 MHz, DMSO-$d_6$) δ 178.4, 155.4, 148.3, 145.2, 141.7, 133.8, 131.6, 128.3, 122.5, 118.9, 115.9, 103.2, 101.3, 93.1, 92.6, 79.6, 57.5; MS (ES+) m/z 307.3 (M+1).

EXAMPLE 11.76

Synthesis of (2'-oxo-2,3-dihydrospiro[furo[2,3-g][1,4]benzodioxine-8,3'-indol]-1'(2'H)-yl)acetic acid

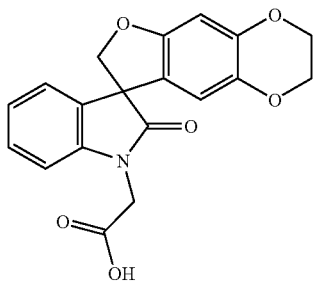

Following the procedure as described in EXAMPLE 11.30 and making non-critical variations using ethyl (2'-oxo-2,3-dihydrospiro[furo[2,3-g][1,4]benzodioxine-8,3'-indol]-1'(2'H)-yl)acetate to replace methyl 2-[(2'-oxo-5,6-dihydrospiro[benzo[1,2-b:5,4-b']difuran-3,3'-indol]-1'(2'H)-yl)methyl]benzoate, (2'-oxo-2,3-dihydrospiro[furo[2,3-g][1,4]benzodioxine-8,3'-indol]-1'(2'H)-yl)acetic acid was obtained (83%): mp 193-196° C. (water); $^1$H NMR (300 MHz, DMSO-$d_6$) δ 7.26-7.21 (m, 1H), 7.09-7.07 (m, 1H), 6.99-6.91 (m, 2H), 6.45 (s, 1H), 6.27 (s, 1H), 4.66 (ABq, 2H), 4.29-4.05 (m, 6H); MS (ES+) m/z 353.7 (M+1).

EXAMPLE 11.77

Synthesis of 1'-methyl-2'-oxo-1',2,2',3-tetrahydrospiro[furo[2,3-g][1,4]benzodioxine-8,3'-indole]-4'-carboxylic acid

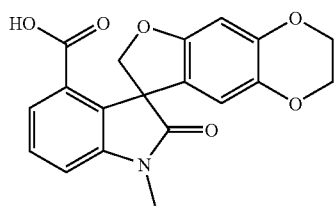

To a solution of phenyl 1'-methyl-2'-oxo-1',2,2',3-tetrahydrospiro[furo[2,3-g][1,4]benzodioxine-8,3'-indole]-4'-carboxylate (2.00 g, 4.65 mmol) in tetrahydrofuran (50 mL) and water (10 mL) was added lithium hydroxide monohydrate (1.00 g, 23.8 mmol) at ambient temperature. The reaction mixture was stirred at ambient temperature for 18 h and concentrated in vacuo. The residue was neutralized to pH 4-5 with 10% w/v hydrochloric acid. The resultant precipitate was filtered and washed with diethyl ether to afford 1'-methyl-2'-oxo-1',2,2',3-tetrahydrospiro[furo[2,3-g][1,4]benzodioxine-8,3'-indole]-4'-carboxylic acid (1.40 g, 85%): mp 297-299° C.; $^1$H NMR (300 MHz, DMSO-$d_6$) δ 7.54-7.43 (m, 3H), 7.32-7.28 (m, 1H), 6.31 (s, 1H), 6.03 (s, 1H), 4.77 (ABq, 2H), 4.12-4.02 (m, 4H), 3.15 (s, 3H); MS (ES+) m/z 376.0 (M+23).

EXAMPLE 11.78

Synthesis of 3'-[(3-bromopyridin-2-yl)methyl]-2,3-dihydrospiro[furo[2,3-g][1,4]benzodioxine-8,1'-inden]-2'(3'H)-one

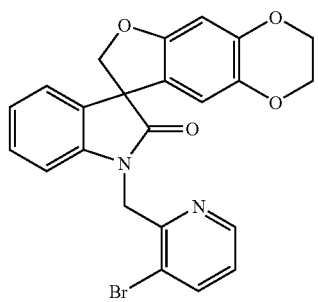

A mixture of (3-bromopyridin-2-yl)methanol (0.100 g, 0.530 mmol) and thionyl chloride (0.070 mL, 0.97 mmol) in dichloromethane (3 mL) and N,N-dimethylformamide (1 drop) was stirred at ambient temperature for 16 h. The reaction mixture was concentrated in vacuo and tetrahydrofuran (5 mL) and N,N-dimethylformamide (5 mL) were added, followed by 2,3-dihydrospiro[furo[2,3-g][1,4]benzodioxine-8,3'-indol]-2'(1'H)-one (0.121 g, 0.41 mmol), cesium carbonate (0.374 g, 1.15 mmol), and potassium iodide (0.038 g, 0.23 mmol). The mixture was heated at 100° C. for 1 h, allowed to cool to ambient temperature and concentrated in vacuo. The residue was triturated sequentially with water and methanol and further purified by column chromatography and eluted with a 0% to 50% gradient of ethyl acetate in dichloromethane to afford 3'-[(3-bromopyridin-2-yl)methyl]-2,3-dihydrospiro[furo[2,3-g][1,4]benzodioxine-8,1-inden]-2' (3'H)-one (0.113 g, 59%) as a colorless solid: mp 217-218° C.; $^1$H NMR (300 MHz, DMSO-$d_6$) δ 8.41 (d, 1H, J=4.0 Hz), 8.15 (d, J=8.1 Hz, 1H), 7.24 (m, 1H), 6.50 (s, 1H), 6.43 (s, 1H), 5.13 (ABq, 2H), 4.75 (ABq, 2H), 4.14-4.09 (m, 4H); $^{13}$C NMR (75 MHz, DMSO-$d_6$) δ 177.3, 155.0, 152.6, 148.3, 144.6, 143.3, 141.3, 138.2, 132.4, 129.1, 125.1, 123.9, 123.3, 122.1, 120.2, 112.3, 109.7, 99.0, 79.7, 64.7, 64.1, 57.7, 44.7; MS (ES+) m/z 464.6 (M+1), 466.6 (M+1).

EXAMPLE 11.79

Synthesis of 3'-{[3-(methylsulfonyl)pyridin-2-yl]methyl}-2,3-dihydrospiro[furo[2,3-g][1,4]benzodioxine-8,1'-inden]-2'(3'H)-one

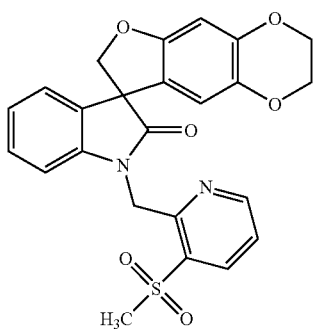

A mixture of 3'-[(3-bromopyridin-2-yl)methyl]-2,3-dihydrospiro[furo[2,3-g][1,4]benzodioxine-8,1'-inden]-2'(3'H)-one (0.233 g, 0.50 mmol), sodium methanesulfonate (0.071 g, 0.60 mmol), copper iodide (0.010 g, 0.05 mmol), and the sodium salt of L-proline (0.014 g, 0.10 mmol) were combined in dimethyl sulfoxide (1 mL) and heated at 95° C. for 48 h, then stirred at ambient temperature for 30 h. The reaction mixture was diluted with ethyl acetate (50 mL) and washed with water (100 mL), dried over sodium sulfate, filtered and concentrated in vacuo. The residue was triturated from methanol and further purified by column chromatography, and eluted with a 0% to 50% gradient of ethyl acetate in dichloromethane to yield 3'-{[3-(methylsulfonyl)pyridin-2-yl]methyl}-2,3-dihydrospiro[furo[2,3-g][1,4]benzodioxine-8,1'-inden]-2'(3'H)-one (0.103 g, 44%) as a colorless solid: mp>250° C.; $^1$H NMR (300 MHz, DMSO-$d_6$) δ 8.69 (d, J=4.2 Hz, 1H), 8.35 (dd, J=8.0, 0.5 Hz, 1H), 7.64 (dd, J=7.9, 4.7 Hz, 1H), 7.24 (dd, J=7.7, 7.7 Hz, 1H), 7.18 (d, J=7.3 Hz, 1H), 7.05-6.99 (m, 2H), 6.50 (s, 1H), 6.39 (s, 1H), 5.50 (ABq, 2H), 4.76 (ABq, 2H), 4.19-4.12 (m, 4H), 3.52 (s, 3H); $^{13}$C NMR (75 MHz, DMSO-$d_6$) δ 177.6, 155.0, 153.7, 153.6, 144.6, 143.4, 138.4, 138.2, 135.9, 132.4, 129.1, 124.1, 123.9, 123.3, 122.1, 112.2, 109.8, 99.1, 79.6, 64.7, 64.1, 57.7, 44.2, 42.7; MS (ES+) m/z 465.0 (M+1).

EXAMPLE 11.80

Synthesis of 2-[(2'-oxo-2,2',3,3'-tetrahydrospiro[furo[2,3-g][1,4]benzodioxine-8,1-inden]-3'-yl)methyl]pyridine-3-carbonitrile

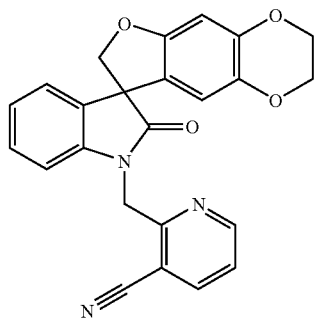

3'-[(3-Bromopyridin-2-yl)methyl]-2,3-dihydrospiro[furo[2,3-g][1,4]-benzodioxine-8,1'-inden]-2'(3'H)-one (0.233 g, 0.500 mmol), nickel (II) chloride hexahydrate (0.113 g, 0.500 mmol), and sodium cyanide (0.050 g, 1.0 mmol) were combined in 1-methyl-2-pyrrolidone (1 mL) and heated at 200° C. for 30 min under microwave irradiation. The reaction mixture was allowed to cool to ambient temperature, poured into water (20 mL) and extracted with ethyl acetate (3×20 mL). The combined organic layers were washed with brine (3×20 mL), dried over sodium sulfate, filtered and concentrated in vacuo. The resulting residue was subjected to column chromatography, and eluted with a 50% to 75% gradient of ethyl acetate in hexanes, to afford 2-[1(2'-oxo-2,2',3,3'-tetrahydrospiro[furo[2,3-g][1,4]benzodioxine-8,1'-inden]-3'-yl)methyl]pyridine-3-carbonitrile (0.593 g, 29%) as a colorless solid: mp 230-233° C.; $^1$H NMR (300 MHz, DMSO-$d_6$) δ 8.71 (dd, J=4.8, 1.4 Hz, 1H), 8.38 (dd, J=7.9, 1.5 Hz, 1H), 7.56 (dd, J=7.8, 4.9 Hz, 1H), 7.27-7.15 (m, 2H), 7.04 (d, J=7.5 Hz, 1H), 6.98 (d, J=7.9 Hz, 1H), 6.50 (s, 1H), 6.38 (s, 1H), 5.30 (s, 2H), 4.74 (ABq, 2H), 4.19-4.11 (m, 4H); $^{13}$C NMR (75 MHz, DMSO-$d_6$) δ 177.3, 158.2, 155.0, 153.1, 144.6, 143.1, 142.1, 138.2, 132.4, 129.1, 124.0, 123.4, 121.9, 116.5, 112.2, 109.8, 108.0, 99.1, 79.8, 64.7, 64.1, 57.7, 44.1; MS (ES+) m/z 412.0 (M+1).

EXAMPLE 11.81

Synthesis of (8S)-1'-{[3-(difluoromethyl)pyridin-2-yl]methyl}-2,3-dihydrospiro[furo[2,3-g][1,4]benzodioxine-8,3'-indol]-2'(1'H)-one

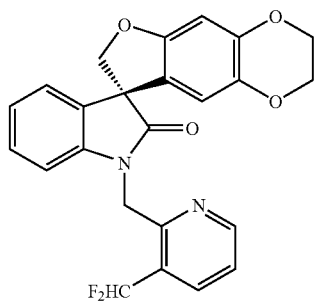

Following the procedure as described in EXAMPLE 11.78 and making non-critical variations using (8S)-2,3-dihydrospiro[furo[2,3-g][1,4]benzodioxine-8,3'-indol]-2'(1'H)- one to replace 2,3-dihydrospiro[furo[2,3-f][1,4]benzodioxine-7,3'-indol]-2'(1'H)-one, and 3-(difluoromethyl)pyridin-2-yl]methanol hydrochloride to replace (3-(trifluoromethyl)pyridin-2-yl)methanol hydrochloride, (8S)-1-{[3-(difluoromethyl)pyridin-2-yl]methyl}-2,3-dihydrospiro[furo[2,3-g][1,4]benzodioxine-8,3'-indol]-2'(1'H)-one was obtained (50%) as a colorless solid: mp 181-182° C.; $^1$H NMR (300 MHz, DMSO-d$_6$) δ 8.56 (d, J=4.9 Hz, 1H), 8.08 (d, J=7.7 Hz, 1H), 7.52-7.50 (m, 1H), 7.52-7.42 (m, 1H), 7.25-7.15 (m, 2H), 7.01 (dd, J=7.5, 7.5 Hz, 1H), 6.91 (d, J=7.8 Hz, 1H), 6.51 (s, 1H), 6.42 (s, 1H), 5.18 (ABq, 2H), 4.72 (ABq, 2H), 4.19-4.12 (m, 4H); $^{13}$C NMR (75 MHz, DMSO-d$_6$) δ 177.4, 155.0, 152.9 (t, $J_{C-F}$=4.3 Hz), 151.4, 144.6, 143.2, 138.2, 135.0 (t, $J_{C-F}$=7.0 Hz), 132.5, 129.1, 128.0 (t, $J_{C-F}$=22.6 Hz), 123.9, 123.5, 123.3, 122.0, 113.8 (t, $J_{C-F}$=236.6 Hz), 112.3, 109.7, 99.1, 79.7, 64.7, 64.1, 57.8, 42.3; MS (ES+) m/z 436.9 (M+1).

EXAMPLE 11.82

Synthesis of N'-hydroxy-3-[(2'-oxo-2,3-dihydrospiro[furo[2,3-g][1,4]benzodioxine-8,3'-indol]-1'(2'H)-yl)methyl]benzenecarboximidamide

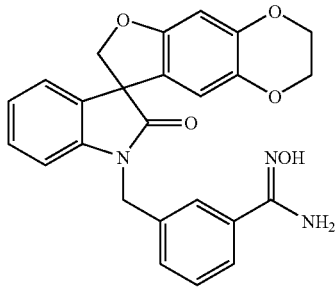

To a solution of 3-[(2'-oxo-2,3-dihydrospiro[furo[2,3-g][1,4]benzodioxine-8,3'-indol]-1'(2'H)-yl)methyl]benzonitrile (0.40 g, 0.98 mmol) in dimethyl sulfoxide (10 mL) was added hydroxylamine (50% w/w solution in water, 0.66 mL, 10.7 mmol). The reaction was stirred at 80° C. for 3 h and allowed to cool to ambient temperature. Water was added, causing a precipitate to be deposited. The solid was collected by filtration and washed with water to afford N'-hydroxy-3-[(2'-oxo-2,3-dihydrospiro[furo[2,3-g][1,4]benzodioxine-8,3'-indol]-1'(2'H)-yl)methyl]benzenecarboximidamide (0.40 g, 93%): $^1$H NMR (300 MHz, CDCl$_3$) δ 7.98 (br s, 1H), 7.64 (s, 2H), 7.43-7.38 (m, 4H), 7.15-7.11 (m, 2H), 7.01-6.96 (m, 1H), 6.79 (s, 1H), 6.67-6.64 (m, 1H), 6.49 (s, 1H), 5.33-5.28 (m, 1H), 4.96-4.58 (m, 3H), 4.19-4.16 (m, 4H); MS (ES+) m/z 444.0 (M+1).

EXAMPLE 11.83

Synthesis of 1'-[3-(5-methyl-1,2,4-oxadiazol-3-yl)benzyl]-2,3-dihydrospiro[furo[2,3-g][1,4]benzodioxine-8,3'-indol]-2'(1'H)-one

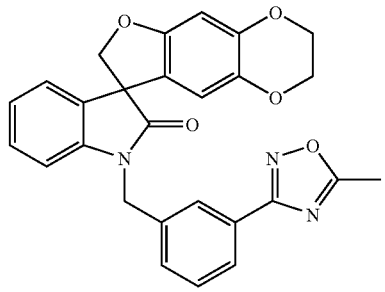

Following the procedure as described in EXAMPLE 11.27 and making non-critical variations using N'-hydroxy-3-[(2'-oxo-2,3-dihydrospiro[furo[2,3-g][1,4]benzodioxine-8,3'-indol]-1'(2'H)-yl)methyl]benzenecarboximidamide to replace N'-hydroxy-3-[(2'-oxo-5,6-dihydrospiro[benzo[1,2-b:5,4-b']difuran-3,3'-indol]-1'(2'H)-yl)methyl]benzenecarboximidamide, 1'-[3-(5-methyl-1,2,4-oxadiazol-3-yl)benzyl]-2,3-dihydrospiro[furo[2,3-g][1,4]benzodioxine-8,3'-indol]-2'(1'H)-one was obtained (65%) as a colorless solid: mp 90-95° C. (ethyl acetate/diethyl ether); $^1$H NMR (300 MHz, CDCl$_3$) δ 7.89-7.87 (m, 2H), 7.58-7.53 (m, 2H), 7.25-7.15 (m, 2H), 7.03-6.95 (m, 2H), 6.50 (s, 1H), 6.20 (s, 1H), 5.15-4.64 (m, 4H), 4.16-4.07 (m, 4H), 2.62 (s, 3H); $^{13}$C NMR (75 MHz, CDCl$_3$) δ 178.1, 177.3, 167.8, 155.2, 144.7, 142.4, 138.4, 137.9, 132.2, 130.8, 130.2, 129.3, 127.2, 126.3, 125.5, 124.2, 123.7, 121.5, 111.6, 109.9, 99.3, 80.0, 64.7, 64.0, 57.8, 43.1, 12.4; MS (ES+) m/z 467.8 (M+1).

EXAMPLE 11.84

Synthesis of 1'-[4-(5-methyl-1,2,4-oxadiazol-3-yl)benzyl]-2,3-dihydrospiro[furo[2,3-g][1,4]benzodioxine-8,3'-indol]-2'(1'H)-one

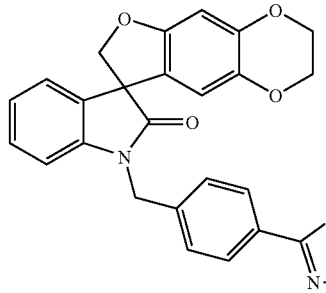

To a solution of 4-[(2'-oxo-2,3-dihydrospiro[furo[2,3-g][1,4]benzodioxine-8,3'-indol]-1'(2'H)-yl)methyl]benzonitrile (0.41 g, 1.0 mmol) in dimethylsulfoxide (20 mL) was added hydroxylamine (50% w/w solution in water, 2.0 mL, 33 mmol). The mixture was heated at 80° C. for 16 h, allowed to cool to ambient temperature and diluted with water (50 mL), causing a precipitate to be deposited. The solid was collected by filtration and combined with pyridine (2.0 mL) and acetic anhydride (0.2 g, 2.0 mmol) in a 10 mL microwave reaction vessel. The mixture was heated at 170° C. for 15 min under microwave irradiation, allowed to cool to ambient temperature and concentrated in vacuo. The residue was purified by column chromatography and eluted with a 15% to 50% gradient of ethyl acetate in hexanes to afford 1'-[4-(5-methyl-1,2,4-oxadiazol-3-yl)benzyl]-2,3-dihydrospiro[furo[2,3-g][1,4]benzodioxine-8,3'-indol]-2'(1'H)-one (0.52 g, 85%) as a colorless solid: mp 174-175° C. (ethyl acetate/hexanes); $^1$H NMR (300 MHz, DMSO-$d_6$) δ 8.06-8.00 (m, 2H), 7.42 (d, J=8.3 Hz, 2H), 7.22-7.13 (m, 2H), 7.04-6.97 (m, 1H), 6.75 (d, J=7.7 Hz, 1H), 6.50 (s, 1H), 6.23 (s, 1H), 5.12 (d, J=15.8 Hz, 1H), 4.94 (d, J=8.9 Hz, 1H), 4.85 (d, J=15.8 Hz, 1H), 4.66 (d, J=8.9 Hz, 1H), 4.21-4.07 (m, 4H), 2.63 (s, 3H); $^{13}$C NMR (75 MHz, DMSO-$d_6$) δ 177.6, 176.6, 168.0, 155.3, 144.7, 141.9, 138.4, 132.2, 128.9, 128.0, 127.8, 126.5, 124.0, 123.6, 120.9, 111.5, 109.2, 99.5, 80.1, 58.1, 43.9, 12.4; MS (ES+) m/z 467.9 (M+1).

EXAMPLE 11.85

Synthesis of 6-(5-methyl-1,2,4-oxadiazol-3-yl)-1'-(pyridin-2-ylmethyl)spiro[1-benzofuran-3,3'-indol]-2'(1'H)-one

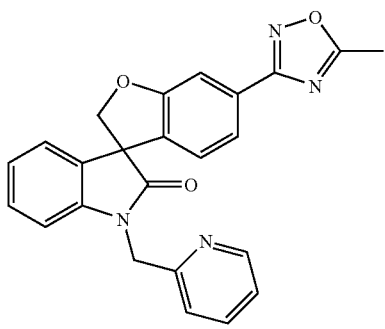

Following the procedure as described in EXAMPLE 11.84 and making non-critical variations using 2'-oxo-1'-(pyridin-2-ylmethyl)-1',2'-dihydrospiro[1-benzofuran-3,3'-indole]-6-carbonitrile to replace 4-[(2'-oxo-2,3-dihydrospiro[furo[2,3-g][1,4]benzodioxine-8,3'-indol]-1'(2'H)-yl)methyl]benzonitrile, 6-(5-methyl-1,2,4-oxadiazol-3-yl)-1'-(pyridin-2-ylmethyl)spiro[1-benzofuran-3,3'-indol]-2'(1'H)-one was obtained (61%) as a colorless solid: mp 147-148° C. (ethyl acetate/hexanes); $^1$H NMR (300 MHz, CDCl$_3$) δ 8.57 (d, J=4.7 Hz, 1H), 7.70-7.61 (m, 2H), 7.56 (d, J=7.9 Hz, 1H), 7.32-7.11 (m, 4H), 7.06-6.98 (m, 3H), 6.95-6.86 (m, 1H), 5.20 (d, J=15.8 Hz, 1H), 5.07 (d, J=9.1 Hz, 1H), 5.00 (d, J=15.8 Hz, 1H), 4.79 (d, J=9.1 Hz, 1H), 2.63 (s, 1H); $^{13}$C NMR (75 MHz, CDCl$_3$) δ 177.0, 176.5, 168.1, 161.1, 155.4, 149.6, 142.2, 137.1, 132.2, 131.9, 129.1, 128.5, 124.0, 123.8, 123.7, 122.9, 121.7, 120.9, 109.7, 109.3, 80.0, 58.1, 46.2, 12.4; MS (ES+) m/z 410.9 (M+1).

EXAMPLE 11.86

Synthesis of 3-[(2'-oxo-2,3-dihydrospiro[furo[2,3-g][1,4]benzodioxine-8,3'-indol]-1'(2'H)-yl)methyl]benzoic acid

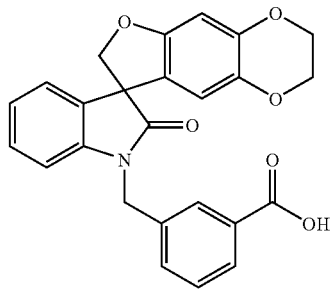

A solution of methyl 3-[(2'-oxo-2,3-dihydrospiro[furo[2,3-g][1,4]benzodioxine-8,3'-indol]-1'(2'H)-yl)methyl]benzoate (5.20 g, 11.73 mmol) in tetrahydrofuran (150 mL) and water (80 mL) was cooled to 0° C. under nitrogen and lithium hydroxide (1.13 g, 47.4 mmol) was slowly added. The reaction mixture was stirred at 0° C. for 30 min, allowed to warm to ambient temperature, stirred for an additional 16 h and concentrated in vacuo. The residue was poured into cold (0° C.) 1 M hydrochloric acid (100 mL), causing a precipitate to be deposited. The mixture was stirred for 2 h at ambient temperature and filtered. The solid was washed with water and hexanes to afford 3-[(2'-oxo-2,3-dihydrospiro[furo[2,3-g][1,4]benzodioxine-8,3'-indol]-1'(2'H)-yl)methyl]benzoic acid (5.08 g, 99%) as a colorless solid: mp 254-258° C. (hexanes); $^1$H NMR (300 MHz, CDCl$_3$) δ 8.03-8.00 (m, 2H), 7.59-7.44 (m, 2H), 7.21-7.16 (m, 2H), 7.04-7.00 (m, 1H), 6.73-6.71 (m, 1H), 6.50 (s, 1H), 6.31 (s, 1H), 5.24-4.60 (m, 5H), 4.15-4.07 (m, 4H); $^{13}$C NMR (75 MHz, CDCl$_3$) δ 177.7, 170.7, 155.2, 144.7, 141.7, 138.5, 136.3, 132.56, 132.3, 130.0, 129.7, 129.3, 128.9, 128.6, 124.1, 123.7, 120.9, 111.6, 109.1, 99.5, 80.0, 64.5, 63.9, 58.1, 43.6; MS (ES+) m/z 429.7 (M+1).

EXAMPLE 11.87

Synthesis of 4-[(2'-oxo-2,3-dihydrospiro[furo[2,3-g][1,4]benzodioxine-8,3'-indol]-1'(2'H)-yl)methyl]benzoic acid

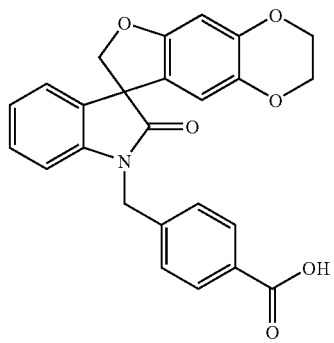

Following the procedure as described in EXAMPLE 11.12 and making non-critical variations using methyl 4-[(2'-oxo-2,3-dihydrospiro[furo[2,3-g][1,4]benzodioxine-8,3'-indol]-1'(2'H)-yl)methyl]benzoate to replace methyl 3-[(2'-oxo-5,6- dihydrospiro[benzo[1,2-b:5,4-b']difuran-3,3'-indol]-1'(2'H)-yl)methyl]benzoate, 4-[(2'-oxo-2,3-dihydrospiro[furo[2,3-g][1,4]benzodioxine-8,3'-indol]-1'(2'H)-yl)methyl]benzoic acid was obtained (89%) as a colorless solid: mp 234-237° C. (water); $^1$H NMR (300 MHz, CDCl$_3$) δ 12.94 (s, 1H), 7.93-7.86 (m, 2H), 7.46-7.40 (m, 2H), 7.26-7.19 (m, 1H), 7.18-7.13 (m, 1H), 7.04-6.92 (m, 2H), 6.50 (s, 1H), 6.12 (s, 1H), 5.07-4.90 (m, 2H), 4.80 (d, J=9.3 Hz, 1H), 4.65 (d, J=9.3 Hz, 1H), 4.19-4.03 (m, 4H); $^{13}$C NMR (75 MHz, CDCl$_3$) δ 177.3, 167.5, 155.2, 144.7, 142.6, 141.9, 138.3, 132.1, 130.5, 130.2, 129.3, 127.8, 124.2, 123.7, 121.6, 111.6, 109.8, 99.3, 79.9, 64.7, 64.1, 57.7, 43.4; MS (ES+) m/z 429.9 (M+1).

EXAMPLE 11.88

Synthesis of 1'-[(4-methylpiperazin-1-yl)methyl]-5,6-dihydrospiro[benzo[1,2-b:5,4-b']difuran-3,3'-indol]-2'(1'H)-one hydrochloride

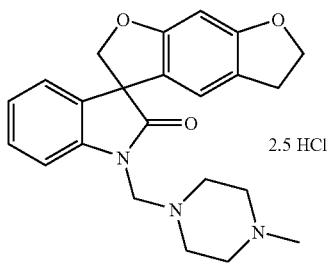

2.5 HCl

A mixture of 5,6-dihydrospiro[benzo[1,2-b:5,4-b']difuran-3,3'-indol]-2'(1'H)-one (0.35 g, 1.2 mmol), N-methylpiperazine (1.4 mL, 11 mmol), 37% w/w aqueous formaldehyde (1.0 mL, 11 mmol) and methanol (2 mL) was heated for 2 h. The reaction mixture was poured into water (100 mL), causing a precipitate to be deposited. The solid was collected by filtration and dissolved in dichloromethane. The resultant solution was dried over magnesium sulfate, filtered and concentrated in vacuo. The residue was dissolved in anhydrous methanol (2 mL) and saturated methanolic hydrogen chloride (5 mL) was added, causing a precipitate to be deposited. The reaction mixture was diluted with diethyl ether (20 mL) and the solid was collected by filtration and washed with diethyl ether (2×10 mL) to afford 1-[(4-methylpiperazin-1-yl)methyl]-5,6-dihydrospiro[benzo[1,2-b:5,4-b']difuran-3,3'-indol]-2'(1'H)-one hydrochloride (0.38 g, 65%) as a colorless solid: mp 181° C. (decomp.) (diethyl ether); $^1$H NMR (300 MHz, CDCl$_3$) δ 11.36 (br s, 1H), 7.37-7.24 (m, 2H), 7.16-7.11 (m, 1H), 7.08-7.00 (m, 1H), 6.71 (s, 1H), 6.36 (s, 1H), 5.99 (br s, 4H), 4.82-4.58 (m, 4H), 4.45 (t, J=8.7 Hz, 2H), 3.45-2.73 (m, 10H), 2.67 (s, 3H); $^{13}$C NMR (75 MHz, CDCl$_3$) δ 179.1, 161.6, 161.0, 143.3, 132.5, 129.0, 124.0, 123.8, 120.8, 120.6, 120.0, 110.6, 92.8, 80.6, 72.6, 60.7, 57.4, 52.0, 47.2, 47.1, 42.3, 28.9, 11.9; MS (ES+) m/z 392.0 (M+1). Anal. Calcd. for C$_{23}$H$_{25}$N$_3$O$_3$.2.5HCl: C, 57.24; H, 5.74; N, 8.71. Found: C, 57.23; H, 5.66; N, 8.34.

EXAMPLE 11.89

Synthesis of N'-hydroxy-2-(2'-oxo-2,3-dihydrospiro[furo[2,3-g][1,4]-benzodioxine-8,3'-indol]-1'(2'H)-yl)ethanimidamide

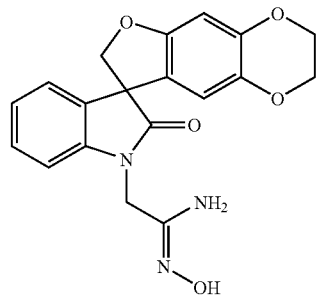

Following the procedure as described in EXAMPLE 11.82 and making non-critical variations using (2'-oxo-2,3-dihydrospiro[furo[2,3-g][1,4]benzodioxine-8,3'-indol]-1'(2'H)-yl)acetonitrile to replace 3-[(2'-oxo-2,3-dihydrospiro[furo[2,3-g][1,4]benzodioxine-8,3'-indol]-1'(2'H)-yl)methyl]benzonitrile, N'-hydroxy-2-(2'-oxo-2,3-dihydrospiro[furo[2,3-g][1,4]benzodioxine-8,3'-indol]-1'(2'H)-yl)ethanimidamide was obtained (75%) as a colorless solid: MS (ES+) m/z 367.9 (M+1).

EXAMPLE 11.90

Synthesis of 1'-{[5-(trifluoromethyl)-1,2,4-oxadiazol-3-yl]methyl}-2,3-dihydrospiro[furo[2,3-g][1,4]benzodioxine-8,3'-indol]-2'(1'H)-one

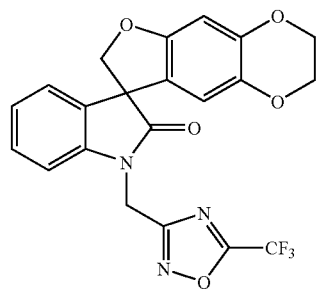

Following the procedure as described in EXAMPLE 11.27 and making non-critical variations using N'-hydroxy-2-(2'-oxo-2,3-dihydrospiro[furo[2,3-g][1,4]benzodioxine-8,3'-indol]-1'(2'H)-yl)ethanimidamide to replace N'-hydroxy-3-[(2'-oxo-5,6-dihydrospiro[benzo[1,2-b:5,4-b']difuran-3,3'-indol]-1'(2'H)-yl)methyl]benzenecarboximidamide, 1-{[5-(trifluoromethyl)-1,2,4-oxadiazol-3-yl]methyl}-2,3-dihydrospiro[furo[2,3-g][1,4]-benzodioxine-8,3'-indol]-2'(1'H)-one was obtained (55%) as a colorless solid: mp 159-160° C. (diethyl ether); $^1$H NMR (300 MHz, CDCl$_3$) δ 7.31-7.23 (m, 1H), 7.22-7.17 (m, 1H), 7.12-7.04 (m, 1H), 6.85 (d, J=7.8 Hz, 1H), 6.48 (s, 1H), 6.33 (s, 1H), 5.27 (d, J=16.8 Hz, 1H), 5.08 (d, J=16.8 Hz, 1H), 4.92 (d, J=9.0 Hz, 1H), 4.66 (d, J=9.0 Hz, 1H), 4.21-4.07 (m, 4H); $^{13}$C NMR (75 MHz, CDCl$_3$) δ 177.3, 167.0, 155.2, 144.8, 140.7, 138.4, 132.2, 129.0, 124.3, 124.2, 120.7, 115.7 (q, J=274.0 Hz), 111.9, 108.5, 99.4, 79.9, 64.5, 63.9, 58.0, 35.6; MS (ES+) m/z 445.9 (M+1).

EXAMPLE 11.91

Synthesis of 2-(2'-oxo-2,3-dihydrospiro[furo[2,3-g][1,4]benzodioxine-8,3'-indol]-1'(2'H)-yl)acetohydrazide

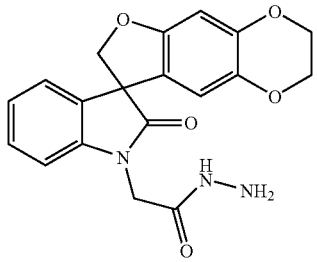

To a solution of ethyl (2'-oxo-2,3-dihydrospiro[furo[2,3-g][1,4]benzodioxine-8,3'-indol]-1'(2'H)-yl)acetate (0.35 g, 0.92 mmol) in ethanol (10 mL) was added hydrazine hydrate (0.15 mL, 1.84 mmol) and the solution was heated at reflux for 16 h. Upon being allowed to cool to ambient temperature a solid precipitate formed. The solid was filtered and washed with ethanol (2 mL) to afford 2-(2'-oxo-2,3-dihydrospiro[furo[2,3-g][1,4]benzodioxine-8,3'-indol]-1'(2'H)-yl)acetohydrazide (0.285 g, 84%) as a colorless solid: MS (ES+) m/z 367.9 (M+1).

EXAMPLE 11.92

Synthesis of 1'-{[5-(trifluoromethyl)-1,3,4-oxadiazol-2-yl]methyl}-2,3-dihydrospiro[furo[2,3-g][1,4]benzodioxine-8,3'-indol]-2'(1'H)-one

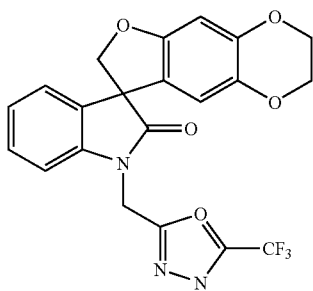

To a solution of 2-(2'-oxo-2,3-dihydrospiro[furo[2,3-g][1,4]benzodioxine-8,3'-indol]-1'(2'H)-yl)acetohydrazide (0.21 g, 0.57 mmol) in pyridine (3.0 mL) at 0° C. was added trifluoroacetic anhydride (0.50 mL, 3.59 mmol) The solution was stirred for 1 h at ambient temperature, poured into 1 M hydrochloric acid (25 mL) and the mixture was extracted with ethyl acetate (3×50 mL). The combined organic extracts were washed with brine (1×50 mL), dried over magnesium sulfate, filtered and concentrated in vacuo. The residue was purified by column chromatography and eluted with a 10% to 50% gradient of ethyl acetate in hexanes followed by recrystallization from diethyl ether to afford 1'-{[5-(trifluoromethyl)-1,3,4-oxadiazol-2-yl]methyl}-2,3-dihydrospiro[furo[2,3-g][1,4]-benzodioxine-8,3'-indol]-2'(1'H)-one (0.05 g, 18%) as a light yellow solid: mp 137-139° C. (diethyl ether); $^1$H NMR (300 MHz, CDCl$_3$) δ 7.34-7.17 (m, 2H), 7.14-7.07 (m, 1H), 6.94 (d, J=7.9 Hz, 1H), 6.49 (s, 1H), 6.24 (s, 1H), 5.36-5.17 (ABq, 2H), 4.91 (d, J=9.06 Hz, 1H), 4.66 (d, J=9.1 Hz, 1H), 4.21-4.07 (m, 4H); $^{13}$C NMR (75 MHz, CDCl$_3$) δ 177.2, 163.4, 155.2, 144.9, 140.3, 138.5, 131.8, 129.2, 124.5, 124.4, 120.3, 111.6, 108.5, 99.5, 79.9, 64.6, 63.9, 58.0, 34.8; MS (ES+) m/z 445.9 (M+1).

EXAMPLE 11.93

Synthesis of 1'-(3-aminobenzyl)-2,3-dihydrospiro[furo[2,3-g][1,4]benzodioxine-8,3'-indol]-2'(1'H)-one

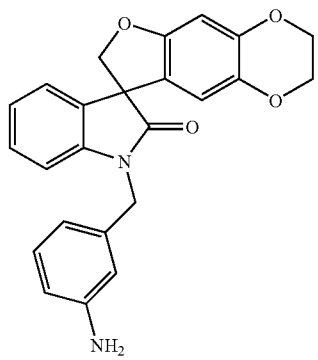

A suspension of 1'-(3-nitrobenzyl)-2,3-dihydrospiro[furo[2,3-g][1,4]benzodioxine-8,3'-indol]-2'(1'H)-one (2.7 g, 6.3 mmol), hydrazine hydrate (2.5 g, 50 mmol) and Raney nickel (0.1 g) in methanol (50 mL) was stirred at ambient temperature under nitrogen for 16 h. The reaction mixture was filtered and the filtrate was concentrated in vacuo. Recrystallization of the residue from chloroform/hexanes (1/1, 20 mL) afforded 1-(3-aminobenzyl)-2,3-dihydrospiro[furo[2,3-g][1,4]-benzodioxine-8,3'-indol]-2'(1'H)-one (1.93 g, 76%) as a colorless solid: MS (ES+) m/z 400.9 (M+1).

EXAMPLE 11.94

Synthesis of N-{3-[(2'-oxo-2,3-dihydrospiro[furo[2,3-g][1,4]benzodioxine-8,3'-indol]-1'(2'H)-yl)methyl]phenyl}methanesulfonamide

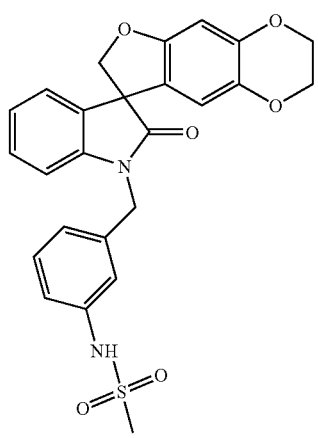

A 50 mL round bottom flask was charged with 1-(3-aminobenzyl)-2,3-dihydrospiro[furo[2,3-g][1,4]benzodioxine-8,3'-indol]-2'(1'H)-one (0.4 g, 1.0 mmol), pyridine (0.16 g, 2.0 mmol) and dichloromethane (10 mL). A solution of methanesulfonyl chloride (0.115 g, 1.0 mmol) in dichloromethane (5 mL) was added at 5° C., the reaction mixture was allowed to warm to ambient temperature and was stirred for 16 h. The reaction mixture was diluted with dichloromethane (50 mL) and was washed with water (50 mL) and 1 M hydrochloric acid (50 mL). The organic phase was dried over magnesium sulfate, filtered and concentrated in vacuo. Purification of the residue by column chromatography and eluted with a 0% to 100% gradient of ethyl acetate in dichloromethane afforded N-{3-[(2'-oxo-2,3-dihydrospiro[furo[2,3-g][1,4]benzodioxine-8,3'-indol]-1'(2'H)-yl)methyl]phenyl}methanesulfonamide (0.39 g, 82%) as an off-white solid: $^1$H NMR (300 MHz, DMSO-$d_6$) δ 9.81 (s, 1H), 7.32-6.90 (m, 8H), 6.49 (s, 1H), 6.18 (s, 1H), 4.89 (ABq, 2H), 4.71 (, 2H), 4.18-4.04 (m, 4H), 2.90 (s, 3H); $^{13}$C NMR (75 MHz, DMSO-$d_6$) δ177.2, 155.2, 144.6, 142.7, 139.3, 138.3, 138.0, 132.0, 130.1, 129.2, 124.1, 123.5, 122.8, 121.4, 118.7, 117.9, 111.7, 109.9, 99.2, 80.0, 64.6, 64.0, 57.7, 43.3; MS (ES+) m/z 478.9 (M+1).

EXAMPLE 11.95

Synthesis of 1'-[(1-oxidopyridin-2-yl)methyl]-2,3-dihydrospiro[furo[2,3-g][1,4]benzodioxine-8,3'-indol]-2'(1'H)-one

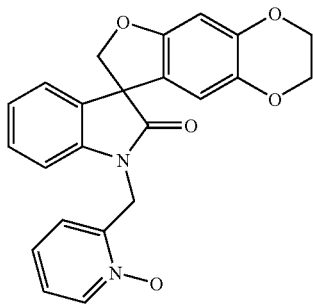

A solution of 1-(pyridin-2-ylmethyl)-2,3-dihydrospiro[furo[2,3-g][1,4]benzodioxine-8,3'-indol]-2'(1'H)-one (0.39 g, 1.0 mmol) and 3-chlorobenzoperoxoic acid (60% w/w, 0.43 g, 1.5 mmol) in dichloromethane (20 mL) was stirred at ambient temperature for 16 h. The reaction mixture was diluted with dichloromethane (50 mL) and washed with saturated aqueous sodium bicarbonate (50 mL). The organic phase was dried over magnesium sulfate, filtered and concentrated in vacuo. The residue was purified by column chromatography and eluted with a 5% to 10% gradient of methanol in dichloromethane to afford 1-[(1-oxidopyridin-2-yl)methyl]-2,3-dihydrospiro[furo[2,3-g][1,4]benzodioxine-8,3'-indol]-2'(1'H)-one (0.23 g, 57%) as an off-white solid: $^1$H NMR (300 MHz, DMSO-$d_6$) δ 8.31-8.26 (m, 1H), 7.30-6.94 (m, 7H), 6.48 (s, 1H), 6.23 (s, 1H), 5.24 (, 2H), 4.78 (ABq, 2H), 4.20-4.06 (m, 4H); $^{13}$C NMR (75 MHz, DMSO-$d_6$) δ177.9, 155.3, 146.0, 144.7, 141.6, 139.8, 138.3, 131.8, 129.2, 125.8, 124.9, 124.4, 124.0, 123.9, 120.6, 111.4, 109.4, 99.5, 80.2, 64.5, 63.9, 58.1, 39.1; MS (ES+) m/z 402.8 (M+1).

EXAMPLE 11.96

Synthesis of 2-[(2'-oxo-2,3-dihydrospiro[furo[2,3-g][1,4]benzodioxine-8,3'-indol]-1'(2'H)-yl)methyl]pyridine-3-carboxylic acid

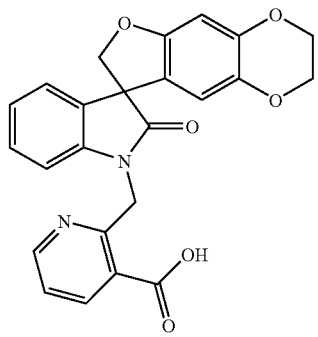

A 250 mL round-bottom flask was charged with ethyl 2-[(2'-oxo-2,3-dihydrospiro[furo[2,3-g][1,4]benzodioxine-8,3'-indol]-1'(2'H)-yl)methyl]pyridine-3-carboxylate (2.3 g, 5.0 mmol), lithium hydroxide (0.48 g, 20.0 mmol), tetrahydrofuran (30.mL), water (50.mL) and methanol (30 mL). The reaction mixture was stirred under nitrogen at reflux for 5 h, allowed to cool to ambient temperature and concentrated in vacuo. The residue was taken up in water (100 mL) and acidified to pH 1 by the addition of 10 M hydrochloric acid, causing a precipitate to be deposited. The solid was collected by filtration, washed with water and recrystallized from ethanol (50 mL) to afford 2-[(2'-oxo-2,3-dihydrospiro[furo[2,3-g][1,4]benzodioxine-8,3'-indol]-1'(2'H)-yl)methyl]pyridine-3-carboxylic acid (1.96 g, 91%) as an off-white solid: $^1$H NMR (300 MHz, DMSO-$d_6$) δ8.57-8.45 (m, 1H), 8.33-8.26 (m, 1H), 7.42 (dd, J=7.82, 4.77 Hz, 1H), 7.21-6.83 (m, 4H), 6.49-6.44 (m, 2H), 5.39 (ABq, 2H), 4.72 (ABq, 2H), 4.24-4.00 (m, 4H).

EXAMPLE 11.97

Synthesis of 1'-[(3-aminopyridin-2-yl)methyl]-2,3-dihydrospiro[furo[2,3-g][1,4]benzodioxine-8,3'-indol]-2'(1'H)-one hydrobromide

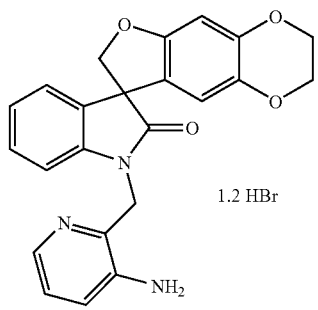

A 50 mL round-bottom Bask was charged with 2-[(2'-oxo-2,3-dihydrospiro[furo[2,3-g][1,4]benzodioxine-8,3'-indol]-1'(2'H)-yl)methyl]pyridine-3-carboxylic acid (0.86 g, 2.0 mmol), diphenyl phosphorazidate (0.69 g, 2.5 mmol), triethylamine (0.25 g, 2.5 mmol), tert-butanol (1.48 g, 20.0 mmol) and toluene (20 mL). The reaction mixture was stirred under nitrogen at reflux for 3 h. The reaction mixture was allowed to cool to ambient temperature and diluted with ethyl acetate (50 mL). The organic phase was washed with water (2×50 mL), dried over anhydrous magnesium sulfate, filtered and concentrated in vacuo. The residue was purified by column chromatography and eluted with a 0% to 50% gradient of ethyl acetate in dichloromethane. The resultant solid was dissolved in dichloromethane (20 mL) and a 30% w/w solution of hydrogen bromide in acetic acid (2.4 g, 10.0 mmol) was added. The reaction mixture was stirred at ambient temperature for 16 h and concentrated in vacuo. The residue was recrystallized three times from methanol (20 mL) to afford [(3-aminopyridin-2-yl)methyl]-2,3-dihydrospiro[furo[2,3-g][1,4]benzodioxine-8,3'-indol]-2'(1'H)-one hydrobromide (0.28 g, 32%) as an off-white solid: $^1$H NMR (300 MHz, CDCl$_3$) δ 8.02-7.72 (m, 3H), 7.54 (dd, J=8.5, 5.5 Hz, 1H), 7.30 (t, J=7.6 Hz, 1H), 7.14-7.00 (m, 2H), 6.43 (s, 1H), 6.14 (s, 1H), 5.49 (s, 2H), 4.67 (ABq, 2H), 4.17-3.98 (m, 4H); MS (ES+) m/z 402.0 (M+1). Anal. Calc'd for $C_{23}H_{20}N_3O_4$.1.2 HBr: C, 55.41; H, 4.08; N, 8.43. Found: C, 55.84; H, 4.36; N, 8.29.

EXAMPLE 11.98

Synthesis of N-{2-[(2'-oxo-2,3-dihydrospiro[furo[2,3-g][1,4]benzodioxine-8,3'-indol]-1'(2'H)-yl)methyl]pyridine-3-yl}methanesulfonamide

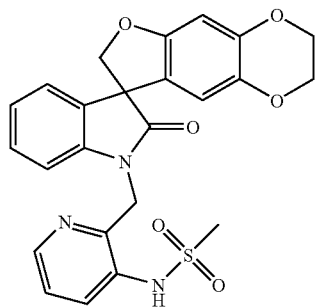

A 50 mL round-bottom flask was charged with 1-[(3-aminopyridin-2-yl)methyl]-2,3-dihydrospiro[furo[2,3-g][1,4]benzodioxine-8,3'-indol]-2'(1'H)-one hydrobromide (0.56 g, 1.0 mmol), methanesulfonyl chloride (0.12 g, 1.1 mmol), pyridine (0.25 g, 3.0 mmol) and dichloromethane (20 mL). The reaction mixture was stirred under nitrogen at ambient temperature for 16 h and diluted with dichloromethane (50 mL). The organic phase was washed with water (2×50 mL), dried over anhydrous magnesium sulfate, filtered and concentrated in vacuo. The residue was purified by column chromatography and eluted with a 0% to 100% gradient of ethyl acetate in dichloromethane, followed by recrystallization from methanol (10 mL) to afford N-{2-[(2'-oxo-2,3-dihydrospiro[furo[2,3-g][1,4]benzodioxine-8,3'-indol]-1'(2'H)-yl)methyl]pyridine-3-yl}methanesulfonamide (0.18 g, 38%) as an off-white solid: $^1$H NMR (300 MHz, DMSO-d$_6$) δ 9.64 (s, 1H), 8.27 (dd, J=4.6, 1.2 Hz, 1H), 7.78 (dd, J=8.0, 1.4 Hz, 1H), 7.34 (dd, J=8.0, 4.7 Hz, 1H), 7.21-7.10 (m, 2H), 6.96 (t, J=7.4 Hz, 1H), 6.77 (d, J=7.8 Hz, 1H), 6.48 (s, 1H), 6.46 (s, 1H), 5.17 (ABq, 2H), 4.73 (ABq, 2H), 4.18-4.05 (m, 4H), 3.14 (s, 3H); $^{13}$C NMR (75 MHz, DMSO-d$_6$) δ 177.6, 154.9, 151.0, 147.1, 144.5, 143.2, 138.1, 134.5, 132.6, 132.2, 132.1, 129.0, 123.8, 123.2, 122.2, 112.3, 109.4, 99.0, 79.6, 64.6, 64.1, 57.8, 41.8, 40.6; MS (ES+) m/z 479.9 (M+1).

EXAMPLE 11.99

Synthesis of 1-(piperidin-4-ylmethyl)-2,3-dihydrospiro[furo[2,3-g][1,4]benzodioxine-8,3'-indol]-2'(1'H)-one hydrochloride

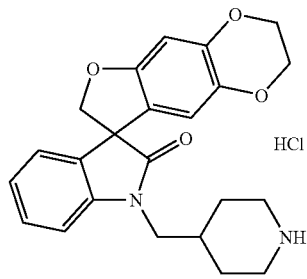

To a solution of tert-butyl 4-[(2'-oxo-2,3-dihydrospiro[furo[2,3-g][1,4]benzodioxine-8,3'-indol]-1'(2'H)-yl)methyl]piperidine-1-carboxylate (4.10 g, 9.53 mmol) in methanol (10 mL) was added 2 M ethereal hydrogen chloride (20 mL, 40 mmol). The mixture was stirred at ambient temperature for 5 h and concentrated in vacuo. The residue was triturated in diethyl ether (50 mL) to afford 1-(piperidin-4-ylmethyl)-2,3-dihydrospiro[furo[2,3-g][1,4]benzodioxine-8,3'-indol]-2'(1'H)-one hydrochloride (3.50 g, 86%): $^1$H NMR (300 MHz, DMSO-d$_6$) δ 9.06-8.50 (br s, 2H), 7.39-7.31 (m, 1H), 7.22-7.02 (m, 3H), 6.51 (s, 1H), 6.19 (s, 1H), 4.73 (d, J=9.3 Hz, 1H), 4.61 (d, J=9.3 Hz, 1H), 4.23-4.06 (m, 4H), 3.73-3.52 (m, 2H), 3.31-3.19 (m, 2H), 2.92-2.70 (m, 2H), 2.16-2.00 (m, 1H), 1.87-1.71 (m, 2H), 1.52-1.30 (m, 2H); MS (ES+) m/z 393.0 (M+1).

EXAMPLE 11.100

Synthesis of 1'-{[1-(1-methylethyl)piperidin-4-yl]methyl}-2,3-dihydrospiro[furo[2,3-g][1,4]benzodioxine-8,3'-indol]-2'(1'H)-one hydrochloride

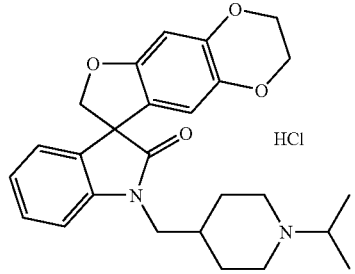

To a mixture of acetone (0.19 mL, 2.5 mmol) and 1,2-dichloroethane (5.0 mL), were added 1'-(piperidin-4-ylmethyl)-2,3-dihydrospiro[furo[2,3-g][1,4]benzodioxine-8,3'-indol]-2'(1'H)-one hydrochloride (0.36 g, 0.84 mmol), triethylamine (0.35 mL, 2.5 mmol) and sodium triacetoxyborohydride (0.534 g, 2.52 mmol). The mixture was stirred at ambient temperature for 16 h and concentrated in vacuo. The residue was purified by column chromatography and eluted with ethyl acetate/methanol/ammonium hydroxide (20/1/0.2) to afford 1'-{[1-(1-methylethyl)piperidin-4-yl]methyl}-2,3-dihydrospiro[furo[2,3-g][1,4]benzodioxine-8,3'-indol]-2'(1'H)-one. To a solution of this compound in methanol (5 mL) was added a 4 M solution of hydrogen chloride in 1,4-dioxane (1.0 mL, 4.0 mmol) and the mixture was stirred at ambient temperature for 30 min and concentrated in vacuo. Sequential trituration of the residue in hexanes and diethyl ether afforded {[1-(1-methylethyl)piperidin-4-yl]methyl}-2,3-dihydrospiro[furo[2,3-g][1,4]benzodioxine-8,3'-indol]-2'(1'H)-one hydrochloride (0.21 g, 53%) as an off-white solid: mp 213-216° C.; $^1$H NMR (300 MHz, DMSO-d$_6$) δ10.02-9.80 (br s, 1H), 7.40-7.02 (m, 4H), 6.51 (s, 1H), 6.18 (s, 1H), 4.74 (d, J=9.3 Hz, 1H), 4.62 (d, J=9.3 Hz, 1H), 4.23-4.06 (m, 4H), 3.73-3.21 (m, 4H), 3.00-2.78 (m, 2H), 2.20-1.52 (m, 5H), 1.32-1.12 (m, 7H); $^{13}$C NMR (75 MHz, DMSO-d$_6$) δ176.8, 154.7, 144.0, 142.5, 137.7, 131.6, 128.7, 123.5, 122.8, 121.0, 111.1, 109.2, 98.6, 79.7, 64.1, 63.5, 57.1, 56.7, 47.1, 44.2, 32.1, 26.6, 26.4, 16.1; MS (ES+) m/z 435.1 (M+1).

EXAMPLE 11.101

Synthesis of 1-[(1-methylpiperidin-4-yl)methyl]-2,3-dihydrospiro[furo[2,3-g][1,4]benzodioxine-8,3'-indol]-2'(1'H)-one hydrochloride

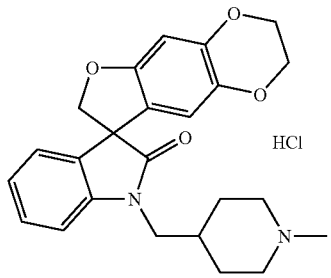

Following the procedure described in EXAMPLE 11.100 and making non-critical variations using 37% w/w aqueous formaldehyde to replace acetone, and tetrahydrofuran to replace dichloromethane, 1-[(1-methylpiperidin-4-yl)methyl]-2,3-dihydrospiro[furo[2,3-g][1,4]benzodioxine-8,3'-indol]-2'(1'H)-one hydrochloride was obtained (60%) as a colorless solid: mp1 86-202° C.; $^1$H NMR (300 MHz, DMSO-d$_5$) δ 10.07-10.03 (br s, 1H), 7.48-6.94 (m, 4H), 6.46 (s, 1H), 6.15 (s, 1H), 4.80-4.50 (m, 2H), 4.25-4.00 (m, 4H), 3.74-2.50 (m, 9H), 2.10-1.38 (m, 5H); MS (ES+) m/z 407.1 (M+1).

EXAMPLE 11.102

Synthesis of 1-(morpholin-2-ylmethyl)-2,3-dihydrospiro[furo[2,3-g][1,4]benzodioxine-8,3'-indol]-2'(1'1-1)-one

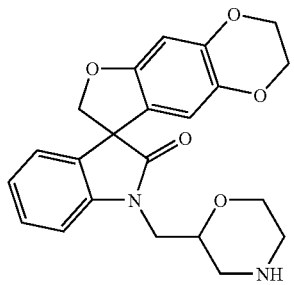

1'-[(4-benzylmorpholin-2-yl)methyl]-2,3-dihydrospiro[furo[2,3-g][1,4]benzodioxine-8,3'-indol]-2'(1'H)-one (3.36 g, 6.93 mmol) was suspended in methanol (20 mL) and ethyl acetate (20 mL) in a Parr bottle, and palladium on carbon (20% w/w, 0.50 g) was added. The mixture was shaken in a Parr hydrogenation apparatus at 50 psi and at ambient temperature for 16 h. The reaction mixture was filtered through a pad of diatomaceous earth and the filtrate was concentrated in vacuo. The residue was purified by column chromatography and eluted with ethyl acetate/methanol/7 N methanolic ammonia (10:1:0.1) to afford 1-(morpholin-2-ylmethyl)-2,3-dihydrospiro[furo[2,3-g][1,4]-benzodioxine-8,3'-indol]-2'(1'H)-one (1.7 g, 62%) as a colorless foam: mp 154-159° C.; $^1$H NMR (mixture of diasteroisomers, 300 MHz, CDCl$_3$) δ 7.33-7.24 (m, 1H), 7.17-7.00 (m, 3H), 6.49 (s, 0.5H), 6.48 (s, 0.5H), 6.24 (s, 0.5H), 6.21 (s, 0.5H), 4.91-4.85 (m, 1H), 4.66-4.60 (m, 1H), 4.22-4.08 (m, 4H), 3.94-3.51 (m, 5H), 3.00-2.61 (m, 4H); MS (ES+) m/z 395.1 (M+1).

EXAMPLE 11.103

Synthesis of 1'-{[4-(1-methylethyl)morpholin-2-yl]methyl}-2,3-dihydrospiro[furo[2,3-g][1,4]benzodioxine-8,3'-indol]-2'(1'H)-one

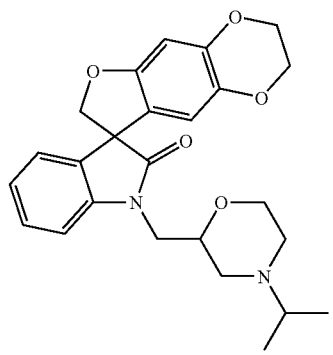

Following the procedure described in EXAMPLE 11.100 and making non-critical variations using 1-(morpholin-2-ylmethyl)-2,3-dihydrospiro[furo[2,3-g][1,4]benzodioxine-8,3'-indol]-2'(1'H)-one to replace 1'-(piperidin-4-ylmethyl)-2,3-dihydrospiro[furo[2,3-g][1,4]benzodioxine-8,3'-indol]-2'(1'H)-one, 1'-{[4-(1-methylethyl)morpholin-2-yl]methyl}-2,3-dihydrospiro[furo[2,3-g][1,4]benzodioxine-8,3'-indol]-2'(1'H)-one was obtained (88%) as a colorless solid: mp 102-125° C.; $^1$H NMR (mixture of diasteroisomers, 300 MHz, CDCl$_3$) δ 7.33-7.26 (m, 1H), 7.20-7.00 (m, 3H), 6.49 (s, 0.5H), 6.48 (s, 0.5H), 6.26 (s, 0.5H), 6.20 (s, 0.5H), 4.88 (d, J=9.0 Hz, 1H), 4.67-4.61 (m, 1H), 4.21-4.07 (m, 4H), 4.00-3.56 (m, 5H), 2.85-2.56 (m, 3H), 2.35-2.05 (m, 2H), 1.02 (d, J=6.6 Hz, 6H); MS (ES+) m/z 437.2 (M+1).

EXAMPLE 11.104

Synthesis of 1-[(4-methylmorpholin-2-yl)methyl]-2,3-dihydrospiro[furo[2,3-g][1,4]benzodioxine-8,3'-indol]-2'(1'H)-one

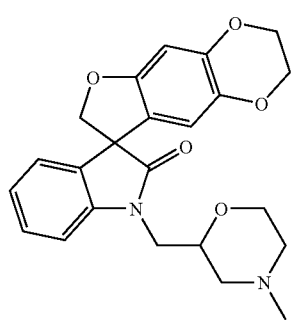

Following the procedure described in EXAMPLE 11.100 and making non-critical variations using 37% w/w aqueous formaldehyde to replace acetone, tetrahydrofuran to replace dichloromethane, and 1-(morpholin-2-ylmethyl)-2,3-dihydrospiro[furo[2,3-g][1,4]-benzodioxine-8,3'-indol]-2'(1'H)- one to replace 1'-(piperidin-4-ylmethyl)-2,3-dihydrospiro[furo[2,3-g][1,4]benzodioxine-8,3'-indol]-2'(1'H)-one, 1'-[(4-methylmorpholin-2-yl)methyl]-2,3-dihydrospiro[furo[2,3-g][1,4]benzodioxine-8,3'-indol]-2'(1'H)-one was obtained (91%) as a colorless solid: mp 102-112° C.; $^1$H NMR (mixture of diasteroisomers, 300 MHz, CDCl$_3$) δ 7.33-7.26 (m, 1H), 7.17-7.00 (m, 3H), 6.48 (s, 1H), 6.26 (s, 0.5H), 6.21 (s, 0.5H), 4.91-4.85 (m, 1H), 4.66-4.60 (m, 1H), 4.22-4.08 (m, 4H), 3.94-3.58 (m, 5H), 2.77 (d, J=11.7 Hz, 1H), 2.61 (d, J=11.7 Hz, 1H), 2.28 (s, 3H), 2.18-2.06 (m, 1H), 1.99-1.89 (m, 1H); MS (ES+) m/z 409.2 (M+1).

EXAMPLE 11.105

Synthesis of (8S)-1'-[(2S)-morpholin-2-ylmethyl]-2,3-dihydrospiro[furo[2,3-g][1,4]benzodioxine-8,3'-indol]-2'(1'H)-one

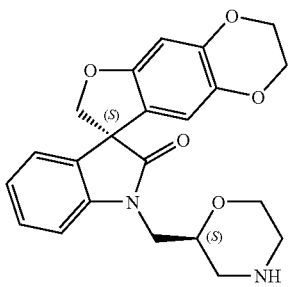

Following the procedure described in EXAMPLE 11.102 and making non-critical variations using (8S)-1'-{[(2S)-4-benzylmorpholin-2-yl]methyl}-2,3-dihydrospiro[furo[2,3-g][1,4]benzodioxine-8,3'-indol]-2'(1'H)-one to replace 1'-[(4-benzylmorpholin-2-yl)methyl]-2,3-dihydrospiro[furo[2,3-g][1,4]benzodioxine-8,3'-indol]-2'(1'H)-one, (8S)-1'-[(2S)-morpholin-2-ylmethyl]-2,3-dihydrospiro[furo[2,3-g][1,4]benzodioxine-8,3'-indol]-2'(1'H)-one was obtained (56%): MS (ES+) m/z 395.1 (M+1).

EXAMPLE 11.106

Synthesis of (8S)-1'-{[(2S)-4-methylmorpholin-2-yl]methyl}-2,3-dihydrospiro[furo[2,3-g][1,4]benzodioxine-8,3'-indol]-2'(1'H)-one

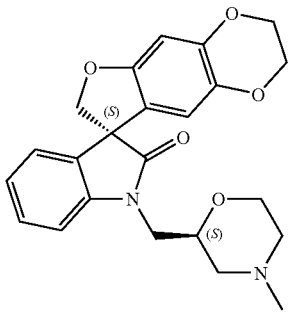

Following the procedure described in EXAMPLE 11.100 and making non-critical variations using 37% w/w aqueous formaldehyde to replace acetone, tetrahydrofuran to replace 1,2-dichloroethane and (8S)-1'-[(2S)-morpholin-2-ylmethyl]-2,3-dihydrospiro[furo[2,3-g][1,4]benzodioxine-8,3'-indol]-2'(1'H)-one to replace 1'-(piperidin-4-ylmethyl)-2,3-dihydrospiro[furo[2,3-g][1,4]benzodioxine-8,3'-indol]-2'(1'H)-one hydrochloride, (8S)-1-{[(2S)-4-methylmorpholin-2-yl]methyl}-2,3-dihydrospiro[furo[2,3-g][1,4]benzodioxine-8,3'-indol]-2'(1'H)-one was obtained (68%) as a colorless solid: mp 85-90° C.; $^1$H NMR (300 MHz, CDCl$_3$) δ 7.27 (d, J=7.5 Hz, 1H), 7.15-6.98 (m, 3H), 6.47 (s, 1H), 6.20 (s, 1H), 4.86 (d, J=9.0 Hz, 1H), 4.61 (d, J=9.0 Hz, 1H), 4.19-4.05 (m, 4H), 3.92-3.56 (m, 5H), 2.76 (d, J=11.4 Hz, 1H), 2.60 (d, J=11.4 Hz, 1H), 2.26 (s, 3H), 2.17-2.05 (m, 1H), 1.97-1.87 (m, 1H); $^{13}$C NMR (300 MHz, CDCl$_3$) δ177.6, 155.1, 144.5, 142.6, 138.2, 132.0, 128.7, 123.6, 123.2, 121.0, 111.4, 109.4, 99.2, 80.0, 73.5, 66.7, 64.4, 63.8, 58.1, 57.8, 54.6, 46.3, 43.1; MS (ES+) m/z 409.2 (M+1).

EXAMPLE 11.107

Synthesis of 1'-{[3-(trifluoromethyl)pyridin-2-yl]methyl}spiro[furo[3,2-e][2,1,3]benzoxadiazole-8,3'-indol]-2'(1'H)-one

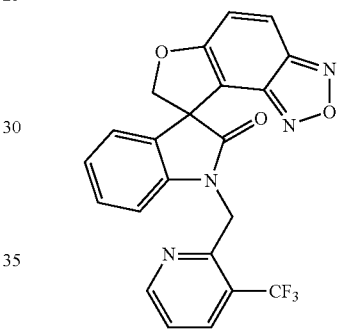

To a cooled (0° C.) solution of 3-trifluoromethyl-pyridin-2-yl)methanol hydrochloride (0.24 g, 1.1 mmol) in dichloromethane (10.mL) was added N,N-dimethylformamide (2 drops, catalytic amount) and thionyl chloride (0.15 mL). The solution was stirred for 16 h at ambient temperature and concentrated in vacuo. The residue was dissolved in N,N-dimethylformamide (10 mL) and cesium carbonate (0.98 g, 3.0 mmol), potassium iodide (100 mg) and spiro[furo[3,2-e][2,1,3]benzoxadiazole-8,3'-indol]-2'(1'H)-one (0.28 g, 1.0 mmol) were added. The reaction was heated at 60° C. for 3 h, allowed to cool to ambient temperature and filtered. The filtrate was concentrated in vacuo and the residue was purified by column chromatography and eluted with a 15% to 30% gradient of ethyl acetate in hexanes to afford 1-{[3-(trifluoromethyl)pyridin-2-yl]methyl}spiro[furo[3,2-e][2,1,3]benzoxadiazole-8,3'-indol]-2'(1'H)-one (0.28 g, 64%) as a colorless solid: mp 212-215° C.; $^1$H NMR (300 MHz, CDCl$_3$) δ8.62 (d, J=4.8 Hz, 1H), 7.97 (d, J=7.8 Hz, 1H), 7.82 (dd, J=9.6, 0.9 Hz, 1H), 7.34-7.27 (m, 2H), 7.23-7.16 (m, 2H), 7.01 (dd, J=7.5, 7.5 Hz, 1H), 6.71 (d, J=7.8 Hz, 1H), 5.46 (d, J=17.4 Hz, 1H), 5.30 (d, J=9.3 Hz, 1H), 5.21 (d, J=17.4 Hz, 1H), 5.01 (d, J=9.3 Hz, 1H); $^{13}$C NMR (75 MHz, CDCl$_3$) δ 176.9, 163.2, 152.5, 152.2, 148.4, 145.0, 142.8, 134.1 (q, J=5.2 Hz), 129.8, 129.6, 125.6, 124.5, 124.1, 123.7, 123.4, 122.1, 121.9, 121.8, 119.3, 82.4, 57.3, 42.7 (q, J=3.3 Hz); MS (ES+) m/z 439.1 (M+1).

EXAMPLE 11.108

Synthesis of 6-chloro-1'-{[3-(trifluoromethyl)pyridin-2-yl]methyl}-2,3-dihydrospiro[furo[3,2-f][1,4]benzodioxine-9,3'-indol]-2'(1'H)-one

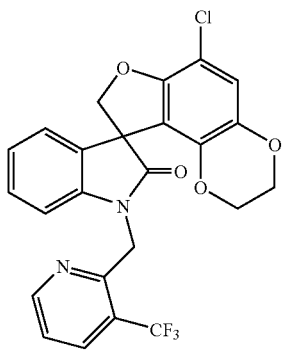

Following the procedure described in EXAMPLE 11.107 and making non-critical variations using 6-chloro-2,3-dihydrospiro[furo[3,2-f][1,4]benzodioxine-9,3'-indol]-2'(1'H)-one to replace spiro[furo[3,2-e][2,1,3]benzoxadiazole-8,3'-indol]-2'(1'H)-one, chloro-1'-{[3-(trifluoromethyl)pyridin-2-yl]methyl}-2,3-dihydrospiro[furo[3,2-f][1,4]benzodioxine-9,3'-indol]-4'1'H)-one was obtained (70%) as a colorless solid: mp 273-275° C.; $^1$H NMR (300 MHz, DMSO-$d_6$) δ8.70 (d, J=4.5 Hz, 1H), 8.26-8.21 (m, 1H), 7.58-7.51 (m, 1H), 7.26-7.18 (m, 2H), 7.08-6.98 (m, 1H), 6.94-6.88 (m, 2H), 5.24 (ABq, 2H), 4.79 (ABq, 2H), 4.14-3.96 (m, 4H); MS (ES+) m/z 489.2 (M+1), 491.2 (M+1).

EXAMPLE 11.109

Synthesis of 1'-{[3-(trifluoromethyl)pyridin-2-yl]methyl}-2,3-dihydrospiro[furo[3,2-f][1,4]benzodioxine-9,3'-indol]-2'(1'H)-one

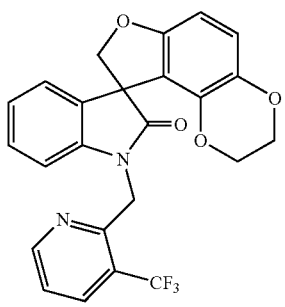

Following the procedure described in EXAMPLE 11.107 and making non-critical variations using 2,3-dihydrospiro[furo[3,2-f][1,4]benzodioxine-9,3'-indol]-2'(1'H)-one to replace spiro[furo[3,2-e][2,1,3]benzoxadiazole-8,3'-indol]-2'(1'H)-one, 1'-{[3-(trifluoromethyl)pyridin-2-yl]methyl}-2,3-dihydrospiro[furo[3,2-f][1,4]benzodioxine-9,3'-indol]-2'(1'H)-one was obtained (70%) as a colorless solid: mp 245-247° C.; $^1$H NMR (300 MHz, CDCl$_3$) δ 8.58 (d, J=4.5 Hz, 1H), 7.98 (d, J=4.5 Hz, 1H), 7.34-7.26 (m, 1H), 7.20-7.12 (m, 2H), 7.04-6.97 (m, 1H), 6.74 (d, J=8.7 Hz, 1H), 6.63-6.58 (m, 1H), 6.46 (d, J=8.7 Hz, 1H), 5.56 (d, J=17.4 Hz, 1H), 5.06 (d, J=16.8 Hz, 1H), 4.97 (d, J=8.7 Hz, 1H), 4.70 (d, J=8.7 Hz, 1H), 4.17-3.92 (m, 4H); $^{13}$C NMR (75 MHz, CDCl$_3$) δ 177.4, 156.2, 152.9, 152.4, 152.3, 142.3, 140.0, 138.6, 138.1, 134.1 (q, J=5.3 Hz), 131.7, 128.3, 124.5, 123.5, 122.9, 122.0, 118.0, 115.6, 108.4, 102.2, 81.8, 64.7, 63.9, 57.2, 42.6 (q, J=3.1 Hz); MS (ES+) m/z 455.2 (M+1).

EXAMPLE 11.110

Synthesis of 1-{[5-(difluoromethyl)furan-2-yl]methyl}-2,3-dihydrospiro[furo[2,3-g][1,4]benzodioxine-8,3'-indol]-2'(1'H)-one

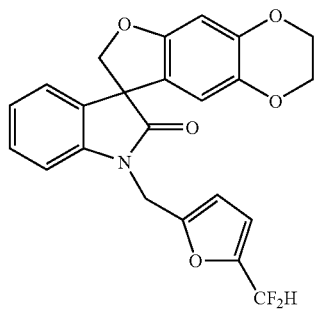

Following the procedure described in EXAMPLE 11.107 and making non-critical variations using 2,3-dihydrospiro[furo[2,3-g][1,4]benzodioxine-8,3'-indol]-41H)-one to replace spiro[furo[3,2-e][2,1,3]benzoxadiazole-8,3'-indol]-2'(1'H)-one and (5-(difluoromethyl)furan-2-yl)methanol to replace 3-trifluoromethyl-pyridin-2-yl)methanol hydrochloride, 1'-{[5-(difluoromethyl)furan-2-yl]methyl}-2,3-dihydrospiro[furo[2,3-g][1,4]benzodioxine-8,3'-indol]-2'(1'H)-one was obtained (35%) as a colorless solid: mp 173-175° C.; $^1$H NMR (300 MHz, CDCl$_3$) δ 7.33-7.25 (m, 1H), 7.21-7.14 (m, 1H), 7.11-6.96 (m, 2H), 6.63-6.58 (m, 1H), 6.57 (t, $J_{H-F}$=54.3 Hz, 1H), 6.50 (s, 1H), 6.37-6.34 (m, 1H), 6.20 (s, 1H), 5.04 (d, J=16.2 Hz, 1H), 4.94-4.83 (m, 2H), 4.65 (d, J=9.0 Hz, 1H), 4.23-4.07 (m, 4H); $^{13}$C NMR (75 MHz, CDCl$_3$) δ177.1, 155.2, 151.1 (t, $J_{C-F}$=2.2 Hz), 146.5, 144.6, 141.5, 138.3, 132.1, 128.9, 123.9, 123.7, 120.8, 111.5, 111.3 (t, $J_{C-F}$=4.1 Hz), 109.2, 108.9, 108.2 (t, $J_{C-F}$=233.6 Hz), 99.4, 80.0, 64.5, 63.9, 57.9, 37.0; MS (ES+) m/z 425.9 (M+1).

EXAMPLE 11.111

Synthesis of 5,6-difluoro-1'-(piperidin-4-ylmethyl)spiro[1-benzofuran-3,3'-indol]-2'(1'H)-one hydrochloride

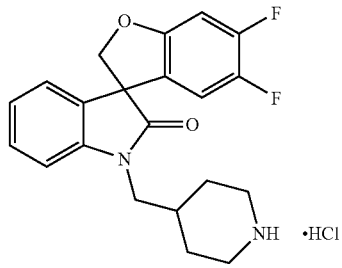

To a solution of tert-butyl 4-[(5,6-difluoro-2'-oxospiro[1-benzofuran-3,3'-indol]-1'(2'H)-yl)methyl]piperidine-1-carboxylate (0.47 g, 1.01 mmol) in anhydrous methanol (8 mL) and anhydrous dichloromethane (3 mL) was added a 4.0 M solution of hydrogen chloride in 1,4-dioxane (4.0 mL, 16 mmol) and the reaction mixture was stirred at ambient temperature for 16 h. Anhydrous diethyl ether (30 mL) was added to the reaction mixture, causing a precipitate to be deposited. Trituration of the resultant solid in diethyl ether (2×30 mL) afforded 5,6-difluoro-1-(piperidin-4-ylmethyl)spiro[1-benzofuran-3,3'-indol]-2'(1'H)-one hydrochloride (0.36 g, 88%) as a colorless solid: mp>200° C.; $^1$H NMR (300 MHz, CD$_3$OD) δ 7.40 (ddd, J=7.6, 7.6, 1.4 Hz, 1H), 7.24-7.12 (m, 3H), 6.92 (dd, J=10.7, 6.4 Hz, 1H), 6.69 (dd, J=9.5, 8.0 Hz, 1H), 4.91 (d, J=9.4 Hz, 1H), 4.76 (d, J=9.4 Hz, 1H), 3.85-3.65 (m, 2H), 3.47-3.37 (m, 2H), 3.05-2.93 (m, 2H), 2.32-2.16 (m, 1H), 2.05-1.92 (m, 2H), 1.64-1.46 (m, 2H); $^{13}$C NMR (75 MHz, CD$_3$OD) δ 179.3, 158.7 (d, $J_{C-F}$=13.0 Hz), 152.6 (dd, $J_{C-F}$=246.7, 14.5 Hz), 146.9 (dd, $J_{C-F}$=239.8, 14.0 Hz), 144.0, 132.7, 130.7, 125.7 (dd, $J_{C-F}$=6.5, 3.2 Hz), 125.1, 112.9 (d, $J_{C-F}$=22.2 Hz), 110.7, 100.9 (d, $J_{C-F}$=22.7 Hz), 82.2, 59.4, 46.1, 44.8, 33.8, 27.8; MS (ES+) m/z 371.3 (M+1). Anal. Calcd for C$_{21}$H$_{20}$F$_2$N$_2$O$_2$.HCl: C, 61.99; H, 5.20; N, 6.89. Found: C, 61.73; H, 5.28; N, 7.03.

EXAMPLE 11.112

Synthesis of 5,6-difluoro-1'-[(1-methylpiperidin-4-yl)methyl]spiro[1-benzofuran-3,3'-indol]-2'(1'H)-one hydrochloride

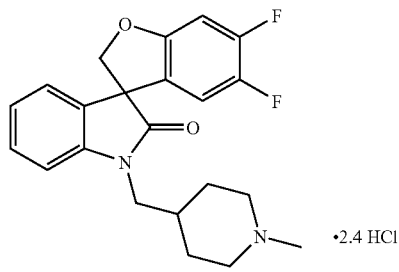

To a solution of 5,6-difluoro-1'-(piperidin-4-ylmethyl)spiro[1-benzofuran-3,3'-indol]-2'(1'H)-one hydrochloride (0.240 g, 0.590 mmol) in tetrahydrofuran (5 mL) was added triethylamine (0.08 mL, 1.18 mmol), formaldehyde (37% w/w in water, 0.18 mL, 2.24 mmol), sodium triacetoxyborohydride (0.375 g, 1.77 mmol), and acetic acid (3 drops). The reaction mixture was stirred at ambient temperature for 3.5 h and concentrated in vacuo. Water (10 mL) was added to the residue and the mixture was extracted with dichloromethane (3×75 mL). The combined organic extracts were dried over sodium sulfate, filtered and concentrated in vacuo. The residue was purified by column chromatography and eluted with dichloromethane/methanol/ammonium hydroxide (10/1/0.2) to afford 5,6-difluoro-1'-[(1-methylpiperidin-4-yl)methyl]spiro[1-benzofuran-3,3'-indol]-2'(1'H)-one hydrochloride (0.205 g, 90%) as a colorless solid: mp 162-164° C.; $^1$H NMR (300 MHz, CDCl$_3$) δ 7.40 (dd, J=7.5, 7.5 Hz, 1H), 7.23-7.12 (m, 3H), 6.92 (dd, J=10.7, 6.4 Hz, 1H), 6.69 (dd, J=9.4, 8.0 Hz, 1H), 4.91 (d, J=9.4 Hz, 1H), 4.76 (d, J=9.4 Hz, 1H), 3.76 (t, J=7.0 Hz, 2H), 3.55-3.48 (m, 2H), 3.02-2.92 (m, 2H), 2.86 (s, 3H), 2.30-1.92 (m, 3H), 1.65-1.56 (m, 2H); $^{13}$C NMR (75 MHz, CDCl$_3$) δ 179.0, 158.5 (d, $J_{C-F}$=10.3 Hz), 152.3 (d, $J_{C-F}$=247.1 Hz), 146.7 (d, $J_{C-F}$=238.3 Hz), 143.9, 132.5, 131.1, 125.4, 125.0, 113.6 (d, $J_{C-F}$=19.8 Hz), 112.3, 100.8 (d, $J_{C-F}$=22.2 Hz), 83.1, 59.0, 57.0, 56.7, 46.7, 34.0, 29.6, 29.5; MS (ES+) m/z 385.3 (M+1). Anal. Calcd for C$_{22}$H$_{22}$F$_2$N$_2$O$_2$.2.4HCl: C, 55.99; H, 5.21; N, 5.94. Found: C, 55.75; H, 5.19; N, 5.97.

EXAMPLE 12

Synthesis of N-(cyclohexylmethyl)-3-[(2'-oxo-5,6-dihydrospiro[benzo[1,2-b:5,4-b']difuran-3,3'-indol]-1'(2'H)-yl)methyl]benzamide

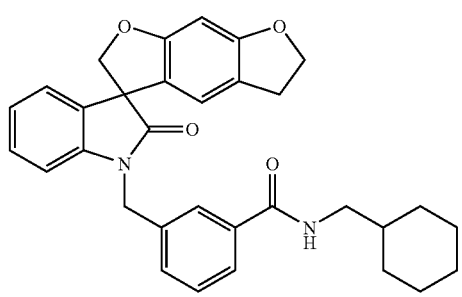

A suspension of 3-[(2'-oxo-5,6-dihydrospiro[benzo[1,2-b:5,4-b']difuran-3,3'-indol]-1'(2'H)-yl)methyl]benzoic acid (2.13 g, 5.1 mmol) and N,N-dimethylformamide (0.001 mL, catalytic amount) in anhydrous dichloromethane (30 mL) was treated with oxalyl chloride (4.50 mL, 5.1 mmol). The reaction mixture was stirred at ambient temperature for 3 h. The crude product was concentrated in vacuo to afford 3-(((2'-oxo-5,6-dihydro-2H-spiro[benzofuro[6,5-b]furan-3,3'-indoline]-1'-yl)methyl)benzoyl chloride as a light yellow solid. A solution of 3-((2'-oxo-5,6-dihydro-2H-spiro[benzofuro[6,5-b]furan-3,3'-indoline]-1'-yl)methyl)benzoyl chloride (0.27 g, 0.6 mmol), cyclohexanemethylamine (0.17 mL, 1.3 mmol), triethylamine (0.44 mL, 3.2 mmol), and 4-(dimethylamino)pyridine (0.005 g, catalytic amount) in anhydrous dichloromethane (5 mL), was stirred at ambient temperature for 20 h under nitrogen. The reaction mixture was diluted with dichloromethane (10 mL) and aqueous citric acid (10 mL) and the phases were separated. The organic phase was washed with water (10 mL) and brine (10 mL), dried over anhydrous sodium sulfate, filtered and concentrated in vacuo. The crude product was purified by column chromatography with ethyl acetate in hexanes (0% to 100% gradient) to afford N-(cyclohexylmethyl)-3-[(2'-oxo-5,6-dihydrospiro[benzo[1,2-b:5,4-b']difuran-3,3'-indol]-1'(2'H)-yl)methyl]benzamide (0.33 g, 65%) as a colourless solid: $^1$H NMR (300 MHz, CDCl$_3$) δ7.80 (s, 1H), 7.63 (d, J=7.4 Hz, 1H), 7.48-7.37 (m, 2H), 7.23-7.15 (m, 2H), 7.08-7.00 (m, 1H), 6.79 (d, J=7.8 Hz, 1H), 6.50 (s, 1H), 6.43 (s, 1H), 6.19-6.09 (m, 1H), 5.08 (d, J=15.7 Hz, 1H), 4.99 (d, J=9.0 Hz, 1H), 4.91 (d, J=15.7 Hz, 1H), 4.72 (d, J=9.0 Hz, 1H), 4.55 (t, J=8.6 Hz, 2H), 3.33-3.23 (m, 2H), 3.07-2.95 (m, 2H), 1.82-1.64 (m, 5H), 1.34-1.13 (m, 4H), 1.07-0.86 (m, 2H); MS (ES+) m/z 509.0 (M+1).

EXAMPLE 12.1

Synthesis of N-(2-methoxyethyl)-3-[(2'-oxo-5,6-dihydrospiro[benzo[1,2-b:5,4-b']difuran-3,3'-indol]-1'(2'H)-yl)methyl]benzamide

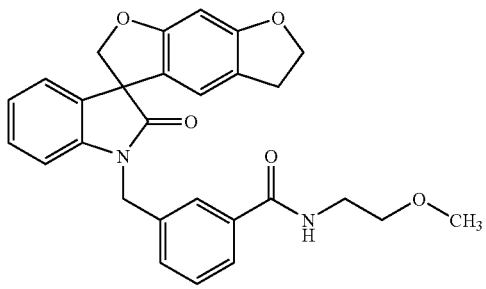

Following the procedure as described in EXAMPLE 12 and making non-critical variations using 2-methoxyethylamine to replace cyclohexanemethylamine, N-(2-methoxyethyl)-3-[(2'-oxo-5,6-dihydrospiro[benzo[1,2-b:5,4-b']difuran-3,3'-indol]-1'(2'H)-yl)methyl]benzamide was obtained (67%) as a colorless solid: mp 72-73° C. (hexanes/ethyl acetate); $^1$H NMR (300 MHz, CDCl$_3$) δ 7.83, (s, 1H), 7.65 (d, J=6.3 Hz, 1H), 7.46-7.36 (m, 2H), 7.22-7.17 (m, 2H), 7.06-7.01 (m, 1H), 6.78 (d, J=7.7 Hz, 1H), 6.56-6.51 (m, 1H), 6.51 (s, 1H), 6.43 (s, 1H), 5.08 (d, J=15.7 Hz, 1H), 4.99 (d, J=9.0 Hz, 1H), 4.91 (d, J=15.7 Hz, 1H), 4.72 (d, J=9.0 Hz, 1H), 4.57-4.51 (m, 2H), 3.67-3.62 (m, 2H), 3.57-3.54 (m, 2H), 3.38 (s, 3H), 3.05-2.98 (m, 2H); MS (ES+) m/z 471.0 (M+1).

EXAMPLE 12.2

Synthesis of N-hexyl-N-methyl-3-[(2'-oxo-5,6-dihydrospiro[benzo[1,2-b:5,4-b']difuran-3,3'-indol]-1'(2'H)-yl)methyl]benzamide

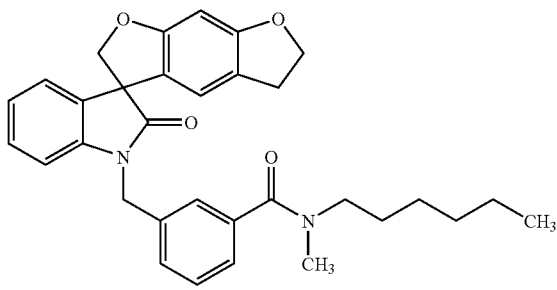

Following the procedure as described in EXAMPLE 12 and making non-critical variations using N-hexylmethylamine to replace cyclohexanemethylamine, N-hexyl-N-methyl-3-[(2'-oxo-5,6-dihydrospiro[benzo[1,2-b:5,4-b']difuran-3,3'-indol]-1'(2'H)-yl)methyl]benzamide was obtained (80%) as a colorless solid: mp 73-74° C. (hexanes/ethyl acetate); $^1$H NMR (300 MHz, CDCl$_3$) δ 7.41-7.36 (m, 3H), 7.31-7.26 (m, 1H), 7.22-7.16 (m, 2H), 7.05-7.00 (m, 1H), 6.82-6.75 (m, 1H), 6.49 (s, 1H), 6.43 (s, 1H), 5.08 (d, J=15.7 Hz, 1H), 4.92 (d, J=9.0 Hz, 1H), 4.86 (d, J=15.7 Hz, 1H), 4.71 (d, J=8.6 Hz, 1H), 4.55 (t, J=8.6 Hz, 2H), 3.19-3.12 (m, 1H), 3.05-2.84 (m, 5H), 1.64 (m, 2H), 1.56-1.47 (m, 1H), 1.38-1.34 (m, 3H), 1.22-1.04 (m, 3H), 0.96-0.79 (m, 3H); MS (ES+) m/z 511.1 (M+1).

EXAMPLE 12.3

Synthesis of N-(2-ethylbutyl)-3-[(2'-oxo-5,6-dihydrospiro[benzo[1,2-b:5,4-b']difuran-3,3'-indol]-1'(2'H)-yl)methyl]benzamide

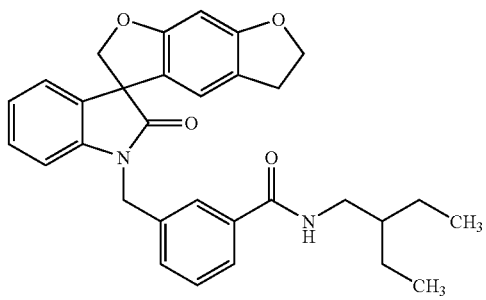

Following the procedure as described in EXAMPLE 12 and making non-critical variations using 2-ethyl-n-butylamine to replace cyclohexanemethylamine, N-(2-ethylbutyl)-3-[(2'-oxo-5,6-dihydrospiro[benzo[1,2-b:5,4-b']difuran-3,3'-indol]-1'(2'H)-yl)methyl]benzamide was obtained (40%) as a colorless solid: mp 105-106° C. (hexanes/ethyl acetate); $^1$H NMR (300 MHz, CDCl$_3$) δ 7.80 (s, 1H), 7.62 (d, J=7.3 Hz, 1H), 7.47-7.38 (m, 2H), 7.23-7.15 (m, 2H), 7.06-7.00 (m, 1H), 6.79 (d, J=7.8 Hz, 1H), 6.51 (s, 1H), 6.43 (s, 1H), 6.10-6.01 (m, 1H), 5.09 (d, J=15.9 Hz, 1H), 4.99 (d, J=9.0 Hz, 1H), 4.91 (d, J=15.9 Hz, 1H), 4.72 (d, J=9.0 Hz, 1H), 4.55 (t, J=8.7 Hz, 2H), 3.44-3.38 (m, 2H), 3.05-2.96 (m, 2H), 1.55-1.46 (m, 1H), 1.42-1.32 (m, 4H), 0.93 (t, J=7.3 Hz, 6H); MS (ES+) m/z 497.0 (M+1).

EXAMPLE 12.4

Synthesis of N-(2,4-dimethylphenyl)-3-[(2'-oxo-5,6-dihydrospiro[benzo[1,2-b:5,4-b']difuran-3,3'-indol]-1'(2'H)-yl)methyl]benzamide

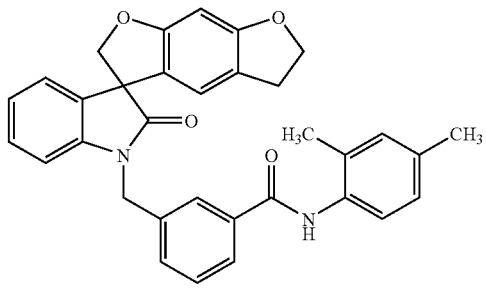

Following the procedure as described in EXAMPLE 12 and making non-critical variations using 2,4-dimethylaniline to replace cyclohexanemethylamine, N-(2,4-dimethylphenyl)-3-[(2'-oxo-5,6-dihydrospiro[benzo[1,2-b:5,4-b']difuran-3,3'-indol]-1'(2'H)-yl)methyl]benzamide was obtained (57%) as a colorless solid: mp 234-235° C. (hexanes/ethyl acetate); $^1$H NMR (300 MHz, CDCl$_3$) δ 7.89 (s, 1H), 7.77 (d, J=7.6 Hz, 2H), 7.57-7.45 (m, 3H), 7.24-7.18 (m, 2H), 7.07 (s, 1H), 7.06-7.02 (m, 2H), 6.82 (d, J=7.8 Hz, 1H), 6.47 (s, 1H), 6.43 (s, 1H), 5.19 (d, J=15.7 Hz, 1H), 5.00 (d, J=9.0 Hz, 1H), 4.88 (d, J=15.7 Hz, 1H), 4.72 (d, J=9.0 Hz, 1H), 4.53-4.35 (m, 2H), 2.91-2.84 (m, 2H), 2.31 (s, 3H), 2.20 (s, 3H); MS (ES+) m/z 516.1 (M+1).

EXAMPLE 12.5

Synthesis of 3-[(2'-oxo-5,6-dihydrospiro[benzo[1,2-b:5,4-b']difuran-3,3'-indol]-1'(2'H)-yl)methyl]-N-(2-phenylpropyl)benzamide

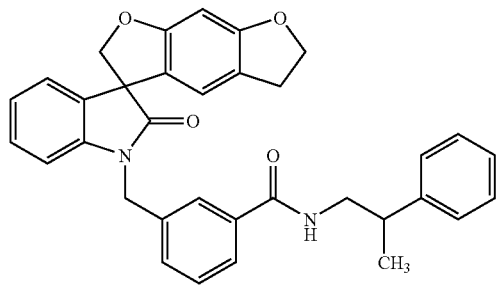

Following the procedure described in EXAMPLE 12 and making non-critical variations using 2-phenylpropan-1-amine to replace cyclohexanemethylamine, 3-[(2'-oxo-5,6-dihydrospiro[benzo[1,2-b:5,4-b']difuran-3,3'-indol]-1'(2'H)-yl)methyl]-N-(2-phenylpropyl)benzamide was obtained (82%) as a colorless solid: $^1$H NMR (300 MHz, (CD$_3$)$_2$CO) δ7.88 (s, 1H), 7.83-7.73 (m, 1H), 7.70 (d, J=7.7 Hz, 1H), 7.54 (d, J=7.7 Hz, 1H), 7.45-7.38 (m, 1H), 7.34-7.14 (m, 7H), 7.09-7.01 (m, 1H), 6.93 (d, J=7.8 Hz, 1H), 6.63 (s, 1H), 6.34 (s, 1H), 5.15 (d, J=15.9 Hz, 1H), 4.94 (d, J=9.2 Hz, 1H), 4.92 (d, J=15.9 Hz, 1H), 4.76 (d, J=9.1 Hz, 1H), 4.53 (t, J=8.7 Hz, 2H), 3.58-3.50 (m, 2H), 3.19-2.93 (m, 3H), 1.28 (d, J=7.0 Hz, 3H); MS (ES+) m/z 531.1 (M+1).

EXAMPLE 12.6

Synthesis of N-[(1S)-1-cyclohexylethyl]-3-[(2'-oxo-5,6-dihydrospiro[benzo[1,2-b:5,4-b']difuran-3,3'-indol]-1'(2'H)-yl)methyl]benzamide

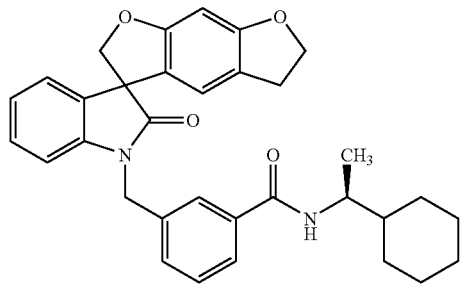

Following the procedure as described in EXAMPLE 12 and making non-critical variations using (S)-(+)-1-cyclohexylethylamine to replace cyclohexanemethylamine, N-[(1S)-1-cyclohexylethyl]-3-[(2'-oxo-5,6-dihydrospiro[benzo[1,2-b:5,4-b']difuran-3,3'-indol]-1'(2'H)-yl)methyl]benzamide was obtained (87%) as a colorless solid: $^1$H NMR (300 MHz, CDCl$_3$) δ7.80 (d, J=6.1, 1H), 7.64-7.57 (m, 1H), 7.46-7.36 (m, 2H), 7.23-7.15 (m, 2H), 7.07-7.00 (m, 1H), 6.79 (d, J=7.7 Hz, 1H), 6.51 (s, 1H), 6.43 (s, 1H), 5.89 (d, J=9.0 Hz, 1H), 5.08 (d, J=15.7 Hz, 1H), 4.99 (d, J=9.0 Hz, 1H), 4.92 (d, J=15.7 Hz, 1H), 4.71 (d, J=9.0 Hz, 1H), 4.55 (t, J=8.6 Hz, 2H), 3.06-2.95 (m, 2H), 1.85-1.61 (m, 5H), 1.58 (s, 3H), 1.49-1.35 (m, 1H), 1.19-0.97 (m, 6H); MS (ES+) m/z 523.1 (M+1).

EXAMPLE 12.7

Synthesis of N-[(1R)-1-cyclohexylethyl]-3-[(2'-oxo-5,6-dihydrospiro[benzo[1,2-b:5,4-b']difuran-3,3'-indol]-1'(2'H)-yl)methyl]benzamide

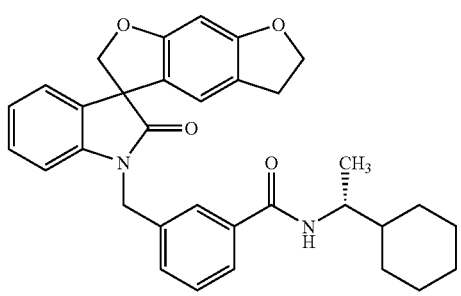

Following the procedure as described in EXAMPLE 12 and making non-critical variations using (R)-(−)-1-cyclohexylethylamine to replace cyclohexanemethylamine, N-[(1R)-1-cyclohexylethyl]-3-[(2'-oxo-5,6-dihydrospiro[benzo[1,2-b:5,4-b']difuran-3,3'-indol]-1'(2'H)-yl)methyl]benzamide was obtained (60%) as a colorless solid: $^1$H NMR (300 MHz, CDCl$_3$) δ7.80 (d, J=6.1, 1H), 7.64-7.57 (m, 1H), 7.46-7.36 (m, 2H), 7.23-7.15 (m, 2H), 7.07-7.00 (m, 1H), 6.79 (d, J=7.7 Hz, 1H), 6.51 (s, 1H), 6.43 (s, 1H), 5.89 (d, J=9.0 Hz, 1H), 5.08 (d, J=15.7 Hz, 1H), 4.99 (d, J=9.0 Hz, 1H), 4.92 (d, J=15.7 Hz, 1H), 4.71 (d, J=9.0 Hz, 1H), 4.55 (t, J=8.6 Hz, 2H), 3.06-2.95 (m, 2H), 1.85-1.61 (m, 5H), 1.58 (s, 3H), 1.49-1.35 (m, 1H), 1.19-0.97 (m, 6H); MS (ES+) m/z 523.1 (M+1).

EXAMPLE 12.8

Synthesis of N-(4-ethylphenyl)-2-[(2'-oxo-5,6-dihydrospiro[benzo[1,2-b:5,4-b']difuran-3,3'-indol]-1'(2'H)-yl)methyl]benzamide

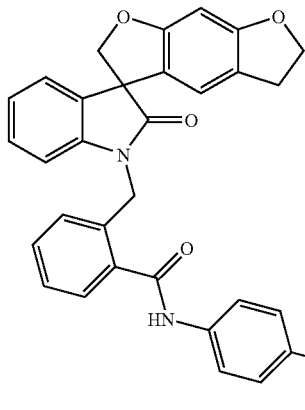

Following the procedure as described in EXAMPLE 12 and making non-critical variations using 4-ethylaniline to replace cyclohexanemethylamine, and 2-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(4-ethylphenyl)-2-[(2'-oxo-5,6-dihydrospiro[benzo[1,2-b:5,4-b']difuran-3,3'-indol]-1'(2'H)-yl)methyl]benzamide was obtained (87%) as a colorless solid: mp>230° C.; $^1$H NMR (300 MHz, DMSO-$d_6$) δ10.50 (s, 1H), 7.68-7.55 (m, 3H), 7.49-7.35 (m, 2H), 7.23-7.10 (m, 5H), 6.99 (dd, J=7.5, 7.5 Hz, 1H), 6.88 (d, J=7.8 Hz, 1H), 6.51 (s, 1H), 6.39 (s, 1H), 5.15-4.99 (m, 2H), 4.83 (d, J=8.9 Hz, 1H), 4.68 (d, J=8.9 Hz, 1H), 4.46 (t, J=8.7 Hz, 2H), 2.99-2.85 (m, 2H), 2.54 (q, J=7.5 Hz, 2H), 1.14 (t, J=7.5 Hz, 3H); $^{13}$C NMR (75 MHz, DMSO-$d_6$) δ177.8, 167.4, 161.6, 161.2, 142.8, 139.7, 137.2, 136.7, 134.4, 132.7, 130.8, 129.1, 129.3, 127.8, 127.1, 124.1, 123.6, 120.9, 120.4, 120.3, 119.6, 109.7, 92.9, 80.4, 72.6, 57.4, 41.5, 28.8, 28.1, 16.3; MS (ES+) m/z 517.2 (M+1).

EXAMPLE 12.9

Synthesis of N-(2-ethylphenyl)-2-[(2'-oxo-5,6-dihydrospiro[benzo[1,2-b:5,4-b']difuran-3,3'-indol]-1'(2'H)-yl)methyl]benzamide

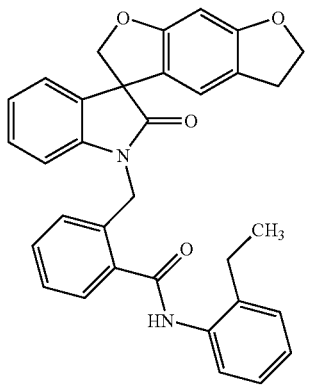

Following the procedure as described in EXAMPLE 12 and making non-critical variations using 2-ethylaniline to replace cyclohexanemethylamine, and 2-[(2'-oxo-5,6-dihydrospiro[benzo[1,2-b:5,4-b']difuran-3,3'-indol]-1'(2'H)-yl)methyl]benzoic acid to replace 3-[4(2'-oxo-5,6-dihydrospiro[benzo[1,2-b:5,4-b']difuran-3,3'-indol]-1'(2'H)-yl)methyl]benzoic acid, N-(2-ethylphenyl)-2-[(2'-oxo-5,6-dihydrospiro[benzo[1,2-b:5,4-b']difuran-3,3'-indol]-1'(2'H)-yl)methyl]benzamide was obtained (95%) as a colorless solid: mp 184-186° C.; $^1$H NMR (300 MHz, DMSO-$d_6$) δ10.06 (s, 1H), 7.69-7.61 (m, 1H), 7.50-7.34 (m, 3H), 7.31-7.13 (m, 6H), 7.01 (dd, J=7.5, 7.5 Hz, 1H), 6.90 (d, J=7.8 Hz, 1H), 6.53 (s, 1H), 6.40 (s, 1H), 5.20-5.01 (m, 2H), 4.86 (d, J=8.9 Hz, 1H), 4.72 (d, J=8.9 Hz, 1H), 4.47 (t, J=8.7 Hz, 2H), 2.93 (t, J=8.7 Hz, 2H), 2.68 (q, J=7.5 Hz, 2H), 1.16 (t, J=7.5 Hz, 3H); $^{13}$C NMR (75 MHz, DMSO-$d_6$) δ 177.9, 168.1, 161.6, 161.2, 142.8, 139.8, 136.4, 135.8, 134.5, 132.7, 130.8, 129.1, 129.0, 128.3, 127.9, 127.8, 127.0, 126.9, 126.5, 124.2, 123.6, 120.9, 120.4, 119.6, 109.7, 92.9, 80.4, 72.6, 57.5, 41.4, 28.8, 24.5, 14.8; MS (ES+) m/z 517.2 (M+1).

EXAMPLE 12.10

Synthesis of N-(2,4-dimethylphenyl)-2-[(2'-oxo-5,6-dihydrospiro[benzo[1,2-b:5,4-b']difuran-3,3'-indol]-1'(2'H)-yl)methyl]benzamide

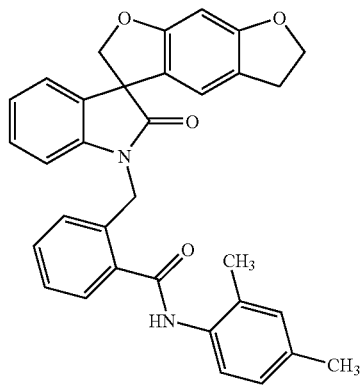

Following the procedure as described in EXAMPLE 12 and making non-critical variations using 2,4-dimethylaniline to replace cyclohexanemethylamine, and 2-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(2,4-dimethylphenyl)-2-[(2'-oxo-5,6-dihydrospiro[benzo[1,2-b:5,4-b']difuran-3,3'-indol]-1'(2'H)-yl)methyl]benzamide was obtained (90%) as a colorless solid: mp 207-208° C.; $^1$H NMR (300 MHz, DMSO-$d_6$) δ9.95 (s, 1H), 7.69-7.61 (m, 1H), 7.49-7.34 (m, 2H), 7.31-7.13 (m, 4H), 7.09-6.95 (m, 3H), 6.89 (d, J=7.8 Hz, 1H), 6.53 (s, 1H), 6.40 (s, 1H), 5.20-5.01 (m, 2H), 4.86 (d, J=8.9 Hz, 1H), 4.71 (d, J=8.9 Hz, 1H), 4.47 (t, J=8.7 Hz, 2H), 2.93 (t, J=8.7 Hz, 2H), 2.25 (s, 6H); $^{13}$C NMR (75 MHz, DMSO-$d_6$) δ177.9, 167.7, 161.6, 161.2, 142.8, 136.6, 135.6, 134.4, 133.9, 133.5, 132.7, 131.3, 130.8, 129.1, 128.4, 127.8, 126.9, 126.7, 124.2, 123.6, 120.9, 120.4, 119.6, 109.7, 92.9, 80.4, 72.6, 65.4, 57.5, 41.4, 28.8, 21.0, 18.4, 15.6; MS (ES+) m/z 517.2 (M+1).

EXAMPLE 12.11

Synthesis of N-(2-methoxyphenyl)-2-[(2'-oxo-5,6-dihydrospiro[benzo[1,2-b:5,4-b']difuran-3,3'-indol]-1'(2'H)-yl)methyl]benzamide

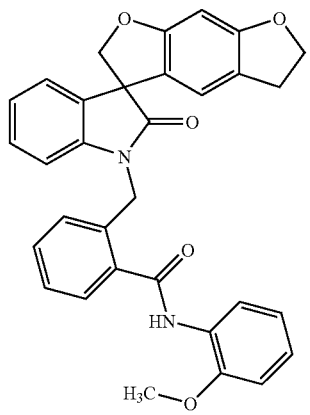

Following the procedure as described in EXAMPLE 12 and making non-critical variations using o-anisidine to replace cyclohexanemethylamine, and 2-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(2-methoxyphenyl)-2-[(2'-oxo-5,6-dihydrospiro[benzo[1,2-b:5,4-b']difuran-3,3'-indol]-1'(2'H)-yl)methyl]benzamide was obtained (84%) as a colorless solid: mp 172-174° C.; $^1$H NMR (300 MHz, DMSO-$d_6$) δ9.66 (s, 1H), 7.78 (d, J=7.6 Hz, 1H), 7.60 (d, J=7.0 Hz, 1H), 7.49-7.32 (m, 2H), 7.24-6.86 (m, 8H), 6.52 (s, 1H), 6.40 (s, 1H), 5.19-5.00 (m, 2H), 4.86 (d, J=9.4 Hz, 1H), 4.70 (d, J=9.4 Hz, 1H), 3.79 (s, 3H), 2.93 (t, J=8.7 Hz, 2H); $^{13}$C NMR (75 MHz, DMSO-$d_6$) δ177.9, 167.6, 161.6, 161.2, 152.1, 142.8, 136.5, 134.4, 132.6, 130.8, 129.1, 128.2, 127.8, 127.1, 126.8, 126.5, 124.9, 124.1, 123.6, 120.9, 120.7, 120.4, 119.6, 112.0, 109.7, 92.9, 80.4, 72.6, 57.4, 56.2, 41.4, 28.8; MS (ES+) m/z 519.2 (M+1).

EXAMPLE 12.12

Synthesis of N-(2-fluorophenyl)-2-[(2'-oxo-5,6-dihydrospiro[benzo[1,2-b:5,4-b']difuran-3,3'-indol]-1'(2'H)-yl)methyl]benzamide

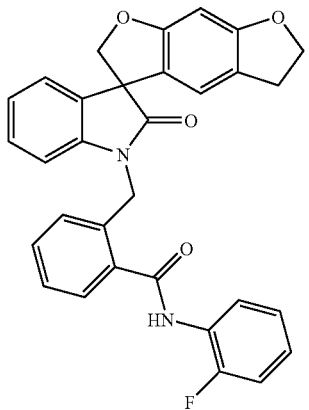

Following the procedure as described in EXAMPLE 12 and making non-critical variations using 2-fluoroaniline to replace cyclohexanemethylamine, and 2-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(2-fluorophenyl)-2-[(2'-oxo-5,6-dihydrospiro[benzo[1,2-b:5,4-b']difuran-3,3'-indol]-1'(2'H)-yl)methyl]benzamide was obtained (57%) as a colorless solid: mp 195-197° C.; $^1$H NMR (300 MHz, DMSO-$d_6$) δ10.37 (s, 1H), 7.75-7.59 (m, 2H), 7.51-7.35 (m, 2H), 7.34-7.11 (m, 6H), 7.00 (dd, J=7.4, 7.4 Hz, 1H), 6.87 (d, J=7.8 Hz, 1H), 6.52 (s, 1H), 6.40 (s, 1H), 5.19-5.00 (m, 2H), 4.85 (d, J=9.4 Hz, 1H), 4.70 (d, J=9.4 Hz, 1H), 4.47 (t, J=8.8 Hz, 2H), 2.93 (t, J=8.8 Hz, 2H); $^{13}$C NMR (75 MHz, DMSO-$d_6$) δ177.8, 161.6, 161.2, 142.8, 135.8, 134.6, 132.7, 131.1, 129.1, 128.6, 127.8, 127.4, 127.3, 127.0, 126.0, 125.8, 124.8, 124.7, 124.2, 123.6, 120.9, 120.4, 119.6, 116.4, 116.2, 109.7, 92.9, 80.5, 72.6, 57.5, 41.4, 28.8; MS (ES+) m/z 529.2 (M+23).

EXAMPLE 12.13

Synthesis of N-(3-chlorophenyl)-2-[(2'-oxo-5,6-dihydrospiro[benzo[1,2-b:5,4-b']difuran-3,3'-indol]-1'(2'H)-yl)methyl]benzamide

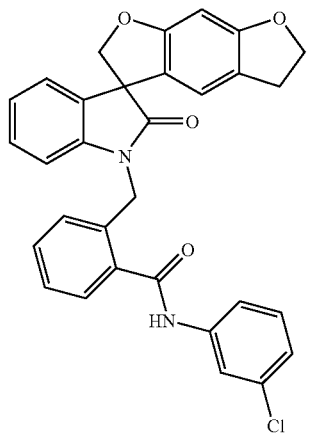

Following the procedure as described in EXAMPLE 12 and making non-critical variations using 3-chloroaniline to replace cyclohexanemethylamine, and 2-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(3-chlorophenyl)-2-[(2'-oxo-5,6-dihydrospiro[benzo[1,2-b:5,4-b']difuran-3,3'-indol]-1'(2'H)-yl)methyl]benzamide was obtained (81%) as a colorless solid: mp>230° C.; $^1$H NMR (300 MHz, DMSO-$d_6$) δ10.71 (s, 1H), 7.96-7.90 (m, 1H), 7.65-7.57 (m, 2H), 7.52-7.31 (m, 3H), 7.26-7.10 (m, 4H), 6.99 (dd, J=7.4, 7.4 Hz, 1H), 6.87 (d, J=7.8 Hz, 1H), 6.50 (s, 1H), 6.38 (s, 1H), 5.16-4.99 (m, 2H), 4.82 (d, J=9.4 Hz, 1H), 4.67 (d, J=9.4 Hz, 1H), 4.46 (t, J=8.8 Hz, 2H), 3.01-2.83 (m, 2H); $^{13}$C NMR (75 MHz, DMSO-$d_6$) δ177.8, 167.8, 161.6, 161.2, 142.8, 140.9, 136.1, 134.5, 133.5, 132.7, 131.1, 130.8, 129.1, 128.5, 127.9, 127.4, 124.1, 123.9, 123.6, 120.9, 120.3, 119.8, 119.6, 118.7, 109.8, 92.9, 80.4, 72.6, 57.4, 41.7, 28.8; MS (ES+) m/z 523.1 (M+1).

EXAMPLE 12.14

Synthesis of N-(3-fluoro-2-methylphenyl)-2-[(2'-oxo-5,6-dihydrospiro[benzo[1,2-b:5,4-b']difuran-3,3'-indol]-1'(2'H)-yl)methyl]benzamide

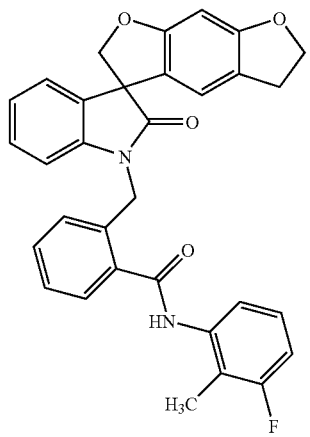

Following the procedure as described in EXAMPLE 12 and making non-critical variations using 3-fluoro-2-methylaniline to replace cyclohexanemethylamine, and 2-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(3-fluoro-2-methylphenyl)-2-[(2'-oxo-5,6-dihydrospiro[benzo[1,2-b:5,4-b']difuran-3,3'-indol]-1'(2'H)-yl)methyl]benzamide was obtained (84%) as a colorless solid: mp>230° C.; $^1$H NMR (300 MHz, DMSO-$d_6$) δ 10.23 (s, 1H), 7.68 (d, J=6.6 Hz, 1H), 7.51-7.37 (m, 2H), 7.33-7.13 (m, 5H), 7.11-6.97 (m, 2H), 6.89 (d, J=7.8 Hz, 1H), 6.58 (s, 1H), 6.39 (s, 1H), 5.16-5.02 (m, 2H), 4.85 (d, J=9.4 Hz, 1H), 4.70 (d, J=9.4 Hz, 1H), 4.47 (t, J=8.8 Hz, 2H), 2.93 (t, J=8.8 Hz, 1H), 2.21-2.14 (m, 3H); $^{13}$C NMR (75 MHz, DMSO-$d_6$) δ177.8, 167.8, 162.8, 161.6, 161.2, 159.6, 142.8, 138.3, 138.2, 136.1, 134.6, 132.7, 131.0, 129.1, 128.5, 127.9, 127.1, 127.0, 126.9, 124.2, 123.6, 122.7, 121.1, 126.9, 120.3, 119.6, 113.0, 112.7, 109.7, 92.9, 80.4, 72.6, 65.4, 57.4, 41.4, 28.8, 15.6, 10.4, 10.3; MS (ES+) m/z 543.1 (M+23).

EXAMPLE 12.15

Synthesis of N-heptyl-2-[(2'-oxo-5,6-dihydrospiro[benzo[1,2-b:5,4-b']difuran-3,3'-indol]-1'(2'H)-yl)methyl]benzamide

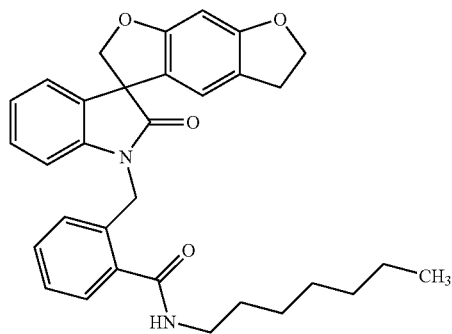

Following the procedure as described in EXAMPLE 12 and making non-critical variations using heptylamine to replace cyclohexanemethylamine, and 2-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-heptyl-2-[(2'-oxo-5,6-dihydrospiro[benzo[1,2-b:5,4-b']difuran-3,3'-indol]-1'(2'H)-yl)methyl]benzamide was obtained (75%) as a colorless solid: mp 196-198° C.; $^1$H NMR (300 MHz, DMSO-$d_6$) δ8.53 (t, J=5.5 Hz, 1H), 7.46-7.27 (m, 3H), 7.23-7.06 (m, 3H), 6.99 (dd, J=7.5, 7.5 Hz, 1H), 6.84 (d, J=7.7 Hz, 1H), 6.51 (s, 1H), 6.40 (s, 1H), 5.10=-4.92 (m, 2H), 4.85 (d, J=9.4 Hz, 1H), 4.71 (d, J=9.4 Hz, 1H), 4.55-4.39 (m, 2H), 3.23 (q, J=6.8 Hz, 2H), 3.03-2.84 (m, 2H), 1.59-1.44 (m, 2H), 1.38-1.14 (m, 8H), 0.81 (t, J=6.6 Hz, 1H); $^{13}$C NMR (75 MHz, DMSO-$d_6$) δ177.8, 168.7, 161.6, 161.2, 142.8, 136.9, 134.1, 132.6, 130.4, 129.1, 128.1, 127.8, 126.8, 124.1, 123.6, 120.9, 120.3, 119.6, 109.6, 92.9, 80.4, 72.6, 57.4, 41.3, 31.7, 29.4, 28.9, 28.8, 26.9, 22.5, 14.4; MS (ES+) m/z 511.2 (M+1).

EXAMPLE 12.16

Synthesis of N-(2-chlorobenzyl)-2-[(2'-oxo-5,6-dihydrospiro[benzo[1,2-b:5,4-b']difuran-3,3'-indol]-1'(2'H)-yl)methyl]benzamide

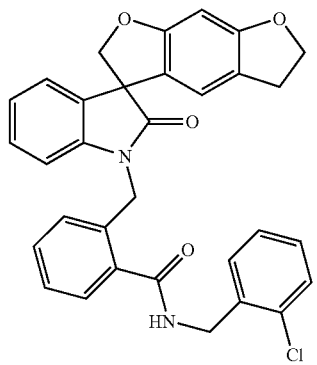

Following the procedure as described in EXAMPLE 12 and making non-critical variations using 2-chlorobenzylamine to replace cyclohexanemethylamine, and 2-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(2-chlorobenzyl)-2-[(2'-oxo-5,6-dihydrospiro[benzo[1,2-b:5,4-b']difuran-3,3'-indol]-1'(2'H)-yl)methyl]benzamide was obtained (88%) as a colorless solid: mp 148-150° C.; $^1$H NMR (300 MHz, DMSO-$d_6$) δ9.12 (t, J=5.8 Hz, 1H), 7.57 (dd, J=7.2, 1.5 Hz, 1H), 7.51-7.24 (m, 6H), 7.23-7.11 (m, 3H), 7.00 (dd, J=7.2, 7.2 Hz, 1H), 6.86 (d, J=7.7 Hz, 1H), 6.52 (s, 1H), 6.40 (s, 1H), 5.15-4.95 (m, 2H), 4.86 (d, J=9.4 Hz, 1H), 4.71 (d, J=9.4 Hz, 1H), 4.57-4.41 (m, 2H), 3.01-2.88 (m, 2H); $^{13}$C NMR (75 MHz, DMSO-$d_6$) δ177.8, 169.0, 161.6, 161.2, 142.8, 136.6, 135.9, 134.6, 132.6, 132.5, 130.8, 129.7, 129.4, 129.2, 129.1, 128.4, 127.7, 127.0, 124.2, 123.6, 120.9, 120.4, 119.6, 109.7, 92.9, 80.4, 72.6, 57.4, 41.4, 41.1, 28.8; MS (ES+) m/z 537.2 (M+1).

EXAMPLE 12.17

Synthesis of 1'-[2-(piperidin-1-ylcarbonyl)benzyl]-5,6-dihydrospiro[benzo[1,2-b:5,4-b']difuran-3,3'-indol]-2'(1'H)-one

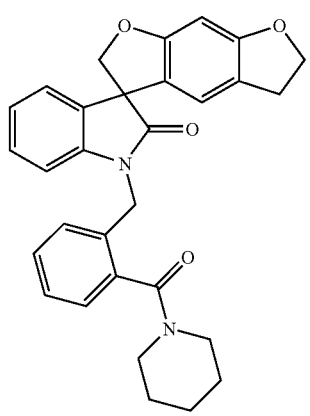

Following the procedure as described in EXAMPLE 12 and making non-critical variations using piperidine to replace cyclohexanemethylamine, and 2-[(2'-oxo-5,6-dihydrospiro

[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, 1'-[2-(piperidin-1-ylcarbonyl)benzyl]-5,6-dihydrospiro[benzo[1,2-b:5,4-b']difuran-3,3'-indol]-2'(1'H)-one was obtained (88%) as a colorless solid: mp 168-170° C.; $^1$H NMR (300 MHz, DMSO-d$_6$) δ7.42-7.10 (m, 6H), 6.99 (dd, J=7.5, 7.5 Hz, 1H), 6.65-6.44 (br, 1H), 6.39 (s, 1H), 4.90-4.64 (m, 4H), 4.54-4.39 (m, 2H), 3.77-3.42 (br, 2H), 3.21-3.07 (m, 2H), 2.94 (t, J=8.2, 1.5 Hz, 1H), 1.66-1.33 (m, 6H); $^{13}$C NMR (75 MHz, DMSO-d$_6$) δ177.7, 167.9, 161.6, 161.2, 142.7, 136.4, 132.6, 129.6, 129.1, 128.1, 126.6, 124.1, 123.5, 120.9, 120.3, 109.8, 92.9, 80.5, 72.6, 65.4, 57.4, 47.9, 42.3, 41.4, 28.8, 26.4, 25.7, 24.4, 15.6; MS (ES+) m/z 481.2 (M+1).

EXAMPLE 12.18

Synthesis of N-butyl-2-[(2'-oxo-5,6-dihydrospiro[benzo[1,2-b:5,4-b']difuran-3,3'-indol]-1'(2'H)-yl)methyl]benzamide

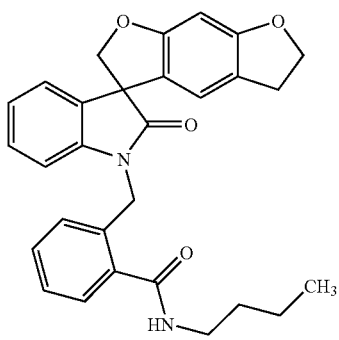

Following the procedure as described in EXAMPLE 12 and making non-critical variations using butylamine to replace cyclohexanemethylamine, and 2-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-butyl-2-[(2'-oxo-5,6-dihydrospiro[benzo[1,2-b:5,4-b']difuran-3,3'-indol]-1'(2'H)-yl)methyl]benzamide was obtained (77%) as a colorless solid: mp 176-178° C.; $^1$H NMR (300 MHz, CDCl$_3$) δ7.48-7.41 (m, 1H), 7.37-7.14 (m, 6H), 7.09-6.99 (m, 3H), 6.55-6.37 (m, 3H), 5.25-5.07 (m, 2H), 4.94 (d, J=9.0 Hz, 1H), 4.70 (d, J=9.0 Hz, 1H), 4.52 (t, J=8.2 Hz, 2H), 3.47 (q, J=6.6 Hz, 2H), 2.98 (t, J=8.7 Hz, 2H), 1.67-1.55 (m, 2H), 1.50-1.35 (m, 2H), 0.95 (t, J=6.6 Hz, 1H); MS (ES+) m/z 491.1 (M+23).

EXAMPLE 12.19

Synthesis of N-(3-methylphenyl)-2-[(2'-oxo-5,6-dihydrospiro[benzo[1,2-b:5,4-b']difuran-3,3'-indol]-1'(2'H)-yl)methyl]benzamide

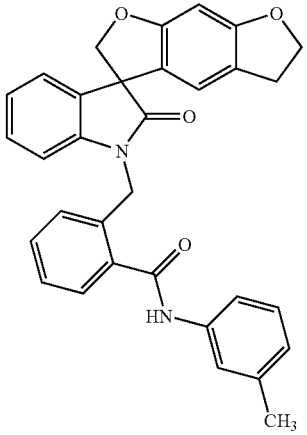

Following the procedure as described in EXAMPLE 12 and making non-critical variations using m-toluidine to replace cyclohexanemethylamine, and 2-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(3-methylphenyl)-2-[(2'-oxo-5,6-dihydrospiro[benzo[1,2-b:5,4-b']difuran-3,3'-indol]-1'(2'H)-yl)methyl]benzamide was obtained (81%) as a colorless solid: mp 229-231° C.; $^1$H NMR (300 MHz, CDCl$_3$) δ8.85 (s, 1H), 7.64-7.55 (m, 2H), 7.49-7.42 (m, 1H), 7.40-7.33 (m, 2H), 7.32-7.16 (m, 4H), 7.11-7.03 (m, 2H), 6.96 (d, J=7.6 Hz, 1H), 6.40 (s, 2H), 5.22-5.05 (m, 2H), 4.93 (d, J=9.0 Hz, 1H), 4.67 (d, J=9.0 Hz, 1H), 4.52 (t, J=8.7 Hz, 2H), 2.96 (t, J=8.5 Hz, 2H), 2.35 (s, 3H); MS (ES+) m/z 525.11 (M+23).

EXAMPLE 12.20

Synthesis of N-(2-fluoro-5-methylphenyl)-2-[(2'-oxo-5,6-dihydrospiro[benzo[1,2-b:5,4-b']difuran-3,3'-indol]-1'(2'H)-yl)methyl]benzamide

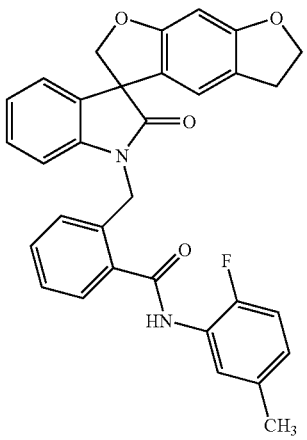

Following the procedure as described in EXAMPLE 12 and making non-critical variations using 2-fluoro-5-methylaniline to replace cyclohexanemethylamine, and 2-[(2'-oxo- 5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(2-fluoro-5-methylphenyl)-2-[(2'-oxo-5,6-dihydrospiro[benzo[1,2-b:5,4-b']difuran-3,3'-indol]-1'(2'H)-yl)methyl]benzamide was obtained (77%) as a colorless solid: mp 214-216° C.; $^1$H NMR (300 MHz, CDCl$_3$) δ 8.25-8.06 (m, 2H), 7.65-7.57 (m, 1H), 7.47-7.33 (m, 2H), 7.33-7.26 (m, 1H), 7.22-7.12 (m, 2H), 7.07-6.86 (m, 4H), 6.46 (s, 1H), 6.40 (s, 1H), 5.27 (s, 2H), 4.95 (d, J=9.0 Hz, 1H), 4.68 (d, J=9.0 Hz, 1H), 4.52 (t, J=8.7 Hz, 2H), 2.96 (t, J=8.5 Hz, 2H), 2.36 (s, 3H); MS (ES+) m/z 543.1 (M+23).

EXAMPLE 12.21

Synthesis of N-(2,3-dimethylphenyl)-2-[(2'-oxo-5,6-dihydrospiro[benzo[1,2-b:5,4-b']difuran-3,3'-indol]-1'(2'H)-yl)methyl]benzamide

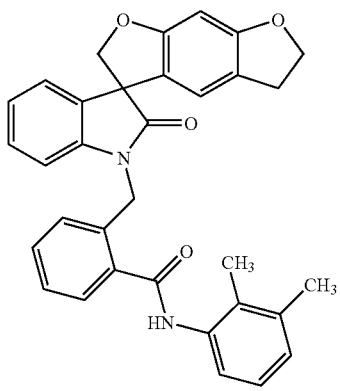

Following the procedure as described in EXAMPLE 12 and making non-critical variations using 2,3-dimethylaniline to replace cyclohexanemethylamine, and 2-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(2,3-dimethylphenyl)-2-[(2'-oxo-5,6-dihydrospiro[benzo[1,2-b:5,4-b']difuran-3,3'-indol]-1'(2'H)-yl)methyl]benzamide was obtained (87%) as a colorless solid: mp>230° C.; $^1$H NMR (300 MHz, CDCl$_3$) δ7.98 (s, 1H), 7.69-7.53 (m, 2H), 7.46-7.33 (m, 2H), 7.33-7.11 (m, 6H), 7.11-6.99 (m, 3H), 6.45 (s, 1H), 6.40 (s, 1H), 5.34-5.17 (m, 2H), 4.93 (d, J=9.0 Hz, 1H), 4.68 (d, J=9.0 Hz, 1H), 4.52 (t, J=8.7 Hz, 2H), 2.96 (t, J=8.5 Hz, 2H), 2.32 (s, 3H), 2.22 (s, 3H); MS (ES+) m/z 539.1 (M+23).

EXAMPLE 12.22

Synthesis of N-[2-(4-methoxyphenyl)ethyl]-2-[(2'-oxo-5,6-dihydrospiro[benzo[1,2-b:5,4-b']difuran-3,3'-indol]-1'(2'H)-yl)methyl]benzamide

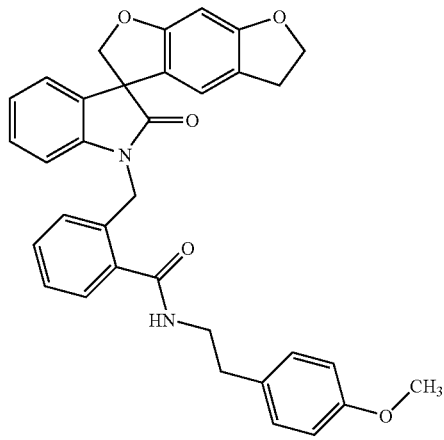

Following the procedure as described in EXAMPLE 12 and making non-critical variations using 2-(4-methoxyphenyl)ethylamine to replace cyclohexanemethylamine, and 2-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-[2-(4-methoxyphenyl)ethyl]-2-[(2'-oxo-5,6-dihydrospiro[benzo[1,2-b:5,4-b']difuran-3,3'-indol]-1'(2'H)-yl)methyl]benzamide was obtained (85%) as a colorless solid: $^1$H NMR (300 MHz, CDCl$_3$) δ7.39-7.13 (m, 8H), 7.08-6.95 (m, 2H), 6.86-6.78 (m, 2H), 6.52-6.39 (m, 3H), 5.10-4.90 (m, 3H), 4.70 (d, J=9.0 Hz, 1H), 3.81-3.62 (m, 5H), 2.98 (t, J=8.7 Hz, 2H), 2.90 (t, J=8.7 Hz, 2H); MS (ES+) m/z 569.2 (M+23).

EXAMPLE 12.23

Synthesis of N-(3-chlorobenzyl)-2-[(2'-oxo-5,6-dihydrospiro[benzo[1,2-b:5,4-b']difuran-3,3'-indol]-1'(2'H)-yl)methyl]benzamide

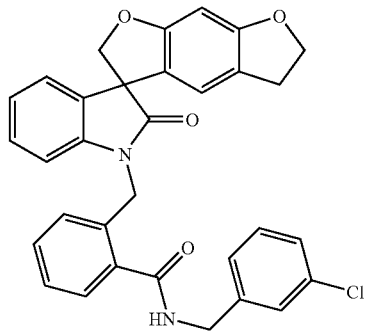

Following the procedure as described in EXAMPLE 12 and making non-critical variations using 3-chlorobenzylamine to replace cyclohexanemethylamine, and 2-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(3-chlorobenzyl)-2-[(2'-oxo-5,6-dihydrospiro[benzo[1,2-b:5,4-b']difuran-3,3'-indol]-1'(2'H)-yl)methyl]benzamide was obtained (84%) as a colorless solid: ¹H NMR (300 MHz, CDCl₃) δ 7.52-7.47 (m, 1H), 7.39-7.15 (m, 9H), 7.09-7.00 (m, 3H), 6.44 (s, 1H), 6.40 (s, 1H), 5.21-5.06 (m, 2H), 4.93 (d, J=9.0 Hz, 1H), 4.69 (d, J=9.0 Hz, 1H), 4.62 (d, J=5.9 Hz, 2H), 4.52 (t, J=8.6 Hz, 2H), 2.95 (t, J=8.6 Hz, 2H); MS (ES+) m/z 559.1 (M+23).

EXAMPLE 12.24

Synthesis of N-[2-(4-chlorophenyl)ethyl]-2-[(2'-oxo-5,6-dihydrospiro[benzo[1,2-b:5,4-b']difuran-3,3'-indol]-1'(2'H)-yl)methyl]benzamide

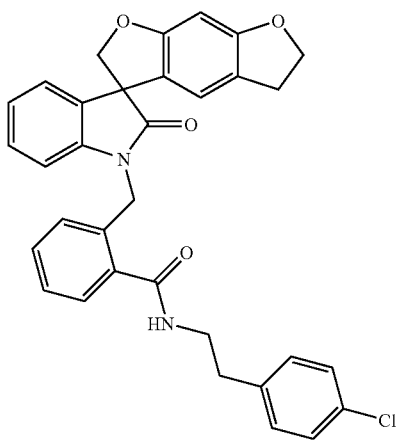

Following the procedure as described in EXAMPLE 12 and making non-critical variations using 2-(4-chlorophenyl)ethylamine to replace cyclohexanemethylamine, and 2-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-[2-(4-chlorophenyl)ethyl]-2-[(2'-oxo-5,6-dihydrospiro[benzo[1,2-b:5,4-b']difuran-3,3'-indol]-1'(2'H)-yl)methyl]benzamide was obtained (78%) as a colorless solid: ¹H NMR (300 MHz, CDCl₃) δ8.59 (br, 1H), 7.44-7.23 (m, 7H), 7.23-6.11 (m, 2H), 7.10-6.94 (m, 2H), 6.73 (d, J=7.7 Hz, 1H), 6.52 (s, 1H), 6.40 (s, 1H), 4.94-4.65 (m, 4H), 4.47 (t, J=8.6 Hz, 2H), 3.57-3.42 (m, 2H), 2.95 (t, J=8.3 Hz, 2H), 2.84 (t, J=6.7 Hz, 2H); MS (ES+) m/z 573.1 (M+23).

EXAMPLE 12.25

Synthesis of N-(2-methoxyphenyl)-4-[(2'-oxo-5,6-dihydrospiro[benzo[1,2-b:5,4-b']difuran-3,3'-indol]-1'(2'H)-yl)methyl]benzamide

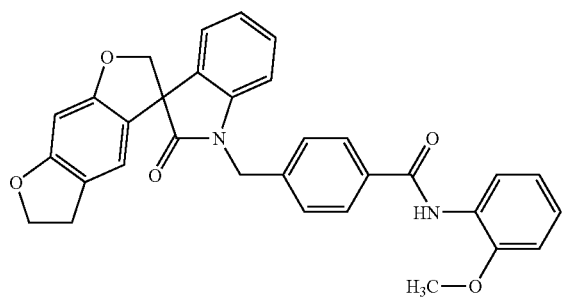

Following the procedure as described in EXAMPLE 12 and making non-critical variations using 2-methoxyaniline to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(2-methoxyphenyl)-4-[(2'-oxo-5,6-dihydrospiro[benzo[1,2-b:5,4-b']difuran-3,3'-indol]-1'(2'H)-yl)methyl]benzamide was obtained (68%) as a colorless solid: ¹H NMR (300 MHz, CDCl₃) δ 8.56-8.43 (m, 2H), 7.87 (d, J=7.9 Hz, 2H), 7.45 (d, J=7.9 Hz, 2H), 7.23-7.15 (m, 2H), 7.11-6.96 (m, 3H), 6.90 (d, J=7.9 Hz, 1H), 6.76 (d, J=7.9 Hz, 1H), 6.48 (s, 1H), 6.42 (s, 1H), 5.01 (ABq, 2H), 4.85 (ABq, 2H), 4.53 (t, J=8.6 Hz, 2H), 3.90 (s, 3H), 3.07-2.92 (m, 2H); ¹³C NMR (75 MHz, CDCl₃) δ178.0, 164.7, 161.9, 161.4, 148.1, 141.8, 139.7, 134.9, 132.7, 128.8, 127.8, 127.7, 127.6, 124.1, 124.0, 123.7, 121.2, 120.1, 120.0, 119.8, 118.9, 109.9, 109.1, 93.4, 93.3, 80.7, 72.4, 57.8, 55.8, 43.9, 29.1; MS (ES+) m/z 519.1 (M+1).

EXAMPLE 12.26

Synthesis of 4-[(2'-oxo-5,6-dihydrospiro[benzo[1,2-b:5,4-b']difuran-3,3'-indol]-1'(2'H)-yl)methyl]-N-[2-(trifluoromethyl)phenyl]benzamide

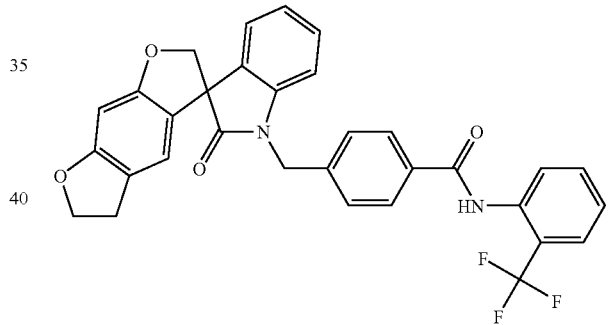

Following the procedure as described in EXAMPLE 12 and making non-critical variations using 2-(trifluoromethyl)aniline to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, 4-[(2'-oxo-5,6-dihydrospiro[benzo[1,2-b:5,4-b']difuran-3,3'-indol]-1'(2'H)-yl)methyl]-N-[2-(trifluoromethyl)phenyl]benzamide was obtained (53%) as a colorless solid: ¹H NMR (300 MHz, CDCl₃) δ8.39 (d, J=8.2 Hz, 1H), 8.17 (s, 1H), 7.85 (d, J=8.2 Hz, 2H), 7.62 (dd, J=15.9, 7.9 Hz, 2H), 7.48 (d, J=8.2 Hz, 2H), 7.31-7.14 (m, 4H), 7.04 (dd, J=7.6, 7.6, 0.7 Hz, 1H), 6.76 (d, J=7.7 Hz, 1H), 6.47 (s, 1H), 6.43 (s, 1H), 5.02 (ABq, 2H), 4.85 (ABq, 2H), 4.54 (t, J=8.7 Hz, 2H), 3.10-2.90 (m, 2H); ¹³C NMR (75 MHz, CDCl₃) δ178.0, 164.9, 161.9, 161.3, 142.6, 141.7, 140.4, 133.8, 133.1, 132.7, 128.8, 128.0, 127.7, 126.2, 124.6, 124.1 (2C), 123.7, 120.0, 118.8, 109.0, 93.3, 80.6, 72.4, 57.7, 43.8, 29.0; MS (ES+) m/z 557.1 (M+1).

EXAMPLE 12.27

Synthesis of 4-[(2'-oxo-5,6-dihydrospiro[benzo[1,2-b:5,4-b']difuran-3,3'-indol]-1'(2'H)-yl)methyl]-N-phenylbenzamide

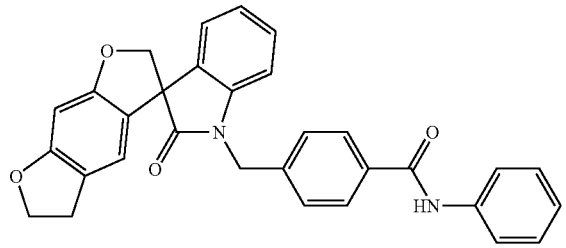

Following the procedure as described in EXAMPLE 12 and making non-critical variations using aniline to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, 4-[(2'-oxo-5,6-dihydrospiro[benzo[1,2-b:5,4-b']difuran-3,3'-indol]-1'(2'H)-yl)methyl]-N-phenylbenzamide was obtained (90%) as a colorless solid: $^1$H NMR (300 MHz, CDCl$_3$) δ8.34 (s, 1H), 7.83 (d, J=7.8 Hz, 2H), 7.60 (d, J=8.3 Hz, 2H), 7.39-7.23 (m, 4H), 7.23-6.97 (m, 4H), 6.72 (d, J=7.7 Hz, 1H), 6.44 (s, 1H), 6.38 (s, 1H), 4.92 (ABq, 2H), 4.77 (ABq, 2H), 4.48 (t, J=8.5 Hz, 2H), 2.89 (t, J=8.5 Hz, 2H); $^{13}$C NMR (75 MHz, CDCl$_3$) δ178.1, 165.2, 161.8, 161.3, 141.6, 139.4, 137.9, 134.6, 132.4, 128.8, 128.7, 127.8, 127.4, 124.4, 123.9, 123.7, 120.2, 119.9, 119.7, 118.7, 109.1, 93.2, 80.4, 72.3, 57.7, 43.7, 28.8; MS (ES+) m/z 489.1 (M+1).

EXAMPLE 12.28

Synthesis of N-methyl-4-[(2'-oxo-5,6-dihydrospiro[benzo[1,2-b:5,4-b']difuran-3,3'-indol]-1'(2'H)-yl)methyl]benzamide

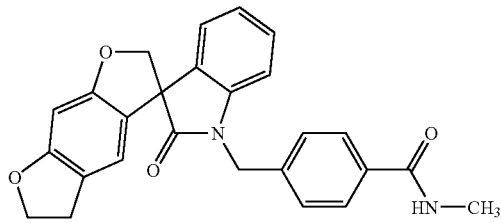

Following the procedure as described in EXAMPLE 12 and making non-critical variations using methylamine hydrochloride to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-methyl-4-[(2'-oxo-5,6-dihydrospiro[benzo[1,2-b:5,4-b']difuran-3,3'-indol]-1'(2'H)-yl)methyl]benzamide was obtained (86%) as a colorless solid: $^1$H NMR (300 MHz, CDCl$_3$) δ7.71 (d, J=8.0 Hz, 2H), 7.34 (d, J=8.0 Hz, 2H), 7.22-7.12 (m, 2H), 7.02 (t, J=7.6 Hz, 1H), 6.73 (d, J=7.6 Hz, 1H), 6.57-6.45 (m, 1H), 6.42 (s, 1H), 6.39 (s, 1H), 4.95 (ABq, 2H), 4.81 (ABq, 2H), 4.53-4.34 (m, 2H), 2.95 (d, J=4.0 Hz, 3H), 2.90-2.73 (m, 2H); $^{13}$C NMR (75 MHz, CDCl$_3$) δ178.2, 167.5, 161.9, 161.4, 141.8, 139.0, 134.2, 132.5, 128.8, 127.6, 127.4, 124.0, 123.7, 120.0, 119.8, 118.7, 109.2, 93.3, 80.6, 72.4, 57.7, 43.8, 28.9, 26.8; MS (ES+) m/z 427.1 (M+1).

EXAMPLE 12.29

Synthesis of N-(2-fluorophenyl)-4-[(2'-oxo-5,6-dihydrospiro[benzo[1,2-b:5,4-b']difuran-3,3'-indol]-1'(2'H)-yl)methyl]benzamide

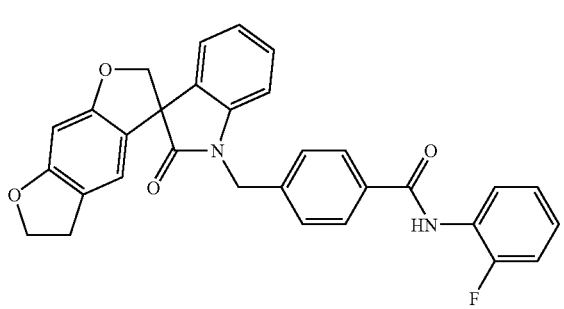

Following the procedure as described in EXAMPLE 12 and making non-critical variations using 2-fluoroaniline to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(2-fluorophenyl)-4-[(2'-oxo-5,6-dihydrospiro[benzo[1,2-b:5,4-b']difuran-3,3'-indol]-1'(2'H)-yl)methyl]benzamide was obtained (75%) as a colorless solid: $^1$H NMR (300 MHz, CDCl$_3$) δ8.42 (ddd, J=8.1, 8.1, 1.2 Hz, 1H), 8.16-7.99 (m, 1H), 7.88 (d, J=8.1 Hz, 2H), 7.47 (d, J=8.1 Hz, 2H), 7.25-7.01 (m, 6H), 6.77 (d, J=7.7 Hz, 1H), 6.49 (s, 1H), 6.43 (s, 1H), 5.03 (ABq, 2H), 4.86 (ABq, 2H), 4.55 (t, J=8.6 Hz, 2H), 3.10-2.91 (m, 2H); $^{13}$C NMR (75 MHz, CDCl$_3$) δ177.9, 164.8, 161.8, 161.3, 152.7 (d, J=243.1 Hz), 141.7, 140.1, 134.0, 132.6, 128.7, 127.7 (2C), 126.3 (d, J=9.8 Hz, 2C), 124.7, 124.6 (d, J=3.9 Hz), 124.0, 123.6, 121.8, 119.9 (2C), 118.7, 114.8 (d, J=19.2 Hz, 2C), 109.0, 93.2, 80.6, 72.3, 57.7, 43.7, 29.0; MS (ES+) m/z 507.1 (M+1).

EXAMPLE 12.30

Synthesis of 4-[(2'-oxo-5,6-dihydrospiro[benzo[1,2-b:5,4-b']difuran-3,3'-indol]-1'(2'H)-yl)methyl]-N-(2-thiophen-2-ylethyl)benzamide

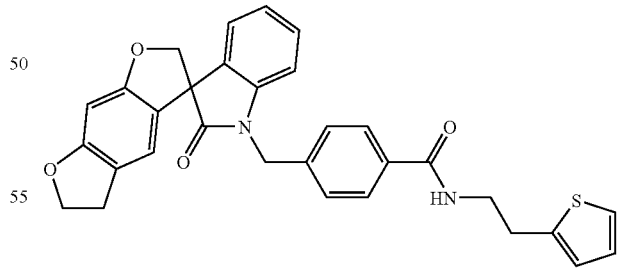

Following the procedure as described in EXAMPLE 12 and making non-critical variations using 2-thiopheneethylamine to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, 4-[(2'-oxo-5,6-dihydrospiro[benzo[1,2-b:5,4-b']difuran-3,3'-indol]-1'(2'H)-yl)methyl]-N-(2-thiophen-2-ylethyl)benzamide was obtained (74%) as a colorless solid: $^1$H NMR (300 MHz, CDCl$_3$) δ7.71 (d, J=7.9 Hz, 2H), 7.37 (d, J=7.9 Hz, 2H), 7.24-7.13 (m, 3H), 7.04 (dd, J=7.5, 7.5 Hz, 1H), 6.95 (dd, J=5.0, 3.5 Hz, 1H), 6.86 (d, J=3.5 Hz, 1H), 6.74 (d, J=7.6 Hz, 1H), 6.51-6.46 (m, 1H), 6.46 (s, 1H), 6.42 (s, 1H), 4.97 (ABq, 2H), 4.83 (ABq, 2H), 4.52 (t, J=8.6 Hz, 2H), 3.78-3.57 (m, 2H), 3.13 (t, J=6.2 Hz, 2H), 2.95 (t, J=8.6 Hz, 2H); $^{13}$C NMR (75 MHz, CDCl$_3$) δ 177.9, 166.8, 161.8, 161.3, 141.7, 141.1, 139.2, 134.1, 132.5, 128.7, 127.5, 127.4, 127.0, 125.4, 123.9 (2C), 123.6, 119.9 (2C), 118.7, 109.0, 93.2, 80.5, 72.3, 57.6, 43.7, 41.2, 29.8, 28.9; MS (ES+) m/z 523.1 (M+1).

EXAMPLE 12.31

Synthesis of 4-[(2'-oxo-5,6-dihydrospiro[benzo[1,2-b:5,4-b']difuran-3,3'-indol]-1'(2'H)-yl)methyl]benzamide

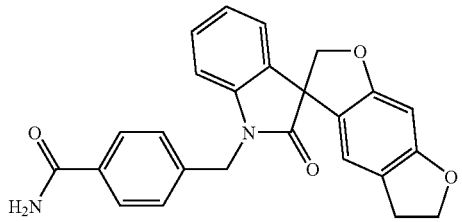

Following the procedure as described in EXAMPLE 12 and making non-critical variations using ammonia in dry dichloromethane to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, 4-[(2'-oxo-5,6-dihydrospiro[benzo[1,2-b:5,4-b']difuran-3,3'-indol]-1'(2'H)-yl)methyl]benzamide was obtained (81%) as a colorless solid: $^1$H NMR (300 MHz, CDCl$_3$) δ7.78 (d, J=7.9 Hz, 2H), 7.34 (d, J=7.9 Hz, 2H), 7.20-7.07 (m, 2H), 6.99 (t, J=7.4 Hz, 1H), 6.85 (s, 1H), 6.71 (d, J=7.6 Hz, 1H), 6.41 (br s, 1H), 6.35 (br s, 1H), 6.20 (s, 1H), 4.94 (ABq, 2H), 4.78 (ABq, 2H), 4.46 (t, J=8.5 Hz, 2H), 2.91 (t, J=8.5 Hz, 2H); $^{13}$C NMR (75 MHz, CDCl$_3$) δ177.6, 168.7, 161.5, 160.9, 141.4, 139.3, 132.7, 132.1, 128.4, 127.8, 127.0, 123.6, 123.3, 119.6, 118.4, 108.8, 92.8, 80.2, 72.0, 57.3, 43.4, 28.6; MS (ES+) m/z 413.1 (M+1).

EXAMPLE 12.32

Synthesis of N-(2,3-dihydro-1H-inden-5-yl)-4-[(2'-oxo-5,6-dihydrospiro[benzo[1,2-b:5,4-b']difuran-3,3'-indol]-1'(2'H)-yl)methyl]benzamide

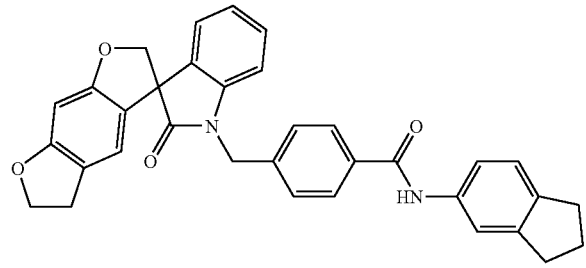

Following the procedure as described in EXAMPLE 12 and making non-critical variations using 5-aminoindan to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(2,3-dihydro-1H-inden-5-yl)-4-[(2'-oxo-5,6-dihydrospiro[benzo[1,2-b:5,4-b']difuran-3,3'-indol]-1'(2'H)-yl)methyl]benzamide was obtained (65%) as a colorless solid: $^1$H NMR (300 MHz, CDCl$_3$) δ7.83 (d, J=8.1 Hz, 2H), 7.79 (s, 1H), 7.56 (s, 1H), 7.42 (d, J=8.1 Hz, 2H), 7.28-7.21 (m, 2H), 7.21-7.14 (m, 2H), 7.08-6.97 (m, 1H), 6.74 (d, J=7.7 Hz, 1H), 6.46 (s, 1H), 6.42 (s, 1H), 4.99 (ABq, 2H), 4.83 (ABq, 2H), 4.53 (t, J=8.6 Hz, 2H), 3.03-2.80 (m, 6H), 2.15-1.97 (m, 2H); MS (ES+) m/z 529.1 (M+1).

EXAMPLE 12.33

Synthesis of 1'-[4(morpholin-4-ylcarbonyl)benzyl]-5,6-dihydrospiro[benzo[1,2-b:5,4-b']difuran-3,3'-indol]-2'(1'H)-one

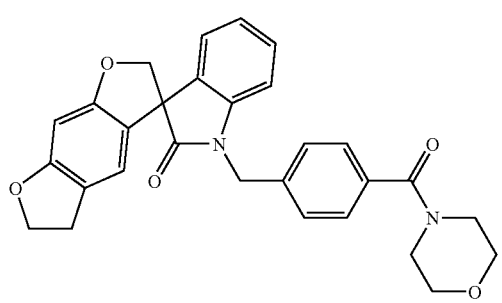

Following the procedure as described in EXAMPLE 12 and making non-critical variations using morpholine to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, 1'-[4-(morpholin-4-ylcarbonyl)benzyl]-5,6-dihydrospiro[benzo[1,2-b:5,4-b']difuran-3,3'-indol]-2'(1'H)-one was obtained (58%) as a colorless solid: $^1$H NMR (300 MHz, CDCl$_3$) δ7.44-7.35 (m, 4H), 7.24-7.15 (m, 2H), 7.04 (dd, J=7.5, 7.5 Hz, 1H), 6.76 (d, J=7.5 Hz, 1H), 6.48 (s, 1H), 6.44 (s, 1H), 4.98 (ABq, 2H), 4.85 (ABq, 2H), 4.55 (t, J=8.6 Hz, 2H), 3.87-3.40 (m, 8H), 3.08-2.93 (m, 2H); MS (ES+) m/z 483.1 (M+1).

EXAMPLE 12.34

Synthesis of N-(2-ethylphenyl)-4-[(2'-oxo-5,6-dihydrospiro[benzo[1,2-b:5,4-b']difuran-3,3'-indol]-1'(2'H)-yl)methyl]benzamide

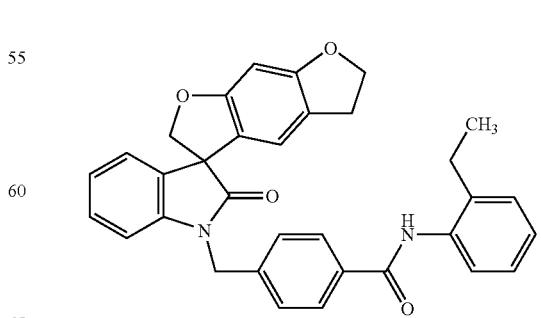

Following the procedure as described in EXAMPLE 12 and making non-critical variations using 2-ethylaniline to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(2-ethylphenyl)-4-[(2'-oxo-5,6-dihydrospiro[benzo[1,2-b:5,4-b']difuran-3,3'-indol]-1'(2'H)-yl)methyl]benzamide was obtained (49%) as a colorless solid: mp 203-204° C.; $^1$H NMR (300 MHz, CDCl$_3$) δ 7.96-7.83 (m, 3H), 7.69 (s, 1H), 7.52-7.44 (m, 2H), 7.31-7.13 (m, 5H), 7.10-7.02 (m, 1H), 6.82-6.74 (m, 1H), 6.49 (s, 1H), 6.44 (s, 1H), 5.03 (ABq, 2H), 4.86 (ABq, 2H), 4.60-4.51 (m, 2H), 3.11-2.92 (m, 2H), 2.67 (q, J=7.5 Hz, 2H), 1.27 (t, J=7.5 Hz, 3H); $^{13}$C NMR (75 MHz, CDCl$_3$) δ 178.0, 165.2, 161.9, 161.3, 141.8, 139.8, 135.1, 134.9, 134.6, 132.7, 128.8, 128.6, 127.8, 127.7, 126.8, 125.8, 124.1, 123.7, 120.0, 119.9, 118.8, 109.1, 93.3, 80.6, 72.4, 57.7, 43.8, 29.0, 24.4, 14.0; MS (ES+) m/z 517.2 (M+1).

EXAMPLE 12.35

Synthesis of N-(2,6-dimethylphenyl)-4-[(2'-oxo-5,6-dihydrospiro[benzo[1,2-b:5,4-b']difuran-3,3'-indol]-1'(2'H)-yl)methyl]benzamide

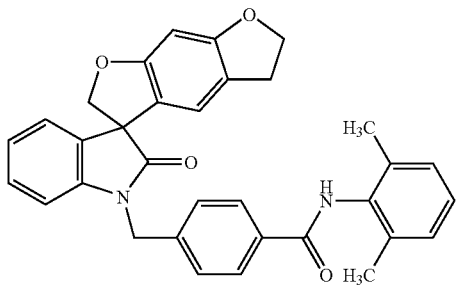

Following the procedure as described in EXAMPLE 12 and making non-critical variations using 2,6-dimethylaniline to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(2,6-dimethylphenyl)-4-[(2'-oxo-5,6-dihydrospiro[benzo[1,2-b:5,4-b']difuran-3,3'-indol]-1'(2'H)-yl)methyl]benzamide was obtained (28%) as a colorless solid: mp>250° C.; $^1$H NMR (300 MHz, CDCl$_3$) δ 7.95-7.89 (m, 2H), 7.51-7.45 (m, 2H), 7.37 (s, 1H), 7.24-7.02 (m, 6H), 6.82-6.75 (m, 1H), 6.49 (s, 1H), 6.44 (s, 1H), 5.04 (ABq, 2H), 4.86 (ABq, 2H), 4.60-4.50 (m, 2H), 3.12-2.91 (m, 2H), 2.27 (s, 6H); $^{13}$C NMR (75 MHz, CDCl$_3$) δ 178.0, 165.3, 161.9, 161.4, 141.8, 139.8, 135.5, 134.1, 133.6, 132.7, 128.8, 128.3, 127.9, 127.8, 127.6, 124.0, 123.7, 120.0, 118.8, 109.1, 93.3, 80.7, 72.4, 57.8, 43.8, 29.0, 18.5; MS (ES+) m/z 517.2 (M+1).

EXAMPLE 12.36

Synthesis of N-(3-fluorophenyl)-4-[(2'-oxo-5,6-dihydrospiro[benzo[1,2-b:5,4-b']difuran-3,3'-indol]-1'(2'H)-yl)methyl]benzamide

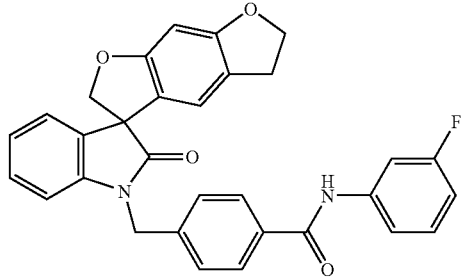

Following the procedure as described in EXAMPLE 12 and making non-critical variations using 3-fluoroaniline to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(3-fluorophenyl)-4-[(2'-oxo-5,6-dihydrospiro[benzo[1,2-b:5,4-b']difuran-3,3'-indol]-1'(2'H)-yl)methyl]benzamide was obtained (50%) as a colorless solid: mp>250° C.; $^1$H NMR (300 MHz, CDCl$_3$) δ 8.03 (s, 1H), 7.89-7.82 (m, 2H), 7.63-7.56 (m, 1H), 7.48-7.41 (m, 2H), 7.34-7.15 (m, 4H), 7.09-7.01 (m, 1H), 6.89-6.80 (m, 1H), 6.78-6.72 (m, 1H), 6.47 (s, 1H), 6.42 (s, 1H), 5.01 (ABq, 2H), 4.82 (ABq, 2H), 4.57-4.48 (m, 2H), 3.01-2.92 (m, 2H); $^{13}$C NMR (75 MHz, CDCl$_3$) δ 178.3, 163.6 (d, $J_{C-F}$=248.0 Hz), 161.4, 141.7, 139.7, 139.5 (d, $J_{C-F}$=10.8 Hz), 134.3, 132.4, 130.0 (d, $J_{C-F}$=9.4 Hz), 128.8, 127.9, 127.6, 124.1, 123.8, 120.0, 119.7, 118.7, 115.4 (d, $J_{C-F}$=2.9 Hz), 111.2 (d, $J_{C-F}$=21.3 Hz), 109.2, 107.6 (d, $J_{C-F}$=26.4 Hz), 93.3, 80.5, 72.4, 57.8, 43.8, 28.9; MS (ES+) m/z 507.2 (M+1).

EXAMPLE 12.37

Synthesis of N-(2,4-dimethylphenyl)-4-[(2'-oxo-5,6-dihydrospiro[benzo[1,2-b:5,4-b']difuran-3,3'-indol]-1'(2'H)-yl)methyl]benzamide

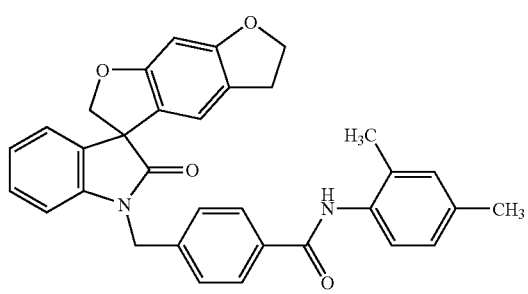

Following the procedure as described in EXAMPLE 12 and making non-critical variations using 2,4-dimethylaniline to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(2,4-dimethylphenyl)-4-[(2'-oxo-5,6-dihydrospiro[benzo[1,2-b:5,4-b']difuran-3,3'-indol]-1'(2'H)-yl)methyl]benzamide was obtained (59%) as a colorless solid: mp 249-251° C.; $^1$H NMR (300 MHz, CDCl$_3$) δ7.91-7.83 (m, 2H), 7.76-7.69 (m, 1H), 7.56 (s, 1H), 7.50-7.43 (m, 2H), 7.28-7.17 (m, 2H), 7.09-7.01 (m, 3H), 6.80-6.74 (m, 1H), 6.49 (s, 1H), 6.44 (s, 1H), 5.03 (ABq, 2H), 4.86 (ABq, 2H), 4.60-4.51 (m, 2H), 3.11-2.92 (m, 2H), 2.32 (s, 3H), 2.28 (s, 3H); $^{13}$C NMR (75 MHz, CDCl$_3$) δ 178.0, 165.2, 161.9, 161.3, 141.7, 139.6, 135.3, 134.6, 132.9, 132.6, 131.2, 129.8, 128.7, 127.7, 127.4, 124.0, 123.6 (2C), 120.0 (2C), 118.8, 109.1, 93.3, 80.6, 72.4, 57.7, 43.8, 29.0, 20.9, 17.8; MS (ES+) m/z 517.2 (M+1).

EXAMPLE 12.38

Synthesis of 4-[(2'-oxo-5,6-dihydrospiro[benzo[1,2-b:5,4-b']difuran-3,3'-indol]-1'(2'H)-yl)methyl]-N-(thiophen-2-ylmethyl)benzamide

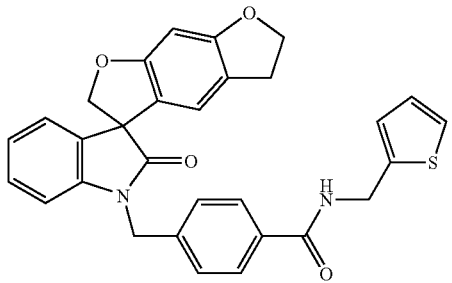

Following the procedure as described in EXAMPLE 12 and making non-critical variations using 2-thiophenemethylamine to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, 4-[(2'-oxo-5,6-dihydrospiro[benzo[1,2-b:5,4-b']difuran-3,3'-indol]-1'(2'H)-yl)methyl]-N-(thiophen-2-ylmethyl)benzamide was obtained (48%) as a colorless solid: mp 167-168° C.; $^1$H NMR (300 MHz, CDCl$_3$) δ7.81-7.73 (m, 2H), 7.43-7.37 (m, 2H), 7.27-7.16 (m, 3H), 7.07-7.00 (m, 2H), 6.99-6.95 (m, 1H), 6.75-6.70 (m, 1H), 6.48-6.40 (m, 3H), 4.99 (ABq, 2H), 4.84 (ABq, 2H), 4.83-4.78 (m, 2H), 4.59-4.50 (m, 2H), 3.09-2.90 (m, 2H); $^{13}$C NMR (75 MHz, CDCl$_3$) δ178.0, 166.5, 161.9, 161.3, 141.7, 140.6, 139.4, 133.7, 132.6, 128.7, 127.7, 127.5, 126.9, 126.2, 125.3, 124.0, 123.6, 120.0 (2C), 118.8, 109.1, 93.3, 80.6, 72.4, 57.7, 43.8, 38.8, 29.0; MS (ES+) m/z 509.2 (M+1).

EXAMPLE 12.39

Synthesis of N-ethyl-4-[(2'-oxo-5,6-dihydrospiro[benzo[1,2-b:5,4-b']difuran-3,3'-indol]-1'(2'H)-yl)methyl]benzamide

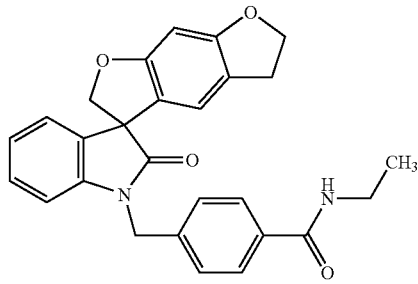

Following the procedure as described in EXAMPLE 12 and making non-critical variations using ethylamine (2 M solution in tetrahydrofuran) to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-ethyl-4-[(2'-oxo-5,6-dihydrospiro[benzo[1,2-b:5,4-b']difuran-3,3'-indol]-1' (2'H)-yl)methyl]benzamide was obtained (57%) as a colorless solid: mp 190-191° C.; $^1$H NMR (300 MHz, CDCl$_3$) δ7.79-7.71 (m, 2H), 7.44-7.36 (m, 2H), 7.24-7.15 (m, 2H), 7.08-6.99 (m, 1H), 6.77-6.70 (m, 1H), 6.47 (s, 1H), 6.43 (s, 1H), 6.14-6.04 (m, 1H), 4.99 (ABq, 2H), 4.85 (ABq, 2H), 4.59-4.50 (m, 2H), 3.54-3.43 (m, 2H), 3.09-2.90 (m, 2H), 1.28-1.21 (m, 3H); $^{13}$C NMR (75 MHz, CDCl$_3$) δ178.0, 166.8, 161.9, 161.3, 141.8, 139.1, 134.4, 132.6, 128.7, 127.5 (2C), 124.0, 123.6, 120.0, 118.8, 109.1, 93.3, 80.6, 72.4, 57.7, 43.8, 34.9, 29.0, 14.8; MS (ES+) m/z 441.2 (M+1).

EXAMPLE 12.40

Synthesis of N-(2-methoxyethyl)-4-[(2'-oxo-5,6-dihydrospiro[benzo[1,2-b:5,4-b']difuran-3,3'-indol]-1'(2'H)-yl)methyl]benzamide

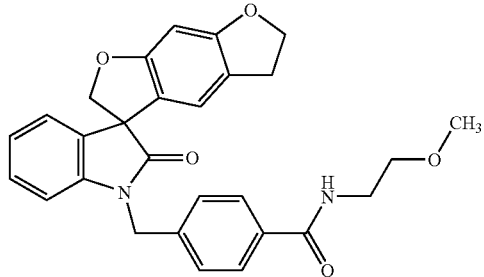

Following the procedure as described in EXAMPLE 12 and making non-critical variations using 2-methoxyethylamine to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(2-methoxyethyl)-4-[(2'-oxo-5,6-dihydrospiro[benzo[1,2-b:5,4-b']difuran-3,3'-indol]-1'(2'H)-yl)methyl]benzamide was obtained (49%) as a colorless solid: mp 182-183° C.; $^1$H NMR (300 MHz, CDCl$_3$) δ7.81-7.73 (m, 2H), 7.44-7.37 (m, 2H), 7.23-7.15 (m, 2H), 7.07-7.00 (m, 1H), 6.77-6.70 (m, 1H), 6.56-6.41 (m, 3H), 5.00

(ABq, 2H), 4.85 (ABq, 2H), 4.60-4.51 (m, 2H), 3.68-3.60 (m, 2H), 3.59-3.52 (m, 2H), 3.38 (s, 3H), 3.08-2.94 (m, 2H); $^{13}$C NMR (75 MHz, CDCl$_3$) δ177.9, 166.9, 161.9, 161.3, 141.8, 139.3, 134.1, 132.6, 128.7, 127.6, 127.5, 124.0, 123.6, 120.0 (2C), 118.8, 109.1, 93.3, 80.6, 72.4, 71.1, 58.8, 57.7, 43.8, 39.7, 29.0; MS (ES+) m/z 471.1 (M+1).

EXAMPLE 12.41

Synthesis of N-(2-ethoxyethyl)-4-[(2'-oxo-5,6-dihydrospiro[benzo[1,2-b:5,4-b']difuran-3,3'-indol]-1'(2'H)-yl)methyl]benzamide

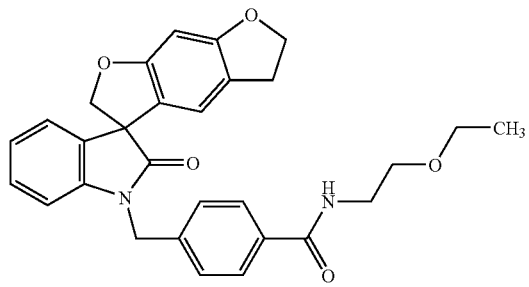

Following the procedure as described in EXAMPLE 12 and making non-critical variations using 2-ethoxyethylamine to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(2-ethoxyethyl)-4-[(2'-oxo-5,6-dihydrospiro[benzo[1,2-b:5,4-b']difuran-3,3'-indol]-1'(2'H)-yl)methyl]benzamide was obtained (48%) as a colorless solid: mp 84-85° C.; $^1$H NMR (300 MHz, CDCl$_3$) δ7.80-7.73 (m, 2H), 7.44-7.38 (m, 2H), 7.23-7.15 (m, 2H), 7.07-7.00 (m, 1H), 6.77-6.71 (m, 1H), 6.58-6.50 (m, 1H), 6.47 (s, 1H), 6.43 (s, 1H), 5.00 (ABq, 2H), 4.85 (ABq, 2H), 4.60-4.50 (m, 2H), 3.68-3.48 (m, 6H), 3.11-2.91 (m, 2H), 1.21 (t, J=7.0, Hz, 3H); $^{13}$C NMR (75 MHz, CDCl$_3$) δ177.9, 166.9, 161.8, 161.3, 141.8, 139.2, 134.2, 132.6, 128.7, 127.6, 127.5, 124.0, 123.6, 120.0 (2C), 118.8, 109.1, 93.2, 80.6, 72.4, 68.9, 66.5, 57.7, 43.8, 39.8, 29.0, 15.1; MS (ES+) m/z 485.1 (M+1).

EXAMPLE 12.42

Synthesis of N-cyclobutyl-4-[(2-oxo-5,6-dihydrospiro[benzo[1,2-b:5,4-b']difuran-3,3-indol]-1(2H)-yl)methyl]benzamide

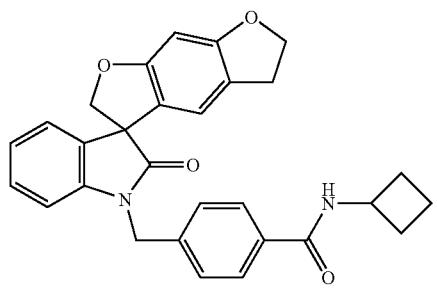

Following the procedure as described in EXAMPLE 12 and making non-critical variations using cyclobutylamine hydrochloride to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3-indol]-1'(2'H)-yl)methyl]benzoic acid, N-cyclobutyl-4-[(2-oxo-5,6-dihydrospiro[benzo[1,2-b:5,4-b']difuran-3,3-indol]-1(2H)-yl)methyl]benzamide was obtained (25%) as a colorless solid: mp>250° C.; $^1$H NMR (300 MHz, CDCl$_3$) δ8.61-8.55 (m, 1H), 7.85-7.78 (m, 2H), 7.46-7.38 (m, 2H), 7.29-7.15 (m, 2H), 7.07-6.93 (m, 2H), 6.46 (s, 1H), 6.44 (s, 1H), 5.08-4.90 (m, 2H), 4.80 (ABq, 2H), 4.55-4.46 (m, 2H), 4.46-4.31 (m, 1H), 3.05-2.91 (m, 2H), 2.26-2.12 (m, 2H), 2.12-1.95 (m, 2H), 1.72-1.60 (m, 2H); $^{13}$C NMR (75 MHz, CDCl$_3$) δ177.1, 164.9, 161.1, 160.7, 142.0, 139.2, 133.7, 132.0, 128.6, 127.7, 126.9, 123.7, 123.1, 120.3, 119.9, 118.8, 109.3, 92.4, 79.8, 72.0, 56.9, 44.4, 42.8, 30.0, 28.3, 14.6; MS (ES+) m/z 467.1 (M+1).

EXAMPLE 12.43

Synthesis of 4-[(2'-oxo-5,6-dihydrospiro[benzo[1,2-b:5,4-b']difuran-3,3'-indol]-1'(2'H)-yl)methyl]-N-1,3-thiazol-2-ylbenzamide

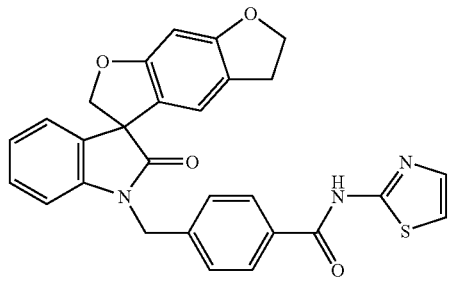

Following the procedure as described in EXAMPLE 12 and making non-critical variations using 2-aminothiazole to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, 4-[(2'-oxo-5,6-dihydrospiro[benzo[1,2-b:5,4-b']difuran-3,3'-indol]-1'(2'H)-yl)methyl]-N-1,3-thiazol-2-ylbenzamide was obtained (46%) as a colorless solid: mp>250° C.; $^1$H NMR (300 MHz, CDCl$_3$) δ12.63 (s, 1H), 8.11-8.05 (m, 2H), 7.57-7.47 (m, 3H), 7.31-7.18 (m, 3H), 7.08-6.98 (m, 2H), 6.49 (s, 1H), 6.44 (s, 1H), 5.12-4.96 (m, 2H), 4.82 (ABq, 2H), 4.58-4.43 (m, 2H), 3.08-2.89 (m, 2H); MS (ES+) m/z 496.1 (M+1).

EXAMPLE 12.44

Synthesis of N-(3-fluoro-2-methylphenyl)-4-[(2'-oxo-5,6-dihydrospiro[benzo[1,2-b:5,4-b']difuran-3,3'-indol]-1'(2'H)-yl)methyl]benzamide

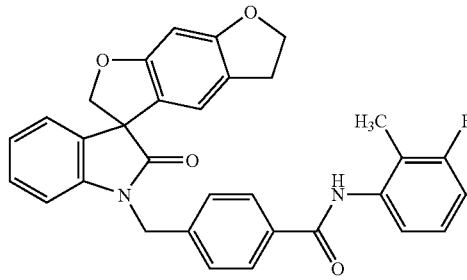

Following the procedure as described in EXAMPLE 12 and making non-critical variations using 3-fluoro-2-methylaniline to replace cyclohexanemethylamine, and 4[(2'-oxo-5,6-dihydrospiro[benzo[1,2-b:5,4-b']difuran-3,3'-indol]-1'(2'H)-yl)methyl]benzoic acid to replace 3-[(2'-oxo-5,6- dihydrospiro[benzo[1,2-b:5,4-b']difuran-3,3'-indol]-1'(2'H)-yl)methyl]benzoic acid, N-(3-fluoro-2-methylphenyl)-4-[(2'-oxo-5,6-dihydrospiro[benzo[1,2-b:5,4-b']difuran-3,3'-indol]-1'(2'H)-yl)methyl]benzamide was obtained (35%) as a colorless solid: mp 143-144° C.; ¹H NMR (300 MHz, CDCl₃) δ 7.91-7.84 (m, 2H), 7.74-7.64 (m, 2H), 7.52-7.45 (m, 2H), 7.29-7.17 (m, 3H), 7.10-7.02 (m, 1H), 6.96-6.87 (m, 1H), 6.80-6.74 (m, 1H), 6.49 (s, 1H), 6.44 (s, 1H), 5.04 (ABq, 2H), 4.85 (ABq, 2H), 4.60-4.51 (m, 2H), 3.10-2.91 (m, 2H), 2.23 (d, J=1.51 Hz, 3H); MS (ES+) m/z 521.0 (M+1).

EXAMPLE 12.45

Synthesis of N-(2-ethylbutyl)-4-[(2'-oxo-5,6-dihydrospiro[benzo[1,2-b:5,4-b']difuran-3,3'-indol]-1'(2'H)-yl)methyl]benzamide

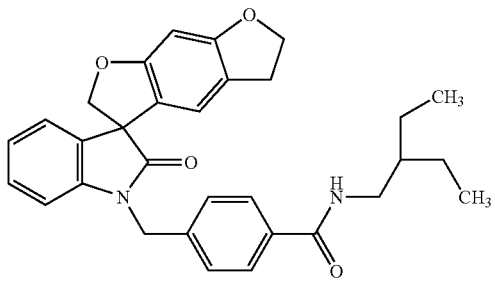

Following the procedure as described in EXAMPLE 12 and making non-critical variations using 2-ethyl-n-butylamine to replace cyclohexanemethylamine, and 4-[(2'-oxo-5,6-dihydrospiro[benzo[1,2-b:5,4-b']difuran-3,3'-indol]-1'(2'H)-yl)methyl]benzoic acid to replace 3-[(2'-oxo-5,6-dihydrospiro[benzo[1,2-b:5,4-b']difuran-3,3'-indol]-1'(2'H)-yl)methyl]benzoic acid, N-(2-ethylbutyl)-4-[(2'-oxo-5,6-dihydrospiro[benzo[1,2-b:5,4-b']difuran-3,3'-indol]-1'(2'H)-yl)methyl]benzamide was obtained (60%) as a colorless solid: mp 211-213° C.; ¹H NMR (300 MHz, CDCl₃) δ7.78-7.70 (m, 2H), 7.44-7.37 (m, 2H), 7.24-7.15 (m, 2H), 7.08-7.00 (m, 1H), 6.77-6.71 (m, 1H), 6.47 (s, 1H), 6.44 (s, 1H), 6.08-5.99 (m, 1H), 4.99 (ABq, 2H), 4.85 (ABq, 2H), 4.59-4.50 (m, 2H), 3.44-3.36 (m, 2H), 3.10-2.91 (m, 2H), 1.55-1.30 (m, 5H), 0.97-0.87 (m, 6H); MS (ES+) m/z 497.0 (M+1).

EXAMPLE 12.46

Synthesis of 2-(2'-oxo-5,6-dihydrospiro[benzo[1,2-b:5,4-b']difuran-3,3'-indol]-1'(2'H)-yl)acetamide

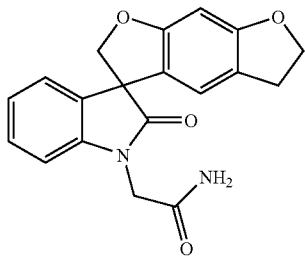

To a stirred solution of (2'-oxo-5,6-dihydrospiro[benzo[1,2-b:5,4-b']difuran-3,3'-indol]-1'(2'H)-yl)acetic acid (0.25 g, 0.74 mmol), triethylamine (0.5 mL), ammonia in dioxane (0.5M, 4.5 mL, 2.3 mmol) in acetonitrile (10 mL) was added 2-(7-aza-1H-benzotriazole-1-yl)-1,1,3,3-tetramethyluronium hexafluorophosphate (0.33 g, 0.9 mmol). The solution was stirred at ambient temperature for 18 h then concentrated in vacuo to dryness. The residue was dissolved in ethyl acetate (50 mL) and washed with 2 M sodium carbonate (2×25 mL) and 1 M hydrochloric acid (2×25 mL). The ethyl acetate layer was dried over anhydrous magnesium sulfate, filtered and concentrated in vacuo to dryness. Recrystallization from diethyl ether (25 mL) in a Branson ultrasonic bench top water bath afforded 2-(2'-oxo-5,6-dihydrospiro[benzo[1,2-b:5,4-b']difuran-3,3'-indol]-1'(2'H)-yl)acetamide (0.06 g, 23%) as a colorless solid: ¹H NMR (300 MHz, DMSO-d₆) δ7.66 (s, 1H), 7.29-7.21 (m, 2H), 7.10 (d, J=6.5 Hz, 1H), 7.03-6.90 (m, 2H), 6.55 (s, 1H), 6.36 (s, 1H), 4.72 (ABq, 2H), 4.53-4.38 (m, 1H), 4.29 (ABq, 2H), 2.92 (t, J=8.6 Hz, 2H); MS (ES+) m/z 337.1 (M+1), 359.1 (M+23).

EXAMPLE 12.47

Synthesis of N-(4-ethylphenyl)-2-(2'-oxo-5,6-dihydrospiro[benzo[1,2-b:5,4-b']difuran-3,3'-indol]-1'(2'H)-yl)acetamide

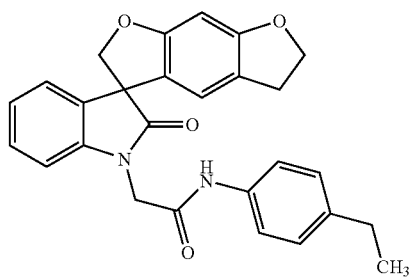

Following the procedure as described in EXAMPLE 12.46 and making non-critical variations using 4-ethylaniline to replace ammonia in dioxane, N-(4-ethylphenyl)-2-(2'-oxo-5,6-dihydrospiro[benzo[1,2-b:5,4-b']difuran-3,3'-indol]-1'(2'H)-yl)acetamide was obtained (69%) as a colorless solid: ¹H NMR (300 MHz, DMSO-d₆) δ 10.25 (s, 1H), 7.45 (d, J=8.4 Hz, 2H), 7.26 (dd, J=7.3, 7.3 Hz, 1H), 7.16-7.09 (m, 3H), 7.08-6.95 (m, 2H), 6.56 (s, 1H), 6.38 (s, 1H), 4.73 (ABq, 2H), 4.56 (ABq, 2H), 4.50-4.41 (m, 2H), 2.94 (t, J=8.6 Hz, 2H), 2.53 (q, J=7.5 Hz, 2H), 1.11 (t, J=7.6 Hz, 3H); ¹³C NMR (75 MHz, DMSO-d₆) δ177.7, 165.3, 161.6, 161.0, 143.2, 139.4, 136.8, 132.6, 129.1, 128.5, 123.9, 123.4, 121.2, 120.3, 119.7, 109.5, 92.9, 80.2, 72.6, 57.3, 43.5, 28.8, 28.0, 16.2; MS (ES+) m/z 441.1 (M+1).

EXAMPLE 12.48

Synthesis of N,N-diethyl-2-(2'-oxo-5,6-dihydrospiro[benzo[1,2-b:5,4-b']difuran-3,3'-indol]-1'(2'H)-yl)acetamide

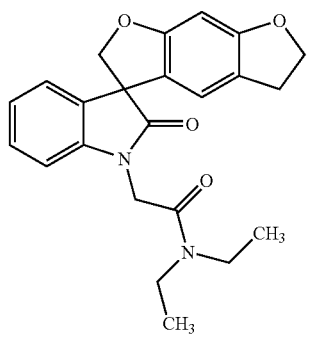

Following the procedure as described in EXAMPLE 12.46 and making non-critical variations using diethylamine to replace ammonia in dioxane, N,N-diethyl-2-(2'-oxo-5,6-dihydrospiro[benzo[1,2-b:5,4-b']difuran-3,3'-indol]-1'(2'H)-yl)acetamide was obtained (54%) as a colorless solid: $^1$H NMR (300 MHz, DMSO-d$_6$) δ 7.28-7.21 (m, 1H), 7.10 (d, J=7.3 Hz, 1H), 6.98 (dd, J=7.5, 7.5 Hz, 1H), 6.91 (d, J=7.8 Hz, 1H), 6.57 (s, 1H), 6.37 (s, 1H), 4.76-4.66 (m, 2H), 4.60 (ABq, 2H), 4.50-4.41 (m, 2H), 3.46-3.36 (m, 2H), 3.31-3.20 (m, 2H), 2.93 (t, J=8.6 Hz, 2H), 1.19 (t, J=7.1 Hz, 3H), 1.00 (t, J=7.1 Hz, 3H); $^{13}$C NMR (75 MHz, DMSO-d$_6$) δ 177.8, 165.0, 161.5, 160.9, 143.4, 132.7, 129.0, 123.8, 123.2, 121.3, 120.2, 119.9, 109.6, 92.8, 80.2, 72.5, 57.3, 41.7, 41.0, 28.8, 14.6, 13.5; MS (ES+) m/z 393.1 (M+1).

EXAMPLE 12.49

Synthesis of N-(3,3-dimethylbutyl)-2-(2'-oxo-5,6-dihydrospiro[benzo[1,2-b:5,4-b']difuran-3,3'-indol]-1'(2'H)-yl)acetamide

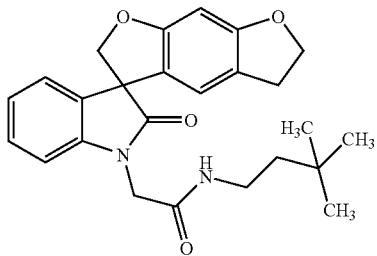

To a stirred solution of (2'-oxo-5,6-dihydrospiro[benzo[1,2-b:5,4-b']difuran-3,3'-indol]-1'(2'H)-yl)acetic acid (0.25 g, 0.74 mmol), isobutylchloroformate (0.11 mL, 0.81 mmol), N-methylmorpholine (0.09 mL, 0.81 mmol) in dichloromethane (10 mL) was added 3,3-dimethylbutylamine (0.11 g, 1.1 mmol). The solution was stirred at ambient temperature for 16 h, diluted with dichloromethane (10 mL) and washed with 2 M sodium carbonate (2×25 mL). The organic layer was dried over magnesium sulfate, filtered and concentrated in vacuo to dryness. The residue was purified by flash chromatography with ethyl acetate in hexanes (30% to 50% gradient) to afford N-(3,3-dimethylbutyl)-2-(2'-oxo-5,6-dihydrospiro[benzo[1,2-b:5,4-b']difuran-3,3'-indol]-1'(2'H)-yl)acetamide (0.13 g, 41%) as a colorless solid: mp 161-163° C.; $^1$H NMR (300 MHz, DMSO-d$_6$) δ 8.14 (dd, J=5.4, 5.4 Hz, 1H), 7.25 (dd, J=7.6, 7.6 Hz, 1H), 7.11 (d, J=6.9 Hz, 1H), 7.03-6.95 (m, 1H), 6.90 (d, J=7.8 Hz, 1H), 6.53 (s, 1H), 6.37 (s, 1H), 4.71 (ABq, 2H), 4.51-4.40 (m, 2H), 4.38-4.20 (m, 2H), 3.12-3.01 (m, 2H), 2.93 (t, J=8.6 Hz, 2H), 1.37-1.27 (m, 2H), 0.85 (s, 9H); $^{13}$C NMR (75 MHz, DMSO-d$_6$) δ 177.6, 166.3, 161.5, 160.9, 143.1, 132.7, 129.0, 123.8, 123.3, 121.3, 120.2, 119.8, 109.4, 92.8, 80.2, 72.5, 57.3, 43.2, 43.0, 35.9, 30.0, 29.7, 28.8; MS (ES+) m/z 421.2 (M+1).

EXAMPLE 12.50

Synthesis of N-[3-(1-methylethoxy)propyl]-2-(2'-oxo-5,6-dihydrospiro[benzo[1,2-b:5,4-b']difuran-3,3'-indol]-1'(2'H)-yl)acetamide

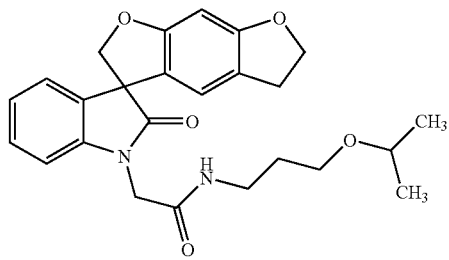

Following the procedure as described in EXAMPLE 12.49 and making non-critical variations using 3-isopropoxypropylamine to replace 3,3-dimethylbutylamine, N-[3-(1-methylethoxy)propyl]-2-(2'-oxo-5,6-dihydrospiro[benzo[1,2-b:5,4-b']difuran-3,3'-indol]-1'(2'H)-yl)acetamide was obtained (22%) as a colorless solid: mp 149-151° C.; $^1$H NMR (300 MHz, DMSO-d$_6$) δ 8.18 (dd, J=5.4, 5.4 Hz, 1H), 7.25 (dd, J=7.7, 7.7 Hz, 1H), 7.11 (d, J=6.9 Hz, 1H), 6.99 (dd, J=7.5, 7.5 Hz, 1H), 6.91 (d, J=7.8 Hz, 1H), 6.53 (s, 1H), 6.37 (s, 1H), 4.71 (dd, J=21.2, 9.3 Hz, 1H), 4.50-4.41 (m, 1H), 4.31 (ABq, 1H), 3.52-3.39 (m, 1H), 3.36-3.30 (m, 1H), 3.11 (dd, J=12.8, 6.7 Hz, 1H), 2.93 (t, J=8.5 Hz, 1H), 1.65-1.52 (m, 1H), 1.02 (d, J=6.1 Hz, 1H); $^{13}$C NMR (75 MHz, DMSO-d$_6$) δ 177.6, 166.5, 161.5, 160.9, 143.1, 132.1, 132.7, 129.0, 123.8, 123.3, 121.3, 120.2, 119.8, 109.4, 92.8, 80.2, 72.5, 71.0, 65.2, 57.3, 43.0, 36.6, 30.2, 28.8, 22.5; MS (ES+) m/z 437.2 (M+1).

EXAMPLE 12.51

Synthesis of 2-(2'-oxo-5,6-dihydrospiro[benzo[1,2-b:5,4-b']difuran-3,3'-indol]-1'(2'H)-yl)-N-propylacetamide

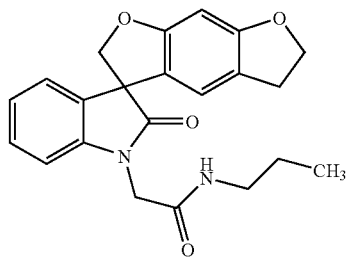

Following the procedure as described in EXAMPLE 12.49 and making non-critical variations using propylamine to replace 3,3-dimethylbutylamine, 2-(2'-oxo-5,6-dihydrospiro[benzo[1,2-b:5,4-b']difuran-3,3'-indol]-1'(2'H)-yl)-N-propylacetamide was obtained (44%) as a colorless solid: mp 207-209° C.; $^1$H NMR (300 MHz, DMSO-d$_6$) δ 8.19 (dd, J=5.5, 5.5 Hz, 1H), 7.25 (dd, J=7.7, 7.7 Hz, 1H), 7.11 (d, J=6.7 Hz, 1H), 6.99 (dd, J=7.2, 7.2 Hz, 1H), 6.91 (d, J=7.8 Hz, 1H), 6.53 (s, 1H), 6.37 (s, 1H), 4.72 (ABq, 2H), 4.50-4.41 (m, 2H), 4.32 (ABq, 2H), 3.03 (dd, J=12.9, 6.7 Hz, 2H), 2.93 (t, J=8.6 Hz, 2H), 1.49-1.30 (m, 2H), 0.82 (t, J=7.39 Hz, 3H); $^{13}$C NMR (75 MHz, DMSO-d$_6$) δ 177.6, 166.4, 161.5, 160.9, 143.2, 132.7, 129.0, 123.8, 123.3, 121.3, 120.2, 119.8, 109.4, 92.8, 80.2, 72.5, 57.3, 43.0, 41.0, 28.8, 22.8, 11.8; MS (ES+) m/z 379.1 (M+1).

EXAMPLE 12.52

Synthesis of N-methyl-2-(2'-oxo-5,6-dihydrospiro[benzo[1,2-b:5,4-b']difuran-3,3'-indol]-1'(2'H)-yl)-N-phenylacetamide

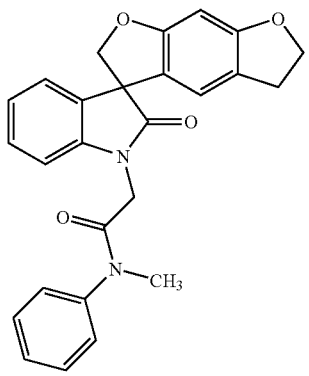

Following the procedure as described in EXAMPLE 12.49 and making non-critical variations using N-methylaniline to replace 3,3-dimethylbutylamine, N-methyl-2-(2'-oxo-5,6-dihydrospiro[benzo[1,2-b:5,4-b']difuran-3,3'-indol]-1'(2'H)-yl)-N-phenylacetamide was obtained (27%) as a colorless solid: mp 234-238° C.; $^1$H NMR (300 MHz, DMSO-$d_6$) δ7.62-7.35 (m, 5H), 7.25 (dd, J=7.6, 7.6 Hz, 1H), 7.09 (d, J=6.7 Hz, 1H), 7.02-6.93 (m, 1H), 6.54 (s, 1H), 6.36 (s, 1H), 4.73-4.61 (m, 2H), 4.50-4.40 (m, 2H), 4.19 (ABq, 2H), 3.18 (br s, 3H), 2.92 (dd, J=8.5, 8.5 Hz, 2H); $^{13}$C NMR (75 MHz, DMSO-$d_6$) δ177.5, 165.9, 161.5, 160.9, 143.1, 132.6, 130.5, 128.9, 127.9, 123.8, 123.3, 121.3, 120.2, 119.8, 109.7, 92.8, 80.0, 72.5, 57.2, 42.4, 37.7, 28.8; MS (ES+) m/z 427.1 (M+1).

EXAMPLE 12.53

Synthesis of N-(2,5-dimethylphenyl)-2-(2'-oxo-5,6-dihydrospiro[benzo[1,2-b:5,4-b']difuran-3,3'-indol]-1'(2'H)-yl)acetamide

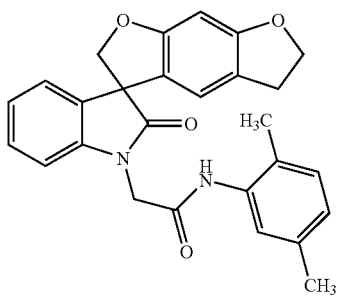

Following the procedure as described in EXAMPLE 12.49 and making non-critical variations using 2,5-dimethylaniline to replace 3,3-dimethylbutylamine, N-(2,5-dimethylphenyl)-2-(2'-oxo-5,6-dihydrospiro[benzo[1,2-b:5,4-b']difuran-3,3'-indol]-1'(2'H)-yl)acetamide was obtained (63%) as a colorless solid: mp 250-252° C.; $^1$H NMR (300 MHz, DMSO-$d_6$) δ9.63 (s, 1H), 7.33-7.25 (m, 1H), 7.21-6.97 (m, 6H), 6.91-6.85 (m, 1H), 6.53 (s, 1H), 6.38 (s, 1H), 4.74 (dd, J=23.9, 9.4 Hz, 2H), 4.60 (dd, J=29.3, 17.3 Hz, 2H), 4.49-4.41 (m, 2H), 2.92 (dd, J=8.6, 8.6 Hz, 2H), 2.20 (s, 3H), 2.14 (s, 3H); $^{13}$C NMR (75 MHz, DMSO-$d_6$) δ177.7, 165.7, 161.6, 160.9, 143.1, 136.0, 135.5, 132.8, 130.7, 129.1, 126.6, 125.9, 123.9, 123.4, 121.3, 120.2, 119.7, 109.4, 92.8, 80.2, 72.5, 57.3, 43.3, 28.8, 21.0, 17.9; MS (ES+) m/z 441.2 (M+1).

EXAMPLE 12.54

Synthesis of N-(2,4-dimethylphenyl)-2-(2'-oxo-5,6-dihydrospiro[benzo[1,2-b:5,4-b']difuran-3,3'-indol]-1'(2'H)-yl)acetamide

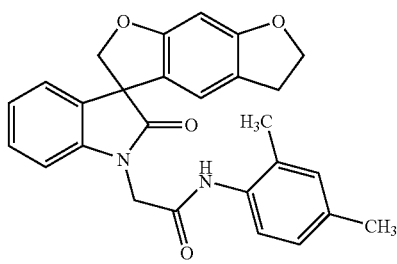

Following the procedure as described in EXAMPLE 12.49 and making non-critical variations using 2,4-dimethylaniline to replace 3,3-dimethylbutylamine, N-(2,4-dimethylphenyl)-2-(2'-oxo-5,6-dihydrospiro[benzo[1,2-b:5,4-b']difuran-3,3'-indol]-1'(2'H)-yl)acetamide was obtained (67%) as a colorless solid: mp 277-279° C.; $^1$H NMR (300 MHz, DMSO-$d_6$) δ9.62 (s, 1H), 7.28 (dd, J=7.6, 7.6 Hz, 1H), 7.21 (d, J=8.0 Hz, H), 7.12 (d, J=6.9 Hz, 1H), 7.08-6.89 (m, 4H), 6.53 (s, 1H), 6.38 (s, 1H), 4.74 (ABq, 2H), 4.59 (m, 2H), 4.49-4.41 (m, 2H), 2.91 (dd, J=8.6, 8.6 Hz, 2H), 2.21 (s, 3H), 2.15 (s, 3H); $^{13}$C NMR (75 MHz, DMSO-$d_6$) δ177.7, 165.7, 161.6, 160.9, 143.1, 135.1, 133.6, 132.8, 132.3, 131.4, 129.0, 128.6, 127.0, 125.5, 123.9, 121.3, 120.2, 119.7, 109.4, 92.8, 80.2, 72.5, 57.4, 55.4, 43.3, 28.8, 20.9, 18.3; MS (ES+) m/z 441.2 (M+1).

EXAMPLE 12.55

Synthesis of N-(2,3-dimethylphenyl)-2-(2'-oxo-5,6-dihydrospiro[benzo[1,2-b:5,4-b']difuran-3,3'-indol]-1'(2'H)-yl)acetamide

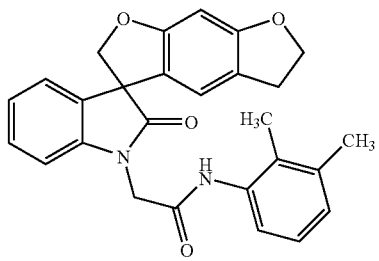

Following the procedure as described in EXAMPLE 12.49 and making non-critical variations using 2,3-dimethylaniline to replace 3,3-dimethylbutylamine, N-(2,3-dimethylphenyl)-2-(2'-oxo-5,6-dihydrospiro[benzo[1,2-b:5,4-b']difuran-3,3'-indol]-1'(2'H)-yl)acetamide was obtained (55%) as a colorless solid: mp 251-253° C.; $^1$H NMR (300 MHz, DMSO-$d_6$) δ9.76 (s, 1H), 7.29 (dd, J=7.4, 7.4 Hz, 1H), 7.15-6.96 (m, 6H), 6.52 (s, 1H), 6.37 (s, 1H), 4.74 (ABq, 2H), 4.60 (ABq, 2H), 4.49-4.40 (m, 2H), 2.91 (dd, J=8.6, 8.6 Hz, 2H), 2.21 (s, 3H), 2.06 (s, 3H); $^{13}$C NMR (75 MHz, DMSO-d$_6$) δ177.7, 165.8, 161.8, 160.9, 143.1, 137.6, 136.0, 132.8, 131.8, 129.0, 127.7, 125.7, 124.0, 123.4, 121.3, 120.2, 119.7, 109.4, 92.8, 80.2, 72.5, 57.3, 43.3, 28.8, 20.6, 14.5; MS (ES+) m/z 441.2 (M+1).

EXAMPLE 12.56

Synthesis of N-(2,6-dimethylphenyl)-2-(2'-oxo-5,6-dihydrospiro[benzo[1,2-b:5,4-b']difuran-3,3'-indol]-1'(2'H)-yl)acetamide

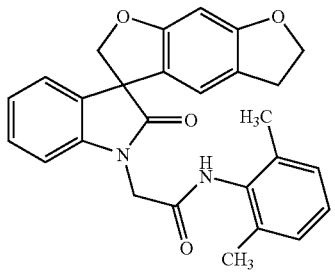

Following the procedure as described in EXAMPLE 12.49 and making non-critical variations using 2,6-dimethylaniline to replace 3,3-dimethylbutylamine, N-(2,6-dimethylphenyl)-2-(2'-oxo-5,6-dihydrospiro[benzo[1,2-b:5,4-b']difuran-3,3'-indol]-1'(2'H)-yl)acetamide was obtained (67%) as a colorless solid: mp 261-262° C.; $^1$H NMR (300 MHz, DMSO-d$_6$) δ9.66 (s, 1H), 7.30 (dd, J=7.7, 7.7 Hz, 1H), 7.16-6.98 (m, 6H), 6.51 (s, 1H), 6.37 (s, 1H), 4.75 (ABq, 2H), 4.67-4.52 (m, 2H), 4.49-4.40 (m, 2H), 2.90 (dd, J=8.6, 8.6 Hz, 2H), 2.12 (s, 6H); $^{13}$C NMR (75 MHz, DMSO-d$_6$) δ177.7, 165.4, 161.5, 160.9, 143.0, 135.7, 135.0, 132.9, 128.9, 128.2, 127.1, 123.9, 123.4, 121.3, 120.2, 119.7, 109.3, 92.8, 80.2, 72.5, 57.4, 43.0, 28.8, 18.6, 15.6; MS (ES+) m/z 441.2 (M+1).

EXAMPLE 12.57

Synthesis of N-methyl-5-[(2'-oxospiro[furo[2,3-f][1,3]benzodioxole-7,3'-indol]-1'(2'H)-yl)methyl]-2-(trifluoromethyl)furan-3-carboxamide

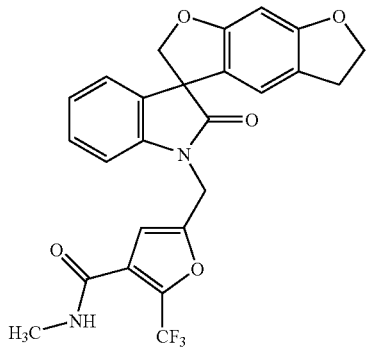

Following the procedure as described in EXAMPLE 12.49 and making non-critical variations using methylamine hydrochloride to replace 3,3-dimethylbutylamine, 5-[(2-oxospiro[furo[2,3-f][1,3]benzodioxole-7,3'-indol]-1'(2'H)-yl)methyl]-2-(trifluoromethyl)furan-3-carboxylic acid to replace (2'-oxo-5,6-dihydrospiro[benzo[1,2-b:5,4-b']difuran-3,3'-indol]-1'(2'H)-yl)acetic acid, N-methyl-5-[(2'-oxospiro[furo[2,3-f][1,3]benzodioxole-7,3'-indol]-1'(2'H)-yl)methyl]-2-(trifluoromethyl)furan-3-carboxamide was obtained (96%) as a colorless solid: mp 202-203° C. (diethyl ether/hexanes); $^1$H NMR (300 MHz, CDCl$_3$) δ 7.31-7.27 (m, 2H), 7.19-7.17 (m, 1H), 7.10-7.05 (m, 1H), 6.95-6.92 (m, 1H), 6.62 (s, 1H), 6.49 (s, 1H), 6.09 (s, 1H), 5.94 (br s, 1H), 5.85-5.84 (m, 2H), 5.03-4.85 (m, 3H), 4.67-4.64 (m, 1H), 2.92 (d, J=3.0 Hz, 3H); MS (ES+) m/z 487.3 (M+1).

EXAMPLE 12.58

Synthesis of 5-[(2'-oxospiro[furo[2,3-f][1,3]benzodioxole-7,3'-indol]-1'(2'H)-yl)methyl]-2-(trifluoromethyl)furan-3-carboxamide

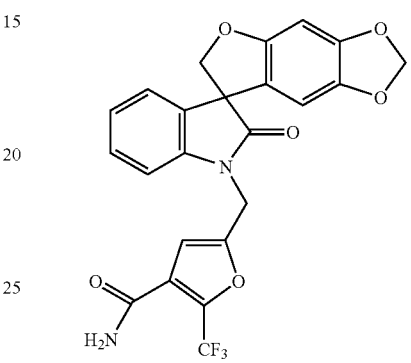

Following the procedure as described in EXAMPLE 12.49 and making non-critical variations using 7 N ammonia solution in methanol to replace 3,3-dimethylbutylamine, and 5-[(2'-oxospiro[furo[2,3-f][1,3]benzodioxole-7,3'-indol]-1'(2'H)-yl)methyl]-2-(trifluoromethyl)furan-3-carboxylic acid to replace (2'-oxo-5,6-dihydrospiro[benzo[1,2-b:5,4-b']difuran-3,3'-indol]-1'(2'H)-yl)acetic acid, 5-[(2'-oxospiro[furo[2,3-f][1,3]benzodioxole-7,3'-indol]-1'(2'H)-yl)methyl]-2-(trifluoromethyl)furan-3-carboxamide was obtained (86%) as a colorless solid: mp 172-174° C. (ethyl acetate/hexanes); $^1$H NMR (300 MHz, CDCl$_3$) δ 7.32-7.27 (m, 1H), 7.20-7.17 (m, 1H), 7.11-7.06 (m, 1H), 6.97-6.94 (m, 1H), 6.70 (s, 1H), 6.49 (s, 1H), 6.09-6.02 (m, 3H), 5.83 (ABq, 2H), 5.85-5.84 (m, 2H), 5.03-4.85 (m, 3H), 4.67-4.64 (m, 1H); MS (ES+) m/z 473.2 (M+1).

EXAMPLE 12.59

Synthesis of N,N-dimethyl-5-[(2'-oxospiro[furo[2,3-f][1,3]benzodioxole-7,3'-indol]-1'(2'H)-yl)methyl]-2-(trifluoromethyl)furan-3-carboxamide

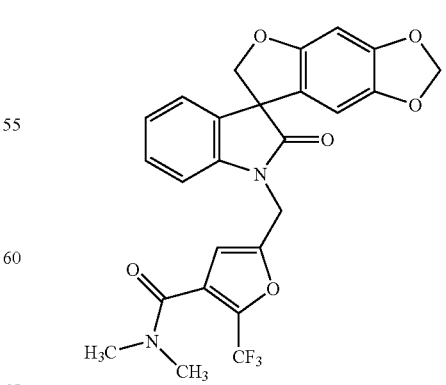

Following the procedure as described in EXAMPLE 12.49 and making non-critical variations using dimethylamine hydrochloride to replace 3,3-dimethylbutylamine, and 5-[(2'-oxospiro[furo[2,3-f][1,3]benzodioxole-7,3'-indol]-1'(2'H)-yl)methyl]-2-(trifluoromethyl)furan-3-carboxylic acid to replace (2'-oxo-5,6-dihydrospiro[benzo[1,2-b:5,4-b']difuran-3,3'-indol]-1'(2'H)-yl)acetic acid, N,N-dimethyl-5-[(2'-oxospiro[furo[2,3-f][1,3]benzodioxole-7,3'-indol]-1'(2'H)-yl)methyl]-2-(trifluoromethyl)furan-3-carboxamide was obtained (32%) as a colorless solid: mp 96-98° C. (ethyl acetate/hexanes); $^1$H NMR (300 MHz, CDCl$_3$) δ 7.32-7.27 (m, 1H), 7.19-7.17 (m, 1H), 7.10-7.05 (m, 1H), 6.96-6.94 (m, 1H), 6.50 (s, 1H), 6.40 (s, 1H), 6.09 (s, 1H), 5.86-5.85 (m, 2H), 5.05-4.87 (m, 3H), 4.68-4.65 (m, 1H); MS (ES+) m/z 501.3 (M+1).

EXAMPLE 12.60

Synthesis of 4-[(2'-oxo-2,3-dihydrospiro[furo[2,3-g][1,4]benzodioxine-8,3'-indol]-1'(2'H)-yl)methyl]benzamide

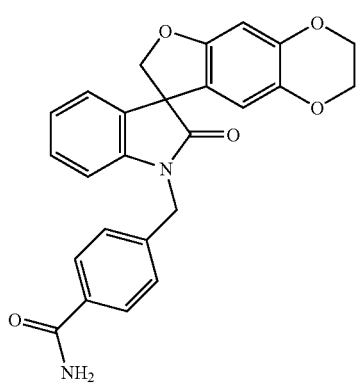

To a solution of 4-[(2'-oxo-2,3-dihydrospiro[furo[2,3-g][1,4]-benzodioxine-8,3'-indol]-1'(2'H)-yl)methyl]benzoic acid (0.43 g, 1.00 mmol) in dichloromethane was added oxalyl chloride (0.2 mL, 2.4 mmol) followed by N,N-dimethylformamide (1 drop). The reaction mixture was stirred at ambient temperature for 5 h and concentrated in vacuo. The residue was dissolved in dichloromethane (10 mL) and added to a 0.5 M solution of ammonia in 1,4-dioxane (5 mL). The reaction mixture was stirred at ambient temperature for 18 h and concentrated in vacuo. The residue was purified by column chromatography and eluted with ethyl acetate to afford 4-[(2'-oxo-2,3-dihydrospiro[furo[2,3-g][1,4]benzodioxine-8,3'-indol]-1'(2'H)-yl)methyl]benzamide (0.15 g, 35%): m.p. 236-238° C. (ethyl acetate); $^1$H NMR (300 MHz, DMSO-d$_6$) δ 7.93-7.80 (m, 3H), 7.39-7.33 (m, 3H), 7.25-7.14 (m, 2H), 7.02-6.94 (m, 2H), 6.50 (s, 1H), 6.08 (s, 1H), 4.94 (ABq, 2H), 4.72 (ABq, 2H), 4.16-4.07 (m, 4H); $^{13}$C NMR (75 MHz, DMSO-d$_6$) δ 177.2, 167.9, 155.2, 144.6, 142.5, 140.0, 138.3, 134.0, 132.1, 129.2, 128.3, 127.4, 124.1, 123.6, 121.6, 111.4, 109.8, 99.3, 79.9, 64.6, 64.0, 57.2, 43.2; MS (ES+) m/z 429.0 (M+1).

EXAMPLE 12.61

Synthesis of 3-[(2'-oxo-2,3-dihydrospiro[furo[2,3-g][1,4]benzodioxine-8,3'-indol]-1'(2'H)-yl)methyl]benzamide

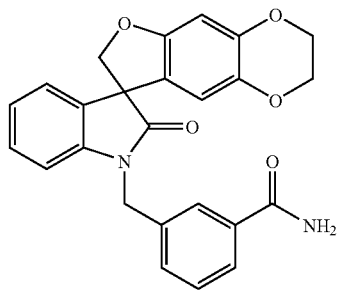

To a solution of 3-[(2'-oxo-2,3-dihydrospiro[furo[2,3-g][1,4]benzodioxine-8,3'-indol]-1'(2'H)-yl)methyl]benzoic acid (1.04 g, 2.42 mmol) in anhydrous chloroform (50 mL) was added oxalyl chloride (0.50 mL, 5.7 mmol) and anhydrous N,N-dimethylformamide (2 drops). The reaction mixture was stirred at ambient temperature for 2 h and concentrated in vacuo. The residue was dissolved in anhydrous tetrahydrofuran (36 mL), cooled to 0° C. and 7 M methanolic ammonia (5.20 mL, 36.3 mmol) was added. The reaction mixture was stirred at 0° C. for 1 h and at ambient temperature for 2 h, filtered and concentrated in vacuo. The residue was purified by column chromatography and eluted with acetone/dichloromethane (1/9), followed by recrystallization from dichloromethane/diethyl ether to afford 3-[(2'-oxo-2,3-dihydrospiro[furo[2,3-g][1,4]benzodioxine-8,3'-indol]-1'(2'H)-yl)methyl]benzamide (1.03 g, 99%) as a colorless solid: mp 130-135° C. (dichloromethane/diethyl ether); $^1$H NMR (300 MHz, CDCl$_3$) δ 7.81 (s, 1H), 7.71-7.69 (m, 1H), 7.48-7.39 (m, 2H), 7.21-7.15 (m, 2H), 7.04-6.99 (m, 1H), 6.76-6.74 (m, 1H), 6.49 (s, 1H), 6.23 (s, 1H), 6.10 (br s, 1H), 5.71 (br s, 1H), 5.14-5.09 (m, 1H), 4.95-4.81 (m, 2H), 4.67-4.64 (m, 1H), 4.19-4.08 (m, 4H); $^{13}$C NMR (75 MHz, CDCl$_3$) δ 177.7, 168.7, 155.3, 144.7, 141.8, 138.4, 136.5, 134.0, 132.1, 130.8, 129.4, 128.9, 126.8, 126.5, 124.0, 123.7, 120.9, 111.4, 109.2, 99.5, 80.0, 64.5, 63.9, 58.1, 43.8; MS (ES+) m/z 428.8 (M+1).

EXAMPLE 12.62

Synthesis of N,N-dimethyl-3-[(2'-oxo-2,3-dihydrospiro[furo[2,3-g][1,4]benzodioxine-8,3'-indol]-1'(2'H)-yl)methyl]benzamide

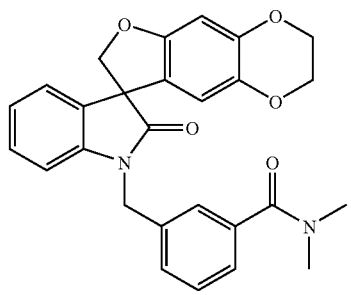

To a solution of 3-[(2'-oxo-2,3-dihydrospiro[furo[2,3-g][1,4]benzodioxine-8,3'-indol]-1'(2'H)-yl)methyl]benzoic acid (0.50 g, 1.16 mmol) in anhydrous chloroform (25 mL) was added oxalyl chloride (0.25 mL, 2.9 mmol) and anhydrous N,N-dimethylformamide (1 drop). The reaction mixture was stirred at ambient temperature for 2 h and concentrated in vacuo. The residue was dissolved in anhydrous dichloromethane (10 mL) and the resultant solution was added dropwise to a cooled (0° C.) solution of dimethylamine hydrochloride (1.56 g, 18.9 mmol) and triethylamine (5.27 mL, 37.8 mmol) in anhydrous dichloromethane (10 mL). The reaction mixture was stirred at 0° C. for 45 min and at ambient temperature for 3 h, filtered and concentrated in vacuo. The residue was recrystallized from hexanes to afford N,N-dimethyl-3-[(2'-oxo-2,3-dihydrospiro[furo[2,3-g][1,4]-benzodioxine-8,3'-indol]-1'(2'H)-yl)methyl]benzamide (0.04 g, 8%) as a light brown solid: mp: 90-96° C. (hexanes); $^1$H NMR (300 MHz, CDCl$_3$) δ 7.37-7.34 (m, 4H), 7.21-7.14 (m, 2H), 7.04-7.00 (m, 1H), 6.77-6.75 (m, 1H), 6.49 (s, 1H), 6.19 (s, 1H), 5.08-5.03 (m, 1H), 4.93-4.82 (m, 2H), 4.67-4.64 (m, 1H), 4.20-4.09 (m, 4H), 3.08 (s, 3H), 2.90 (s, 3H); $^{13}$C NMR (75 MHz, CDCl$_3$) δ 177.6, 171.1, 155.3, 144.7, 141.9, 138.3, 137.0, 136.0, 132.1, 129.1, 128.9, 128.3, 126.6, 126.0, 124.0, 123.6, 120.9, 111.5, 109.2, 99.5, 80.2, 64.5, 63.9, 58.0, 43.9, 39.6, 35.3; MS (ES+) m/z 456.8 (M+1).

EXAMPLE 12.63

Synthesis of N-methyl-2-[(2'-oxo-2,3-dihydrospiro[furo[2,3-g][1,4]benzodioxine-8,3'-indol]-1'(2'H)-yl)methyl]pyridine-3-carboxamide

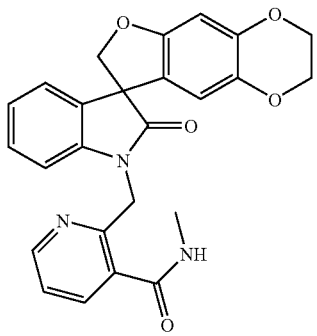

A 50 mL round-bottom flask was charged with 2-[(2'-oxo-2,3-dihydrospiro[furo[2,3-g][1,4]benzodioxine-8,3'-indol]-1'(2'H)-yl)methyl]pyridine-3-carboxylic acid (0.43 g, 1.0 mmol), methylamine hydrochloride (0.14 g, 2.0 mmol), 1-ethyl-3-(3-dimethylaminopropyl)carbodiimide hydrochloride (0.26 g, 1.4 mmol), 1-hydroxybenzotriazole (0.20 g, 1.5 mmol), N-methylmorpholine (0.4 mL, 3.6 mmol) and N,N-dimethylformamide (7 mL). The reaction mixture was stirred under nitrogen at ambient temperature for 20 h, and poured into water (200 mL). The solid was collected by filtration, washed with water, dried and purified by column chromatography and eluted with a 0% to 50% gradient of ethyl acetate in dichloromethane to afford N-methyl-2-[(2'-oxo-2,3-dihydrospiro[furo[2,3-g][1,4]benzodioxine-8,3'-indol]-1' (2'H)-yl)methyl]pyridine-3-carboxamide (0.41 g, 92%) as an off-white solid: $^1$H NMR (300 MHz, CDCl$_3$) δ 8.43 (d, J=4.8 Hz, 1H), 7.85 (d, J=7.7 Hz, 1H), 7.36 (dd, J=7.5, 5.0 Hz, 1H), 7.20-7.07 (m, 2H), 6.95 (t, J=7.5, 1H), 6.81 (d, J=7.8 Hz, 1H), 6.46 (d, J=1.2 Hz, 1H), 6.43 (d, J=1.2 Hz, 1H), 5.16 (ABq, 2H), 4.70 (ABq, 2H), 4.20-4.05 (m, 4H), 2.77 (s, 3H); $^{13}$C NMR (75 MHz, CDCl$_3$) δ 177.3, 167.6, 154.9, 152.7, 150.1, 144.5, 143.3, 138.1, 136.2, 132.5, 131.6, 129.0, 123.7, 123.1, 122.9, 122.2, 112.4, 109.6, 99.0, 79.7, 64.6, 64.1, 57.7, 43.3, 26.5; MS (ES+) m/z 443.9 (M+1).

EXAMPLE 12.64

Synthesis of N-(2-aminoethyl)-2-[(2'-oxo-2,3-dihydrospiro[furo[2,3-g][1,4]benzodioxine-8,3'-indol]-1'(2'H)-yl)methyl]pyridine-3-carboxamide dihydrochloride

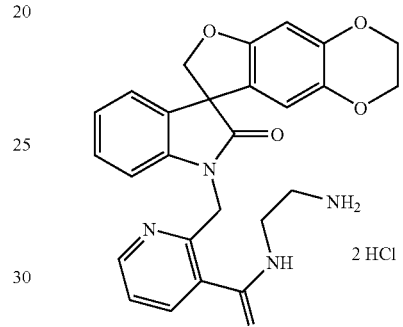

A 50 mL round-bottom flask was charged with 2-[(2'-oxo-2,3-dihydrospiro[furo[2,3-g][1,4]benzodioxine-8,3'-indol]-1'(2'H)-yl)methyl]pyridine-3-carboxylic acid (0.43 g, 1.0 mmol), tert-butyl 2-aminomethylcarbamate (0.32 g, 2.0 mmol), 1-ethyl-3-(3-dimethyllaminopropyl)carbodiimide hydrochloride (0.26 g, 1.35 mmol), 1-hydroxybenzotriazole (0.20 g, 1.5 mmol), N-methylmorpholine (0.4 mL, 3.6 mmol) and N,N-dimethylformamide (7 mL). The reaction mixture was stirred under nitrogen at ambient temperature for 20 h and poured into water (200 mL). The solid was collected by filtration, washed with water, dried and dissolved in tetrahydrofuran (20 mL). A 4 M solution of hydrochloric acid in dioxane was added and the reaction mixture was stirred for 16 h, diluted with diethyl ether (50 mL) and filtered to afford N-(2-aminoethyl)-2-[(2'-oxo-2,3-dihydrospiro[furo[2,3-g][1,4]benzodioxine-8,3'-indol]-1'(2'H)-yl)methyl]pyridine-3-carboxamide dihydrochloride (0.31 g, 57%) as an off-white solid: $^1$H NMR (300 MHz, CDCl$_3$) δ 10.01 (s, 2H), 9.02 (t, J=5.4 Hz, 1H), 8.45 (dd, J=4.8, 1.5 Hz, 1H), 8.20 (s, 2H), 8.10 (dd, J=7.8, 1.5 Hz, 1H), 7.41 (dd, J=7.8, 4.9 Hz, 1H), 7.20-7.08 (m, 2H), 6.99-6.86 (m, 2H), 6.46 (s, 1H), 6.43 (s, 1H), 5.26 (ABq, 2H), 4.71 (ABq, 2H), 4.19-4.05 (m, 4H), 3.58-3.47 (m, 2H), 3.06-2.93 (m, 2H); $^{13}$C NMR (75 MHz, CDCl$_3$) δ 177.4, 167.6, 154.9, 152.9, 150.0, 144.5, 143.3, 138.1, 137.1, 132.5, 130.9, 129.0, 123.8, 123.1, 122.9, 122.2, 112.3, 109.7, 99.0, 79.7, 64.6, 64.1, 57.7, 43.2, 38.8, 37.6; MS (ES+) m/z 472.9 (M+1).

EXAMPLE 12.65

Synthesis of N-(2-fluorophenyl)-4-[(2'-oxo-2,3-dihydrospiro[furo[2,3-g][1,4]benzodioxine-8,3'-indol]-1'(2'H)-yl)methyl]benzamide

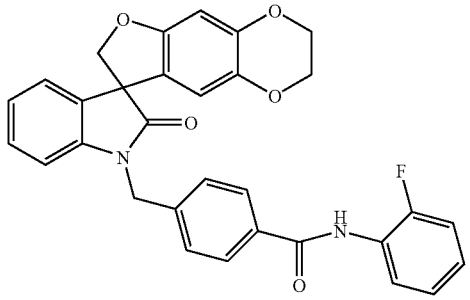

To a stirred solution of 4-[(2'-oxo-2,3-dihydrospiro[furo[2,3-g][1,4]benzodioxine-8,3'-indol]-1'(2'H)-yl)methyl]benzoic acid (0.400 g, 0.93 mmol) in anhydrous chloroform (20 mL) was added thionyl chloride (0.27 mL, 3.7 mmol). The solution was heated at reflux for 2 h and concentrated in vacuo to afford 4-[(2'-oxo-2,3-dihydrospiro[furo[2,3-g][1,4]benzodioxine-8,3'-indol]-1'(2'H)-yl)methyl]benzoyl chloride (0.45 g) as a pale yellow solid. To a solution of 2-fluoroaniline (0.1 mL, 1.0 mmol) and triethylamine (0.43 mL, 3.1 mmol) in anhydrous dichloromethane (10 mL) at 0° C. under nitrogen was added 4-((2'-oxo-3,7-dihydro-2H-spiro[benzofuro[5,6-b][1,4]dioxine-8,3'-indoline]-1'-yl)methyl)benzoyl chloride (0.46 g, 1.0 mmol). The reaction mixture was stirred at ambient temperature for 42 h and was washed with 10% w/v hydrochloric acid (10 mL), water (10 mL) and brine (10 mL). The organic phase was dried over anhydrous magnesium sulfate, filtered and concentrated in vacuo. The residue was purified by column chromatography and eluted with hexanes/ethyl acetate (1/1) to afford N-(2-fluorophenyl)-4-[(2'-oxo-2,3-dihydrospiro[furo[2,3-g][1,4]benzodioxine-8,3'-indol]-1'(2'H)-yl)methyl]benzamide (0.262 g, 49%) as a colorless solid: mp 245-251° C.; $^1$H NMR (300 MHz, CDCl$_3$) δ 8.48-8.43 (m, 1H), 8.11-8.04 (m, 1H), 7.88 (d, J=8.1 Hz, 2H), 7.46 (d, J=8.1 Hz, 2H), 7.24-7.02 (m, 6H), 6.75 (d, J=7.8 Hz, 1H), 6.52 (s, 1H), 6.24 (s, 1H), 5.16 (d, J=15.9 Hz, 1H), 4.95 (d, J=8.7 Hz, 1H), 4.89 (d, J=15.9 Hz, 1H), 4.68 (d, J=9.0 Hz, 1H), 4.21-4.10 (m, 4H); $^{13}$C NMR (75 MHz, CDCl$_3$) δ 177.6, 164.9, 155.3, 152.7 (d, J=241.4 Hz), 144.7, 141.7, 140.0, 138.3, 134.1, 132.2, 128.8, 127.8 (d, J=4.1 Hz), 126.4 (d, J=9.8 Hz), 124.7-124.6 (m), 124.1, 123.7, 121.8, 120.8, 114.8 (d, J=19.1 Hz), 111.4, 109.1, 99.5, 80.1, 64.5, 63.9, 58.0, 43.8; MS (ES+) m/z 523.0 (M+1).

EXAMPLE 13

Synthesis of 5-[(2'-oxo-5,6-dihydrospiro[benzo[1,2-b:5,4-b']difuran-3,3'-indol]-1'(2'H)-yl)methyl]furan-2-carboxylic acid

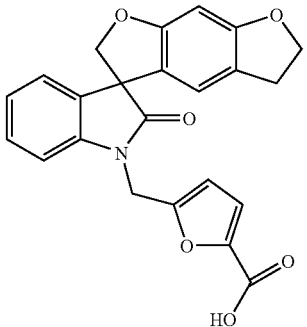

A solution of methyl 5-[(2'-oxo-5,6-dihydrospiro[benzo[1,2-b:5,4-b']difuran-3,3'-indol]-1'(2'H)-yl)methyl]furan-2-carboxylate (5.5 g, 13.0 mmol) and sodium hydroxide (1.04 g, 26.0 mmol) in water 100 ml) and methanol (40 mL) was stirred at 65° C. for 16 h. The solvent methanol was evaporated under reduced pressure, and the residue was cooled in ice-bath and acidified with 10% hydrochloric acid to pH 1-2. The solid precipitate was filtered off, and recrystallized from ethanol (100 mL) to afford 5-[(2'-oxo-5,6-dihydrospiro[benzo[1,2-b:5,4-b']difuran-3,3'-indol]-1'(2'H)-yl)methyl]furan-2-carboxylic acid (5.10 g, 92%) as a colorless solid: $^1$H NMR (300 MHz, CDCl$_3$) δ7.36-6.92 (m, 5H), 6.51 (s, 1H), 6.44 (d, J=3.5 Hz, 1H), 6.40 (s, 1H), 5.02 (ABq, 2H), 4.81 (ABq, 2H), 4.51 (t, J=8.6 Hz, 2H), 3.04-2.91 (m, 2H); $^{13}$C NMR (75 MHz, CDCl$_3$) δ177.2, 161.6, 160.9, 159.6, 153.7, 145.0, 142.1, 132.7, 129.1, 124.0, 123.7, 121.0, 120.4, 119.6, 119.1, 111.1, 109.7, 92.9, 80.0, 72.6, 57.4, 37.3, 28.8; MS (ES+) m/z 403.8 (M+1).

EXAMPLE 13.1

Synthesis of N,N-dimethyl-5-[(2'-oxo-5,6-dihydrospiro[benzo[1,2-b:5,4-b']difuran-3,3'-indol]-1'(2'H)-yl)methyl]furan-2-carboxamide

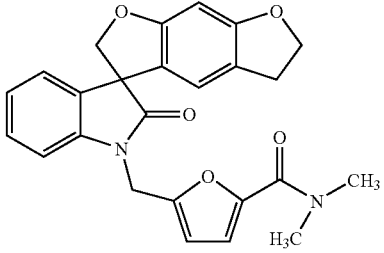

A mixture of 5-[(2'-oxo-5,6-dihydrospiro[benzo[1,2-b:5,4-b']difuran-3,3-indol]-1'(2'H)-yl)methyl]furan-2-carboxylic acid (4.85 g, 12 mmol), thionyl chloride (11.90 g, 100 mmol) and a few drops of N,N-dimethylformamide in chloroform (60 mL) was stirred at ambient temperature for 16 h. The solvent and excess of thionyl chloride were evaporated under reduced pressure. The residue was dissolved in dichloromethane (50 mL). To the above solution (5 mL, 1.2 mmol) was added dimethylamine hydrochloride (0.81 g, 10 mmol) and triethylamine (1.01 g, 10 mmol). The mixture was stirred at ambient temperature for 3 h. The reaction mixture was diluted with dichloromethane (100 mL) and extracted with water (2×100 mL), dried over magnesium sulfate and filtered. The filtrate was evaporated under reduced pressure, and the residue was purified by column chromatography with dichloromethanemethanol (100:1-20:1) to afford N,N-dimethyl-5-[(2'-oxo-5,6-dihydrospiro[benzo[1,2-b:5,4-b']difuran-3,3'-indol]-1'(2'H)-yl)methyl]furan-2-carboxamide (0.22 g, 42%) as a colorless solid: $^1$H NMR (300 MHz, CDCl$_3$) δ7.31-6.90 (m, 5H), 6.43-6.37 (m, 3H), 4.97 (ABq, 2H), 4.78 (ABq, 2H), 4.52 (t, J=8.6 Hz, 2H), 3.11 (s, 6H), 2.96 (t, J=8.6 Hz, 2H); $^{13}$C NMR (75 MHz, CDCl$_3$) δ177.2, 161.6, 161.0, 159.4, 151.3, 147.5, 142.2, 132.6, 129.1, 124.1, 123.7, 121.0, 120.4, 119.5, 116.8, 110.4, 109.8, 92.9, 80.1, 72.6, 57.4, 37.1, 28.8; MS (ES+) m/z 431.1 (M+1).

EXAMPLE 13.2

Synthesis of N-methyl-5-[(2'-oxo-5,6-dihydrospiro [benzo[1,2-b:5,4-b']difuran-3,3'-indol]-1'(2'H)-yl) methyl]furan-2-carboxamide

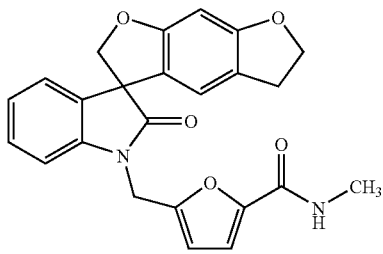

Following the procedure as described in EXAMPLE 13.1 and making non-critical variations using methylamine hydrochloride to replace dimethylamine hydrochloride, N-methyl-5-[(2'-oxo-5,6-dihydrospiro[benzo[1,2-b:5,4-b']difuran-3,3'-indol]-1'(2'H)-yl)methyl]furan-2-carboxamide was obtained (37%) as a colorless solid: $^1$H NMR (300 MHz, CDCl$_3$) δ7.29-6.89 (m, 5H), 6.66 (s, 1H), 6.42-6.35 (m, 3H), 4.91 (ABq, 2H), 4.78 (ABq, 2H), 4.53 (t, J=8.5 Hz, 2H) 2.98-2.87 (m, 5H); $^{13}$C NMR (75 MHz, CDCl$_3$) δ177.8, 161.9, 161.3, 158.7, 150.5, 148.0, 141.3, 132.5, 128.9, 124.1, 123.9, 120.0, 119.9, 118.8, 114.8, 111.1, 108.8, 93.3, 80.4, 72.4, 57.7, 37.2, 29.0, 25.8; MS (ES+) m/z 417.2 (M+1).

EXAMPLE 13.3

Synthesis of 2-[(2'-oxo-5,6-dihydrospiro[benzo[1,2-b:5,4-b']difuran-3,3'-indol]-1'(2'H)-yl)methyl]-1,3-oxazole-4-carboxamide

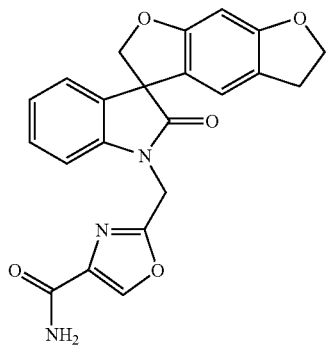

Following the procedure as described in EXAMPLE 13.1 and making non-critical variations using 4 M ammonia solution in dioxane to replace dimethylamine hydrochloride, 2-[(2'-oxo-5,6-dihydrospiro[benzo[1,2-b:5,4-b']difuran-3,3'-indol]-1'(2'H)-yl)methyl]-1,3-oxazole-4-carboxylic acid to replace 5-[(2'-oxo-5,6-dihydrospiro[benzo[1,2-b:5,4-b'] difuran-3,3-indol]-1'(2'H)-yl)methyl]furan-2-carboxylic acid, 2-[(2'-oxo-5,6-dihydrospiro[benzo[1,2-b:5,4-b']difuran-3,3'-indol]-1'(2'H)-yl)methyl]-1,3-oxazole-4-carboxamide was obtained (19%) as a colorless solid: $^1$H NMR (300 MHz, CDCl$_3$) δ $^1$H NMR (300 MHz, CDCl$_3$) δ 8.55 (s, 1H), 7.53 (d, J=10.2 Hz, 2H), 7.33-6.99 (m, 4H), 6.54 (s, 1H), 6.38 (s, 1H), 5.22-5.01 (m, 2H), 4.75 (ABq, 2H), 4.46 (t, J=8.8 Hz, 2H), 2.92 (t, J=8.6 Hz, 2H); $^{13}$C NMR (75 MHz, CDCl$_3$) δ177.3, 161.9, 161.6, 160.9, 159.2, 143.2, 142.2, 136.8, 132.5, 129.2, 124.1, 123.8, 120.8, 120.4, 119.7, 109.6, 92.8, 80.0, 72.5, 57.3, 37.4, 28.7; MS (ES+) m/z 403.8 (M+1).

EXAMPLE 13.4

Synthesis of N,N-dimethyl-2-[1(2'-oxo-5,6-dihydrospiro[benzo[1,2-b:5,4-b']difuran-3,3'-indol]-1' (2'H)-yl)methyl]-1,3-oxazole-4-carboxamide

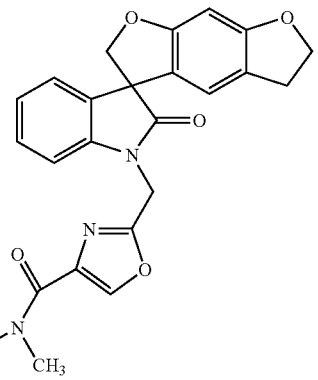

Following the procedure as described in EXAMPLE 13.1 and making non-critical variations using 2-[(2'-oxo-5,6-dihydrospiro[benzo[1,2-b:5,4-b']difuran-3,3'-indol]-1'(2'H)-yl) methyl]-1,3-oxazole-4-carboxylic acid to replace 5-[(2'-oxo-5,6-dihydrospiro[benzo[1,2-b:5,4-b']difuran-3,3-indol]-1' (1'H)-yl)methyl]furan-2-carboxylic acid, N,N-dimethyl-2-[(2'-oxo-5,6-dihydrospiro[benzo[1,2-b:5,4-b']difuran-3,3'-indol]-1'(2'H)-yl)methyl]-1,3-oxazole-4-carboxamide was obtained (3.0%) as a colorless solid: $^1$H NMR (300 MHz, CDCl$_3$) δ8.09 (s, 1H), 7.27-6.86 (m, 4H), 6.50 (s, 1H), 6.40 (s, 1H), 5.08 (ABq, 2H), 4.82 (ABq, 2H), 4.52 (t, J=8.6 Hz, 2H), 3.29 (s, 3H), 3.06 (s, 3H), 2.97 (t, J=8.6 Hz, 2H); MS (ES+) m/z 431.8 (M+1).

EXAMPLE 13.5

Synthesis of N-cyclopropyl-2-[(2'-oxospiro[furo[2,3-f][1,3]benzodioxole-7,3'-indol]-1'(2'H)-yl)methyl]-1,3-oxazole-4-carboxamide

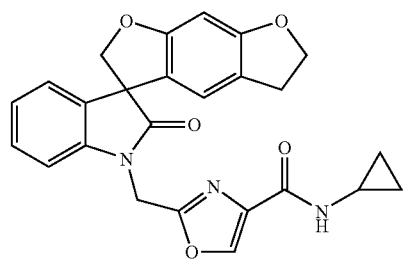

A solution of 24(2'-oxo-6H-spiro[benzofuro[6,5-d][1,3]dioxole-7,3'-indoline]-1-yl)methyl)oxazole-4-carboxylic acid (0.41 g, 1.0 mmol), N-hydroxybenzotriazole (0.20 g, 1.5 mmol) and 1-ethyl-3-(3-dimethyllaminopropyl)carbodiimide hydrochloride (0.29 g, 1.5 mmol) in dichloromethane (10 mL) was stirred for 30 min, followed by the addition of cyclopropylamine (0.8 mL). The solution was stirred at ambient temperature for 16 h, diluted with dichloromethane (100 mL), washed with distilled water (2×50 mL), dried over magnesium sulfate, filtered and concentrated in vacuo to dryness. The residue was purified by flash chromatography with ethyl acetate in hexanes (gradient: 50% to 75%) to afford N-(1-methylethyl)-2-[(2'-oxospiro[furo[2,3-f][1,3]benzodioxole-7,3'-indol]-1'(2'H)-yl)methyl]-1,3-oxazole-4-carboxamide (0.40 g, 91%) as a colorless solid: mp 188-191° C.; $^1$H NMR (300 MHz, CDCl$_3$) δ8.14 (s, 1H), 7.28-7.22 (m, 1H), 7.19 (d, J=6.8 Hz, 1H), 7.07 (dd, J=7.4, 7.4 Hz, 1H), 6.85 (d, J=7.7 Hz, 2H), 6.49 (s, 1H), 6.16 (s, 1H), 5.85 (ABq, 2H), 5.04 (ABq, 2H), 4.81 (ABq, 2H), 2.82 (m, 1H), 0.85-0.77 (m, 2H), 0.64-0.58 (m, 2H); $^{13}$C NMR (75M Hz, CDCl$_3$) δ177.2, 161.3, 158.1, 155.8, 149.0, 142.4, 141.8, 141.0, 136.6, 132.0, 129.1, 124.15, 124.10, 119.2, 108.6, 103.0, 101.6, 93.7, 80.2, 58.2, 37.1, 22.3, 6.60, 6.55; MS (ES+) m/z 446.2 (M+1).

EXAMPLE 13.6

Synthesis of N-(1-methylethyl)-2-[(2'-oxospiro[furo[2,3-f][1,3]benzodioxole-7,3'-indol]-1'(2'H)-yl)methyl]-1,3-oxazole-4-carboxamide

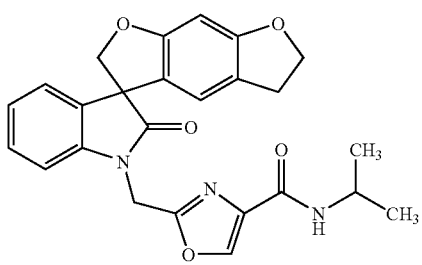

Following the procedure as described in EXAMPLE 13.5 and making non-critical variations using isopropylamine to replace cyclopropylamine, N-(1-methylethyl)-2-[(2'-oxospiro[furo[2,3-f][1,3]benzodioxole-7,3'-indol]-1'(2'H)-yl)methyl]-1,3-oxazole-4-carboxamide was obtained (17%) as a colorless solid: mp 182-183° C.; $^1$H NMR (300 MHz, CDCl$_3$) δ8.12 (s, 1H), 7.31-7.17 (m, 2H), 7.08 (dd, J=7.5, 7.5 Hz, 1H), 6.88 (s, J=7.8 Hz, 1H), 6.61 (d, J=7.5 Hz, 1H), 6.50 (s, 1H), 6.17 (s, 1H), 5.85 (d, J=4.6 Hz, 2H), 5.05 (ABq, 2H), 4.82 (ABq, 2H), 4.20 (m, 1H), 1.22 (d, J=6.5 Hz, 6H); $^{13}$C NMR (75 MHz, CDCl$_3$) δ177.2, 159.1, 158.0, 155.8, 149.1, 142.4, 141.8, 141.0, 136.9, 132.0, 129.1, 124.2, 119.2, 108.7, 103.0, 101.6, 93.7, 80.2, 58.2, 41.2, 37.1, 29.7, 22.7; MS (ES+) m/z 448.2 (M+1).

EXAMPLE 13.7

Synthesis of N-(2-fluorophenyl)-2-(2'-oxo-2,3-dihydrospiro[furo[2,3-g][1,4]benzodioxine-8,3'-indol]-1'(2'H)-yl)acetamide

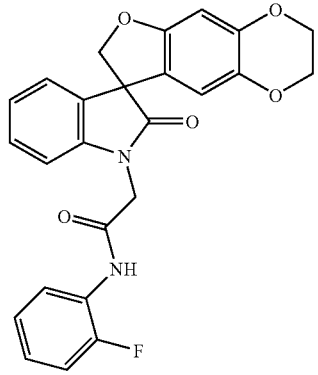

To a solution of (2'-oxo-2,3-dihydrospiro[furo[2,3-g][1,4]benzodioxine-8,3'-indol]-1'(2'H)-yl)acetic acid (0.53 g, 1.50 mmol), 2-fluoroaniline (0.2 mL, 2.1 mmol) and triethylamine (0.5 mL, 3.5 mmol) in chloroform (30 mL) was added 2-ethoxy-1-ethoxycarbonyl-1,2-dihydroquinoline (0.48 g, 1.94 mmol). The reaction mixture was heated at reflux for 26 h, allowed to cool to ambient temperature, diluted with ethyl acetate and washed sequentially with water, 10% w/v hydrochloric acid, water, 10% w/v aqueous sodium hydroxide, water and brine. The organic phase was dried over anhydrous sodium sulfate and filtered. The filtrate was concentrated in vacuo. The residue was purified by column chromatography and eluted with ethyl acetate/hexanes (1/3) to afford N-(2-fluorophenyl)-2-(2'-oxo-2,3-dihydrospiro[furo[2,3-g][1,4]benzodioxine-8,3'-indol]-1'(2'H)-yl)acetamide (0.08 g, 12%): mp 117-119° C. (ethyl acetate/hexanes); $^1$H NMR (300 MHz, CDCl$_3$) δ 8.24-8.22 (m, 1H), 8.05-7.90 (m, 1H), 7.33-6.95 (m, 6H), 6.50-6.47 (m, 1H), 6.33-6.30 (m, 1H), 4.94-4.89 (m, 1H), 4.68-4.49 (m, 4H), 4.17-4.09 (m, 4H); $^{13}$C NMR (75 MHz, CDCl$_3$) δ 178.2, 164.6, 155.2, 144.7, 141.3, 138.4, 131.9, 129.1, 125.6, 124.9, 121.8, 120.4, 115.0, 114.8, 111.7, 108.9, 99.4, 80.0, 64.6, 63.8, 58.0, 45.1; MS (ES+) m/z 446.8 (M+1).

EXAMPLE 13.8

Synthesis of 2-[(3-methyl-2'-oxospiro[furo[3,2-f][1,2]benzisoxazole-5,3'-indol]-1'(2'H)-yl)methyl]-1,3-oxazole-4-carboxylic acid

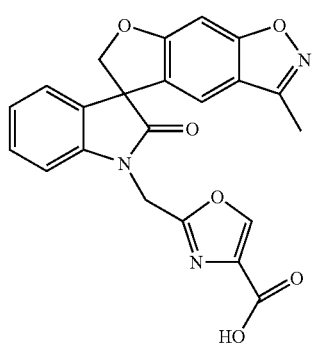

Following the procedure as described in EXAMPLE 13 and making non-critical variations using methyl 2-[(3-methyl-2'-oxospiro[furo[3,2-f][1,2]benzisoxazole-5,3'-indol]-1'(2'H)-yl)methyl]-1,3-oxazole-4-carboxylate to replace methyl 5-[(2'-oxo-5,6-dihydrospiro[benzo[1,2-b:5,4-b']difuran-3,3'-indol]-1'(2'H)-yl)methyl]furan-2-carboxylate, 2-[(3-methyl-2'-oxospiro[furo[3,2-f][1,2]benzisoxazole-5,3'-indol]-1'(2'H)-yl)methyl]-1,3-oxazole-4-carboxylic acid was obtained (69%) as a colorless solid: $^1$H NMR (300 MHz, DMSO-$d_6$) δ 13.13 (s, 1H), 8.70 (s, 1H), 7.74-7.71 (m, 1H), 7.40-7.34 (m, 1H), 7.26-7.23 (m, 2H), 7.07-7.02 (m, 2H), 5.28-5.22 (m, 2H), 5.00-4.90 (m, 2H), 2.39 (s, 3H); MS (ES+) m/z 417.8 (M+1).

EXAMPLE 13.9

Synthesis of N,N-dimethyl-2-[(3-methyl-2'-oxospiro[furo[3,2-f][1,2]benzisoxazole-5,3'-indol]-1'(2'H)-yl)methyl]-1,3-oxazole-4-carboxamide

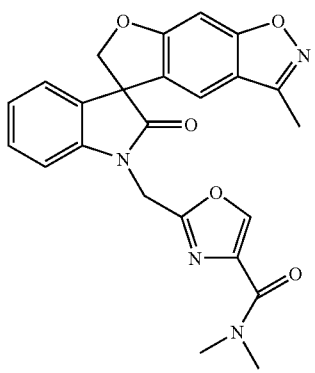

A mixture of 2-[(3-methyl-2'-oxospiro[furo[3,2-f][1,2]benzisoxazole-5,3'-indol]-1'(2'H)-yl)methyl]-1,3-oxazole-4-carboxylic acid (0.32 g, 0.76 mmol), dimethylamine hydrochloride (0.13 g, 1.52 mmol), 1-hydroxybenzotriazole hydrate (0.16 g, 1.17 mmol), 1-ethyl-3-(3-dimethylaminopropyl)-carbodiimide hydrochloride (0.21 g, 1.07 mmol), 4-methylmorpholine (0.23 mL, 2.07 mmol) and anhydrous N,N-dimethylformamide (10 mL) was stirred at ambient temperature for 16 h. The reaction mixture was concentrated in vacuo, and the residue recrystallized from diethyl ether to afford N,N-dimethyl-2-[(3-methyl-2'-oxospiro[furo[3,2-f][1,2]benzisoxazole-5,3'-indol]-1'(2'H)-yl)methyl]-1,3-oxazole-4-carboxamide (0.23 g, 68%) as a colorless solid: mp 87-89° C. (diethyl ether); $^1$H NMR (300 MHz, CDCl$_3$) δ 8.10 (s, 1H), 7.48-7.5 (m, 1H), 7.31-7.25 (m, 1H), 7.14-7.11 (m, 1H), 7.05-6.95 (m, 3H), 5.28-5.06 (m, 3H), 4.87-4.84 (m, 1H), 3.32 (s, 3H), 3.06 (s, 3H), 2.43 (s, 3H); $^{13}$C NMR (75 MHz, CDCl$_3$) δ 175.8, 164.0, 161.7, 158.2, 157.1, 154.9, 143.7, 141.3, 137.2, 130.1, 129.5, 124.0, 123.9, 123.2, 118.0, 109.3, 108.6, 107.9, 81.3, 56.3, 38.4, 37.5, 36.2, 9.8; MS (ES+) m/z 444.8 (M+1).

EXAMPLE 13.10

Synthesis of 1'-(3-aminopropyl)-5,6-dihydrospiro[benzo[1,2-b:5,4-b']difuran-3,3'-indol]

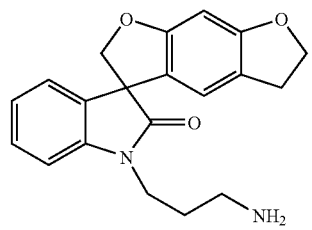

To a suspension of 2-[3-(2'-oxo-5,6-dihydrospiro[benzo[1,2-b:5,4-b']difuran-3,3'-indol]-1'(2'H)-yl)propyl]-1H-isoindole-1,3(2H)-dione (1.25 g, 2.70 mmol) in ethanol (25 mL) was added hydrazine monohydrate (0.70 mL, 8.2 mmol). The reaction mixture was stirred at ambient temperature for 3 days, over which time a precipitate was deposited. The solid was collected by filtration and purified by column chromatography and eluted with ethyl acetate/methanol/7 N methanolic ammonia (10/1/0.2) to afford 1'-(3-aminopropyl)-5,6-dihydrospiro[benzo[1,2-b:5,4-b']difuran-3,3'-indol]-2'(1'H)-one as a yellow oil: MS (ES+) m/z 336.9 (M+1).

EXAMPLE 13.11

Synthesis of N-[3-(2'-oxo-5,6-dihydrospiro[benzo[1,2-b:5,4-b']difuran-3,3'-indol]-1'(2'H)-yl)propyl]-2-(trifluoromethoxy)benzamide

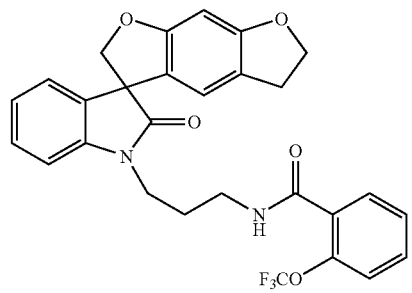

To a solution of 1'-(3-aminopropyl)-5,6-dihydrospiro[benzo[1,2-b:5,4-b']difuran-3,3'-indol]-2'(1'H)-one (0.20 g, 0.59 mmol) in anhydrous dichloromethane (10 mL) was added triethylamine (0.10 mL, 0.71 mmol) followed by 2-(trifluoromethoxy)benzoyl chloride. The reaction mixture was stirred at ambient temperature for 20 h and concentrated in vacuo. The residue was purified by column chromatography to afford N-[3-(2'-oxo-5,6-dihydrospiro[benzo[1,2-b:5,4-b']difuran-3,3'-indol]-1'(2'H)-yl)propyl]-2-(trifluoromethoxy)benzamide (0.21 g, 67%) as a colorless foam: mp 65-70° C.; $^1$H NMR (300 MHz, CDCl$_3$) δ 7.81 (dd, J=7.6, 1.7 Hz, 1H), 7.47 (ddd, J=9.4, 7.6, 1.5 Hz, 1H), 7.39-7.30 (m, 3H), 7.20 (d, J=6.9 Hz, 1H), 7.09 (dd, J=7.5, 7.5 Hz, 1H), 6.95 (d, J=7.9 Hz, 1H), 6.47 (s, 1H), 6.41 (s, 1H), 4.90 (d, J=9.0 Hz, 1H), 4.67 (d, J=9.0 Hz, 1H), 4.53 (t, J=8.6 Hz, 1H), 4.02-3.83 (m, 2H), 3.58-3.33 (m, 2H), 2.99 (t, J=8.6 Hz, 2H), 2.05-2.01 (m, 2H); $^{13}$C NMR (75 MHz, CDCl$_3$) δ 179.0, 164.9, 161.9, 161.3, 145.7, 141.8, 132.8, 131.8, 130.7, 129.3, 128.9, 127.3, 124.1, 123.7, 121.5, 120.3 (d, $J_{C-F}$=259.2 Hz), 120.0, 119.8, 118.7, 108.4, 93.3, 80.5, 72.4, 57.8, 37.1, 36.1, 29.0, 27.0; MS (ES+) m/z 524.5 (M+1).

EXAMPLE 14

Synthesis of 1'-[(2S)-2-hydroxypropyl]-5,6-dihydrospiro[benzo[1,2-b:5,4-b']difuran-3,3'-indol]-2'(1'H)-one

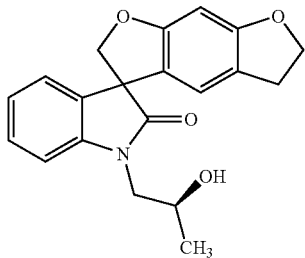

A stirred mixture of 1'-{(2S)-2-[(benzyloxy)methoxy]propyl}-5,6-dihydrospiro[benzo[1,2-b:5,4-b']difuran-3,3'-indol]-2'(1'H)-one (2.4 g, 5.2 mmol), palladium on carbon (0.24 g, 10% wt) and 3 M hydrochloric acid (5 mL) in absolute ethanol (50 mL) was hydrogenated for 6 h at 50 psi using a Parr hydrogenation apparatus. The mixture was filtered through celite and concentrated in vacuo to dryness. The residue was purified by flash chromatography with ethyl acetate in hexanes (25% to 50% gradient) to afford 1-[(2S)-2-hydroxypropyl]-5,6-dihydrospiro[benzo[1,2-b:5,4-b']difuran-3,3'-indol]-2'(1'H)-one (1.37 g, 78%) as a colorless solid: mp 171-174° C.; $^1$H NMR (300 MHz, DMSO-$d_6$) δ7.28 (dd, J=7.7, 7.7 Hz, 1H), 7.16 (d, J=7.4 Hz, 1H), 7.04 (dd, J=7.5, 7.5 Hz, 1H), 6.97 (dd, J=7.8, 3.5 Hz, 1H), 6.49 (d, J=10.2 Hz, 1H), 6.39 (d, J=1.4 Hz, 1H), 4.91 (dd, J=9.0, 0.5 Hz, 1H), 4.66 (dd, J=9.0, 0.6 Hz, 1H), 4.51 (dt, J=8.6, 1.0 Hz, 1H), 4.29-4.11 (m, 1H), 3.90-3.66 (m, 2H), 3.07-2.87 (m, 2H), 2.41 (dd, J=32.9, 5.5 Hz, 1H), 1.28 (dd, J=6.3, 1.1 Hz, 3H); $^{13}$C NMR (75 MHz, DMSO-$d_6$) δ179.2, 161.8 (2), 161.3 (2), 142.6 (2), 132.9 (2), 128.7 (2), 123.9 (2), 123.5, 120.2 (2), 120.0 (2), 118.8 (2), 108.9 (2), 93.2 (2), 80.6 (2), 72.4 (2), 66.5 (2), 57.8 (2), 48.1 (2), 29.0 (2), 21.4; MS (ES+) m/z 338.0 (M+1).

EXAMPLE 14.1

Synthesis of 1'-[(2S)-2-(benzyloxy)propyl]-5,6-dihydrospiro[benzo[1,2-b:5,4-b']difuran-3,3'-indol]-2'(1'H)-one

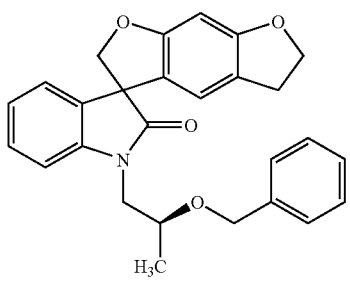

To a stirred solution of 1'-[(2S)-2-hydroxypropyl]-5,6-dihydrospiro[benzo[1,2-b:5,4-b']difuran-3,3'-indol]-2'(1'H)-one (0.19 mg, 0.56 mmol) in anhydrous tetrahydrofuran (10 mL) was added sodium hydride (60% dispersion in mineral oil, 0.03 g, 0.71 mmol). The solution was stirred at ambient temperature for 30 min, then benzylbromide (0.14 g, 0.84 mmol) was added. The reaction mixture was stirred for 16 h. The solution was cooled to ambient temperature, filtered and concentrated in vacuo to dryness. The residue was purified by flash chromatography with ethyl acetate in hexanes (25%) to afford 1'-[(2S)-2-(benzyloxy)propyl]-5,6-dihydrospiro[benzo[1,2-b:5,4-b']difuran-3,3'-indol]-2'(1'H)-one (0.20 g, 77%) as a colorless solid: mp 45-47° C.; $^1$H NMR (300 MHz, CDCl$_3$) (diastereomers) δ7.30-6.97 (m, 9H), 6.38 (s, 1H), 6.33 (d, J=36.0 Hz, 1H), 4.84 (dd, J=21.7, 8.9 Hz, 1H), 4.68-4.55 (m, 2H), 4.49 (dt, J=8.6, 0.8 Hz, 2H), 4.40 (dd, J=12.0, 3.8 Hz, 1H), 4.01-3.83 (m, 2H), 3.80-3.68 (m, 1H), 2.88 (t, J=8.6 Hz, 3H); $^{13}$C NMR (75 MHz, CDCl$_3$) (diastereomers) δ178.1 (2), 161.7 (2), 161.3 (2), 143.0 (2), 138.3 (2), 132.7, 128.6, 128.3 (2), 127.5 (2), 127.3, 123.6 (2), 123.2, 120.3 (2), 119.8 (2), 118.9 (2), 109.7 (2), 93.2, 80.7 (2), 73.2, 72.8, 72.4, 70.9, 70.7, 57.6, 46.1 (2), 29.0 (2), 17.7 (2); MS (ES+) m/z 428.0 (M+23).

EXAMPLE 14.2

Synthesis of 1'-{(2S)-2-[(4-fluorobenzyl)oxy]propyl}-5,6-dihydrospiro[benzo[1,2-b:5,4-b']difuran-3,3'-indol]-2'(1'H)-one

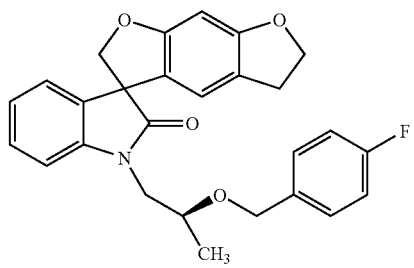

Following the procedure as described in EXAMPLE 14.1 and making non-critical variations using 4-fluorobenzyl bromide to replace benzylbromide, 1'-{(2S)-2-[(4-fluorobenzyl)oxy]propyl}-5,6-dihydrospiro[benzo[1,2-b:5,4-b']difuran-3,3'-indol]-2'(1'H)-one was obtained (70%) as a colorless solid: mp 55-60° C.; $^1$H NMR (300 MHz, CDCl$_3$) δ7.30-7.20 (m, 1H), 7.17-6.97 (m, 5H), 6.93-6.84 (m, 2H), 6.38 (s, 1H), 6.30 (d, J=36.9 Hz, 1H), 4.84 (dd, J=13.8, 8.9 Hz, 1H), 4.65-4.53 (m, 2H), 4.49 (dt, J=8.6, 1.2 Hz, 2H), 4.36 (dd, J=11.8, 5.4 Hz, 1H), 4.00-3.83 (m, 2H), 3.79-3.66 (m, 1H), 2.96-2.80 (m, 2H), 1.29 (d, J=6.0 Hz, 3H); $^{13}$C NMR (75 MHz, CDCl$_3$) δ178.1, 162.2, 161.3, 143.0, 134.0, 132.7, 129.0, 128.5, 123.7, 123.2, 120.2, 119.8, 118.8, 115.2, 114.9, 93.2, 80.6, 73.3, 72.9, 72.4, 70.0, 57.6, 46.0, 29.0, 17.6; MS (ES+) m/z 445.8 (M+1).

EXAMPLE 14.3

Synthesis of 1'-[(2S)-2-(pyridin-2-ylmethoxy)propyl]-5,6-dihydrospiro[benzo[1,2-b:5,4-b']difuran-3,3'-indol]-2'(1'H)-one

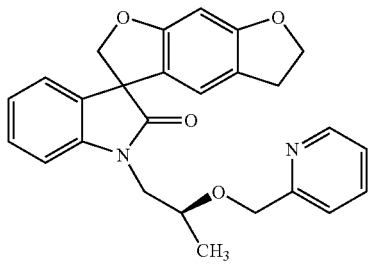

Following the procedure as described in EXAMPLE 14.1 and making non-critical variations using 2-(bromomethyl)pyridine hydrobromide to replace benzylbromide, 1'-[(2S)-2-(pyridin-2-ylmethoxy)propyl]-5,6-dihydrospiro[benzo[1,2-b:5,4-b']difuran-3,3'-indol]-2'(1'H)-one was obtained (69%) as a colorless solid: mp 46-54° C.; $^1$H NMR (300 MHz, CDCl$_3$) δ8.49-8.41 (m, 1H), 7.50 (m, 1H), 7.35-6.87 (m, 6H), 6.54-6.13 (m, 2H), 4.94-4.80 (m, 1H), 4.80-4.67 (m, 1H), 4.66-4.32 (m, 4H), 4.10-3.63 (m, 3H), 2.97-2.57 (m, 2H), 1.62-0.76 (m, 3H); $^{13}$C NMR (75 MHz, CDCl$_3$) δ178.1, 161.7, 158.5, 148.8, 143.0, 136.6, 132.7, 128.6, 123.7, 123.2, 122.2, 121.0, 120.3, 119.8, 118.8, 109.4, 93.1, 80.5, 73.5, 72.3, 71.7, 57.6, 45.9, 28.9, 17.5; MS (ES+) m/z 428.74 (M+1).

EXAMPLE 14.4

Synthesis of 1'-(3-hydroxybutyl)-5,6-dihydrospiro[benzo[1,2-b:5,4-b']difuran-3,3'-indol]-2'(1'H)-one

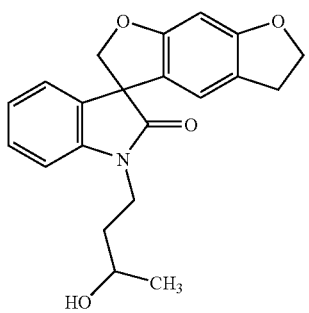

To a stirred solution of 3-(2'-oxo-5,6-dihydrospiro[benzo[1,2-b:5,4-b']difuran-3,3'-indol]-1'(2'H)-yl)propanal (0.34 g, 1.00 mmol) in tetrahydrofuran (10 mL) was added methylmagnesium bromide (0.35 mL, 3 M diethyl ether solution, 1.05 mmol) at 0° C. The reaction mixture was stirred at 0° C. for 3 h, quenched with saturated ammonium chloride solution, and extracted with ethyl acetate. The organic layer was washed with water, brine, dried over anhydrous sodium sulfate and filtered. The filtrate was concentrated in vacuo. The residue was subjected to column chromatography with ethyl acetate in hexanes (20% to 40% gradient) to afford 1-(3-hydroxybutyl)-5,6-dihydrospiro[benzo[1,2-b:5,4-b']difuran-3,3'-indol]-2'(1'H)-one (0.21 g, 59%): mp 64-66° C. (diethyl ether/hexanes); $^1$H NMR (300 MHz, CDCl$_3$) δ7.33-7.28 (m, 1H), 7.19-7.15 (m, 1H), 7.09-7.03 (m, 1H), 6.94 (d, J=6.0 Hz, 1H), 6.46-6.40 (m, 2H), 4.92-4.87 (m, 1H), 4.69-4.62 (m, 1H), 4.56-4.49 (m, 2H), 4.21-4.09 (m, 1H), 3.76-3.62 (m, 2H), 3.22 (br s, 1H), 3.03-2.95 (m, 2H), 1.88-1.63 (m, 2H), 1.24-1.19 (m, 3H); MS (ES+) m/z 352.1 (M+1).

EXAMPLE 14.5

Synthesis of 1'-(4,4,4-trifluoro-3-hydroxybutyl)-5,6-dihydrospiro[benzo[1,2-b:5,4-b']difuran-3,3'-indol]-2'(1'H)-one

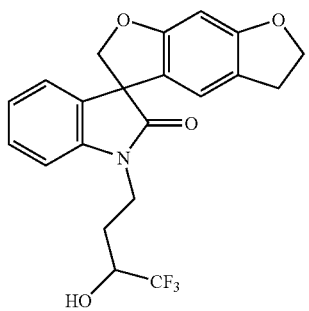

To a stirred solution of 3-(2'-oxo-5,6-dihydrospiro[benzo[1,2-b:5,4-b']difuran-3,3'-indol]-1'(2'H)-yl)propanal (0.34 g, 1.00 mmol) in tetrahydrofuran (10 mL) were added cesium fluoride (0.80 g, 5.26 mmol) and trifluoromethyltrimethylsilane (0.25 mL, 1.69 mmol) at −78° C. The reaction mixture was stirred for 18 h while the temperature was slowly warmed to ambient temperature, quenched with methanol, stirred for 1 h at ambient temperature, and extracted with ethyl acetate. The organic layer was washed with water, brine, dried over anhydrous sodium sulfate and filtered. The filtrate was concentrated in vacuo. The residue was subjected to column chromatography with ethyl acetate in hexanes (20% to 40% gradient) to give 1-(4,4,4-trifluoro-3-hydroxybutyl)-5,6-dihydrospiro[benzo[1,2-b:5,4-b']difuran-3,3'-indol]-2'(1'H)-one (0.24 g, 58%): mp 124-126° C. (diethyl ether/hexanes); $^1$H NMR (300 MHz, CDCl$_3$) δ7.36-7.31 (m, 1H), 7.22-7.19 (m, 1H), 7.13-7.08 (m, 1H), 6.94 (d, J=9.0 Hz, 1H), 6.45-6.41 (m, 2H), 4.89-4.70 (m, 1H), 4.67-4.63 (m, 1H), 4.56-4.49 (m, 2H), 4.24-4.10 (m, 1H), 4.01-3.73 (m, 3H), 3.02-2.95 (m, 2H), 2.11-2.05 (m, 2H); $^{13}$C NMR (75 MHz, CDCl$_3$) δ 179.5, 162.1, 162.0, 161.4, 161.3, 141.5, 132.7, 129.1, 124.3, 124.0, 120.2, 119.6, 118.8, 118.5, 108.4, 93.4, 80.3, 72.4, 67.8, 57.9, 36.2, 28.9; MS (ES+) m/z 405.7 (M+1).

EXAMPLE 15

Synthesis of 3-(2'-oxo-5,6-dihydrospiro[benzo[1,2-b:5,4-b']difuran-3,3'-indol]-1'(2'H)-yl)propanal

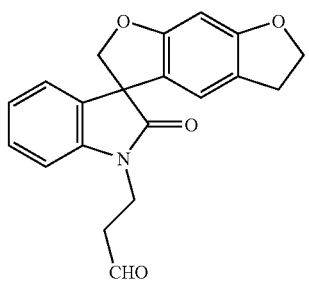

To a solution of 1'-(3-hydroxypropyl)-5,6-dihydrospiro[benzo[1,2-b:5,4-b']difuran-3,3'-indol]-2'(1'H)-one (2.00 g, 5.92 mmol) in dichloromethane (100 mL) was added Dess-Martin periodinane (3.70 g, 8.46 mmol). The reaction mixture was stirred at 0° C. for 17 h, diluted with ethyl acetate, washed with 10% sodium thiosulfate solution and saturated sodium bicarbonate solution and brine. The organic layer was dried over anhydrous sodium sulfate and filtered. The filtrate was concentrated in vacuo, the residue was subjected to column chromatography with ethyl acetate in hexanes (20% to 50% gradient) to afford 3-(2'-oxo-5,6-dihydrospiro[benzo[1,2-b:5,4-b']difuran-3,3'-indol]-1'(2'H)-yl)propanal (1.74 g, 87%): MS (ES+) m/z 336.1 (M+1).

EXAMPLE 15.1

Synthesis of 1'-{3-[(3-methylbutyl)amino]propyl}-5,6-dihydrospiro[benzo[1,2-b:5,4-b']difuran-3,3'-indol]-2'(1'H)-one hydrochloride

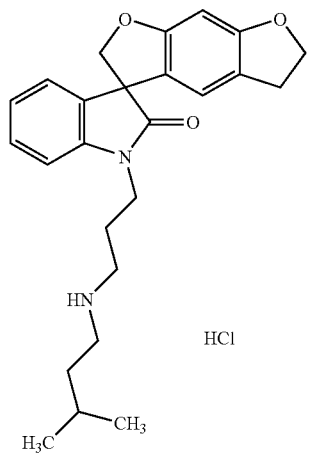

To a solution of 3-(2'-oxo-5,6-dihydrospiro[benzo[1,2-b:5,4-b']difuran-3,3'-indol]-1'(2'H)-yl)propanal (0.34 g, 1.00 mmol) and isoamylamine (0.20 mL, 1.72 mmol) in 1,2-dichloroethane (20 mL) was added sodium triacetoxy borohydride (0.43 g, 1.92 mmol). The reaction mixture was stirred at ambient temperature for 18 h. The reaction was quenched with saturated sodium bicarbonate solution, and extracted with dichloromethane. The combined organic solution was washed with water, brine, dried over anhydrous sodium sulfate and filtered. The filtrate was concentrated in vacuo, the residue was subjected to column chromatography with ethyl acetate in hexanes (30% plus 1% 7 M ammonia in methanol) to afford 1-{3-[(3-methylbutyl)amino]propyl}-5,6-dihydrospiro[benzo[1,2-b:5,4-b']difuran-3,3'-indol]-2'(1'H)-one (0.37 g, 91%). The compound was then converted to its hydrogen chloride salt (0.36 g) by treatment with hydrogen chloride (2 M solution in diethyl ether, 0.5 mL, 1.0 mmol): mp 98-101° C. (diethyl ether); $^1$H NMR (300 MHz, DMSO-d$_6$) δ 8.79 (br s, 2H), 7.32-7.03 (m, 4H), 6.49 (s, 1H), 6.38 (s, 1H), 4.71 (ABq, 2H), 4.49-4.43 (m, 2H), 3.82-3.65 (m, 2H), 2.94-2.82 (m, 6H), 2.00-1.96 (m, 2H), 1.60-1.41 (m, 3H), 0.83 (d, J=9 Hz, 6H); MS (ES+) m/z 407.2 (M+1).

EXAMPLE 15.2

Synthesis of 1'-{3-[butyl(methyl)amino]propyl}-5,6-dihydrospiro[benzo[1,2-b:5,4-b']difuran-3,3'-indol]-2'(1'H)-one hydrochloride

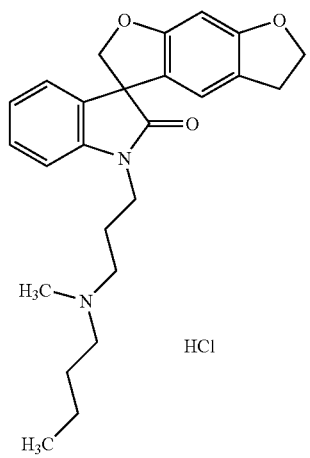

Following the procedure as described in EXAMPLE 15.1 and making non-critical variations using N-methylbutylamine to replace isoamylamine, 1-{3-[butyl(methyl)amino]propyl}-5,6-dihydrospiro[benzo[1,2-b:5,4-b']difuran-3,3'-indol]-2'(1'H)-one hydrochloride was obtained (80%) as a colorless solid: mp 96-99° C. (diethyl ether); $^1$H NMR (300 MHz, DMSO-d$_6$) δ 10.5 (br s, 1H), 7.35-7.00 (m, 4H), 6.49 (s, 1H), 6.37 (s, 1H), 4.71 (ABq, 2H), 4.49-4.43 (m, 2H), 4.15 (br, 1H), 3.82-3.73 (m, 2H), 3.12-2.89 (m, 6H), 2.69-2.63 (m, 2H), 2.12-1.97 (m, 2H), 1.66-1.52 (m, 2H), 1.32-1.20 (m, 2H), 0.85 (t, J=6.0 Hz, 3H); MS (ES+) m/z 407.2 (M+1).

EXAMPLE 15.3

Synthesis of 1'-{3-[(2,2,2-trifluoroethyl)amino]propyl}-5,6-dihydrospiro[benzo[1,2-b:5,4-b']difuran-3,3'-indol]-2'(1'H)-one hydrochloride

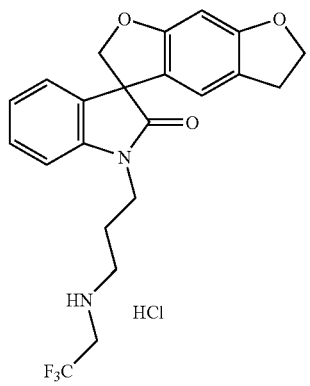

Following the procedure as described in EXAMPLE 15.1 and making non-critical variations using 2,2,2-trifluoroethylamine to replace isoamylamine, 1'-{3-[(2,2,2-trifluoroethyl)amino]propyl}-5,6-dihydrospiro[benzo[1,2-b:5,4-b']difuran-3,3'-indol]-2'(1'H)-one hydrochloride was obtained (86%) as a colorless solid: mp 124-126° C. (diethyl ether); $^1$H NMR (300 MHz, DMSO-d$_6$) δ 7.35-7.29 (m, 1H), 7.21-7.12 (m, 2H), 7.06-7.01 (m, 1H), 6.48 (s, 1H), 6.37 (s, 1H), 4.71

(AB, 2H), 4.49-4.43 (m, 2H), 4.06-3.97 (m, 2H), 3.87-3.70 (m, 2H), 3.04-2.89 (m, 4H), 2.11-2.00 (m, 2H); $^{13}$C NMR (75 MHz, DMSO-d$_6$) δ177.6, 161.6, 161.1, 142.6, 132.7, 129.2, 124.1, 123.4, 120.9, 120.3, 119.5, 92.9, 80.3, 72.5, 57.3, 46.0, 37.5, 28.8, 24.3, 22.5, 14.4; MS (ES+) m/z 419.1 (M+1).

EXAMPLE 15.4

Synthesis of 3-{[3-(2'-oxo-5,6-dihydrospiro[benzo[1,2-b:5,4-b']difuran-3,3'-indol]-1'(2'H)-yl)propyl]amino}propanenitrile hydrochloride

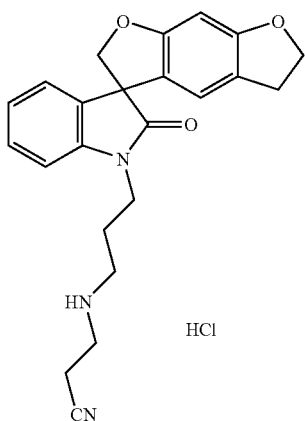

Following the procedure as described in EXAMPLE 15.1 and making non-critical variations using 3-aminopropiontrile to replace isoamylamine, 3-{[3-(2'-oxo-5,6-dihydrospiro[benzo[1,2-b:5,4-b']difuran-3,3'-indol]-1'(2'H)-yl)propyl]amino}propanenitrile hydrochloride was obtained (61%) as a colorless solid: mp 214-216° C. (diethyl ether); $^1$H NMR (300 MHz, DMSO-d$_6$) δ 7.33-7.29 (m, 1H), 7.20-7.12 (m, 2H), 7.04-6.99 (m, 1H), 6.45 (s, 1H), 6.37 (s, 1H), 4.65 (ABq, 2H), 4.49-4.43 (m, 2H), 3.82-3.69 (m, 2H), 3.01-2.76 (m, 8H), 1.92-1.79 (m, 2H); $^{13}$C NMR (75 MHz, DMSO-d$_6$) δ177.5, 161.6, 161.1, 142.8, 132.7, 129.2, 124.1, 123.4, 121.0, 120.3, 119.4, 109.5, 92.9, 80.2, 72.5, 57.3, 45.4, 43.6, 37.8, 28.8, 25.8, 16.2; MS (ES+) m/z 390.1 (M+1).

EXAMPLE 16

Synthesis of 4'-[6-(dimethylamino)pyridin-3-yl]-1'-[(2R)-tetrahydrofuran-2-ylmethyl]-5,6-dihydrospiro[benzo[1,2-b:5,4-b']difuran-3,3'-indol]-2'(1'H)-one

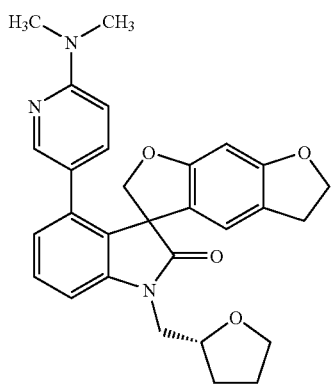

A stirred solution of 4'-bromo-1'-[(2R)-tetrahydrofuran-2-ylmethyl]-5,6-dihydrospiro[benzo[1,2-b:5,4-b']difuran-3,3'-indol]-2'(1'H)-one (0.125 g, 0.3 mmol), 2-(dimethylamino)pyridine 5-boronic acid hydrate (0.08 g, 0.45 mmol), tetrakis(triphenylphosphine)palladium(0) (0.04 g, 0.03 mmol), 2 M sodium carbonate (1 mL) in N,N-dimethylformamide (4 mL) was heated with stirring at 150° C. for 15 min in a microwave reactor. The solution was poured into distilled water (15 mL) and washed with ethyl acetate (75 mL). The ethyl acetate layer was washed with brine (3×25 mL), dried on magnesium sulfate, filtered and concentrated in vacuo to dryness. The residue was purified by flash chromatography with ethyl acetate in hexanes (gradient: 30% to 60%) to afford 4'-[6-(dimethylamino)pyridin-3-yl]-1'-[(2R)-tetrahydrofuran-2-ylmethyl]-5,6-dihydrospiro[benzo[1,2-b:5,4-b']difuran-3,3'-indol]-2'(1'H)-one (0.11 g, 73%) as a colorless solid: $^1$H NMR (300 MHz, DMSO-d$_6$) δ7.53 (d, J=2.4 Hz, 1H), 7.33 (dd, J=7.8 Hz, 1H), 7.18 (dd, J=7.4, 4.7 Hz, 1H), 6.77 (d, J=7.2 Hz, 1H), 6.71 (ddd, J=8.8, 2.4, 0.9 Hz, 1H), 6.51 (d, J=5.6 Hz, 1H), 6.31 (d, J=8.8 Hz, 1H), 6.12 (d, J=0.9 Hz, 1H), 4.59-4.41 (m, 3H), 4.33 (dd, J=9.4, 3.1 Hz, 1H), 4.23-4.08 (m, 1H), 3.89-3.55 (m, 4H), 3.09-2.86 (m, 2H), 2.95 (s, 6H), 2.05-1.69 (m, 3H), 1.67-1.51 (m, 1H); MS (ES+) m/z 484.1 (M+1).

EXAMPLE 16.1

Synthesis of 4'-[(E)-2-(4-fluorophenyl)ethenyl]-1'-[(2R)-tetrahydrofuran-2-ylmethyl]-5,6-dihydrospiro[benzo[1,2-b:5,4-b']difuran-3,3'-indol]-2'(1'H)-one

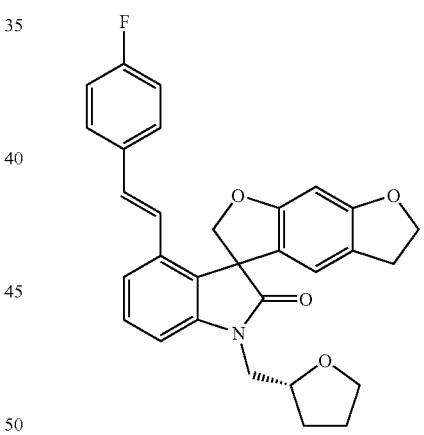

Following the procedure as described in EXAMPLE 16 and making non-critical variations using trans-2-(4-fluorophenyl)vinyl boronic acid to replace 2-(dimethylamino)pyridine 5-boronic acid hydrate, 4'-[(E)-2-(4-fluorophenyl)ethenyl]-1'-[(2R)-tetrahydrofuran-2-ylmethyl]-5,6-dihydrospiro[benzo[1,2-b:5,4-b']difuran-3,3'-indol]-2'(1'H)-one was obtained (47%) as a colorless solid: $^1$H NMR (300 MHz, DMSO-d$_6$) δ7.44-7.25 (m, 4H), 7.24-7.06 (m, 4H), 6.75 (d, J=16.4 Hz, 1H), 6.52 (s, 1H), 6.48 (s, 1H), 4.78 (ABq, J=26.1, 9.6 Hz, 2H), 4.52-4.36 (m, 2H), 4.23-4.09 (m, 1H), 3.90-3.54 (m, 4H), 2.92 (t, J=8.51, 8.51 Hz, 2H), 2.04-1.69 (m, 3H), 1.68-1.53 (m, 1H); MS (ES+) m/z 484.1 (M+1).

EXAMPLE 16.2

Synthesis of 4'-dibenzo[b,d]thiophen-4-yl-1'-[(2R)-tetrahydrofuran-2-ylmethyl]-5,6-dihydrospiro[benzo[1,2-b:5,4-b']difuran-3,3'-indol]-2'(1'H)-one

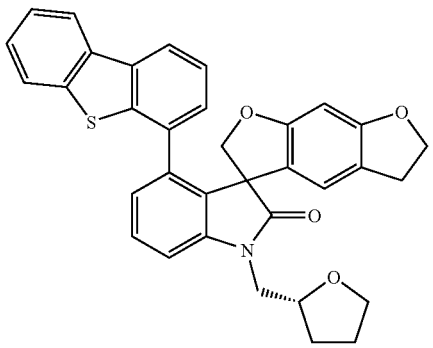

Following the procedure as described in EXAMPLE 16 and making non-critical variations using dibenzothiophene-4-boronic acid to replace 2-(dimethylamino)pyridine 5-boronic acid hydrate, 4'-dibenzo[b,d]thiophen-4-yl-t-[(2R)-tetrahydrofuran-2-ylmethyl]-5,6-dihydrospiro[benzo[1,2-b:5,4-b']difuran-3,3'-indol]-2'(1'H)-one was obtained (45%) as a colorless solid: $^1$H NMR (300 MHz, DMSO-$d_6$) (diastereomers) δ 8.53-8.02 (m, 2H), 8.02-7.70 (m, 1H), 7.67-7.21 (m, 5H), 7.20-6.91 (m, 2H), 6.59 (s, 0.5H), 6.19 (s, 1H), 5.96 (s, 0.5H), 5.28 (s, 0.5H), 5.01-4.76 (m, 0.5H), 4.68-4.31 (m, 2H), 4.29-4.13 (m, 1H), 4.11-3.52 (m, 5H), 3.20-2.67 (m, 2H), 2.13-1.71 (m, 3H), 1.71-1.50 (m, 1H); MS (ES+) m/z 546.0 (M+1).

EXAMPLE 16.3

Synthesis of 4'-(1-benzothiophen-3-yl)-1'-[(2R)-tetrahydrofuran-2-ylmethyl]-5,6-dihydrospiro[benzo[1,2-b:5,4-b']difuran-3,3'-indol]-2'(1'H)-one

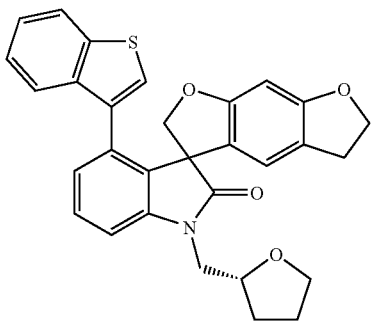

Following the procedure as described in EXAMPLE 16 and making non-critical variations using thianaphthene-3-boronic acid to replace 2-(dimethylamino)pyridine 5-boronic acid hydrate, 4'-(1-benzothiophen-3-yl)-1'-[(2R)-tetrahydrofuran-2-ylmethyl]-5,6-dihydrospiro[benzo[1,2-b:5,4-b']difuran-3,3'-indol]-2'(1'H)-one was obtained (49%) as a colorless solid: $^1$H NMR (300 MHz, DMSO-$d_6$) δ7.86 (d, J=7.2 Hz, 1H), 7.57-6.70 (m, 7H), 6.48-6.31 (br s, 1H), 5.76 (br s, 1H), 4.52-4.09 (m, 5H), 3.93-3.57 (m, 4H), 2.97-2.66 (m, 2H), 2.05-1.71 (m, 3H), 1.70-1.54 (m, 1H); MS (ES+) m/z 496.1 (M+1).

EXAMPLE 16.4

Synthesis of 4'-(1-methyl-1H-indol-5-yl)-1'-[(2R)-tetrahydrofuran-2-ylmethyl]-5,6-dihydrospiro[benzo[1,2-b:5,4-b']difuran-3,3'-indol]-2'(1'H)-one

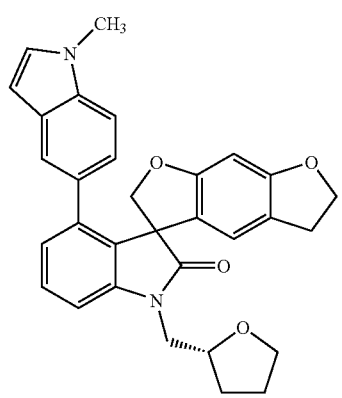

Following the procedure as described in EXAMPLE 16 and making non-critical variations using 1-methyl-5-(4,4,5,5-tetramethyl-1,3,2-dioxaborolen-2-yl)-1H-indole to replace 2-(dimethylamino)pyridine 5-boronic acid hydrate, 4'-(1-methyl-1H-indol-5-yl)-1'-[(2R)-tetrahydrofuran-2-ylmethyl]-5,6-dihydrospiro[benzo[1,2-b:5,4-b']difuran-3,3'-indol]-2'(1'H)-one was obtained (65%) as a colorless solid: $^1$H NMR (300 MHz, DMSO-$d_6$) δ7.34 (dd, J=7.8, 7.82 Hz, 1H), 7.26 (d, J=3.0 Hz, 1H), 7.23-7.14 (m, 2H), 6.85 (d, J=7.2 Hz, 1H), 6.73-6.71 (m, 1H), 6.63-6.57 (m, 2H), 6.09 (d, J=3.0 Hz, 1H), 6.03 (s, 1H), 4.62-4.46 (m, 2H), 4.40 (dd, J=9.2, 2.7 Hz, 1H), 4.26-4.12 (m, 1H), 4.09 (dd, J=9.2, 1.1 Hz, 1H), 3.92-3.56 (m, 4H), 3.79 (s, 3H), 3.16-2.90 (m, 2H), 2.04-1.71 (m, 3H), 1.69-1.54 (m, 1H); MS (ES+) m/z 493.2 (M+1).

EXAMPLE 16.5

Synthesis of 4'-[3,5-bis(trifluoromethyl)phenyl]-1'-[(2R)-tetrahydrofuran-2-ylmethyl]-5,6-dihydrospiro[benzo[1,2-b:5,4-b']difuran-3,3'-indol]-2'(1'H)-one

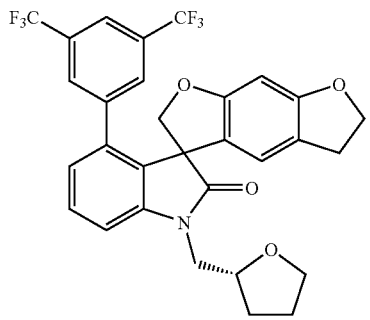

Following the procedure as described in EXAMPLE 16 and making non-critical variations using 3,5-bis(trifluorom ethyl)phenyl boronic acid to replace 2-(dimethylamino)pyridine 5-boronic acid hydrate, 4'-[3,5-bis(trifluoromethyl)phenyl]-1'-[(2R)-tetrahydrofuran-2-ylmethyl]-5,6-dihydrospiro[benzo[1,2-b:5,4-b']difuran-3,3'-indol]-2'(1'H)-one was obtained (40%) as a colorless solid: $^1$H NMR (300 MHz, CDCl$_3$) δ7.73 (s, 1H), 7.36 (dd, J=7.9, 7.9 Hz, 1H), 7.26-7.23 (m, 2H), 7.19 (dd, J=7.2, 7.2 Hz, 1H), 6.83 (d, J=7.7 Hz, 1H), 6.53 (s, 1H), 5.90 (s, 1H), 4.70 (d, J=8.9 Hz, 1H), 4.51 (t, J=8.9, 8.9 Hz, 2H), 4.39 (d, J=9.1 Hz, 1H), 4.34-4.23 (m, 1H), 4.05-3.67 (m, 4H), 2.98 (t, J=8.5 Hz, 2H), 2.15-1.83 (m, 3H), 1.79-1.65 (m, 1H); MS (ES+) m/z 576.1 (M+1).

EXAMPLE 16.6

Synthesis of 4'-(4-phenoxyphenyl)-1'-[(2R)-tetrahydrofuran-2-ylmethyl]-5,6-dihydrospiro[benzo[1,2-b:5,4-b']difuran-3,3'-indol]-2'(1'H)-one

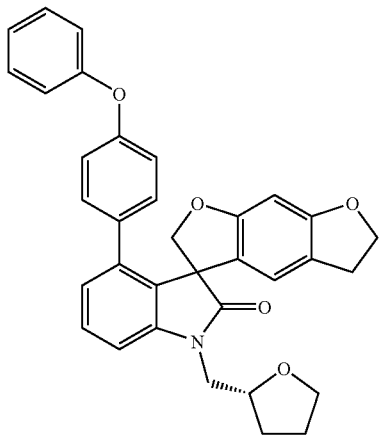

Following the procedure as described in EXAMPLE 16 and making non-critical variations using p-phenoxyphenyl boronic acid to replace 2-(dimethylamino)pyridine 5-boronic acid hydrate, 4'-(4-phenoxyphenyl)-1'-[(2R)-tetrahydrofuran-2-ylmethyl]-5,6-dihydrospiro[benzo[1,2-b:5,4-b']difuran-3,3'-indol]-2'(1'H)-one was obtained (35%) as a colorless solid: $^1$H NMR (300 MHz, DMSO-d$_6$) δ7.42-7.30 (m, 3H), 7.22 (dd, J=7.6, 4.3 Hz, 1H), 7.11 (dd, J=7.4, 7.4 Hz, 1H), 6.95 (d, J=8.4 Hz, 2H), 6.82 (d, J=7.6 Hz, 1H), 6.78-6.70 (m, 4H), 6.50 (d, J=5.8 Hz, 1H), 6.03 (s, 1H), 4.54-4.33 (m, 4H), 4.25-4.10 (m, 1H), 3.90-3.55 (m, 4H), 3.08-2.83 (m, 2H), 2.05-1.70 (m, 3H), 1.68-1.54 (m, 1H); MS (ES+) m/z 532.1 (M+1).

EXAMPLE 16.7

Synthesis of 4'-[4-(2-methylpropoxy)phenyl]-1'-[(2R)-tetrahydrofuran-2-ylmethyl]-5,6-dihydrospiro[benzo[1,2-b:5,4-b']difuran-3,3'-indol]-2'(1'H)-one

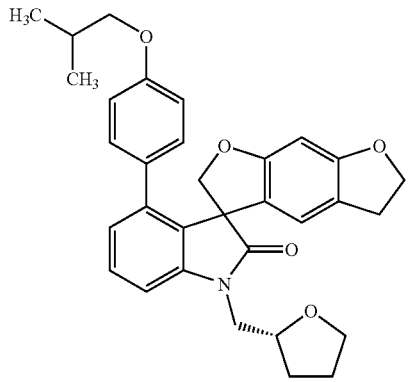

Following the procedure as described in EXAMPLE 16 and making non-critical variations using p-(2-methylpropoxy)phenyl boronic acid to replace 2-(dimethylamino)pyridine 5-boronic acid hydrate, 4'-[4-(2-methylpropoxy)phenyl]-1'-[(2R)-tetrahydrofuran-2-ylmethyl]-5,6-dihydrospiro[benzo[1,2-b:5,4-b']difuran-3,3'-indol]-2'(1'H)-one was obtained (34%) as a colorless solid: $^1$H NMR (300 MHz, CDCl$_3$) δ7.31 (dd, J=7.8, 7.8 Hz, 1H), 7.08 (ddd, J=10.3, 7.9, 0.9 Hz, 1H), 6.88 (d, J=7.7 Hz, 1H), 6.71-6.62 (m, 4H), 6.58 (s, 1H), 6.18-6.15 (m, 1H), 4.68-4.48 (m, 3H), 4.39-4.23 (m, 2H), 4.07-3.57 (m, 6H), 3.13-2.92 (m, 2H), 2.14-1.81 (m, 4H), 1.80-1.66 (m, 1H), 1.00 (dd, J=6.7, 1.2 Hz, 6H); MS (ES+) m/z 512.2 (M+1).

EXAMPLE 16.8

Synthesis of 4'-(4-butoxyphenyl)-1'-[(2R)-tetrahydrofuran-2-ylmethyl]-5,6-dihydrospiro[benzo[1,2-b:5,4-b']difuran-3,3'-indol]-2'(1'H)-one

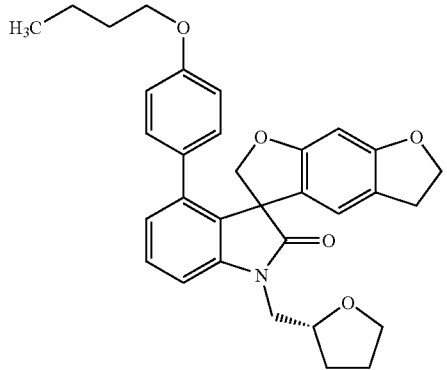

Following the procedure as described in EXAMPLE 16 and making non-critical variations using p-butoxylphenyl boronic acid to replace 2-(dimethylamino)pyridine 5-boronic acid hydrate, 4'-(4-butoxyphenyl)-1'-[(2R)-tetrahydrofuran-2-ylmethyl]-5,6-dihydrospiro[benzo[1,2-b:5,4-b']difuran-3,3'-indol]-2'(1'H)-one was obtained (34%) as a colorless solid: $^1$H NMR (300 MHz, CDCl$_3$) δ7.31 (dd, J=7.8, 7.8 Hz, 1H), 7.14-7.03 (m, 1H), 6.88 (d, J=7.7 Hz, 1H), 6.72-6.61 (m, 4H), 6.58 (s, 1H), 6.16 (s, 1H), 4.69-4.46 (m, 3H), 4.39-4.23 (m, 2H), 4.09-3.56 (m, 6H), 3.14-2.92 (m, 2H), 2.14-1.82 (m, 3H), 1.81-1.65 (m, 3H), 1.55-1.40 (m, 2H), 0.96 (t, J=7.3 Hz, 3H); MS (ES+) m/z 512.1 (M+1).

EXAMPLE 16.9

Synthesis of 4'-(4-methoxyphenyl)-1'-[(2R)-tetrahydrofuran-2-ylmethyl]-5,6-dihydrospiro[benzo[1,2-b:5,4-b']difuran-3,3'-indol]-2'(1'H)-one

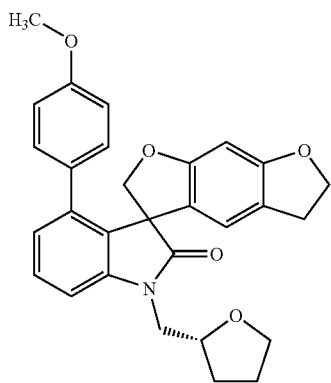

Following the procedure as described in EXAMPLE 16 and making non-critical variations using p-methoxyphenyl boronic acid to replace 2-(dimethylamino)pyridine 5-boronic acid hydrate, 4'-(4-methoxyphenyl)-1'-[(2R)-tetrahydrofuran-2-ylmethyl]-5,6-dihydrospiro[benzo[1,2-b:5,4-b']difuran-3,3'-indol]-2'(1'H)-one was obtained (41%) as a colorless solid: $^1$H NMR (300 MHz, CDCl$_3$) δ7.32 (dd, J=7.8, 7.8 Hz, 1H), 7.19 (dd, J=7.2, 4.8 Hz, 1H), 6.78 (d, J=7.1 Hz, 1H), 6.70-6.59 (m, 4H), 6.52 (d, J=5.2 Hz, 1H), 6.11 (s, 1H), 4.58-4.40 (m, 3H), 4.26-4.09 (m, 2H), 3.90-3.54 (m, 7H), 3.09-2.87 (m, 2H), 2.05-1.70 (m, 3H), 1.68-1.54 (m, 1H); MS (ES+) m/z 469.9 (M+1).

EXAMPLE 16.10

Synthesis of 4'-pyrimidin-5-yl-1'-[(2R)-tetrahydrofuran-2-ylmethyl]-5,6-dihydrospiro[benzo[1,2-b:5,4-b']difuran-3,3'-indol]-2'(1'H)-one

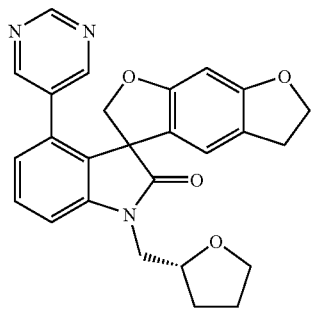

Following the procedure as described in EXAMPLE 16 and making non-critical variations using pyrimidine-5-boronic acid to replace 2-(dimethylamino)pyridine 5-boronic acid hydrate, 4'-pyrimidin-5-yl-1'-[(2R)-tetrahydrofuran-2-ylmethyl]-5,6-dihydrospiro[benzo[1,2-b:5,4-b']difuran-3,3'-indol]-2'(1'H)-one was obtained (38%) as a colorless solid: $^1$H NMR (300 MHz, CDCl$_3$) δ9.08 (s, 1H), 8.12 (d, J=1.16 Hz, 1H), 7.38 (dd, J=7.8, 7.8 Hz, 2H), 7.24-7.16 (m, 1H), 6.83 (d, J=7.6 Hz, 1H), 6.58-6.53 (m, 1H), 6.04 (s, 1H), 4.72 (dd, J=9.3, 1.3 Hz, 1H), 4.63-4.46 (m, 2H), 4.39 (dd, J=9.3, 1.3 Hz, 1H), 4.35-4.23 (m, 1H), 4.06-3.65 (m, 4H), 3.01 (t, J=8.6 Hz, 2H), 2.16-1.84 (m, 3H), 1.79-1.63 (m, 1H); MS (ES+) m/z 442.0 (M+1).

EXAMPLE 16.11

Synthesis of 4'-[6-(dimethylamino)pyridin-3-yl]-1'-{[5-(trifluoromethyl)furan-2-yl]methyl}-5,6-dihydrospiro[benzo[1,2-b:5,4-b']difuran-3,3'-indol]-2'(1'H)-one

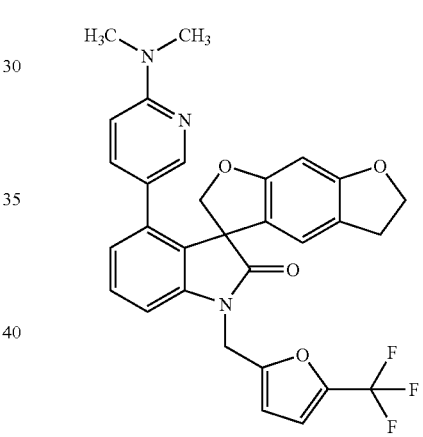

Following the procedure as described in EXAMPLE 16 and making non-critical variations using 4'-bromo-1'-{[5-(trifluoromethyl)furan-2-yl]methyl}-5,6-dihydrospiro[benzo[1,2-b:5,4-b']difuran-3,3'-indol]-2'(1'H)-one to replace 4'-bromo-1'-[(2R)-tetrahydrofuran-2-ylmethyl]-5,6-dihydrospiro[benzo[1,2-b:5,4-b']difuran-3,3'-indol]-2'(1'H)-one, 4'-[6-(dimethylamino)pyridin-3-yl]-1'-{[5-(trifluoromethyl)furan-2-yl]methyl}-5,6-dihydrospiro[benzo[1,2-b:5,4-b']difuran-3,3'-indol]-2'(1'H)-one was obtained (73%) as a colorless solid: mp 223-225° C.; $^1$H NMR (300 MHz, CDCl$_3$) δ 7.82-7.77 (m, 1H), 7.32 (dd, J=7.8, 7.8 Hz, 1H), 7.25-7.23 (m, 1H), 6.93 (dd, J=16.6, 7.8 Hz, 2H), 6.78-6.71 (m, 1H), 6.65-6.58 (m, 1H), 6.53 (s, 1H), 6.44 (d, J=2.5 Hz, 1H), 6.28-6.16 (m, 2H), 5.19 (d, J=16.1 Hz, 1H), 4.78 (d, J=16.2 Hz, 1H), 4.71 (d, J=9.2 Hz, 1H), 4.64-4.50 (m, 2H), 4.47 (d, J=9.2 Hz, 1H), 3.07-2.97 (m, 8H); MS (ES+) m/z 548.0 (M+1).

EXAMPLE 16.12

Synthesis of 1'-[(5-chloro-2-thienyl)methyl]-4'-[6-(dimethylamino)pyridin-3-yl]spiro[furo[2,3-f][1,3]benzodioxole-7,3'-indol]-2'(1'H)-one

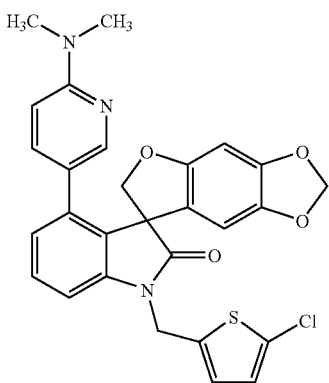

A round bottom flask (25 mL) equipped with condenser was charged with 4'-bromo-1'-[(5-chloro-2-thienyl)methyl]spiro[furo[2,3-f][1,3]benzodioxole-7,3'-indol]-2'(1'H)-one (0.18 g, 0.50 mmol), 6-(dimethylamino)pyridin-3-ylboronic acid (0.084 g, 0.75 mmol) and tetrakis(triphenylphosphine)palladium(0) (0.06 g, 10 mol %). The flask was flushed with nitrogen for 5 min, then anhydrous dioxane (7 mL) and 2 M sodium carbonate (0.5 mL). The reaction mixture was heated at reflux for 16 h, cooled to ambient temperature and the solvent was removed under reduced pressure. The residue was dissolved in ethyl acetate (20 mL), washed with saturated ammonium chloride (10 mL), brine (10 mL), dried over anhydrous sodium sulfate and filtered. The filtrate was concentrated in vacuo to dryness. The residue was purified by flash column chromatography with ethyl acetate in hexanes (70%) to afford 1-[(5-chloro-2-thienyl)methyl]-4'-[6-(dimethylamino)pyridin-3-yl]spiro[furo[2,3-f][1,3]benzodioxole-7,3'-indol]-2'(1'H)-one (0.10 g, 70%) as a colourless solid: mp 215-218° C.; $^1$H NMR (300 MHz, DMSO-$d_6$) δ 7.54 (d, J=2.0 Hz, 1H), 7.34 (dd, J=7.8, 7.8 Hz, 1H), 7.22 (d, J=7.2 Hz, 1H), 7.13 (d, J=3.8 Hz, 1H), 6.98 (d, J=3.8 Hz, 1H), 6.80 (d, J=8.0 Hz, 1H), 6.74 (dd, J=8.8, 2.5 Hz, 1H), 6.38 (s, 1H), 6.33 (d, J=8.8 Hz, 1H), 6.20 (s, 1H), 5.93 (d, J=18.0 Hz, 2H), 5.05 (ABq, 2H), 4.44 (ABq, 2H), 2.95 (s, 6H); $^{13}$C NMR (75 MHz, DMSO-$d_6$) δ 177.5, 158.4, 156.0, 148.9, 147.1, 142.3, 142.0, 138.4, 137.6, 137.3, 129.6, 129.4, 128.2, 127.9, 127.1, 126.1, 122.1, 121.1, 109.0, 104.7, 102.8, 101.9, 93.7, 77.9, 58.2, 38.1, 31.2; MS (ES+) m/z 534.1 (M+1), 532.2 (M+1).

EXAMPLE 16.13

Synthesis of 1'-[(5-chloro-2-thienyl)methyl]-4'-(3-furyl)spiro[furo[2,3-f][1,3]benzodioxole-7,3'-indol]-2'(1'1-1)-one

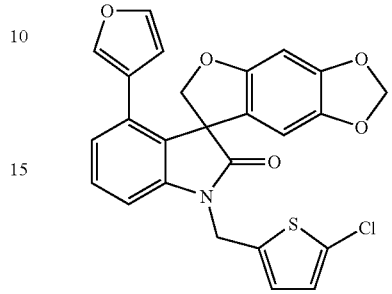

Following the procedure as described in EXAMPLE 16.12 and making non-critical variations using 3-furanboronic acid to replace 6-(dimethylamino)pyridin-3-ylboronic acid, 1-[(5-chloro-2-thienyl)methyl]-4'-(3-furyl)spiro[furo[2,3-f][1,3]benzodioxole-7,3'-indol]-2'(1'H)-one was obtained (95%) as a colorless solid: mp 166-168° C.; $^1$H NMR (300 MHz, DMSO-$d_6$) δ 7.57 (dd, J=1.7, 1.7 Hz, 1H), 7.34 (dd, J=7.9, 7.9 Hz, 1H), 7.20 (d, J=7.2 Hz, 1H), 7.11 (d, J=3.8 Hz, 1H), 7.04 (s, 1H), 6.99-6.96 (m, 2H), 6.77 (s, 1H), 6.19 (s, 1H), 6.03 (dd, J=1.7, 0.8 Hz, 1H), 5.93 (d, J=2.7 Hz, 2H), 5.04 (ABq, 2H), 4.55 (ABq, 2H); $^{13}$C NMR (75 MHz, DMSO-$d_6$) δ177.4, 156.2, 149.1, 143.8, 142.9, 142.0, 140.6, 138.4, 130.7, 129.6, 128.2, 127.7, 127.0, 125.6, 122.9, 120.8, 111.4, 109.3, 102.9, 102.0, 93.9, 77.6, 58.1, 39.1; MS (ES+) m/z 480.3 (M+1), 478.3 (M+1).

EXAMPLE 16.14

Synthesis of 4'-[6-(dimethylamino)pyridin-3-yl]spiro[furo[2,3-f][1,3]benzodioxole-7,3'-indol]-2'(1'H)-one

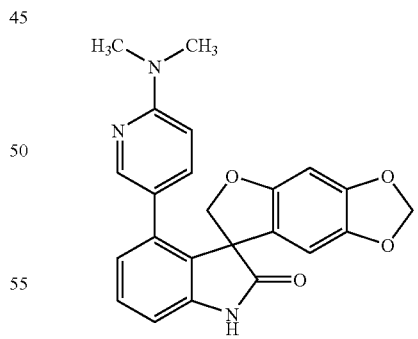

To a suspended mixture of 4'-bromospiro[furo[2,3-f][1,3]benzodioxole-7,3'-indol]-2'(1'H)-one (1.00 g, 2.78 mmol), 6-(dimethylamino)pyridin-3-ylboronic acid (0.69 g, 4.17 mmol) and tetrakis(triphenylphosphine)palladium (0) (0.32 g, 0.28 mmol) in N,N-dimethylformamide (30 mL) was added aqueous 2 M sodium carbonate (2.8 mL, 5.6 mmol).

The reaction mixture was refluxed for 3 h. The solid was filtered and washed with ethyl acetate (40 mL). The filtrate was concentrated in vacuo to dryness. The residue was purified by column chromatography with ethyl acetate in hexanes (20% to 50% gradient) to afford 4'-[6-(dimethylamino)pyridin-3-yl]spiro[furo[2,3-f][1,3]benzodioxole-7,3'-indol]-2'(1'H)-one (0.60 g, 54%) as a white powder: mp>245° C. (ethyl acetate); $^1$H NMR (300 MHz, DMSO-$d_6$) δ10.69 (s, 1H), 7.59 (d, J=2.4 Hz, 1H), 7.29 (dd, J=7.8, 7.8 Hz, 1H), 6.93 (d, J=7.8 Hz, 1H), 6.79-6.74 (m, 2H), 6.40-6.35 (m, 3H), 5.95 (d, J=19.9 Hz, 2H), 4.52 (d, J=9.3 Hz, 1H), 4.36 (d, J=9.3 Hz, 1H), 2.99 (s, 6H); $^{13}$C NMR (75 MHz, DMSO-$d_6$) δ 178.8, 157.9, 155.5, 148.1, 146.6, 142.2, 141.5, 137.0, 136.8, 129.8, 128.9, 124.4, 121.9, 121.2, 109.0, 104.2, 102.5, 101.3, 93.1, 77.5, 58.2, 37.6; MS (ES+) m/z 402.3 (M+1).

EXAMPLE 16.15

Synthesis of 1'-methyl-4'-(2-oxo-2H-chromen-7-yl)-2,3-dihydrospiro[furo[2,3-g][1,4]benzodioxine-8,3'-indol]-2'(1'H)-one

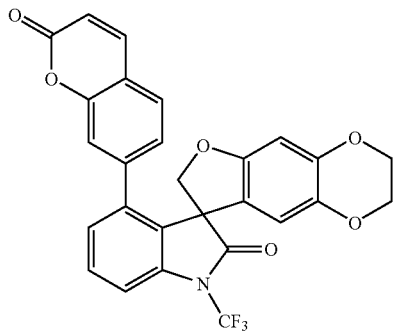

Following the procedure as described in EXAMPLE 16 and making non-critical variations using 4'-bromo-1'-methyl-2,3-dihydrospiro[furo[2,3-g][1,4]benzodioxine-8,3'-indol]-2'(1'H)-one to replace 4'-bromo-1'-[(2R)-tetrahydrofuran-2-ylmethyl]-5,6-dihydrospiro[benzo[1,2-b:5,4-b']difuran-3,3'-indol]-2'(1'H)-one, and 7-(4,4,5,5-tetramethyl-1,3,2-dioxaborolan-2-yl)-2H-chromen-2-one (Isihiyama et al., *Tetrahedron Lett.* (1997) 38:3447-3450) to replace 2-(dimethylamino)pyridine 5-boronic acid hydrate, 1-methyl-4'-(2-oxo-2H-chromen-7-yl)-2,3-dihydrospiro[furo[2,3-g][1,4]benzodioxine-8,3'-indol]-2'(1'H)-one was obtained (55%) as an off-white solid: mp 228-229° C. (hexanes/ethyl acetate); $^1$H NMR (300 MHz, CDCl$_3$) δ7.71-7.63 (m, 1H), 7.42-7.36 (m, 1H), 7.32-7.27 (m, 1H), 6.99-6.94 (m, 1H), 6.93-6.86 (m, 1H), 6.80-6.74 (m, 1H), 6.69-6.64 (m, 1H), 6.43-6.36 (m, 1H), 6.34-6.29 (m, 1H), 6.00-5.94 (m, 1H), 4.67-4.60 (m, 1H), 4.35-4.04 (m, 5H), 3.32 (s, 3H); $^{13}$C NMR (75 MHz, CDCl$_3$) δ 177.5, 160.5, 155.3, 153.1, 145.0, 143.2, 143.1, 142.1, 138.3, 138.2, 129.8, 128.9, 126.9, 124.8, 124.5, 121.1, 117.7, 117.1, 116.6, 111.2, 108.2, 98.8, 78.4, 64.5, 63.9, 58.3, 26.9; MS (ES+) m/z 453.8 (M+1).

EXAMPLE 16.16

Synthesis of 1'-methyl-4'-(2-oxopyrrolidin-1-yl)-2,3-dihydrospiro[furo[2,3-g][1,4]benzodioxine-8,3'-indol]-2'(1'H)-one

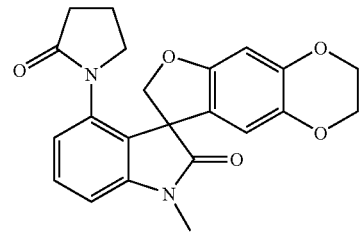

To a degassed solution of 4'-bromo-1'-methyl-2,3-dihydrospiro[furo[2,3-g][1,4]benzodioxine-8,3'-indol]-2'(1'H)-one (1.00 g, 2.57 mmol), 2-pyrrolidinone (0.30 mL, 3.9 mmol), potassium carbonate (0.71 g, 5.1 mmol) and rac-trans-N,N' dimethylcyclohexane-1,2-diamine (0.10 mL, 0.63 mmol) in dimethyl sulfoxide (20 mL) was added copper(I) iodide (0.06 g, 0.31 mmol). The mixture was stirred at 150° C. under nitrogen for 48 h, allowed to cool to ambient temperature, diluted with ethyl acetate and washed sequentially with 10% v/v ammonium hydroxide, water and brine. The organic phase was dried over anhydrous sodium sulfate and filtered. The filtrate was concentrated in vacuo. The residue was subjected to column chromatography and eluted with ethyl acetate to afford 1-methyl-4'-(2-oxopyrrolidin-1-yl)-2,3-dihydrospiro[furo[2,3-g][1,4]benzodioxine-8,3'-indol]-2'(1'H)-one (0.28 g, 28%): mp 256-258° C. (ethyl acetate/hexanes); $^1$H NMR (300 MHz, CDCl$_3$) δ 7.38-7.32 (m, 1H), 6.90-6.87 (m, 1H), 6.78-6.76 (m, 1H), 6.44 (s, 1H), 6.23 (s, 1H), 4.84 (ABq, 2H), 4.18-4.06 (m, 4H), 3.34-3.24 (m, 4H), 2.56-2.27 (m, 3H), 1.98-1.80 (m, 2H); $^{13}$C NMR (75 MHz, CDCl$_3$) δ 177.1, 175.9, 155.6, 144.7, 143.9, 138.1, 135.5, 131.4, 130.3, 122.8, 119.8, 111.5, 108.5, 98.8, 78.3, 64.5, 63.9, 57.7, 50.6, 30.6, 27.1, 18.8; MS (ES+) m/z 393.1 (M+1).

EXAMPLE 16.17

Synthesis of 1'-methyl-4'-morpholin-4-yl-2,3-dihydrospiro[furo[2,3-g][1,4]benzodioxine-8,3'-indol]-2'(1'H)-one

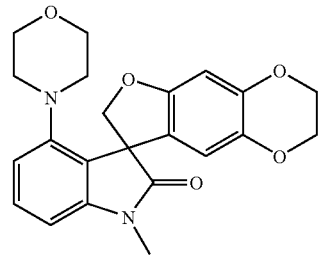

To a degassed solution of 4'-bromo-1'-methyl-2,3-dihydrospiro[furo[2,3-g][1,4]benzodioxine-8,3'-indol]-2'(1'H)-one (1.00 g, 2.57 mmol), morpholine (0.34 mL, 3.9 mmol), sodium tert-butoxide (0.45 g, 4.7 mmol) and 9,9-dimethyl-4,5-bis(diphenylphosphino)xanthene (0.30 g, 0.52 mmol) in toluene (40 mL) was added tris(dibenzylideneacetone)dipalladium(0) (0.24 g, 0.26 mmol). The mixture was stirred at reflux under nitrogen for 48 h, allowed to cool to ambient temperature, diluted with ethyl acetate, washed with water and brine, dried over anhydrous sodium sulfate and filtered. The filtrate was concentrated in vacuo. The residue was subjected to column chromatography eluted with ethyl acetate/hexanes (1/1) to afford 1'-methyl-4'-morpholin-4-yl-2,3-dihydrospiro[furo[2,3-g][1,4]benzodioxine-8,3'-indol]-2'(1'H)-one (0.04 g, 4%): mp 246-249° C. (ethyl acetate/hexanes); $^1$H NMR (300 MHz, DMSO-d$_6$) δ 7.35-7.29 (m, 1H), 6.94-6.87 (m, 2H), 6.42 (s, 1H), 6.17 (s, 1H), 4.75 (ABq, 2H), 4.14-4.02 (m, 4H), 3.30 (t, J=4.2 Hz, 4H), 3.12 (s, 3H), 2.52-2.27 (m, 4H); $^{13}$C NMR (75 MHz, DMSO-d$_6$) δ 177.8, 155.6, 149.9, 144.7, 144.3, 137.6, 130.3, 127.1, 121.6, 117.1, 111.3, 106.4, 98.6, 77.8, 66.7, 64.6, 64.0, 57.7, 53.0, 27.0; MS (ES+) m/z 395.0 (M+1).

EXAMPLE 16.18

Synthesis of 1'-methyl-4'-(2-oxopyridin-1(2H)-yl)-2,3-dihydrospiro[furo[2,3-g][1,4]benzodioxine-8,3'-indol]-2'(1'H)-one

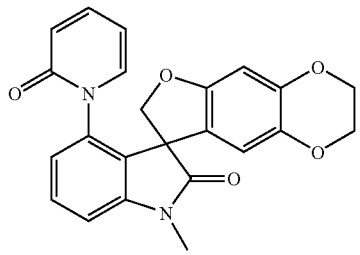

To a degassed solution of 4'-bromo-1'-methyl-2,3-dihydrospiro[furo[2,3-g][1,4]benzodioxine-8,3'-indol]-2'(1'H)-one (1.00 g, 2.57 mmol), 2-hydroxypyridine (0.49 g, 5.2 mmol), potassium carbonate (1.10 g, 7.95 mmol) and 8-hydroxyquinoline (0.15 g, 1.04 mmol) in dimethyl sulfoxide (30 mL) was added copper(I) iodide (0.10 g, 0.52 mmol). The reaction mixture was heated at 150° C. for 72 h, allowed to cool to ambient temperature, diluted with dichloromethane, washed sequentially with 10% v/v ammonium hydroxide, water and brine, dried over anhydrous sodium sulfate and filtered. The filtrate was concentrated in vacuo. The residue was subjected to column chromatography and eluted with ethyl acetate/hexanes (1/1) to afford 1'-methyl-4'-(2-oxopyridin-1(2H)-yl)-2,3-dihydrospiro[furo[2,3-g][1,4]benzodioxine-8,3'-indol]-2'(1'H)-one (0.02 g, 3%): mp 212-214° C. (ethyl acetate/hexanes); $^1$H NMR (300 MHz, CDCl$_3$) δ 7.99-7.96 (m, 1H), 7.57-7.50 (m, 1H), 7.38-7.34 (m, 1H), 6.88-6.76 (m, 3H), 6.69-6.66 (m, 1H), 6.18 (s, 2H), 4.73 (s, 2H), 4.11-4.01 (m, 4H), 3.28 (3H); $^{13}$C NMR (75 MHz, CDCl$_3$) δ 177.3, 155.3, 149.9, 144.5, 144.2, 139.0, 137.7, 129.9, 123.6, 118.9, 117.9, 111.6, 105.3, 98.7, 78.9, 64.4, 63.7, 57.4, 27.0; MS (ES+) m/z 403.0 (M+1).

EXAMPLE 16.19

Synthesis of 4'-amino-1'-methyl-2,3-dihydrospiro[furo[2,3-g][1,4]benzodioxine-8,3'-indol]-2'(1'H)-one

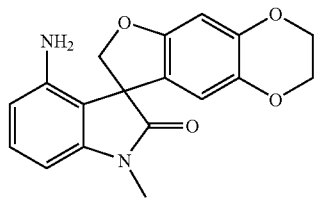

To a degassed solution of 4'-bromo-1'-methyl-2,3-dihydrospiro[furo[2,3-g][1,4]benzodioxine-8,3'-indol]-2'(1'H)-one (11.58 g, 30.0 mmol), benzophenone imine (7.8 mL, 46 mmol) and rac-2,2'-bis(diphenylphosphino)-1,1'-binaphtyl (5.64 g, 9.00 mmol) in toluene (250 mL) was added tris(dibenzylideneacetone)dipalladium(0) (2.75 g, 3.00 mmol) followed by sodium tert-butoxide (5.40 g, 56.2 mmol). The mixture was stirred at reflux under nitrogen for 20 h and filtered through a pad of diatomaceous earth. The filtrate was concentrated in vacuo and the residue was dissolved in tetrahydrofuran (100 mL). 10% w/v hydrochloric acid (20 mL) was added and the mixture was stirred at ambient temperature for 5 h and concentrated in vacuo to remove most of the tetrahydrofuran. The mixture was neutralized with 10% w/v aqueous sodium hydroxide and extracted with dichloromethane (3×150 mL). The combined organic extracts was washed with water and brine, dried over anhydrous sodium sulfate and filtered. The filtrate was concentrated in vacuo. The residue was recrystallized sequentially from ethyl acetate/hexanes followed by methanol to afford 4'-amino-t-methyl-2,3-dihydrospiro[furo[2,3-g][1,4]benzodioxine-8,3'-indol]-2'(1'H)-one (8.90 g, 90%): mp 252-254° C. (ethyl acetate/hexanes); $^1$H NMR (300 MHz, CDCl$_3$) δ 7.11-7.05 (m, 1H), 6.46 (s, 1H), 6.36-6.31 (m, 3H), 4.75 (ABq, 2H), 4.19-4.06 (m, 4H), 3.59 (br s, 2H), 3.23 (3H); MS (ES+) m/z 325.0 (M+1).

EXAMPLE 16.20

Synthesis of N-(1'-methyl-2'-oxo-1',2,2',3-tetrahydrospiro[furo[2,3-g][1,4]benzodioxine-8,3'-indol]-4'-yl)cyclobutanecarboxamide

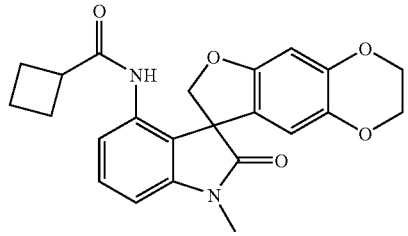

To a solution of 4'-amino-1'-methyl-2,3-dihydrospiro[furo[2,3-g][1,4]benzodioxine-8,3'-indol]-2'(1'H)-one (700 mg, 1.72 mmol) in dichloromethane (50 mL) and pyridine (5 mL) was added cyclobutanecarbonyl chloride (0.17 mL, 1.48 mmol) at 0° C. The reaction mixture was stirred at ambient temperature for 18 h, diluted with dichloromethane (150 mL), washed sequentially with water, 10% w/v hydrochloric acid, water and brine, dried over anhydrous sodium sulfate and filtered. The filtrate was concentrated in vacuo. The residue was subjected to column chromatography and eluted with ethyl acetate/hexanes (1/3) to afford N-(1-methyl-2'-oxo-1', 2,2',3-tetrahydrospiro[furo[2,3-g][1,4]benzodioxine-8,3'-indol]-4'-yl)cyclobutanecarboxamide (0.50 g, 71%): mp 234-236° C. (ethyl acetate/hexanes); $^1$H NMR (300 MHz, DMSO-$d_6$) δ 8.15 (s, 1H), 7.32-7.26 (m, 1H), 7.11-7.08 (m, 1H), 6.94-6.91 (m, 1H), 6.43 (s, 1H), 6.17 (s, 1H), 4.68 (ABq, 2H), 4.13-4.05 (m, 4H), 3.15 (s, 3H), 2.96-2.90 (m, 1H), 2.05-1.64 (m, 6H); $^{13}$C NMR (75 MHz, DMSO-$d_6$) δ 176.6, 173.5, 155.1, 144.6, 144.3, 138.3, 134.6, 129.5, 125.3, 120.8, 119.4, 112.0, 106.8, 98.8, 78.2, 64.6, 64.0, 57.1, 27.1, 25.0, 24.9, 17.9; MS (ES+) m/z 406.9 (M+1).

EXAMPLE 16.21

Synthesis of N-(1'-methyl-2'-oxo-1',2,2',3-tetrahydrospiro[furo[2,3-g][1,4]benzodioxine-8,3'-indol]-4'-yl)-2-(trifluoromethyl)benzamide

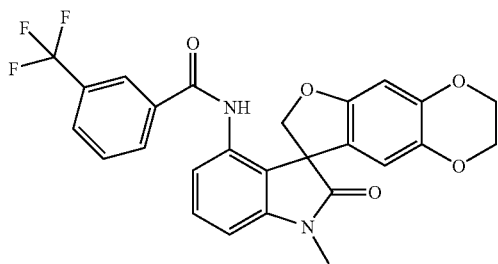

Following the procedure as described in EXAMPLE 16.20 and making non-critical variations using 2-(trifluoromethyl)benzoyl chloride to replace cyclobutanecarbonyl chloride, N-(1'-methyl-2'-oxo-1',2,2',3-tetrahydrospiro[furo[2,3-g][1,4]benzodioxine-8,3'-indol]-4'-yl)-2-(trifluoromethyl)benzamide was obtained (66%): mp 241-243° C. (ethyl acetate/hexanes); $^1$H NMR (300 MHz, CDCl$_3$) δ 8.02-7.98 (m, 1H), 7.74-7.70 (m, 1H), 7.62-7.56 (m, 2H), 7.41-7.33 (m, 2H), 7.28-7.23 (m, 1H), 6.76-6.73 (m, 1H), 6.33 (s, 1H), 6.03 (s, 1H), 4.71 (ABq, 2H), 4.18-4.08 (m, 4H), 3.29 (s, 3H); $^{13}$C NMR (75 MHz, CDCl$_3$) δ 175.9, 165.7, 153.8, 145.0, 142.8, 139.4, 134.3, 131.9, 130.3, 130.0, 127.5, 126.7, 120.7, 118.0, 116.5, 112.1, 105.2, 99.3, 78.8, 64.5, 63.8, 57.2, 27.1; MS (ES+) m/z 497.0 (M+1).

EXAMPLE 16.22

Synthesis of N-(1'-methyl-2'-oxo-1',2,2',3-tetrahydrospiro[furo[2,3-g][1,4]benzodioxine-8,3'-indol]-4'-yl)methanesulfonamide

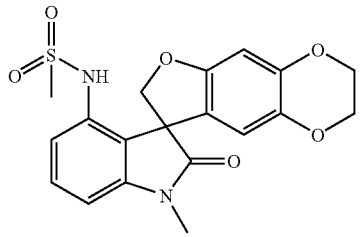

Following the procedure as described in EXAMPLE 16.20 and making non-critical variations using methanesulfonyl chloride to replace cyclobutanecarbonyl chloride, N-(1'-methyl-2'-oxo-1',2,2',3-tetrahydrospiro[furo[2,3-g][1,4]benzodioxine-8,3'-indol]-4'-yl)methanesulfonamide was obtained (89%): mp 184-186° C. (ethyl acetate/hexanes); $^1$H NMR (300 MHz, CDCl$_3$) δ 7.34-7.25 (m, 2H), 6.75-6.71 (m 1H), 6.61 (s, 1H), 6.56 (br s, 1H), 6.34 (s, 1H), 4.70 (ABq, 2H), 4.19-4.06 (m, 4H), 3.29 (s, 3H), 2.35 (s, 3H); $^{13}$C NMR (75 MHz, CDCl$_3$) δ 175.5, 154.1, 145.3, 143.2, 139.6, 133.9, 130.3, 121.1, 118.5, 114.9, 111.6, 105.2, 100.4, 78.7, 64.4, 63.9, 57.0, 38.7, 27.1; MS (ES+) m/z 402.9 (M+1).

EXAMPLE 16.23

Synthesis of N-(1'-methyl-2'-oxo-1',2,2',3-tetrahydrospiro[furo[2,3-g][1,4]benzodioxine-8,3'-indol]-4'-yl)cyclohexanecarboxamide

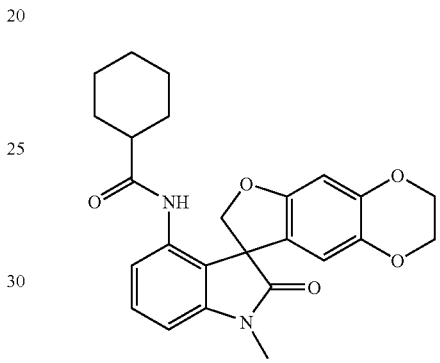

Following the procedure as described in EXAMPLE 16.20 and making non-critical variations using cyclohexanecarbonyl chloride to replace cyclobutanecarbonyl chloride, N-(1'-methyl-2'-oxo-1',2,2',3-tetrahydrospiro[furo[2,3-g][1,4]benzodioxine-8,3'-indol]-4'-yl)cyclohexanecarboxamide was obtained (23%): mp 96-98° C. (ethyl acetate/hexanes); $^1$H NMR (300 MHz, CDCl$_3$) δ 7.99-7.95 (m, 1H), 7.31-7.25 (m 1H), 7.04 (br s, 1H), 6.67-6.64 (m, 1H), 6.53 (s, 1H), 6.34 (s, 1H), 4.74 (ABq, 2H), 4.21-4.10 (m, 4H), 3.26 (s, 3H), 2.04-1.69 (m, 11H); $^{13}$C NMR (75 MHz, CDCl$_3$) δ 176.3, 174.5, 154.4, 145.3, 142.8, 139.3, 135.1, 129.8, 119.1, 118.0, 115.8, 112.3, 104.2, 99.4, 78.6, 64.5, 63.8, 57.1, 46.7, 29.4, 29.0, 27.0, 25.6; MS (ES+) m/z 435.0 (M+1).

EXAMPLE 16.24

Synthesis of N-(1'-methyl-2'-oxo-1,2,2',3-tetrahydrospiro[furo[2,3-g][1,4]benzodioxine-8,3'-indol]-4'-yl)cyclopentanecarboxamide

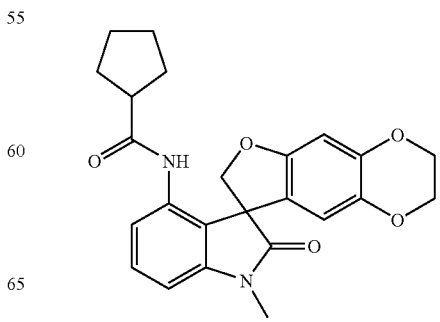

Following the procedure as described in EXAMPLE 16.20 and making non-critical variations using cyclopentanecarbonyl chloride to replace cyclobutanecarbonyl chloride, N-(1'-methyl-2'-oxo-1',2,2',3-tetrahydrospiro[furo[2,3-g][1,4]benzodioxine-8,3'-indol]-4'-yl)cyclopentanecarboxamide was obtained (52%): mp 196-198° C. (ethyl acetate/hexanes); $^1$H NMR (300 MHz, CDCl$_3$) δ 7.98-7.94 (m, 1H), 7.30-7.24 (m 1H), 7.09 (br s, 1H), 6.67-6.64 (m, 1H), 6.53 (s, 1H), 6.32 (s, 1H), 4.74 (ABq, 2H), 4.20-4.09 (m, 4H), 3.26 (s, 3H), 2.45-2.39 (m, 1H), 1.89-1.51 (m, 8H); $^{13}$C NMR (75 MHz, CDCl$_3$) δ 176.2, 174.7, 154.3, 145.2, 142.7, 139.3, 135.1, 129.8, 119.2, 118.2, 115.9, 112.2, 104.2, 99.4, 78.4, 64.5, 63.8, 57.1, 46.7, 30.1, 29.9, 27.0, 25.9; MS (ES+) m/z 421.1 (M+1).

EXAMPLE 16.25

Synthesis of N-(1'-methyl-2'-oxo-1',2,2',3-tetrahydrospiro[furo[2,3-g][1,4]benzodioxine-8,3'-indol]-4'-yl)acetamide

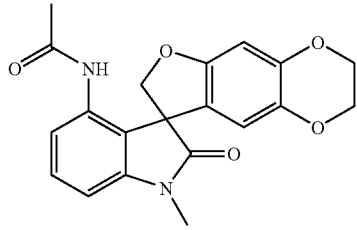

Following the procedure as described in EXAMPLE 16.20 and making non-critical variations using acetyl chloride to replace cyclobutanecarbonyl chloride, N-1'-methyl-2'-oxo-1',2,2',3-tetrahydrospiro[furo[2,3-g][1,4]benzodioxine-8,3'-indol]-4'-yl)acetamide was obtained (27%): mp 182-184° C. (ethyl acetate/hexanes); $^1$H NMR (300 MHz, CDCl$_3$) δ 7.89-7.85 (m, 1H), 7.31-7.24 (m, 1H), 7.14 (br s, 1H), 6.69-6.65 (m 1H), 6.53 (s, 1H), 6.32 (br s, 1H), 4.74 (ABq, 2H), 4.19-4.10 (m, 4H), 3.27 (s, 3H), 1.95 (s, 3H); $^{13}$C NMR (75 MHz, CDCl$_3$) δ 176.0, 168.5, 154.0, 145.1, 142.6, 139.4, 134.7, 129.7, 119.9, 116.1, 112.1, 104.5, 99.2, 78.6, 64.5, 63.8, 57.1, 27.0, 24.3; MS (ES+) m/z 367.0 (M+1).

EXAMPLE 16.26

Synthesis of N-(1'-methyl-2'-oxo-1',2,2',3-tetrahydrospiro[furo[2,3-g][1,4]benzodioxine-8,3'-indol]-4'-yl)cyclopropanecarboxamide

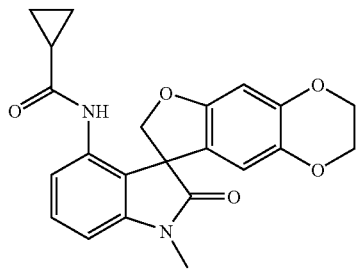

Following the procedure as described in EXAMPLE 16.20 and making non-critical variations using cyclopropanecarbonyl chloride to replace cyclobutanecarbonyl chloride, N-(1'-methyl-2'-oxo-1',2,2',3-tetrahydrospiro[furo[2,3-g][1,4]benzodioxine-8,3'-indol]-4'-yl)cyclopropanecarboxamide was obtained (78%): mp 266-268° C. (ethyl acetate/hexanes); $^1$H NMR (300 MHz, CDCl$_3$) δ 7.93-7.89 (m, 1H), 7.33 (br s, 1H), 7.28-7.23 (m, 1H), 6.67-6.63 (m 1H), 6.53 (s, 1H), 6.33 (s, 1H), 4.77 (ABq, 2H), 4.20-4.10 (m, 4H), 3.27 (s, 3H), 1.26-1.17 (m, 1H), 0.99-0.73 (m, 4H); $^{13}$C NMR (75 MHz, CDCl$_3$) δ 176.1, 172.1, 154.1, 145.1, 142.6, 139.4, 135.0, 129.7, 119.4, 118.3, 116.0, 112.1, 104.5, 99.3, 78.5, 64.5, 63.8, 57.2, 27.0, 15.6, 8.1, 8.0; MS (ES+) m/z 393.0 (M+1).

EXAMPLE 16.27

Synthesis of N-(1-methyl-2'-oxo-1,2,2',3-tetrahydrospiro[furo[2,3-g][1,4]benzodioxine-8,3'-indol]-4'-yl)benzamide

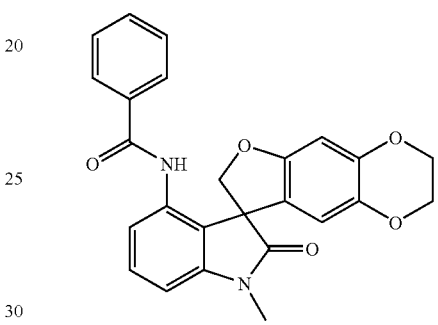

Following the procedure as described in EXAMPLE 16.20 and making non-critical variations using benzoyl chloride to replace cyclobutanecarbonyl chloride, N-(1'-methyl-2'-oxo-1',2,2',3-tetrahydrospiro[furo[2,3-g][1,4]benzodioxine-8,3'-indol]-4'-yl)benzamide was obtained (60%): mp 192-194° C. (ethyl acetate/hexanes); $^1$H NMR (300 MHz, CDCl$_3$) δ 8.21-8.18 (m, 1H), 7.76 (br s, 1H), 7.63-7.59 (m, 2H), 7.53-7.32 (m, 4H), 6.73-6.70 (m 1H), 6.46 (s, 1H), 6.38 (s, 1H), 4.80 (ABq, 2H), 4.17-4.08 (m, 4H), 3.28 (s, 3H); $^{13}$C NMR (75 MHz, CDCl$_3$) δ 176.3, 165.4, 154.2, 145.2, 143.0, 139.4, 135.0, 134.0, 132.1, 130.0, 128.6, 127.0, 119.4, 117.9, 115.9, 112.2, 104.6, 99.8, 78.5, 64.5, 63.8, 60.4, 57.2, 27.0; MS (ES+) m/z 428.9 (M+1).

EXAMPLE 16.28

Synthesis of 2-methoxy-N-(1'-methyl-2'-oxo-1',2,2',3-tetrahydrospiro[furo[2,3-g][1,4]benzodioxine-8,3'-indol]-4'-yl)acetamide

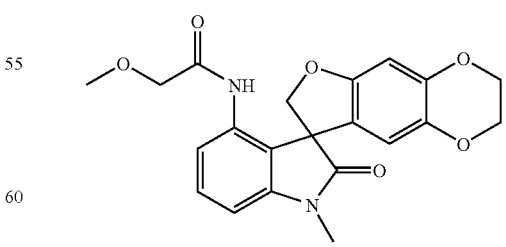

Following the procedure as described in EXAMPLE 16.20 and making non-critical variations using methoxyacetyl chloride to replace cyclobutanecarbonyl chloride, 2-methoxy-N-(1'-methyl-2'-oxo-1,2,2',3-tetrahydrospiro[furo[2,3-g][1,4]benzodioxine-8,3'-indol]-4'-yl)acetamide was obtained (70%): mp 237-239° C. (ethyl acetate/hexanes); $^1$H NMR (300 MHz, CDCl$_3$) δ 8.07 (br s, 1H), 7.98-7.95 (m, 1H), 7.33-7.27 (m, 1H), 6.71-6.67 (m 1H), 6.50 (s, 1H), 6.29 (s, 1H), 4.73 (ABq, 2H), 4.20-4.09 (m, 4H), 3.89 (ABq, 2H), 3.31 (s, 3H), 3.25 (s, 3H); $^{13}$C NMR (75 MHz, CDCl$_3$) δ 176.7, 168.2, 155.2, 145.1, 143.4, 138.7, 134.0, 129.8, 119.4, 117.5, 116.2, 111.8, 104.8, 99.7, 78.1, 71.9, 64.5, 63.8, 59.1, 57.1, 26.9; MS (ES+) m/z 396.9 (M+1).

EXAMPLE 16.29

Synthesis of N-(1'-methyl-2'-oxo-1',2,2',3-tetrahydrospiro[furo[2,3-g][1,4]benzodioxine-8,3'-indol]-4'-yl)propanamide

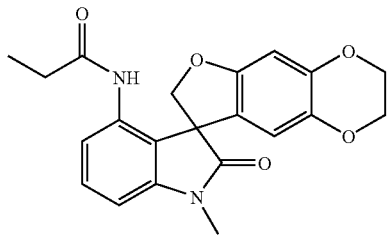

Following the procedure as described in EXAMPLE 16.20 and making non-critical variations using propionyl chloride to replace cyclobutanecarbonyl chloride, N-(1'-methyl-2'-oxo-1',2,2',3-tetrahydrospiro[furo[2,3-g][1,4]benzodioxine-8,3'-indol]-4'-yl)propanamide was obtained (42%): mp 224-226° C. (ethyl acetate/hexanes); $^1$H NMR (300 MHz, CDCl$_3$) δ 7.93-7.90 (m, 1H), 7.31-7.23 (m, 1H), 7.09 (br s, 1H), 6.68-6.64 (m, 1H), 6.52 (s, 1H), 6.32 (s, 1H), 4.73 (ABq, 2H), 4.20-4.08 (m, 4H), 3.31 (s, 3H), 3.27 (s, 3H), 2.28-2.07 (m, 2H), 1.07 (t, J=7.5 Hz, 3H); $^{13}$C NMR (75 MHz, CDCl$_3$) δ 176.7, 172.2, 154.1, 145.1, 142.7, 139.4, 134.8, 129.8, 119.7, 118.2, 116.1, 112.1, 104.3, 99.3, 78.5, 64.5, 63.8, 57.1, 30.6, 27.0, 9.2; MS (ES+) m/z 381.0 (M+1).

EXAMPLE 16.30

Synthesis of N-(1'-methyl-2'-oxo-1',2,2',3-tetrahydrospiro[furo[2,3-g][1,4]benzodioxine-8,3'-indol]-4'-yl)pentanamide

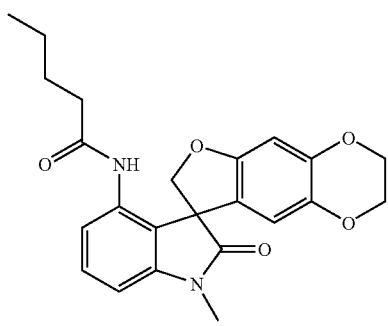

Following the procedure as described in EXAMPLE 16.20 and making non-critical variations using valeryl chloride to replace cyclobutanecarbonyl chloride, N-(1'-methyl-2'-oxo-1',2,2',3-tetrahydrospiro[furo[2,3-g][1,4]benzodioxine-8,3'-indol]-4'-yl)pentanamide was obtained (30%): mp 182-183° C. (ethyl acetate/hexanes); $^1$H NMR (300 MHz, CDCl$_3$) δ 7.96-7.92 (m, 1H), 7.31-7.23 (m, 1H), 7.09 (br s, 1H), 6.68-6.64 (m, 1H), 6.52 (s, 1H), 6.33 (s, 1H), 4.74 (ABq, 2H), 4.19-4.10 (m, 4H), 3.27 (s, 3H), 2.19-2.05 (m, 2H), 1.55-1.45 (m, 2H), 1.32-1.22 (m, 2H), 0.88 (t, J=7.2 Hz, 3H); $^{13}$C NMR (75 MHz, CDCl$_3$) δ 176.1, 171.6, 154.2, 145.1, 142.7, 139.4, 134.9, 129.8, 119.5, 118.2, 116.0, 112.2, 104.3, 99.3, 78.6, 64.5, 63.8, 57.1, 37.5, 27.3, 27.0, 22.2, 13.7; MS (ES+) m/z 409.0 (M+1).

EXAMPLE 16.31

Synthesis of 2,2-dimethyl-N-(1'-methyl-2'-oxo-1',2,2',3-tetrahydrospiro[furo[2,3-g][1,4]benzodioxine-8,3'-indol]-4'-yl)propanamide

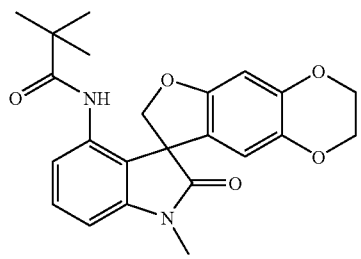

Following the procedure as described in EXAMPLE 16.20 and making non-critical variations using trimethylacetyl chloride to replace cyclobutanecarbonyl chloride, 2,2-dimethyl-N-(1'-methyl-2'-oxo-1',2,2',3-tetrahydrospiro[furo[2,3-g][1,4]benzodioxine-8,3'-indol]-4'-yl)propanamide was obtained (47%): mp 182-184° C. (ethyl acetate/hexanes); $^1$H NMR (300 MHz, CDCl$_3$) δ 7.87 (br s, 1H), 7.33-7.27 (m, 1H), 7.22-7.18 (m, 1H), 6.94-6.91 (m, 1H), 6.43 (s, 1H), 6.22 (s, 1H), 4.70 (ABq, 2H), 4.15-4.01 (m, 4H), 3.15 (s, 3H), 0.97 (s, 9H); $^{13}$C NMR (75 MHz, CDCl$_3$) δ 177.0, 176.7, 155.0, 144.7, 144.4, 138.3, 135.0, 129.6, 124.3, 120.2, 119.1, 112.2, 106.6, 99.1, 78.1, 64.6, 64.0, 57.1, 39.2, 27.3, 27.1; MS (ES+) m/z 409.0 (M+1).

EXAMPLE 16.32

Synthesis of N-(1'-methyl-2'-oxo-1',2,2',3-tetrahydrospiro[furo[2,3-g][1,4]benzodioxine-8,3'-indol]-4'-yl)hexanamide

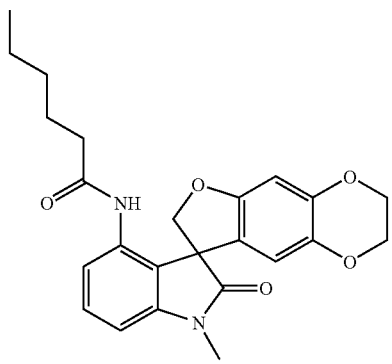

Following the procedure as described in EXAMPLE 16.20 and making non-critical variations using hexanoyl chloride to replace cyclobutanecarbonyl chloride, N-(1'-methyl-2'-oxo-1',2,2',3-tetrahydrospiro[furo[2,3-g][1,4]benzodioxine-8,3'-indol]-4'-yl)hexanamide was obtained (67%): mp 151-153° C. (ethyl acetate/hexanes); $^1$H NMR (300 MHz, CDCl$_3$) δ 7.96-7.92 (m, 1H), 7.31-7.23 (m, 1H), 7.10 (br s, 1H), 6.68-6.64 (m, 1H), 6.52 (s, 1H), 6.32 (s, 1H), 4.74 (ABq, 2H), 4.20-4.09 (m, 4H), 3.27 (s, 3H), 3.21-2.02 (m, 2H), 1.56-1.47 (m, 2H), 1.30-1.23 (m, 4H), 0.86 (t, J=6.6 Hz, 3H); $^{13}$C NMR (75 MHz, CDCl$_3$) δ 176.1, 171.6, 154.1, 145.1, 142.6, 139.4, 134.9, 129.8, 119.5, 118.2, 116.0, 112.2, 104.3, 99.3, 78.5, 64.5, 63.8, 57.1, 37.7, 31.3, 27.0, 24.9, 22.3, 13.9; MS (ES+) m/z 423.0 (M+1).

EXAMPLE 16.33

Synthesis of N-(1'-methyl-2'-oxo-1',2,2',3-tetrahydrospiro[furo[2,3-g][1,4]benzodioxine-8,3'-indol]-4'-yl)heptanamide

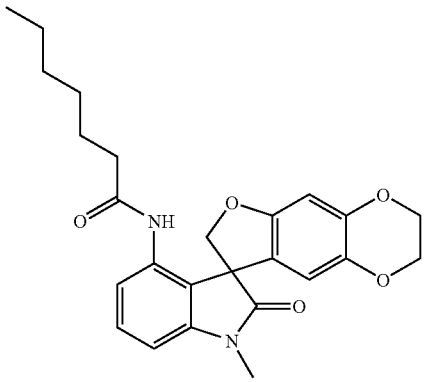

Following the procedure described in EXAMPLE 16.20 and making non-critical variations using heptanoyl chloride to replace cyclobutanecarbonyl chloride, N-(1-methyl-2'-oxo-1,2,2',3-tetrahydrospiro[furo[2,3-g][1,4]benzodioxine-8,3'-indol]-4'-yl)heptanamide was obtained (46%): mp 123-124° C. (ethyl acetate/hexanes); $^1$H NMR (300 MHz, CDCl$_3$) δ 7.96-7.92 (m, 1H), 7.31-7.23 (m, 1H), 7.10 (br s, 1H), 6.68-6.64 (m, 1H), 6.52 (s, 1H), 6.32 (s, 1H), 4.74 (ABq, 2H), 4.19-4.05 (m, 4H), 3.27 (s, 3H), 3.21-2.03 (m, 2H), 1.53-1.47 (m, 2H), 1.35-1.14 (m, 6H), 0.86 (t, J=7.2 Hz, 3H); $^{13}$C NMR (75 MHz, CDCl$_3$) δ 176.1, 171.7, 154.1, 145.1, 142.6, 139.3, 134.9, 129.8, 119.5, 118.2, 116.0, 112.2, 104.3, 99.3, 78.5, 64.5, 63.8, 57.1, 37.8, 31.4, 28.8, 27.0, 25.2, 22.4, 14.0; MS (ES+) m/z 437.1 (M+1).

EXAMPLE 16.34

Synthesis of 2-(2-methoxyethoxy)-N-(1'-methyl-2'-oxo-1',2,2',3-tetrahydrospiro[furo[2,3-g][1,4]benzodioxine-8,3'-indol]-4'-yl)acetamide

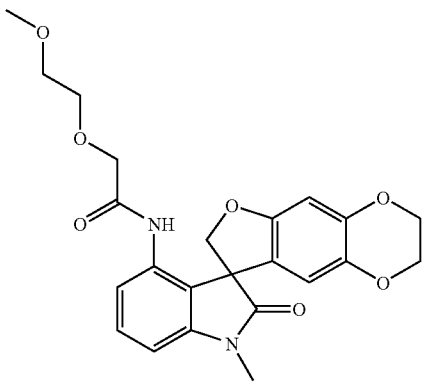

Following the procedure as described in EXAMPLE 16.20 and making non-critical variations using 2-(2-methoxyethoxy)acetyl chloride to replace cyclobutanecarbonyl chloride, 2-(2-methoxyethoxy)-N-(1'-methyl-2'-oxo-1',2,2',3-tetrahydrospiro[furo[2,3-g][1,4]-benzodioxine-8,3'-indol]-4'-yl)acetamide was obtained (77%): mp 122-123° C. (ethyl acetate/hexanes); $^1$H NMR (300 MHz, CDCl$_3$) δ 8.08 (br s, 1H), 7.85-7.81 (m, 1H), 7.33-7.26 (m, 1H), 6.72-6.68 (m, 1H), 6.46 (s, 1H), 6.26 (s, 1H), 4.78 (ABq, 2H), 4.18-4.06 (m, 4H), 3.99 (ABq, 2H), 3.65-3.40 (m, 4H), 3.32 (s, 3H), 3.24 (s, 3H); $^{13}$C NMR (75 MHz, CDCl$_3$) δ 176.7, 168.5, 155.1, 144.9, 143.4, 138.7, 133.8, 129.8, 120.4, 117.9, 117.2, 111.7, 105.1, 99.6, 77.8, 71.7, 70.8, 64.5, 63.8, 58.9, 57.1, 26.9; MS (ES+) m/z 441.1 (M+1).

EXAMPLE 16.35

Synthesis of 1-hexyl-3-(1'-methyl-2'-oxo-1',2,2',3-tetrahydrospiro[furo[2,3-g][1,4]-benzodioxine-8,3'-indol]-4'-yl)urea

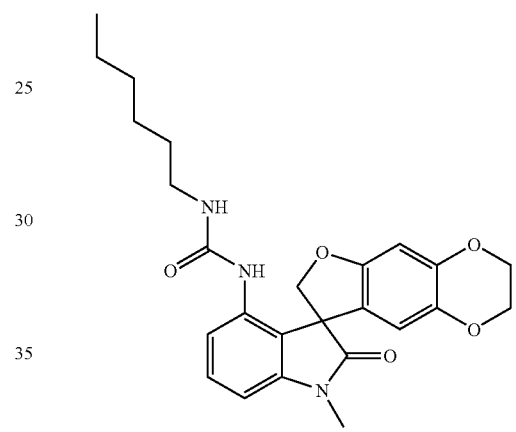

To a stirred solution of 4'-amino-1'-methyl-2,3-dihydrospiro[furo[2,3-g][1,4]benzodioxine-8,3'-indol]-2'(1'H)-one (0.33 g, 1.00 mmol) in 1,4-dioxane (20 mL) was added trichloromethyl chloroformate (0.14 mL, 1.2 mmol). The reaction mixture was heated at 65° C. for 24 h, allowed to cool to ambient temperature and concentrated in vacuo. The residue was dissolved in tetrahydrofuran (10 mL) and the resultant solution was cooled to 0° C. in an ice bath. n-Hexylamine (0.40 mL, 3.0 mmol) and triethylamine (0.70 mL, 5.0 mmol) were added. The reaction mixture was allowed to warm to ambient temperature, stirred for 24 h and concentrated in vacuo. The residue was dissolved in ethyl acetate and washed with water (4×150 mL). The organic phase was dried over anhydrous sodium sulfate, filtered and concentrated in vacuo. The residue was recrystallized from ethyl acetate/hexanes to afford 1-hexyl-3-(1'-methyl-2'-oxo-1',2,2',3-tetrahydrospiro[furo[2,3-g][1,4]benzodioxine-8,3'-indol]-4'-yl)urea (0.294 g, 64%) as a pale brown solid: mp 154-155° C. (ethyl acetate/hexanes); $^1$H NMR (300 MHz, CDCl$_3$) δ 7.78-7.75 (m, 1H), 7.30-7.25 (m, 1H), 6.63-6.60 (m, 1H), 6.52 (s, 1H), 6.34 (s, 1H), 6.09 (s, 1H), 4.76 (ABq, 2H), 4.22-4.11 (m, 5H), 3.28 (s, 3H), 3.14-3.00 (m, 2H), 1.48-1.41 (m, 2H), 1.32-1.25 (m, 6H), 0.89 (t, J=6.7 Hz, 3H); $^{13}$C NMR (75 MHz, CDCl$_3$) δ 176.3, 154.6, 154.2, 145.1, 142.8, 139.4, 135.9, 129.8, 119.0, 118.3, 115.8, 112.2, 103.3, 99.3, 78.2, 64.5, 63.8, 57.1, 40.5, 31.5, 29.8, 27.0, 26.4, 22.5, 14.0; MS (ES+) m/z 452.2 (M+1).

EXAMPLE 16.36

Synthesis of 1-cyclopentyl-3-(1'-methyl-2'-oxo-1',2, 2',3-tetrahydrospiro[furo[2,3-g][1,4]benzodioxine-8, 3'-indol]-4'-yl)urea

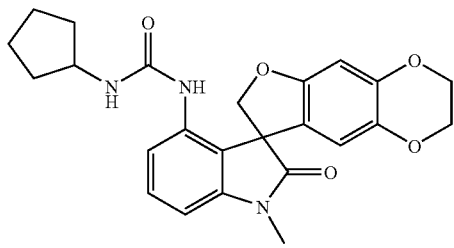

Following the procedure as described in EXAMPLE 16.35 and making non-critical variations using cyclopentylamine to replace n-hexylamine, 1-cyclopentyl-3-(1'-methyl-2'-oxo-1', 2,2',3-tetrahydrospiro[furo[2,3-g][1,4]benzodioxine-8,3'-indol]-4'-yl)urea was obtained (61%) as a pale yellow solid: mp 133-135° C. (ethyl acetate/hexanes); $^1$H NMR (300 MHz, CDCl$_3$) δ 7.76-7.73 (m, 1H), 7.31-7.25 (m, 1H), 6.63-6.60 (m, 1H), 6.52 (s, 1H), 6.34 (s, 1H), 6.07 (s, 1H), 4.77 (ABq, 2H), 4.20-4.11 (m, 5H), 3.81-3.76 (m, 1H), 3.28 (s, 3H), 1.94-1.80 (m, 2H), 1.70-1.54 (m, 4H), 1.35-1.28 (m, 2H); $^{13}$C NMR (75 MHz, CDCl$_3$) δ 176.3, 154.3, 145.2, 142.9, 139.3, 135.9, 129.8, 118.9, 118.3, 116.0, 112.3, 103.3, 99.2, 78.2, 64.5, 63.9, 57.1, 52.3, 33.6, 33.4, 27.0, 23.5, 23.5; MS (ES+) m/z 436.2 (M+1).

EXAMPLE 16.37

Synthesis of 1-cyclohexyl-3-(1'-methyl-2'-oxo-1',2, 2',3-tetrahydrospiro[furo[2,3-g][1,4]benzodioxine-8, 3'-indol]-4'-yl)urea

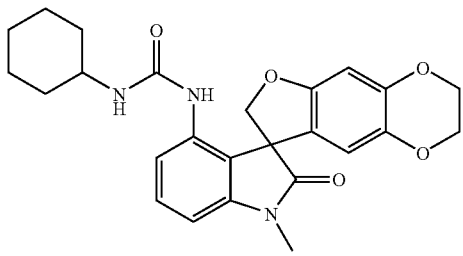

Following the procedure as described in EXAMPLE 16.35 and making non-critical variations using cyclohexylamine to replace n-hexylamine, 1-cyclohexyl-3-(1'-methyl-2'-oxo-1', 2,2',3-tetrahydrospiro[furo[2,3-g][1,4]benzodioxine-8,3'-indol]-4'-yl)urea was obtained (57%) as a colorless solid: mp 175-177° C. (ethyl acetate); $^1$H NMR (300 MHz, CDCl$_3$) δ 7.72-7.69 (m, 1H), 7.30-7.24 (m, 1H), 6.63-6.60 (m, 1H), 6.53 (s, 1H), 6.34 (s, 1H), 6.05 (s, 1H), 4.76 (ABq, 2H), 4.20-4.12 (m, 5H), 3.41 (s, 1H), 3.28 (s, 3H), 1.90-1.82 (m, 2H), 1.71-1.58 (m, 3H), 1.41-1.01 (m, 5H); $^{13}$C NMR (75 MHz, CDCl$_3$) δ 176.3, 154.2, 153.9, 145.1, 142.9, 139.3, 135.9, 129.8, 119.3, 118.4, 116.1, 112.2, 103.3, 99.2, 78.3, 64.5, 63.8, 57.2, 49.2, 33.6, 33.5, 27.0, 25.5, 24.7; MS (ES+) m/z 450.1 (M+1).

EXAMPLE 16.38

Synthesis of N-cyclohexyl-1'-methyl-2'-oxo-1',2,2',3-tetrahydrospiro[furo[2,3-g][1,4]benzodioxine-8,3'-indole]-4'-carboxamide

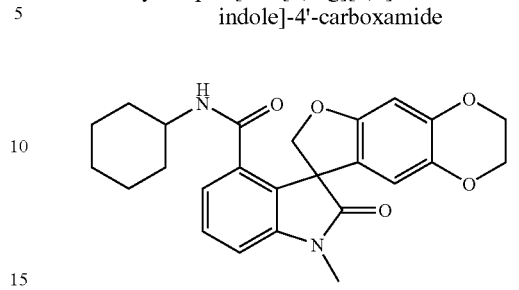

To a stirred solution of 1'-methyl-2'-oxo-1,2,2',3-tetrahydrospiro[furo[2,3-g][1,4]benzodioxine-8,3'-indole]-4'-carboxylic acid (0.200 g, 0.566 mmol) and 1-ethyl-3-(3-dimethylaminopropyl)-carbodiimide (0.114 g, 0.736 mmol) in N,N-dimethylformamide (20 mL) was added N,N-diisoproylethylamine (0.30 mL, 1.72 mmol) and hydroxybenzotriazole (0.092 g, 0.68 mmol). The reaction mixture was stirred at ambient temperature for 10 min and cyclohexylamine (0.10 mL, 0.87 mmol) was added. The reaction mixture was stirred at ambient temperature for 40 h and concentrated in vacuo to remove most of the N,N-dimethylformamide. The mixture was diluted with ethyl acetate (150 mL), washed with water (3×150 mL) and brine (3×100 mL), dried over anhydrous sodium sulfate, filtered and concentrated in vacuo. The residue was purified by column chromatography and eluted with ethyl acetate/hexanes (1/1) to afford N-cyclohexyl-1'-methyl-2'-oxo-1',2,2',3-tetrahydrospiro[furo[2,3-g][1,4]benzodioxine-8,3'-indole]-4'-carboxamide (0.127 g, 51%) as a colorless solid: mp 139-140° C.; $^1$H NMR (300 MHz, CDCl$_3$) δ7.42-7.36 (m, 1H), 7.24-7.20 (m, 1H), 6.98-6.94 (m, 1H), 6.51 (s, 1H), 6.17 (s, 1H), 5.30-5.27 (m, 1H), 4.95 (ABq, 2H), 4.24-4.04 (m, 4H), 3.71-3.61 (m, 1H), 3.26 (s, 3H), 1.78-1.57 (m, 5H), 1.36-1.22 (m, 2H), 1.12-0.99 (m, 1H), 0.89-0.82 (m, 2H); $^{13}$C NMR (75 MHz, CDCl$_3$) δ177.6, 166.3, 155.9, 145.0, 144.3, 137.9. 134.7, 129.5, 127.4, 122.8, 120.4, 110.7, 109.9, 100.1. 78.0, 64.5, 64.0, 58.2, 48.7, 32.4, 32.1, 26.7, 25.5, 24.9, 24.7; MS (ES+) m/z 435.0 (M+1).

EXAMPLE 16.39

Synthesis of N-cyclopentyl-1'-methyl-2'-oxo-1',2,2', 3-tetrahydrospiro[furo[2,3-g][1,4]benzodioxine-8,3'-indole]-4'-carboxamide

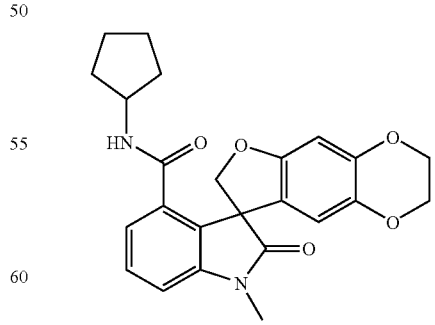

Following the procedure described in EXAMPLE 16.38 and making non-critical variations using cyclopentylamine to replace cyclohexylamine, N-cyclopentyl-1'-methyl-2'-oxo-1',2,2',3-tetrahydrospiro[furo[2,3-g][1,4]benzodioxine-8,3'-indole]-4'-carboxamide was obtained (28%) as a colorless solid: mp 135-136° C. (ethyl acetate/hexanes); ¹H NMR (300 MHz, CDCl₃) δ 7.43-7.36 (m, 1H), 7.24-7.22 (m, 1H), 6.98-6.95 (m, 1H), 6.50 (s, 1H), 6.17 (s, 1H), 5.38-5.36 (m, 1H), 4.95 (ABq, 2H), 4.20-4.06 (m, 5H), 3.26 (s, 1H), 1.92-1.78 (m, 2H), 1.52-1.49 (m, 4H), 1.13-0.93 (m, 2H); ¹³C NMR (75 MHz, CDCl₃) δ 177.6, 166.8, 155.9, 145.0, 144.3, 137.9, 134.6, 129.5, 127.3, 122.8, 120.5, 110.7, 109.9, 100.0, 78.9, 64.5, 64.0, 58.1, 51.5, 32.6, 32.4, 26.9, 23.9, 23.7; MS (ES+) m/z 421.1 (M+1).

EXAMPLE 16.40

Synthesis of N-cyclopropyl-1'-methyl-2'-oxo-1',2,2',3-tetrahydrospiro[furo[2,3-g][1,4]benzodioxine-8,3'-indole]-4'-carboxamide

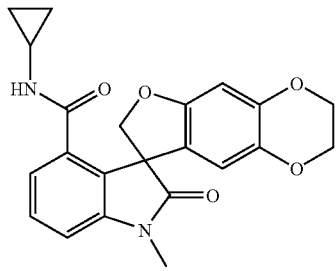

Following the procedure described in EXAMPLE 16.38 and making non-critical variations using cyclopropylamine to replace cyclohexylamine, N-cyclopropyl-1'-methyl-2'-oxo-1',2,2',3-tetrahydrospiro[furo[2,3-g][1,4]benzodioxine-8,3'-indole]-4'-carboxamide was obtained (36%) as a colorless solid: mp 127-128° C. (ethyl acetate/hexanes); ¹H NMR (300 MHz, CDCl₃) δ 7.42-7.36 (m, 1H), 7.24-7.22 (m, 1H), 6.98-6.96 (m, 1H), 6.52 (s, 1H), 6.17 (s, 1H), 5.41 (s, 1H), 4.90 (m, 2H), 4.21-4.11 (m, 4H), 3.26 (s, 3H), 2.67-2.60 (m, 1H), 0.68-0.63 (m, 2H), 0.18-0.17 (m, 2H); ¹³C NMR (75 MHz, CDCl₃) δ 177.5, 168.5, 155.7, 145.1, 144.1, 137.9, 134.1, 129.6, 127.4, 122.9, 120.5, 110.6, 110.0, 100.1, 78.7, 64.6, 64.0, 58.0, 26.9, 22.8, 6.4, 6.2; MS (ES+) m/z 415.0 (M+23).

EXAMPLE 16.41

Synthesis of 1'-methyl-4'-(pyrrolidin-1-ylcarbonyl)-2,3-dihydrospiro[furo[2,3-g][1,4]-benzodioxine-8,3'-indol]-2'(1'H)-one

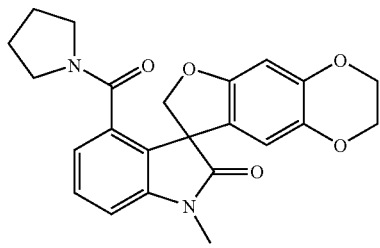

Following the procedure described in EXAMPLE 16.38 and making non-critical variations using pyrrolidine to replace cyclohexylamine, 1'-methyl-4'-(pyrrolidin-1-ylcarbonyl)-2,3-dihydrospiro[furo[2,3-g][1,4]benzodioxine-8,3'-indol]-2'(1'H)-one was obtained (8%) as a colorless solid: mp 242-244° C. (ethyl acetate/hexanes); ¹H NMR (300 MHz, CDCl₃) δ 7.36-7.30 (m, 1H), 6.92-6.89 (m, 2H), 6.45 (s, 1H), 6.21 (s, 1H), 5.01 (ABq, 2H), 4.22-4.01 (m, 4H), 3.49-3.40 (m, 1H), 3.29 (s, 3H), 3.21-3.11 (m, 1H), 3.02-2.93 (m, 1H), 2.43-2.35 (m, 1H), 1.77-1.62 (m, 3H), 1.39-1.29 (m, 1H); ¹³C NMR (75 MHz, CDCl₃) δ 177.6, 166.7, 156.2, 144.6, 143.4, 137.5, 135.4, 129.1, 128.4, 120.4, 119.8, 111.1, 108.6, 99.0, 79.5, 64.6, 64.0, 58.2, 48.0, 44.9, 26.9, 25.5, 24.4; MS (ES+) m/z 407.0 (M+1).

EXAMPLE 16.42

Synthesis of 1'-methyl-2'-oxo-N-pentyl-1',2,2',3-tetrahydrospiro[furo[2,3-g][1,4]benzodioxine-8,3'-indole]-4'-carboxamide

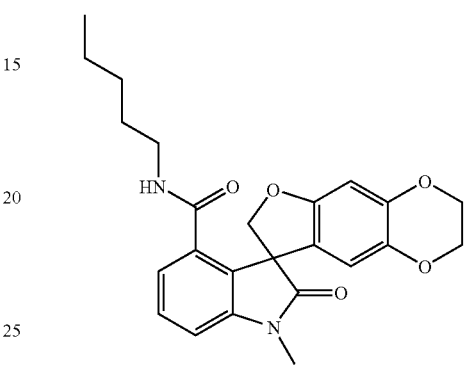

Following the procedure described in EXAMPLE 16.38 and making non-critical variations using n-pentylamine to replace cyclohexylamine, 1-methyl-2'-oxo-N-pentyl-1',2,2',3-tetrahydrospiro[furo[2,3-g][1,4]benzodioxine-8,3'-indole]-4'-carboxamide was obtained (29%) as a pale yellow solid: mp 191-193° C. (ethyl acetate/hexanes); ¹H NMR (300 MHz, CDCl₃) δ 7.42-7.36 (m, 1H), 7.24-7.22 (m, 1H), 6.99-6.95 (m, 1H), 6.50 (s, 1H), 6.20 (s, 1H), 5.32-5.25 (m, 1H), 4.92 (ABq, 2H), 4.21-4.09 (m, 4H), 3.30-3.17 (m, 1H), 3.27 (s, 3H), 3.06-2.95 (m, 1H), 1.30-1.11 (m, 6H), 0.87 (t, J=7.1 Hz, 3H); 130 NMR (75 MHz, CDCl₃) δ 177.6, 167.0, 155.8, 145.0, 144.1, 137.9, 134.4, 129.5, 127.8, 122.9, 120.6, 110.7, 109.9, 99.8, 78.8, 64.5, 64.0, 58.1, 39.9, 29.0, 28.7, 26.9, 22.3, 13.9; MS (ES+) m/z 423.1 (M+1).

EXAMPLE 16.43

Synthesis of N-(2-methoxyethyl)-1'-methyl-2'-oxo-1',2,2',3-tetrahydrospiro[furo[2,3-g][1,4]benzodioxine-8,3'-indole]-4'-carboxamide

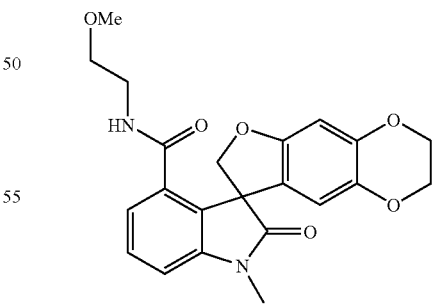

Following the procedure described in EXAMPLE 16.38 and making non-critical variations using 2-methoxyethylamine to replace cyclohexylamine, N-(2-methoxyethyl)-1'-methyl-2'-oxo-1',2,2',3-tetrahydrospiro[furo[2,3-g][1,4]-benzodioxine-8,3'-indole]-4'-carboxamide was obtained (14%) as a colorless solid: mp 97-100° C. (ethyl acetate/hexanes); ¹H NMR (300 MHz, CDCl₃) δ 7.41-7.36 (m, 1H), 7.21-7.18 (m, 1H), 6.99-6.96 (m, 1H), 6.45 (s, 1H), 6.18 (s, 1H), 5.75-5.69 (m, 1H), 4.95 (ABq, 2H), 4.19-4.10 (m, 4H), 3.48-3.15 (m, 10H); $^{13}$C NMR (75 MHz, CDCl$_3$) δ 177.8, 167.2, 155.9, 144.8, 144.1, 137.8, 134.0, 129.4, 128.4, 122.4, 120.4, 110.8, 110.0, 99.4, 79.0, 70.9, 64.5, 63.9, 58.6, 58.3, 39.4, 26.9; MS (ES+) m/z 411.0 (M+1).

EXAMPLE 16.44

Synthesis of N-(4-fluorobenzyl)-1'-methyl-2'-oxo-1', 2,2',3-tetrahydrospiro[furo[2,3-g][1,4]benzodioxine-8,3'-indole]-4'-carboxamide

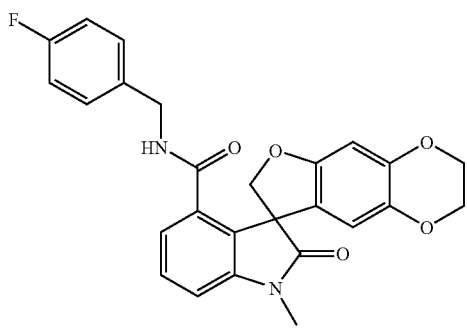

Following the procedure described in EXAMPLE 16.38 and making non-critical variations using 4-fluorobenzylamine to replace cyclohexylamine, N-(4-fluorobenzyl)-1'-methyl-2'-oxo-1',2,2',3-tetrahydrospiro[furo[2,3-g][1,4]benzodioxine-8,3'-indole]-4'-carboxamide was obtained (13%) as a colorless solid: mp 149-150° C. (ethyl acetate/hexanes); $^1$H NMR (300 MHz, CDCl$_3$) δ 7.43-7.38 (m, 1H), 7.30-7.27 (m, 1H), 7.08-6.93 (m, 5H), 6.43 (s, 1H), 6.14 (s, 1H), 5.56-5.53 (m, 1H), 4.96 (ABq, 2H), 4.53-4.46 (m, 1H), 4.20-3.93 (m, 5H), 3.27 (s, 1H); $^{13}$C NMR (75 MHz, CDCl$_3$) δ 177.5, 166.9, 163.8, 155.7, 144.9, 144.2, 137.9, 133.7, 133.3, 129.9, 129.8-129.6, 128.2, 123.0, 120.3, 115.6, 115.3, 110.6, 110.3, 99.7, 78.9, 64.4, 63.8, 58.2, 43.4, 26.9; MS (ES+) m/z 461.0 (M+1).

EXAMPLE 16.45

Synthesis of N-hexyl-1'-methyl-2'-oxo-1',2,2',3-tetrahydrospiro[furo[2,3-g][1,4]benzodioxine-8,3'-indole]-4'-carboxamide

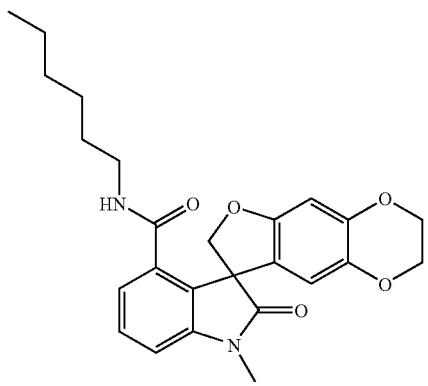

To a stirred solution of 1'-methyl-2'-oxo-1',2,2',3-tetrahydrospiro[furo[2,3-g][1,4]benzodioxine-8,3'-indole]-4'-carboxylic acid (0.200 g, 0.566 mmol) in N,N-dimethylformamide (12 mL) were added hydroxybenzotriazole (0.151 g, 1.13 mmol), 0-(benzotriazol-1-yl)-N,N,N',N'-tetramethyluronium tetrafluoroborate (0.364 g, 1.13 mmol) and N,N-diisopropylethylamine (0.81 mL, 4.5 mmol). The reaction mixture was stirred at ambient temperature for 15 min and N-hexylamine (0.15 mL, 1.1 mmol) was added. The reaction mixture stirred for 72 h at ambient temperature and concentrated in vacuo. The residue was dissolved in ethyl acetate and was washed with water (3×150 mL), 1 M aqueous sodium hydroxide (2×100 mL) and brine (2×100 mL). The organic layer was dried over anhydrous sodium sulfate and concentrated in vacuo. The residue was recrystallized from hexanes/ethyl acetate to afford N-hexyl-1'-methyl-2'-oxo-1',2,2',3-tetrahydrospiro[furo[2,3-g][1,4]benzodioxine-8,3'-indole]-4'-carboxamide (0.180 g, 73%) as a colorless solid: mp 172-173° C. (ethyl acetate/hexanes); $^1$H NMR (300 MHz, CDCl$_3$) δ 7.42-7.36 (m 1H), 7.26-7.22 (m, 1H), 6.99-6.96 (m, 1H), 6.49 (s, 1H), 6.20 (s, 1H), 5.30-5.26 (m, 1H), 4.92 (ABq, 2H), 4.25-4.07 (m, 4H), 3.27-2.97 (m, 5H), 1.30-1.18 (m, 8H), 0.87 (t, J=6.8 Hz, 3H); $^{13}$C NMR (75 MHz, CDCl$_3$) δ 177.6, 167.0, 155.8, 145.0, 144.1, 137.9, 134.4, 129.5, 127.8, 122.9, 120.6, 110.7, 109.9, 99.8, 78.8, 64.5, 64.0, 58.1, 40.0, 31.4, 28.9, 26.9, 26.5, 22.5, 14.0; MS (ES+) m/z 437.1 (M+1).

EXAMPLE 16.46

Synthesis of 1'-methyl-2'-oxo-N-(pyridin-2-ylmethyl)-1',2,2',3-tetrahydrospiro[furo[2,3-g][1,4]benzodioxine-8,3'-indole]-4'-carboxamide

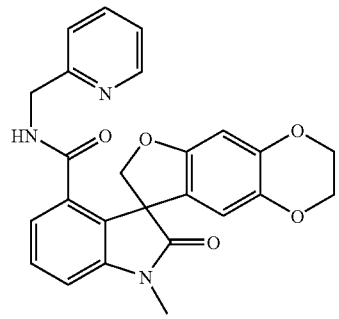

Following the procedure described in EXAMPLE 16.45 and making non-critical variations using 2-(aminomethyl) pyridine to replace n-hexylamine, 1'-methyl-2'-oxo-N-(pyridin-2-ylmethyl)-1',2,2',3-tetrahydrospiro[furo[2,3-g][1,4] benzodioxine-8,3'-indole]-4'-carboxamide was obtained (38%) as a colorless solid: mp 214-215° C. (ethyl acetate); $^1$H NMR (300 MHz, CDCl$_3$) δ 8.46-8.44 (m, 1H), 7.70-7.64 (m, 1H), 7.43-7.37 (m, 1H), 7.26-7.14 (m, 3H), 7.00-6.97 (m, 1H), 6.62 (s, 1H), 6.30 (s, 1H), 6.16 (s, 1H), 4.97 (ABq, 2H), 4.66-4.31 (m, 2H), 4.11-3.90 (m, 4H), 3.28 (s, 3H); $^{13}$C NMR (75 MHz, CDCl$_3$) δ 177.8, 167.2, 155.8, 155.7, 148.5, 144.5, 144.1, 137.7, 137.1, 133.9, 129.4, 128.9, 122.4, 122.3, 122.2, 120.4, 110.8, 110.0, 99.2, 79.1, 64.3, 63.7, 58.4, 44.7, 26.9; MS (ES+) m/z 444.1 (M+1).

EXAMPLE 16.47

Synthesis of N-(4-fluorophenyl)-1'-methyl-2'-oxo-1,2,2',3-tetrahydrospiro[furo[2,3-g][1,4]benzodioxine-8,3'-indole]-4'-carboxamide

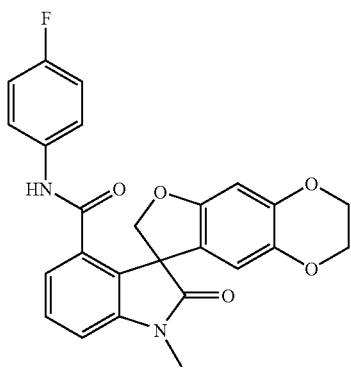

Following the procedure described in EXAMPLE 16.45 and making non-critical variations using 4-fluoroaniline to replace n-hexylamine, N-(4-fluorophenyl)-1'-methyl-2'-oxo-1',2,2',3-tetrahydrospiro[furo[2,3-g][1,4]benzodioxine-8,3'-indole]-4'-carboxamide was obtained (59%) as a pale pink solid: mp>250° C. (ethyl acetate/hexanes); $^1$H NMR (300 MHz, DMSO-$d_6$) δ 10.00 (br s, 1H), 7.52-7.47 (m, 1H), 7.39-7.34 (m, 2H), 7.26-7.20 (m, 2H), 7.12-7.06 (m, 2H), 6.21 (s, 1H), 6.13 (s, 1H), 4.85 (ABq, 2H), 4.13-3.91 (m, 4H), 3.21 (s, 3H); $^{13}$C NMR (75 MHz, DMSO-$d_6$) δ 177.6, 165.7, 158.7 (d, $J_{C-F}$=238.5 Hz), 156.1, 144.7, 144.2, 137.5, 135.4, 135.3, 134.5, 129.5, 128.8, 122.5, 122.4, 121.6, 120.1, 115.4 (d, $J_{C-F}$=21.8 Hz), 111.7, 110.8, 98.5, 79.8, 64.6, 64.0, 58.3, 27.1; MS (ES+) m/z 447.2 (M+1).

EXAMPLE 16.48

Synthesis of 4'-amino-1'-pentyl-2,3-dihydrospiro[furo[2,3-g][1,4]benzodioxine-8,3'-indol]-2'(1'H)-one

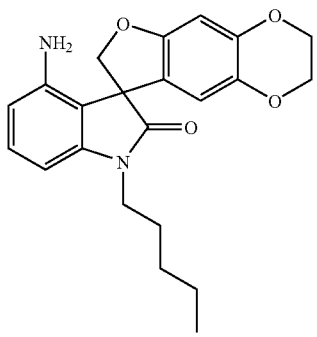

Following the procedure described in EXAMPLE 16.19 and making non-critical variations using 4'-bromo-1'-pentyl-2,3-dihydrospiro[furo[2,3-g][1,4]benzodioxine-8,3'-indol]-2'(1'H)-one to replace 4'-bromo-1'-methyl-2,3-dihydrospiro[furo[2,3-g][1,4]benzodioxine-8,3'-indol]-2'(1'H)-one, 4'-amino-1'-pentyl-2,3-dihydrospiro[furo[2,3-g][1,4]benzodioxine-8,3'-indol]-2'(1'H)-one was obtained (79%) as an orange solid: $^1$H NMR (300 MHz, CDCl$_3$) δ 7.11-7.05 (m, 1H), 6.48 (s, 1H), 6.36-6.32 (m, 3H), 4.78 (s, 2H), 4.21-4.11 (m, 4H), 3.84-3.58 (m, 2H), 1.76-1.66 (m, 2H), 1.39-1.33, (m, 4H), 0.91 (t, J=6.6 Hz, 3H); MS (ES+) m/z 380.9 (M+1).

EXAMPLE 16.49

Synthesis of 4'-(benzylamino)-1'-{[3-(trifluoromethyl)pyridin-2-yl]methyl}-2,3-dihydrospiro[furo[2,3-g][1,4]benzodioxine-8,3'-indol]-2'(1'H)-one

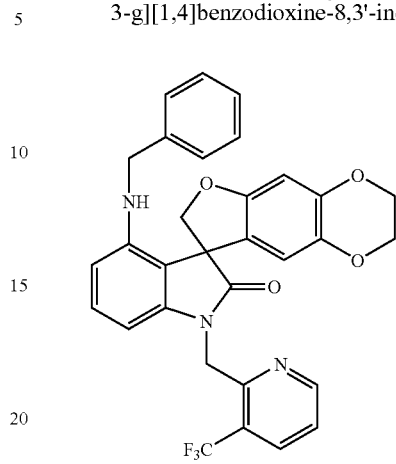

4'-Bromo-1'-{[3-(trifluoromethyl)pyridin-2-yl]methyl}-2,3-dihydrospiro[furo[2,3-g][1,4]benzodioxine-8,3'-indol]-2'(1'H)-one (0.700 g, 1.31 mmol), tris(dibenzylideneacetone)dipalladium(0) (0.14 g, 0.16 mmol), sodium tert-butoxide (0.252 g, 2.62 mmol), 2,2'-bis(diphenylphosphino)-1,1'-binaphthalene (0.29 g, 0.47 mmol) and benzylamine (0.22 mL, 2.0 mmol) were combined in anhydrous toluene (20 mL) and heated at 105° C. for 60 h. The reaction mixture was filtered through a pad of diatomaceous earth and the pad was washed with ethyl acetate (150 mL). The filtrate was washed with saturated aqueous sodium bicarbonate (100 mL), water (100 mL) and brine (100 mL), dried over anhydrous sodium sulfate, filtered and concentrated in vacuo. The residue was purified by column chromatography and eluted with a 0% to 25% gradient of ethyl acetate in dichloromethane to afford 4'-(benzylamino)-1'-{[3-(trifluoromethyl)pyridin-2-yl]methyl}-2,3-dihydrospiro[furo[2,3-g][1,4]benzodioxine-8,3'-indol]-2'(1'H)-one (0.227 g, 31%) as a colorless solid: $^1$H NMR (300 MHz, CDCl$_3$) δ 8.67 (d, J=4.5 Hz, 1H), 7.95 (d, J=7.9 Hz, 1H), 7.34-7.17 (m, 5H), 7.02 (d, J=7.7 Hz, 1H), 6.95 (dd, J=8.3, 8.3 Hz, 1H), 6.83 (s, 1H), 6.40 (s, 1H), 6.15 (ABq, 2H), 5.23 (ABq, 2H), 4.86 (ABq, 2H), 4.20-4.15 (m, 4H).

EXAMPLE 16.50

Synthesis of 4'-amino-1'-{[3-(trifluoromethyl)pyridin-2-yl]methyl}-2,3-dihydrospiro[furo[2,3-g][1,4]benzodioxine-8,3'-indol]-2'(1'H)-one

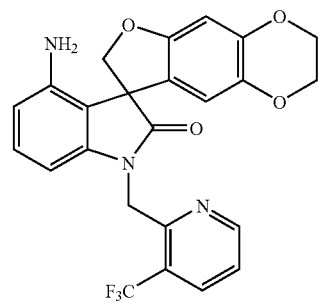

A mixture of 4'-(benzylamino)-1'-{[3-(trifluoromethyl)pyridin-2-yl]methyl}-2,3-dihydrospiro[furo[2,3-g][1,4]benzodioxine-8,3'-indol]-2'(1'H)-one (0.251 g, 0.45 mmol) and palladium hydroxide on carbon (0.251 g, 20 dry wt %, contains ~50% water, 0.18 mmol), methanol (20 mL), glacial acetic acid (1 drop, catalytic amount) was placed under an atmosphere of hydrogen (1 atm) and stirred at ambient temperature for 16 h. Further, palladium hydroxide on carbon (0.100 g, 20 dry wt %, contains ~50% water, 0.072 mmol) and acetic acid (1 drop, catalytic amount) were added, the reaction mixture was again placed under an atmosphere of hydrogen (1 atm) and allowed to react at ambient temperature for 72 h. The reaction mixture was filtered through a pad of diatomaceous earth and the pad was washed with ethyl acetate (50 mL). The filtrate was washed with water (100 mL) and brine (100 mL). The organic phase was dried over sodium sulfate, filtered and concentrated in vacuo. The residue was purified by column chromatography and eluted with a 0% to 25% gradient of ethyl acetate in dichloromethane, to yield 4'-amino-1'-{[3-(trifluoromethyl)pyridin-2-yl]methyl}-2,3-dihydrospiro[furo[2,3-g][1,4]benzodioxine-8,3'-indol]-2'(1'H)-one (0.070 g, 33%) as a colorless solid: mp 243-245° C.; $^1$H NMR (300 MHz, DMSO-d$_6$) δ 8.68 (d, J=4.6 Hz, 1H), 8.25 (d, J=7.9 Hz, 1H), 7.58 (dd, J=7.7 Hz, J=5.0 Hz, 1H), 6.91 (dd, J=8.0 Hz, J=8.0 Hz, 1H), 6.54 (d, J=12.1 Hz, 1H), 6.33 (d, J=8.2 Hz, 1H), 6.08 (d, J=7.6 Hz, 1H), 5.14 (ABq, 2H), 4.71 (ABq, 2H), 4.52 (s, 2H), 4.17 (m, 4H); $^{13}$C NMR (75 MHz, CDCl$_3$) δ 178.0, 154.9, 152.6, 152.4, 144.7, 142.9, 142.8, 138.8, 134.2, 134.1, 129.4, 122.0, 118.6, 114.5, 112.8, 111.3, 99.0, 77.2, 64.5, 63.9, 57.2, 42.4; MS (ES+) m/z 469.9 (M+1).

EXAMPLE 16.51

Synthesis of 4'-hydroxy-2,3-dihydrospiro[furo[2,3-g][1,4]benzodioxine-8,3'-indol]

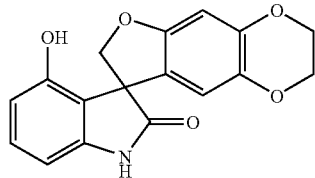

To a solution of 4'-bromo-1,2,2',3-tetrahydrospiro[furo[2,3-g][1,4]benzodioxine-8,3'-indole] (0.30 g, 0.80 mmol) in anhydrous tetrahydrofuran (20 mL) at −98° C. was added tert-butyllithium (1.90 mL, 1.7 M solution in pentane, 3.2 mmol) and stirred for 15 min. Trimethyl borate (0.36 mL, 3.2 mmol) was added and the reaction mixture was allowed to warm to ambient temperature and stirred for 16 h. A solution of hydrogen peroxide in water (0.28 mL, 35% w/w, 3.2 mmol) was added to the reaction mixture at 0° C., and the mixture was allowed to warm to ambient temperature, stirred for 0.5 h and concentrated in vacuo. The residue was triturated with water and filtered. The resultant solid was purified by column chromatography and eluted with a 0% to 50% gradient of ethyl acetate in dichloromethane to afford 4'-hydroxy-2,3-dihydrospiro[furo[2,3-g][1,4]benzodioxine-8,3'-indol]-2'(1'H)-one (0.004 g, 2%) as a colorless solid: mp>250° C.; $^1$H NMR (300 MHz, DMSO-d$_6$) δ 10.37 (s, 1H), 9.50 (s, 1H), 7.00 (dd, J=8.0, 8.0 Hz, 1H), 6.39-6.34 (m, 3H), 6.08 (s, 1H), 4.64 (ABq, 2H), 4.09 (m, 4H); $^{13}$C NMR (75 MHz, DMSO-d$_6$) δ 179.3, 155.5, 154.1, 144.0, 143.6, 137.7, 130.1, 121.0, 116.1, 111.1, 110.5, 101.8, 98.7, 76.8, 64.6, 64.0, 57.2; MS (ES+) m/z 311.7 (M+1).

EXAMPLE 16.52

Synthesis of 4'-hydroxy-1'-methyl-2,3-dihydrospiro[furo[2,3-g][1,4]benzodioxine-8,3'-indol]-2'(1'H)-one

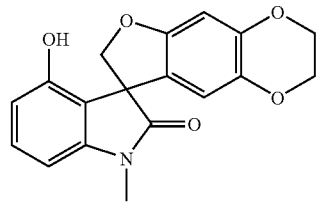

Following the procedure as described in EXAMPLE 16.51 and making non-critical variations using 4'-bromo-1'-methyl-2,3-dihydrospiro[furo[2,3-g][1,4]benzodioxine-8,3'-indol]-2'(1'H)-one to replace 4'-bromo-1',2,2',3-tetrahydrospiro[furo[2,3-g][1,4]benzodioxine-8,3'-indol], 4'-hydroxy-1'-methyl-2,3-dihydrospiro[furo[2,3-g][1,4]benzodioxine-8,3'-indol]-2'(1'7-1)-one was obtained (37%) as a colorless solid: mp>250° C.; $^1$H NMR (300 MHz, DMSO-d$_6$) δ 9.61 (s, 1H), 7.14 (dd, J=8.0, 8.0 Hz, 1H), 6.56 (d, J=7.7 Hz, 1H), 6.50 (d, J=8.3 Hz, 1H), 6.40 (s, 1H), 6.12 (s, 1H), 4.67 (ABq, 2H), 4.17-4.09 (m, 4H), 3.12 (s, 3H); $^{13}$C NMR (75 MHz, DMSO-d$_6$) δ 177.0, 155.0, 153.3, 144.7, 143.6, 137.1, 129.6, 120.2, 114.6, 110.9, 110.8, 100.2, 98.1, 76.2, 64.1, 63.5, 56.3, 26.5; MS (ES+) m/z 325.8 (M+1).

EXAMPLE 16.53

Synthesis of 1'-methyl-4'-(pyridin-2-yloxy)-2,3-dihydrospiro[furo[2,3-g][1,4]benzodioxine-8,3'-indol]-2'(1'H)-one

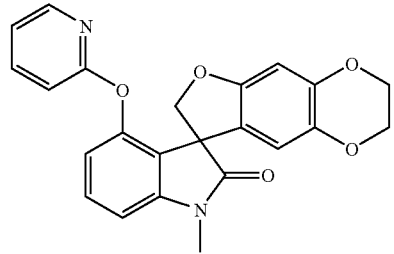

4'-Hydroxy-t-methyl-2,3-dihydrospiro[furo[2,3-g][1,4]benzodioxine-8,3'-indol]-2'(1'H)-one (0.120 g, 0.37 mmol), copper(I) iodide (0.007 g, 0.04 mmol), potassium carbonate (0.066 g, 0.48 mmol), 2-bromopyridine (0.070 mL, 0.74 mmol), and 1-butyl-1H-imidazole (0.024 mL, 0.18 mmol) were combined in anhydrous toluene (1 mL) and heated in a sealed tube at 120° C. for 50 h. Dichloromethane (25 mL) was added and the mixture was washed with water (3×25 mL). The organic phase was dried over magnesium sulfate, filtered and concentrated in vacuo. The residue was triturated in methanol to afford 1'-methyl-4'-(pyridin-2-yloxy)-2,3-dihydrospiro[furo[2,3-g][1,4]benzodioxine-8,3'-indol]-2'(1'H)-one (0.080 g, 54%) as a colorless solid: mp 219-221° C.; $^1$H NMR (300 MHz, DMSO-d$_6$) δ 7.91-7.89 (m, 1H), 7.67-7.62 (m, 1H), 7.35 (dd, J=8.1, 8.1 Hz, 1H), 6.98-6.94 (m, 2H), 6.72 (d, J=8.3 Hz, 1H), 6.65 (d, J=8.3 Hz, 1H), 6.11 (d, J=10.4 Hz, 1H), 4.57 (ABq, 2H), 4.10-3.93 (m, 4H), 3.18 (s, 3H); $^{13}$C NMR (75 MHz, DMSO-d$_6$) δ 176.3, 162.4, 154.6, 149.4, 146.6, 144.7, 143.7, 139.5, 137.1, 129.8, 123.0, 118.9, 118.5, 117.3, 111.5, 110.6, 105.7, 97.9, 77.6, 64.0, 63.4, 56.5, 26.8; MS (ES+) m/z 403.2 (M+1).

EXAMPLE 16.54

Synthesis of 4'-[2-(2-methoxyethoxy)ethoxy]-1'-methyl-2,3-dihydrospiro[furo[2,3-g][1,4]benzodioxine-8,3'-indol]-2'(1'H)-one

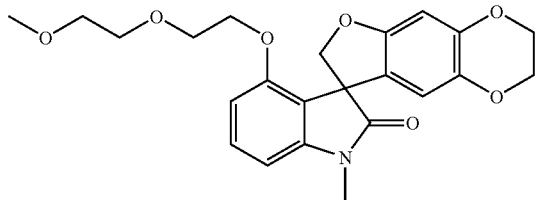

Following the procedure as described in EXAMPLE 16.53 and making non-critical variations using 1-bromo-2-(2-methoxyethoxy)ethane to replace 2-bromopyridine, 4'-[2-(2-methoxyethoxy)ethoxy]-1'-methyl-2,3-dihydrospiro[furo[2,3-g][1,4]benzodioxine-8,3'-indol]-2'(1'H)-one was obtained (26%) as a colorless solid: mp 109-110° C.; $^1$H NMR (300 MHz, DMSO-d$_6$) δ 7.30 (dd, J=8.1, 8.1 Hz, 1H), 6.73 (dd, J=8.1, 5.6 Hz, 1H), 6.39 (s, 1H), 6.12 (s, 1H), 4.69 (ABq, 2H), 4.17-4.07 (m, 4H), 4.01-3.91 (m, 2H), 3.49 (t, J=4.5 Hz, 2H), 3.38-3.31 (m, 4H), 3.20 (s, 3H), 3.15 (s, 3H); $^{13}$C NMR (75 MHz, DMSO-d$_6$) δ 177.0, 155.1, 154.3, 144.4, 143.6, 137.0, 130.1, 120.0, 116.7, 110.7, 107.4, 102.1, 98.0, 76.5, 71.2, 69.7, 68.7, 68.0, 64.1, 63.5, 57.9, 56.5, 26.5; MS (ES+) m/z 428.1 (M+1).

EXAMPLE 16.55

Synthesis of 1'-methyl-4'-{[3-(trifluoromethyl)pyridin-2-yl]oxy}-2,3-dihydrospiro[furo[2,3-g][1,4]benzodioxine-8,3'-indol]-2'(1'H)-one

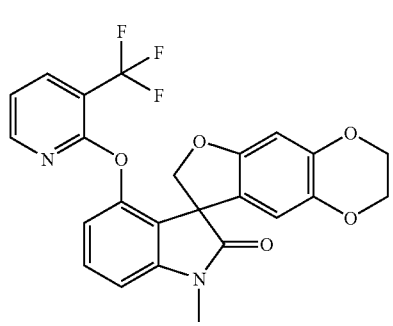

Following the procedure as described in EXAMPLE 16.53 and making non-critical variations using 2-bromo-3-(trifluoromethyl)pyridine to replace 2-bromopyridine, 1'-methyl-4'-{[3-(trifluoromethyl)pyridin-2-yl]oxy}-2,3-dihydrospiro[furo[2,3-g][1,4]benzodioxine-8,3'-indol]-2'(1'H)-one was obtained (44%) as a colorless solid: mp>250° C.; $^1$H NMR (300 MHz, DMSO-d$_6$) δ 8.11-8.06 (m, 2H), 7.42 (dd, J=8.0, 8.0 Hz, 1H), 7.17 (dd, J=7.5, 5.0 Hz, 1H), 7.05 (d, J=7.8 Hz, 1H), 6.78 (d, J=8.3 Hz, 1H), 6.07 (s, 1H), 6.04 (s, 1H), 4.61 (ABq, 2H), 4.11-3.93 (m, 4H), 3.21 (s, 3H); $^{13}$C NMR (75 MHz, DMSO-d$_6$) δ 176.7, 159.0, 155.2, 151.1, 148.7, 145.6, 144.1, 137.8 (m), 137.4, 130.6, 125.0, 123.3, 118.8, 117.9, 112.3, 112.1, 111.6, 107.0, 98.2, 78.1, 64.5, 63.9, 57.0, 27.3; MS (ES+) m/z 470.9 (M+1).

EXAMPLE 16.56

Synthesis of 1'-methyl-4'-[4-(trifluoromethyl)phenoxy]-2,3-dihydrospiro[furo[2,3-g][1,4]benzodioxine-8,3'-indol]-2'(1'H)-one

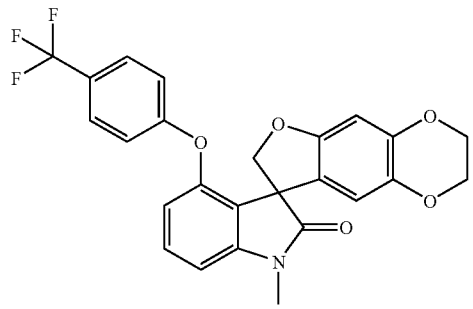

Following the procedure as described in EXAMPLE 16.53 and making non-critical variations using 1-bromo-4-(trifluoromethyl)benzene to replace 2-bromopyridine, 1'-methyl-4'-[4-(trifluoromethyl)phenoxy]-2,3-dihydrospiro[furo[2,3-g][1,4]benzodioxine-8,3'-indol]-2'(1'H)-one was obtained (36%) as a colorless solid: mp 198-201° C.; $^1$H NMR (300 MHz, DMSO-d$_6$) δ 7.52 (d, J=8.7 Hz, 2H), 7.44 (dd, J=8.1, 8.1 Hz, 1H), 7.06 (d, J=7.8 Hz, 1H), 6.74 (dd, J=8.3, 1.9 Hz, 3H), 6.19 (s, 1H), 6.10 (s, 1H), 4.66 (ABq, 2H), 4.12-3.93 (m, 4H), 3.23 (s, 3H); $^{13}$C NMR (75 MHz, DMSO-d$_6$) δ 176.2, 154.6, 149.8, 145.1, 143.8, 137.2, 130.6, 126.6 (m), 123.1, 122.8, 122.4, 118.8, 116.2, 115.4, 111.1, 106.2, 98.0, 77.6, 64.0, 63.3, 56.4, 26.8; MS (ES+) m/z 470.1 (M+1).

EXAMPLE 16.57

Synthesis of 4'-(benzyloxy)-1'-methyl-2,3-dihydrospiro[furo[2,3-g][1,4]benzodioxine-8,3'-indol]-2'(1'H)-one

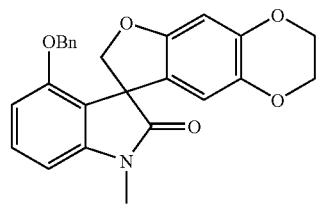

4'-Hydroxy-1'-methyl-2,3-dihydrospiro[furo[2,3-g][1,4]benzodioxine-8,3'-indol]-2'(1'H)-one (0.25 g, 0.77 mmol), benzyl bromide (0.13 mL, 1.1 mmol), and cesium carbonate (0.751 g, 2.30 mmol) were combined in anhydrous N,N-dimethylformamide (10 mL) at ambient temperature and stirred for 16 h. The reaction mixture was concentrated in vacuo and the residue was taken up in water (25 mL) and extracted with dichloromethane (3×25 mL). The organic layer was dried over magnesium sulfate, filtered and concentrated in vacuo. The residue was purified by column chromatography and eluted with a 0% to 10% gradient of ethyl acetate in dichloromethane, followed by recrystallization from methanol/dichloromethane to afford 4'-(benzyloxy)-1'-methyl-2,3-dihydrospiro[furo[2,3-g][1,4]benzodioxine-8,3'-indol]-2'(1'H)-one (0.130 g, 41%) as a colorless solid: mp 198-200° C.; $^1$H NMR (300 MHz, DMSO-d$_6$) δ 7.32-7.23 (m, 4H), 7.03-7.01 (m, 2H), 6.81 (d, J=8.5 Hz, 1H) 6.74 (d, J=7.8

Hz, 1H), 6.44 (s, 1H), 6.20 (s, 1H), 5.06 (s, 2H), 4.70 (ABq, 2H), 4.19-4.11 (m, 4H), 3.16 (s, 3H); $^{13}$C NMR (75 MHz, DMSO-d$_6$) δ 177.4, 155.8, 154.4, 145.0, 144.3, 137.8, 137.3, 130.6, 128.5, 127.9, 127.0, 120.5, 117.6, 111.5, 108.1, 102.8, 98.8, 77.5, 69.1, 64.7, 64.1, 57.7, 27.1; MS (ES+) m/z 416.0 (M+1).

EXAMPLE 16.58

Synthesis of 1'-methyl-4'-{[3-(trifluoromethyl)pyridin-2-yl]methoxy}-2,3-dihydrospiro[furo[2,3-g][1,4]benzodioxine-8,3'-indol]-2'(1'H)-one

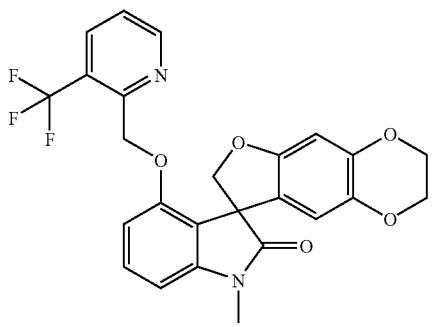

Following the procedure as described in EXAMPLE 16.57 and making non-critical variations using 2-(chloromethyl)-3-(trifluoromethyl)pyridine hydrochloride to replace benzyl bromide, 1'-methyl-4'-{[3-(trifluoromethyl)pyridin-2-yl]methoxy}-2,3-dihydrospiro[furo[2,3-g][1,4]benzodioxine-8,3'-indol]-2'(1'H)-one was obtained (44%) as a colorless solid: mp 157-159° C.; $^1$H NMR (300 MHz, DMSO-d$_6$) δ 8.77 (d, J=4.7 Hz, 1H), 8.17 (d, J=7.9 Hz, 1H), 7.61 (dd, J=8.0, 4.9 Hz, 1H), 7.31 (dd, J=8.1, 8.1 Hz, 1H), 6.83 (d, J=8.5 Hz, 1H), 6.75 (d, J=7.8 Hz, 1H), 6.06 (s, 1H), 6.01 (s, 1H), 5.16 (ABq, 2H), 4.59 (ABq, 2H), 4.14-4.06 (m, 4H), 3.14 (s, 3H); $^{13}$C NMR (75 MHz, DMSO-d$_6$) δ 177.4, 155.5, 154.8, 153.2, 153.0, 137.5, 135.3, 130.6, 125.8, 124.6, 124.2, 124.1, 122.2, 120.1, 117.6, 111.2, 107.9, 103.0, 98.0, 77.1, 69.2, 64.6, 64.0, 57.0, 27.1; MS (ES+) m/z 484.8 (M+1).

EXAMPLE 16.59

Synthesis of 4'-(6-(dimethylamino)pyridin-3-yl)-1'-(pyridin-2-ylmethyl)-3,7-dihydro-2H-spiro[benzofuro[5,6-b][1,4]dioxine-8,3'-indolin]-2'-one

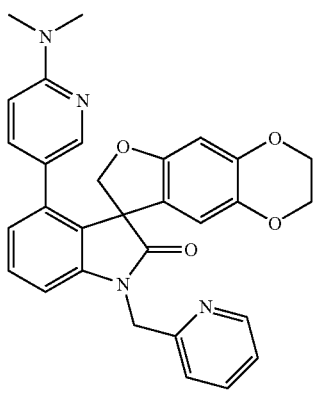

Following the procedure as described in EXAMPLE 2.46 and making non-critical variations using 2-(dimethylamino)pyridine-5-boronic acid to replace quinolin-3-ylboronic acid, and 4'-bromo-1'-(pyridin-2-ylmethyl)-2,3-dihydrospiro[furo[2,3-g][1,4]benzodioxine-8,3'-indol]-2'(1'H)-one to replace 4'-bromo-1'-(diphenylmethyl)-2,3-dihydrospiro[furo[2,3-g][1,4]benzodioxine-8,3'-indol]-2'(1'H)-one, 4'-(6-(dimethylamino)pyridin-3-yl)-1'-(pyridin-2-ylmethyl)-3,7-dihydro-2H-spiro[benzofuro[5,6-b][1,4]dioxine-8,3'-indolin]-2'-one was obtained (44%) as a colorless solid: mp 187-188° C. (methanol/dichloromethane); $^1$H NMR (300 MHz, CDCl$_3$) δ 8.61-8.56 (m, 1H), 7.80-7.77 (m, 1H), 7.70-7.62 (m, 1H), 7.32-7.17 (m, 3H), 6.91-6.81 (m, 2H), 6.66 (dd, J=8.8, 2.5 Hz, 1H), 6.40 (s, 1H), 6.27 (s, 1H), 6.21 (d, J=8.8 Hz, 1H), 5.25 (d, J=15.8 Hz, 1H), 4.93 (d, J=15.8 Hz, 1H), 4.71 (d, J=9.0 Hz, 1H), 4.46 (d, J=9.0 Hz, 1H), 4.30-4.08 (m, 4H), 3.05 (s, 6H); $^{13}$C NMR (75 MHz, CDCl$_3$) δ 178.2, 158.5, 155.6, 155.4, 149.5, 147.4, 144.7, 142.7, 138.0, 137.6, 137.2, 137.1, 129.5, 128.8, 125.9, 122.8, 122.7, 122.0, 121.7, 111.2, 108.6, 104.3, 99.4, 64.6, 64.0, 58.4, 46.2, 38.1; MS (ES+) m/z 507.0 (M+1).

EXAMPLE 16.60

Synthesis of 4'-(4-methoxyphenyl)-1'-(pyridin-2-ylmethyl)-3,7-dihydro-2H-spiro[benzofuro[5,6-b][1,4]dioxine-8,3'-indolin]-2'-one

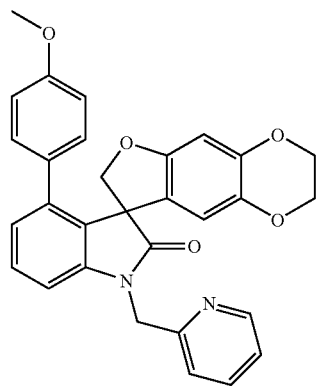

Following the procedure as described in EXAMPLE 2.46 and making non-critical variations using 4-methoxyphenyl boronic acid to replace quinolin-3-ylboronic acid, and 4'-bromo-1'-(pyridin-2-ylmethyl)-2,3-dihydrospiro[furo[2,3-g][1,4]benzodioxine-8,3'-indol]-2'(1'H)-one to replace 4'-bromo-1'-(diphenylmethyl)-2,3-dihydrospiro[furo[2,3-g][1,4]benzodioxine-8,3'-indol]-2'(1'H)-one, 4'-(4-methoxyphenyl)-1'-(pyridin-2-ylmethyl)-3,7-dihydro-2H-spiro[benzofuro[5,6-b][1,4]dioxine-8,3'-indolin]-2'-one was obtained (68%) as a colorless solid: mp 205-206° C. (ethyl acetate/hexanes); $^1$H NMR (300 MHz, CDCl$_3$) δ 8.59 (d, J=4.7 Hz, 1H), 7.65-7.68 (m, 1H), 7.32-7.17 (m, 3H), 6.91-6.84 (m, 2H), 6.78-6.61 (m, 4H), 6.41 (s, 1H), 6.25 (s, 1H), 5.26 (d, J=15.8 Hz, 1H), 4.92 (d, J=15.8 Hz, 1H), 4.68 (d, J=9.0 Hz, 1H), 4.36 (d, J=9.0 Hz, 1H), 4.27-4.08 (m, 4H), 3.77 (s, 3H); $^{13}$C NMR (75 MHz, CDCl$_3$) δ 178.3, 158.9, 155.6, 155.5, 149.5, 144.6, 142.6, 140.0, 137.9, 137.1, 130.9, 129.8, 129.0, 128.7, 125.7, 122.9, 122.8, 121.7, 113.2, 111.1, 108.5, 99.4, 64.6, 64.0, 58.5, 55.3, 46.2; MS (ES+) m/z 493.0 (M+1).

EXAMPLE 16.61

Synthesis of (7S)-4'-furan-3-yl-1'-methylspiro[furo[2,3-d][1,3]benzodioxole-7,3'-indol]-2'(1'H)-one

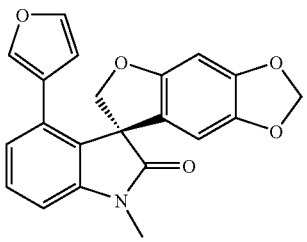

4'-Furan-3-yl-1'-methylspiro[furo[2,3-f][1,3]benzodioxole-7,3'-indol]-2'(1'H)-one (950 mg, 2.63 mmol) was resolved on a semi-preparative chiral column (CHIRALPAK-IA, Chiral Technologies, Inc.) eluted with 2% acetonitrile in tert-butylmethylether at 30 mL/min (25 min run time). Each run consisted of 50 mg of the racemate dissolved in acetonitrile/tert-butylmethylether (1:1). (7S)-4'-furan-3-yl-1'-methylspiro[furo[2,3-f][1,3]benzodioxole-7,3'-indol]-2'(1'H)-one was the first enantiomer to elute. Recrystallization from dichloromethane and diethyl ether afforded (7S)-4'-furan-3-yl-t-methylspiro[furo[2,3-f][1,3]benzodioxole-7,3'-indol]-2'(1'H)-one (0.38 g, 79%) as a colorless solid: mp 144-145° C. (dichloromethane/diethyl ether); $^1$H NMR (300 MHz, CDCl$_3$) δ 7.38-7.30 (m, 2H), 7.00 (dd, J=7.9, 0.9 Hz, 1H), 6.89-6.81 (m, 1H), 6.42 (s, 1H), 6.21 (s, 1H), 6.05-6.03 (m, 1H), 5.89 (d, J=1.3 Hz, 1H), 5.85 (d, J=1.3 Hz, 1H), 4.72 (d, J=9.1 Hz, 1H), 4.57 (d, J=9.1 Hz, 1H), 3.27 (s, 3H); $^{13}$C NMR (75 MHz, CDCl$_3$) δ 178.1, 156.2, 149.1, 144.2, 142.8, 142.0, 140.4, 131.0, 129.1, 128.2, 125.4, 122.5, 120.8, 111.1, 107.5, 102.8, 101.6, 93.9, 58.5, 26.9; MS (ES+) m/z 361.9 (M+1).

EXAMPLE 16.62

Synthesis of (7R)-4'-furan-3-yl-1'-methylspiro[furo[2,3-f][1,3]-benzodioxole-7,3'-indol]-2'(1'H)-one

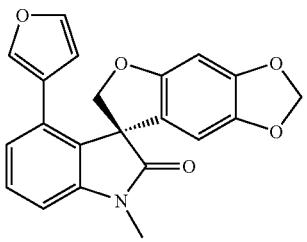

4'-Furan-3-yl-1'-methylspiro[furo[2,3-f][1,3]benzodioxole-7,3'-indol]-2'(1'H)-one (950 mg, 2.63 mmol) was resolved on a semi-preparative chiral column (CHIRALPAK-IA, Chiral Technologies, Inc.) and eluted with 2% acetonitrile in tert-butylmethylether at 30 mL/min (25 min run time). Each run consisted of 50 mg of the racemate dissolved in acetonitrile/tert-butylmethylether (1:1). (7R)-4'-furan-3-yl-1'-methylspiro[furo[2,3-f][1,3]benzodioxole-7,3'-indol]-2'(1'H)-one was the second enantiomer to elute. Recrystallization from dichloromethane and diethyl ether afforded (7R)-4'-furan-3-yl-t-methylspiro[furo[2,3-f][1,3]benzodioxole-7,3'-indol]-2'(1'H)-one (0.39 g, 82%) as a colorless solid: mp 144-145° C. (dichloromethane/diethyl ether); $^1$H NMR (300 MHz, CDCl$_3$) δ 7.38-7.30 (m, 2H), 7.00 (dd, J=7.9, 0.6 Hz, 1H), 6.89-6.81 (m, 1H), 6.42 (s, 1H), 6.21 (s, 1H), 6.05-6.03 (m, 1H), 5.89 (d, J=1.2 Hz, 1H), 5.85 (d, J=1.2 Hz, 1H), 4.72 (d, J=9.1 Hz, 1H), 4.57 (d, J=9.1 Hz, 1H), 3.27 (s, 3H); $^{13}$C NMR (75 MHz, CDCl$_3$) δ 178.1, 156.2, 149.1, 144.2, 142.8, 142.0, 140.4, 131.0, 129.1, 128.2, 125.4, 122.5, 120.8, 111.1, 107.5, 102.8, 101.6, 93.9, 58.5, 26.9; MS (ES+) m/z 361.9 (M+1).

EXAMPLE 16.63

Synthesis of (7R)-4'-bromo-1'-methylspiro[furo[2,3-f][1,3]benzodioxole-7,3'-indol]-2'(1'H)-one

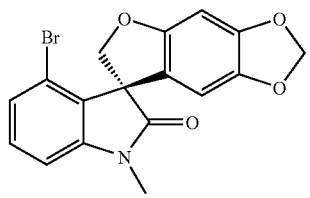

4'-Bromo-1'-methylspiro[furo[2,3-f][1,3]benzodioxole-7,3'-indol]-2'(1'H)-one (0.32 g, 8.58 mmol) was resolved on a semi-preparative chiral column (CHIRALPAK-IA, Chiral Technologies, Inc.) eluted with 5% acetonitrile in tert-butylmethylether at 30 mL/min. Each run consisted of 50 mg of the racemate dissolved in acetonitrile/tert-butylmethylether (1:1). (7R)-4'-bromo-1'-methylspiro[furo[2,3-f][1,3]benzodioxole-7,3'-indol]-2'(1'H)-one (0.14 g, 86%) was the first enantiomer to elute and was obtained as a crystalline colorless solid:. mp 226-228° C. (acetonitrile/tert-butylmethylether); $^1$H NMR (300 MHz, DMSO-d$_6$) δ 7.31-7.23 (m, 1H), 7.20-7.15 (m, 1H), 7.12-7.08 (m, 1H), 6.59 (s, 1H), 6.28 (s, 1H), 5.92-5.87 (m, 2H), 4.82 (d, J=9.7 Hz, 1H), 4.67 (d, J=9.7 Hz, 1H), 3.15 (s, 3H); MS (ES+) m/z 373.8, 375.8 (M+1).

EXAMPLE 16.64

Synthesis of (7S)-4'-bromo-1'-methylspiro[furo[2,3-f][1,3]benzodioxole-7,3'-indol]-2'(1'H)-one

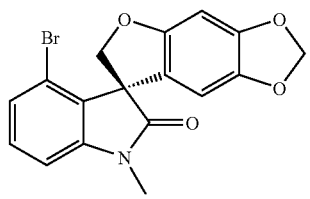

4'-Bromo-1'-methylspiro[furo[2,3-f][1,3]benzodioxole-7,3'-indol]-2'(1'H)-one (0.32 g, 8.58 mmol) was resolved on a semi-preparative chiral column (CHIRALPAK-IA, Chiral Technologies, Inc.) and eluted with 5% acetonitrile in tent-butylmethylether at 30 mL/min. Each run consisted of 50 mg of the racemate dissolved in acetonitrile/tert-butylmethylether (1:1). (7S)-4'-bromo-1'-methylspiro[furo[2,3-f][1,3] benzodioxole-7,3'-indol]-2'(1'H)-one (0.13 g, 81%) was the second enantiomer to elute and was isolated as a crystalline colorless solid: mp 226-227° C. (acetonitrile/tert-butylmethylether); $^1$H NMR (300 MHz, DMSO-d$_6$) δ 7.31-7.23 (m, 1H), 7.20-7.15 (m, 1H), 7.12-7.08 (m, 1H), 6.59 (s, 1H), 6.28 (s, 1H), 5.92-5.87 (m, 2H), 4.82 (d, J=9.7 Hz, 1H), 4.67 (d, J=9.7 Hz, 1H), 3.15 (s, 3H); MS (ES+) m/z 373.8, 375.8 (M+1).

EXAMPLE 16.65

Synthesis of (7S)-4'-furan-3-ylspiro[furo[2,3-f][1,3]benzodioxole-7,3'-indol]-2'(1'H)-one

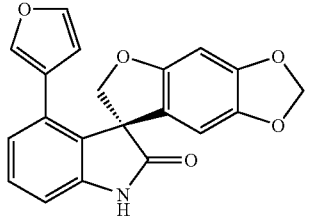

4'-Furan-3-ylspiro[furo[2,3-f][1,3]benzodioxole-7,3'-indol]-2'(1'H)-one (0.25 g) was resolved on a semi-preparative chiral column (CHIRALPAK-IA, Chiral Technologies, Inc.) and eluted with 5% acetonitrile in tert-butylmethylether at 30 mL/min. Each run consisted of 50 mg of the racemate dissolved first in dimethylsulfoxide (0.15 mL) and diluted with acetonitrile (0.85 mL) and tert-butylmethylether (1.00 mL). The product was dissolved in dimethylsulfoxide (2.0 mL), precipitated with water (50.0 mL), filtered and air dried to afford (7S)-4'-furan-3-ylspiro[furo[2,3-f][1,3]benzodioxole-7,3'-indol]-2'(1'H)-one (0.11 g, 88%) as a colorless solid. This enantiomer was the first to elute. mp 230-231° C. (water); $^1$H NMR (300 MHz, DMSO-d$_6$) δ 10.64 (s, 1H), 7.57 (dd, J=1.6, 1.6 Hz, 1H), 7.27 (dd, J=7.8, 7.8 Hz, 1H), 7.03 (s, 1H), 6.90 (dd, J=7.1, 7.1 Hz, 2H), 6.55 (s, 1H), 6.32 (s, 1H), 6.06 (d, J=0.8 Hz, 1H), 5.92 (d, J=4.8 Hz, 2H), 4.60 (d, J=9.4 Hz, 1H), 4.44 (d, J=9.4 Hz, 1H); $^{13}$C NMR (75 MHz, DMSO-d$_6$) δ 179.2, 156.1, 148.8, 143.8, 143.3, 142.0, 140.5, 130.5, 129.6, 128.9, 124.3, 123.2, 121.4, 111.3, 109.7, 103.3, 101.9, 93.7, 77.6, 58.6; MS (ES+) m/z 347.9 (M+1).

EXAMPLE 16.66

Synthesis of (7R)-4'-furan-3-ylspiro[furo[2,3-f][1,3]benzodioxole-7,3'-indol]-2'(1'H)-one

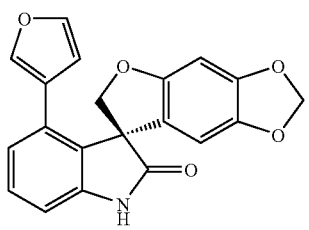

4'-Furan-3-ylspiro[furo[2,3-f][1,3]benzodioxole-7,3'-indol]-2'(1'H)-one (0.25 g) was resolved on a semi-preparative chiral column (CHIRALPAK-IA, Chiral Technologies, Inc.) and eluted with 5% acetonitrile in tert-butylmethylether at 30 mL/min. Each run consisted of 50 mg of the racemate dissolved first in dimethylsulfoxide (0.15 mL) and diluted with acetonitrile (0.85 mL) and tert-butylmethylether (1.00 mL). The product isolated was dissolved in dimethylsulfoxide (2.0 mL), precipitated with water (50.0 mL), filtered and air dried to afford (7R)-4'-furan-3-ylspiro[furo[2,3-f][1,3]benzodioxole-7,3'-indol]-2'(1'H)-one (0.10 g, 75%) as a colorless solid. This enantiomer was the second to elute: mp 229-231° C. (water); $^1$H NMR (300 MHz, DMSO-d$_6$) δ 10.64 (s, 1H), 7.57 (dd, J=1.6, 1.6 Hz, 1H), 7.27 (dd, J=7.8, 7.8 Hz, 1H), 7.03 (s, 1H), 6.90 (dd, J=7.1, 7.1 Hz, 2H), 6.55 (s, 1H), 6.32 (s, 1H), 6.06 (d, J=0.8 Hz, 1H), 5.92 (d, J=4.8 Hz, 2H), 4.60 (d, J=9.4 Hz, 1H), 4.44 (d, J=9.4 Hz, 1H); $^{13}$C NMR (75 MHz, DMSO-d$_6$) δ 179.2, 156.1, 148.8, 143.8, 143.3, 142.0, 140.5, 130.5, 129.6, 128.9, 124.3, 123.2, 121.4, 111.3, 109.7, 103.3, 101.9, 93.7, 77.6, 58.6; MS (ES+) m/z 347.9 (M+1).

EXAMPLE 16.67

Synthesis of 1'-methyl-4'-(1H-pyrazol-3-yl)-2,3-dihydrospiro[furo[2,3-g][1,4]benzodioxine-8,3'-indol]-2'(1'H)-one

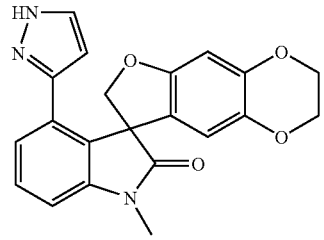

Following the procedure as described in EXAMPLE 2.46 and making non-critical variations using 1H-pyrazol-3-boronic acid to replace quinolin-3-ylboronic acid, and 4'-bromo-1'-methylspiro[furo[2,3-f][1,3]benzodioxole-7,3'-indol]-2'(1'H)-one to replace 4'-bromo-1'-(diphenylmethyl)-2,3-dihydrospiro[furo[2,3-g][1,4]benzodioxine-8,3'-indol]-2'(1'H)-one, 1'-methyl-4'-(1H-pyrazol-3-yl)-2,3-dihydrospiro[furo[2,3-g][1,4]benzodioxine-8,3'-indol]-2'(1'H)-one was obtained (63%) as a colorless solid: mp 201-202° C. (dichloromethane/diethyl ether); $^1$H NMR (300 MHz, CDCl$_3$) δ 7.46-7.35 (m, 2H), 7.25-7.20 (m, 1H), 6.92 (d, J=7.7 Hz, 1H), 6.40 (s, 1H), 6.24 (s, 1H), 5.94 (d, J=2.0 Hz, 1H), 4.74-4.61 (m, 2H), 4.20-4.07 (m, 4H), 3.27 (s, 3H); $^{13}$C NMR (75 MHz, CDCl$_3$) δ 178.0, 155.6, 144.7, 144.5, 137.8, 129.2, 128.0, 124.6, 121.6, 111.0, 108.2, 105.5, 99.5, 77.4, 64.5, 63.9, 58.4, 26.9; MS (ES+) m/z 375.9 (M+1).

EXAMPLE 16.68

Synthesis of 4'-furan-3-yl-1'-methyl-2,3-dihydrospiro[furo[2,3-g][1,4]benzodioxine-8,3'-indol]-2'(1'H)-one

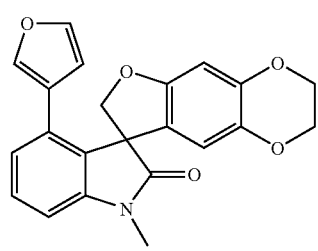

Following the procedure as described in EXAMPLE 2.46 and making non-critical variations using 3-furanboronic acid to replace quinolin-3-ylboronic acid, and 4'-bromo-1'-methylspiro[furo[2,3-f][1,3]benzodioxole-7,3'-indol]-2'(1'H)-one to replace 4'-bromo-1'-(diphenylmethyl)-2,3-dihydrospiro

[furo[2,3-g][1,4]benzodioxine-8,3'-indol]-2'(1'H)-one, 4'-furan-3-yl-1'-methyl-2,3-dihydrospiro[furo[2,3-g][1,4]-benzodioxine-8,3'-indol]-2'(1'H)-one was obtained (65%) as a colorless solid: mp 178-180° C. (ethyl acetate/hexanes); $^1$H NMR (300 MHz, CDCl$_3$) δ 7.38-7.29 (m, 2H), 7.00 (d, J=7.9 Hz, 1H), 6.86 (d, J=7.8 Hz, 1H), 6.76 (s, 1H), 6.41 (s, 1H), 6.28 (s, 1H), 6.04-6.01 (m, 1H), 4.68 (d, J=9.0 Hz, 1H), 4.53 (d, J=9.0 Hz, 1H), 4.23-4.09 (m, 4H), 3.26 (s, 3H); $^{13}$C NMR (75 MHz, CDCl$_3$) δ 178.0, 155.5, 144.7, 144.3, 142.8, 140.5, 137.9, 130.8, 129.1, 128.1, 125.2, 122.6, 122.5, 111.2, 111.1, 107.4, 99.7, 76.7, 64.6, 64.0, 58.3, 26.8; MS (ES+) m/z 375.9 (M+1).

EXAMPLE 16.69

Synthesis of 1'-methyl-4'-(1H-pyrazol-4-yl)-2,3-dihydrospiro[furo[2,3-g][1,4]benzodioxine-8,3'-indol]-2'(1'H)-one

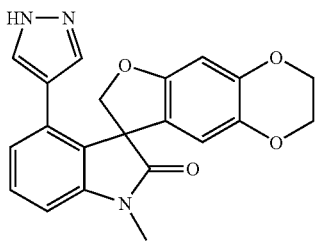

Following the procedure as described in EXAMPLE 2.46 and making non-critical variations using 1H-pyrazole-4-boronic acid to replace quinolin-3-ylboronic acid, and 4'-bromo-1'-methylspiro[furo[2,3-f][1,3]benzodioxole-7,3'-indol]-2'(1'H)-one to replace 4'-bromo-1'-(diphenylmethyl)-2,3-dihydrospiro[furo[2,3-g][1,4]benzodioxine-8,3'-indol]-2'(1'H)-one, 1-methyl-4'-(1H-pyrazol-4-yl)-2,3-dihydrospiro[furo[2,3-g][1,4]benzodioxine-8,3'-indol]-2'(1'H)-one was obtained (54%) as a colorless solid: mp 250-251° C. (ethyl acetate/hexanes); $^1$H NMR (300 MHz, CDCl$_3$) δ 7.35 (dd, J=7.9, 7.9 Hz, 1H), 7.10-7.00 (m, 3H), 6.86 (d, J=7.8 Hz, 1H), 6.40 (s, 1H), 6.31 (s, 1H), 4.66 (d, J=9.1 Hz, 1H), 4.47 (d, J=9.1 Hz, 1H), 4.23-4.08 (m, 4H), 3.26 (s, 3H); $^{13}$C NMR (75 MHz, CDCl$_3$) δ 178.0, 155.4, 144.8, 144.3, 138.0, 130.6, 129.2, 127.9, 125.4, 122.5, 111.4, 107.3, 99.6, 64.6, 63.9, 58.2, 26.8; MS (ES+) m/z 376.0 (M+1).

EXAMPLE 16.70

Synthesis of 1'-methyl-4'-(1-methyl-1H-pyrazol-4-yl)-2,3-dihydrospiro[furo[2,3-g][1,4]benzodioxine-8,3'-indol]-2'(1'H)-one

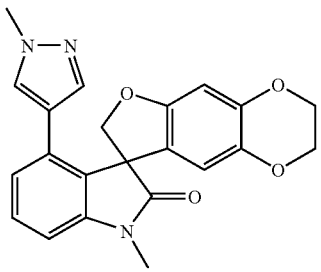

Following the procedure as described in EXAMPLE 2.46 and making non-critical variations using 1-methyl-4-(4,4,5,5-tetramethyl-1,3,2-dioxaborolan-2-yl)-1H-pyrazole to replace quinolin-3-ylboronic acid, and 4'-bromo-1'-methylspiro[furo[2,3-f][1,3]benzodioxole-7,3'-indol]-2'(1'H)-one to replace 4'-bromo-1'-(diphenylmethyl)-2,3-dihydrospiro[furo[2,3-g][1,4]benzodioxine-8,3'-indol]-2'(1'H)-one, 1'-methyl-4'-(1-methyl-1H-pyrazol-4-yl)-2,3-dihydrospiro[furo[2,3-g][1,4]benzodioxine-8,3'-indol]-2'(1'H)-one was obtained (58%) as a colorless solid: mp 220-222° C. (ethyl acetate/hexanes); $^1$H NMR (300 MHz, CDCl$_3$) δ 7.32 (dd, J=7.9, 7.9 Hz, 1H), 7.16 (s, 1H), 6.99 (d, J=7.8 Hz, 1H), 6.83 (d, J=7.8 Hz, 1H), 6.53 (s, 1H), 6.42 (s, 1H), 6.31 (s, 1H), 4.66 (d, J=9.1 Hz, 1H), 4.48 (d, J=9.1 Hz, 1H), 4.23-4.09 (m, 4H), 3.75 (s, 3H), 3.25 (s, 3H); 130 NMR (75 MHz, CDCl$_3$) δ 178.0, 155.6, 144.8, 144.2, 138.7, 138.0, 130.8, 129.3, 129.1, 127.8, 125.2, 122.7, 119.0, 111.5, 107.0, 99.4, 76.7, 64.6, 64.0, 58.3, 38.9, 26.8; MS (ES+) m/z 390.0 (M+1).

EXAMPLE 16.71

Synthesis of 1'-methyl-2'-oxo-1',2,2',3-tetrahydrospiro[furo[2,3-g][1,4]-benzodioxine-8,3'-indole]-4'-carbonitrile

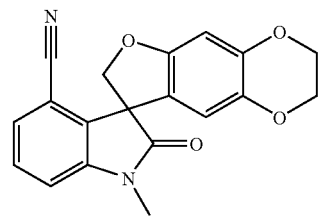

Following the procedure as described in EXAMPLE 2.48 and making non-critical variations using 4'-bromo-1'-methylspiro[furo[2,3-f][1,3]benzodioxole-7,3'-indol]-2'(1'H)-one to replace 6-bromo-1'-(diphenylmethyl)spiro[1-benzofuran-3,3'-indol]-2'(1'H)-one, 1'-methyl-2'-oxo-1',2,2',3-tetrahydrospiro[furo[2,3-g][1,4]benzodioxine-8,3'-indole]-4'-carbonitrile was obtained (74%) as a colorless solid: mp 196-197° C. (ethyl acetate/hexanes); $^1$H NMR (300 MHz, CDCl$_3$) δ 7.47-7.36 (m, 1H), 7.32-7.27 (m, 1H), 7.11-7.07 (m, 1H), 6.52 (s, 1H), 6.14 (s, 1H), 4.94-4.83 (m, 2H), 4.22-4.06 (m, 4H), 3.28 (s, 3H); MS (ES+) m/z 334.9 (M+1).

EXAMPLE 16.72

Synthesis of 1'-methyl-2'-oxo-1',2,2',3-tetrahydrospiro[furo[2,3-g][1,4]benzodioxine-8,3'-indole]-4'-carboxamide

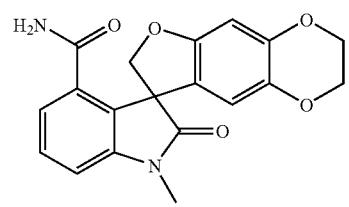

To a suspension of 1'-methyl-2'-oxo-1,2,2',3-tetrahydrospiro[furo[2,3-g][1,4]benzodioxine-8,3'-indole]-4'-carbonitrile (0.25 g, 0.75 mmol) in ethanol (30 mL) was added saturated aqueous sodium carbonate (3 mL) and 30% w/w aqueous hydrogen peroxide (3 mL). The reaction mixture was heated at reflux for 3 h, allowed to cool to ambient temperature and concentrated in vacuo. The residue was triturated in water to afford 1'-methyl-2'-oxo-1',2,2',3-tetrahydrospiro[furo[2,3-g][1,4]benzodioxine-8,3'-indole]-4'-carboxamide (0.09 g, 33%) as a colorless solid: mp>250° C. (water); $^1$H NMR (300 MHz, CDCl$_3$) δ 7.59 (s, 1H), 7.43-7.36 (m, 1H), 7.24-7.13 (m, 3H), 6.28 (s, 1H), 5.98 (s, 1H), 5.15 (d, J=8.1 Hz, 1H), 4.57 (d, J=8.1 Hz, 1H), 4.16-3.99 (m, 4H), 3.13 (s, 3H); MS (ES+) m/z 352.9 (M+1).

EXAMPLE 16.73

Synthesis of 1'-methyl-4'-(tetrahydrofuran-3-yl)spiro[furo[2,3-f][1,3]benzodioxole-7,3'-indol]-2'(1'H)-one

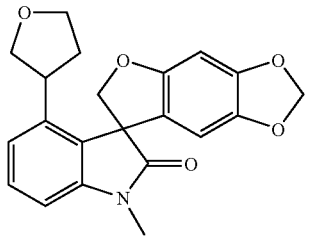

To a solution of 4'-furan-3-yl-1'-methylspiro[furo[2,3-f][1,3]benzodioxole-7,3'-indol]-2'(1'H)-one (0.60 g, 1.66 mmol) in ethyl acetate (30 mL) was added palladium on carbon (10% w/w, 0.40 g). The reaction mixture was shaken under a pressure of hydrogen gas (60 psi) in a Parr hydrogenation apparatus at ambient temperature for 16 h and filtered through a pad of diatomaceous earth. The filtrate was concentrated in vacuo and the residue recrystallized from dichloromethane/diethyl ether to afford methyl-4'-(tetrahydrofuran-3-yl)spiro[furo[2,3-f][1,3]benzodioxole-7,3'-indol]-2'(1'H)-one (0.44 g, 73%) as a colorless solid: mp 182-184° C. (dichloromethane/ether); $^1$H NMR (300 MHz, CDCl$_3$) δ 7.31-7.35 (m, 1H), 7.08-7.01 (m, 1H), 6.77 (d, J=7.7 Hz, 1H), 6.52-6.48 (m, 1H), 6.15 (d, J=13.3 Hz, 1H), 5.90-5.84 (m, 2H), 4.96 (dd, J=9.26, 1.0 Hz, 1H), 4.78-4.67 (m, 1H), 4.11-3.59 (m, 3H), 3.39-3.18 (m, 2H), 2.40-1.94 (m, 1H), 1.63-1.36 (m, 1H); MS (ES+) m/z 365.9 (M+1).

EXAMPLE 16.74

Synthesis of 1'-methyl-4'-(5-methyl-1,2,4-oxadiazol-3-yl)-2,3-dihydrospiro[furo[2,3-g][1,4]benzodioxine-8,3'-indol]-2'(1'H)-one

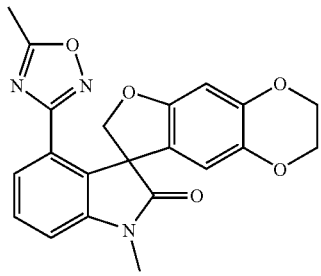

To a solution of 1'-methyl-2'-oxo-1',2,2',3-tetrahydrospiro[furo[2,3-g][1,4]benzodioxine-8,3'-indole]-4'-carbonitrile (0.35 g, 1.05 mmol) in dimethylsulfoxide (10 mL) was added hydroxylamine (50% w/w solution in water, 3.0 mL). The reaction mixture was stirred for 16 h at ambient temperature, poured into water (50 mL) and extracted with ethyl acetate (3×100 mL). The combined organic extracts were washed with brine (2×50 mL), dried over magnesium sulfate, filtered and concentrated in vacuo. The residue was triturated in hexanes to afford N'-hydroxy-1'-methyl-2'-oxo-3,7-dihydro-2H-spiro[benzofuro[5,6-b][1,4]dioxine-8,3'-indoline]-4'-carboximidamide (0.37 g) as a colorless solid. To a 10 mL microwave reaction vessel were added N'-hydroxy-1'-methyl-2'-oxo-3,7-dihydro-2H-spiro[benzofuro[5,6-b][1,4]dioxine-8,3'-indoline]-4'-carboximidamide (0.20 g, 0.54 mmol), acetic anhydride (0.50 mL) and pyridine (2.00 mL). The solution was heated at 160° C. for 0.5 h in a microwave reactor, allowed to cool to ambient temperature and concentrated in vacuo. The residue was purified by column chromatography and eluted with hexanes/ethyl acetate (3/1) followed by recrystallization from diethyl ether to afford 1-methyl-4'-(5-methyl-1,2,4-oxadiazol-3-yl)-2,3-dihydrospiro[furo[2,3-g][1,4]benzodioxine-8,3'-indol]-2'(1'H)-one (0.08 g, 37%) as a colorless solid: mp 199-201° C. (diethyl ether); $^1$H NMR (300 MHz, CDCl$_3$) δ 7.70 (dd, J=8.0, 0.8 Hz, 1H), 7.46 (t, J=7.9 Hz, 1H), 7.03 (dd, J=7.8, 0.8 Hz, 1H), 6.39 (s, 1H), 6.03 (s, 1H), 5.14 (d, J=8.6 Hz, 1H), 4.82 (d, J=8.6 Hz, 1H), 4.16-4.00 (m, 4H), 3.28 (s, 3H), 2.50 (s, 3H); MS (ES+) m/z 391.9 (M+1).

EXAMPLE 16.75

Synthesis of 4'-(3,5-dimethylisoxazol-4-yl)-1'-methyl-2,3-dihydrospiro[furo[2,3-g][1,4]benzodioxine-8,3'-indol]-2'(1'H)-one

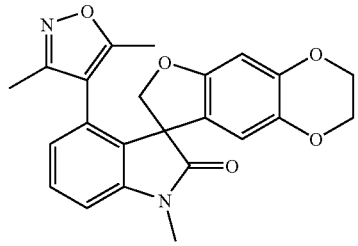

To a 10 mL reaction vessel were added 4'-bromo-1'-methylspiro[furo[2,3-f][1,3]benzodioxole-7,3'-indol]-2'(1'H)-one (0.50 g, 1.3 mmol), 3,5-dimethylisoxazole-4-boronic acid (0.37 g, 2.6 mmol), palladium acetate (0.018 g, 0.026 mmol), dicyclohexylphosphino-2',6'-dimethoxybiphenyl (0.021 g, 0.052 mmol), potassium carbonate (0.54 g, 3.9 mmol), acetonitrile (2.0 mL) and water (1.5 mL). The vessel was heated for 16 h at 100° C. under microwave irradiation, allowed to cool to ambient temperature, diluted with water (25 mL) and extracted with ethyl acetate (3×75 mL). The combined organic extracts were washed with brine (50 mL), dried over magnesium sulfate, filtered and concentrated in vacuo. The residue was purified by column chromatography and eluted with a 20% to 60% gradient of ethyl acetate in hexanes to afford 4'-(3,5-dimethylisoxazol-4-yl)-t-methyl-2,3-dihydrospiro[furo[2,3-g][1,4]benzodioxine-8,3'-indol]-2'(1'H)-one (0.422 g, 80%) as a colorless solid: mp 228-230° C. (ethyl acetate/hexanes); $^1$H NMR (mixture of atropisomers, 300 MHz, CDCl$_3$) δ 7.39-7.29 (m, 1H), 6.95 (d, J=7.79 Hz, 1H), 6.73 (d, J=7.76 Hz, 1H), 6.26 (s, 1H), 6.21 (d, J=7.14 Hz, 1H), 4.70 (dd, J=8.9, 3.4 Hz, 1H), 4.39 (dd, J=17.4, 9.0 Hz, 1H), 4.17-4.03 (m, 4H), 3.31 (s, 1.5H), 3.30 (s, 1.5H), 2.24 (s, 1.5H), 2.07 (s, 1.5H), 1.40 (s, 1.5H), 1.32 (s, 1.5H); MS (ES+) m/z 405.0 (M+1).

EXAMPLE 16.76

Synthesis of N,1'-dimethyl-2'-oxo-1',2,2',3-tetrahydrospiro[furo[2,3-g][1,4]benzodioxine-8,3'-indole]-4'-carboxamide

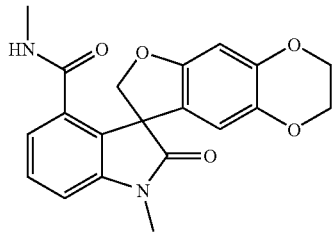

Phenyl 1'-methyl-2'-oxo-1',2,2',3-tetrahydrospiro[furo[2,3-g][1,4]benzodioxine-8,3'-indole]-4'-carboxylate (0.30 g, 0.70 mmol), methylamine hydrochloride (0.12 g, 1.8 mmol), potassium carbonate (0.39 g, 2.8 mmol) and N,N-dimethylformamide (3.0 mL) were added to a microwave reaction vessel. The reaction was heated at 100° C. for 0.5 h in a microwave reactor. Further, methylamine hydrochloride (0.20 g, 3.0 mmol) was added and the mixture was heated at 100° C. for an additional 45 min in a microwave reactor. The mixture allowed to cool to ambient temperature, poured into water (25 mL) and extracted with ethyl acetate (3×50 mL). The combined organic extracts were washed with brine (2×50 mL), dried over magnesium sulfate, filtered and concentrated in vacuo. The product was precipitated from dichloromethane with diethyl ether and subsequently recrystallized from ethyl acetate to afford N, t-dimethyl-2'-oxo-1',2,2',3-tetrahydrospiro[furo[2,3-g][1,4]benzodioxine-8,3'-indole]-4'-carboxamide (0.08 g, 32%) as a colorless solid: mp 120-122° C. (ethyl acetate); $^1$H NMR (300 MHz, CDCl$_3$) δ 7.41-7.31 (m, 1H), 7.25-7.19 (m, 1H), 6.98-6.93 (m, 1H), 6.49 (s, 1H), 6.20 (s, 1H), 5.19 (d, J=3.2 Hz, 1H), 4.87 (s, 2H), 4.21-4.08 (m, 4H), 3.26 (s, 3H), 2.64 (d, J=4.9 Hz, 3H); MS (ES+) m/z 366.9 (M+1).

EXAMPLE 16.77 and Example 16.78

Synthesis of N-cyclobutyl-1'-methyl-2'-oxo-1',2,2',3-tetrahydrospiro[furo[2,3-g][1,4]-benzodioxine-8,3'-indole]-4'-carboxamide and N,N,1'-trimethyl-2'-oxo-1',2,2',3-tetrahydrospiro[furo[2,3-g][1,4]benzodioxine-8,3'-indole]-4'-carboxamide

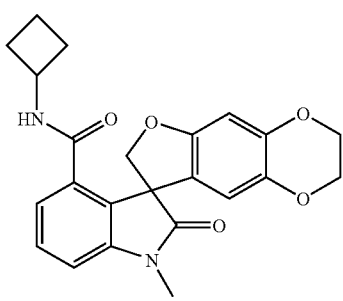

-continued

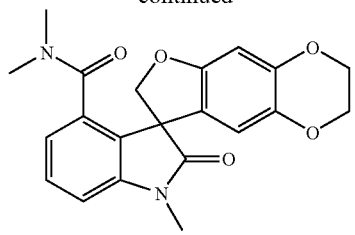

Phenyl 1'-methyl-2'-oxo-1',2,2',3-tetrahydrospiro[furo[2,3-g][1,4]-benzodioxine-8,3'-indole]-4'-carboxylate (0.30 g, 0.70 mmol), cyclobutylamine hydrochloride (0.23 g, 2.1 mmol), potassium carbonate (0.39 g, 2.8 mmol) and N,N-dimethylformamide (3.0 mL) were added to a microwave reaction vessel. The reaction was heated at 110° C. for 1 h in a microwave reactor, allowed to cool to ambient temperature, poured into water (25 mL) and extracted with ethyl acetate (3×50 mL). The combined organic extracts were washed with 1 M hydrochloric acid (50 mL) and brine (50 mL), dried over magnesium sulfate, filtered and concentrated in vacuo. The residue was purified by column chromatography and eluted with a 20% to 100% gradient of ethyl acetate in hexanes followed by recrystallization from dichloromethane/diethyl ether to afford N-cyclobutyl-1'-methyl-2'-oxo-1',2,2',3-tetrahydrospiro[furo[2,3-g][1,4]benzodioxine-8,3'-indole]-4'-carboxamide (0.045 g, 17%) as a colorless solid: mp 128-129° C. (dichloromethane/diethyl ether); $^1$H NMR (300 MHz, CDCl$_3$) δ 7.41-7.33 (m, 1H), 7.26-7.21 (m, 1H), 6.97-6.93 (m, 1H), 6.51 (s, 1H), 6.20 (s, 1H), 5.46 (d, J=6.65 Hz, 1H), 4.96-4.81 (m, 2H), 4.35-4.01 (m, 5H), 3.25 (s, 3H), 2.27-2.09 (m, 2H), 1.70-1.40 (m, 4H); MS (ES+) m/z 407.0 (M+1). N,N,1'-trimethyl-2'-oxo-1,2,2',3-tetrahydrospiro[furo[2,3-g][1,4]benzodioxine-8,3'-indole]-4'-carboxamide (0.12 g, 37%) was isolated as a byproduct from the synthesis of N-cyclobutyl-1'-methyl-2'-oxo-1',2,2',3-tetrahydrospiro[furo[2,3-g][1,4]benzodioxine-8,3'-indole]-4'-carboxamide, obtained as colorless solid: mp 218-221° C. (dichloromethane/diethyl ether); $^1$H NMR (300 MHz, CDCl$_3$) δ 7.32 (dd, J=7.8, 7.8 Hz, 1H), 6.91-6.84 (m, 2H), 6.44 (s, 1H), 6.22 (s, 1H), 5.05 (d, J=8.8 Hz, 1H), 4.79 (d, J=8.8 Hz, 1H), 4.20-4.04 (m, 4H), 3.28 (s, 3H), 2.79 (s, 3H), 2.19 (s, 3H); MS (ES+) m/z 381.0 (M+1).

EXAMPLE 16.79

Synthesis of 4'-(3-methoxyphenoxy)-1'-methyl-2,3-dihydrospiro[furo[2,3-g][1,4]benzodioxine-8,3'-indol]-2'(1'H)-one

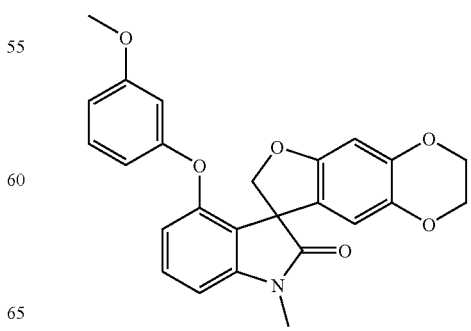

A 10 mL sealed tube was charged with 4'-bromo-t-methyl-3,7-dihydro-2H-spiro[benzofuro[5,6-b][1,4]dioxine-8,3'-indolin]-2'-one (0.77 g, 2.0 mmol), 3-methoxyphenol (0.50 g, 4.0 mmol), potassium carbonate (0.36 g, 2.6 mmol), copper (I) iodide (0.038 g, 0.2 mmol), 1-methylimidazole (0.082 g, 1.0 mmol) and anhydrous toluene (3 mL). The reaction mixture was heated at 150° C. for 16 h, allowed to cool to ambient temperature and filtered. The filtrate was concentrated in vacuo and the residue was purified by column chromatography and eluted with a 15% to 50% gradient of ethyl acetate in hexanes to afford 4'-(3-methoxyphenoxy)-1'-methyl-2,3-dihydrospiro[furo[2,3-g][1,4]benzodioxine-8,3'-indol]-2'(1'H)-one (0.27 g, 31%) as an off-white solid: mp 166-168° C. (ethyl acetate/hexanes); $^1$H NMR (300 MHz, CDCl$_3$ δ 7.20-7.27 (m, 1H), 7.02-7.10 (m, 1H), 6.68 (d, J=7.7 Hz, 1H), 6.58 (d, J=8.4 Hz, 1H), 6.50-6.58 (m, 1H), 6.35-6.29 (m, 1H), 6.25 (s, 1H), 6.21 (t, J=2.0, Hz, 1H), 6.19 (s, 1H), 4.83 (ABq, 2H), 4.15-4.01 (m, 4H), 3.69 (s, 3H), 3.27 (s, 3H); $^{13}$C NMR (75 MHz, CDCl$_3$) δ177.5, 160.5, 157.7, 155.5, 152.7, 144.8, 144.3, 137.7, 130.1, 129.7, 121.7, 119.2, 114.6, 111.0, 110.2, 109.0, 104.0, 103.9, 99.0, 77.7, 64.4, 63.8, 57.3, 55.2, 27.0; MS (ES+) m/z 432.0 (M+1).

EXAMPLE 16.80

Synthesis of 1'-methyl-4-phenoxy-2,3-dihydrospiro[furo[2,3-g][1,4]benzodioxine-8,3'-indol]-2'(1'H)-one

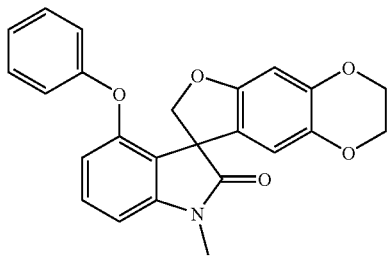

Following the procedure as described in EXAMPLE 16.79 and making non-critical variations using phenol to replace 3-methoxyphenol, 1'-methyl-4-phenoxy-2,3-dihydrospiro[furo[2,3-g][1,4]benzodioxine-8,3'-indol]-2'(1'H)-one was obtained (49%) as a colorless solid: $^1$H NMR (300 MHz, CDCl$_3$) δ7.35-7.11 (m, 3H), 6.93-7.04 (m, 1H), 6.76-6.63 (m, 3H), 6.54 (d, J=8.4 Hz, 1H), 6.25 (s, 1H), 6.21 (s, 1H), 4.84 (ABq, 2H), 4.17-3.98 (m, 4H), 3.27 (s, 3H); $^{13}$C NMR (75 MHz, CDCl$_3$) δ 177.5, 156.4, 155.5, 153.0, 144.8, 144.3, 137.7, 130.1, 129.3, 123.2, 121.4, 119.3, 118.2, 114.1, 111.0, 103.8, 99.0, 77.6, 64.4, 63.8, 57.4, 27.0; MS (ES+) m/z 402.0 (M+1).

EXAMPLE 16.81

Synthesis of 1'-methyl-4'-(3-morpholin-4-ylphenoxy)-2,3-dihydrospiro[furo[2,3-g][1,4]benzodioxine-8,3'-indol]-2'(1'H)-one

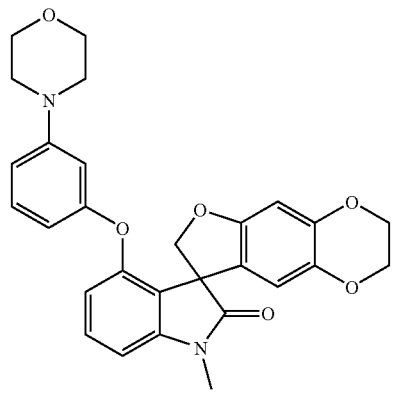

Following the procedure as described in EXAMPLE 16.79 and making non-critical variations using 3-morpholinophenol to replace 3-methoxyphenol, 1'-methyl-4'-(3-morpholin-4-ylphenoxy)-2,3-dihydrospiro[furo[2,3-g][1,4]benzodioxine-8,3'-indol]-2'(1'H)-one was obtained (53%) as a colorless solid: $^1$H NMR (300 MHz, CDCl$_3$) δ7.18-7.24 (m, 1H), 7.01-7.09 (m, 1H), 6.65 (d, J=7.7 Hz, 1H), 6.55 (d, J=8.5 Hz, 2H), 6.27 (s, 1H), 6.26-6.21 (m, 2H), 6.20 (s, 1H), 4.84 (ABq, 2H), 4.13-4.00 (m, 4H), 3.82-3.74 (m, 4H), 3.25 (s, 3H), 3.07-3.00 (m, 4H); $^{13}$C NMR (75 MHz, CDCl$_3$) δ177.6, 157.5, 155.6, 153.3, 152.5, 144.8, 144.3, 137.6, 130.1, 129.7, 121.1, 119.4, 114.0, 111.0, 110.5, 109.7, 105.9, 103.6, 99.1, 77.6, 66.7, 64.4, 63.8, 57.3, 48.9, 27.0; MS (ES+) m/z 486.9 (M+1).

EXAMPLE 16.82

Synthesis of 4'-[(6-methoxypyridin-3-yl)oxy]-1'-methyl-2,3-dihydrospiro[furo[2,3-g][1,4]benzodioxine-8,3'-indol]-2'(1'H)-one

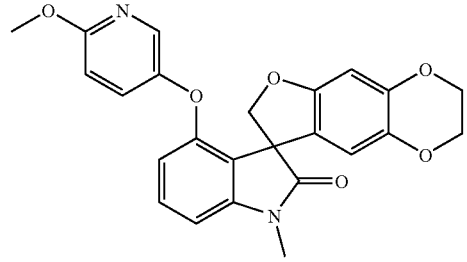

Following the procedure as described in EXAMPLE 16.79 and making non-critical variations using 6-methoxypyridin-3-ol to replace 3-methoxyphenol, and 1-butylimidazole to replace 1-methylimidazole, 4'-[(6-methoxypyridin-3-yl)oxy]-1'-methyl-2,3-dihydrospiro[furo[2,3-g][1,4]-benzodioxine-8,3'-indol]-2'(1'H)-one was obtained (33%) as a colorless solid: $^1$H NMR (300 MHz, CDCl$_3$) δ7.64 (s, 1H), 7.27-7.18 (m, 1H), 6.91-6.99m, 1H), 6.62-6.69 (m, 1H), 6.54-6.58 (m, 1H), 6.42-6.48 (m, 1H), 6.27-6.30 (m, 1H), 6.18-

6.22 (m, 1H), 4.85 (ABq, 2H), 4.15-4.03 (m, 4H), 3.85 (s, 3H), 3.26 (s, 3H); $^{13}$C NMR (75 MHz, CDCl$_3$) δ 177.4, 160.2, 155.5, 153.6, 147.5, 144.9, 144.4, 137.8, 136.9, 130.2, 130.1, 120.8, 119.2, 112.7, 111.0, 103.8, 99.1, 77.7, 64.4, 63.8, 57.3, 53.6, 27.0; MS (ES+) m/z 432.9 (M+1).

EXAMPLE 16.83

Synthesis of 4'-(1,3-benzodioxol-5-yloxy)-1'-methyl-2,3-dihydrospiro[furo[2,3-g][1,4]benzodioxine-8,3'-indol]-2'(1'H)-one

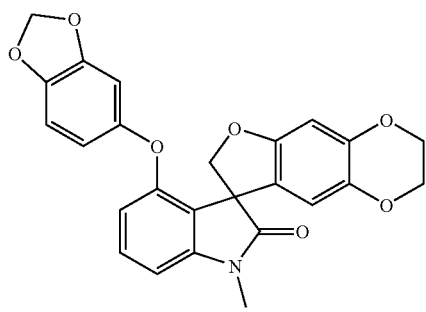

Following the procedure as described in EXAMPLE 16.79 and making non-critical variations using benzo[d][1,3]dioxol-5-ol to replace 3-methoxyphenol and 1-butylimidazole to replace 1-methylimidazole, 4'-(1,3-benzodioxol-5-yloxy)-1'-methyl-2,3-dihydrospiro[furo[2,3-g][1,4]benzodioxine-8,3'-indol]-2'(1'H)-one was obtained (8%) as a colorless solid: $^1$H NMR (300 MHz, CDCl$_3$) δ 7.21 (s, 1H), 6.67-6.57 (m, 2H), 6.50 (d, J=8.5 Hz, 1H), 6.32 (s, 1H), 6.25-6.15 (m, 3H), 5.89 (s, 2H), 4.84 (ABq, 2H), 4.18-4.04 (m, 4H), 3.26 (s, 3H); $^{13}$C NMR (75 MHz, CDCl$_3$) δ 177.5, 155.6, 153.9, 150.9, 148.0, 144.8, 144.3, 143.7, 137.7, 130.0, 120.6, 119.4, 113.1, 111.2, 111.0, 107.8, 103.4, 101.5, 101.4, 99.0, 77.5, 64.4, 63.9, 57.3, 27.0; MS (ES+) m/z 445.8 (M+1).

EXAMPLE 16.84

Synthesis of 4'-(4-methoxyphenoxy)-1'-methyl-2,3-dihydrospiro[furo[2,3-g][1,4]benzodioxine-8,3'-indol]-2'(1'H)-one

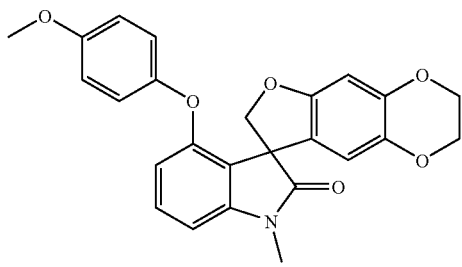

A 10 mL microwave reaction vessel was charged with 4'-bromo-1'-methyl-3,7-dihydro-2H-spiro[benzofuro[5,6-b][1,4]dioxine-8,3'-indolin]-2'-one (0.19 g, 0.5 mmol), 4-methoxyphenol (0.12 g, 1.0 mmol), potassium tert-butoxide (0.11 g, 1.0 mmol), copper (I) bromide (0.012 g, 0.08 mmol) and anhydrous 1-methylpyrrolidin-2-one (2 mL). The reaction mixture was irradiated at 250° C. for 75 min in a microwave reactor and was allowed to cool to ambient temperature. The reaction mixture was poured into water (15 mL) and extracted with ethyl acetate (50 mL). The combined organic extracts were washed with water (3×50 mL) and brine (50 mL), dried over magnesium sulfate, filtered and concentrated in vacuo. Purification of the residue by column chromatography and eluted with a 15% to 50% gradient of ethyl acetate in hexanes afforded 4'-(4-methoxyphenoxy)-1'-methyl-2,3-dihydrospiro[furo[2,3-g][1,4]benzodioxine-8,3'-indol]-2'(1'H)-one (0.084 g, 39%) as an off-white solid: mp 55-58° C. (ethyl acetate/hexanes); $^1$H NMR (300 MHz, CDCl$_3$) δ 7.27-7.14 (m, 1H), 6.78-6.59 (m, 5H), 6.44 (d, J=8.48 Hz, 1H), 6.31 (d, J=1.08 Hz, 1H), 6.22 (d, J=1.08 Hz, 1H), 4.86 (ABq, 2H), 4.16-4.03 (m, 4H), 3.74 (s, 3H), 3.26 (s, 3H); $^{13}$C NMR (75 MHz, CDCl$_3$) δ 177.6, 155.8, 155.6, 154.3, 149.6, 144.8, 144.3, 137.7, 130.0, 120.2, 120.1, 119.5, 114.5, 112.7, 111.0, 103.1, 99.1, 64.4, 63.9, 57.4, 55.6, 27.0; MS (ES+) m/z 432.0 (M+1).

EXAMPLE 16.85

Synthesis of 1'-methyl-4-(pyridine-2-ylmethoxy)-2,3-dihydrospiro[furo[2,3-g][1,4]benzodioxine-8,3'-indol]-2'(1'H)-one

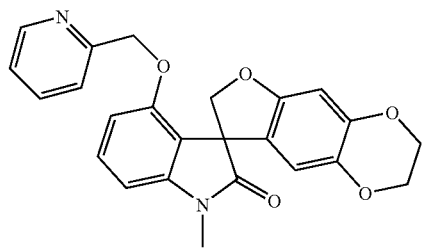

A 25 mL flask was charged with 4-hydroxy-1'-methyl-3,7-dihydro-2H-spiro[benzofuro[5,6-b][1,4]dioxine-8,3'-indolin]-2'-one (0.33 g, 1.0 mmol), 2-(bromomethyl)pyridine hydrobromide (0.4 g, 1.6 mmol), cesium carbonate (0.98 g, 3.0 mmol) and anhydrous N,N-dimethylformamide (6 mL). The reaction mixture was heated at 100° C. for 1.5 h and was allowed to cool to ambient temperature and filtered. The filtrate was concentrated in vacuo and the residue was purified column chromatography and eluted with a 15% to 80% gradient of ethyl acetate in hexanes to afford 1'-methyl-4-(pyridine-2-ylmethoxy)-2,3-dihydrospiro[furo[2,3-g][1,4]benzodioxine-8,3'-indol]-2'(1'H)-one (0.202 g, 49%) as an off-white solid: mp 181-183° C. (methanol); $^1$H NMR (300 MHz, CDCl$_3$) δ 8.46 (d, J=4.7 Hz, 1H), 7.56-7.60 (m, 1H), 7.24-7.26 (m, 1H), 7.17-7.10 (m, 1H), 6.99 (d, J=7.9 Hz, 1H), 6.66 (d, J=8.5 Hz, 1H), 6.57 (d, J=7.8 Hz, 1H), 6.44 (s, 1H), 6.25 (s, 1H), 5.14-5.01 (m, 2H), 4.86 (ABq, 2H), 5.18-4.99 (m, 1H), 4.17-4.03 (m, 4H), 3.24 (s, 3H); $^{13}$C NMR (75 MHz, CDCl$_3$) δ 177.9, 156.7, 155.8, 154.3, 148.6, 144.5, 144.3, 137.8, 136.8, 130.3, 122.4, 120.7, 119.8, 117.6, 111.4, 107.3, 102.0, 98.9, 77.5, 70.1, 64.5, 63.9, 57.4, 26.9; MS (ES+) m/z 417.0 (M+1).

EXAMPLE 16.86

Synthesis of 1'-methyl-4-(4-fluorobenzyloxy)-2,3-dihydrospiro[furo[2,3-g][1,4]benzodioxine-8,3'-indol]-2'(1'H)-one

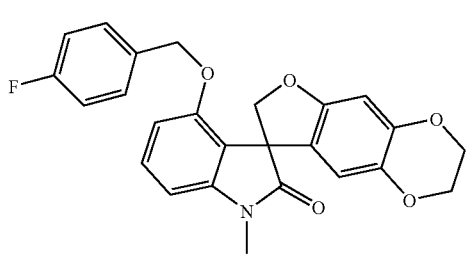

Following the procedure as described in EXAMPLE 16.85 and making non-critical variations using 1-(bromomethyl)-4-fluorobenzene to replace 2-(bromomethyl)pyridine hydrobromide, t-methyl-4-(4-fluorobenzyloxy)-2,3-dihydrospiro[furo[2,3-g][1,4]benzodioxine-8,3'-indol]-2'(1'H)-one was obtained (62%) as a colorless solid: $^1$H NMR (300 MHz, CDCl$_3$) δ 7.21-7.28 (m, 1H), 7.04-6.88 (m, 4H), 6.63 (d, J=8.5 Hz, 1H), 6.56 (d, J=7.8 Hz, 1H), 6.41 (s, 1H), 6.23 (s, 1H), 4.93 (ABq, 2H), 4.81 (ABq, 2H), 4.21-4.05 (m, 4H), 3.23 (s, 3H); $^{13}$C NMR (75 MHz, CDCl$_3$) δ 177.9, 163.8, 160.6, 155.9, 154.5, 144.6, 144.3, 137.7, 132.1, 132.0, 130.1, 128.4, 128.3, 119.8, 117.9, 115.2, 115.0, 111.2, 107.5, 101.9, 99.0, 77.5, 68.9, 64.5, 63.9, 57.4, 26.9; MS (ES+) m/z 434.2 (M+1).

EXAMPLE 16.87

Synthesis of 4'-(4-fluorophenoxy)-1'-methyl-2,3-dihydrospiro[furo[2,3-g][1,4]benzodioxine-8,3'-indol]-2'(1'H)-one

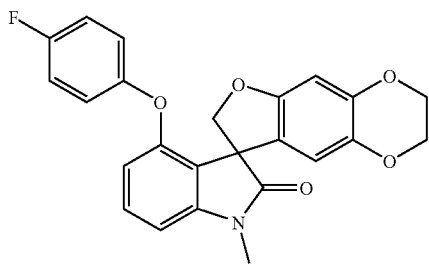

Following the procedure as described in EXAMPLE 16.53 and making non-critical variations using 1-bromo-4-fluorobenzene to replace 2-bromopyridine, 4'-(4-fluorophenoxy)-1'-methyl-2,3-dihydrospiro[furo[2,3-g][1,4]benzodioxine-8,3'-indol]-2'(1'H)-one was obtained (41%) as an off-white solid: mp 151-153° C. (methanol); $^1$H NMR (300 MHz, CDCl$_3$) δ 7.21-7.27 (m, 1H), 6.80-6.88 (m, 2H), 6.71-6.60 (m, 3H), 6.51 (d, J=8.4 Hz, 1H), 6.25 (s, 1H), 6.17 (s, 1H), 4.83 (ABq, 2H), 4.14-4.01 (m, 4H), 3.26 (s, 3H); $^{13}$C NMR (75 MHz, CDCl$_3$) δ 177.4, 160.2, 157.0, 155.5, 153.1, 152.4, 152.4, 144.9, 144.3, 137.7, 130.2, 121.5, 119.4, 119.3, 119.1, 115.9, 115.6, 113.9, 111.0, 104.0, 99.0, 77.7, 64.4, 63.9, 57.3, 27.0; MS (ES+) m/z 420.0 (M+1).

EXAMPLE 16.88

Synthesis of 1'-[(5-chloro-2-thienyl)methyl]-5-(6-methoxypyridin-3-yl)spiro[1-benzofuran-3,3'-indol]-2'(1'H)-one

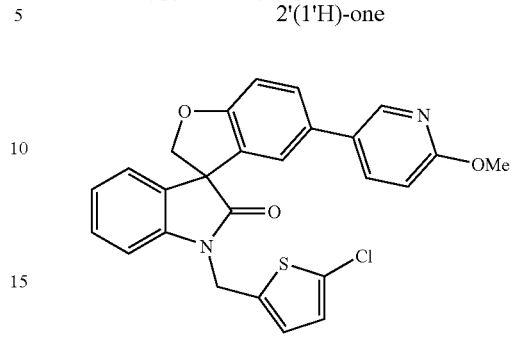

Following the procedure as described in EXAMPLE 16.12 and making non-critical variations using (6-methoxypyridin-3-yl)boronic acid to replace 6-(dimethylamino)pyridin-3-ylboronic acid, and 5-bromo-1'-[(5-chloro-2-thienyl)methyl]spiro[1-benzofuran-3,3'-indol]-2'(1'H)-one to replace 4'-bromo-1'-[(5-chloro-2-thienyl)methyl]spiro[furo[2,3-f][1,3]benzodioxole-7,3'-indol]-2'(1'H)-one, 1'-[(5-chloro-2-thienyl)methyl]-5-(6-methoxypyridin-3-yl)spiro[1-benzofuran-3,3'-indol]-2'(1'H)-one was obtained (20%) as a colorless solid: mp 60-62° C.; $^1$H NMR (300 MHz, CDCl$_3$) δ 8.16 (d, J=2.5 Hz, 1H), 7.54 (dd, J=8.6, 2.2 Hz, 1H), 7.35 (dd, J=8.4, 1.6 Hz, 1H), 7.27 (t, J=7.7 Hz, 1H), 7.17 (d, J=7.3 Hz, 1H), 7.07-6.98 (m, 2H), 6.95 (d, J=7.8 Hz, 1H), 6.88 (d, J=2.2 Hz, 1H), 6.69 (d, J=8.6 Hz, 1H), 5.12 (d, J=15.8 Hz, 1H), 5.00 (d, J=9.2 Hz, 1H), 4.91 (d, J=15.8 Hz, 1H), 4.73 (d, J=9.2 Hz, 1H), 3.89 (s, 3H); $^{13}$C NMR (75 MHz, CDCl$_3$) δ 176.9, 163.2, 160.3, 144.5, 141.3, 137.2, 136.9, 132.2, 131.7, 130.1, 129.8, 129.6, 129.1, 128.5, 126.4, 126.0, 124.1, 123.9, 121.7, 110.9, 110.6, 109.0, 79.7, 60.4, 58.0, 53.5, 39.2; MS (ES+) 475.5 (M+1) 477.5 (M+1).

EXAMPLE 17

Synthesis of 1'-(4-hydroxybenzyl)-5,6-dihydrospiro[benzo[1,2-b:5,4-b']difuran-3,3'-indol]-2'(1'H)-one

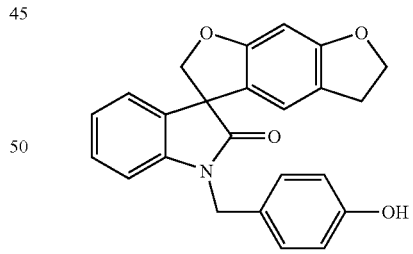

A mixture of 1'-[4-(benzyloxy)benzyl]-5,6-dihydrospiro[benzo[1,2-b:5,4-b']difuran-3,3'-indol]-2'(1'H)-one (2.4 g, 5.1 mmol) and palladium on carbon (10% w/w, 0.49 g) in anhydrous methanol (10 mL) and ethyl acetate (50 mL) was hydrogenated at ambient temperature under a balloon pressure for 16 h. The mixture was filtered through a pad of diatomaceous earth The pad was washed with ethyl acetate (50 mL) and the filtrate was concentrated in vacuo. The residue was purified by column chromatography and eluted with a 25% to 50% gradient of ethyl acetate in hexanes to afford 1-(4-hydroxybenzyl)-5,6-dihydrospiro[benzo[1,2-b:5,4-b']difuran-3,3'-indol]-2'(1'H)-one (1.86 g, 94%) as a colorless solid: mp 226-227° C.; ¹H NMR (300 MHz, CDCl₃) δ 7.25-7.13 (m, 4H), 7.06-6.99 (m, 1H), 6.87-6.82 (m, 1H), 6.78-6.72 (m, 2H), 6.44-6.41 (m, 2H), 5.27 (s, 1H), 4.88 (ABq, J=69.0, 15.3 Hz, 2H), 4.84 (ABq, J=82.9, 9.0 Hz, 2H), 4.55-4.46 (m, 2H), 2.96-2.86 (m, 2H); ¹³C NMR (75 MHz, CDCl₃) δ 178.2, 161.8, 161.3, 155.5, 142.1, 132.8, 128.8, 128.7, 127.5, 123.9, 123.5, 120.0, 119.9, 118.8, 115.8, 109.4, 93.3, 80.5, 72.4, 70.0, 57.8, 43.7, 28.9; MS (ES+) m/z 385.9 (M+1).

EXAMPLE 17.1

Synthesis of 1'-(4-hydroxybenzyl)-2,3-dihydrospiro[furo[2,3-g][1,4]benzodioxine-8,3'-indol]-2'(1'H)-one

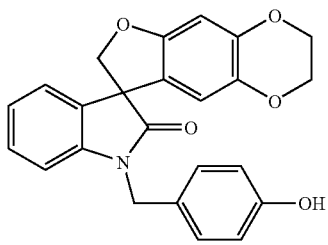

Following the procedure as described in Example 17 and making non-critical variations using 1'-[4-(benzyloxy)benzyl]-2,3-dihydrospiro[furo[2,3-g][1,4]benzodioxine-8,3'-indol]-2'(1'H)-one to replace 1'-[4(benzyloxy)benzyl]-5,6-dihydrospiro[benzo[1,2-b:5,4-b']difuran-3,3'-indol]-2'(1'H)-one, 1-(4-hydroxybenzyl)-2,3-dihydrospiro[furo[2,3-g][1,4]benzodioxine-8,3'-indol]-2'(1'H)-one was obtained (93%) as a colorless solid: mp 243-244° C.; ¹H NMR (300 MHz, CDCl₃) δ 9.42 (s, 1H), 7.30-7.22 (m, 1H), 7.20-7.13 (m, 3H), 7.05-6.97 (m, 2H), 6.76-6.68 (m, 2H), 6.52 (s, 1H), 6.04 (s, 1H), 4.89-4.63 (m, 4H), 4.21-4.07 (m, 4H); ¹³C NMR (75 MHz, CDCl₃) δ 176.6, 156.7, 154.6, 144.1, 142.1, 137.7, 131.7, 128.6, 126.4, 123.5, 122.9, 121.2, 115.3, 110.8, 109.5, 98.8, 79.3, 64.1, 63.5, 57.1, 42.5; MS (ES+) m/z 401.9 (M+1).

EXAMPLE 17.2

Synthesis of 1'-(3-hydroxypropyl)-2,3-dihydrospiro[furo[2,3-g][1,4]benzodioxine-8,3'-indol]-2'(1'H)-one

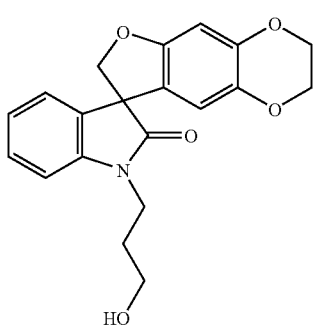

Following the procedure as described in Example 17 and making non-critical variations using 1'-[3-(benzyloxy)propyl]-2,3-dihydrospiro[furo[2,3-g][1,4]benzodioxine-8,3'-indol]-2'(1'H)-one to replace 1'-[4(benzyloxy)benzyl]-5,6-dihydrospiro[benzo[1,2-b:5,4-b']difuran-3,3'-indol]-2'(1'H)-one, 1-(3-hydroxypropyl)-2,3-dihydrospiro[furo[2,3-g][1,4]benzodioxine-8,3'-indol]-2'(1'H)-one was obtained (83%): mp 157-158° C. (ethyl acetate/hexanes); ¹H NMR (300 MHz, CDCl₃) δ 7.33-7.27 (m, 1H), 7.18-7.15 (m, 1H), 7.08-7.03 (m, 1H), 6.95-6.92 (m, 1H), 6.48 (s, 1H), 6.19 (s 1H), 4.73 (ABq, 2H), 4.19-4.08 (m, 4H), 3.02-3.80 (m, 2H), 3.61-3.55 (m, 2H), 2.98 (d, J=6.0 Hz, 1H), 1.98-1.85 (m, 2H); ¹³C NMR (75 MHz, CDCl₃) δ 178.8, 155.3, 144.6, 141.9, 138.3, 132.4, 128.9, 124.1, 123.6, 120.6, 111.4, 108.5, 99.4, 80.0, 64.5, 63.9, 58.3, 58.1, 36.4, 29.8; MS (ES+) m/z 353.8 (M+1).

EXAMPLE 18

Synthesis of ethyl 2'-oxo-2,3-dihydrospiro[furo[2,3-g][1,4]benzodioxine-8,3'-indole]-1'(2'H)-carboxylate

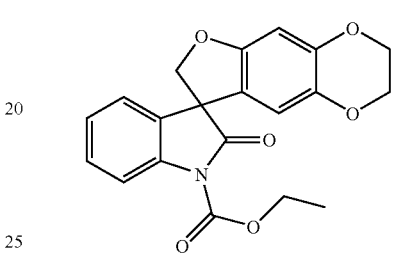

To a cooled (0° C.) suspension of sodium hydride (60% w/w in mineral oil, 0.16 g, 3.7 mmol) in anhydrous N,N-dimethylformamide (30 mL) was added 2,3-dihydrospiro[furo[2,3-g][1,4]benzodioxine-8,3'-indol]-2'(1'H)-one (0.99 g, 3.39 mmol), followed by ethyl chloroformate (0.35 mL, 3.7 mmol). The reaction mixture was stirred at ambient temperature for 18 h and was concentrated in vacuo. The residue was purified by column chromatography and eluted with a 5% to 66% gradient of ethyl acetate in hexanes to afford ethyl 2'-oxo-2,3-dihydrospiro[furo[2,3-g][1,4]benzodioxine-8,3'-indole]-1'(2'H)-carboxylate (0.68 g, 55%) as a colourless solid: mp 198-200° C. (hexanes/ethyl acetate); ¹H NMR (300 MHz, CDCl₃) δ7.96 (d, J=7.7 Hz, 1H), 7.39-7.34 (m, 1H), 7.19-7.18 (m, 2H), 6.50 (s, 1H), 6.27 (s, 1H), 4.93 (d, J=9.1 Hz, 1H), 4.63 (d, J=9.1 Hz, 1H), 4.49 (q, J=7.1 Hz, 2H), 4.21-4.18 (m, 2H), 4.13-4.10 (m, 2H) 1.45 (t, J=7.1 Hz, 3H); ¹³C NMR (75 MHz, CDCl₃) δ175.7, 155.1, 150.8, 144.9, 138.7, 138.4, 130.7, 129.2, 125.5, 123.8, 121.0, 115.2, 111.7, 99.4, 80.8, 64.5, 63.9, 63.7, 58.6, 14.2; MS (ES+) m/z 367.7 (M+1).

EXAMPLE 18.1

Synthesis of tert-butyl 4'-bromo-2'-oxospiro[furo[2,3-f][1,3]benzodioxole-7,3'-indole]-1'(2'H)-carboxylate

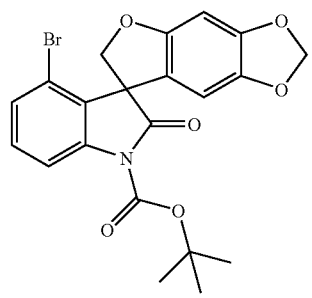

A mixture of 4'-bromospiro[furo[2,3-f][1,3]benzodioxole-7,3'-indol]-2'(1'H)-one (0.99 g, 2.8 mmol), di-tert-butyl dicarbonate (1.0 mL, 4.4 mmol) and sodium hydroxide (0.28 g, 6.9 mmol) and tetrahydrofuran/water (5/2, 46 mL) was stirred at ambient temperature for 16 h. Most of the tetrahydrofuran was removed in vacuo and the resultant mixture was extracted with ethyl acetate (4×50 mL). The combined organic extracts were dried over sodium sulfate, filtered and concentrated in vacuo. The residue was purified by column chromatography and eluted with a 10% to 20% gradient of ethyl acetate in hexanes to afford tert-butyl 4'-bromo-2'-oxospiro[furo[2,3-f][1,3]benzodioxole-7,3'-indole]-1'(2'H)-carboxylate (0.93 g, 74%) as a colorless solid: mp 154-156° C.; $^1$H NMR (300 MHz, DMSO-$d_6$) δ7.85 (dd, J=1.8 Hz, 7.3 Hz, 1H), 7.34 (d, J=1.8 Hz, 1H), 7.32 (dd, J=8.1, 8.1 Hz, 1H), 6.59 (s, 1H), 6.44 (s, 1H), 5.90 (d, J=4.9 Hz, 2H), 4.79 (ABq, 2H), 1.53 (s, 9H); $^{13}$C NMR (75 MHz, DMSO-$d_6$) 175.4, 157.1, 149.1, 148.8, 141.9, 141.8, 131.1, 129.1, 129.0, 119.0, 117.4, 114.5, 103.9, 101.9, 93.2, 84.7, 78.7, 59.9, 28.1; MS (ES+) m/z 460.2 (M+1), 462.2 (M+1).

EXAMPLE 18.2

Synthesis of tert-butyl 2'-oxo-2,3-dihydrospiro[furo[2,3-g][1,4]benzodioxine-8,3'-indole]-1'(2'H)-carboxylate

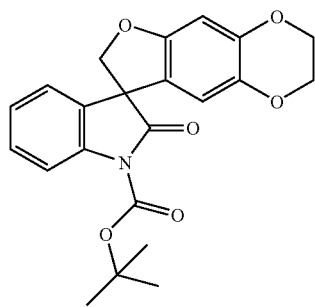

To a stirred solution of 2,3-dihydrospiro[furo[2,3-g][1,4]benzodioxine-8,3'-indol]-2'(1'H)-one (2.00 g, 6.77 mmol), triethylamine (1.6 mL, 11.mmol) and 4-(dimethylamino)pyridine (0.02 g, 0.16 mmol) in N,N-dimethylformamide (30 mL) was added di-tert-butyl dicarbonate (2.50 g, 11.4 mmol). The reaction mixture was stirred at ambient temperature for 50 h, diluted with ethyl acetate and washed with water and brine. The organic phase was dried over anhydrous sodium sulfate and filtered. The filtrate was concentrated in vacuo. The residue was purified by column chromatography and eluted with ethyl acetate/hexanes (1/3) to afford tert-butyl 2'-oxo-2,3-dihydrospiro[furo[2,3-g][1,4]-benzodioxine-8,3'-indole]-1'(2'H)-carboxylate (2.12 g, 79%): mp 171-172° C. (ethyl acetate/hexanes); $^1$H NMR (300 MHz, CDCl$_3$) δ 7.91-7.88 (m, 1H), 7.36-7.29 (m, 1H), 7.16-7.14 (m, 1H), 6.47 (s, 1H), 6.39 (s, 1H), 6.26 (s, 1H), 4.75 (ABq, 2H), 4.19-4.08 (m, 4H), 1.62 (s, 9H); MS (ES+) m/z 417.9 (M+23).

EXAMPLE 19

Synthesis of 1'-{[(3aR,5R,5aS,8aS,8bR)-2,2,7,7-tetramethyltetrahydro-3aH-bis[1,3]dioxolo[4,5-b:4',5'-d]pyran-5-yl]methyl}-2,3-dihydrospiro[furo[2,3-g][1,4]benzodioxine-8,3'-indol]-2'(1'H)-one

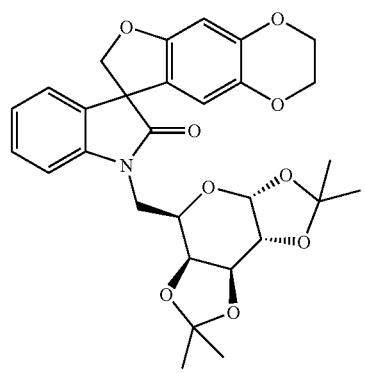

To a suspension of 2,3-dihydrospiro[furo[2,3-g][1,4]benzodioxine-8,3'-indol]-2'(1'H)-one (0.40 g, 1.35 mmol) in anhydrous N,N-dimethylformamide (30 mL) was added cesium carbonate (1.32 g, 4.06 mmol) and the reaction mixture was allowed to stir at ambient temperature under nitrogen for 1 h. Potassium iodide (0.05 g, 0.3 mmol) and 6-O-tosyl-1,2,3,4-di-O-isopropylidene-α-D-galactopyranose (0.35 mL, 3.7 mmol) were then added and the reaction mixture was stirred at 80° C. for 72 h and concentrated in vacuo. The residue was triturated with ethyl acetate and filtered through a pad of diatomaceous earth. The filtrate was concentrated in vacuo and the residue was purified by column chromatography and eluted with a 5% to 66% gradient of ethyl acetate in hexanes to afford 1-{[(3aR,5R,5aS,8aS,8bR)-2,2,7,7-tetramethyltetrahydro-3aH-bis[1,3]dioxolo[4,5-b:4',5'-d]pyran-5-yl]methyl}-2,3-dihydrospiro[furo[2,3-g][1,4]benzodioxine-8,3'-indol]-2'(1'H)-one (0.56 g, 77%) as a colourless solid: mp 112-118° C. (ethanol); $^1$H NMR (300 MHz, CDCl$_3$) δ7.29-7.21 (m, 1H), 7.12-7.08 (m, 1H) 7.02-6.95 (m, 2H), 6.55-6.31 (m, 2H), 5.48-5.42 (m, 1H), 4.91-4.82 (m, 1H), 4.68-4.59 (m, 2H), 4.33-4.22 (m, 3H), 4.18-4.10 (m, 4H), 4.07-3.98 (m, 1H), 3.88-3.80 (m, 1H), 1.38-1.26 (m, 12H); $^{13}$C NMR (75 MHz, CDCl$_3$) δ 177.7, 177.6, 155.3, 154.9, 144.4, 144.3, 143.0, 142.9, 138.3, 138.0, 132.6, 132.1, 128.5, 128.4, 123.6, 123.2, 122.9, 122.8, 121.7, 121.0, 112.4, 111.9, 109.7, 109.6, 109.5, 109.2, 109.0, 108.8, 99.1, 99.0, 96.4, 96.2, 80.3, 79.6, 71.6, 71.5, 71.0, 70.9, 70.5, 70.2, 65.9, 65.2, 64.5, 63.8, 57.9, 57.8, 41.0, 40.8, 26.1, 26.0, 25.8, 25.5, 25.0, 24.5, 24.5; MS (ES+) m/z 538.0 (M+1).

EXAMPLE 20

Synthesis of 6-deoxy-6-(2'-oxo-2,3-dihydrospiro[furo[2,3-g][1,4]benzodioxine-8,3'-indol]-1'(2'H)-yl)-D-galactopyranose

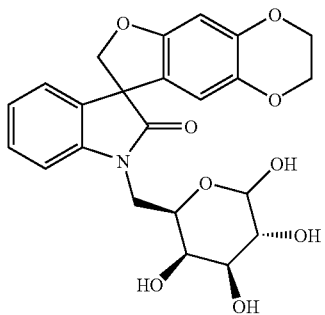

1'-{[(3aR,5R,5aS,8aS,8bR)-2,2,7,7-tetramethyltetrahydro-3aH-bis[1,3]dioxolo[4,5-b:4',5'-d]pyran-5-yl]methyl}-2,3-dihydrospiro[furo[2,3-g][1,4]benzodioxine-8,3'-indol]-2'(1'H)-one (0.45 g, 0.83 mmol) was suspended in 80% v/v aqueous trifluoroacetic acid (40 mL) and the reaction mixture was stirred at ambient temperature for 3 h. The reaction mixture was concentrated in vacuo and the residue recrystallized from ethanol to afford 6-deoxy-6-(2'-oxo-2,3-dihydrospiro[furo[2,3-g][1,4]-benzodioxine-8,3'-indol]-1'(2'H)-yl)-D-galactopyranose (0.025 g, 7%) as an off white solid: mp 122-126° C. (ethanol); $^{13}$C NMR (75 MHz, CDCl$_3$) δ178.5, 155.2, 155.2, 155.1, 155.0, 144.5, 142.6, 142.2, 142.1, 138.0, 138.0, 132.3, 132.0, 129.0, 123.5, 123.4, 121.0, 120.9, 111.6, 111.4, 109.9, 109.7 99.2, 92.7, 79.9, 64.4, 63.8, 60.4, 58.0, 21.0, 14.2; MS (ES+) m/z 480.0 (M+23).

EXAMPLE 21

Synthesis of 1'-cyclopropyl-2,3-dihydrospiro[furo[2,3-g][1,4]benzodioxine-8,3'-indol]-2'(1'H)-one

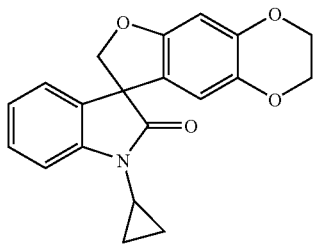

To a suspension of 2,3-dihydrospiro[furo[2,3-g][1,4]benzodioxine-8,3'-indol]-2'(1'H)-one (0.59 g, 2.0 mmol), cyclopropylboronic acid (0.34 g, 4.0 mmol), cupric acetate (0.36 g, 2.0 mmol) and 4-(N,N-dimethylamino)pyridine (0.73 g, 6.0 mmol) in anhydrous toluene (10 mL) was added dropwise sodium hexamethyldisilazide (1 M solution in tetrahydrofuran, 2.0 mL, 2.0 mmol). The reaction vessel was fitted with a condenser topped with a calcium chloride drying tube and the mixture was heated at 95° C. for 16 h. The reaction mixture was allowed to cool to ambient temperature, diluted with 1 M hydrochloric acid (40 mL) and extracted with ethyl acetate (2×25 mL). The combined organic extracts were washed with brine (25 mL), dried over anhydrous sodium sulfate, filtered and concentrated in vacuo. Trituration of the residue in diethyl ether/ethyl acetate (1/1, 20 mL) afforded 1-cyclopropyl-2,3-dihydrospiro[furo[2,3-g][1,4]benzodioxine-8,3'-indol]-2'(1'H)-one (0.48 g, 72%) as an off-white solid: mp 227-228° C. (ethyl acetate/diethyl ether); $^1$H NMR (300 MHz, CDCl$_3$) δ7.36-7.28 (m, 1H), 7.18-7.11 (m, 2H), 7.08-7.02 (m, 1H), 6.48 (s, 1H), 6.14 (s, 1H), 4.88 (d, J=8.9 Hz, 1H), 4.62 (d, J=8.9 Hz, 1H), 4.20-4.06 (m, 4H), 2.74-2.65 (m, 1H), 1.14-0.88 (m, 4H); $^{13}$C NMR (75 MHz, CDCl$_3$) δ178.1, 155.2, 144.6, 143.4, 138.3, 132.0, 128.8, 123.7, 123.3, 121.3, 111.4, 109.7, 99.4, 80.1, 64.6, 64.0, 58.1, 22.5, 6.4; MS (ES+) m/z 336.0 (M+1).

EXAMPLE 22

Synthesis of 1'-acetyl-2,3-dihydrospiro[furo[2,3-g][1,4]benzodioxine-8,3'-indol]-2'(1'H)-one

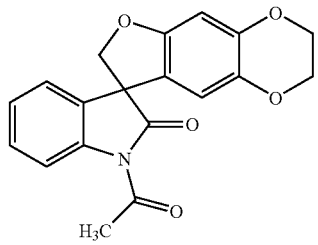

A mixture of 2,3-dihydrospiro[furo[2,3-g][1,4]benzodioxine-8,3'-indol]-2'(1'H)-one (1.00 g, 3.39 mmol), sodium acetate (0.556 g, 6.78 mmol) and acetic anhydride (20 mL) was heated at reflux for 0.5 h. The reaction mixture was allowed to cool to ambient temperature and was concentrated in vacuo. Trituration of the residue in water (20 mL), followed by recrystallization of the resultant solid from hexanes/diethyl ether, afforded 1'-acetyl-2,3-dihydrospiro[furo[2,3-g][1,4]benzodioxine-8,3'-indol]-2'(1'H)-one (0.802 g, 70%) as a colorless solid: mp 236-238° C. (hexanes/diethyl ether); $^1$H NMR (300 MHz, CDCl$_3$) δ8.32-8.25 (m, 1H), 7.42-7.33 (m, 1H), 7.25-7.15 (m, 2H), 6.52 (s, 1H), 6.25 (s, 1H), 4.97-4.90 (m, 1H), 4.68-4.60 (m, 1H), 4.25-4.04 (m, 4H), 2.68 (s, 3H); $^{13}$C NMR (75 MHz, CDCl$_3$) δ178.5, 171.0, 155.2, 145.1, 139.6, 138.6, 130.8, 129.4, 126.2, 123.7, 121.0, 116.8, 111.7, 99.6, 80.9, 64.6, 64.0, 58.8, 26.7; MS (ES+) m/z 360.1 (M+23).

EXAMPLE 23

Synthesis of 1'-{[4-(trifluoromethyl)pyridin-2-yl]methyl}-2,3-dihydrospiro[furo[2,3-g][1,4]benzodioxine-8,3'-indol]-2'(1'H)-one

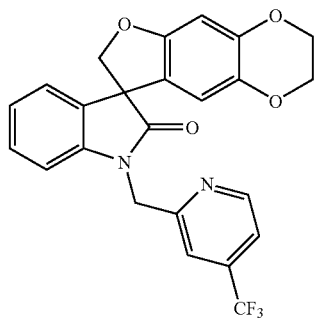

To a solution of 2,3-dihydrospiro[furo[2,3-g][1,4]benzodioxine-8,3'-indol]-2'(1'H)-one (0.753 g, 2.55 mmol), [4-(trifluoromethyl)pyridin-2-yl]methanol (Ashimori et al., *Chem. Pharm. Bull.* (1990) 38:2446-2458) (0.655 g, 3.70 mmol) and tri-n-butylphosphine (0.93 mL, 3.7 mmol) in anhydrous tetrahydrofuran (20 mL) and anhydrous dimethylsulfoxide (0.2 mL) at ambient temperature was added over a period of 10 min a solution of diethyl azodicarboxylate (0.64 mL, 4.1 mmol) in anhydrous tetrahydrofuran (10 mL). The reaction mixture was stirred at ambient temperature for 3 h and was poured into 1 M hydrochloric acid (50 mL). The mixture was extracted with diethyl ether (3×50 mL) and the combined organic extracts were washed with brine (50 mL), dried over anhydrous sodium sulfate, filtered and concentrated in vacuo. Purification of the residue by column chromatography and eluted with a 80% to 100% gradient of dichloromethane in hexanes, followed by a 0% to 20% gradient of ethyl acetate in dichloromethane and recrystallization from methanol afforded 1'-{[4-(trifluoromethyl)pyridin-2-yl]methyl}-2,3-dihydrospiro[furo[2,3-g][1,4]benzodioxine-8,3'-indol]-2'(1'H)-one (0.164 g, 10%) as a colorless solid: mp 154-155° C. (methanol); $^1$H NMR (300 MHz, CDCl$_3$) δ8.76 (d, J=5.1 Hz, 1H), 7.51 (s, 1H), 7.44 (d, J=5.1 Hz, 1H), 7.24-7.16 (m, 2H), 7.08-7.01 (m, 1H), 6.86 (d, J=7.7 Hz, 1H), 6.52 (s, 1H), 6.31 (s, 1H), 5.27 (d, J=16.1 Hz, 1H), 5.04 (d, J=16.1 Hz, 1H), 4.95 (d, J=9.0 Hz, 1H), 4.69 (d, J=9.0 Hz, 1H), 4.23-4.11 (m, 4H); $^{13}$C NMR (75 MHz, CDCl$_3$) δ177.8, 157.3, 155.3, 150.8, 144.8, 141.9, 139.8, 138.5, 132.3, 129.0, 124.1, 123.9, 121.1, 118.7, 117.6, 111.8, 109.3, 99.5, 80.1, 64.7, 64.0, 58.2, 45.8; MS (ES+) m/z 455.0 (M+1).

EXAMPLE 24

Synthesis of 4'-acetyl-t-methyl-2,3-dihydrospiro[furo[2,3-g][1,4]benzodioxine-8,3'-indol]-2'(1'H)-one

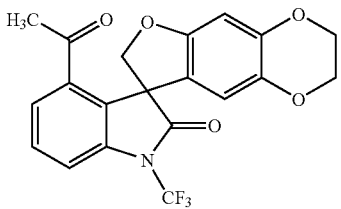

A 10 mL septum-capped microwave pressure tube was charged with 4'-bromo-1'-methyl-2,3-dihydrospiro[furo[2,3-g][1,4]benzodioxine-8,3'-indol]-2'(1'H)-one (0.39 g, 1.0 mmol), palladium (II) acetate (0.022 g, 0.1 mmol), 1,3-bis(diphenylphosphino)propane (0.10 g, 0.25 mmol) and potassium carbonate (0.17 g, 1.2 mmol). The tube was capped and purged for 5 min with dry nitrogen, and butyl vinyl ether (0.52 mL, 4.0 mmol), N,N-dimethylformamide (2.0 mL) and water (0.2 mL) were added. The reaction mixture was heated for 1 h under microwave irradiation (100 W, 120° C.) and was allowed to cool to ambient temperature, poured into 10% v/v aqueous hydrochloric acid (5 mL) and stirred at ambient temperature for 1 h. The mixture was diluted with water (20 mL) and was neutralized with 2 M aqueous sodium carbonate. Ethyl acetate (20 mL) was added and the biphasic mixture was filtered through a pad of diatomaceous earth. The pad was washed with ethyl acetate (20 mL) and the filtrate was transferred to a separatory funnel. The aqueous phase was extracted with ethyl acetate (3×20 mL). The combined organic extracts were washed with water (3×20 mL) and brine (20 mL), dried over anhydrous sodium sulfate, filtered and concentrated in vacuo. The crude product was purified by column chromatography and eluted with a 0% to 100% gradient of ethyl acetate in hexanes, followed by recrystallization from dichloromethane/diethyl ether to afford 4'-acetyl-1'-methyl-2,3-dihydrospiro[furo[2,3-g][1,4]benzodioxine-8,3'-indol]-2'(1'N)-one (0.264 g, 75%) as an off-white solid: mp 234-235° C. (dichloromethane/diethyl ether); $^1$H NMR (300 MHz, CDCl$_3$) δ7.55-7.44 (m, 2H), 7.14-7.08 (m, 1H), 6.50 (s, 1H), 5.99 (s, 1H), 4.95-4.77 (m, 2H), 4.19-4.04 (m, 4H), 3.28 (m, 3H), 2.43 (m, 3H); $^{13}$C NMR (75 MHz, CDCl$_3$) δ198.3, 178.6, 157.2, 145.4, 144.3, 137.4, 134.5, 130.6, 129.5, 124.4, 119.9, 112.1, 110.2, 98.9, 78.9, 64.5, 64.0, 59.4, 28.5, 27.0; MS (ES+) m/z 351.8 (M+1).

EXAMPLE 25

Synthesis of 1'-methyl-4'-(2-methyl-1,3-thiazol-4-yl)-2,3-dihydrospiro[furo[2,3-g][1,4]benzodioxine-8,3'-indol]-2'(1'H)-one

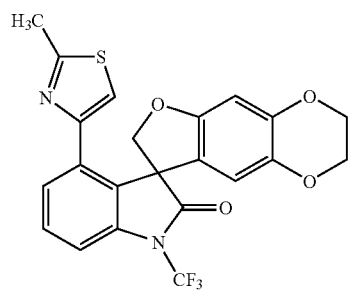

To a suspension of 4'-(bromoacetyl)-1'-methyl-2,3-dihydrospiro[furo[2,3-g][1,4]benzodioxine-8,3'-indol]-2'(1'H)-one (0.25 g, 0.57 mmol) in p-dioxane (15 mL) was added thioacetamide (0.047 g, 0.63 mmol) and the reaction mixture, which became homogeneous upon heating, was heated at 80° C. for 1 h. The reaction mixture was allowed to cool to ambient temperature and was concentrated to dryness in vacuo. The crude product was purified by column chromatography and eluted with a 0% to 100% gradient of ethyl acetate in hexanes to afford 1'-methyl-4'-(2-methyl-1,3-thiazol-4-yl)-2,3-dihydrospiro[furo[2,3-g][1,4]benzodioxine-8,3'-indol]-2'(1'H)-one (0.076 g, 33%) as an off-white solid: mp 219-220° C. (hexanes/ethyl acetate); $^1$H NMR (300 MHz, CDCl$_3$) δ7.42-7.36 (m, 1H), 7.32-7.27 (m, 1H), 6.91 (d, J=7.7 Hz, 1H), 6.54 (s, 1H), 6.36 (s, 1H), 6.22 (s, 1H), 4.81-4.71 (m, 2H), 4.21-4.07 (m, 4H), 3.29 (s, 3H), 2.64 (s, 3H); $^{13}$C NMR (75 MHz, CDCl$_3$) δ178.4, 165.2, 156.1, 151.8, 144.4, 137.7, 133.2, 129.2, 128.6, 124.7, 122.2, 116.6, 111.2, 108.2, 99.1, 78.3, 77.4, 64.7, 64.0, 58.8, 27.0, 19.1; MS (ES+) m/z 406.9 (M+1).

EXAMPLE 26

Synthesis of 4'-(2-amino-1,3-thiazol-4-yl)-1'-methyl-2,3-dihydrospiro[furo[2,3-g][1,4]benzodioxine-8,3'-indol]-2'(1'H)-one

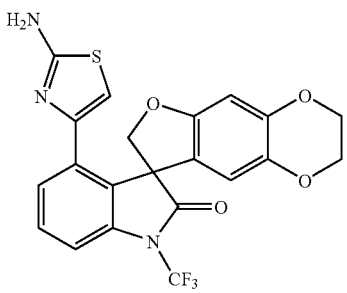

To a solution of 4'-(bromoacetyl)-t-methyl-2,3-dihydrospiro[furo[2,3-g][1,4]benzodioxine-8,3'-indol]-2'(1'H)-one (0.20 g, 0.47 mmol) in anhydrous ethanol (10 mL) was added thiourea (0.039 g, 0.51 mmol) and the reaction mixture was heated at reflux for 1 h. The reaction mixture was allowed to cool to ambient temperature and was concentrated to dryness in vacuo. The crude product was purified by column chromatography and eluted with a 0% to 10% gradient of methanol in dichloromethane to afford 4'-(2-amino-1,3-thiazol-4-yl)-1'-methyl-2,3-dihydrospiro[furo[2,3-g][1,4]benzodioxine-8,3'-indol]-2'(1'H)-one (0.159 g, 84%) as a pale yellow solid: mp 233-234° C. (dec.) (dichloromethane/methanol); $^1$H NMR (300 MHz, CDCl$_3$) δ 7.44-7.37 (m, 1H), 7.23 (d, J=7.9 Hz, 1H), 6.95 (d, J=7.9 Hz, 1H), 6.57-6.42 (br m, 2H), 6.37 (s, 1H), 6.22 (s, 1H), 5.80 (s, 1H), 4.80-4.73 (m, 2H), 4.22-4.07 (m, 4H), 3.28 (s, 3H); $^{13}$C NMR (75 MHz, CDCl$_3$) δ 178.0, 168.2, 155.7, 144.8, 144.4, 138.1, 129.7, 129.4, 124.3, 121.9, 111.4, 109.4, 105.9, 99.2, 78.4, 77.4, 64.7, 64.0, 58.6, 27.1; MS (ES+) m/z 408.3 (M+1).

EXAMPLE 27

Synthesis of 4'-(5-hydroxy-1H-pyrazol-3-yl)-1'-methyl-2,3-dihydrospiro[furo[2,3-g][1,4]benzodioxine-8,3'-indol]-2'(1'H)-one

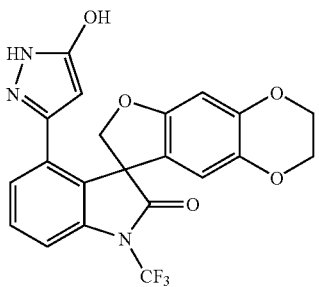

To a suspension of 4'-(bromoacetyl)-1'-methyl-2,3-dihydrospiro[furo[2,3-g][1,4]benzodioxine-8,3'-indol]-2'(1'H)-one (0.23 g, 0.53 mmol) in glacial acetic acid (5 mL) was added dropwise hydrazine hydrate (0.03 mL, 0.59 mmol) and the reaction mixture was heated at reflux for 16 h, allowed to cool to ambient temperature and was concentrated in vacuo. The crude product was triturated in dichloromethane (10 mL) and the resultant solid was recrystallized from dichloromethane/diethyl ether. Following a second recrystallization from methanol, 4'-(5-hydroxy-1H-pyrazol-3-yl)-1'-methyl-2,3-dihydrospiro[furo[2,3-g][1,4]benzodioxine-8,3'-indol]-2'(1'H)-one (0.029 g, 14%) was obtained as a colorless solid: mp>250° C. (methanol); $^1$H NMR (300 MHz, DMSO-d$_6$) δ 11.77 (br s, 1H), 9.51 (br s, 1H), 7.49-7.39 (m, 1H), 7.22-7.09 (m, 2H), 6.41 (s, 1H), 6.15 (s, 1H), 4.76-4.42 (m, 3H), 4.25-4.02 (m, 4H), 3.19 (s, 3H); $^{13}$C NMR (75 MHz, DMSO-d$_6$) δ 177.1, 155.0, 144.7, 144.0, 137.2, 129.1, 126.5, 123.1, 121.8, 110.6, 108.8, 98.7, 90.6, 76.2, 64.2, 63.6, 57.7, 26.5; MS (ES+) m/z 391.8 (M+1).

EXAMPLE 28

Synthesis of 1'-[3-(3-methyl-1,2,4-oxadiazol-5-yl)benzyl]-2,3-dihydrospiro[furo[2,3-g][1,4]benzodioxine-8,3'-indol]-2'(1'H)-one

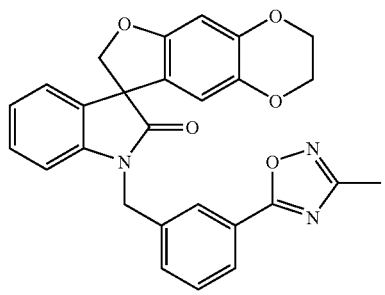

A solution of 3-[(2'-oxo-2,3-dihydrospiro[furo[2,3-g][1,4]benzodioxine-8,3'-indol]-1'(2'H)-yl)methyl]benzamide (0.50 g, 1.17 mmol) and N,N-dimethylacetamide dimethyl acetal (0.60 mL, 4.1 mmol) in 1,4-dioxane (10 mL) was stirred at 110° C. for 3 h, allowed to cool to ambient temperature and concentrated in vacuo. Hydroxylamine hydrochloride (0.11 g, 1.6 mmol), 1,4-dioxane (10 mL), glacial acetic acid (10 mL) and 2 M aqueous sodium hydroxide (0.85 mL, 1.70 mmol) were then added and the mixture was heated at 90° C. for 2 h. The mixture was allowed to cool to ambient temperature and water was added, causing a precipitate to be deposited. The solid was collected by filtration, washed with water and hexanes and recrystallized from dichloromethane/hexanes to afford 1'-[3-(3-methyl-1,2,4-oxadiazol-5-yl)benzyl]-2,3-dihydrospiro[furo[2,3-g][1,4]benzodioxine-8,3'-indol]-2'(1'H)-one (0.038 g, 6%) as a colorless solid: mp 80-89° C. (dichloromethane/hexanes); $^1$H NMR (300 MHz, CDCl$_3$) δ 8.09-8.12 (m, 2H), 7.54-7.57 (m, 2H), 7.15-7.18 (m, 2H), 7.00-7.03 (m, 1H), 6.74-6.77 (m, 1H), 6.50 (s, 1H), 6.29 (s, 1H), 5.14-5.17 (m, 1H), 4.89-4.92 (m, 2H), 4.65-4.67 (m, 1H), 4.13-4.17 (m, 4H), 2.43 (s, 3H); $^{13}$C NMR (75 MHz, CDCl$_3$) δ 177.6, 174.9, 167.9, 155.3, 144.7, 141.7, 138.4, 137.0, 132.3, 131.4, 129.9, 128.9, 127.4, 126.8, 124.8, 124.1, 123.7, 120.8, 111.6, 109.1, 99.5, 80.2, 64.5, 63.9, 58.1, 43.7, 11.7; MS (ES+) m/z 467.8 (M+1).

EXAMPLE 29

Synthesis of 3-{4-[(3-methyl-2'-oxospiro[furo[3,2-f][1,2]benzisoxazole-5,3'-indol]-1'(2'H)-yl)methyl]phenyl}-3-oxopropanenitrile

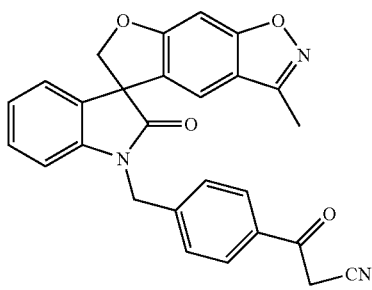

To a solution of 3-methylspiro[furo[3,2-f][1,2]benzisoxazole-5,3'-indol]-2'(1'H)-one (0.35 g, 1.20 mmol) in anhydrous N,N-dimethylformamide (20 mL) at 0° C. was added slowly sodium hydride (60% w/w dispersion in mineral oil, 0.072 g, 1.50 mmol). The solution was stirred at ambient temperature for 30 min, 5-(4-(bromomethyl)phenyl)isoxazole (Sasaki et al., *Biorg. Med. Chem. Lett.* (1998) 8:2241-2246) (0.24 g, 1.00 mmol) was added and the mixture was stirred for 16 h at ambient temperature. The reaction mixture was poured into water (200 mL) and extracted with ethyl acetate (3×200 mL). The combined organic extracts were washed with brine (3×100 mL), dried over magnesium sulfate, filtered and concentrated in vacuo. The residue was purified by column chromatography and eluted with a 15% to 50% gradient of ethyl acetate in hexanes to afford 3-{4-[(3-methyl-2'-oxospiro[furo[3,2-f][1,2]benzisoxazole-5,3'-indol]-1'(2'H)-yl)methyl]phenyl}-3-oxopropanenitrile (0.33 g, 61%) as a colorless solid: $^1$H NMR (300 MHz, CDCl$_3$) δ 7.96-7.92 (m, 2H), 7.63-7.60 (m, 2H), 7.50-7.46 (m, 1H), 7.23-7.13 (m, 2H), 7.04 6.97 (m, 2H), 6.71-6.67 (m, 1H), 5.43-4.76 (m, 4H), 4.06 (s, 2H), 2.46 (s, 3H).

EXAMPLE 29.1

Synthesis of 1'-[4-(3-amino-1H-pyrazol-5-yl)benzyl]-3-methylspiro[furo[3,2-f][1,2]benzisoxazole-5,3'-indol]-2'(1'H)-one hydrochloride

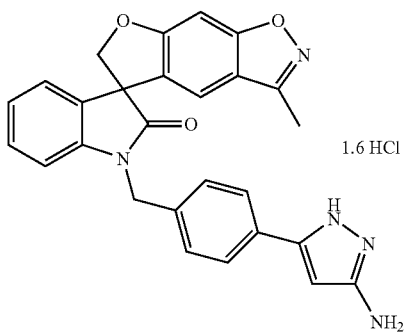

To a solution of 3-(4-((3-methyl-2'-oxo-6H-spiro[benzofuro[5,6-d]isoxazole-5,3'-indoline]-1'-yl)methyl)phenyl)-3-oxopropanenitrile in ethanol (20 mL) was added hydrazine hydrate (0.40 mL, 15 mmol). The solution was heated at reflux for 4 h, allowed to cool to ambient temperature and concentrated in vacuo. The resultant solid was dissolved in anhydrous methanol (10 mL) and a saturated solution of hydrogen chloride in anhydrous methanol (1.5 mL) was added, causing a precipitate to be deposited. The solid was collected by filtration to obtain 1'-[4-(3-amino-1H-pyrazol-5-yl)benzyl]-3-methylspiro[furo[3,2-f][1,2]benzisoxazole-5,3'-indol]-2'(1'H)-one (0.14 g, 43%) as a pale yellow solid: mp 191-195° C. (methanol); $^1$H NMR (300 MHz, DMSO-d$_6$) δ 7.82-7.71 (m, 3H), 7.52 (d, J=8.3 Hz, 2H), 7.31-7.18 (m, 2H), 7.10 (d, J=8.6 Hz, 1H), 7.04-6.97 (m, 2H), 6.40 (s, 1H), 5.16 (d, J=16.3 Hz, 1H), 5.05 (d, J=9.7 Hz, 1H), 4.98-4.89 (m, 2H), 2.42 (s, 3H); $^{13}$C NMR (75 MHz, DMSO-d$_6$) δ 176.3, 164.3, 157.8, 155.9, 145.7, 142.7, 138.0, 130.5, 129.7, 128.3, 127.5, 126.6, 124.7, 124.4, 123.8, 117.8, 109.2, 108.5, 108.4, 81.5, 56.1, 43.5, 9.8; MS (ES+) m/z 463.9 (M+1). Anal. Calcd. for C$_{27}$H$_{21}$N$_6$O$_3$.1.6HCl: C, 62.15; H, 4.37; N, 13.42. Found: C, 61.97; H, 4.52; N, 13.15.

EXAMPLE 29.2

Synthesis of 1'-[4-(3-amino-1H-pyrazol-5-yl)benzyl]-2,3-dihydrospiro[furo[2,3-g][1,4]benzodioxine-8,3'-indol]-2'(1'H)-one hydrochloride

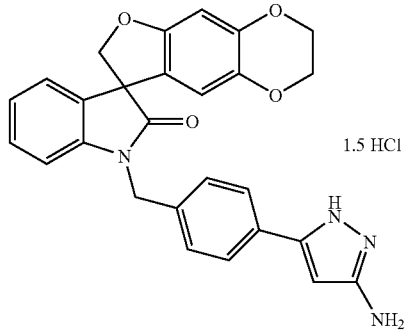

Following the procedure as described in EXAMPLE 29 and EXAMPLE 29.1 and making non-critical variations using 2,3-dihydrospiro[furo[2,3-g][1,4]benzodioxine-8,3'-indol]-2'(1'H)-one to replace 3-methylspiro[furo[3,2-f][1,2]benzisoxazole-5,3'-indol]-2'(1'H)-one, 1'-[4-(3-amino-1H-pyrazol-5-yl)benzyl]-2,3-dihydrospiro[furo[2,3-g][1,4]benzodioxine-8,3'-indol]-2'(1'H)-one hydrochloride was obtained (25%) as a pale yellow solid: mp 198-201° C. (methanol); $^1$H NMR (300 MHz, DMSO-d$_6$) δ 7.79 (d, J=8.3 Hz, 2H), 7.43 (d, J=8.3 Hz, 2H), 7.21-7.25 (m, 1H), 7.15 (d, J=7.1 Hz, 1H), 7.00 (t, J=7.8 Hz, 2H), 6.50 (s, 1H), 6.38 (s, 1H), 6.08 (s, 1H), 5.06-4.86 (m, 2H), 4.80 (d, J=9.3 Hz, 1H), 4.66 (d, J=9.3 Hz, 1H), 4.21-4.01 (m, 4H); $^{13}$C NMR (75 MHz, DMSO-d$_6$) δ 177.3, 155.2, 145.6, 144.7, 142.6, 138.3, 138.3, 132.2, 129.3, 128.4, 127.6, 126.7, 124.2, 123.7, 121.6, 111.4, 109.9, 99.3, 80.0, 64.7, 64.1, 57.7, 43.3; MS (ES+) m/z 467.0 (M+1). Anal. Calcd. for C$_{27}$H$_{22}$N$_4$O$_4$.1.5HCl: C, 62.22; H, 4.54; N, 10.75. Found: C, 62.19; H, 4.59; N, 10.55.

EXAMPLE 30

Synthesis of 1'-[4(3-methyl-1,2,4-oxadiazol-5-yl)benzyl]-2,3-dihydrospiro[furo[2,3-g][1,4]benzodioxine-8,3'-indol]-2'(1'H)-one

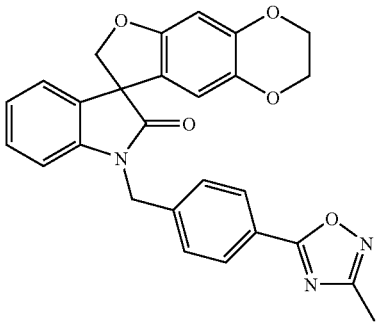

To a solution of 4-[(2'-oxo-2,3-dihydrospiro[furo[2,3-g][1,4]benzodioxine-8,3'-indol]-1'(2'H)-yl)methyl]benzoic acid (0.75 g, 1.7 mmol) in dichloromethane (10 mL) was added oxalyl chloride (0.50 mL, 5.77 mmol) and N,N-dimethylformamide (2 drops, catalytic amount). The mixture was stirred for 16 h at ambient temperature and concentrated in vacuo. The residue was dissolved in pyridine (1 mL) and transferred into a 10 mL microwave reaction vessel with pyridine rinses (2×1 mL). To this solution was added N-hydroxyacetamidine (0.25 g, 3.4 mmol) and the reaction mixture was irradiated at 170° C. for 30 min in a microwave reactor. The reaction mixture was allowed to cool to ambient temperature, concentrated in vacuo and the residue was purified by column chromatography and eluted with a 15% to 50% gradient of ethyl acetate in hexanes, followed by recrystallization from dichloromethane/diethyl ether to afford 1'-[4(3-methyl-1,2,4-oxadiazol-5-yl)benzyl]-2,3-dihydrospiro[furo[2,3-g][1,4]benzodioxine-8,3'-indol]-2'(1'H)-one (0.50 g, 63%) as a colorless solid: mp 177-178° C. (dichloromethane); $^1$H NMR (300 MHz, CDCl$_3$) δ 8.08 (d, J=8.1 Hz, 2H), 7.46 (d, J=8.1 Hz, 2H), 7.26-7.13 (m, 2H), 7.06-6.98 (m, 1H), 6.74 (d, J=7.6 Hz, 1H), 6.49 (s, 1H), 6.21 (s, 1H), 5.14 (d, J=16.0 Hz, 1H), 4.94 (d, J=9.0 Hz, 1H), 4.87 (d, J=16.0 Hz, 1H), 4.66 (d, J=8.9 Hz, 1H), 4.21-4.07 (m, 4H), 2.44 (s, 3H); $^{13}$C NMR (75 MHz, CDCl$_3$) δ 177.6, 174.9, 167.8, 155.3, 144.7, 141.7, 138.4, 132.2, 128.9, 128.6, 128.0, 124.1, 123.8, 123.8, 120.8, 111.5, 109.1, 99.5, 80.1, 64.5, 63.9, 58.1, 43.9, 11.7; MS (ES+) m/z 467.9 (M+1).

EXAMPLE 31

Synthesis of 2'-oxo-1'-(pyridin-2-ylmethyl)-1',2,2',3-tetrahydrospiro[furo[2,3-g][1,4]benzodioxine-8,3'-indole]-5'-carboxamide

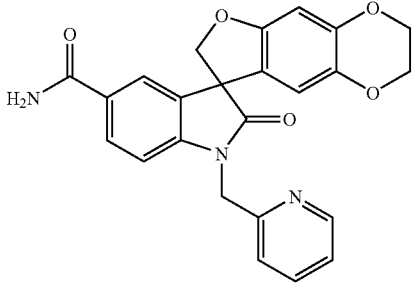

To a suspension of 2'-oxo-1'-(pyridin-2-ylmethyl)-1',2,2',3-tetrahydrospiro[furo[2,3-g][1,4]benzodioxine-8,3'-indole]-5'-carbonitrile (0.24 g, 0.57 mmol) in ethanol (20 mL) was added 3 M aqueous sodium carbonate (2 mL) and 30% w/w aqueous hydrogen peroxide (2 mL). The reaction mixture was stirred at ambient temperature for 16 h and concentrated in vacuo. The residue was triturated in water to afford 2'-oxo-1'-(pyridin-2-ylmethyl)-1',2,2',3-tetrahydrospiro[furo[2,3-g][1,4]benzodioxine-8,3'-indole]-5'-carboxamide (0.23 g, 93%) as a colorless solid: mp 220-222° C. (water); $^1$H NMR (300 MHz, CDCl$_3$) δ 8.46-8.42 (m, 1H), 7.82 (s, 1H), 7.81-7.74 (m, 2H), 7.65 (d, J=1.5 Hz, 1H), 7.38 (d, J=7.8 Hz, 1H), 7.28 (dd, J=7.0, 5.0 Hz, 1H), 7.19 (s, 1H), 6.98 (d, J=8.3 Hz, 1H), 6.50 (s, 1H), 6.33 (s, 1H), 5.14-4.97 (ABq, 2H), 4.81-4.68 (ABq, 2H), 4.19-4.06 (m, 4H); $^{13}$C NMR (75 MHz, CDCl$_3$) δ 177.6, 167.6, 155.4, 155.1, 149.7, 145.7, 144.7, 138.3, 137.6, 132.4, 129.4, 129.2, 123.3, 123.3, 122.3, 121.6, 112.1, 109.3, 99.2, 79.8, 64.7, 64.1, 57.7, 45.3; MS (ES+) m/z 429.9 (M+1).

EXAMPLE 32

Synthesis of 1'-[(6-morpholin-4-ylpyridin-3-yl)methyl]-2,3-dihydrospiro[furo[2,3-g][1,4]benzodioxine-8,3'-indol]-2'(1'H)-one

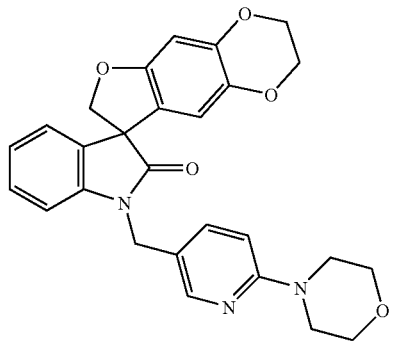

A 10 mL microwave reaction vessel was charged with 1-[(6-chloropyridin-3-yl)methyl]-2,3-dihydrospiro[furo[2,3-g][1,4]benzodioxine-8,3'-indol]-2'(1'H)-one (0.13 g, 0.31 mmol) and morpholine (0.5 mL, 6.1 mmol). The reaction mixture was irradiated at 180° C. for 20 min in a microwave reactor. The reaction mixture was poured into a mixture of water (15 mL) and ethyl acetate (30 mL). The layers were separated and the aqueous layer was extracted with ethyl acetate (2×30 mL). The combined organic layers was washed with brine (40 mL), dried over anhydrous magnesium sulfate, filtered and concentrated in vacuo. The residue was purified by column chromatography and eluted with 50% ethyl acetate in hexanes to afford 1'-[(6-morpholin-4-ylpyridin-3-yl)methyl]-2,3-dihydrospiro[furo[2,3-g][1,4]benzodioxine-8,3'-indol]-2'(1'H)-one (0.13 g, 92%) as a colorless solid: mp 117-119° C.; $^1$H NMR (300 MHz, DMSO-d$_6$) δ8.22-8.19 (m, 1H), 7.56-7.49 (m, 1H), 7.32-7.24 (m, 1H), 7.18-7.08 (m, 2H), 7.06-6.99 (m, 1H), 6.87-6.80 (m, 1H), 6.52 (s, 1H), 6.02 (s, 1H), 4.81 (q, J=15.5 Hz, 2H), 4.72 (ABq, J=40.6, 9.3 Hz, 2H), 4.22-4.06 (m, 4H), 3.70-3.63 (m, 4H), 3.44-3.38 (m, 4H); $^{13}$C NMR (75 MHz, DMSO-d$_6$) δ 176.6, 158.5, 154.6, 146.7, 144.1, 141.9, 137.7, 137.1, 131.7, 128.7, 123.6, 123.0, 121.1, 121.0, 110.8, 109.4, 107.1, 98.8, 79.3, 65.8, 64.1, 63.5, 57.1, 45.0; MS (ES+) m/z 471.9 (M+1).

EXAMPLE 32.1

Synthesis of 1'-{[6-(dimethylamino)pyridin-3-yl]methyl}-2,3-dihydrospiro[furo[2,3-g][1,4]benzodioxine-8,3'-indol]-2'(1'H)-one

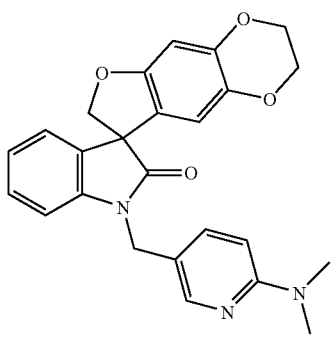

Following the procedure as described in EXAMPLE 32 and making non-critical variations using dimethylamine (40% w/w in water) to replace morpholine, 1'-{[6-(dimethylamino)pyridin-3-yl]methyl}-2,3-dihydrospiro[furo[2,3-g][1,4]benzodioxine-8,3'-indol]-2'(1'H)-one was obtained (82%) as a colorless solid: mp 93-95° C.; $^1$H NMR (300 MHz, DMSO-d$_6$) δ 8.18-8.14 (m, 1H), 7.49-7.43 (m, 1H), 7.31-7.24 (m, 1H), 7.18-7.07 (m, 2H), 7.05-6.98 (m, 1H), 6.65-6.59 (m, 1H), 6.52 (s, 1H), 6.02 (s, 1H), 4.87-4.62 (m, 4H), 4.21-4.07 (m, 4H), 2.98 (s, 6H); $^{13}$C NMR (75 MHz, DMSO-d$_6$) δ 176.6, 158.4, 154.6, 146.9, 144.1, 141.9, 137.7, 136.7, 131.7, 128.7, 123.5, 122.9, 121.1, 118.8, 110.8, 109.4, 105.8, 98.7, 79.3, 64.1, 63.5, 57.2, 37.6; MS (ES+) m/z 429.9 (M+1).

EXAMPLE 32.2

Synthesis of 1-{[6-(dimethylamino)pyridin-2-yl]methyl}-2,3-dihydrospiro[furo[2,3-g][1,4]benzodioxine-8,3'-indol]-2'(1'H)-one

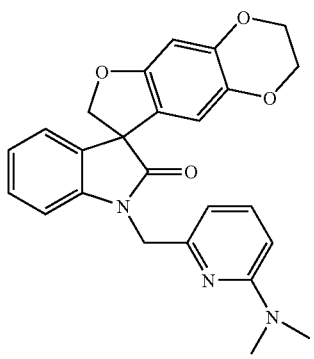

Following the procedure as described in EXAMPLE 32 and making non-critical variations using dimethylamine (40% w/w in water) to replace morpholine and 1'-[(6-chloropyridin-2-yl)methyl]-2,3-dihydrospiro[furo[2,3-g][1,4]benzodioxine-8,3'-indol]-2'(1'H)-one to replace 1'-[(6-chloropyridin-3-yl)methyl]-2,3-dihydrospiro[furo[2,3-g][1,4]benzodioxine-8,3'-indol]-2'(1'H)-one, 1-{[6-(dimethylamino)pyridin-2-yl]methyl}-2,3-dihydrospiro[furo[2,3-g][1,4]benzodioxine-8,3'-indol]-2'(1'H)-one was obtained (44%) as a colorless solid: mp 196-197° C.; $^1$H NMR (300 MHz, CDCl$_3$) δ 7.45-7.34 (m, 1H), 7.24-7.11 (m, 2H), 7.06-6.94 (m, 2H), 6.52-6.46 (m, 2H), 6.42-6.35 (m, 1H), 6.28 (s, 1H), 4.91 (ABq, J=53.2, 15.3 Hz, 2H), 4.80 (ABq, J=84.8, 9.1 Hz, 2H), 4.23-4.07 (m, 4H), 3.04 (s, 6H); $^{13}$C NMR (300 MHz, CDCl$_3$) δ 177.4, 159.0, 155.3, 153.3, 144.5, 142.7, 138.2, 137.9, 132.2, 128.6, 123.5, 123.1, 121.2, 111.7, 109.9, 108.8, 104.5, 99.3, 80.3, 64.5, 63.9, 58.1, 46.0, 37.8; MS (ES+) m/z 430.0 (M+1).

EXAMPLE 33

Synthesis of 1'-({6-[(diphenylmethylidene)amino]pyridin-2-yl}methyl)-2,3-dihydrospiro[furo[2,3-g][1,4]benzodioxine-8,3'-indol]-2'(1'H)-one

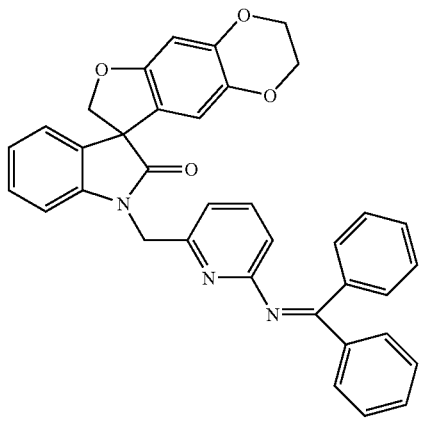

A mixture of 1'-[(6-chloropyridin-2-yl)methyl]-2,3-dihydrospiro[furo[2,3-g][1,4]-benzodioxine-8,3'-indol]-2'(1'H)-one (0.2 g, 0.5 mmol) and sodium tert-butoxide (0.06 g, 0.67 mmol) in 1,2-dimethoxyethane (3 mL) was degassed with argon for 15 min. (R)-(−)-1'-[(S)-2-(dicyclohexylphosphino)ferrocenyl]ethyldi-tert-butylphosphine (0.006 g, 0.01 mmol), palladium(II) acetate (0.01 g, 0.05 mmol), and benzophenone imine (0.1 mL, 0.6 mmol) were added. The reaction mixture was stirred at 70° C. for 24 h, allowed to cool to ambient temperature, diluted with dichloromethane (20 mL) and filtered through a pad of diatomaceous earth. The pad was washed with dichloromethane (20 mL) and the filtrate was concentrated in vacuo. The residue was purified by column chromatography and eluted with a 25% to 35% gradient of ethyl acetate in hexanes to afford 1'-({6-[(diphenylmethylidene)amino]pyridin-2-yl}methyl)-2,3-dihydrospiro[furo[2,3-g][1,4]benzodioxine-8,3'-indol]-2'(1'H)-one (0.19 g, 70%) as a colorless solid: MS (ES+) m/z 565.8 (M+1).

EXAMPLE 33.1

Synthesis of tert-butyl (3R)-3-({4-[(5,6-difluoro-2'-oxospiro[1-benzofuran-3,3'-indol]-1'(2'H)-yl)methyl]phenyl}amino)pyrrolidine-1-carboxylate

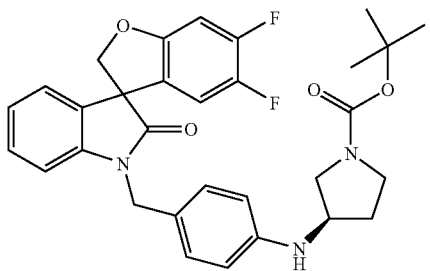

To a solution of 1'-(4-bromobenzyl)-5,6-difluorospiro[1-benzofuran-3,3'-indol]-2'(1'H)-one (0.44 g, 1.0 mmol) in anhydrous toluene (10 mL) was added (±)-(1,1'-binaphthalene-2,2'-diyl)bis(diphenylphosphine) (0.093 g, 0.15 mmol) and (R)-(+)-1-Boc-3-aminopyrrolidine (0.26 g, 1.4 mmol), followed by tris(dibenzylideneacetone)dipalladium (0) (0.458 g, 0.1 mmol) and sodium tert-butoxide (0.19 g, 2.0 mmol). The reaction mixture was heated at reflux for 16 h, allowed to cool to ambient temperature and filtered through a pad of diatomaceous earth. The filtrate was concentrated in vacuo and the residue dissolved in ethyl acetate (100 mL). The mixture was washed with water (2×75 mL) and brine (75 mL), dried over sodium sulfate, filtered and concentrated in vacuo. The residue was purified by column chromatography and eluted with a 20% to 40% gradient of ethyl acetate in hexanes to afford tert-butyl (3R)-3-({4-[(5,6-difluoro-2'-oxospiro[1-benzofuran-3,3'-indol]-1'(2'H)-yl)methyl]phenyl}amino)pyrrolidine-1-carboxylate (0.403 g, 74%) as a brown oil: $^1$H NMR (300 MHz, CDCl$_3$) δ 7.25-7.11 (m, 4H), 7.05-7.00 (m, 1H), 6.89 (d, J=7.7 Hz, 1H), 6.78 (dd, J=10.3, 6.3 Hz, 1H), 6.59 (s, 1H), 6.56 (s, 1H), 6.49 (dd, J=7.9, 7.9 Hz, 1H), 5.02-4.93 (m, 2H), 4.74-4.69 (m, 2H), 4.01 (br s, 1H), 3.76-3.68 (m, 2H), 3.46 (m, 2H), 3.20 (m, 1H), 2.21-2.12 (m, 1H), 1.87 (br s, 1H), 1.46 (s, 9H).

EXAMPLE 33.2

Synthesis of 5,6-difluoro-1'-{4-[(3R)-pyrrolidin-3-ylamino]benzyl}spiro[1-benzofuran-3,3'-indol]-2'(1'H)-one hydrochloride

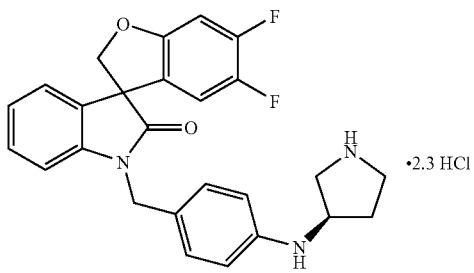

Following the procedure as described in EXAMPLE 11.111 and making non-critical variations using tert-butyl (3R)-3-({4-[(5,6-difluoro-2'-oxospiro[1-benzofuran-3,3'-indol]-1'(2'H)-yl)methyl]phenyl}amino)pyrrolidine-1-carboxylate to replace tert-butyl 4-[(5,6-difluoro-2'-oxospiro[1-benzofuran-3,3'-indol]-1'(2'H)-yl)methyl]piperidine-1-carboxylate, 5,6-difluoro-1'-{4-[(3R)-pyrrolidin-3-ylamino]benzyl}spiro[1-benzofuran-3,3'-indol]-2'(1'H)-one hydrochloride was obtained (78%) as a beige solid: mp 153-162° C.; $^1$H NMR (300 MHz, CDCl$_3$) δ 7.36-7.27 (m, 3H), 7.19 (d, J=7.3 Hz, 1H), 7.10 (d, J=7.4 Hz, 1H), 7.06-6.97 (m, 3H), 6.92 (dd, J=10.7, 6.4 Hz, 1H), 6.53 (dd, J=8.4, 8.4 Hz, 1H), 5.02-4.77 (m, 4H), 4.31 (s, 1H), 3.54-3.35 (m, 4H), 2.37 (s, 1H), 2.16 (s, 1H); $^{13}$C NMR (75 MHz, CDCl$_3$) δ 178.6, 158.4 (d, $J_{C-F}$=10.7 Hz), 152.3 (dd, $J_{C-F}$=246.1, 12.8 Hz), 146.6 (dd, $J_{C-F}$=239.5, 13.4 Hz), 143.3, 141.0, 133.4, 132.4, 130.5, 130.4, 125.5 (d, $J_{C-F}$=3.3 Hz), 125.0, 124.9, 120.2, 112.7 (d, $J_{C-F}$=20.3 Hz), 111.3, 100.8 (d, $J_{C-F}$=22.5 Hz), 82.1, 59.1, 57.7, 50.2, 46.3, 44.7, 30.4; MS (ES+) m/z 448.2 (M+1). Anal. Calcd for C$_{26}$H$_{23}$F$_2$N$_3$O$_2$.2.3HCl: C, 58.77; H, 4.80; N, 7.91. Found: C, 58.69; H, 4.37; N, 8.33.

EXAMPLE 33.3

Synthesis of 1'-[(5-morpholin-4-ylpyridin-2-yl)methyl]-2,3-dihydrospiro[furo[2,3-g][1,4]benzodioxine-8,3'-indol]-2'(1'H)-one

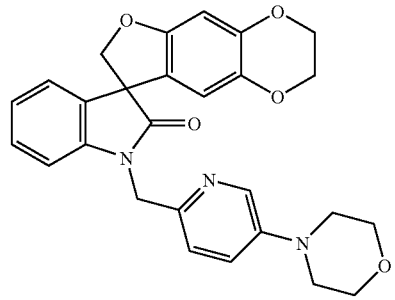

Following the procedure as described in EXAMPLE 33.1 and making non-critical variations using morpholine to replace (R)-(+)-1-Boc-3-aminopyrrolidine, and 1'-[(5-bromopyridin-2-yl)methyl]-2,3-dihydrospiro[furo[2,3-g][1,4]benzodioxine-8,3'-indol]-2'(1'H)-one to replace 1'-(4-bromobenzyl)-5,6-difluorospiro[1-benzofuran-3,3'-indol]-2'(1'H)-one, 1'-[(5-morpholin-4-ylpyridin-2-yl)methyl]-2,3-dihydrospiro[furo[2,3-g][1,4]benzodioxine-8,3'-indol]-2'(1'H)-one was obtained (60%) as a pale yellow solid: mp 204-206° C.; $^1$H NMR (300 MHz, CDCl$_3$) δ 8.23 (d, J=2.4 Hz, 1H), 7.23-7.11 (m, 4H), 7.01 (dd, J=7.5, 7.5 Hz, 1H), 6.95 (d, J=7.8 Hz, 1H), 6.50 (s, 1H), 6.27 (s, 1H), 5.13 (d, J=15.3 Hz, 1H), 4.94 (d, J=9.0 Hz, 1H), 4.89 (d, J=15.6 Hz, 1H), 4.66 (d, J=9.0 Hz, 1H), 4.21-4.11 (m, 4H), 3.87 (t, J=4.8 Hz, 4H), 3.17 (t, J=5.0 Hz, 4H); $^{13}$C NMR (75 MHz, CDCl$_3$) δ 177.4, 155.3, 146.3, 146.2, 144.6, 142.2, 138.3, 137.3, 132.2, 128.8, 123.7, 123.4, 123.2, 122.0, 121.1, 111.7, 109.7, 99.4, 80.2, 66.6, 64.5, 63.9, 58.1, 48.5, 45.6; MS (ES+) m/z 472.2 (M+1).

EXAMPLE 33.4

Synthesis of 1'-{[5-(dimethylamino)pyridin-2-yl]methyl}-2,3-dihydrospiro[furo[2,3-g][1,4]benzodioxine-8,3'-indol]-2'(1'H)-one

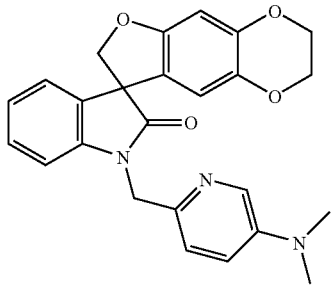

Following the procedure as described in EXAMPLE 33.1 and making non-critical variations using dimethylamine hydrochloride to replace (R)-(+)-1-Boc-3-aminopyrrolidine, and 1'-[(5-bromopyridin-2-yl)methyl]-2,3-dihydrospiro[furo[2,3-g][1,4]benzodioxine-8,3'-indol]-2'(1'H)-one to replace 1'-(4-bromobenzyl)-5,6-difluorospiro[1-benzofuran-3,3'-indol]-2'(1'H)-one, 1'-{[5-(dimethylamino)pyridin-2-yl]methyl}-2,3-dihydrospiro[furo[2,3-g][1,4]benzodioxine-8,3'-indol]-2'(1'H)-one was obtained (23%) as a beige solid: mp 229-236° C.; $^1$H NMR (300 MHz, CDCl$_3$) δ8.06 (d, J=2.7 Hz, 1H), 7.22-6.92 (m, 6H), 6.50 (s, 1H), 6.27 (s, 1H), 5.11 (d, J=15.3 Hz, 1H), 4.94 (d, J=9.0 Hz, 1H), 4.87 (d, J=15.3 Hz, 1H), 4.65 (d, J=8.7 Hz, 1H), 4.21-4.11 (m, 4H), 2.96 (s, 6H); $^{13}$C NMR (75 MHz, CDCl$_3$) δ177.4, 155.3, 145.5, 144.5, 142.8, 142.4, 138.3, 134.1, 132.3, 128.8, 123.6, 123.2, 122.0, 121.2, 119.8, 111.7, 109.9, 99.3, 80.2, 64.5, 63.9, 58.1, 45.7, 40.1; MS (ES+) m/z 430.1 (M+1).

EXAMPLE 34

Synthesis of 1'-[(6-aminopyridin-2-yl)methyl]-2,3-dihydrospiro[furo[2,3-g][1,4]benzodioxine-8,3'-indol]-2'(1'H)-one

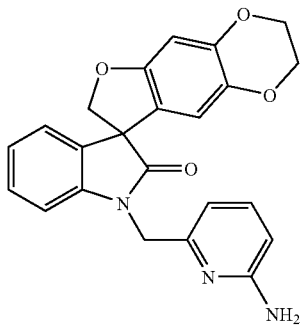

To a solution of 1'-({6-[(diphenylmethylidene)amino]pyridin-2-yl}methyl)-2,3-dihydrospiro[furo[2,3-g][1,4]benzodioxine-8,3'-indol]-2'(1'H)-one (0.18 g, 0.32 mmol) in tetrahydrofuran (10 mL) was added 2 M aqueous hydrochloric acid (0.5 mL). The reaction mixture was stirred at ambient temperature for 10 min, cooled to 0° C. and saturated aqueous sodium bicarbonate (10 mL) was added. The mixture was diluted with ethyl acetate (30 mL). The layers were separated and the aqueous layer was extracted with ethyl acetate (2×25 mL). The combined organic layers was washed with brine (45 mL), dried over anhydrous magnesium sulfate, filtered and concentrated in vacuo. The residue was purified by column chromatography and eluted with 65% ethyl acetate in hexanes to afford 1'-[(6-aminopyridin-2-yl)methyl]-2,3-dihydrospiro[furo[2,3-g][1,4]benzodioxine-8,3'-indol]-2'(1'H)-one (0.10 g, 76%) as a colorless solid: mp 240-241° C.; $^1$H NMR (300 MHz, CDCl$_3$) δ7.45-7.35 (m, 1H), 7.25-7.14 (m, 2H), 7.06-6.98 (m, 1H), 6.91-6.86 (m, 1H), 6.59-6.54 (m, 1H), 6.50 (s, 1H), 6.45-6.39 (m, 1H), 6.37 (s, 1H), 5.12-5.03 (m, 1H), 4.99-4.92 (m, 1H), 4.80-4.63 (m, 4H), 4.25-4.05 (m, 4H); $^{13}$C NMR (300 MHz, CDCl$_3$) δ 177.5, 157.9, 155.2, 153.0, 144.6, 142.1, 139.0, 138.2, 132.2, 128.8, 123.7, 123.4, 121.2, 111.7, 111.1, 109.6, 107.9, 99.3, 80.0, 64.5, 63.9, 58.1, 45.2; MS (ES+) m/z 401.9 (M+1).

EXAMPLE 35

Synthesis of 1'-[(6-oxo-1,6-dihydropyridin-3-yl)methyl]-2,3-dihydrospiro[furo[2,3-g][1,4]benzodioxine-8,3'-indol]-2'(1'H)-one

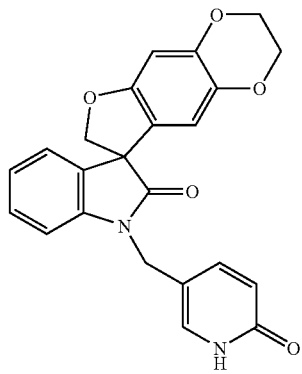

To a stirred mixture of 1'-[(6-methoxypyridin-3-yl)methyl]-2,3-dihydrospiro[furo[2,3-g][1,4]benzodioxine-8,3'-indol]-2'(1'H)-one (0.24 g, 0.58 mmol), sodium iodide (0.29 g, 1.9 mmol), and water (2 drops) in acetonitrile (5 mL) was added chlorotrimethylsilane (0.23 mL, 1.8 mmol). The reaction mixture was stirred at ambient temperature for 16 h. Further, sodium iodide (0.14 g, 0.95 mmol) and chlorotrimethylsilane (0.12 mL, 0.95 mmol) were added and the reaction mixture was stirred at ambient temperature for 24 h. Further, sodium iodide (0.29 g, 1.9 mmol) and chlorotrimethylsilane (0.23 mL, 1.8 mmol) were added and the reaction mixture was stirred at ambient temperature for 5 days. A solution of sodium bisulfite (0.51 g, 4.9 mmol) in water (30 mL) and ethyl acetate (150 mL) were added. The layers were separated and the organic layer was washed with brine (2×50 mL), dried over anhydrous magnesium sulfate, filtered and concentrated in vacuo. The residue was triturated with diethyl ether and the crude product was purified by preparative thin layer chromatography and eluted with 30% acetone in dichloromethane to afford 1'-[(6-oxo-1,6-dihydropyridin-3-yl)methyl]-2,3-dihydrospiro[furo[2,3-g][1,4]benzodioxine-8,3'-indol]-2'(1'H)-one (0.15 g, 63%) as a colorless solid: mp 249-250° C.; $^1$H NMR (300 MHz, CDCl$_3$) δ7.61-7.46 (m, 2H), 7.31-7.21 (m, 1H), 7.20-7.14 (m, 1H), 7.09-7.02 (m, 1H), 6.86-6.81 (m, 1H), 6.66-6.59 (m, 1H), 6.50 (s, 1H), 6.15

(s, 1H), 4.92-4.60 (m, 4H), 4.24-4.06 (m, 4H); $^{13}$C NMR (75 MHz, CDCl$_3$) δ 177.7, 164.4, 155.2, 144.7, 142.2, 141.4, 138.3, 133.5, 132.2, 129.0, 124.2, 123.8, 120.9, 120.7, 115.8, 111.4, 108.7, 99.5, 80.0, 64.5, 63.9, 58.0, 40.6; MS (ES+) m/z 403.0 (M+1).

EXAMPLE 35.1

Synthesis of 1'-[(2-hydroxypyrimidin-5-yl)methyl]-2,3-dihydrospiro[furo[2,3-g][1,4]benzodioxine-8,3'-indol]-2'(1'H)-one

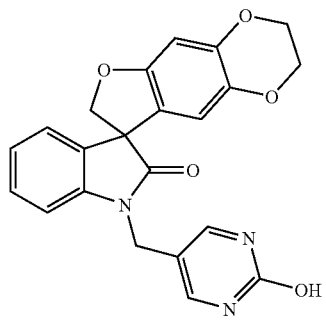

Following the procedure as described in EXAMPLE 35 and making non-critical variations using 1'-[(2-methoxypyrimidin-5-yl)methyl]-2,3-dihydrospiro[furo[2,3-g][1,4]benzodioxine-8,3'-indol]-2'(1'H)-one to replace 1'-[(6-methoxypyridin-3-yl)methyl]-2,3-dihydrospiro[furo[2,3-g][1,4]benzodioxine-8,3'-indol]-2'(1'H)-one, 1'-[(2-hydroxypyrimidin-5-yl)methyl]-2,3-dihydrospiro[furo[2,3-g][1,4]benzodioxine-8,3'-indol]-2'(1'H)-one was obtained (19%) as a colorless solid: mp>250° C.; $^1$H NMR (300 MHz, DMSO-d$_6$) δ 8.31 (s, 2H), 7.37-7.28 (m, 1H), 7.28-7.21 (m, 1H), 7.20-7.12 (m, 1H), 7.10-7.00 (m, 1H), 6.50 (s, 1H), 6.08 (s, 1H), 4.71 (s, 2H), 4.71 (ABq, J=47.0, 9.4 Hz, 2H), 4.23-4.04 (m, 4H); $^{13}$C NMR (300 MHz, CDCl$_3$) δ 176.9, 154.7, 144.2, 141.7, 137.8, 131.9, 128.8, 123.7, 123.2, 121.2, 112.1, 111.0, 109.3, 98.8, 79.4, 64.2, 63.6, 57.2, 37.6; MS (ES+) m/z 403.9 (M+1).

EXAMPLE 36

Synthesis of 1'-[(1-methyl-6-oxo-1,6-dihydropyridin-3-yl)methyl]-2,3-dihydrospiro[furo[2,3-g][1,4]benzodioxine-8,3'-indol]-2'(1'H)-one

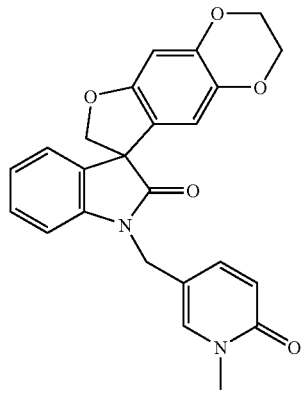

To a cooled (0° C.) solution of 1'-[(6-oxo-1,6-dihydropyridin-3-yl)methyl]-2,3-dihydrospiro[furo[2,3-g][1,4]benzodioxine-8,3'-indol]-2'(1'H)-one (0.07 g, 0.17 mmol) in anhydrous N,N-dimethylformamide (3 mL) was added sodium hydride (60% in mineral oil, 0.01 g, 0.25 mmol). The mixture was stirred at ambient temperature for 1 h, and iodomethane (0.02 mL, 0.27 mmol) was added. The mixture was stirred at ambient temperature for 16 h, diluted with water (15 mL) and extracted with ethyl acetate (3×30 mL). The combined organic layers was washed with brine (35 mL), dried over anhydrous magnesium sulfate, filtered and concentrated in vacuo. The residue was purified by column chromatography and eluted with a 10% to 30% gradient of acetone in dichloromethane to afford 1'-[(1-methyl-6-oxo-1,6-dihydropyridin-3-yl)methyl]-2,3-dihydrospiro[furo[2,3-g][1,4]benzodioxine-8,3'-indol]-2'(1'H)-one (0.03 g, 42%) as a colorless solid: mp 205-207° C.; $^1$H NMR (300 MHz, CDCl$_3$) δ7.40-7.34 (m, 2H), 7.33-7.26 (m, 1H), 7.21-7.16 (m, 1H), 7.11-7.04 (m, 1H), 6.91-6.85 (m, 1H), 6.60-6.54 (m, 1H), 6.50 (s, 1H), 6.12 (s, 1H), 4.77 (ABq, J=75.6, 9.0 Hz, 2H), 4.66 (ABq, J=58.2, 15.3 Hz, 2H), 4.22-4.08 (m, 4H), 3.53 (s, 3H); $^{13}$C NMR (75 MHz, CDCl$_3$) δ 177.7, 162.5, 155.2, 144.7, 141.5, 139.6, 138.3, 137.4, 132.2, 128.9, 124.3, 123.8, 121.3, 120.7, 114.0, 111.2, 108.5, 99.5, 79.8, 64.5, 63.9, 57.9, 40.8, 37.9; MS (ES+) m/z 416.9 (M+1).

EXAMPLE 37

Synthesis of 1'-[(6-aminopyridin-3-yl)methyl]-2,3-dihydrospiro[furo[2,3-g][1,4]benzodioxine-8,3'-indol]-2'(1'H)-one

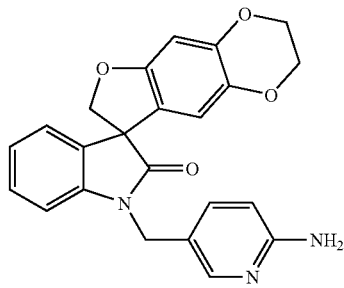

To a cooled (0° C.) suspension of tert-butyl {5-[(2'-oxo-2,3-dihydrospiro[furo[2,3-g][1,4]benzodioxine-8,3'-indol]-1'(2'H)-yl]methyl]pyridin-2-yl}carbamate (0.27 g, 0.53 mmol) in anhydrous dichloromethane (12 mL) was added trifluoroacetic acid (4 mL). The mixture was stirred at ambient temperature for 3 h and concentrated in vacuo. The residue was dissolved in dichloromethane (100 mL), washed with saturated aqueous sodium bicarbonate (35 mL) and brine (35 mL), dried over anhydrous magnesium sulfate, filtered and concentrated in vacuo to afford 1-'[(6-aminopyridin-3-yl)methyl]-2,3-dihydrospiro[furo[2,3-g][1,4]benzodioxine-8,3'-indol]-2'(1'H)-one (0.20 g, 93%) as a colorless solid: mp 117-119° C.; $^1$H NMR (300 MHz, DMSO-d$_6$) 8.00-7.96 (m, 1H), 7.37-7.24 (m, 2H), 7.19-7.07 (m, 2H), 7.07-6.98 (m, 1H), 6.52 (s, 1H), 6.43-6.38 (m, 1H), 6.01-5.96 (m, 3H), 4.82-4.62 (m, 4H), 4.21-4.07 (m, 4H); $^{13}$C NMR (75 MHz, DMSO-d$_6$) δ 176.6, 159.2, 154.6, 147.0, 144.1, 141.9, 137.7, 136.7, 131.7, 128.7, 123.5, 122.9, 121.2, 119.3, 110.7, 109.4, 108.0, 98.7, 79.2, 64.1, 63.5, 57.1; MS (ES+) m/z 401.9 (M+1).

EXAMPLE 38

Synthesis of N'-hydroxy-N-{5-[(2'-oxo-2,3-dihydrospiro[furo[2,3-g][1,4]benzodioxine-8,3'-indol]-1'(2'H)-yl)methyl]pyridin-2-yl}imidoformamide

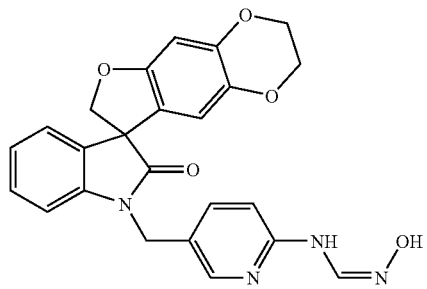

To a solution of 1'-[(6-aminopyridin-3-yl)methyl]-2,3-dihydrospiro[furo[2,3-g][1,4]benzodioxine-8,3'-indol]-2'(1'H)-one (0.40 g, 1.0 mmol) in 2-propanol was added N,N-dimethylformamide dimethyl acetal (0.17 mL, 1.3 mmol). The mixture was heated at reflux for 3 h, allowed to cool to ambient temperature and further N,N-dimethylformamide dimethyl acetal (0.12 mL, 0.9 mmol) was added. The mixture was heated at reflux for 6 h and allowed to cool to 50° C. Hydroxylamine hydrochloride (0.15 g, 2.2 mmol) was added and the mixture was stirred at 50° C. for 16 h. The mixture was allowed to cool to ambient temperature, during which time a precipitate was deposited. The solid was filtered, washed with 2-propanol and diethyl ether and dried to afford N'-hydroxy-N-{5-[(2'-oxo-2,3-dihydrospiro[furo[2,3-g][1,4]benzodioxine-8,3'-indol]-1'(2'H)-yl)methyl]pyridin-2-yl}imidoformamide (0.37 g, 82%) as a colorless solid: mp 231-232° C.; $^1$H NMR (300 MHz, DMSO-$d_6$) δ 10.07 (s, 1H), 9.41-9.35 (m, 1H), 8.23-8.19 (m, 1H), 7.84-7.78 (m, 1H), 7.59-7.53 (m, 1H), 7.32-7.24 (m, 1H), 7.19-7.13 (m, 1H), 7.13-7.07 (m, 1H), 7.07-6.99 (m, 2H), 6.52 (s, 1H), 6.05 (s, 1H), 4.86-4.83 (m, 2H), 4.73 (ABq, J=44.3, 9.4 Hz, 2H), 4.22-4.06 (m, 4H); $^{13}$C NMR (75 MHz, DMSO-$d_6$) δ 176.7, 154.6, 152.0, 146.6, 144.1, 141.8, 137.7, 137.5, 135.4, 131.7, 128.7, 124.0, 123.6, 123.0, 121.1, 110.8, 110.4, 109.4, 98.8, 79.3, 64.1, 63.5, 57.2; MS (ES+) m/z 444.9 (M+1).

EXAMPLE 39

Synthesis of 1'-([1,2,4]triazolo[1,5-a]pyridin-6-ylmethyl)-2,3-dihydrospiro[furo[2,3-g][1,4]benzodioxine-8,3'-indol]-2'(1'H)-one

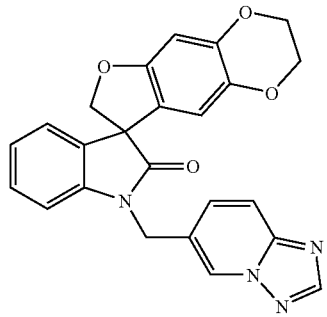

To a cooled (0° C.) suspension of N'-hydroxy-N-{5-[(2'-oxo-2,3-dihydrospiro[furo[2,3-g][1,4]benzodioxine-8,3'-indol]-1'(2'H)-yl)methyl]pyridin-2-yl}imidoformamide (0.22 g, 0.5 mmol) in tetrahydrofuran (7 mL) was slowly added trifluoroacetic anhydride (0.08 mL, 0.54 mmol). The mixture was stirred at ambient temperature for 3 h, diluted with saturated aqueous sodium bicarbonate (10 mL) and extracted with ethyl acetate (3×50 mL). The combined organic layers was washed with saturated aqueous sodium bicarbonate (50 mL) and brine (50 mL), dried over anhydrous magnesium sulfate, filtered and concentrated in vacuo. The residue was purified by column chromatography and eluted with a 50% to 65% gradient of ethyl acetate in hexanes to afford 1'-([1,2,4]triazolo[1,5-a]pyridin-6-ylmethyl)-2,3-dihydrospiro[furo[2,3-g][1,4]benzodioxine-8,3'-indol]-2'(1'H)-one (0.11 g, 54%) as a colorless solid: mp 207-209° C.; $^1$H NMR (300 MHz, DMSO-$d_6$) δ 8.65 (s, 1H), 8.37 (s, 1H), 7.82-7.77 (m, 1H), 7.61-7.55 (m, 1H), 7.30-7.17 (m, 2H), 7.11-7.04 (m, 1H), 6.90-6.85 (m, 1H), 6.52 (s, 1H), 6.18 (s, 1H), 5.03 (ABq, J=40.9, 15.6 Hz, 2H), 4.80 (ABq, J=79.6, 9.0 Hz, 2H), 4.23-4.09 (m, 4H); $^{13}$C NMR (75 MHz, DMSO-$d_6$) δ 177.7, 155.2, 154.2, 149.9, 144.8, 141.2, 138.4, 132.1, 129.8, 129.0, 127.0, 124.4, 124.0, 123.0, 120.5, 117.4, 111.4, 108.6, 99.5, 80.0, 64.5, 63.9, 58.0, 41.2; MS (ES+) m/z 426.9 (M+1).

EXAMPLE 40

Synthesis of 1'-[(2S)-2,3-dihydroxypropyl]-2,3-dihydrospiro[furo[2,3-g][1,4]benzodioxine-8,3'-indol]-2'(1'H)-one

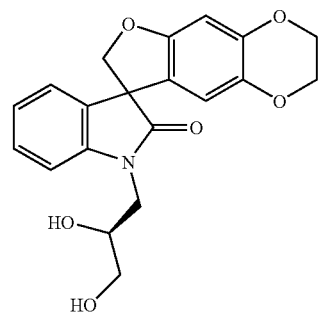

A solution of 1'-{[(4S)-2,2-dimethyl-1,3-dioxolan-4-yl]methyl}-2,3-dihydrospiro[furo[2,3-g][1,4]benzodioxine-8,3'-indol]-2'(1'H)-one (0.66 g, 1.61 mmol) in glacial acetic acid (10 mL) and water (5 mL) was stirred at ambient temperature for 18 h and concentrated in vacuo. The residue was recrystallized from ethyl acetate to afford 1'-[(2S)-2,3-dihydroxypropyl]-2,3-dihydrospiro[furo[2,3-g][1,4]benzodioxine-8,3'-indol]-2'(1'H)-one (0.59 g, 99%): mp 179-181° C. (ethyl acetate/hexane); $^1$H NMR (300 MHz, DMSO-$d_6$) δ 7.30-7.25 (m, 1H), 7.13-7.07 (m, 2H), 7.01-6.95 (m, 1H), 6.46 (s, 1H), 6.21-6.19 (m, 1H), 5.02-4.94 (m, 1H), 4.71-4.57 (m, 3H), 4.14-4.06 (m, 4H), 3.81-3.54 (m, 3H), 3.39-3.32 (m, 2H); MS (ES+) m/z 369.9 (M+1).

EXAMPLE 41 AND EXAMPLE 42

Synthesis of 6-[(2'-oxo-2,3-dihydrospiro[furo[2,3-g][1,4]benzodioxine-8,3'-indol]-1'(2'H)-yl)methyl]pyridine-2-carbonitrile and 6-[(2'-oxo-2,3-dihydrospiro[furo[2,3-g][1,4]benzodioxine-8,3'-indol]-1'(2'H)-yl)methyl]pyridine-2-carboxamide

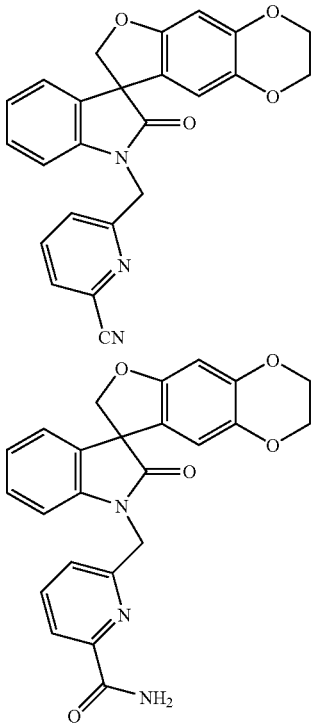

A mixture of 1'-[(6-chloropyridin-2-yl)methyl]-2,3-dihydrospiro[furo[2,3-g][1,4]benzodioxine-8,3'-indol]-2'(1'H)-one (0.50 g, 1.2 mmol), sodium cyanide (0.12 g, 2.4 mmol) and nickel(II) bromide trihydrate (0.026 g, 1.2 mmol) in 1-methyl-2-pyrrolidinone (5 mL) was heated under microwave irradiation at 200° C. for 30 min, allowed to cooled to ambient temperature, diluted with ethyl acetate and washed with water and brine. The organic phase was dried over anhydrous sodium sulfate and filtered. The filtrate was concentrated in vacuo. The residue was subjected to column chromatography and eluted with ethyl acetate/hexanes (1/1) to afford two products:

The first compound to elute was 6-[(2'-oxo-2,3-dihydrospiro[furo[2,3-g][1,4]benzodioxine-8,3'-indol]-1'(2'H)-yl)methyl]pyridine-2-carbonitrile (0.23 g, 48%): mp 213-215° C. (ethyl acetate/hexanes); $^1$H NMR (300 MHz, DMSO-$d_6$) δ 8.06-8.01 (m, 1H), 7.95-7.92 (m, 1H), 7.71-7.67 (m, 1H), 7.26-7.14 (m, 2H), 7.04-6.98 (m, 1H), 6.94-6.90 (m, 1H), 6.48 (s, 1H), 6.25 (s, 1H), 5.09 (ABq, 2H), 4.71 (ABq, 2H), 4.15-4.06 (m, 4H); MS (ES+) m/z 412.0 (M+1).

The second compound to elute was 6-[(2'-oxo-2,3-dihydrospiro[furo[2,3-g][1,4]benzodioxine-8,3'-indol]-1'(2'H)-yl)methyl]pyridine-2-carboxamide (0.06 g, 12%): mp 113-115° C. (ethyl acetate/hexanes); $^1$H NMR (300 MHz, DMSO-$d_6$) δ 7.97-7.88 (m, 2H), 7.71-7.68 (m, 2H), 7.50-7.46 (m, 1H), 7.27-6.99 (m, 4H), 6.48 (s, 1H), 6.12 (s, 1H), 5.06 (ABq, 2H), 4.79 (ABq, 2H), 4.15-4.06 (m, 4H); $^{13}$C NMR (75 MHz, DMSO-$d_6$) δ 177.2, 165.9, 155.4, 155.1, 144.6, 143.0, 139.3, 138.3, 132.0, 129.2, 124.5, 124.1, 121.6, 121.1, 111.6, 109.9, 99.2, 79.9, 64.6, 64.0, 57.7, 45.2; MS (ES+) m/z 430.0 (M+1).

EXAMPLE 43

Synthesis of N',6-dihydroxy-1'-(4-methoxybenzyl)-2'-oxo-1',2'-dihydrospiro[1-benzofuran-3,3'-indole]-5-carboximidamide

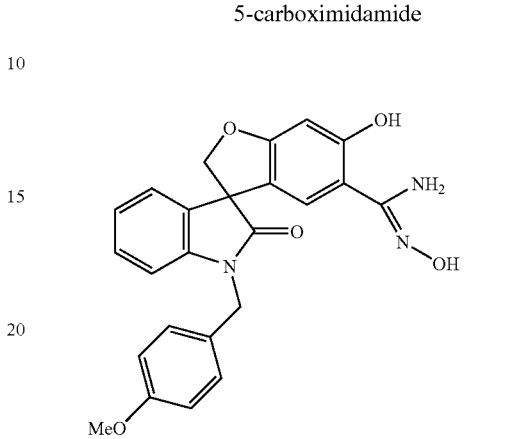

To a stirred solution of 6-hydroxy-1'-(4-methoxybenzyl)-2'-oxo-1',2'-dihydrospiro[1-benzofuran-3,3'-indole]-5-carbonitrile (0.84 g, 2.10 mmol) and hydroxylamine hydrochloride (0.20 g, 2.9 mmol) in ethanol (50 mL) was added triethylamine (0.40 mL, 2.9 mmol). The reaction mixture was stirred at reflux for 18 h and concentrated in vacuo. The residue was extracted with ethyl acetate (3×50 mL). The combined organic extracts were washed with water and brine, dried over anhydrous sodium sulfate and filtered. The filtrate was concentrated in vacuo to afford N',6-dihydroxy-1'-(4-methoxybenzyl)-2'-oxo-1',2'-dihydrospiro[1-benzofuran-3,3'-indole]-5-carboximidamide (0.90 g, 99%): MS (ES+) m/z 431.9 (M+1).

EXAMPLE 44

Synthesis of 3-amino-1'-(4-methoxybenzyl)spiro[furo[3,2-f][1,2]benzisoxazole-5,3'-indol]-2'(1'H)-one

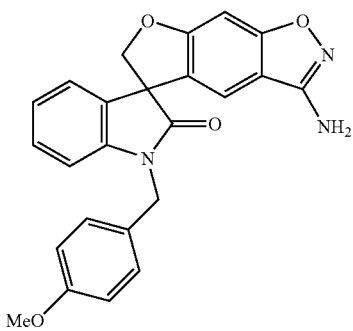

To a solution of N',6-dihydroxy-1'-(4-methoxybenzyl)-2'-oxo-1',2'-dihydrospiro[1-benzofuran-3,3'-indole]-5-carboximidamide (0.90 g, 2.1 mmol) and triphenylphosphine (0.71 g, 2.7 mmol) in tetrahydrofuran (30 mL) was added diethyl azodicarboxylate (0.43 mL, 2.7 mmol) at 0° C. The reaction mixture was allowed to warm to ambient temperature and was stirred for 16 h. 10% w/v aqueous sodium hydroxide (10 mL) was added and the mixture was stirred for 3 h. Most of the tetrahydrofuran was removed in vacuo and the resultant mixture was extracted with ethyl acetate (3×50 mL). The combined organic extracts were washed with water and brine, dried over anhydrous sodium sulfate and filtered. The filtrate was concentrated in vacuo. The residue was purified by column chromatography to afford 3-amino-1'-(4-methoxybenzyl)spiro[furo[3,2-f][1,2]benzisoxazole-5,3'-indol]-2'(1'H)-one (0.16 g, 19%): mp 214-216° C.; $^1$H NMR (300 MHz, DMSO-d$_6$) δ 7.29-7.20 (m, 5H), 7.14-7.12 (m, 1H), 7.05 (s, 1H), 7.02-6.98 (m, 2H), 6.90-6.87 (m, 2H), 6.29 (s, 1H), 4.92-4.69 (m, 4H), 3.69 (s, 3H); $^{13}$C NMR (75 MHz, DMSO-d$_6$) δ 177.3, 162.8, 159.1, 155.3, 148.8, 142.6, 138.1, 132.5, 129.1, 128.7, 124.5, 124.1, 123.4, 114.5, 109.9, 109.2, 93.0, 79.9, 57.9, 55.5, 42.9; MS (ES+) m/z 413.9 (M+1).

EXAMPLE 44.1

Synthesis of 3-amino-1'-(pyridin-2-ylmethyl)spiro[furo[3,2-f][1,2]benzisoxazole-5,3'-indol]-2'(1'H)-one

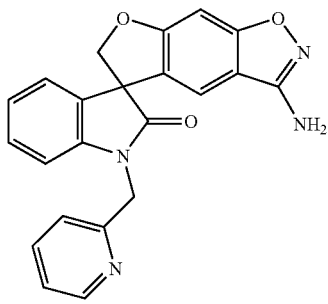

To a stirred solution of 6-fluoro-2'-oxo-1'-(pyridin-2-ylmethyl)-1',2'-dihydrospiro[1-benzofuran-3,3'-indole]-5-carbonitrile (0.40 g, 2.7 mol) and acetohydroxamic acid (0.60 g, 8.0 mmol) in N,N-dimethylformamide (20 mL) was added cesium carbonate (2.60 g, 8.0 mmol). The reaction mixture was stirred at ambient temperature for 18 h and water was added. The aqueous phase was extracted with ethyl acetate. The combined organic extracts were washed with water and brine, dried over anhydrous sodium sulfate and filtered. The filtrate was concentrated in vacuo. The residue was purified by column chromatography and eluted with (ethyl acetate/hexanes (2/3)+0.1% v/v 7 N methanolic ammonia) to afford 3-amino-1'-(pyridin-2-ylmethyl)spiro[furo[3,2-f][1,2]benzisoxazole-5,3'-indol]-2'(1'H)-one (0.05 g, 5%): mp 190-192° C. (ethyl acetate/hexanes); $^1$H NMR (300 MHz, DMSO-d$_6$) δ 8.54-8.52 (m, 1H), 7.79-7.73 (m, 1H), 7.35-7.20 (m, 5H), 7.08-6.96 (m, 3H), 6.15 (s, 2H), 5.09-4.85 (m, 4H); $^{13}$C NMR (75 MHz, DMSO-d$_6$) δ 177.2, 164.2, 163.3, 158.7, 155.6, 149.9, 143.5, 137.6, 131.7, 129.4, 126.4, 124.5, 123.6, 123.1, 121.9, 116.8, 111.5, 109.9, 91.4, 81.0, 56.8, 45.3; MS (ES+) m/z 384.9 (M+1).

EXAMPLE 44.2

Synthesis of 3-amino-1'-[(2R)-tetrahydrofuran-2-ylmethyl]spiro[furo[3,2-f][1,2]benzisoxazole-5,3'-indol]-2'(1'H)-one

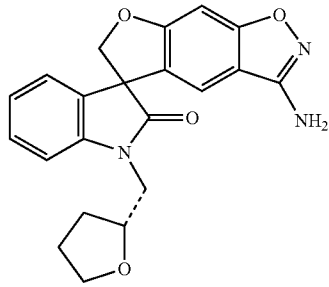

To a stirred solution of 6-fluoro-2'-oxo-1'-[(2R)-tetrahydrofuran-2-ylmethyl]-1',2'-dihydrospiro[1-benzofuran-3,3'-indole]-5-carbonitrile (0.59 g, 1.6 mol) and acetone oxime (0.35 g, 4.8 mmol) in N,N-dimethylformamide (20 mL) was added cesium carbonate (1.56 g, 4.8 mmol). The reaction mixture was stirred at ambient temperature for 19 h, then heated at 60° C. for 7 h and allowed to cool to ambient temperature. Water was added and the mixture was extracted with ethyl acetate (3×50 mL). The combined organic extracts were washed with water and brine, dried over anhydrous sodium sulfate and filtered. The filtrate was concentrated in vacuo. The residue was dissolved in a mixture of ethanol (30 mL), water (10 mL), and concentrated hydrochloric acid (2 mL) and stirred at reflux for 4 h. The mixture was allowed to cool to ambient temperature and neutralized with saturated aqueous sodium bicarbonate. The mixture was extracted with ethyl acetate (3×100 mL). The combined organic extracts were washed with water and brine, dried over anhydrous sodium sulfate and filtered. The filtrate was concentrated in vacuo. The residue was subjected to column chromatography and eluted with (ethyl acetate/hexanes (1/3)+0.1% v/v 7 N methanolic ammonia) to afford 3-amino-1'-[(2R)-tetrahydrofuran-2-ylmethyl]spiro[furo[3,2-f][1,2]benzisoxazole-5,3'-indol]-2'(1'H)-one (0.37 g, 60%): mp 116-119° C. (ethyl acetate/hexanes); $^1$H NMR (300 MHz, CDCl$_3$) δ 7.35-7.32 (m, 1H), 7.13-7.02 (m, 3H), 6.09 (s, 1H), 6.84-6.81 (m, 1H), 4.91 (ABq, 2H), 4.31-4.25 (m, 1H), 4.13-4.09 (m, 2H), 3.86-3.66 (m, 4H), 2.12-1.87 (m, 4H); (ES+) m/z 377.9 (M+1).

EXAMPLE 44.3

Synthesis of 3-amino-1'-[2-(trifluoromethyl)benzyl]spiro[furo[3,2-f][1,2]benzisoxazole-5,3'-indol]-2'(1'H)-one

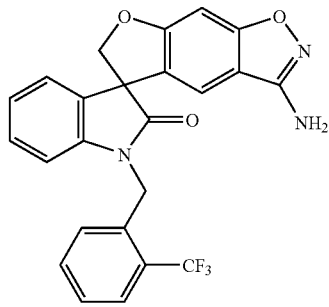

Following the procedure as described in EXAMPLE 44.2 and making non-critical variations using 6-fluoro-2'-oxo-1'-[2-(trifluoromethyl)benzyl]-1',2'-dihydrospiro[1-benzofuran-3,3'-indole]-5-carbonitrile to replace 6-fluoro-2'-oxo-1'-[(2R)-tetrahydrofuran-2-ylmethyl]-1',2'-dihydrospiro[1- benzofuran-3,3'-indole]-5-carbonitrile, 3-amino-1'-[2-(trifluoromethyl)benzyl]spiro[furo[3,2-f][1,2]benzisoxazole-5,3'-indol]-2'(1'H)-one was obtained (62%): mp 262-264° C. (ethyl acetate); $^1$H NMR (300 MHz, DMSO-d$_6$+CDCl$_3$) δ 7.68-7.65 (m, 1H), 7.56-7.51 (m, 1H), 7.39-7.34 (m, 1H), 7.25 (s, 1H), 7.18-7.13 (m, 3H), 7.02-6.97 (m, 1H), 6.76 (s, 1H), 6.61-6.58 (m, 1H), 5.62 (s, 2H), 5.19-4.79 (m, 4H); MS (ES+) m/z 452.1 (M+1).

EXAMPLE 45

Synthesis of 6-hydroxy-2'-oxo-1'-[(2R)-tetrahydrofuran-2-ylmethyl]-1',2'-dihydrospiro[1-benzofuran-3,3'-indole]-5-carbonitrile

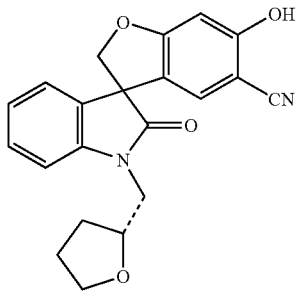

To a stirred solution of concentrated sulfuric acid (2.5 mL) in water (1.5 mL) was added sodium nitrite (0.10 g, 1.5 mmol) in small portions at 0° C., followed by hypophosphorous acid (0.50 mL, 4.6 mmol) and a solution of 3-amino-t-[(2R)-tetrahydrofuran-2-ylmethyl]spiro[furo[3,2-f][1,2]benzisoxazole-5,3'-indol]-2'(1'H)-one (0.17 g, 0.45 mmol) in glacial acetic acid (2 mL) and ethanol (5 mL). The reaction mixture was stirred at 0° C. for 6 h and at ambient temperature for 18 h, diluted with ethyl acetate, washed with water and brine, dried over anhydrous sodium sulfate and filtered. The filtrate was concentrated in vacuo. The residue was subjected to column chromatography and eluted with ethyl acetate/hexanes (1/1) to afford 6-hydroxy-2'-oxo-1'-[(2R)-tetrahydrofuran-2-ylmethyl]-1',2'-dihydrospiro[1-benzofuran-3,3'-indole]-5-carbonitrile (0.09 g, 57%): mp 218-221° C. (ethyl acetate/hexanes); $^1$H NMR (300 MHz, DMSO-d$_6$) δ 11.27 (s, 1H), 7.32-7.27 (m, 1H), 7.19-7.14 (m, 2H), 7.03-6.98 (m, 1H), 6.86 (d, J=6.0 Hz, 1H), 4.86-4.75 (m, 2H), 4.17-4.11 (m, 1H), 3.80-3.54 (m, 4H), 1.97-1.53 (m, 4H); $^{13}$C NMR (75 MHz, DMSO-d$_6$) δ 176.8, 165.5, 163.2, 143.4, 131.6, 129.4, 128.1, 123.9, 122.4, 122.3, 117.4, 110.3, 98.1, 92.0, 81.0, 76.1, 67.6, 56.4, 29.1, 25.5; MS (ES+) m/z 363.0 (M+1).

EXAMPLE 45.1

Synthesis of 6-hydroxy-2'-oxo-1'-[2-(trifluoromethyl)benzyl]-1',2'-dihydrospiro[1-benzofuran-3,3'-indole]-5-carbonitrile

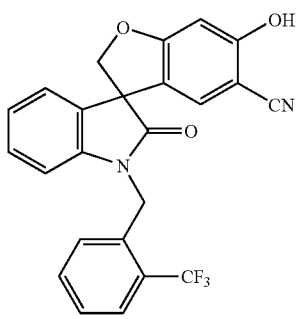

Following the procedure as described in EXAMPLE 45 and making non-critical variations using 3-amino-1'-[2-(trifluoromethyl)benzyl]spiro[furo[3,2-f][1,2]benzisoxazole-5,3'-indol]-2'(1'H)-one to replace 3-amino-1'-[(2R)-tetrahydrofuran-2-ylmethyl]spiro[furo[3,2-f][1,2]benzisoxazole-5,3'-indol]-2'(1'H)-one, 6-hydroxy-2'-oxo-1'-[2-(trifluoromethyl)benzyl]-1',2'-dihydrospiro[1-benzofuran-3,3'-indole]-5-carbonitrile was obtained (38%): mp 122-124° C. (ethyl acetate); $^1$H NMR (300 MHz, DMSO-d$_6$) δ 11.30 (s, 1H), 7.81-7.78 (m, 1H), 7.62-7.47 (m, 2H), 7.30-7.23 (m, 3H), 7.18 (s, 1H), 7.08-7.03 (m, 1H), 6.73-6.70 (m, 1H), 6.53 (s, 1H), 5.11-4.83 (m, 4H); $^{13}$C NMR (75 MHz, DMSO-d$_6$) δ 178.8, 165.7, 162.1, 141.6, 132.9, 132.7, 131.0, 129.8, 128.1, 127.7, 126.7, 124.7, 124.1, 120.9, 116.7, 110.0, 99.0, 93.2, 81.1, 57.2, 41.0; MS (ES−) m/z 435.1 (M−1).

EXAMPLE 46

Synthesis of 1'-[2-(trifluoromethyl)benzyl]-1H-spiro[furo[3,2-f]indazole-5,3'-indol]-2'(1'H)-one

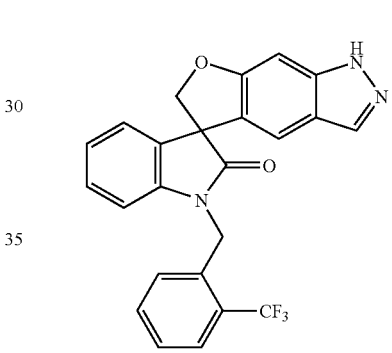

To a stirred solution of 6-fluoro-2'-oxo-1'-[2-((trifluoromethyl)benzyl]-1',2'-dihydrospiro[1-benzofuran-3,3'-indole]-5-carbonitrile (0.44 g, 1.0 mmol) in 1,2-dimethoxyethane (20 mL) was added hydrazine monohydrate (1.0 mL, 21 mmol). The reaction mixture was stirred at reflux for 19 h and concentrated in vacuo. The residue was dissolved in ethanol (20 mL) and isoamyl nitrite (1.50 mL, 10.7 mmol), and hypophosphorous acid (2.0 mL, 18 mmol) was added. The reaction mixture was allowed to stir at ambient temperature for 18 h, neutralized with saturated aqueous sodium bicarbonate and extracted with ethyl acetate (3×100 mL). The combined organic extracts was dried over anhydrous sodium sulfate and filtered. The filtrate was concentrated in vacuo. The residue was subjected to column chromatography and eluted with ethyl acetate/hexanes (1/1) to afford 1'-[2-(trifluoromethyl)benzyl]-1H-spiro[furo[3,2-f]indazole-5,3'-indol]-2'(1'H)-one (0.04 g, 10%): mp 124-126° C. (ethyl acetate/hexanes); $^1$H NMR (300 MHz, DMSO-d$_6$) δ 12.83 (s, 1H), 7.83-7.0 (m, 2H), 7.67-7.63 (m, 1H), 7.54-7.49 (m, 1H), 7.27-7.18 (m, 4H), 7.08-7.03 (m, 1H), 6.95-6.94 (m, 1H), 6.81-6.77 (m, 1H), 5.07-4.83 (m, 4H); MS (ES−) m/z 436.2 (M−1).

EXAMPLE 46.1

Synthesis of 1'-(pyridin-2-ylmethyl)-1H-spiro[furo[3,2-f]indazole-5,3'-indol]-2'(1'H)-one

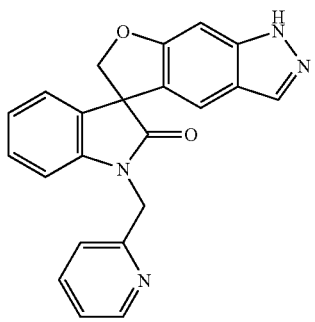

Following the procedure as described in EXAMPLE 46 and making non-critical variations using 6-fluoro-2'-oxo-1'-(pyridin-2-ylmethyl)-1',2'-dihydrospiro[1-benzofuran-3,3'-indole]-5-carbonitrile to replace 6-fluoro-2'-oxo-1'-[2-(trifluoromethyl)benzyl]-1',2'-dihydrospiro[1-benzofuran-3,3'-indole]-5-carbonitrile, 1'-(pyridin-2-ylmethyl)-1H-spiro[furo[3,2-f]indazole-5,3'-indol]-2'(1'H)-one was obtained (33%): mp 117-119° C. (ethyl acetate/hexanes); $^1$H NMR (300 MHz, CDCl$_3$) δ 10.21 (br s, 1H), 8.60-7.59 (m, 1H), 7.79 (s, 1H), 7.70-7.65 (m, 1H), 7.31-6.89 (m, 7H), 5.24-4.77 (m, 4H); $^{13}$C NMR (75 MHz, CDCl$_3$) δ 177.5, 160.7, 155.4, 149.6, 142.3, 141.7, 137.1, 134.9, 132.3, 129.0, 126.3, 123.7, 123.6, 122.8, 121.7, 119.1, 115.6, 109.7, 89.6, 80.6, 57.3, 46.1; MS (ES+) m/z 369.2 (M+1).

EXAMPLE 46.2

Synthesis of 1'-((3-(trifluoromethyl)pyridin-2-yl)methyl)-1,6-dihydrospiro[furo[3,2-f]indazole-5,3'-indolin]-2'-one

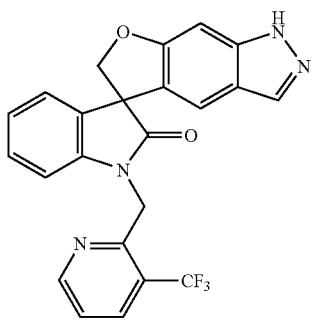

Following the procedure as described in EXAMPLE 46 and making non-critical variations using 6-fluoro-2'-oxo-1'-{[3-(trifluoromethyl)pyridin-2-yl]methyl}-1',2'-dihydrospiro[1-benzofuran-3,3'-indole]-5-carbonitrile to replace 6-fluoro-2'-oxo-1'-[2-(trifluoromethyl)benzyl]-1',2'-dihydrospiro[1-benzofuran-3,3'-indole]-5-carbonitrile, 1'-((3-(trifluoromethyl)pyridin-2-yl)methyl)-1,6-dihydrospiro[furo[3,2-f]indazole-5,3'-indolin]-2'-one was obtained (47%): mp 152-154° C. (ethyl acetate/hexanes); $^1$H NMR (300 MHz, DMSO-d$_6$) δ 12.79 (br s, 1H), 8.80 (d, J=6.0 Hz, 1H), 8.24-8.21 (m, 1H), 7.87 (s, 1H), 7.57-7.53 (m, 1H), 7.26-7.17 (m, 3H), 7.02-6.89 (m, 3H), 5.25 (ABq, 2H), 4.87 (ABq, 2H); $^{13}$C NMR (75 MHz, DMSO-d$_6$) δ 172.5, 160.1, 153.2, 152.9, 143.5, 141.6, 135.5, 135.4, 134.1, 132.7, 129.1, 126.7, 124.0, 123.6, 123.2, 122.5, 119.1, 116.0, 109.5, 89.4, 80.0, 56.9, 42.4; MS (ES+) m/z 436.9 (M+1).

BIOLOGICAL ASSAYS

Various techniques are known in the art for testing the activity of the compound of the invention or determining their solubility in known pharmaceutically acceptable excipients. In order that the invention described herein may be more fully understood, the following biological assays are set forth. It should be understood that these examples are for illustrative purposes only and are not to be construed as limiting this invention in any manner.

Biological Example 1

Guanidine Influx Assay (In Vitro Assay)

This example describes an in vitro assay for testing and profiling test agents against human or rat sodium channels stably expressed in cells of either an endogenous or recombinant origin. The assay is also useful for determining the IC$_{50}$ of a sodium channel blocking compound. The assay is based on the guanidine flux assay described by Reddy, N. L., et al., *J. Med. Chem.* (1998), 41(17):3298-302.

The guanidine influx assay is a radiotracer flux assay used to determine ion flux activity of sodium channels in a high-throughput microplate-based format. The assay uses $^{14}$C-guanidine hydrochloride in combination with various known sodium channel modulators, to assay the potency of test agents. Potency is determined by an IC$_{50}$ calculation. Selectivity is determined by comparing potency of the compound for the channel of interest to its potency against other sodium channels (also called 'selectivity profiling').

Each of the test agents is assayed against cells that express the channels of interest. Voltage gated sodium channels are either TTX sensitive or insensitive. This property is useful when evaluating the activities of a channel of interest when it resides in a mixed population with other sodium channels. The following Table 1 summarizes cell lines useful in screening for a certain channel activity in the presence or absence of TTX.

TABLE 1

| CELL LINE | mRNA Expression | Functional Characterization |
|---|---|---|
| CHO-K1 (Chinese Hamster Ovary; recommended host cell line) ATTC accession number CCL-61 | Na$_v$1.4 expression has been shown by RT-PCR No other Na$_v$ expression has been detected | The 18- to 20-fold increase in [$^{14}$C] guanidine influx was completely blocked using TTX. (Na$_v$1.4 is a TTX sensitive channel) |

TABLE 1-continued

| CELL LINE | mRNA Expression | Functional Characterization |
|---|---|---|
| L6 (rat myoblast cell) ATTC Number CRL-1458 | Expression of $Na_v1.4$ and 1.5 | The 10- to 15-fold increase in [$^{14}$C] guanidine influx was only partially blocked by TTX at 100 nM ($Na_v1.5$ is TTX resistant) |
| SH-SY5Y (Human neuroblastoma) ATTC Number CRL-2266 | Published Expression of $Na_v1.9$ and $Na_v1.7$ (Blum et al.) | The 10- to 16-fold increase in [$^{14}$C] guanidine influx above background was partially blocked by TTX ($Na_v1.9$ is TTX resistant) |
| SK-N-BE2C (a human neuroblastoma cell line ATCC Number CRL-2268) | Expression of $Na_v1.8$ | Stimulation of BE2C cells with pyrethroids results in a 6-fold increase in [$^{14}$C] guanidine influx above background. TTX partially blocked influx ($Na_v1.8$ is TTX resistant) |
| PC12 (rat pheochromocytoma) ATTC Number CRL-1721 | Expression of $Na_v1.2$ expression | The 8- to 12-fold increase in [$^{14}$C] guanidine influx was completely blocked using TTX. ($Na_v1.2$ is a TTX sensitive channel) |

It is also possible to employ recombinant cells expressing these sodium channels. Cloning and propagation of recombinant cells are known to those skilled in the art (see, for example, Klugbauer, N, et al., *EMBO J.* (1995), 14(6):1084-90; and Lossin, C., et al., *Neuron* (2002), 34, pp. 877-884).

Cells expressing the channel of interest are grown according to the supplier or in the case of a recombinant cell in the presence of selective growth media such as G418 (Gibco/Invitrogen). The cells are disassociated from the culture dishes with an enzymatic solution (Ix) Trypsin/EDTA (Gibco/Invitrogen) and analyzed for density and viability using haemocytometer (Neubauer). Disassociated cells are washed and resuspended in their culture media then plated into Scintiplates (Beckman Coulter Inc.) (approximately 100,000 cells/well) and incubated at 37° C./5% $CO_2$ for 20-24 hours. After an extensive wash with Low sodium HEPES-buffered saline solution (LNHBSS) (150 mM Choline Chloride, 20 nM HEPES (Sigma), 1 mM Calcium Chloride, 5 mM Potassium Chloride, 1 mM Magnesium Chloride, 10 mM Glucose) agents diluted with LNHBSS are added to each well. (Varying concentrations of test agent may be used). The activation/radiolabel mixture contains aconitine (Sigma) to increase the percentage of time that the sodium channels are open, and $^{14}$C-guanidine hydrochloride (ARC) to measure flux through the voltage-gated sodium channels.

After loading the cells with test agent and activation/radiolabel mixture, the Scintiplates are incubated at ambient temperature. Following the incubation, the Scintplates are extensively washed with LNHBSS supplemented with guanidine (Sigma). The Scintiplates are dried and then counted using a Wallac MicroBeta TriLux (Perkin-Elmer Life Sciences). The ability of the test agent to block sodium channel activity is determined by comparing the amount of $^{14}$C-guanidine present inside the cells expressing the different sodium channels. Based on this data, a variety of calculations, as set out elsewhere in this specification, may be used to determine whether a test agent is selective for a particular sodium channel.

The $IC_{50}$ value of a test agent for a specific sodium channel may be determined using the above general method. The $IC_{50}$ may be determined using a 3, 8, 10, 12 or 16 point curve in duplicate or triplicate with a starting concentration of 1, 5 or 10 μM diluted serially with a final concentration reaching the sub-nanomolar, nanomolar and low micromolar ranges. Typically the mid-point concentration of test agent is set at 1 μM, and sequential concentrations of half dilutions greater or smaller are applied (e.g. 0.5 μM; 5 μM and 0.25 μM; 10 μM and 0.125 μM; 20 μM etc.). The $IC_{50}$ curve is calculated using the 4 Parameter Logistic Model or Sigmoidal Dose-Response Model formula (fit=(A+((B−A)/(1+((C/x)^D)))).

The fold selectivity, factor of selectivity or multiple of selectivity, is calculated by dividing the $IC_{50}$ value of the test sodium channel by the reference sodium channel, for example, $Na_v1.5$.

Representative compounds of the invention, when tested in the above assay using a known cell line that expresses a sodium channel, demonstrated an $IC_{50}$ (nM) activity level as set forth below in Table 2 wherein "A" refers to an $IC_{50}$ activity level of from 1 nM to 100 nM, "B" refers to an $IC_{50}$ activity level from 100 nM to 1 μM, "C" refers to an $IC_{50}$ activity level from 1 μM to 10 μM, and "D" refers to an $IC_{50}$ activity level equal to or greater than 10 μM. The Example numbers provided in Table 2 correspond to the Examples herein:

TABLE 2

| Ex. No. | Compound Name | $IC_{50}$ |
|---|---|---|
| 1 | 2-methylspiro[furo[2 3-f][1,3]benzothiazole-7,3'-indol]-2'(1'H)-one | C |
| 1.1 | 1'-[(6-methylpyridin-2-yl)methyl]-2,3-dihydrospiro[furo[2,3-g][1,4]benzodioxine-8,3'-indol]-2'(1'H)-one | A |
| 1.2 | 1'-(pyridin-3-ylmethyl)-2,3-dihydrospiro[furo[2,3-g][1,4]benzodioxine-8,3'-indol]-2'(1'H)-one | A |
| 1.3 | 1'-{[2,5-dimethyl-1-(1-methylethyl)-1H-pyrrol-3-yl]methyl}spiro[furo[2,3-f][1,3]benzodioxole-7,3'-indol]-2'(1'H)-one | A |
| 1.4 | 5-(benzyloxy)-1'-[(5-chloro-2-thienyl)methyl]spiro[1-benzofuran-3,3'-indol]-2'(1'H)-one | C |
| 1.5 | 7'-bromospiro[furo[2,3-f][1,3]benzodioxole-7,3'-indol]-2'(1'H)-one | A |
| 1.6 | 1'-[(3-isopropylisoxazol-5-yl)methyl]spiro[furo[2,3-f][1,3]benzodioxole-7,3'-indol]-2'(1'H)-one | A |

TABLE 2-continued

| Ex. No. | Compound Name | IC$_{50}$ |
|---|---|---|
| 1.7 | 1'-[(4-bromo-2-thienyl)methyl]spiro[furo[2,3-f][1,3]benzodioxole-7,3'-indol]-2'(1'H)-one | A |
| 1.9 | 1'-{[2-methyl-5-(trifluoromethyl)-1,3-oxazol-4-yl]methyl}spiro[furo[2,3-f][1,3]benzodioxole-7,3'-indol]-2'(1'H)-one | A |
| 1.10 | (3R)-5,6-dihydrospiro[benzo[1,2-b:5,4-b']difuran-3,3'-indol]-2'(1'H)-one | C |
| 1.10 | (3S)-5,6-dihydrospiro[benzo[1,2-b:5,4-b']difuran-3,3'-indol]-2'(1'H)-one | A |
| 1.11 | (R)-3,7-dihydro-2H-spiro[benzofuro[5,6-b][1,4]dioxine-8,3'-indolin]-2'-one | C |
| 1.11 | (S)-2,3-dihydrospiro[furo[2,3-g][1,4]benzodioxine-8,3'-indol]-2'(1'H)-one | A |
| 1.12 | (8S)-1'-{[3-(trifluoromethyl)pyridin-2-yl]methyl}-2,3-dihydrospiro[furo[2,3-g][1,4]benzodioxine-8,3'-indol]-2'(1'H)-one | A |
| 1.13 | (8S)-1'-[(5-hydroxypyridin-2-yl)methyl]-2,3-dihydrospiro[furo[2,3-g][1,4]benzodioxine-8,3'-indol]-2'(1'H)-one | B |
| 1.14 | 1'-[(5-bromopyridin-2-yl)methyl]-2,3-dihydrospiro[furo[2,3-g][1,4]benzodioxine-8,3'-indol]-2'(1'H)-one | A |
| 1.15 | 1'-{[5-(4-chlorophenyl)-2-(trifluoromethyl)furan-3-yl]methyl}spiro[furo[2,3-f][1,3]benzodioxole-7,3'-indol]-2'(1'H)-one | C |
| 1.16 | 1'-{[5-chloro-1-methyl-3-(trifluoromethyl)-1H-pyrazol-4-yl]methyl}spiro[furo[2,3-f][1,3]benzodioxole-7,3'-indol]-2'(1'H)-one | A |
| 1.17 | 1'-(5-methoxypyridin-3-yl)spiro[furo[2,3-f][1,3]benzodioxole-7,3'-indol]-2'(1'H)-one | B |
| 2.3 | 1'-(diphenylmethyl)-5,6-dimethylspiro[1-benzofuran-3,3'-indol]-2'(1'H)-one | C |
| 2.6 | 1'-(4-methoxybenzyl)-3-methylspiro[furo[3,2-f][1,2]benzisoxazole-5,3'-indol]-2'(1'H)-one | A |
| 2.9 | 1'-(diphenylmethyl)-5-fluorospiro[1-benzofuran-3,3'-indol]-2'(1'H)-one | C |
| 2.11 | 1'-(diphenylmethyl)-2,3-dihydrospiro[furo[2,3-g][1,4]benzodioxine-8,3'-indol]-2'(1'H)-one | C |
| 2.14 | 1'-(diphenylmethyl)-2-methylspiro[furo[2,3-f][1,3]benzoxazole-7,3'-indol]-2'(1'H)-one | D |
| 2.16 | 1'-(diphenylmethyl)-3-methylspiro[furo[2,3-f][1,3]benzoxazole-7,3'-indole]-2,2'(1'H,3H)-dione | D |
| 2.22 | 6-bromo-1'-((5-(trifluoromethyl)furan-2-yl)methyl)-2H-spiro[benzofuran-3,3'-indolin]-2'-one | C |
| 2.23 | 5-bromo-1'-((5-(trifluoromethyl)furan-2-yl)methyl)-2H-spiro[benzofuran-3,3'-indolin]-2'-one | B |
| 2.24 | 6'-isopentyl-3,7-dihydro-2H-spiro[benzofuro[5,6-b][1,4]dioxine-8,8'-thiazolo[5,4-e]indol]-7'(6'H)-one | A |
| 2.25 | 6-((5-(trifluoromethyl)furan-2-yl)methyl)-2,3,5',6'-tetrahydro-2'H-spiro[[1,4]dioxino[2,3-f]indole-8,3'-benzofuro[6,5-b]furan]-7(6H)-one | B |
| 2.26 | 6-(((R)-tetrahydrofuran-2-yl)methyl)-2,3,5',6'-tetrahydro-2'H-spiro[[1,4]dioxino[2,3-f]indole-8,3'-benzofuro[6,5-b]furan]-7(6H)-one | C |
| 2.27 | 6-((5-(trifluoromethyl)furan-2-yl)methyl)-2,3,3',7'-tetrahydro-2'H-spiro[[1,4]dioxino[2,3-f]indole-8,8'-benzofuro[5,6-b][1,4]dioxin]-7(6H)-one | B |
| 2.28 | 1-methyl-1'-{[5-(trifluoromethyl)furan-2-yl]methyl}-2,3-dihydro-1H-spiro[furo[3,2-g][1,4]benzoxazine-8,3'-indol]-2'(1'H)-one hydrochloride | B |
| 2.29 | 1-methyl-1'-[(2R)-tetrahydrofuran-2-ylmethyl]-2,3-dihydro-1H-spiro[furo[3,2-g][1,4]benzoxazine-8,3'-indol]-2'(1'H)-one hydrochloride | B |
| 2.30 | 4-methyl-1'-[(2R)-tetrahydrofuran-2-ylmethyl]-3,4-dihydro-2H-spiro[furo[2,3-g][1,4]benzoxazine-8,3'-indol]-2'(1'H)-one | C |
| 2.31 | 1'-[(2R)-tetrahydrofuran-2-ylmethyl]-4H-spiro[furo[3,2-g][1,3]benzodioxine-6,3'-indol]-2'(1'H)-one | C |
| 2.34 | 2,2-difluoro-1'-{[5-(trifluoromethyl)furan-2-yl]methyl}spiro[furo[2,3-f][1,3]benzodioxole-7,3'-indol]-2'(1'H)-one | B |
| 2.35 | 2,2-difluoro-1'-{[5-(trifluoromethyl)furan-2-yl]methyl}spiro[furo[2,3-f][1,3]benzodioxole-7,3'-indol]-2'(1'H)-one | C |
| 2.36 | 2,2-difluoro-1'-{[3-(trifluoromethyl)pyridin-2-yl]methyl}spiro[furo[2,3-f][1,3]benzodioxole-7,3'-indol]-2'(1'H)-one | C |
| 2.38 | 3'-(4-methoxybenzyl)-5,6-dihydrospiro[benzo[1,2-b:5,4-b']difuran-3,1'-pyrrolo[3,2-f]quinolin]-2'(3'H)-one | B |

TABLE 2-continued

| Ex. No. | Compound Name | IC$_{50}$ |
|---|---|---|
| 2.39 | 6-hydroxy-1'-(4-methoxybenzyl)-2'-oxo-1',2'-dihydrospiro[1-benzofuran-3,3'-indole]-5-carbonitrile | C |
| 2.40 | 6-fluoro-1'-(4-methoxybenzyl)-2'-oxo-1',2'-dihydrospiro[1-benzofuran-3,3'-indole]-5-carbonitrile | C |
| 2.41 | 1'-(4-methoxybenzyl)-3-methylspiro[furo[2,3-f][1,2]benzisoxazole-7,3'-indol]-2'(1'H)-one | C |
| 2.44 | 1'-(diphenylmethyl)-4'-fluoro-2,3-dihydrospiro[furo[2,3-g][1,4]benzodioxine-8,3'-indol]-2'(1'H)-one | B |
| 2.45 | 1'-(4-fluorophenyl)-2,3-dihydrospiro[furo[2,3-g][1,4]benzodioxine-8,3'-indol]-2'(1'H)-one | A |
| 2.49 | 5'-bromo-1'-(pyridin-2-ylmethyl)-2,3-dihydrospiro[furo[2,3-g][1,4]benzodioxine-8,3'-indol]-2'(1'H)-one | A |
| 2.50 | 2'-oxo-1'-(pyridin-2-ylmethyl)-1',2,2',3-tetrahydrospiro[furo[2,3-g][1,4]benzodioxine-8,3'-indole]-5'-carbonitrile | A |
| 2.61 | 1'-(diphenylmethyl)-5,6-difluorospiro[1-benzofuran-3,3'-indol]-2'(1'H)-one | D |
| 2.63 | 4',5'-dimethoxy-1'-{[5-(trifluoromethyl)furan-2-yl]methyl}-2,3-dihydrospiro[furo[2,3-g][1,4]benzodioxine-8,3'-indol]-2'(1'H)-one | B |
| 2.64 | 4',7'-dimethoxy-1'-[2-(2-methoxyethoxy)ethyl]-2,3-dihydrospiro[furo[2,3-g][1,4]benzodioxine-8,3'-indol]-2'(1'H)-one | B |
| 2.65 | 6-[2-(2-methoxyethoxy)ethyl]-2,2',3,3'-tetrahydrospiro[1,4-dioxino[2,3-f]indole-8,8'-furo[2,3-g][1,4]benzodioxin]-7(6H)-one | C |
| 2.66 | 6'-(4-methoxybenzyl)-2,3-dihydrospiro[furo[2,3-g][1,4]benzodioxine-8,8'-[1,3]thiazolo[5,4-e]indol]-7'(6'H)-one | B |
| 3 | 6-methoxy-5-methylspiro[1-benzofuran-3,3'-indol]-2'(1'H)-one | C |
| 3.1 | 4'-chloro-5,6-dihydrospiro[benzo[1,2-b:5,4-b']difuran-3,3'-indol]-2'(1'H)-one | A |
| 3.2 | 6-bromospiro[1-benzofuran-3,3'-indol]-2'(1'H)-one | C |
| 3.3 | 5,6-dimethylspiro[1-benzofuran-3,3'-indol]-2'(1'H)-one | B |
| 3.4 | 5'-fluoro-5,6-dihydrospiro[benzo[1,2-b:5,4-b']difuran-3,3'-indol]-2'(1'H)-one | C |
| 3.5 | 6'-fluoro-5,6-dihydrospiro[benzo[1,2-b:5,4-b']difuran-3,3'-indol]-2'(1H)-one | C |
| 3.6 | 3-methylspiro[furo[3,2-f][1,2]benzisoxazole-5,3'-indol]-2'(1'H)-one | B |
| 3.7 | 5-fluoro-6-methoxyspiro[1-benzofuran-3,3'-indol]-2'(1'H)-one | C |
| 3.8 | 5-fluoro-spiro[1-benzofuran-3,3'-indol]-2'(1'H)-one | C |
| 3.10 | 2,3-dihydrospiro[furo[2,3-g][1,4]benzodioxine-8,3'-indol]-2'(1'H)-one | A |
| 3.11 | 3,4-dihydro-2H-spiro[furo[2,3-h][1,5]benzodioxepine-9,3'-indol]-2'(1'H)-one | C |
| 3.12 | 2-methylspiro[furo[2,3-f][1,3]benzoxazole-7,3'-indol]-2'(1'H)-one | D |
| 3.13 | 3-methylspiro[furo[2,3-f][1,3]benzoxazole-7,3'-indole]-2,2'(1'H,3H)-dione | C |
| 3.14 | 1-methylspiro[furo[3,2-f][1,3]benzoxazole-7,3'-indole]-2,2'(1H,1'H)-dione | C |
| 3.15 | 7'-chloro-5,6-dihydrospiro[benzo[1,2-b:5,4-b']difuran-3,3'-indol]-2'(1'H)-one | B |
| 3.16 | 7'-fluoro-5,6-dihydrospiro[benzo[1,2-b:5,4-b']difuran-3,3'-indol]-2'(1'H)-one | B |
| 3.17 | 4'-fluoro-7'-methyl-5,6-dihydrospiro[benzo[1,2-b:5,4-b']difuran-3,3'-indol]-2'(1'H)-one | B |
| 3.21 | 6,7-dihydro-5H-spiro[furo[3,2-g]chromene-3,3'-indol]-2'(1'H)-one | B |
| 3.22 | 1-methyl-1H-spiro[furo[3,2-g][1,4]benzoxazine-8,3'-indole]-2,2'(1'H,3H)-dione | C |
| 3.23 | 4-methyl-4,7-dihydrospiro[benzofuro[5,6-b][1,4]oxazine-8,3'-indoline]-2',3(2H)-dione | C |
| 3.24 | 2,3,6,7-tetrahydrospiro[furo[3,2-g]chromene-5,3'-indol]-2'(1'H)-one | C |
| 3.25 | (3S)-6-methoxy-5-methylspiro[1-benzofuran-3,3'-indol]-2'(1'H)-one | C |
| 3.26 | (3R)-6-methoxy-5-methylspiro[1-benzofuran-3,3'-indol]-2'(1'H)-one | C |
| 3.28 | 2',3',5,6-tetrahydrospiro[benzo[1,2-b:5,4-b']difuran-3,8'-[1,4]dioxino[2,3-f]indol]-7'(6'H)-one | C |
| 3.29 | 6-methoxy-2'-oxo-1',2'-dihydrospiro[1-benzofuran-3,3'-indole]-5-carbonitrile | C |
| 3.30 | 6-fluoro-2'-oxo-1',2'-dihydrospiro[1-benzofuran-3,3'-indole]-5-carbonitrile | C |

TABLE 2-continued

| Ex. No. | Compound Name | IC$_{50}$ |
|---|---|---|
| 3.32 | 4'-bromo-2,3-dihydrospiro[furo[2,3-g][1,4]benzodioxine-8,3'-indol]-2'(1'H)-one | B |
| 3.33 | 4'-fluoro-2,3-dihydrospiro[furo[2,3-g][1,4]benzodioxine-8,3'-indol]-2'(1'H)-one | A |
| 3.34 | 4'-quinolin-3-yl-2,3-dihydrospiro[furo[2,3-g][1,4]benzodioxine-8,3'-indol]-2'(1'H)-one | B |
| 3.35 | 4'-(4-phenoxyphenyl)-2,3-dihydrospiro[furo[2,3-g][1,4]benzodioxine-8,3'-indol]-2'(1'H)-one | B |
| 3.40 | spiro[indole-3,3'-thieno[2,3-f][1]benzofuran]-2(1H)-one 5,5'-dioxide | C |
| 3.41 | spiro[furo[3,2-e][2,1,3]benzoxadiazole-8,3'-indol]-2'(1'H)-one | C |
| 3.42 | 6-chloro-2,3-dihydrospiro[furo[3,2-f][1,4]benzodioxine-9,3'-indol]-2'(1'H)-one | C |
| 3.44 | 5,6-difluorospiro[1-benzofuran-3,3'-indol]-2'(1'H)-one | C |
| 3.45 | 5',6',7',8'-tetrahydrospiro[indole-3,3'-naphtho[2,3-b]furan]-2(1H)-one | C |
| 3.46 | 6-(2-methoxyethoxy)spiro[1-benzofuran-3,3'-indol]-2'(1'H)-one | C |
| 3.47 | 5-(2-methoxyethoxy)spiro[1-benzofuran-3,3'-indol]-2'(1'H)-one | C |
| 3.48 | 2,3-dihydrospiro[furo[2,3-f][1,4]benzodioxine-7,3'-indol]-2'(1'H)-one | C |
| 3.49 | 2,3-dihydrospiro[furo[2,3-g][1,4]benzodioxine-8,8'-[1,3]thiazolo[5,4-e]indol]-7'(6'H)-one | C |
| 3.50 | 4',6'-dimethoxy-2,3-dihydrospiro[furo[2,3-g][1,4]benzodioxine-8,3'-indol]-2'(1'H)-one | C |
| 3.51 | spiro[furo[2,3-g]quinoxaline-8,3'-indol]-2'(1'H)-one | C |
| 4 | 1'-(tetrahydro-2H-pyran-2-ylmethyl)-5,6-dihydrospiro[benzo[1,2-b:5,4-b']difuran-3,3'-indol]-2'(1'H)-one | A |
| 4.2 | 1'-[(2-chloro-1-methyl-1H-imidazol-5-yl)methyl]-5,6-dihydrospiro[benzo[1,2-b:5,4-b']difuran-3,3'-indol]-2'(1'H)-one | A |
| 4.3 | 1'-[(2R)-tetrahydrofuran-2-ylmethyl]-5,6-dihydrospiro[benzo[1,2-b:5,4-b']difuran-3,3'-indol]-2'(1'H)-one | A |
| 4.4 | 1'-(3-methylbutyl)-5,6-dihydrospiro[benzo[1,2-b:5,4-b']difuran-3,3'-indol]-2'(1'H)-one | A |
| 4.5 | 1'-[(2S)-tetrahydrofuran-2-ylmethyl]-5,6-dihydrospiro[benzo[1,2-b:5,4-b']difuran-3,3'-indol]-2'(1'H)-one | A |
| 4.6 | 1'-(tetrahydro-2H-pyran-4-ylmethyl)-5,6-dihydrospiro[benzo[1,2-b:5,4-b']difuran-3,3'-indol]-2'(1'H)-one | B |
| 4.7 | methyl 5-[(2'-oxo-5,6-dihydrospiro[benzo[1,2-b:5,4-b']difuran-3,3'-indol]-1'(2'H)-yl)methyl]furan-2-carboxylate | A |
| 4.8 | 1'-(1,4-dioxan-2-ylmethyl)-5,6-dihydrospiro[benzo[1,2-b:5,4-b']difuran-3,3'-indol]-2'(1'H)-one | A |
| 4.9 | 1'-{[1-methyl-3-(trifluoromethyl)-1H-pyrazol-4-yl]methyl}-5,6-dihydrospiro[benzo[1,2-b:5,4-b']difuran-3,3'-indol]-2'(1'H)-one | B |
| 4.10 | 1'-(tetrahydro-2H-pyran-3-ylmethyl)-5,6-dihydrospiro[benzo[1,2-b:5,4-b']difuran-3,3'-indol]-2'(1'H)-one | A |
| 4.11 | methyl 2-[(2'-oxo-5,6-dihydrospiro[benzo[1,2-b:5,4-b']difuran-3,3'-indol]-1'(2'H)-yl)methyl]-1,3-oxazole-4-carboxylate | A |
| 4.12 | 1'-(2-fluorobenzyl)-5,6-dihydrospiro[benzo[1,2-b:5,4-b']difuran-3,3'-indol]-2'(1'H)-one | A |
| 4.13 | 1'-(4-fluorobenzyl)-5,6-dihydrospiro[benzo[1,2-b:5,4-b']difuran-3,3'-indol]-2'(1'H)-one | A |
| 4.14 | 1'-benzyl-5,6-dihydrospiro[benzo[1,2-b:5,4-b']difuran-3,3'-indol]-2'(1'H)-one | A |
| 4.15 | 1'-(biphenyl-4-ylmethyl)-5,6-dihydrospiro[benzo[1,2-b:5,4-b']difuran-3,3'-indol]-2'(1'H)-one | A |
| 4.16 | 1'-(tetrahydrofuran-3-ylmethyl)-5,6-dihydrospiro[benzo[1,2-b:5,4-b']difuran-3,3'-indol]-2'(1'H)-one | B |
| 4.17 | 1'-[(3-bromoisoxazol-5-yl)methyl]-5,6-dihydrospiro[benzo[1,2-b:5,4-b']difuran-3,3'-indol]-2'(1'H)-one | A |
| 4.18 | 1'-[(5-bromofuran-2-yl)methyl]-5,6-dihydrospiro[benzo[1,2-b:5,4-b']difuran-3,3'-indol]-2'(1'H)-one | A |
| 4.20 | 1'-(oxetan-2-ylmethyl)-5,6-dihydrospiro[benzo[1,2-b:5,4-b']difuran-3,3'-indol]-2'(1'H)-one | B |
| 4.21 | 1'-[(1-ethyl-1H-imidazol-5-yl)methyl]-5,6-dihydrospiro[benzo[1,2-b:5,4-b']difuran-3,3'-indol]-2'(1'H)-one | B |

TABLE 2-continued

| Ex. No. | Compound Name | IC$_{50}$ |
|---|---|---|
| 4.22 | 3-[(2'-oxo-5,6-dihydrospiro[benzo[1,2-b:5,4-b']difuran-3,3'-indol]-1'(2'H)-yl)methyl]benzonitrile | A |
| 4.23 | 4-((2'-oxo-5,6-dihydro-2H-spiro[benzofuro[6,5-b]furan-3,3'-indoline]-1'-yl)methyl)benzonitrile | A |
| 4.24 | 4'-[(2'-oxo-5,6-dihydrospiro[benzo[1,2-b:5,4-b']difuran-3,3'-indol]-1'(2'H)-yl)methyl]biphenyl-2-carbonitrile | B |
| 4.25 | 1'-{(2S)-2-[(benzyloxy)methoxy]propyl}-5,6-dihydrospiro[benzo[1,2-b:5,4-b']difuran-3,3'-indol]-2'(1'H)-one | B |
| 4.26 | 1'-(2,3-dihydro-1,4-benzodioxin-6-ylmethyl)-5,6-dihydrospiro[benzo[1,2-b:5,4-b']difuran-3,3'-indol]-2'(1'H)-one | A |
| 4.27 | 1'-(2,1,3-benzoxadiazol-5-ylmethyl)-5,6-dihydrospiro[benzo[1,2-b:5,4-b']difuran-3,3'-indol]-2'(1'H)-one | A |
| 4.28 | 1'-(2,1,3-benzothiadiazol-5-ylmethyl)-5,6-dihydrospiro[benzo[1,2-b:5,4-b']difuran-3,3'-indol]-2'(1'H)-one | A |
| 4.29 | 1'-[(4-benzylmorpholin-2-yl)methyl]-5,6-dihydrospiro[benzo[1,2-b:5,4-b']difuran-3,3'-indol]-2'(1'H)-one | C |
| 4.33 | 4'-chloro-1'-{[5-(trifluoromethyl)furan-2-yl]methyl}-5,6-dihydrospiro[benzo[1,2-b:5,4-b']difuran-3,3'-indol]-2'(1'H)-one | A |
| 4.34 | 4'-chloro-1'-[(2R)-tetrahydrofuran-2-ylmethyl]-5,6-dihydrospiro[benzo[1,2-b:5,4-b']difuran-3,3'-indol]-2'(1'H)-one | A |
| 4.35 | 4'-bromo-1'-[(2R)-tetrahydrofuran-2-ylmethyl]-5,6-dihydrospiro[benzo[1,2-b:5,4-b']difuran-3,3'-indol]-2'(1'H)-one | A |
| 4.36 | 1'-(3-methylbutyl)-2,3-dihydrospiro[furo[2,3-g][1,4]benzodioxine-8,3'-indol]-2'(1'H)-one | A |
| 4.37 | 1'-(tetrahydro-2H-pyran-4-ylmethyl)-2,3-dihydrospiro[furo[2,3-g][1,4]benzodioxine-8,3'-indol]-2'(1'H)-one | A |
| 4.38 | 1'-(tetrahydro-2H-pyran-2-ylmethyl)-2,3-dihydrospiro[furo[2,3-g][1,4]benzodioxine-8,3'-indol]-2'(1'H)-one | A |
| 4.39 | 1'-[(5-chloro-1-methyl-1H-imidazol-2-yl)methyl]-2,3-dihydrospiro[furo[2,3-g][1,4]benzodioxine-8,3'-indol]-2'(1'H)-one | A |
| 4.41 | 1'-(pyridin-2-ylmethyl)-2,3-dihydrospiro[furo[2,3-g][1,4]benzodioxine-8,3'-indol]-2'(1'H)-one | A |
| 4.43 | 1'-[(2S)-tetrahydrofuran-2-ylmethyl]-2,3-dihydrospiro[furo[2,3-g][1,4]benzodioxine-8,3'-indol]-2'(1'H)-one | A |
| 4.44 | 1'-[(2R)-tetrahydrofuran-2-ylmethyl]-2,3-dihydrospiro[furo[2,3-g][1,4]benzodioxine-8,3'-indol]-2'(1'H)-one | A |
| 4.45 | 1'-(1,4-dioxan-2-ylmethyl)-2,3-dihydrospiro[furo[2,3-g][1,4]benzodioxine-8,3'-indol]-2'(1'H)-one | A |
| 4.46 | 1'-(3,4-dimethoxybenzyl)-2,3-dihydrospiro[furo[2,3-g][1,4]benzodioxine-8,3'-indol]-2'(1'H)-one | A |
| 4.47 | 1'-(3,5-dimethoxybenzyl)-2,3-dihydrospiro[furo[2,3-g][1,4]benzodioxine-8,3'-indol]-2'(1'H)-one | A |
| 4.48 | 1'-(2,3-dihydro-1,4-benzodioxin-6-ylmethyl)-2,3-dihydrospiro[furo[2,3-g][1,4]benzodioxine-8,3'-indol]-2'(1'H)-one | A |
| 4.49 | (R)-1'-{[5-(trifluoromethyl)furan-2-yl]methyl}-2,3-dihydrospiro[furo[2,3-g][1,4]benzodioxine-8,3'-indol]-2'(1'H)-one | A |
| 4.50 | (S)-1'-{[5-(trifluoromethyl)furan-2-yl]methyl}-2,3-dihydrospiro[furo[2,3-g][1,4]benzodioxine-8,3'-indol]-2'(1'H)-one | A |
| 4.51 | (S)-1'-(pyridin-2-ylmethyl)-2,3-dihydrospiro[furo[2,3-g][1,4]benzodioxine-8,3'-indol]-2'(1'H)-one | A |
| 4.52 | 1'-(pyridin-2-ylmethyl)-6,7-dihydrospiro[benzo[1,2-b:4,5-b']difuran-3,3'-indol]-2'(1'H)-one | A |
| 4.53 | 1'-[(2R)-tetrahydrofuran-2-ylmethyl]-6,7-dihydro-5H-spiro[furo[3,2-g]chromene-3,3'-indol]-2'(1'H)-one | B |
| 4.54 | 1'-{[5-(trifluoromethyl)furan-2-yl]methyl}-3,4-dihydro-2H-spiro[furo[2,3-h][1,5]benzodioxepine-9,3'-indol]-2'(1'H)-one | B |
| 4.55 | 1'-(pyridin-2-ylmethyl)-3,4-dihydro-2H-spiro[furo[2,3-h][1,5]benzodioxepine-9,3'-indol]-2'(1'H)-one | B |
| 4.56 | 2-methyl-1'-(3-methylbutyl)spiro[furo[2,3-f][1,3]benzothiazole-7,3'-indol]-2'(1'H)-one | C |

TABLE 2-continued

| Ex. No. | Compound Name | IC$_{50}$ |
|---|---|---|
| 4.57 | 2-methyl-1'-(tetrahydro-2H-pyran-4-ylmethyl)spiro[furo[2,3-f][1,3]benzothiazole-7,3'-indol]-2'(1'H)-one | C |
| 4.58 | 2-methyl-1'-[(2R)-tetrahydrofuran-2-ylmethyl]spiro[furo[2,3-f][1,3]benzoxazole-7,3'-indol]-2'(1'H)-one | C |
| 4.59 | 1-methyl-1'-[(2R)-tetrahydrofuran-2-ylmethyl]-1H-spiro[furo[3,2-g][1,4]benzoxazine-8,3'-indole]-2,2'(1'H,3H)-dione | C |
| 4.60 | 1-methyl-1'-[(2R)-tetrahydrofuran-2-ylmethyl]spiro[furo[3,2-f][1,3]benzoxazole-7,3'-indole]-2,2'(1H,1'H)-dione | C |
| 4.61 | 6-methoxy-5-methyl-1'-[(2R)-tetrahydrofuran-2-ylmethyl]spiro[1-benzofuran-3,3'-indol]-2'(1'H)-one | C |
| 4.62 | 6-methoxy-5-methyl-1'-(pyridin-2-ylmethyl)spiro[1-benzofuran-3,3'-indol]-2'(1'H)-one | C |
| 4.63 | 6-methoxy-5-methyl-1'-(tetrahydro-2H-pyran-2-ylmethyl)spiro[1-benzofuran-3,3'-indol]-2'(1'H)-one | C |
| 4.64 | 5-fluoro-6-methoxy-1'-(tetrahydro-2H-pyran-2-ylmethyl)spiro[1-benzofuran-3,3'-indol]-2'(1'H)-one | B |
| 4.65 | 5-fluoro-6-methoxy-1'-(pyridin-2-ylmethyl)spiro[1-benzofuran-3,3'-indol]-2'(1'H)-one | B |
| 4.66 | 5-fluoro-6-methoxy-1'-[(2R)-tetrahydrofuran-2-ylmethyl]spiro[1-benzofuran-3,3'-indol]-2'(1'H)-one | B |
| 4.67 | 1'-benzyl-5-fluoro-6-methoxyspiro[1-benzofuran-3,3'-indol]-2'(1'H)-one | B |
| 4.68 | 6-methoxy-1'-[(2R)-tetrahydrofuran-2-ylmethyl]spiro[1-benzofuran-3,3'-indol]-2'(1'H)-one | B |
| 4.70 | 1'-{[5-(trifluoromethyl)furan-2-yl]methyl}-2,3,6,7-tetrahydrospiro[furo[3,2-g]chromene-5,3'-indol]-2'(1'H)-one | C |
| 4.72 | 1'-{[(2S)-5-oxopyrrolidin-2-yl]methyl}spiro[furo[2,3-f][1,3]benzodioxole-7,3'-indol]-2'(1'H)-one | C |
| 4.73 | (2'-oxospiro[furo[2,3-f][1,3]benzodioxole-7,3'-indol]-1'(2'H)-yl)acetonitrile | A |
| 4.74 | 7'-(trifluoromethyl)-1'-{[5-(trifluoromethyl)-2-furyl]methyl}spiro[furo[2,3-f][1,3]benzodioxole-7,3'-indol]-2'(1'H)-one | B |
| 4.75 | 1'-[(5-chloro-2-thienyl)methyl]-7'-(trifluoromethyl)spiro[furo[2,3-f][1,3]benzodioxole-7,3'-indol]-2'(1'H)-one | B |
| 4.76 | 1'-[(2-isopropyl-1,3-thiazol-5-yl)methyl]-7'-(trifluoromethyl)spiro[furo[2,3-f][1,3]benzodioxole-7,3'-indol]-2'(1'H)-one | B |
| 4.77 | 1'-[(2-isopropyl-1,3-oxazol-5-yl)methyl]spiro[furo[2,3-f][1,3]benzodioxole-7,3'-indol]-2'(1'H)-one | A |
| 4.78 | tert-butyl [1-cyclopropyl-3-(2'-oxospiro[furo[2,3-f][1,3]benzodioxole-7,3'-indol]-1'(2'H)-yl)propyl]carbamate | A |
| 4.79 | 1'-[4-(methylsulfanyl)benzyl]spiro[furo[2,3-f][1,3]benzodioxole-7,3'-indol]-2'(1'H)-one | A |
| 4.80 | 3-(2'-oxospiro[furo[2,3-f][1,3]benzodioxole-7,3'-indol]-1'(2'H)-yl)propanenitrile | A |
| 4.81 | 1'-[(2-bromo-1,3-thiazol-5-yl)methyl]spiro[furo[2,3-f][1,3]benzodioxole-7,3'-indol]-2'(1'H)-one | A |
| 4.82 | 1'-{[2-amino-4-(trifluoromethyl)-1,3-thiazol-5-yl]methyl}spiro[furo[2,3-f][1,3]benzodioxole-7,3'-indol]-2'(1'H)-one | B |
| 4.83 | 6-Fluoro-5-methoxy-1'-{[5-(trifluoromethyl)furan-2-yl]methyl}spiro[1-benzofuran-3,3'-indol]-2'(1'H)-one | C |
| 4.84 | 4'-chloro-2'-oxospiro[furo[2,3-f][1,3]benzodioxole-7,3'-indol]-1'(2'H)-yl)acetonitrile | B |
| 4.85 | 1'-[(2-amino-1,3-thiazol-4-yl)methyl]spiro[furo[2,3-f][1,3]benzodioxole-7,3'-indol]-2'(1'H)-one | B |
| 4.86 | 4'-bromo-1'-[(5-chloro-2-thienyl)methyl]spiro[furo[2,3-f][1,3]benzodioxole-7,3'-indol]-2'(1'H)-one | A |
| 4.87 | 1'-[(5-chloro-2-thienyl)methyl]-2'-oxo-1',2'-dihydrospiro[furo[2,3-f][1,3]benzodioxole-7,3'-indole]-7'-carbonitrile | A |
| 4.88 | 1'-[(2-isopropyl-1,3-thiazol-4-yl)methyl]-2'-oxo-1',2'-dihydrospiro[furo[2,3-f][1,3]benzodioxole-7,3'-indole]-7'-carbonitrile | A |
| 4.89 | 4'-chloro-1'-[(5-chloro-2-thienyl)methyl]spiro[furo[2,3-f][1,3]benzodioxole-7,3'-indol]-2'(1'H) | A |
| 4.90 | 4'-chloro-1'-{[5-(trifluoromethyl)-2-furyl]methyl}spiro[furo[2,3-f][1,3]benzodioxole-7,3'-indol]-2'(1'H)-one | A |
| 4.91 | 4'-chloro-1'-[(2-isopropyl-1,3-thiazol-4-yl)methyl]spiro[furo[2,3-f][1,3]benzodioxole-7,3'-indol]-2'(1'H)-one | A |

TABLE 2-continued

| Ex. No. | Compound Name | IC$_{50}$ |
|---|---|---|
| 4.92 | 4'-[6-(dimethylamino)pyridin-3-yl]-1'-{[2-(1-methylethyl)-1,3-thiazol-4-yl]methyl}spiro[furo[2,3-f][1,3]benzodioxole-7,3'-indol]-2'(1'H)-one | B |
| 4.93 | 3'-[2-(fluoromethyl)benzyl]-2,3-dihydrospiro[furo[2,3-g][1,4]benzodioxine-8,1'-inden]-2'(3'H)-one | A |
| 4.94 | 3-[(2'-oxo-2,3-dihydrospiro[furo[2,3-g][1,4]benzodioxine-8,3'-indol]-1'(2'H)-yl)methyl]benzonitrile | A |
| 4.95 | 1'-(4-fluoro-3-methoxybenzyl)-2,3-dihydrospiro[furo[2,3-g][1,4]benzodioxine-8,3'-indol]-2'(1'H)-one | A |
| 4.96 | 4-[(2'-oxo-2,3-dihydrospiro[furo[2,3-g][1,4]benzodioxine-8,3'-indol]-1'(2'H)-yl)methyl]benzonitrile | A |
| 4.97 | 1'-(4-isoxazol-5-ylbenzyl)-2,3-dihydrospiro[furo[2,3-g][1,4]benzodioxine-8,3'-indol]-2'(1'H)-one | A |
| 4.98 | 1'-{[6-(trifluoromethyl)pyridin-3-yl]methyl}-2,3-dihydrospiro[furo[2,3-g][1,4]benzodioxine-8,3'-indol]-2'(1'H)-one | A |
| 4.99 | 1'-(4-isoxazol-5-ylbenzyl)-3-methylspiro[furo[3,2-f][1,2]benzisoxazole-5,3'-indol]-2'(1'H)-one | B |
| 4.100 | 1'-[(5-fluoropyridin-2-yl)methyl]-2,3-dihydrospiro[furo[2,3-g][1,4]benzodioxine-8,3'-indol]-2'(1'H)-one | A |
| 4.101 | 1'-[(3-fluoropyridin-2-yl)methyl]-2,3-dihydrospiro[furo[2,3-g][1,4]benzodioxine-8,3'-indol]-2'(1'H)-one | A |
| 4.102 | 1'-(pyridin-2-ylmethyl)-4'-quinolin-3-yl-2,3-dihydrospiro[furo[2,3-g][1,4]benzodioxine-8,3'-indol]-2'(1'H)-one | B |
| 4.103 | 4'-(4-phenoxyphenyl)-1'-(pyridin-2-ylmethyl)-2,3-dihydrospiro[furo[2,3-g][1,4]benzodioxine-8,3'-indol]-2'(1'H)-one | B |
| 4.104 | 1'-[(3,5-difluoropyridin-2-yl)methyl]-2,3-dihydrospiro[furo[2,3-g][1,4]benzodioxine-8,3'-indol]-2'(1'H)-one | A |
| 4.105 | 2'-oxo-1'-(pyridin-2-ylmethyl)-1',2'-dihydrospiro[1-benzofuran-3,3'-indole]-6-carbonitrile | C |
| 4.106 | 3-{[(8S)-2'-oxo-2,3-dihydrospiro[furo[2,3-g][1,4]benzodioxine-8,3'-indol]-1'(2'H)-yl]methyl}benzonitrile | A |
| 4.107 | (8S)-1'-[(5-fluoropyridin-2-yl)methyl]-2,3-dihydrospiro[furo[2,3-g][1,4]benzodioxine-8,3'-indol]-2'(1'H)-one | A |
| 4.108 | (8S)-1'-[(3-fluoropyridin-2-yl)methyl]-2,3-dihydrospiro[furo[2,3-g][1,4]benzodioxine-8,3'-indol]-2'(1'H)-one | A |
| 4.109 | (S)-1'-(2-oxobutyl)-3,7-dihydro-2H-spiro[benzofuro[5,6-b][1,4]dioxine-8,3'-indolin]-2'-one | A |
| 4.110 | 1'-[(4-fluoropyridin-2-yl)methyl]-2,3-dihydrospiro[furo[2,3-g][1,4]benzodioxine-8,3'-indol]-2'(1'H)-one | A |
| 4.111 | 1'-(2,3-dihydro-1,4-benzodioxin-6-ylmethyl)-2'-oxo-1',2'-dihydrospiro[1-benzofuran-3,3'-indole]-6-carbonitrile | B |
| 4.112 | 1'-[(3-chloropyridin-2-yl)methyl]-2,3-dihydrospiro[furo[2,3-g][1,4]benzodioxine-8,3'-indol]-2'(1'H)-one | A |
| 4.113 | 1'-[2-(trifluoromethyl)benzyl]-2,3-dihydrospiro[furo[2,3-g][1,4]benzodioxine-8,3'-indol]-2'(1'H)-one | A |
| 4.114 | (8R)-1'-[2-(trifluoromethyl)benzyl]-2,3-dihydrospiro[furo[2,3-g][1,4]benzodioxine-8,3'-indol]-2'(1'H)-one | B |
| 4.116 | (8S)-1'-[2-(trifluoromethyl)benzyl]-2,3-dihydrospiro[furo[2,3-g][1,4]benzodioxine-8,3'-indol]-2'(1'H)-one | A |
| 4.118 | 1'-(2,1,3-benzothiadiazol-5-ylmethyl)-2,3-dihydrospiro[furo[2,3-g][1,4]benzodioxine-8,3'-indol]-2'(1'H)-one | A |
| 4.119 | 1'-(1,3-benzothiazol-2-ylmethyl)-2,3-dihydrospiro[furo[2,3-g][1,4]benzodioxine-8,3'-indol]-2'(1'H)-one | A |
| 4.120 | 1'-[(1-methyl-1H-benzimidazol-2-yl)methyl]-2,3-dihydrospiro[furo[2,3-g][1,4]benzodioxine-8,3'-indol]-2'(1'H)-one | A |
| 4.121 | 1'-{[2-(1-methylethyl)-1,3-thiazol-4-yl]methyl}-2,3-dihydrospiro[furo[2,3-g][1,4]benzodioxine-8,3'-indol]-2'(1'H)-one | A |
| 4.122 | 1'-(2,1,3-benzoxadiazol-5-ylmethyl)-2,3-dihydrospiro[furo[2,3-g][1,4]benzodioxine-8,3'-indol]-2'(1'H)-one | A |
| 4.124 | 1'-(pyridin-2-ylmethyl)spiro[furo[3,2-e][2,1,3]benzoxadiazole-8,3'-indol]-2'(1'H)-one | A |
| 4.125 | 1'-(pyridin-3-ylmethyl)spiro[furo[3,2-e][2,1,3]benzoxadiazole-8,3'-indol]-2'(1'H)-one | C |
| 4.126 | 6-chloro-1'-(pyridin-2-ylmethyl)-2,3-dihydrospiro[furo[3,2-f][1,4]benzodioxine-9,3'-indol]-2'(1'H)-one | C |
| 4.127 | 1'-(pyridin-2-ylmethyl)-2,3-dihydrospiro[furo[3,2-f][1,4]benzodioxine-9,3'-indol]-2'(1'H)-one | C |

TABLE 2-continued

| Ex. No. | Compound Name | IC$_{50}$ |
|---|---|---|
| 4.129 | 1-[(2R)-tetrahydrofuran-2-ylmethyl]-5',6',7',8'-tetrahydrospiro[indole-3,3'-naphtho[2,3-b]furan]-2(1H)-one | C |
| 4.130 | 1'-(pyridin-2-ylmethyl)spiro[furo[2,3-g]quinoxaline-8,3'-indol]-2'(1'H)-one | C |
| 5 | 1'-[(2-methoxypyrimidin-5-yl)methyl]-5,6-dihydrospiro[benzo[1,2-b:5,4-b']difuran-3,3'-indol]-2'(1'H)-one | B |
| 5.1 | 7'-chloro-1'-((5-(trifluoromethyl)furan-2-yl)methyl)-5,6-dihydro-2H-spiro[benzofuro[6,5-b]furan-3,3'-indolin]-2'-one | B |
| 5.2 | (3R)-1'-(3-methylbutyl)-5,6-dihydrospiro[benzo[1,2-b:5,4-b']difuran-3,3'-indol]-2'(1'H)-one | C |
| 5.3 | (3R)-1'-pentyl-5,6-dihydrospiro[benzo[1,2-b:5,4-b']difuran-3,3'-indol]-2'(1'H)-one | C |
| 5.4 | (3R)-1'-(pyridin-2-ylmethyl)-5,6-dihydrospiro[benzo[1,2-b:5,4-b']difuran-3,3'-indol]-2'(1'H)-one | C |
| 5.5 | (3R)-1'-{[5-(trifluoromethyl)furan-2-yl]methyl}-5,6-dihydrospiro[benzo[1,2-b:5,4-b']difuran-3,3'-indol]-2'(1'H)-one | C |
| 5.6 | (3S)-1'-(pyridin-2-ylmethyl)-5,6-dihydrospiro[benzo[1,2-b:5,4-b']difuran-3,3'-indol]-2'(1'H)-one | A |
| 5.7 | (3S)-1'-{[5-(trifluoromethyl)furan-2-yl]methyl}-5,6-dihydrospiro[benzo[1,2-b:5,4-b']difuran-3,3'-indol]-2'(1'H)-one | A |
| 5.8 | 3-methyl-1'-{[5-(trifluoromethyl)furan-2-yl]methyl}spiro[furo[2,3-f][1,3]benzoxazole-7,3'-indole]-2,2'(1'H,3H)-dione | C |
| 5.13 | 1'-[(6-chloropyridin-2-yl)methyl]-2,3-dihydrospiro[furo[2,3-g][1,4]benzodioxine-8,3'-indol]-2'(1'H)-one | A |
| 5.15 | 1'-[(6-methoxypyridin-3-yl)methyl]-2,3-dihydrospiro[furo[2,3-g][1,4]benzodioxine-8,3'-indol]-2'(1'H)-one | A |
| 5.16 | (8S)-1'-(pyrazin-2-ylmethyl)-2,3-dihydrospiro[furo[2,3-g][1,4]benzodioxine-8,3'-indol]-2'(1'H)-one | A |
| 5.17 | (8S)-1'-[(2-methoxypyrimidin-5-yl)methyl]-2,3-dihydrospiro[furo[2,3-g][1,4]benzodioxine-8,3'-indol]-2'(1'H)-one | A |
| 5.18 | (8S)-1'-(pyrimidin-2-ylmethyl)-2,3-dihydrospiro[furo[2,3-g][1,4]benzodioxine-8,3'-indol]-2'(1'H)-one | A |
| 5.19 | 6-methyl-1'-(pyridin-2-ylmethyl)-2,3-dihydrospiro[1,4-dioxino[2,3-f]indole-8,3'-indole'-2',7(1'H,6H)-dione | C |
| 5.20 | 4'-fluoro-1'-{[3-(trifluoromethyl)pyridin-2-yl]methyl}-2,3-dihydrospiro[furo[2,3-g][1,4]benzodioxine-8,3'-indol]-2'(1'H)-one | A |
| 5.21 | 1'-[(2,2-difluorocyclopropyl)methyl]-2,3-dihydrospiro[furo[2,3-g][1,4]benzodioxine-8,3'-indol]-2'(1'H)-one | A |
| 5.22 | 1'-methyl-2,3-dihydrospiro[furo[2,3-g][1,4]benzodioxine-8,3'-indol]-2'(1'H)-one | A |
| 5.23 | 1'-{[4-(trifluoromethyl)-1,3-thiazol-2-yl]methyl}-2,3-dihydrospiro[furo[2,3-g][1,4]benzodioxine-8,3'-indol]-2'(1'H)-one | A |
| 5.25 | 9-fluoro-1'-(pyridin-2-ylmethyl)-2,3-dihydro-spiro[furo[2,3-g][1,4]benzodioxine-8,3'-indol]-2'(1'H)-one | A |
| 5.26 | 9-fluoro-1'-{[3-(trifluoromethyl)pyridin-2-yl]methyl}-2,3-dihydrospiro[furo[2,3-g][1,4]benzodioxine-8,3'-indol]-2'(1'H)-one | A |
| 5.27 | 9-fluoro-1'-[(5-hydroxypyridin-2-yl)methyl]-2,3-dihydrospiro[furo[2,3-g][1,4]benzodioxine-8,3'-indol]-2'(1'H)-one | B |
| 5.28 | 1'-(pyridin-2-ylmethyl)-7,8-dihydro-6H-spiro-[furo[2,3-g]chromene-3,3'-indol]-2'(1'H)-one | A |
| 5.29 | 1'-{[3-(trifluoromethyl)pyridin-2-yl]methyl}-7,8-dihydro-6H-spiro[furo[2,3-g]chromene-3,3'-indol]-2'(1'H)-one | B |
| 5.31 | 1-(pyridin-2-ylmethyl)spiro[indole-3,3'-thieno[2,3-f][1]benzofuran]-2(1H)-one 5,5'-dioxide | C |
| 5.32 | 1'-(pyrimidin-2-ylmethyl)-2,3-dihydrospiro[furo[2,3-g][1,4]benzodioxine-8,3'-indol]-2'(1'H)-one | A |
| 5.33 | 1'-[(4,6-dimethoxypyrimidin-2-yl)methyl]-2,3-dihydrospiro[furo[2,3-g][1,4]benzodioxine-8,3'-indol]-2'(1'H)-one | A |
| 5.34 | 6-(2-methoxyethoxy)-1'-(pyridin-2-ylmethyl)spiro[1-benzofuran-3,3'-indol]-2'(1'H)-one | B |
| 5.35 | 5-(2-methoxyethoxy)-1'-(pyridin-2-ylmethyl)spiro[1-benzofuran-3,3'-indol]-2'(1'H)-one | B |
| 5.36 | 1'-(pyridin-2-ylmethyl)-2,3-dihydrospiro[furo[2,3-f][1,4]benzodioxine-7,3'-indol]-2'(1'H)-one | B |

TABLE 2-continued

| Ex. No. | Compound Name | IC$_{50}$ |
|---|---|---|
| 5.37 | 1'-{[3-(trifluoromethyl)pyridin-2-yl]methyl}-2,3-dihyrospiro[furo[2,3-f][1,4]benzodioxine-7,3'-indol]-2'(1'H)-one | B |
| 5.38 | 6-[(2'-oxospiro[furo[2,3-f][1,3]benzodioxole-7,3'-indol]-1'(2'H)-yl)methyl]pyrimidine-2,4(1H,3H)-dione | C |
| 6 | 1'-[(5-Chloro-1,2,4-thiadiazol-3-yl)methyl]spiro[furo[2,3-f][1,3]benzodioxole-7,3'-indol]-2'(1'H)-one | A |
| 6.1 | 4'-chloro-1'-[(5-chloro-1,2,4-thiadiazol-3-yl)methyl]spiro[furo[2,3-f][1,3]benzodioxole-7,3'-indol]-2'(1'H)-one | A |
| 6.2 | 5,6-dimethyl-1'-(tetrahydro-2H-pyran-2-ylmethyl)spiro[1-benzofuran-3,3'-indol]-2'(1'H)-one | B |
| 6.3 | 1'-[(3-chlorothiophen-2-yl)methyl]spiro[furo[2,3-f][1,3]benzodioxole-7,3'-indol]-2'(1'H)-one | A |
| 6.4 | 1'-{[3-(2,6-dichlorophenyl)-5-methylisoxazol-4-yl]methyl}spiro[furo[2,3-f][1,3]benzodioxole-7,3'-indol]-2'(1'H)-one | C |
| 6.5 | 1'-({2-[4-(trifluoromethyl)phenyl]-1,3-thiazol-4-yl}methyl)spiro[furo[2,3-f][1,3]benzodioxole-7,3'-indol]-2'(1'H)-one | B |
| 6.6 | 1'-[(5-phenyl-1,3,4-oxadiazol-2-yl)methyl]spiro[furo[2,3-f][1,3]benzodioxole-7,3'-indol]-2'(1'H)-one | B |
| 6.7 | 1'-{[5-(4-chlorophenyl)-1,3,4-oxadiazol-2-yl]methyl}spiro[furo[2,3-f][1,3]benzodioxole-7,3'-indol]-2'(1'H)-one | B |
| 6.8 | 1'-([1,3]oxazolo[4,5-b]pyridin-2-ylmethyl)spiro[furo[2,3-f][1,3]benzodioxole-7,3'-indol]-2'(1'H)-one | A |
| 7.1 | 1'-[3-(trifluoromethyl)benzyl]-2,3-dihydrospiro[furo[2,3-g][1,4]benzodioxine-8,3'-indol]-2'(1'H)-one | A |
| 7.2 | methyl 5-[(2'-oxo-2,3-dihydrospiro[furo[2,3-g][1,4]benzodioxine-8,3'-indol]-1'(2'H)-yl)methyl]furan-2-carboxylate | A |
| 7.10 | 1'-(3-nitrobenzyl)-2,3-dihydrospiro[furo[2,3-g][1,3]benzodioxine-8,3'-indol]-2'(1'H)-one | A |
| 7.11 | 1'-(1,3-thiazol-5-ylmethyl)-2,3-dihydrospiro[furo[2,3-g][1,3]benzodioxine-8,3'-indol]-2'(1'H)-one | A |
| 7.12 | 1'-{[5-(trifluoromethyl)pyridin-2-yl]methyl}-2,3-dihydrospiro[furo[2,3-g][1,3]benzodioxine-8,3'-indol]-2'(1'H)-one | A |
| 7.13 | 1'-{[3-(trifluoromethyl)pyridin-2-yl]methyl}-2,3-dihydrospiro[furo[2,3-g][1,3]benzodioxine-8,3'-indol]-2'(1'H)-one | A |
| 7.14 | 1'-[(3-pyridin-3-ylisoxazol-5-yl)methyl]-2,3-dihydrospiro[furo[2,3-g][1,3]benzodioxine-8,3'-indol]-2'(1'H)-one | A |
| 7.15 | (8R)-1'-{[3-(trifluoromethyl)pyridin-2-yl]methyl}-2,3-dihydrospiro[furo[2,3-g][1,3]benzodioxine-8,3'-indol]-2'(1'H)-one | B |
| 7.16 | N,N-dimethyl-3-[(2'-oxo-2,3-dihydrospiro[furo[2,3-g][1,4]benzodioxine-8,3'-indol]-1'-(2'H)-yl)methyl]benzenesulfonamide | C |
| 7.17 | 1'-[3-(morpholin-4-ylsulfonyl)benzyl]-2,3-dihydrospiro[furo[2,3-g][1,4]benzodioxine-8,3'-indol]-2'(1'H)-one | C |
| 7.18 | 1'-[(4-methyl-1,2,5-oxadiazol-3-yl)methyl]-2,3-dihydrospiro[furo[2,3-g][1,4]benzodioxine-8,3'-indol]-2'(1'H)-one | A |
| 7.19 | 1'-(2,3-difluorobenzyl)-2,3-dihydrospiro[furo[2,3-g][1,4]benzodioxine-8,3'-indol]-2'(1'H)-one | A |
| 7.20 | 1'-(3,5-difluorobenzyl)-2,3-dihydrospiro[furo[2,3-g][1,4]benzodioxine-8,3'-indol]-2'(1'H)-one | A |
| 7.21 | 1'-(4-fluorobenzyl)-2,3-dihydrospiro[furo[2,3-g][1,4]benzodioxine-8,3'-indol]-2'(1'H)-one | A |
| 7.22 | 1'-(2-chloro-4-fluorobenzyl)-2,3-dihydrospiro[furo[2,3-g][1,4]benzodioxine-8,3'-indol]-2'(1'H)-one | A |
| 7.23 | 1'-[(1-methyl-1H-benzotriazol-5-yl)methyl]-2,3-dihydrospiro[furo[2,3-g][1,4]benzodioxine-8,3'-indol]-2'(1'H)-one | A |
| 7.24 | 1'-[(3-trifluoromethoxy)benzyl]-2,3-dihydrospiro[furo[2,3-g][1,4]benzodioxine-8,3'-indol]-2'(1'H)-one | A |
| 7.25 | 1'-[(2-fluoro-6-trifluoromethyl)benzyl]-2,3-dihydrospiro[furo[2,3-g][1,4]benzodioxine-8,3'-indol]-2'(1'H)-one | A |
| 7.26 | 1'-[(2-fluoro-5-trifluoromethyl)benzyl]-2,3-dihydrospiro[furo[2,3-g][1,4]benzodioxine-8,3'-indol]-2'(1'H)-one | A |
| 7.27 | 1'-[(2-trifluoromethoxy)benzyl]-2,3-dihydrospiro[furo[2,3-g][1,4]benzodioxine-8,3'-indol]-2'(1'H)-one | A |

TABLE 2-continued

| Ex. No. | Compound Name | IC$_{50}$ |
|---|---|---|
| 7.28 | 1'-[2-(2,2,5-trimethyl-1,3-dioxan-2-yl)ethyl]-2,3-dihydrospiro[furo[2,3-g][1,4]benzodioxine-8,3'-indol]-2'(1'H)-one | A |
| 8 | 1'-[(2S)-1,4-dioxan-2-ylmethyl]spiro[furo[2,3-f][1,3]benzodioxole-7,3'-indol]-2'(1'H)-one | A |
| 8.1 | 7'-chloro-1'-[(2R)-tetrahydrofuran-2-ylmethyl]-5,6-dihydrospiro[benzo[1,2-b:5,4-b']difuran-3,3'-indol]-2'(1'H)-one | B |
| 8.2 | 7'-fluoro-1'-[(2R)-tetrahydrofuran-2-ylmethyl]-5,6-dihydrospiro[benzo[1,2-b:5,4-b']difuran-3,3'-indol]-2'(1'H)-one | A |
| 8.3 | 4'-fluoro-7'-methyl-1'-[(2R)-tetrahydrofuran-2-ylmethyl]-5,6-dihydrospiro[benzo[1,2-b:5,4-b']difuran-3,3'-indol]-2'(1'H)-one | A |
| 8.4 | 1'-pentyl-2,3-dihydrospiro[furo[2,3-g][1,4]benzodioxine-8,3'-indol]-2'(1'H)-one | A |
| 8.5 | (8R)-1'-[(2R)-1,4-dioxan-2-ylmethyl]-2,3-dihydrospiro[furo[2,3-g][1,4]benzodioxine-8,3'-indol]-2'(1'H)-one | C |
| 8.6 | (8R)-1'-[(2S)-1,4-dioxan-2-ylmethyl]-2,3-dihydrospiro[furo[2,3-g][1,4]benzodioxine-8,3'-indol]-2'(1'H)-one | C |
| 8.7 | (8S)-1'-[(2S)-1,4-dioxan-2-ylmethyl]-2,3-dihydrospiro[furo[2,3-g][1,4]benzodioxine-8,3'-indol]-2'(1'H)-one | A |
| 8.8 | (8S)-1'-[(2R)-1,4-dioxan-2-ylmethyl]-2,3-dihydrospiro[furo[2,3-g][1,4]benzodioxine-8,3'-indol]-2'(1'H)-one | A |
| 8.9 | 1'-[(2R)-tetrahydrofuran-2-ylmethyl]-6,7-dihydrospiro[benzo[1,2-b:4,5-b']difuran-3,3'-indol]-2'(1'H)-one | B |
| 8.10 | 1'-[(2R)-1,4-dioxan-2-ylmethyl]-6,7-dihydrospiro[benzo[1,2-b:4,5-b']difuran-3,3'-indol]-2'(1'H)-one | B |
| 8.11 | 1'-[(2R)-tetrahydrofuran-2-ylmethyl]-3,4-dihydro-2H-spiro[furo[2,3-h][1,5]benzodioxepine-9,3'-indol]-2'(1'H)-one | C |
| 8.12 | 1'-[(2R)-1,4-dioxan-2-ylmethyl]-3,4-dihydro-2H-spiro[furo[2,3-h][1,5]benzodioxepine-9,3'-indol]-2'(1'H)-one | B |
| 8.14 | 3-methyl-1'-(((R)-tetrahydrofuran-2-yl)methyl)-2H-spiro[benzofuro[6,5-d]oxazole-7,3'-indoline]-2,2'(3H,6H)-dione | C |
| 8.15 | 7'-fluoro-1'-(pyridin-2-ylmethyl)-3,7-dihydro-2H-spiro[benzofuro[5,6-b][1,4]dioxine-8,3'-indolin]-2'-one | A |
| 8.16 | 7'-fluoro-1'-((3-(trifluoromethyl)pyridin-2-yl)methyl)-3,7-dihydro-2H-spiro[benzofuro[5,6-b][1,4]dioxine-8,3'-indolin]-2'-one | A |
| 8.17 | 3'-[2-(difluoromethyl)benzyl]-2,3-dihydrospiro[furo[2,3-g][1,4]benzodioxine-8,1'-inden]-2'(3'H)-one | A |
| 8.18 | 1'-[(5-fluoropyridin-3-yl)methyl]-2,3-dihydrospiro[furo[2,3-g][1,4]benzodioxine-8,3'-indol]-2'(1'H)-one | A |
| 8.19 | (8S)-1'-[(5-fluoropyridin-3-yl)methyl]-2,3-dihydrospiro[furo[2,3-g][1,4]benzodioxine-8,3'-indol]-2'(1'H)-one | A |
| 9 | 3-methyl-1'-{[5-(trifluoromethyl)furan-2-yl]methyl}spiro[furo[3,2-f][1,2]benzisoxazole-5,3'-indol]-2'(1'H)-one | A |
| 9.1 | 1'-[2-(2-methoxyethoxy)ethyl]-5,6-dihydrospiro[benzo[1,2-b:5,4-b']difuran-3,3'-indol]-2'(1'H)-one | B |
| 9.2 | 1'-{[(2S)-5-oxopyrrolidin-2-yl]methyl}-5,6-dihydrospiro[benzo[1,2-b:5,4-b']difuran-3,3'-indol]-2'(1'H)-one | C |
| 9.3 | 1'-[2-(2-oxo-1,3-oxazolidin-3-yl)ethyl]-5,6-dihydrospiro[benzo[1,2-b:5,4-b']difuran-3,3'-indol]-2'(1'H)-one | C |
| 9.4 | 1'-(4-pyridin-2-ylbenzyl)-5,6-dihydrospiro[benzo[1,2-b:5,4-b']difuran-3,3'-indol]-2'(1'H)-one | B |
| 9.5 | 1'-(pyrimidin-2-ylmethyl)-5,6-dihydrospiro[benzo[1,2-b:5,4-b']difuran-3,3'-indol]-2'(1'H)-one | A |
| 9.6 | 1'-(pyrimidin-4-ylmethyl)-5,6-dihydrospiro[benzo[1,2-b:5,4-b']difuran-3,3'-indol]-2'(1'H)-one | A |
| 9.7 | 1'-(pyrazin-2-ylmethyl)-5,6-dihydrospiro[benzo[1,2-b:5,4-b']difuran-3,3'-indol]-2'(1'H)-one | A |
| 9.8 | 1'-[(7-fluoro-1-benzofuran-2-yl)methyl]-5,6-dihydrospiro[benzo[1,2-b:5,4-b']difuran-3,3'-indol]-2'(1'H)-one | A |
| 9.9 | 1'-(pyridazin-3-ylmethyl)-5,6-dihydrospiro[benzo[1,2-b:5,4-b']difuran-3,3'-indol]-2'(1'H)-one | B |

TABLE 2-continued

| Ex. No. | Compound Name | IC$_{50}$ |
|---|---|---|
| 9.10 | 1'-[(2-oxo-1,3-oxazolidin-5-yl)methyl]-5,6-dihydrospiro[benzo[1,2-b:5,4-b']difuran-3,3'-indol]-2'(1'H)-one | C |
| 9.11 | 1'-[3-(benzyloxy)benzyl]-5,6-dihydrospiro[benzo[1,2-b:5,4-b']difuran-3,3'-indol]-2'(1'H)-one | B |
| 9.12 | 1'-[(1-methyl-1H-benzimidazol-2-yl)methyl]-5,6-dihydrospiro[benzo[1,2-b:5,4-b']difuran-3,3'-indol]-2'(1'H)-one | B |
| 9.13 | 1'-(2H-benzotriazol-2-ylmethyl)-5,6-dihydrospiro[benzo[1,2-b:5,4-b']difuran-3,3'-indol]-2'(1'H)-one | A |
| 9.14 | methyl 2-[(2'-oxo-5,6-dihydrospiro[benzo[1,2-b:5,4-b']difuran-3,3'-indol]-1'(2'H)-yl)methyl]benzoate | A |
| 9.15 | methyl 3-[(2'-oxo-5,6-dihydrospiro[benzo[1,2-b:5,4-b']difuran-3,3'-indol]-1'(2'H)-yl)methyl]benzoate | A |
| 9.16 | methyl 4-[(2'-oxo-5,6-dihydrospiro[benzo[1,2-b:5,4-b']difuran-3,3'-indol]-1'(2'H)-yl)methyl]benzoate | A |
| 9.17 | 1'-[3-(benzyloxy)propyl]-5,6-dihydrospiro[benzo[1,2-b:5,4-b']difuran-3,3'-indol]-2'(1'H)-one | B |
| 9.18 | 5'-fluoro-1'-[(2R)-tetrahydrofuran-2-ylmethyl]-5,6-dihydrospiro[benzo[1,2-b:5,4-b']difuran-3,3'-indol]-2'(1'H)-one | B |
| 9.19 | 6'-fluoro-1'-[(2R)-tetrahydrofuran-2-ylmethyl]-5,6-dihydrospiro[benzo[1,2-b:5,4-b']difuran-3,3'-indol]-2'(1'H)-one | B |
| 9.20 | 1'-[2-(2-methoxyethoxy)ethyl]-2,3-dihydrospiro[furo[2,3-g][1,4]benzodioxine-8,3'-indol]-2'(1'H)-one | A |
| 9.21 | 2-methyl-1'-(pyridin-2-ylmethyl)spiro[furo[2,3-f][1,3]benzothiazole-7,3'-indol]-2'(1'H)-one | C |
| 9.22 | 1'-[(5-chloro-1-methyl-1H-imidazol-2-yl)methyl]-2-methylspiro[furo[2,3-f][1,3]benzothiazole-7,3'-indol]-2'(1'H)-one | C |
| 9.23 | 4-methyl-1'-(((R)-tetrahydrofuran-2-yl)methyl)-4,7-dihydrospiro[benzofuro[5,6-b][1,4]oxazine-8,3'-indoline]-2',3(2H)-dione | A |
| 9.24 | 3-methyl-1'-(pyridin-2-ylmethyl)spiro[furo[3,2-f][1,2]benzisoxazole-5,3'-indol]-2'(1'H)-one | A |
| 9.25 | 3-methyl-1'-(pyridin-3-ylmethyl)spiro[furo[3,2-f][1,2]benzisoxazole-5,3'-indol]-2'(1'H)-one | A |
| 9.26 | 3-methyl-1'-[(2R)-tetrahydrofuran-2-ylmethyl]spiro[furo[3,2-f][1,2]benzisoxazole-5,3'-indol]-2'(1'H)-one | B |
| 9.27 | 5,6-dimethyl-1'-(tetrahydro-2H-pyran-4-ylmethyl)spiro[1-benzofuran-3,3'-indol]-2'(1'H)-one | C |
| 9.28 | 5,6-dimethyl-1'-(pyridin-2-ylmethyl)spiro[1-benzofuran-3,3'-indol]-2'(1'H)-one | B |
| 9.29 | 5-fluoro-6-methoxy-1'-(tetrahydro-2H-pyran-4-ylmethyl)spiro[1-benzofuran-3,3'-indol]-2'(1'H)-one | C |
| 9.30 | 5-fluoro-6-methoxy-1'-{[5-(trifluoromethyl)furan-2-yl]methyl}spiro[1-benzofuran-3,3'-indol]-2'(1'H)-one | B |
| 9.31 | 5,6-difluoro-1'-(pyridin-3-ylmethyl)spiro[1-benzofuran-3,3'-indol]-2'(1'H)-one | C |
| 9.32 | 5,6-difluoro-1'-{[5-(trifluoromethyl)furan-2-yl]methyl}spiro[1-benzofuran-3,3'-indol]-2'(1'H)-one | C |
| 9.33 | 6-methoxy-1'-(pyridin-2-ylmethyl)-2H-spiro[benzofuran-3,3'-indolin]-2'-one | A |
| 9.34 | 6-methoxy-1'-(pyridin-3-ylmethyl)spiro[1-benzofuran-3,3'-indol]-2'(1'H)-one | A |
| 9.35 | 6-methoxy-1'-(tetrahydro-2H-pyran-4-ylmethyl)spiro[1-benzofuran-3,3'-indol]-2'(1'H)-one | B |
| 9.36 | 6-methoxy-1'-(tetrahydro-2H-pyran-2-ylmethyl)spiro[1-benzofuran-3,3'-indol]-2'(1'H)-one | A |
| 9.37 | 1'-[4-(benzyloxy)benzyl]-2,3-dihydrospiro[furo[2,3-g][1,4]benzodioxine-8,3'-indol]-2'(1'H)-one | B |
| 9.38 | 1'-[4-(benzyloxy)benzyl]-5,6-dihydrospiro[benzo[1,2-b:5,4-b']difuran-3,3'-indol]-2'-(1'H)-one | B |
| 9.39 | (8S)-1'-[4-(benzyloxy)benzyl]-2,3-dihydrospiro[furo[2,3-g][1,4]benzodioxine-8,3'-indol]-2'(1'H)-one | B |
| 9.40 | tert-butyl {5-[(2'-oxo-2,3-dihydrospiro[furo[2,3-g][1,4]benzodioxine-8,3'-indol]-1'(2'H)-yl)methyl]pyridin-2-yl}carbamate | B |
| 9.41 | 3-methyl-1'-[2-(trifluoromethyl)benzyl]spiro[furo[3,2-f][1,2]benzisoxazole-5,3'-indol]-2'(1'H)-one | B |
| 9.42 | 3-methyl-1'-{[3-(trifluoromethyl)pyridin-2-yl]methyl}spiro[furo[3,2-f][1,2]benzisoxazole-5,3'-indol]-2'(1'H)-one | B |
| 9.43 | 1'-[3-(benzyloxy)propyl]-2,3-dihydrospiro[furo[2,3-g][1,4]benzodioxine-8,3'-indol]-2'(1'H)-one | A |
| 9.44 | ethyl (2'-oxo-2,3-dihydrospiro[furo[2,3-g][1,4]benzodioxine-8,3'-indol]-1'(2'H)-yl)acetate | A |

TABLE 2-continued

| Ex. No. | Compound Name | IC$_{50}$ |
|---|---|---|
| 9.45 | 1'-{[(4S)-2,2-dimethyl-1,3-dioxolan-4-yl]methyl}-2,3-dihydrospiro[furo[2,3-g][1,4]benzodioxine-8,3'-indol]-2'(1'H)-one | A |
| 9.46 | 6-methoxy-1'-(4-methoxybenzyl)-2'-oxo-1',2'-dihydrospiro[1-benzofuran-3,3'-indole]-5-carbonitrile | B |
| 9.47 | 6-methoxy-2'-oxo-1'-(pyridin-2-ylmethyl)-1',2'-dihydrospiro[1-benzofuran-3,3'-indole]-5-carbonitrile | C |
| 9.48 | 6-fluoro-2'-oxo-1'-(pyridin-2-ylmethyl)-1',2'-dihydrospiro[1-benzofuran-3,3'-indole]-5-carbonitrile | C |
| 9.50 | 6-fluoro-2'-oxo-1'-[2-(trifluoromethyl)benzyl]-1',2'-dihydrospiro[1-benzofuran-3,3'-indole]-5-carbonitrile | C |
| 9.51 | 6-fluoro-2'-oxo-1'-{[3-(trifluoromethyl)pyridin-2-yl]methyl}-1',2'-dihydrospiro[1-benzofuran-3,3'-indole]-5-carbonitrile | C |
| 9.53 | methyl 3-[(2'-oxo-2,3-dihydrospiro[furo[2,3-g][1,4]benzodioxine-8,3'-indol]-1'(2'H)-yl)methyl]benzoate | A |
| 9.54 | 1'-[2-(2-methoxyethoxy)ethyl]-3-methylspiro[furo[3,2-f][1,2]benzisoxazole-5,3'-indol]-2'(1'H)-one | B |
| 9.55 | 3-methyl-1'-(3-methylbutyl)spiro[furo[3,2-f][1,2]benzisoxazole-5,3'-indol]-2'(1'H)-one | A |
| 9.56 | 3-methyl-1'-(pyrazin-2-ylmethyl)spiro[furo[3,2-f][1,2]benzisoxazole-5,3'-indol]-2'(1'H)-one | A |
| 9.57 | 1'-[(3-fluoropyridin-2-yl)methyl]-3-methylspiro[furo[3,2-f][1,2]benzisoxazole-5,3'-indol]-2'(1'H)-one | B |
| 9.58 | methyl 2-[(3-methyl-2'-oxospiro[furo[3,2-f][1,2]benzisoxazole-5,3'-indol]-1'(2'H)-yl)methyl]-1,3-oxazole-4-carboxylate | B |
| 9.59 | methyl 4-[(2'-oxo-2,3-dihydrospiro[furo[2,3-g][1,4]benzodioxine-8,3'-indol]-1'(2'H)-yl)methyl]benzoate | A |
| 9.60 | 1'-[(4-benzylmorpholin-2-yl)methyl]-2,3-dihydrospiro[furo[2,3-g][1,4]benzodioxine-8,3'-indol]-2'(1'H)-one | B |
| 9.64 | 5,6-difluoro-1'-(pyridin-2-ylmethyl)spiro[1-benzofuran-3,3'-indol]-2'(1'H)-one | B |
| 9.65 | 5,6-difluoro-1'-(tetrahydro-2H-pyran-4-ylmethyl)spiro[1-benzofuran-3,3'-indol]-2'(1'H)-one | C |
| 9.66 | 2-[3-(2'-oxo-5,6-dihydrospiro[benzo[1,2-b:5,4-b']difuran-3,3'-indol]-1'(2'H)-yl)propyl]-1H-isoindole-1,3(2H)-dione | A |
| 9.67 | 1'-{[5-(benzyloxy)pyridin-2-yl]methyl}spiro[furo[3,2-e][2,1,3]benzoxadiazole-8,3'-indol]-2'(1'H)-one | B |
| 9.70 | (8S)-1'-[2-(2-methoxyethoxy)ethyl]-2,3-dihydrospiro[furo[2,3-g][1,4]benzodioxine-8,3'-indol]-2'(1'H)-one | A |
| 9.71 | 6'-[2-(2-methoxyethoxy)ethyl]-2,3-dihydrospiro[furo[2,3-g][1,4]benzodioxine-8,8'-[1,3]thiazolo[5,4-e]indol]-7'(6'H)-one | B |
| 9.72 | 6'-(pyridin-2-ylmethyl)-2,3-dihydrospiro[furo[2,3-g][1,4]benzodioxine-8,8'-[1,3]thiazolo[5,4-e]indol]-7'(6'H)-one | B |
| 9.73 | 4',6'-dimethoxy-1'-[2-(2-methoxyethoxy)ethyl]-2,3-dihydrospiro[furo[2,3-g][1,4]benzodioxine-8,3'-indol]-2'(1'H)-one | C |
| 9.74 | 4',6'-dimethoxy-1'-(pyridin-2-ylmethyl)-2,3-dihydrospiro[furo[2,3-g][1,4]benzodioxine-8,3'-indol]-2'(1'H)-one | B |
| 9.75 | 6-(2-methoxyethoxy)-1'-[2-(2-methoxyethoxy)ethyl]spiro[1-benzofuran-3,3'-indol]-2'(1'H)-one | B |
| 9.76 | 5-(2-methoxyethoxy)-1'-[2-(2-methoxyethoxy)ethyl]spiro[1-benzofuran-3,3'-indol]-2'(1'H)-one | B |
| 10 | 1-(pyridazin-4-ylmethy)-5,6-dihydrospiro[benzo[1,2-b:5,4-b']difuran-3,3'-indo]-2'(1'H)-one | B |
| 11 | 1'-[(2-chloro-1,3-thiazol-5-yl)methyl]spiro[furo[2,3-f][1,3]benzodioxole-7,3'-indol]-2'(1'H)-one | A |
| 11.1 | 1'-{[2-(dimethylamino)-1,3-thiazol-5-yl]methyl}spiro[furo[2,3-f][1,3]benzodioxole-7,3'-indol]-2'(1'H)-one | A |
| 11.2 | 1'-[(2-morpholin-4-yl-1,3-thiazol-5-yl)methyl]spiro[furo[2,3-f][1,3]benzodioxole-7,3'-indol]-2'(1'H)-one | B |
| 11.3 | 1'-[(2-piperidin-1-yl-1,3-thiazol-5-yl)methyl]spiro[furo[2,3-f][1,3]benzodioxole-7,3'-indol]-2'(1'H)-one | B |
| 11.4 | 1'-[(2-methoxy-1,3-thiazol-5-yl)methyl]spiro[furo[2,3-f][1,3]benzodioxole-7,3'-indol]-2'(1'H)-one | A |
| 11.5 | 1'-(piperidin-4-ylmethyl)-5,6-dihydrospiro[benzo[1,2-b:5,4-b']difuran-3,3'-indol]-2'(1'H)-one | C |
| 11.6 | 1'-{[1-(1-methylethyl)piperidin-4-yl]methyl}-5,6-dihydrospiro[benzo[1,2-b:5,4-b']difuran-3,3'-indol]-2'(1'H)-one | C |

TABLE 2-continued

| Ex. No. | Compound Name | IC$_{50}$ |
|---|---|---|
| 11.8 | 1'-[(1-ethylpiperidin-4-yl)methyl]-5,6-dihydrospiro[benzo[1,2-b:5,4-b']difuran-3,3'-indol]-2'(1'H)-one | C |
| 11.10 | 1'-[(1-methylpiperidin-4-yl)methyl]-5,6-dihydrospiro[benzo[1,2-b:5,4-b']difuran-3,3'-indol]-2'(1'H)-one | D |
| 11.12 | 3-[(2'-oxo-5,6-dihydrospiro[benzo[1,2-b:5,4-b']difuran-3,3'-indol]-1'(2'H)-yl)methyl]benzoic acid | C |
| 11.13 | 1'-{4-[5-(trifluoromethyl)-1,2,4-oxadiazol-3-yl]benzyl}-5,6-dihydrospiro[benzo[1,2-b:5,4-b']difuran-3,3'-indol]-2'(1'H)-one | B |
| 11.14 | 1'-[4-(5-methyl-1,2,4-oxadiazol-3-yl)benzyl]-5,6-dihydrospiro[benzo[1,2-b:5,4-b']difuran-3,3'-indol]-2'(1'H)-one | A |
| 11.15 | 1'-[(5-pyridin-4-ylfuran-2-yl)methyl]-5,6-dihydrospiro[benzo[1,2-b:5,4-b']difuran-3,3'-indol]-2'(1'H)-one | B |
| 11.16 | 1'-(4-pyridin-3-ylbenzyl)-5,6-dihydrospiro[benzo[1,2-b:5,4-b']difuran-3,3'-indol]-2'(1'H)-one | B |
| 11.17 | 1'-[(2'-fluorobiphenyl-4-yl)methyl]-5,6-dihydrospiro[benzo[1,2-b:5,4-b']difuran-3,3'-indol]-2'(1'H)-one | B |
| 11.18 | 1'-{2-[5-(trifluoromethyl)-1,2,4-oxadiazol-3-yl]ethyl}spiro[furo[2,3-f][1,3]benzodioxole-7,3'-indol]-2'(1'H)-one | A |
| 11.19 | 4'-chloro-1'-{[5-(trifluoromethyl)-1,2,4-oxadiazol-3-yl]methyl}spiro[furo[2,3-f][1,3]benzodioxole-7,3'-indol]-2'(1'H)-one | A |
| 11.20 | 4'-chloro-1'-[(5-cyclopropyl-1,2,4-oxadiazol-3-yl)methyl]spiro[furo[2,3-f][1,3]benzodioxole-7,3'-indol]-2'(1'H)-one | A |
| 11.21 | 4'-chloro-1'-{1-[5-(difluoromethyl)-1,2,4-oxadiazol-3-yl]ethyl}spiro[furo[2,3-f][1,3]benzodioxole-7,3'-indol]-2'(1'H)-one | A |
| 11.22 | 1'-{[5-(difluoromethyl)-1,2,4-oxadiazol-3-yl]methyl}spiro[furo[2,3-f][1,3]benzodioxole-7,3'-indol]-2'(1'H)-one | A |
| 11.23 | 1'-[(5-tert-butyl-1,2,4-oxadiazol-3-yl)methyl]spiro[furo[2,3-f][1,3]benzodioxole-7,3'-indol]-2'(1'H)-one | A |
| 11.24 | 1'-[(5-cyclopropyl-1,2,4-oxadiazol-3-yl)methyl]spiro[furo[2,3-f][1,3]benzodioxole-7,3'-indol]-2'(1'H)-one | A |
| 11.25 | 4'-chloro-1'-{[5-(1-methylethyl)-1,2,4-oxadiazol-3-yl]methyl}spiro[furo[2,3-f][1,3]benzodioxole-7,3'-indol]-2'(1'H)-one | A |
| 11.26 | 1'-{[5-(1-methylethyl)-1,2,4-oxadiazol-3-yl]methyl}spiro[furo[2,3-f][1,3]benzodioxole-7,3'-indol]-2'(1'H)-one | A |
| 11.27 | 1'-[3-(5-methyl-1,2,4-oxadiazol-3-yl)benzyl]-5,6-dihydrospiro[benzo[1,2-b:5,4-b']difuran-3,3'-indol]-2'(1'H)-one | A |
| 11.28 | 1'-{3-[5-(trifluoromethyl)-1,2,4-oxadiazol-3-yl]benzyl}-5,6-dihydrospiro[benzo[1,2-b:5,4-b']difuran-3,3'-indol]-2'(1'H)-one | B |
| 11.29 | 1'-[4-(5-methyl-4H-1,2,4-triazol-3-yl)benzyl]-5,6-dihydrospiro[benzo[1,2-b:5,4-b']difuran-3,3'-indol]-2'(1'H)-one | B |
| 11.30 | 2-[(2'-oxo-5,6-dihydrospiro[benzo[1,2-b:5,4-b']difuran-3,3'-indol]-1'(2'H)-yl)methyl]benzoic acid | C |
| 11.31 | 4-[(2'-oxo-5,6-dihydrospiro[benzo[1,2-b:5,4-b']difuran-3,3'-indol]-1'(2'H)-yl)methyl]benzoic acid | B |
| 11.32 | 5-[(2'-oxo-2,3-dihydrospiro[furo[2,3-g][1,4]benzodioxine-8,3'-indol]-1'(2'H)-yl)methyl]furan-2-carboxylic acid | C |
| 11.33 | N,N-dimethyl-5-[(2'-oxo-2,3-dihydrospiro[furo[2,3-g][1,4]benzodioxine-8,3'-indol]-1'(2'H)-yl)methyl]furan-2-carboxamide | B |
| 11.34 | 1'-(3-hydroxypropyl)-5,6-dihydrospiro[benzo[1,2-b:5,4-b']difuran-3,3'-indol]-2'(1'H)-one | B |
| 11.35 | 2'-oxo-1'-[(2R)-tetrahydrofuran-2-ylmethyl]-1',2',5,6-tetrahydrospiro[benzo[1,2-b:5,4-b']difuran-3,3'-indole]-4'-carbonitrile | B |
| 11.37 | 4'-[(dimethylamino)methyl]-1'-[(2R)-tetrahydrofuran-2-ylmethyl]-5,6-dihydrospiro[benzo[1,2-b:5,4-b']difuran-3,3'-indol]-2'(1'H)-one | C |
| 11.38 | 4'-(pyrrolidin-1-ylmethyl)-1'-[(2R)-tetrahydrofuran-2-ylmethyl]-5,6-dihydrospiro[benzo[1,2-b:5,4-b']difuran-3,3'-indol]-2'(1'H)-one | C |
| 11.39 | 4'-amino-1'-[(2R)-tetrahydrofuran-2-ylmethyl]-5,6-dihydrospiro[benzo[1,2-b:5,4-b']difuran-3,3'-indol]-2'(1'H)-one | B |

TABLE 2-continued

| Ex. No. | Compound Name | IC$_{50}$ |
|---|---|---|
| 11.41 | 1'-[(4-methylmorpholin-2-yl)methyl]-5,6-dihydrospiro[benzo[1,2-b:5,4-b']difuran-3,3'-indol]-2'(1'H)-one | B |
| 11.42 | 1'-{[4-(1-methylethyl)morpholin-2-yl]methyl}-5,6-dihydrospiro[benzo[1,2-b:5,4-b']difuran-3,3'-indol]-2'(1'H)-one | C |
| 11.43 | 1'-methyl-5,6-dihydrospiro[benzo[1,2-b:5,4-b']difuran-3,3'-indol]-2'(1'H)-one | B |
| 11.44 | 1'-[4-(1H-tetrazol-5-yl)benzyl]-5,6-dihydrospiro[benzo[1,2-b:5,4-b']difuran-3,3'-indol]-2'(1'H)-one | C |
| 11.45 | 1'-(3-hydroxybenzyl)-5,6-dihydrospiro[benzo[1,2-b:5,4-b']difuran-3,3'-indol]-2'(1'H)-one | B |
| 11.46 | 1'-(4-morpholin-4-ylbenzyl)-5,6-dihydrospiro[benzo[1,2-b:5,4-b']difuran-3,3'-indol]-2'(1'H)-one | B |
| 11.47 | 6-amino-1'-[(2R)-tetrahydrofuran-2-ylmethyl]spiro[1-benzofuran-3,3'-indol]-2'(1'H)-one | C |
| 11.48 | N-{2'-oxo-1'-[(2R)-tetrahydrofuran-2-ylmethyl]-1',2'-dihydrospiro[1-benzofuran-3,3'-indol]-6-yl}methanesulfonamide | C |
| 11.49 | 6-hydroxy-1'-(3-methylbutyl)spiro[1-benzofuran-3,3'-indol]-2'(1'H)-one | A |
| 11.50 | 6-hydroxy-1'-(3-methylbutyl)-5-(trifluoroacetyl)spiro[1-benzofuran-3,3'-indol]-2'(1'H)-one | C |
| 11.52 | 6-[(3R)-pyrrolidin-3-ylamino]-1'-{[5-(trifluoromethyl)furan-2-yl]methyl}spiro[1-benzofuran-3,3'-indol]-2'(1'H)-one | B |
| 11.53 | 6-hydroxy-1'-[(2R)-tetrahydrofuran-2-ylmethyl]spiro[1-benzofuran-3,3'-indol]-2'(1'H)-one | B |
| 11.54 | 6-(1-methylethoxy)-1'-[(2R)-tetrahydrofuran-2-ylmethyl]spiro[1-benzofuran-3,3'-indol]-2'(1'H)-one | B |
| 11.56 | 6-[(3S)-pyrrolidin-3-yloxy]-1'-[(2R)-tetrahydrofuran-2-ylmethyl]spiro[1-benzofuran-3,3'-indol]-2'(1'H)-one hydrochloride | C |
| 11.58 | 6-[(3R)-pyrrolidin-3-yloxy]-1'-[(2R)-tetrahydrofuran-2-ylmethyl]spiro[1-benzofuran-3,3'-indol]-2'(1'H)-one hydrochloride | C |
| 11.60 | 1'-[(2R)-tetrahydrofuran-2-ylmethyl]spiro[benzo[1,2-b:5,4-b']difuran-3,3'-indole]-2',5(1'H,6H)-dione | B |
| 11.61 | 1'-(pyrrolidin-3-ylmethyl)-5,6-dihydrospiro[benzo[1,2-b:5,4-b']difuran-3,3'-indol]-2'(1'H)-one | C |
| 11.62 | N-(1-methylethyl)-3-[(2'-oxo-5,6-dihydrospiro[benzo[1,2-b:5,4-b']difuran-3,3'-indol]-1'(2'H)-yl)methyl]pyrrolidine-1-carboxamide | C |
| 11.63 | 1'-[(4-methylpiperazin-1-yl)methyl]spiro[furo[2,3-f][1,3]benzodioxole-7,3'-indol]-2'(1'H)-one hydrogen chloride | A |
| 11.64 | (3S)-6-methoxy-5-methyl-1'-[(4-methylpiperazin-1-yl)methyl]spiro[1-benzofuran-3,3'-indol]-2'(1'H)-one hydrogen chloride | A |
| 11.65 | (3R)-6-methoxy-5-methyl-1'-[(4-methylpiperazin-1-yl)methyl]spiro[1-benzofuran-3,3'-indol]-2'(1'H)-one hydrogen chloride | B |
| 11.66 | (3S)-1'-[(2R)-tetrahydrofuran-2-ylmethyl]-5,6-dihydrospiro[benzo[1,2-b:5,4-b']difuran-3,3'-indol]-2'(1'H)-one | A |
| 11.67 | (3R)-1'-[(2R)-tetrahydrofuran-2-ylmethyl]-5,6-dihydrospiro[benzo[1,2-b:5,4-b']difuran-3,3'-indol]-2'(1'H)-one | C |
| 11.68 | (3R)-1'-[(2S)-tetrahydrofuran-2-ylmethyl]-5,6-dihydrospiro[benzo[1,2-b:5,4-b']difuran-3,3'-indol]-2'(1'H)-one | A |
| 11.69 | (3S)-1'-[(2S)-tetrahydrofuran-2-ylmethyl]-5,6-dihydrospiro[benzo[1,2-b:5,4-b']difuran-3,3'-indol]-2''(1'H)-one | C |
| 11.70 | 1'-{[(2S)-1-methyl-5-oxopyrrolidin-2-yl]methyl}-5,6-dihydrospiro[benzo[1,2-b:5,4-b']difuran-3,3'-indol]-2'(1'H)-one | C |
| 11.71 | 1'-[(3-methyl-2-oxo-1,3-oxazolidin-5-yl)methyl]spiro[furo[2,3-f][1,3]benzodioxole-7,3'-indol]-2'(1'H)-one | C |
| 11.72 | 1'-{[5-(trifluoromethyl)-1,2,4-oxadiazol-3-yl]methyl}spiro[furo[2,3-f][1,3]benzodioxole-7,3'-indol]-2'(1'H)-one | A |
| 11.73 | N-isopropyl-3-[2-(2'-oxospiro[furo[2,3-f][1,3]benzodioxole-7,3'-indol]-1'(2'H)-yl)ethyl]piperidine-1-carboxamide | B |
| 11.74 | 5-[(2'-oxospiro[furo[2,3-f][1,3]benzodioxole-7,3'-indol]-1'(2'H)-yl)methyl]thiophene-3-carbonitrile | A |
| 11.75 | 2'-oxo-1',2'-dihydrospiro[furo[2,3-f][1,3]benzodioxole-7,3'-indole]-7'-carbonitrile | B |

TABLE 2-continued

| Ex. No. | Compound Name | IC$_{50}$ |
|---|---|---|
| 11.78 | 3'-[(3-bromopyridin-2-yl)methyl]-2,3-dihydrospiro[furo[2,3-g][1,4]benzodioxine-8,1'-inden]-2'(3'H)-one | A |
| 11.79 | 3'-{[3-(methylsulfonyl)pyridin-2-yl]methyl}-2,3-dihydrospiro[furo[2,3-g][1,4]benzodioxine-8,1'-inden]-2'(3'H)-one | B |
| 11.80 | 2-[(2'-oxo-2,2',3,3'-tetrahydrospiro[furo[2,3-g][1,4]benzodioxine-8,1'-inden]-3'-yl)methyl]pyridine-3-carbonitrile | A |
| 11.81 | (8S)-1'-{[3-(difluoromethyl)pyridin-2-yl]methyl}-2,3-dihydrospiro[furo[2,3-g][1,4]benzodioxine-8,3'-indol]-2'(1'H)-one | A |
| 11.83 | 1'-[3-(5-methyl-1,2,4-oxadiazol-3-yl)benzyl]-2,3-dihydrospiro[furo[2,3-g][1,4]benzodioxine-8,3'-indol]-2'(1'H)-one | A |
| 11.84 | 1'-[4-(5-methyl-1,2,4-oxadiazol-3-yl)benzyl]-2,3-dihydrospiro[furo[2,3-g][1,4]benzodioxine-8,3'-indol]-2'(1'H)-one | A |
| 11.85 | 6-(5-methyl-1,2,4-oxadiazol-3-yl)-1'-(pyridin-2-ylmethyl)spiro[1-benzofuran-3,3'-indol]-2'(1'H)-one | B |
| 11.86 | 3-[(2'-oxo-2,3-dihydrospiro[furo[2,3-g][1,4]benzodioxine-8,3'-indol]-1'(2'H)-yl)methyl]benzoic acid | C |
| 11.87 | 4-[(2'-oxo-2,3-dihydrospiro[furo[2,3-g][1,4]benzodioxine-8,3'-indol]-1'(2'H)-yl)methyl]benzoic acid | C |
| 11.90 | 1'-{[5-(trifluoromethyl)-1,2,4-oxadiazol-3-yl]methyl}-2,3-dihydrospiro[furo[2,3-g][1,4]benzodioxine-8,3'-indol]-2'(1'H)-one | A |
| 11.92 | 1'-{[5-(trifluoromethyl)-1,3,4-oxadiazol-2-yl]methyl}-2,3-dihydrospiro[furo[2,3-g][1,4]benzodioxine-8,3'-indol]-2'(1'H)-one | A |
| 11.94 | N-{3-[(2'-oxo-2,3-dihydrospiro[furo[2,3-g][1,4]benzodioxine-8,3'-indol]-1'(2'H)-yl)methyl]phenyl}methanesulfonamide | B |
| 11.95 | 1'-[(1-oxydopyridin-2-yl)methyl]-2,3-dihydrospiro[furo[2,3-g][1,4]benzodioxine-8,3'-indol]-2'(1'H)-one | B |
| 11.97 | 1'-[(3-aminopyridin-2-yl)methyl]-2,3-dihydrospiro[furo[2,3-g][1,4]benzodioxine-8,3'-indol]-2'(1'H)-one hydrobromide | A |
| 11.98 | N-{2-[(2'-oxo-2,3-dihydrospiro[furo[2,3-g][1,4]benzodioxine-8,3'-indol]-1'(2'H)-yl)methyl]pyridine-3-yl}methanesulfonamide | B |
| 11.99 | 1'-(piperidin-4-ylmethyl)-2,3-dihydrospiro[furo[2,3-g][1,4]benzodioxine-8,3'-indol]-2'(1'H)-one hydrochloride | C |
| 11.100 | 1'-{[1-(1-methylethyl)piperidin-4-yl]methyl}-2,3-dihydrospiro[furo[2,3-g][1,4]benzodioxine-8,3'-indol]-2'(1'H)-one hydrochloride | C |
| 11.101 | 1'-[(1-methylpiperidin-4-yl)methyl]-2,3-dihydrospiro[furo[2,3-g][1,4]benzodioxine-8,3'-indol]-2'(1'H)-one hydrochloride | C |
| 11.102 | 1'-(morpholin-2-ylmethyl)-2,3-dihydrospiro[furo[2,3-g][1,4]benzodioxine-8,3'-indol]-2'(1'H)-one | C |
| 11.103 | 1'-{[4-(1-methylethyl)morpholin-2-yl]methyl}-2,3-dihydrospiro[furo[2,3-g][1,4]benzodioxine-8,3'-indol]-2'(1'H)-one | B |
| 11.104 | 1'-[(4-methylmorpholin-2-yl)methyl]-2,3-dihydrospiro[furo[2,3-g][1,4]benzodioxine-8,3'-indol]-2'(1'H)-one | B |
| 11.106 | (8S)-1'-{[(2S)-4-methylmorpholin-2-yl]methyl}-2,3-dihydrospiro[furo[2,3-g][1,4]benzodioxine-8,3'-indol]-2'(1'H)-one | A |
| 11.107 | 1'-{[3-(trifluoromethyl)pyridin-2-yl]methyl}spiro[furo[3,2-e][2,1,3]benzoxadiazole-8,3'-indol]-2'(1'H)-one | C |
| 11.108 | 6-chloro-1'-{[3-(trifluoromethyl)pyridin-2-yl]methyl}-2,3-dihydrospiro[furo[3,2-f][1,4]benzodioxine-9,3'-indol]-2'(1'H)-one | C |
| 11.109 | 1'-{[3-(trifluoromethyl)pyridin-2-yl]methyl}-2,3-dihydrospiro[furo[3,2-f][1,4]benzodioxine-9,3'-indol]-2'(1'H)-one | C |
| 11.110 | 1'-{[5-(difluoromethyl)furan-2-yl]methyl}-2,3-dihydrospiro[furo[2,3-g][1,4]benzodioxine-8,3'-indol]-2'(1'H)-one | A |
| 11.111 | 5,6-difluoro-1'-(piperidin-4-ylmethyl)spiro[1-benzofuran-3,3'-indol]-2'(1'H)-one hydrochloride | A |
| 11.112 | 5,6-difluoro-1'-[(1-methylpiperidin-4-yl)methyl]spiro[1-benzofuran-3,3'-indol]-2'(1'H)-one hydrochloride | A |
| 12 | N-(cyclohexylmethyl)-3-[(2'-oxo-5,6-dihydrospiro[benzo[1,2-b:5,4-b']difuran-3,3'-indol]-1'(2'H)-yl)methyl]benzamide | B |

TABLE 2-continued

| Ex. No. | Compound Name | IC$_{50}$ |
|---|---|---|
| 12.1 | N-(2-methoxyethyl)-3-[(2'-oxo-5,6-dihydrospiro[benzo[1,2-b:5,4-b']difuran-3,3'-indol]-1'(2'H)-yl)methyl]benzamide | B |
| 12.2 | N-hexyl-N-methyl-3-[(2'-oxo-5,6-dihydrospiro[benzo[1,2-b:5,4-b']difuran-3,3'-indol]-1'(2'H)-yl)methyl]benzamide | B |
| 12.3 | N-(2-ethylbutyl)-3-[(2'-oxo-5,6-dihydrospiro[benzo[1,2-b:5,4-b']difuran-3,3'-indol]-1'(2'H)-yl)methyl]benzamide | B |
| 12.4 | N-(2,4-dimethylphenyl)-3-[(2'-oxo-5,6-dihydrospiro[benzo[1,2-b:5,4-b']difuran-3,3'-indol]-1'(2'H)-yl)methyl]benzamide | B |
| 12.5 | 3-[(2'-oxo-5,6-dihydrospiro[benzo[1,2-b:5,4-b']difuran-3,3'-indol]-1'(2'H)-yl)methyl]-N-(2-phenylpropyl)benzamide | B |
| 12.6 | N-[(1S)-1-cyclohexylethyl]-3-[(2'-oxo-5,6-dihydrospiro[benzo[1,2-b:5,4-b']difuran-3,3'-indol]-1'(2'H)-yl)methyl]benzamide | B |
| 12.7 | N-[(1R)-1-cyclohexylethyl]-3-[(2'-oxo-5,6-dihydrospiro[benzo[1,2-b:5,4-b']difuran-3,3'-indol]-1'(2'H)-yl)methyl]benzamide | C |
| 12.8 | N-(4-ethylphenyl)-2-[(2'-oxo-5,6-dihydrospiro[benzo[1,2-b:5,4-b']difuran-3,3'-indol]-1'(2'H)-yl)methyl]benzamide | D |
| 12.9 | N-(2-ethylphenyl)-2-[(2'-oxo-5,6-dihydrospiro[benzo[1,2-b:5,4-b']difuran-3,3'-indol]-1'(2'H)-yl)methyl]benzamide | C |
| 12.10 | N-(2,4-dimethylphenyl)-2-[(2'-oxo-5,6-dihydrospiro[benzo[1,2-b:5,4-b']difuran-3,3'-indol]-1'(2'H)-yl)methyl]benzamide | C |
| 12.11 | N-(2-methoxyphenyl)-2-[(2'-oxo-5,6-dihydrospiro[benzo[1,2-b:5,4-b']difuran-3,3'-indol]-1'(2'H)-yl)methyl]benzamide | C |
| 12.12 | N-(2-fluorophenyl)-2-[(2'-oxo-5,6-dihydrospiro[benzo[1,2-b:5,4-b']difuran-3,3'-indol]-1'(2'H)-yl)methyl]benzamide | B |
| 12.13 | N-(3-chlorophenyl)-2-[(2'-oxo-5,6-dihydrospiro[benzo[1,2-b:5,4-b']difuran-3,3'-indol]-1'(2'H)-yl)methyl]benzamide | C |
| 12.14 | N-(3-fluoro-2-methylphenyl)-2-[(2'-oxo-5,6-dihydrospiro[benzo[1,2-b:5,4-b']difuran-3,3'-indol]-1'(2'H)-yl)methyl]benzamide | B |
| 12.15 | N-heptyl-2-[(2'-oxo-5,6-dihydrospiro[benzo[1,2-b:5,4-b']difuran-3,3'-indol]-1'(2'H)-yl)methyl]benzamide | C |
| 12.16 | N-(2-chlorobenzyl)-2-[(2'-oxo-5,6-dihydrospiro[benzo[1,2-b:5,4-b']difuran-3,3'-indol]-1'(2'H)-yl)methyl]benzamide | B |
| 12.17 | 1'-[2-(piperidin-1-ylcarbonyl)benzyl]-5,6-dihydrospiro[benzo[1,2-b:5,4-b']difuran-3,3'-indol]-2'(1'H)-one | C |
| 12.18 | N-butyl-2-[(2'-oxo-5,6-dihydrospiro[benzo[1,2-b:5,4-b']difuran-3,3'-indol]-1'(2'H)-yl)methyl]benzamide | C |
| 12.19 | N-(3-methylphenyl)-2-[(2'-oxo-5,6-dihydrospiro[benzo[1,2-b:5,4-b']difuran-3,3'-indol]-1'(2'H)-yl)methyl]benzamide | C |
| 12.20 | N-(2-fluoro-5-methylphenyl)-2-[(2'-oxo-5,6-dihydrospiro[benzo[1,2-b:5,4-b']difuran-3,3'-indol]-1'(2'H)-yl)methyl]benzamide | C |
| 12.21 | N-(2,3-dimethylphenyl)-2-[(2'-oxo-5,6-dihydrospiro[benzo[1,2-b:5,4-b']difuran-3,3'-indol]-1'(2'H)-yl)methyl]benzamide | C |
| 12.22 | N-[2-(4-methoxyphenyl)ethyl]-2-[(2'-oxo-5,6-dihydrospiro[benzo[1,2-b:5,4-b']difuran-3,3'-indol]-1'(2'H)-yl)methyl]benzamide | C |
| 12.23 | N-(3-chlorobenzyl)-2-[(2'-oxo-5,6-dihydrospiro[benzo[1,2-b:5,4-b']difuran-3,3'-indol]-1'(2'H)-yl)methyl]benzamide | C |
| 12.24 | N-[2-(4-chlorophenyl)ethyl]-2-[(2'-oxo-5,6-dihydrospiro[benzo[1,2-b:5,4-b']difuran-3,3'-indol]-1'(2'H)-yl)methyl]benzamide | C |
| 12.25 | N-(2-methoxyphenyl)-4-[(2'-oxo-5,6-dihydrospiro[benzo[1,2-b:5,4-b']difuran-3,3'-indol]-1'(2'H)-yl)methyl]benzamide | C |
| 12.26 | 4-[(2'-oxo-5,6-dihydrospiro[benzo[1,2-b:5,4-b']difuran-3,3'-indol]-1'(2'H)-yl)methyl]-N-[2-(trifluoromethyl)phenyl]benzamide | C |
| 12.27 | 4-[(2'-oxo-5,6-dihydrospiro[benzo[1,2-b:5,4-b']difuran-3,3'-indol]-1'(2'H)-yl)methyl]-N-phenylbenzamide | B |

TABLE 2-continued

| Ex. No. | Compound Name | IC$_{50}$ |
|---|---|---|
| 12.28 | N-methyl-4-[(2'-oxo-5,6-dihydrospiro[benzo[1,2-b:5,4-b']difuran-3,3'-indol]-1'(2'H)-yl)methyl]benzamide | B |
| 12.29 | N-(2-fluorophenyl)-4-[(2'-oxo-5,6-dihydrospiro[benzo[1,2-b:5,4-b']difuran-3,3'-indol]-1'(2'H)-yl)methyl]benzamide | B |
| 12.30 | 4-[(2'-oxo-5,6-dihydrospiro[benzo[1,2-b:5,4-b']difuran-3,3'-indol]-1'(2'H)-yl)methyl]-N-(2-thiophen-2-ylethyl)benzamide | B |
| 12.31 | 4-[(2'-oxo-5,6-dihydrospiro[benzo[1,2-b:5,4-b']difuran-3,3'-indol]-1'(2'H)-yl)methyl]benzamide | A |
| 12.32 | N-(2,3-dihydro-1H-inden-5-yl)-4-[(2'-oxo-5,6-dihydrospiro[benzo[1,2-b:5,4-b']difuran-3,3'-indol]-1'(2'H)-yl)methyl]benzamide | C |
| 12.33 | 1'-[4-(morpholin-4-ylcarbonyl)benzyl]-5,6-dihydrospiro[benzo[1,2-b:5,4-b']difuran-3,3'-indol]-2'(1'H)-one | C |
| 12.34 | N-(2-ethylphenyl)-4-[(2'-oxo-5,6-dihydrospiro[benzo[1,2-b:5,4-b']difuran-3,3'-indol]-1'(2'H)-yl)methyl]benzamide | C |
| 12.35 | N-(2,6-dimethylphenyl)-4-[(2'-oxo-5,6-dihydrospiro[benzo[1,2-b:5,4-b']difuran-3,3'-indol]-1'(2'H)-yl)methyl]benzamide | C |
| 12.36 | N-(3-fluorophenyl)-4-[(2'-oxo-5,6-dihydrospiro[benzo[1,2-b:5,4-b']difuran-3,3'-indol]-1'(2'H)-yl)methyl]benzamide | B |
| 12.37 | N-(2,4-dimethylphenyl)-4-[(2'-oxo-5,6-dihydrospiro[benzo[1,2-b:5,4-b']difuran-3,3'-indol]-1'(2'H)-yl)methyl]benzamide | B |
| 12.38 | 4-[(2'-oxo-5,6-dihydrospiro[benzo[1,2-b:5,4-b']difuran-3,3'-indol]-1'(2'H)-yl)methyl]-N-(thiophen-2-ylmethyl)benzamide | B |
| 12.39 | N-ethyl-4-[(2'-oxo-5,6-dihydrospiro[benzo[1,2-b:5,4-b']difuran-3,3'-indol]-1'(2'H)-yl)methyl]benzamide | B |
| 12.40 | N-(2-methoxyethyl)-4-[(2'-oxo-5,6-dihydrospiro[benzo[1,2-b:5,4-b']difuran-3,3'-indol]-1'(2'H)-yl)methyl]benzamide | B |
| 12.41 | N-(2-ethoxyethyl)-4-[(2'-oxo-5,6-dihydrospiro[benzo[1,2-b:5,4-b']difuran-3,3'-indol]-1'(2'H)-yl)methyl]benzamide | B |
| 12.42 | N-cyclobutyl-4-[(2-oxo-5,6-dihydrospiro[benzo[1,2-b:5,4-b']difuran-3,3-indol]-1(2H)-yl)methyl]benzamide | B |
| 12.43 | 4-[(2'-oxo-5,6-dihydrospiro[benzo[1,2-b:5,4-b']difuran-3,3'-indol]-1'(2'H)-yl)methyl]-N-1,3-thiazol-2-ylbenzamide | B |
| 12.44 | N-(3-fluoro-2-methylphenyl)-4-[(2'-oxo-5,6-dihydrospiro[benzo[1,2-b:5,4-b']difuran-3,3'-indol]-1'(2'H)-yl)methyl]benzamide | C |
| 12.45 | N-(2-ethylbutyl)-4-[(2'-oxo-5,6-dihydrospiro[benzo[1,2-b:5,4-b']difuran-3,3'-indol]-1'(2'H)-yl)methyl]benzamide | C |
| 12.46 | 2-(2'-oxo-5,6-dihydrospiro[benzo[1,2-b:5,4-b']difuran-3,3'-indol]-1'(2'H)-yl)acetamide | C |
| 12.47 | N-(4-ethylphenyl)-2-(2'-oxo-5,6-dihydrospiro[benzo[1,2-b:5,4-b']difuran-3,3'-indol]-1'(2'H)-yl)acetamide | C |
| 12.48 | N,N-diethyl-2-(2'-oxo-5,6-dihydrospiro[benzo[1,2-b:5,4-b']difuran-3,3'-indol]-1'(2'H)-yl)acetamide | B |
| 12.49 | N-(3,3-dimethylbutyl)-2-(2'-oxo-5,6-dihydrospiro[benzo[1,2-b:5,4-b']difuran-3,3'-indol]-1'(2'H)-yl)acetamide | B |
| 12.50 | N-[3-(1-methylethoxy)propyl]-2-(2'-oxo-5,6-dihydrospiro[benzo[1,2-b:5,4-b']difuran-3,3'-indol]-1'(2'H)-yl)acetamide | B |
| 12.51 | 2-(2'-oxo-5,6-dihydrospiro[benzo[1,2-b:5,4-b']difuran-3,3'-indol]-1'(2'H)-yl)-N-propylacetamide | B |
| 12.52 | N-methyl-2-(2'-oxo-5,6-dihydrospiro[benzo[1,2-b:5,4-b']difuran-3,3'-indol]-1'(2'H)-yl)-N-phenylacetamide | B |
| 12.53 | N-(2,5-dimethylphenyl)-2-(2'-oxo-5,6-dihydrospiro[benzo[1,2-b:5,4-b']difuran-3,3'-indol]-1'(2'H)-yl)acetamide | C |
| 12.54 | N-(2,4-dimethylphenyl)-2-(2'-oxo-5,6-dihydrospiro[benzo[1,2-b:5,4-b']difuran-3,3'-indol]-1'(2'H)-yl)acetamide | C |
| 12.55 | N-(2,3-dimethylphenyl)-2-(2'-oxo-5,6-dihydrospiro[benzo[1,2-b:5,4-b']difuran-3,3'-indol]-1'(2'H)-yl)acetamide | C |
| 12.56 | N-(2,6-dimethylphenyl)-2-(2'-oxo-5,6-dihydrospiro[benzo[1,2-b:5,4-b']difuran-3,3'-indol]-1'(2'H)-yl)acetamide | C |
| 12.57 | N-methyl-5-[(2'-oxospiro[furo[2,3-f][1,3]benzodioxole-7,3'-indol]-1'(2'H)-yl)methyl]-2-(trifluoromethyl)furan-3-carboxamide | B |

TABLE 2-continued

| Ex. No. | Compound Name | IC$_{50}$ |
|---|---|---|
| 12.58 | 5-[(2'-oxospiro[furo[2,3-f][1,3]benzodioxole-7,3'-indol]-1'(2'H)-yl)methyl]-2-(trifluoromethyl)furan-3-carboxamide | A |
| 12.59 | N,N-dimethyl-5-[(2'-oxospiro[furo[2,3-f][1,3]benzodioxole-7,3'-indol]-1'(2'H)-yl)methyl]-2-(trifluoromethyl)furan-3-carboxamide | B |
| 12.60 | 4-[(2'-oxo-2,3-dihydrospiro[furo[2,3-g][1,4]benzodioxine-8,3'-indol]-1'(2'H)-yl)methyl]benzamide | A |
| 12.61 | 3-[(2'-oxo-2,3-dihydrospiro[furo[2,3-g][1,4]benzodioxine-8,3'-indol]-1'(2'H)-yl)methyl]benzamide | B |
| 12.62 | N,N-dimethyl-3-[(2'-oxo-2,3-dihydrospiro[furo[2,3-g][1,4]benzodioxine-8,3'-indol]-1'(2'H)-yl)methyl]benzamide | B |
| 12.63 | N-methyl-2-[(2'-oxo-2,3-dihydrospiro[furo[2,3-g][1,4]benzodioxine-8,3'-indol]-1'(2'H)-yl)methyl]pyridine-3-carboxamide | C |
| 12.64 | N-(2-aminoethyl)-2-[(2'-oxo-2,3-dihydrospiro[furo[2,3-g][1,4]benzodioxine-8,3'-indol]-1'(2'H)-yl)methyl]pyridine-3-carboxamide dihydrochloride | B |
| 12.65 | N-(2-fluorophenyl)-4-[(2'-oxo-2,3-dihydrospiro[furo[2,3-g][1,4]benzodioxine-8,3'-indol]-1'(2'H)-yl)methyl]benzamide | B |
| 13 | 5-[(2'-oxo-5,6-dihydrospiro[benzo[1,2-b:5,4-b']difuran-3,3'-indol]-1'(2'H)-yl)methyl]furan-2-carboxylic acid | C |
| 13.1 | N,N-dimethyl-5-[(2'-oxo-5,6-dihydrospiro[benzo[1,2-b:5,4-b']difuran-3,3'-indol]-1'(2'H)-yl)methyl]furan-2-carboxamide | A |
| 13.2 | N-methyl-5-[(2'-oxo-5,6-dihydrospiro[benzo[1,2-b:5,4-b']difuran-3,3'-indol]-1'(2'H)-yl)methyl]furan-2-carboxamide | B |
| 13.3 | 2-[(2'-oxo-5,6-dihydrospiro[benzo[1,2-b:5,4-b']difuran-3,3'-indol]-1'(2'H)-yl)methyl]-1,3-oxazole-4-carboxamide | B |
| 13.4 | N,N-dimethyl-2-[(2'-oxo-5,6-dihydrospiro[benzo[1,2-b:5,4-b']difuran-3,3'-indol]-1'(2'H)-yl)methyl]-1,3-oxazole-4-carboxamide | B |
| 13.5 | N-cyclopropyl-2-[(2'-oxospiro[furo[2,3-f][1,3]benzodioxole-7,3'-indol]-1'(2'H)-yl)methyl]-1,3-oxazole-4-carboxamide | A |
| 13.6 | N-(1-methylethyl)-2-[(2'-oxospiro[furo[2,3-f][1,3]benzodioxole-7,3'-indol]-1'(2'H)-yl)methyl]-1,3-oxazole-4-carboxamide | A |
| 13.7 | N-(2-fluorophenyl)-2-(2'-oxo-2,3-dihydrospiro[furo[2,3-g][1,4]benzodioxine-8,3'-indol]-1'(2'H)-yl)acetamide | A |
| 13.11 | N-[3-(2'-oxo-5,6-dihydrospiro[benzo[1,2-b:5,4-b']difuran-3,3'-indol]-1'(2'H)-yl)propyl]-2-(trifluoromethoxy)benzamide | B |
| 14 | 1'-[(2S)-2-hydroxypropyl]-5,6-dihydrospiro[benzo[1,2-b:5,4-b']difuran-3,3'-indol]-2'(1'H)-one | B |
| 14.1 | 1'-[(2S)-2-(benzyloxy)propyl]-5,6-dihydrospiro[benzo[1,2-b:5,4-b']difuran-3,3'-indol]-2'(1'H)-one | B |
| 14.2 | 1'-{(2S)-2-[(4-fluorobenzyl)oxy]propyl}-5,6-dihydrospiro[benzo[1,2-b:5,4-b']difuran-3,3'-indol]-2'(1'H)-one | B |
| 14.3 | 1'-[(2S)-2-(pyridin-2-ylmethoxy)propyl]-5,6-dihydrospiro[benzo[1,2-b:5,4-b']difuran-3,3'-indol]-2'(1'H)-one | C |
| 14.4 | 1'-(3-hydroxybutyl)-5,6-dihydrospiro[benzo[1,2-b:5,4-b']difuran-3,3'-indol]-2'(1'H)-one | B |
| 14.5 | 1'-(4,4,4-trifluoro-3-hydroxybutyl)-5,6-dihydrospiro[benzo[1,2-b:5,4-b']difuran-3,3'-indol]-2'(1'H)-one | B |
| 15.1 | 1'-{3-[(3-methylbutyl)amino]propyl}-5,6-dihydrospiro[benzo[1,2-b:5,4-b']difuran-3,3'-indol]-2'(1'H)-one hydrochloride | C |
| 15.2 | 1'-{3-[butyl(methyl)amino]propyl}-5,6-dihydrospiro[benzo[1,2-b:5,4-b']difuran-3,3'-indol]-2'(1'H)-one hydrochloride | C |
| 15.3 | 1'-{3-[(2,2,2-trifluoroethyl)amino]propyl}-5,6-dihydrospiro[benzo[1,2-b:5,4-b']difuran-3,3'-indol]-2'(1'H)-one hydrochloride | B |
| 15.4 | 3-{[3-(2'-oxo-5,6-dihydrospiro[benzo[1,2-b:5,4-b']difuran-3,3'-indol]-1'(2'H)-yl)propyl]amino}propanenitrile hydrochloride | B |
| 16 | 4'-[6-(dimethylamino)pyridin-3-yl]-1'-[(2R)-tetrahydrofuran-2-ylmethyl]-5,6-dihydrospiro[benzo[1,2-b:5,4-b']difuran-3,3'-indol]-2'(1'H)-one | B |

TABLE 2-continued

| Ex. No. | Compound Name | IC$_{50}$ |
|---|---|---|
| 16.1 | 4'-[(E)-2-(4-fluorophenyl)ethenyl]-1'-[(2R)-tetrahydrofuran-2-ylmethyl]-5,6-dihydrospiro[benzo[1,2-b:5,4-b']difuran-3,3'-indol]-2'(1'H)-one | B |
| 16.2 | 4'-dibenzo[b,d]thiophen-4-yl-1'-[(2R)-tetrahydrofuran-2-ylmethyl]-5,6-dihydrospiro[benzo[1,2-b:5,4-b']difuran-3,3'-indol]-2'(1'H)-one | B |
| 16.3 | 4'-(1-benzothiophen-3-yl)-1'-[(2R)-tetrahydrofuran-2-ylmethyl]-5,6-dihydrospiro[benzo[1,2-b:5,4-b']difuran-3,3'-indol]-2'(1'H)-one | C |
| 16.4 | 4'-(1-methyl-1H-indol-5-yl)-1'-[(2R)-tetrahydrofuran-2-ylmethyl]-5,6-dihydrospiro[benzo[1,2-b:5,4-b']difuran-3,3'-indol]-2'(1'H)-one | B |
| 16.5 | 4'-[3,5-bis(trifluoromethyl)phenyl]-1'-[(2R)-tetrahydrofuran-2-ylmethyl]-5,6-dihydrospiro[benzo[1,2-b:5,4-b']difuran-3,3'-indol]-2'(1'H)-one | B |
| 16.6 | 4'-(4-phenoxyphenyl)-1'-[(2R)-tetrahydrofuran-2-ylmethyl]-5,6-dihydrospiro[benzo[1,2-b:5,4-b']difuran-3,3'-indol]-2'(1'H)-one | B |
| 16.7 | 4'-[4-(2-methylpropoxy)phenyl]-1'-[(2R)-tetrahydrofuran-2-ylmethyl]-5,6-dihydrospiro[benzo[1,2-b:5,4-b']difuran-3,3'-indol]-2'(1'H)-one | B |
| 16.8 | 4'-(4-butoxyphenyl)-1'-[(2R)-tetrahydrofuran-2-ylmethyl]-5,6-dihydrospiro[benzo[1,2-b:5,4-b']difuran-3,3'-indol]-2'(1'H)-one | B |
| 16.9 | 4'-(4-methoxyphenyl)-1'-[(2R)-tetrahydrofuran-2-ylmethyl]-5,6-dihydrospiro[benzo[1,2-b:5,4-b']difuran-3,3'-indol]-2'(1'H)-one | A |
| 16.10 | 4'-pyrimidin-5-yl-1'-[(2R)-tetrahydrofuran-2-ylmethyl]-5,6-dihydrospiro[benzo[1,2-b:5,4-b']difuran-3,3'-indol]-2'(1'H)-one | C |
| 16.11 | 4'-[6-(dimethylamino)pyridin-3-yl]-1'-{[5-(trifluoromethyl)furan-2-yl]methyl}-5,6-dihydrospiro[benzo[1,2-b:5,4-b']difuran-3,3'-indol]-2'(1'H)-one | B |
| 16.12 | 1'-[(5-chloro-2-thienyl)methyl]-4'-[6-(dimethylamino)pyridin-3-yl]spiro[furo[2,3-f][1,3]benzodioxole-7,3'-indol]-2'(1'H)-one | B |
| 16.13 | 1'-[(5-chloro-2-thienyl)methyl]-4'-(3-furyl)spiro[furo[2,3-f][1,3]benzodioxole-7,3'-indol]-2'(1'H)-one | B |
| 16.14 | 4'-[6-(dimethylamino)pyridin-3-yl]spiro[furo[2,3-f][1,3]benzodioxole-7,3'-indol]-2'(1'H)-one | C |
| 16.59 | 4'-(6-(dimethylamino)pyridin-3-yl)-1'-(pyridin-2-ylmethyl)-3,7-dihydro-2H-spiro[benzofuro[5,6-b][1,4]dioxine-8,3'-indolin]-2'-one | B |
| 16.60 | 4'-(4-methoxyphenyl)-1'-(pyridin-2-ylmethyl)-3,7-dihydro-2H-spiro[benzofuro[5,6-b][1,4]dioxine-8,3'-indolin]-2'-one | A |
| 16.61 | (7S)-4'-furan-3-yl-1'-methylspiro[furo[2,3-f][1,3]benzodioxole-7,3'-indol]-2'(1'H)-one | A |
| 16.62 | (7R)-4'-furan-3-yl-1'-methylspiro[furo[2,3-f][1,3]benzodioxole-7,3'-indol]-2'(1'H)-one | B |
| 16.88 | 1'-[(5-chloro-2-thienyl)methyl]-5-(6-methoxypyridin-3-yl)spiro[1-benzofuran-3,3'-indol]-2'(1'H)-one | C |
| 17 | 1'-(4-hydroxybenzyl)-5,6-dihydrospiro[benzo[1,2-b:5,4-b']difuran-3,3'-indol]-2'(1'H)-one | A |
| 17.1 | 1'-(4-hydroxybenzyl)-2,3-dihydrospiro[furo[2,3-g][1,4]benzodioxine-8,3'-indol]-2'(1'H)-one | A |
| 17.2 | 1'-(3-hydroxypropyl)-2,3-dihydrospiro[furo[2,3-g][1,4]benzodioxine-8,3'-indol]-2'(1'H)-one | A |
| 18 | ethyl 2'-oxo-2,3-dihydrospiro[furo[2,3-g][1,4]benzodioxine-8,3'-indole]-1'(2'H)-carboxylate | A |
| 18.1 | tert-butyl 4'-bromo-2'-oxospiro[furo[2,3-f][1,3]benzodioxole-7,3'-indole]-1'(2'H)-carboxylate | A |
| 18.2 | tert-butyl 2'-oxo-2,3-dihydrospiro[furo[2,3-g][1,4]benzodioxine-8,3'-indole]-1'(2'H)-carboxylate | B |
| 19 | 1'-{[(3aR,5R,5aS,8aS,8bR)-2,2,7,7-tetramethyltetrahydro-3aH-bis[1,3]dioxolo[4,5-b:4',5'-d]pyran-5-yl]methyl}-2,3-dihydrospiro[furo[2,3-g][1,4]benzodioxine-8,3'-indol]-2'(1'H)-one | C |
| 20 | 6-deoxy-6-(2'-oxo-2,3-dihydrospiro[furo[2,3-g][1,4]benzodioxine-8,3'-indol]-1'(2'H)-yl)-D-galactopyranose | C |
| 21 | 1'-cyclopropyl-2,3-dihydrospiro[furo[2,3-g][1,4]benzodioxine-8,3'-indol]-2'(1'H)-one | A |
| 22 | 1'-acetyl-2,3-dihydrospiro[furo[2,3-g][1,4]benzodioxine-8,3'-indol]-2'(1'H)-one | A |
| 23 | 1'-{[4-(trifluoromethyl)pyridin-2-yl]methyl}-2,3-dihydrospiro[furo[2,3-g][1,4]benzodioxine-8,3'-indol]-2'(1'H)-one | A |

TABLE 2-continued

| Ex. No. | Compound Name | IC$_{50}$ |
|---|---|---|
| 28 | 1'-[3-(3-methyl-1,2,4-oxadiazol-5-yl)benzyl]-2,3-dihydrospiro[furo[2,3-g][1,4]benzodioxine-8,3'-indol]-2'(1'H)-one | A |
| 29.1 | 1'-[4-(3-amino-1H-pyrazol-5-yl)benzyl]-3-methylspiro[furo[3,2-f][1,2]benzisoxazole-5,3'-indol]-2'(1'H)-one hydrochloride | B |
| 29.2 | 1'-[4-(3-amino-1H-pyrazol-5-yl)benzyl]-2,3-dihydrospiro[furo[2,3-g][1,4]benzodioxine-8,3'-indol]-2'(1'H)-one hydrochloride | B |
| 30 | 1'-[4-(3-methyl-1,2,4-oxadiazol-5-yl)benzyl]-2,3-dihydrospiro[furo[2,3-g][1,4]benzodioxine-8,3'-indol]-2'(1'H)-one | A |
| 31 | 2'-oxo-1'-(pyridin-2-ylmethyl)-1',2,2',3-tetrahydrospiro[furo[2,3-g][1,4]benzodioxine-8,3'-indole]-5'-carboxamide | B |
| 32 | 1'-[(6-morpholin-4-ylpyridin-3-yl)methyl]-2,3-dihydrospiro[furo[2,3-g][1,4]benzodioxine-8,3'-indol]-2'(1'H)-one | A |
| 32.1 | 1'-{[6-(dimethylamino)pyridin-3-yl]methyl}-2,3-dihydrospiro[furo[2,3-g][1,4]benzodioxine-8,3'-indol]-2'(1'H)-one | A |
| 32.2 | 1'-{[6-(dimethylamino)pyridin-2-yl]methyl}-2,3-dihydrospiro[furo[2,3-g][1,4]benzodioxine-8,3'-indol]-2'(1'H)-one | A |
| 33.2 | 5,6-difluoro-1'-{4-[(3R)-pyrrolidin-3-ylamino]benzyl}spiro[1-benzofuran-3,3'-indol]-2'(1'H)-one hydrochloride | C |
| 33.3 | 1'-[(5-morpholin-4-ylpyridin-2-yl)methyl]-2,3-dihydrospiro[furo[2,3-g][1,4]benzodioxine-8,3'-indol]-2'(1'H)-one | B |
| 33.4 | 1'-{[5-(dimethylamino)pyridin-2-yl]methyl}-2,3-dihydrospiro[furo[2,3-g][1,4]benzodioxine-8,3'-indol]-2'(1'H)-one | A |
| 35 | 1'-[(6-oxo-1,6-dihydropyridin-3-yl)methyl]-2,3-dihydrospiro[furo[2,3-g][1,4]benzodioxine-8,3'-indol]-2'(1'H)-one | B |
| 35.1 | 1'-[(2-hydroxypyrimidin-5-yl)methyl]-2,3-dihydrospiro[furo[2,3-g][1,4]benzodioxine-8,3'-indol]-2'(1'H)-one | C |
| 36 | 1'-[(1-methyl-6-oxo-1,6-dihydropyridin-3-yl)methyl]-2,3-dihydrospiro[furo[2,3-g][1,4]benzodioxine-8,3'-indol]-2'(1'H)-one | B |
| 37 | 1'-[(6-aminopyridin-3-yl)methyl]-2,3-dihydrospiro[furo[2,3-g][1,4]benzodioxine-8,3'-indol]-2'(1'H)-one | A |
| 38 | N'-hydroxy-N-{5-[(2'-oxo-2,3-dihydrospiro[furo[2,3-g][1,4]benzodioxine-8,3'-indol]-1'(2'H)-yl)methyl]pyridin-2-yl}imidoformamide | A |
| 39 | 1'-([1,2,4]triazolo[1,5-a]pyridin-6-ylmethyl)-2,3-dihydrospiro[furo[2,3-g][1,4]benzodioxine-8,3'-indol]-2'(1'H)-one | A |
| 40 | 1'-[(2S)-2,3-dihydroxypropyl]-2,3-dihydrospiro[furo[2,3-g][1,4]benzodioxine-8,3'-indol]-2'(1'H)-one | B |
| 41 | 6-[(2'-oxo-2,3-dihydrospiro[furo[2,3-g][1,4]benzodioxine-8,3'-indol]-1'(2'H)-yl)methyl]pyridine-2-carbonitrile | A |
| 42 | 6-[(2'-oxo-2,3-dihydrospiro[furo[2,3-g][1,4]benzodioxine-8,3'-indol]-1'(2'H)-yl)methyl]pyridine-2-carboxamide | A |
| 44 | 3-amino-1'-(4-methoxybenzyl)spiro[furo[3,2-f][1,2]benzisoxazole-5,3'-indol]-2'(1'H)-one | B |
| 44.1 | 3-amino-1'-(pyridin-2-ylmethyl)spiro[furo[3,2-f][1,2]benzisoxazole-5,3'-indol]-2'(1'H)-one | B |
| 44.2 | 3-amino-1'-[(2R)-tetrahydrofuran-2-ylmethyl]spiro[furo[3,2-f][1,2]benzisoxazole-5,3'-indol]-2'(1'H)-one | C |
| 44.3 | 3-amino-1'-[2-(trifluoromethyl)benzyl]spiro[furo[3,2-f][1,2]benzisoxazole-5,3'-indol]-2'(1'H)-one | C |
| 45 | 6-hydroxy-2'-oxo-1'-[(2R)-tetrahydrofuran-2-ylmethyl]-1',2'-dihydrospiro[1-benzofuran-3,3'-indole]-5-carbonitrile | C |
| 45.1 | 6-hydroxy-2'-oxo-1'-[2-(trifluoromethyl)benzyl]-1',2'-dihydrospiro[1-benzofuran-3,3'-indole]-5-carbonitrile | C |
| 46 | 1'-[2-(trifluoromethyl)benzyl]-1H-spiro[furo[3,2-f]indazole-5,3'-indol]-2'(1'H)-one | C |
| 46.1 | 1'-(pyridin-2-ylmethyl)-1H-spiro[furo[3,2-f]indazole-5,3'-indol]-2'(1'H)-one | B |
| 46.2 | 1'-((3-(trifluoromethyl)pyridin-2-yl)methyl)-1,6-dihydrospiro[furo[3,2-f]indazole-5,3'-indolin]-2'-one | B |

Biological Example 2

Electrophysiological Assay (In Vitro Assay)

Cells expressing the channel of interest are cultured in DMEM growth media (Gibco) with 0.5 mg/mL G418, +/−1% PSG, and 10% heat-inactivated fetal bovine serum at 37° C. and 5% $CO_2$. For electrophysiological recordings, cells are plated on 10 mm dishes.

Whole cell recordings are examined by established methods of whole cell voltage clamp (Bean et al., op. cit.) using an Axopatch 200B amplifier and Clampex software (Axon Instruments, Union City, Calif.). All experiments are performed at ambient temperature. Electrodes are fire-polished to resistances of 2-4 Mohms Voltage errors and capacitance artifacts are minimized by series resistance compensation and capacitance compensation, respectively. Data are acquired at 40 kHz and filtered at 5 kHz. The external (bath) solution consists of: NaCl (140 mM), KCl (5 mM), $CaCl_2$ (2 mM), $MgCl_2$ (1 mM), HEPES (10 mM) at pH 7.4. The internal (pipette) solution consists of (in mM): NaCl (5), $CaCl_2$ (0.1), $MgCl_2$ (2), CsCl (10), CsF (120), HEPES (10), EGTA (10), at pH 7.2.

To estimate the steady-state affinity of compounds for the resting and inactivated state of the channel ($K_r$ and $K_i$, respectively), 12.5 ms test pulses to depolarizing voltages from −60 to +90 mV from a holding potential of −120 mV is used to construct current-voltage relationships (I-V curves). A voltage near the peak of the IV-curve (−30 to 0 mV) is used as the test pulse throughout the remainder of the experiment. Steady-state inactivation (availability) curves are then constructed by measuring the current activated during a 8.75 ms test pulse following 1 second conditioning pulses to potentials ranging from −120 to −10 mV.

The steady-state voltage-dependence of binding of a compound to a sodium channel is determined by measuring the blockage of the ionic current at two holding potentials. Binding to rested-state channels is determined by using a holding potential of −120 mV, so that maximal availability is achieved. Binding to inactivated-state channels is evaluated at a holding potential such that only 10% of the channels are available to open. The membrane potential is held at this voltage for at least 10 seconds so that drug binding can equilibrate.

The apparent dissociation constant at each voltage is calculated with the equation:

$$\% \text{ inhibition} = \frac{[\text{Drug}]}{([\text{Drug}] + K_d)}$$

where $K_d$ is the dissociation constant (either $K_r$ or $K_i$), and [Drug] is the concentration of the test compound.

Representative compounds of the invention, when tested in this model, demonstrated affinities for the inactivated state of the channel of interest as set forth below in Table 3 wherein "A" refers to $K_i$ of less than 300 nM and "B" refers to $K_i$ of greater than 300 nM. The Example numbers provided in Table 3 correspond to the Examples herein:

TABLE 3

| Ex. No. | Compound Name | $K_i$ (μM) |
|---|---|---|
| 1.2 | 1'-(pyridin-3-ylmethyl)-2,3-dihydrospiro[furo[2,3-g][1,4]benzodioxine-8,3'-indol]-2'(1'H)-one | B |
| 1.10 | (3S)-5,6-dihydrospiro[benzo[1,2-b:5,4-b']difuran-3,3'-indol]-2'(1'H)-one | A |
| 1.11 | (S)-2,3-dihydrospiro[furo[2,3-g][1,4]benzodioxine-8,3'-indol]-2'(1'H)-one | B |
| 1.12 | (8S)-1'-{[3-(trifluoromethyl)pyridin-2-yl]methyl}-2,3-dihydrospiro[furo[2,3-g][1,4]benzodioxine-8,3'-indol]-2'(1'H)-one | A |
| 1.13 | (8S)-1'-[(5-hydroxypyridin-2-yl)methyl]-2,3-dihydrospiro[furo[2,3-g][1,4]benzodioxine-8,3'-indol]-2'(1'H)-one | A |
| 2.27 | 6-((5-(trifluoromethyl)furan-2-yl)methyl)-2,3,3',7'-tetrahydro-2'H-spiro[[1,4]dioxino[2,3-f]indole-8,8'-benzofuro[5,6-b][1,4]dioxin]-7(6H)-one | A |
| 2.34 | 2,2-difluoro-1'-{[5-(trifluoromethyl)furan-2-yl]methyl}spiro[furo[2,3-f][1,3]benzodioxole-7,3'-indol]-2'(1'H)-one | B |
| 2.35 | 2,2-difluoro-1'-{[5-(trifluoromethyl)furan-2-yl]methyl}spiro[furo[2,3-f][1,3]benzodioxole-7,3'-indol]-2'(1'H)-one | B |
| 2.54 | 1'-{[3-(trifluoromethyl)pyridin-2-yl]methyl}-7,8-dihyrdospiro[1,4-dioxino[2,3-g][1,3]benzodioxine-4,3'-indol]-2'(1'H)-one | B |
| 2.65 | 6-[2-(2-methoxyethoxy)ethyl]-2,2',3,3'-tetrahydrospiro[1,4-dioxino[2,3-f]indole-8,8'-furo[2,3-g][1,4]benzodioxin]-7(6H)-one | B |
| 3 | 6-methoxy-5-methylspiro[1-benzofuran-3,3'-indol]-2'(1'H)-one | B |
| 3.29 | 6-methoxy-2'-oxo-1',2'-dihydrospiro[1-benzofuran-3,3'-indole]-5-carbonitrile | B |
| 3.33 | 4'-fluoro-2,3-dihydrospiro[furo[2,3-g][1,4]benzodioxine-8,3'-indol]-2'(1'H)-one | A |
| 3.34 | 4'-quinolin-3-yl-2,3-dihydrospiro[furo[2,3-g][1,4]benzodioxine-8,3'-indol]-2'(1'H)-one | B |
| 3.35 | 4'-(4-phenoxyphenyl)-2,3-dihydrospiro[furo[2,3-g][1,4]benzodioxine-8,3'-indol]-2'(1'H)-one | B |
| 3.41 | spiro[furo[3,2-e][2,1,3]benzoxadiazole-8,3'-indol]-2'(1'H)-one | B |
| 4 | 1'-(tetrahydro-2H-pyran-2-ylmethyl)-5,6-dihydrospiro[benzo[1,2-b:5,4-b']difuran-3,3'-indol]-2'(1'H)-one | B |

TABLE 3-continued

| Ex. No. | Compound Name | $K_i$ (μM) |
|---|---|---|
| 4.3 | 1'-[(2R)-tetrahydrofuran-2-ylmethyl]-5,6-dihydrospiro[benzo[1,2-b:5,4-b']difuran-3,3'-indol]-2'(1'H)-one | B |
| 4.6 | 1'-(tetrahydro-2H-pyran-4-ylmethyl)-5,6-dihydrospiro[benzo[1,2-b:5,4-b']difuran-3,3'-indol]-2'(1'H)-one | B |
| 4.8 | 1'-(1,4-dioxan-2-ylmethyl)-5,6-dihydrospiro[benzo[1,2-b:5,4-b']difuran-3,3'-indol]-2'(1'H)-one | B |
| 4.10 | 1'-(tetrahydro-2H-pyran-3-ylmethyl)-5,6-dihydrospiro[benzo[1,2-b:5,4-b']difuran-3,3'-indol]-2'(1'H)-one | B |
| 4.16 | 1'-(tetrahydrofuran-3-ylmethyl)-5,6-dihydrospiro[benzo[1,2-b:5,4-b']difuran-3,3'-indol]-2'(1'H)-one | B |
| 4.20 | 1'-(oxetan-2-ylmethyl)-5,6-dihydrospiro[benzo[1,2-b:5,4-b']difuran-3,3'-indol]-2'(1'H)-one | B |
| 4.22 | 3-[(2'-oxo-5,6-dihydrospiro[benzo[1,2-b:5,4-b']difuran-3,3'-indol]-1'(2'H)-yl)methyl]benzonitrile | B |
| 4.22 | 3-[(2'-oxo-5,6-dihydrospiro[benzo[1,2-b:5,4-b']difuran-3,3'-indol]-1'(2'H)-yl)methyl]benzonitrile | B |
| 4.27 | 1'-(2,1,3-benzoxadiazol-5-ylmethyl)-5,6-dihydrospiro[benzo[1,2-b:5,4-b']difuran-3,3'-indol]-2'(1'H)-one | B |
| 4.28 | 1'-(2,1,3-benzothiadiazol-5-ylmethyl)-5,6-dihydrospiro[benzo[1,2-b:5,4-b']difuran-3,3'-indol]-2'(1'H)-one | A |
| 4.29 | 1'-[(4-benzylmorpholin-2-yl)methyl]-5,6-dihydrospiro[benzo[1,2-b:5,4-b']difuran-3,3'-indol]-2'(1'H)-one | B |
| 4.36 | 1'-(3-methylbutyl)-2,3-dihydrospiro[furo[2,3-g][1,4]benzodioxine-8,3'-indol]-2'(1'H)-one | A |
| 4.38 | 1'-(tetrahydro-2H-pyran-2-ylmethyl)-2,3-dihydrospiro[furo[2,3-g][1,4]benzodioxine-8,3'-indol]-2'(1'H)-one | A |
| 4.43 | 1'-[(2S)-tetrahydrofuran-2-ylmethyl]-2,3-dihydrospiro[furo[2,3-g][1,4]benzodioxine-8,3'-indol]-2'(1'H)-one | B |
| 4.45 | 1'-(1,4-dioxan-2-ylmethyl)-2,3-dihydrospiro[furo[2,3-g][1,4]benzodioxine-8,3'-indol]-2'(1'H)-one | B |
| 4.48 | 1'-(2,3-dihydro-1,4-benzodioxin-6-ylmethyl)-2,3-dihydrospiro[furo[2,3-g][1,4]benzodioxine-8,3'-indol]-2'(1'H)-one | A |
| 4.49 | (R)-1'-{[5-(trifluoromethyl)furan-2-yl]methyl}-2,3-dihydrospiro[furo[2,3-g][1,4]benzodioxine-8,3'-indol]-2'(1'H)-one | A |
| 4.50 | (S)-1'-{[5-(trifluoromethyl)furan-2-yl]methyl}-2,3-dihydrospiro[furo[2,3-g][1,4]benzodioxine-8,3'-indol]-2'(1'H)-one | A |
| 4.51 | (S)-1'-(pyridin-2-ylmethyl)-2,3-dihydrospiro[furo[2,3-g][1,4]benzodioxine-8,3'-indol]-2'(1'H)-one | A |
| 4.54 | 1'-{[5-(trifluoromethyl)furan-2-yl]methyl}-3,4-dihydro-2H-spiro[furo[2,3-h][1,5]benzodioxepine-9,3'-indol]-2'(1'H)-one | A |
| 4.55 | 1'-(pyridin-2-ylmethyl)-3,4-dihydro-2H-spiro[furo[2,3-h][1,5]benzodioxepine-9,3'-indol]-2'(1'H)-one | B |
| 4.68 | 6-methoxy-1'-[(2R)-tetrahydrofuran-2-ylmethyl]spiro[1-benzofuran-3,3'-indol]-2'(1'H)-one | B |
| 4.103 | 4'-(4-phenoxyphenyl)-1'-(pyridin-2-ylmethyl)-2,3-dihydrospiro[furo[2,3-g][1,4]benzodioxine-8,3'-indol]-2'(1'H)-one | A |
| 5.1 | 7'-chloro-1'-((5-(trifluoromethyl)furan-2-yl)methyl)-5,6-dihydro-2H-spiro[benzofuro[6,5-b]furan-3,3'-indolin]-2'-one | A |
| 5.4 | (3R)-1'-(pyridin-2-ylmethyl)-5,6-dihydrospiro[benzo[1,2-b:5,4-b']difuran-3,3'-indol]-2'(1'H)-one | B |
| 5.5 | (3R)-1'-{[5-(trifluoromethyl)furan-2-yl]methyl}-5,6-dihydrospiro[benzo[1,2-b:5,4-b']difuran-3,3'-indol]-2'(1'H)-one | B |
| 5.6 | (3S)-1'-(pyridin-2-ylmethyl)-5,6-dihydrospiro[benzo[1,2-b:5,4-b']difuran-3,3'-indol]-2'(1'H)-one | B |
| 5.7 | (3S)-1'-{[5-(trifluoromethyl)furan-2-yl]methyl}-5,6-dihydrospiro[benzo[1,2-b:5,4-b']difuran-3,3'-indol]-2'(1'H)-one | A |
| 5.17 | (8S)-1'-[(2-methoxypyrimidin-5-yl)methyl]-2,3-dihydrospiro[furo[2,3-g][1,4]benzodioxine-8,3'-indol]-2'(1'H)-one | A |
| 5.18 | (8S)-1'-(pyrimidin-2-ylmethyl)-2,3-dihydrospiro[furo[2,3-g][1,4]benzodioxine-8,3'-indol]-2'(1'H)-one | A |
| 7.4 | (R)-1'-pentyl-2,3-dihydrospiro[furo[2,3-g][1,4]benzodioxine-8,3'-indol]-2'(1'H)-one | B |

TABLE 3-continued

| Ex. No. | Compound Name | $K_i$ (μM) |
|---|---|---|
| 7.8 | 1'-(4-methoxybutyl)-2,3-dihydrospiro[furo[2,3-g][1,3]benzodioxine-8,3'-indol]-2'(1'H)-one | A |
| 7.15 | (8R)-1'-{[3-(trifluoromethyl)pyridin-2-yl]methyl}-2,3-dihydrospiro[furo[2,3-g][1,3]benzodioxine-8,3'-indol]-2'(1'H)-one | B |
| 8.4 | 1'-pentyl-2,3-dihydrospiro[furo[2,3-g][1,4]benzodioxine-8,3'-indol]-2'(1'H)-one | A |
| 8.6 | (8R)-1'-[(2S)-1,4-dioxan-2-ylmethyl]-2,3-dihydrospiro[furo[2,3-g][1,4]benzodioxine-8,3'-indol]-2'(1'H)-one | B |
| 8.7 | (8S)-1'-[(2S)-1,4-dioxan-2-ylmethyl]-2,3-dihydrospiro[furo[2,3-g][1,4]benzodioxine-8,3'-indol]-2'(1'H)-one | B |
| 8.8 | (8S)-1'-[(2R)-1,4-dioxan-2-ylmethyl]-2,3-dihydrospiro[furo[2,3-g][1,4]benzodioxine-8,3'-indol]-2'(1'H)-one | A |
| 8.12 | 1'-[(2R)-1,4-dioxan-2-ylmethyl]-3,4-dihydro-2H-spiro[furo[2,3-h][1,5]benzodioxepine-9,3'-indol]-2'(1'H)-one | B |
| 9 | 3-methyl-1'-{[5-(trifluoromethyl)furan-2-yl]methyl}spiro[furo[3,2-f][1,2]benzisoxazole-5,3'-indol]-2'(1'H)-one | A |
| 9.6 | 1'-(pyrimidin-4-ylmethyl)-5,6-dihydrospiro[benzo[1,2-b:5,4-b']difuran-3,3'-indol]-2'(1'H)-one | B |
| 9.20 | 1'-[2-(2-methoxyethoxy)ethyl]-2,3-dihydrospiro[furo[2,3-g][1,4]benzodioxine-8,3'-indol]-2'(1'H)-one | A |
| 9.23 | 4-methyl-1'-[(2R)-tetrahydrofuran-2-ylmethyl]-2H-spiro[furo[2,3-g][1,4]benzoxazine-8,3'-indole]-2',3(1'H,4H)-dione | B |
| 9.24 | 3-methyl-1'-(pyridin-2-ylmethyl)spiro[furo[3,2-f][1,2]benzisoxazole-5,3'-indol]-2'(1'H)-one | B |
| 10.1 | 1'-(pyridin-3-ylmethyl)-2,3-dihydrospiro[furo[2,3-g][1,4]benzodioxine-8,3'-indol]-2'(1'H)-one | B |
| 11.14 | 1'-[4-(5-methyl-1,2,4-oxadiazol-3-yl)benzyl]-5,6-dihydrospiro[benzo[1,2-b:5,4-b']difuran-3,3'-indol]-2'(1'H)-one | A |
| 11.27 | 1'-[3-(5-methyl-1,2,4-oxadiazol-3-yl)benzyl]-5,6-dihydrospiro[benzo[1,2-b:5,4-b']difuran-3,3'-indol]-2'(1'H)-one | A |
| 11.33 | N,N-dimethyl-5-[(2'-oxo-2,3-dihydrospiro[furo[2,3-g][1,4]benzodioxine-8,3'-indol]-1'(2'H)-yl)methyl]furan-2-carboxamide | A |
| 11.64 | (3S)-6-methoxy-5-methyl-1'-[(4-methylpiperazin-1-yl)methyl]spiro[1-benzofuran-3,3'-indol]-2'(1'H)-one hydrogen chloride | B |
| 11.66 | (3S)-1'-[(2R)-tetrahydrofuran-2-ylmethyl]-5,6-dihydrospiro[benzo[1,2-b:5,4-b']difuran-3,3'-indol]-2'(1'H)-one | B |
| 11.67 | (3R)-1'-[(2R)-tetrahydrofuran-2-ylmethyl]-5,6-dihydrospiro[benzo[1,2-b:5,4-b']difuran-3,3'-indol]-2'(1'H)-one | B |
| 11.69 | (3S)-1'-[(2S)-tetrahydrofuran-2-ylmethyl]-5,6-dihydrospiro[benzo[1,2-b:5,4-b']difuran-3,3'-indol]-2"(1'H)-one | B |
| 11.85 | 6-(5-methyl-1,2,4-oxadiazol-3-yl)-1'-(pyridin-2-ylmethyl)spiro[1-benzofuran-3,3'-indol]-2'(1'H)-one | B |
| 16 | 4'-[6-(dimethylamino)pyridin-3-yl]-1'-[(2R)-tetrahydrofuran-2-ylmethyl]-5,6-dihydrospiro[benzo[1,2-b:5,4-b']difuran-3,3'-indol]-2'(1'H)-one | B |
| 16.6 | 4'-(4-phenoxyphenyl)-1'-[(2R)-tetrahydrofuran-2-ylmethyl]-5,6-dihydrospiro[benzo[1,2-b:5,4-b']difuran-3,3'-indol]-2'(1'H)-one | A |
| 16.7 | 4'-[4-(2-methylpropoxy)phenyl]-1'-[(2R)-tetrahydrofuran-2-ylmethyl]-5,6-dihydrospiro[benzo[1,2-b:5,4-b']difuran-3,3'-indol]-2'(1'H)-one | A |
| 16.9 | 4'-(4-methoxyphenyl)-1'-[(2R)-tetrahydrofuran-2-ylmethyl]-5,6-dihydrospiro[benzo[1,2-b:5,4-b']difuran-3,3'-indol]-2'(1'H)-one | A |
| 16.10 | 4'-pyrimidin-5-yl-1'-[(2R)-tetrahydrofuran-2-ylmethyl]-5,6-dihydrospiro[benzo[1,2-b:5,4-b']difuran-3,3'-indol]-2'(1'H)-one | B |
| 16.80 | 1'-methyl-4-phenoxy-2,3-dihydrospiro[furo[2,3-g][1,4]benzodioxine-8,3'-indol]-2'(1'H)-one | A |

Biological Example 3

Analgesia Induced by Sodium Channel Blockers

Heat Induced Tail Flick Latency Test

In this test, the analgesia effect produced by administering a compound of the invention can be observed through heat-induced tail-flick in mice. The test includes a heat source consisting of a projector lamp with a light beam focused and directed to a point on the tail of a mouse being tested. The tail-flick latencies, which are assessed prior to drug treatment, and in response to a noxious heat stimulus, i.e., the response time from applying radiant heat on the dorsal surface of the tail to the occurrence of tail flick, are measured and recorded at 40, 80, 120, and 160 minutes.

For the first part of this study, 65 animals undergo assessment of baseline tail flick latency once a day over two consecutive days. These animals are then randomly assigned to one of the 11 different treatment groups including a vehicle control, a morphine control, and 9 compounds at 30 mg/Kg are administered intramuscularly. Following dose administration, the animals are closely monitored for signs of toxicity including tremor or seizure, hyperactivity, shallow, rapid or depressed breathing and failure to groom. The optimal incubation time for each compound is determined via regression analysis. The analgesic activity of the test compounds is expressed as a percentage of the maximum possible effect (% MPE) and is calculated using the following formula:

$$\% \, MPE = \frac{\text{Postdrug latency} - \text{Predrug latency}}{\text{Cut-off time (10 s)} - \text{Predrug latency}} \times 100\%$$

where:

Postdrug latency=the latency time for each individual animal taken before the tail is removed (flicked) from the heat source after receiving drug.

Predrug latency=the latency time for each individual animal taken before the tail is flicked from the heat source prior to receiving drug.

Cut-off time (10 s)=is the maximum exposure to the heat source.

Acute Pain (Formalin Test)

The formalin test is used as an animal model of acute pain. In the formalin test, animals are briefly habituated to the plexiglass test chamber on the day prior to experimental day for 20 minutes. On the test day, animals are randomly injected with the test articles. At 30 minutes after drug administration, 50 µL of 10% formalin is injected subcutaneously into the plantar surface of the left hind paw of the rats. Video data acquisition begins immediately after formalin administration, for duration of 90 minutes.

The images are captured using the Actimetrix Limelight software which stores files under the *.llii extension, and then converts it into the MPEG-4 coding. The videos are then analyzed using behaviour analysis software "The Observer 5.1", (Version 5.0, Noldus Information Technology, Wageningen, The Netherlands). The video analysis is conducted by watching the animal behaviour and scoring each according to type, and defining the length of the behaviour (Dubuisson and Dennis, 1977). Scored behaviours include: (1) normal behaviour, (2) putting no weight on the paw, (3) raising the paw, (4) licking/biting or scratching the paw. Elevation, favoring, or excessive licking, biting and scratching of the injected paw indicate a pain response. Analgesic response or protection from compounds is indicated if both paws are resting on the floor with no obvious favoring, excessive licking, biting or scratching of the injected paw.

Analysis of the formalin test data is done according to two factors: (1) Percent Maximal Potential Inhibitory Effect (% MPIE) and (2) pain score. The % MPIEs is calculated by a series of steps, where the first is to sum the length of non-normal behaviours (behaviours 1,2,3) of each animal. A single value for the vehicle group is obtained by averaging all scores within the vehicle treatment group. The following calculation yields the MPIE value for each animal:

$MPIE(\%)=100-[(\text{treatment sum/average vehicle value})\times 100\%]$

The pain score is calculated from a weighted scale as described above. The duration of the behaviour is multiplied by the weight (rating of the severity of the response), and divided by the total length of observation to determine a pain rating for each animal. The calculation is represented by the following formula:

$\text{Pain rating}=[0(T0)+1(T1)+2(T2)+3(T3)]/(T0+T1+T2+T3)$

CFA Induced Chronic Inflammatory Pain

In this test, tactile allodynia is assessed with calibrated von Frey filaments. Following a full week of acclimatization to the vivarium facility, 150 µL of the "Complete Freund's Adjuvant" (CFA) emulsion (CFA suspended in an oil/saline (1:1) emulsion at a concentration of 0.5 mg/mL) is injected subcutaneously into the plantar surface of the left hind paw of rats under light isoflurane anaesthesia. Animals are allowed to recover from the anaesthesia and the baseline thermal and mechanical nociceptive thresholds of all animals are assessed one week after the administration of CFA. All animals are habituated to the experimental equipment for 20 minutes on the day prior to the start of the experiment. The test and control articles are administered to the animals, and the nociceptive thresholds measured at defined time points after drug administration to determine the analgesic responses to each of the six available treatments. The time points used are previously determined to show the highest analgesic effect for each test compound.

Thermal nociceptive thresholds of the animals are assessed using the Hargreaves test. Animals are placed in a Plexiglas enclosure set on top of an elevated glass platform with heating units. The glass platform is thermostatically controlled at a temperature of approximately 30° C. for all test trials. Animals are allowed to accommodate for 20 minutes following placement into the enclosure until all exploration behaviour ceases. The Model 226 Plantar/Tail Stimulator Analgesia Meter (IITC, Woodland Hills, Calif.) is used to apply a radiant heat beam from underneath the glass platform to the plantar surface of the hind paws. During all test trials, the idle intensity and active intensity of the heat source are set at 1 and 45 respectively, and a cut off time of 20 seconds is employed to prevent tissue damage.

The response thresholds of animals to tactile stimuli are measured using the Model 2290 Electrovonfrey anesthesiometer (IITC Life Science, Woodland Hills, Calif.) following the Hargreaves test. Animals are placed in an elevated Plexiglas enclosure set on a mire mesh surface. After 10 minutes of accommodation, pre-calibrated Von Frey hairs are applied perpendicularly to the plantar surface of both paws of the animals in an ascending order starting from the 0.1 g hair, with sufficient force to cause slight buckling of the hair against the paw. Testing continues until the hair with the lowest force to induce a rapid flicking of the paw is determined or when the cut off force of approximately 20 g is reached. This cut off force is used because it represent approximately 10% of the animals' body weight and it serves to prevent raising of the entire limb due to the use of stiffer hairs, which would change the nature of the stimulus.

Postoperative Models of Nociception

In this model, the hypealgesia caused by an intra-planar incision in the paw is measured by applying increased tactile stimuli to the paw until the animal withdraws its paw from the applied stimuli. While animals are anaesthetized under 3.5% isofluorane, which is delivered via a nose cone, a 1 cm longitudinal incision is made using a number 10 scalpel blade in the plantar aspect of the left hind paw through the skin and fascia, starting 0.5 cm from the proximal edge of the heel and extending towards the toes. Following the incision, the skin is apposed using 2, 3-0 sterilized silk sutures. The injured site is covered with Polysporin and Betadine. Animals are returned to their home cage for overnight recovery.

The withdrawal thresholds of animals to tactile stimuli for both operated (ipsilateral) and unoperated (contralateral) paws can be measured using the Model 2290 Electrovonfrey anesthesiometer (IITC Life Science, Woodland Hills, Calif.). Animals are placed in an elevated Plexiglas enclosure set on a mire mesh surface. After at least 10 minutes of acclimatization, pre-calibrated Von Frey hairs are applied perpendicularly to the plantar surface of both paws of the animals in an ascending order starting from the 10 g hair, with sufficient force to cause slight buckling of the hair against the paw. Testing continues until the hair with the lowest force to induce a rapid flicking of the paw is determined or when the cut off force of approximately 20 g is reached. This cut off force is used because it represent approximately 10% of the animals' body weight and it serves to prevent raising of the entire limb due to the use of stiffer hairs, which would change the nature of the stimulus.

Neuropathic pain model; Chronic Constriction Injury

Briefly, an approximately 3 cm incision is made through the skin and the fascia at the mid thigh level of the animals' left hind leg using a no. 10 scalpel blade. The left sciatic nerve is exposed via blunt dissection through the biceps femoris with care to minimize haemorrhagia. Four loose ligatures are tied along the sciatic nerve using 4-0 non-degradable sterilized silk sutures at intervals of 1 to 2 mm apart. The tension of the loose ligatures is tight enough to induce slight constriction of the sciatic nerve when viewed under a dissection microscope at a magnification of 4 fold. In the sham-operated animal, the left sciatic nerve is exposed without further manipulation. Antibacterial ointment is applied directly into the wound, and the muscle is closed using sterilized sutures. Betadine is applied onto the muscle and its surroundings, followed by skin closure with surgical clips.

The response thresholds of animals to tactile stimuli are measured using the Model 2290 Electrovonfrey anesthesiometer (IITC Life Science, Woodland Hills, Calif.). Animals are placed in an elevated Plexiglas enclosure set on a mire mesh surface. After 10 minutes of accommodation, pre-calibrated Von Frey hairs are applied perpendicularly to the plantar surface of both paws of the animals in an ascending order starting from the 0.1 g hair, with sufficient force to cause slight buckling of the hair against the paw. Testing continues until the hair with the lowest force to induce a rapid flicking of the paw is determined or when the cut off force of approximately 20 g is reached. This cut off force is used because it represents approximately 10% of the animals' body weight and it serves to prevent raising of the entire limb due to the use of stiffer hairs, which would change the nature of the stimulus.

Thermal nociceptive thresholds of the animals are assessed using the Hargreaves test. Following the measurement of tactile thresholds, animals are placed in a Plexiglass enclosure set on top of an elevated glass platform with heating units. The glass platform is thermostatically controlled at a temperature of approximately 24 to 26° C. for all test trials. Animals are allowed to accommodate for 10 minutes following placement into the enclosure until all exploration behaviour ceases. The Model 226 Plantar/Tail Stimulator Analgesia Meter (IITC, Woodland Hills, Calif.) is used to apply a radiant heat beam from underneath the glass platform to the plantar surface of the hind paws. During all test trials, the idle intensity and active intensity of the heat source are set at 1 and 55 respectively, and a cut off time of 20 seconds is used to prevent tissue damage.

Neuropathic Pain Model: Spinal Nerve Ligation

The spinal nerve ligation (SNL) neuropathic pain model is used as an animal (i.e. rat) model of neuropathic pain. In the SNL test, the lumbar roots of spinal nerves L5 and L6 are tightly ligated to cause nerve injury, which results in the development of mechanical hyperalgesia, mechanical allodynia and thermal hypersensitivity. The surgery is performed two weeks before the test day in order for the pain state to fully develop in the animals. Several spinal nerve ligation variations are used to characterize the analgesic properties of a compound of the invention.

(1) Ligation of the L5 spinal nerve;
(2) Ligation of the L5 and L6 spinal nerves;
(3) Ligation and transection of the L5 spinal nerve;
(4) Ligation and transection of the L5 and L6 spinal nerves; or
(5) Mild irritation of the L4 spinal nerve in combination with any one of the above (1)-(4).

While the animals are anaesthetized under 3.5% isofluorane delivered via a nose cone, an approximately 2.5 cm longitudinal incision is made using a number 10 scalpel blade in the skin just lateral to the dorsal midline, using the level of the posterior iliac crests as the midpoint of the incision. Following the incision, the isoflourane is readjusted to maintenance levels (1.5%–2.5%). At mid-sacral region, an incision is made with the scalpel blade, sliding the blade along the side of the vertebral column (in the saggital plane) until the blade hits the sacrum. Scissors tips are introduced through the incision and the muscle and ligaments are removed from the spine to expose 2-3 cm of the vertebral column. The muscle and fascia are cleared from the spinal vertebra in order to locate the point where the nerve exits from the vertebra. A small glass hook is placed medial to the spinal nerves and the spinal nerves are gently elevated from the surrounding tissues. Once the spinal nerves have been isolated, a small length of non-degradable 6-0 sterilized silk thread is wound twice around the ball at the tip of the glass hook and passed back under the nerve. The spinal nerves are then firmly ligated by tying a knot, ensuring that the nerve bulges on both sides of the ligature. The procedure may be repeated as needed. In some animals, the L4 spinal nerve may be lightly rubbed (up to 20 times) with the small glass hook to maximize the development of neuropathic pain. Antibacterial ointment is applied directly into the incision, and the muscle is closed using sterilized sutures. Betadine is applied onto the muscle and its surroundings, followed by skin closure with surgical staples or sterile non-absorbable monofilament 5-0 nylon sutures.

The analgesic effect produced by topical administration of a compound of the invention to the animals can then be observed by measuring the paw withdrawal threshold of animals to mechanical tactile stimuli. These may be measured using either the mechanical allodynia procedure or the mechanical hyperalgesia procedure as described below. After establishment of the appropriate baseline measurements by either method, topical formulation of a compound of the invention is applied on the ipsilateral ankle and foot. The animals are then placed in plastic tunnels for 15 minutes to prevent them from licking the treated area and removing the compound. Animals are placed in the acrylic enclosure for 15 minutes before testing the ipsilateral paw by either of the methods described below, and the responses are recorded at 0.5, 1.0 and 2.0 hour post treatment.

A. Mechanical Allodynia Method

The pain threshold of animals to mechanical alloydnia for both operated and control animals can be measured approximately 14 days post-surgery using manual calibrated von Frey filaments as follows. Animals are placed in an elevated plexiglass enclosure set on a mire mesh surface. Animals are allowed to acclimate for 20-30 minutes. Pre-calibrated Von Frey hairs are applied perpendicularly to the plantar surface of the ipsilateral paw of the animals starting from the 2.0 g hair, with sufficient force to cause slight buckling of the hair against the paw to establish the baseline measurements. Stimuli are presented in a consecutive manner, either in an ascending or descending order until the first change in response is noted, after which four additional reponses are recorded for a total of six responses. The six responses measured in grams are entered into a formula as described by Chaplan, S. R. et al., *J. Neurosci. Methods,* 1994 July; 53(1): 55-63, and a 50% withdrawal threshold is calculated. This constitutes the mechanical allodynia value.

B. Mechanical Hyperalgesia Method

The response thresholds of animals to tactile stimuli were measured using the Model 2290 Electrovonfrey anesthesiometer (IITC Life Science, Woodland Hills, Calif.). Animals were placed in an elevated Plexiglas enclosure set on a wire mesh surface. After 15 minutes of accommodation in this enclosure, a von Frey hair was applied perpendicularly to the plantar surface of the ipsilateral hind paws of the animals, with sufficient force, measured in grams, to elicit a crisp response of the paw. The response indicated a withdrawal from the painful stimulus and constituted the efficacy endpoint. The data were expressed as percent change from baseline threshold measured in grams.

Biological Example 4

Aconitine Induced Arrhythmia Test

The antiarrhythmic activity of compounds of the invention is demonstrated by the following test. Arrhythmia is provoked by intravenous administration of aconitine (2.0 µg/Kg) dissolved in physiological saline solution. Test compounds of the invention are intravenously administered 5 minutes after the administration of aconitine. Evaluation of the anti-arrhythmic activity is conducted by measuring the time from the aconitine administration to the occurrence of extrasystole (ES) and the time from the aconitine administration to the occurrence of ventricular tachycardia (VT).

In rates under isoflurane anaesthesia (¼ to ⅓ of 2%), a tracheotomy is performed by first creating an incision in the neck area, then isolating the trachea and making a 2 mm incision to insert tracheal tube 2 cm into the trachea such that the opening of the tube is positioned just on top of the mouth. The tubing is secured with sutures and attached to a ventilator for the duration of the experiment.

Incisions (2.5 cm) are then made into the femoral areas and using a blunt dissection probe, the femoral vessels are isolated. Both femoral veins are cannulated, one for pentobarbital anaesthetic maintenance (0.02-0.05 mL) and one for the infusion and injection of drug and vehicle. The femoral artery is cannulated with the blood pressure gel catheter of the transmitter.

The ECG leads are attached to the thoracic muscle in the Lead II position (upper right/above heart—white lead and lower left/below heart—red lead). The leads are secured with sutures.

All surgical areas are covered with gauze moistened with 0.9% saline. Saline (1-1.5 mL of a 0.9% solution) is supplied to moisten the areas post-surgery. The animals' ECG and ventilation are allowed to equilibrate for at least 30 minutes.

The arrhythmia is induced with a 2 µg/Kg/min aconitine infusion for 5 minutes. During this time the ECG is recorded and continuously monitored. Compounds of the present invention can be tested in these assays to determine their effectiveness in treating arrhythmia.

Biological Example 5

Ischemia Induced Arrhythmia Test

Rodent models of ventricular arrhythmias, in both acute cardioversion and prevention paradigms have been employed in testing potential therapeutics for both atrial and ventricular arrhythmias in humans. Cardiac ischemia leading to myocardial infarction is a common cause of morbidity and mortality. The ability of a compound to prevent ischemia-induced ventricular tachycardia and fibrillation is an accepted model for determining the efficacy of a compound in a clinical setting for both atrial and ventricular tachycardia and fibrillation.

Anaesthesia is first induced by pentobarbital (i.p.), and maintained by an i.v. bolus infusion. Male SD rats have their trachea cannulated for artificial ventilation with room air at a stroke volume of 10 mL/Kg, 60 strokes/minute. The right femoral artery and vein are cannulated with PE50 tubing for mean arterial blood pressure (MAP) recording and intravenous administration of compounds, respectively.

The chest is opened between the $4^{th}$ and $5^{th}$ ribs to create a 1.5 cm opening such that the heart is visible. Each rat is placed on a notched platform and metal restraints are hooked onto the rib cage opening the chest cavity. A suture needle is used to penetrate the ventricle just under the lifted atrium and exited the ventricle in a downward diagonal direction so that a >30% to <50% occlusion zone (OZ) would be obtained. The exit position is ~0.5 cm below where the aorta connects to the left ventricle. The suture is tightened such that a loose loop (occluder) is formed around a branch of the artery. The chest is then closed with the end of the occluder accessible outside of the chest.

Electrodes are placed in the Lead II position (right atrium to apex) for ECG measurement as follows: one electrode inserted into the right forepaw and the other electrode inserted into the left hind paw.

The body temperature, MAP, ECG, and heart rate are constantly recorded throughout the experiment. Once the critical parameters has stabilized, a 1-2 minute recording is taken to establish the baseline values. Infusion of a compound of the invention or control substance is initiated once baseline values are established. After a 5-minute infusion of compound or control, the suture is pulled tight to ligate the LCA and create ischemia in the left ventricle. The critical parameters are recorded continuously for 20 minutes after ligation, unless the MAP reached the critical level of 20-30 mmHg for at least 3 minutes, in which case the recording is stopped because the animal would be declared deceased and is then sacrificed. The ability of compounds of the invention to prevent arrhythmias and sustain near-normal MAP and HR is scored and compared to control.

Biological Example 6

In Vivo Assay for Benign Prostate Hyperplasia (BPH)

The effectiveness of the compounds of the present invention for treating BPH can be demonstrated by the following in vivo assay.

Dogs are dosed orally with compounds of the present invention at oral doses of between 0 mg/Kg and 100 mg/Kg for a period of 4 weeks. A control group receives placebo. The animals are sacrificed and the prostate glands dissected out, dabbed dry and then weighed.

Biological Example 7

In Vivo Assay for Antihypercholesterlemia Efficacy and Antiatherosclerotic Efficacy Dogs have cardiovascular systems similar to that of humans, making them ideal for studying the effects of medicinal compounds designed to treat cardiovascular disorders.

Dogs are dosed orally at a range of 0 mg/Kg to 100 mg/Kg daily with compounds of the present invention for a period of 2-4 weeks. After 2 and 4 weeks the animals are bled and their serum collected for total cholesterol analysis and compared to the animals dosed with vehicle alone (0 mg/Kg).

The measurement of cholesterol is one of the most common tests performed in the clinical laboratory setting. Simple fluorometric methods for the sensitive quantitation of total cholesterol in plasma or serum are commonly used. In one assay, cholesteryl esters in the sample are first hydrolyzed by cholesterol esterase. All cholesterol, whether previously esterified or existing free in the circulation, is then oxidized by cholesterol oxidase to the corresponding ketone and hydrogen peroxide. ADHP (10-acetyl-3,7-dihydroxyphenoxazine) is utilized as a highly sensitive and stable probe for hydrogen peroxide. Horseradish peroxidase catalyzes the reaction of ADHP with hydrogen peroxide to yield the highly fluorescent product resorufin, which can be monitored using excitation wavelengths of 565-580 nm and emission wavelengths of 585-595 nm.

Biological Example 8

In Vivo Assay for Treatment of Pruritis

The compounds of the invention can be evaluated for their activity as antipruritic agents by in vivo test using rodent models. One established model for peripherally elicited pruritus is through the injection of serotonin into the rostral back area (neck) in hairless rats. Prior to serotonin injections (e.g., 2 mg/mL, 50 µL), a dose of a compound of the present invention can be applied systemically through oral, intravenous or intraperitoneal routes or topically to a circular area fixed diameter (e.g. 18 mm). Following dosing, the serotonin injections are given in the area of the topical dosing. After serotonin injection the animal behaviour is monitored by video recording for 20 min-1.5 h, and the number of scratches in this time compared to vehicle treated animals. Thus, application of a compound of the current invention could suppress serotonin-induced scratching in rats.

Biological Example 9

Cytochrome P450 (CYP450) Inhibition Assay

CYP450 (CYP) is the designation for a superfamily of enzymes. Each family consists of one or more subfamilies and each subfamily contains one or more specific CYP isoforms. The Cytochrome P450 (CYP450) Inhibition Assay is a fluorescence-based assay using a CYP isozyme for screening of compounds of the invention to determine the level of CYP450 inhibition by a specific compound. The assay is based on the CYP inhibition kit described by Vivid CYP450 Screening Kit Protocol, 2005, Invitrogen Corporation (Invitrogen Corporation, 1600 Faraday Avenue, Carlsbad, Calif. 92008, USA).

This assay is designed to assess compounds by quantifying the inhibition of the predominant human CYP450 isozymes involved in hepatic drug metabolism. It is based on the principle derived from the testing of many pharmacologically active compounds for their ability to serve as substrates and inhibitors for the major Drug Metabolizing Enzymes, primarily CYPs, or for their interference with the metabolism of existing drugs. The standard method for evaluating specific CYP isozyme inhibition is to determine the conversion of a probe substrate (Table 4) into its metabolite, in the presence and absence of the potential inhibitor. Quantification of the metabolite is achieved by HPLC or by using a probe substrate that is metabolized into a fluorescent product (fluorescent assay).

Four CYP isozymes were investigated: CYP3A4, 2C9, 2C19 and 2D6. In particular, CYP3A4 is shown to be one of the most important isozyme involved in the metabolism of drugs in the body (see http://medicine.iupui.edu/flockhart/table.htm). A drug that inhibits a specific CYP isozyme may decrease the metabolism of the drug and increase serum concentrations of drugs that are substrates for that isoenzyme. The CYP3A4 data reported below can be useful to predict potential clinical drug-drug interactions for a particular compound.

TABLE 4

CYP450 ISOZYMES (CYP) AND SUBSTRATES USED

| CYP | Substrate Acronym | Structure Name |
|---|---|---|
| 3A4 | BOMCC | 7-(benzyloxymethoxy)-3-cyanocoumarin |
| 2C19 | EOMCC | 7-(ethoxymethoxy)-3-cyanocoumarin |
| 2C9 | BOMF | (benzyloxymethoxy)fluorescein |
| 2D6 | MOBFC | 7-(4-methoxybenzyloxy)-4-trifluoromethylcoumarin |

TABLE 5

CYP450 ISOZYME INHIBITORS

| Isozyme | Inhibitor | Concentration in 10 µM assay | % Inhibition in 10 µM assay | IC$_{50}$ (nM) |
|---|---|---|---|---|
| 3A4 | Ketoconazole | 0.1 µM | 50 +/− 10% | 88 +/− 30 nM |
| 2C9 | Sulfaphenazole | 0.420 µM | 50 +/− 15% | 345 +/− 20 nM |
| 2C19 | Ketoconazole | 7.62 µM | 65 +/− 10% | 3132 +/− 680 nM |
| 2D6 | Quinidine | 0.0137 µM | 55 +/− 15% | 15 +/− 5 nM |

TABLE 6

TERMINOLOGY

| Name | Definition |
|---|---|
| Regeneration System (RS) | 100x consists of 333 mM Glucose-6-phosphate and 40 U/mL Glucose-6-phosphate dehydrogenase in 100 mM Potassium Phosphate Buffer (pH 8.0). |
| Baculosomes (Bac) | Microsomes prepared from insect cells that were infected with baculovirus containing the cDNAs for human CYP isozyme (1 µM specific P450 content) and rabbit NADPH reductase. |
| NADP$^+$ | Nicotinamide adenine dinucleotide phosphate at 10 µM in potassium phosphate buffer (100 mM, pH 8.0). Conversion of NADP+ into NADPH by the regeneration system is required to start the CYP450 reaction. |
| Reaction Buffer | Contains 100 or 200 mM potassium phosphate buffer. |
| Pre-Mix | Contains reaction buffer, RS, Bac. Prepare separately for each isozyme. |
| Substrate Mix | Contains reaction buffer, substrate (BOMCC, EOMCC, BOMF, or MOBFC), and NADP+. Prepare separately for each isozyme. |

This assay can be used for single concentration screening or for IC$_{50}$ determination. In a single concentration screening assay, the final assay concentration of the test compound is 10 µM. In an IC$_{50}$ determination assay, IC$_{50}$ may be determined using a 3, 6, or 12 point curve in triplicate with a chosen starting concentration diluted serially.

Preparation Stage:

In the Preparation Stage, the test compounds, controls (acetonitrile (ACN) or dimethyl sulfoxide (DMSO) and No Baculosomes), and known inhibitors (Table 5) were diluted to 10% ACN or DMSO in water at appropriate concentrations. The Premix and Substrate Mix solutions were also prepared per kit instructions. The Premix consisted of P450 Baculosomes, regeneration system (RS), and Vivid® CYP450 reaction buffer. The Substrate Mix consisted of Vivid® substrate, NADP+ and Vivid® CYP450 reaction buffer.

Assay Stage:

In the Assay Stage, 30 µL water was added to each well of a 96-well assay plate. Then 10 µL of the 10% ACN or DMSO in water stocks of the test compounds, negative controls, or known inhibitors were added to designated wells according to the assay plate layout. The third step was to add 50 µL of the Premix solution to each working well (except for No Baculosomes control wells, 50 µL buffer was added instead). The assay plate was then pre-warmed at ambient temperature in the dark for 20 minutes. When pre-warming was completed, 10 µL of the Substrate Mix solution was added to each working well (including the No Baculosomes control wells). This resulted in a final 1% ACN or DMSO concentration. The assay plate was immediately placed in a PolarStar plate reader to read initial fluorescence. The assay plate was again incubated at ambient temperature in the dark for 20, 30, or 60 minutes depending on the reaction time of the isozyme (Table 7). 10 µL of the stop reagent was added to each working well and final fluorescence was read.

TABLE 7

ISOZYME REACTION TIME AND STOP REAGENT

| Isozyme | Reaction Time (min) | Concentration of Stop Reagent |
|---|---|---|
| 3A4 | 20 | 10 µM Ketoconazole |
| 2C19 | 20 | 30 µM Ketoconazole |
| 2C9 | 30 | 10 µM Sulfaphenazole |
| 2D6 | 60 | 1 µM Quinidine |

Data Analysis:

The difference between the initial and final fluorescence readings was used to calculate percent inhibition. The ACN or DMSO readings represented 0% inhibition and the No Baculosomes readings represented 100% inhibition. Percent inhibition by the compound or known inhibitor was calculated based on comparison with the solvent (ACN or DMSO) control and the No Baculosomes control. To minimize any fluorescence compound or background effect, the relative fluorescence unit (RFU) initial was substrated from the RFU final.

Determine the % inhibition for each compound or control for each CYP450 isozyme:

$$\% \text{ Inhibition} = \frac{\text{Compound } (RFU \text{ final-intial}) - DMSO \text{ control } (RFU \text{ final-intial})}{NoBac \, (RFU \text{ final-intial}) - DMSO \text{ control } (RFU \text{ final-intial})} \times 100$$

Representative compounds of the invention, when tested in the above assay demonstrated percent inhibition of the CYP3A4 isozyme as set forth below in Table 8 wherein "A" refers to percent inhibition of less than 50% at 10 µM and "B" refers to percent inhibition of greater than 50% at 10 µM. The Example numbers provided in Table 8 correspond to the Examples herein:

TABLE 8

| Ex. No. | Compound Name | % Inhibition of CYP3A4 |
|---|---|---|
| 1 | 2-methylspiro[furo[2,3-f][1,3]benzothiazole-7,3'-indol]-2'(1'H)-one | A |
| 1.1 | 1'-[(6-methylpyridin-2-yl)methyl]-2,3-dihydrospiro[furo[2,3-g][1,4]benzodioxine-8,3'-indol]-2'(1'H)-one | B |
| 1.2 | 1'-(pyridin-3-ylmethyl)-2,3-dihydrospiro[furo[2,3-g][1,4]benzodioxine-8,3'-indol]-2'(1'H)-one | A |
| 1.3 | 1'-{[2,5-dimethyl-1-(1-methylethyl)-1H-pyrrol-3-yl]methyl}spiro[furo[2,3-f][1,3]benzodioxole-7,3'-indol]-2'(1'H)-one | B |
| 1.4 | 5-(benzyloxy)-1'-[(5-chloro-2-thienyl)methyl]spiro[1-benzofuran-3,3'-indol]-2'(1'H)-one | B |

TABLE 8-continued

| Ex. No. | Compound Name | % Inhibition of CYP3A4 |
|---|---|---|
| 1.5 | 7'-bromospiro[furo[2,3-f][1,3]benzodioxole-7,3'-indol]-2'(1'H)-one | B |
| 1.6 | 1'-[(3-isopropylisoxazol-5-yl)methyl]spiro[furo[2,3-f][1,3]benzodioxole-7,3'-indol]-2'(1'H)-one | B |
| 1.7 | 1'-[(4-bromo-2-thienyl)methyl]spiro[furo[2,3-f][1,3]benzodioxole-7,3'-indol]-2'(1'H)-one | B |
| 1.8 | 1'-(1-benzofuran-2-ylmethyl)spiro[furo[2,3-f][1,3]benzodioxole-7,3'-indol]-2'(1'H)-one | B |
| 1.9 | 1'-{[2-methyl-5-(trifluoromethyl)-1,3-oxazol-4-yl]methyl}spiro[furo[2,3-f][1,3]benzodioxole-7,3'-indol]-2'(1'H)-one | B |
| 1.10 | (3R)-5,6-dihydrospiro[benzo[1,2-b:5,4-b']difuran-3,3'-indol]-2'(1'H)-one | A |
| 1.10 | (3S)-5,6-dihydrospiro[benzo[1,2-b:5,4-b']difuran-3,3'-indol]-2'(1'H)-one | B |
| 1.11 | (R)-3,7-dihydro-2H-spiro[benzofuro[5,6-b][1,4]dioxine-8,3'-indolin]-2'-one | A |
| 1.11 | (S)-2,3-dihydrospiro[furo[2,3-g][1,4]benzodioxine-8,3'-indol]-2'(1'H)-one | A |
| 1.12 | (8S)-1'-{[3-(trifluoromethyl)pyridin-2-yl]methyl}-2,3-dihydrospiro[furo[2,3-g][1,4]benzodioxine-8,3'-indol]-2'(1'H)-one | A |
| 1.13 | (8S)-1'-[(5-hydroxypyridin-2-yl)methyl]-2,3-dihydrospiro[furo[2,3-g][1,4]benzodioxine-8,3'-indol]-2'(1'H)-one | A |
| 1.14 | 1'-[(5-bromopyridin-2-yl)methyl]-2,3-dihydrospiro[furo[2,3-g][1,4]benzodioxine-8,3'-indol]-2'(1'H)-one | B |
| 1.15 | 1'-{[5-(4-chlorophenyl)-2-(trifluoromethyl)furan-3-yl]methyl}spiro[furo[2,3-f][1,3]benzodioxole-7,3'-indol]-2'(1'H)-one | A |
| 1.16 | 1'-{[5-chloro-1-methyl-3-(trifluoromethyl)-1H-pyrazol-4-yl]methyl}spiro[furo[2,3-f][1,3]benzodioxole-7,3'-indol]-2'(1'H)-one | B |
| 1.17 | 1'-(5-methoxypyridin-3-yl)spiro[furo[2,3-f][1,3]benzodioxole-7,3'-indol]-2'(1'H)-one | B |
| 2.3 | 1'-(diphenylmethyl)-5,6-dimethylspiro[1-benzofuran-3,3'-indol]-2'(1'H)-one | A |
| 2.6 | 1'-(4-methoxybenzyl)-3-methylspiro[furo[3,2-f][1,2]benzisoxazole-5,3'-indol]-2'(1'H)-one | B |
| 2.9 | 1'-(diphenylmethyl)-5-fluorospiro[1-benzofuran-3,3'-indol]-2'(1'H)-one | A |
| 2.11 | 1'-(diphenylmethyl)-2,3-dihydrospiro[furo[2,3-g][1,4]benzodioxine-8,3'-indol]-2'(1'H)-one | A |
| 2.14 | 1'-(diphenylmethyl)-2-methylspiro[furo[2,3-f][1,3]benzoxazole-7,3'-indol]-2'(1'H)-one | A |
| 2.16 | 1'-(diphenylmethyl)-3-methylspiro[furo[2,3-f][1,3]benzoxazole-7,3'-indole]-2,2'(1'H,3H)-dione | A |
| 2.22 | 6-bromo-1'-((5-(trifluoromethyl)furan-2-yl)methyl)-2H-spiro[benzofuran-3,3'-indolin]-2'-one | B |
| 2.23 | 5-bromo-1'-((5-(trifluoromethyl)furan-2-yl)methyl)-2H-spiro[benzofuran-3,3'-indolin]-2'-one | B |
| 2.24 | 6'-isopentyl-3,7-dihydro-2H-spiro[benzofuro[5,6-b][1,4]dioxine-8,8'-thiazolo[5,4-e]indol]-7'(6'H)-one | B |
| 2.25 | 6-((5-(trifluoromethyl)furan-2-yl)methyl)-2,3,5',6'-tetrahydro-2'H-spiro[[1,4]dioxino[2,3-f]indole-8,3'-benzofuro[6,5-b]furan]-7(6H)-one | B |
| 2.26 | 6-(((R)-tetrahydrofuran-2-yl)methyl)-2,3,5',6'-tetrahydro-2'H-spiro[[1,4]dioxino[2,3-f]indole-8,3'-benzofuro[6,5-b]furan]-7(6H)-one | A |
| 2.27 | 6-((5-(trifluoromethyl)furan-2-yl)methyl)-2,3,3',7'-tetrahydro-2'H-spiro[[1,4]dioxino[2,3-f]indole-8,8'-benzofuro[5,6-b][1,4]dioxin]-7(6H)-one | B |
| 2.28 | 1-methyl-1'-{[5-(trifluoromethyl)furan-2-yl]methyl}-2,3-dihydro-1H-spiro[furo[3,2-g][1,4]benzoxazine-8,3'-indol]-2'(1'H)-one hydrochloride | B |
| 2.29 | 1-methyl-1'-[(2R)-tetrahydrofuran-2-ylmethyl]-2,3-dihydro-1H-spiro[furo[3,2-g][1,4]benzoxazine-8,3'-indol]-2'(1'H)-one hydrochloride | A |
| 2.30 | 4-methyl-1'-[(2R)-tetrahydrofuran-2-ylmethyl]-3,4-dihydro-2H-spiro[furo[2,3-g][1,4]benzoxazine-8,3'-indol]-2'(1'H)-one | B |
| 2.31 | 1'-[(2R)-tetrahydrofuran-2-ylmethyl]-4H-spiro[furo[3,2-g][1,3]benzodioxine-6,3'-indol]-2'(1'H)-one | B |
| 2.34 | 2,2-difluoro-1'-{[5-(trifluoromethyl)furan-2-yl]methyl}spiro[furo[2,3-f][1,3]benzodioxole-7,3'-indol]-2'(1'H)-one | B |

TABLE 8-continued

| Ex. No. | Compound Name | % Inhibition of CYP3A4 |
|---|---|---|
| 2.35 | 2,2-difluoro-1'-{[5-(trifluoromethyl)furan-2-yl]methyl}spiro[furo[2,3-f][1,3]benzodioxole-7,3'-indol]-2'(1'H)-one | B |
| 2.36 | 2,2-difluoro-1'-{[3-(trifluoromethyl)pyridin-2-yl]methyl}spiro[furo[2,3-f][1,3]benzodioxole-7,3'-indol]-2'(1'H)-one | A |
| 2.38 | 3'-(4-methoxybenzyl)-5,6-dihydrospiro[benzo[1,2-b:5,4-b']difuran-3,1'-pyrrolo[3,2-f]quinolin]-2'(3'H)-one | B |
| 2.39 | 6-hydroxy-1'-(4-methoxybenzyl)-2'-oxo-1',2'-dihydrospiro[1-benzofuran-3,3'-indole]-5-carbonitrile | B |
| 2.40 | 6-fluoro-1'-(4-methoxybenzyl)-2'-oxo-1',2'-dihydrospiro[1-benzofuran-3,3'-indole]-5-carbonitrile | B |
| 2.41 | 1'-(4-methoxybenzyl)-3-methylspiro[furo[2,3-f][1,2]benzisoxazole-7,3'-indol]-2'(1'H)-one | B |
| 2.45 | 1'-(4-fluorophenyl)-2,3-dihydrospiro[furo[2,3-g][1,4]benzodioxine-8,3'-indol]-2'(1'H)-one | A |
| 2.49 | 5'-bromo-1'-(pyridin-2-ylmethyl)-2,3-dihydrospiro[furo[2,3-g][1,4]benzodioxine-8,3'-indol]-2'(1'H)-one | B |
| 2.50 | 2'-oxo-1'-(pyridin-2-ylmethyl)-1',2,2',3-tetrahydrospiro[furo[2,3-g][1,4]benzodioxine-8,3'-indole]-5'-carbonitrile | A |
| 2.53 | phenyl 1'-methyl-2'-oxo-1',2,2',3-tetrahydrospiro[furo[2,3-g][1,4]benzodioxine-8,3'-indole]-4'-carboxylate | B |
| 2.54 | 1'-{[3-(trifluoromethyl)pyridin-2-yl]methyl}-7,8-dihyrdospiro[1,4-dioxino[2,3-g][1,3]benzodioxine-4,3'-indol]-2'(1'H)-one | A |
| 2.61 | 1'-(diphenylmethyl)-5,6-difluorospiro[1-benzofuran-3,3'-indol]-2'(1'H)-one | A |
| 2.63 | 4',5'-dimethoxy-1'-{[5-(trifluoromethyl)furan-2-yl]methyl}-2,3-dihydrospiro[furo[2,3-g][1,4]benzodioxine-8,3'-indol]-2'(1'H)-one | B |
| 2.64 | 4',7'-dimethoxy-1'-[2-(2-methoxyethoxy)ethyl]-2,3-dihydrospiro[furo[2,3-g][1,4]benzodioxine-8,3'-indol]-2'(1'H)-one | A |
| 2.65 | 6-[2-(2-methoxyethoxy)ethyl]-2,2',3,3'-tetrahydrospiro[1,4-dioxino[2,3-f]indole-8,8'-furo[2,3-g][1,4]benzodioxin]-7'(6H)-one | A |
| 2.66 | 6'-(4-methoxybenzyl)-2,3-dihydrospiro[furo[2,3-g][1,4]benzodioxine-8,8'-[1,3]thiazolo[5,4-e]indol]-7'(6H)-one | B |
| 3 | 6-methoxy-5-methylspiro[1-benzofuran-3,3'-indol]-2'(1'H)-one | B |
| 3.1 | 4'-chloro-5,6-dihydrospiro[benzo[1,2-b:5,4-b']difuran-3,3'-indol]-2'(1'H)-one | B |
| 3.2 | 6-bromospiro[1-benzofuran-3,3'-indol]-2'(1'H)-one | B |
| 3.3 | 5,6-dimethylspiro[1-benzofuran-3,3'-indol]-2'(1'H)-one | B |
| 3.4 | 5'-fluoro-5,6-dihydrospiro[benzo[1,2-b:5,4-b']difuran-3,3'-indol]-2'(1'H)-one | B |
| 3.5 | 6'-fluoro-5,6-dihydrospiro[benzo[1,2-b:5,4-b']difuran-3,3'-indol]-2'(1'H)-one | B |
| 3.6 | 3-methylspiro[furo[3,2-f][1,2]benzisoxazole-5,3'-indol]-2'(1'H)-one | A |
| 3.7 | 5-fluoro-6-methoxyspiro[1-benzofuran-3,3'-indol]-2'(1'H)-one | A |
| 3.8 | 5-fluoro-spiro[1-benzofuran-3,3'-indol]-2'(1'H)-one | B |
| 3.10 | 2,3-dihydrospiro[furo[2,3-g][1,4]benzodioxine-8,3'-indol]-2'(1'H)-one | A |
| 3.11 | 3,4-dihydro-2H-spiro[furo[2,3-h][1,5]benzodioxepine-9,3'-indol]-2'(1'H)-one | A |
| 3.12 | 2-methylspiro[furo[2,3-f][1,3]benzoxazole-7,3'-indol]-2'(1'H)-one | A |
| 3.13 | 3-methylspiro[furo[2,3-f][1,3]benzoxazole-7,3'-indole]-2,2'(1'H,3H)-dione | A |
| 3.14 | 1-methylspiro[furo[3,2-f][1,3]benzoxazole-7,3'-indole]-2,2'(1H,1'H)-dione | A |
| 3.15 | 7'-chloro-5,6-dihydrospiro[benzo[1,2-b:5,4-b']difuran-3,3'-indol]-2'(1'H)-one | A |
| 3.16 | 7'-fluoro-5,6-dihydrospiro[benzo[1,2-b:5,4-b']difuran-3,3'-indol]-2'(1'H)-one | A |
| 3.17 | 4'-fluoro-7'-methyl-5,6-dihydrospiro[benzo[1,2-b:5,4-b']difuran-3,3'-indol]-2'(1'H)-one | B |
| 3.21 | 6,7-dihydro-5H-spiro[furo[3,2-g]chromene-3,3'-indol]-2'(1'H)-one | A |
| 3.22 | 1-methyl-1H-spiro[furo[3,2-g][1,4]benzoxazine-8,3'-indole]-2,2'(1'H,3H)-dione | A |
| 3.23 | 4-methyl-4,7-dihydrospiro[benzofuro[5,6-b][1,4]oxazine-8,3'-indoline]-2',3(2H)-dione | A |
| 3.24 | 2,3,6,7-tetrahydrospiro[furo[3,2-g]chromene-5,3'-indol]-2'(1'H)-one | A |
| 3.25 | (3S)-6-methoxy-5-methylspiro[1-benzofuran-3,3'-indol]-2'(1'H)-one | A |

TABLE 8-continued

| Ex. No. | Compound Name | % Inhibition of CYP3A4 |
|---|---|---|
| 3.26 | (3R)-6-methoxy-5-methylspiro[1-benzofuran-3,3'-indol]-2'(1'H)-one | B |
| 3.28 | 2',3',5,6-tetrahydrospiro[benzo[1,2-b:5,4-b']difuran-3,8'-[1,4]dioxino[2,3-f]indol]-7'(6'H)-one | B |
| 3.29 | 6-methoxy-2'-oxo-1',2'-dihydrospiro[1-benzofuran-3,3'-indole]-5-carbonitrile | A |
| 3.30 | 6-fluoro-2'-oxo-1',2'-dihydrospiro[1-benzofuran-3,3'-indole]-5-carbonitrile | A |
| 3.32 | 4'-bromo-2,3-dihydrospiro[furo[2,3-g][1,4]benzodioxine-8,3'-indol]-2'(1'H)-one | A |
| 3.33 | 4'-fluoro-2,3-dihydrospiro[furo[2,3-g][1,4]benzodioxine-8,3'-indol]-2'(1'H)-one | A |
| 3.34 | 4'-quinolin-3-yl-2,3-dihydrospiro[furo[2,3-g][1,4]benzodioxine-8,3'-indol]-2'(1'H)-one | B |
| 3.35 | 4'-(4-phenoxyphenyl)-2,3-dihydrospiro[furo[2,3-g][1,4]benzodioxine-8,3'-indol]-2'(1'H)-one | B |
| 3.40 | spiro[indole-3,3'-thieno[2,3-f][1]benzofuran]-2(1H)-one 5,5'-dioxide | A |
| 3.41 | spiro[furo[3,2-e][2,1,3]benzoxadiazole-8,3'-indol]-2'(1'H)-one | A |
| 3.42 | 6-chloro-2,3-dihydrospiro[furo[3,2-f][1,4]benzodioxine-9,3'-indol]-2'(1'H)-one | A |
| 3.44 | 5,6-difluorospiro[1-benzofuran-3,3'-indol]-2'(1'H)-one | B |
| 3.45 | 5',6',7',8'-tetrahydrospiro[indole-3,3'-naphtho[2,3-b]furan]-2(1H)-one | B |
| 3.46 | 6-(2-methoxyethoxy)spiro[1-benzofuran-3,3'-indol]-2'(1'H)-one | A |
| 3.47 | 5-(2-methoxyethoxy)spiro[1-benzofuran-3,3'-indol]-2'(1'H)-one | A |
| 3.48 | 2,3-dihydrospiro[furo[2,3-f][1,4]benzodioxine-7,3'-indol]-2'(1'H)-one | A |
| 3.49 | 2,3-dihydrospiro[furo[2,3-g][1,4]benzodioxine-8,8'-[1,3]thiazolo[5,4-e]indol]-7'(6'H)-one | B |
| 3.50 | 4',6'-dimethoxy-2,3-dihydrospiro[furo[2,3-g][1,4]benzodioxine-8,3'-indol]-2'(1'H)-one | A |
| 3.51 | spiro[furo[2,3-g]quinoxaline-8,3'-indol]-2'(1'H)-one | A |
| 4 | 1'-(tetrahydro-2H-pyran-2-ylmethyl)-5,6-dihydrospiro[benzo[1,2-b:5,4-b']difuran-3,3'-indol]-2'(1'H)-one | A |
| 4.2 | 1'-[(2-chloro-1-methyl-1H-imidazol-5-yl)methyl]-5,6-dihydrospiro[benzo[1,2-b:5,4-b']difuran-3,3'-indol]-2'(1'H)-one | B |
| 4.3 | 1'-[(2R)-tetrahydrofuran-2-ylmethyl]-5,6-dihydrospiro[benzo[1,2-b:5,4-b']difuran-3,3'-indol]-2'(1'H)-one | A |
| 4.4 | 1'-(3-methylbutyl)-5,6-dihydrospiro[benzo[1,2-b:5,4-b']difuran-3,3'-indol]-2'(1'H)-one | B |
| 4.5 | 1'-[(2S)-tetrahydrofuran-2-ylmethyl]-5,6-dihydrospiro[benzo[1,2-b:5,4-b']difuran-3,3'-indol]-2'(1'H)-one | A |
| 4.6 | 1'-(tetrahydro-2H-pyran-4-ylmethyl)-5,6-dihydrospiro[benzo[1,2-b:5,4-b']difuran-3,3'-indol]-2'(1'H)-one | A |
| 4.7 | methyl 5-[(2'-oxo-5,6-dihydrospiro[benzo[1,2-b:5,4-b']difuran-3,3'-indol]-1'(2'H)-yl)methyl]furan-2-carboxylate | B |
| 4.8 | 1'-(1,4-dioxan-2-ylmethyl)-5,6-dihydrospiro[benzo[1,2-b:5,4-b']difuran-3,3'-indol]-2'(1'H)-one | A |
| 4.9 | 1'-{[1-methyl-3-(trifluoromethyl)-1H-pyrazol-4-yl]methyl}-5,6-dihydrospiro[benzo[1,2-b:5,4-b']difuran-3,3'-indol]-2'(1'H)-one | B |
| 4.10 | 1'-(tetrahydro-2H-pyran-3-ylmethyl)-5,6-dihydrospiro[benzo[1,2-b:5,4-b']difuran-3,3'-indol]-2'(1'H)-one | A |
| 4.11 | methyl 2-[(2'-oxo-5,6-dihydrospiro[benzo[1,2-b:5,4-b']difuran-3,3'-indol]-1'(2'H)-yl)methyl]-1,3-oxazole-4-carboxylate | A |
| 4.12 | 1'-(2-fluorobenzyl)-5,6-dihydrospiro[benzo[1,2-b:5,4-b']difuran-3,3'-indol]-2'(1'H)-one | A |
| 4.13 | 1'-(4-fluorobenzyl)-5,6-dihydrospiro[benzo[1,2-b:5,4-b']difuran-3,3'-indol]-2'(1'H)-one | B |
| 4.14 | 1'-benzyl-5,6-dihydrospiro[benzo[1,2-b:5,4-b']difuran-3,3'-indol]-2'(1'H)-one | B |
| 4.15 | 1'-(biphenyl-4-ylmethyl)-5,6-dihydrospiro[benzo[1,2-b:5,4-b']difuran-3,3'-indol]-2'(1'H)-one | A |
| 4.16 | 1'-(tetrahydrofuran-3-ylmethyl)-5,6-dihydrospiro[benzo[1,2-b:5,4-b']difuran-3,3'-indol]-2'(1'H)-one | A |
| 4.17 | 1'-[(3-bromoisoxazol-5-yl)methyl]-5,6-dihydrospiro[benzo[1,2-b:5,4-b']difuran-3,3'-indol]-2'(1'H)-one | B |
| 4.18 | 1'-[(5-bromofuran-2-yl)methyl]-5,6-dihydrospiro[benzo[1,2-b:5,4-b']difuran-3,3'-indol]-2'(1'H)-one | B |

TABLE 8-continued

| Ex. No. | Compound Name | % Inhibition of CYP3A4 |
|---|---|---|
| 4.20 | 1'-(oxetan-2-ylmethyl)-5,6-dihydrospiro[benzo[1,2-b:5,4-b']difuran-3,3'-indol]-2'(1'H)-one | A |
| 4.21 | 1'-[(1-ethyl-1H-imidazol-5-yl)methyl]-5,6-dihydrospiro[benzo[1,2-b:5,4-b']difuran-3,3'-indol]-2'(1'H)-one | B |
| 4.22 | 3-[(2'-oxo-5,6-dihydrospiro[benzo[1,2-b:5,4-b']difuran-3,3'-indol]-1'(2'H)-yl)methyl]benzonitrile | B |
| 4.23 | 4-((2'-oxo-5,6-dihydro-2H-spiro[benzofuro[6,5-b]furan-3,3'-indoline]-1'-yl)methyl)benzonitrile | A |
| 4.24 | 4'-[(2'-oxo-5,6-dihydrospiro[benzo[1,2-b:5,4-b']difuran-3,3'-indol]-1'(2'H)-yl)methyl]biphenyl-2-carbonitrile | A |
| 4.25 | 1'-{(2S)-2-[(benzyloxy)methoxy]propyl}-5,6-dihydrospiro[benzo[1,2-b:5,4-b']difuran-3,3'-indol]-2'(1'H)-one | B |
| 4.26 | 1'-(2,3-dihydro-1,4-benzodioxin-6-ylmethyl)-5,6-dihydrospiro[benzo[1,2-b:5,4-b']difuran-3,3'-indol]-2'(1'H)-one | A |
| 4.27 | 1'-(2,1,3-benzoxadiazol-5-ylmethyl)-5,6-dihydrospiro[benzo[1,2-b:5,4-b']difuran-3,3'-indol]-2'(1'H)-one | B |
| 4.28 | 1'-(2,1,3-benzothiadiazol-5-ylmethyl)-5,6-dihydrospiro[benzo[1,2-b:5,4-b']difuran-3,3'-indol]-2'(1'H)-one | B |
| 4.29 | 1'-[(4-benzylmorpholin-2-yl)methyl]-5,6-dihydrospiro[benzo[1,2-b:5,4-b']difuran-3,3'-indol]-2'(1'H)-one | B |
| 4.33 | 4'-chloro-1'-{[5-(trifluoromethyl)furan-2-yl]methyl}-5,6-dihydrospiro[benzo[1,2-b:5,4-b']difuran-3,3'-indol]-2'(1'H)-one | B |
| 4.34 | 4'-chloro-1'-[(2R)-tetrahydrofuran-2-ylmethyl]-5,6-dihydrospiro[benzo[1,2-b:5,4-b']difuran-3,3'-indol]-2'(1'H)-one | A |
| 4.35 | 4'-bromo-1'-[(2R)-tetrahydrofuran-2-ylmethyl]-5,6-dihydrospiro[benzo[1,2-b:5,4-b']difuran-3,3'-indol]-2'(1'H)-one | B |
| 4.36 | 1'-(3-methylbutyl)-2,3-dihydrospiro[furo[2,3-g][1,4]benzodioxine-8,3'-indol]-2'(1'H)-one | A |
| 4.37 | 1'-(tetrahydro-2H-pyran-4-ylmethyl)-2,3-dihydrospiro[furo[2,3-g][1,4]benzodioxine-8,3'-indol]-2'(1'H)-one | A |
| 4.38 | 1'-(tetrahydro-2H-pyran-2-ylmethyl)-2,3-dihydrospiro[furo[2,3-g][1,4]benzodioxine-8,3'-indol]-2'(1'H)-one | A |
| 4.40 | 1'-[(5-chloro-1-methyl-1H-imidazol-2-yl)methyl]-2,3-dihydrospiro[furo[2,3-g][1,4]benzodioxine-8,3'-indol]-2'(1'H)-one hydrochloride | B |
| 4.41 | 1'-(pyridin-2-ylmethyl)-2,3-dihydrospiro[furo[2,3-g][1,4]benzodioxine-8,3'-indol]-2'(1'H)-one | A |
| 4.42 | 1'-(pyridin-2-ylmethyl)-2,3-dihydrospiro[furo[2,3-g][1,4]benzodioxine-8,3'-indol]-2'(1'H)-one hydrochloride | A |
| 4.43 | 1'-[(2S)-tetrahydrofuran-2-ylmethyl]-2,3-dihydrospiro[furo[2,3-g][1,4]benzodioxine-8,3'-indol]-2'(1'H)-one | A |
| 4.44 | 1'-[(2R)-tetrahydrofuran-2-ylmethyl]-2,3-dihydrospiro[furo[2,3-g][1,4]benzodioxine-8,3'-indol]-2'(1'H)-one | A |
| 4.45 | 1'-(1,4-dioxan-2-ylmethyl)-2,3-dihydrospiro[furo[2,3-g][1,4]benzodioxine-8,3'-indol]-2'(1'H)-one | A |
| 4.46 | 1'-(3,4-dimethoxybenzyl)-2,3-dihydrospiro[furo[2,3-g][1,4]benzodioxine-8,3'-indol]-2'(1'H)-one | B |
| 4.47 | 1'-(3,5-dimethoxybenzyl)-2,3-dihydrospiro[furo[2,3-g][1,4]benzodioxine-8,3'-indol]-2'(1'H)-one | B |
| 4.48 | 1'-(2,3-dihydro-1,4-benzodioxin-6-ylmethyl)-2,3-dihydrospiro[furo[2,3-g][1,4]benzodioxine-8,3'-indol]-2'(1'H)-one | A |
| 4.49 | (R)-1'-{[5-(trifluoromethyl)furan-2-yl]methyl}-2,3-dihydrospiro[furo[2,3-g][1,4]benzodioxine-8,3'-indol]-2'(1'H)-one | B |
| 4.50 | (S)-1'-{[5-(trifluoromethyl)furan-2-yl]methyl}-2,3-dihydrospiro[furo[2,3-g][1,4]benzodioxine-8,3'-indol]-2'(1'H)-one | B |
| 4.51 | (S)-1'-(pyridin-2-ylmethyl)-2,3-dihydrospiro[furo[2,3-g][1,4]benzodioxine-8,3'-indol]-2'(1'H)-one | A |
| 4.52 | 1'-(pyridin-2-ylmethyl)-6,7-dihydrospiro[benzo[1,2-b:4,5-b']difuran-3,3'-indol]-2'(1'H)-one | A |
| 4.53 | 1'-[(2R)-tetrahydrofuran-2-ylmethyl]-6,7-dihydro-5H-spiro[furo[3,2-g]chromene-3,3'-indol]-2'(1'H)-one | A |
| 4.54 | 1'-{[5-(trifluoromethyl)furan-2-yl]methyl}-3,4-dihydro-2H-spiro[furo[2,3-h][1,5]benzodioxepine-9,3'-indol]-2'(1'H)-one | B |

TABLE 8-continued

| Ex. No. | Compound Name | % Inhibition of CYP3A4 |
|---|---|---|
| 4.55 | 1'-(pyridin-2-ylmethyl)-3,4-dihydro-2H-spiro[furo[2,3-h][1,5]benzodioxepine-9,3'-indol]-2'(1'H)-one | A |
| 4.56 | 2-methyl-1'-(3-methylbutyl)spiro[furo[2,3-f][1,3]benzothiazole-7,3'-indol]-2'(1'H)-one | B |
| 4.57 | 2-methyl-1'-(tetrahydro-2H-pyran-4-ylmethyl)spiro[furo[2,3-f][1,3]benzothiazole-7,3'-indol]-2'(1'H)-one | B |
| 4.58 | 2-methyl-1'-[(2R)-tetrahydrofuran-2-ylmethyl]spiro[furo[2,3-f][1,3]benzoxazole-7,3'-indol]-2'(1'H)-one | A |
| 4.59 | 1-methyl-1'-[(2R)-tetrahydrofuran-2-ylmethyl]-1H-spiro[furo[3,2-g][1,4]benzoxazine-8,3'-indole]-2,2'(1'H,3H)-dione | A |
| 4.60 | 1-methyl-1'-[(2R)-tetrahydrofuran-2-ylmethyl]spiro[furo[3,2-f][1,3]benzoxazole-7,3'-indole]-2,2'(1H,1'H)-dione | A |
| 4.61 | 6-methoxy-5-methyl-1'-[(2R)-tetrahydrofuran-2-ylmethyl]spiro[1-benzofuran-3,3'-indol]-2'(1'H)-one | A |
| 4.62 | 6-methoxy-5-methyl-1'-(pyridin-2-ylmethyl)spiro[1-benzofuran-3,3'-indol]-2'(1'H)-one | B |
| 4.63 | 6-methoxy-5-methyl-1'-(tetrahydro-2H-pyran-2-ylmethyl)spiro[1-benzofuran-3,3'-indol]-2'(1'H)-one | B |
| 4.64 | 5-fluoro-6-methoxy-1'-(tetrahydro-2H-pyran-2-ylmethyl)spiro[1-benzofuran-3,3'-indol]-2'(1'H)-one | A |
| 4.65 | 5-fluoro-6-methoxy-1'-(pyridin-2-ylmethyl)spiro[1-benzofuran-3,3'-indol]-2'(1'H)-one | A |
| 4.66 | 5-fluoro-6-methoxy-1'-[(2R)-tetrahydrofuran-2-ylmethyl]spiro[1-benzofuran-3,3'-indol]-2'(1'H)-one | A |
| 4.67 | 1'-benzyl-5-fluoro-6-methoxyspiro[1-benzofuran-3,3'-indol]-2'(1'H)-one | A |
| 4.68 | 6-methoxy-1'-[(2R)-tetrahydrofuran-2-ylmethyl]spiro[1-benzofuran-3,3'-indol]-2'(1'H)-one | A |
| 4.70 | 1'-{[5-(trifluoromethyl)furan-2-yl]methyl}-2,3,6,7-tetrahydrospiro[furo[3,2-g]chromene-5,3'-indol]-2'(1'H)-one | B |
| 4.72 | 1'-{[(2S)-5-oxopyrrolidin-2-yl]methyl}spiro[furo[2,3-f][1,3]benzodioxole-7,3'-indol]-2'(1'H)-one | B |
| 4.73 | (2'-oxospiro[furo[2,3-f][1,3]benzodioxole-7,3'-indol]-1'(2'H)-yl)acetonitrile | B |
| 4.74 | 7'-(trifluoromethyl)-1'-{[5-(trifluoromethyl)-2-furyl]methyl}spiro[furo[2,3-f][1,3]benzodioxole-7,3'-indol]-2'(1'H)-one | B |
| 4.75 | 1'-[(5-chloro-2-thienyl)methyl]-7'-(trifluoromethyl)spiro[furo[2,3-f][1,3]benzodioxole-7,3'-indol]-2'(1'H)-one | B |
| 4.76 | 1'-[(2-isopropyl-1,3-thiazol-5-yl)methyl]-7'-(trifluoromethyl)spiro[furo[2,3-f][1,3]benzodioxole-7,3'-indol]-2'(1'H)-one | B |
| 4.77 | 1'-[(2-isopropyl-1,3-oxazol-5-yl)methyl]spiro[furo[2,3-f][1,3]benzodioxole-7,3'-indol]-2'(1'H)-one | B |
| 4.78 | tert-butyl [1-cyclopropyl-3-(2'-oxospiro[furo[2,3-f][1,3]benzodioxole-7,3'-indol]-1'(2'H)-yl)propyl]carbamate | B |
| 4.79 | 1'-[4-(methylsulfanyl)benzyl]spiro[furo[2,3-f][1,3]benzodioxole-7,3'-indol]-2'(1'H)-one | B |
| 4.80 | 3-(2'-oxospiro[furo[2,3-f][1,3]benzodioxole-7,3'-indol]-1'(2'H)-yl)propanenitrile | B |
| 4.81 | 1'-[(2-bromo-1,3-thiazol-5-yl)methyl]spiro[furo[2,3-f][1,3]benzodioxole-7,3'-indol]-2'(1'H)-one | B |
| 4.82 | 1'-{[2-amino-4-(trifluoromethyl)-1,3-thiazol-5-yl]methyl}spiro[furo[2,3-f][1,3]benzodioxole-7,3'-indol]-2'(1'H)-one | B |
| 4.83 | 6-Fluoro-5-methoxy-1'-{[5-(trifluoromethyl)furan-2-yl]methyl}spiro[1-benzofuran-3,3'-indol]-2'(1'H)-one | B |
| 4.84 | 4'-chloro-2'-oxospiro[furo[2,3-f][1,3]benzodioxole-7,3'-indol]-1'(2'H)-yl)acetonitrile | A |
| 4.85 | 1'-[(2-amino-1,3-thiazol-4-yl)methyl]spiro[furo[2,3-f][1,3]benzodioxole-7,3'-indol]-2'(1'H)-one | B |
| 4.86 | 4'-bromo-1'-[(5-chloro-2-thienyl)methyl]spiro[furo[2,3-f][1,3]benzodioxole-7,3'-indol]-2'(1'H)-one | B |
| 4.87 | 1'-[(5-chloro-2-thienyl)methyl]-2'-oxo-1',2'-dihydrospiro[furo[2,3-f][1,3]benzodioxole-7,3'-indole]-7'-carbonitrile | B |
| 4.88 | 1'-[(2-isopropyl-1,3-thiazol-4-yl)methyl]-2'-oxo-1',2'-dihydrospiro[furo[2,3-f][1,3]benzodioxole-7,3'-indole]-7'-carbonitrile | B |
| 4.89 | 4'-chloro-1'-[(5-chloro-2-thienyl)methyl]spiro[furo[2,3-f][1,3]benzodioxole-7,3'-indol]-2'(1'H)-one | B |
| 4.90 | 4'-chloro-1'-{[5-(trifluoromethyl)-2-furyl]methyl}spiro[furo[2,3-f][1,3]benzodioxole-7,3'-indol]-2'(1'H)-one | B |
| 4.91 | 4'-chloro-1'-[(2-isopropyl-1,3-thiazol-4-yl)methyl]spiro[furo[2,3-f][1,3]benzodioxole-7,3'-indol]-2'(1'H)-one | B |

TABLE 8-continued

| Ex. No. | Compound Name | % Inhibition of CYP3A4 |
|---|---|---|
| 4.92 | 4'-[6-(dimethylamino)pyridin-3-yl]-1'-{[2-(1-methylethyl)-1,3-thiazol-4-yl]methyl}spiro[furo[2,3-f][1,3] benzodioxole-7,3'-indol]-2'(1'H)-one | B |
| 4.93 | 3'-[2-(fluoromethyl)benzyl]-2,3-dihydrospiro[furo[2,3-g][1,4]benzodioxine-8,1'-inden]-2'(3'H)-one | B |
| 4.94 | 3-[(2'-oxo-2,3-dihydrospiro[furo[2,3-g][1,4]benzodioxine-8,3'-indol]-1'(2'H)-yl)methyl]benzonitrile | B |
| 4.95 | 1'-(4-fluoro-3-methoxybenzyl)-2,3-dihydrospiro[furo[2,3-g][1,4]benzodioxine-8,3'-indol]-2'(1'H)-one | B |
| 4.96 | 4-[(2'-oxo-2,3-dihydrospiro[furo[2,3-g][1,4]benzodioxine-8,3'-indol]-1'(2'H)-yl)methyl]benzonitrile | B |
| 4.97 | 1'-(4-isoxazol-5-ylbenzyl)-2,3-dihydrospiro[furo[2,3-g][1,4]benzodioxine-8,3'-indol]-2'(1'H)-one | A |
| 4.98 | 1'-{[6-(trifluoromethyl)pyridin-3-yl]methyl}-2,3-dihydrospiro[furo[2,3-g][1,4]benzodioxine-8,3'-indol]-2'(1'H)-one | B |
| 4.99 | 1'-(4-isoxazol-5-ylbenzyl)-3-methylspiro[furo[3,2-f][1,2]benzisoxazole-5,3'-indol]-2'(1'H)-one | A |
| 4.100 | 1'-[(5-fluoropyridin-2-yl)methyl]-2,3-dihydrospiro[furo[2,3-g][1,4]benzodioxine-8,3'-indol]-2'(1'H)-one | A |
| 4.101 | 1'-[(3-fluoropyridin-2-yl)methyl]-2,3-dihydrospiro[furo[2,3-g][1,4]benzodioxine-8,3'-indol]-2'(1'H)-one | A |
| 4.102 | 1'-(pyridin-2-ylmethyl)-4'-quinolin-3-yl-2,3-dihydrospiro[furo[2,3-g][1,4]benzodioxine-8,3'-indol]-2'(1'H)-one | B |
| 4.103 | 4'-(4-phenoxyphenyl)-1'-(pyridin-2-ylmethyl)-2,3-dihydrospiro[furo[2,3-g][1,4]benzodioxine-8,3'-indol]-2'(1'H)-one | A |
| 4.104 | 1'-[(3,5-difluoropyridin-2-yl)methyl]-2,3-dihydrospiro[furo[2,3-g][1,4]benzodioxine-8,3'-indol]-2'(1'H)-one | A |
| 4.105 | 2'-oxo-1'-(pyridin-2-ylmethyl)-1',2'-dihydrospiro[1-benzofuran-3,3'-indole]-6-carbonitrile | A |
| 4.106 | 3-{[(8S)-2'-oxo-2,3-dihydrospiro[furo[2,3-g][1,4]benzodioxine-8,3'-indol]-1'(2'H)-yl]methyl}benzonitrile | A |
| 4.107 | (8S)-1'-[(5-fluoropyridin-2-yl)methyl]-2,3-dihydrospiro[furo[2,3-g][1,4]benzodioxine-8,3'-indol]-2'(1'H)-one | A |
| 4.108 | (8S)-1'-[(3-fluoropyridin-2-yl)methyl]-2,3-dihydrospiro[furo[2,3-g][1,4]benzodioxine-8,3'-indol]-2'(1'H)-one | A |
| 4.109 | (S)-1'-(2-oxobutyl)-3,7-dihydro-2H-spiro[benzofuro[5,6-b][1,4]dioxine-8,3'-indolin]-2'-one | A |
| 4.110 | 1'-[(4-fluoropyridin-2-yl)methyl]-2,3-dihydrospiro[furo[2,3-g][1,4]benzodioxine-8,3'-indol]-2'(1'H)-one | A |
| 4.111 | 1'-(2,3-dihydro-1,4-benzodioxin-6-ylmethyl)-2'-oxo-1',2'-dihydrospiro[1-benzofuran-3,3'-indole]-6-carbonitrile | A |
| 4.112 | 1'-[(3-chloropyridin-2-yl)methyl]-2,3-dihydrospiro[furo[2,3-g][1,4]benzodioxine-8,3'-indol]-2'(1'H)-one | B |
| 4.113 | 1'-[2-(trifluoromethyl)benzyl]-2,3-dihydrospiro[furo[2,3-g][1,4]benzodioxine-8,3'-indol]-2'(1'H)-one | A |
| 4.114 | (8R)-1'-[2-(trifluoromethyl)benzyl]-2,3-dihydrospiro[furo[2,3-g][1,4]benzodioxine-8,3'-indol]-2'(1'H)-one | A |
| 4.116 | (8S)-1'-[2-(trifluoromethyl)benzyl]-2,3-dihydrospiro[furo[2,3-g][1,4]benzodioxine-8,3'-indol]-2'(1'H)-one | A |
| 4.118 | 1'-(2,1,3-benzothiadiazol-5-ylmethyl)-2,3-dihydrospiro[furo[2,3-g][1,4]benzodioxine-8,3'-indol]-2'(1'H)-one | B |
| 4.119 | 1'-(1,3-benzothiazol-2-ylmethyl)-2,3-dihydrospiro[furo[2,3-g][1,4]benzodioxine-8,3'-indol]-2'(1'H)-one | B |
| 4.120 | 1'-[(1-methyl-1H-benzimidazol-2-yl)methyl]-2,3-dihydrospiro[furo[2,3-g][1,4]benzodioxine-8,3'-indol]-2'(1'H)-one | B |
| 4.121 | 1'-{[2-(1-methylethyl)-1,3-thiazol-4-yl]methyl}-2,3-dihydrospiro[furo[2,3-g][1,4]benzodioxine-8,3'-indol]-2'(1'H)-one | B |
| 4.122 | 1'-(2,1,3-benzoxadiazol-5-ylmethyl)-2,3-dihydrospiro[furo[2,3-g][1,4]benzodioxine-8,3'-indol]-2'(1'H)-one | B |
| 4.124 | 1'-(pyridin-2-ylmethyl)spiro[furo[3,2-e][2,1,3]benzoxadiazole-8,3'-indol]-2'(1'H)-one | A |
| 4.125 | 1'-(pyridin-3-ylmethyl)spiro[furo[3,2-e][2,1,3]benzoxadiazole-8,3'-indol]-2'(1'H)-one | A |
| 4.126 | 6-chloro-1'-(pyridin-2-ylmethyl)-2,3-dihydrospiro[furo[3,2-f][1,4]benzodioxine-9,3'-indol]-2'(1'H)-one | B |
| 4.129 | 1-[(2R)-tetrahydrofuran-2-ylmethyl]-5',6',7',8'-tetrahydrospiro[indole-3,3'-naphtho[2,3-b]furan]-2(1H)-one | A |
| 4.130 | 1'-(pyridin-2-ylmethyl)spiro[furo[2,3-g]quinoxaline-8,3'-indol]-2'(1'H)-one | A |
| 5 | 1'-[(2-methoxypyrimidin-5-yl)methyl]-5,6-dihydrospiro[benzo[1,2-b:5,4-b']difuran-3,3'-indol]-2'(1'H)-one | A |

TABLE 8-continued

| Ex. No. | Compound Name | % Inhibition of CYP3A4 |
|---|---|---|
| 5.1 | 7'-chloro-1'-((5-(trifluoromethyl)furan-2-yl)methyl)-5,6-dihydro-2H-spiro[benzofuro[6,5-b]furan-3,3'-indolin]-2'-one | B |
| 5.2 | (3R)-1'-(3-methylbutyl)-5,6-dihydrospiro[benzo[1,2-b:5,4-b']difuran-3,3'-indol]-2'(1'H)-one | B |
| 5.3 | (3R)-1'-pentyl-5,6-dihydrospiro[benzo[1,2-b:5,4-b']difuran-3,3'-indol]-2'(1'H)-one | B |
| 5.4 | (3R)-1'-(pyridin-2-ylmethyl)-5,6-dihydrospiro[benzo[1,2-b:5,4-b']difuran-3,3'-indol]-2'(1'H)-one | A |
| 5.5 | (3R)-1'-{[5-(trifluoromethyl)furan-2-yl]methyl}-5,6-dihydrospiro[benzo[1,2-b:5,4-b']difuran-3,3'-indol]-2'(1'H)-one | B |
| 5.6 | (3S)-1'-(pyridin-2-ylmethyl)-5,6-dihydrospiro[benzo[1,2-b:5,4-b']difuran-3,3'-indol]-2'(1'H)-one | A |
| 5.7 | (3S)-1'-{[5-(trifluoromethyl)furan-2-yl]methyl}-5,6-dihydrospiro[benzo[1,2-b:5,4-b']difuran-3,3'-indol]-2'(1'H)-one | B |
| 5.8 | 3-methyl-1'-{[5-(trifluoromethyl)furan-2-yl]methyl}spiro[furo[2,3-f][1,3]benzoxazole-7,3'-indole]-2,2'(1'H,3H)-dione | B |
| 5.9 | 1'-{[6-(trifluoromethyl)pyridin-2-yl]methyl}-2,3-dihydrospiro[furo[2,3-g][1,4]benzodioxine-8,3'-indol]-2'(1'H)-one | B |
| 5.10 | 1'-{[2-(trifluoromethyl)pyridin-3-yl]methyl}-2,3-dihydrospiro[furo[2,3-g][1,4]benzodioxine-8,3'-indol]-2'(1'H)-one | A |
| 5.11 | 1'-{[3-(trifluoromethyl)pyrazin-2-yl]methyl}-2,3-dihydrospiro[furo[2,3-g][1,4]benzodioxine-8,3'-indol]-2'(1'H)-one | A |
| 5.12 | 1'-{[4-(trifluoromethyl)pyridin-3-yl]methyl}-2,3-dihydrospiro[furo[2,3-g][1,4]benzodioxine-8,3'-indol]-2'(1'H)-one | B |
| 5.13 | 1'-[(6-chloropyridin-2-yl)methyl]-2,3-dihydrospiro[furo[2,3-g][1,4]benzodioxine-8,3'-indol]-2'(1'H)-one | B |
| 5.14 | 1'-[(2-methoxypyrimidin-5-yl)methyl]-2,3-dihydrospiro[furo[2,3-g][1,4]benzodioxine-8,3'-indol]-2'(1'H)-one | A |
| 5.15 | 1'-[(6-methoxypyridin-3-yl)methyl]-2,3-dihydrospiro[furo[2,3-g][1,4]benzodioxine-8,3'-indol]-2'(1'H)-one | A |
| 5.16 | (8S)-1'-(pyrazin-2-ylmethyl)-2,3-dihydrospiro[furo[2,3-g][1,4]benzodioxine-8,3'-indol]-2'(1'H)-one | A |
| 5.17 | (8S)-1'-[(2-methoxypyrimidin-5-yl)methyl]-2,3-dihydrospiro[furo[2,3-g][1,4]benzodioxine-8,3'-indol]-2'(1'H)-one | A |
| 5.18 | (8S)-1'-(pyrimidin-2-ylmethyl)-2,3-dihydrospiro[furo[2,3-g][1,4]benzodioxine-8,3'-indol]-2'(1'H)-one | A |
| 5.19 | 6-methyl-1'-(pyridin-2-ylmethyl)-2,3-dihydrospiro[1,4-dioxino[2,3-f]indole-8,3'-indole]-2',7(1'H,6H)-dione | A |
| 5.20 | 4'-fluoro-1'-{[3-(trifluoromethyl)pyridin-2-yl]methyl}-2,3-dihydrospiro[furo[2,3-g][1,4]benzodioxine-8,3'-indol]-2'(1'H)-one | A |
| 5.21 | 1'-[(2,2-difluorocyclopropyl)methyl]-2,3-dihydrospiro[furo[2,3-g][1,4]benzodioxine-8,3'-indol]-2'(1'H)-one | A |
| 5.22 | 1'-methyl-2,3-dihydrospiro[furo[2,3-g][1,4]benzodioxine-8,3'-indol]-2'(1'H)-one | A |
| 5.23 | 1'-{[4-(trifluoromethyl)-1,3-thiazol-2-yl]methyl}-2,3-dihydrospiro[furo[2,3-g][1,4]benzodioxine-8,3'-indol]-2'(1'H)-one | B |
| 5.25 | 9-fluoro-1'-(pyridin-2-ylmethyl)-2,3-dihydro-spiro[furo[2,3-g][1,4]benzodioxine-8,3'-indol]-2'(1'H)-one | B |
| 5.26 | 9-fluoro-1'-{[3-(trifluoromethyl)pyridin-2-yl]methyl}-2,3-dihydrospiro[furo[2,3-g][1,4]benzodioxine-8,3'-indol]-2'(1'H)-one | A |
| 5.27 | 9-fluoro-1'-[(5-hydroxypyridin-2-yl)methyl]-2,3-dihydrospiro[furo[2,3-g][1,4]benzodioxine-8,3'-indol]-2'(1'H)-one | B |
| 5.28 | 1'-(pyridin-2-ylmethyl)-7,8-dihydro-6H-spiro-[furo[2,3-g]chromene-3,3'-indol]-2'(1'H)-one | B |
| 5.29 | 1'-{[3-(trifluoromethyl)pyridin-2-yl]methyl}-7,8-dihydro-6H-spiro[furo[2,3-g]chromene-3,3'-indol]-2'(1'H)-one | A |
| 5.31 | 1-(pyridin-2-ylmethyl)spiro[indole-3,3'-thieno[2,3-f][1]benzofuran]-2(1H)-one 5,5'-dioxide | A |
| 5.32 | 1'-(pyrimidin-2-ylmethyl)-2,3-dihydrospiro[furo[2,3-g][1,4]benzodioxine-8,3'-indol]-2'(1'H)-one | A |
| 5.33 | 1'-[(4,6-dimethoxypyrimidin-2-yl)methyl]-2,3-dihydrospiro[furo[2,3-g][1,4]benzodioxine-8,3'-indol]-2'(1'H)-one | B |
| 5.34 | 6-(2-methoxyethoxy)-1'-(pyridin-2-ylmethyl)spiro[1-benzofuran-3,3'-indol]-2'(1'H)-one | A |

TABLE 8-continued

| Ex. No. | Compound Name | % Inhibition of CYP3A4 |
|---|---|---|
| 5.35 | 5-(2-methoxyethoxy)-1'-(pyridin-2-ylmethyl)spiro[1-benzofuran-3,3'-indol]-2'(1'H)-one | A |
| 5.36 | 1'-(pyridin-2-ylmethyl)-2,3-dihydrospiro[furo[2,3-f][1,4]benzodioxine-7,3'-indol]-2'(1'H)-one | A |
| 5.37 | 1'-{[3-(trifluoromethyl)pyridin-2-yl]methyl}-2,3-dihyrospiro[furo[2,3-f][1,4]benzodioxine-7,3'-indol]-2'(1'H)-one | A |
| 5.38 | 6-[(2'-oxospiro[furo[2,3-f][1,3]benzodioxole-7,3'-indol]-1'(2'H)-yl)methyl]pyrimidine-2,4(1H,3H)-dione | A |
| 6 | 1'-[(5-Chloro-1,2,4-thiadiazol-3-yl)methyl]spiro[furo[2,3-f][1,3]benzodioxole-7,3'-indol]-2'(1'H)-one | B |
| 6.1 | 4'-chloro-1'-[(5-chloro-1,2,4-thiadiazol-3-yl)methyl]spiro[furo[2,3-f][1,3]benzodioxole-7,3'-indol]-2'(1'H)-one | B |
| 6.2 | 5,6-dimethyl-1'-(tetrahydro-2H-pyran-2-ylmethyl)spiro[1-benzofuran-3,3'-indol]-2'(1'H)-one | B |
| 6.3 | 1'-[(3-chlorothiophen-2-yl)methyl]spiro[furo[2,3-f][1,3]benzodioxole-7,3'-indol]-2'(1'H)-one | B |
| 6.4 | 1'-{[3-(2,6-dichlorophenyl)-5-methylisoxazol-4-yl]methyl}spiro[furo[2,3-f][1,3]benzodioxole-7,3'-indol]-2'(1'H)-one | B |
| 6.5 | 1'-({2-[4-(trifluoromethyl)phenyl]-1,3-thiazol-4-yl}methyl)spiro[furo[2,3-f][1,3]benzodioxole-7,3'-indol]-2'(1'H)-one | B |
| 6.6 | 1'-[(5-phenyl-1,3,4-oxadiazol-2-yl)methyl]spiro[furo[2,3-f][1,3]benzodioxole-7,3'-indol]-2'(1'H)-one | B |
| 6.7 | 1'-{[5-(4-chlorophenyl)-1,3,4-oxadiazol-2-yl]methyl}spiro[furo[2,3-f][1,3]benzodioxole-7,3'-indol]-2'(1'H)-one | B |
| 6.8 | 1'-([1,3]oxazolo[4,5-b]pyridin-2-ylmethyl)spiro[furo[2,3-f][1,3]benzodioxole-7,3'-indol]-2'(1'H)-one | A |
| 7.1 | 1'-[3-(trifluoromethyl)benzyl]-2,3-dihydrospiro[furo[2,3-g][1,4]benzodioxine-8,3'-indol]-2'(1'H)-one | A |
| 7.2 | methyl 5-[(2'-oxo-2,3-dihydrospiro[furo[2,3-g][1,4]benzodioxine-8,3'-indol]-1'(2'H)-yl)methyl]furan-2-carboxylate | B |
| 7.4 | (R)-1'-pentyl-2,3-dihydrospiro[furo[2,3-g][1,4]benzodioxine-8,3'-indol]-2'(1'H)-one | B |
| 7.5 | 1'-hexyl-2,3-dihydrospiro[furo[2,3-g][1,4]benzodioxine-8,3'-indol]-2'(1'H)-one | B |
| 7.6 | 1'-(2-cyclopropylethyl)-2,3-dihydrospiro[furo[2,3-g][1,3]benzodioxine-8,3'-indol]-2'(1'H)-one | A |
| 7.7 | 1'-(2-ethoxyethyl)-2,3-dihydrospiro[furo[2,3-g][1,3]benzodioxine-8,3'-indol]-2'(1'H)-one | A |
| 7.8 | 1'-(4-methoxybutyl)-2,3-dihydrospiro[furo[2,3-g][1,3]benzodioxine-8,3'-indol]-2'(1'H)-one | A |
| 7.9 | 1'-(3-methoxypropyl)-2,3-dihydrospiro[furo[2,3-g][1,3]benzodioxine-8,3'-indol]-2'(1'H)-one | A |
| 7.10 | 1'-(3-nitrobenzyl)-2,3-dihydrospiro[furo[2,3-g][1,3]benzodioxine-8,3'-indol]-2'(1'H)-one | A |
| 7.11 | 1'-(1,3-thiazol-5-ylmethyl)-2,3-dihydrospiro[furo[2,3-g][1,3]benzodioxine-8,3'-indol]-2'(1'H)-one | B |
| 7.12 | 1'-{[5-(trifluoromethyl)pyridin-2-yl]methyl}-2,3-dihydrospiro[furo[2,3-g][1,3]benzodioxine-8,3'-indol]-2'(1'H)-one | B |
| 7.13 | 1'-{[3-(trifluoromethyl)pyridin-2-yl]methyl}-2,3-dihydrospiro[furo[2,3-g][1,3]benzodioxine-8,3'-indol]-2'(1'H)-one | B |
| 7.14 | 1'-[(3-pyridin-3-ylisoxazol-5-yl)methyl]-2,3-dihydrospiro[furo[2,3-g][1,3]benzodioxine-8,3'-indol]-2'(1'H)-one | B |
| 7.15 | (8R)-1'-{[3-(trifluoromethyl)pyridin-2-yl]methyl}-2,3-dihydrospiro[furo[2,3-g][1,3]benzodioxine-8,3'-indol]-2'(1'H)-one | A |
| 7.16 | N,N-dimethyl-3-[(2'-oxo-2,3-dihydrospiro[furo[2,3-g][1,4]benzodioxine-8,3'-indol]-1'-(2'H)-yl)methyl]benzenesulfonamide | B |
| 7.17 | 1'-[3-(morpholin-4-ylsulfonyl)benzyl]-2,3-dihydrospiro[furo[2,3-g][1,4]benzodioxine-8,3'-indol]-2'(1'H)-one | B |
| 7.18 | 1'-[(4-methyl-1,2,5-oxadiazol-3-yl)methyl]-2,3-dihydrospiro[furo[2,3-g][1,4]benzodioxine-8,3'-indol]-2'(1'H)-one | A |
| 7.19 | 1'-(2,3-difluorobenzyl)-2,3-dihydrospiro[furo[2,3-g][1,4]benzodioxine-8,3'-indol]-2'(1'H)-one | B |
| 7.20 | 1'-(3,5-difluorobenzyl)-2,3-dihydrospiro[furo[2,3-g][1,4]benzodioxine-8,3'-indol]-2'(1'H)-one | B |
| 7.21 | 1'-(4-fluorobenzyl)-2,3-dihydrospiro[furo[2,3-g][1,4]benzodioxine-8,3'-indol]-2'(1'H)-one | B |

TABLE 8-continued

| Ex. No. | Compound Name | % Inhibition of CYP3A4 |
|---|---|---|
| 7.22 | 1'-(2-chloro-4-fluorobenzyl)-2,3-dihydrospiro[furo[2,3-g][1,4]benzodioxine-8,3'-indol]-2'(1'H)-one | A |
| 7.23 | 1'-[(1-methyl-1H-benzotriazol-5-yl)methyl]-2,3-dihydrospiro[furo[2,3-g][1,4]benzodioxine-8,3'-indol]-2'(1'H)-one | A |
| 7.24 | 1'-[(3-trifluoromethoxy)benzyl]-2,3-dihydrospiro[furo[2,3-g][1,4]benzodioxine-8,3'-indol]-2'(1'H)-one | B |
| 7.25 | 1'-[(2-fluoro-6-trifluoromethyl)benzyl]-2,3-dihydrospiro[furo[2,3-g][1,4]benzodioxine-8,3'-indol]-2'(1'H)-one | A |
| 7.26 | 1'-[(2-fluoro-5-trifluoromethyl)benzyl]-2,3-dihydrospiro[furo[2,3-g][1,4]benzodioxine-8,3'-indol]-2'(1'H)-one | A |
| 7.27 | 1'-[(2-trifluoromethoxy)benzyl]-2,3-dihydrospiro[furo[2,3-g][1,4]benzodioxine-8,3'-indol]-2'(1'H)-one | A |
| 7.28 | 1'-[2-(2,2,5-trimethyl-1,3-dioxan-2-yl)ethyl]-2,3-dihydrospiro[furo[2,3-g][1,4]benzodioxine-8,3'-indol]-2'(1'H)-one | B |
| 8 | 1'-[(2S)-1,4-dioxan-2-ylmethyl]spiro[furo[2,3-f][1,3]benzodioxole-7,3'-indol]-2'(1'H)-one | B |
| 8.1 | 7'-chloro-1'-[(2R)-tetrahydrofuran-2-ylmethyl]-5,6-dihydrospiro[benzo[1,2-b:5,4-b']difuran-3,3'-indol]-2'(1'H)-one | A |
| 8.2 | 7'-fluoro-1'-[(2R)-tetrahydrofuran-2-ylmethyl]-5,6-dihydrospiro[benzo[1,2-b:5,4-b']difuran-3,3'-indol]-2'(1'H)-one | A |
| 8.3 | 4'-fluoro-7'-methyl-1'-[(2R)-tetrahydrofuran-2-ylmethyl]-5,6-dihydrospiro[benzo[1,2-b:5,4-b']difuran-3,3'-indol]-2'(1'H)-one | B |
| 8.4 | 1'-pentyl-2,3-dihydrospiro[furo[2,3-g][1,4]benzodioxine-8,3'-indol]-2'(1'H)-one | B |
| 8.5 | (8R)-1'-[(2R)-1,4-dioxan-2-ylmethyl]-2,3-dihydrospiro[furo[2,3-g][1,4]benzodioxine-8,3'-indol]-2'(1'H)-one | A |
| 8.6 | (8R)-1'-[(2S)-1,4-dioxan-2-ylmethyl]-2,3-dihydrospiro[furo[2,3-g][1,4]benzodioxine-8,3'-indol]-2'(1'H)-one | A |
| 8.8 | (8S)-1'-[(2R)-1,4-dioxan-2-ylmethyl]-2,3-dihydrospiro[furo[2,3-g][1,4]benzodioxine-8,3'-indol]-2'(1'H)-one | A |
| 8.9 | 1'-[(2R)-tetrahydrofuran-2-ylmethyl]-6,7-dihydrospiro[benzo[1,2-b:4,5-b']difuran-3,3'-indol]-2'(1'H)-one | A |
| 8.10 | 1'-[(2R)-1,4-dioxan-2-ylmethyl]-6,7-dihydrospiro[benzo[1,2-b:4,5-b']difuran-3,3'-indol]-2'(1'H)-one | A |
| 8.11 | 1'-[(2R)-tetrahydrofuran-2-ylmethyl]-3,4-dihydro-2H-spiro[furo[2,3-h][1,5]benzodioxepine-9,3'-indol]-2'(1'H)-one | A |
| 8.12 | 1'-[(2R)-1,4-dioxan-2-ylmethyl]-3,4-dihydro-2H-spiro[furo[2,3-h][1,5]benzodioxepine-9,3'-indol]-2'(1'H)-one | A |
| 8.13 | 1'-[(2S)-1,4-dioxan-2-ylmethyl]-3,4-dihydro-2H-spiro[furo[2,3-h][1,5]benzodioxepine-9,3'-indol]-2'(1'H)-one | A |
| 8.14 | 3-methyl-1'-(((R)-tetrahydrofuran-2-yl)methyl)-2H-spiro[benzofuro[6,5-d]oxazole-7,3'-indoline]-2,2'(3H,6H)-dione | A |
| 8.15 | 7'-fluoro-1'-(pyridin-2-ylmethyl)-3,7-dihydro-2H-spiro[benzofuro[5,6-b][1,4]dioxine-8,3'-indolin]-2'-one | A |
| 8.16 | 7'-fluoro-1'-((3-(trifluoromethyl)pyridin-2-yl)methyl)-3,7-dihydro-2H-spiro[benzofuro[5,6-b][1,4]dioxine-8,3'-indolin]-2'-one | A |
| 8.17 | 3'-[2-(difluoromethyl)benzyl]-2,3-dihydrospiro[furo[2,3-g][1,4]benzodioxine-8,1'-inden]-2'(3'H)-one | A |
| 8.18 | 1'-[(5-fluoropyridin-3-yl)methyl]-2,3-dihydrospiro[furo[2,3-g][1,4]benzodioxine-8,3'-indol]-2'(1'H)-one | B |
| 8.19 | (8S)-1'-[(5-fluoropyridin-3-yl)methyl]-2,3-dihydrospiro[furo[2,3-g][1,4]benzodioxine-8,3'-indol]-2'(1'H)-one | A |
| 9 | 3-methyl-1'-{[5-(trifluoromethyl)furan-2-yl]methyl}spiro[furo[3,2-f][1,2]benzisoxazole-5,3'-indol]-2'(1'H)-one | B |
| 9.1 | 1'-[2-(2-methoxyethoxy)ethyl]-5,6-dihydrospiro[benzo[1,2-b:5,4-b']difuran-3,3'-indol]-2'(1'H)-one | B |
| 9.2 | 1'-{[(2S)-5-oxopyrrolidin-2-yl]methyl}-5,6-dihydrospiro[benzo[1,2-b:5,4-b']difuran-3,3'-indol]-2'(1'H)-one | A |
| 9.3 | 1'-[2-(2-oxo-1,3-oxazolidin-3-yl)ethyl]-5,6-dihydrospiro[benzo[1,2-b:5,4-b']difuran-3,3'-indol]-2'(1'H)-one | B |
| 9.4 | 1'-(4-pyridin-2-ylbenzyl)-5,6-dihydrospiro[benzo[1,2-b:5,4-b']difuran-3,3'-indol]-2'(1'H)-one | A |
| 9.5 | 1'-(pyrimidin-2-ylmethyl)-5,6-dihydrospiro[benzo[1,2-b:5,4-b']difuran-3,3'-indol]-2'(1'H)-one | A |
| 9.6 | 1'-(pyrimidin-4-ylmethyl)-5,6-dihydrospiro[benzo[1,2-b:5,4-b']difuran-3,3'-indol]-2'(1'H)-one | A |

TABLE 8-continued

| Ex. No. | Compound Name | % Inhibition of CYP3A4 |
|---|---|---|
| 9.7 | 1'-(pyrazin-2-ylmethyl)-5,6-dihydrospiro[benzo[1,2-b:5,4-b']difuran-3,3'-indol]-2'(1'H)-one | A |
| 9.8 | 1'-[(7-fluoro-1-benzofuran-2-yl)methyl]-5,6-dihydrospiro[benzo[1,2-b:5,4-b']difuran-3,3'-indol]-2'(1'H)-one | B |
| 9.9 | 1'-(pyridazin-3-ylmethyl)-5,6-dihydrospiro[benzo[1,2-b:5,4-b']difuran-3,3'-indol]-2'(1'H)-one | A |
| 9.10 | 1'-[(2-oxo-1,3-oxazolidin-5-yl)methyl]-5,6-dihydrospiro[benzo[1,2-b:5,4-b']difuran-3,3'-indol]-2'(1'H)-one | A |
| 9.11 | 1'-[3-(benzyloxy)benzyl]-5,6-dihydrospiro[benzo[1,2-b:5,4-b']difuran-3,3'-indol]-2'(1'H)-one | A |
| 9.12 | 1'-[(1-methyl-1H-benzimidazol-2-yl)methyl]-5,6-dihydrospiro[benzo[1,2-b:5,4-b']difuran-3,3'-indol]-2'(1'H)-one | B |
| 9.13 | 1'-(2H-benzotriazol-2-ylmethyl)-5,6-dihydrospiro[benzo[1,2-b:5,4-b']difuran-3,3'-indol]-2'(1'H)-one | B |
| 9.14 | methyl 2-[(2'-oxo-5,6-dihydrospiro[benzo[1,2-b:5,4-b']difuran-3,3'-indol]-1'(2'H)-yl)methyl]benzoate | A |
| 9.15 | methyl 3-[(2'-oxo-5,6-dihydrospiro[benzo[1,2-b:5,4-b']difuran-3,3'-indol]-1'(2'H)-yl)methyl]benzoate | B |
| 9.16 | methyl 4-[(2'-oxo-5,6-dihydrospiro[benzo[1,2-b:5,4-b']difuran-3,3'-indol]-1'(2'H)-yl)methyl]benzoate | A |
| 9.17 | 1'-[3-(benzyloxy)propyl]-5,6-dihydrospiro[benzo[1,2-b:5,4-b']difuran-3,3'-indol]-2'(1'H)-one | B |
| 9.18 | 5'-fluoro-1'-[(2R)-tetrahydrofuran-2-ylmethyl]-5,6-dihydrospiro[benzo[1,2-b:5,4-b']difuran-3,3'-indol]-2'(1'H)-one | B |
| 9.19 | 6'-fluoro-1'-[(2R)-tetrahydrofuran-2-ylmethyl]-5,6-dihydrospiro[benzo[1,2-b:5,4-b']difuran-3,3'-indol]-2'(1'H)-one | A |
| 9.20 | 1'-[2-(2-methoxyethoxy)ethyl]-2,3-dihydrospiro[furo[2,3-g][1,4]benzodioxine-8,3'-indol]-2'(1'H)-one | A |
| 9.21 | 2-methyl-1'-(pyridin-2-ylmethyl)spiro[furo[2,3-f][1,3]benzothiazole-7,3'-indol]-2'(1'H)-one | A |
| 9.22 | 1'-[(5-chloro-1-methyl-1H-imidazol-2-yl)methyl]-2-methylspiro[furo[2,3-f][1,3]benzothiazole-7,3'-indol]-2'(1'H)-one | B |
| 9.23 | 4-methyl-1'-(((R)-tetrahydrofuran-2-yl)methyl)-4,7-dihydrospiro[benzofuro[5,6-b][1,4]oxazine-8,3'-indoline]-2',3(2H)-dione | A |
| 9.24 | 3-methyl-1'-(pyridin-2-ylmethyl)spiro[furo[3,2-f][1,2]benzisoxazole-5,3'-indol]-2'(1'H)-one | B |
| 9.25 | 3-methyl-1'-(pyridin-3-ylmethyl)spiro[furo[3,2-f][1,2]benzisoxazole-5,3'-indol]-2'(1'H)-one | B |
| 9.26 | 3-methyl-1'-[(2R)-tetrahydrofuran-2-ylmethyl]spiro[furo[3,2-f][1,2]benzisoxazole-5,3'-indol]-2'(1'H)-one | A |
| 9.27 | 5,6-dimethyl-1'-(tetrahydro-2H-pyran-4-ylmethyl)spiro[1-benzofuran-3,3'-indol]-2'(1'H)-one | B |
| 9.28 | 5,6-dimethyl-1'-(pyridin-2-ylmethyl)spiro[1-benzofuran-3,3'-indol]-2'(1'H)-one | A |
| 9.29 | 5-fluoro-6-methoxy-1'-(tetrahydro-2H-pyran-4-ylmethyl)spiro[1-benzofuran-3,3'-indol]-2'(1'H)-one | A |
| 9.30 | 5-fluoro-6-methoxy-1'-{[5-(trifluoromethyl)furan-2-yl]methyl}spiro[1-benzofuran-3,3'-indol]-2'(1'H)-one | B |
| 9.31 | 5,6-difluoro-1'-(pyridin-3-ylmethyl)spiro[1-benzofuran-3,3'-indol]-2'(1'H)-one | B |
| 9.32 | 5,6-difluoro-1'-{[5-(trifluoromethyl)furan-2-yl]methyl}spiro[1-benzofuran-3,3'-indol]-2'(1'H)-one | B |
| 9.33 | 6-methoxy-1'-(pyridin-2-ylmethyl)-2H-spiro[benzofuran-3,3'-indolin]-2'-one | A |
| 9.34 | 6-methoxy-1'-(pyridin-3-ylmethyl)spiro[1-benzofuran-3,3'-indol]-2'(1'H)-one | B |
| 9.35 | 6-methoxy-1'-(tetrahydro-2H-pyran-4-ylmethyl)spiro[1-benzofuran-3,3'-indol]-2'(1'H)-one | B |
| 9.36 | 6-methoxy-1'-(tetrahydro-2H-pyran-2-ylmethyl)spiro[1-benzofuran-3,3'-indol]-2'(1'H)-one | A |
| 9.37 | 1'-[4-(benzyloxy)benzyl]-2,3-dihydrospiro[furo[2,3-g][1,4]benzodioxine-8,3'-indol]-2'(1'H)-one | A |
| 9.38 | 1'-[4-(benzyloxy)benzyl]-5,6-dihydrospiro[benzo[1,2-b:5,4-b']difuran-3,3'-indol]-2'(1'H)-one | A |
| 9.39 | (8S)-1'-[4-(benzyloxy)benzyl]-2,3-dihydrospiro[furo[2,3-g][1,4]benzodioxine-8,3'-indol]-2'(1'H)-one | A |
| 9.40 | tert-butyl {5-[(2'-oxo-2,3-dihydrospiro[furo[2,3-g][1,4]benzodioxine-8,3'-indol]-1'(2'H)-yl)methyl]pyridin-2-yl}carbamate | A |

TABLE 8-continued

| Ex. No. | Compound Name | % Inhibition of CYP3A4 |
|---|---|---|
| 9.41 | 3-methyl-1'-[2-(trifluoromethyl)benzyl]spiro[furo[3,2-f][1,2]benzisoxazole-5,3'-indol]-2'(1'H)-one | B |
| 9.42 | 3-methyl-1'-{[3-(trifluoromethyl)pyridin-2-yl]methyl}spiro[furo[3,2-f][1,2]benzisoxazoie-5,3'-indol]-2'(1'H)-one | B |
| 9.43 | 1'-[3-(benzyloxy)propyl]-2,3-dihydrospiro[furo[2,3-g][1,4]benzodioxine-8,3'-indol]-2'(1'H)-one | A |
| 9.44 | ethyl (2'-oxo-2,3-dihydrospiro[furo[2,3-g][1,4]benzodioxine-8,3'-indol]-1'(2'H)-yl)acetate | A |
| 9.45 | 1'-{[(4S)-2,2-dimethyl-1,3-dioxolan-4-yl]methyl}-2,3-dihydrospiro[furo[2,3-g][1,4]benzodioxine-8,3'-indol]-2'(1'H)-one | B |
| 9.46 | 6-methoxy-1'-(4-methoxybenzyl)-2'-oxo-1',2'-dihydrospiro[1-benzofuran-3,3'-indole]-5-carbonitrile | B |
| 9.47 | 6-methoxy-2'-oxo-1'-(pyridin-2-ylmethyl)-1',2'-dihydrospiro[1-benzofuran-3,3'-indole]-5-carbonitrile | B |
| 9.48 | 6-fluoro-2'-oxo-1'-(pyridin-2-ylmethyl)-1',2'-dihydrospiro[1-benzofuran-3,3'-indole]-5-carbonitrile | B |
| 9.50 | 6-fluoro-2'-oxo-1'-[2-(trifluoromethyl)benzyl]-1',2'-dihydrospiro[1-benzofuran-3,3'-indole]-5-carbonitrile | B |
| 9.51 | 6-fluoro-2'-oxo-1'-{[3-(trifluoromethyl)pyridin-2-yl]methyl}-1',2'-dihydrospiro[1-benzofuran-3,3'-indole]-5-carbonitrile | A |
| 9.53 | methyl 3-[(2'-oxo-2,3-dihydrospiro[furo[2,3-g][1,4]benzodioxine-8,3'-indol]-1'(2'H)-yl)methyl]benzoate | B |
| 9.54 | 1'-[2-(2-methoxyethoxy)ethyl]-3-methylspiro[furo[3,2-f][1,2]benzisoxazole-5,3'-indol]-2'(1'H)-one | A |
| 9.55 | 3-methyl-1'-(3-methylbutyl)spiro[furo[3,2-f][1,2]benzisoxazole-5,3'-indol]-2'(1'H)-one | B |
| 9.56 | 3-methyl-1'-(pyrazin-2-ylmethyl)spiro[furo[3,2-f][1,2]benzisoxazole-5,3'-indol]-2'(1'H)-one | A |
| 9.57 | 1'-[(3-fluoropyridin-2-yl)methyl]-3-methylspiro[furo[3,2-f][1,2]benzisoxazole-5,3'-indol]-2'(1'H)-one | A |
| 9.58 | methyl 2-[(3-methyl-2'-oxospiro[furo[3,2-f][1,2]benzisoxazole-5,3'-indol]-1'(2'H)-yl)methyl]-1,3-oxazole-4-carboxylate | A |
| 9.59 | methyl 4-[(2'-oxo-2,3-dihydrospiro[furo[2,3-g][1,4]benzodioxine-8,3'-indol]-1'(2'H)-yl)methyl]benzoate | A |
| 9.60 | 1'-[(4-benzylmorpholin-2-yl)methyl]-2,3-dihydrospiro[furo[2,3-g][1,4]benzodioxine-8,3'-indol]-2'(1'H)-one | B |
| 9.64 | 5,6-difluoro-1'-(pyridin-2-ylmethyl)spiro[1-benzofuran-3,3'-indol]-2'(1'H)-one | A |
| 9.65 | 5,6-difluoro-1'-(tetrahydro-2H-pyran-4-ylmethyl)spiro[1-benzofuran-3,3'-indol]-2'(1'H)-one | A |
| 9.66 | 2-[3-(2'-oxo-5,6-dihydrospiro[benzo[1,2-b:5,4-b']difuran-3,3'-indol]-1'(2'H)-yl)propyl]-1H-isoindole-1,3(2H)-dione | B |
| 9.67 | 1'-{[5-(benzyloxy)pyridin-2-yl]methyl}spiro[furo[3,2-e][2,1,3]benzoxadiazole-8,3'-indol]-2'(1'H)-one | A |
| 9.70 | (8S)-1'-[2-(2-methoxyethoxy)ethyl]-2,3-dihydrospiro[furo[2,3-g][1,4]benzodioxine-8,3'-indol]-2'(1'H)-one | A |
| 9.71 | 6'-[2-(2-methoxyethoxy)ethyl]-2,3-dihydrospiro[furo[2,3-g][1,4]benzodioxine-8,8'-[1,3]thiazolo[5,4-e]indol]-7'(6'H)-one | B |
| 9.72 | 6'-(pyridin-2-ylmethyl)-2,3-dihydrospiro[furo[2,3-g][1,4]benzodioxine-8,8'-[1,3]thiazolo[5,4-e]indol]-7'(6'H)-one | B |
| 9.73 | 4',6'-dimethoxy-1'-[2-(2-methoxyethoxy)ethyl]-2,3-dihydrospiro[furo[2,3-g][1,4]benzodioxine-8,3'-indol]-2'(1'H)-one | B |
| 9.74 | 4',6'-dimethoxy-1'-(pyridin-2-ylmethyl)-2,3-dihydrospiro[furo[2,3-g][1,4]benzodioxine-8,3'-indol]-2'(1'H)-one | B |
| 9.75 | 6-(2-methoxyethoxy)-1'-[2-(2-methoxyethoxy)ethyl]spiro[1-benzofuran-3,3'-indol]-2'(1'H)-one | A |
| 9.76 | 5-(2-methoxyethoxy)-1'-[2-(2-methoxyethoxy)ethyl]spiro[1-benzofuran-3,3'-indol]-2'(1'H)-one | A |
| 10 | 1-(pyridazin-4-ylmethyl)-5,6-dihydrospiro[benzo[1,2-b:5,4-b']difuran-3,3'-indol]-2'(1'H)-one | B |
| 11 | 1'-[(2-chloro-1,3-thiazol-5-yl)methyl]spiro[furo[2,3-f][1,3]benzodioxole-7,3'-indol]-2'(1'H)-one | B |
| 11.1 | 1'-{[2-(dimethylamino)-1,3-thiazol-5-yl]methyl}spiro[furo[2,3-f][1,3]benzodioxole-7,3'-indol]-2'(1'H)-one | B |
| 11.2 | 1'-[(2-morpholin-4-yl-1,3-thiazol-5-yl)methyl]spiro[furo[2,3-f][1,3]benzodioxole-7,3'-indol]-2'(1'H)-one | B |
| 11.3 | 1'-[(2-piperidin-1-yl-1,3-thiazol-5-yl)methyl]spiro[furo[2,3-f][1,3]benzodioxole-7,3'-indol]-2'(1'H)-one | B |
| 11.4 | 1'-[(2-methoxy-1,3-thiazol-5-yl)methyl]spiro[furo[2,3-f][1,3]benzodioxole-7,3'-indol]-2'(1'H)-one | B |

TABLE 8-continued

| Ex. No. | Compound Name | % Inhibition of CYP3A4 |
|---|---|---|
| 11.5 | 1'-(piperidin-4-ylmethyl)-5,6-dihydrospiro[benzo[1,2-b:5,4-b']difuran-3,3'-indol]-2'(1'H)-one | A |
| 11.6 | 1'-{[1-(1-methylethyl)piperidin-4-yl]methyl}-5,6-dihydrospiro[benzo[1,2-b:5,4-b']difuran-3,3'-indol]-2'(1'H)-one | B |
| 11.8 | 1'-[(1-ethylpiperidin-4-yl)methyl]-5,6-dihydrospiro[benzo[1,2-b:5,4-b']difuran-3,3'-indol]-2'(1'H)-one | B |
| 11.10 | 1'-[(1-methylpiperidin-4-yl)methyl]-5,6-dihydrospiro[benzo[1,2-b:5,4-b']difuran-3,3'-indol]-2'(1'H)-one | B |
| 11.12 | 3-[(2'-oxo-5,6-dihydrospiro[benzo[1,2-b:5,4-b']difuran-3,3'-indol]-1'(2'H)-yl)methyl]benzoic acid | A |
| 11.13 | 1'-{4-[5-(trifluoromethyl)-1,2,4-oxadiazol-3-yl]benzyl}-5,6-dihydrospiro[benzo[1,2-b:5,4-b']difuran-3,3'-indol]-2'(1'H)-one | A |
| 11.14 | 1'-[4-(5-methyl-1,2,4-oxadiazol-3-yl)benzyl]-5,6-dihydrospiro[benzo[1,2-b:5,4-b']difuran-3,3'-indol]-2'(1'H)-one | A |
| 11.15 | 1'-[(5-pyridin-4-ylfuran-2-yl)methyl]-5,6-dihydrospiro[benzo[1,2-b:5,4-b']difuran-3,3'-indol]-2'(1'H)-one | B |
| 11.16 | 1'-(4-pyridin-3-ylbenzyl)-5,6-dihydrospiro[benzo[1,2-b:5,4-b']difuran-3,3'-indol]-2'(1'H)-one | B |
| 11.17 | 1'-[(2'-fluorobiphenyl-4-yl)methyl]-5,6-dihydrospiro[benzo[1,2-b:5,4-b']difuran-3,3'-indol]-2'(1'H)-one | A |
| 11.18 | 1'-{2-[5-(trifluoromethyl)-1,2,4-oxadiazol-3-yl]ethyl}spiro[furo[2,3-f][1,3]benzodioxole-7,3'-indol]-2'(1'H)-one | B |
| 11.19 | 4'-chloro-1'-{[5-(trifluoromethyl)-1,2,4-oxadiazol-3-yl]methyl}spiro[furo[2,3-f][1,3]benzodioxole-7,3'-indol]-2'(1'H)-one | B |
| 11.20 | 4'-chloro-1'-[(5-cyclopropyl-1,2,4-oxadiazol-3-yl)methyl]spiro[furo[2,3-f][1,3]benzodioxole-7,3'-indol]-2'(1'H)-one | B |
| 11.21 | 4'-chloro-1'-{1-[5-(difluoromethyl)-1,2,4-oxadiazol-3-yl]ethyl}spiro[furo[2,3-f][1,3]benzodioxole-7,3'-indol]-2'(1'H)-one | B |
| 11.22 | 1'-{[5-(difluoromethyl)-1,2,4-oxadiazol-3-yl]methyl}spiro[furo[2,3-f][1,3]benzodioxole-7,3'-indol]-2'(1'H)-one | B |
| 11.23 | 1'-[(5-tert-butyl-1,2,4-oxadiazol-3-yl)methyl]spiro[furo[2,3-f][1,3]benzodioxole-7,3'-indol]-2'(1'H)-one | B |
| 11.24 | 1'-[(5-cyclopropyl-1,2,4-oxadiazol-3-yl)methyl]spiro[furo[2,3-f][1,3]benzodioxole-7,3'-indol]-2'(1'H)-one | B |
| 11.25 | 4'-chloro-1'-{[5-(1-methylethyl)-1,2,4-oxadiazol-3-yl]methyl}spiro[furo[2,3-f][1,3]benzodioxole-7,3'-indol]-2'(1'H)-one | B |
| 11.26 | 1'-{[5-(1-methylethyl)-1,2,4-oxadiazol-3-yl]methyl}spiro[furo[2,3-f][1,3]benzodioxole-7,3'-indol]-2'(1'H)-one | B |
| 11.27 | 1'-[3-(5-methyl-1,2,4-oxadiazol-3-yl)benzyl]-5,6-dihydrospiro[benzo[1,2-b:5,4-b']difuran-3,3'-indol]-2'(1'H)-one | B |
| 11.28 | 1'-{3-[5-(trifluoromethyl)-1,2,4-oxadiazol-3-yl]benzyl}-5,6-dihydrospiro[benzo[1,2-b:5,4-b']difuran-3,3'-indol]-2'(1'H)-one | B |
| 11.29 | 1'-[4-(5-methyl-4H-1,2,4-triazol-3-yl)benzyl]-5,6-dihydrospiro[benzo[1,2-b:5,4-b']difuran-3,3'-indol]-2'(1'H)-one | B |
| 11.30 | 2-[(2'-oxo-5,6-dihydrospiro[benzo[1,2-b:5,4-b']difuran-3,3'-indol]-1'(2'H)-yl)methyl]benzoic acid | A |
| 11.31 | 4-[(2'-oxo-5,6-dihydrospiro[benzo[1,2-b:5,4-b']difuran-3,3'-indol]-1'(2'H)-yl)methyl]benzoic acid | A |
| 11.33 | N,N-dimethyl-5-[(2'-oxo-2,3-dihydrospiro[furo[2,3-g][1,4]benzodioxine-8,3'-indol]-1'(2'H)-yl)methyl]furan-2-carboxamide | B |
| 11.34 | 1'-(3-hydroxypropyl)-5,6-dihydrospiro[benzo[1,2-b:5,4-b']difuran-3,3'-indol]-2'(1'H)-one | A |
| 11.35 | 2'-oxo-1'-[(2R)-tetrahydrofuran-2-ylmethyl]-1',2',5,6-tetrahydrospiro[benzo[1,2-b:5,4-b']difuran-3,3'-indole]-4'-carbonitrile | A |
| 11.37 | 4'-[(dimethylamino)methyl]-1'-[(2R)-tetrahydrofuran-2-ylmethyl]-5,6-dihydrospiro[benzo[1,2-b:5,4-b']difuran-3,3'-indol]-2'(1'H)-one | A |
| 11.38 | 4'-(pyrrolidin-1-ylmethyl)-1'-[(2R)-tetrahydrofuran-2-ylmethyl]-5,6-dihydrospiro[benzo[1,2-b:5,4-b']difuran-3,3'-indol]-2'(1'H)-one | A |
| 11.39 | 4'-amino-1'-[(2R)-tetrahydrofuran-2-ylmethyl]-5,6-dihydrospiro[benzo[1,2-b:5,4-b']difuran-3,3'-indol]-2'(1'H)-one | B |

TABLE 8-continued

| Ex. No. | Compound Name | % Inhibition of CYP3A4 |
|---|---|---|
| 11.41 | 1'-[(4-methylmorpholin-2-yl)methyl]-5,6-dihydrospiro[benzo[1,2-b:5,4-b']difuran-3,3'-indol]-2'(1'H)-one | B |
| 11.42 | 1'-{[4-(1-methylethyl)morpholin-2-yl]methyl}-5,6-dihydrospiro[benzo[1,2-b:5,4-b']difuran-3,3'-indol]-2'(1'H)-one | B |
| 11.43 | 1'-methyl-5,6-dihydrospiro[benzo[1,2-b:5,4-b']difuran-3,3'-indol]-2'(1'H)-one | A |
| 11.44 | 1'-[4-(1H-tetrazol-5-yl)benzyl]-5,6-dihydrospiro[benzo[1,2-b:5,4-b']difuran-3,3'-indol]-2'(1'H)-one | B |
| 11.45 | 1'-(3-hydroxybenzyl)-5,6-dihydrospiro[benzo[1,2-b:5,4-b']difuran-3,3'-indol]-2'(1'H)-one | B |
| 11.46 | 1'-(4-morpholin-4-ylbenzyl)-5,6-dihydrospiro[benzo[1,2-b:5,4-b']difuran-3,3'-indol]-2'(1'H)-one | B |
| 11.47 | 6-amino-1'-[(2R)-tetrahydrofuran-2-ylmethyl]spiro[1-benzofuran-3,3'-indol]-2'(1'H)-one | B |
| 11.48 | N-{2'-oxo-1'-[(2R)-tetrahydrofuran-2-ylmethyl]-1',2'-dihydrospiro[1-benzofuran-3,3'-indol]-6-yl}methanesulfonamide | A |
| 11.49 | 6-hydroxy-1'-(3-methylbutyl)spiro[1-benzofuran-3,3'-indol]-2'(1'H)-one | B |
| 11.50 | 6-hydroxy-1'-(3-methylbutyl)-5-(trifluoroacetyl)spiro[1-benzofuran-3,3'-indol]-2'(1'H)-one | B |
| 11.52 | 6-[(3R)-pyrrolidin-3-ylamino]-1'-{[5-(trifluoromethyl)furan-2-yl]methyl}spiro[1-benzofuran-3,3'-indol]-2'(1'H)-one | B |
| 11.53 | 6-hydroxy-1'-[(2R)-tetrahydrofuran-2-ylmethyl]spiro[1-benzofuran-3,3'-indol]-2'(1'H)-one | A |
| 11.54 | 6-(1-methylethoxy)-1'-[(2R)-tetrahydrofuran-2-ylmethyl]spiro[1-benzofuran-3,3'-indol]-2'(1'H)-one | A |
| 11.56 | 6-[(3S)-pyrrolidin-3-yloxy]-1'-[(2R)-tetrahydrofuran-2-ylmethyl]spiro[1-benzofuran-3,3'-indol]-2'(1'H)-one hydrochloride | A |
| 11.58 | 6-[(3R)-pyrrolidin-3-yloxy]-1'-[(2R)-tetrahydrofuran-2-ylmethyl]spiro[1-benzofuran-3,3'-indol]-2'(1'H)-one hydrochloride | A |
| 11.60 | 1'-[(2R)-tetrahydrofuran-2-ylmethyl]spiro[benzo[1,2-b:5,4-b']difuran-3,3'-indole]-2',5(1'H,6H)-dione | A |
| 11.61 | 1'-(pyrrolidin-3-ylmethyl)-5,6-dihydrospiro[benzo[1,2-b:5,4-b']difuran-3,3'-indol]-2'(1'H)-one | A |
| 11.62 | N-(1-methylethyl)-3-[(2'-oxo-5,6-dihydrospiro[benzo[1,2-b:5,4-b']difuran-3,3'-indol]-1'(2'H)-yl)methyl]pyrrolidine-1-carboxamide | B |
| 11.63 | 1'-[(4-methylpiperazin-1-yl)methyl]spiro[furo[2,3-f][1,3]benzodioxole-7,3'-indol]-2'(1'H)-one hydrogen chloride | B |
| 11.64 | (3S)-6-methoxy-5-methyl-1'-[(4-methylpiperazin-1-yl)methyl]spiro[1-benzofuran-3,3'-indol]-2'(1'H)-one hydrogen chloride | A |
| 11.65 | (3R)-6-methoxy-5-methyl-1'-[(4-methylpiperazin-1-yl)methyl]spiro[1-benzofuran-3,3'-indol]-2'(1'H)-one hydrogen chloride | B |
| 11.62 | (3S)-1'-[(2R)-tetrahydrofuran-2-ylmethyl]-5,6-dihydrospiro[benzo[1,2-b:5,4-b']difuran-3,3'-indol]-2'(1'H)-one | A |
| 11.67 | (3R)-1'-[(2R)-tetrahydrofuran-2-ylmethyl]-5,6-dihydrospiro[benzo[1,2-b:5,4-b']difuran-3,3'-indol]-2'(1'H)-one | A |
| 11.68 | (3R)-1'-[(2S)-tetrahydrofuran-2-ylmethyl]-5,6-dihydrospiro[benzo[1,2-b:5,4-b']difuran-3,3'-indol]-2'(1'H)-one | B |
| 11.69 | (3S)-1'-[(2S)-tetrahydrofuran-2-ylmethyl]-5,6-dihydrospiro[benzo[1,2-b:5,4-b']difuran-3,3'-indol]-2"(1'H)-one | A |
| 11.70 | 1'-{[(2S)-1-methyl-5-oxopyrrolidin-2-yl]methyl}-5,6-dihydrospiro[benzo[1,2-b:5,4-b']difuran-3,3'-indol]-2'(1'H)-one | B |
| 11.71 | 1'-[(3-methyl-2-oxo-1,3-oxazolidin-5-yl)methyl]spiro[furo[2,3-f][1,3]benzodioxole-7,3'-indol]-2'(1'H)-one | B |
| 11.72 | 1'-{[5-(trifluoromethyl)-1,2,4-oxadiazol-3-yl]methyl}spiro[furo[2,3-f][1,3]benzodioxole-7,3'-indol]-2'(1'H)-one | B |
| 11.73 | N-isopropyl-3-[2-(2'-oxospiro[furo[2,3-f][1,3]benzodioxole-7,3'-indol]-1'(2'H)-yl)ethyl]piperidine-1-carboxamide | B |
| 11.74 | 5-[(2'-oxospiro[furo[2,3-f][1,3]benzodioxole-7,3'-indol]-1'(2'H)-yl)methyl]thiophene-3-carbonitrile | B |
| 11.75 | 2'-oxo-1',2'-dihydrospiro[furo[2,3-f][1,3]benzodioxole-7,3'-indole]-7'-carbonitrile | B |

TABLE 8-continued

| Ex. No. | Compound Name | % Inhibition of CYP3A4 |
|---|---|---|
| 11.77 | 1'-methyl-2'-oxo-1',2,2',3-tetrahydrospiro[furo[2,3-g][1,4]benzodioxine-8,3'-indole]-4'-carboxylic acid | A |
| 11.78 | 3'-[(3-bromopyridin-2-yl)methyl]-2,3-dihydrospiro[furo[2,3-g][1,4]benzodioxine-8,1'-inden]-2'(3'H)-one | A |
| 11.79 | 3'-{[3-(methylsulfonyl)pyridin-2-yl]methyl}-2,3-dihydrospiro[furo[2,3-g][1,4]benzodioxine-8,1'-inden]-2'(3'H)-one | A |
| 11.80 | 2-[(2'-oxo-2,2',3,3'-tetrahydrospiro[furo[2,3-g][1,4]benzodioxine-8,1'-inden]-3'-yl)methyl]pyridine-3-carbonitrile | A |
| 11.81 | (8S)-1'-{[3-(difluoromethyl)pyridin-2-yl]methyl}-2,3-dihydrospiro[furo[2,3-g][1,4]benzodioxine-8,3'-indol]-2'(1'H)-one | A |
| 11.83 | 1'-[3-(5-methyl-1,2,4-oxadiazol-3-yl)benzyl]-2,3-dihydrospiro[furo[2,3-g][1,4]benzodioxine-8,3'-indol]-2'(1'H)-one | B |
| 11.84 | 1'-[4-(5-methyl-1,2,4-oxadiazol-3-yl)benzyl]-2,3-dihydrospiro[furo[2,3-g][1,4]benzodioxine-8,3'-indol]-2'(1'H)-one | A |
| 11.85 | 6-(5-methyl-1,2,4-oxadiazol-3-yl)-1'-(pyridin-2-ylmethyl)spiro[1-benzofuran-3,3'-indol]-2'(1'H)-one | A |
| 11.86 | 3-[(2'-oxo-2,3-dihydrospiro[furo[2,3-g][1,4]benzodioxine-8,3'-indol]-1'(2'H)-yl)methyl]benzoic acid | A |
| 11.87 | 4-[(2'-oxo-2,3-dihydrospiro[furo[2,3-g][1,4]benzodioxine-8,3'-indol]-1'(2'H)-yl)methyl]benzoic acid | A |
| 11.90 | 1'-{[5-(trifluoromethyl)-1,2,4-oxadiazol-3-yl]methyl}-2,3-dihydrospiro[furo[2,3-g][1,4]benzodioxine-8,3'-indol]-2'(1'H)-one | B |
| 11.92 | 1'-{[5-(trifluoromethyl)-1,3,4-oxadiazol-2-yl]methyl}-2,3-dihydrospiro[furo[2,3-g][1,4]benzodioxine-8,3'-indol]-2'(1'H)-one | A |
| 11.94 | N-{3-[(2'-oxo-2,3-dihydrospiro[furo[2,3-g][1,4]benzodioxine-8,3'-indol]-1'(2'H)-yl)methyl]phenyl}methanesulfonamide | B |
| 11.95 | 1'-[(1-oxydopyridin-2-yl)methyl]-2,3-dihydrospiro[furo[2,3-g][1,4]benzodioxine-8,3'-indol]-2'(1'H)-one | A |
| 11.97 | 1'-[(3-aminopyridin-2-yl)methyl]-2,3-dihydrospiro[furo[2,3-g][1,4]benzodioxine-8,3'-indol]-2'(1'H)-one hydrobromide | B |
| 11.98 | N-{2-[(2'-oxo-2,3-dihydrospiro[furo[2,3-g][1,4]benzodioxine-8,3'-indol]-1'(2'H)-yl)methyl]pyridine-3-yl}methanesulfonamide | B |
| 11.99 | 1'-(piperidin-4-ylmethyl)-2,3-dihydrospiro[furo[2,3-g][1,4]benzodioxine-8,3'-indol]-2'(1'H)-one hydrochloride | A |
| 11.100 | 1'-{[1-(1-methylethyl)piperidin-4-yl]methyl}-2,3-dihydrospiro[furo[2,3-g][1,4]benzodioxine-8,3'-indol]-2'(1'H)-one hydrochloride | B |
| 11.101 | 1'-[(1-methylpiperidin-4-yl)methyl]-2,3-dihydrospiro[furo[2,3-g][1,4]benzodioxine-8,3'-indol]-2'(1'H)-one hydrochloride | A |
| 11.102 | 1'-(morpholin-2-ylmethyl)-2,3-dihydrospiro[furo[2,3-g][1,4]benzodioxine-8,3'-indol]-2'(1'H)-one | A |
| 11.103 | 1'-{[4-(1-methylethyl)morpholin-2-yl]methyl}-2,3-dihydrospiro[furo[2,3-g][1,4]benzodioxine-8,3'-indol]-2'(1'H)-one | B |
| 11.104 | 1'-[(4-methylmorpholin-2-yl)methyl]-2,3-dihydrospiro[furo[2,3-g][1,4]benzodioxine-8,3'-indol]-2'(1'H)-one | B |
| 11.106 | (8S)-1'-{[(2S)-4-methylmorpholin-2-yl]methyl}-2,3-dihydrospiro[furo[2,3-g][1,4]benzodioxine-8,3'-indol]-2'(1'H)-one | A |
| 11.107 | 1'-{[3-(trifluoromethyl)pyridin-2-yl]methyl}spiro[furo[3,2-e][2,1,3]benzoxadiazole-8,3'-indol]-2'(1'H)-one | B |
| 11.108 | 6-chloro-1'-{[3-(trifluoromethyl)pyridin-2-yl]methyl}-2,3-dihydrospiro[furo[3,2-f][1,4]benzodioxine-9,3'-indol]-2'(1'H)-one | A |
| 11.109 | 1'-{[3-(trifluoromethyl)pyridin-2-yl]methyl}-2,3-dihydrospiro[furo[3,2-f][1,4]benzodioxine-9,3'-indol]-2'(1'H)-one | A |
| 11.110 | 1'-{[5-(difluoromethyl)furan-2-yl]methyl}-2,3-dihydrospiro[furo[2,3-g][1,4]benzodioxine-8,3'-indol]-2'(1'H)-one | B |
| 11.111 | 5,6-difluoro-1'-(piperidin-4-ylmethyl)spiro[1-benzofuran-3,3'-indol]-2'(1'H)-one hydrochloride | B |
| 11.112 | 5,6-difluoro-1'-[(1-methylpiperidin-4-yl)methyl]spiro[1-benzofuran-3,3'-indol]-2'(1'H)-one hydrochloride | B |
| 12 | N-(cyclohexylmethyl)-3-[(2'-oxo-5,6-dihydrospiro[benzo[1,2-b:5,4-b']difuran-3,3'-indol]-1'(2'H)-yl)methyl]benzamide | B |

TABLE 8-continued

| Ex. No. | Compound Name | % Inhibition of CYP3A4 |
|---|---|---|
| 12.1 | N-(2-methoxyethyl)-3-[(2'-oxo-5,6-dihydrospiro[benzo[1,2-b:5,4-b']difuran-3,3'-indol]-1'(2'H)-yl)methyl]benzamide | B |
| 12.2 | N-hexyl-N-methyl-3-[(2'-oxo-5,6-dihydrospiro[benzo[1,2-b:5,4-b']difuran-3,3'-indol]-1'(2'H)-yl)methyl]benzamide | B |
| 12.3 | N-(2-ethylbutyl)-3-[(2'-oxo-5,6-dihydrospiro[benzo[1,2-b:5,4-b']difuran-3,3'-indol]-1'(2'H)-yl)methyl]benzamide | B |
| 12.4 | N-(2,4-dimethylphenyl)-3-[(2'-oxo-5,6-dihydrospiro[benzo[1,2-b:5,4-b']difuran-3,3'-indol]-1'(2'H)-yl)methyl]benzamide | B |
| 12.5 | 3-[(2'-oxo-5,6-dihydrospiro[benzo[1,2-b:5,4-b']difuran-3,3'-indol]-1'(2'H)-yl)methyl]-N-(2-phenylpropyl)benzamide | B |
| 12.6 | N-[(1S)-1-cyclohexylethyl]-3-[(2'-oxo-5,6-dihydrospiro[benzo[1,2-b:5,4-b']difuran-3,3'-indol]-1'(2'H)-yl)methyl]benzamide | B |
| 12.7 | N-[(1R)-1-cyclohexylethyl]-3-[(2'-oxo-5,6-dihydrospiro[benzo[1,2-b:5,4-b']difuran-3,3'-indol]-1'(2'H)-yl)methyl]benzamide | B |
| 12.8 | N-(4-ethylphenyl)-2-[(2'-oxo-5,6-dihydrospiro[benzo[1,2-b:5,4-b']difuran-3,3'-indol]-1'(2'H)-yl)methyl]benzamide | A |
| 12.9 | N-(2-ethylphenyl)-2-[(2'-oxo-5,6-dihydrospiro[benzo[1,2-b:5,4-b']difuran-3,3'-indol]-1'(2'H)-yl)methyl]benzamide | B |
| 12.10 | N-(2,4-dimethylphenyl)-2-[(2'-oxo-5,6-dihydrospiro[benzo[1,2-b:5,4-b']difuran-3,3'-indol]-1'(2'H)-yl)methyl]benzamide | B |
| 12.11 | N-(2-methoxyphenyl)-2-[(2'-oxo-5,6-dihydrospiro[benzo[1,2-b:5,4-b']difuran-3,3'-indol]-1'(2'H)-yl)methyl]benzamide | B |
| 12.12 | N-(2-fluorophenyl)-2-[(2'-oxo-5,6-dihydrospiro[benzo[1,2-b:5,4-b']difuran-3,3'-indol]-1'(2'H)-yl)methyl]benzamide | B |
| 12.13 | N-(3-chlorophenyl)-2-[(2'-oxo-5,6-dihydrospiro[benzo[1,2-b:5,4-b']difuran-3,3'-indol]-1'(2'H)-yl)methyl]benzamide | B |
| 12.14 | N-(3-fluoro-2-methylphenyl)-2-[(2'-oxo-5,6-dihydrospiro[benzo[1,2-b:5,4-b']difuran-3,3'-indol]-1'(2'H)-yl)methyl]benzamide | B |
| 12.15 | N-heptyl-2-[(2'-oxo-5,6-dihydrospiro[benzo[1,2-b:5,4-b']difuran-3,3'-indol]-1'(2'H)-yl)methyl]benzamide | B |
| 12.16 | N-(2-chlorobenzyl)-2-[(2'-oxo-5,6-dihydrospiro[benzo[1,2-b:5,4-b']difuran-3,3'-indol]-1'(2'H)-yl)methyl]benzamide | B |
| 12.17 | 1'-[2-(piperidin-1-ylcarbonyl)benzyl]-5,6-dihydrospiro[benzo[1,2-b:5,4-b']difuran-3,3'-indol]-2'(1'H)-one | B |
| 12.18 | N-butyl-2-[(2'-oxo-5,6-dihydrospiro[benzo[1,2-b:5,4-b']difuran-3,3'-indol]-1'(2'H)-yl)methyl]benzamide | B |
| 12.19 | N-(3-methylphenyl)-2-[(2'-oxo-5,6-dihydrospiro[benzo[1,2-b:5,4-b']difuran-3,3'-indol]-1'(2'H)-yl)methyl]benzamide | B |
| 12.20 | N-(2-fluoro-5-methylphenyl)-2-[(2'-oxo-5,6-dihydrospiro[benzo[1,2-b:5,4-b']difuran-3,3'-indol]-1'(2'H)-yl)methyl]benzamide | B |
| 12.21 | N-(2,3-dimethylphenyl)-2-[(2'-oxo-5,6-dihydrospiro[benzo[1,2-b:5,4-b']difuran-3,3'-indol]-1'(2'H)-yl)methyl]benzamide | B |
| 12.22 | N-[2-(4-methoxyphenyl)ethyl]-2-[(2'-oxo-5,6-dihydrospiro[benzo[1,2-b:5,4-b']difuran-3,3'-indol]-1'(2'H)-yl)methyl]benzamide | B |
| 12.23 | N-(3-chlorobenzyl)-2-[(2'-oxo-5,6-dihydrospiro[benzo[1,2-b:5,4-b']difuran-3,3'-indol]-1'(2'H)-yl)methyl]benzamide | B |
| 12.24 | N-[2-(4-chlorophenyl)ethyl]-2-[(2'-oxo-5,6-dihydrospiro[benzo[1,2-b:5,4-b']difuran-3,3'-indol]-1'(2'H)-yl)methyl]benzamide | B |
| 12.25 | N-(2-methoxyphenyl)-4-[(2'-oxo-5,6-dihydrospiro[benzo[1,2-b:5,4-b']difuran-3,3'-indol]-1'(2'H)-yl)methyl]benzamide | A |
| 12.26 | 4-[(2'-oxo-5,6-dihydrospiro[benzo[1,2-b:5,4-b']difuran-3,3'-indol]-1'(2'H)-yl)methyl]-N-[2-(trifluoromethyl)phenyl]benzamide | B |
| 12.27 | 4-[(2'-oxo-5,6-dihydrospiro[benzo[1,2-b:5,4-b']difuran-3,3'-indol]-1'(2'H)-yl)methyl]-N-phenylbenzamide | A |
| 12.28 | N-methyl-4-[(2'-oxo-5,6-dihydrospiro[benzo[1,2-b:5,4-b']difuran-3,3'-indol]-1'(2'H)-yl)methyl]benzamide | B |
| 12.29 | N-(2-fluorophenyl)-4-[(2'-oxo-5,6-dihydrospiro[benzo[1,2-b:5,4-b']difuran-3,3'-indol]-1'(2'H)-yl)methyl]benzamide | A |
| 12.30 | 4-[(2'-oxo-5,6-dihydrospiro[benzo[1,2-b:5,4-b']difuran-3,3'-indol]-1'(2'H)-yl)methyl]-N-(2-thiophen-2-ylethyl)benzamide | B |
| 12.31 | 4-[(2'-oxo-5,6-dihydrospiro[benzo[1,2-b:5,4-b']difuran-3,3'-indol]-1'(2'H)-yl)methyl]benzamide | B |
| 12.32 | N-(2,3-dihydro-1H-inden-5-yl)-4-[(2'-oxo-5,6-dihydrospiro[benzo[1,2-b:5,4-b']difuran-3,3'-indol]-1'(2'H)-yl)methyl]benzamide | A |
| 12.33 | 1'-[4-(morpholin-4-ylcarbonyl)benzyl]-5,6-dihydrospiro[benzo[1,2-b:5,4-b']difuran-3,3'-indol]-2'(1'H)-one | B |

TABLE 8-continued

| Ex. No. | Compound Name | % Inhibition of CYP3A4 |
|---|---|---|
| 12.34 | N-(2-ethylphenyl)-4-[(2'-oxo-5,6-dihydrospiro[benzo[1,2-b:5,4-b']difuran-3,3'-indol]-1'(2'H)-yl)methyl]benzamide | B |
| 12.35 | N-(2,6-dimethylphenyl)-4-[(2'-oxo-5,6-dihydrospiro[benzo[1,2-b:5,4-b']difuran-3,3'-indol]-1'(2'H)-yl)methyl]benzamide | B |
| 12.36 | N-(3-fluorophenyl)-4-[(2'-oxo-5,6-dihydrospiro[benzo[1,2-b:5,4-b']difuran-3,3'-indol]-1'(2'H)-yl)methyl]benzamide | A |
| 12.37 | N-(2,4-dimethylphenyl)-4-[(2'-oxo-5,6-dihydrospiro[benzo[1,2-b:5,4-b']difuran-3,3'-indol]-1'(2'H)-yl)methyl]benzamide | A |
| 12.38 | 4-[(2'-oxo-5,6-dihydrospiro[benzo[1,2-b:5,4-b']difuran-3,3'-indol]-1'(2'H)-yl)methyl]-N-(thiophen-2-ylmethyl)benzamide | B |
| 12.39 | N-ethyl-4-[(2'-oxo-5,6-dihydrospiro[benzo[1,2-b:5,4-b']difuran-3,3'-indol]-1'(2'H)-yl)methyl]benzamide | B |
| 12.40 | N-(2-methoxyethyl)-4-[(2'-oxo-5,6-dihydrospiro[benzo[1,2-b:5,4-b']difuran-3,3'-indol]-1'(2'H)-yl)methyl]benzamide | A |
| 12.41 | N-(2-ethoxyethyl)-4-[(2'-oxo-5,6-dihydrospiro[benzo[1,2-b:5,4-b']difuran-3,3'-indol]-1'(2'H)-yl)methyl]benzamide | B |
| 12.42 | N-cyclobutyl-4-[(2-oxo-5,6-dihydrospiro[benzo[1,2-b:5,4-b']difuran-3,3-indol]-1(2H)-yl)methyl]benzamide | B |
| 12.43 | 4-[(2'-oxo-5,6-dihydrospiro[benzo[1,2-b:5,4-b']difuran-3,3'-indol]-1'(2'H)-yl)methyl]-N-1,3-thiazol-2-ylbenzamide | A |
| 12.44 | N-(3-fluoro-2-methylphenyl)-4-[(2'-oxo-5,6-dihydrospiro[benzo[1,2-b:5,4-b']difuran-3,3'-indol]-1'(2'H)-yl)methyl]benzamide | A |
| 12.45 | N-(2-ethylbutyl)-4-[(2'-oxo-5,6-dihydrospiro[benzo[1,2-b:5,4-b']difuran-3,3'-indol]-1'(2'H)-yl)methyl]benzamide | A |
| 12.46 | 2-(2'-oxo-5,6-dihydrospiro[benzo[1,2-b:5,4-b']difuran-3,3'-indol]-1'(2'H)-yl)acetamide | A |
| 12.47 | N-(4-ethylphenyl)-2-(2'-oxo-5,6-dihydrospiro[benzo[1,2-b:5,4-b']difuran-3,3'-indol]-1'(2'H)-yl)acetamide | A |
| 12.48 | N,N-diethyl-2-(2'-oxo-5,6-dihydrospiro[benzo[1,2-b:5,4-b']difuran-3,3'-indol]-1'(2'H)-yl)acetamide | A |
| 12.49 | N-(3,3-dimethylbutyl)-2-(2'-oxo-5,6-dihydrospiro[benzo[1,2-b:5,4-b']difuran-3,3'-indol]-1'(2'H)-yl)acetamide | B |
| 12.50 | N-[3-(1-methylethoxy)propyl]-2-(2'-oxo-5,6-dihydrospiro[benzo[1,2-b:5,4-b']difuran-3,3'-indol]-1'(2'H)-yl)acetamide | B |
| 12.51 | 2-(2'-oxo-5,6-dihydrospiro[benzo[1,2-b:5,4-b']difuran-3,3'-indol]-1'(2'H)-yl)-N-propylacetamide | B |
| 12.52 | N-methyl-2-(2'-oxo-5,6-dihydrospiro[benzo[1,2-b:5,4-b']difuran-3,3'-indol]-1'(2'H)-yl)-N-phenylacetamide | B |
| 12.53 | N-(2,5-dimethylphenyl)-2-(2'-oxo-5,6-dihydrospiro[benzo[1,2-b:5,4-b']difuran-3,3'-indol]-1'(2'H)-yl)acetamide | A |
| 12.54 | N-(2,4-dimethylphenyl)-2-(2'-oxo-5,6-dihydrospiro[benzo[1,2-b:5,4-b']difuran-3,3'-indol]-1'(2'H)-yl)acetamide | B |
| 12.55 | N-(2,3-dimethylphenyl)-2-(2'-oxo-5,6-dihydrospiro[benzo[1,2-b:5,4-b']difuran-3,3'-indol]-1'(2'H)-yl)acetamide | B |
| 12.56 | N-(2,6-dimethylphenyl)-2-(2'-oxo-5,6-dihydrospiro[benzo[1,2-b:5,4-b']difuran-3,3'-indol]-1'(2'H)-yl)acetamide | B |
| 12.57 | N-methyl-5-[(2'-oxospiro[furo[2,3-f][1,3]benzodioxole-7,3'-indol]-1'(2'H)-yl)methyl]-2-(trifluoromethyl)furan-3-carboxamide | B |
| 12.58 | 5-[(2'-oxospiro[furo[2,3-f][1,3]benzodioxole-7,3'-indol]-1'(2'H)-yl)methyl]-2-(trifluoromethyl)furan-3-carboxamide | B |
| 12.59 | N,N-dimethyl-5-[(2'-oxospiro[furo[2,3-f][1,3]benzodioxole-7,3'-indol]-1'(2'H)-yl)methyl]-2-(trifluoromethyl)furan-3-carboxamide | B |
| 12.60 | 4-[(2'-oxo-2,3-dihydrospiro[furo[2,3-g][1,4]benzodioxine-8,3'-indol]-1'(2'H)-yl)methyl]benzamide | B |
| 12.61 | 3-[(2'-oxo-2,3-dihydrospiro[furo[2,3-g][1,4]benzodioxine-8,3'-indol]-1'(2'H)-yl)methyl]benzamide | B |
| 12.62 | N,N-dimethyl-3-[(2'-oxo-2,3-dihydrospiro[furo[2,3-g][1,4]benzodioxine-8,3'-indol]-1'(2'H)-yl)methyl]benzamide | B |
| 12.63 | N-methyl-2-[(2'-oxo-2,3-dihydrospiro[furo[2,3-g][1,4]benzodioxine-8,3'-indol]-1'(2'H)-yl)methyl]pyridine-3-carboxamide | A |
| 12.64 | N-(2-aminoethyl)-2-[(2'-oxo-2,3-dihydrospiro[furo[2,3-g][1,4]benzodioxine-8,3'-indol]-1'(2'H)-yl)methyl]pyridine-3-carboxamide dihydrochloride | B |
| 12.65 | N-(2-fluorophenyl)-4-[(2'-oxo-2,3-dihydrospiro[furo[2,3-g][1,4]benzodioxine-8,3'-indol]-1'(2'H)-yl)methyl]benzamide | A |
| 13 | 5-[(2'-oxo-5,6-dihydrospiro[benzo[1,2-b:5,4-b']difuran-3,3'-indol]-1'(2'H)-yl)methyl]furan-2-carboxylic acid | A |

TABLE 8-continued

| Ex. No. | Compound Name | % Inhibition of CYP3A4 |
|---|---|---|
| 13.1 | N,N-dimethyl-5-[(2'-oxo-5,6-dihydrospiro[benzo[1,2-b:5,4-b']difuran-3,3'-indol]-1'(2'H)-yl)methyl]furan-2-carboxamide | B |
| 13.2 | N-methyl-5-[(2'-oxo-5,6-dihydrospiro[benzo[1,2-b:5,4-b']difuran-3,3'-indol]-1'(2'H)-yl)methyl]furan-2-carboxamide | B |
| 13.3 | 2-[(2'-oxo-5,6-dihydrospiro[benzo[1,2-b:5,4-b']difuran-3,3'-indol]-1'(2'H)-yl)methyl]-1,3-oxazole-4-carboxamide | A |
| 13.4 | N,N-dimethyl-2-[(2'-oxo-5,6-dihydrospiro[benzo[1,2-b:5,4-b']difuran-3,3'-indol]-1'(2'H)-yl)methyl]-1,3-oxazole-4-carboxamide | A |
| 13.5 | N-cyclopropyl-2-[(2'-oxospiro[furo[2,3-f][1,3]benzodioxole-7,3'-indol]-1'(2'H)-yl)methyl]-1,3-oxazole-4-carboxamide | B |
| 13.6 | N-(1-methylethyl)-2-[(2'-oxospiro[furo[2,3-f][1,3]benzodioxole-7,3'-indol]-1'(2'H)-yl)methyl]-1,3-oxazole-4-carboxamide | B |
| 13.7 | N-(2-fluorophenyl)-2-(2'-oxo-2,3-dihydrospiro[furo[2,3-g][1,4]benzodioxine-8,3'-indol]-1'(2'H)-yl)acetamide | A |
| 13.11 | N-[3-(2'-oxo-5,6-dihydrospiro[benzo[1,2-b:5,4-b']difuran-3,3'-indol]-1'(2'H)-yl)propyl]-2-(trifluoromethoxy)benzamide | B |
| 14 | 1'-[(2S)-2-hydroxypropyl]-5,6-dihydrospiro[benzo[1,2-b:5,4-b']difuran-3,3'-indol]-2'(1'H)-one | A |
| 14.1 | 1'-[(2S)-2-(benzyloxy)propyl]-5,6-dihydrospiro[benzo[1,2-b:5,4-b']difuran-3,3'-indol]-2'(1'H)-one | B |
| 14.2 | 1'-{(2S)-2-[(4-fluorobenzyl)oxy]propyl}-5,6-dihydrospiro[benzo[1,2-b:5,4-b']difuran-3,3'-indol]-2'(1'H)-one | B |
| 14.3 | 1'-[(2S)-2-(pyridin-2-ylmethoxy)propyl]-5,6-dihydrospiro[benzo[1,2-b:5,4-b']difuran-3,3'-indol]-2'(1'H)-one | B |
| 14.4 | 1'-(3-hydroxybutyl)-5,6-dihydrospiro[benzo[1,2-b:5,4-b']difuran-3,3'-indol]-2'(1'H)-one | A |
| 14.5 | 1'-(4,4,4-trifluoro-3-hydroxybutyl)-5,6-dihydrospiro[benzo[1,2-b:5,4-b']difuran-3,3'-indol]-2'(1'H)-one | B |
| 15.1 | 1'-{3-[(3-methylbutyl)amino]propyl}-5,6-dihydrospiro[benzo[1,2-b:5,4-b']difuran-3,3'-indol]-2'(1'H)-one hydrochloride | B |
| 15.2 | 1'-{3-[butyl(methyl)amino]propyl}-5,6-dihydrospiro[benzo[1,2-b:5,4-b']difuran-3,3'-indol]-2'(1'H)-one hydrochloride | B |
| 15.3 | 1'-{3-[(2,2,2-trifluoroethyl)amino]propyl}-5,6-dihydrospiro[benzo[1,2-b:5,4-b']difuran-3,3'-indol]-2'(1'H)-one hydrochloride | B |
| 15.4 | 3-{[3-(2'-oxo-5,6-dihydrospiro[benzo[1,2-b:5,4-b']difuran-3,3'-indol]-1'(2'H)-yl)propyl]amino}propanenitrile hydrochloride | B |
| 16 | 4'-[6-(dimethylamino)pyridin-3-yl]-1'-[(2R)-tetrahydrofuran-2-ylmethyl]-5,6-dihydrospiro[benzo[1,2-b:5,4-b']difuran-3,3'-indol]-2'(1'H)-one | B |
| 16.1 | 4'-[(E)-2-(4-fluorophenyl)ethenyl]-1'-[(2R)-tetrahydrofuran-2-ylmethyl]-5,6-dihydrospiro[benzo[1,2-b:5,4-b']difuran-3,3'-indol]-2'(1'H)-one | B |
| 16.2 | 4'-dibenzo[b,d]thiophen-4-yl-1'-[(2R)-tetrahydrofuran-2-ylmethyl]-5,6-dihydrospiro[benzo[1,2-b:5,4-b']difuran-3,3'-indol]-2'(1'H)-one | B |
| 16.3 | 4'-(1-benzothiophen-3-yl)-1'-[(2R)-tetrahydrofuran-2-ylmethyl]-5,6-dihydrospiro[benzo[1,2-b:5,4-b']difuran-3,3'-indol]-2'(1'H)-one | B |
| 16.4 | 4'-(1-methyl-1H-indol-5-yl)-1'-[(2R)-tetrahydrofuran-2-ylmethyl]-5,6-dihydrospiro[benzo[1,2-b:5,4-b']difuran-3,3'-indol]-2'(1'H)-one | B |
| 16.5 | 4'-[3,5-bis(trifluoromethyl)phenyl]-1'-[(2R)-tetrahydrofuran-2-ylmethyl]-5,6-dihydrospiro[benzo[1,2-b:5,4-b']difuran-3,3'-indol]-2'(1'H)-one | B |
| 16.6 | 4'-(4-phenoxyphenyl)-1'-[(2R)-tetrahydrofuran-2-ylmethyl]-5,6-dihydrospiro[benzo[1,2-b:5,4-b']difuran-3,3'-indol]-2'(1'H)-one | A |
| 16.7 | 4'-[4-(2-methylpropoxy)phenyl]-1'-[(2R)-tetrahydrofuran-2-ylmethyl]-5,6-dihydrospiro[benzo[1,2-b:5,4-b']difuran-3,3'-indol]-2'(1'H)-one | A |
| 16.8 | 4'-(4-butoxyphenyl)-1'-[(2R)-tetrahydrofuran-2-ylmethyl]-5,6-dihydrospiro[benzo[1,2-b:5,4-b']difuran-3,3'-indol]-2'(1'H)-one | A |
| 16.9 | 4'-(4-methoxyphenyl)-1'-[(2R)-tetrahydrofuran-2-ylmethyl]-5,6-dihydrospiro[benzo[1,2-b:5,4-b']difuran-3,3'-indol]-2'(1'H)-one | B |
| 16.10 | 4'-pyrimidin-5-yl-1'-[(2R)-tetrahydrofuran-2-ylmethyl]-5,6-dihydrospiro[benzo[1,2-b:5,4-b']difuran-3,3'-indol]-2'(1'H)-one | B |

TABLE 8-continued

| Ex. No. | Compound Name | % Inhibition of CYP3A4 |
|---|---|---|
| 16.11 | 4'-[6-(dimethylamino)pyridin-3-yl]-1'-{[5-(trifluoromethyl)furan-2-yl]methyl}-5,6-dihydrospiro[benzo[1,2-b:5,4-b']difuran-3,3'-indol]-2'(1'H)-one | B |
| 16.12 | 1'-[(5-chloro-2-thienyl)methyl]-4'-[6-(dimethylamino)pyridin-3-yl]spiro[furo[2,3-f][1,3]benzodioxole-7,3'-indol]-2'(1'H)-one | B |
| 16.13 | 1'-[(5-chloro-2-thienyl)methyl]-4'-(3-furyl)spiro[furo[2,3-f][1,3]benzodioxole-7,3'-indol]-2'(1'H)-one | B |
| 16.14 | 4'-[6-(dimethylamino)pyridin-3-yl]spiro[furo[2,3-f][1,3]benzodioxole-7,3'-indol]-2'(1'H)-one | B |
| 16.15 | 1'-methyl-4'-(2-oxo-2H-chromen-7-yl)-2,3-dihydrospiro[furo[2,3-g][1,4]benzodioxine-8,3'-indol]-2'(1'H)-one | B |
| 16.16 | 1'-methyl-4'-(2-oxopyrrolidin-1-yl)-2,3-dihydrospiro[furo[2,3-g][1,4]benzodioxine-8,3'-indol]-2'(1'H)-one | A |
| 16.17 | 1'-methyl-4'-morpholin-4-yl-2,3-dihydrospiro[furo[2,3-g][1,4]benzodioxine-8,3'-indol]-2'(1'H)-one | A |
| 16.18 | 1'-methyl-4'-(2-oxopyridin-1(2H)-yl)-2,3-dihydrospiro[furo[2,3-g][1,4]benzodioxine-8,3'-indol]-2'(1'H)-one | A |
| 16.19 | 4'-amino-1'-methyl-2,3-dihydrospiro[furo[2,3-g][1,4]benzodioxine-8,3'-indol]-2'(1'H)-one | A |
| 16.20 | N-(1'-methyl-2'-oxo-1',2,2',3-tetrahydrospiro[furo[2,3-g][1,4]benzodioxine-8,3'-indol]-4'-yl)cyclobutanecarboxamide | A |
| 16.21 | N-(1'-methyl-2'-oxo-1',2,2',3-tetrahydrospiro[furo[2,3-g][1,4]benzodioxine-8,3'-indol]-4'-yl)-2-(trifluoromethyl)benzamide | A |
| 16.22 | N-(1'-methyl-2'-oxo-1',2,2',3-tetrahydrospiro[furo[2,3-g][1,4]benzodioxine-8,3'-indol]-4'-yl)methanesulfonamide | A |
| 16.23 | N-(1'-methyl-2'-oxo-1',2,2',3-tetrahydrospiro[furo[2,3-g][1,4]benzodioxine-8,3'-indol]-4'-yl)cyclohexanecarboxamide | A |
| 16.24 | N-(1'-methyl-2'-oxo-1',2,2',3-tetrahydrospiro[furo[2,3-g][1,4]benzodioxine-8,3'-indol]-4'-yl)cyclopentanecarboxamide | A |
| 16.25 | N-(1'-methyl-2'-oxo-1',2,2',3-tetrahydrospiro[furo[2,3-g][1,4]benzodioxine-8,3'-indol]-4'-yl)acetamide | A |
| 16.26 | N-(1'-methyl-2'-oxo-1',2,2',3-tetrahydrospiro[furo[2,3-g][1,4]benzodioxine-8,3'-indol]-4'-yl)cyclopropanecarboxamide | A |
| 16.27 | N-(1'-methyl-2'-oxo-1',2,2',3-tetrahydrospiro[furo[2,3-g][1,4]benzodioxine-8,3'-indol]-4'-yl)benzamide | B |
| 16.28 | 2-methoxy-N-(1'-methyl-2'-oxo-1',2,2',3-tetrahydrospiro[furo[2,3-g][1,4]benzodioxine-8,3'-indol]-4'-yl)acetamide | A |
| 16.29 | N-(1'-methyl-2'-oxo-1',2,2',3-tetrahydrospiro[furo[2,3-g][1,4]benzodioxine-8,3'-indol]-4'-yl)propanamide | A |
| 16.30 | N-(1'-methyl-2'-oxo-1',2,2',3-tetrahydrospiro[furo[2,3-g][1,4]benzodioxine-8,3'-indol]-4'-yl)pentanamide | A |
| 16.31 | 2,2-dimethyl-N-(1'-methyl-2'-oxo-1',2,2',3-tetrahydrospiro[furo[2,3-g][1,4]benzodioxine-8,3'-indol]-4'-yl)propanamide | A |
| 16.32 | N-(1'-methyl-2'-oxo-1',2,2',3-tetrahydrospiro[furo[2,3-g][1,4]benzodioxine-8,3'-indol]-4'-yl)hexanamide | A |
| 16.33 | N-(1'-methyl-2'-oxo-1',2,2',3-tetrahydrospiro[furo[2,3-g][1,4]benzodioxine-8,3'-indol]-4'-yl)heptanamide | B |
| 16.34 | 2-(2-methoxyethoxy)-N-(1'-methyl-2'-oxo-1',2,2',3-tetrahydrospiro[furo[2,3-g][1,4]benzodioxine-8,3'-indol]-4'-yl)acetamide | A |
| 16.35 | 1-hexyl-3-(1'-methyl-2'-oxo-1'2,2',3-tetrahydrospiro[furo[2,3-g][1,4]benzodioxine-8,3'-indol]-4'-yl)urea | B |
| 16.36 | 1-cyclopentyl-3-(1'-methyl-2'-oxo-1',2,2',3-tetrahydrospiro[furo[2,3-g][1,4]benzodioxine-8,3'-indol]-4'-yl)urea | A |
| 16.37 | 1-cyclohexyl-3-(1'-methyl-2'-oxo-1',2,2',3-tetrahydrospiro[furo[2,3-g][1,4]benzodioxine-8,3'-indol]-4'-yl)urea | A |
| 16.38 | N-cyclohexyl-1'-methyl-2'-oxo-1',2,2',3-tetrahydrospiro[furo[2,3-g][1,4]benzodioxine-8,3'-indole]-4'-carboxamide | A |
| 16.39 | N-cyclopentyl-1'-methyl-2'-oxo-1',2,2',3-tetrahydrospiro[furo[2,3-g][1,4]benzodioxine-8,3'-indole]-4'-carboxamide | A |
| 16.41 | 1'-methyl-4'-(pyrrolidin-1-ylcarbonyl)-2,3-dihydrospiro[furo[2,3-g][1,4]benzodioxine-8,3'-indol]-2'(1'H)-one | A |
| 16.42 | 1'-methyl-2'-oxo-N-pentyl-1',2,2',3-tetrahydrospiro[furo[2,3-g][1,4]benzodioxine-8,3'-indole]-4'-carboxamide | A |

TABLE 8-continued

| Ex. No. | Compound Name | % Inhibition of CYP3A4 |
|---|---|---|
| 16.43 | N-(2-methoxyethyl)-1'-methyl-2'-oxo-1',2,2',3-tetrahydrospiro[furo[2,3-g][1,4]benzodioxine-8,3'-indole]-4'-carboxamide | A |
| 16.44 | N-(4-fluorobenzyl)-1'-methyl-2'-oxo-1',2,2',3-tetrahydrospiro[furo[2,3-g][1,4]benzodioxine-8,3'-indole]-4'-carboxamide | A |
| 16.45 | N-hexyl-1'-methyl-2'-oxo-1',2,2',3-tetrahydrospiro[furo[2,3-g][1,4]benzodioxine-8,3'-indole]-4'-carboxamide | B |
| 16.46 | 1'-methyl-2'-oxo-N-(pyridin-2-ylmethyl)-1',2,2',3-tetrahydrospiro[furo[2,3-g][1,4]benzodioxine-8,3'-indole]-4'-carboxamide | A |
| 16.47 | N-(4-fluorophenyl)-1'-methyl-2'-oxo-1',2,2',3-tetrahydrospiro[furo[2,3-g][1,4]benzodioxine-8,3'-indole]-4'-carboxamide | A |
| 16.50 | 4'-amino-1'-{[3-(trifluoromethyl)pyridin-2-yl]methyl}-2,3-dihydrospiro[furo[2,3-g][1,4]benzodioxine-8,3'-indol]-2'(1'H)-one | A |
| 16.51 | 4'-hydroxy-2,3-dihydrospiro[furo[2,3-g][1,4]benzodioxine-8,3'-indol]-2'(1'H)-one | A |
| 16.52 | 4'-hydroxy-1'-methyl-2,3-dihydrospiro[furo[2,3-g][1,4]benzodioxine-8,3'-indol]-2'(1'H)-one | A |
| 16.53 | 1'-methyl-4'-(pyridin-2-yloxy)-2,3-dihydrospiro[furo[2,3-g][1,4]benzodioxine-8,3'-indol]-2'(1'H)-one | B |
| 16.54 | 4'-[2-(2-methoxyethoxy)ethoxy]-1'-methyl-2,3-dihydrospiro[furo[2,3-g][1,4]benzodioxine-8,3'-indol]-2'(1'H)-one | A |
| 16.55 | 1'-methyl-4'-{[3-(trifluoromethyl)pyridin-2-yl]oxy}-2,3-dihydrospiro[furo[2,3-g][1,4]benzodioxine-8,3'-indol]-2'(1'H)-one | B |
| 16.56 | 1'-methyl-4'-[4-(trifluoromethyl)phenoxy]-2,3-dihydrospiro[furo[2,3-g][1,4]benzodioxine-8,3'-indol]-2'(1'H)-one | B |
| 16.57 | 4'-(benzyloxy)-1'-methyl-2,3-dihydrospiro[furo[2,3-g][1,4]benzodioxine-8,3'-indol]-2'(1'H)-one | B |
| 16.58 | 1'-methyl-4'-{[3-(trifluoromethyl)pyridin-2-yl]methoxy}-2,3-dihydrospiro[furo[2,3-g][1,4]benzodioxine-8,3'-indol]-2'(1'H)-one | B |
| 16.59 | 4'-(6-(dimethylamino)pyridin-3-yl)-1'-(pyridin-2-ylmethyl)-3,7-dihydro-2H-spiro[benzofuro[5,6-b][1,4]dioxine-8,3'-indolin]-2'-one | B |
| 16.60 | 4'-(4-methoxyphenyl)-1'-(pyridin-2-ylmethyl)-3,7-dihydro-2H-spiro[benzofuro[5,6-b][1,4]dioxine-8,3'-indolin]-2'-one | B |
| 16.61 | (7S)-4'-furan-3-yl-1'-methylspiro[furo[2,3-f][1,3]benzodioxole-7,3'-indol]-2'(1'H)-one | B |
| 16.62 | (7R)-4'-furan-3-yl-1'-methylspiro[furo[2,3-f][1,3]benzodioxole-7,3'-indol]-2'(1'H)-one | B |
| 16.63 | (7R)-4'-bromo-1'-methylspiro[furo[2,3-f][1,3]benzodioxole-7,3'-indol]-2'(1'H)-one | B |
| 16.64 | (7S)-4'-bromo-1'-methylspiro[furo[2,3-f][1,3]benzodioxole-7,3'-indol]-2'(1'H)-one | B |
| 16.65 | (7S)-4'-furan-3-ylspiro[furo[2,3-f][1,3]benzodioxole-7,3'-indol]-2'(1'H)-one | B |
| 16.66 | (7R)-4'-furan-3-ylspiro[furo[2,3-f][1,3]benzodioxole-7,3'-indol]-2'(1'H)-one | B |
| 16.67 | 1'-methyl-4'-(1H-pyrazol-3-yl)-2,3-dihydrospiro[furo[2,3-g][1,4]benzodioxine-8,3'-indol]-2'(1'H)-one | B |
| 16.68 | 4'-furan-3-yl-1'-methyl-2,3-dihydrospiro[furo[2,3-g][1,4]benzodioxine-8,3'-indol]-2'(1'H)-one | B |
| 16.69 | 1'-methyl-4'-(1H-pyrazol-4-yl)-2,3-dihydrospiro[furo[2,3-g][1,4]benzodioxine-8,3'-indol]-2'(1'H)-one | A |
| 16.70 | 1'-methyl-4'-(1-methyl-1H-pyrazol-4-yl)-2,3-dihydrospiro[furo[2,3-g][1,4]benzodioxine-8,3'-indol]-2'(1'H)-one | A |
| 16.71 | 1'-methyl-2'-oxo-1',2,2',3-tetrahydrospiro[furo[2,3-g][1,4]benzodioxine-8,3'-indole]-4'-carbonitrile | A |
| 16.73 | 1'-methyl-4'-(tetrahydrofuran-3-yl)spiro[furo[2,3-f][1,3]benzodioxole-7,3'-indol]-2'(1'H)-one | B |
| 16.74 | 1'-methyl-4'-(5-methyl-1,2,4-oxadiazol-3-yl)-2,3-dihydrospiro[furo[2,3-g][1,4]benzodioxine-8,3'-indol]-2'(1'H)-one | A |
| 16.75 | 4'-(3,5-dimethylisoxazol-4-yl)-1'-methyl-2,3-dihydrospiro[furo[2,3-g][1,4]benzodioxine-8,3'-indol]-2'(1'H)-one | B |
| 16.77 | N-cyclobutyl-1'-methyl-2'-oxo-1',2,2',3-tetrahydrospiro[furo[2,3-g][1,4]benzodioxine-8,3'-indole]-4'-carboxamide | A |
| 16.78 | N,N,1'-trimethyl-2'-oxo-1',2,2',3-tetrahydrospiro[furo[2,3-g][1,4]benzodioxine-8,3'-indole]-4'-carboxamide | A |

TABLE 8-continued

| Ex. No. | Compound Name | % Inhibition of CYP3A4 |
|---|---|---|
| 16.79 | 4'-(3-methoxyphenoxy)-1'-methyl-2,3-dihydrospiro[furo[2,3-g][1,4]benzodioxine-8,3'-indol]-2'(1'H)-one | B |
| 16.80 | 1'-methyl-4-phenoxy-2,3-dihydrospiro[furo[2,3-g][1,4]benzodioxine-8,3'-indol]-2'(1'H)-one | B |
| 16.81 | 1'-methyl-4'-(3-morpholin-4-ylphenoxy)-2,3-dihydrospiro[furo[2,3-g][1,4]benzodioxine-8,3'-indol]-2'(1'H)-one | B |
| 16.82 | 4'-[(6-methoxypyridin-3-yl)oxy]-1'-methyl-2,3-dihydrospiro[furo[2,3-g][1,4]benzodioxine-8,3'-indol]-2'(1'H)-one | A |
| 16.83 | 4'-(1,3-benzodioxol-5-yloxy)-1'-methyl-2,3-dihydrospiro[furo[2,3-g][1,4]benzodioxine-8,3'-indol]-2'(1'H)-one | B |
| 16.84 | 4'-(4-methoxyphenoxy)-1'-methyl-2,3-dihydrospiro[furo[2,3-g][1,4]benzodioxine-8,3'-indol]-2'(1'H)-one | B |
| 16.85 | 1'-methyl-4-(pyridine-2-ylmethoxy)-2,3-dihydrospiro[furo[2,3-g][1,4]benzodioxine-8,3'-indol]-2'(1'H)-one | B |
| 16.86 | 1'-methyl-4-(4-fluorobenzyloxy)-2,3-dihydrospiro[furo[2,3-g][1,4]benzodioxine-8,3'-indol]-2'(1'H)-one | B |
| 16.87 | 4'-(4-fluorophenoxy)-1'-methyl-2,3-dihydrospiro[furo[2,3-g][1,4]benzodioxine-8,3'-indol]-2'(1'H)-one | B |
| 16.88 | 1'-[(5-chloro-2-thienyl)methyl]-5-(6-methoxypyridin-3-yl)spiro[1-benzofuran-3,3'-indol]-2'(1'H)-one | B |
| 17 | 1'-(4-hydroxybenzyl)-5,6-dihydrospiro[benzo[1,2-b:5,4-b']difuran-3,3'-indol]-2'(1'H)-one | B |
| 17.1 | 1'-(4-hydroxybenzyl)-2,3-dihydrospiro[furo[2,3-g][1,4]benzodioxine-8,3'-indol]-2'(1'H)-one | B |
| 17.2 | 1'-(3-hydroxypropyl)-2,3-dihydrospiro[furo[2,3-g][1,4]benzodioxine-8,3'-indol]-2'(1'H)-one | A |
| 18 | ethyl 2'-oxo-2,3-dihydrospiro[furo[2,3-g][1,4]benzodioxine-8,3'-indole]-1'(2'H)-carboxylate | A |
| 18.1 | tert-butyl 4'-bromo-2'-oxospiro[furo[2,3-f][1,3]benzodioxole-7,3'-indole]-1'(2'H)-carboxylate | B |
| 18.2 | tert-butyl 2'-oxo-2,3-dihydrospiro[furo[2,3-g][1,4]benzodioxine-8,3'-indole]-1'(2'H)-carboxylate | A |
| 19 | 1'-{[(3aR,5R,5aS,8aS,8bR)-2,2,7,7-tetramethyltetrahydro-3aH-bis[1,3]dioxolo[4,5-b:4',5'-d]pyran-5-yl]methyl}-2,3-dihydrospiro[furo[2,3-g][1,4]benzodioxine-8,3'-indol]-2'(1'H)-one | A |
| 20 | 6-deoxy-6-(2'-oxo-2,3-dihydrospiro[furo[2,3-g][1,4]benzodioxine-8,3'-indol]-1'(2'H)-yl)-D-galactopyranose | A |
| 21 | 1'-cyclopropyl-2,3-dihydrospiro[furo[2,3-g][1,4]benzodioxine-8,3'-indol]-2'(1'H)-one | A |
| 22 | 1'-acetyl-2,3-dihydrospiro[furo[2,3-g][1,4]benzodioxine-8,3'-indol]-2'(1'H)-one | A |
| 23 | 1'-{[4-(trifluoromethyl)pyridin-2-yl]methyl}-2,3-dihydrospiro[furo[2,3-g][1,4]benzodioxine-8,3'-indol]-2'(1'H)-one | A |
| 24 | 4'-acetyl-1'-methyl-2,3-dihydrospiro[furo[2,3-g][1,4]benzodioxine-8,3'-indol]-2'(1'H)-one | A |
| 25 | 1'-methyl-4'-(2-methyl-1,3-thiazol-4-yl)-2,3-dihydrospiro[furo[2,3-g][1,4]benzodioxine-8,3'-indol]-2'(1'H)-one | B |
| 26 | 4'-(2-amino-1,3-thiazol-4-yl)-1'-methyl-2,3-dihydrospiro[furo[2,3-g][1,4]benzodioxine-8,3'-indol]-2'(1'H)-one | B |
| 27 | 4'-(5-hydroxy-1H-pyrazol-3-yl)-1'-methyl-2,3-dihydrospiro[furo[2,3-g][1,4]benzodioxine-8,3'-indol]-2'(1'H)-one | A |
| 28 | 1'-[3-(3-methyl-1,2,4-oxadiazol-5-yl)benzyl]-2,3-dihydrospiro[furo[2,3-g][1,4]benzodioxine-8,3'-indol]-2'(1'H)-one | A |
| 29.1 | 1'-[4-(3-amino-1H-pyrazol-5-yl)benzyl]-3-methylspiro[furo[3,2-f][1,2]benzisoxazole-5,3'-indol]-2'(1'H)-one hydrochloride | B |
| 29.2 | 1'-[4-(3-amino-1H-pyrazol-5-yl)benzyl]-2,3-dihydrospiro[furo[2,3-g][1,4]benzodioxine-8,3'-indol]-2'(1'H)-one hydrochloride | B |
| 30 | 1'-[4-(3-methyl-1,2,4-oxadiazol-5-yl)benzyl]-2,3-dihydrospiro[furo[2,3-g][1,4]benzodioxine-8,3'-indol]-2'(1'H)-one | A |
| 31 | 2'-oxo-1'-(pyridin-2-ylmethyl)-1',2,2',3-tetrahydrospiro[furo[2,3-g][1,4]benzodioxine-8,3'-indole]-5'-carboxamide | A |
| 32 | 1'-[(6-morpholin-4-ylpyridin-3-yl)methyl]-2,3-dihydrospiro[furo[2,3-g][1,4]benzodioxine-8,3'-indol]-2'(1'H)-one | B |

TABLE 8-continued

| Ex. No. | Compound Name | % Inhibition of CYP3A4 |
|---|---|---|
| 32.1 | 1'-{[6-(dimethylamino)pyridin-3-yl]methyl}-2,3-dihydrospiro[furo[2,3-g][1,4]benzodioxine-8,3'-indol]-2'(1'H)-one | A |
| 32.2 | 1'-{[6-(dimethylamino)pyridin-2-yl]methyl}-2,3-dihydrospiro[furo[2,3-g][1,4]benzodioxine-8,3'-indol]-2'(1'H)-one | B |
| 33.2 | 5,6-difluoro-1'-{4-[(3R)-pyrrolidin-3-ylamino]benzyl}spiro[1-benzofuran-3,3'-indol]-2'(1'H)-one hydrochloride | B |
| 33.3 | 1'-[(5-morpholin-4-ylpyridin-2-yl)methyl]-2,3-dihydrospiro[furo[2,3-g] [1,4]benzodioxine-8,3'-indol]-2'(1'H)-one | A |
| 33.4 | 1'-{[5-(dimethylamino)pyridin-2-yl]methyl}-2,3-dihydrospiro[furo[2,3-g][1,4]benzodioxine-8,3'-indol]-2'(1'H)-one | B |
| 34 | 1'-[(6-aminopyridin-2-yl)methyl]-2,3-dihydrospiro[furo[2,3-g][1,4]benzodioxine-8,3'-indol]-2'(1'H)-one | B |
| 35 | 1'-[(6-oxo-1,6-dihydropyridin-3-yl)methyl]-2,3-dihydrospiro[furo[2,3-g][1,4]benzodioxine-8,3'-indol]-2'(1'H)-one | A |
| 35.1 | 1'-[(2-hydroxypyrimidin-5-yl)methyl]-2,3-dihydrospiro[furo[2,3-g][1,4]benzodioxine-8,3'-indol]-2'(1'H)-one | A |
| 36 | 1'-[(1-methyl-6-oxo-1,6-dihydropyridin-3-yl)methyl]-2,3-dihydrospiro[furo[2,3-g][1,4]benzodioxine-8,3'-indol]-2'(1'H)-one | A |
| 37 | 1'-[(6-aminopyridin-3-yl)methyl]-2,3-dihydrospiro[furo[2,3-g][1,4]benzodioxine-8,3'-indol]-2'(1'H)-one | A |
| 38 | N'-hydroxy-N-{5-[(2'-oxo-2,3-dihydrospiro[furo[2,3-g][1,4]benzodioxine-8,3'-indol]-1'(2'H)-yl)methyl]pyridin-2-yl}imidoformamide | A |
| 39 | 1'-([1,2,4]triazolo[1,5-a]pyridin-6-ylmethyl)-2,3-dihydrospiro[furo[2,3-g][1,4]benzodioxine-8,3'-indol]-2'(1'H)-one | B |
| 41 | 6-[(2'-oxo-2,3-dihydrospiro[furo[2,3-g][1,4]benzodioxine-8,3'-indol]-1'(2'H)-yl)methyl]pyridine-2-carbonitrile | A |
| 42 | 6-[(2'-oxo-2,3-dihydrospiro[furo[2,3-g][1,4]benzodioxine-8,3'-indol]-1'(2'H)-yl)methyl]pyridine-2-carboxamide | B |
| 44 | 3-amino-1'-(4-methoxybenzyl)spiro[furo[3,2-f][1,2]benzisoxazole-5,3'-indol]-2'(1'H)-one | B |
| 44.1 | 3-amino-1'-(pyridin-2-ylmethyl)spiro[furo[3,2-f][1,2]benzisoxazole-5,3'-indol]-2'(1'H)-one | A |
| 44.2 | 3-amino-1'-[(2R)-tetrahydrofuran-2-ylmethyl]spiro[furo[3,2-f][1,2]benzisoxazole-5,3'-indol]-2'(1'H)-one | A |
| 44.3 | 3-amino-1'-[2-(trifluoromethyl)benzyl]spiro[furo[3,2-f][1,2]benzisoxazole-5,3'-indol]-2'(1'H)-one | B |
| 45 | 6-hydroxy-2'-oxo-1'-[(2R)-tetrahydrofuran-2-ylmethyl]-1',2'-dihydrospiro[1-benzofuran-3,3'-indole]-5-carbonitrile | A |
| 45.1 | 6-hydroxy-2'-oxo-1'-[2-(trifluoromethyl)benzyl]-1',2'-dihydrospiro[1-benzofuran-3,3'-indole]-5-carbonitrile | A |
| 46 | 1'-[2-(trifluoromethyl)benzyl]-1H-spiro[furo[3,2-f]indazole-5,3'-indol]-2'(1'H)-one | B |
| 46.1 | 1'-(pyridin-2-ylmethyl)-1H-spiro[furo[3,2-f]indazole-5,3'-indol]-2'(1'H)-one | A |
| 46.2 | 1'-((3-(trifluoromethyl)pyridin-2-yl)methyl)-1,6-dihydrospiro[furo[3,2-f]indazole-5,3'-indolin]-2'-one | B |

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A compound of formula (I):

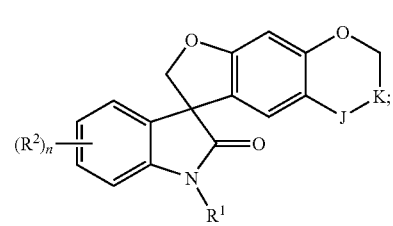

wherein:

n is 1 or 2;

one of J and K is —CH$_2$— and the other is —O—;

or both J and K are each —CH$_2$—;

R$^1$ is (6-methylpyridin-2-yl)methyl, pyridin-3-ylmethyl, diphenylmethyl, pentyl, isopentyl, (5-(trifluoromethyl)furan-2-yl)methyl, tetrahydrofuran-2-ylmethyl, 3-methylbutyl, tetrahydro-2H-pyran-4-ylmethyl, tetrahydro-2H-pyran-2-ylmethyl, (5-chloro-1-methyl-1H-imidazol-2-yl)methyl, pyridin-2-ylmethyl, (2R)-1,4-dioxan-2-ylmethyl, 1,4-dioxan-2-ylmethyl, 3,4-dimethoxybenzyl, 3,5-dimethoxybenzyl, 2,3-dihydro-1,4-benzodioxin-6-ylmethyl, [5-(trifluoromethyl)furan-2-yl]methyl, 3-(trifluoromethyl)benzyl, (5-methoxycarbonylfuran-2-yl)methyl, 2(2-methoxyethoxy)ethyl, 5-carboxyfuran-2-ylmethyl, 5-(dimethylaminocarbonyl)furan-2ylmethyl, 3-(trifluoromethyl)pyridin-2-yl]methyl or (5-hydroxypyridin-2-yl)methyl;

each R$^2$ is hydrogen;

or two adjacent R$^2$'s, together with the adjacent carbons to which they are attached, form a fused thiazolyl ring or a fused dioxinyl ring;

as a stereoisomer, enantiomer, tautomer thereof or mixtures thereof;

or a pharmaceutically acceptable salt or prodrug thereof.

2. The compound of claim 1 wherein J is —O— and K is —CH$_2$—.

3. The compound of claim 2 selected from:
(8R)-1'-[(2R)-1,4-dioxan-2-ylmethyl]-2,3-dihydrospiro[furo[2,3-g][1,4]benzodioxine-8,3'-indol]-2'(1'H)-one;
1'-[(6-methylpyridin-2-yl)methyl]-2,3-dihydrospiro[furo[2,3-g][1,4]benzodioxine-8,3'-indol]-2'(1'H)-one;
1'-(pyridin-3-ylmethyl)-2,3-dihydrospiro[furo[2,3-g][1,4]benzodioxine-8,3'-indol]-2'(1'H)-one;
(8S)-1'-{[3-(trifluoromethyl)pyridin-2-yl]methyl}-2,3-dihydrospiro[furo[2,3-g][1,4]benzodioxine-8,3'-indol]-2'(1'H)-one;
(8S)-1'-[(5-hydroxypyridin-2-yl)methyl]-2,3-dihydrospiro[furo[2,3-g][1,4]benzodioxine-8,3'-indol]-2'(1'H)-one;
1'-(diphenylmethyl)-2,3-dihydrospiro[furo[2,3-g][1,4]benzodioxine-8,3'-indol]-2'(1'H)-one;
6'-isopentyl-3,7-dihydro-2H-spiro[benzofuro[5,6-b][1,4]dioxine-8,8'-thiazolo[5,4-e]indol]-7'(6'H)-one;
6-((5-(trifluoromethyl)furan-2-yl)methyl)-2,3,3',7'-tetrahydro-2'H-spiro[[1,4]dioxino[2,3-f]indole-8,8'-benzofuro[5,6-b][1,4]dioxin]-7(6H)-one;
2,3-dihydrospiro[furo[2,3-g][1,4]benzodioxine-8,3'-indol]-2'(1'H)-one;
1'-(3-methylbutyl)-2,3-dihydrospiro[furo[2,3-g][1,4]benzodioxine-8,3'-indol]-2'(1'H)-one;
1'-(tetrahydro-2H-pyran-4-ylmethyl)-2,3-dihydrospiro[furo[2,3-g][1,4]benzodioxine-8,3'-indol]-2'(1'H)-one;
1'-(tetrahydro-2H-pyran-2-ylmethyl)-2,3-dihydrospiro[furo[2,3-g][1,4]benzodioxine-8,3'-indol]-2'(1'H)-one;
1'-[(5-chloro-1-methyl-1H-imidazol-2-yl)methyl]-2,3-dihydrospiro[furo[2,3-g][1,4]benzodioxine-8,3'-indol]-2'(1'H)-one;
1-[(5-chloro-1-methyl-1H-imidazol-2-yl)methyl]-2,3-dihydrospiro[furo[2,3-g][1,4]benzodioxine-8,3'-indol]-2'(1'H)-one hydrochloride;
1'-(pyridin-2-ylmethyl)-2,3-dihydrospiro[furo[2,3-g][1,4]benzodioxine-8,3'-indol]-2'(1'H)-one;
(S)-1'-(pyridin-2-ylmethyl)-2,3-dihydrospiro[furo[2,3-g][1,4]benzodioxine-8,3'-indol]-2'(1'H)-one hydrochloride;
1'-[(2S)-tetrahydrofuran-2-ylmethyl]-2,3-dihydrospiro[furo[2,3-g][1,4]benzodioxine-8,3'-indol]-2'(1'H)-one;
1'-[(2R)-tetrahydrofuran-2-ylmethyl]-2,3-dihydrospiro[furo[2,3-g][1,4]benzodioxine-8,3'-indol]-2'(1'H)-one;
1'-(1,4-dioxan-2-ylmethyl)-2,3-dihydrospiro[furo[2,3-g][1,4]benzodioxine-8,3'-indol]-2'(1'H)-one;
1'-(3,4-dimethoxybenzyl)-2,3-dihydrospiro[furo[2,3-g][1,4]benzodioxine-8,3'-indol]-2'(1'H)-one;
1'-(3,5-dimethoxybenzyl)-2,3-dihydrospiro[furo[2,3-g][1,4]benzodioxine-8,3'-indol]-2'(1'H)-one;
1'-(2,3-dihydro-1,4-benzodioxin-6-ylmethyl)-2,3-dihydrospiro[furo[2,3-g][1,4]benzodioxine-8,3'-indol]-2'(1'H)-one;
(R)-1'-{[5-(trifluoromethyl)furan-2-yl]methyl}-2,3-dihydrospiro[furo[2,3-g][1,4]benzodioxine-8,3'-indol]-2'(1'H)-one;
(S)-1'-{[5-(trifluoromethyl)furan-2-yl]methyl}-2,3-dihydrospiro[furo[2,3-g][1,4]benzodioxine-8,3'-indol]-2'(1'H)-one;
(S)-1'-(pyridin-2-ylmethyl)-2,3-dihydrospiro[furo[2,3-g][1,4]benzodioxine-8,3'-indol]-2'(1'H)-one;
1'-[3-(trifluoromethyl)benzyl]-2,3-dihydrospiro[furo[2,3-g][1,4]benzodioxine-8,3'-indol]-2'(1'H)-one;
methyl 5-[(2'-oxo-2,3-dihydrospiro[furo[2,3-g][1,4]benzodioxine-8,3'-indol]-1'(2'H)-yl)methyl]furan-2-carboxylate;
1'-pentyl-2,3-dihydrospiro[furo[2,3-g][1,4]benzodioxine-8,3'-indol]-2'(1'H)-one;
(8R)-1'-[(2S)-1,4-dioxan-2-ylmethyl]-2,3-dihydrospiro[furo[2,3-g][1,4]benzodioxine-8,3'-indol]-2'(1'H)-one;
(8S)-1'-[(2S)-1,4-dioxan-2-ylmethyl]-2,3-dihydrospiro[furo[2,3-g][1,4]benzodioxine-8,3'-indol]-2'(1'H)-one;
(8S)-1'-[(2R)-1,4-dioxan-2-ylmethyl]-2,3-dihydrospiro[furo[2,3-g][1,4]benzodioxine-8,3'-indol]-2'(1'H)-one;
1'-[2-(2-methoxyethoxy)ethyl]-2,3-dihydrospiro[furo[2,3-g][1,4]benzodioxine-8,3'-indol]-2'(1'H)-one;
5-[(2'-oxo-2,3-dihydrospiro[furo[2,3-g][1,4]-benzodioxine-8,3'-indol]-1'(2'H)-yl)methyl]furan-2-carboxylic acid; or
N,N-dimethyl-5-[(2'-oxo-2,3-dihydrospiro[furo[2,3-g][1,4]benzodioxine-8,3'-indol]-1'(2'H)-yl)methyl]furan-2-carboxamide.

4. The compound of claim 1 wherein J is —CH$_2$— and K is —O—.

5. The compound of claim 4 which is 1'-[(2R)-tetrahydrofuran-2-ylmethyl]-4H-spiro[furo[3,2-g][1,3]benzodioxine-6,3'-indol]-2'(1'H)-one.

6. The compound of claim 1 where both J and K are each —CH$_2$—.

7. The compound of claim 6 selected from:
1'-(diphenylmethyl)-6,7-dihydro-5H-spiro[furo[3,2-g]chromene-3,3'-indol]-2'(1'H)-one; or
1'-[(2R)-tetrahydrofuran-2-ylmethyl]-6,7-dihydro-5H-spiro[furo[3,2-g]chromene-3,3'-indol]-2'(1'H)-one.

8. A pharmaceutical composition comprising a pharmaceutically acceptable excipient and a compound of claim 1, as a stereoisomer, enantiomer, tautomer thereof or mixtures thereof; or a pharmaceutically acceptable salt or prodrug thereof.

9. A method of treating pain in a mammal, wherein the method comprises administering to the mammal in need thereof a therapeutically effective amount of a compound of claim 1, as a stereoisomer, enantiomer, tautomer thereof or mixtures thereof; or a pharmaceutically acceptable salt or prodrug thereof.

10. The method of claim 9, wherein the pain is selected from the group consisting of neuropathic pain, inflammatory pain, visceral pain, cancer pain, dental pain, chemotherapy pain, trauma pain, surgical pain, labor pain, neurogenic bladder, ulcerative colitis, chronic pain, persistent pain, peripherally mediated pain, centrally mediated pain, chronic headache, migraine headache, sinus headache, tension headache, phantom limb pain, and peripheral nerve injury, and combinations thereof.

11. The method of claim 9, wherein the pain is associated with a disease or condition selected from HIV, HIV treatment induced neuropathy, heat sensitivity, sarcoidosis, irritable bowel syndrome, Crohns disease, multiple sclerosis, amyotrophic lateral sclerosis, pruritis, hypercholesterolemia, benign prostatic hyperplasia, diabetic neuropathy, peripheral neuropathy, rheumatoid arthritis, osteoarthritis, paroxysmal dystonia, myasthenia syndromes, myotonia, malignant hyperthermia, cystic fibrosis, pseudoaldosteronism, rhabdomyolysis, bipolar depression, anxiety, schizophrenia, sodium channel toxin related illnesses, Paroxysmal Episodic Pain Disorder, cancer, epilepsy, partial and general tonic seizures, restless leg syndrome, arrhythmias, ischaemic conditions caused by stroke or neural trauma, tachy-arrhythmias, atrial fibrillation and ventricular fibrillation.

12. A method of treating pain in a mammal by the inhibition of ion flux through a voltage-dependent sodium channel in the mammal, wherein the method comprises administering to the mammal in need thereof a therapeutically effective amount of a compound of claim 1, as a stereoisomer, enantiomer, tautomer thereof or mixtures thereof; or a pharmaceutically acceptable salt or prodrug thereof.

13. A method of decreasing ion flux through a voltage-dependent sodium channel in a cell in a mammal, wherein the method comprises contacting the cell with a compound of claim 1, as a stereoisomer, enantiomer, tautomer thereof or mixtures thereof; or a pharmaceutically acceptable salt or prodrug thereof.

14. A method of treating hypercholesterolemia in a mammal, wherein the method comprises administering to the mammal in need thereof a therapeutically effective amount of a compound of claim 1, as a stereoisomer, enantiomer, tautomer thereof or mixtures thereof; or a pharmaceutically acceptable salt or prodrug thereof.

15. A method of treating benign prostatic hyperplasia in a mammal, wherein the method comprises administering to the mammal in need thereof a therapeutically effective amount of a compound of claim 1, as a stereoisomer, enantiomer, tautomer thereof or mixtures thereof; or a pharmaceutically acceptable salt or prodrug thereof.

16. A method of treating pruritis in a mammal, wherein the method comprises administering to the mammal in need thereof a therapeutically effective amount of a compound of claim 1, as a stereoisomer, enantiomer, tautomer thereof or mixtures thereof; or a pharmaceutically acceptable salt or prodrug thereof.

17. The method of claim 9 wherein the pain is selected from trigeminal neuralgia, post-herpetic neuralgia, eudynia, familial erythromelalgia, primary erythromelalgia, familial rectal pain or fibromyalgia.

18. A compound of formula (I):

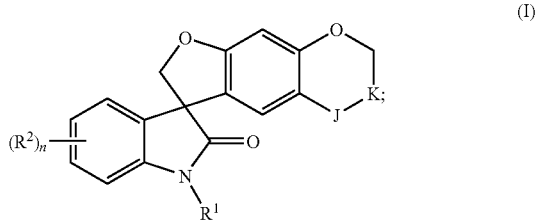

(I)

wherein:
n is 1 or 2;
one of J and K is —CH$_2$— and the other is —O—;
or both J and K are each —CH$_2$—;
R$^1$ is methyl, cyclopropyl, carboxymethyl, (3-carboxy)benzyl, (3-methylsulfonylamino)benzyl, [(3-methylsulfonylamino)pyridin-2-yl]methyl, [(3-carboxy)pyridin-2-yl]methyl, [(ethoxy)carbonyl]methyl, 2-cyclopropylethyl, 1,3-thiazol-5-ylmethyl, 3-methoxypropyl, (6-methylpyridin-2-yl)methyl, pyridin-3-ylmethyl, [3-(cyano)pyridine-2-yl]methyl, [3-(difluoromethyl)pyridin-2-yl]methyl, 3-(5-methyl-1,2,4-oxadiazol-3-yl)benzyl, 4-(5-methyl-1,2,4-oxadiazol-3-yl)benzyl, [5-(trifluoromethyl)-1,2,4-oxadiazol-3-yl]methyl, [5-(trifluoromethyl)-1,3,4-oxadiazol-2-yl]methyl, [4-(trifluoromethyl)pyridin-2-yl]methyl, (4-methyl-1,2,5-oxadiazol-3-yl)methyl, pyrazin-2-ylmethyl, pyrimidin-2-ylmethyl, (1-methyl-1H-benzotriazol-5-yl)methyl, [2-(tert-butoxycarbonylamino)pyridin-5-yl]methyl, [6-(dimethylamino)pyridin-3-yl]methyl, [6-(dimethylamino)pyridin-2-yl]methyl, {6-[(diphenylmethylidene)amino]pyridin-2-yl}methyl, (5-morpholin-4-ylpyridin-2-yl)methyl, [5-(dimethylamino)pyridin-2-yl]methyl, (6-aminopyridin-2-yl)methyl, (6-oxo-1,6-dihydropyridin-3-yl)methyl, (2-hydroxypyrimidin-5-yl)methyl, (1-methyl-6-oxo-1,6-dihydropyridin-3-yl)methyl, (6-aminopyridin-3-yl)methyl, [1,2,4]triazolo[1,5-a]pyridin-6-ylmethyl, (5-hydroxypyridin-2-yl)methyl, (5-bromopyridin-2-yl)methyl, hydrazinocarbonylmethyl, [6-deoxy-D-galactopyranose]-6-yl, (6-morpholin-4-ylpyridin-3-yl)methyl, [3-(methylsulfonyl)pyridin-2-yl]methyl, (4S)-2,2-dimethyl-1,3-dioxolan-4-yl]methyl, (3-bromopyridin-2-yl)methyl, [(2-imidoformamido)pyridine-5-yl]methyl, (6-cyanopyridin-2-yl)methyl, (6-aminocarbonylpyridin-2-yl)methyl, diphenylmethyl, 4-methoxybenzyl, 2-(fluoromethyl)benzyl, 2-ethoxyethyl, 4-fluorophenyl, (2-fluorophenylaminocarbonyl)methyl, 2-(2-methoxyethoxy)ethyl, 4-isoxazol-5-ylbenzyl, 3-(benzyloxy)propyl, (2S)-2,3-dihydroxypropyl, 4-methoxybutyl, pentyl, isopentyl, hexyl, 3-nitrobenzyl, [3-(trifluoromethyl)pyridin-2-yl]methyl, [5-(trifluoromethyl)pyridin-2-yl]methyl, [(tert-butoxycarbonylamino)pyridin-2-yl]methyl, (3-(trifluoromethyl)pyridin-2-yl)methyl, (5-(trifluoromethyl)furan-2-yl)methyl, tetrahydrofuran-2-ylmethyl, 3-methylbutyl, cyanomethyl, 4-hydroxybenzyl, 3-cyanobenzyl, 4-fluoro-3-methoxybenzyl, 4-cyanobenzyl, [6-(trifluoromethyl)pyridin-3-yl]methyl, [4-(trifluoromethyl)-1,3-thiazol-2-yl]methyl, (3-fluoropyridin-2-yl)methyl, (4-fluoropyridin-2-yl)methyl, (5-fluoropyridin-3-yl)methyl, (5-fluoropyridin-2-yl)methyl, (3-chloropyridin-2-yl)methyl, (3,5-difluoropyridin-2-yl)methyl, (3-pyridin-3-ylisoxazol-5-yl)methyl, (2,2-difluorocyclopropyl)methyl, 2-oxobutyl, 2,1,3-benzothiadiazol-5-ylmethyl, 2,1,3-benzoxadiazol-5-ylmethyl, 1,3-benzothiazol-2-ylmethyl, (1-methyl-1H-benzimidazol-2-yl)methyl, [2-(1-methylethyl)-1,3-thiazol-4-yl]methyl, tert-butoxycarbonyl, [1-(tert-butoxycarbonyl)piperidin-4-yl]methyl, (2-methoxypyrimidin-5-yl)methyl, (6-methoxypyridin-3-yl)methyl, (1-oxydopyridin-2-yl)methyl, (3-aminopyridin-2-yl)methyl, piperidin-4-ylmethyl, [1-(1-methylethyl)piperidin-4-yl]methyl, (1-methylpiperidin-4-yl)methyl, morpholin-2-ylmethyl, [4-(1-methylethyl)morpholin-2-yl]methyl, (4-methylmorpholin-2-yl)methyl, (2S)-morpholin-2-ylmethyl, [(2S)-4- methylmorpholin-2-yl]methyl, [5-(difluoromethyl)furan-2-yl]methyl, tetrahydro-2H-pyran-4-ylmethyl, tetrahydro-2H-pyran-2-ylmethyl, (5-chloro-1-methyl-1H-imidazol-2-yl)methyl, (6-chloropyridin-2-yl)methyl, (4,6-dimethoxypyrimidin-2-yl)methyl, [(3-methylaminocarbonyl)pyridin-2-yl]methyl, 1-[2-(aminoethyl)aminocarbonylpyridin-3-yl]methyl, pyridin-2-ylmethyl, (2R)-1,4-dioxan-2-ylmethyl, 1,4-dioxan-2-ylmethyl, 3,4-dimethoxybenzyl, 3,5-dimethoxybenzyl, 3-hydroxypropyl, 3-phthalimidopropyl, 3-aminobenzyl, (3-aminocarbonyl)benzyl, (4-aminocarbonyl)benzyl, (3-N,N-dimethylaminocarbonyl)benzyl, 4-(benzyloxy)benzy, 4-fluorobenzyl, 2,3-difluorobenzyl, 3,5-difluorobenzyl, 2-chloro-4-fluorobenzyl, [3-(2-fluorophenyl)aminocarbonyl]benzyl, 3-(methoxycarbonyl)benzyl, 4-(methoxycarbonyl)benzyl, 4-(ethoxycarbonyl)benzyl, 3-(dimethylamino-sulfonyl)benzyl, 3-(3-methyl-1,2,4-oxadiazol-5-yl)benzyl, 4-(3-amino-1H-pyrazol-5-yl)benzyl, 4-(3-methyl-1,2,4-oxadiazol-5-yl)benzyl, 3-(morpholin-4-ylsulfonyl)benzyl, 2-(difluoromethyl)benzyl, (3-trifluoromethoxy)benzyl, (2-fluoro-6-trifluoromethyl)benzyl, (2-fluoro-5-trifluoromethyl)benzyl, (2-trifluoromethoxy)benzyl, 3-(amino(hydroxyimino)methyl)benzyl, 2-amino-2-(hydroxyimino)ethyl, (6-(N'-hydroxyformimidamido)pyridin-3-yl)methyl, 2-(2,2,5-trimethyl-1,3-dioxan-2-yl)ethyl, (4-benzylmorpholin-2-yl)methyl, [(2S)-4-benzylmorpholin-2-yl]methyl, 2,3-dihydro-1,4-benzodioxin-6-ylmethyl, [5-(trifluoromethyl)furan-2-yl]methyl, 3-(trifluoromethyl)benzyl, [3-(trifluoromethyl)pyrazin-2-yl]methyl, [4-(trifluoromethyl)pyridin-3-yl]methyl, (5-methoxycarbonylfuran-2-yl)methyl, 5-carboxyfuran-2-ylmethyl, 5-(dimethylaminocarbonyl)furan-2ylmethyl, [2-(trifluoromethyl)pyridin-3-yl]methyl, methylcarbonyl, ethoxycarbonyl, tert-butoxycarbonyl or [(3aR,5R,5aS,8aS,8bR)-2,2,7,7-tetramethyltetrahydro-3aH-bis[1,3]dioxolo[4,5-b:4',5'-d]pyran-5-yl]methyl;

each $R^2$ is independently hydrogen, hydroxy, amino, (hexanylaminocarbonyl)amino, (cyclopentylaminocarbonyl)amino, benzylamino, (cyclohexylaminocarbonyl)amino, methylsulfonylamino, (methyl)carbonylamino, N,N-dimethylaminocarbonyl, (ethyl)carbonylamino, (butyl)carbonylamino, (tert-butyl)carbonylamino, (pentanyl)carbonylamino, (hexanyl)carbonylamino, (methoxymethyl)carbonylamino, cyclobutylcarbonylamino, [2-methoxy(ethoxymethyl)]carbonylamino, (methylsulfonyl)amino, (2-trifluoromethylphenyl)carbonylamino, (cyclohexanyl)carbonylamino, (cyclopentanyl)carbonylamino, (cyclopropanyl)carbonylamino, (phenyl)carbonylamino, bromo, cyano, fluoro, methyl, methoxy, hydroxycarbonyl, methylcarbonyl, pyrrolidinylcarbonyl, aminocarbonyl, methylaminocarbonyl, (2-methoxyethyl)aminocarbonyl, (cyclopropyl)aminocarbonyl, pentylaminocarbonyl, (cyclobutyl)aminocarbonyl, (cyclopentyl)aminocarbonyl, hexanylaminocarbonyl, (cyclohexyl)aminocarbonyl, (4-fluorophenyl)aminocarbonyl, (4-fluorobenzyl)aminocarbonyl, (pyridin-2-ylmethyl)aminocarbonyl, 2-(2-methoxyethoxy)ethoxy, [3-(trifluoromethyl)pyridin-2-yl]oxyl, quinolinyl, phenoxycarbonyl, 2-oxochromenyl, 2-oxopyrrolidinyl, morpholinyl, 2-oxopyridinyl, benzyloxyl, [3-(trifluoromethyl)pyridin-2-yl]methoxy, pyridine-2-ylmethoxy, pyridin-2-yloxy, 4-(trifluoromethyl)phenoxy, 2-methyl-1,3-thiazol-4-yl, 2-amino-1,3-thiazol-4-yl, 6-(dimethylamino)pyridin-3-yl, furan-3-yl, 1H-pyrazol-3-yl, 1H-pyrazol-4-yl, 1-methyl-1H-pyrazol-4-yl , 5-hydroxy-1H-pyrazol-3-yl, 5-methyl-1,2,4-oxadiazol-3-yl, (6-methoxypyridin-3-yl)oxy, 1,3-benzodioxol-5-yloxy, 4-fluorobenzyloxy, 3,5-dimethylisoxazol-4-yl, phenoxy, 3-methoxyphenoxy, 4-methoxyphenoxy, 3-morpholin-4-ylphenoxy, 4-fluorophenoxy, 4-methoxyphenyl or 4-phenoxyphenyl;

or two adjacent $R^2$'s, together with the adjacent carbons to which they are attached, form a fused thiazolyl ring, a fused pyridyl ring or a fused dioxinyl ring;

as a stereoisomer, enantiomer, tautomer thereof or mixtures thereof;

or a pharmaceutically acceptable salt or prodrug thereof.

19. The compound of claim 18 wherein J is —O— and K is —CH$_2$—.

20. The compound of claim 19 selected from:

1'-methyl-2'-oxo-N-pentyl-1',2,2',3-tetrahydrospiro[furo[2,3-g][1,4]benzodioxine-8,3'-indole]-4'carboxamide;

1'-(diphenylmethyl)-4',6'-dimethoxy-2,3-dihydrospiro[furo[2,3-g][1,4]benzodioxine-8,3'-indol]-2'(1'H)-one;

1'-[(5-bromopyridin-2-yl)methyl]-2,3-dihydrospiro[furo[2,3-g] [1,4]benzodioxine-8,3'-indol]-2'(1'H)-one;

1'-(diphenylmethyl)-7'-fluoro-2,3-dihydrospiro[furo[2,3-g][1,4]benzodioxine-8,3'-indol]-2'(1'H)-one;

4'-bromo-1'-(diphenylmethyl)-2,3-dihydrospiro[furo[2,3-g][1,4]benzodioxine-8,3'-indol]-2'(1'H)-one;

4'-bromo-1'-methyl-2,3-dihydrospiro[furo[2,3-g][1,4]benzodioxine-8,3'-indol]-2'(1'H)-one;

1'-(diphenylmethyl)-4'-fluoro-2,3-dihydrospiro[furo[2,3-g][1,4]benzodioxine-8,3'-indol]-2'(1'H)-one;

1'-(4-fluorophenyl)-2,3-dihydrospiro[furo[2,3-g][1,4]benzodioxine-8,3'-indol]-2'(1'H)-one;

1'-(diphenylmethyl)-4'-quinolin-3-yl-2,3-dihydrospiro[furo[2,3-g][1,4]benzodioxine-8,3'-indol]-2'(1'H)-one;

1'-(diphenylmethyl)-4'-(4-phenoxyphenyl)-2,3-dihydrospiro[furo[2,3-g][1,4]benzodioxine-8,3'-indol]-2'(1'H)-one;

5'-bromo-1'-(pyridin-2-ylmethyl)-2,3-dihydrospiro[furo[2,3-g][1,4]benzodioxine-8,3'-indol]-2'(1'H) -one;

2'-oxo-1'-(pyridin-2-ylmethyl)-1',2,2',3-tetrahydrospiro[furo[2,3-g][1,4]benzodioxine-8,3'-indole]-5'-carbonitrile;

5'-bromo-1'-(diphenylmethyl)-2,3-dihydrospiro[furo[2,3-g][1,4]benzodioxine-8,3'-indol]-2'(1'H)-one;

1'-(diphenylmethyl)-5'-methyl-2,3-dihydrospiro[furo[2,3-g][1,4]benzodioxine-8,3'-indol]-2'(1'H)-one;

phenyl 1'-methyl-2'-oxo-1',2,2',3-tetrahydrospiro[furo[2,3-g][1,4]benzodioxine-8,3'-indole]-4'-carboxylate;

4',5'-dimethoxy-1'-{[5-(trifluoromethyl)furan-2-yl]methyl}-2,3-dihydrospiro[furo[2,3-g][1,4]benzodioxine-8,3'-indol]-2'(1'H)-one;

4',7'-dimethoxy-1'-[2-(2-methoxyethoxy)ethyl]2,3-dihydrospiro[furo[2,3-g][1,4]benzodioxine-8,3'-indol]-2'(1'H)-one;

6-[2-(2-methoxyethoxy)ethyl]-2,2',3,3'-tetrahydrospiro[1,4-dioxino[2,3-f]indole-8,8'-furo[2,3-g][1,4]benzodioxin]-7(6H)-one;

6'-(4-methoxybenzyl)-2,3-dihydrospiro[furo[2,3-g][1,4]benzodioxine-8,8'-[1,3]thiazolo[5,4-e]indol]-7'(6'H)-one;

3'-[2-(fluoromethyl)benzyl]-2,3-dihydrospiro[furo[2,3-g][1,4]benzodioxine-8,1'-inden]-2'(3'H)-one;

3-[(2'-oxo-2,3-dihydrospiro[furo[2,3-g][1,4]benzodioxine-8,3'-indol]-1'(2'H)-yl)methyl]benzonitrile;

1'-(4-fluoro-3-methoxybenzyl)-2,3-dihydrospiro[furo[2,3-g][1,4]benzodioxine-8,3'-indol]-2'(1'H)-one;

4-[(2'-oxo-2,3-dihydrospiro[furo[2,3-g]][1,4]benzodioxine-8,3'-indol]-1'(2'H)-yl)methyl]benzonitrile;

1'-(4-isoxazol-5-ylbenzyl)-2,3-dihydrospiro[furo[2,3-g][1,4]benzodioxine-8,3'-indol]-2'(1'H)-one;

1'-{[6-(trifluoromethyl)pyridin-3-yl]methyl}-2,3-dihydrospiro[furo[2,3-g][1,4]benzodioxine-8,3'-indol]-2'(1'H)-one;

1'-[(5-fluoropyridin-2-yl)methyl]-2,3-dihydrospiro[furo[2,3-g][1,4]benzodioxine-8,3'-indol]-2'(1'H)-one;

1'-[(3-fluoropyridin-2-yl)methyl]-2,3-dihydrospiro[furo[2,3-g][1,4]benzodioxine-8,3'-indol]-2'(1'H)-one;

1'-(pyridin-2-ylmethyl)-4'-quinolin-3-yl-2,3-dihydrospiro[furo[2,3-g][1,4]benzodioxine-8,3'-indol]-2'(1'H)-one;

4'-(4-phenoxyphenyl)-1'-(pyridin-2-ylmethyl)-2,3-dihydrospiro[furo[2,3-g][1,4]benzodioxine-8,3'-indol]-2'(1'H)-one;

1'-[(3,5-difluoropyridin-2-yl)methyl]-2,3-dihydrospiro[furo[2,3-g][1,4]benzodioxine-8,3'-indol]-2'(1'H)-one;

3-{[(8S)-2'-oxo-2,3-dihydrospiro[furo[2,3-g][1,4]benzodioxine-8,3'-indol]-1'(2'H)-yl]methyl}benzonitrile;

(8S)-1'-[(5-fluoropyridin-2-yl)methyl]-2,3-dihydrospiro[furo[2,3-g][1,4]benzodioxine-8,3'-indol]-2'(1'H)-one;

(8S)-1'-[(3-fluoropyridin-2-yl)methyl]-2,3-dihydrospiro[furo[2,3-g][1,4]benzodioxine-8,3'-indol]-2'(1'H)-one;

(S)-1'-(2-oxobutyl)-3,7-dihydro-2H-spiro[benzofuro[5,6-b][1,4]dioxine-8,3'-indolin]-2'-one;

1'-[(4-fluoropyridin-2-yl)methyl]-2,3-dihydrospiro[furo[2,3-g][1,4]benzodioxine-8,3'-indol]-2'(1'H)-one;

1'-[(3-chloropyridin-2-yl)methyl]-2,3-dihydrospiro[furo[2,3-g][1,4]benzodioxine-8,3'-indol]-2'(1'H)-one;

1'-[2-(trifluoromethyl)benzyl]-2,3-dihydrospiro[furo[2,3-g][1,4]benzodioxine-8,3'-indol]-2'(1'H)-one;

(8R)-1'-[2-(trifluoromethyl)benzyl]-2,3-dihydrospiro[furo[2,3-g][1,4]benzodioxine-8,3'-indol]-2'(1'H)-one;

5'-methyl-1'-{[3-(trifluoromethyl)pyridin-2-yl]methyl}-2,3-dihydrospiro[furo[2,3-g][1,4]benzodioxine-8,3'-indol]-2'(1'H)-one;

(8S)-1'-[2-(trifluoromethyl)benzyl]-2,3-dihydrospiro[furo[2,3-g][1,4]benzodioxine-8,3'-indol]-2'(1'H)-one;

4'-bromo-1'-(pyridin-2-ylmethyl)-2,3-dihydrospiro[furo[2,3-g][1,4]benzodioxine-8,3'-indol]-2'(1'H)-one;

1'-(2,1,3-benzothiadiazol-5-ylmethyl)-2,3-dihydrospiro[furo[2,3-g][1,4]benzodioxine-8,3'-indol]-2'(1'H)-one;

1'-(1,3-benzothiazol-2-ylmethyl)-2,3-dihydrospiro[furo[2,3-g][1,4]benzodioxine-8,3'-indol]-2'(1'H)-one;

1'[(1-methyl-1H-benzimidazol-2-yl)methyl]-2,3-dihydrospiro[furo[2,3-g][1,4]benzodioxine-8,3'-indol]-2'(1'H)-one;

1'-{[2-(1-methylethyl)-1,3-thiazol-4-yl]methyl}-2,3-dihydrospiro[furo[2,3-g][1,4]benzodioxine-8,3'-indol]-2'(1'H)-one;

1'-(2,1,3-benzoxadiazol-5-ylmethyl)-2,3-dihydrospiro[furo[2,3-g][1,4]benzodioxine-8,3'-indol]-2'(1'H)-one;

tert-butyl 4-[(2'-oxo-2,3-dihydrospiro[furo[2,3-g][1,4]benzodioxine-8,3'-indol]-1'(2'H)-yl)methyl]piperidine-1-carboxylate;

1'-{[6-(trifluoromethyl)pyridin-2-yl]methyl}-2,3-dihydrospiro[furo[2,3-g][1,4]benzodioxine-8,3'-indol]-2'(1'H)-one;

1'-{[2-(trifluoromethyl)pyridin-3-yl]methyl}-2,3-dihydrospiro[furo[2,3-g][1,4]benzodioxine-8,3'-indol]2'(1'H)-one;

1'-{[3-(trifluoromethyl)pyrazin-2-yl]methyl}-2,3-dihydrospiro[furo[2,3-g][1,4]benzodioxine-8,3'-indol]-2'(1'H)-one;

1'-{[4-(trifluoromethyl)pyridin-3-yl]methyl}-2,3-dihydrospiro[furo[2,3-g][1,4]benzodioxine-8,3'-indol]-2'(1'H)-one;

1'-[(6-chloropyridin-2-yl)methyl]-2,3-dihydrospiro[furo[2,3-g][1,4]benzodioxine-8,3'-indol]-2'(1'H)-one;

1'-[(2-methoxypyrimidin-5-yl)methyl]-2,3-dihydrospiro[furo[2,3-g][1,4]benzodioxine-8,3'-indol]-2'(1'H)-one;

1'-[(6-methoxypyridin-3-yl)methyl]-2,3-dihydrospiro[furo[2,3-g][1,4]benzodioxine-8,3'-indol]-2'(1'H)-one;

(8S)-1'-(pyrazin-2-ylmethyl)-2,3-dihydrospiro[furo[2,3-g][1,4]benzodioxine-8,3'-indol]-2'(1'H)-one;

(8S)-1'-[(2-methoxypyrimidin-5-yl)methyl]-2,3-dihydrospiro[furo[2,3-g][1,4]benzodioxine-8,3'-indol]-2'(1'H)-one;

(8S)-1'-(pyrimidin-2-ylmethyl)-2,3-dihydrospiro[furo[2,3-g][1,4]benzodioxine-8,3'-indol]-2'(1'H)-one;

4'-fluoro-1'-{[3-(trifluoromethyl)pyridin-2-yl]methyl}-2,3-dihydrospiro[furo[2,3-g][1,4]benzodioxine-8,3'-indol]-2'(1'H)-one;

1'-[(2,2-difluorocyclopropyl)methyl]-2,3-dihydrospiro[furo[2,3-g][1,4]benzodioxine-8,3'-indol]-2'(1'H)-one;

1'-methyl-2,3-dihydrospiro[furo[2,3-g][1,4]benzodioxine-8,3'-indol]-2'(1'H)-one;

1'-{[4-(trifluoromethyl)-1,3-thiazol-2-yl]methyl}-2,3-dihydrospiro[furo[2,3-g][1,4]benzodioxine-8,3'-indol]-2'(1'H)-one;

(2'-oxo-2,3-dihydrospiro[furo[2,3-g][1,4]benzodioxine-8,3'-indol]-1'(2'H)-yl)acetonitrile;

ethyl 2-[(2'-oxo-2,3-dihydrospiro[furo[2,3-g][1,4]benzodioxine-8,3'-indol]-1'(2'H)-yl)methyl]pyridine-3-carboxylate;

1-(pyrimidin-2-ylmethyl)-2,3-dihydrospiro[furo[2,3-g][1,4]benzodioxine-8,3'-indol]2'(1'H)-one;

1'-[(4,6-dimethoxypyrimidin-2-yl)methyl]-2,3-dihydrospiro[furo[2,3-g][1,4]benzodioxine-8,3'-indol]-2'(1'H)-one;

(S)-1'-pentyl-2,3-dihydrospiro[furo[2,3-g][1,4]benzodioxine-8,3'-indol]-2'(1'H)-one;

(R)-1'-pentyl-2,3-dihydrospiro[furo[2,3-g][1,4]benzodioxine-8,3'-indol]-2'(1'H)-one;

1'-hexyl-2,3-dihydrospiro[furo[2,3-g][1,4]benzodioxine-8,3'-indol]-2'(1'H)-one;

1'-(2-cyclopropylethyl)-2,3-dihydrospiro[furo[2,3-g][1,3]benzodioxine-8,3'-indol]-2'(1'H)-one;

1'-(2-ethoxyethyl)-2,3-dihydrospiro[furo[2,3-g][1,3]benzodioxine-8,3'-indol]-2'(1'H)-one;

1'-(4-methoxybutyl)-2,3-dihydrospiro[furo[2,3-g][1,3]benzodioxine-8,3'-indol]-2'(1'H)-one;

1'-(3-methoxypropyl)-2,3-dihydrospiro[furo[2,3-g][1,3]benzodioxine-8,3'-indol]-2'(1'H)-one;

1'-(3-nitrobenzyl)-2,3-dihydrospiro[furo[2,3-g][1,3]benzodioxine-8,3'-indol]-2'(1'H)-one;

1'-(1,3-thiazol-5-ylmethyl)-2,3-dihydrospiro[furo[2,3-g][1,3]benzodioxine-8,3'-indol]-2'(1'H)-one;

1'-{[5-(trifluoromethyl)pyridin-2-yl]methyl}-2,3-dihydrospiro[furo[2,3-g][1,3]benzodioxine-8,3'-indol]-2'(1'H)-one;

1'-{[3-(trifluoromethyl)pyridin-2-yl]methyl}-2,3-dihydrospiro[furo[2,3-g][1,3]benzodioxine-8,3'-indol]-2'(1'H)-one;

1'-[(3-pyridin-3-ylisoxazol-5-yl)methyl]-2,3-dihydrospiro[furo[2,3-g][1,3]benzodioxine-8,3'-indol]-2'(1'H)-one;

(8R)-1'-{[3-(trifluoromethyl)pyridin-2-yl]methyl}-2,3-dihydrospiro[furo[2,3-g][1,3]benzodioxine-8,3'-indol]-2'(1'H)-one;

N,N-dimethyl-3-[(2'-oxo-2,3-dihydrospiro[furo[2,3-g][1,4]benzodioxine-8,3'-indol]-1'-(2'H)-yl)methyl]benzenesulfonamide;

1'-[3-(morpholin-4-ylsulfonyl)benzyl]-2,3-dihydrospiro[furo[2,3-g][1,4]benzodioxine-8,3'-indol]-2'(1'H)-one;

1'-[(4-methyl-1,2,5-oxadiazol-3-yl)methyl]-2,3-dihydrospiro[furo[2,3-g][1,4]benzodioxine-8,3'-indol]-2'(1'H)-one;

1'-(2,3-difluorobenzyl)-2,3-dihydrospiro[furo[2,3-g][1,4]benzodioxine-8,3'-indol]-2'(1'H)-one;

1'-(3,5-difluorobenzyl)-2,3-dihydrospiro[furo[2,3-g][1,4]benzodioxine-8,3'-indol]-2'(1'H)-one;

1'-(4-fluorobenzyl)-2,3-dihydrospiro[furo[2,3-g][1,4]benzodioxine-8,3'-indol]-2'(1'H)-one;

1'-(2-chloro-4-fluorobenzyl)-2,3-dihydrospiro[furo[2,3-g][1,4]benzodioxine-8,3'-indol]-2'(1'H)-one;

1'-[(1-methyl-1H-benzotriazol-5-yl)methyl]-2,3-dihydrospiro[furo[2,3-g][1,4]benzodioxine-8,3'-indol]-2'(1'H)-one;

1'-[(3-trifluoromethoxy)benzyl]-2,3-dihydrospiro[furo[2,3-g][1,4]benzodioxine-8,3'-indol]-2'(1'H)-one;

1'-[(2-fluoro-6-trifluoromethyl)benzyl]-2,3-dihydrospiro[furo[2,3-g][1,4]benzodioxine-8,3'-indol]-2'(1'H)-one;

1'-[(2-fluoro-5-trifluoromethyL)benzyl]-2,3-dihydrospiro[furo[2,3-g][1,4]benzodioxine-8,3'-indol]-2'(1'H)-one;

1'-[(2-trifluoromethoxy)benzyl]-2,3-dihydrospiro[furo[2,3-g][1,4]benzodioxine-8,3'-indol]-2'(1'H)-one;

1'-[2-(2,2,5-trimethyl-1,3-dioxan-2-yl)ethyl]-2,3-dihydrospiro[furo[2,3-g][1,4]benzodioxine-8,3'-indol]-2'(1'H)-one;

7'-fluoro-1'-(pyridin-2-ylmethyl)-3,7-dihydro-2H-spiro[benzofuro[5,6-b][1,4]dioxine-8,3'-indolin]-2'-one;

7'-fluoro-1'-((3-(trifluoromethyl)pyridin-2-yl)methyl)-3,7-dihydro-2H-spiro[benzofuro[5,6-b][1,4]dioxine-8,3'-indolin]-2'-one;

3'-[2-(difluoromethyl)benzyl]-2,3-dihydrospiro[furo[2,3-g][1,4]benzodioxine-8,1'-inden]-2'(3'H)-one;

1'-[(5-fluoropyridin-3-yl)methyl]-2,3-dihydrospiro[furo[2,3-g][1,4]benzodioxine-8,3'-indol]-2'(1'H)-one;

(8S)-1'-[(5-fluoropyridin-3-yl)methyl]-2,3-dihydrospiro[furo[2,3-g][1,4]benzodioxine-8,3'-indol]-2'(1'H)-one;

1'-[4-(benzyloxy)benzyl]-2,3-dihydrospiro[furo[2,3-g][1,4]benzodioxine-8,3'-indol]-2'(1'H)-one;

(8S)-1'-[4-(benzyloxy)benzyl]-2,3-dihydrospiro[furo[2,3-g][1,4]benzodioxine-8,3'-indol]-2'(1'H)-one;

tert-butyl {5-[(2'-oxo-2,3-dihydrospiro[furo[2,3-g][1,4]benzodioxine-8,3'-indol]-1'(2'H)-yl)methyl]pyridin-2-yl}carbamate;

1'-3-(benzyloxy)propyl]-2,3-dihydrospiro[furo[2,3-g][1,4]benzodioxine-8,3'-indol]-2'(1'H)-one;

ethyl (2'-oxo-2,3-dihydrospiro[furo[2,3-g][1,4]benzodioxine-8,3'-indol]-1'(2'H)-yl)acetate;

1'-{[(4S)-2,2-dimethyl-1,3-dioxolan-4-yl]methyl}-2,3-dihydrospiro[furo[2,3-g][1,4]benzodioxine-8,3'-indol]-2'(1'H)-one;

4'-bromo-1'-pentyl-2,3-dihydrospiro[furo[2,3-g][1,4]benzodioxine-8,3'-indol]-2'(1'H)-one;

methyl 3-[(2'-oxo-2,3-dihydrospiro[furo[2,3-g][1,4]benzodioxine-8,3'-indol]-1'(2'H)-yl)methyl]benzoate;

methyl 4-[(2'-oxo-2,3-dihydrospiro[furo[2,3-g][1,4]benzodioxine-8,3'-indol]-1'(2'H)-yl)methyl]benzoate;

1'-[(4-benzylmorpholin-2-yl)methyl]-2,3-dihydrospiro[furo[2,3-g][1,4]benzodioxine-8,3'-indol]-2'(1'H)-one;

(8S)-1'-{[(2S)-4-benzylmorpholin-2-yl]methyl}-2,3-dihydrospiro[furo[2,3-g][1,4]benzodioxine-8,3'-indol]-2'(1'H)-one;

ethyl 4-[(2'-oxo-2,3-dihydrospiro[furo[2,3-g][1,4]benzodioxine-8,3'-indol]-1'(2'H)-yl)methyl]benzoate;

2-[3-(2'-oxo-2,3-dihydrospiro[furo[2,3-g][1,4]benzodioxine-8,3'-indol]-1'(2'H)-yl)propyl]-1H-isoindole-1,3(2H)-dione;

(8S)-1'-[2-(2-methoxyethoxy)ethyl]-2,3-dihydrospiro[furo[2,3-g][1,4]benzodioxine-8,3'-indol]-2'(1'H)-one;

6'-[2-(2-methoxyethoxy)ethyl]-2,3-dihydrospiro[furo[2,3-g][1,4]benzodioxine-8,8'-[1,3]thiazolo[5,4-e]indol]-7'(6'H)-one;

6'-(pyridin-2-ylmethyl)-2,3-dihydrospiro[furo[2,3-g][1,4]benzodioxine-8,8'-[1,3]thiazolo[5,4-e]indol]-7'(6'H)-one;

4',6'-dimethoxy-1'-[2-(2-methoxyethoxy)ethyl]-2,3-dihydrospiro[furo[2,3-g][1,4]benzodioxine-8,3'-indol]-2'(1'H)-one;

4',6'-dimethoxy-1'-(pyridin-2-ylmethyl)-2,3-dihydrospiro[furo[2,3-g][1,4]benzodioxine-8,3'-indol]-2'(1'H)-one;

(2'-oxo-2,3-dihydrospiro[furo[2,3-1,4]benzodioxine-8,3'-indol]-1'(2'H)-yl)acetic acid;

1'-methyl-2'-oxo-1',2,2',3-tetrahydrospiro[furo[2,3-g][1,4]benzodioxine-8,3'-indole]-4'-carboxylic acid;

3'-[(3-bromopyridin-2-yl)methyl]-2,3-dihydrospiro[furo[2,3-g][1,4]benzodioxine-8,1'-inden]-2'(3'H)-one;

3'-{[3-(methylsulfonyl)pyridin-2-yl]methyl}-2,3-dihydrospiro[furo[2,3-g][1,4]benzodioxine-8,1'-inden]-2'(3'H)-one;

2[(2'-oxo-2,2',3,3'-tetrahydrospiro[furo[2,3-g][1,4]benzodioxine-8,1'-inden]-3'-yl)methyl]pyridine-3-carbonitrile;

(8S)-1'-{[3-(difluoromethyl)pyridin-2-yl]methyl}-2,3-dihydrospiro[furo[2,3-g][1,4]benzodioxine-8,3'-indol]-2'(1'H)-one;

N'-hydroxy-3-[(2'-oxo-2,3-dihydrospiro[furo[2,3-g][1,4]benzodioxine-8,3'-indol]-1'(2'H)-yl)methyl]benzenecarboximidamide;

1'-[3-(5-methyl-1,2,4-oxadiazol-3-yl)benzyl]-2,3-dihydrospiro[furo[2,3-g][1,4]benzodioxine-8,3'-indol]-2'(1'H)-one;

1'-[4(5-methyl-1,2,4-oxadiazol-3-yl)benzyl]-2,3-dihydrospiro[furo[2,3-g][1,4]benzodioxine-8,3'-indol]-2'(1'H)-one;

3-[(2'-oxo-2,3-dihydrospiro[furo[2,3-g][1,4]benzodioxine-8,3'-indol]1'(2'H)-yl)methyl]benzoic acid;

4-[(2'-oxo-2,3-dihydrospiro[furo[2,3-g][1,4]benzodioxine-8,3'-indol]-1'(2'H)-yl)methyl]benzoic acid;

N'-hydroxy-2-(2'-oxo-2,3-dihydrospiro[furo[2,3-g][1,4]benzodioxine-8,3'-indol]-1'(2'H)-yl)ethanimidamide;

1'-{[5-(trifluoromethyl)-1,2,4-oxadiazol-3-yl]methyl}-2,3-dihydrospiro[furo[2,3-g][1,4]benzodioxine-8,3'-indol]-2'(1'H)-one;

2-(2'-oxo-2,3-dihydrospiro[furo[2,3-g][1,4]benzodioxine-8,3'-indol]-1'(1'H)-yl)acetohydrazide;

1'-{[5-(trifluoromethyl)-1,3,4-oxadiazol-2-yl]methyl}-2,3-dihydrospiro[furo[2,3-g][1,4]benzodioxine-8,3'-indol]-2'(1'H)-one;

1'-(3-aminobenzyl)-2,3-dihydrospiro[furo[2,3-g][1,4]benzodioxine-8,3'-indol]-2'(1'H)-one;

N-{3[(2'-oxo-2,3-dihydrospiro[furo[2,3-g][1,4]benzodioxine-8,3'-indol]-1'(1'H)-yl)methyl]phenyl}methanesulfonamide;

1'-[(1-oxydopyridin-2-yl)methyl]-2,3-dihydrospiro[furo[2,3-g][1,4]benzodioxine-8,3'-indol]-2'(1'H)-one;

2-[(2'-oxo-2,3-dihydrospiro[furo[2,3-g][1,4]benzodioxine-8,3'-indol]-1'(2'H)-yl)methyl]pyridine-3-carboxylic acid;

1'-[(3-aminopyridin-2-yl)methyl]-2,3-dihydrospiro[furo[2,3-g][1,4]benzodioxine-8,3'-indol]-2'(1'H)-one hydrobromide;

N-{2-[(2'-oxo-2,3-dihydrospiro[furo[2,3-g][1,4]benzodioxine-8,3'-indol]-1'(2'H)-yl)methyl]pyridine-3-yl}methanesulfonamide;

1'-(piperidin-4-ylmethyl)-2,3-dihydrospiro[furo[2,3-g][1,4]benzodioxine-8,3'-indol]-2'(1'H)-one hydrochloride;

1'-{[1-(1-methylethyl)piperidin-4-yl]methyl}-2,3-dihydrospiro[furo[2,3-g][1,4]benzodioxine-8,3'-indol]-2'(1'H)-one hydrochloride;

1'-[(1-methylpiperidin-4-yl)methyl]-2,3-dihydrospiro[furo[2,3-g][1,4]benzodioxine-8,3'-indol]-2'(1'H)-one hydrochloride;

1'-(morpholin-2-ylmethyl)-2,3-dihydrospiro[furo[2,3-g][1,4]benzodioxine-8,3'-indol]-2'(1'H)-one;

1'-{[4-(1-methylethyl)morpholin-2-yl]methyl}-2,3-dihydrospiro[furo[2,3-g][1,4]benzodioxine-8,3'-indol]-2'(1'H)-one;

1'-[(4-methylmorpholin-2-yl)methyl]-2,3-dihydrospiro[furo[2,3-g][1,4]benzodioxine-8,3'-indol]-2'(1'H)-one;

(8S)-1'-[(2S)-morpholin-2-ylmethyl]-2,3-dihydrospiro[furo[2,3-g][1,4]benzodioxine-8,3'-indol]-2'(1'H)-one;

(8S)-1'-{[(2S)-4-methylmorpholin-2-yl]methyl}-2,3-dihydrospiro[furo[2,3-g][1,4]benzodioxine-8,3'-indol]-2'(1'H)-one;

1'-{[5-(difluoromethyl)furan-2-yl]methyl}-2,3-dihydrospiro[furo[2,3-g][1,4]benzodioxine-8,3'-indol]-2'(1'H)-one;

4-[(2'-oxo-2,3-dihydrospiro[furo[2,3-g][1,4]benzodioxine-8,3'-indol]-1'(2'H)-yl)methyl]benzamide;

3-[(2'-oxo-2,3-dihydrospiro[furo[2,3-g][1,4]benzodioxine-8,3'-indol]-1'(2'H)-yl)methyl]benzamide;

N,N-dimethyl-3-[(2'-oxo-2,3-dihydrospiro[furo[2,3-g][1,4]benzodioxine-8,3'-indol]-1'(2'H)-yl)methyl]benzamide;

N-methyl-2-[(2'-oxo-2,3-dihydrospiro[furo[2,3-g][1,4]benzodioxine-8,3'-indol]-1'(2'H)-yl)methyl]pyridine-3-carboxamide;

N-(2-aminoethyl)-2-[(2'-oxo-2,3-dihydrospiro[furo[2,3-g][1,4]benzodioxine-8,3'-indol]-1'(2'H)-yl)methyl]pyridine-3-carboxamide dihydrochloride;

N-(2-fluorophenyl)-4-[(2'-oxo-2,3-dihydrospiro[furo[2,3-g][1,4]benzodioxine-8,3'-indol]-1'(2H)-yl)methyl]benzamide;

N-(2-fluorophenyl)-2-(2'-oxo-2,3-dihydrospiro[furo[2,3-g][1,4]benzodioxine-8,3'-indol]-1'(2'H)-yl)acetamide;

1'-methyl-4'-(2-oxo-2H-chromen-7-yl)-2,3-dihydrospiro[furo[2,3-g][1,4]benzodioxine-8,3'-indol]-2'(1'H)-one;

1'-methyl-4'-(2-oxopyrrolidin-1-yl)-2,3-dihydrospiro[furo[2,3-g][1,4]benzodioxine-8,3'-indol]-2'(1'H)-one;

1'-methyl-4'-morpholin-4-yl-2,3-dihydrospiro[furo[2,3-g][1,4]benzodioxine-8,3'-indol]-2'(1'H)-one;

1'-methyl-4'-(2-oxopyridin-1(2H)-yl)-2,3-dihydrospiro[furo[2,3-g][1,4]benzodioxine-8,3'-indol]-2'(1'H)-one;

4'-amino-1'-methyl-2,3-dihydrospiro[furo[2,3-g][1,4]benzodioxine-8,3'-indol]-2'(1'H)-one;

N-(1'-methyl-2'-oxo-1',2,2',3-tetrahydrospiro[furo[2,3-g][1,4]benzodioxine-8,3'-indol]-4'-yl)cyclobutanecarboxamide;

N-(1'-methyl-2'-oxo-1',2,2',3-tetrahydrospiro[furo[2,3-g][1,4]benzodioxine-8,3'-indol]-4'-yl)-2-(trifluoromethyl)benzamide;

N-(1'-methyl-2'-oxo-1',2,2',3-tetrahydrospiro[furo[2,3-g][1,4]benzodioxine-8,3'-indol]-4'-yl)methanesulfonamide;

N-(1'-methyl-2'-oxo-1',2,2',3-tetrahydrospiro[furo[2,3-g][1,4]benzodioxine-8,3'-indol]-4'-yl)cyclohexanecarboxamide;

N-(1'-methyl-2'-oxo-1',2,2',3-tetrahydrospiro[furo[2,3-g][1,4]benzodioxine-8,3'-indol]-4'-yl)cyclopentanecarboxamide;

N-(1'-methyl-2'-oxo-1',2,2',3-tetrahydrospiro[furo[2,3-g][1,4]benzodioxine-8,3'-indol]-4'-yl)acetamide;

N-(1'-methyl-2'-oxo-1',2,2',3-tetrahydrospiro[furo[2,3-g][1,4]benzodioxine-8,3'-indol]-4'-yl)cyclopropanecarboxamide;

N-(1'-methyl-2'-oxo-1',2,2',3-tetrahydrospiro[furo[2,3-g][1,4]benzodioxine-8,3'-indol]-4'-yl)benzamide;

2-methoxy-N-(1'-methyl-2'-oxo-1',2,2',3-tetrahydrospiro[furo[2,3-g][1,4]benzodioxine-8,3'-indol]-4'-yl)acetamide;

N-(1'-methyl-2'-oxo-1',2,2',3-tetrahydrospiro[furo[2,3-g][1,4]benzodioxine-8,3'-indol]-4'-yl)propanamide;

N-(1'-methyl-2'-oxo-1',2,2',3-tetrahydrospiro[furo[2,3-g][1,4]benzodioxine-8,3'-indol]-4'-yl)pentanamide;

2,2-dimethyl-N-(1'-methyl-2'-oxo-1',2,2',3-tetrahydrospiro[furo[2,3-g][1,4]benzodioxine-8,3'-indol]-4'-yl)propanamide;

N-(1'-methyl-2'-oxo-1',2,2',3-tetrahydrospiro[furo[2,3-g][1,4]benzodioxine-8,3'-indol]-4'-yl)hexanamide;

N-(1'-methyl-2'-oxo-1',2,2',3-tetrahydrospiro[furo[2,3-g][1,4]benzodioxine-8,3'-indol]-4'-yl)heptanamide;

2-(2-methoxyethoxy)-N-(1'-methyl-2'-oxo-1',2,2',3-tetrahydrospiro[furo[2,3-g][1,4]benzodioxine-8,3'-indol]-4'-yl)acetamide;

1-hexyl-3-(1'-methyl-2'-oxo-1',2,2',3-tetrahydrospiro[furo[2,3-g][1,4]benzodioxine-8,3'-indol]-4'-yl)urea;

1-cyclopentyl-3-(1'-methyl-2'-oxo-1',2,2',3-tetrahydrospiro[furo[2,3-g][1,4]benzodioxine-8,3'-indol]-4'-yl)urea;

1-cyclohexyl-3-(1'-methyl-2'-oxo-1',2,2',3-tetrahydrospiro[furo[2,3-g][1,4]benzodioxine-8,3'-indol]-4'-yl)urea;

N-cyclohexyl-1'-methyl-2'-oxo-1',2,2',3-tetrahydrospiro[furo[2,3-g][1,4]benzodioxine-8,3'-indole]-4'-carboxamide;

N-cyclopentyl-1'-methyl-2'-oxo-1',2,2',3-tetrahydrospiro[furo[2,3-g][1,4]benzodioxine-8,3'-indole]-4'-carboxamide;

N-cyclopropyl-1'-methyl-2'-oxo-1',2,2',3-tetrahydrospiro[furo[2,3-g][1,4]benzodioxine-8,3'-indole]-4'-carboxamide;

1-methyl-4'-(pyrrolidin-1-ylcarbonyl)-2,3-dihydrospiro[furo[2,3-g][1,4]benzodioxine-8,3'-indol]-2'(1'H)-one;

N-(2-methoxyethyl)-1'-methyl-2'-oxo-1',2,2',3-tetrahydrospiro[furo[2,3-g][1,4]benzodioxine-8,3'-indole]-4'-carboxamide;

N-(4-fluorobenzyl)-1'-methyl-2'-oxo-1',2,2',3-tetrahydrospiro[furo[2,3-g][1,4]benzodioxine-8,3'-indole]-4'-carboxamide;

N-hexyl-1'-methyl-2'-oxo-1',2,2',3-tetrahydrospiro[furo[2,3-g][1,4]benzodioxine-8,3'-indole]-4'-carboxamide;

1'-methyl-2'-oxo-N-(pyridin-2-ylmethyl)-1',2,2',3-tetrahydrospiro[furo[2,3-g][1,4]benzodioxine-8,3'-indole]-4'-carboxamide;

N-(4-fluorophenyl)-1'-methyl-2'-oxo-1',2,2',3-tetrahydrospiro[furo[2,3-g][1,4]benzodioxine-8,3'-indole]-4'-carboxamide;

4'-amino-1'-pentyl-2,3-dihydrospiro[furo[2,3-g][1,4]benzodioxine-8,3'-indol]-2'(1'H)-one;

4'-(benzylamino)-1'-{[3-(trifluoromethyl)pyridin-2-yl]methyl}-2,3-dihydrospiro[furo[2,3-g][1,4]benzodioxine-8,3'-indol]-2'(1'H)-one;

4'-amino-1'-{[3-(trifluoromethyl)pyridin-2-yl]methyl}-2,3-dihydrospiro[furo[2,3-g][1,4]benzodioxine-8,3'-indol]-2'(1'H)-one;

4'-hydroxy-1'-methyl-2,3-dihydrospiro[furo[2,3-g][1,4]benzodioxine-8,3'-indol]-2'(1'H)-one;

1'-methyl-4'-(pyridin-2-yloxy)-2,3-dihydrospiro[furo[2,3-g][1,4]benzodioxine-8,3'-indol]-2'(1'H)-one;

4'-[2-(2-methoxyethoxy)ethoxy]-1'-methyl-2,3-dihydrospiro[furo[2,3-g][1,4]benzodioxine-8,3'-indol]-2'(1'H)-one;

1'-methyl-4'-{[3-(trifluoromethyl)pyridin-2-yl]oxy}-2,3-dihydrospiro[furo[2,3-g][1,4]benzodioxine-8,3'-indol]-2'(1'H)-one;

1'-methyl-4'-[4-(trifluoromethyl)phenoxy]-2,3-dihydrospiro[furo[2,3-g][1,4]benzodioxine-8,3'-indol]-2'(1'H)-one;

4'-(benzyloxy)-1'-methyl-2,3-dihydrospiro[furo[2,3-g][1,4]benzodioxine-8,3'-indol]-2'(1'H)-one;

1-methyl-4'-{[3-(trifluoromethyl)pyridin-2-yl]methoxy}-2,3-dihydrospiro[furo[2,3-g][1,4]benzodioxine-8,3'-indol]-2'(1'H)-one;

4'-(6-(dimethylamino)pyridin-3-yl)-1'-(pyridin-2-ylmethyl)-3,7-dihydro-2H-spiro[benzofuro[5,6-b][1,4]dioxine-8,3'-indolin]-2'-one;

4'-(4-methoxyphenyl)-1'-(pyridin-2-ylmethyl)-3,7-dihydro-2H-spiro[benzofuro[5,6-b][1,4]dioxine-8,3'-indolin]-2'-one;

1'-methyl-4'-(1H-pyrazol-3-yl)-2,3-dihydrospiro[furo[2,3-g][1,4]benzodioxine-8,3'-indol]-2'(1'H)-one;

4'-furan-3-yl1'-methyl-2,3-dihydrospiro[furo[2,3-g][1,4]benzodioxine-8,3'-indol]-2'(1'H)-one;

1-methyl-4'-(1H-pyrazol-4-yl)-2,3-dihydrospiro[furo[2,3-g][1,4]benzodioxine-8,3'-indol]-2'(1'H)-one;

1'-methyl-4'-(1-methyl-1H-pyrazol-4-yl)-2,3-dihydrospiro[furo[2,3-g][1,4]benzodioxine-8,3'-indol]-2'(1'H)-one;

1'-methyl-2'-oxo-1',2,2',3-tetrahydrospiro[furo[2,3-g][1,4]benzodioxine-8,3'-indole]-4'-carbonitrile;

1'-methyl-2'-oxo-1',2,2',3-tetrahydrospiro[furo[2,3-g][1,4]benzodioxine-8,3'-indole]-4'-carboxamide;

1'-methyl-4'-(5-methyl-1,2,4-oxadiazol-3-yl)-2,3-dihydrospiro[furo[2,3-g][1,4]benzodioxine-8,3'-indol]-2'(1'H)-one;

4'-(3,5-dimethylisoxazol-4-yl)-1'-methyl-2,3-dihydrospiro[furo[2,3-g][1,4]benzodioxine-8,3'-indol]-2'(1'H)-one;

N,1'-dimethyl-2'-oxo-1',2,2',3-tetrahydrospiro[furo[2,3-g][1,4]benzodioxine-8,3'-indole]-4'-carboxamide;

N-cyclobutyl-1'-methyl-2'-oxo-1',2,2',3-tetrahydrospiro[furo[2,3-1,4]benzodioxine-8,3'-indole]-4'-carboxamide;

N,N,1'-trimethyl-2'-oxo-1',2,2',3-tetrahydrospiro[furo[2,3-g][1,4]benzodioxine-8,3'-indole]-4'-carboxamide;

4'-(3-methoxyphenoxy)-1'-methyl-2,3-dihydrospiro[furo[2,3-g][1,4]benzodioxine-8,3'-indol]-2'(1'H)-one;

1-methyl-4-phenoxy-2,3-dihydrospiro[furo[2,3-g][1,4]benzodioxine-8,3'-indol]-2'(1'H)-one;

1-methyl-4'-(3-morpholin-4-ylphenoxy)-2,3-dihydrospiro[furo[2,3-g][1,4]benzodioxine-8,3'-indol]-2'(1'H)-one;

4'-[(6-methoxypyridin-3-yl)oxy]-1'-methyl-2,3-dihydrospiro[furo[2,3-1,4]benzodioxine-8,3'-indol]-2'(1'H)-one;

4'-(1,3-benzodioxol-5-yloxy)-1'-methyl-2,3-dihydrospiro[furo[2,3-g][1,4]benzodioxine-8,3'-indol]-2'(1'H)-one;

4'-(4-methoxyphenoxy)-1-methyl-2,3-dihydrospiro[furo[2,3-g][1,4]benzodioxine-8,3'-indol]-2'(1'H)-one;

1'-methyl-4-(pyridine-2-ylmethoxy)-2,3-dihydrospiro[furo[2,3-g][1,4]benzodioxine-8,3'-indol]-2'(1'H)-one;

1'-methyl-4-(4-fluorobenzyloxy)-2,3-dihydrospiro[furo[2,3-g][1,4]benzodioxine-8,3'-indol]-2'(1'H)-one;

4'-(4-fluorophenoxy)-1'-methyl-2,3-dihydrospiro[furo[2,3-g][1,4]benzodioxine-8,3'-indol]-2'(1'H)-one;

1'-(4-hydroxybenzyl)-2,3-dihydrospiro[furo[2,3-g][1,4]benzodioxine-8,3'-indol]-2'(1'H)-one;

1'-(3-hydroxypropyl)-2,3-dihydrospiro[furo[2,3-g][1,4]benzodioxine-8,3'-indol]-2'(1'H)-one;

ethyl 2'-oxo-2,3-dihydrospiro[furo[2,3-g][1,4]benzodioxine-8,3'-indole]-1'(2'H)-carboxylate;

tert-butyl 2'-oxo-2,3-dihydrospiro[furo[2,3-g][1,4]benzodioxine-8,3'-indole]-1'(2'H)-carboxylate;

1'-{[(3aR,5R,5aS,8aS,8bR)-2,2,7,7-tetramethyltetrahydro-3aH-bis[1,3]dioxolo[4,5-b:4',5'-d]pyran-5-yl]methyl}-2,3-dihydrospiro[furo[2,3-g][1,4]benzodioxine-8,3'-indol]-2'(1'H)-one;

6-deoxy-6-(2'-oxo-2,3-dihydrospiro[furo[2,3-g][1,4]benzodioxine-8,3'-indol]-1'(2'H)-yl)-D-galactopyranose;

1'-cyclopropyl-2,3-dihydrospiro[furo[2,3-g][1,4]benzodioxine-8,3'-indol]-2'(1'H)-one;

1'-acetyl-2,3-dihydrospiro[furo[2,3-g][1,4]benzodioxine-8,3'-indol]-2'(1'H)-one;

1'-{[4-(trifluoromethyl)pyridin-2-yl]methyl}-2,3-dihydrospiro[furo[2,3-g][1,4]benzodioxine-8,3'-indol]-2'(1'H)-one;

4'-acetyl-1'-methyl-2,3-dihydrospiro[furo[2,3-g][1,4]benzodioxine-8,3'-indol]-2'(1'H)-one;

1'-methyl-4'-(2-methyl-1,3-thiazol-4-yl)-2,3-dihydrospiro[furo[2,3-g][1,4]benzodioxine-8,3'-indol]-2'(1'H)-one;

4'-(2-amino-1,3-thiazol-4-yl)-1'-methyl-2,3-dihydrospiro[furo[2,3-g][1,4]benzodioxine-8,3'-indol]-2'(1'H)-one;

4'-(5-hydroxy-1H-pyrazol-3-yl)-1'-methyl-2,3-dihydrospiro[furo[2,3-g][1,4]benzodioxine-8,3'-indol]-2'(1'H)-one;

1'-[3-(3-methyl-1,2,4-oxadiazol-5-yl)benzyl]-2,3-dihydrospiro[furo[2,3-g][1,4]benzodioxine-8,3'-indol]-2'(1'H)-one;

1'-[4-(3-amino-1H-pyrazol-5-yl)benzyl]-2,3-dihydrospiro[furo[2,3-g][1,4]benzodioxine-8,3'-indol]-2'(1'H)-one hydrochloride;

1'-[4-(3-methyl-1,2,4-oxadiazol-5-yl)benzyl]-2,3-dihydrospiro[furo[2,3-g][1,4]benzodioxine-8,3'-indol]-2'(1'H)-one;

2'-oxo-1'-(pyridin-2-ylmethyl)-1',2,2',3-tetrahydrospiro[furo[2,3-g][1,4]benzodioxine-8,3'-indole]-5'-carboxamide;

1'-[(6-morpholin-4-ylpyridin-3-yl)methyl]-2,3-dihydrospiro[furo[2,3-g][1,4]benzodioxine-8,3'-indol]-2'(1'H)-one;

1'-{[6-(dimethylamino)pyridin-3-yl]methyl}-2,3-dihydrospiro[furo[2,3-g][1,4]benzodioxine-8,3'-indol]-2'(1'H)-one;

1'-{[6-(dimethylamino)pyridin-2-yl]methyl}-2,3-dihydrospiro[furo[2,3-g][1,4]benzodioxine-8,3'-indol]-2'(1'H)-one;

1'-({6-[(diphenylmethylidene)amino]pyridin-2-yl}methyl)-2,3-dihydrospiro[furo[2,3-1,4]benzodioxine-8,3'-indol]-2'(1'H)-one;

1'-[(5-morpholin-4-ylpyridin-2-yl)methyl]-2,3-dihydrospiro[furo[2,3-g] [1,4]benzodioxine-8,3'-indol]-2'(1'H)-one;

1'-{[5-(dimethylamino)pyridin-2-yl]methyl}-2,3-dihydrospiro[furo[2,3-g][1,4]benzodioxine-8,3'-indol]-2'(1'H)-one;

1'-[(6-aminopyridin-2-yl)methyl]-2,3-dihydrospiro[furo[2,3-g][1,4]benzodioxine-8,3'-indol]-2'(1'H)-one;

1'-[(6-oxo-1,6-dihydropyridin-3-yl)methyl]-2,3-dihydrospiro[furo[2,3-g][1,4]benzodioxine-8,3'-indol]-2'(1'H)-one;

1'-[(2-hydroxypyrimidin-5-yl)methyl]-2,3-dihydrospiro[furo[2,3-g][1,4]benzodioxine-8,3'-indol]-2'(1'H)-one;

1'-[(1-methyl-6-oxo-1,6-dihydropyridin-3-yl)methyl]-2,3-dihydrospiro[furo[2,3-g][1,4]benzodioxine-8,3'-indol]-2'(1'H)-one;

1'-[(6-aminopyridin-3-yl)methyl]-2,3-dihydrospiro[furo[2,3-g][1,4]benzodioxine-8,3'-indol]-2'(1'H)-one;

N'-hydroxy-N-{5-[(2'-oxo-2,3-dihydrospiro[furo[2,3-g][1,4]benzodioxine-8,3'-indol]-1'(2'H)-yl)methyl]pyridin-2-yl}imidoformamide;

1'-([1,2,4]triazolo[1,5-a]pyridin-6-ylmethyl)-2,3-dihydrospiro[furo[2,3-g][1,4]benzodioxine-8,3'-indol]-2'(1'H)-one;

1'-[(2S)-2,3-dihydroxypropyl]-2,3-dihydrospiro[furo[2,3-g][1,4]benzodioxine-8,3'-indol]-2'(1'H)-one;

6-[(2'-oxo-2,3-dihydrospiro[furo[2,3-g][1,4]benzodioxine-8,3'-indol]-1'(2'H)-yl)methyl]pyridine-2-carbonitrile; or 6-[(2'-oxo-2,3-dihydrospiro[furo[2,3-g][1,4]benzodioxine-8,3'-indol]-1'(2'H)-yl)methyl]pyridine-2-carboxamide.

21. A pharmaceutical composition comprising a pharmaceutically acceptable excipient and a compound of claim 18, as a stereoisomer, enantiomer, tautomer thereof or mixtures thereof; or a pharmaceutically acceptable salt or prodrug thereof.

22. A method of treating pain in a mammal, wherein the method comprises administering to the mammal in need thereof a therapeutically effective amount of a compound of claim 18, as a stereoisomer, enantiomer, tautomer thereof or mixtures thereof; or a pharmaceutically acceptable salt or prodrug thereof.

23. The method of claim 22, wherein the pain is selected from the group consisting of neuropathic pain, inflammatory pain, visceral pain, cancer pain, dental pain, chemotherapy pain, trauma pain, surgical pain, labor pain, neurogenic bladder, ulcerative colitis, chronic pain, persistent pain, peripherally mediated pain, centrally mediated pain, chronic headache, migraine headache, sinus headache, tension headache, phantom limb pain, and peripheral nerve injury, and combinations thereof.

24. The method of claim 22, wherein the pain is associated with a disease or condition selected from HIV, HIV treatment induced neuropathy, heat sensitivity, sarcoidosis, irritable bowel syndrome, Crohns disease, multiple sclerosis, amyotrophic lateral sclerosis, pruritis, hypercholesterolemia, benign prostatic hyperplasia, diabetic neuropathy, peripheral neuropathy, rheumatoid arthritis, osteoarthritis, paroxysmal dystonia, myasthenia syndromes, myotonia, malignant hyperthermia, cystic fibrosis, pseudoaldosteronism, rhabdomyolysis, bipolar depression, anxiety, schizophrenia, sodium channel toxin related illnesses, Paroxysmal Episodic Pain Disorder, cancer, epilepsy, partial and general tonic seizures, restless leg syndrome, arrhythmias, ischaemic conditions caused by stroke or neural trauma, tachy-arrhythmias, atrial fibrillation and ventricular fibrillation.

25. The method of claim 22 wherein the pain is selected from trigeminal neuralgia, post-herpetic neuralgia, eudynia, familial erythromelalgia, primary erythromelalgia, familial rectal pain or fibromyalgia.

* * * * *

UNITED STATES PATENT AND TRADEMARK OFFICE
CERTIFICATE OF CORRECTION

PATENT NO. : 8,263,606 B2
APPLICATION NO. : 12/578148
DATED : September 11, 2012
INVENTOR(S) : Mikhail Chafeev et al.

Page 1 of 1

It is certified that error appears in the above-identified patent and that said Letters Patent is hereby corrected as shown below:

In the Claims

Column 737, Claim 1, Line 12:
"(5-methoxycarbonylfuran-2-yl)methyl, 2(2-methoxyethoxy)ethyl," should read,
--(5-methoxycarbonylfuran-2-yl)methyl, 2-(2-methoxyethoxy)ethyl,--.

Column 737, Claim 3, Line 61:
"(S)-1'-(pyridine-2-ylmethyl)-2,3-dihydrospiro[furo[2,3-g]" should read, --1'-(pyridine-2-ylmethyl)-2,3-dihydrospiro[furo[2,3-g]--.

Column 742, Claim 20, Line 18:
"[2,3-g][1,4]benzodioxine-8,3'-indole]-4'carboxamide;" should read, --[2,3-g][1,4]benzodioxine-8,3'-indole]-4'-carboxamide;--.

Column 742, Claim 20, Line 52:
"4',7'-dimethoxy-1'-[2-(2-methoxyethoxy)ethyl]2,3-dihydrospiro" should read, --4',7'-dimethoxy-1'-[2-(2-methoxyethoxy)ethyl]-2,3-dihydrospiro--.

Column 743, Claim 20, Line 1:
"4-[(2'-oxo-2,3-dihydrospiro[furo[2,3-g][]1,4]benzodioxine" should read, --4-[(2'-oxo-2,3-dihydrospiro[furo[2,3-g][1,4]benzodioxine--.

Column 745, Claim 20, Line 24:
"1'-[(2-fluoro-5-trifluoromethyL)benzyl]-2,3-dihydrospiro" should read, --1'-[(2-fluoro-5-trifluoromethyl)benzyl]-2,3-dihydrospiro--.

Column 745, Claim 20, Line 49:
"1'-3-(benzyloxy)propyl]-2,3-dihydrospiro[furo[2,3-g][1," should read, --1'-[3-(benzyloxy)propyl]-2,3-dihydrospiro[furo[2,3-g][1,--.

Signed and Sealed this
Seventh Day of January, 2014

Margaret A. Focarino
*Commissioner for Patents of the United States Patent and Trademark Office*

UNITED STATES PATENT AND TRADEMARK OFFICE
CERTIFICATE OF CORRECTION

PATENT NO. : 8,263,606 B2
APPLICATION NO. : 12/578148
DATED : September 11, 2012
INVENTOR(S) : Mikhail Chafeev et al.

It is certified that error appears in the above-identified patent and that said Letters Patent is hereby corrected as shown below:

In the Claims

Column 745, Line 56, Claim 20,
"4'-bromo-11'-pentyl-2,3-dihydrospiro[furo[2,3-g][1,4]" should read,
--4'-bromo-1'-pentyl-2,3-dihydrospiro[furo[2,3-g][1,4]--.

Column 746, Line 19, Claim 20,
"(2'-oxo-2,3-dihydrospiro[furo[2,3-1,4]benzodioxine-8,3'" should read,
--(2'-oxo-2,3-dihydrospiro[furo[2,3-g][1,4]benzodioxine-8,3'--.

Column 746, Line 40, Claim 20,
"1'-[4(5-methyl-1,2,4-oxadiazol-3-yl)benzyl]-2,3-dihydrospiro" should read,
--1'-[4-(5-methyl-1,2,4-oxadiazol-3-yl)benzyl]-2,3-dihydrospiro--.

Column 746, Lines 43-44, Claim 20,
"3-[(2'-oxo-2,3-dihydrospiro[furo[2,3-g][1,4]benzodioxine-8,3'indol]1'(2'H)-yl)methyl]benzoic acid;" should read, --3-[(2'-oxo-2,3-dihydrospiro[furo[2,3-g][1,4]benzodioxine-8,3'-indol]-1'(2'*H*)-yl)methyl]benzoic acid;--.

Column 746, Lines 52-53, Claim 20,
"2-(2'-oxo-2,3-dihydrospiro[furo[2,3-g][1,4]benzodioxine-8,3'-indol]-1'(1'H)-yl)acetohydrazide;" should read, --2-(2'-oxo-2,3-dihydrospiro[furo[2,3-g][1,4]benzodioxine-8,3'-indol]-1'(2'*H*)-yl)acetohydrazide;--.

Column 746, Lines 59-60, Claim 20,
"N-{3[2'-oxo-2,3-dihydrospiro[furo[2,3-g][1,4]benzodioxine-8,3'-indol]-1'(1'H)-yl)methyl]" should read, --N-{3[2'-oxo-2,3-dihydrospiro[furo[2,3-g][1,4]benzodioxine-8,3'-indol]-1'(2'*H*)-yl)methyl]--.

Signed and Sealed this
Seventeenth Day of February, 2015

Michelle K. Lee
*Deputy Director of the United States Patent and Trademark Office*

CERTIFICATE OF CORRECTION (continued)
U.S. Pat. No. 8,263,606 B2

Column 749, Line 33, Claim 20,
"4'-furan-3-yl1'methyl-2,3-dihydrospiro[furo[2,3-g][1,4]" should read,
--4'-furan-3-yl-1'methyl-2,3-dihydrospiro[furo[2,3-g][1,4]--.

Column 749, Lines 53-54, Claim 20,
"[furo[2,3-1,4]benzodioxine-8,3'-indole]-4'-carboxamide;" should read,
--[furo[2,3-g][1,4]benzodioxine-8,3'-indole]-4'-carboxamide;--.

Column 749, Line 65, Claim 20,
"dihydrospiro[furo[2,3-1,4]benzodioxine-8,3'-indol]-2'" should read,
--dihydrospiro[furo[2,3-g][1,4]benzodioxine-8,3'-indol]-2'--.

Column 750, Line 3, Claim 20,
"4'-(4-methoxyphenoxy)-1-methyl-2,3-dihydrospiro[furo" should read,
--4'-(4-methoxyphenoxy)-1'-methyl-2,3-dihydrospiro[furo--.

Column 750, Line 64, Claim 20,
"yl}methyl)-2,3-dihydrospiro[furo[2,3-1,4]benzodioxine" should read,
--yl}methyl)-2,3-dihydrospiro[furo[2,3-g][1,4]benzodioxine--.